(12) United States Patent
Sakuma

(10) Patent No.: US 11,968,887 B2
(45) Date of Patent: Apr. 23, 2024

(54) ORGANIC ELECTROLUMINESCENCE DEVICE AND DIAMINE COMPOUND FOR ORGANIC ELECTROLUMINESCENCE DEVICE

(71) Applicant: Samsung Display Co., Ltd., Yongin-si (KR)

(72) Inventor: Takao Sakuma, Yokohama (JP)

(73) Assignee: Samsung Display Co., Ltd., Yongin-si (KR)

( * ) Notice: Subject to any disclaimer, the term of this patent is extended or adjusted under 35 U.S.C. 154(b) by 327 days.

(21) Appl. No.: 17/099,550

(22) Filed: Nov. 16, 2020

(65) Prior Publication Data

US 2022/0344589 A1   Oct. 27, 2022

(30) Foreign Application Priority Data

Nov. 27, 2019  (KR) .................. 10-2019-0154806
Jul. 2, 2020    (KR) .................. 10-2020-0081721

(51) Int. Cl.
*C07C 211/54*        (2006.01)
*C07C 211/58*        (2006.01)
(Continued)

(52) U.S. Cl.
CPC .......... *H10K 85/633* (2023.02); *C07C 211/54* (2013.01); *C07C 211/58* (2013.01);
(Continued)

(58) Field of Classification Search
None
See application file for complete search history.

(56) References Cited

U.S. PATENT DOCUMENTS 6,872,475 B2   3/2005 Chen et al.
7,901,793 B2   3/2011 Kim et al.
(Continued)

FOREIGN PATENT DOCUMENTS

CN   101400643 A   4/2009
CN   101668730 A   3/2010
(Continued)

OTHER PUBLICATIONS

Machine translation of JP-2008056625, translation generated Apr. 2023, 30 pages. (Year: 2023).*

(Continued)

*Primary Examiner* — Robert S Loewe
(74) *Attorney, Agent, or Firm* — Lewis Roca Rothgerber Christie LLP

(57) ABSTRACT

An organic electroluminescence device of an embodiment includes a first electrode, a hole transport region disposed on the first electrode, an emission layer disposed on the hole transport region, an electron transport region disposed on the emission layer, and a second electrode disposed on the electron transport region, wherein the hole transport region includes a diamine compound represented by Formula 1, thereby showing high emission efficiency:

(Continued)

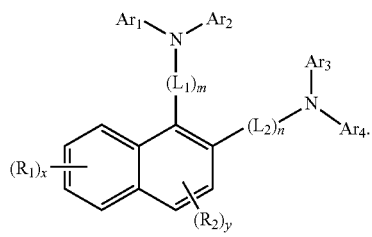

[Formula 1]

24 Claims, 2 Drawing Sheets

(51) Int. Cl.
*C07D 333/76* (2006.01)
*C09K 11/06* (2006.01)
*H10K 85/60* (2023.01)
*H10K 50/11* (2023.01)
*H10K 50/15* (2023.01)
*H10K 50/16* (2023.01)
*H10K 50/17* (2023.01)
*H10K 50/18* (2023.01)

(52) U.S. Cl.
CPC ............ *C07D 333/76* (2013.01); *C09K 11/06* (2013.01); *H10K 85/636* (2023.02); *C09K 2211/1007* (2013.01); *C09K 2211/1011* (2013.01); *C09K 2211/1014* (2013.01); *C09K 2211/1018* (2013.01); *H10K 50/11* (2023.02); *H10K 50/15* (2023.02); *H10K 50/166* (2023.02); *H10K 50/17* (2023.02); *H10K 50/18* (2023.02); *H10K 85/615* (2023.02); *H10K 85/626* (2023.02); *H10K 85/6576* (2023.02)

(56) References Cited

U.S. PATENT DOCUMENTS

| | | |
|---|---|---|
| 8,026,514 B2 | 9/2011 | Jang et al. |
| 8,329,316 B2 | 12/2012 | Kim et al. |
| 2002/0051918 A1 | 5/2002 | Miyamoto et al. |
| 2004/0061136 A1 | 4/2004 | Tyan et al. |
| 2009/0174312 A1* | 7/2009 | Kim ............... H10K 85/322 548/440 |
| 2012/0032152 A1 | 2/2012 | Kim et al. |
| 2018/0123048 A1 | 5/2018 | So et al. |
| 2022/0158095 A1* | 5/2022 | Huang ............. C07C 211/61 |

FOREIGN PATENT DOCUMENTS

| | | |
|---|---|---|
| CN | 107531684 A | 1/2018 |
| CN | 111217714 A | 6/2020 |
| CN | 112142605 A | 12/2020 |
| EP | 2 139 846 B1 | 9/2016 |
| JP | H08 87122 A | 4/1996 |
| JP | 2002-91031 A | 3/2002 |
| JP | 3780279 B2 | 5/2006 |
| JP | 2008056625 A * | 3/2008 ............ C07C 211/58 |
| JP | 4541511 B2 | 9/2010 |
| JP | 5088097 B2 | 12/2012 |
| JP | 5373769 B2 | 12/2013 |
| KR | 10-0670185 B1 | 2/2007 |
| KR | 10-1012578 B1 | 2/2011 |
| KR | 10-2016-0013692 A | 2/2016 |
| KR | 10-2016-0113783 A | 10/2016 |
| KR | 10-2016-0127429 A | 11/2016 |
| KR | 10-2019-0056336 A | 5/2019 |
| TW | I478898 B | 4/2015 |
| WO | WO 2007/063986 A1 | 6/2007 |
| WO | WO 2007/105884 A1 | 9/2007 |
| WO | WO 2008/133459 A1 | 11/2008 |

OTHER PUBLICATIONS

Machine translation of CN-111217714, translation generated Apr. 2023, 11 pages. (Year: 2023).*
EPO EESR dated Jun. 7, 2021 for EP Application No. 20206001.8, 13 pages.
R.F. Bridger, "Radical Coupling Products from the Permanganate Oxidation of N-Phenyl-2-naphthylamine," *J. Org. Chem.*, vol. 35, No. 6, 1970, pp. 1746-1750.
EPO ESR dated Mar. 22, 2021 for EP Application No. 20206001.8, 7 pgs.

* cited by examiner

ORGANIC ELECTROLUMINESCENCE DEVICE AND DIAMINE COMPOUND FOR ORGANIC ELECTROLUMINESCENCE DEVICE

CROSS-REFERENCE TO RELATED APPLICATION

This application claims priority to and the benefit of Korean Patent Application No. 10-2019-0154806, filed on Nov. 27, 2019, and Korean Patent Application No. 10-2020-0081721, filed on Jul. 2, 2020, the entire content of each of which is hereby incorporated by reference.

BACKGROUND

1. Field

One or more aspects of embodiments of the present disclosure relate to an organic electroluminescence device and a diamine compound for an organic electroluminescence device.

2. Description of the Related Art

Organic electroluminescence displays are being actively developed as image displays. Different from a liquid crystal display, the organic electroluminescence display is a so-called self-luminescent display, in which holes and electrons respectively injected from a first electrode and a second electrode recombine in an emission layer, and a light-emitting material including an organic compound in the emission layer emits light to attain display.

In the application of an organic electroluminescence device to a display, a decreased driving voltage, increased emission efficiency, and increased life (lifespan) of the organic electroluminescence device are desired, and development of materials for an organic electroluminescence device stably attaining such demands are desired.

SUMMARY

One or more aspects of embodiments of the present disclosure are directed toward an organic electroluminescence device and a diamine compound for an organic electroluminescence device, for example, to an organic electroluminescence device having high efficiency and a diamine compound included in the hole transport region of an organic electroluminescence device.

One or more example embodiments of the present disclosure provide an organic electroluminescence device including a first electrode, a hole transport region on the first electrode, an emission layer on the hole transport region, an electron transport region on the emission layer and a second electrode on the electron transport region, wherein the hole transport region includes a diamine compound represented by Formula 1:

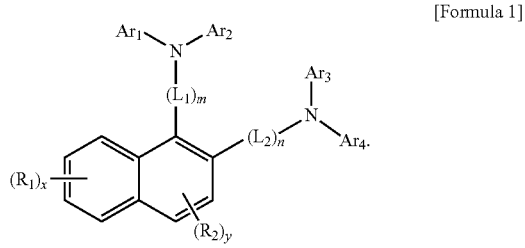

[Formula 1]

In Formula 1, $Ar_1$ to $Ar_4$ may each independently be a substituted or unsubstituted aryl group of 6 to 30 carbon atoms for forming a ring or a substituted or unsubstituted heteroaryl group of 2 to 30 carbon atoms for forming a ring, $L_1$ may be a direct linkage or a substituted or unsubstituted phenylene group, $L_2$ may be a direct linkage, a substituted or unsubstituted arylene group of 6 to 30 carbon atoms for forming a ring, or a substituted or unsubstituted heteroarylene group of 2 to 30 carbon atoms for forming a ring, $R_1$ and $R_2$ may each be independently a hydrogen atom, a deuterium atom, a halogen atom, a cyano group, a substituted or unsubstituted thiol group, a substituted or unsubstituted oxy group, a substituted or unsubstituted silyl group, a substituted or unsubstituted alkyl group of 1 to 20 carbon atoms, a substituted or unsubstituted aryl group of 6 to 30 carbon atoms for forming a ring, or a substituted or unsubstituted heteroaryl group of 2 to 30 carbon atoms for forming a ring, "x" may be an integer of 0 to 4, "y" may be an integer of 0 to 2, and "m" and "n" may each independently be an integer of 0 to 4, where m+n is not 0.

In an embodiment, Formula 1 may be represented by Formula 2 or Formula 3:

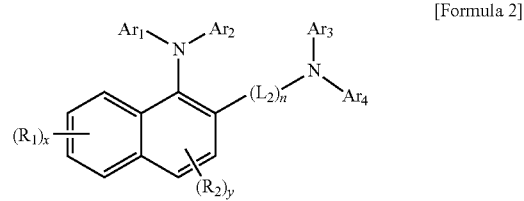

[Formula 2]

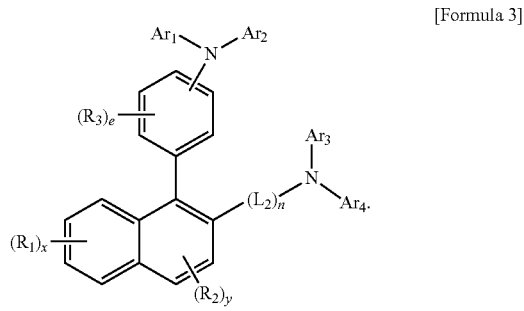

[Formula 3]

In Formula 2 and Formula 3, $R_3$ may be a hydrogen atom, a deuterium atom, a halogen atom, a substituted or unsubstituted alkyl group of 1 to 20 carbon atoms, a substituted or unsubstituted aryl group of 6 to 30 carbon atoms for forming a ring, or a substituted or unsubstituted heteroaryl group of 2 to 30 carbon atoms for forming a ring, "e" may be an integer of 0 to 4, and $Ar_1$ to $Ar_4$, $L_2$, $R_1$, $R_2$, "n", "x" and "y" may each independently be the same as defined in Formula 1.

In an embodiment, $L_2$ may be a direct linkage, a substituted or unsubstituted phenylene group, a substituted or unsubstituted biphenylene group, a substituted or unsubstituted naphthylene group, or a substituted or unsubstituted anthracenyl group.

In an embodiment, Formula 2 may be represented by Formula 2-1 or Formula 2-2:

[Formula 2-1]

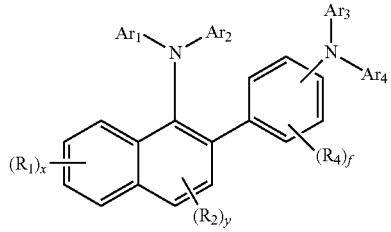

[Formula 2-2]

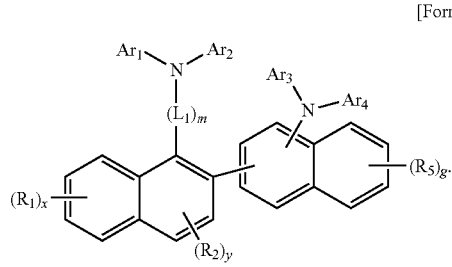

In Formula 2-1 and Formula 2-2, $R_4$ and $R_5$ may each independently be a hydrogen atom, a deuterium atom, a halogen atom, a substituted or unsubstituted alkyl group of 1 to 20 carbon atoms, a substituted or unsubstituted aryl group of 6 to 30 carbon atoms for forming a ring, or a substituted or unsubstituted heteroaryl group of 2 to 30 carbon atoms for forming a ring, "f" and "g" may each independently be an integer of 0 to 4, and $Ar_1$ to $Ar_4$, $R_1$, $R_2$, "x" and "y" may each independently be the same as defined in Formula 2.

In an embodiment, Formula 3 may be represented by any one of Formula 3-1 to Formula 3-3:

[Formula 3-1]

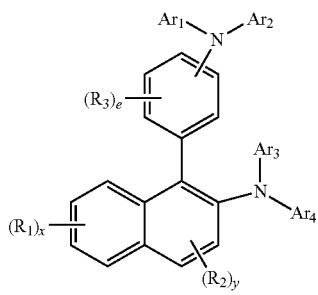

[Formula 3-2]

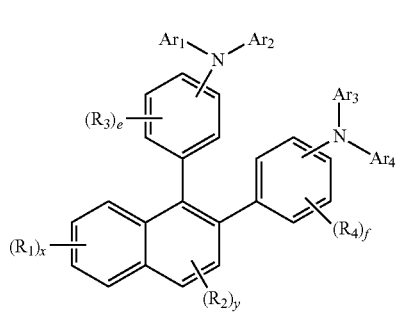

[Formula 3-3]

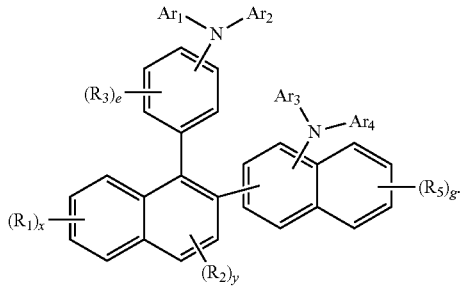

In Formula 3-1 to Formula 3-3, $R_4$ and $R_5$ may each independently be a hydrogen atom, a deuterium atom, a halogen atom, a substituted or unsubstituted alkyl group of 1 to 20 carbon atoms, a substituted or unsubstituted aryl group of 6 to 30 carbon atoms for forming a ring, or a substituted or unsubstituted heteroaryl group of 2 to 30 carbon atoms for forming a ring, "f" and "g" may each independently be an integer of 0 to 4, and $Ar_1$ to $Ar_4$, $R_1$ to $R_3$, "e", "x" and "y" may each independently be the same as defined in Formula 3.

In an embodiment, Formula 3 may be represented by Formula 4 or Formula 5:

[Formula 4]

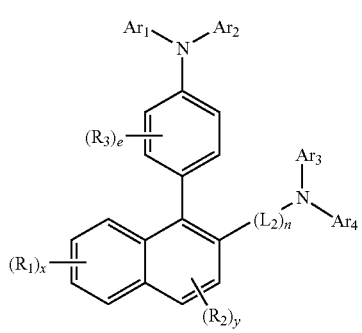

[Formula 5]

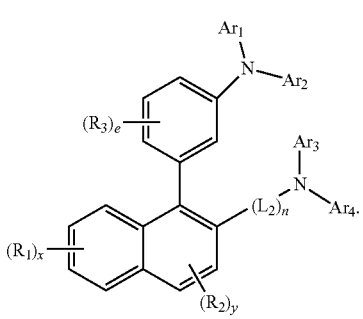

In Formula 4 and Formula 5, $Ar_1$ to $Ar_4$, $L_2$, $R_1$ to $R_3$, "e", "n", "x" and "y" may each independently be the same as defined in Formula 3.

In an embodiment, $Ar_1$ and $Ar_3$ may each independently be a substituted or unsubstituted phenyl group, a substituted or unsubstituted biphenyl group, a substituted or unsubstituted triphenyl group, or a substituted or unsubstituted naphthyl group.

In an embodiment, $R_1$ and $R_2$ may each independently be a hydrogen atom, a deuterium atom, a substituted or unsubstituted alkyl group of 1 to 5 carbon atoms, a substituted or unsubstituted phenyl group, or a substituted or unsubstituted carbazole group.

In an embodiment, the hole transport region may include a hole injection layer disposed on the first electrode, and a hole transport layer disposed on the hole injection layer, and the hole transport layer may include the diamine compound represented by Formula 1.

In an embodiment, the hole transport region may further include an electron blocking layer disposed on the hole transport layer.

In an embodiment, the diamine compound represented by Formula 1 may be at least one selected from the compounds represented in Compound Group 1 to Compound Group 5.

One or more example embodiments of the present disclosure provide a diamine compound represented by Formula 1.

BRIEF DESCRIPTION OF THE DRAWINGS

The accompanying drawings are included to provide a further understanding of the present disclosure and are incorporated in and constitute a part of this specification. The drawings illustrate example embodiments of the present disclosure and, together with the description, serve to explain principles of the present disclosure. In the drawings.

DETAILED DESCRIPTION

Figure 1:
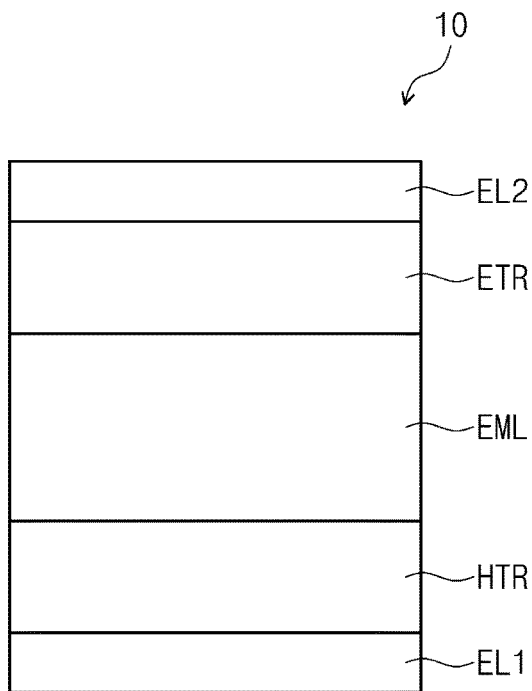
FIG. 1 is a schematic cross-sectional view illustrating an organic electroluminescence device according to an embodiment of the present disclosure.

The present disclosure may have various modifications and may be embodied in different forms, and example embodiments will be explained in detail with reference to the accompany drawings. However, the present disclosure may be embodied in different forms, and should not be construed as being limited to the embodiments set forth herein. Rather, all modifications, equivalents, and substituents that are included in the spirit and technical scope of the present disclosure should be included in the present disclosure.

It will be understood that when an element (or region, layer, part, etc.) is referred to as being "on", "connected to" or "coupled to" another element, it can be directly on, connected or coupled to the other element, or a third intervening element(s) may be present.

Like reference numerals refer to like elements throughout, and duplicative descriptions thereof may not be provided. In addition, in the drawings, the thickness, the ratio, and the dimensions of constituent elements may be exaggerated for effective explanation of technical contents.

As used herein, the singular forms "a," "an," and "the" are intended to include the plural forms as well, unless the context clearly indicates otherwise. The term "and/or" includes one or more combinations which may be defined by relevant elements.

It will be understood that, although the terms first, second, etc. may be used herein to describe various elements, these elements should not be limited by these terms. These terms are only used to distinguish one element from another element. Thus, a first element could be termed a second element without departing from the teachings of the present disclosure. Similarly, a second element could be termed a first element. As used herein, the singular forms are intended to include the plural forms as well, unless the context clearly indicates otherwise.

In addition, the terms "below," "beneath," "on," and "above" are used for explaining the relation of elements shown in the drawings. The terms are relative concepts, and are explained based on the directions shown in the drawing.

Unless otherwise defined, all terms (including technical and scientific terms) used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the relevant art, and will not be interpreted in an idealized or overly formal sense unless expressly so defined herein.

It will be further understood that the terms "includes," "including," "comprises," and/or "comprising," when used in this specification, specify the presence of stated features, numerals, steps, operations, elements, parts, or the combination thereof, but do not preclude the presence or addition of one or more other features, numerals, steps, operations, elements, parts, or the combination thereof.

As used herein, expressions such as "at least one of," "one of," and "selected from," when preceding a list of elements, modify the entire list of elements and do not modify the individual elements of the list. Further, the use of "may" when describing embodiments of the present disclosure refers to "one or more embodiments of the present disclosure".

Hereinafter, the organic electroluminescence device according to an embodiment of the present disclosure and a compound of an embodiment, included therein will be explained with reference to the attached drawings.

FIG. 1 to FIG. 4 are schematic cross-sectional views showing organic electroluminescence devices according to example embodiments of the present disclosure. Referring to FIG. 1 to FIG. 4, in an organic electroluminescence device 10 of an embodiment, a first electrode EL1 and a second electrode EL2 are oppositely disposed, and between the first electrode EL1 and the second electrode EL2, an emission layer EML may be disposed.

In some embodiments, the organic electroluminescence device 10 of an embodiment further includes a plurality of functional layers between the first electrode EL1 and the second electrode EL2 in addition to the emission layer EML. The plurality of the functional layers may include a hole transport region HTR and an electron transport region ETR. For example, the organic electroluminescence device 10 according to an embodiment may include the first electrode EL1, a hole transport region HTR, the emission layer EML, an electron transport region ETR, and the second electrode EL2, stacked in order. In some embodiments, the organic electroluminescence device 10 of an embodiment may include a capping layer CPL disposed on the second electrode EL2.

The organic electroluminescence device 10 of an embodiment may include a diamine compound of an embodiment, which will be explained later, in the emission layer EML disposed between the first electrode EL1 and the second electrode EL2. However, embodiments of the present disclosure are not limited thereto. In some embodiments, the organic electroluminescence device 10 may include the compound according to an embodiment in a hole transport region HTR and/or an electron transport region ETR, (which are among the plurality of functional layers disposed between the first electrode EL1 and the second electrode EL2 in addition to the emission layer EML), or may include the compound according to an embodiment in a capping layer CPL disposed on the second electrode EL2.

Figure 2:
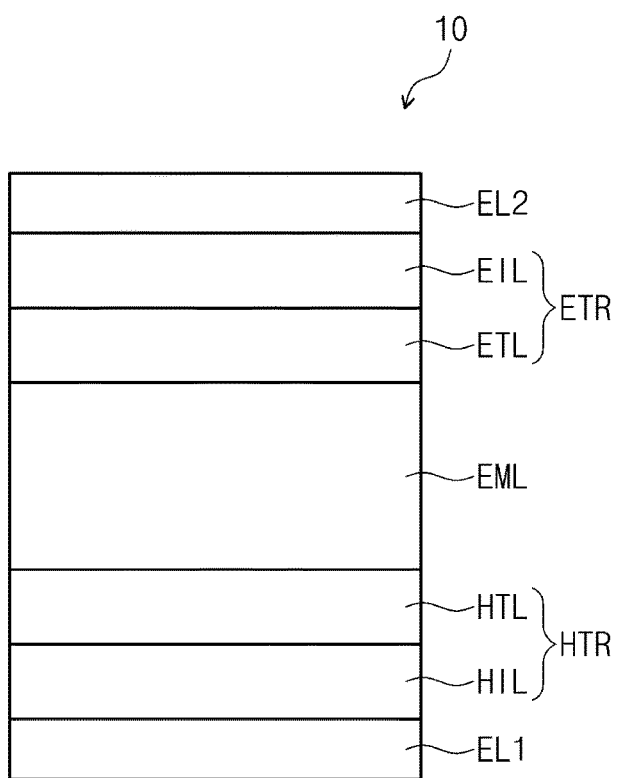
FIG. 2 is a schematic cross-sectional view illustrating an organic electroluminescence device according to an embodiment of the present disclosure.
Figure 3:
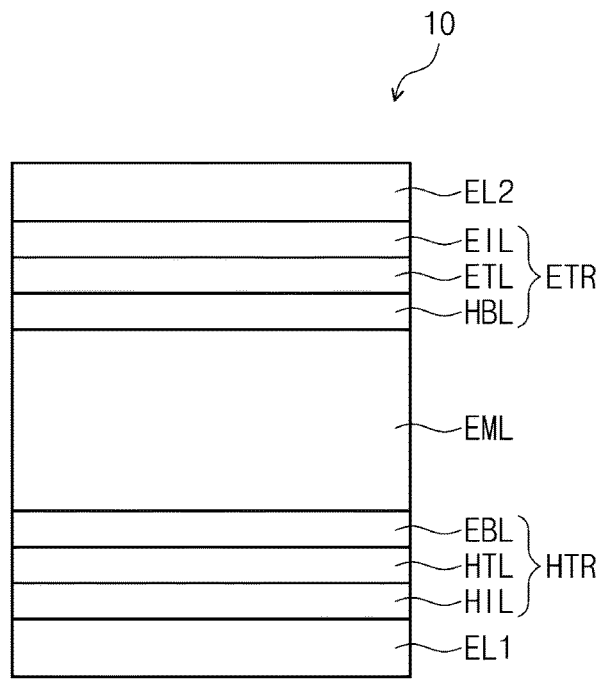
FIG. 3 is a schematic cross-sectional view illustrating an organic electroluminescence device according to an embodiment of the present disclosure.
Figure 4:
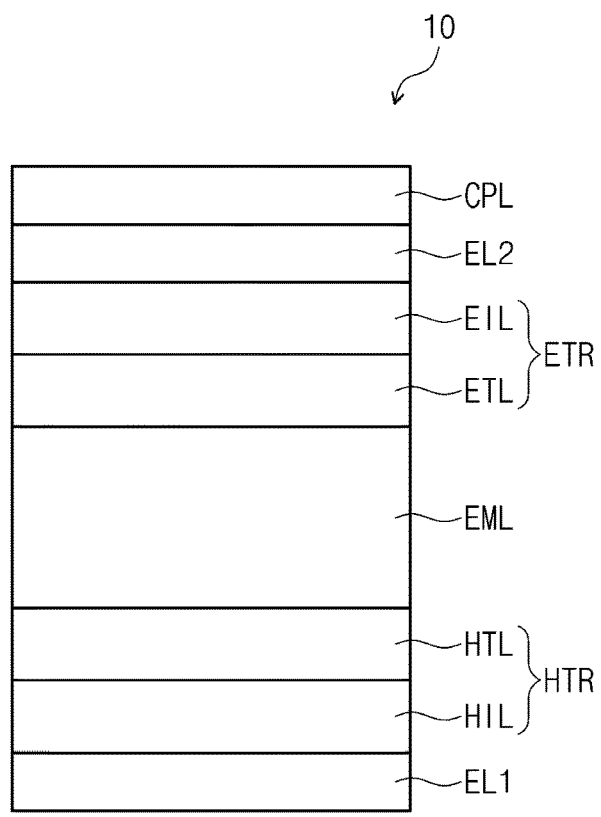
FIG. 4 is a schematic cross-sectional view illustrating an organic electroluminescence device according to an embodiment of the present disclosure.

Compared with FIG. 1, FIG. 2 shows a cross-sectional view of an organic electroluminescence device 10 of an embodiment, wherein the hole transport region HTR includes a hole injection layer HIL and a hole transport layer HTL, and the electron transport region ETR includes an electron injection layer EIL and an electron transport layer ETL. Compared with FIG. 1, FIG. 3 shows a cross-sectional view of an organic electroluminescence device 10 of an embodiment, wherein the hole transport region HTR includes the hole injection layer HIL, the hole transport layer HTL, and an electron blocking layer EBL, and the electron transport region ETR includes the electron injection layer EIL, the electron transport layer ETL, and a hole blocking layer HBL. Compared with FIG. 2, FIG. 4 shows a cross-sectional view of an organic electroluminescence device 10 of an embodiment, including a capping layer CPL disposed on the second electrode EL2.

The first electrode EL1 may have conductivity (e.g., be conductive). The first electrode EL1 may be formed using a metal alloy or a conductive compound. The first electrode EL1 may be a pixel electrode or an anode. The first electrode EL1 may be a transmissive electrode, a transflective electrode, or a reflective electrode. When the first electrode EL1 is a transmissive electrode, the first electrode EL1 may include a transparent metal oxide (such as indium tin oxide (ITO), indium zinc oxide (IZO), zinc oxide (ZnO), and/or indium tin zinc oxide (ITZO)). When the first electrode EL1 is a transflective electrode or a reflective electrode, the first electrode EL1 may include silver (Ag), magnesium (Mg), copper (Cu), aluminum (Al), platinum (Pt), palladium (Pd), gold (Au), nickel (Ni), neodymium (Nd), iridium (Ir), chromium (Cr), lithium (Li), calcium (Ca), LiF/Ca, LiF/Al, molybdenum (Mo), titanium (Ti), a compound thereof, or a mixture thereof (for example, a mixture of Ag and Mg). In some embodiments, the first electrode EL1 may have a structure including a plurality of layers including a reflective layer or a transflective layer formed using the above materials, and a transmissive conductive layer formed using ITO, IZO, ZnO, and/or ITZO. For example, the first electrode EL1 may include a three-layer structure of ITO/Ag/ITO. However, an embodiment of the present disclosure is not limited thereto. The thickness of the first electrode EL1 may be about 1,000 Å to about 10,000 Å, for example, about 1,000 Å to about 3,000 Å.

The hole transport region HTR is provided on the first electrode EL1. The hole transport region HTR may include at least one of a hole injection layer HIL, a hole transport layer HTL, a hole buffer layer, or an electron blocking layer EBL.

The hole transport region HTR may have a single layer formed using a single material, a single layer formed using a plurality of different materials, or a multilayer structure including a plurality of layers formed using a plurality of different materials.

For example, the hole transport region HTR may have the structure of a single layer of a hole injection layer HIL or a hole transport layer HTL, or may have a structure of a single layer formed using a hole injection material and a hole transport material. In some embodiments, the hole transport region HTR may have a structure of a single layer formed using a plurality of different materials, or a structure stacked from the first electrode EL1 of hole injection layer HIL/hole transport layer HTL, hole injection layer HIL/hole transport layer HTL/hole buffer layer, hole injection layer HIL/hole buffer layer, hole transport layer HTL/hole buffer layer, or hole injection layer HIL/hole transport layer HTL/electron blocking layer EBL, without limitation.

The hole transport region HTR of the organic electroluminescence device 10 of an embodiment may include the diamine compound according to an embodiment of the present disclosure.

In the description, the term "substituted or unsubstituted" refers to a state of being unsubstituted, or substituted with at least one substituent selected from the group consisting of a deuterium atom, a halogen atom, a cyano group, a nitro group, an amino group, a silyl group, an oxy group, a thio group, a sulfinyl group, a sulfonyl group, a carbonyl group, a boron group, a phosphine oxide group, a phosphine sulfide group, an alkyl group, an alkenyl group, an alkoxy group, a hydrocarbon ring group, an aryl group, and a heterocyclic group. In addition, each of the example substituents may be further substituted or unsubstituted. For example, a biphenyl group may be interpreted as a named aryl group, or as a phenyl group substituted with a phenyl group.

In the description, the term "halogen atom" includes a fluorine atom, a chlorine atom, a bromine atom, and an iodine atom.

In the description, the term "alkyl" may refer to a linear, branched or cyclic alkyl group. The carbon number of the alkyl may be 1 to 50, 1 to 30, 1 to 20, 1 to 10, or 1 to 6. Non-limiting examples of the alkyl include methyl, ethyl, n-propyl, isopropyl, n-butyl, s-butyl, t-butyl, i-butyl, 2-ethylbutyl, 3,3-dimethylbutyl, n-pentyl, i-pentyl, neopentyl, t-pentyl, cyclopentyl, 1-methylpentyl, 3-methylpentyl, 2-ethylpentyl, 4-methyl-2-pentyl, n-hexyl, 1-methylhexyl, 2-ethylhexyl, 2-butylhexyl, cyclohexyl, 4-methylcyclohexyl, 4-t-butylcyclohexyl, n-heptyl, 1-methylheptyl, 2,2-dimethylheptyl, 2-ethylheptyl, 2-butylheptyl, n-octyl, t-octyl, 2-ethyloctyl, 2-butyloctyl, 2-hexyloctyl, 3,7-dimethyloctyl, cyclooctyl, n-nonyl, n-decyl, adamantyl, 2-ethyldecyl, 2-butyldecyl, 2-hexyldecyl, 2-octyldecyl, n-undecyl, n-dodecyl, 2-ethyldodecyl, 2-butyldodecyl, 2-hexyldocecyl, 2-octyldodecyl, n-tridecyl, n-tetradecyl, n-pentadecyl, n-hexadecyl, 2-ethylhexadecyl, 2-butylhexadecyl, 2-hexylhexadecyl, 2-octylhexadecyl, n-heptadecyl, n-octadecyl, n-nonadecyl, n-eicosyl, 2-ethyleicosyl, 2-butyleicosyl, 2-hexyleicosyl, 2-octyleicosyl, n-henicosyl, n-docosyl, n-tricosyl, n-tetracosyl, n-pentacosyl, n-hexacosyl, n-heptacosyl, n-octacosyl, n-nonacosyl, n-triacontyl, etc.

In the description, the term "alkenyl group" may refer to a hydrocarbon group including one or more carbon-carbon double bonds in the middle or at the terminal end of an alkyl group including 2 or more carbon atoms. The alkenyl group may be a linear chain or a branched chain. The carbon number is not specifically limited, and may be 2 to 30, 2 to 20, or 2 to 10. Non-limiting examples of the alkenyl group include a vinyl group, a 1-butenyl group, a 1-pentenyl group, a 1,3-butadienyl group, a styrenyl group, a styrylvinyl group, etc.

In the description, the term "alkynyl group" may refer to a hydrocarbon group including one or more carbon-carbon triple bonds in the middle or at the terminal end of an alkyl group including 2 or more carbon atoms. The alkynyl group may be a linear chain or a branched chain. The carbon number is not specifically limited, and may be 2 to 30, 2 to 20, or 2 to 10. Non-limiting examples of the alkynyl group include an ethynyl group, a propynyl group, etc.

In the description, the term "hydrocarbon ring group" may refer to an optional functional group or substituent derived from an aliphatic hydrocarbon ring, or an optional functional group or substituent derived from an aromatic hydrocarbon ring. The carbon number of the hydrocarbon ring for forming a ring may be 5 to 60, 5 to 30, or 5 to 20.

In the description, the term "aryl group" may refer to an optional functional group or substituent derived from an aromatic hydrocarbon ring. The aryl group may be a monocyclic aryl group or a polycyclic aryl group. The carbon number for forming a ring in the aryl group may be 6 to 30, 6 to 20, or 6 to 15. Non-limiting examples of the aryl group include phenyl, naphthyl, fluorenyl, anthracenyl, phenanthryl, biphenyl, terphenyl, quaterphenyl, quinqphenyl, sexiphenyl, triphenylenyl, pyrenyl, benzofluoranthenyl, chrysenyl, etc.

In the description, the fluorenyl group may be substituted, and two substituents thereof may be combined with each other to form a spiro structure. Examples of a substituted fluorenyl group are as follows. However, an embodiment of the present disclosure is not limited thereto.

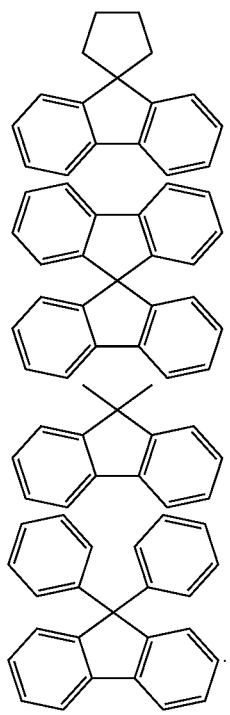

In the description, the term "heterocyclic group" may refer to an optional functional group or substituent derived from a ring including one or more heteroatoms among B, O, N, P, Si and S. The heterocyclic group may be an aliphatic heterocyclic group or an aromatic heterocyclic group. The aromatic heterocyclic group may be a heteroaryl group. The aliphatic heterocycle and the aromatic heterocycle may be a monocycle or polycycle.

In the description, the heterocyclic group may include one or more among B, O, N, P, Si and S as heteroatoms. When the heterocyclic group includes two or more heteroatoms, the two or more heteroatoms may be the same or different. The heterocyclic group may be a monocyclic heterocyclic group or a polycyclic heterocyclic group, and in some embodiments may be a heteroaryl group. The carbon number for forming a ring of the heterocyclic group may be 2 to 30, 2 to 20, or 2 to 10.

In the description, the aliphatic heterocyclic group may include one or more among B, O, N, P, Si and S as heteroatoms. The carbon number for forming a ring of the aliphatic heterocyclic group may be 2 to 30, 2 to 20, or 2 to 10. Non-limiting examples of the aliphatic heterocyclic group include an oxirane group, a thiirane group, a pyrrolidine group, a piperidine group, a tetrahydrofuran group, a tetrahydrothiophene group, a thiane group, a tetrahydropyrane group, a 1,4-dioxane group, etc.

In the description, the heteroaryl group may include one or more among B, O, N, P, Si and S as heteroatoms. When the heteroaryl group includes two or more heteroatoms, the two or more heteroatoms may be the same or different. The heteroaryl group may be a monocyclic heterocyclic group or a polycyclic heterocyclic group. The carbon number for forming a ring of the heteroaryl group may be 2 to 30, 2 to 20, or 2 to 10. Non-limiting examples of the heteroaryl group include thiophene, furan, pyrrole, imidazole, triazole, pyridine, bipyridine, pyrimidine, triazine, triazole, acridyl, pyridazine, pyrazinyl, quinoline, quinazoline, quinoxaline, phenoxazine, phthalazine, pyrido pyrimidine, pyrido pyrazine, pyrazino pyrazine, isoquinoline, indole, carbazole, N-arylcarbazole, N-heteroarylcarbazole, N-alkylcarbazole, benzoxazole, benzimidazole, benzothiazole, benzocarbazole, benzothiophene, dibenzothiophene, thienothiophene, benzofuran, phenanthroline, thiazole, isooxazole, oxazole, oxadiazole, thiadiazole, phenothiazine, dibenzosilole, dibenzofuran, etc.

In the description, the carbon number of the amine group is not specifically limited, and may be 1 to 30. The amine group may be an alkyl amine group, an aryl amine group, or a heteroaryl amine group. Non-limiting examples of the amine group include a methylamine group, a dimethylamine group, a phenylamine group, a diphenylamine group, a naphthylamine group, a 9-methyl-anthracenylamine group, a triphenylamine group, etc.

In the description, the arylene group may be substantially the same as the aryl group, except that the arylene group is a divalent group.

In the description, the heteroarylene group may be substantially the same as the heteroaryl group, except that the heteroarylene group is a divalent group.

In the description, a thiol group may include an alkylthio group and an arylthio group. In the description, the oxy group may include an alkoxy group and an aryl oxy group. In the description, the aryl group in the aryl oxy group and the aryl thio group may be the same as described herein.

In the description, "-*" indicates a connected position.

The diamine compound according to an embodiment of the present disclosure is represented by Formula 1:

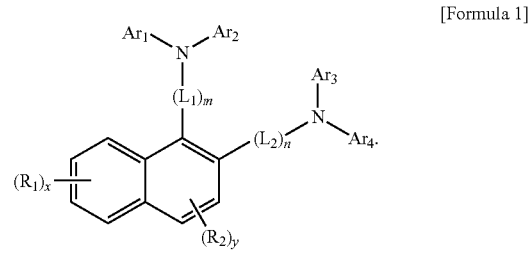

[Formula 1]

In Formula 1, $Ar_1$ to $Ar_4$ may each independently be a substituted or unsubstituted aryl group of 6 to 30 carbon atoms for forming a ring or a substituted or unsubstituted heteroaryl group of 2 to 30 carbon atoms for forming a ring.

In Formula 1, $L_1$ may be a direct linkage or a substituted or unsubstituted phenylene group.

In Formula 1, $L_2$ may be a direct linkage, a substituted or unsubstituted arylene group of 6 to 30 carbon atoms for forming a ring, or a substituted or unsubstituted heteroarylene group of 2 to 30 carbon atoms for forming a ring.

In Formula 1, $R_1$ and $R_2$ may each independently be a hydrogen atom, a deuterium atom, a halogen atom, a cyano group, a substituted or unsubstituted thiol group, a substituted or unsubstituted oxy group, a substituted or unsubstituted silyl group, a substituted or unsubstituted alkyl group of 1 to 20 carbon atoms, a substituted or unsubstituted aryl group of 6 to 30 carbon atoms for forming a ring, or a substituted or unsubstituted heteroaryl group of 2 to 30 carbon atoms for forming a ring.

In Formula 1, "x" may be an integer of 0 to 4. When "x" is 2 or more, a plurality of $R_1$ groups may be the same or different.

In Formula 1, "y" may be an integer of 0 to 2. When "y" is 2, a plurality of $R_2$ groups may be the same or different.

In Formula 1, "m" and "n" may each independently be an integer of 0 to 4, or an integer of 0 to 3, an integer of 0 to 2, or an integer of 0 to 1. However, m+n is not 0. When "m" is 2 or more, a plurality of $L_1$ groups may be the same or different, and when "n" is 2 or more, a plurality of $L_2$ groups may be the same or different.

In an embodiment, $L_1$ of Formula 1 may be a direct linkage. In this case, Formula 1 may be represented by Formula 2:

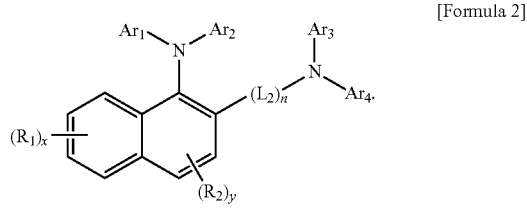

[Formula 2]

In Formula 2, $Ar_1$ to $Ar_4$, $L_2$, $R_1$, $R_2$, "n", "x" and "y" may each independently be the same as defined in Formula 1.

In an embodiment, "m" of Formula 1 may be 1, and $L_1$ may be a substituted or unsubstituted phenylene group. In this case, Formula 1 may be represented by Formula 3:

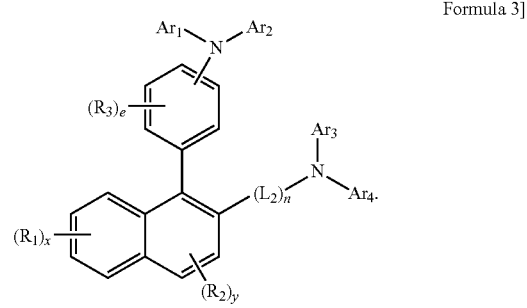

Formula 3]

In Formula 3, $R_3$ may be a hydrogen atom, a deuterium atom, a halogen atom, a substituted or unsubstituted alkyl group of 1 to 20 carbon atoms, a substituted or unsubstituted aryl group of 6 to 30 carbon atoms for forming a ring, or a substituted or unsubstituted heteroaryl group of 2 to 30 carbon atoms for forming a ring.

In Formula 3, "e" may be an integer of 0 to 4. When "e" is 2 or more, a plurality of $R_3$ groups may be the same or different.

In Formula 3, $Ar_1$ to $Ar_4$, $L_2$, $R_1$, $R_2$, "n", "x" and "y" may each independently be the same as defined in Formula 1.

In an embodiment, $L_2$ in Formula 1 may be a direct linkage, a substituted or unsubstituted phenylene group, a substituted or unsubstituted biphenylene group, a substituted or unsubstituted naphthylene group, or a substituted or unsubstituted anthracenylene group.

In an embodiment, "n" in Formula 2 may be 1, and $L_2$ may be a substituted or unsubstituted phenylene group. In this case, Formula 2 may be represented by Formula 2-1:

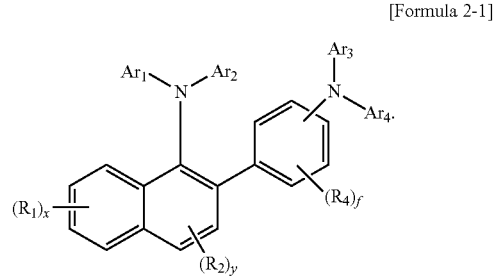

[Formula 2-1]

In Formula 2-1, $R_4$ may be a hydrogen atom, a deuterium atom, a halogen atom, a substituted or unsubstituted alkyl group of 1 to 20 carbon atoms, a substituted or unsubstituted aryl group of 6 to 30 carbon atoms for forming a ring, or a substituted or unsubstituted heteroaryl group of 2 to 30 carbon atoms for forming a ring.

In Formula 2-1, "f" may be an integer of 0 to 4. When "f" is 2 or more, a plurality of $R_4$ groups may be the same or different.

In Formula 2-1, $Ar_1$ to $Ar_4$, $R_1$, $R_2$, "x" and "y" may each independently be the same as defined in Formula 2.

In an embodiment, "n" in Formula 2 may be 1, and $L_2$ may be a substituted or unsubstituted naphthylene group. In this case, Formula 2 may be represented by Formula 2-2:

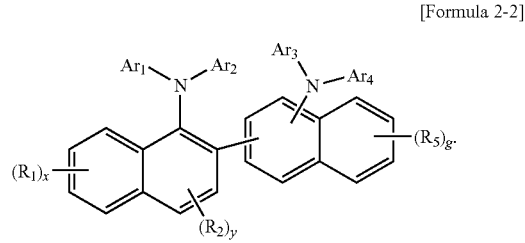

[Formula 2-2]

In Formula 2-2, $R_5$ may be a hydrogen atom, a deuterium atom, a halogen atom, a substituted or unsubstituted alkyl group of 1 to 20 carbon atoms, a substituted or unsubstituted aryl group of 6 to 30 carbon atoms for forming a ring, or a substituted or unsubstituted heteroaryl group of 2 to 30 carbon atoms for forming a ring.

In Formula 2-2, "g" may be an integer of 0 to 4. When "g" is 2 or more, a plurality of $R_5$ groups may be the same or different.

In Formula 2-2, $Ar_1$ to $Ar_4$, $R_1$, $R_2$, "x" and "y" may each independently be the same as defined in Formula 2.

In an embodiment, $L_2$ in Formula 3 may be a direct linkage. In this case, Formula 3 may be represented by Formula 3-1:

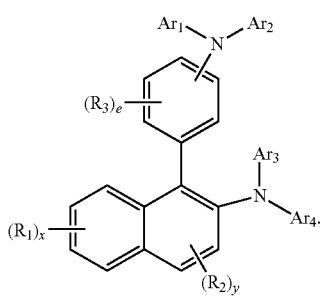

[Formula 3-1]

In Formula 3-1, $Ar_1$ to $Ar_4$, $R_1$ to $R_3$, "e", "x" and "y" may each independently be the same as defined in Formula 3.

In an embodiment, "n" in Formula 3 may be 1, and $L_2$ may be a substituted or unsubstituted phenylene group. In this case, Formula 3 may be represented by Formula 3-2:

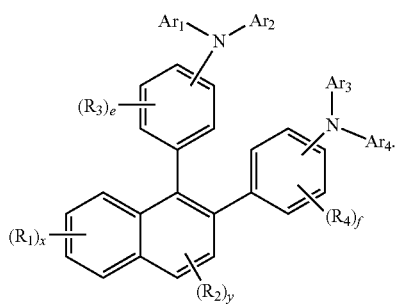

[Formula 3-2]

In Formula 3-2, $R_4$ may be a hydrogen atom, a deuterium atom, a halogen atom, a substituted or unsubstituted alkyl group of 1 to 20 carbon atoms, a substituted or unsubstituted aryl group of 6 to 30 carbon atoms for forming a ring, or a substituted or unsubstituted heteroaryl group of 2 to 30 carbon atoms for forming a ring.

In Formula 3-2, "f" may be an integer of 0 to 4. When "f" is 2 or more, a plurality of $R_4$ groups may be the same or different.

In Formula 3-2, $Ar_1$ to $Ar_4$, $R_1$ to $R_3$, "e", "x" and "y" may each independently be the same as defined in Formula 3.

In an embodiment, "n" in Formula 3 may be 1, and $L_2$ may be a substituted or unsubstituted naphthylene group. In this case, Formula 3 may be represented by Formula 3-3:

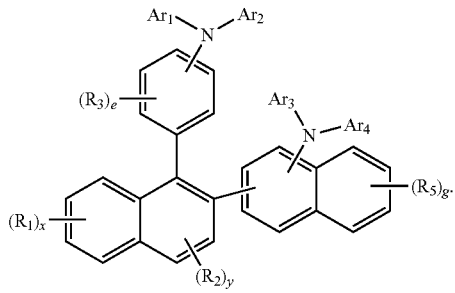

[Formula 3-3]

In Formula 3-3, $R_5$ may be a hydrogen atom, a deuterium atom, a halogen atom, a substituted or unsubstituted alkyl group of 1 to 20 carbon atoms, a substituted or unsubstituted aryl group of 6 to 30 carbon atoms for forming a ring, or a substituted or unsubstituted heteroaryl group of 2 to 30 carbon atoms for forming a ring.

In Formula 3-3, "g" may be an integer of 0 to 4. When "g" is 2 or more, a plurality of $R_5$ groups may be the same or different.

In Formula 3-3, $Ar_1$ to $Ar_4$, $R_1$ to $R_3$, "e", "x" and "y" may each independently be the same as defined in Formula 3.

In an embodiment, "m" (e.g., in Formula 1) may be 1, $L_1$ may be a substituted or unsubstituted phenylene group, and naphthylene and amine may be substituted at para positions to each other on the $L_1$ phenylene group.

In an embodiment, Formula 3 may be represented by Formula 4:

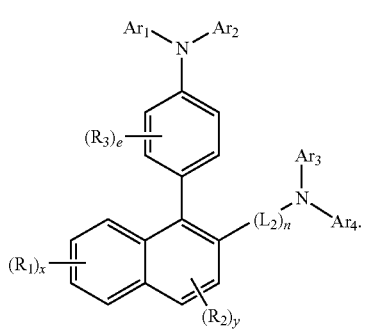

[Formula 4]

In Formula 4, $Ar_1$ to $Ar_4$, $L_2$, $R_1$ to $R_3$, "e", "n", "x" and "y" may each independently be the same as defined in Formula 3.

In an embodiment, "m" (e.g., in Formula 1) may be 1, $L_1$ may be a substituted or unsubstituted phenylene group, and naphthylene and amine may be substituted at meta positions to each other on the $L_1$ phenylene group.

In an embodiment, Formula 3 may be represented by Formula 5:

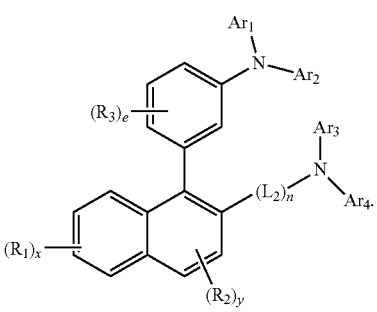

[Formula 5]

In Formula 5, $Ar_1$ to $Ar_4$, $L_2$, $R_1$ to $R_3$, "e", "n", "x" and "y" may each independently be the same as defined in Formula 3.

In an embodiment, $Ar_1$ and $Ar_3$ in Formula 1 to Formula 5 may each independently be a substituted or unsubstituted phenyl group, a substituted or unsubstituted biphenyl group, a substituted or unsubstituted triphenyl group, or a substituted or unsubstituted naphthyl group.

In an embodiment, $R_1$ and $R_2$ in Formula 1 to Formula 5 may each independently be a hydrogen atom, a deuterium atom, a substituted or unsubstituted alkyl group of 1 to 5 carbon atoms, a substituted or unsubstituted phenyl group, or a substituted or unsubstituted carbazole group.

The diamine compound represented by Formula 1 according to an embodiment of the present disclosure may be any or at least one selected among the compounds represented in Compound Groups 1 to 5, but an embodiment of the present disclosure is not limited thereto.

[Compound Group 1]

| | m | n | L₁ | L₂ | Ar₁ | Ar₂ | Ar₃ | Ar₄ | (naphthalene with (R₁)ₓ, (R₂)ᵧ) |
|---|---|---|---|---|---|---|---|---|---|
| A1-1 | 1 | 0 | phenylene | — | phenyl | phenyl | phenyl | phenyl | naphthyl |
| A1-2 | 1 | 0 | phenylene | — | biphenyl | biphenyl | biphenyl | biphenyl | naphthyl |
| A1-3 | 1 | 0 | phenylene | — | phenyl | biphenyl | phenyl | biphenyl | naphthyl |

-continued
[Compound Group 1]
| | m | n | L₁ | L₂ | Ar₁ | Ar₂ | Ar₃ | Ar₄ |  |
|---|---|---|---|---|---|---|---|---|---|
| A1-4 | 1 | 0 |  | — |  |  |  | 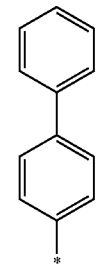 [SMILES: *c1ccc(-c2ccccc2)cc1] |  |
| A1-5 | 1 | 0 |  | — |  |  |  |  |  |
| A1-6 | 1 | 0 |  | — |  | 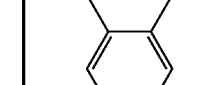 |  |  | 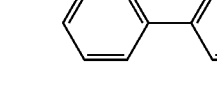 |

-continued
[Compound Group 1]
| | m | n | L₁ | L₂ | Ar₁ | Ar₂ | Ar₃ | Ar₄ | 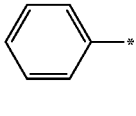 |
|---|---|---|---|---|---|---|---|---|---|
| A1-7 | 1 | 0 | 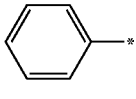 | — | 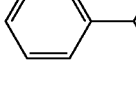 |  | 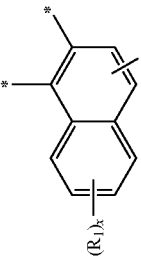 | 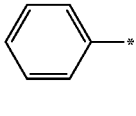 | 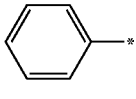 |
| A1-8 | 1 | 0 | 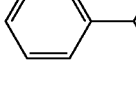 | — |  | 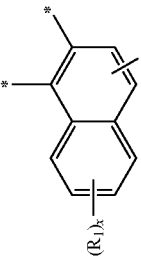 | 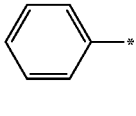 | 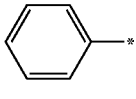 | 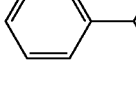 |
| A1-9 | 1 | 0 |  | — | 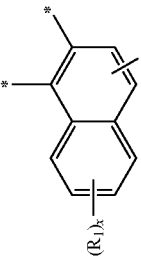 | | | | |

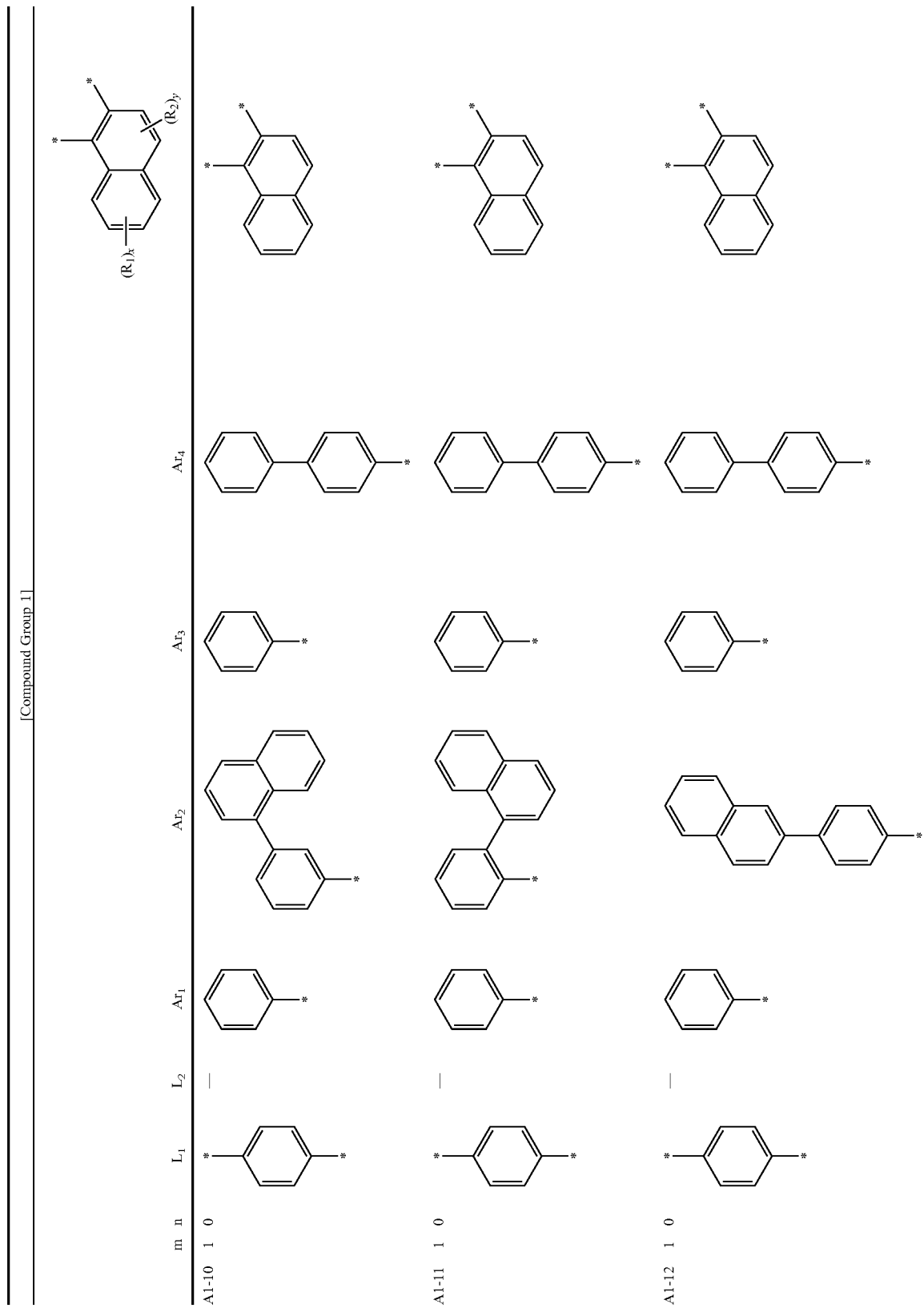

-continued
[Compound Group 1]
| m | n | L₁ | L₂ | Ar₁ | Ar₂ | Ar₃ | Ar₄ | 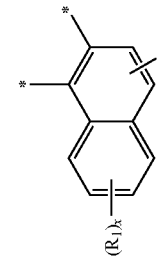 |
|---|---|----|----|-----|-----|-----|-----|---|
| A1-13 | 1 | 0 | 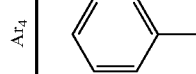 | — | 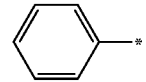 | 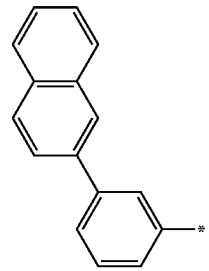 | 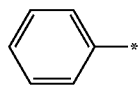 |  | 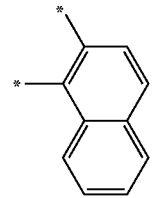 |
| A1-14 | 1 | 0 |  | — | 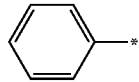 | 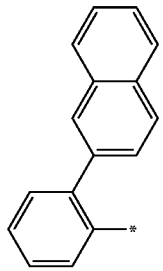 | 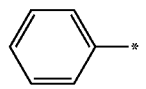 |  | 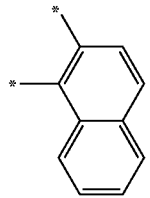 |
| A1-15 | 1 | 0 |  | — | 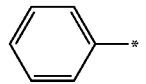 | 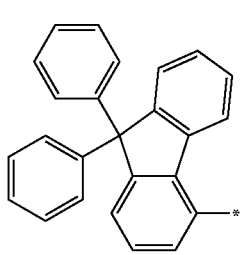 | |  | 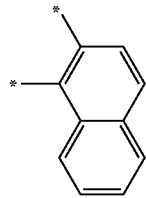 |

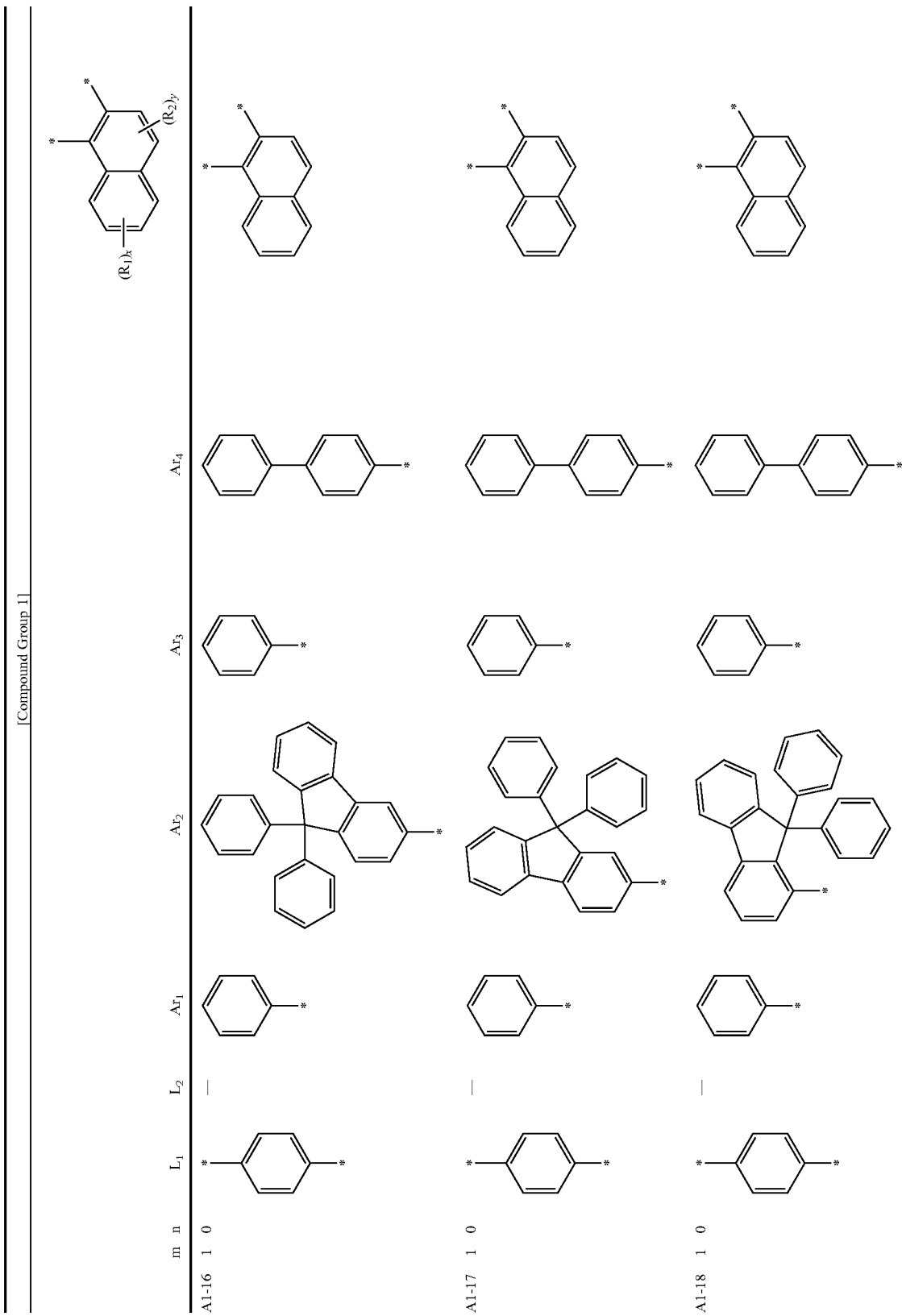

-continued
[Compound Group 1]
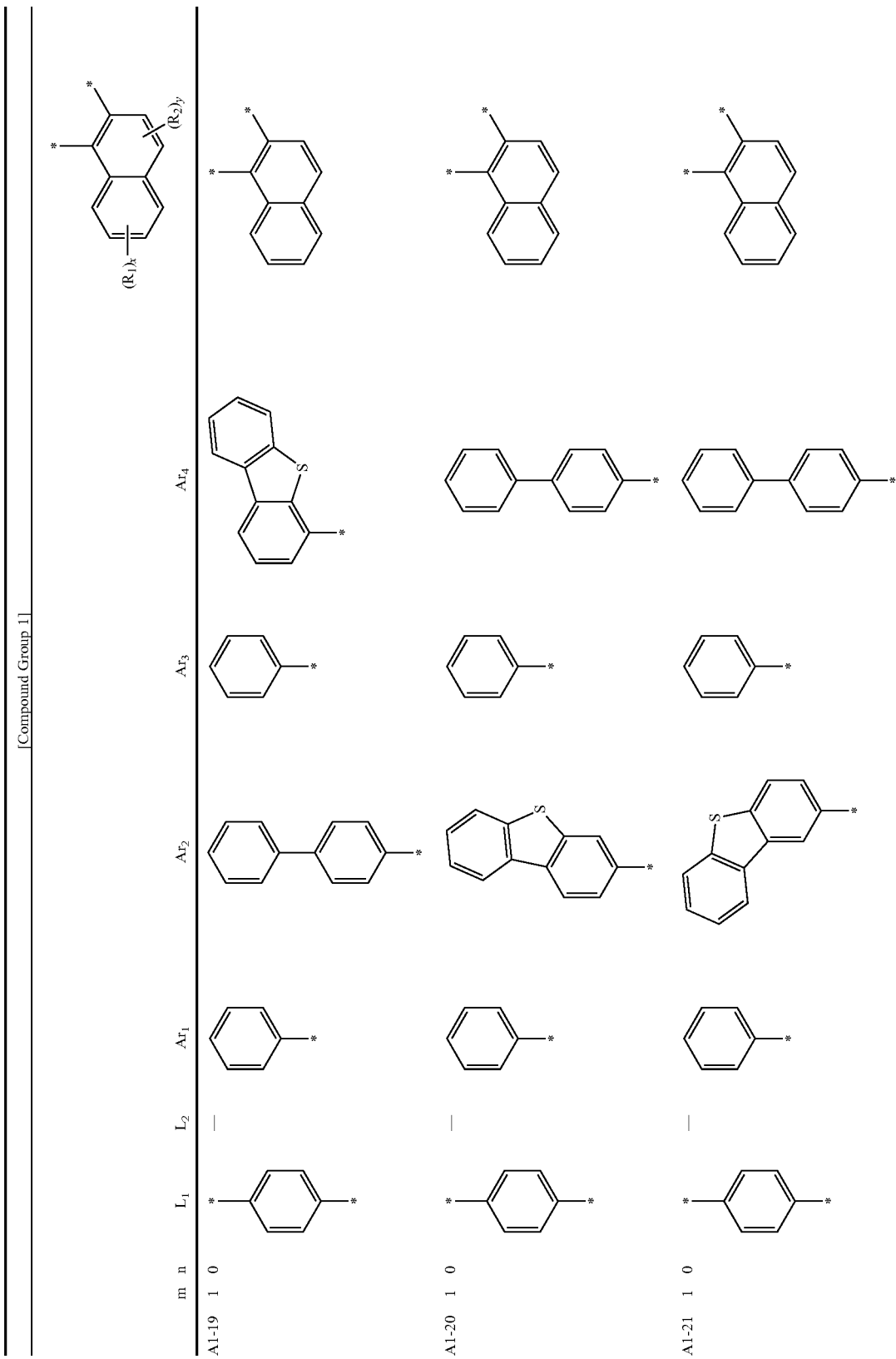

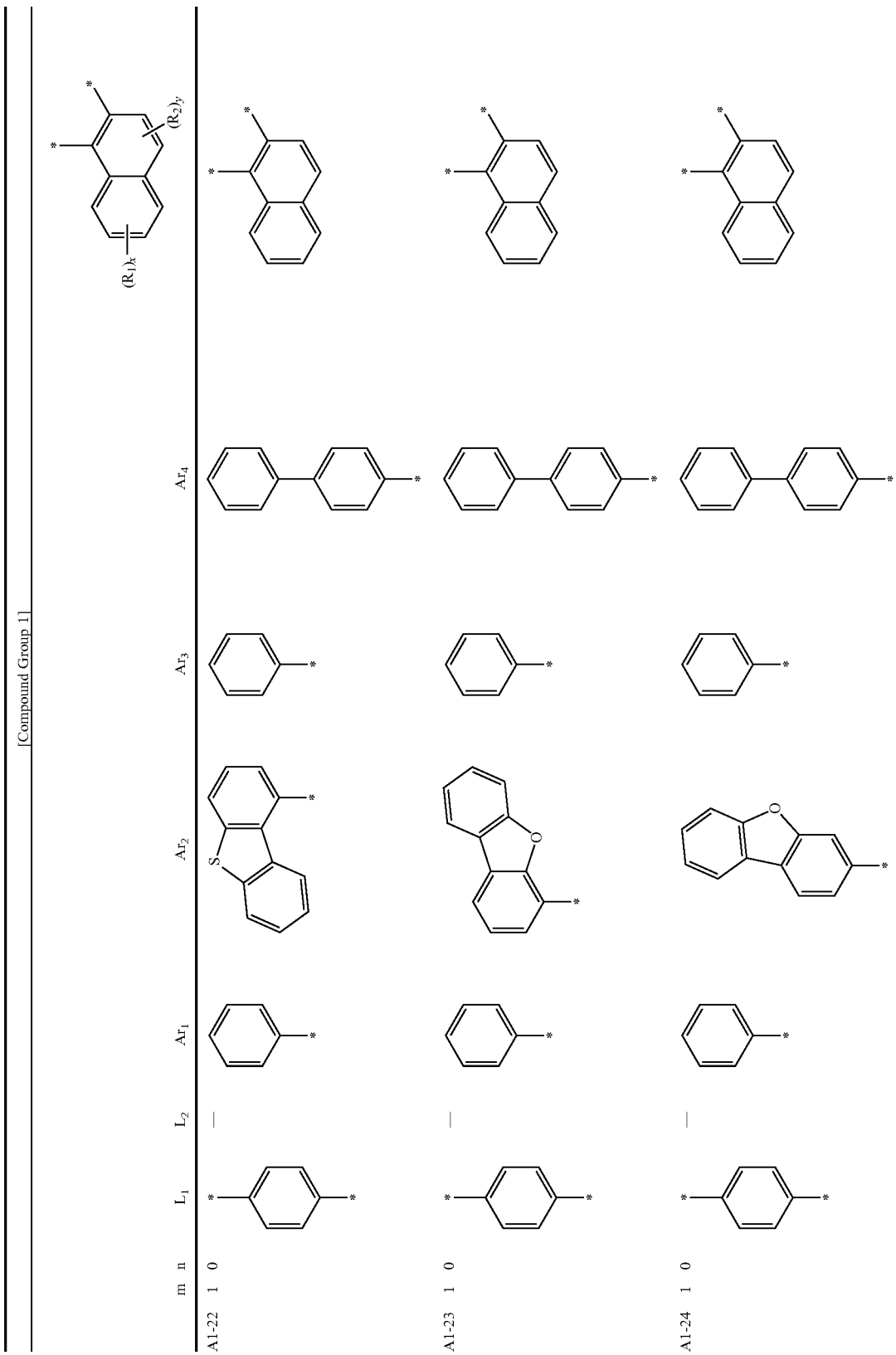

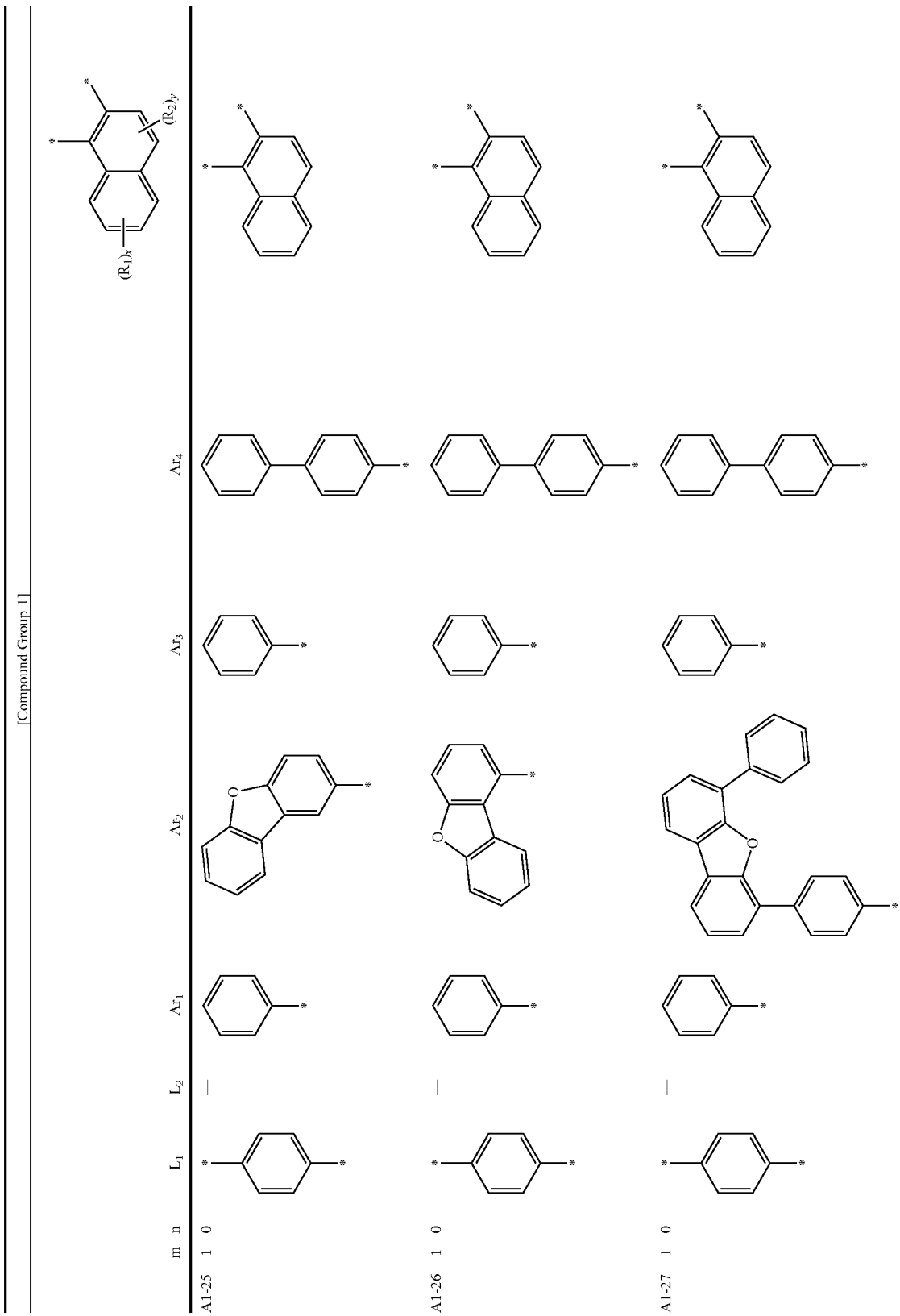

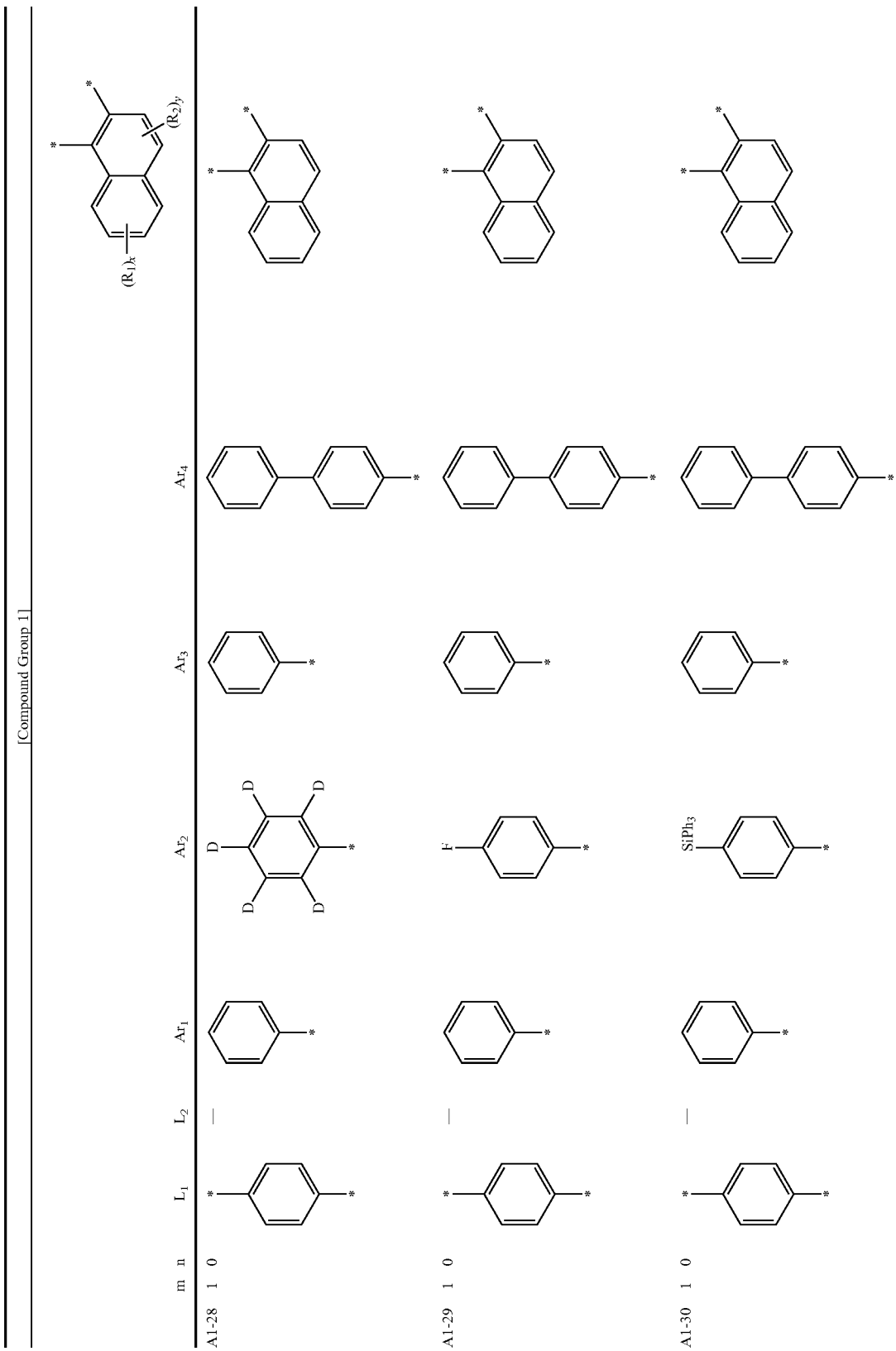

-continued
[Compound Group 1]
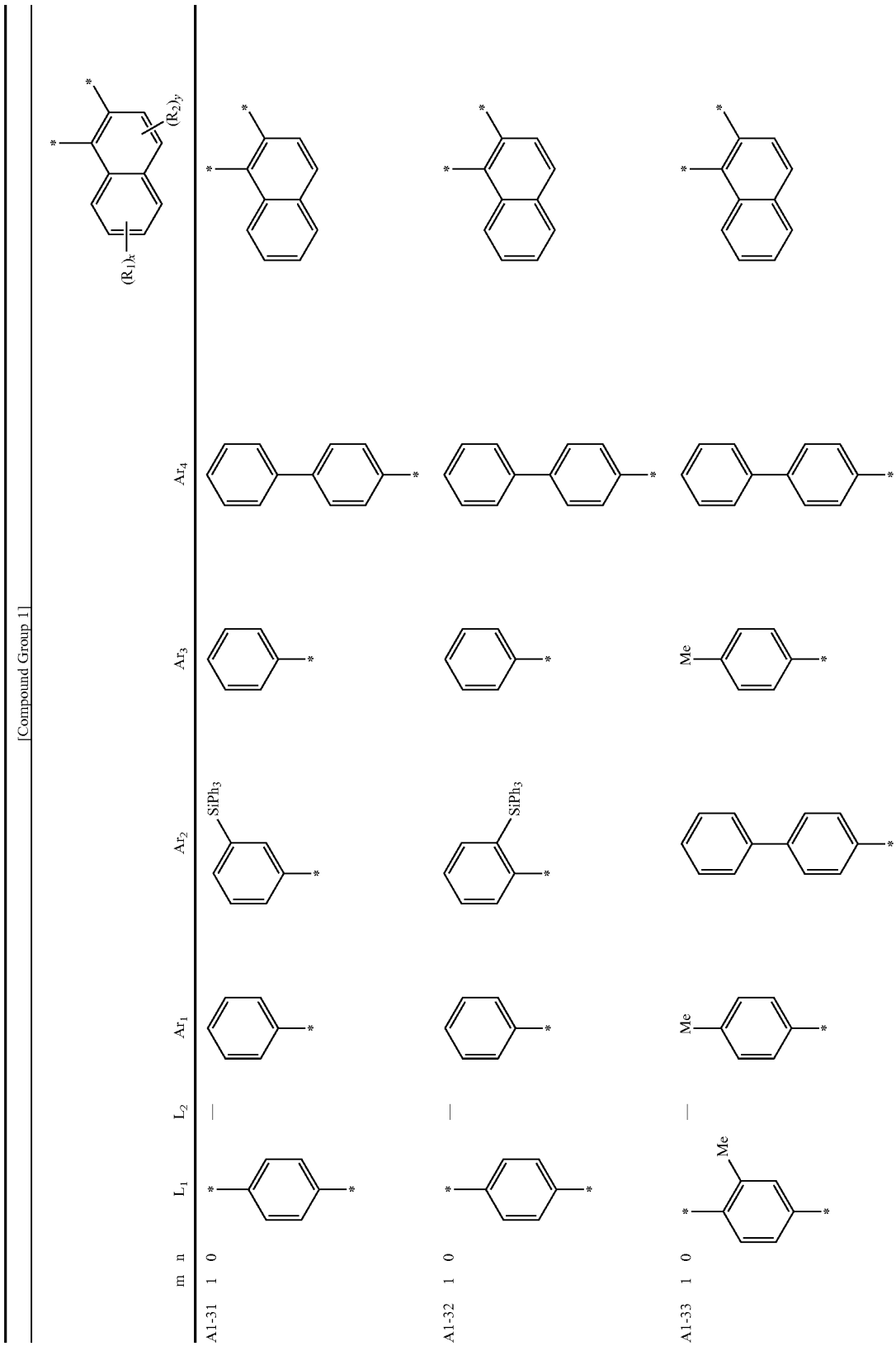

-continued
[Compound Group 1]
| | m | n | L₁ | L₂ | Ar₁ | Ar₂ | Ar₃ | Ar₄ | 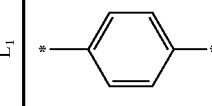 |
|---|---|---|---|---|---|---|---|---|---|
| B1-1 | 1 | 0 | 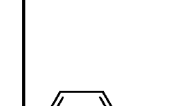 | — | 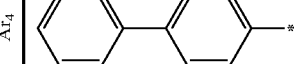 | 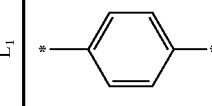 | 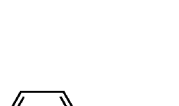 | 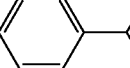 | 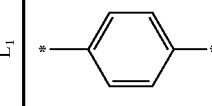 |
| B1-2 | 1 | 0 |  | — | 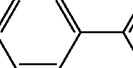 | 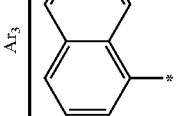 | 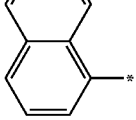 |  |  |
| B1-3 | 1 | 0 | 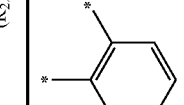 | — | 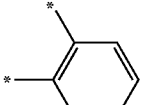 |  |  | | |

-continued
[Compound Group 1]
| | m | n | $L_1$ | $L_2$ | $Ar_1$ | $Ar_2$ | $Ar_3$ | $Ar_4$ | 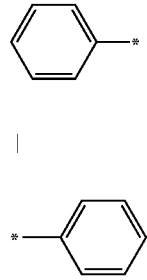 |
|---|---|---|---|---|---|---|---|---|---|
| B1-4 | 1 | 0 | 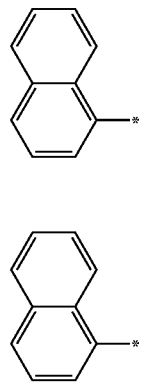 | — | 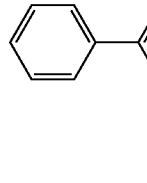 | 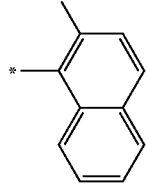 | 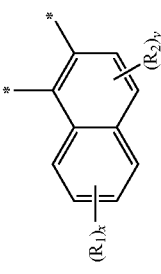 | 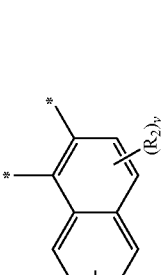 | 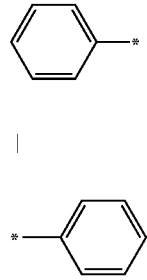 |
| B1-5 | 1 | 0 | 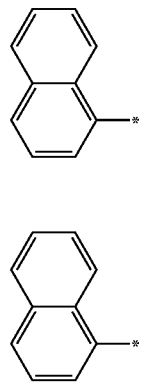 | — | 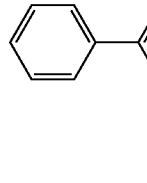 | 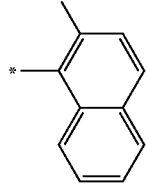 | 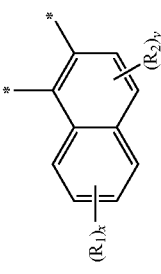 | 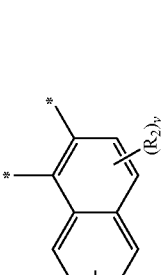 | 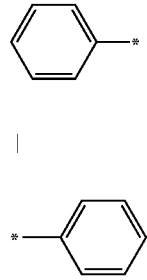 |
| B1-6 | 1 | 0 | 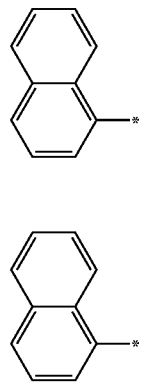 | — | 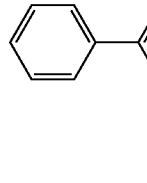 | 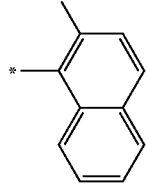 | 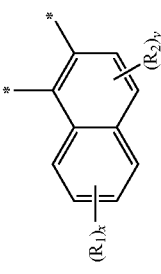 | 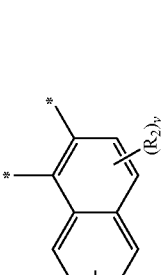 | |

-continued
[Compound Group 1]
| | m | n | L₁ | L₂ | Ar₁ | Ar₂ | Ar₃ | Ar₄ | |
|---|---|---|---|---|---|---|---|---|---|
| B1-7 | 1 | 0 | 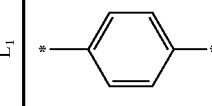 | — |  | 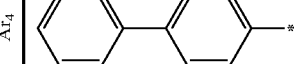 | 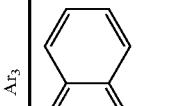 | 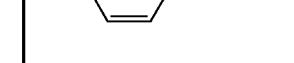 | 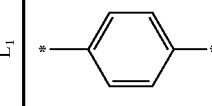 |
| B1-8 | 1 | 0 |  | — | 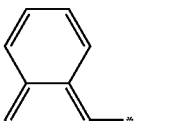 | 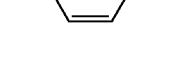 |  | 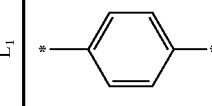 |  |
| B1-9 | 1 | 0 | 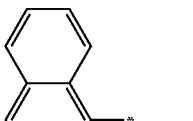 | — | 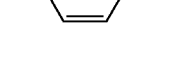 |  |  |  |  |

-continued

[Compound Group 1]

| | m | n | L₁ | L₂ | Ar₁ | Ar₂ | Ar₃ | Ar₄ | (naphthalene with R₁, R₂) |
|---|---|---|---|---|---|---|---|---|---|
| B1-10 | 1 | 0 | *-⌬-* | — | phenyl | 2-naphthyl-phenyl | 1-naphthyl | biphenyl | 2-naphthyl |
| B1-11 | 1 | 0 | *-⌬-* | — | phenyl | 2-naphthyl-phenyl (meta) | 1-naphthyl | biphenyl | 1-naphthyl |
| B1-12 | 1 | 0 | *-⌬-* | — | phenyl | 2-naphthyl-phenyl (ortho) | 1-naphthyl | biphenyl | 1-naphthyl |

-continued
[Compound Group 1]
| | m | n | L₁ | L₂ | Ar₁ | Ar₂ | Ar₃ | Ar₄ | 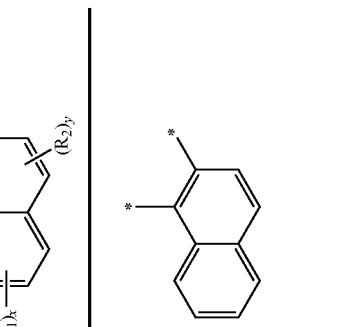 |
|---|---|---|---|---|---|---|---|---|---|
| B1-13 | 1 | 0 | 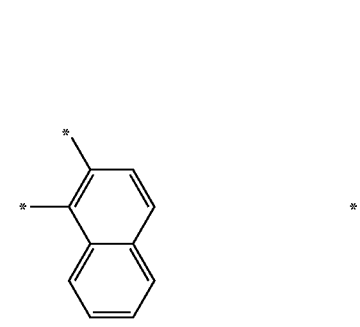 | — | 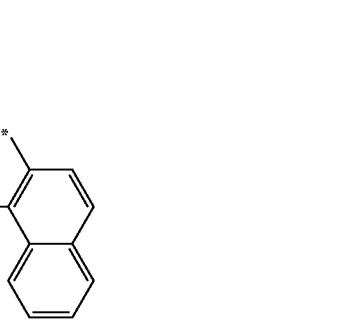 | 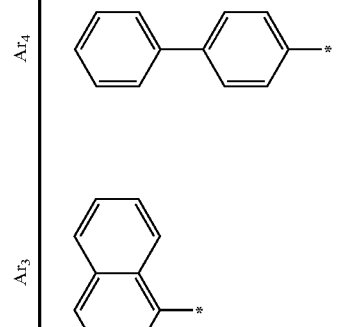 | 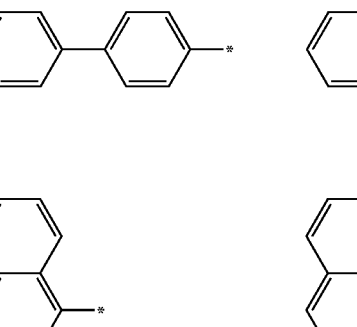 | 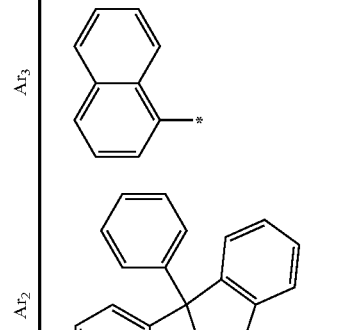 | 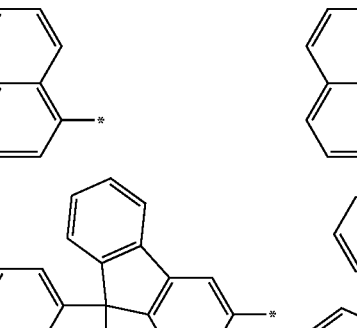 |
| B1-14 | 1 | 0 | 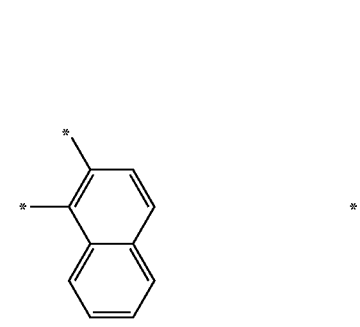 | — | 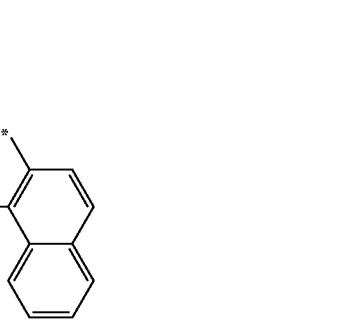 | 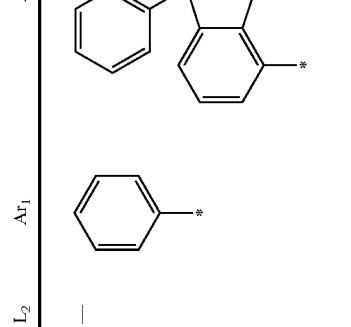 | 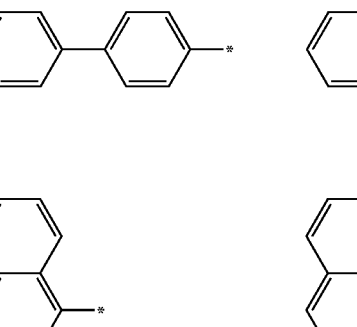 | 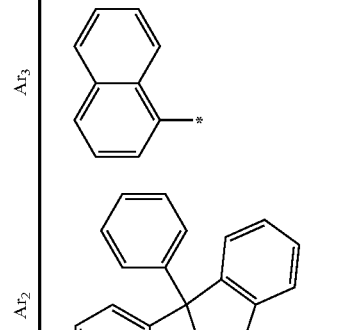 | 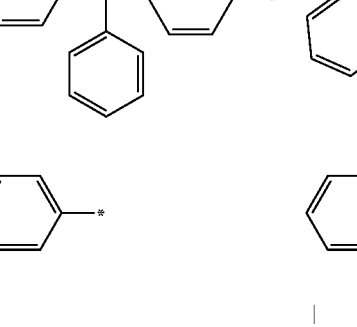 |
| B1-15 | 1 | 0 | 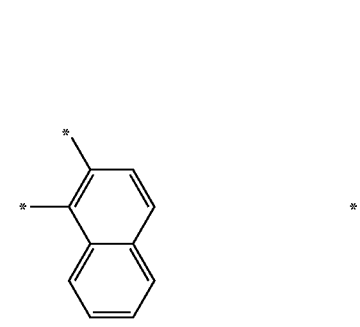 | — | 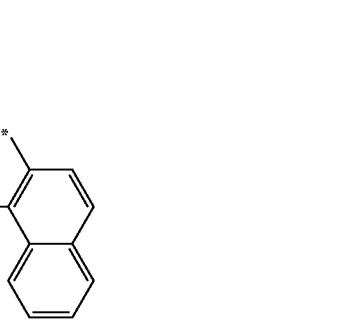 | 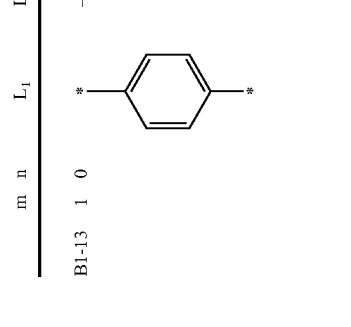 | 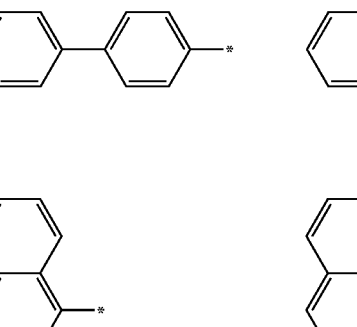 | 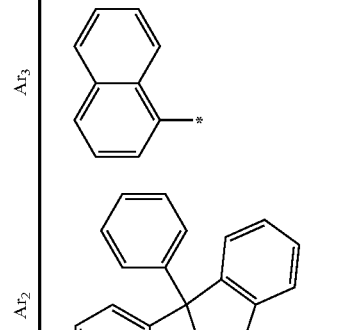 | 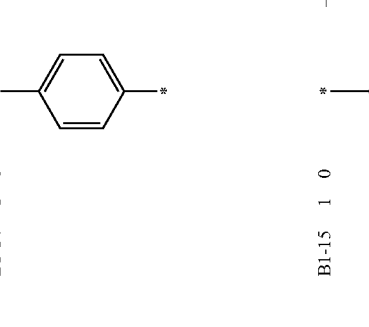 |

-continued

[Compound Group 1]

| | m | n | L₁ | L₂ | Ar₁ | Ar₂ | Ar₃ | Ar₄ | |
|---|---|---|---|---|---|---|---|---|---|
| B1-16 | 1 | 0 | | | | | | | |
| B1-17 | 1 | 0 | | | | | | | |
| B1-18 | 1 | 0 | | | | | | | |

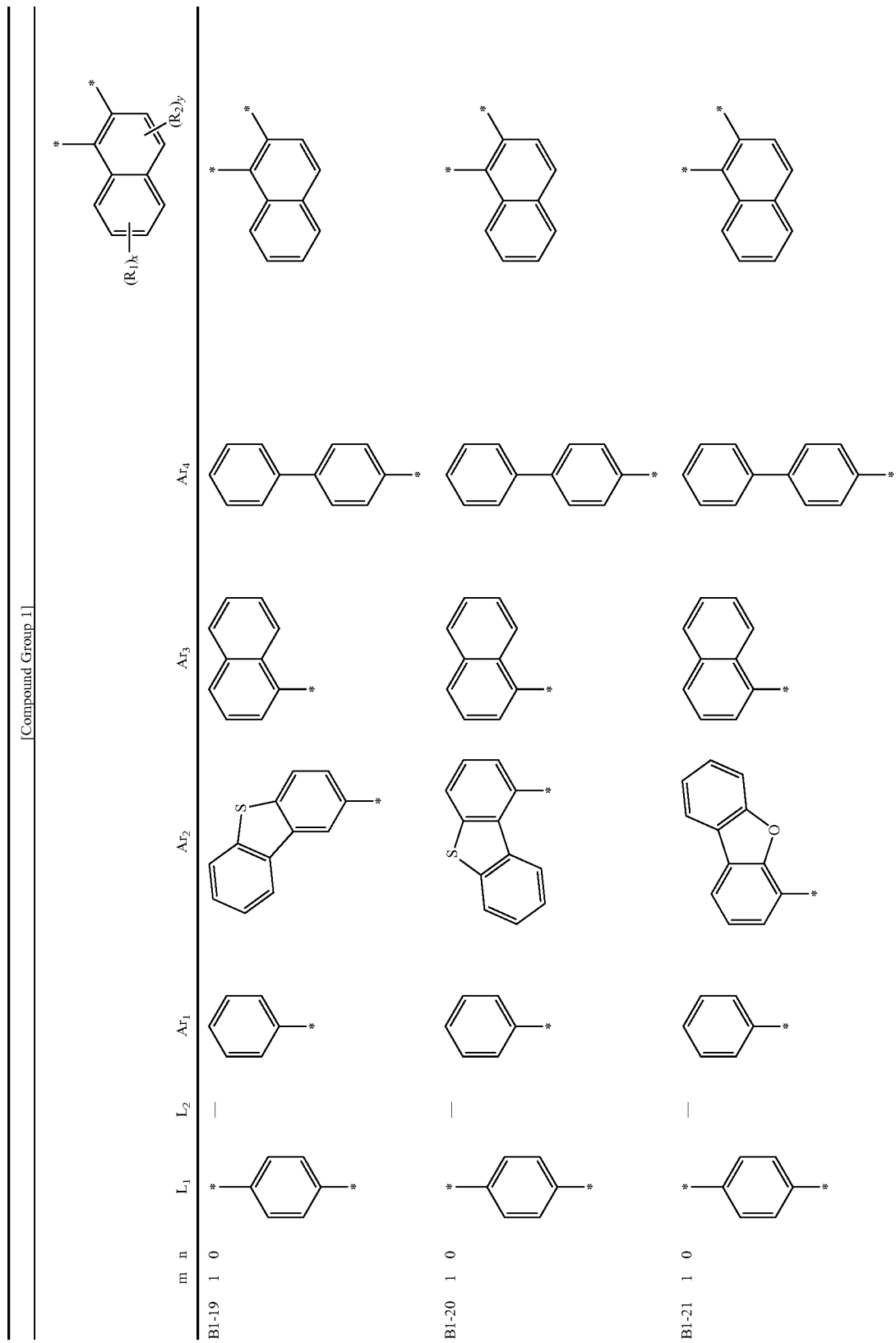

-continued

[Compound Group 1]

| | m | n | L₁ | L₂ | Ar₁ | Ar₂ | Ar₃ | Ar₄ | |
|---|---|---|---|---|---|---|---|---|---|
| B1-22 | 1 | 0 | *–⟨phenyl⟩–* | — | phenyl* | dibenzofuran-3-yl* | naphth-1-yl* | biphenyl-4-yl* | naphthyl |
| B1-23 | 1 | 0 | *–⟨phenyl⟩–* | — | phenyl* | dibenzofuran-2-yl* | naphth-1-yl* | biphenyl-4-yl* | naphthyl |
| B1-24 | 1 | 0 | *–⟨phenyl⟩–* | — | phenyl* | dibenzofuran-1-yl* | naphth-1-yl* | biphenyl-4-yl* | naphthyl |

-continued
[Compound Group 1]
| | m | n | L₁ | L₂ | Ar₁ | Ar₂ | Ar₃ | Ar₄ |  |
|---|---|---|---|---|---|---|---|---|---|
| B1-25 | 1 | 0 |  | — |  | 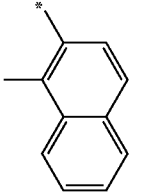 |  |  |  |
| B1-26 | 1 | 0 | 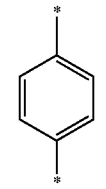 [SMILES: *c1ccc(*)cc1] | — |  |  | 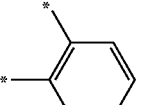 |  |  |
| B1-27 | 1 | 0 |  | — |  |  |  | 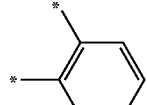 |  |

-continued
[Compound Group 1]
| | m | n | L₁ | L₂ | Ar₁ | Ar₂ | Ar₃ | Ar₄ | |
|---|---|---|---|---|---|---|---|---|---|
| B1-28 | 1 | 0 | 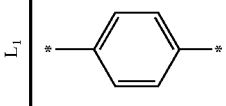 | — | 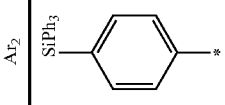 | 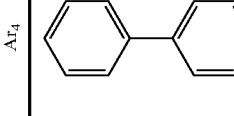 | 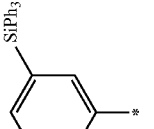 | 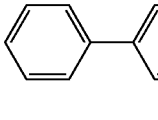 | 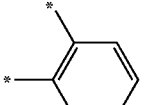 |
| B1-29 | 1 | 0 |  | — | 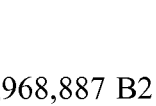 | 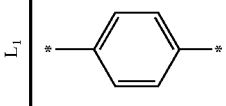 | 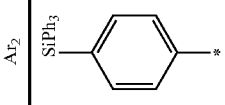 | 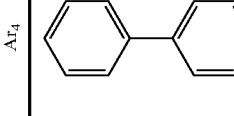 | 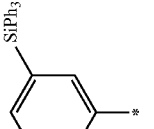 |
| B1-30 | 1 | 0 | 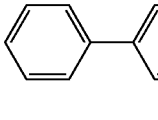 | — | 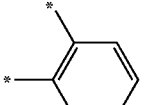 |  | 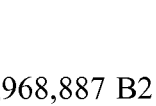 | 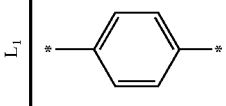 | 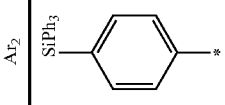 |

-continued
[Compound Group 1]
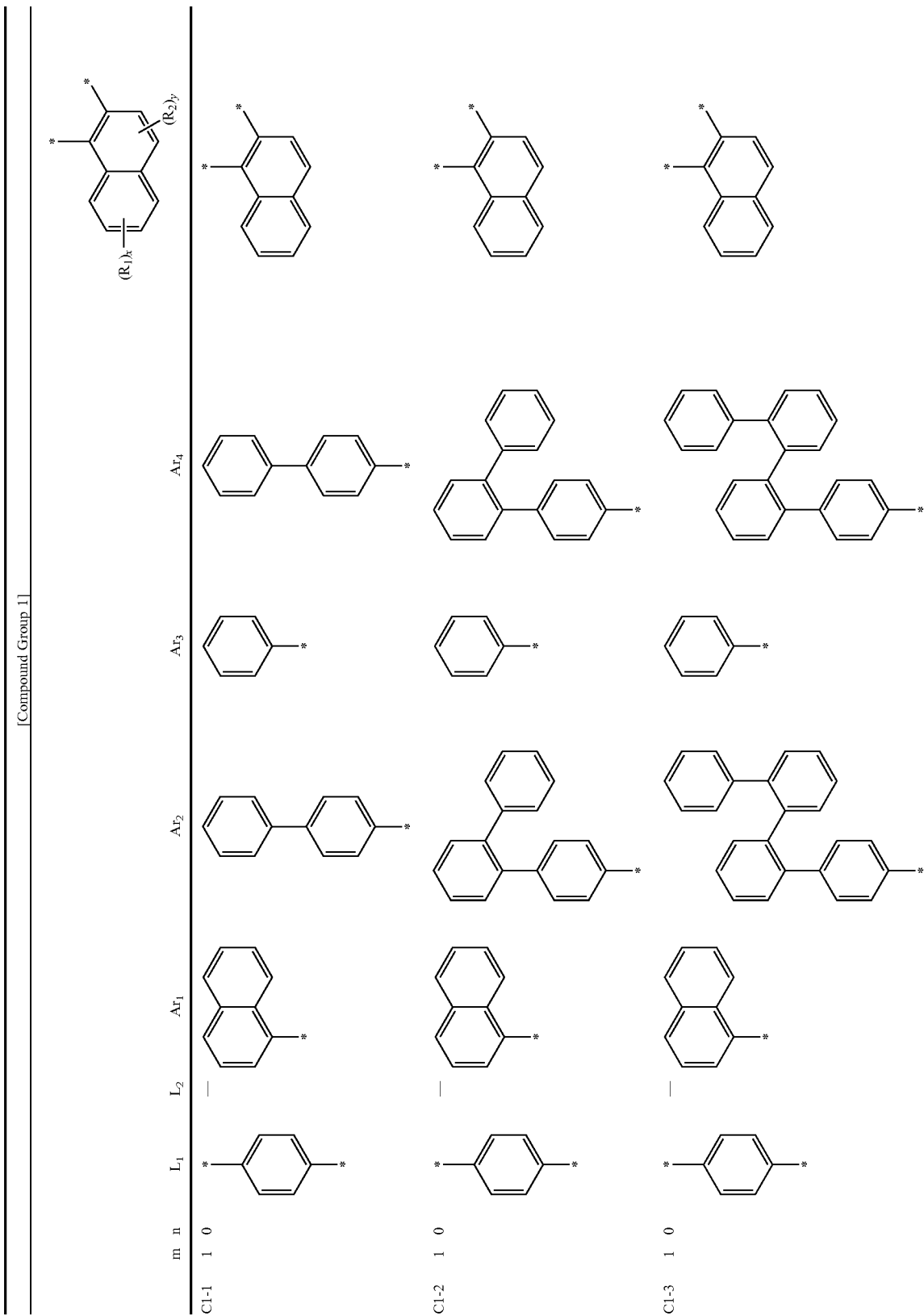

-continued
[Compound Group 1]
| | m | n | L₁ | L₂ | Ar₁ | Ar₂ | Ar₃ | Ar₄ | |
|---|---|---|---|---|---|---|---|---|---|
| C1-4 | 1 | 0 | 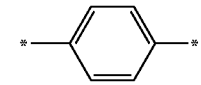 | — | 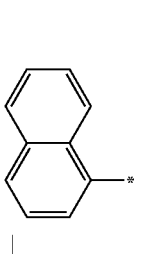 | 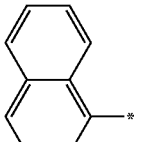 | 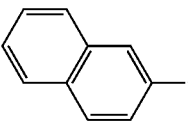 | 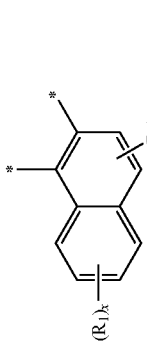 | 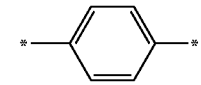 |
| C1-5 | 1 | 0 | 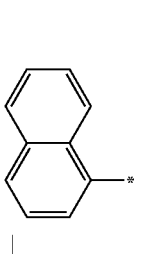 | — | 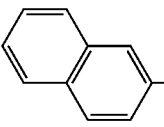 | 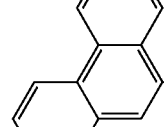 | 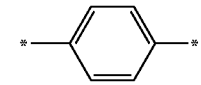 | 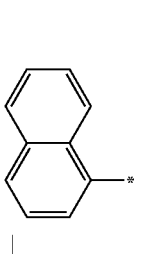 | 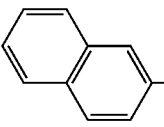 |
| C1-6 | 1 | 0 | 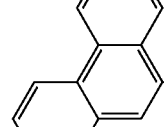 | — | | | | | |

-continued
[Compound Group 1]
| | m | n | L₁ | L₂ | Ar₁ | Ar₂ | Ar₃ | Ar₄ |  |
|---|---|---|---|---|---|---|---|---|---|
| C1-7 | 1 | 0 |  | — |  |  |  |  | 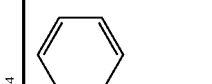 |
| C1-8 | 1 | 0 | 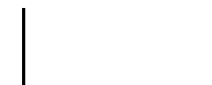 | — | 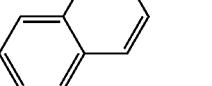 | 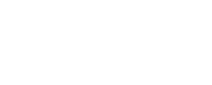 |  |  |  |
| C1-9 | 1 | 0 |  | — | | | | | |

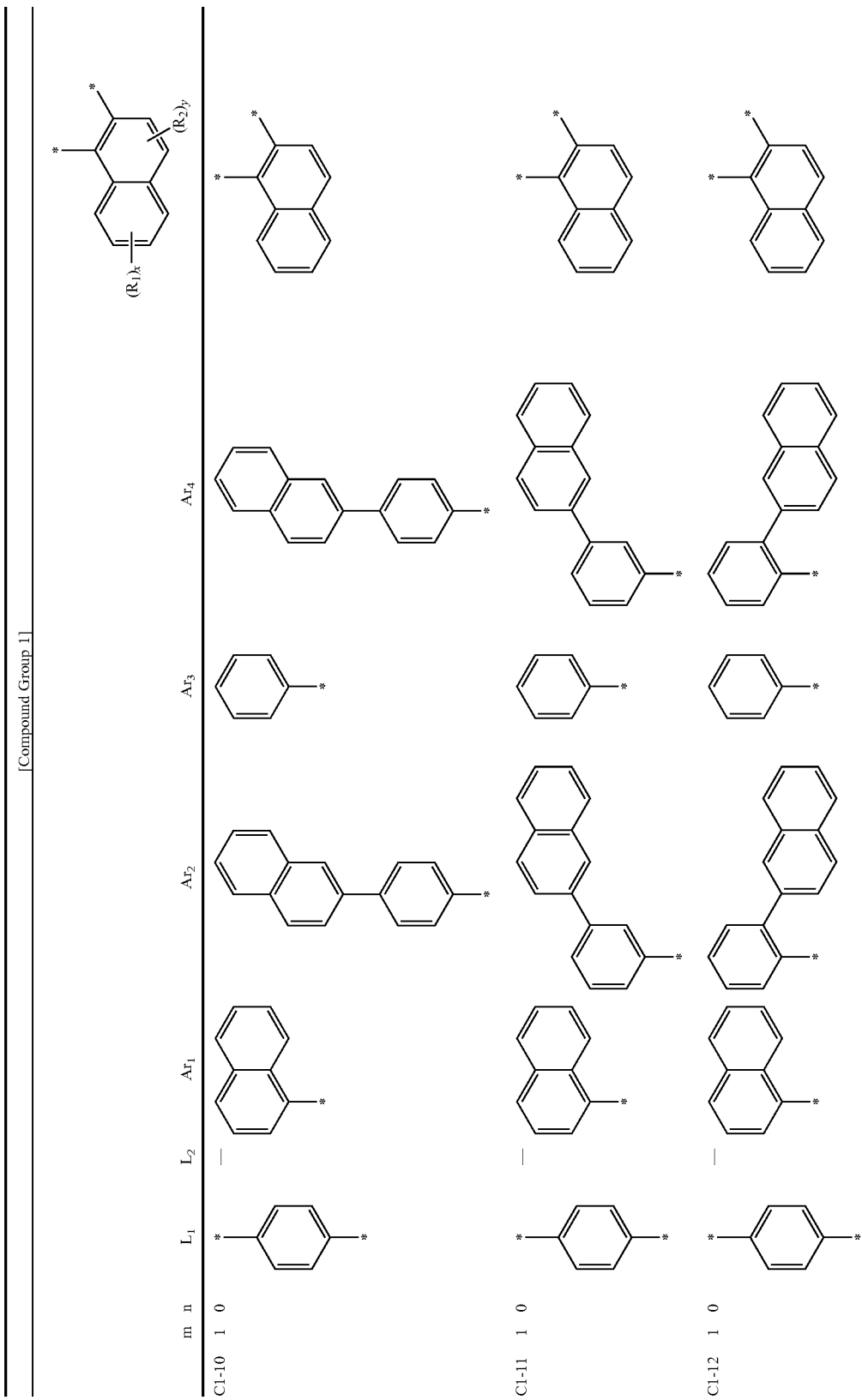

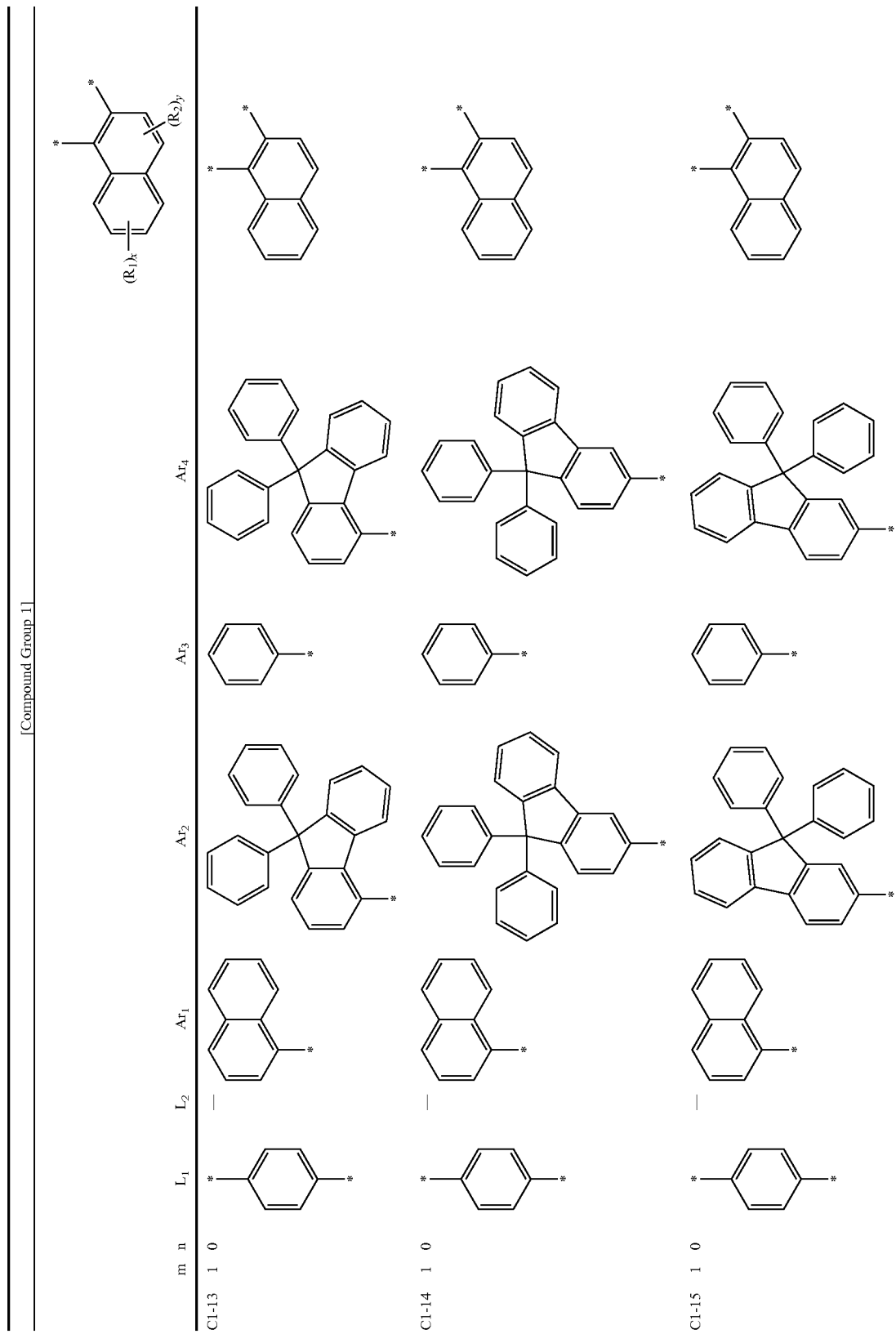

-continued
[Compound Group 1]
| | m | n | L₁ | L₂ | Ar₁ | Ar₂ | Ar₃ | Ar₄ | 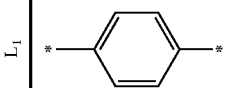 |
|---|---|---|---|---|---|---|---|---|---|
| C1-16 | 1 | 0 | | — | | | | | |
| C1-17 | 1 | 0 | | — | | | | | |
| C1-18 | 1 | 0 | | — | | | | | |

-continued
[Compound Group 1]
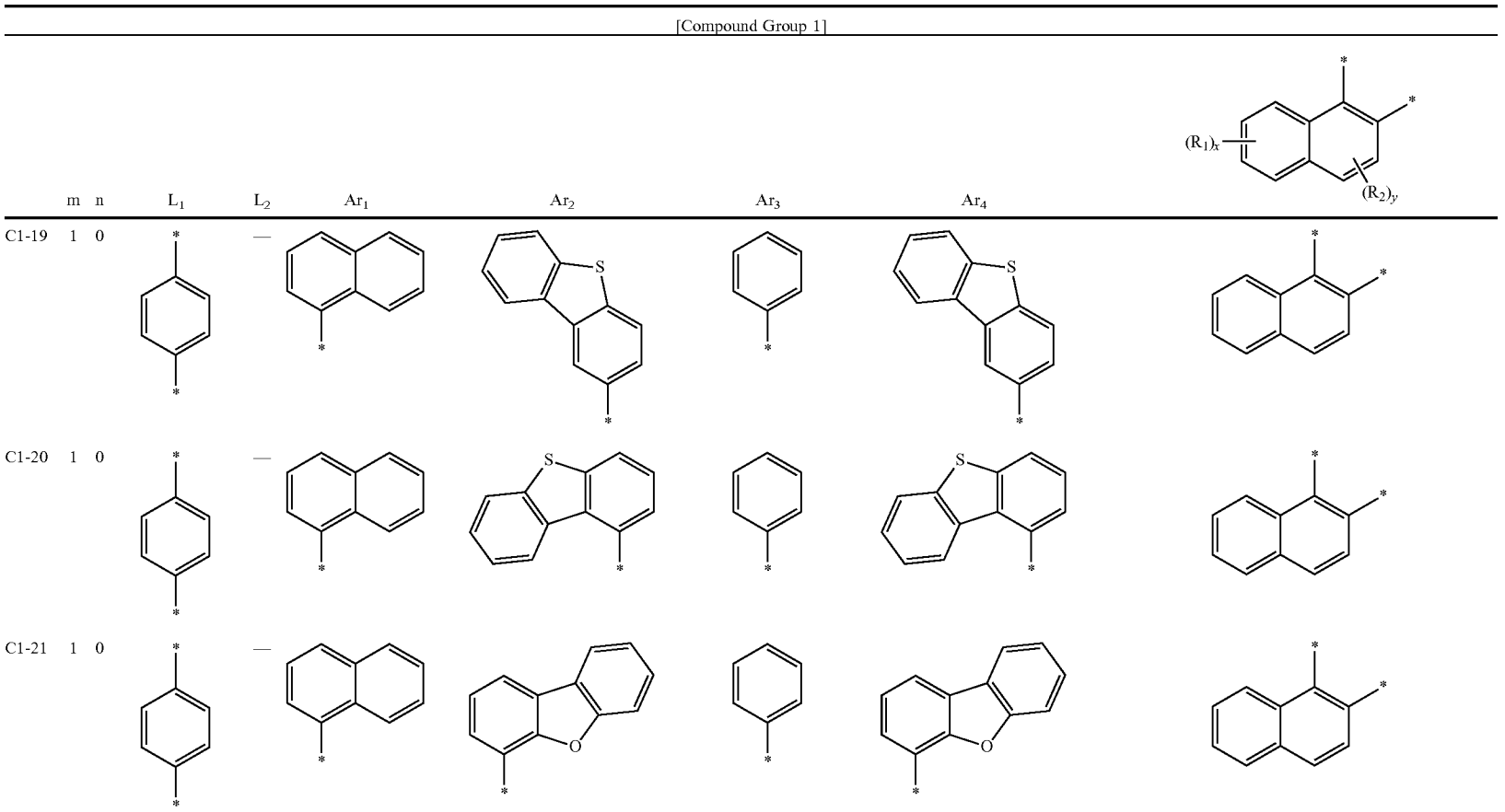

-continued
[Compound Group 1]
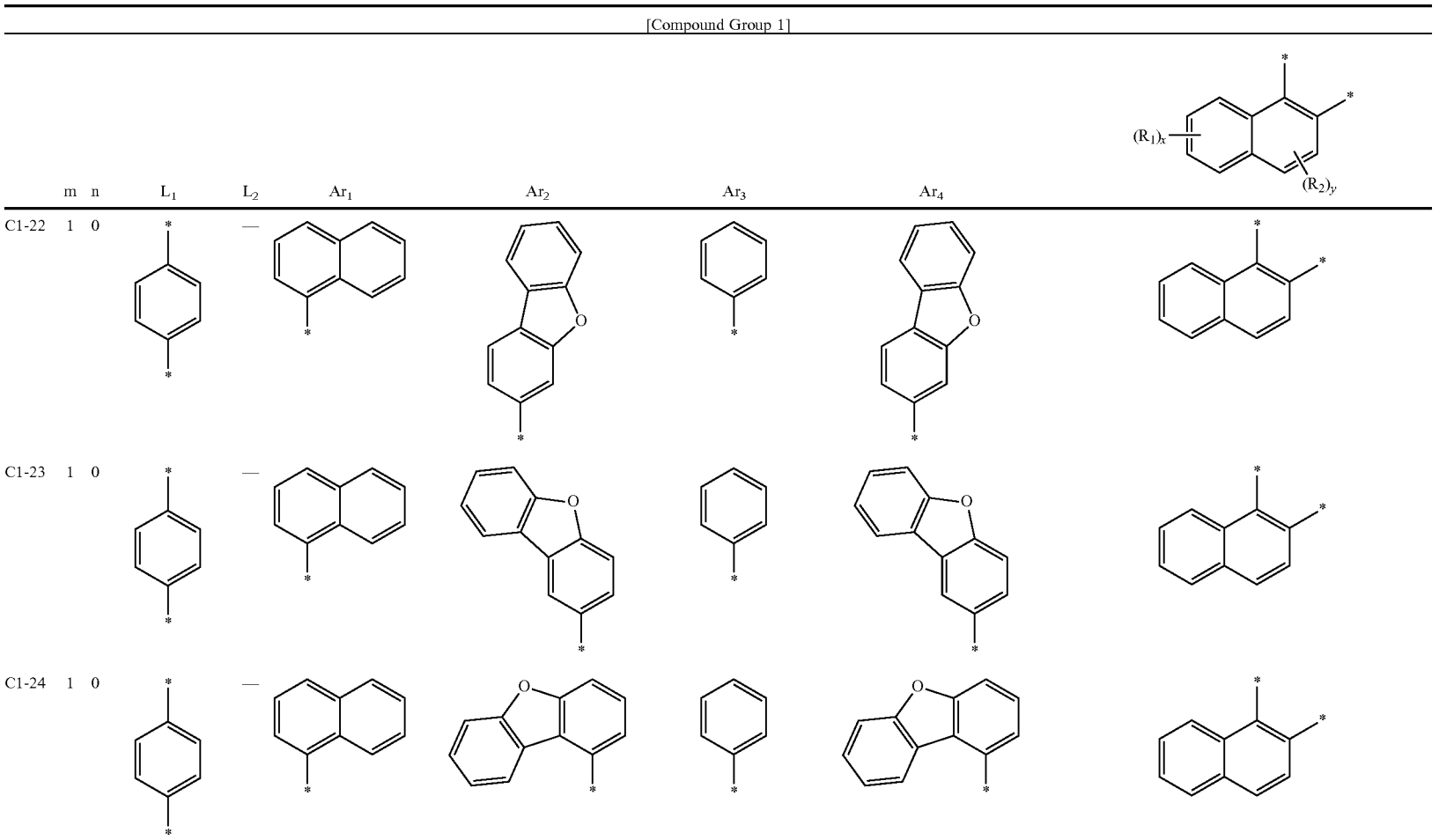

-continued
[Compound Group 1]
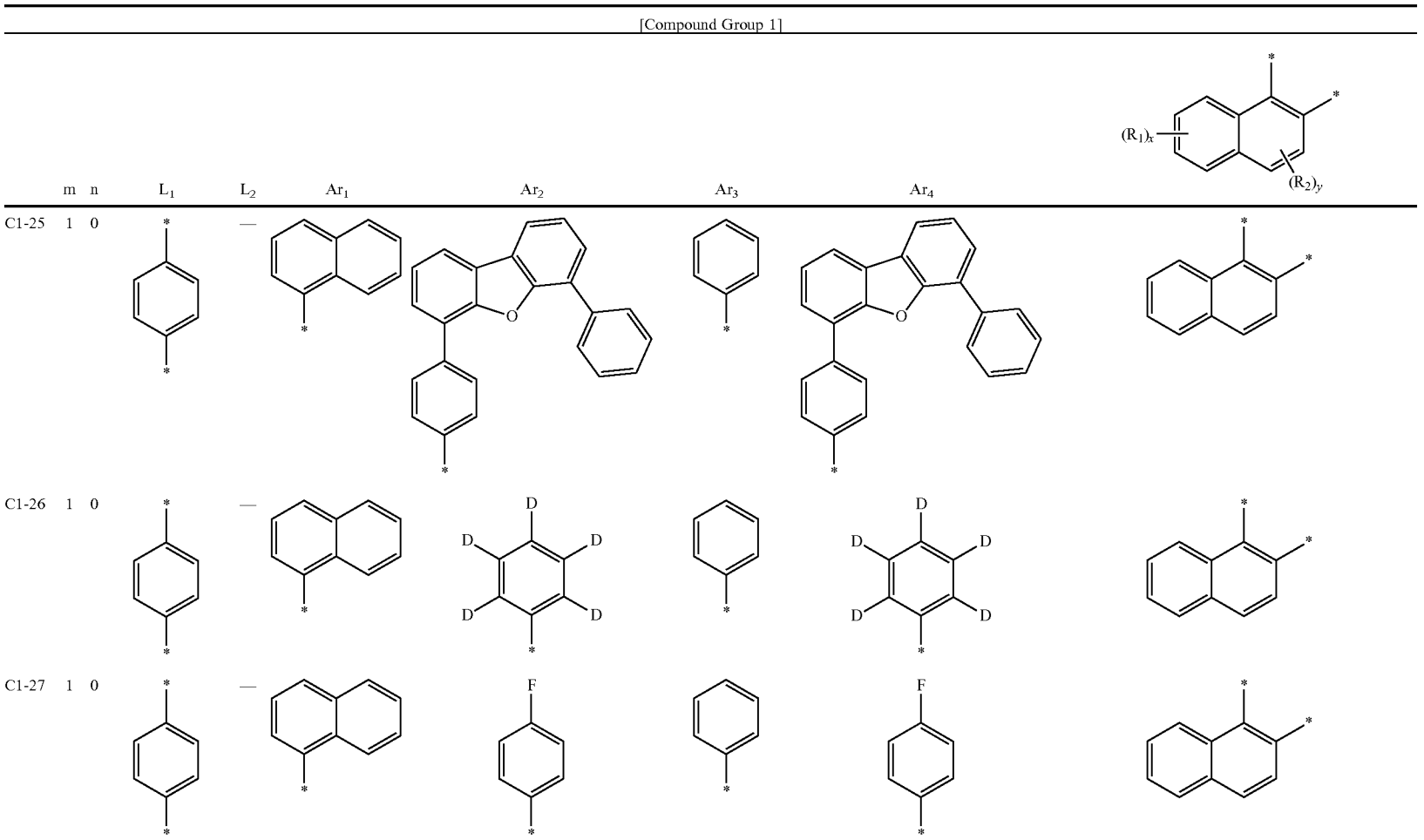

-continued
[Compound Group 1]

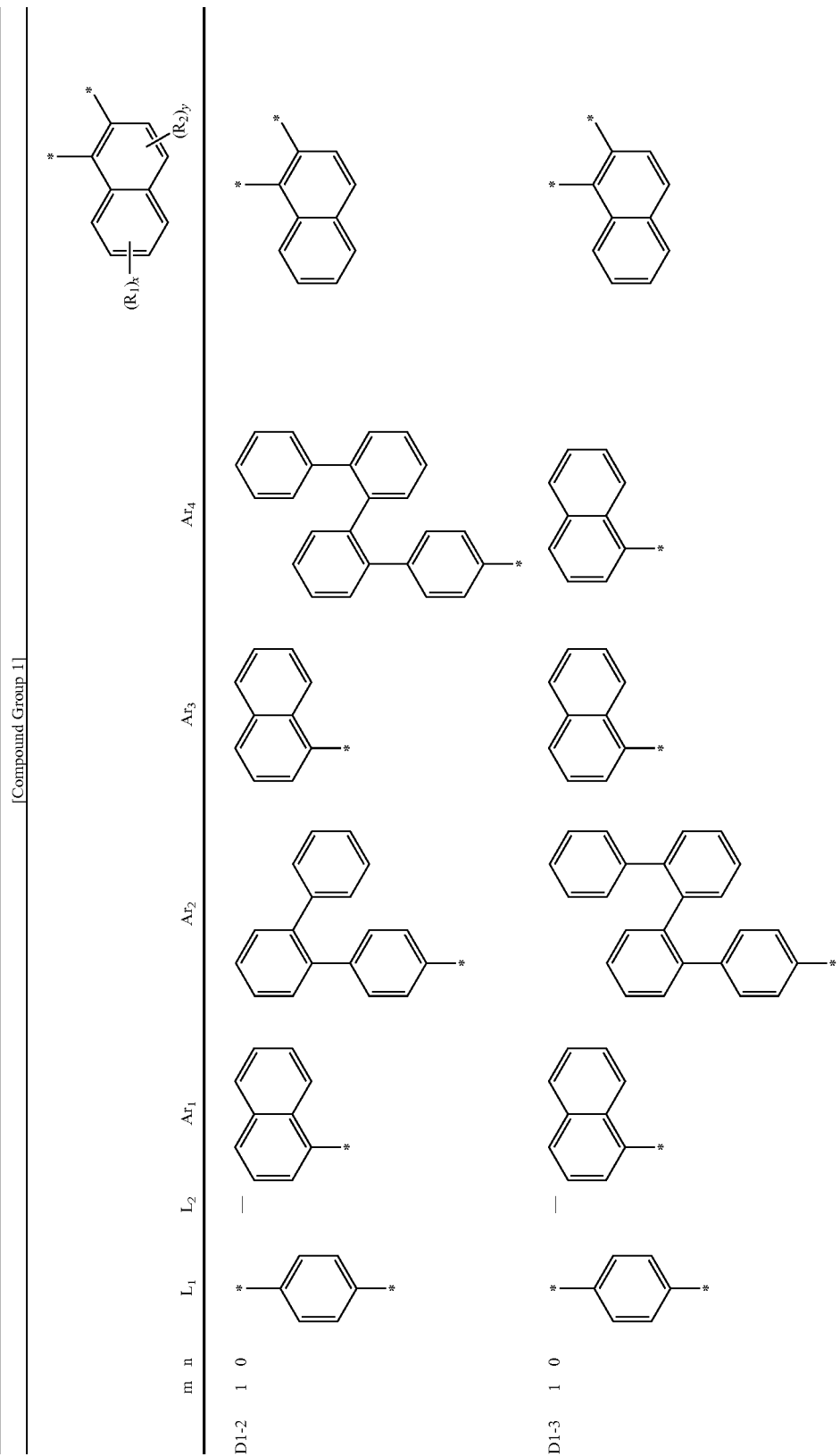

-continued
[Compound Group 1]
| | m | n | L₁ | L₂ | Ar₁ | Ar₂ | Ar₃ | Ar₄ |  |
|---|---|---|---|---|---|---|---|---|---|
| D1-4 | 1 | 0 |  | — |  |  |  |  |  |
| D1-5 | 1 | 0 |  | — |  |  |  |  |  |
| D1-6 | 1 | 0 |  | — |  |  |  |  |  |

-continued
[Compound Group 1]
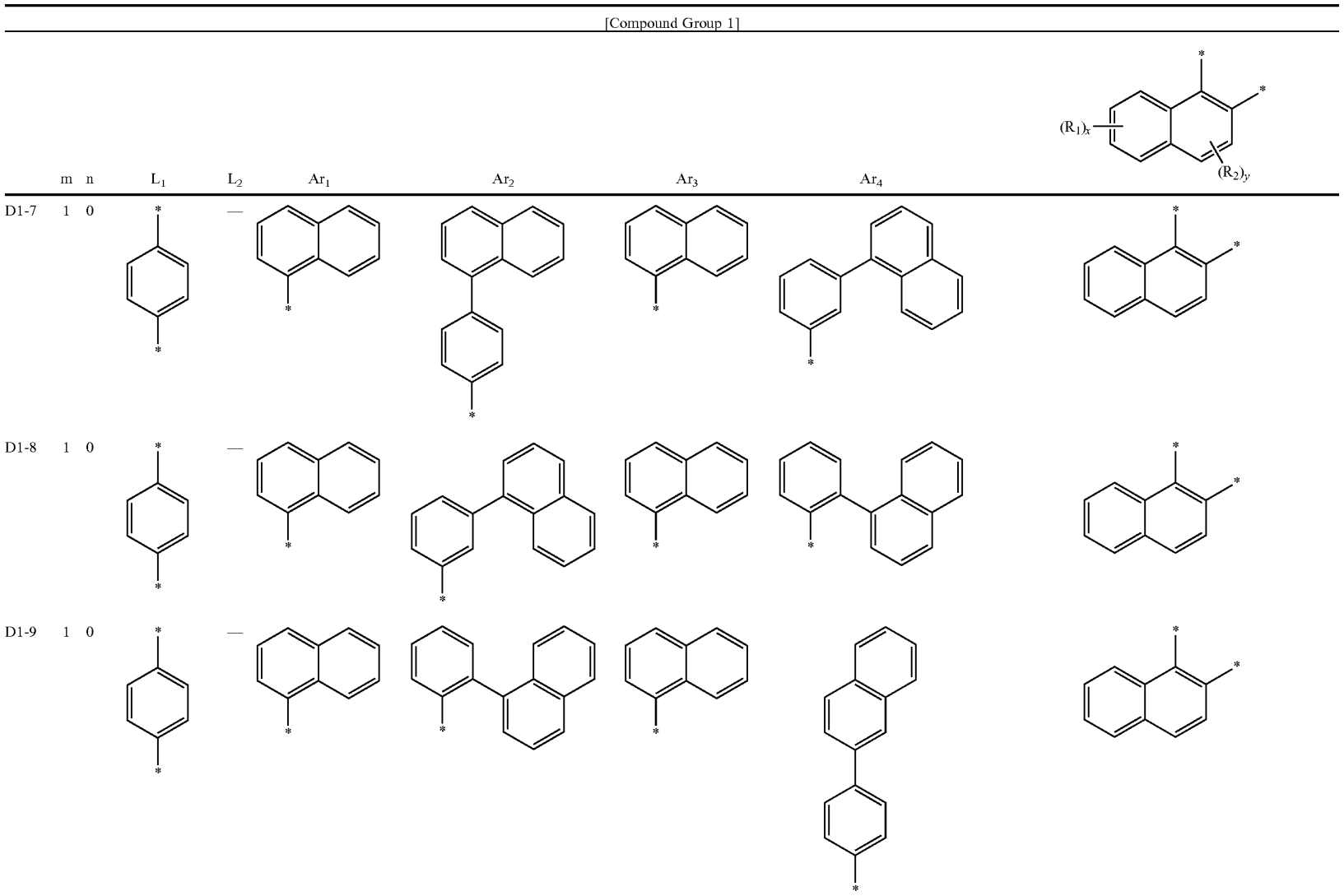

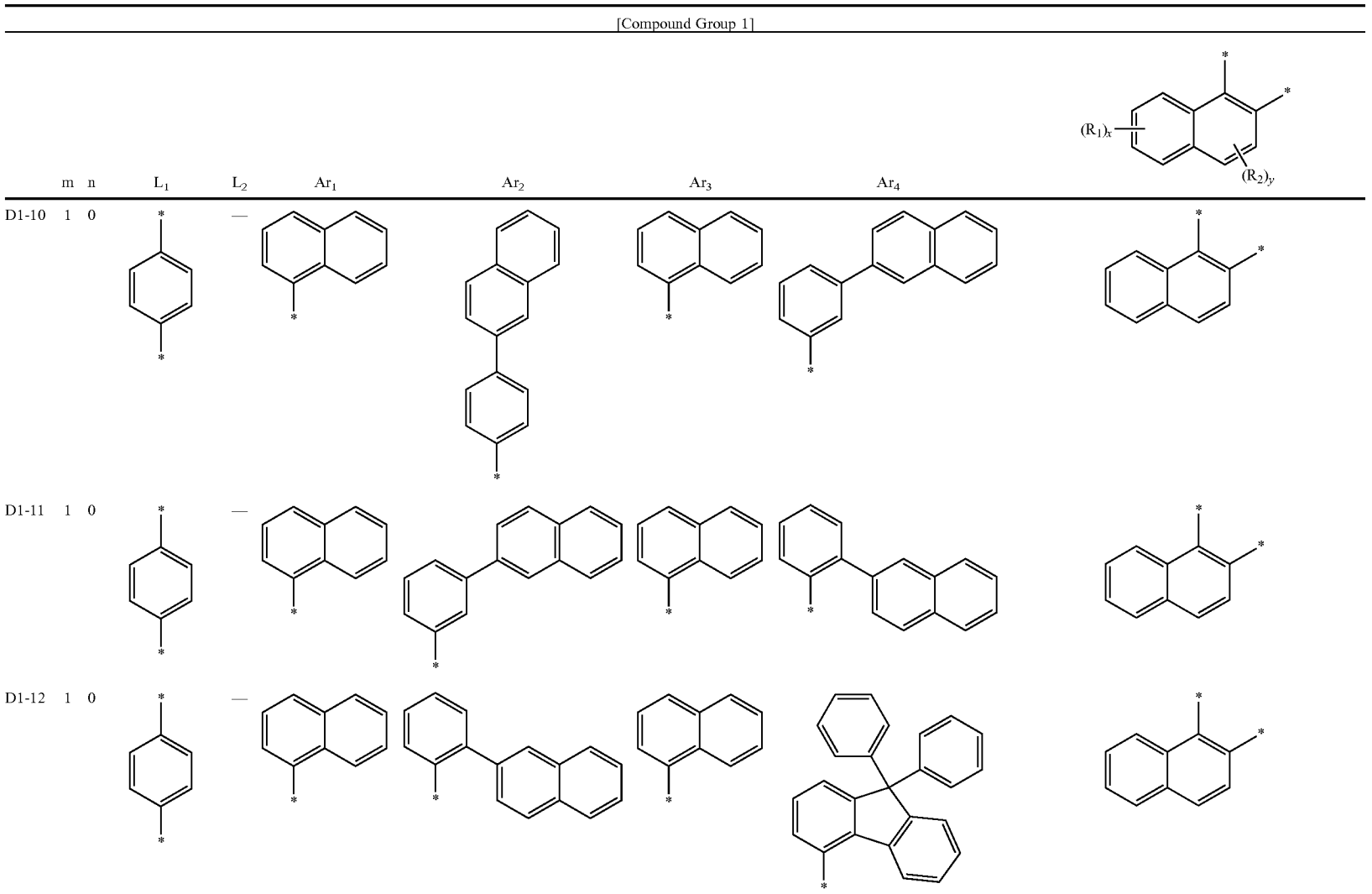

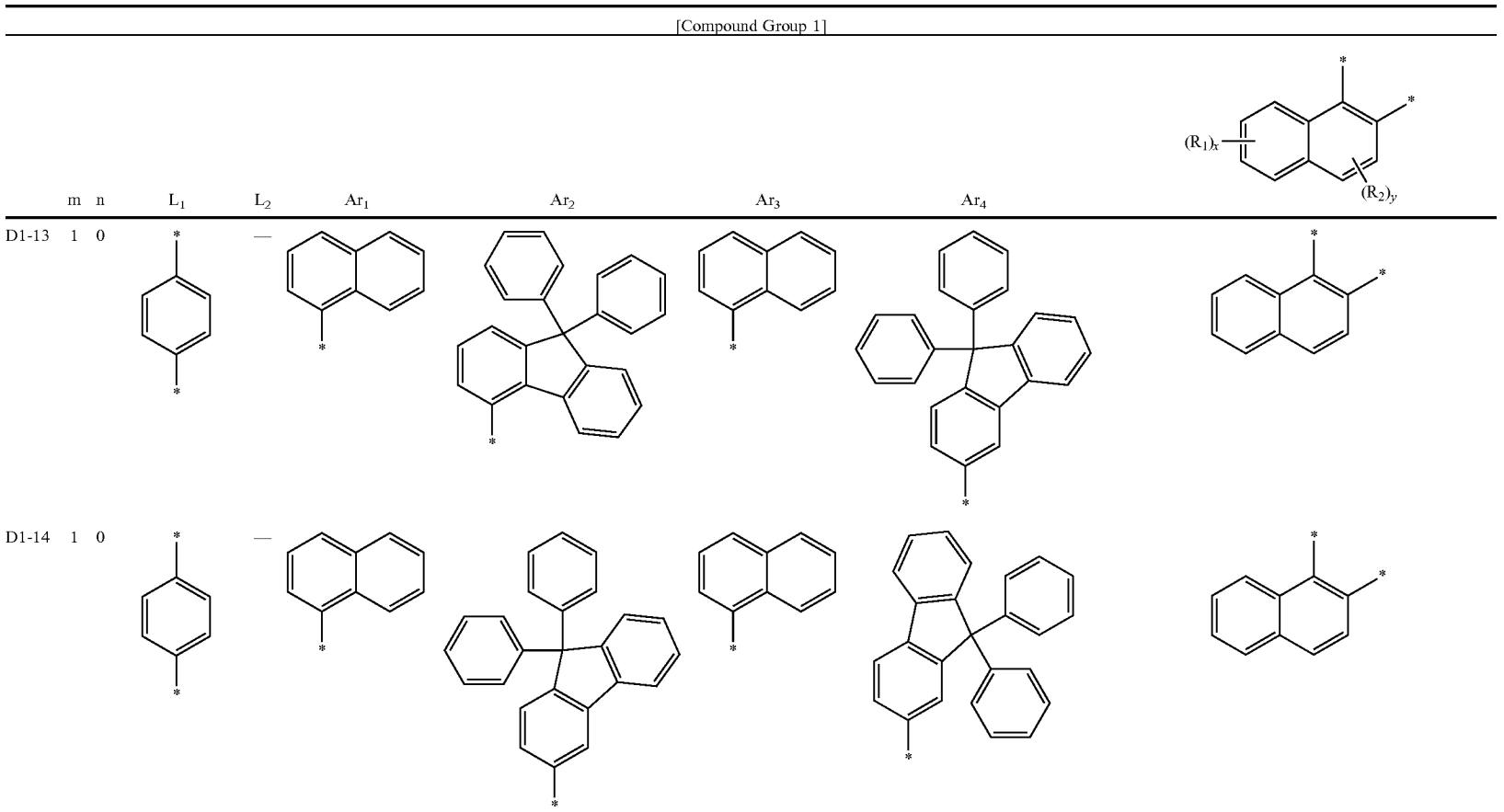

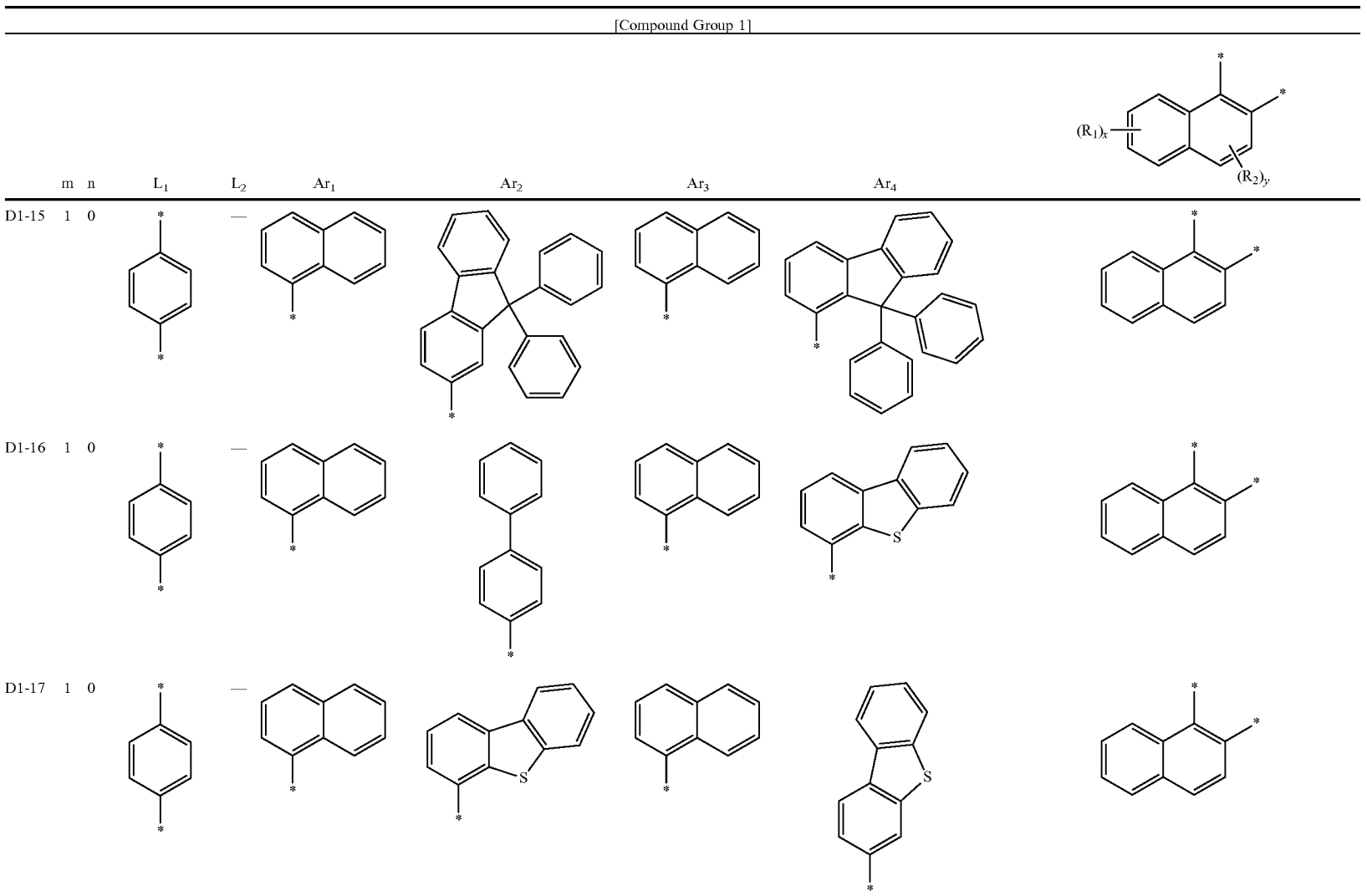

-continued
[Compound Group 1]
| | m | n | L₁ | L₂ | Ar₁ | Ar₂ | Ar₃ | Ar₄ | (R₁)ₓ / (R₂)ᵧ |
|---|---|---|---|---|---|---|---|---|---|
| D1-18 | 1 | 0 |  | — |  |  |  |  |  |
| D1-19 | 1 | 0 |  | — |  |  |  |  |  |
| D1-20 | 1 | 0 |  | — |  |  |  |  |  |

-continued

[Compound Group 1]

| | m | n | L₁ | L₂ | Ar₁ | Ar₂ | Ar₃ | Ar₄ | (R₁)ₓ / (R₂)ᵧ naphthalene |
|---|---|---|---|---|---|---|---|---|---|
| D1-21 | 1 | 0 | *-C₆H₄-* | — | 1-naphthyl | dibenzofuran-4-yl | 1-naphthyl | dibenzofuran-3-yl | naphthyl |
| D1-22 | 1 | 0 | *-C₆H₄-* | — | 1-naphthyl | dibenzofuran-3-yl | 1-naphthyl | dibenzofuran-2-yl | naphthyl |
| D1-23 | 1 | 0 | *-C₆H₄-* | — | 1-naphthyl | dibenzofuran-2-yl | 1-naphthyl | dibenzofuran-4-yl | naphthyl |

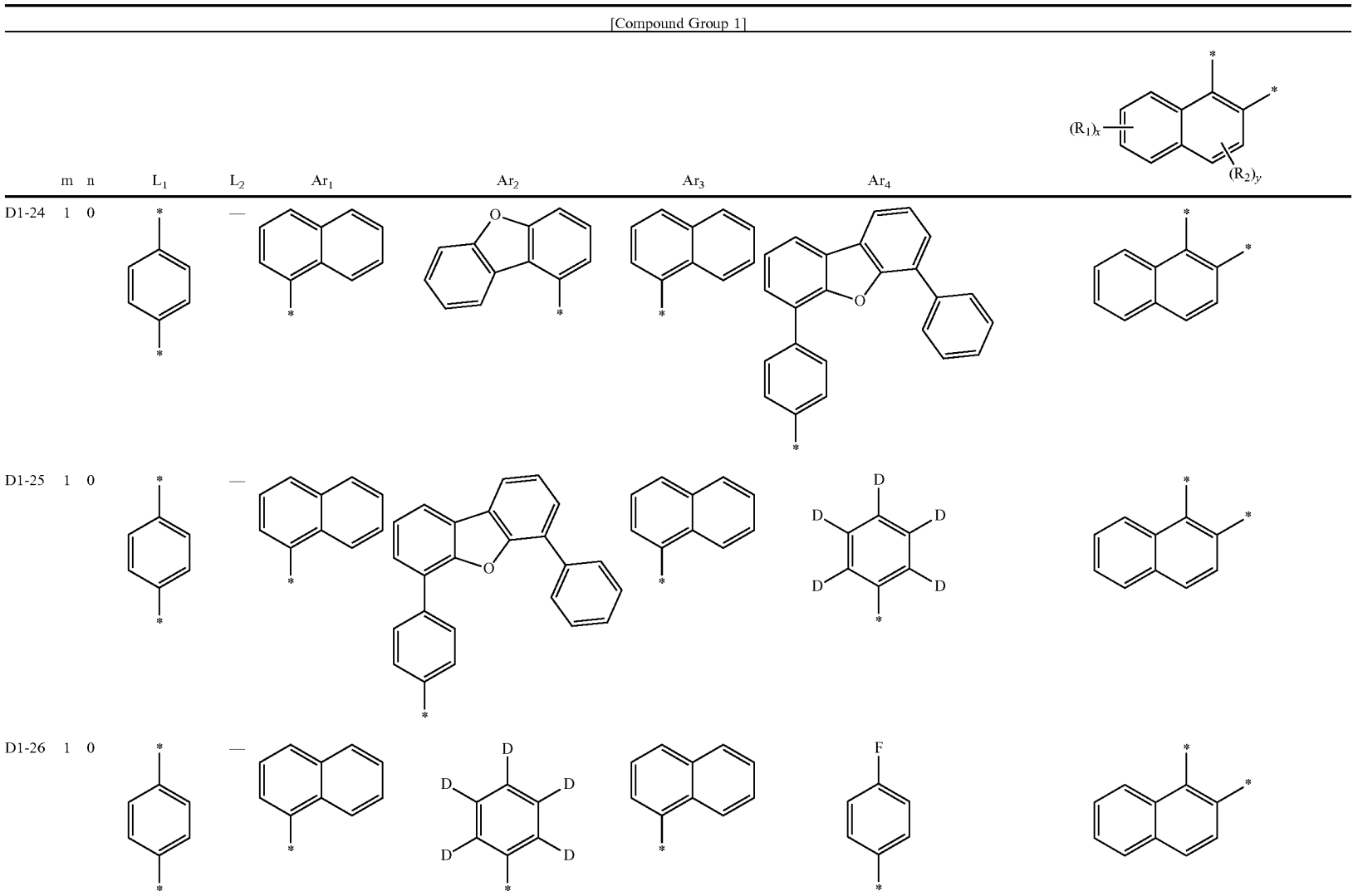

-continued
[Compound Group 1]

-continued
[Compound Group 1]
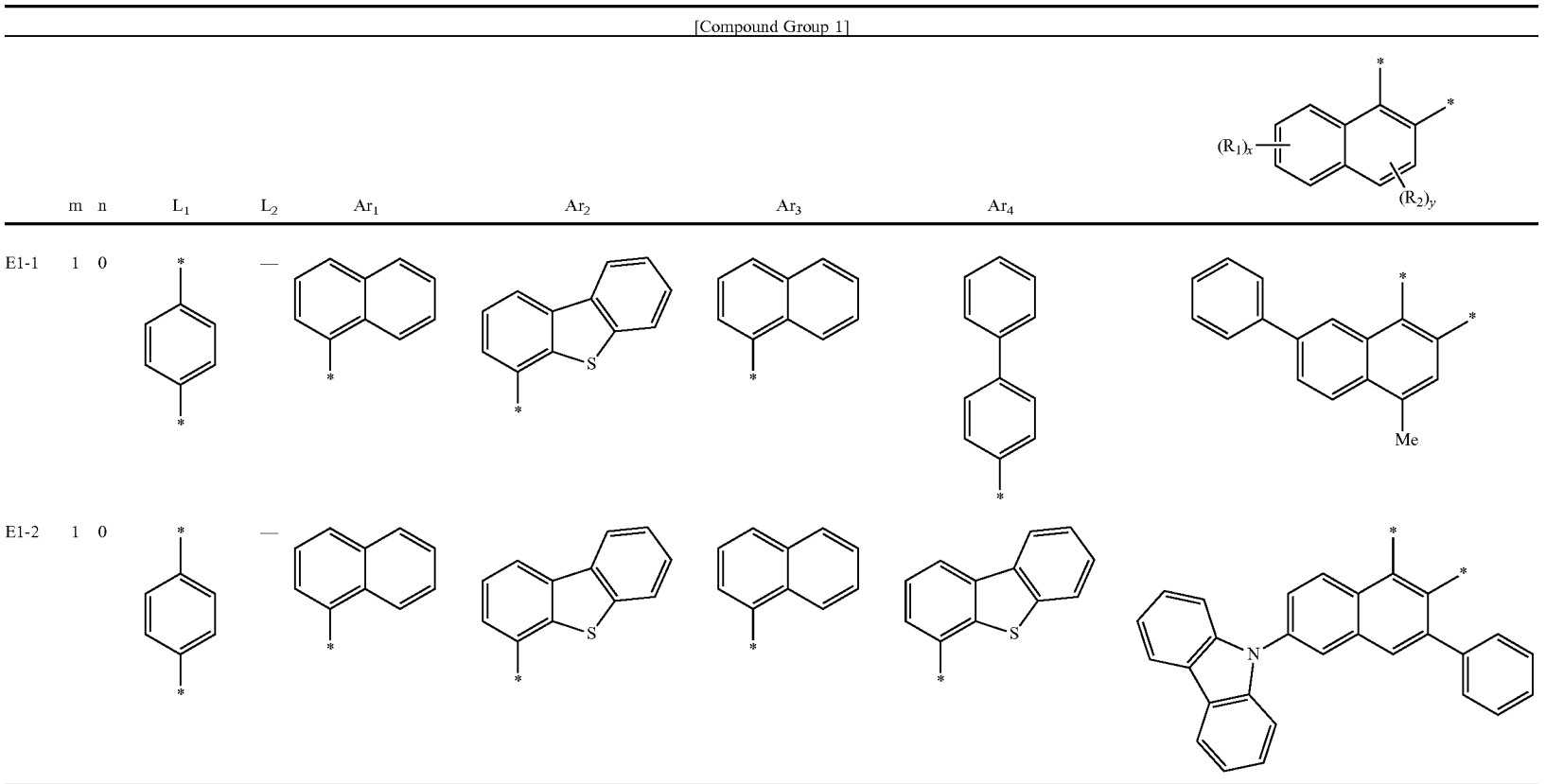

[Compound Group 2]
| | m | n | L₁ | L₂ | Ar₁ | Ar₂ | Ar₃ | Ar₄ | 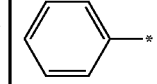 |
|---|---|---|---|---|---|---|---|---|---|
| A2-1 | 1 | 1 | phenylene | phenylene | phenyl | phenyl | phenyl | phenyl | 1-naphthyl (2-substituted) |
| A2-2 | 1 | 1 | phenylene | phenylene | biphenyl | biphenyl | biphenyl | biphenyl | 1-naphthyl (2-substituted) |
| A2-3 | 1 | 1 | phenylene | phenylene | phenyl | biphenyl | phenyl | biphenyl | 1-naphthyl (2-substituted) |

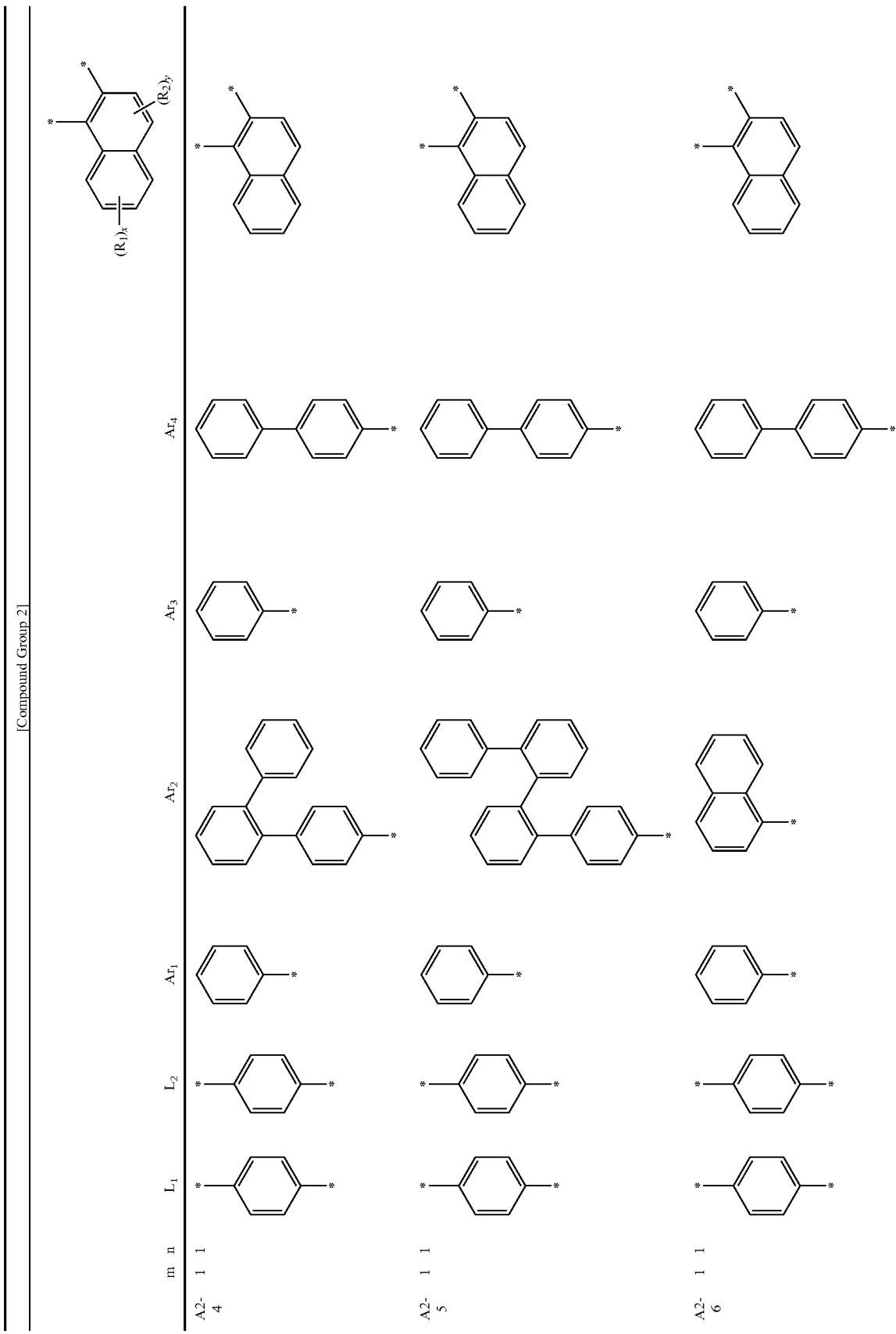

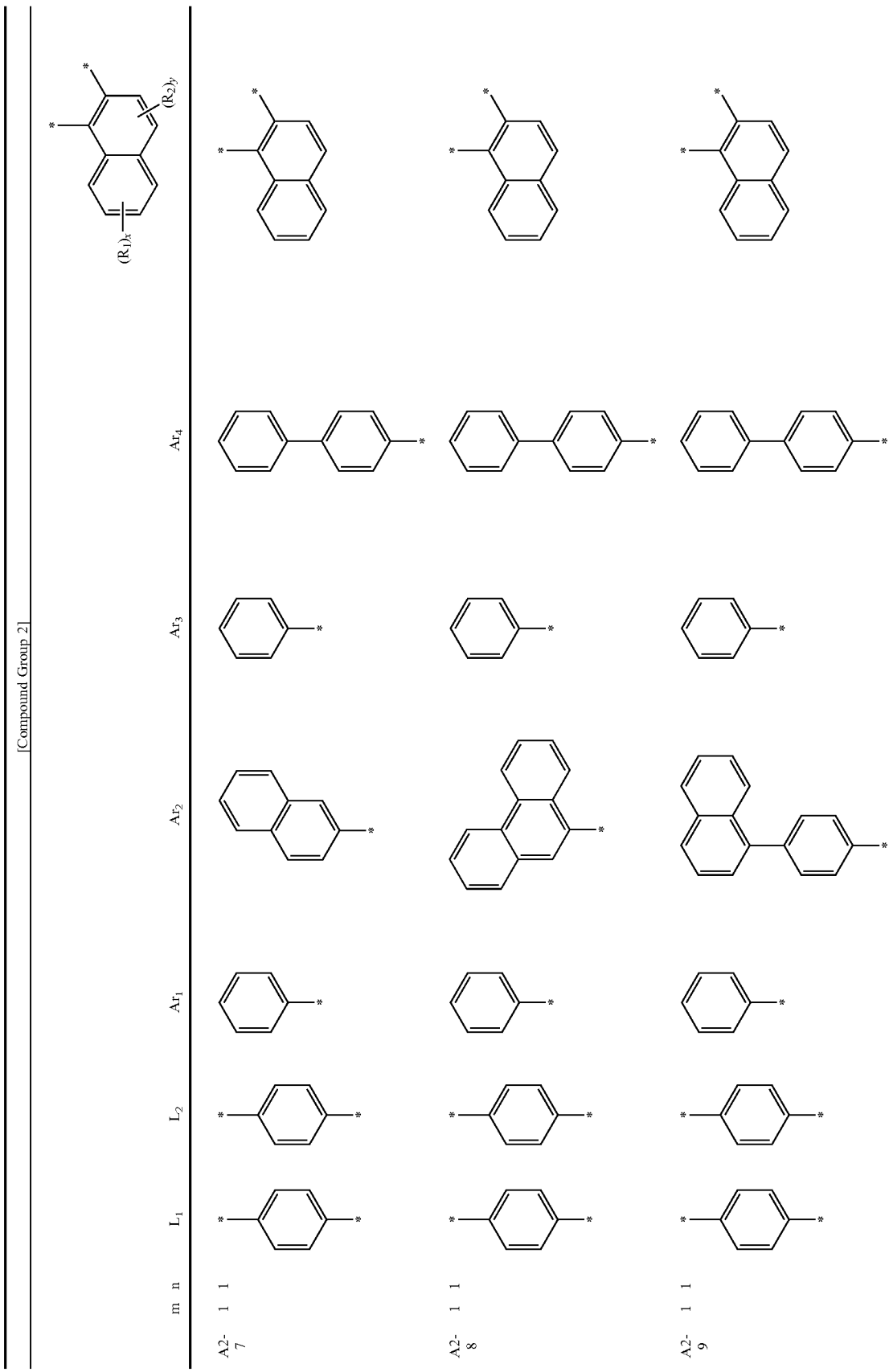

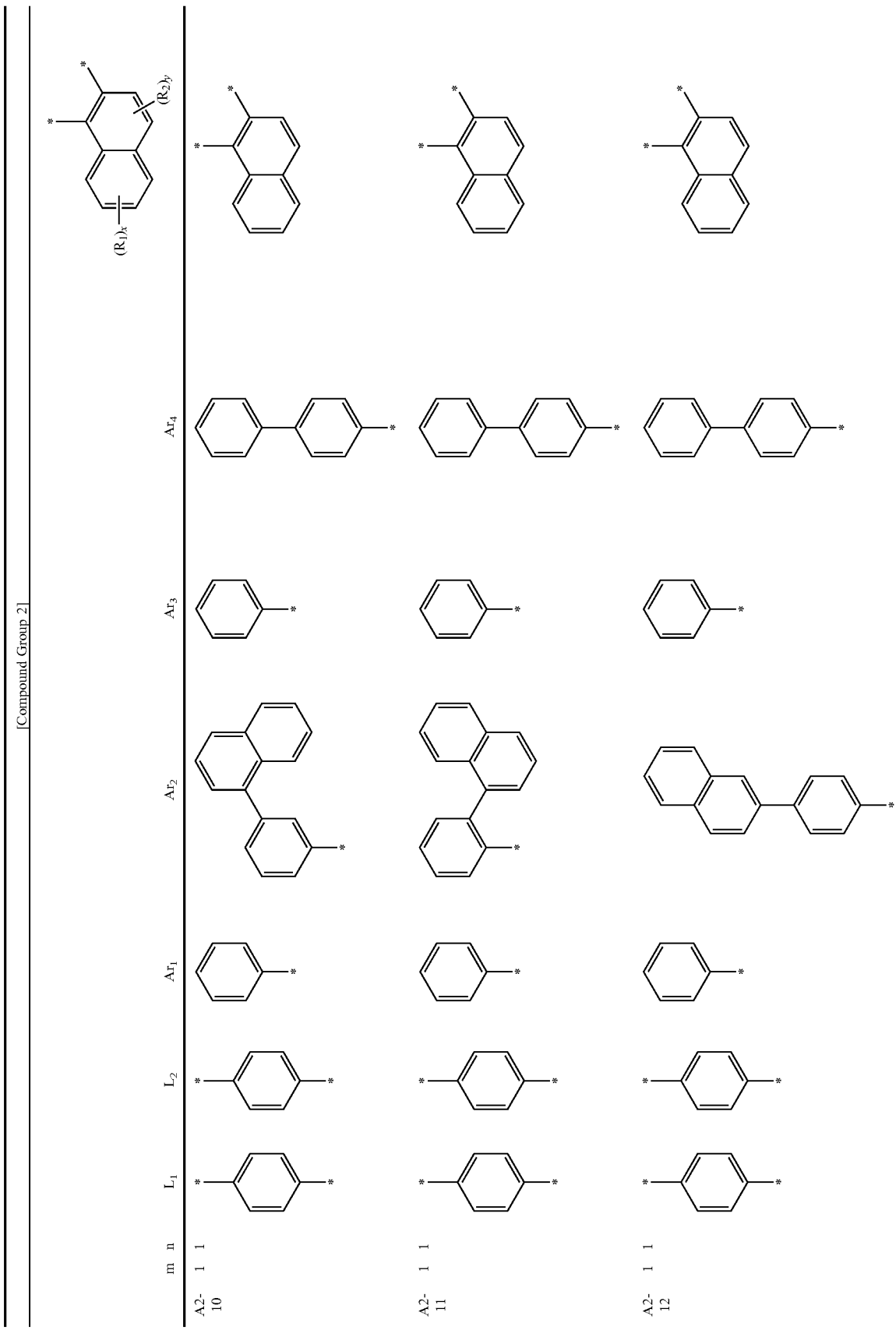

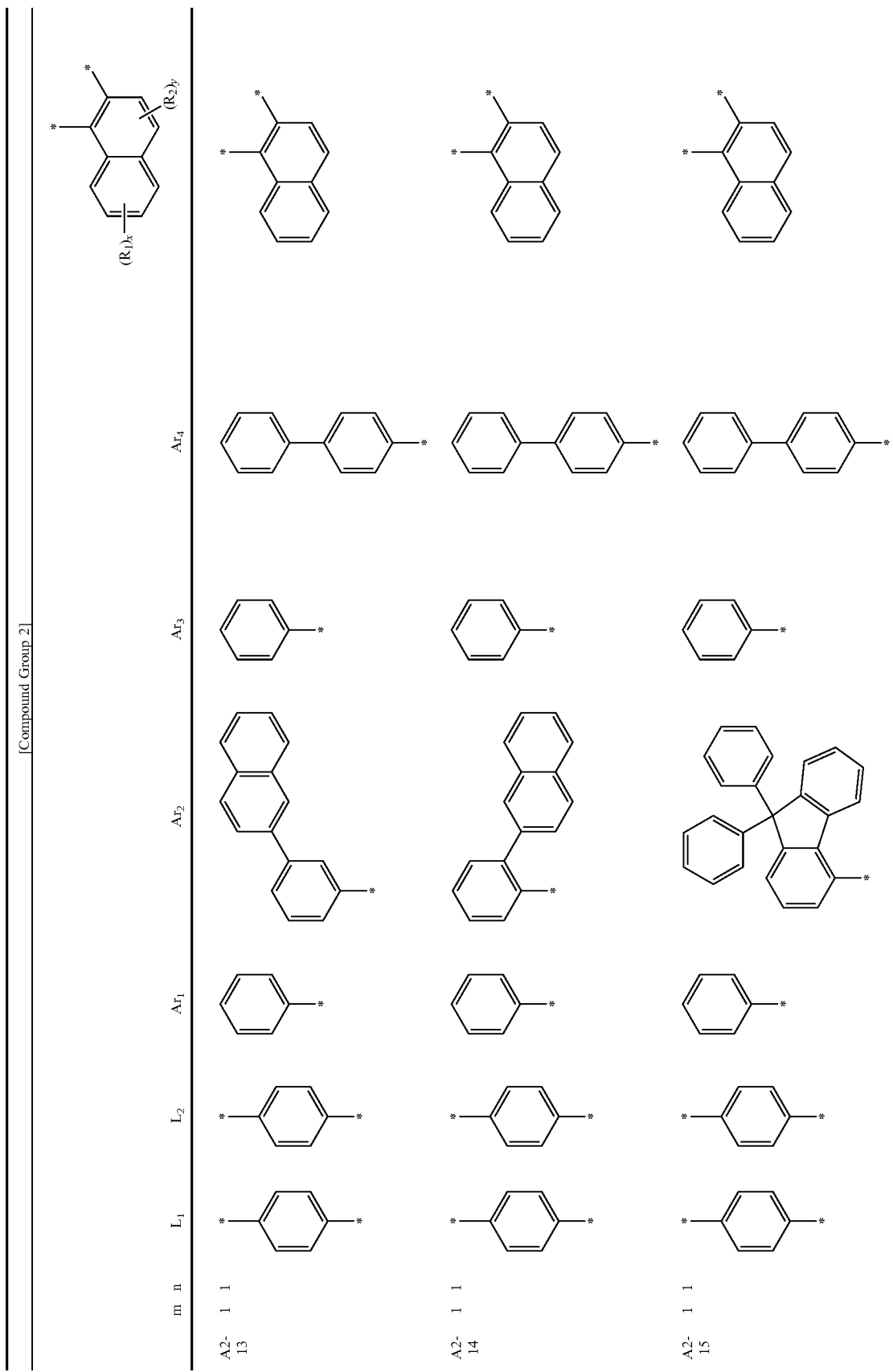

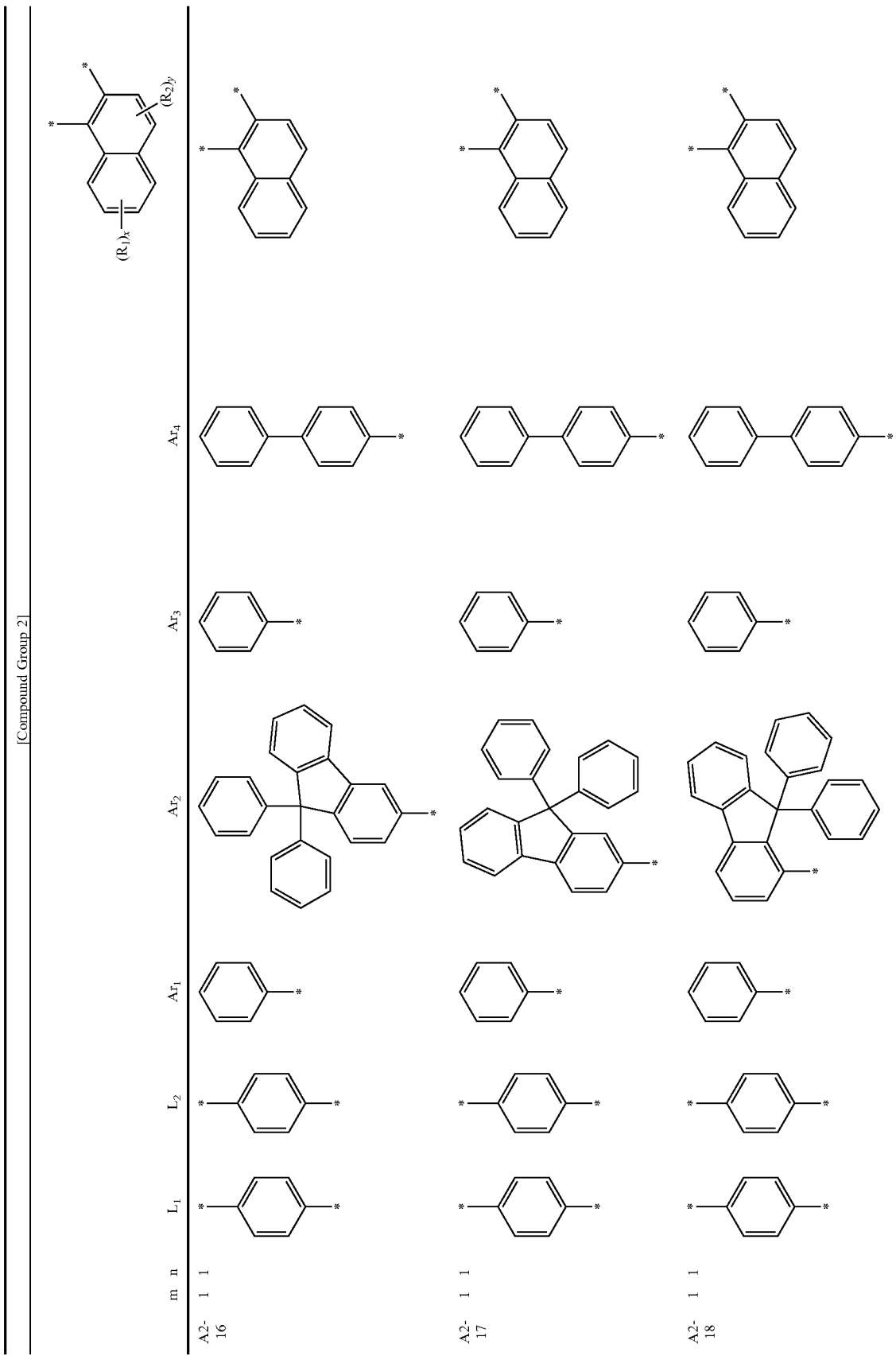

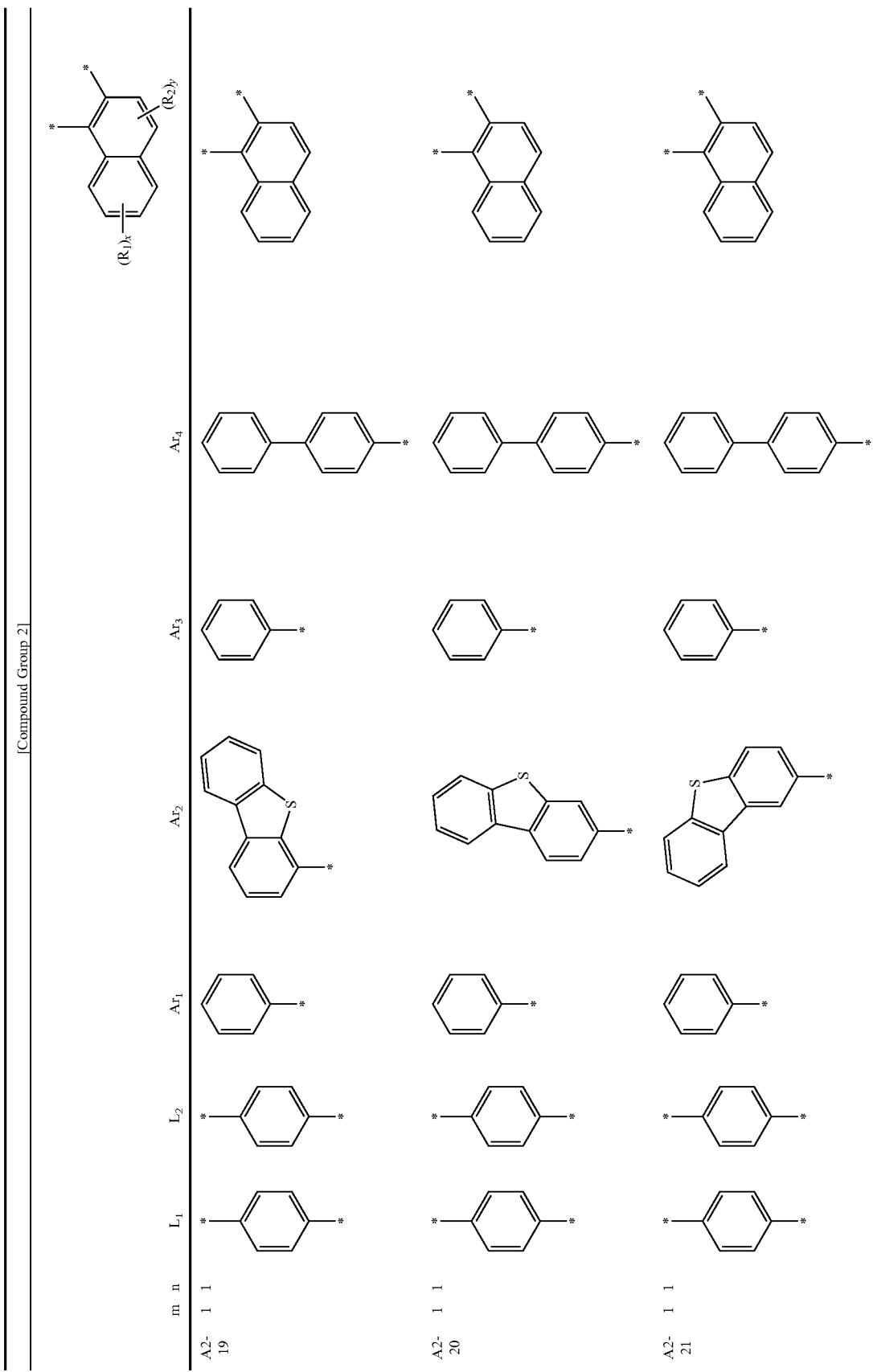

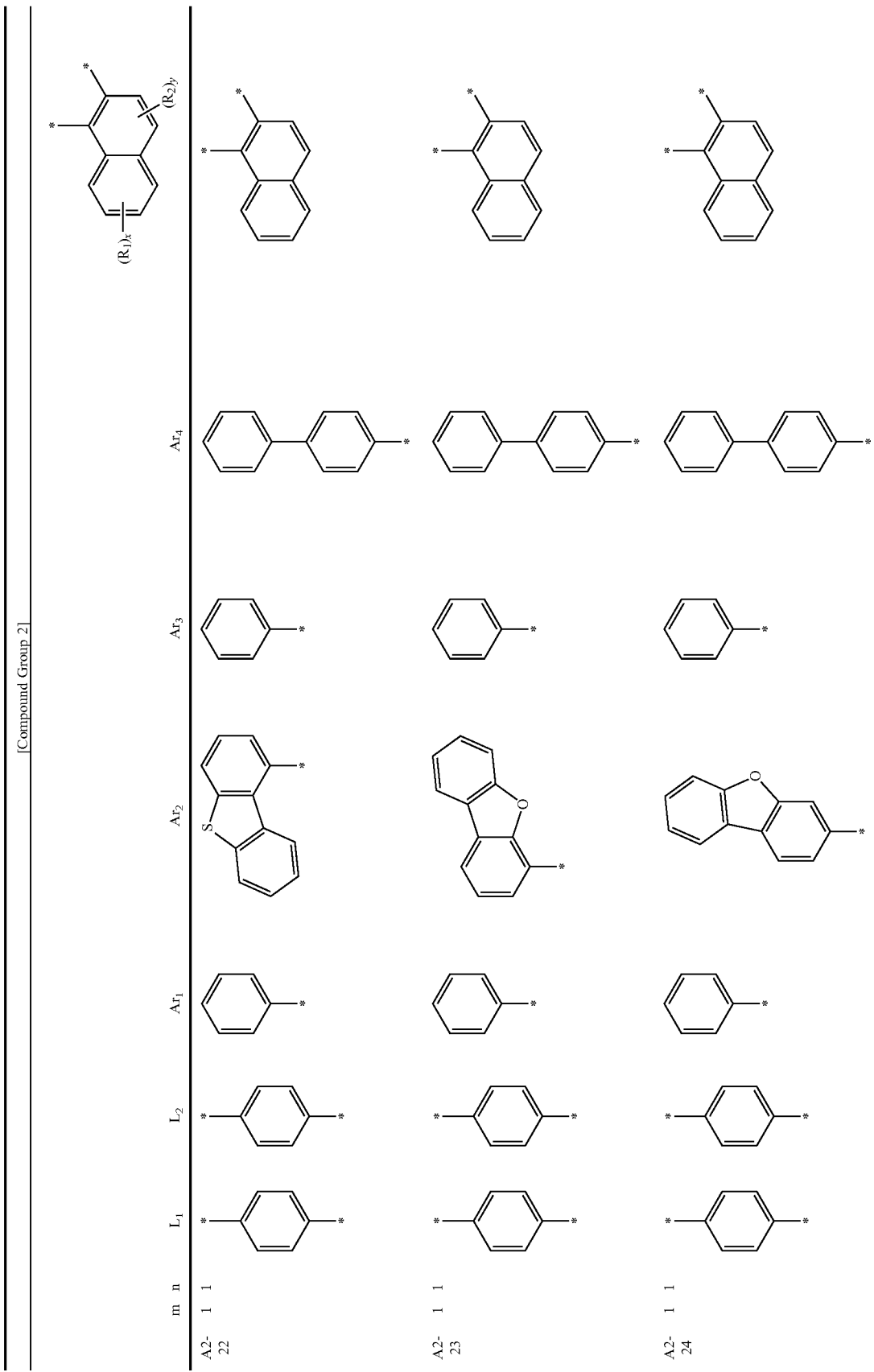

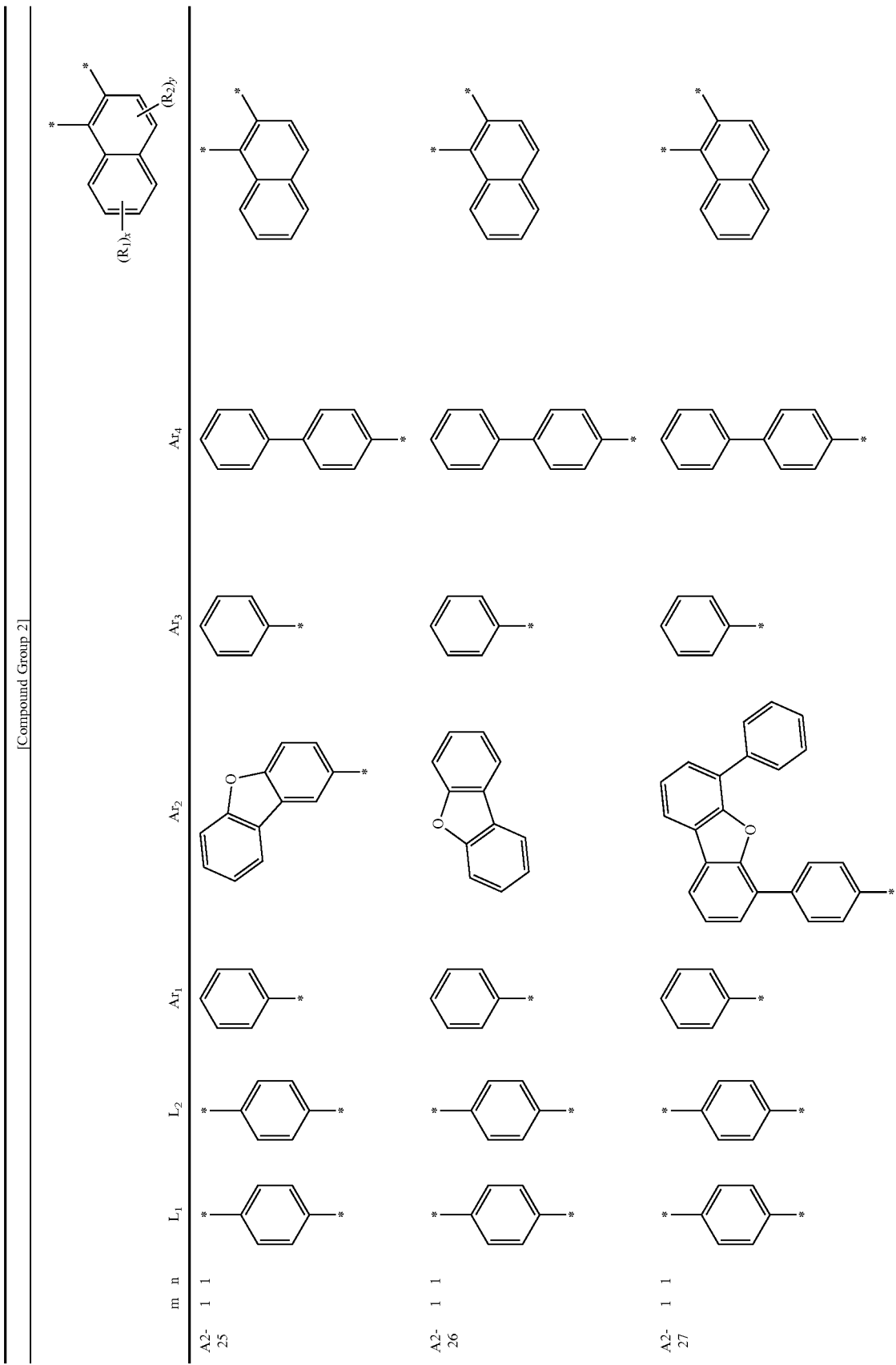

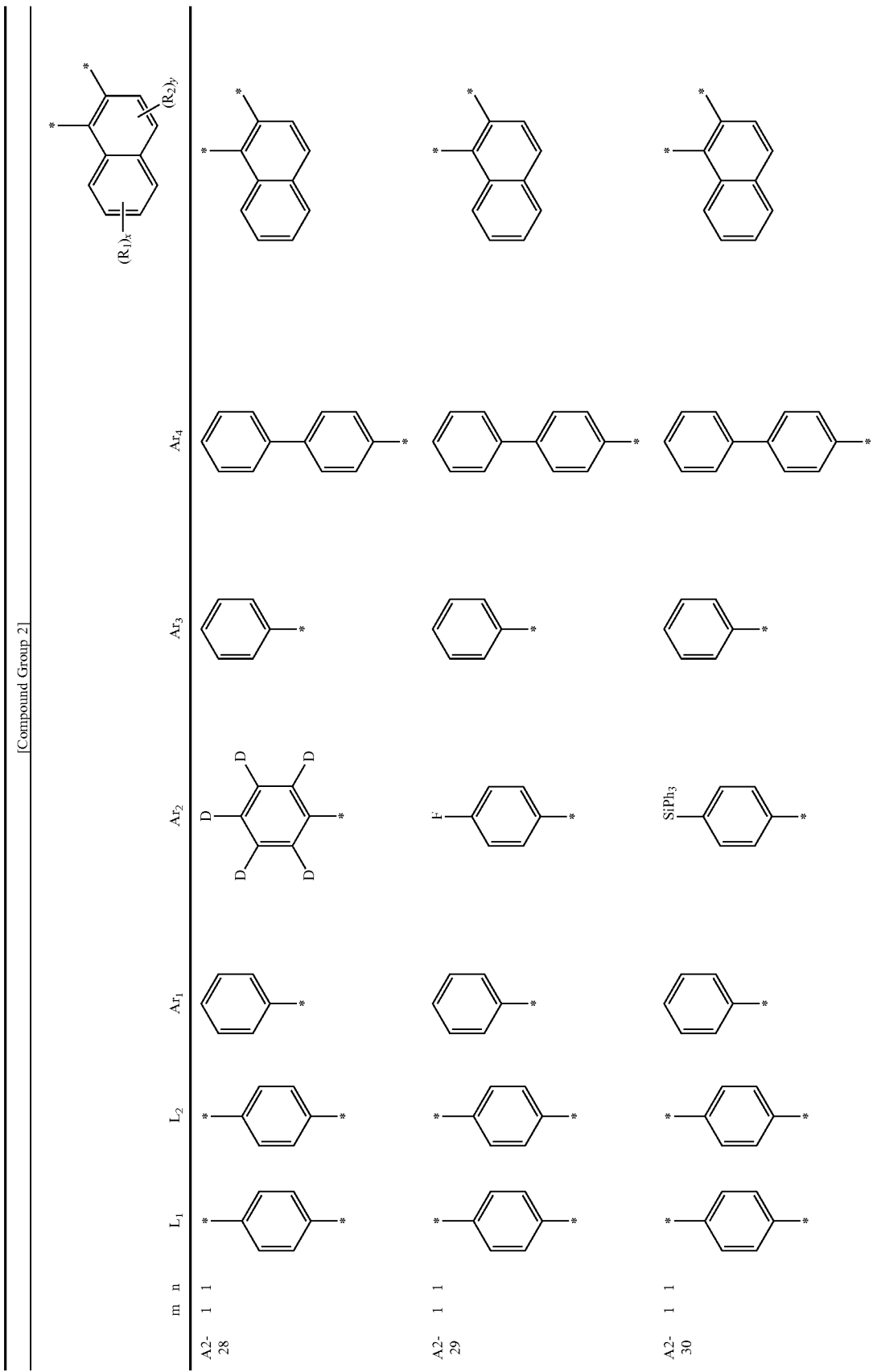

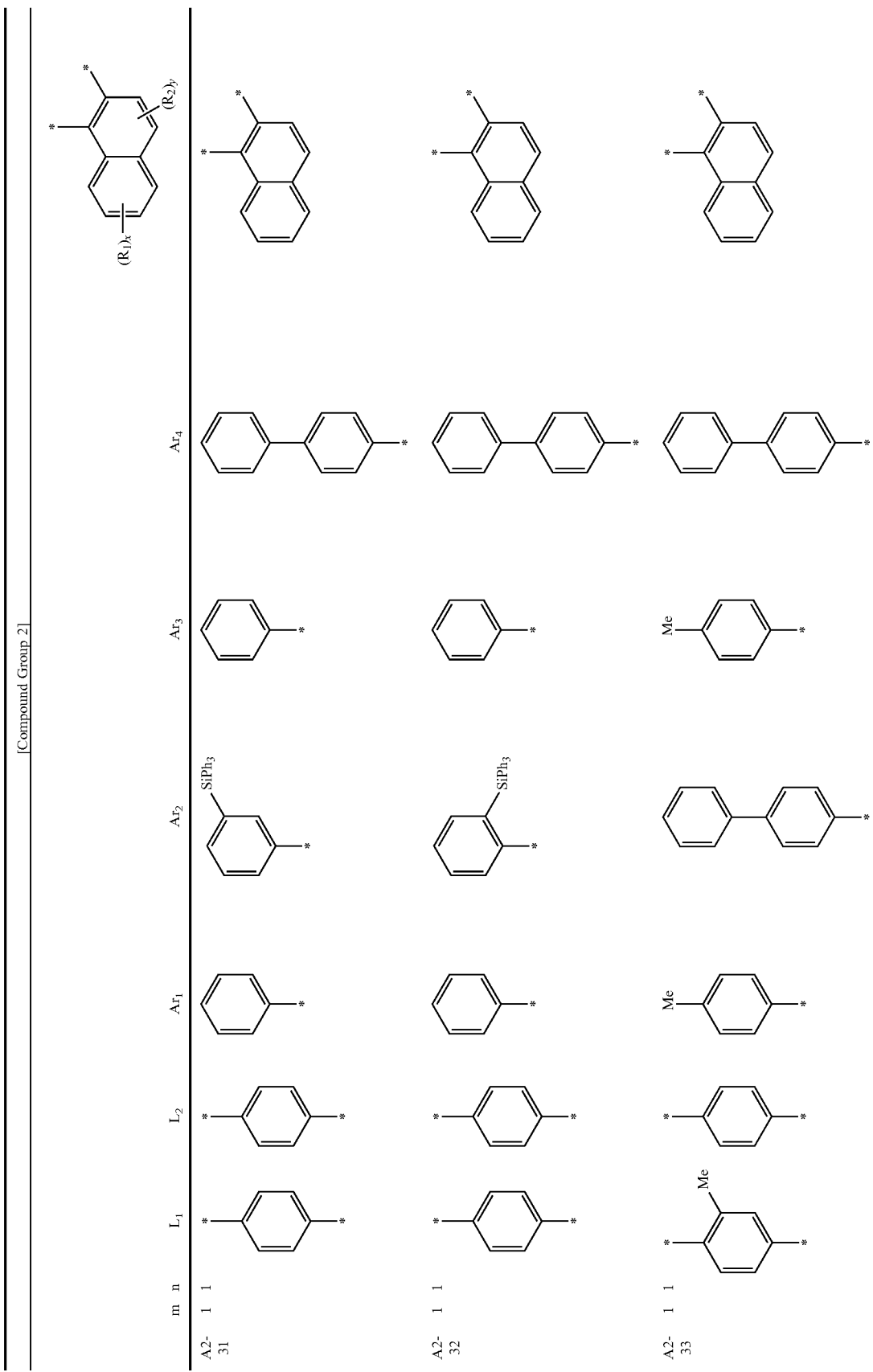

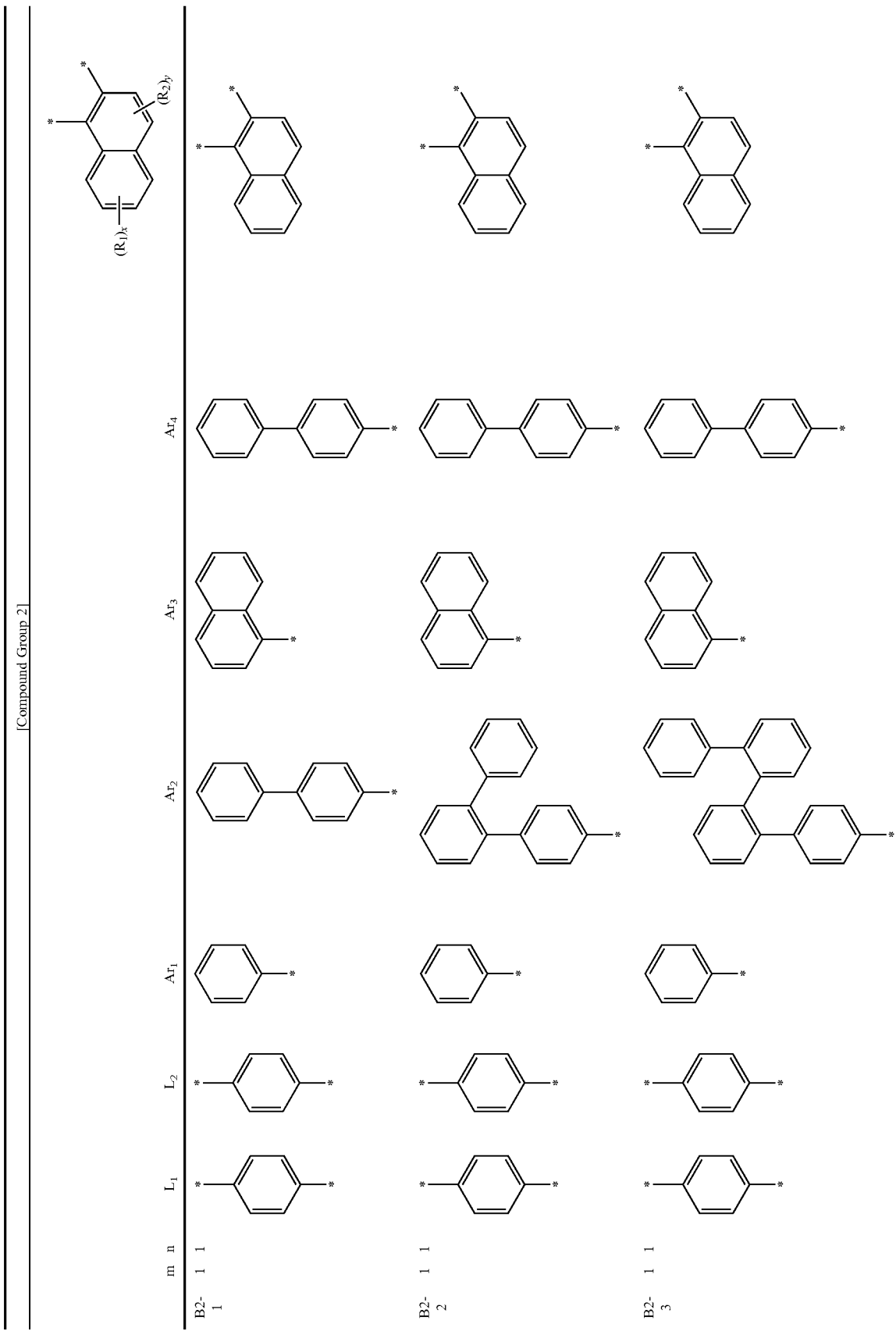

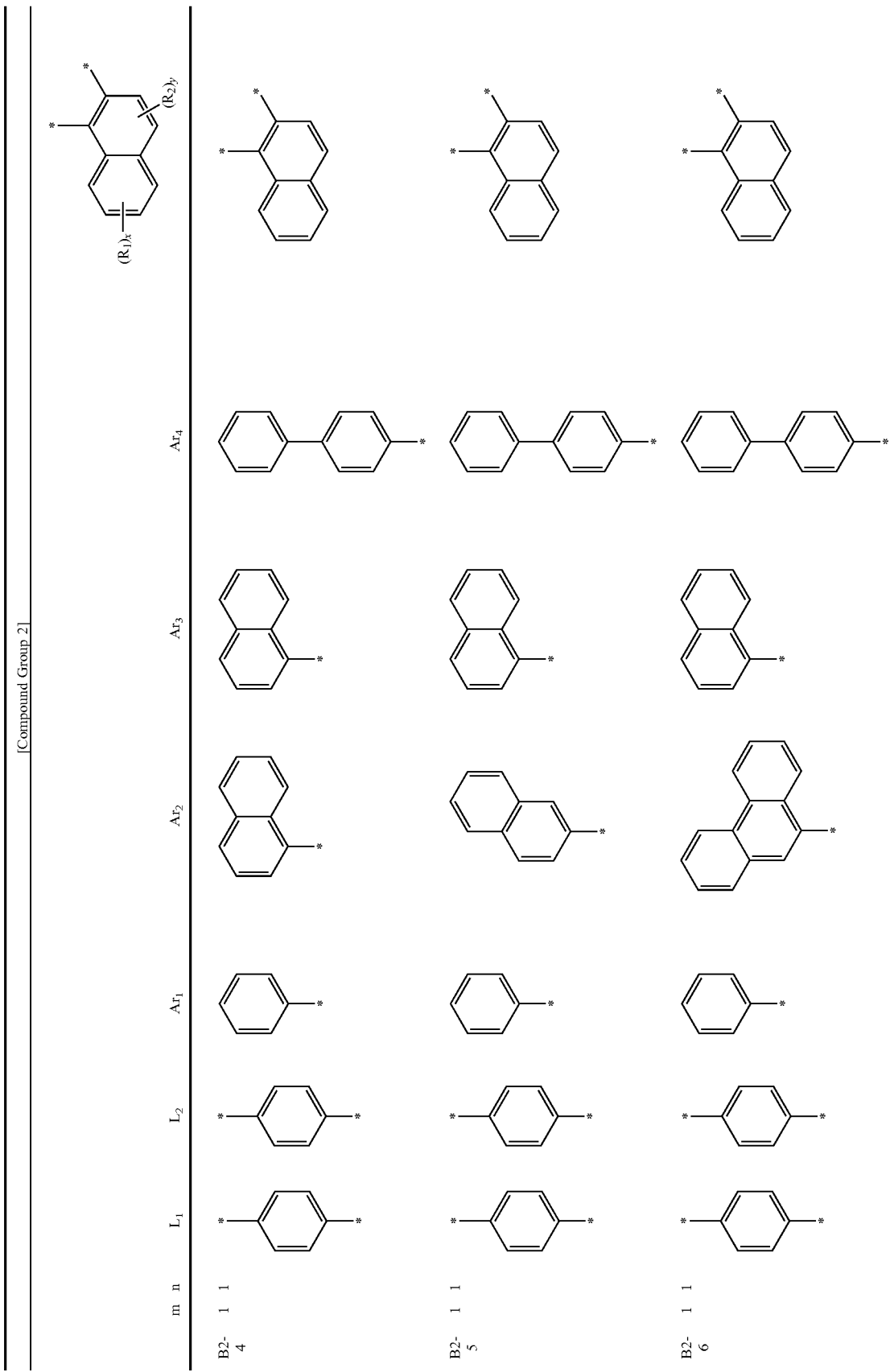

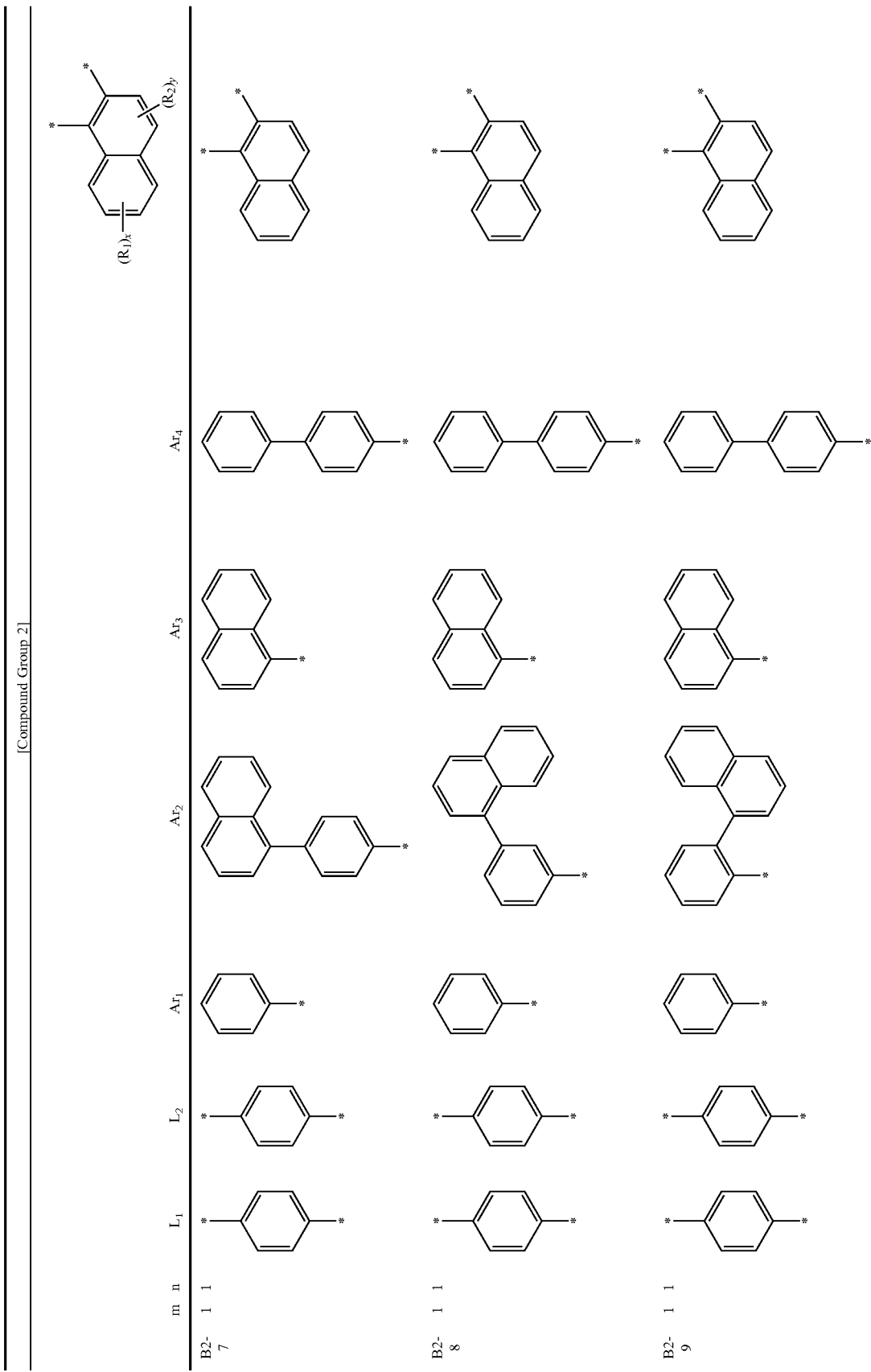

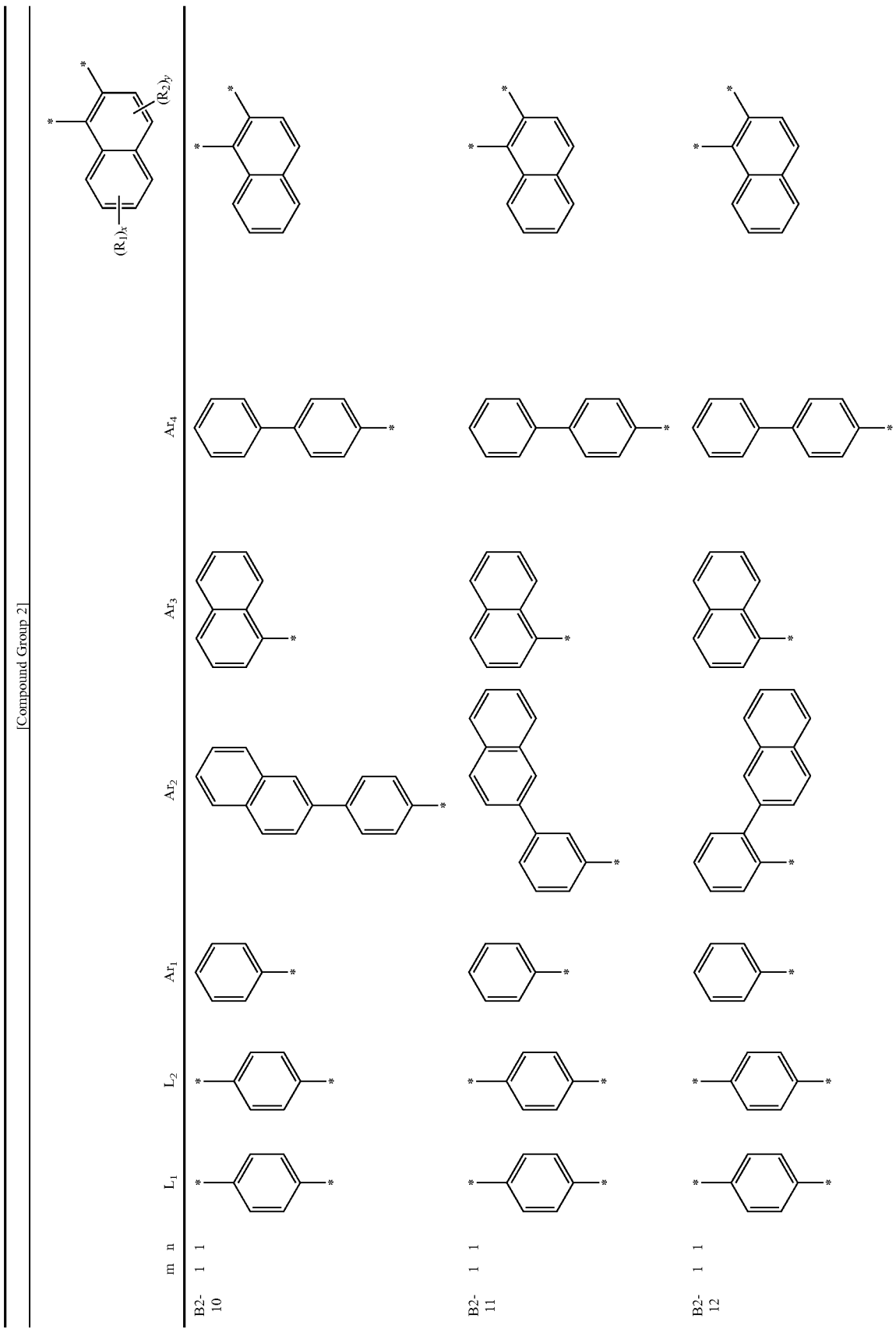

-continued
[Compound Group 2]
| | m | n | L₁ | L₂ | Ar₁ | Ar₂ | Ar₃ | Ar₄ | |
|---|---|---|---|---|---|---|---|---|---|
| B2-13 | 1 | 1 |  |  |  |  |  |  |  |
| B2-14 | 1 | 1 |  |  |  |  |  |  |  |
| B2-15 | 1 | 1 |  |  |  |  |  |  |  |

-continued
[Compound Group 2]
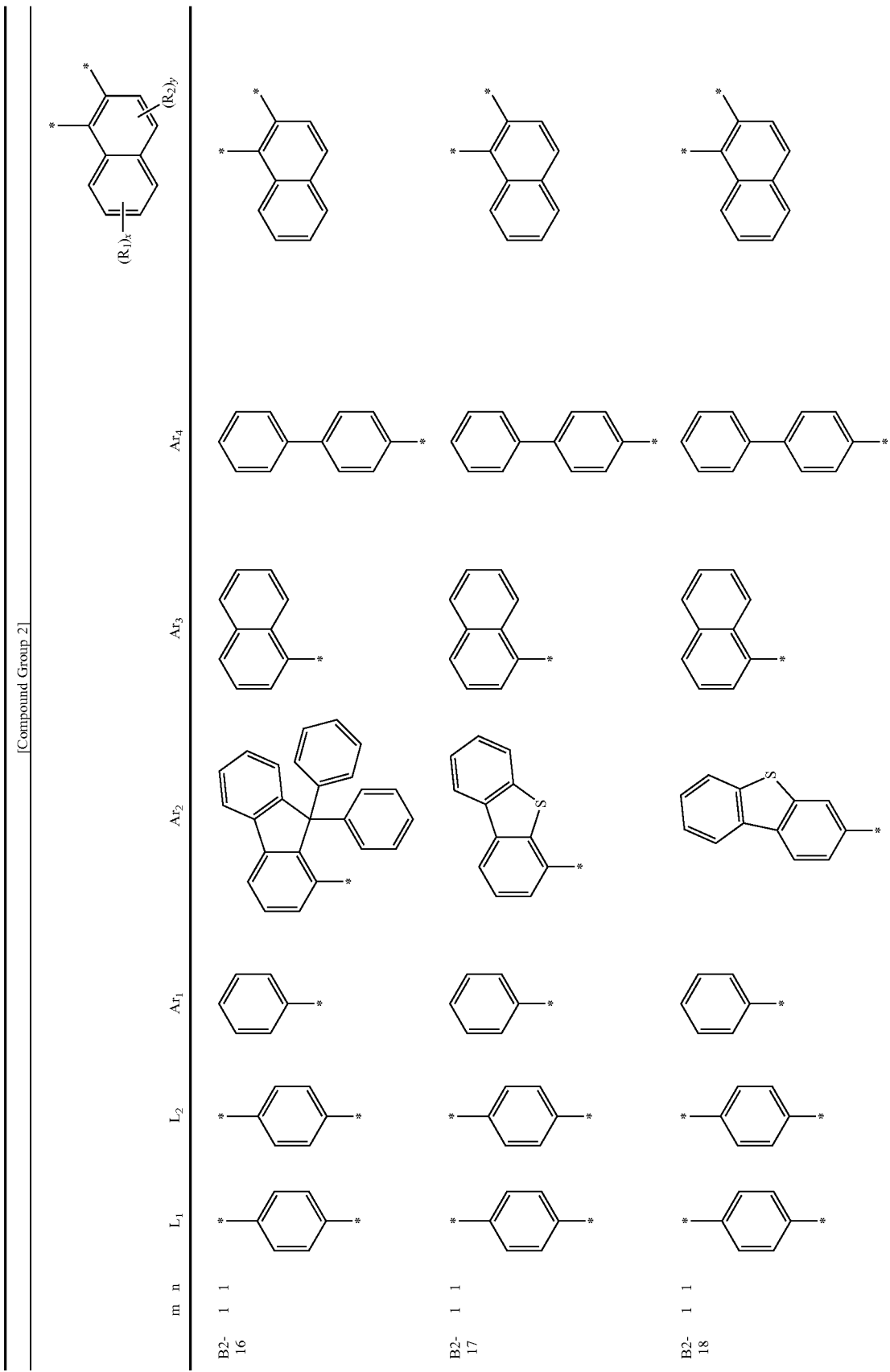

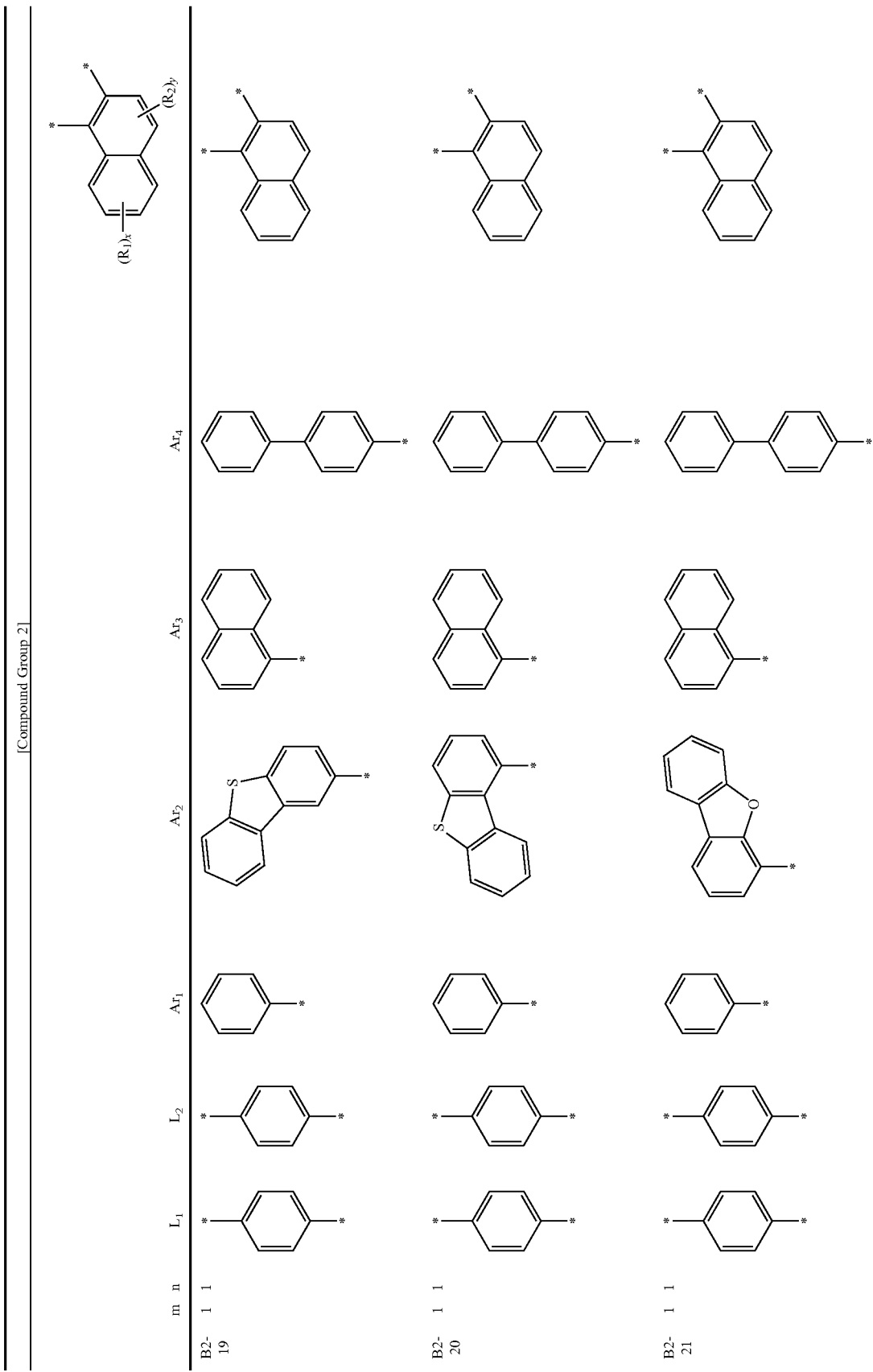

-continued
[Compound Group 2]
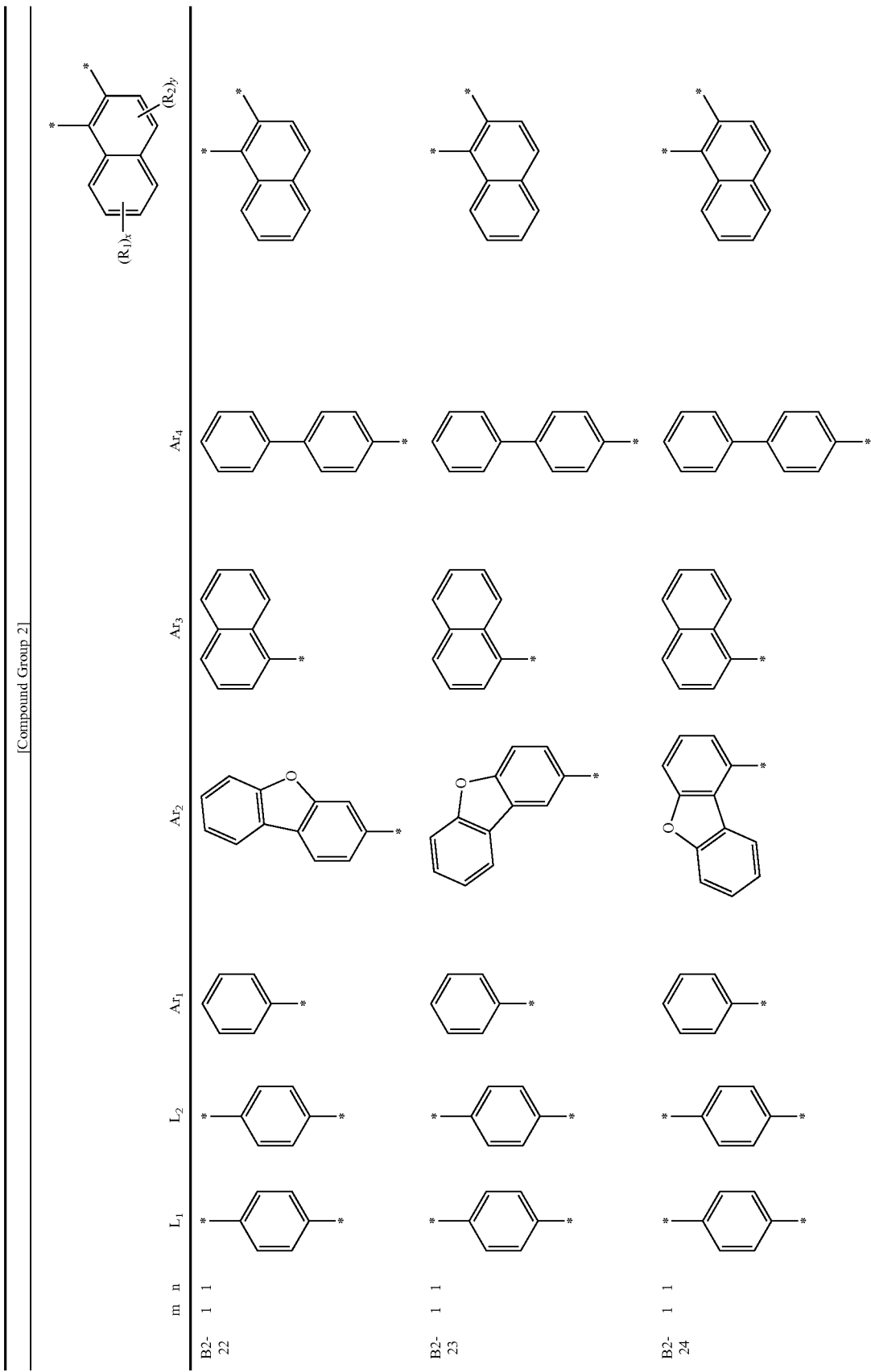

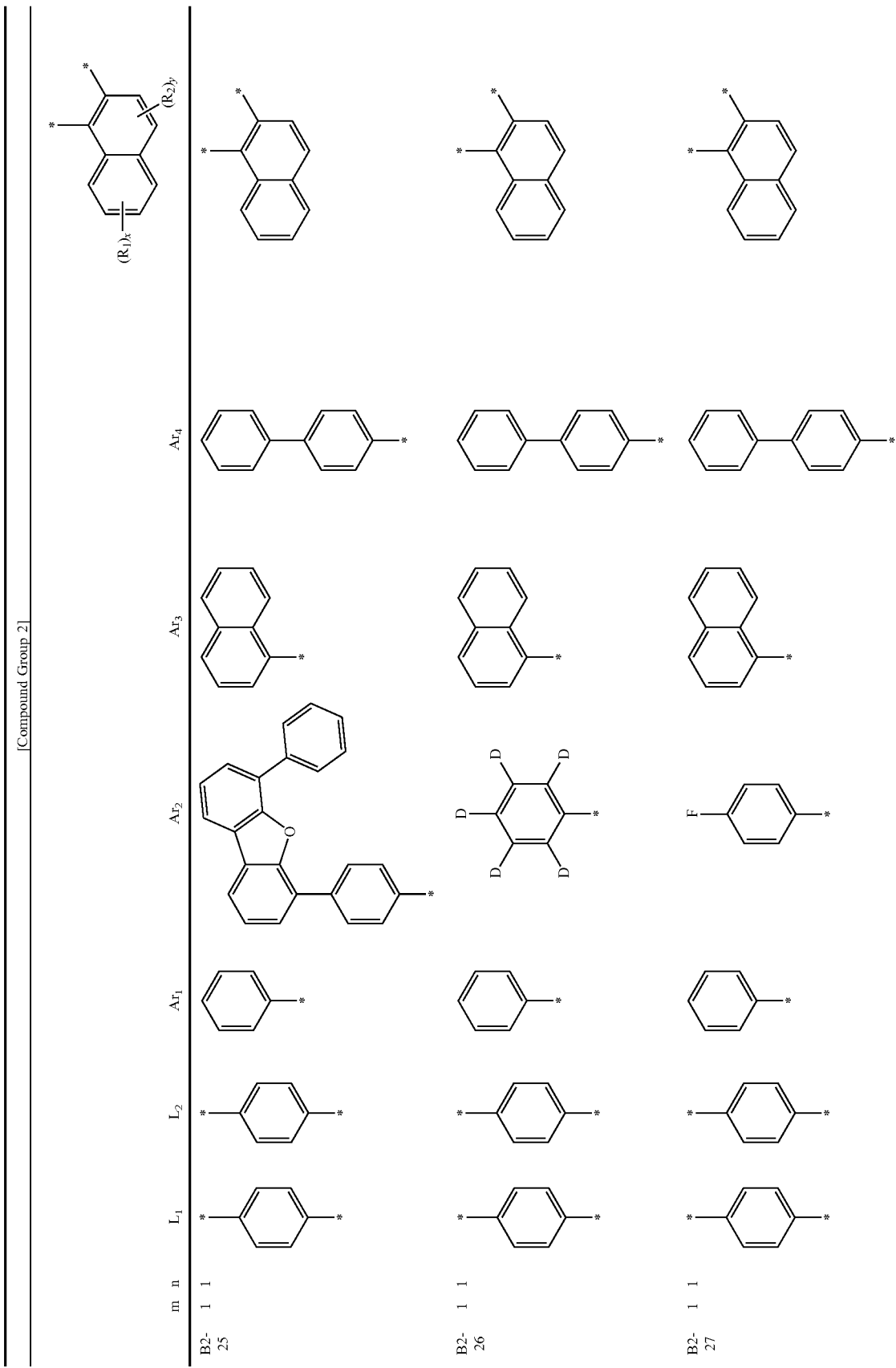

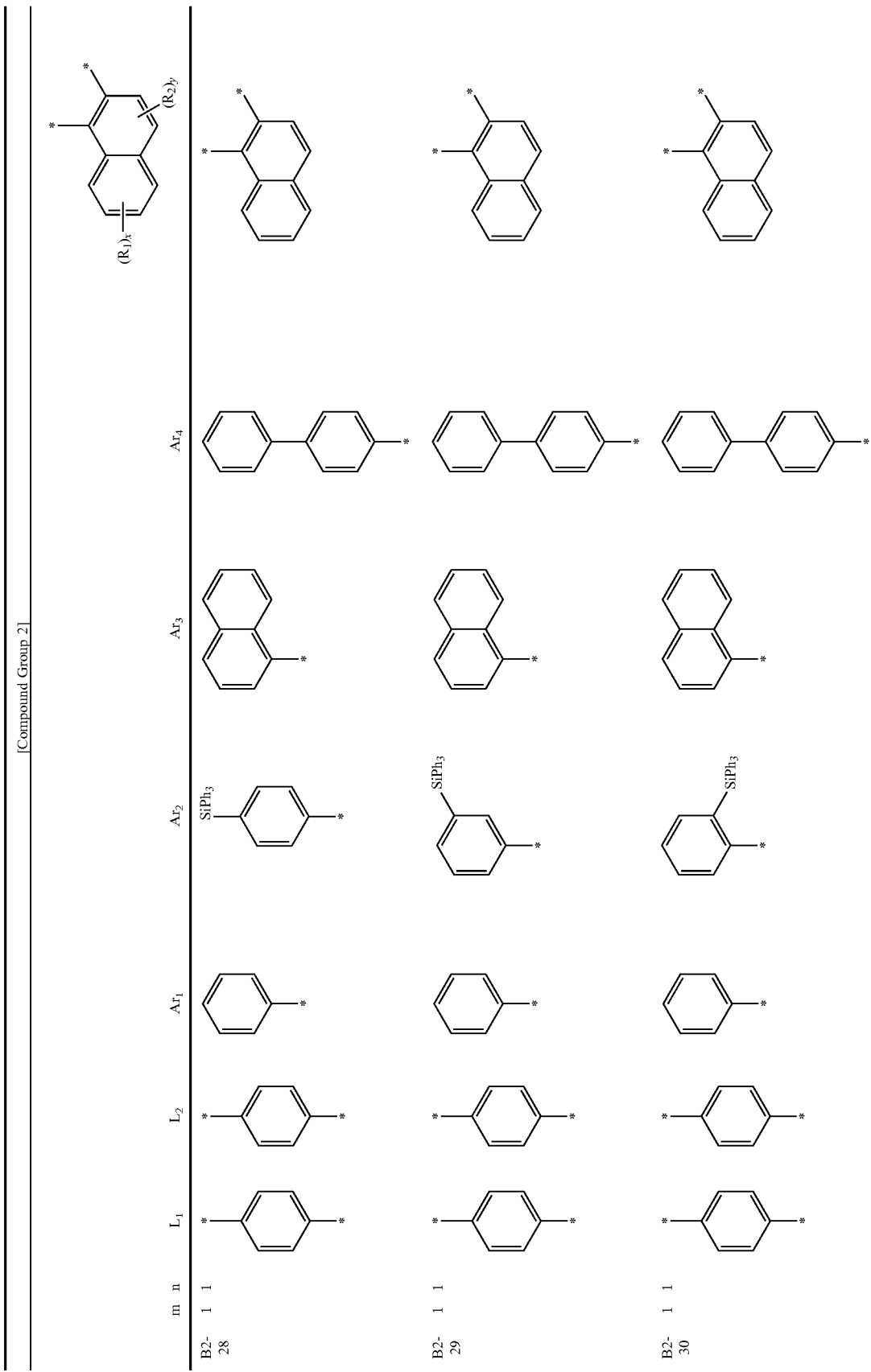

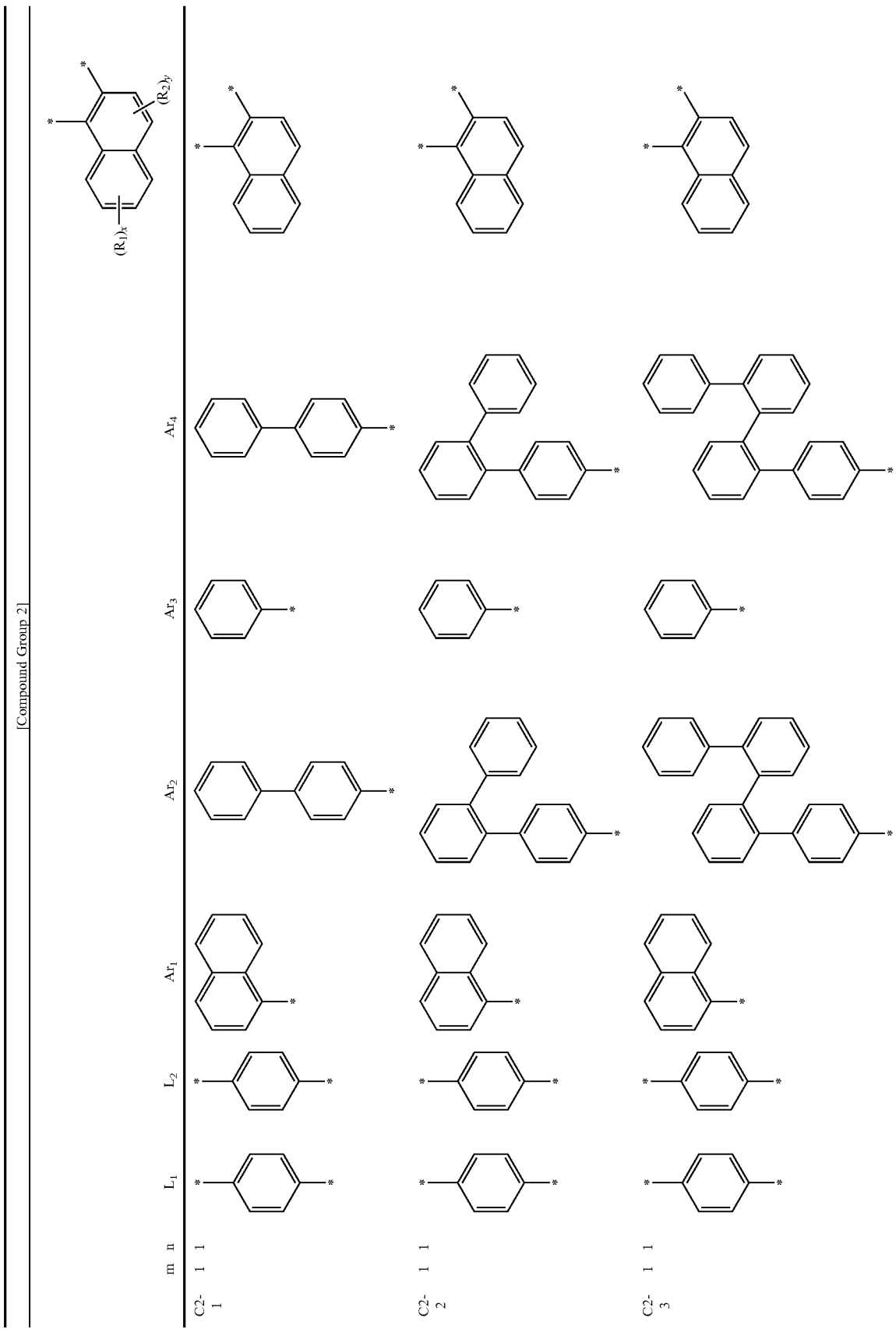

-continued
[Compound Group 2]
| m n | L₁ | L₂ | Ar₁ | Ar₂ | Ar₃ | Ar₄ | |
|---|---|---|---|---|---|---|---|
| C2-4 1 1 | 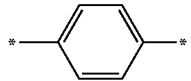 | 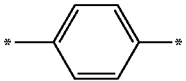 | 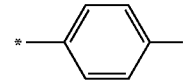 |  | 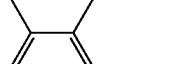 | 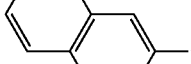 | 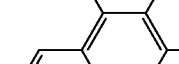 |
| C2-5 1 1 |  |  |  |  |  |  |  |
| C2-6 1 1 | 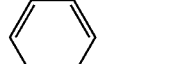 | 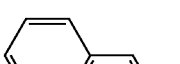 | 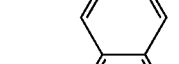 |  |  |  |  |

-continued
[Compound Group 2]
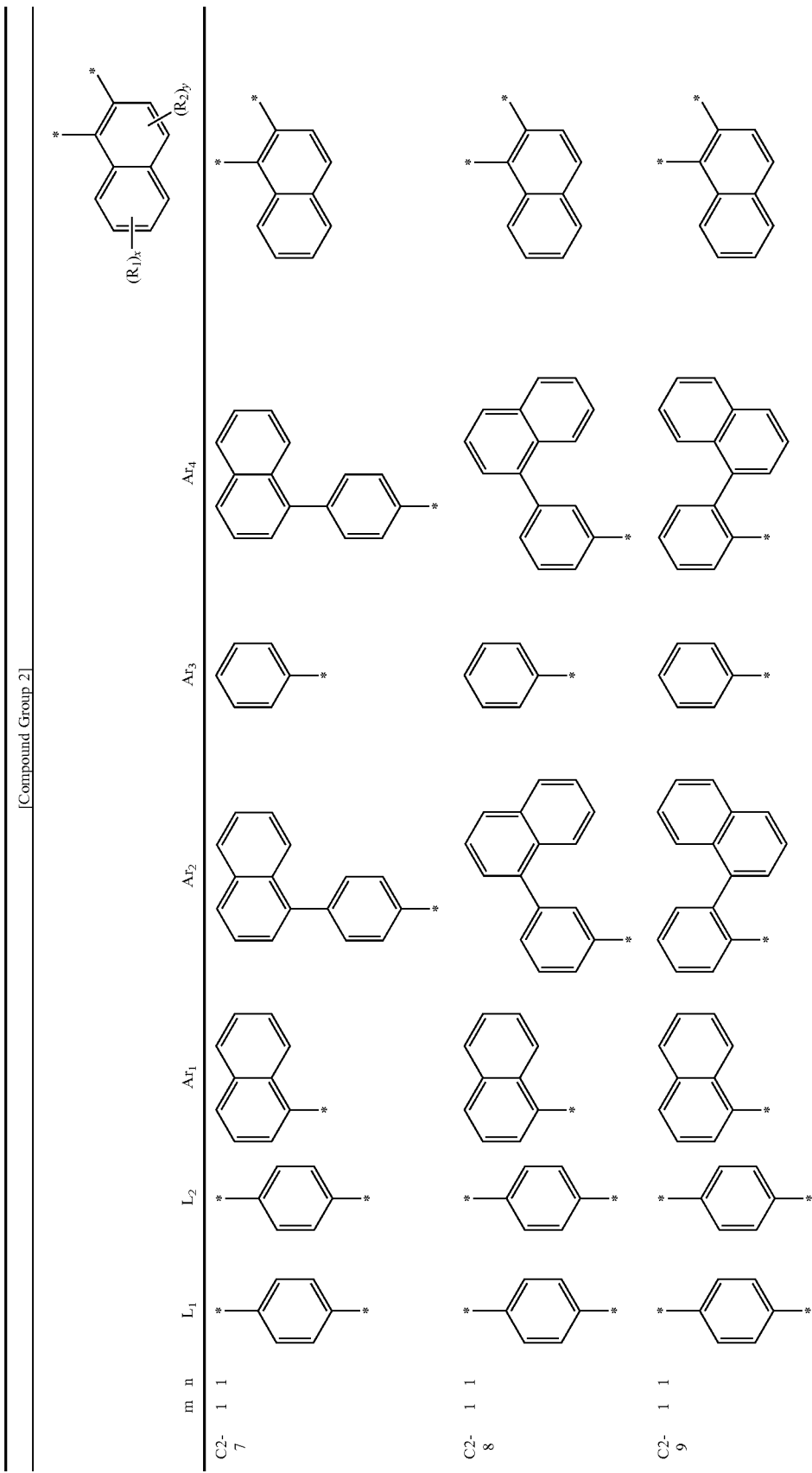

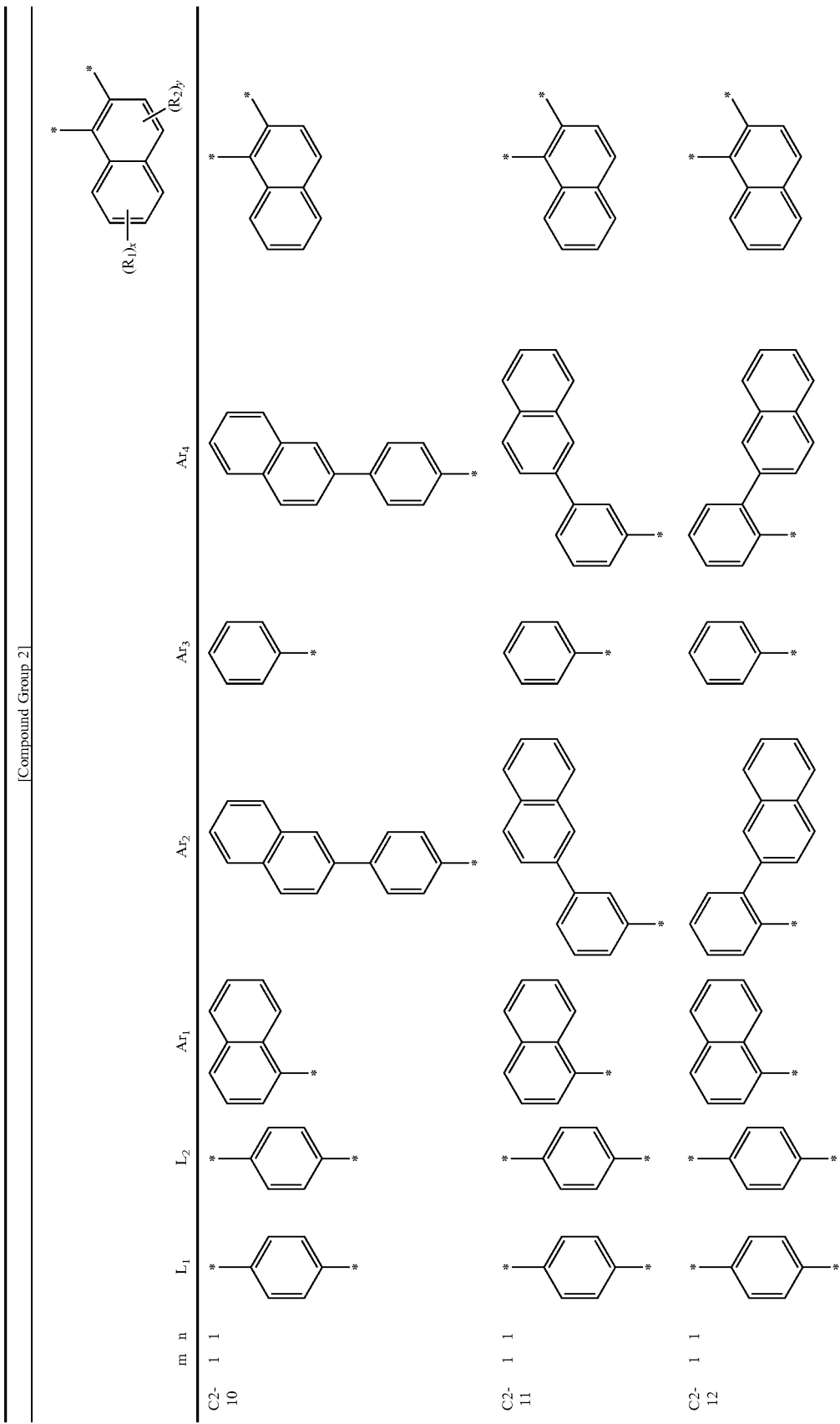

-continued
[Compound Group 2]
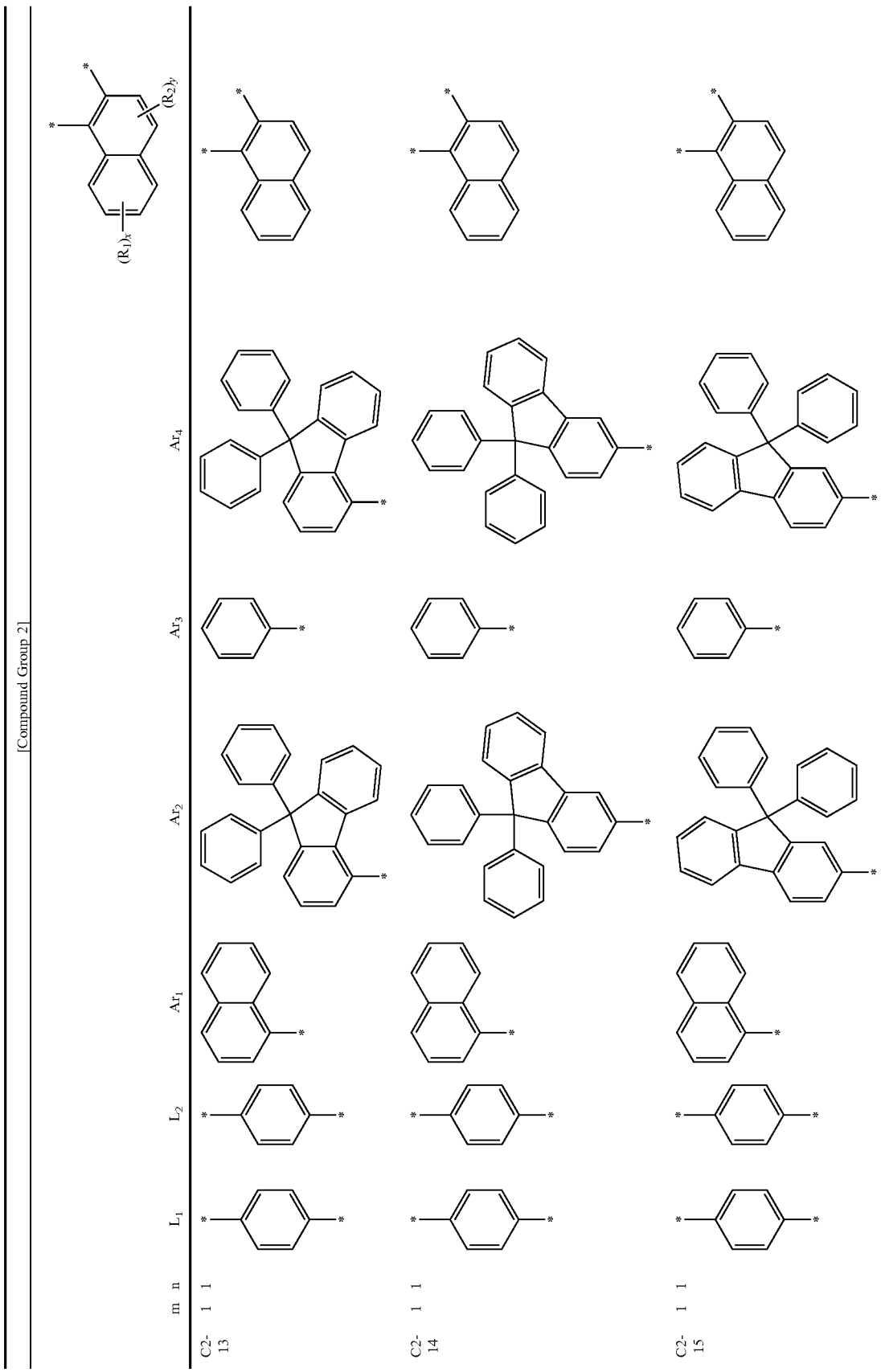

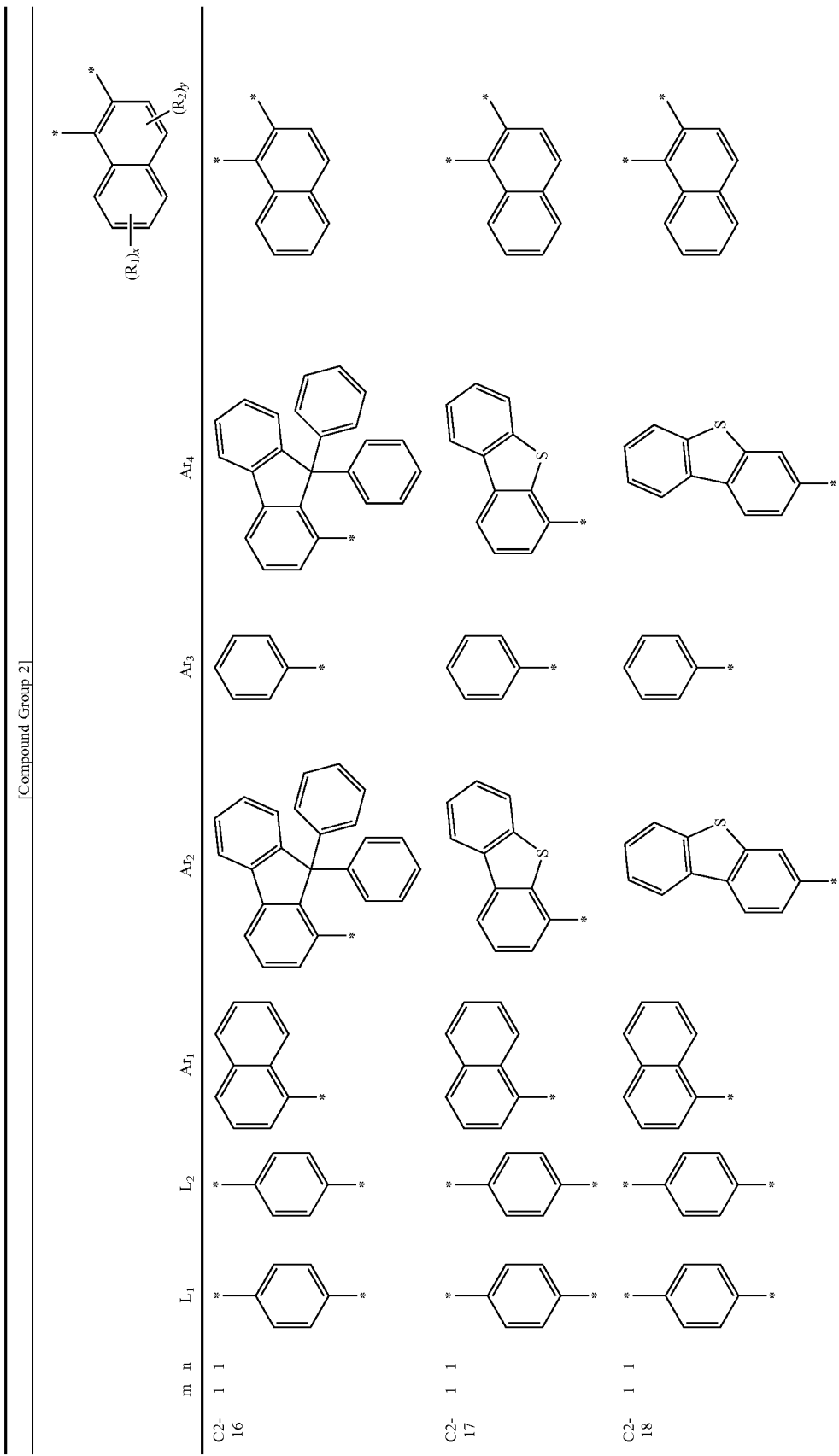

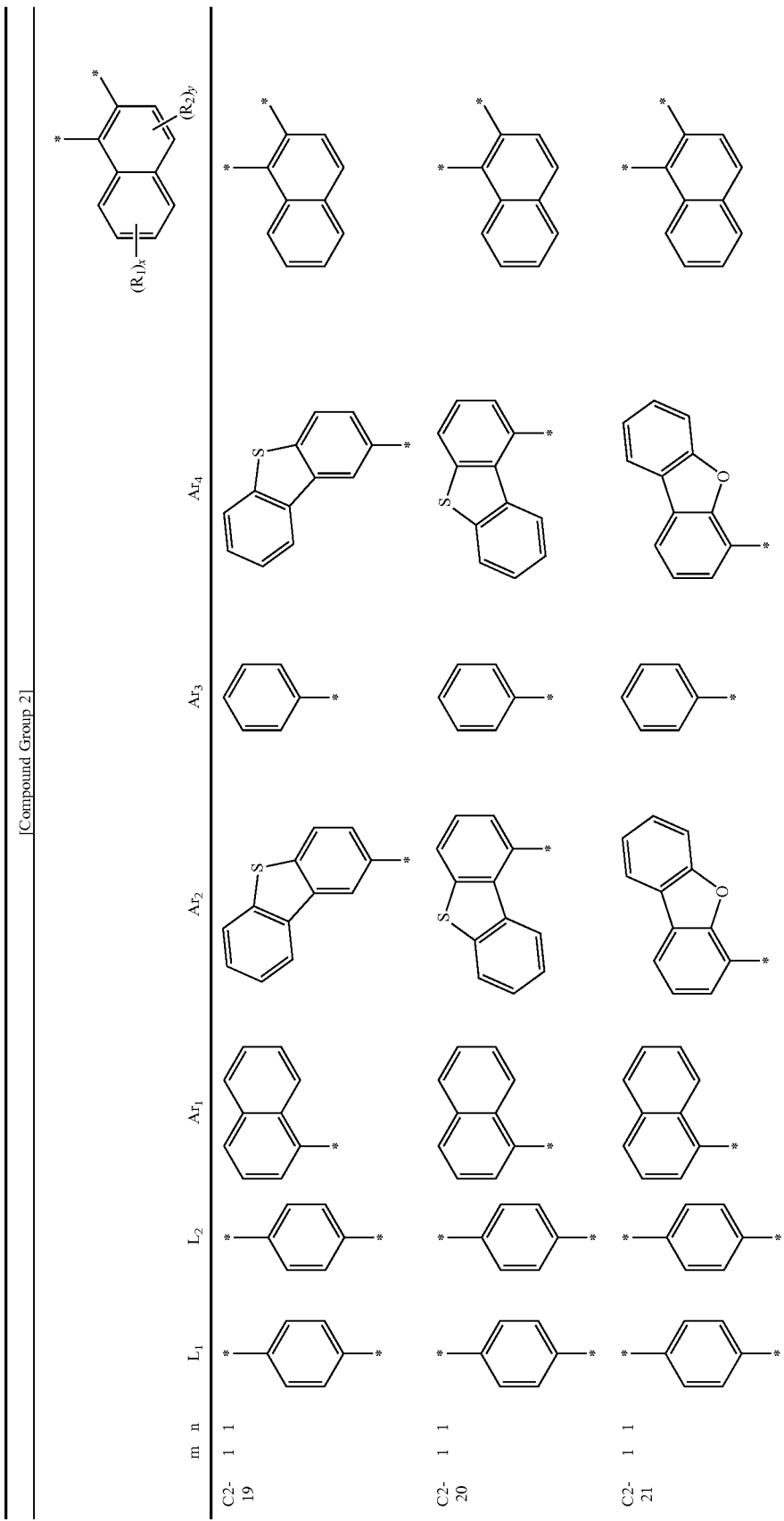

-continued
[Compound Group 2]
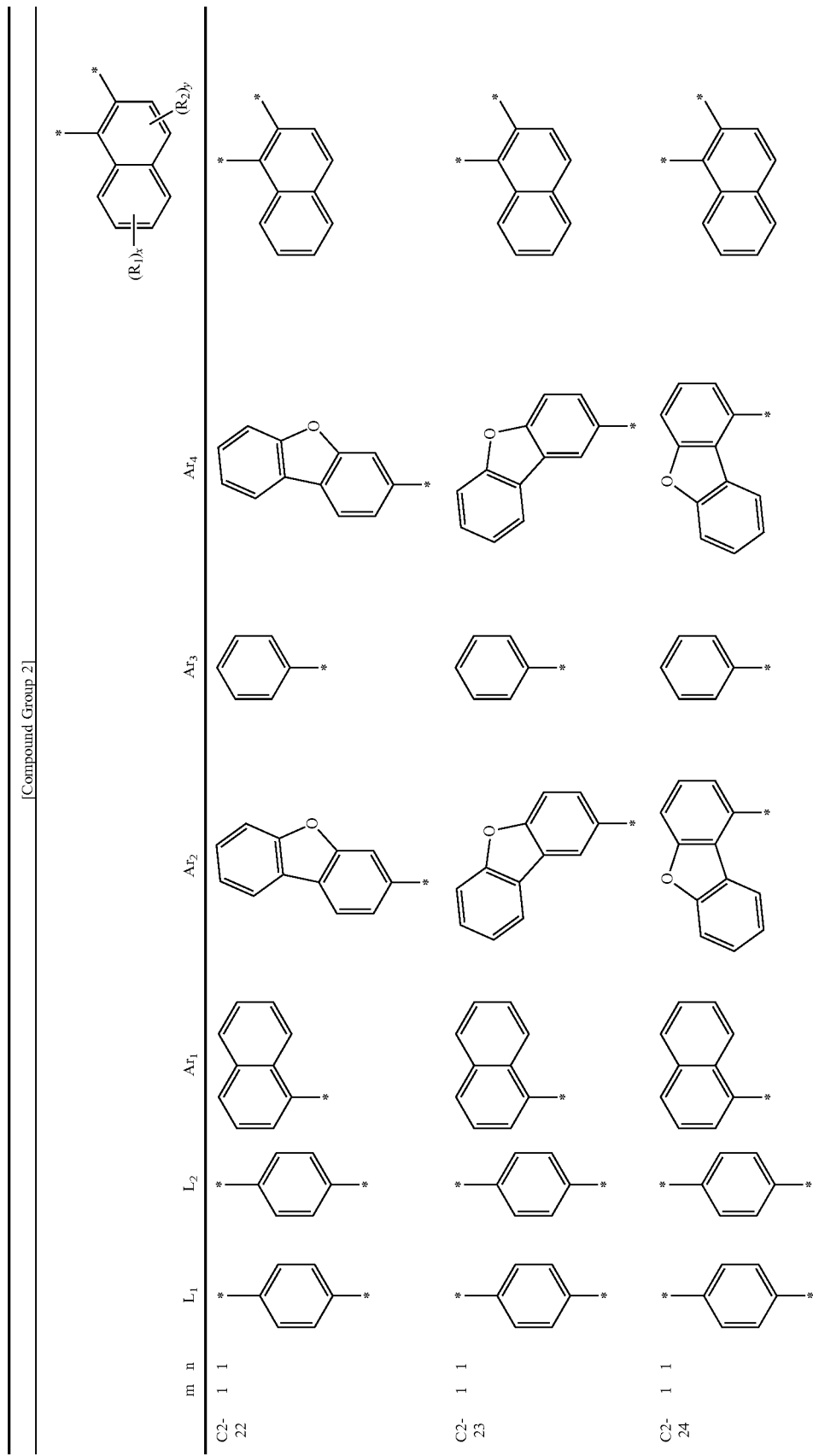

-continued
[Compound Group 2]
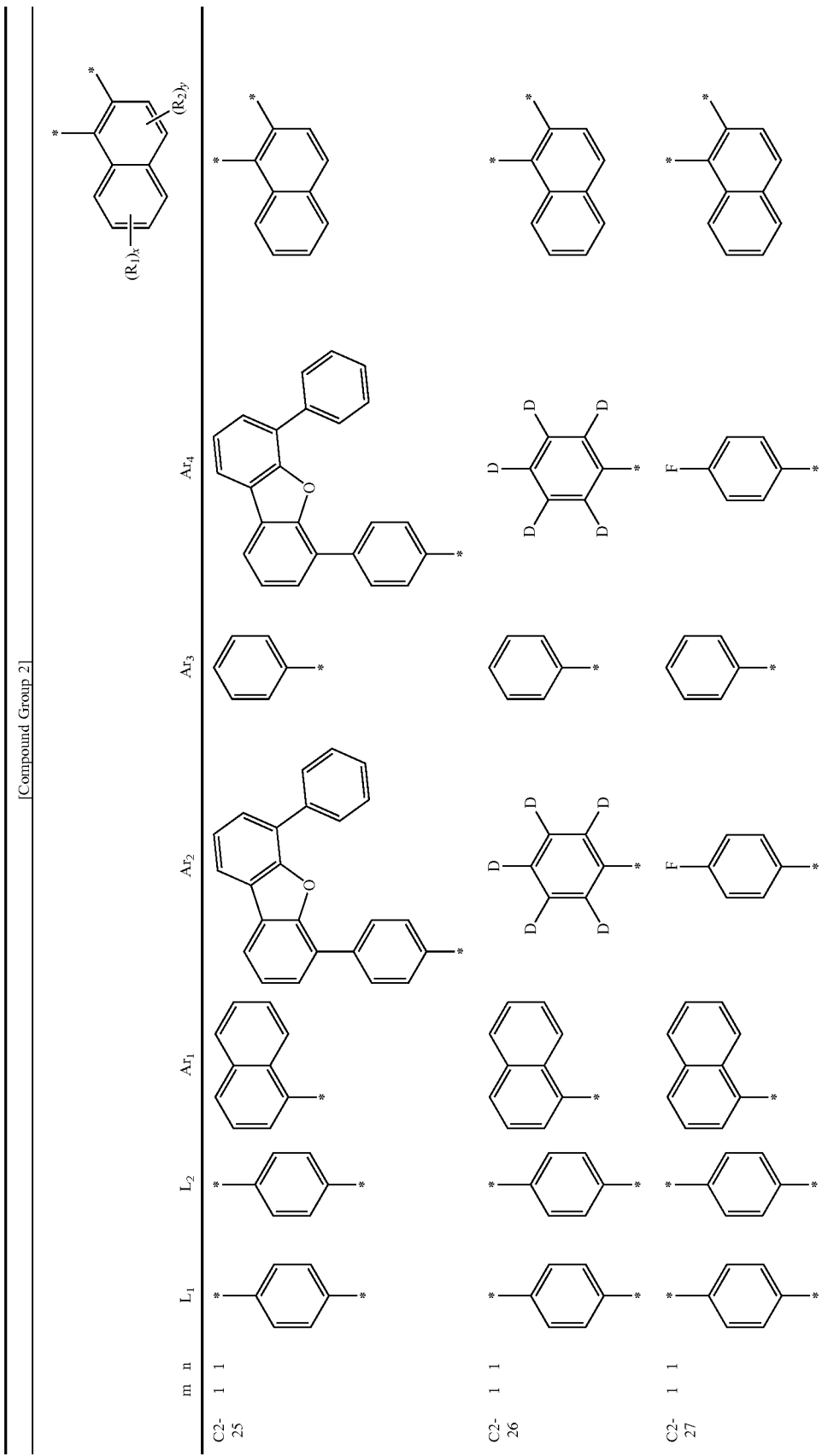

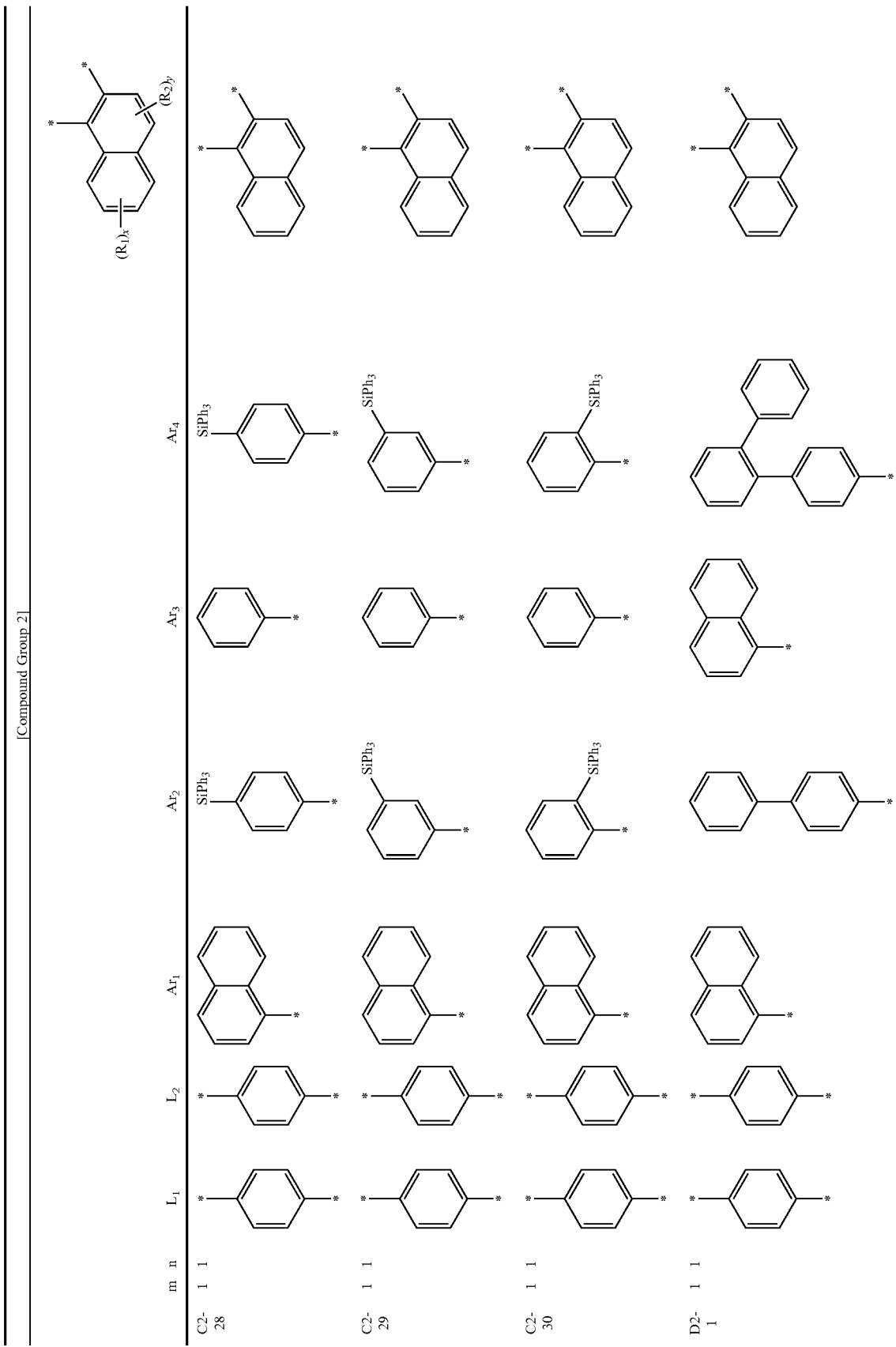

-continued
[Compound Group 2]
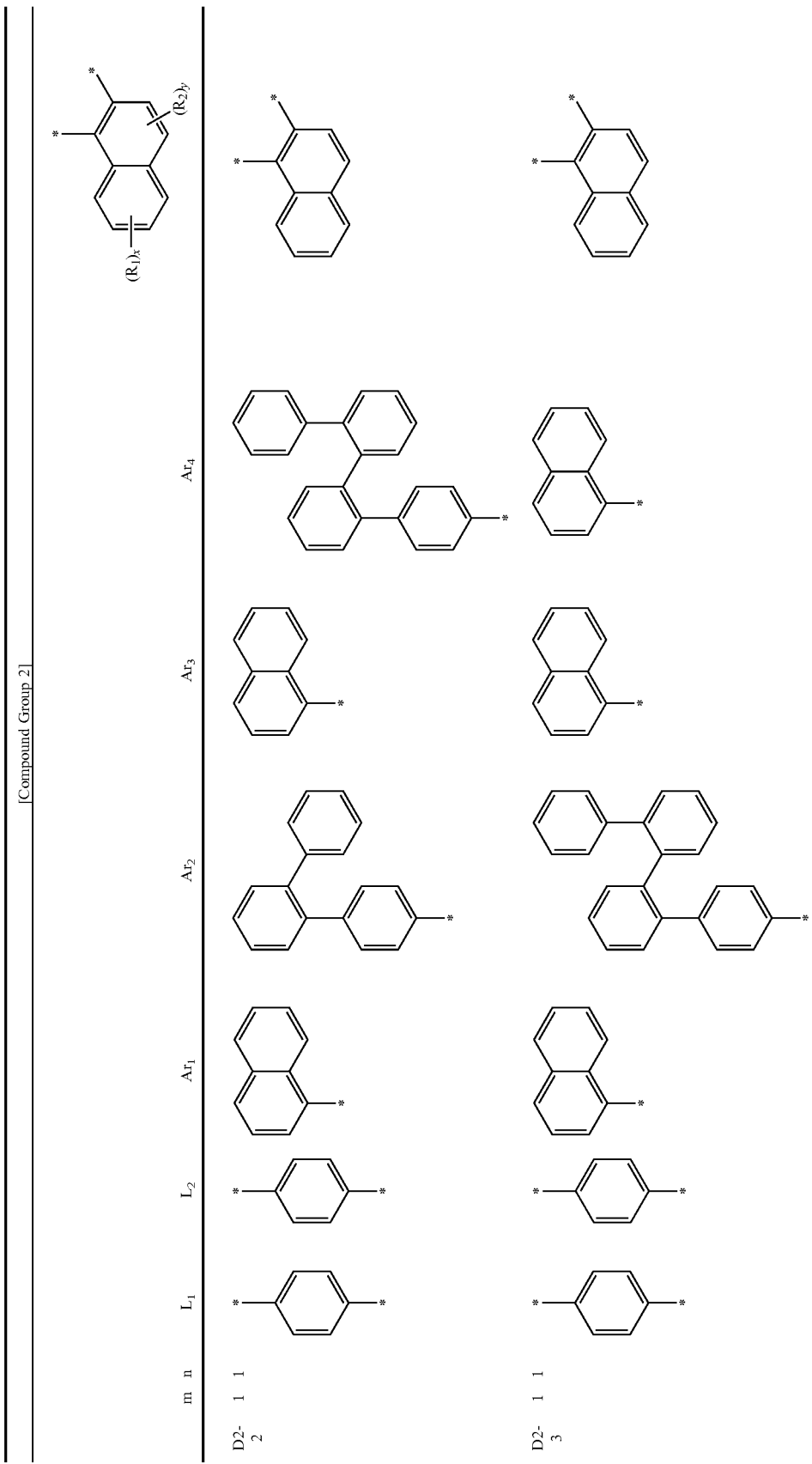

-continued
[Compound Group 2]
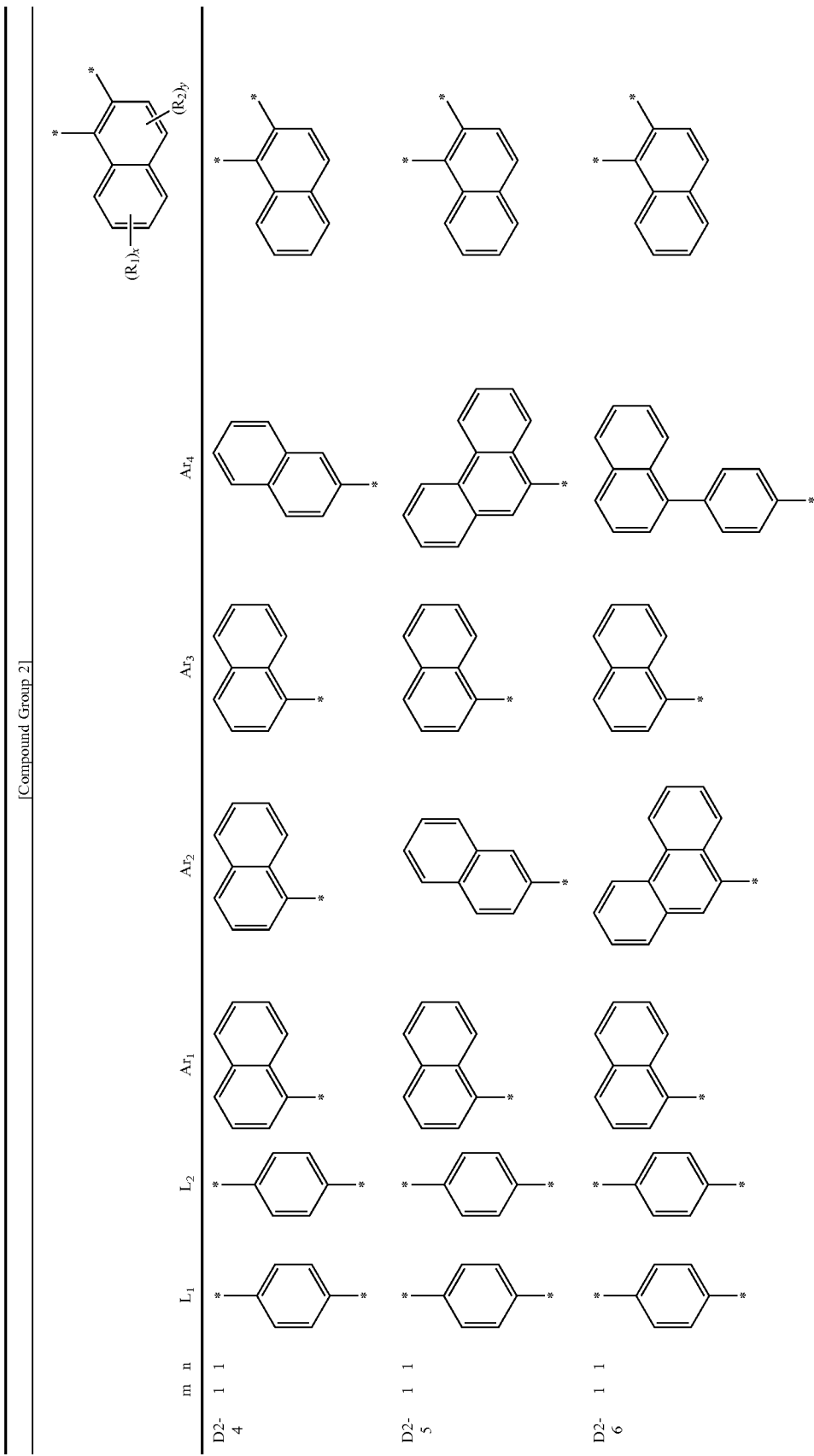

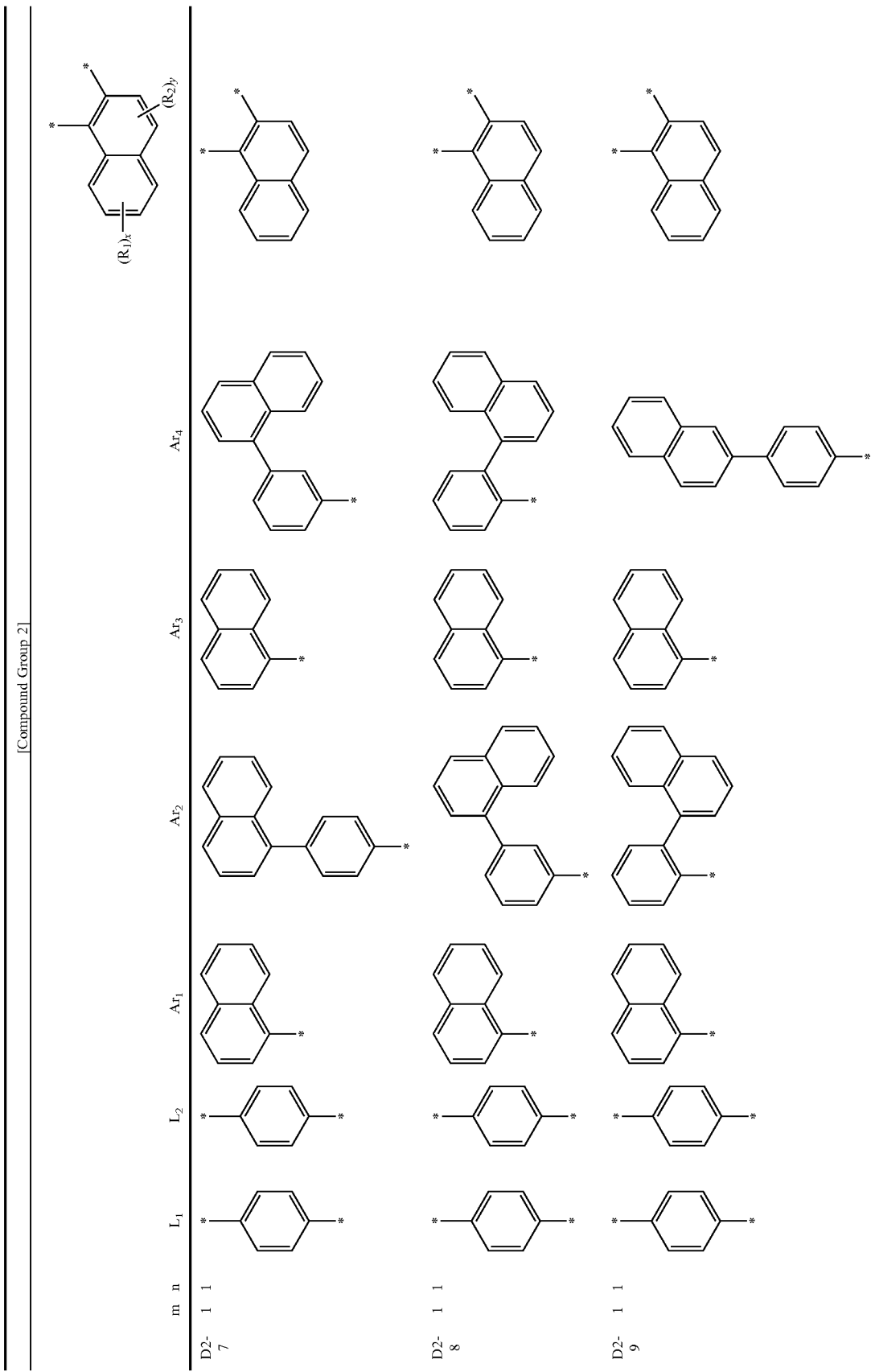

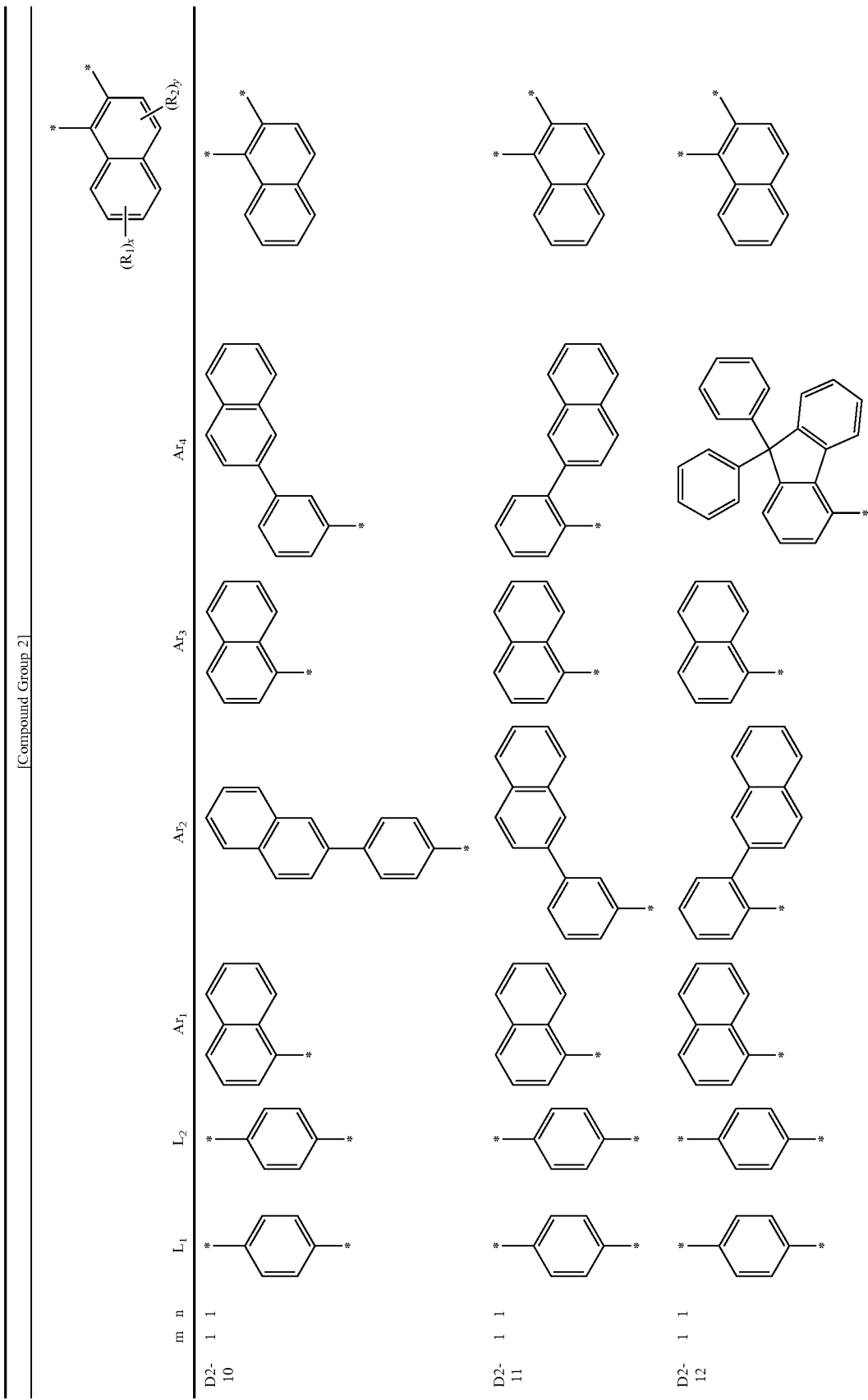

-continued
[Compound Group 2]
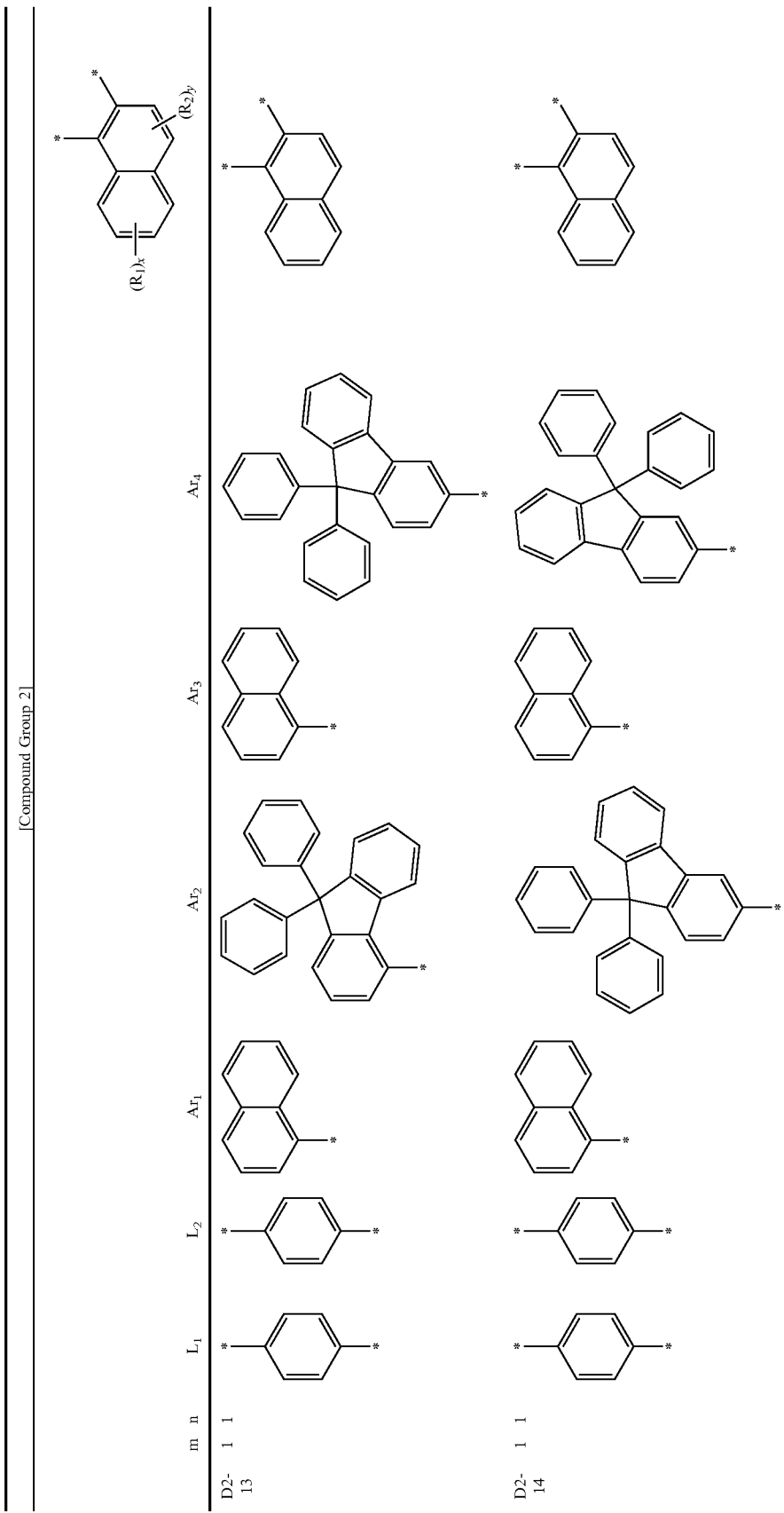

-continued
[Compound Group 2]
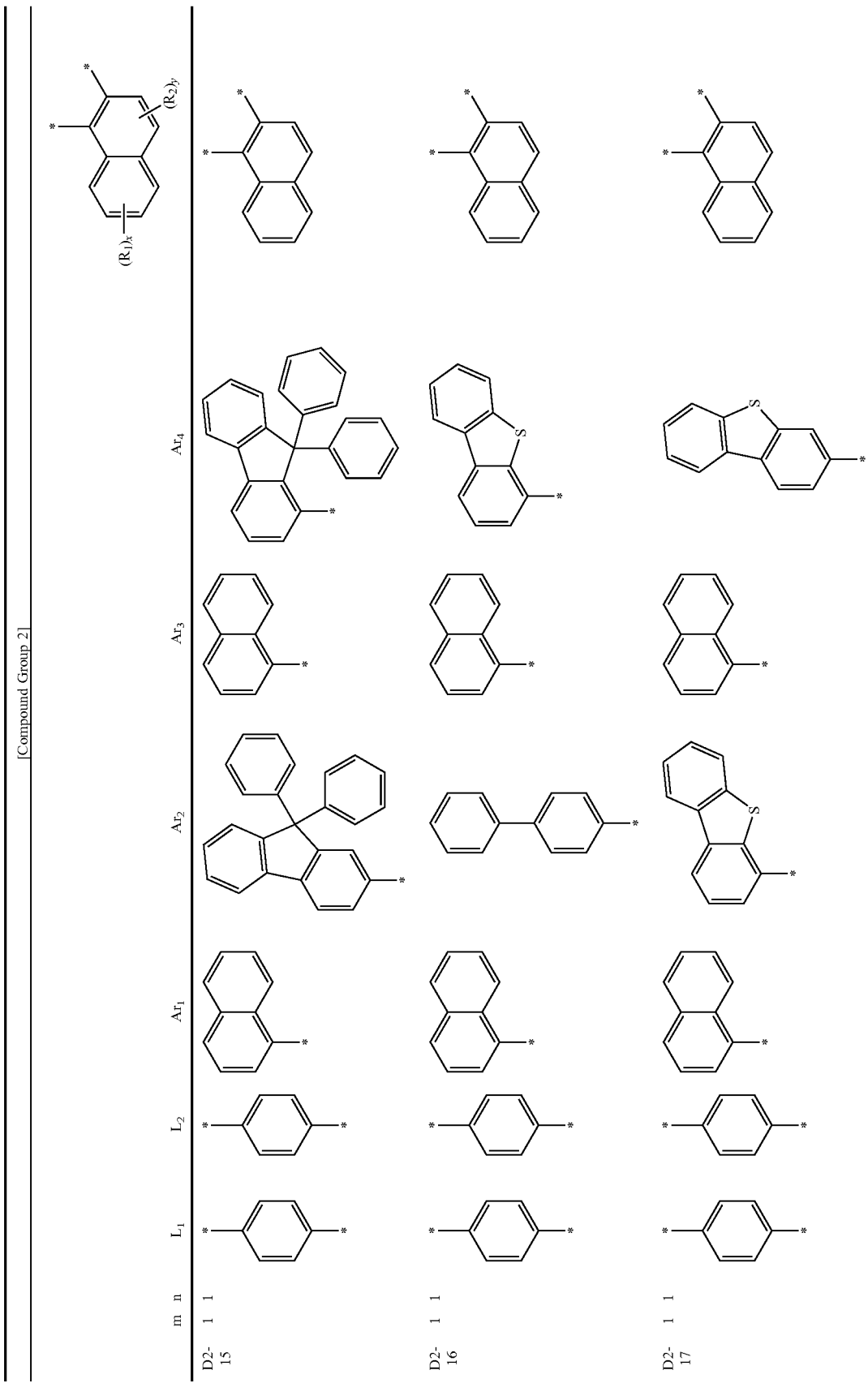

-continued
[Compound Group 2]
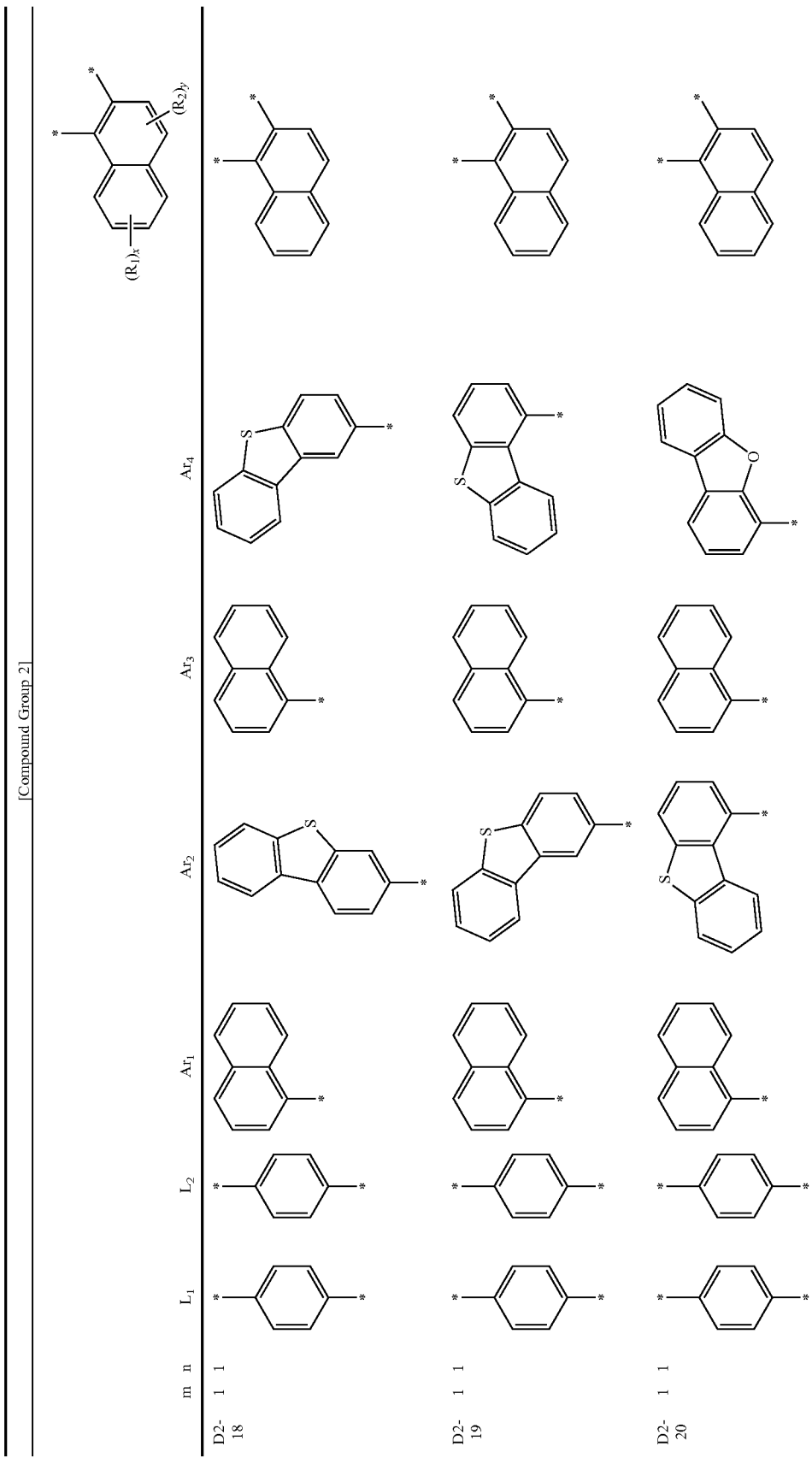

-continued
[Compound Group 2]
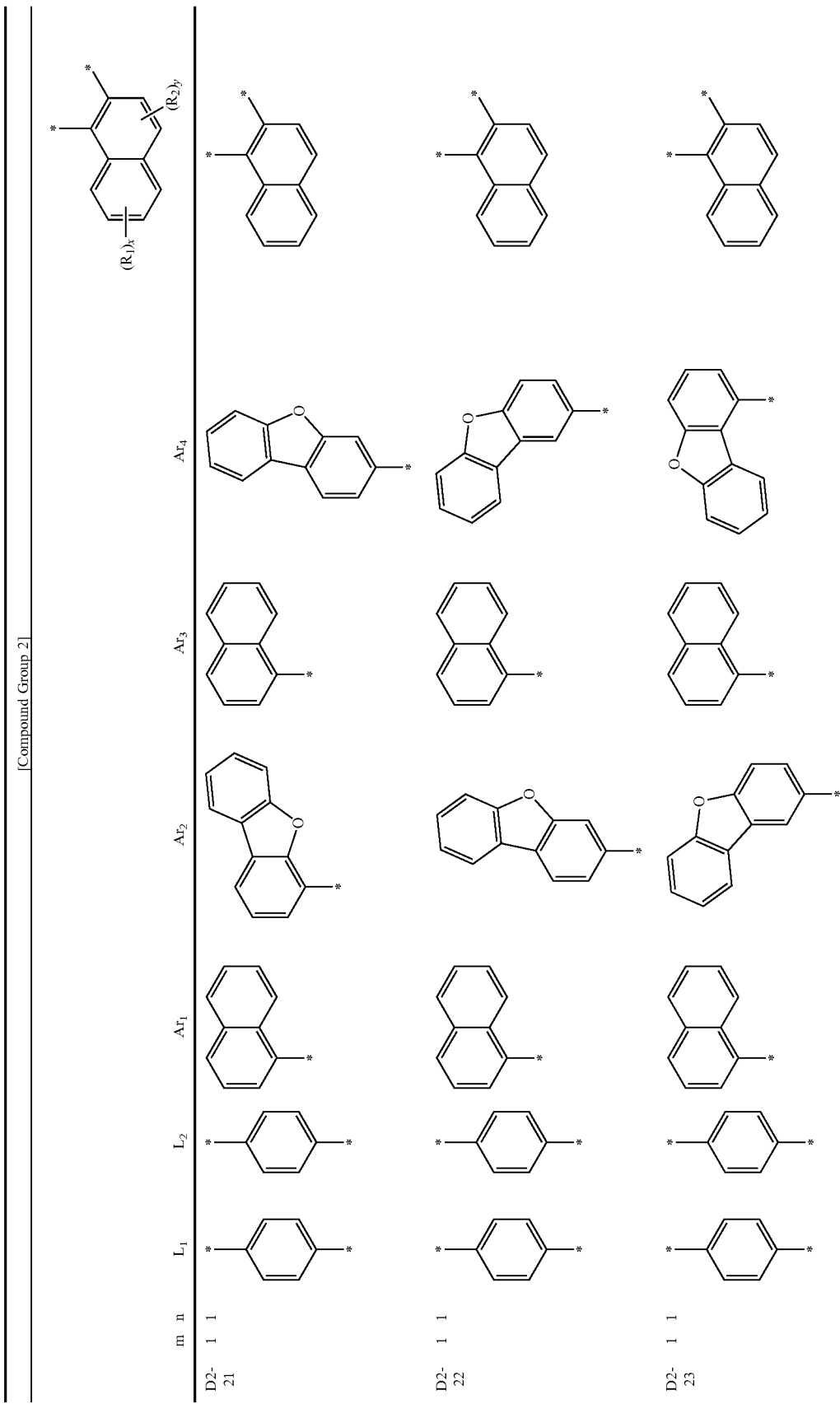

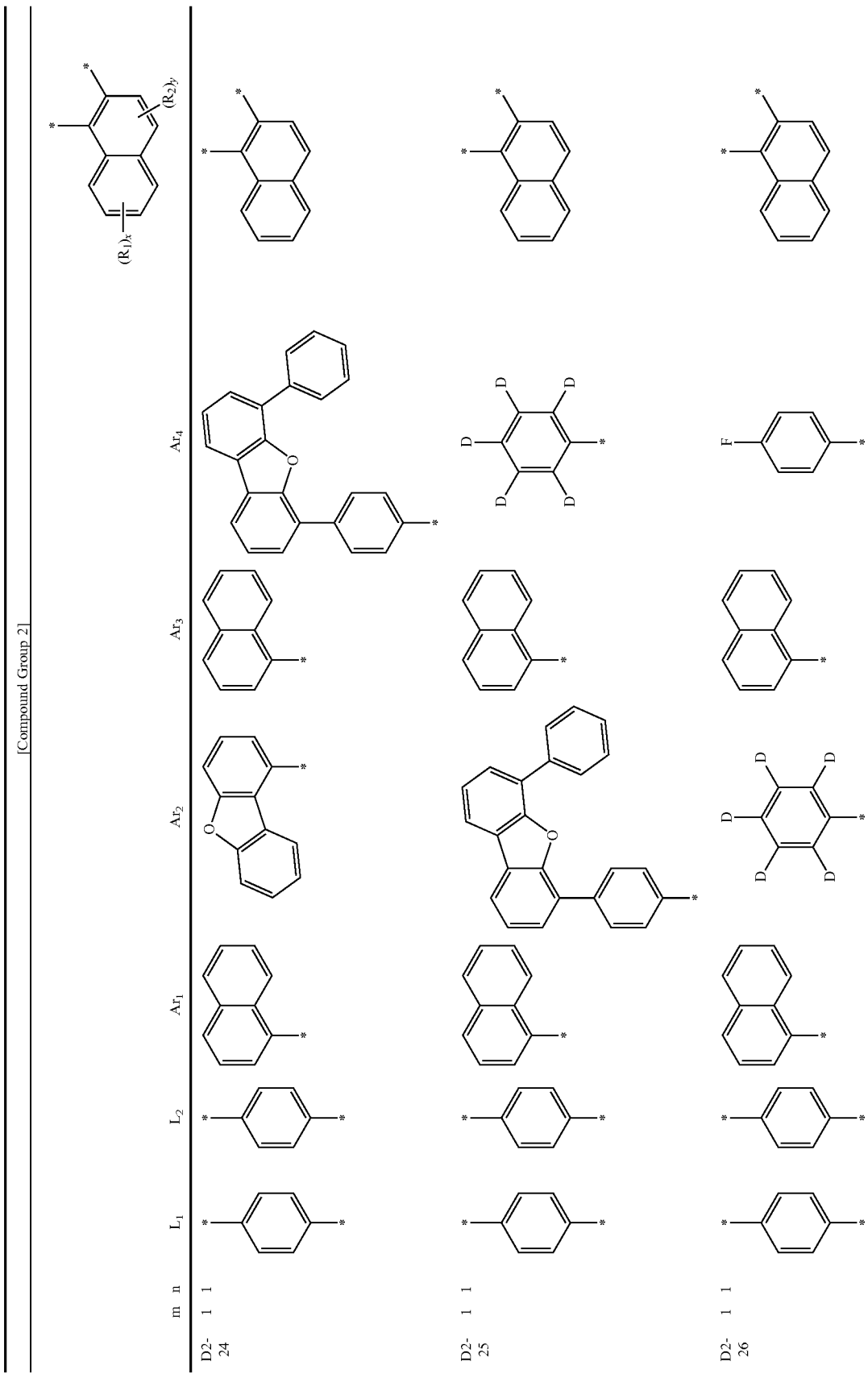

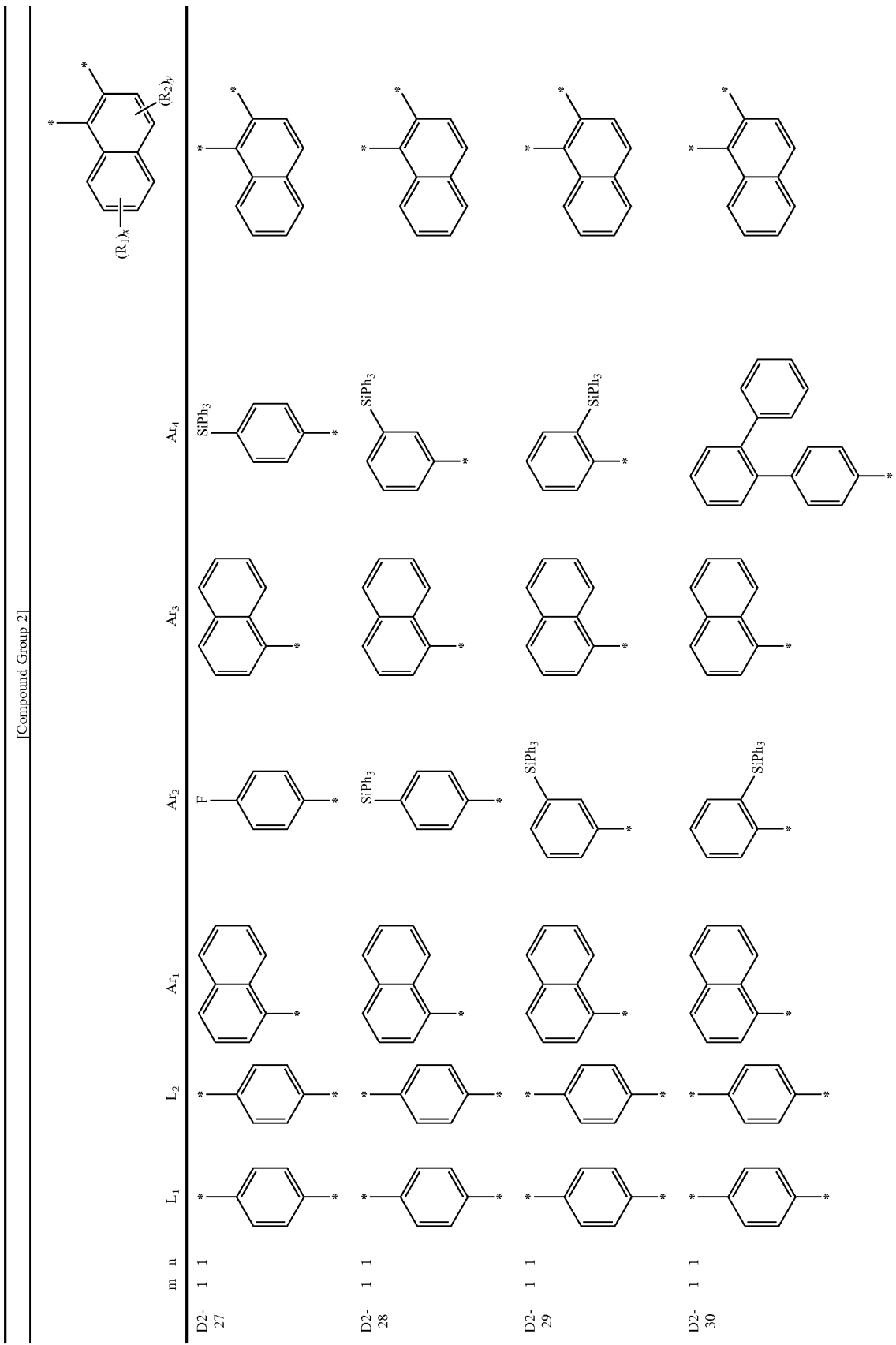

-continued
[Compound Group 2]
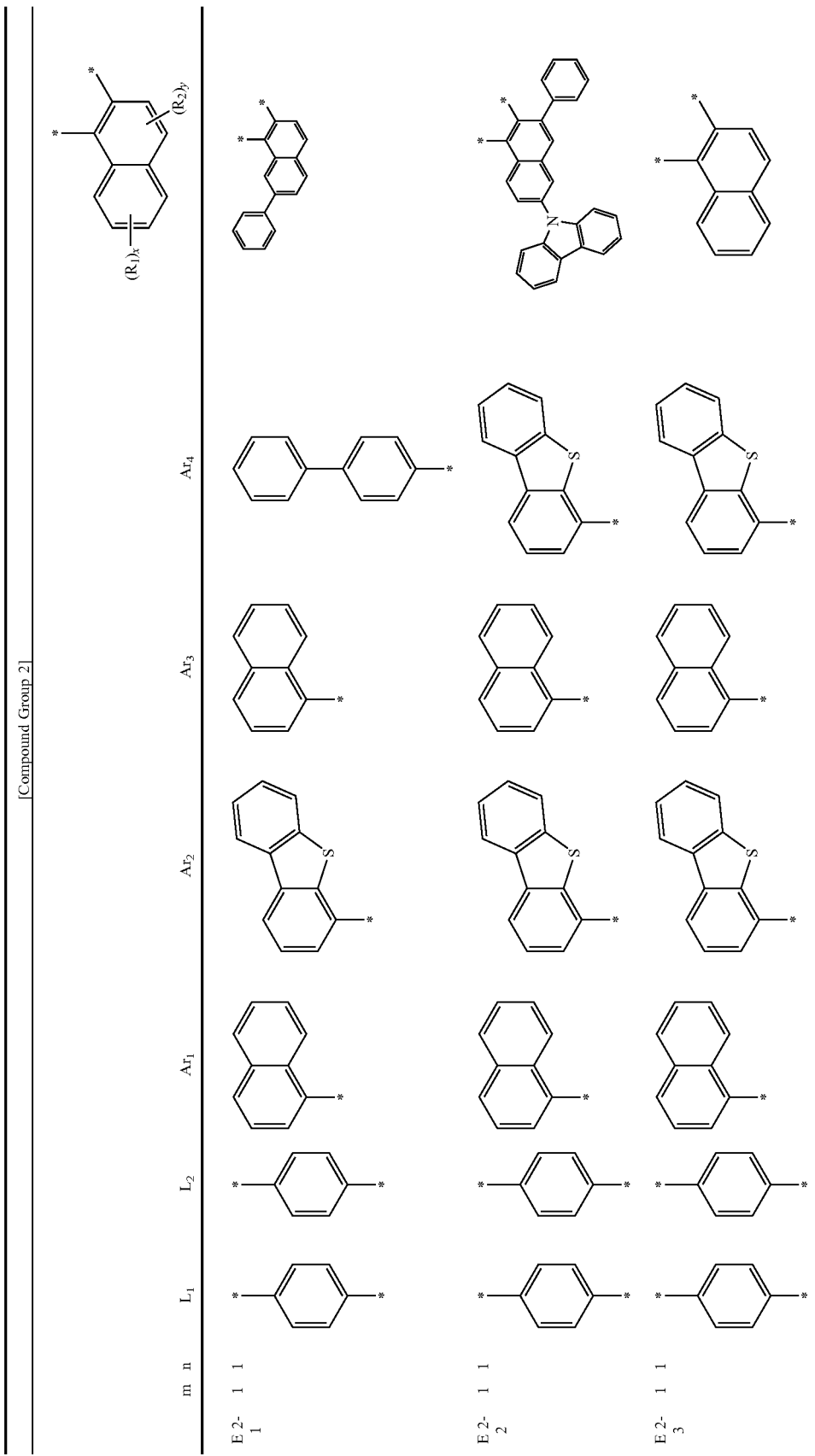

[Compound Group 3]
| | m | n | L₁ | L₂ | Ar₁ | Ar₂ | Ar₃ | Ar₄ | 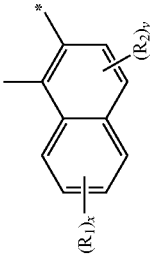 |
|---|---|---|---|---|---|---|---|---|---|
| A3-1 | 0 | 1 | — | 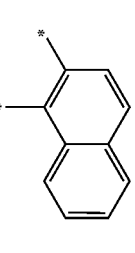 | 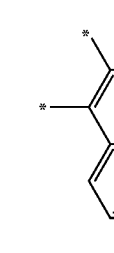 | 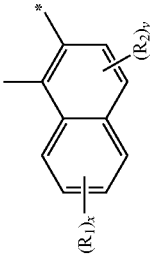 | 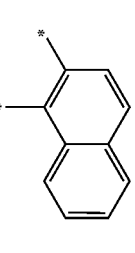 | 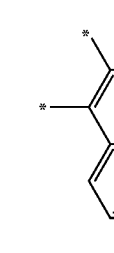 | 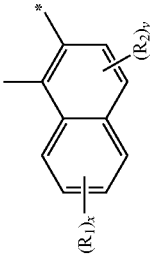 |
| A3-2 | 0 | 1 | — | 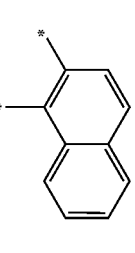 | 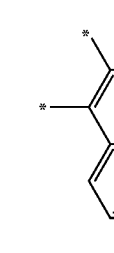 | 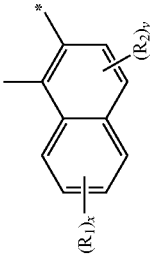 | 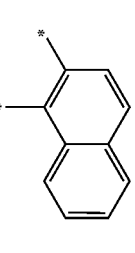 | 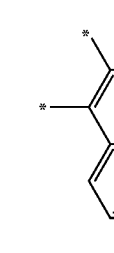 | 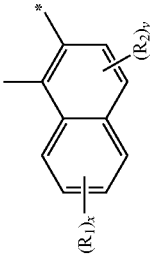 |
| A3-3 | 0 | 1 | — | 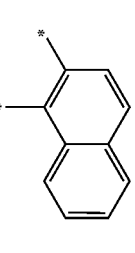 | 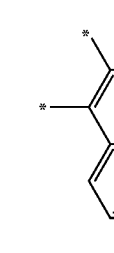 | 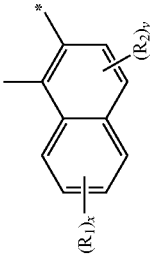 | 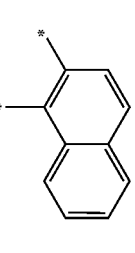 | 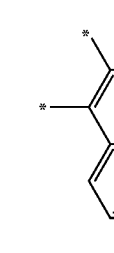 | 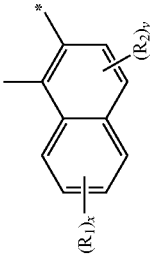 |

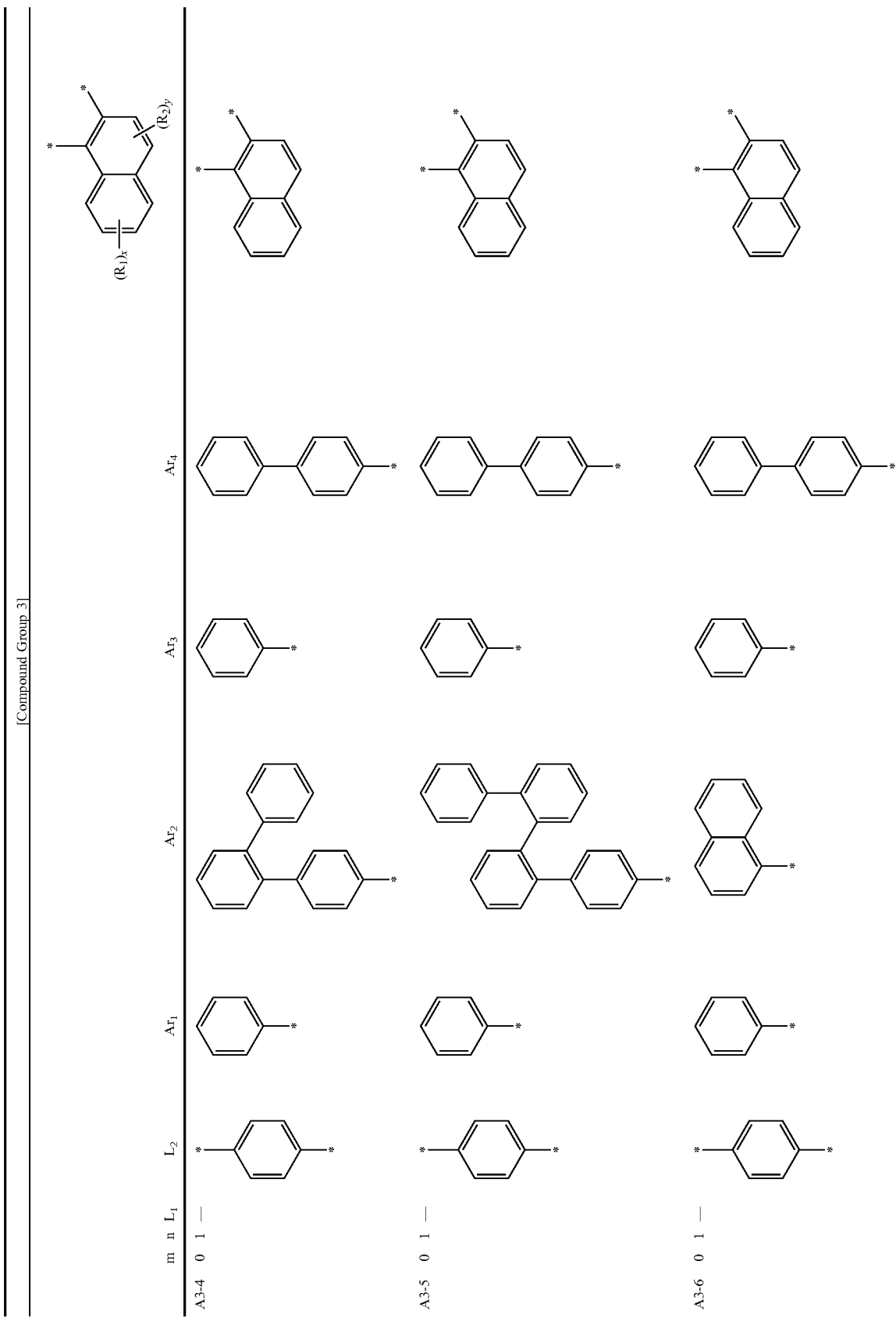

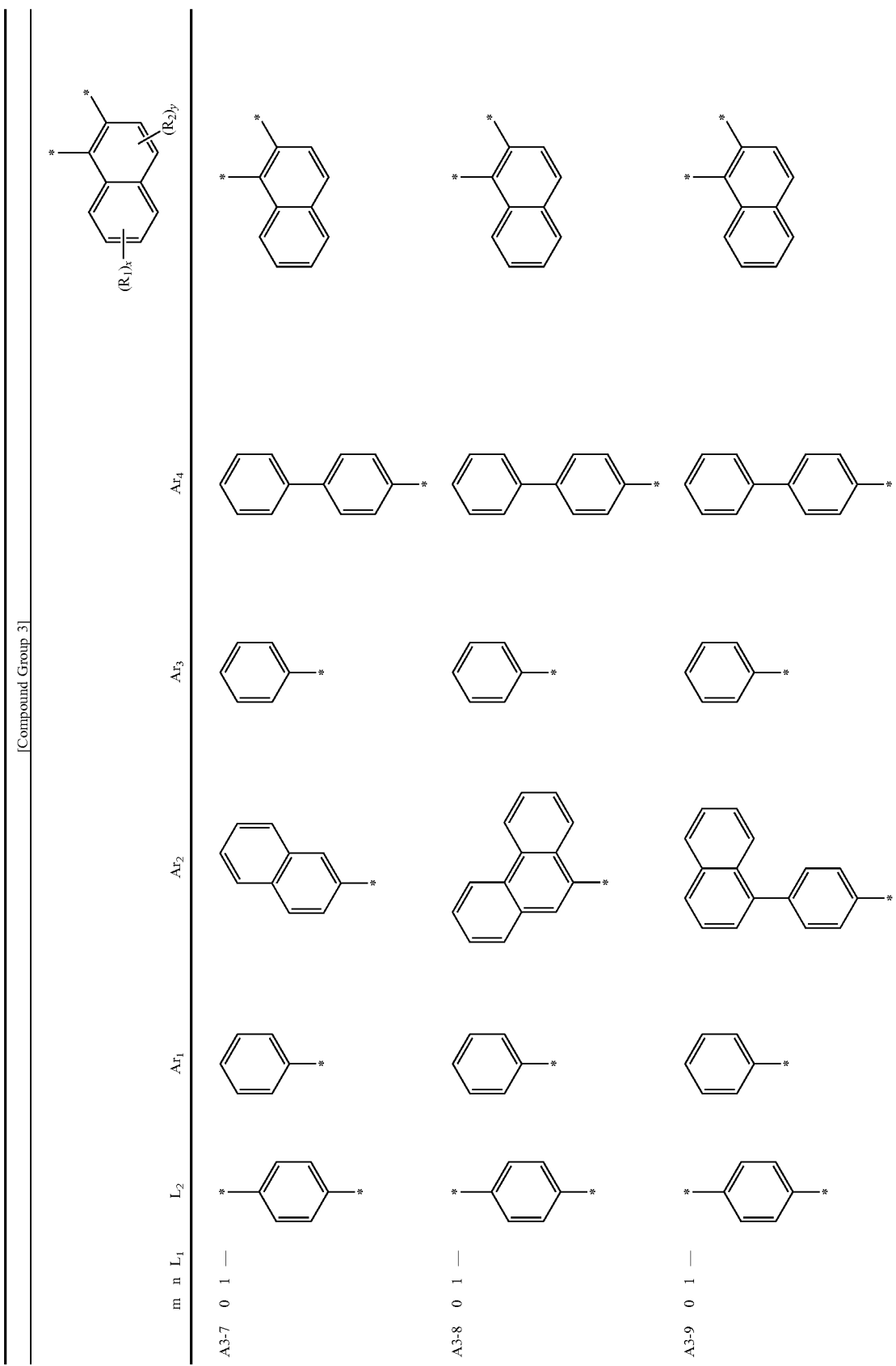

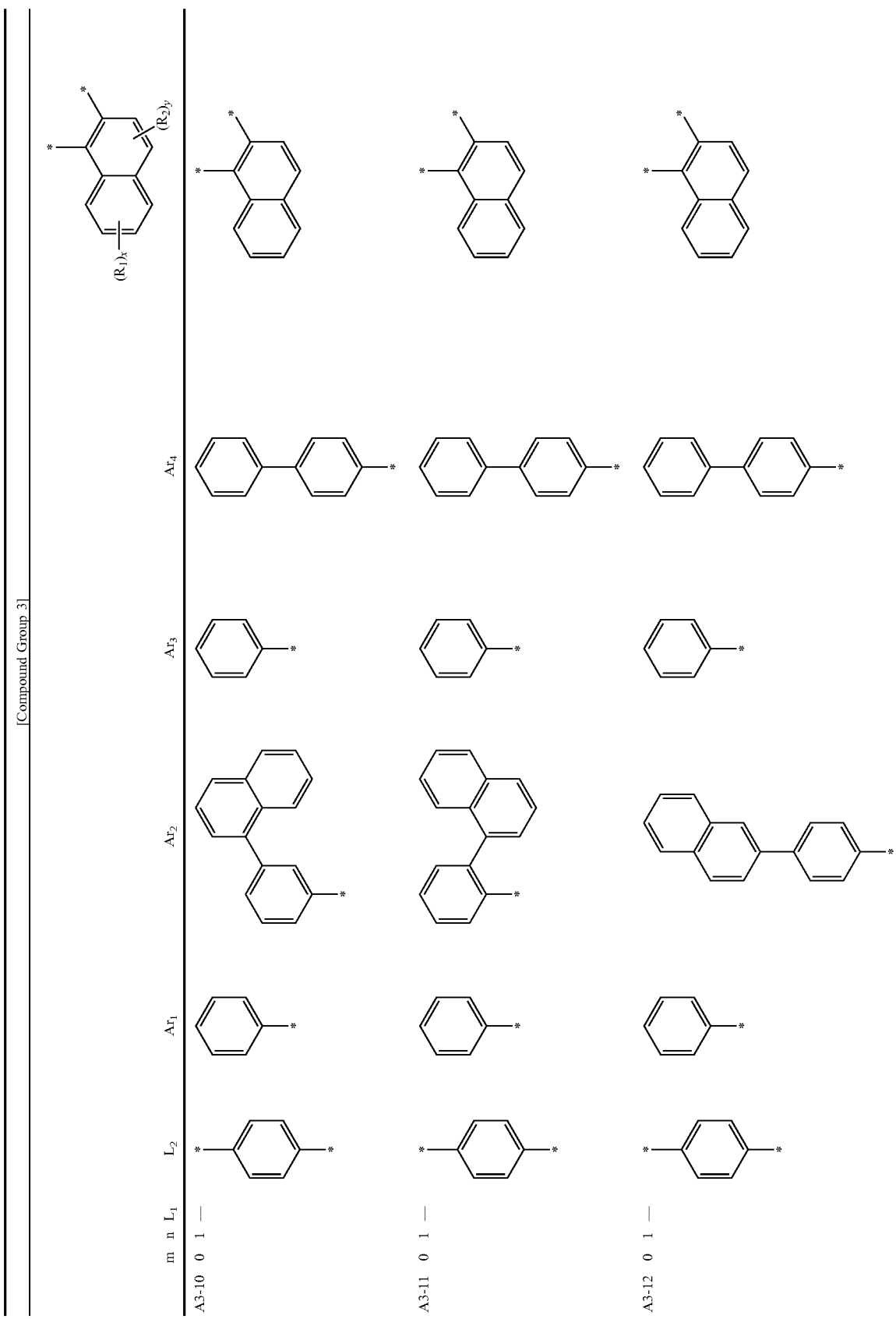

-continued

[Compound Group 3]

| | m | n | L₁ | L₂ | Ar₁ | Ar₂ | Ar₃ | Ar₄ | (R₁)x, (R₂)y naphthalene |
|---|---|---|---|---|---|---|---|---|---|
| A3-13 | 0 | 1 | — | *–⟨phenyl⟩–* | phenyl* | 3-(naphthalen-2-yl)phenyl* | phenyl* | biphenyl* | 1,2-naphthyl |
| A3-14 | 0 | 1 | — | *–⟨phenyl⟩–* | phenyl* | 2-(naphthalen-2-yl)phenyl* | phenyl* | biphenyl* | 1,2-naphthyl |
| A3-15 | 0 | 1 | — | *–⟨phenyl⟩–* | phenyl* | 9,9-diphenylfluoren-4-yl* | phenyl* | biphenyl* | 1,2-naphthyl |

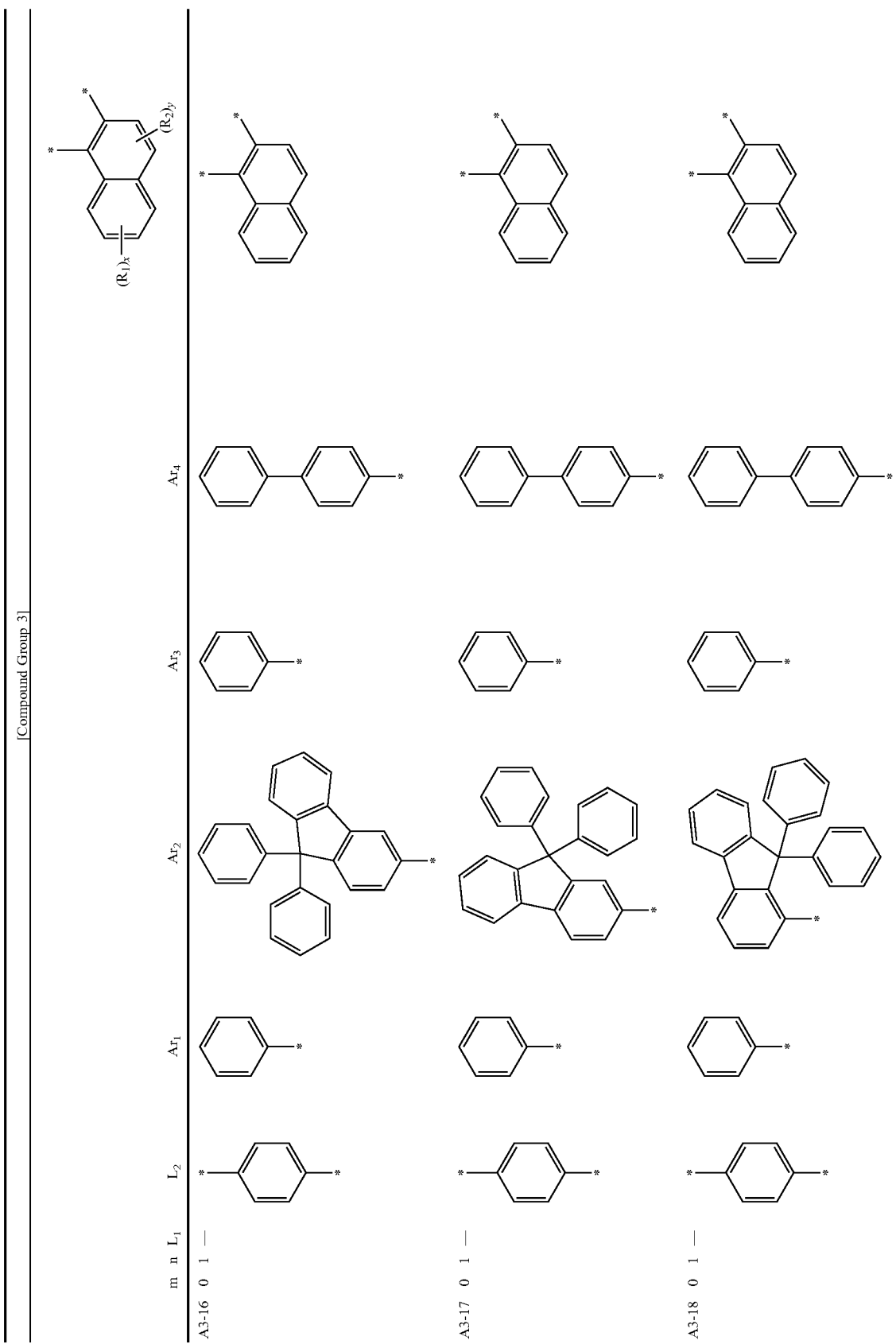

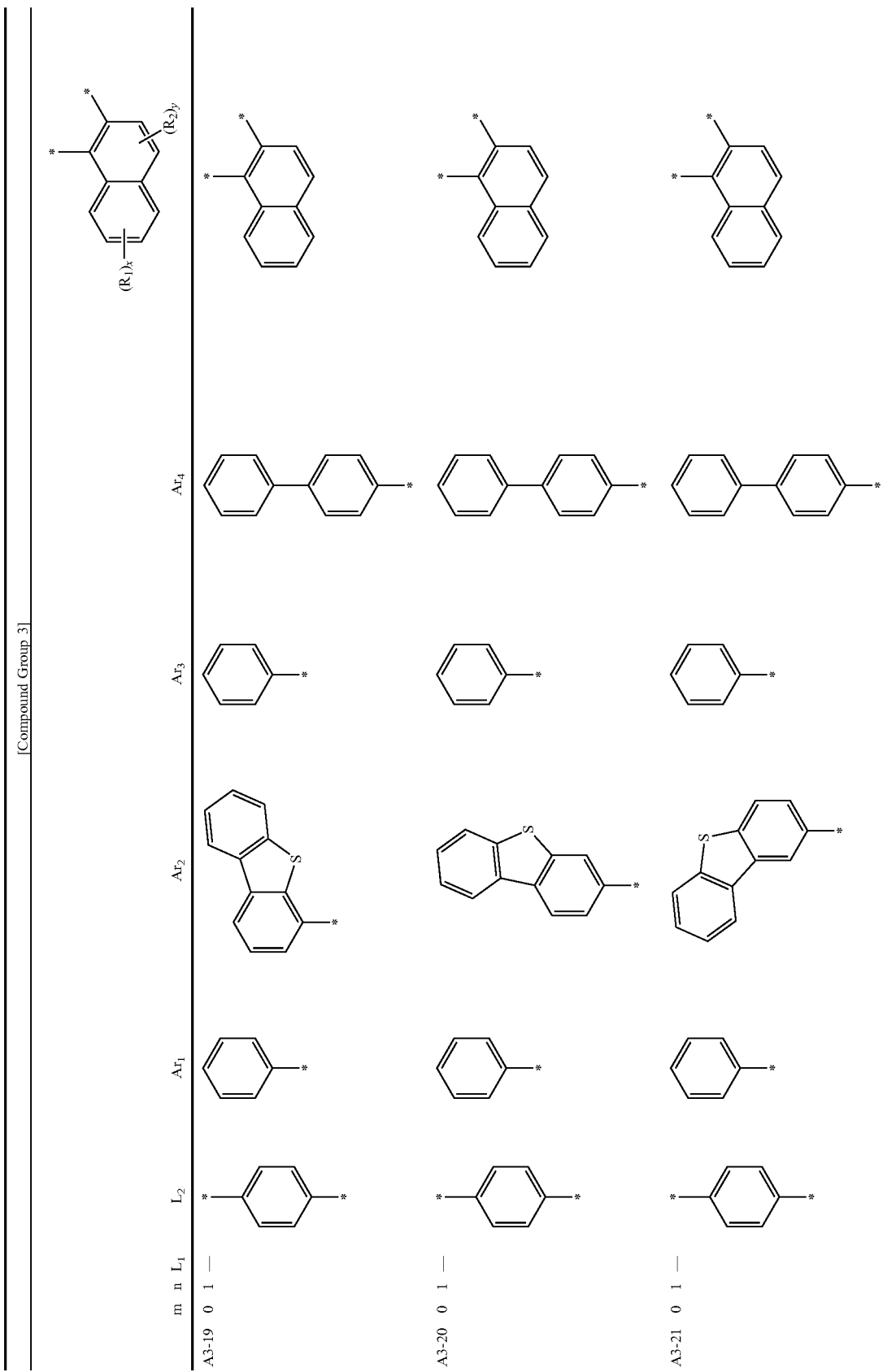

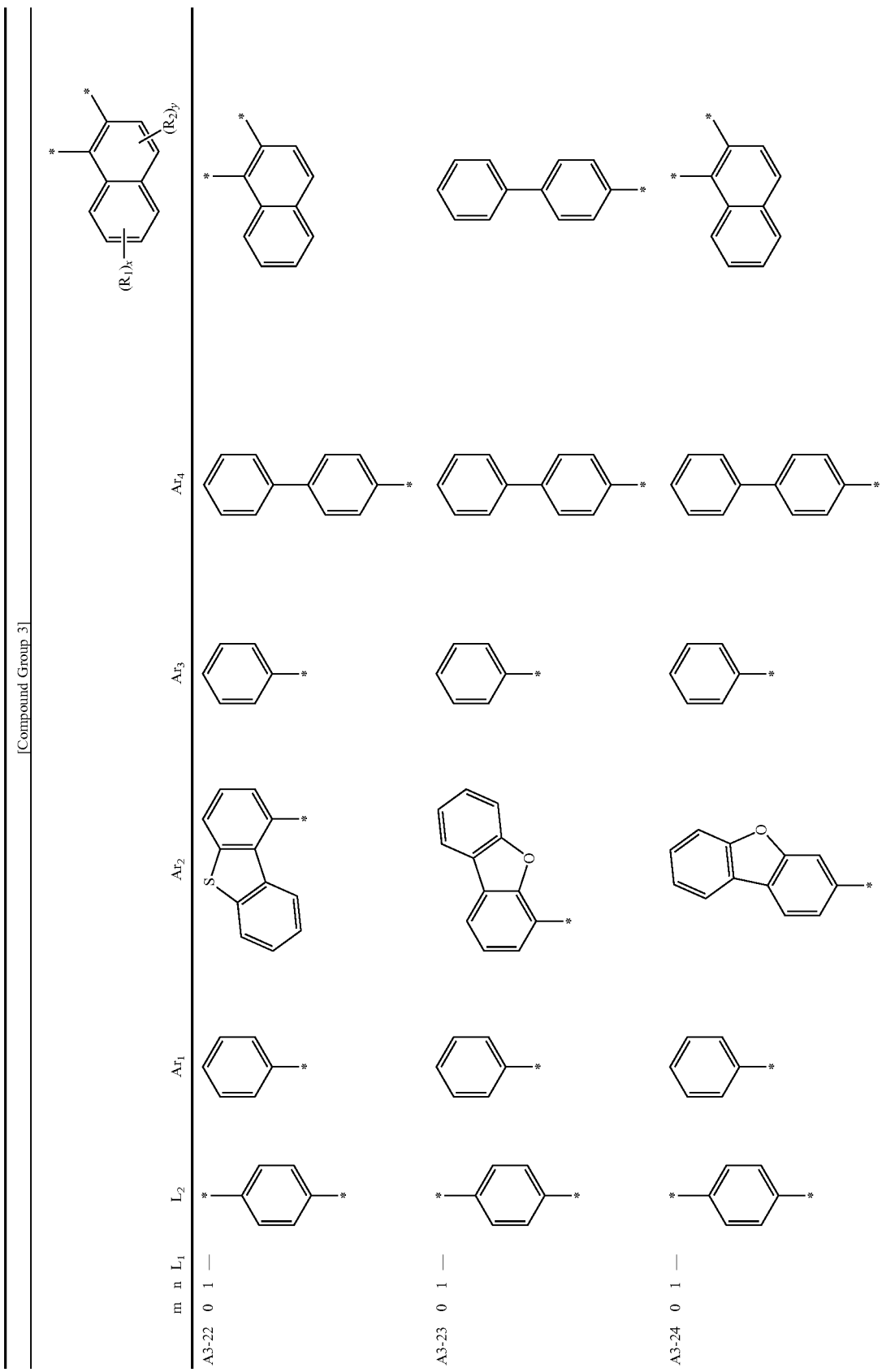

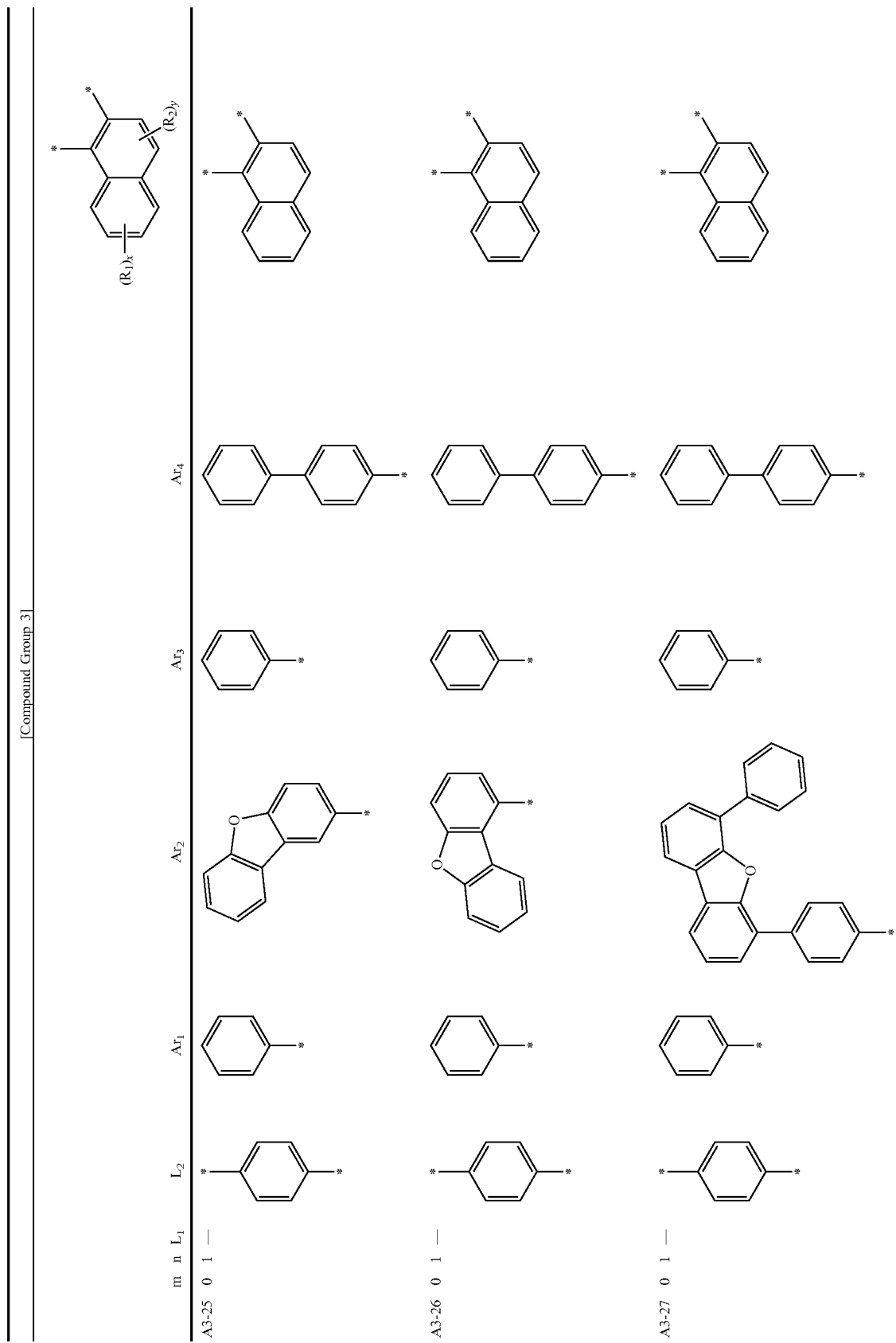

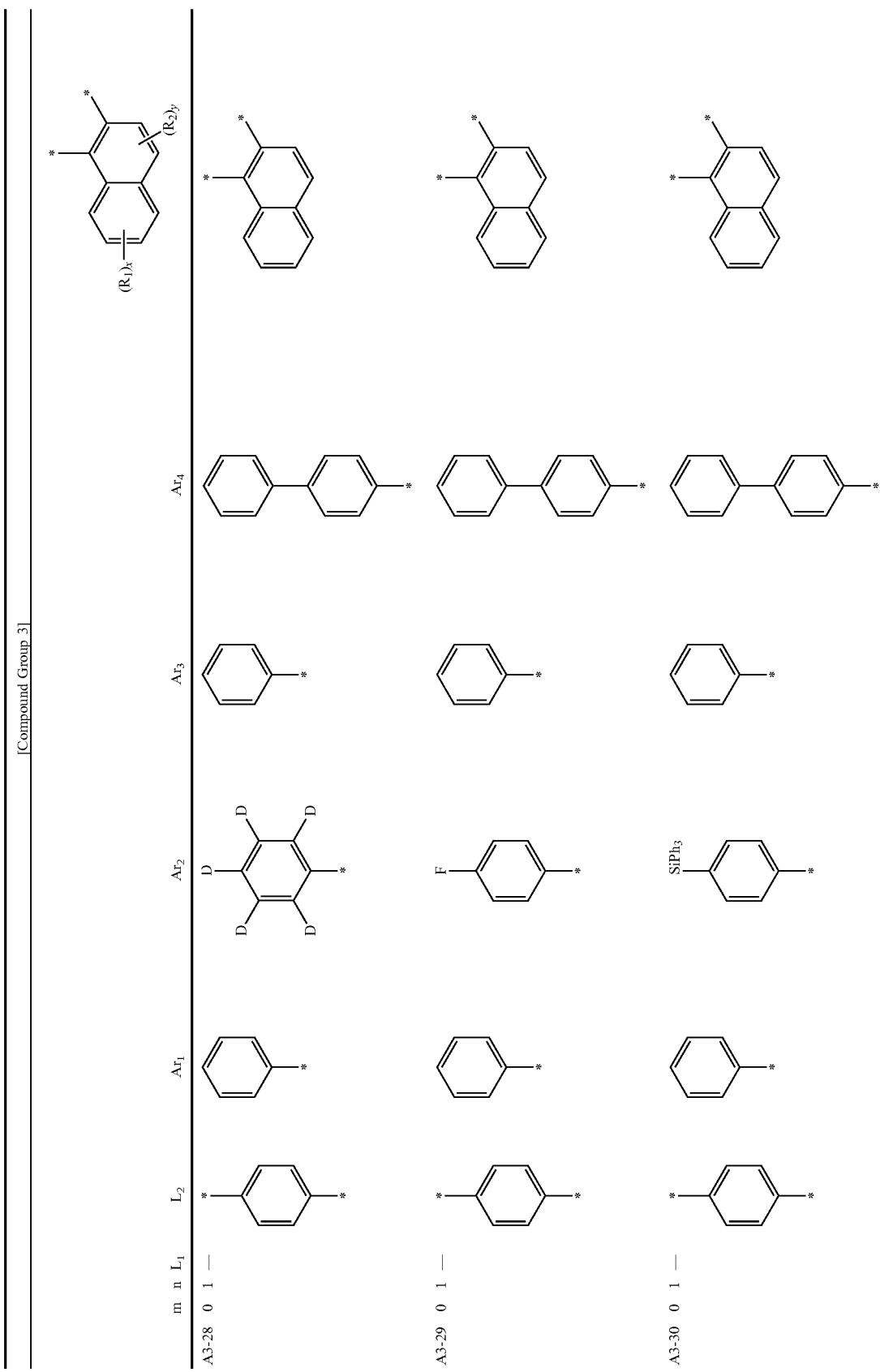

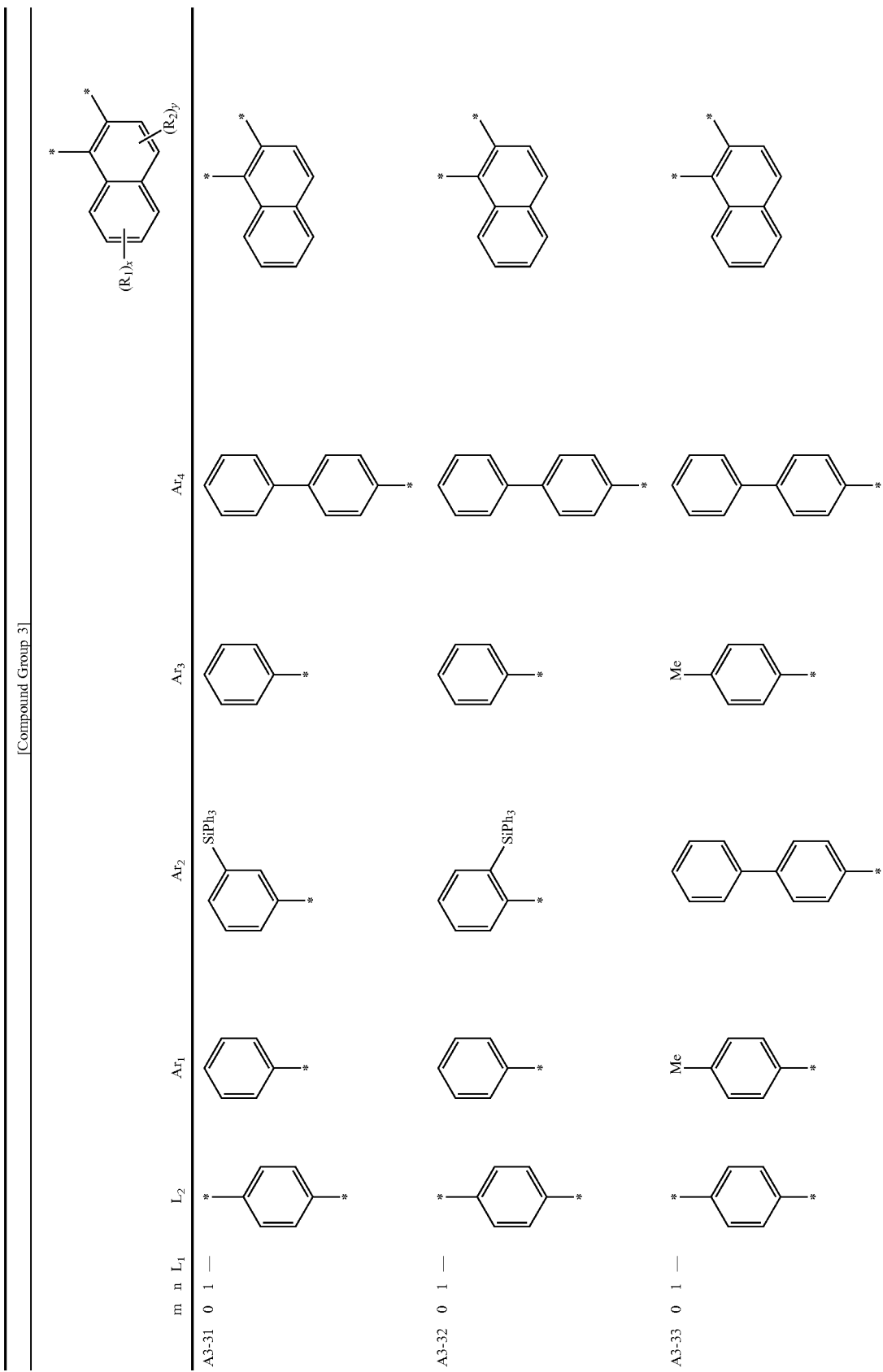

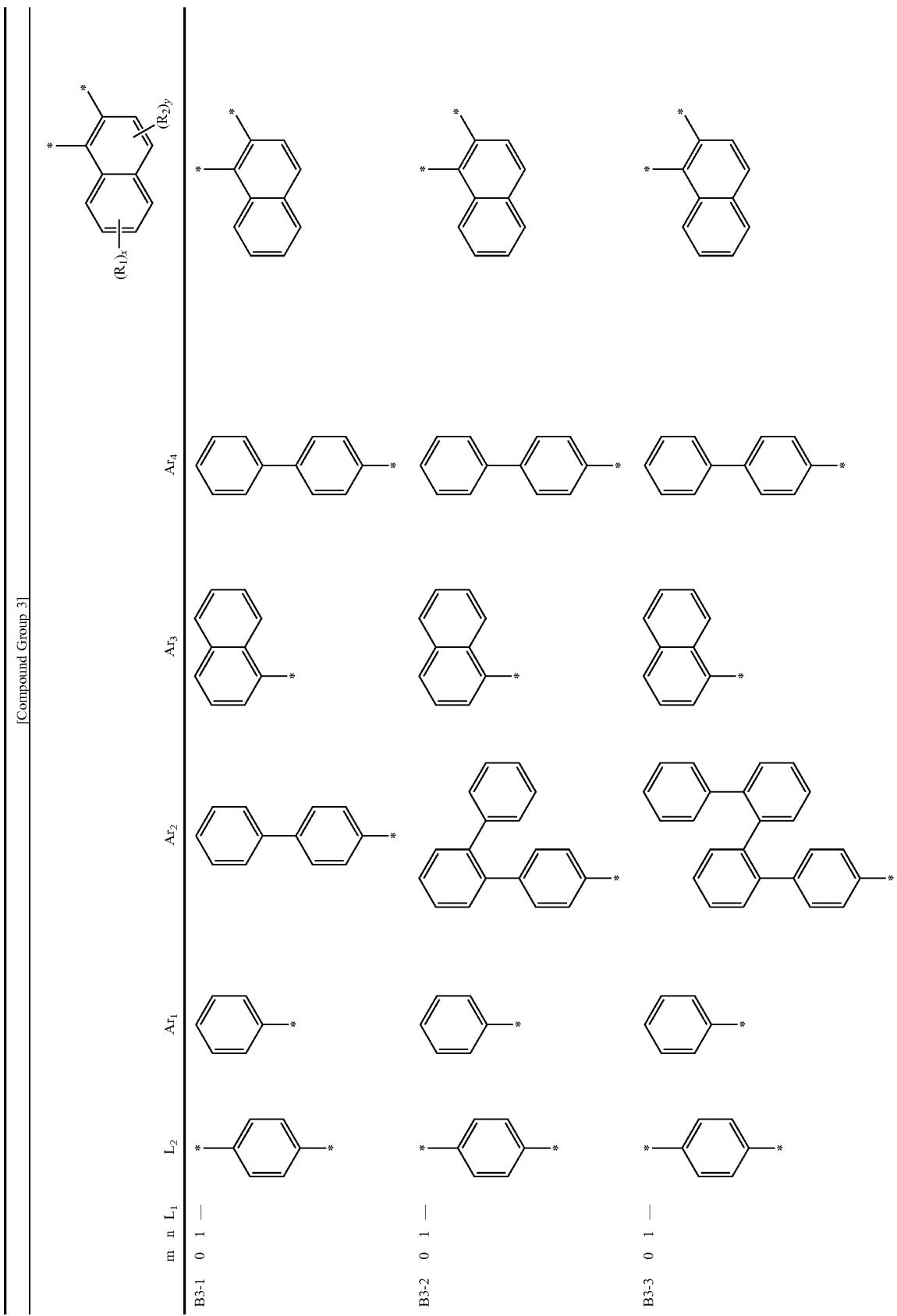

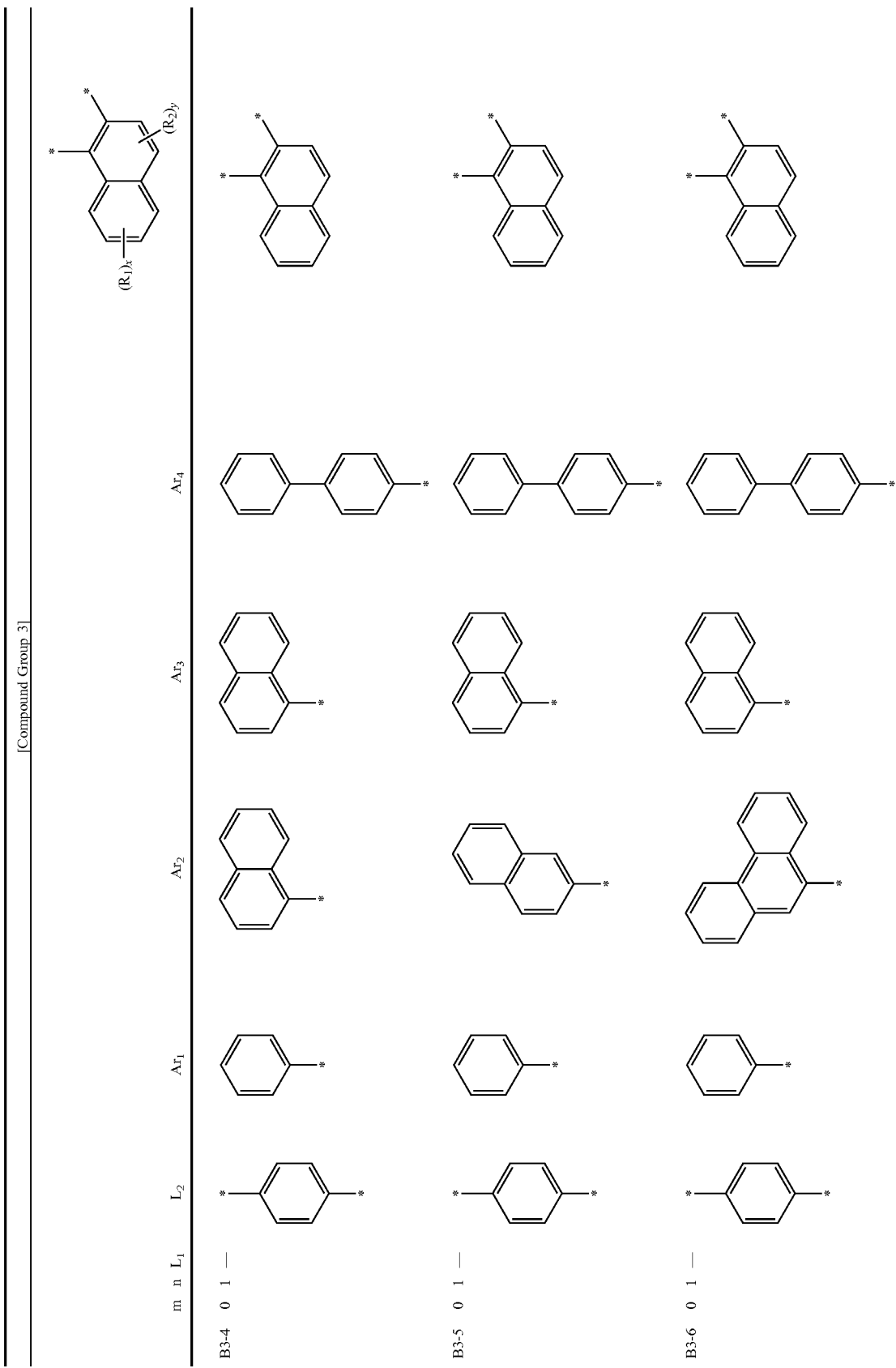

-continued
[Compound Group 3]
| | m | n | L₁ | L₂ | Ar₁ | Ar₂ | Ar₃ | Ar₄ | |
|---|---|---|---|---|---|---|---|---|---|
| B3-7 | 0 | 1 | — | 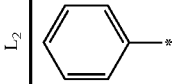 |  |  | 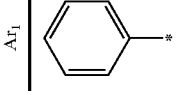 |  |  |
| B3-8 | 0 | 1 | — | 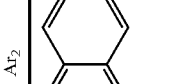 |  |  | 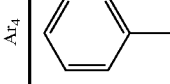 | 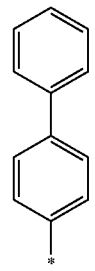 [SMILES: *c1ccc(-c2ccccc2)cc1] |  |
| B3-9 | 0 | 1 | — | 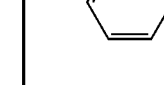 |  |  |  |  |  |

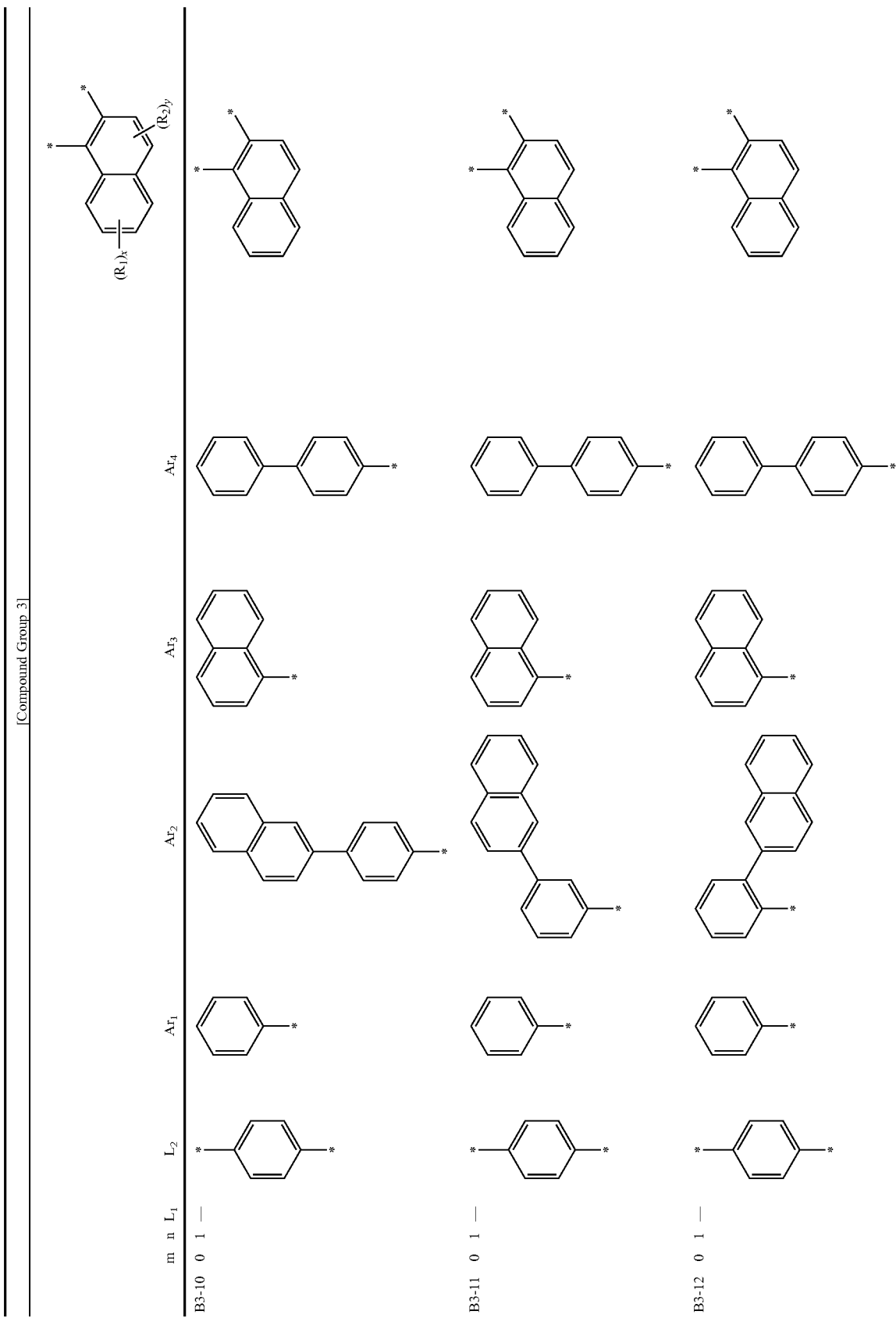

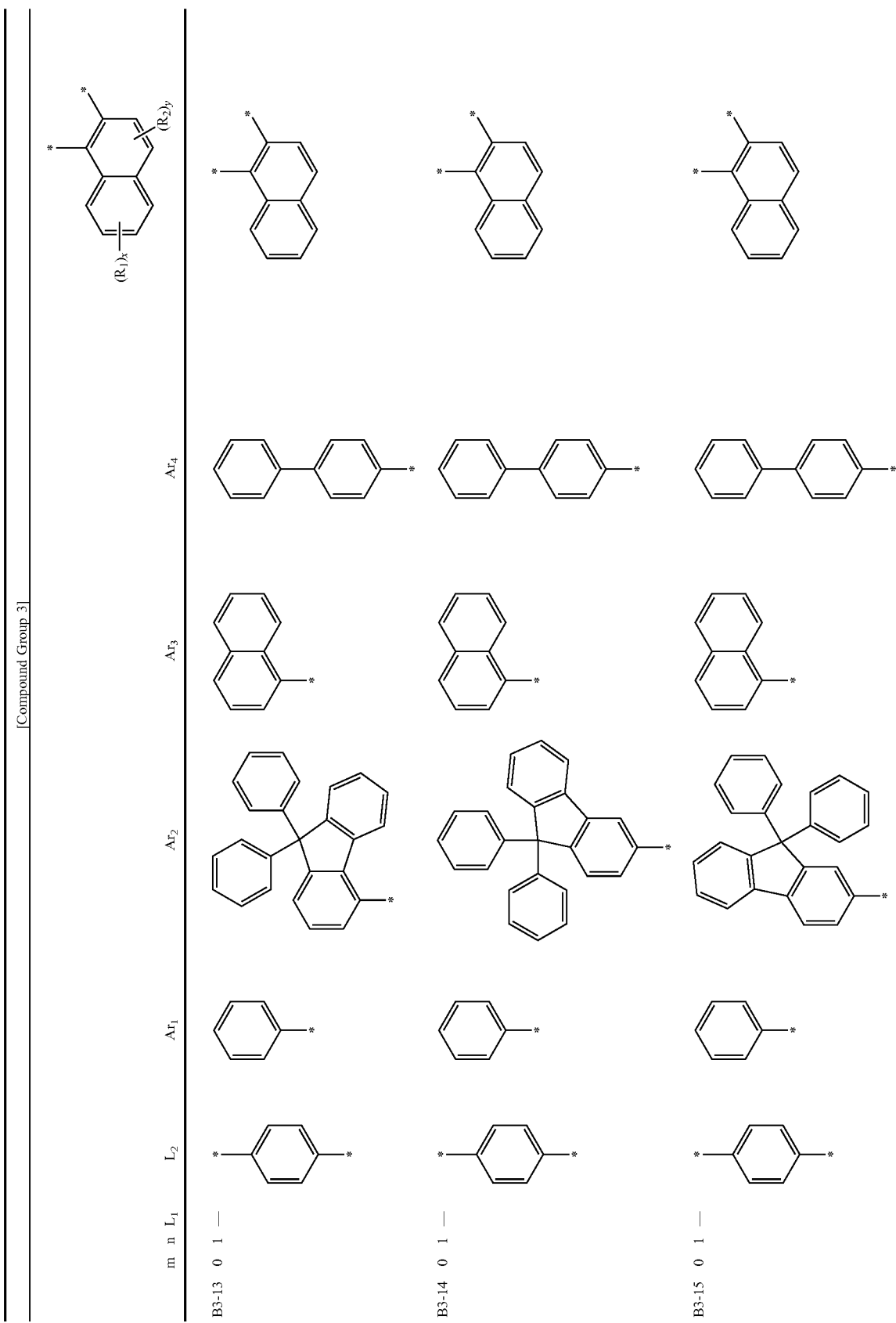

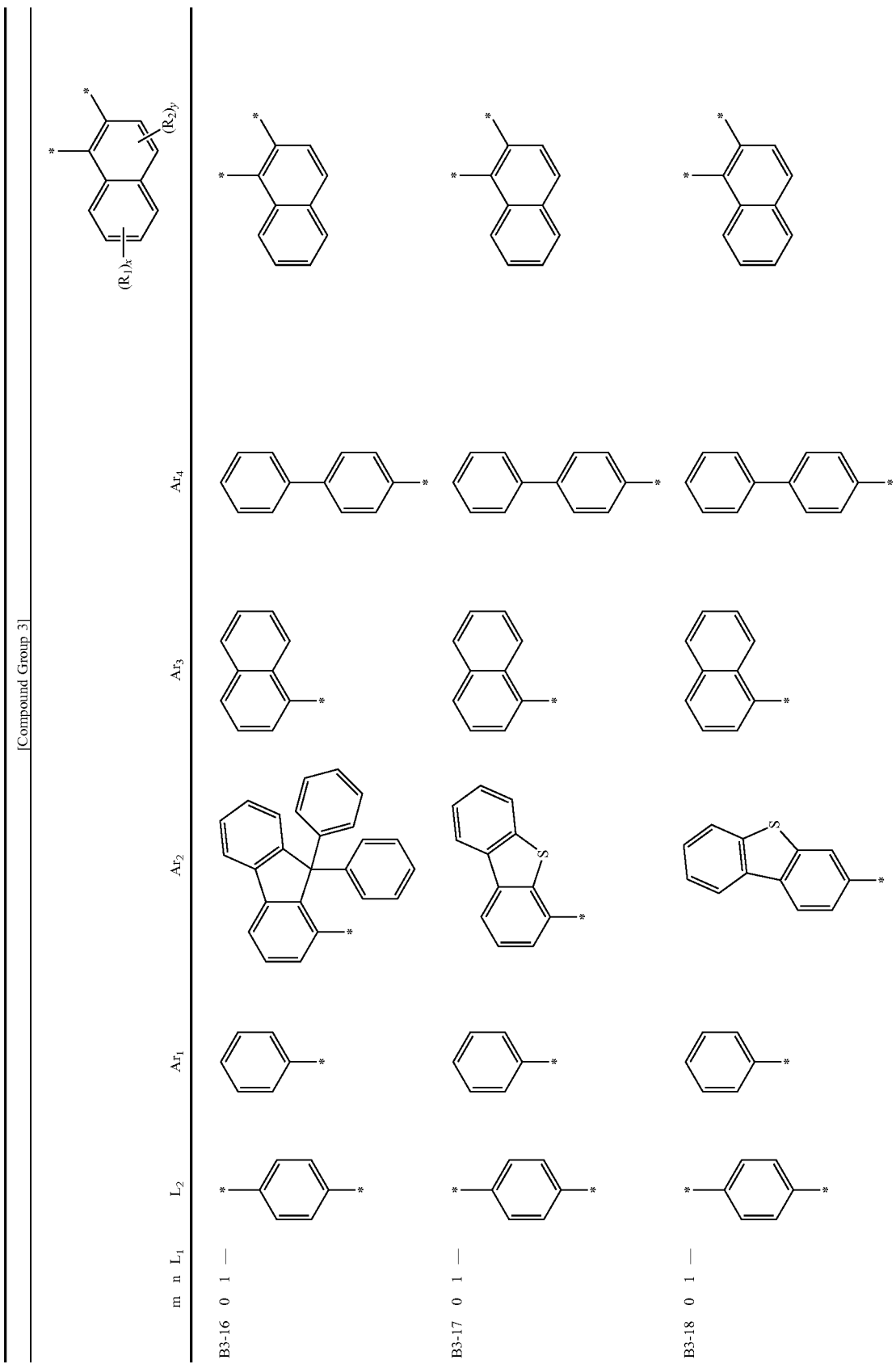

-continued
[Compound Group 3]
| | m | n | L₁ | L₂ | Ar₁ | Ar₂ | Ar₃ | Ar₄ | |
|---|---|---|---|---|---|---|---|---|---|
| B3-19 | 0 | 1 | — | 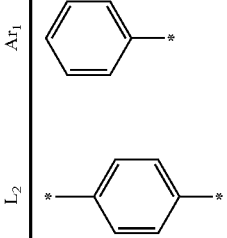 | 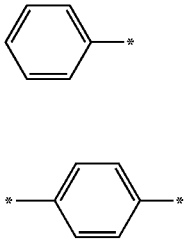 | 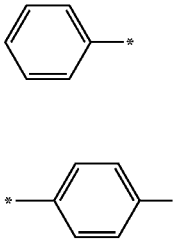 |  | 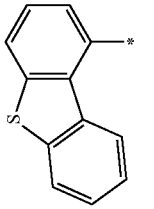 | 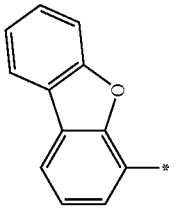 |
| B3-20 | 0 | 1 | — |  |  |  |  |  |  |
| B3-21 | 0 | 1 | — |  |  |  | | | |

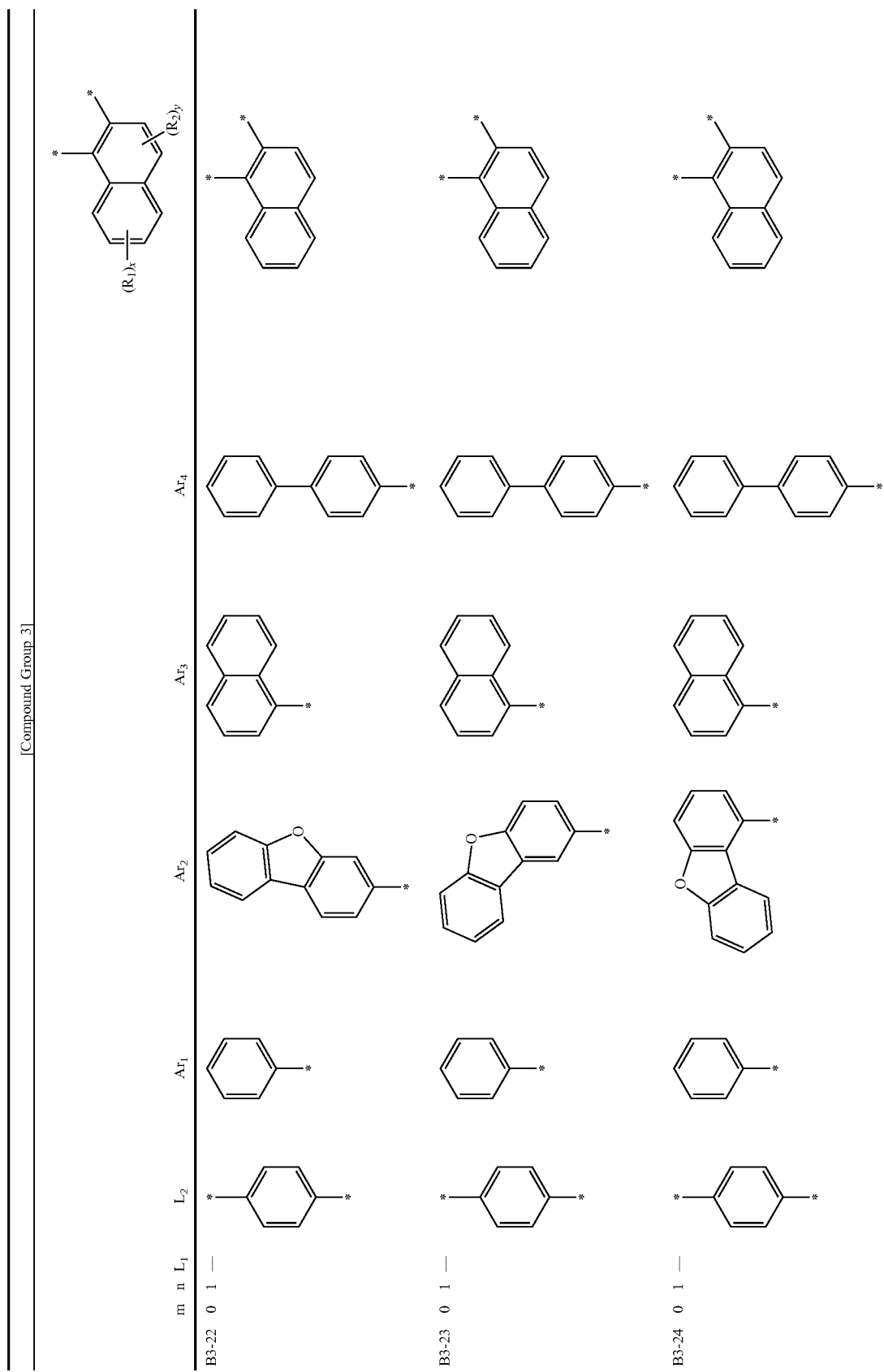

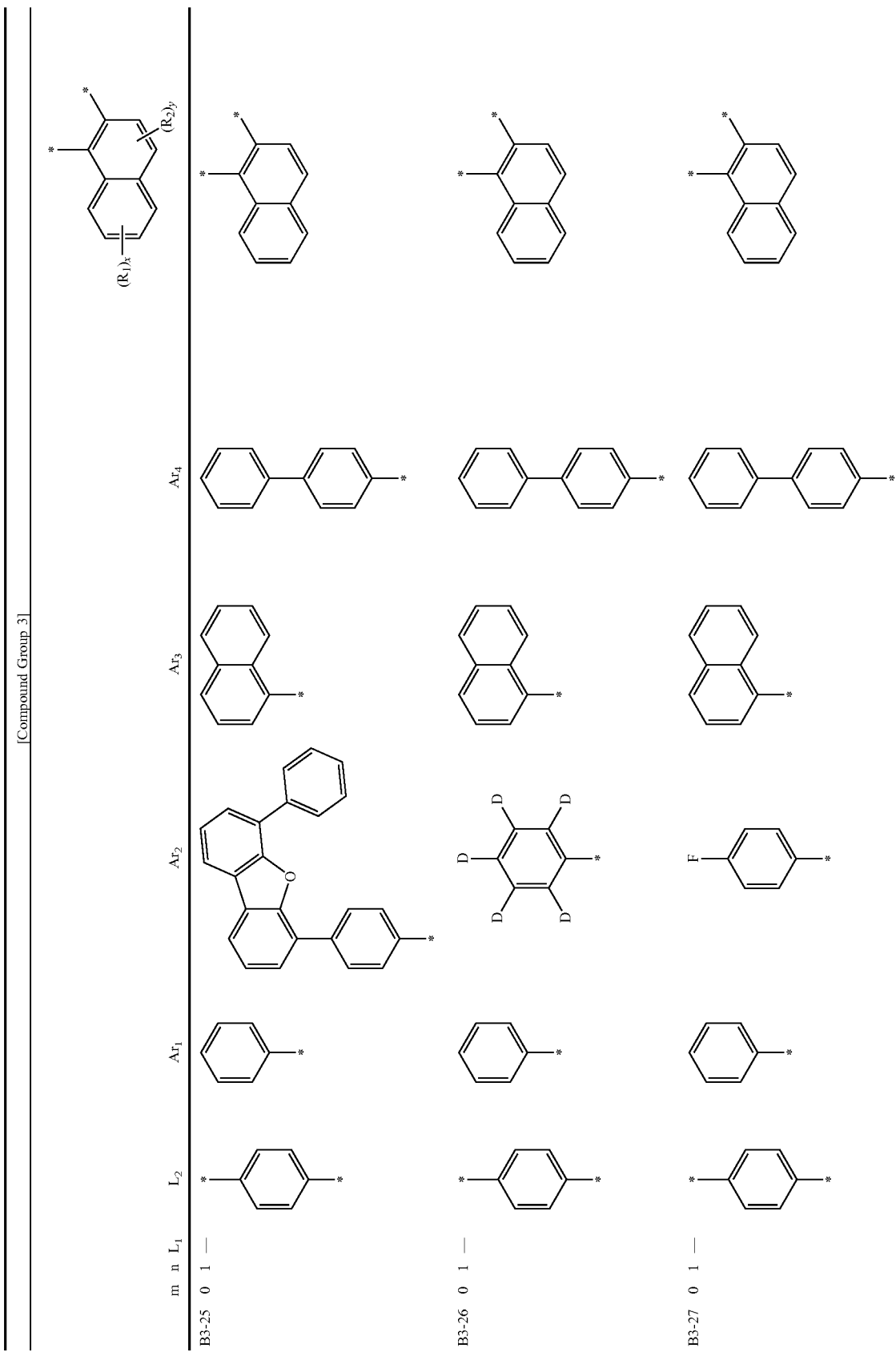

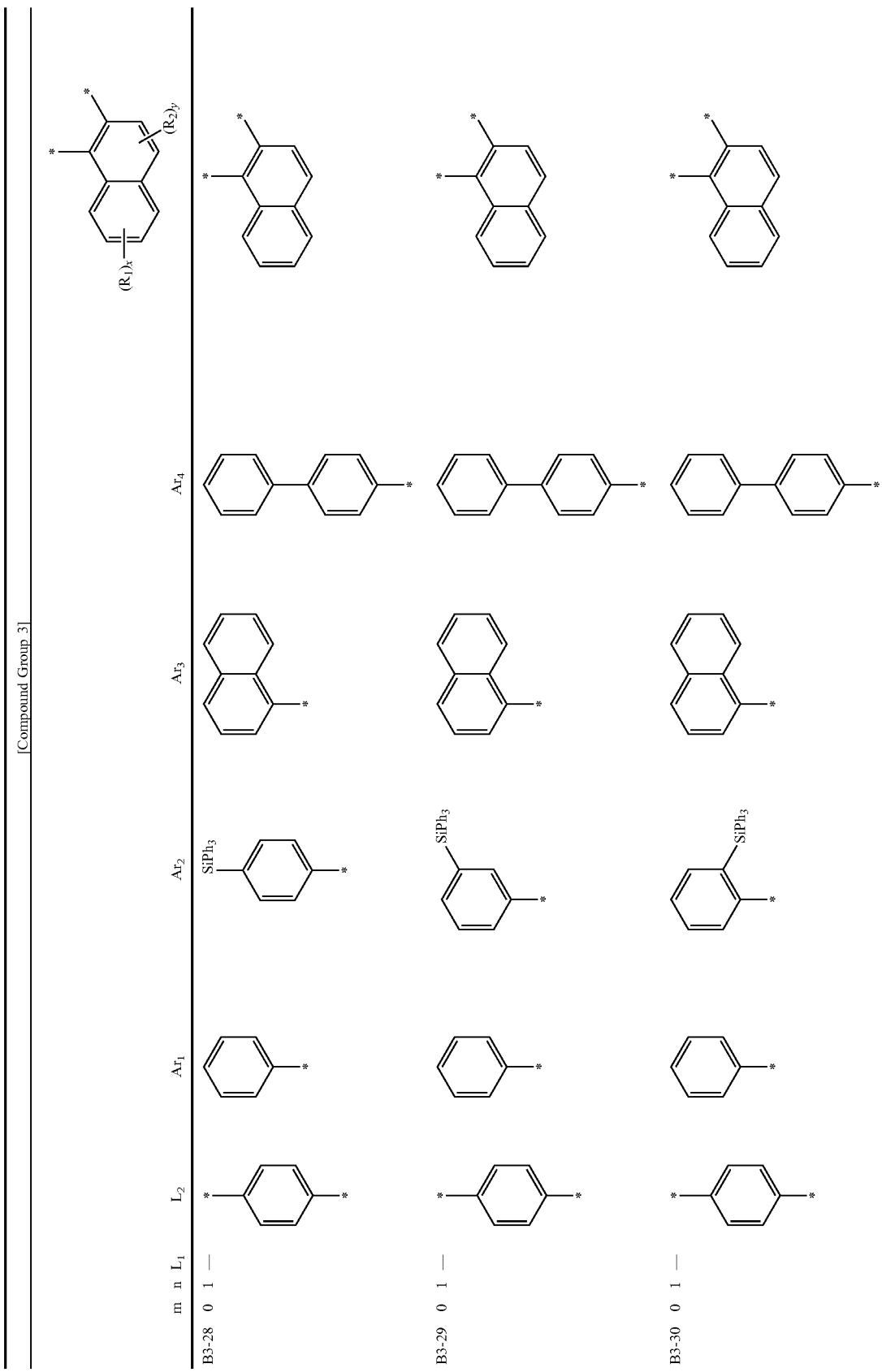

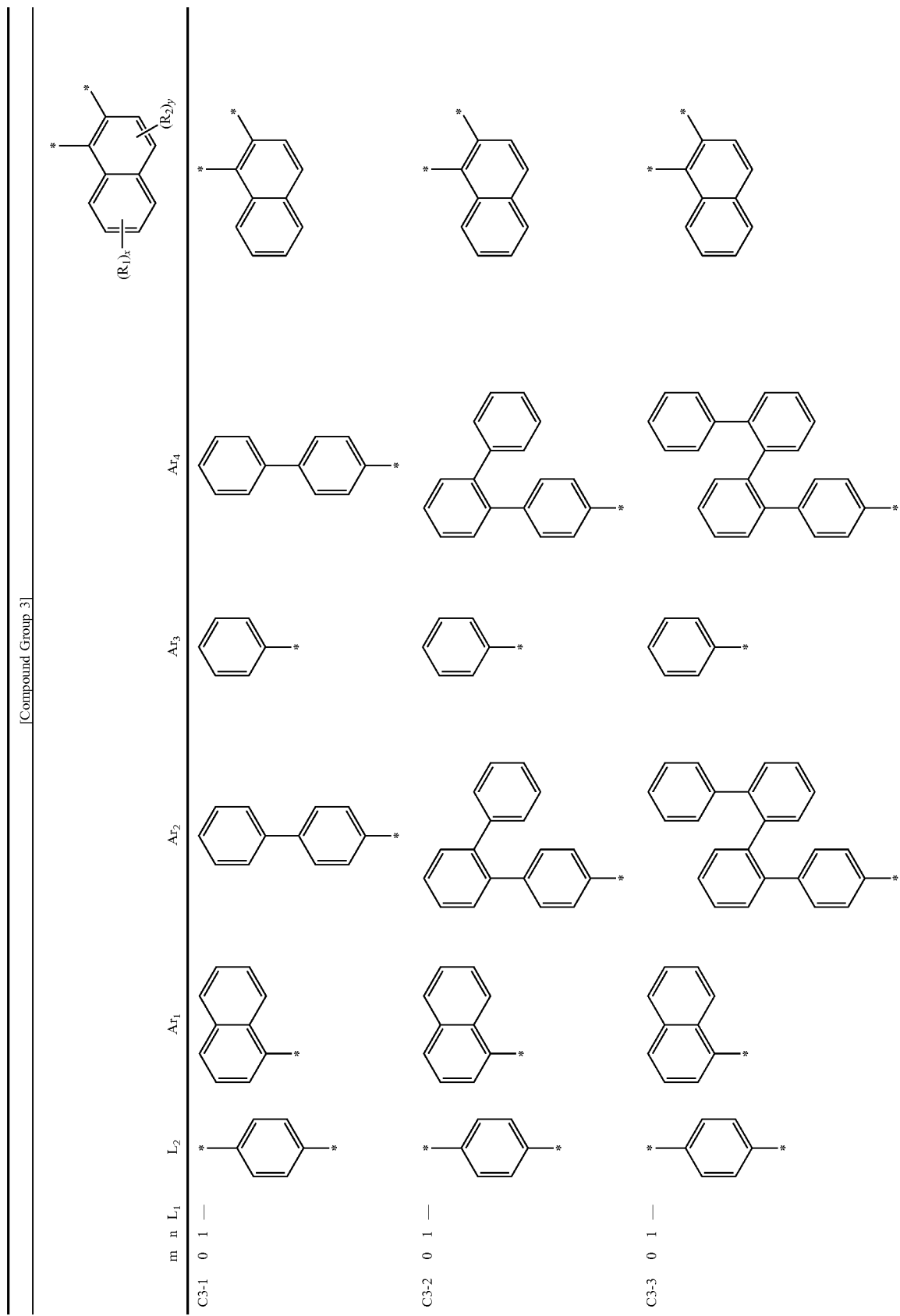

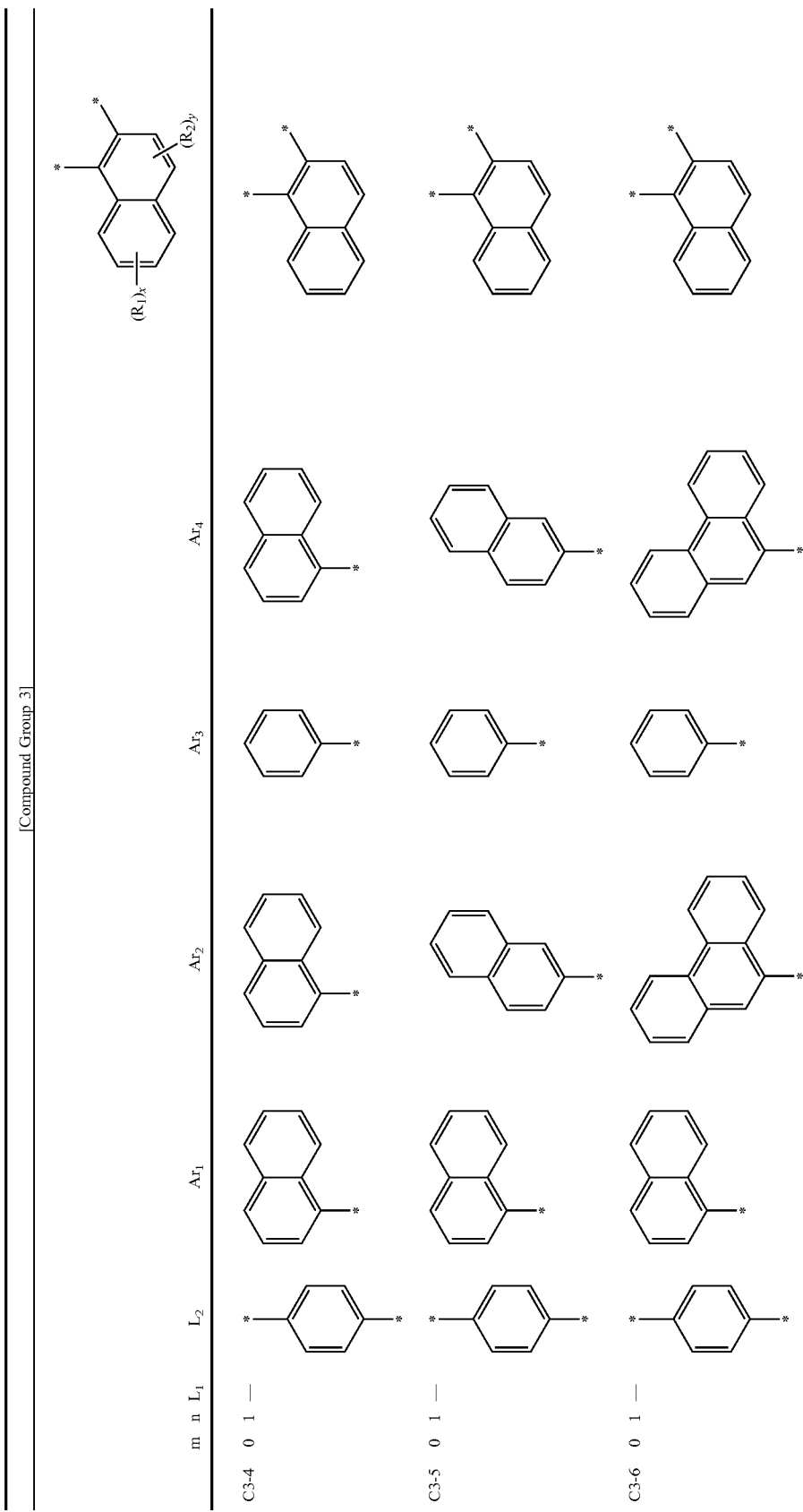

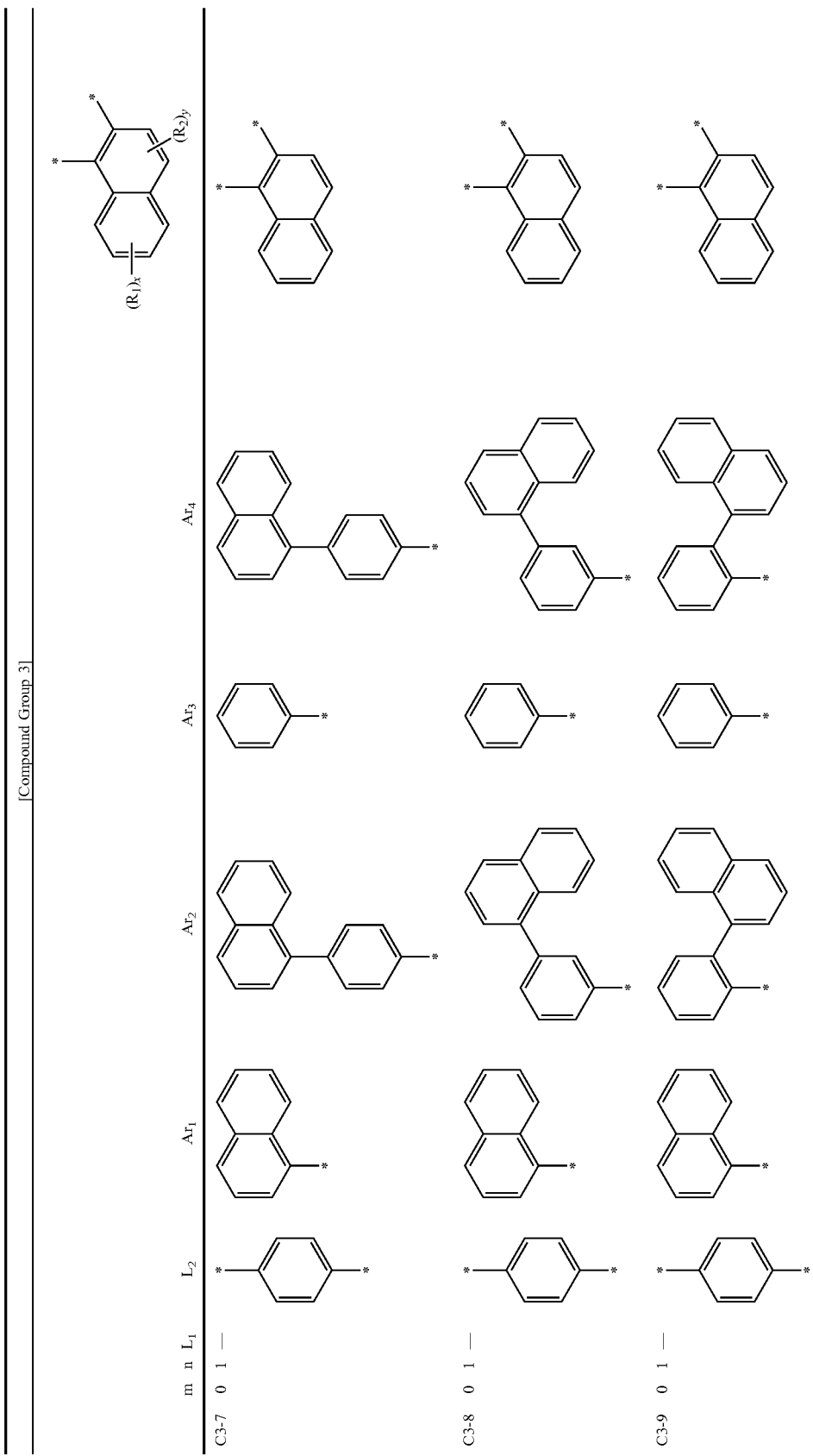

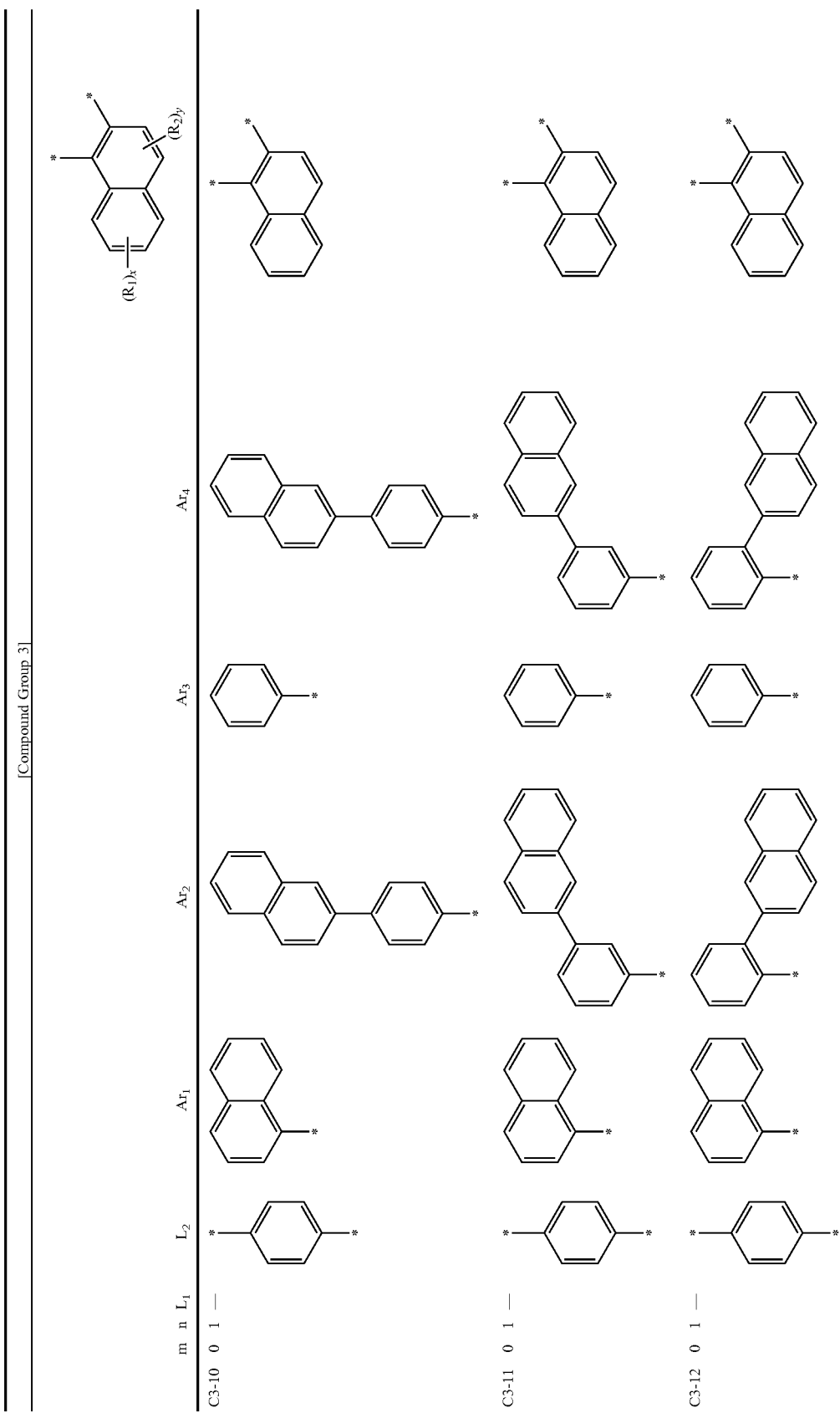

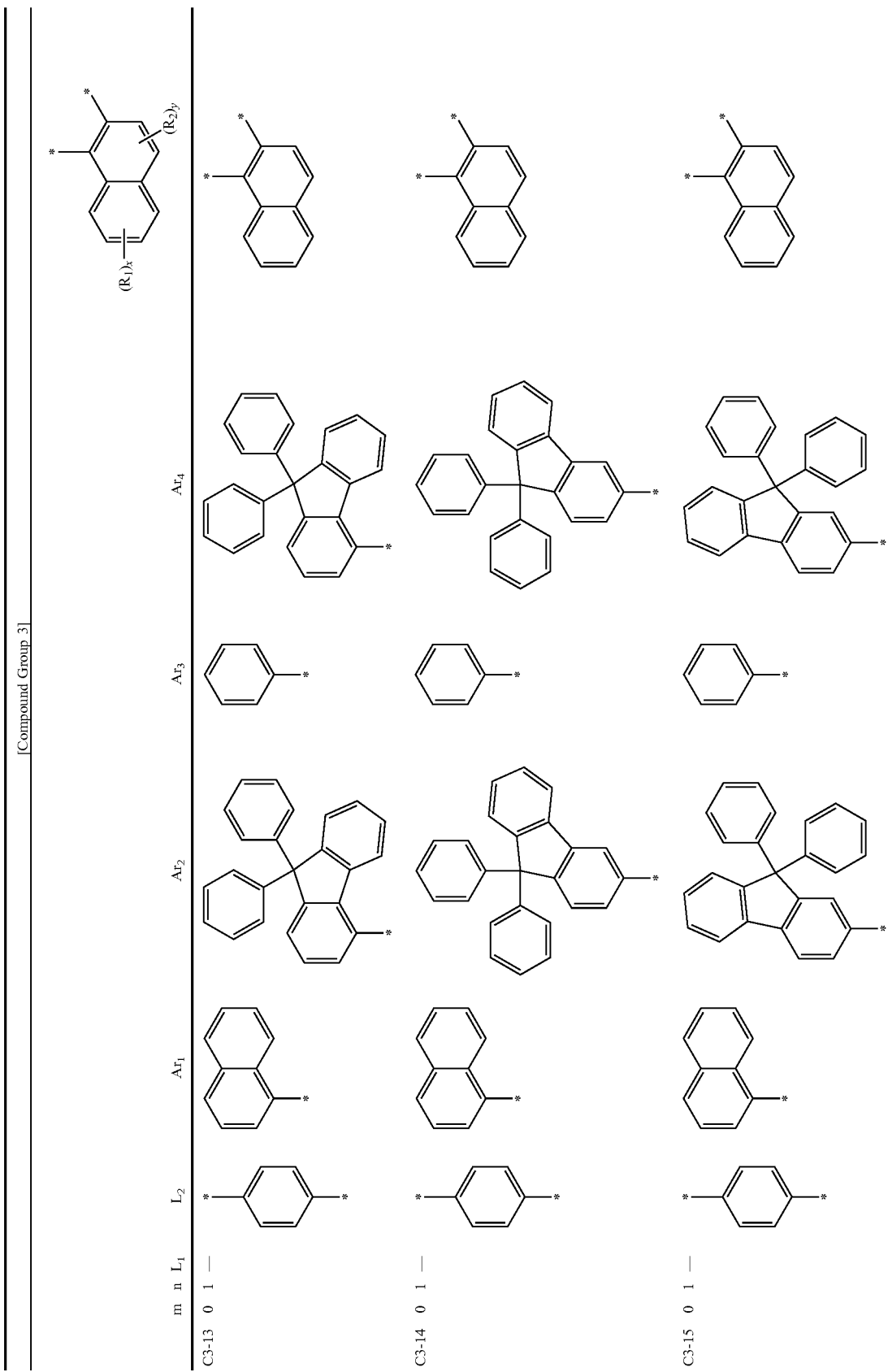

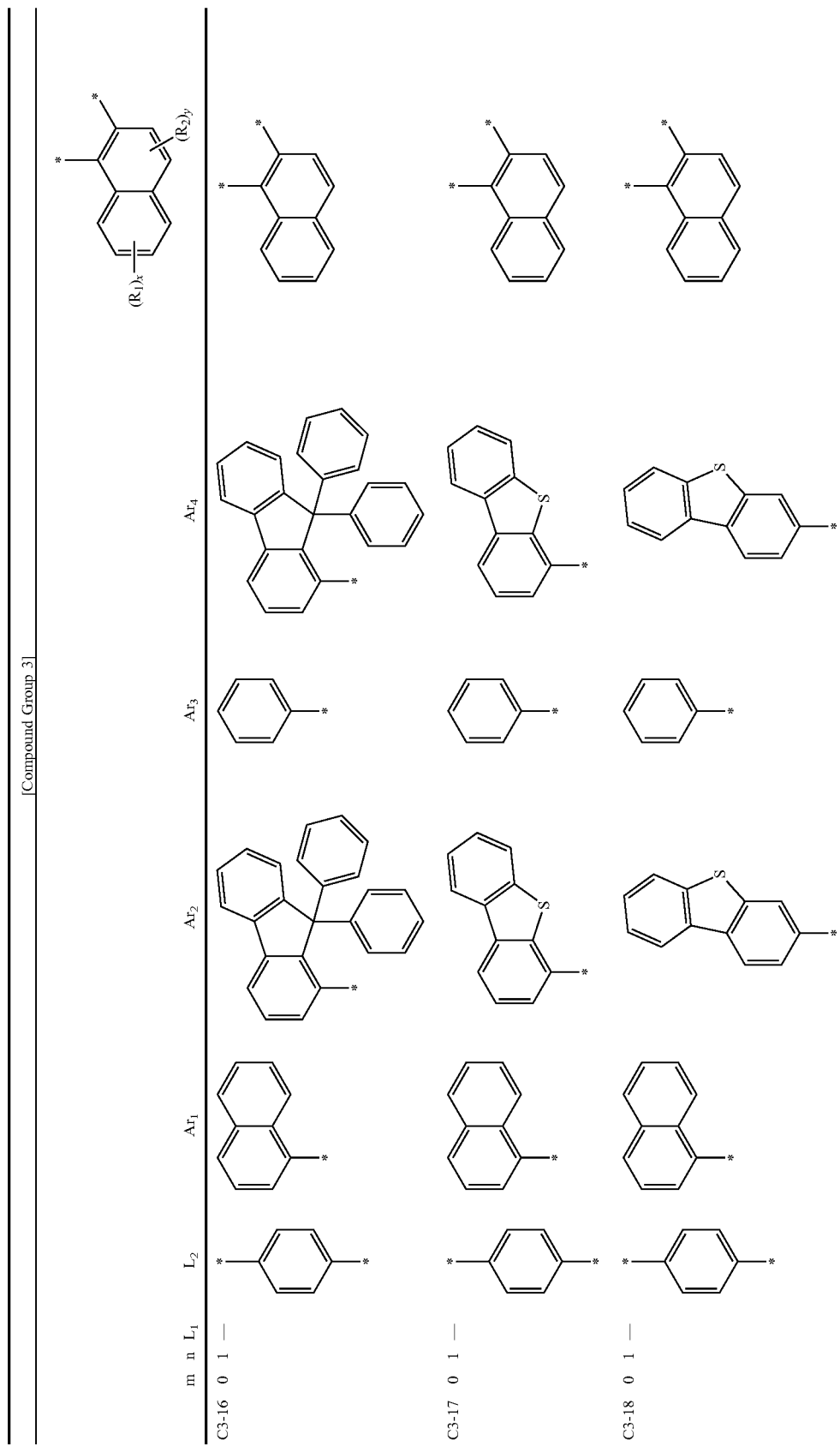

-continued
[Compound Group 3]
| | m | n | L₁ | L₂ | Ar₁ | Ar₂ | Ar₃ | Ar₄ | 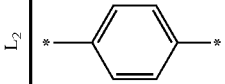 |
|---|---|---|---|---|---|---|---|---|---|
| C3-19 | 0 | 1 | — | | | | | | |
| C3-20 | 0 | 1 | — | | | | | | |
| C3-21 | 0 | 1 | — | | | | | | |


-continued
[Compound Group 3]

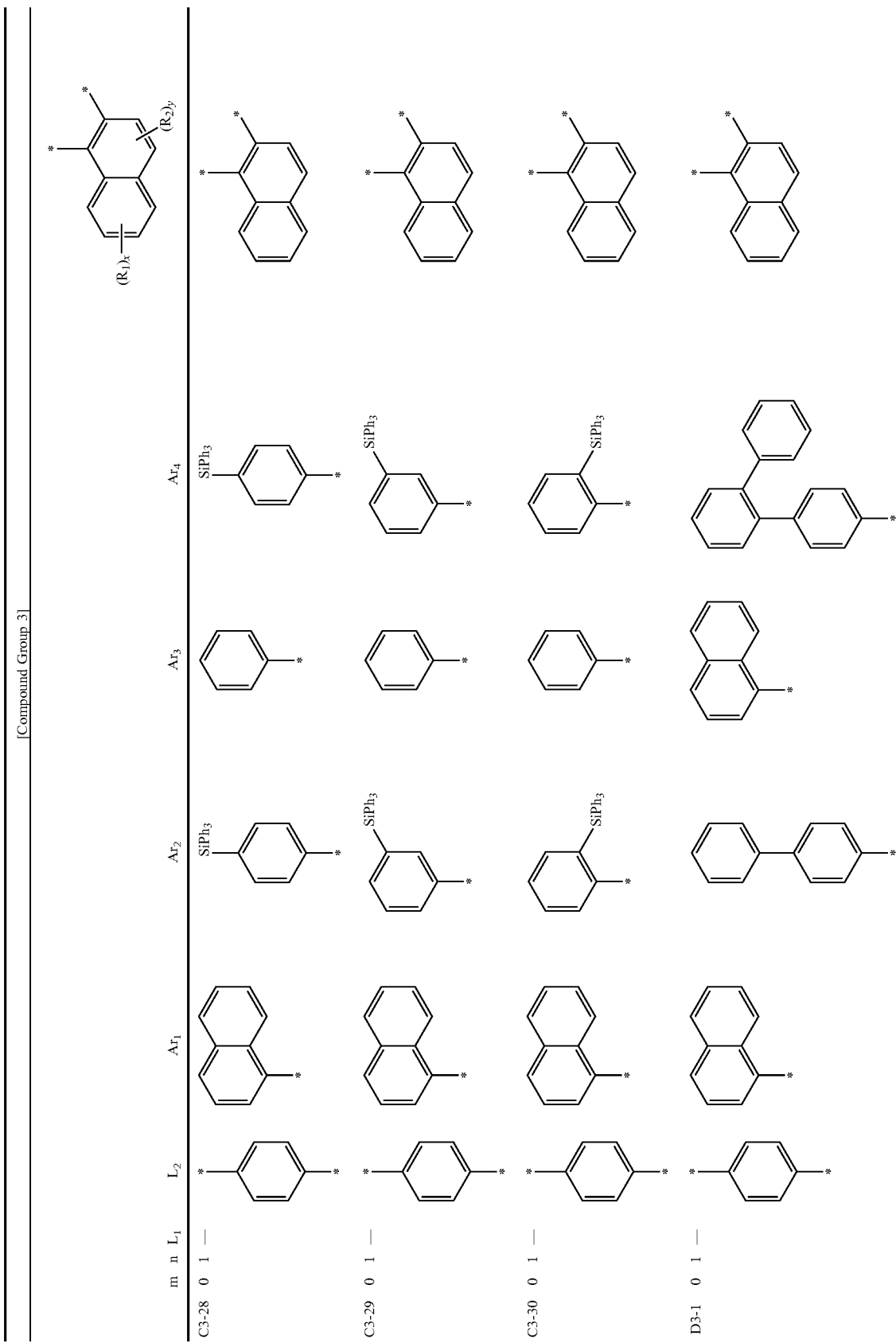

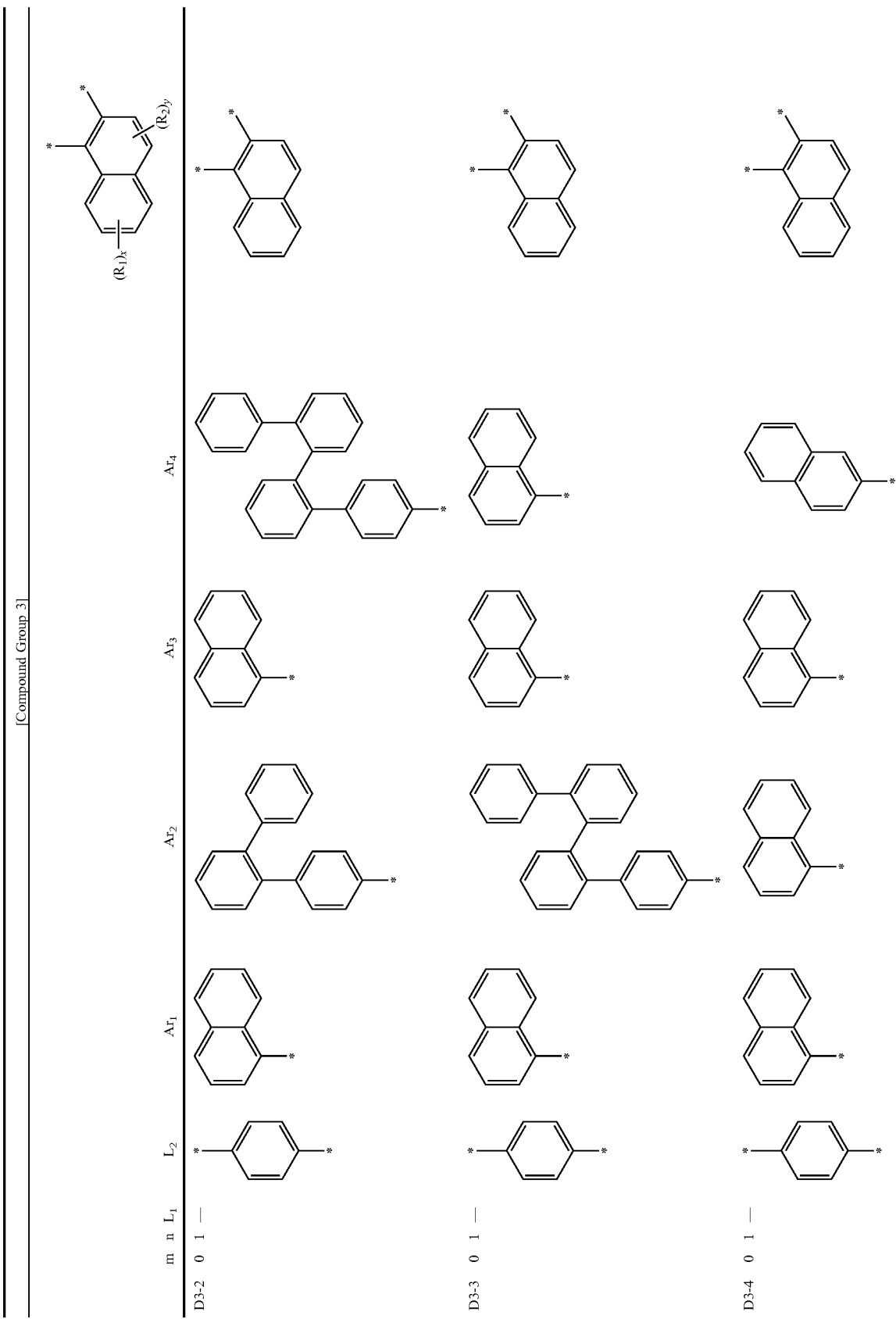

















-continued

[Compound Group 4]

| | m | n | L₁ | L₂ | Ar₁ | Ar₂ | Ar₃ | Ar₄ | |
|---|---|---|---|---|---|---|---|---|---|
| A4-22 | 1 | 1 | | | | | | | |
| A4-23 | 1 | 1 | | | | | | | |
| A4-24 | 1 | 1 | | | | | | | |

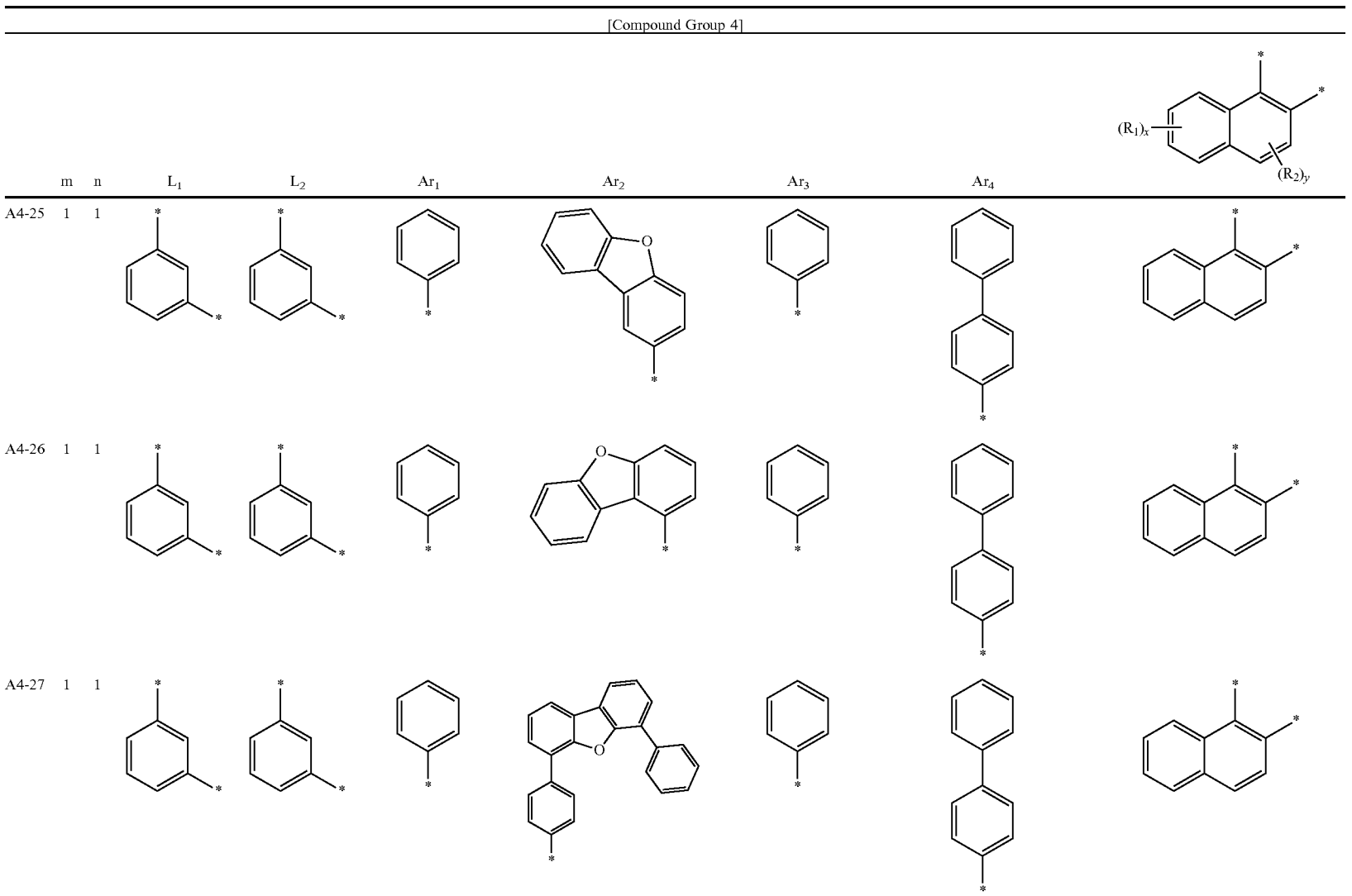

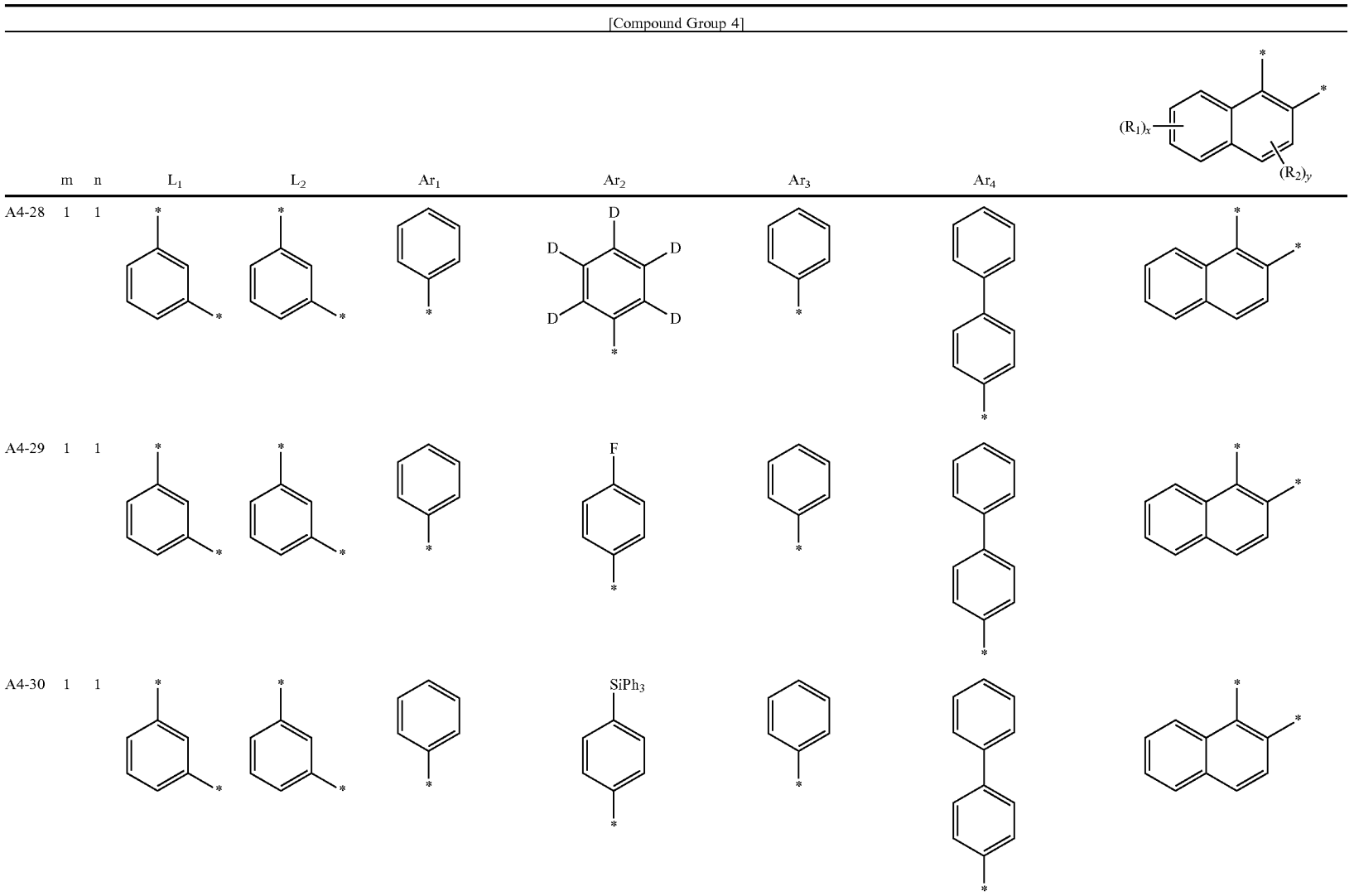

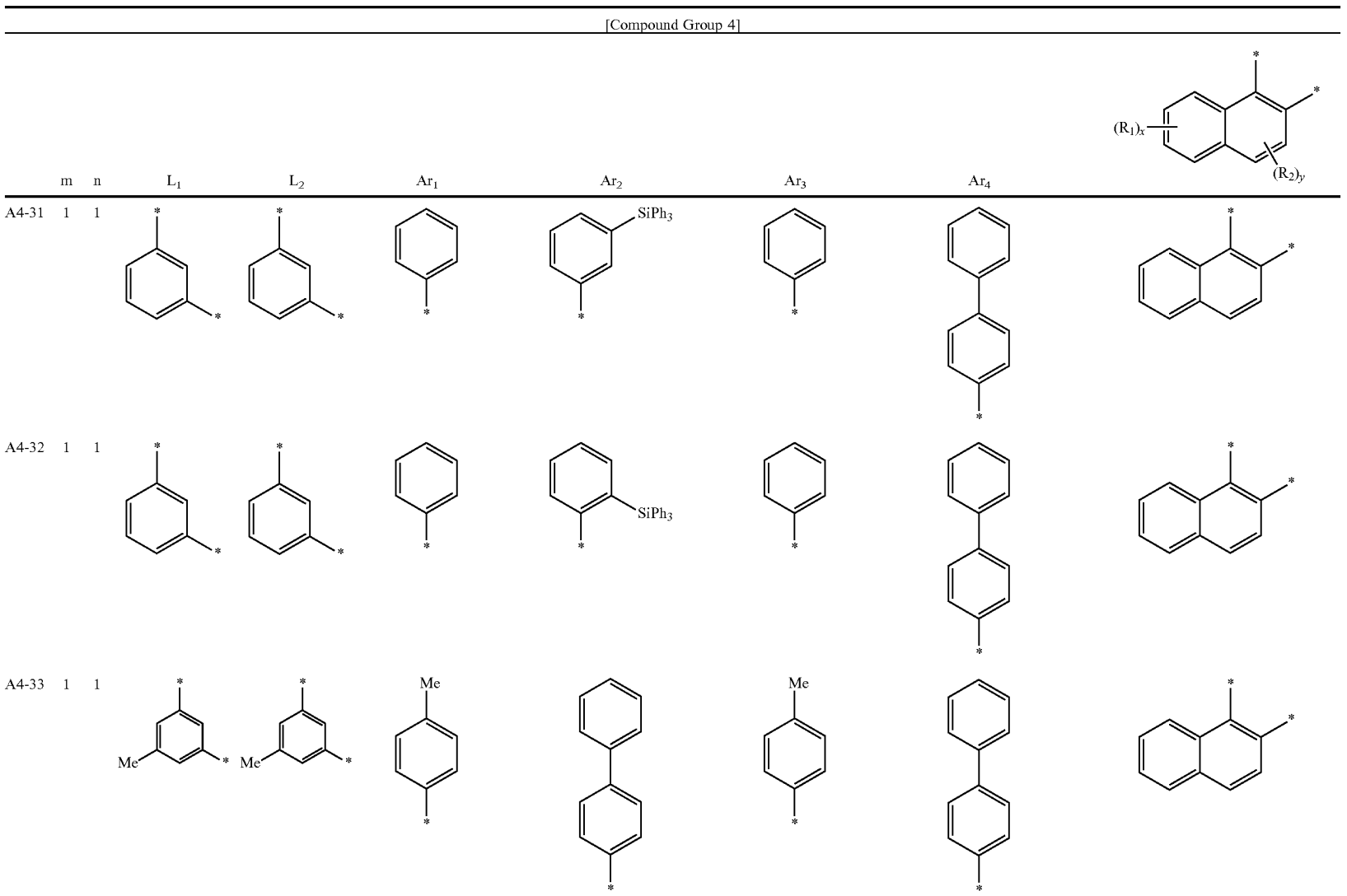

-continued

[Compound Group 4]

| | m | n | L₁ | L₂ | Ar₁ | Ar₂ | Ar₃ | Ar₄ | |
|---|---|---|---|---|---|---|---|---|---|
| B4-1 | 1 | 1 | | | | | | | |
| B4-2 | 1 | 1 | | | | | | | |
| B4-3 | 1 | 1 | | | | | | | |

-continued
[Compound Group 4]
| | m | n | $L_1$ | $L_2$ | $Ar_1$ | $Ar_2$ | $Ar_3$ | $Ar_4$ | 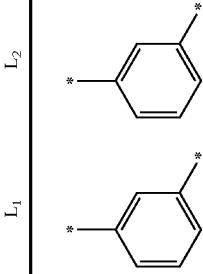 |
|---|---|---|---|---|---|---|---|---|---|
| B4-4 | 1 | 1 | | | | | | | |
| B4-5 | 1 | 1 | | | | | | | |
| B4-6 | 1 | 1 | | | | | | | |

-continued

[Compound Group 4]

| | m | n | L₁ | L₂ | Ar₁ | Ar₂ | Ar₃ | Ar₄ | |
|---|---|---|---|---|---|---|---|---|---|
| B4-7 | 1 | 1 | | | | | | | |
| B4-8 | 1 | 1 | | | | | | | |
| B4-9 | 1 | 1 | | | | | | | |


[Compound Group 4]


-continued
[Compound Group 4]
| | m | n | L₁ | L₂ | Ar₁ | Ar₂ | Ar₃ | Ar₄ |  |
|---|---|---|---|---|---|---|---|---|---|
| B4-19 | 1 | 1 | | | | | | | |
| B4-20 | 1 | 1 | | | | | | | |
| B4-21 | 1 | 1 | | | | | | | |

-continued
[Compound Group 4]
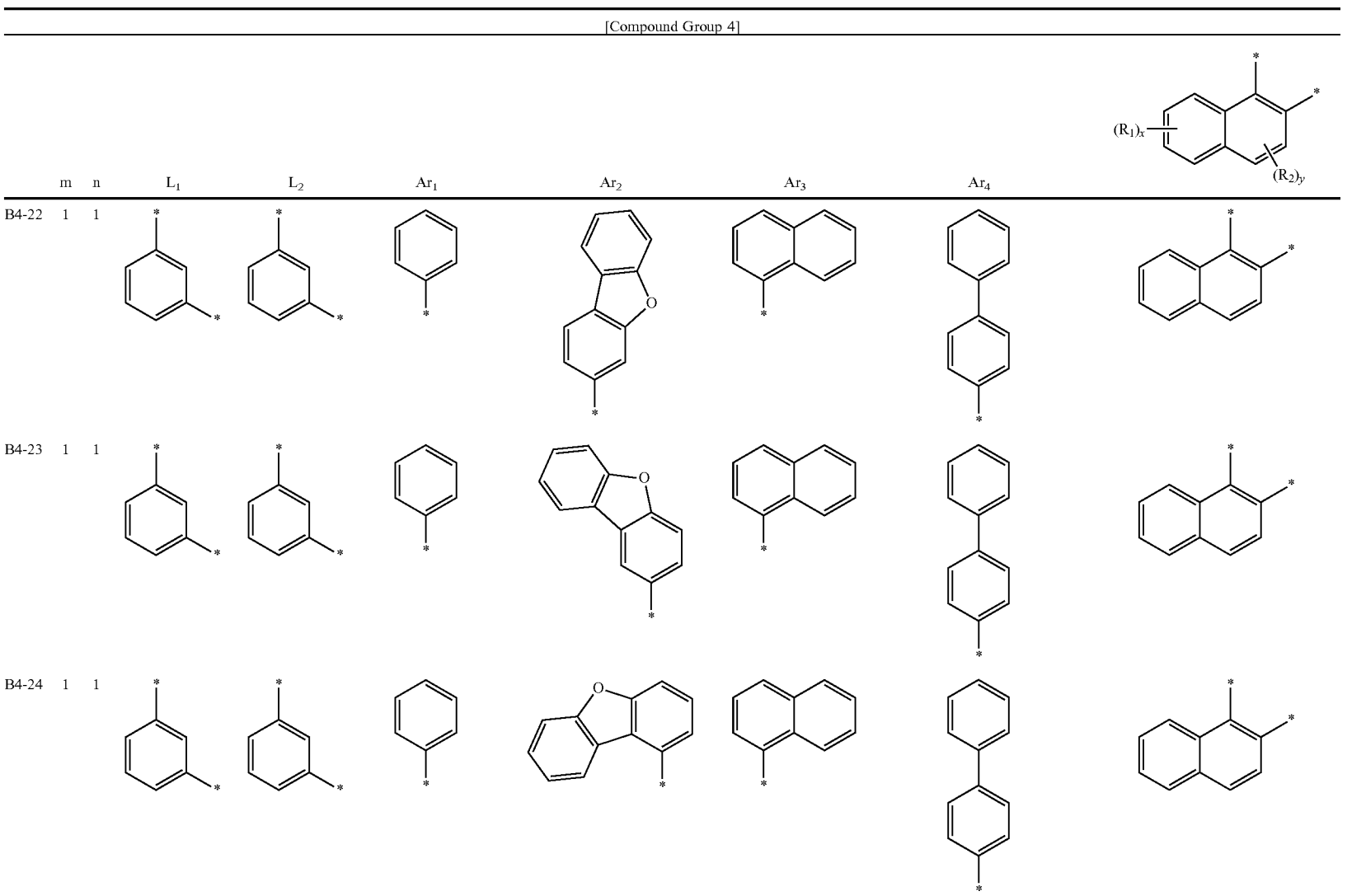

-continued
[Compound Group 4]
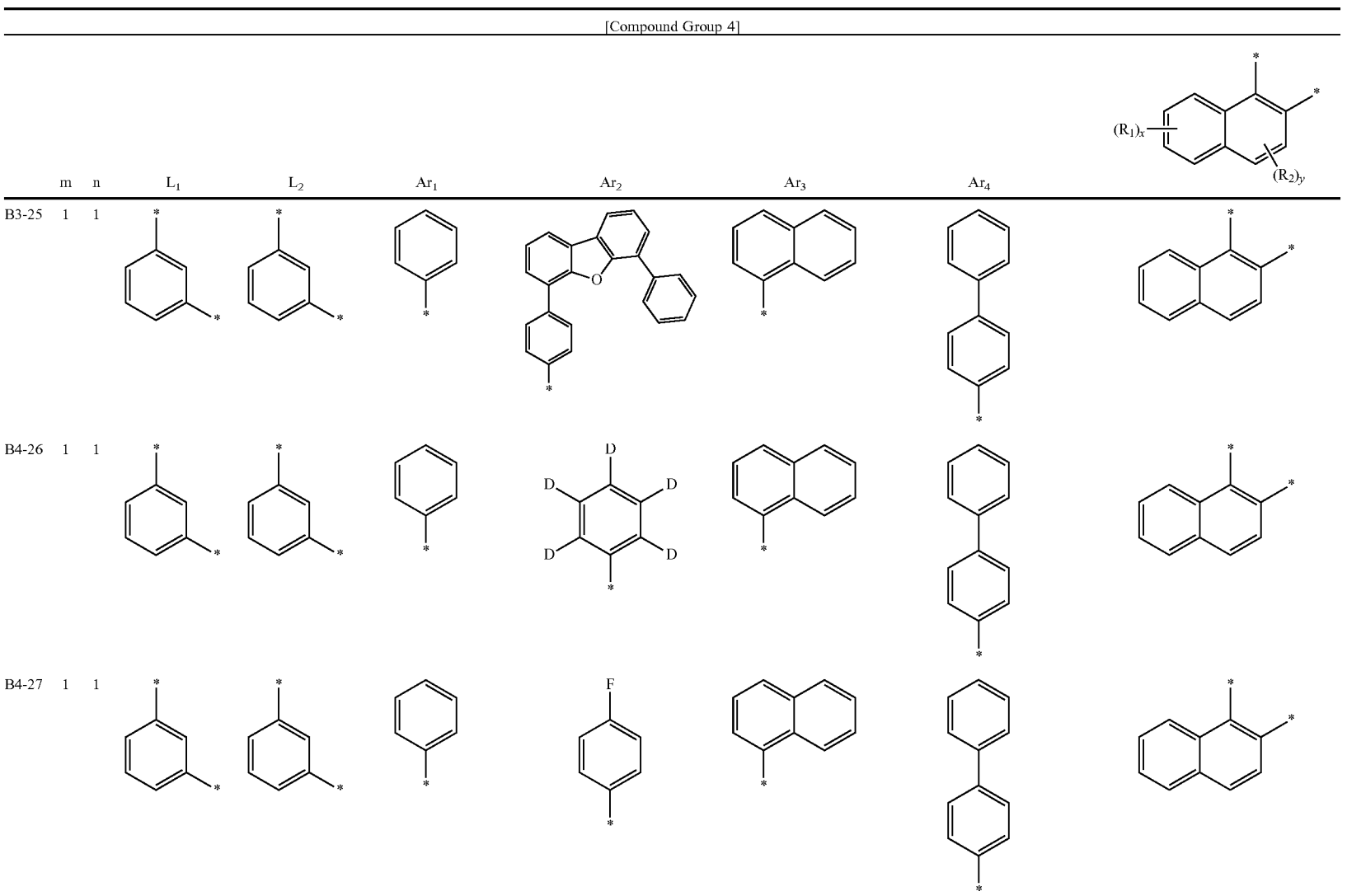

-continued

[Compound Group 4]

| | m | n | L₁ | L₂ | Ar₁ | Ar₂ | Ar₃ | Ar₄ | (R₁)ₓ / (R₂)ᵧ naphthalene |
|---|---|---|---|---|---|---|---|---|---|
| B4-28 | 1 | 1 | meta-phenylene | meta-phenylene | phenyl | 4-SiPh₃-phenyl | 1-naphthyl | biphenyl-4-yl | naphthalene |
| B4-29 | 1 | 1 | meta-phenylene | meta-phenylene | phenyl | 3-SiPh₃-phenyl | 1-naphthyl | biphenyl-4-yl | naphthalene |
| B4-30 | 1 | 1 | meta-phenylene | meta-phenylene | phenyl | 2-SiPh₃-phenyl | 1-naphthyl | biphenyl-4-yl | naphthalene |

-continued
[Compound Group 4]
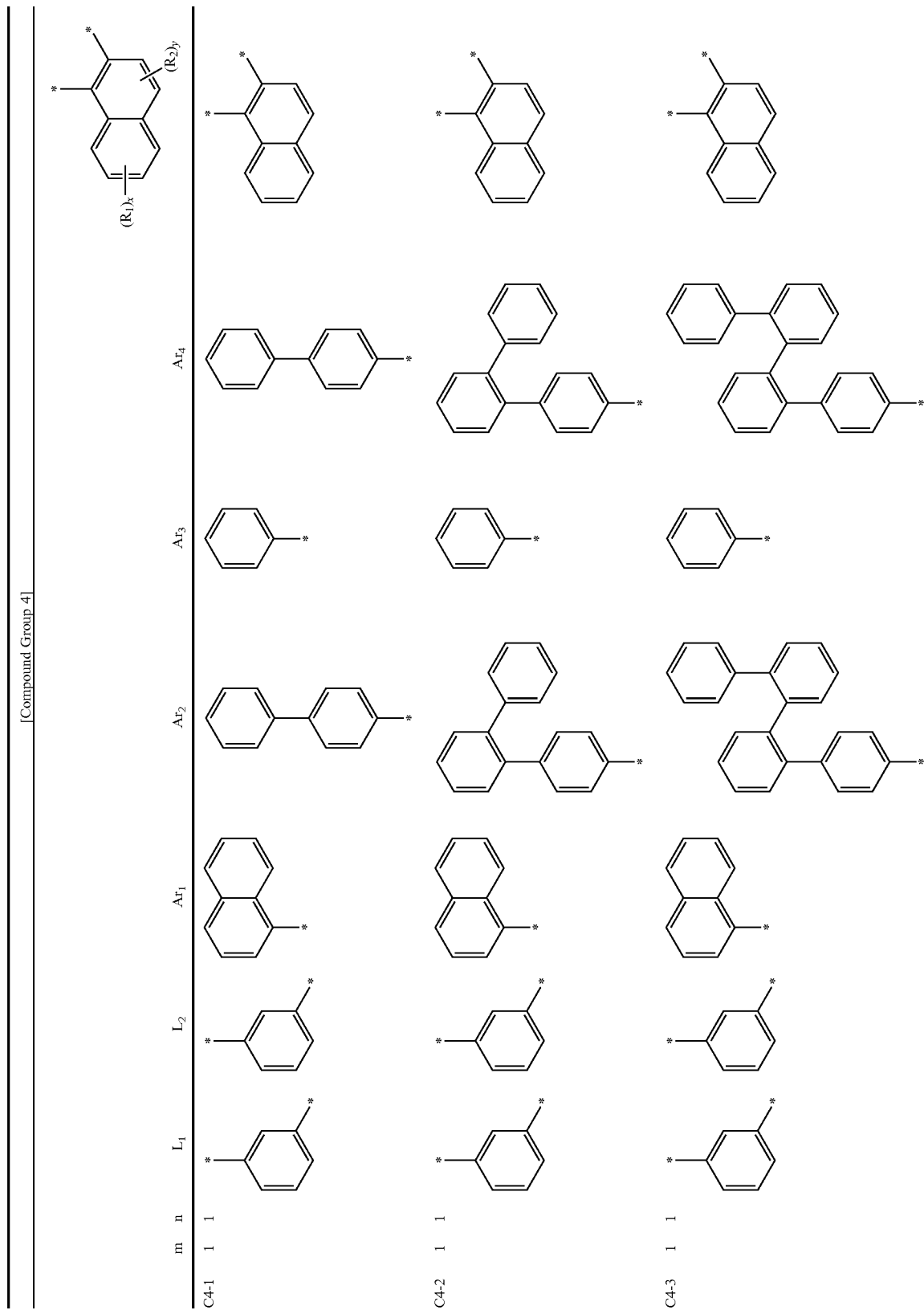

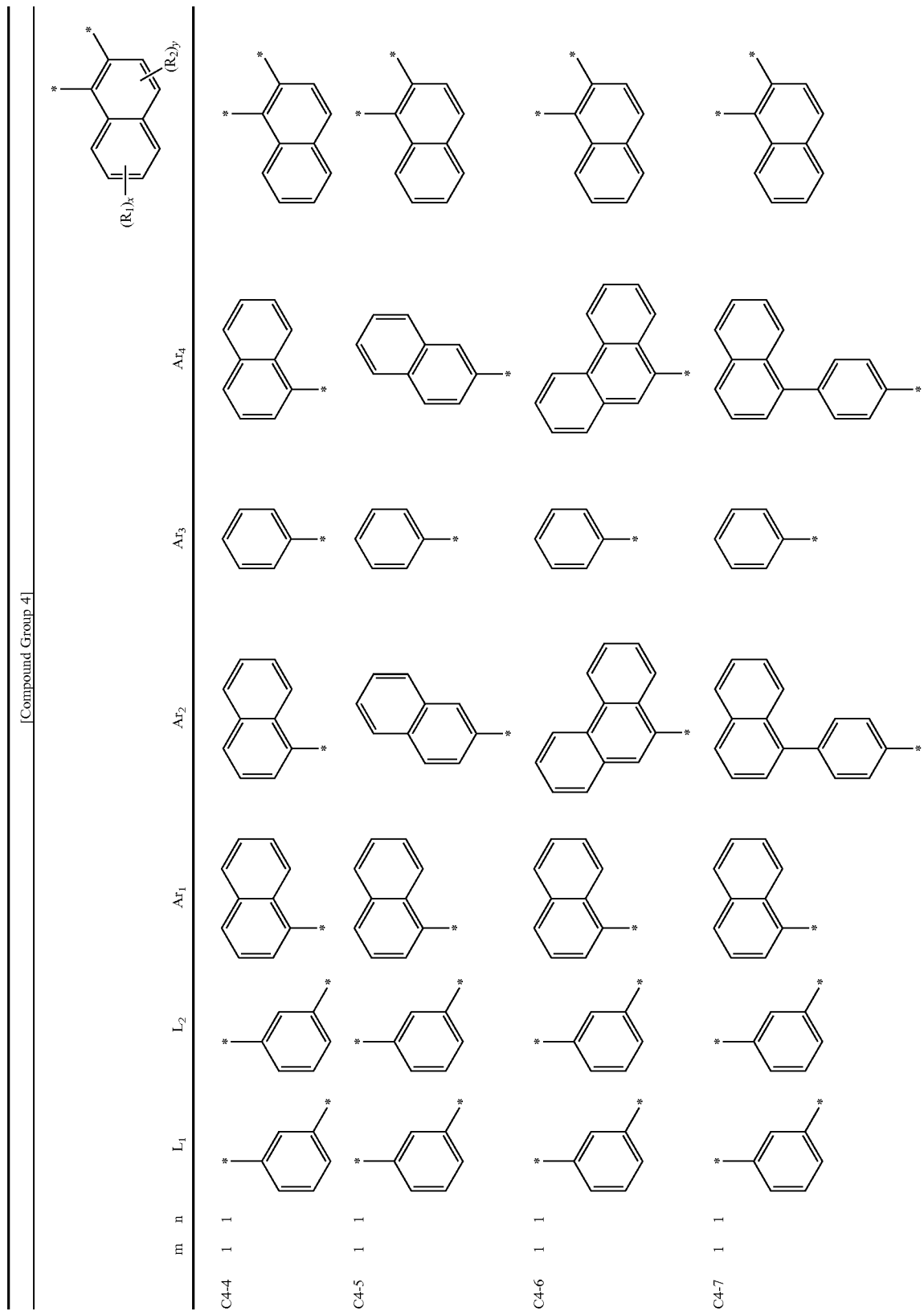

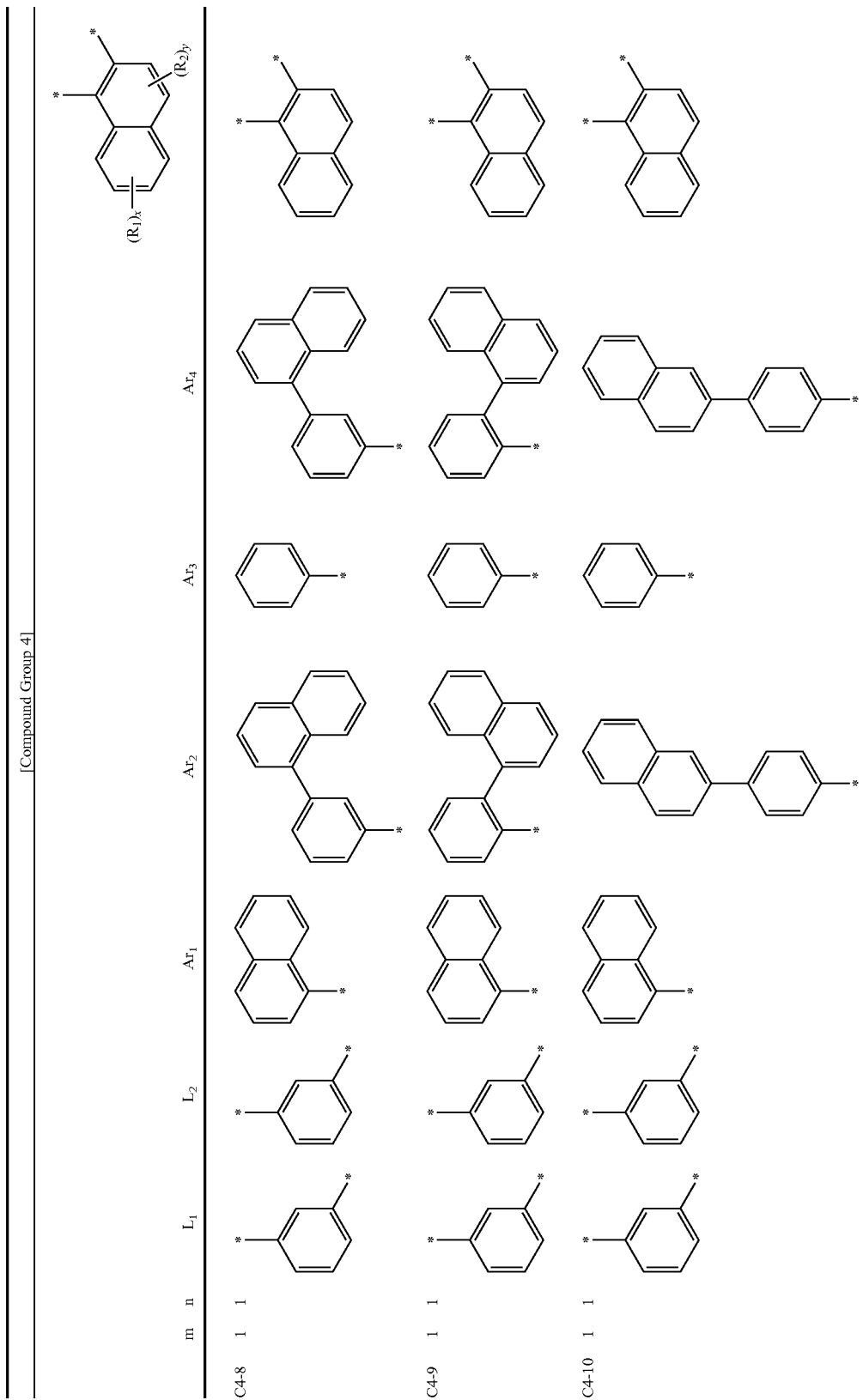

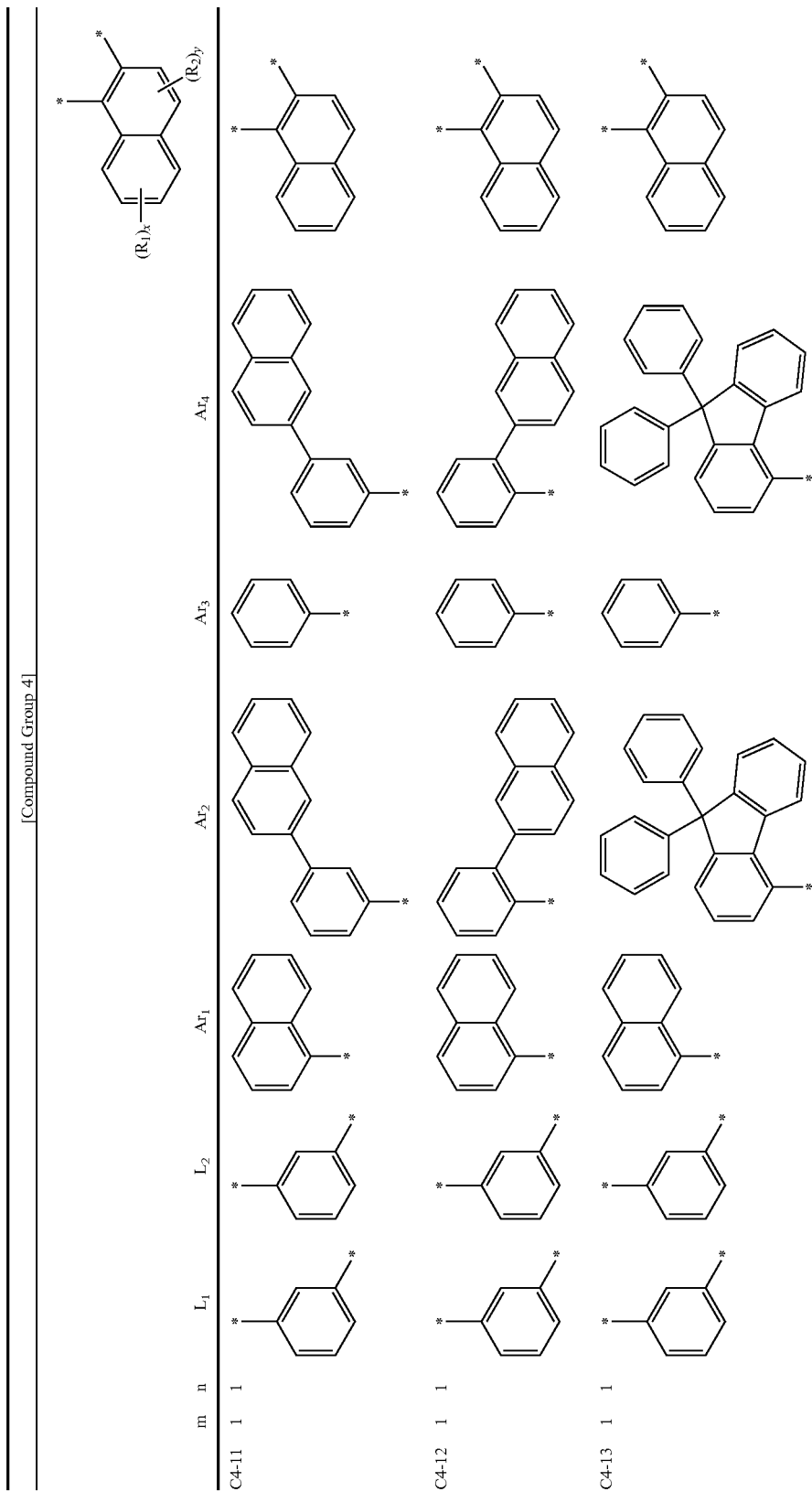

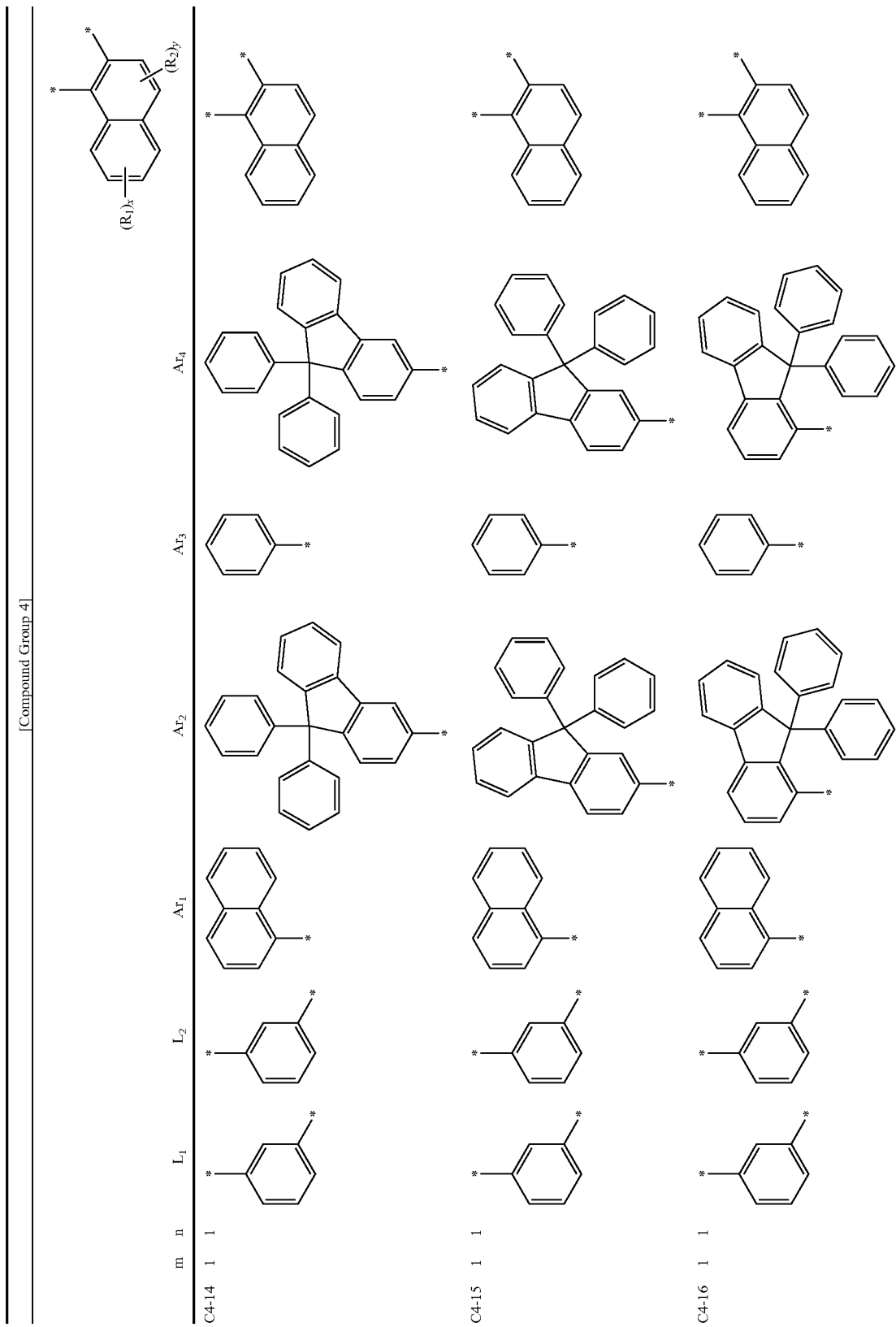

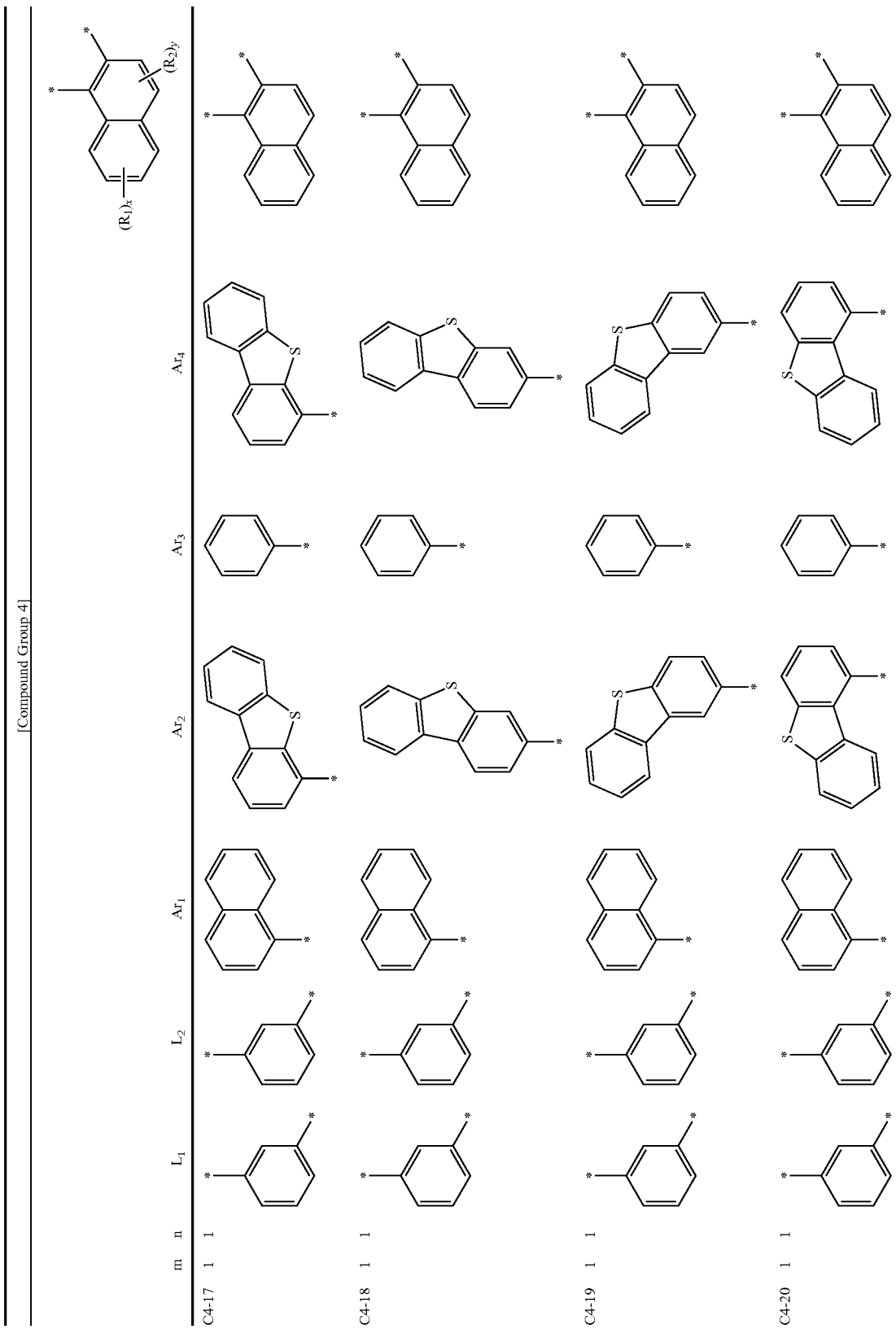

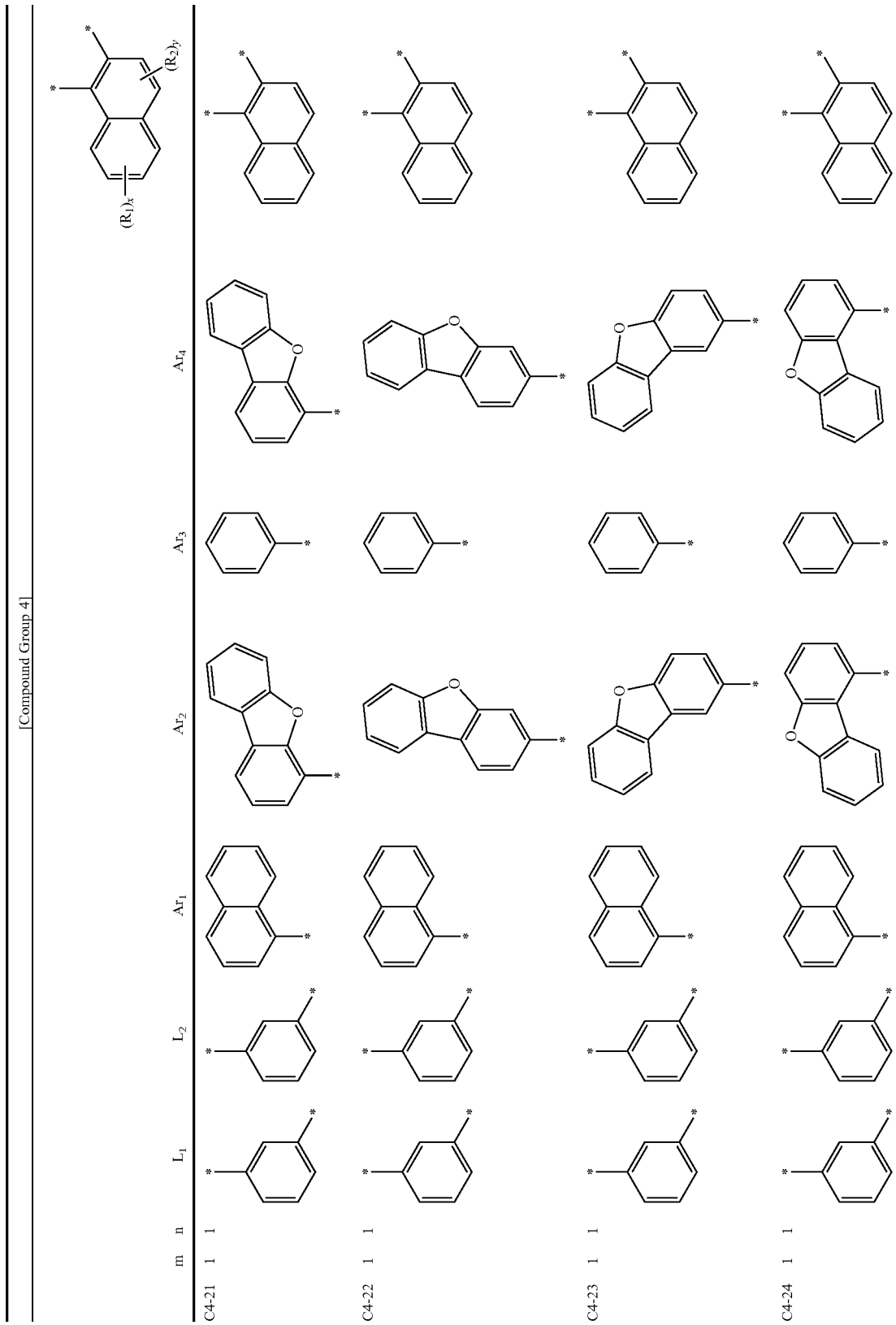

-continued
[Compound Group 4]
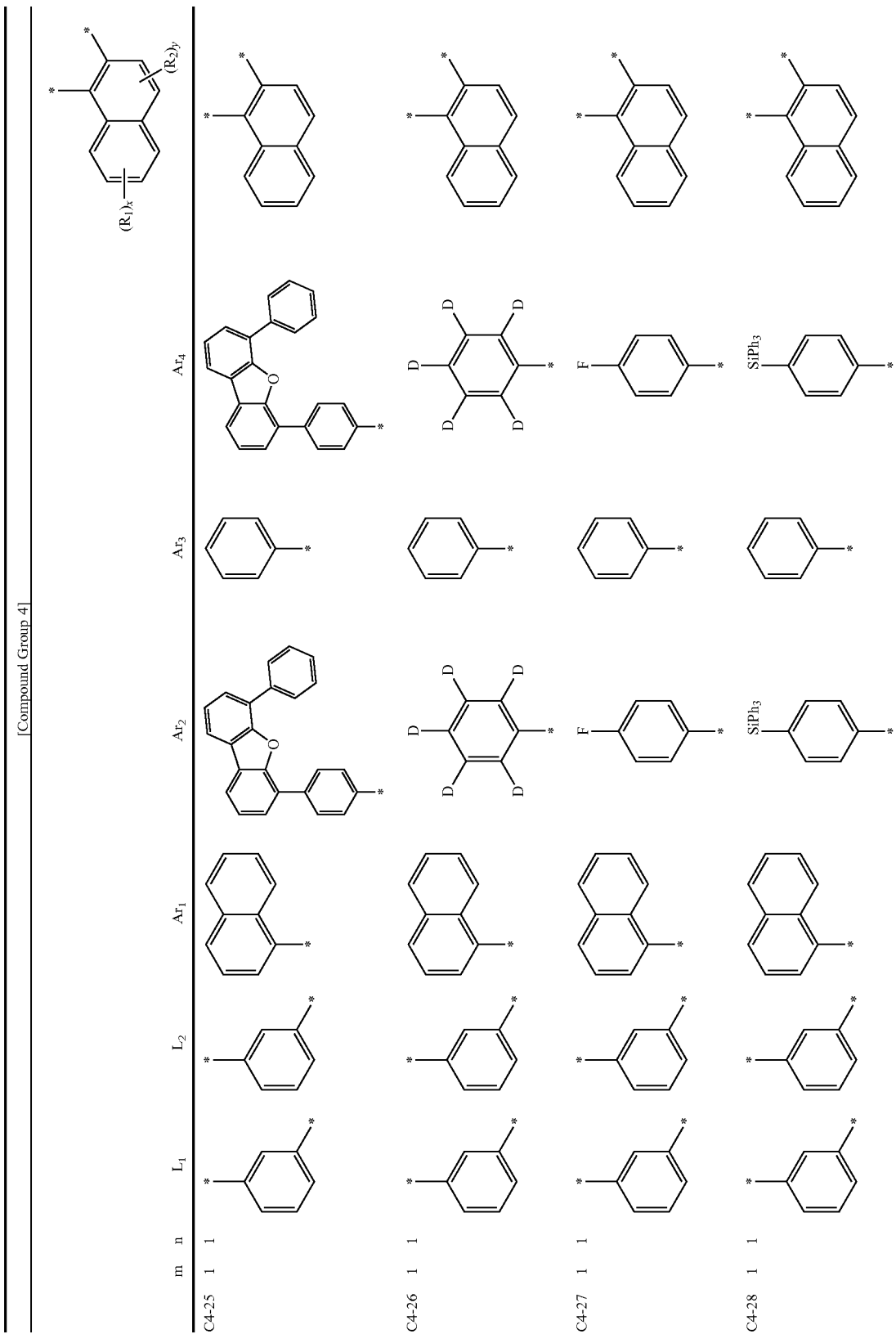

-continued

[Compound Group 4]

| | m | n | L₁ | L₂ | Ar₁ | Ar₂ | Ar₃ | Ar₄ |
|---|---|---|---|---|---|---|---|---|
| C4-29 | 1 | 1 | phenyl-1,3 | phenyl-1,3 | naphthalen-1-yl | 3-SiPh₃-phenyl | phenyl | 3-SiPh₃-phenyl |
| C4-30 | 1 | 1 | phenyl-1,3 | phenyl-1,3 | naphthalen-1-yl | 2-SiPh₃-phenyl | phenyl | 2-SiPh₃-phenyl |
| D4-1 | 1 | 1 | phenyl-1,3 | phenyl-1,3 | naphthalen-1-yl | biphenyl-4-yl | naphthalen-1-yl | biphenyl-2,4'-diyl |

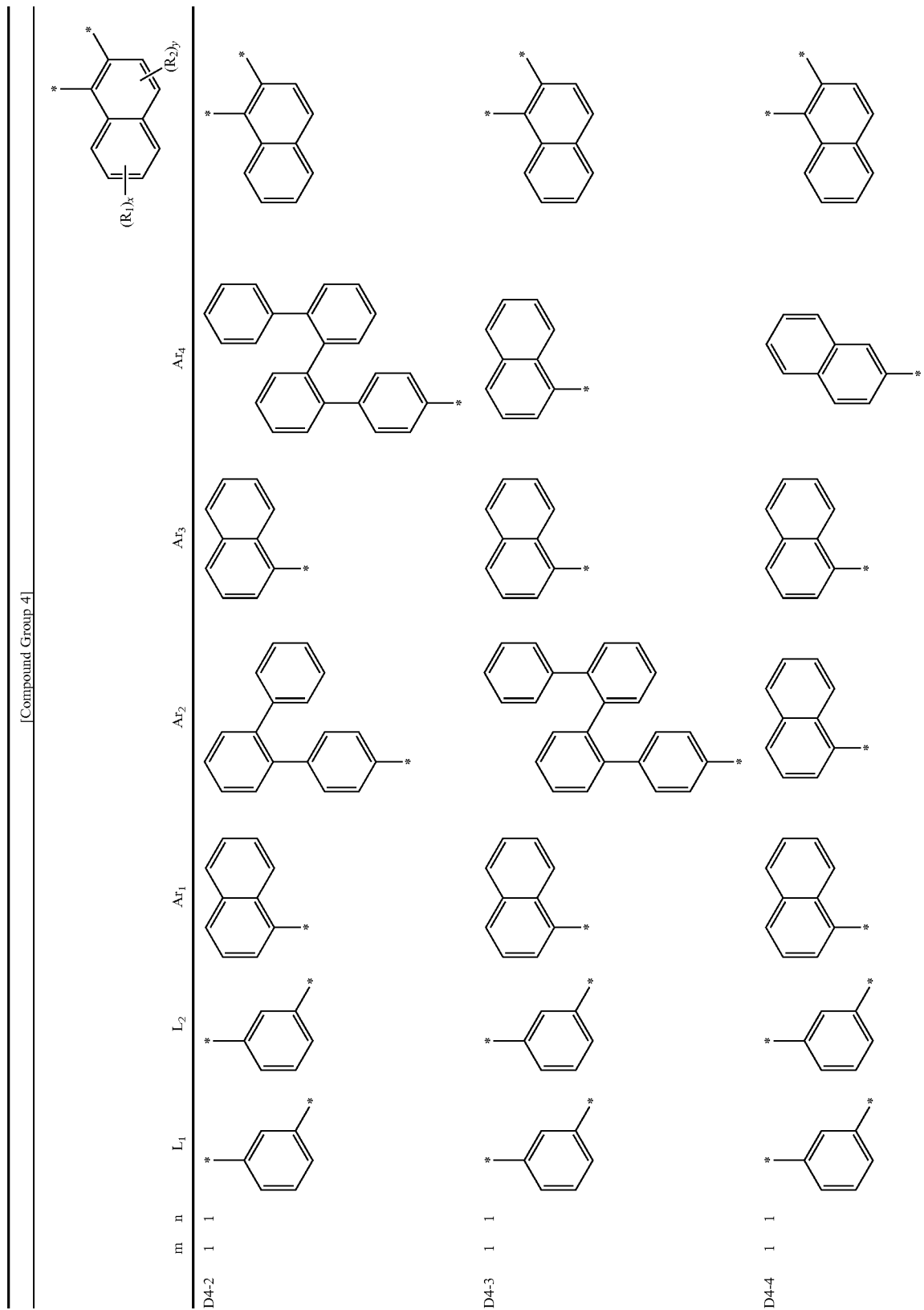

-continued
[Compound Group 4]
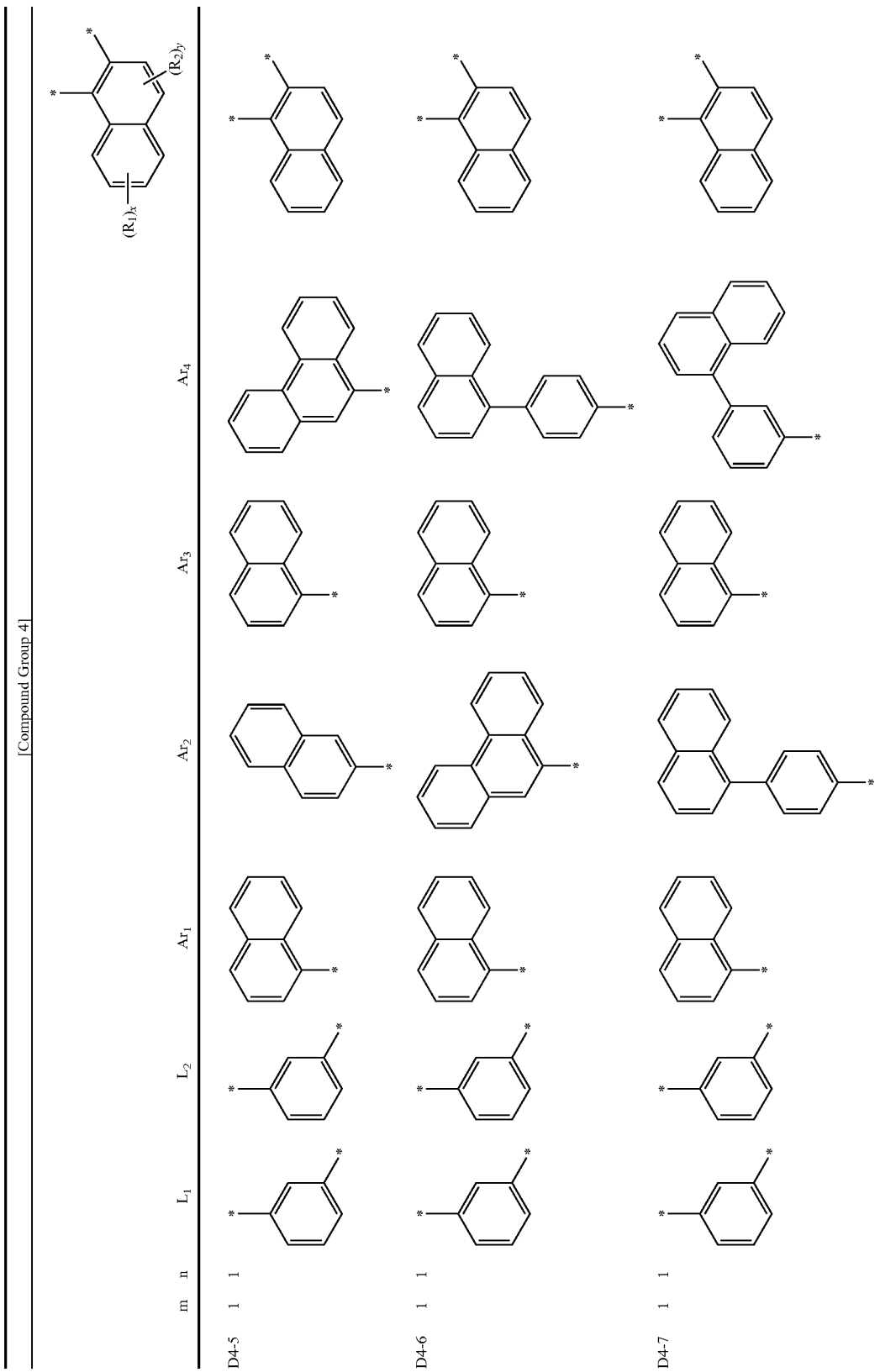

-continued

[Compound Group 4]




-continued

[Compound Group 4]

| | m | n | L₁ | L₂ | Ar₁ | Ar₂ | Ar₃ | Ar₄ | |
|---|---|---|---|---|---|---|---|---|---|
| D4-20 | 1 | 1 | | | | | | | |
| D4-21 | 1 | 1 | | | | | | | |
| D4-22 | 1 | 1 | | | | | | | |

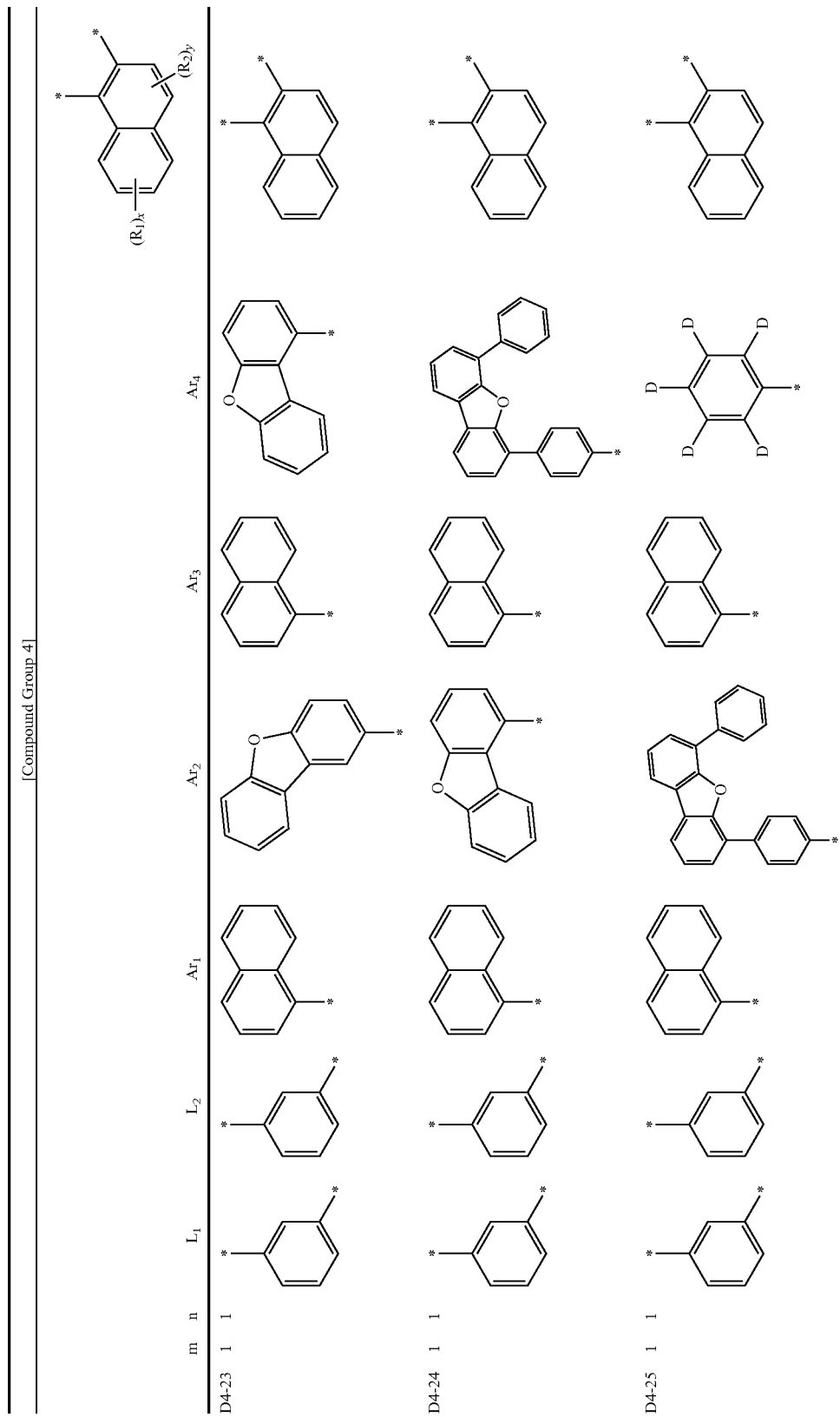

-continued
[Compound Group 4]
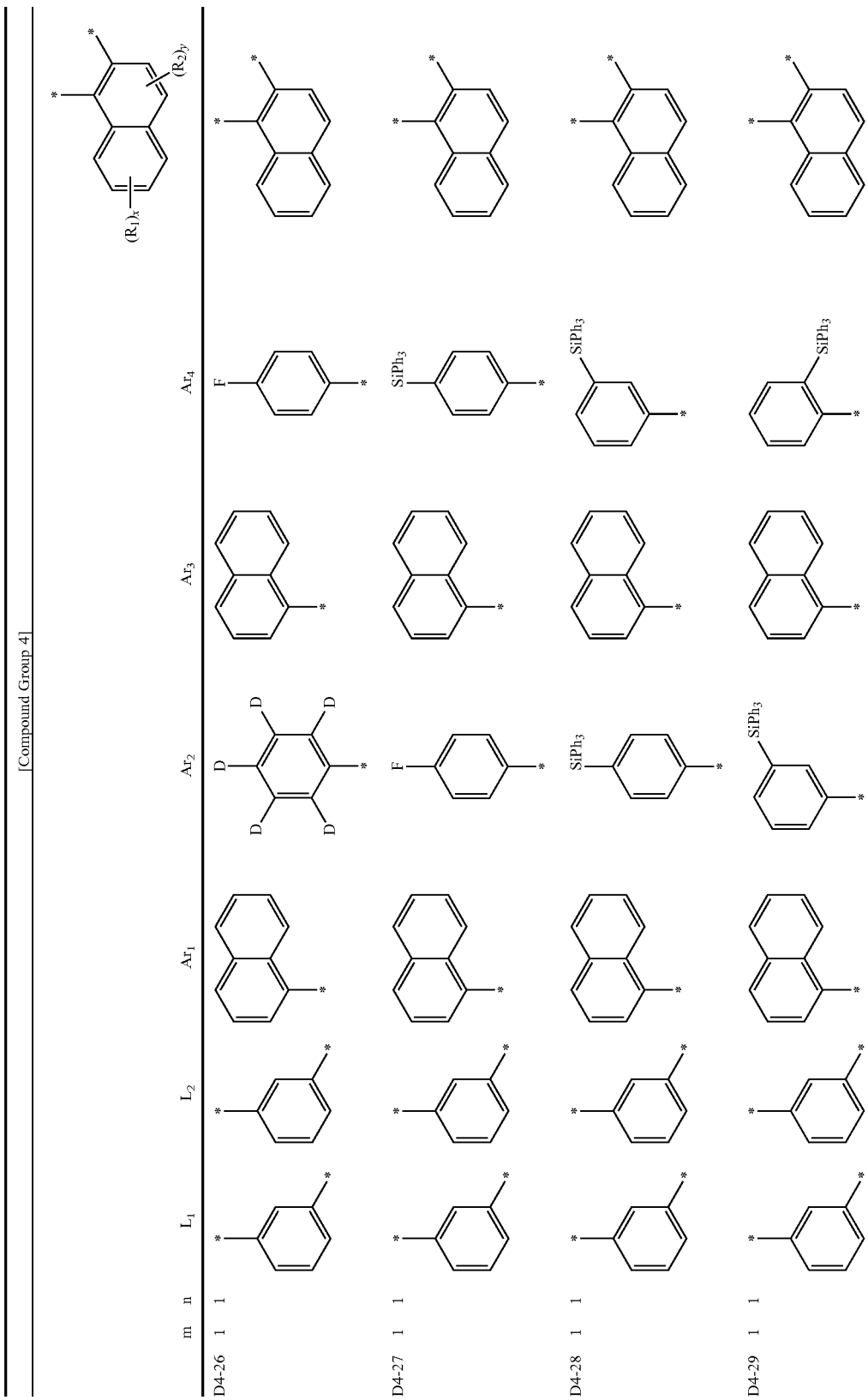

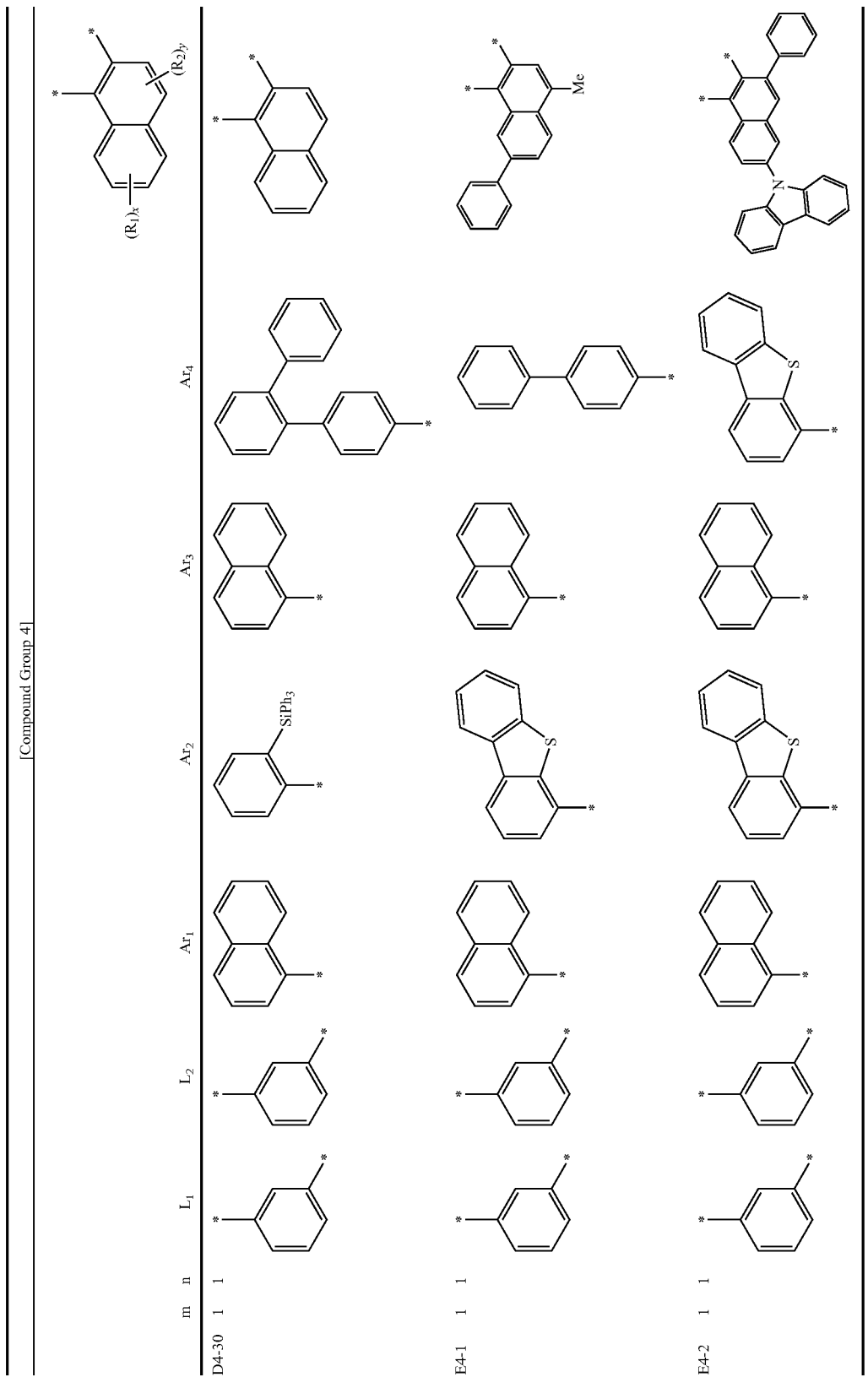

Compound Group 5

| | m | n | L₁ | L₂ | Ar₁ | Ar₂ | Ar₃ | Ar₄ | |
|---|---|---|---|---|---|---|---|---|---|
| A5-1 | 0 | 1 | — | naphthalene-1,4-diyl | phenyl | phenyl | phenyl | phenyl | naphthalen-1-yl (2-sub) |
| A5-2 | 0 | 1 | — | naphthalene-1,4-diyl | biphenyl | biphenyl | biphenyl | biphenyl | naphthalen-1-yl (2-sub) |
| A5-3 | 0 | 1 | — | naphthalene-1,4-diyl | phenyl | biphenyl | phenyl | biphenyl | naphthalen-1-yl (2-sub) |

-continued
Compound Group 5
| | m | n | L₁ | L₂ | Ar₁ | Ar₂ | Ar₃ | Ar₄ | (R₁)ₓ / (R₂)ᵧ |
|---|---|---|---|---|---|---|---|---|---|
| A5-4 | 0 | 1 | — | 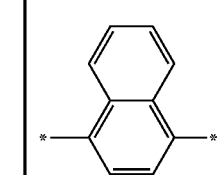 | 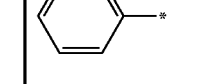 | 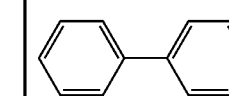 | 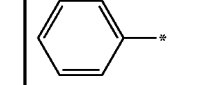 |  | 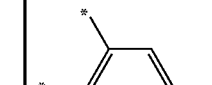 |
| A5-5 | 0 | 1 | — | 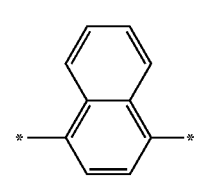 | 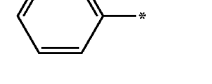 | 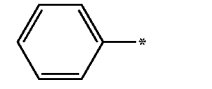 | 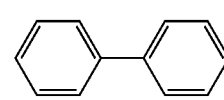 | 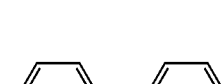 | 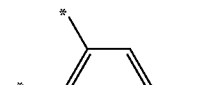 |

-continued
Compound Group 5
| | m | n | $L_1$ | $L_2$ | $Ar_1$ | $Ar_2$ | $Ar_3$ | $Ar_4$ | 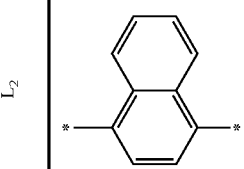 |
|---|---|---|---|---|---|---|---|---|---|
| A5-6 | 0 | 1 | — | 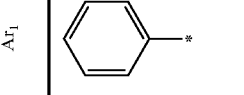 | 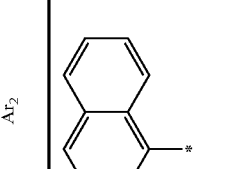 | 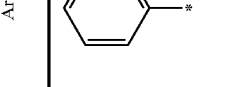 | 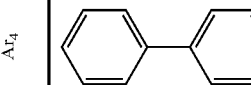 |  | 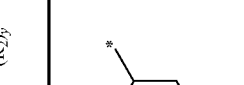 |
| A5-7 | 0 | 1 | — | 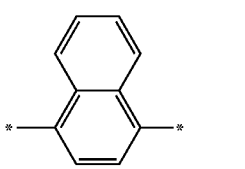 | 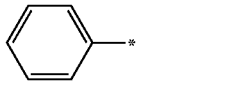 | 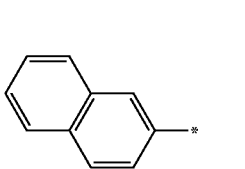 | 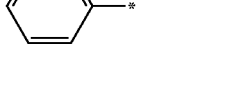 | 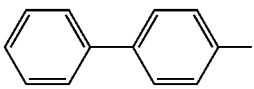 |  |
| A5-8 | 0 | 1 | — |  | 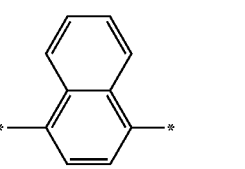 | 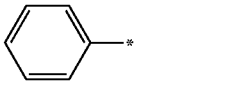 | 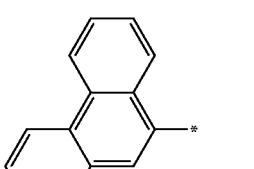 | 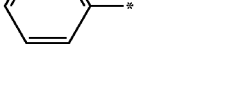 | 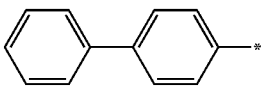 |

-continued
Compound Group 5
| | m | n | L₁ | L₂ | Ar₁ | Ar₂ | Ar₃ | Ar₄ |  |
|---|---|---|---|---|---|---|---|---|---|
| A5-9 | 0 | 1 | — | | | | | | |
| A5-10 | 0 | 1 | — | | | | | | |
| A5-11 | 0 | 1 | — | | | | | | |

-continued
Compound Group 5
| | m | n | L₁ | L₂ | Ar₁ | Ar₂ | Ar₃ | Ar₄ | 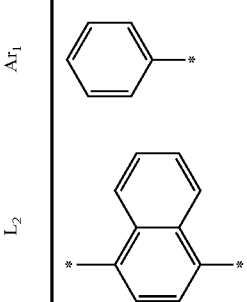 |
|---|---|---|---|---|---|---|---|---|---|
| A5-12 | 0 | 1 | — | 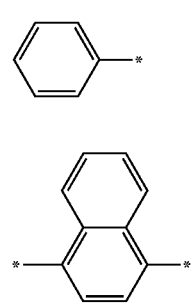 | 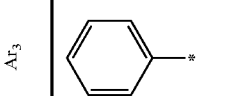 | 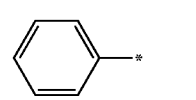 | 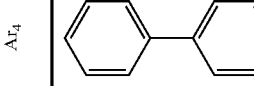 | 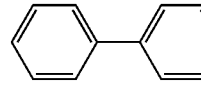 |  |
| A5-13 | 0 | 1 | — |  | 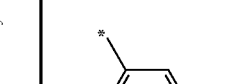 | 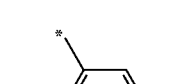 |  |  | |

-continued
Compound Group 5
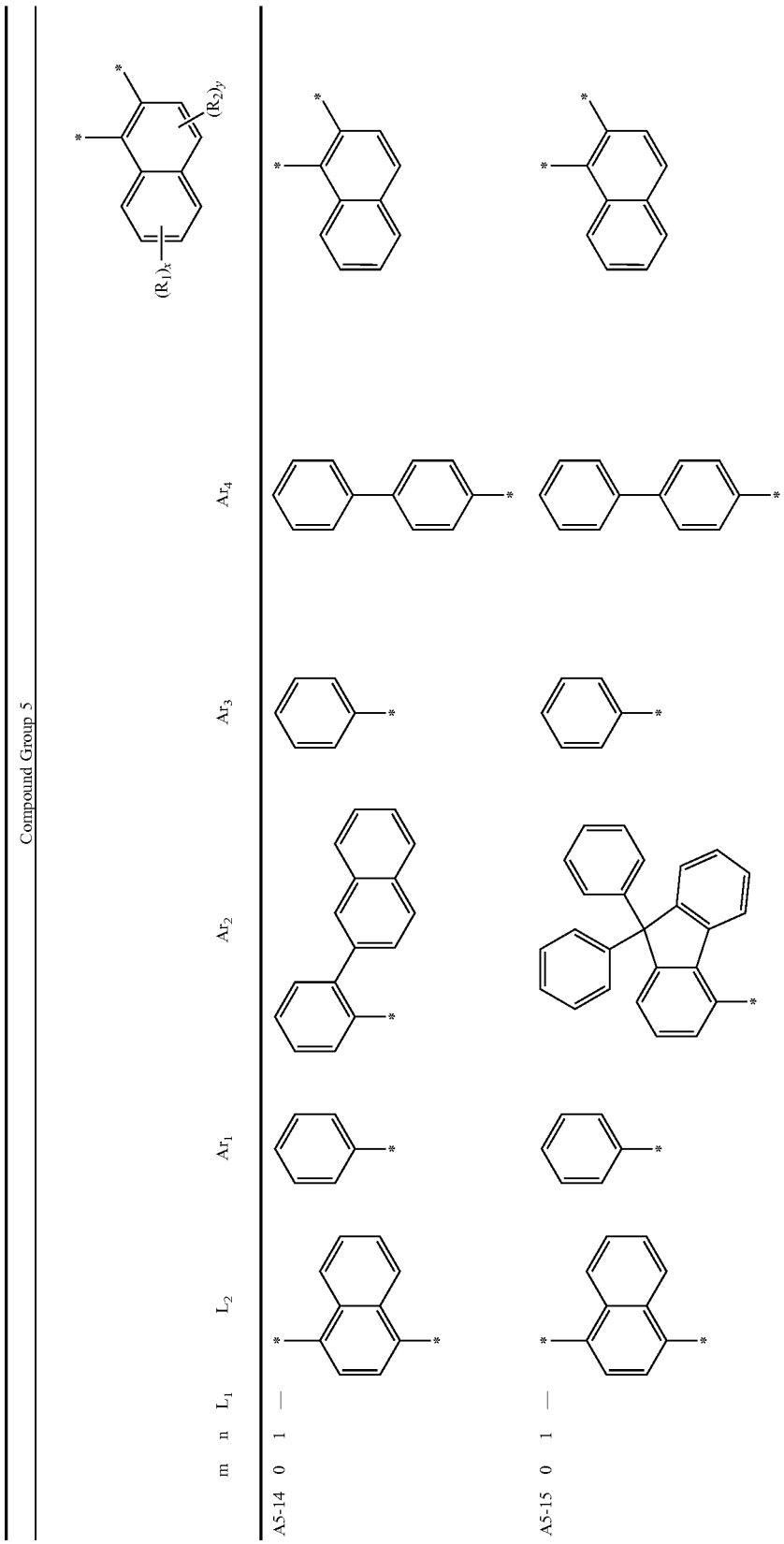

-continued
Compound Group 5
| | m | n | L₁ | L₂ | Ar₁ | Ar₂ | Ar₃ | Ar₄ | 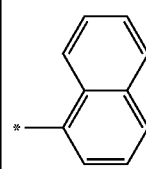 |
|---|---|---|---|---|---|---|---|---|---|
| A5-16 | 0 | 1 | — | 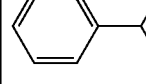 | 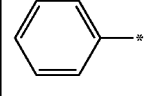 | 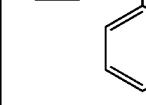 |  |  | 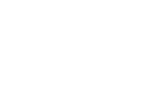 |
| A5-17 | 0 | 1 | — | 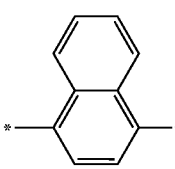 | 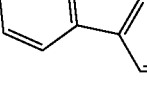 | 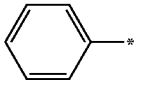 |  |  |  |

-continued
Compound Group 5
| | m | n | L₁ | L₂ | Ar₁ | Ar₂ | Ar₃ | Ar₄ | 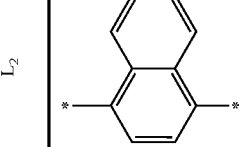 |
|---|---|---|---|---|---|---|---|---|---|
| A5-18 | 0 | 1 | — | 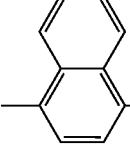 |  |  |  |  | 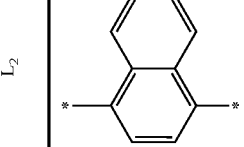 |
| A5-19 | 0 | 1 | — | 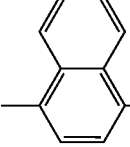 |  |  |  |  | 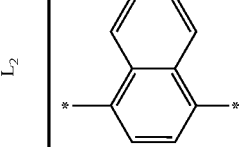 |
| A5-20 | 0 | 1 | — | 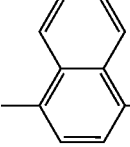 |  |  |  |  | |

-continued

Compound Group 5

| | m | n | L₁ | L₂ | Ar₁ | Ar₂ | Ar₃ | Ar₄ | |
|---|---|---|---|---|---|---|---|---|---|
| A5-21 | 0 | 1 | — | naphthalene-1,4-diyl | phenyl | dibenzothiophen-2-yl | phenyl | biphenyl-4-yl | naphthalene |
| A5-22 | 0 | 1 | — | naphthalene-1,4-diyl | phenyl | dibenzothiophen-4-yl | phenyl | biphenyl-4-yl | naphthalene |
| A5-23 | 0 | 1 | — | naphthalene-1,4-diyl | phenyl | dibenzofuran-4-yl | phenyl | biphenyl-4-yl | naphthalene |

-continued
Compound Group 5
| m | n | L₁ | L₂ | Ar₁ | Ar₂ | Ar₃ | Ar₄ | 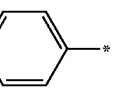 |
|---|---|---|---|---|---|---|---|---|
| A5-24 | 0 | 1 | — | 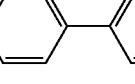 | 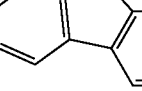 | 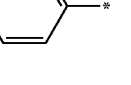 | 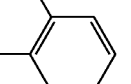 |  |  |
| A5-25 | 0 | 1 | — | 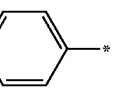 | 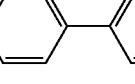 | 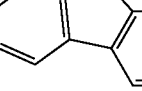 | 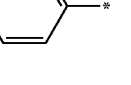 | 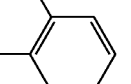 |  |
| A5-26 | 0 | 1 | — |  | 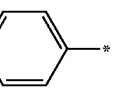 | 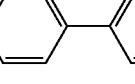 | 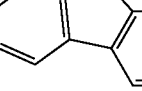 | 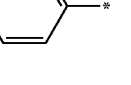 | 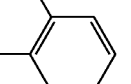 |

-continued
Compound Group 5
| | m | n | L₁ | L₂ | Ar₁ | Ar₂ | Ar₃ | Ar₄ | 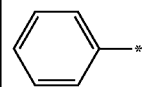 |
|---|---|---|---|---|---|---|---|---|---|
| A5-27 | 0 | 1 | — | 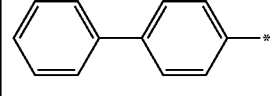 | 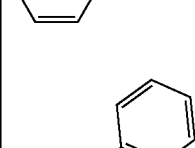 | 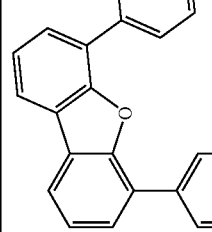 |  | 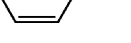 |  |
| A5-28 | 0 | 1 | — |  | 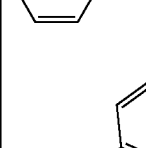 |  | 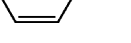 | 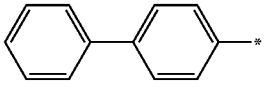 |  |

-continued
Compound Group 5
| | m | n | L₁ | L₂ | Ar₁ | Ar₂ | Ar₃ | Ar₄ | 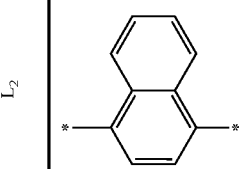 |
|---|---|---|---|---|---|---|---|---|---|
| A5-29 | 0 | 1 | — | 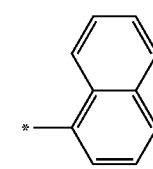 | 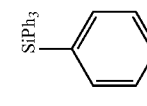 | 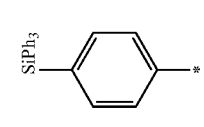 | 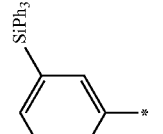 | 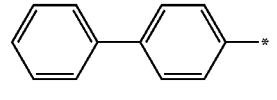 | 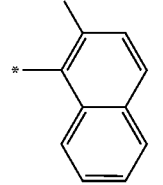 |
| A5-30 | 0 | 1 | — | 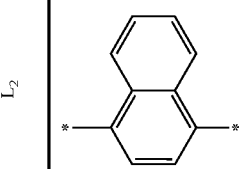 | 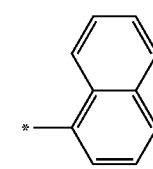 | 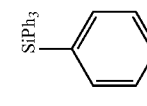 | 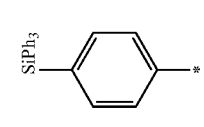 | 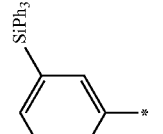 | 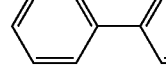 |
| A5-31 | 0 | 1 | — | 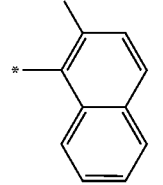 | 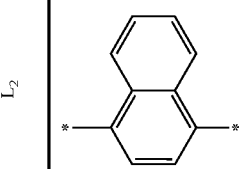 | 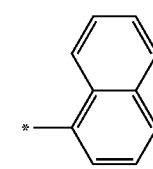 | 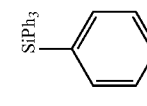 | 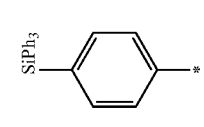 | 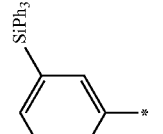 |

-continued
Compound Group 5
| | m | n | L₁ | L₂ | Ar₁ | Ar₂ | Ar₃ | Ar₄ | 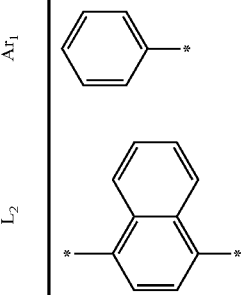 |
|---|---|---|---|---|---|---|---|---|---|
| A5-32 | 0 | 1 | — | 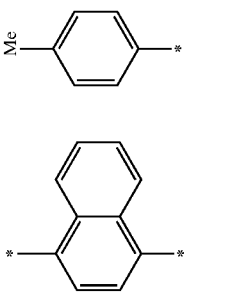 |  |  | 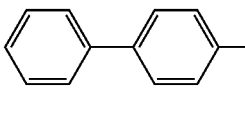 | 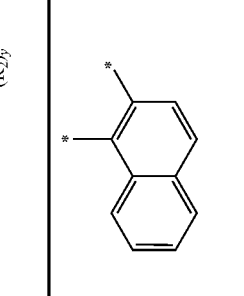 |  |
| A5-33 | 0 | 1 | — | 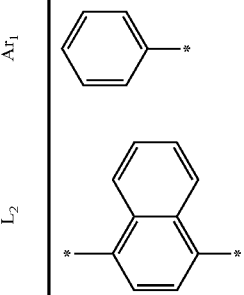 | 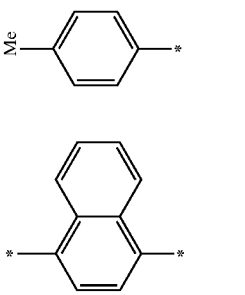 |  |  | 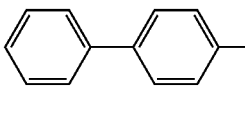 |  |
| B5-1 | 0 | 1 | — |  |  |  | 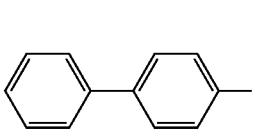 | 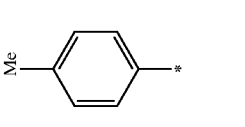 | 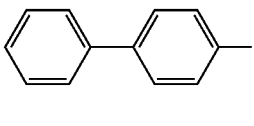 |

-continued
Compound Group 5
| m | n | L₁ | L₂ | Ar₁ | Ar₂ | Ar₃ | Ar₄ | 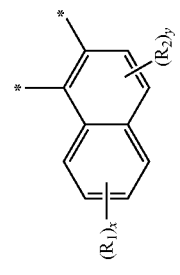 |
|---|---|---|---|---|---|---|---|---|
| B5-2 | 0 | 1 | — | 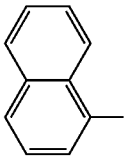 | 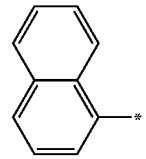 | 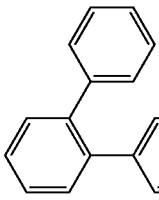 | 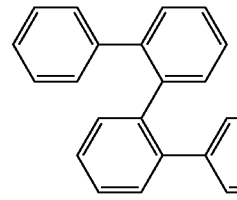 | 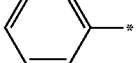 |
| B5-3 | 0 | 1 | — | 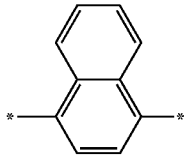 | 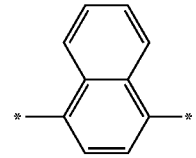 | | | |

-continued
Compound Group 5
| | m | n | L₁ | L₂ | Ar₁ | Ar₂ | Ar₃ | Ar₄ | 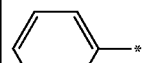 |
|---|---|---|---|---|---|---|---|---|---|
| B5-4 | 0 | 1 | — | 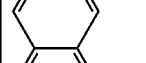 | 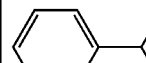 | 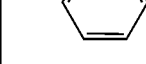 |  |  | 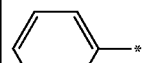 |
| B5-5 | 0 | 1 | — | 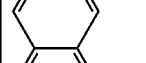 | 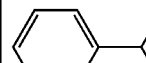 | 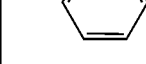 |  |  | 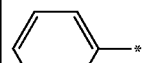 |
| B5-6 | 0 | 1 | — | 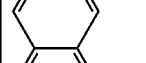 | 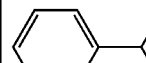 | 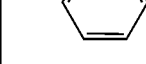 |  |  | |

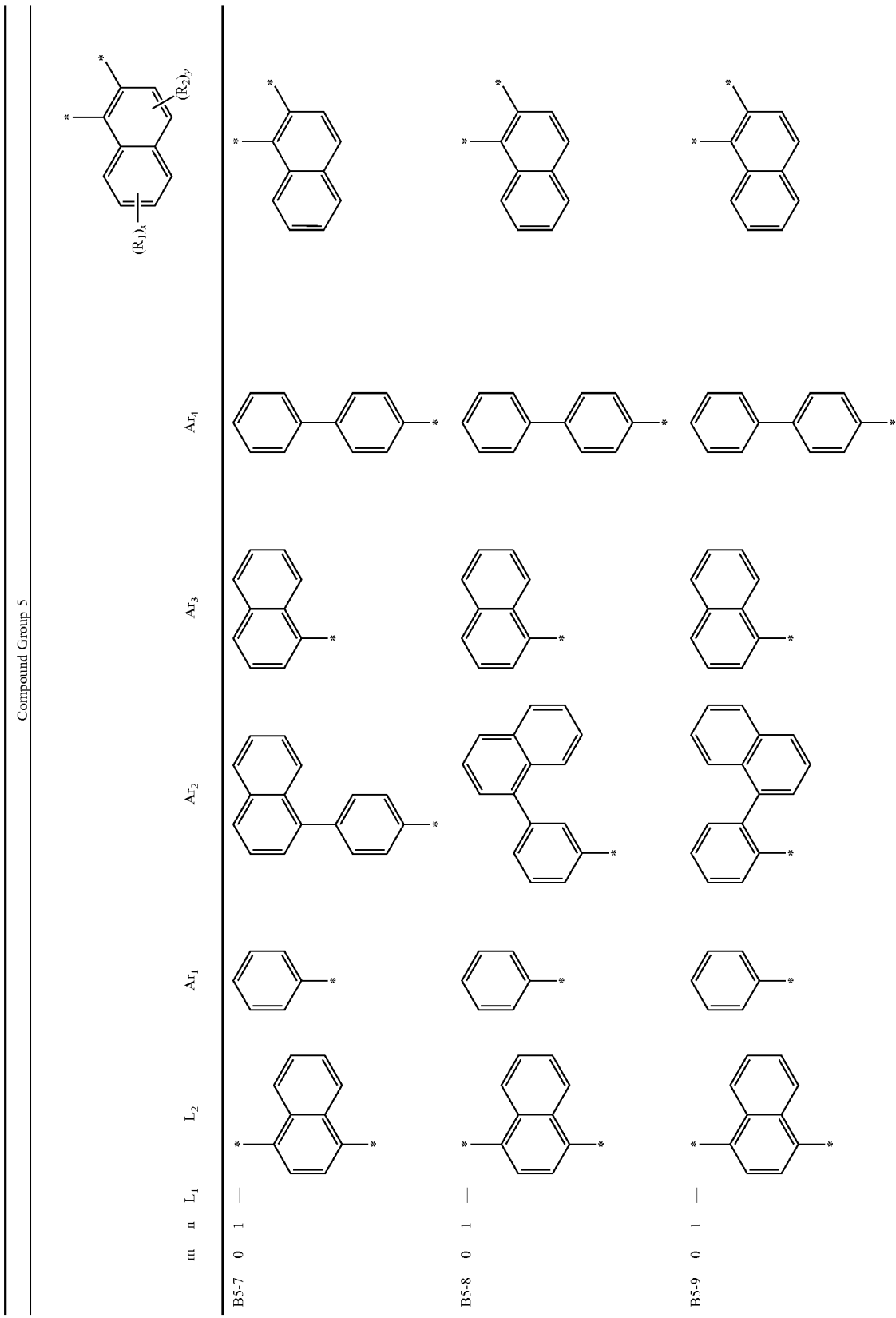

-continued
Compound Group 5
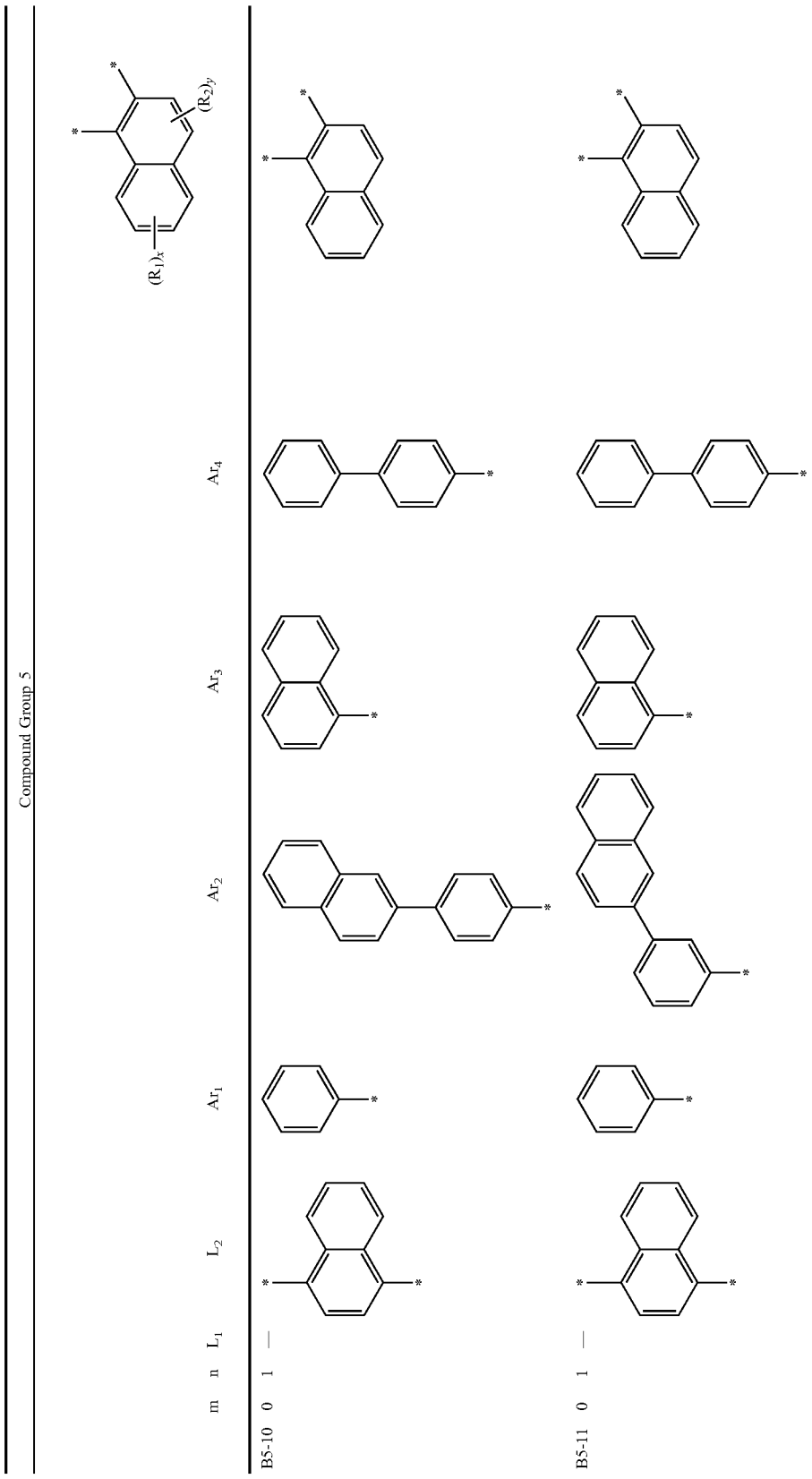

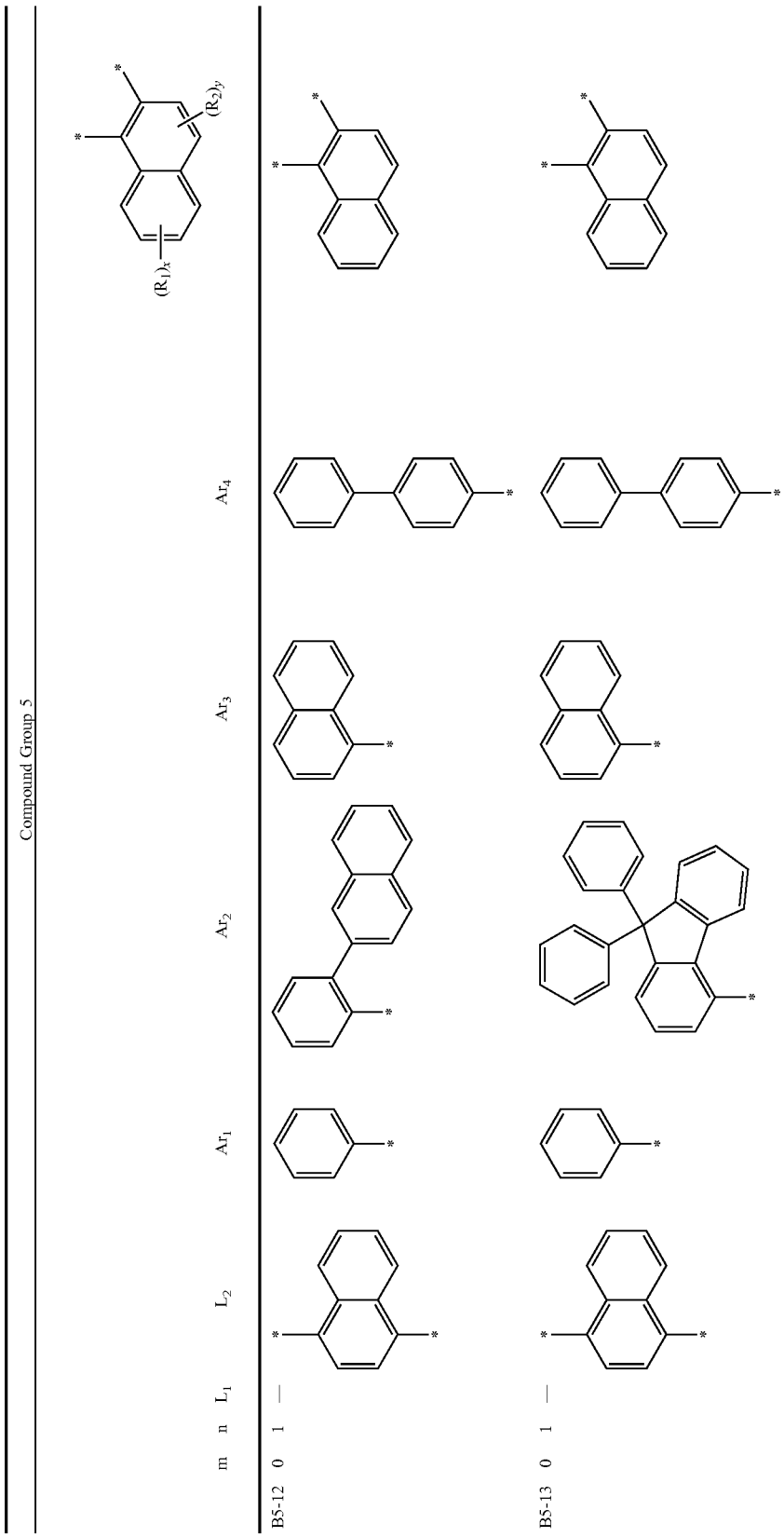

-continued
Compound Group 5
| | m | n | L$_1$ | L$_2$ | Ar$_1$ | Ar$_2$ | Ar$_3$ | Ar$_4$ | 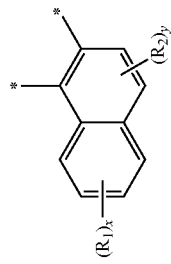 |
|---|---|---|---|---|---|---|---|---|---|
| B5-14 | 0 | 1 | — | 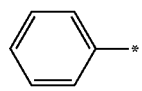 | 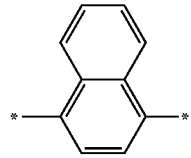 | 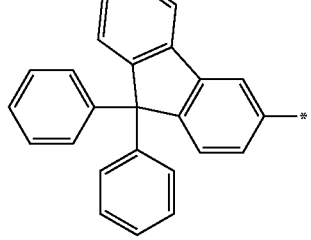 | 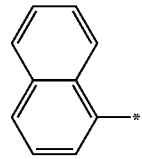 |  | 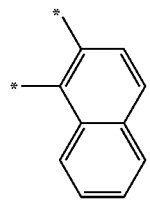 |
| B5-15 | 0 | 1 | — | 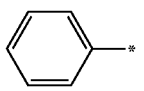 | 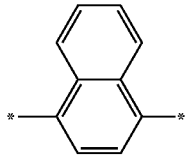 | 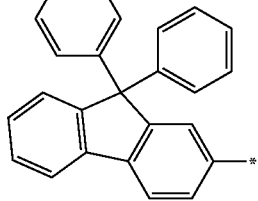 | 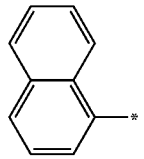 | 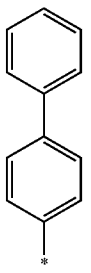 | 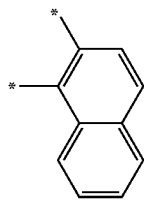 |

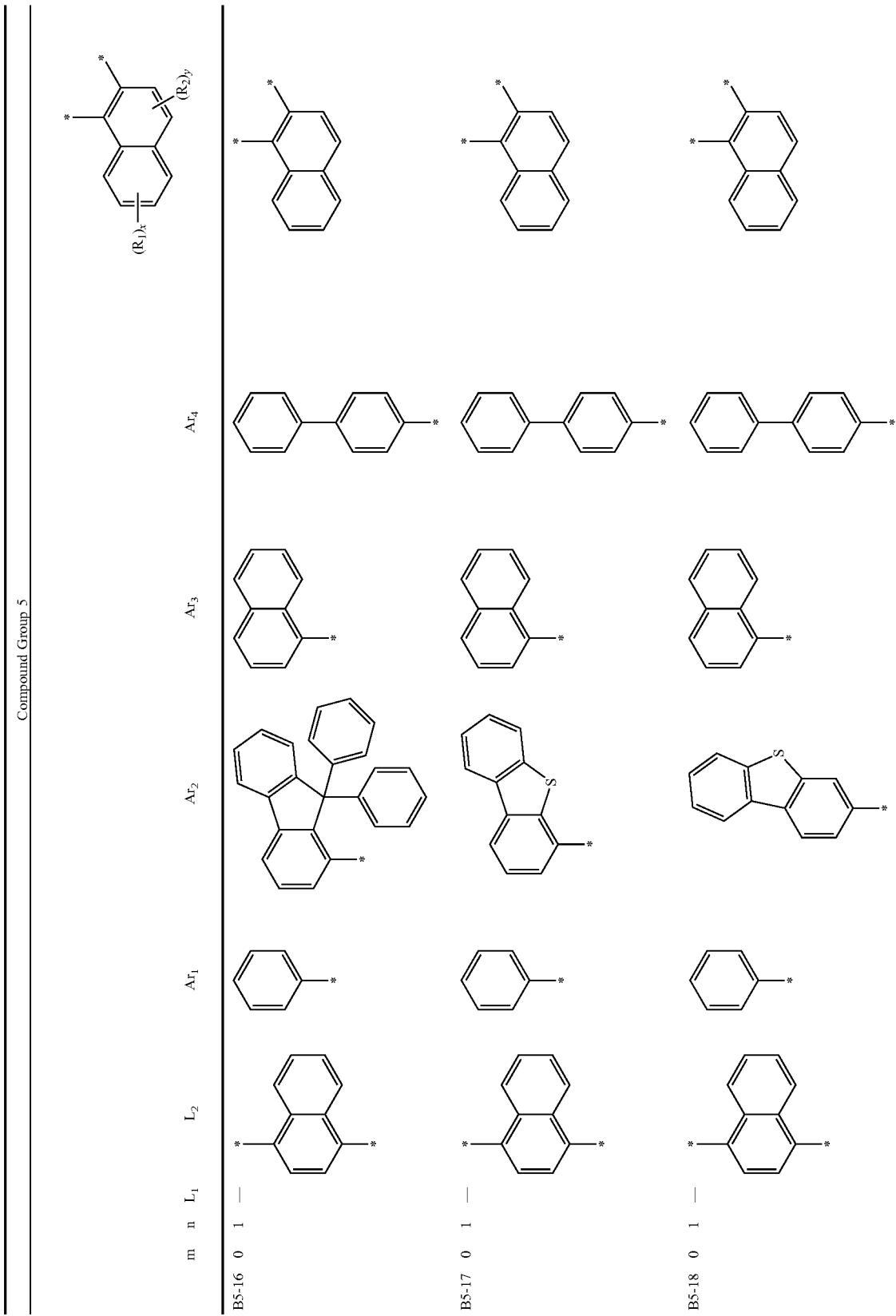

-continued

Compound Group 5

| | m | n | L₁ | L₂ | Ar₁ | Ar₂ | Ar₃ | Ar₄ | |
|---|---|---|---|---|---|---|---|---|---|
| B5-19 | 0 | 1 | — | naphthalene-1,4-diyl | phenyl | dibenzothiophen-2-yl | naphthalen-1-yl | biphenyl | naphthalene |
| B5-20 | 0 | 1 | — | naphthalene-1,4-diyl | phenyl | dibenzothiophen-4-yl | naphthalen-1-yl | biphenyl | naphthalene |
| B5-21 | 0 | 1 | — | naphthalene-1,4-diyl | phenyl | dibenzofuran-4-yl | naphthalen-1-yl | biphenyl | naphthalene |

-continued

Compound Group 5

| | m | n | L₁ | L₂ | Ar₁ | Ar₂ | Ar₃ | Ar₄ | (R₁)ₓ / (R₂)ᵧ naphthyl |
|---|---|---|---|---|---|---|---|---|---|
| B5-22 | 0 | 1 | — | 1,4-naphthylene | phenyl | dibenzofuran-3-yl | naphthalen-1-yl | biphenyl-4-yl | 1,2-naphthyl |
| B5-23 | 0 | 1 | — | 1,4-naphthylene | phenyl | dibenzofuran-2-yl | naphthalen-1-yl | biphenyl-4-yl | 1,2-naphthyl |
| B5-24 | 0 | 1 | — | 1,4-naphthylene | phenyl | dibenzofuran-4-yl | naphthalen-1-yl | biphenyl-4-yl | 1,2-naphthyl |

-continued
Compound Group 5
| | m | n | L₁ | L₂ | Ar₁ | Ar₂ | Ar₃ | Ar₄ | |
|---|---|---|---|---|---|---|---|---|---|
| B5-25 | 0 | 1 | — | 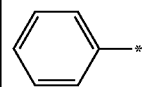 | 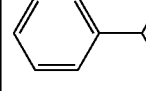 | 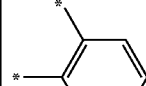 | 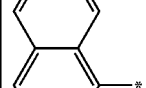 |  |  |
| B5-26 | 0 | 1 | — | 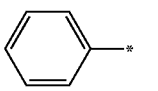 | 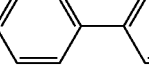 | 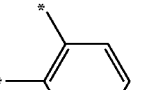 | 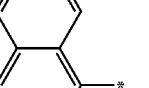 | 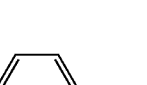 |  |

-continued
Compound Group 5
| | m | n | L₁ | L₂ | Ar₁ | Ar₂ | Ar₃ | Ar₄ | 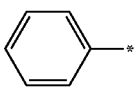 |
|---|---|---|---|---|---|---|---|---|---|
| B5-27 | 0 | 1 | — | 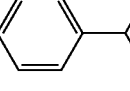 | 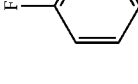 | 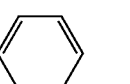 |  |  | 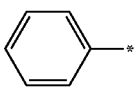 |
| B5-28 | 0 | 1 | — | 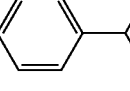 | 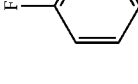 | 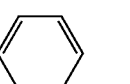 |  |  | 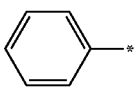 |
| B5-29 | 0 | 1 | — | 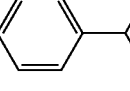 | 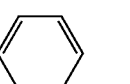 |  |  |  |  |

-continued
Compound Group 5
| | m | n | $L_1$ | $L_2$ | $Ar_1$ | $Ar_2$ | $Ar_3$ | $Ar_4$ |  |
|---|---|---|---|---|---|---|---|---|---|
| B5-30 | 0 | 1 | — |  |  |  | 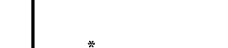 | 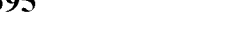 |  |
| C5-1 | 0 | 1 | — |  |  |  | 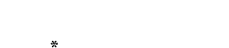 |  |  |
| C5-2 | 0 | 1 | — |  |  | 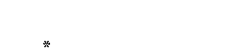 | | | |

-continued
Compound Group 5
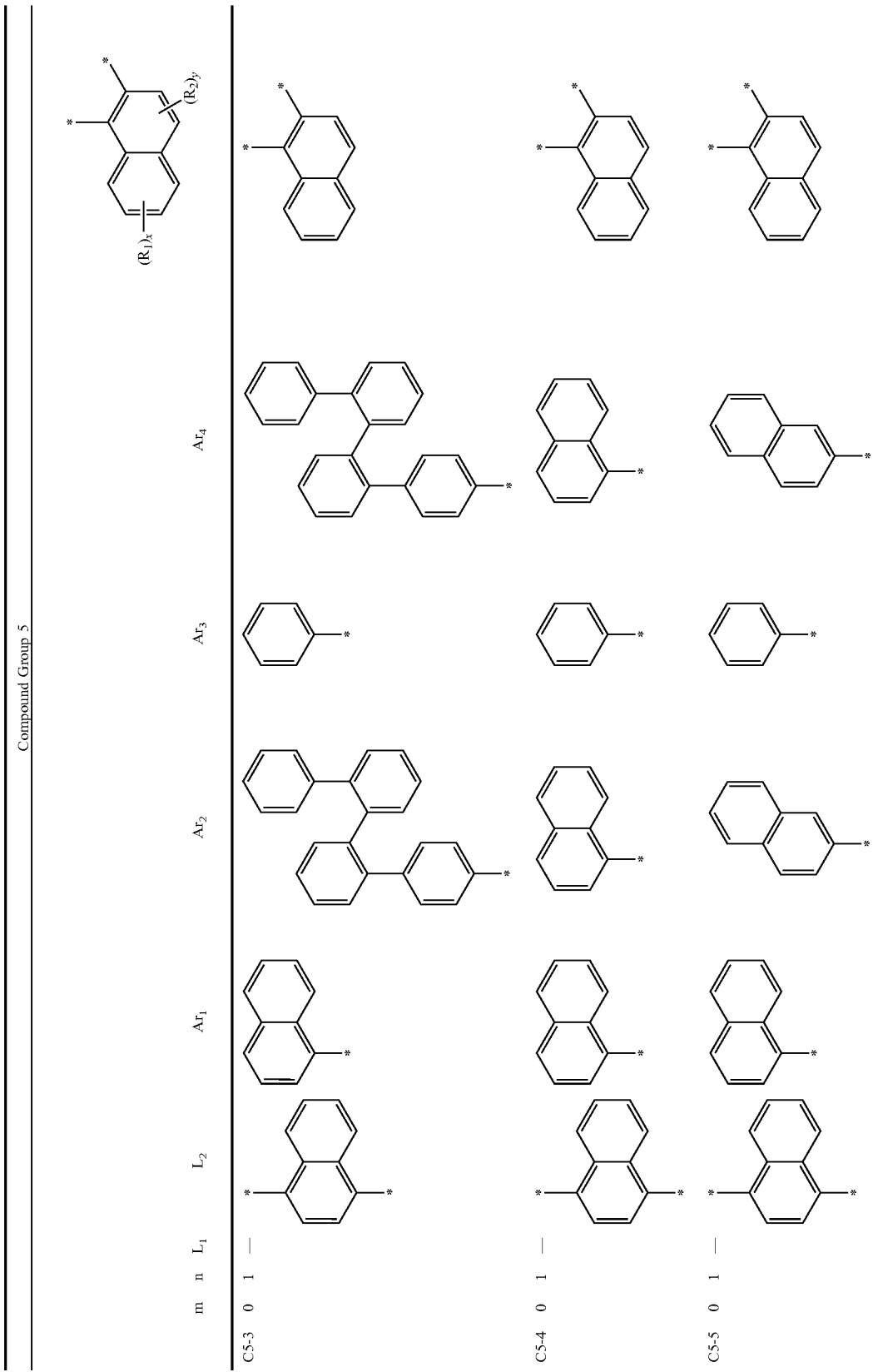

-continued
Compound Group 5
| | m | n | L₁ | L₂ | Ar₁ | Ar₂ | Ar₃ | Ar₄ | 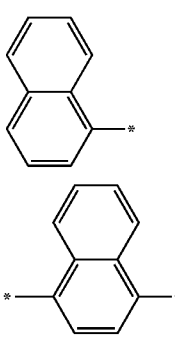 |
|---|---|---|---|---|---|---|---|---|---|
| C5-6 | 0 | 1 | — | 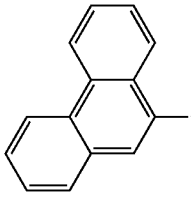 | 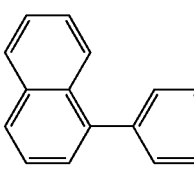 | 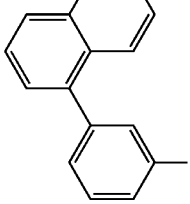 | 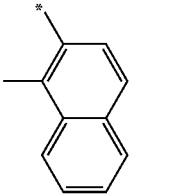 | 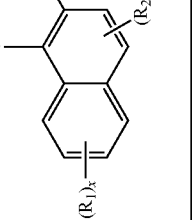 | 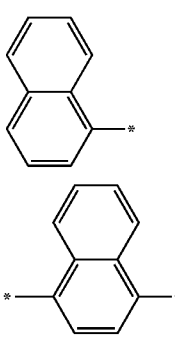 |
| C5-7 | 0 | 1 | — | 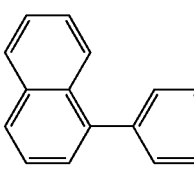 | 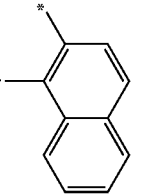 | 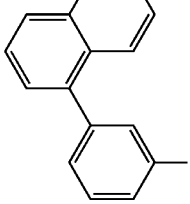 | 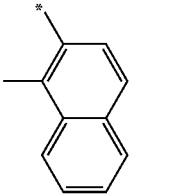 | 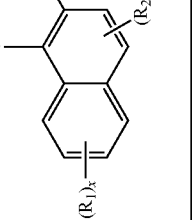 | 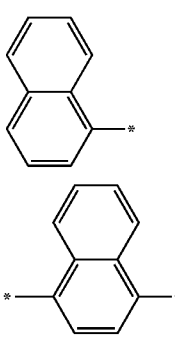 |
| C5-8 | 0 | 1 | — | 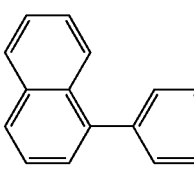 | 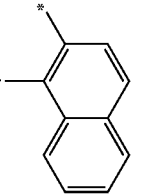 | 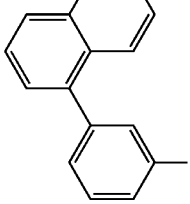 | 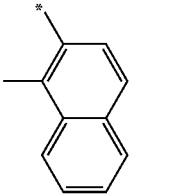 | 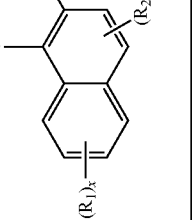 | |

-continued
Compound Group 5
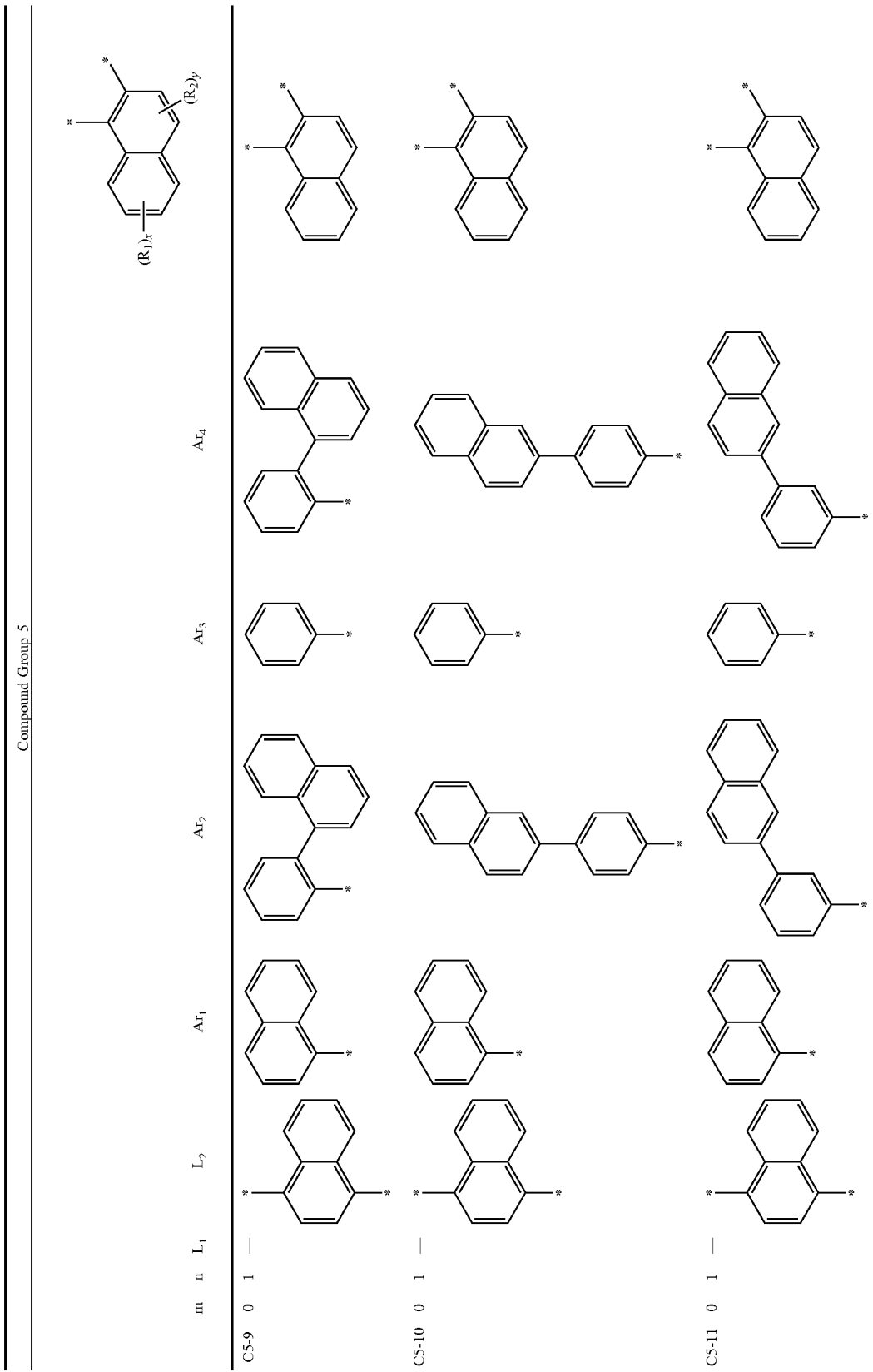

-continued
Compound Group 5
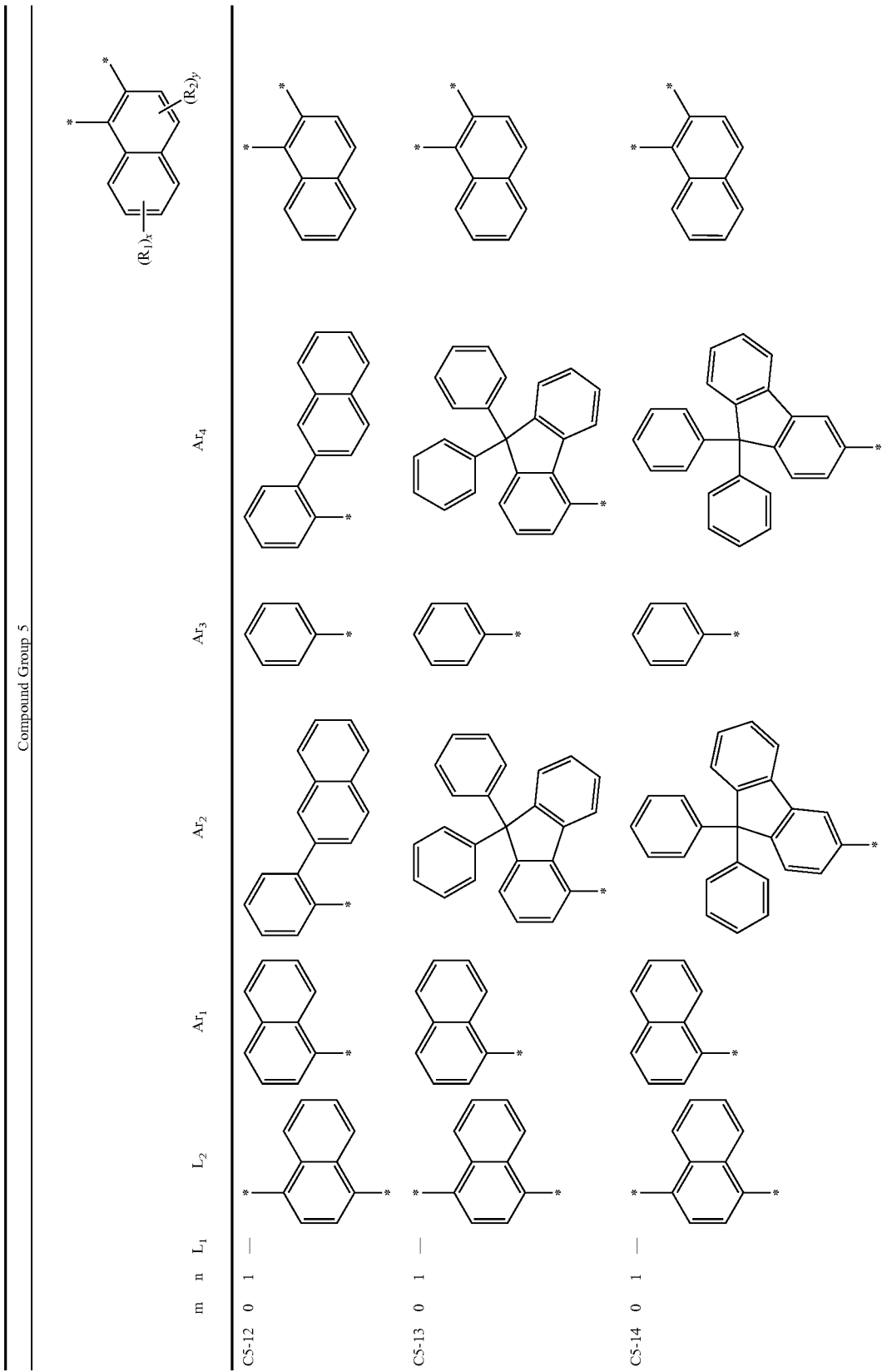

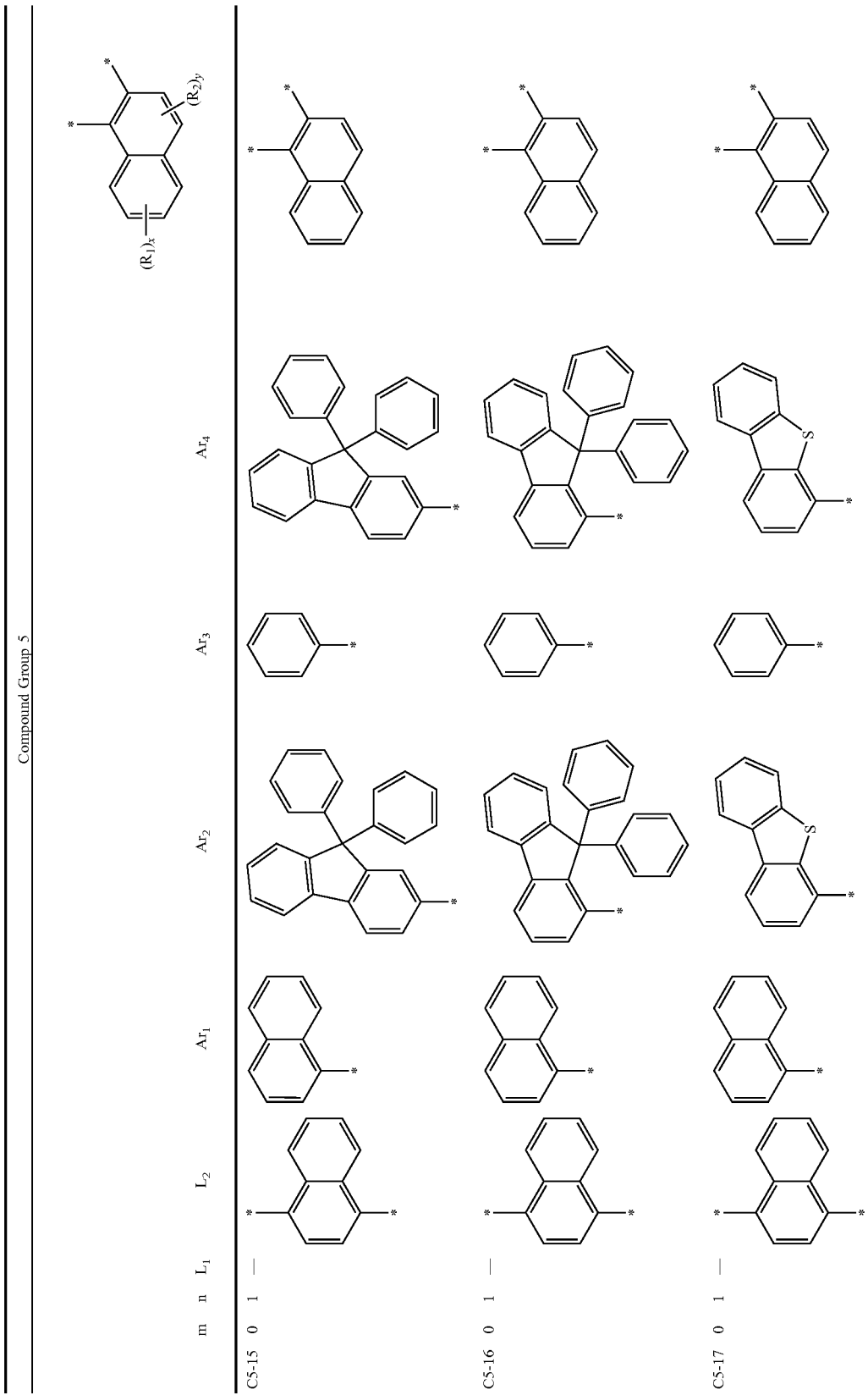

-continued
Compound Group 5
| | m | n | L₁ | L₂ | Ar₁ | Ar₂ | Ar₃ | Ar₄ | 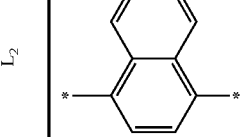 |
|---|---|---|---|---|---|---|---|---|---|
| C5-18 | 0 | 1 | — | 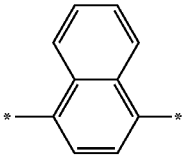 | 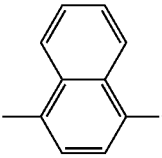 | 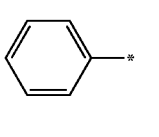 | 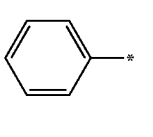 | 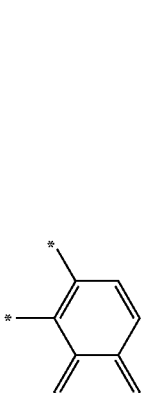 | 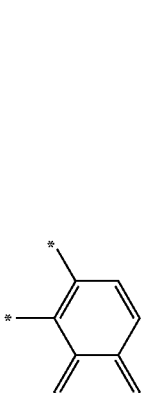 |
| C5-19 | 0 | 1 | — | 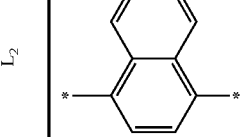 | 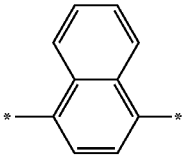 | 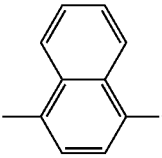 | 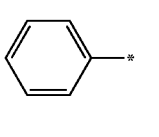 | 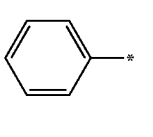 | 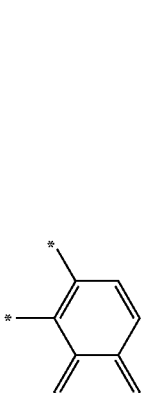 |
| C5-20 | 0 | 1 | — | 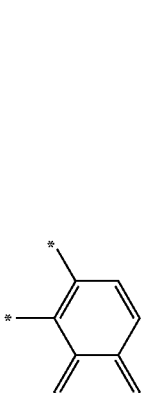 | 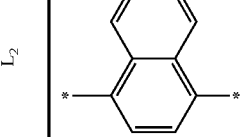 | 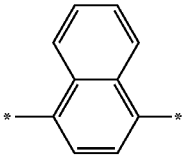 | 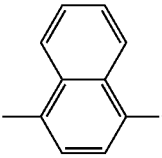 | 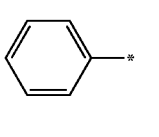 | 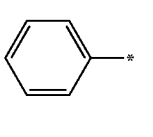 |

-continued
Compound Group 5
| | m | n | L₁ | L₂ | Ar₁ | Ar₂ | Ar₃ | Ar₄ | 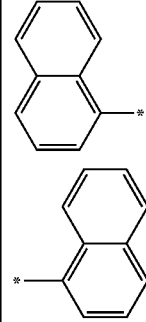 |
|---|---|---|---|---|---|---|---|---|---|
| C5-21 | 0 | 1 | — | 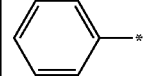 | 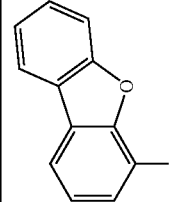 | 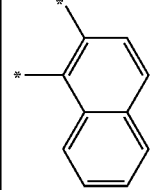 | 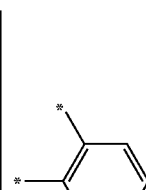 | 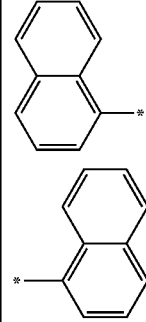 | 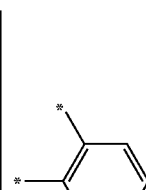 |
| C5-22 | 0 | 1 | — | 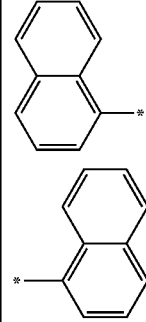 | 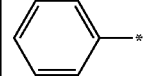 | 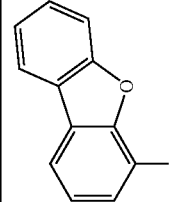 | 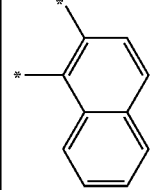 | 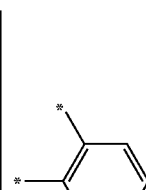 | 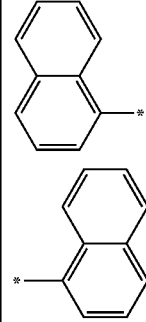 |
| C5-23 | 0 | 1 | — | 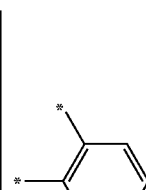 | 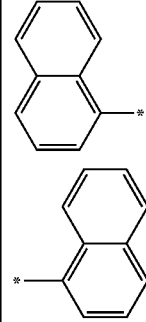 | 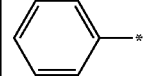 | 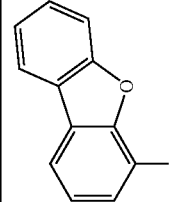 | 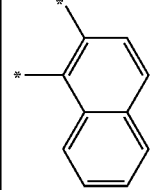 | 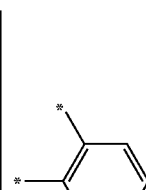 |

-continued
Compound Group 5
| | m | n | L₁ | L₂ | Ar₁ | Ar₂ | Ar₃ | Ar₄ | 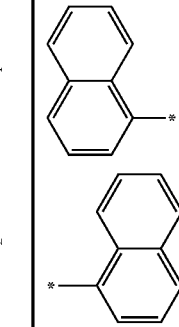 |
|---|---|---|---|---|---|---|---|---|---|
| C5-24 | 0 | 1 | — |  | 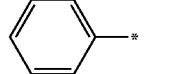 | 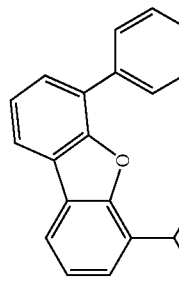 | 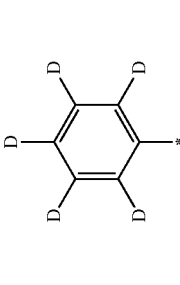 | 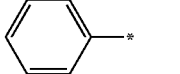 | 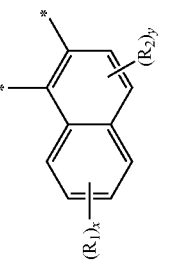 |
| C5-25 | 0 | 1 | — | 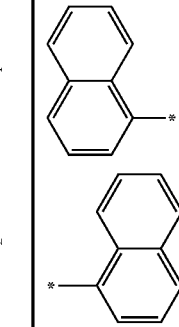 |  | 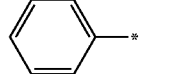 | 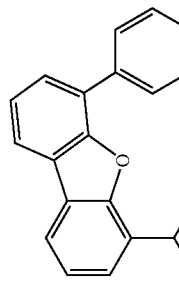 | 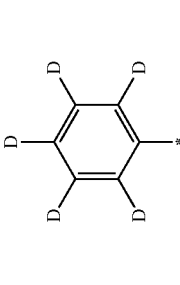 | 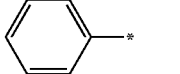 |
| C5-26 | 0 | 1 | — | 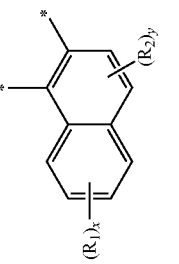 | 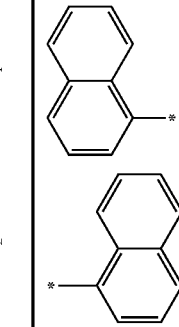 |  | 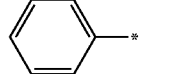 | 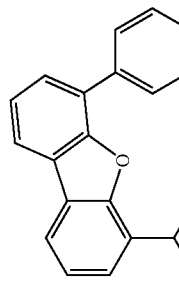 | 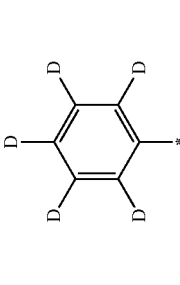 |

-continued
Compound Group 5
| | m | n | L₁ | L₂ | Ar₁ | Ar₂ | Ar₃ | Ar₄ | |
|---|---|---|---|---|---|---|---|---|---|
| C5-27 | 0 | 1 | — |  |  |  |  |  |  |
| C5-28 | 0 | 1 | — |  |  |  |  |  |  |
| C5-29 | 0 | 1 | — |  |  |  |  |  |  |
| C5-30 | 0 | 1 | — |  |  | | | | |

-continued
Compound Group 5
| | m | n | L₁ | L₂ | Ar₁ | Ar₂ | Ar₃ | Ar₄ | 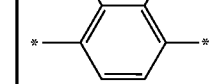 |
|---|---|---|---|---|---|---|---|---|---|
| D5-1 | 0 | 1 | — | 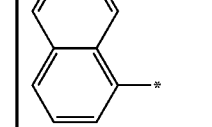 | 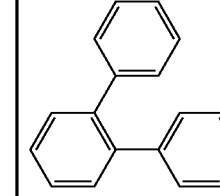 | 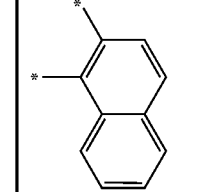 |  | 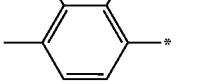 | 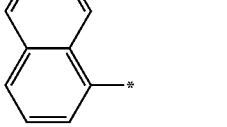 |
| D5-2 | 0 | 1 | — | 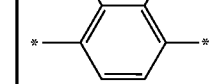 | 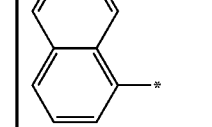 | 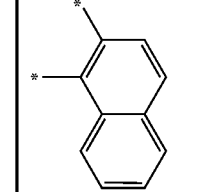 |  | 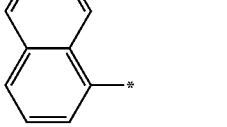 | 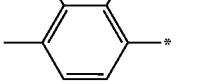 |

-continued
Compound Group 5
| | m | n | L₁ | L₂ | Ar₁ | Ar₂ | Ar₃ | Ar₄ | 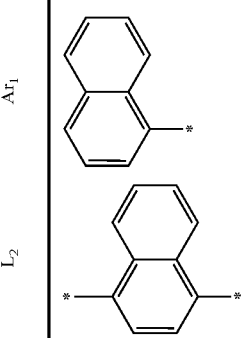 |
|---|---|---|---|---|---|---|---|---|---|
| D5-3 | 0 | 1 | — | 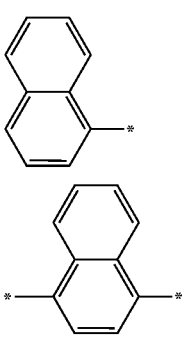 | 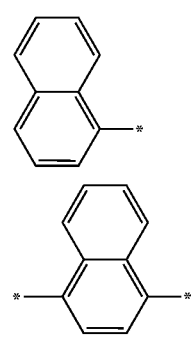 | 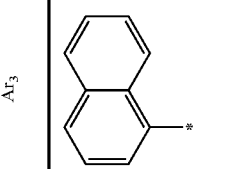 | 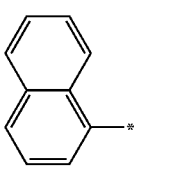 | 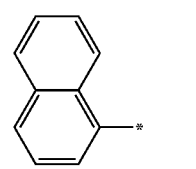 | 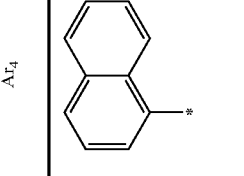 |
| D5-4 | 0 | 1 | — | 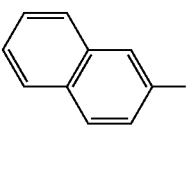 | 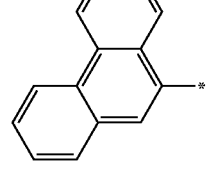 | 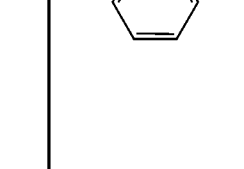 | 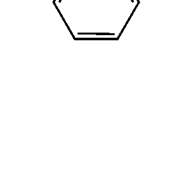 | 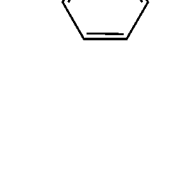 | 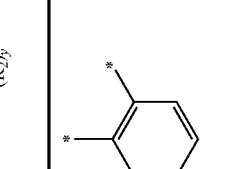 |
| D5-5 | 0 | 1 | — | 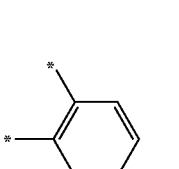 | 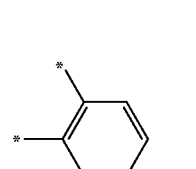 | 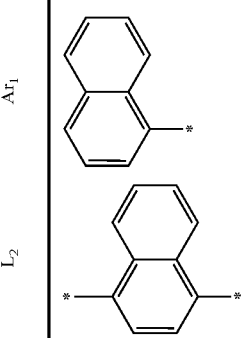 | 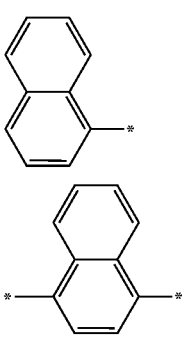 | 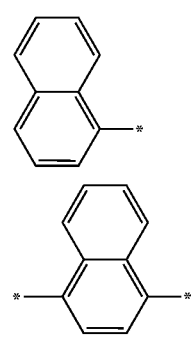 | 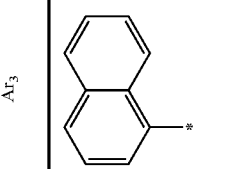 |

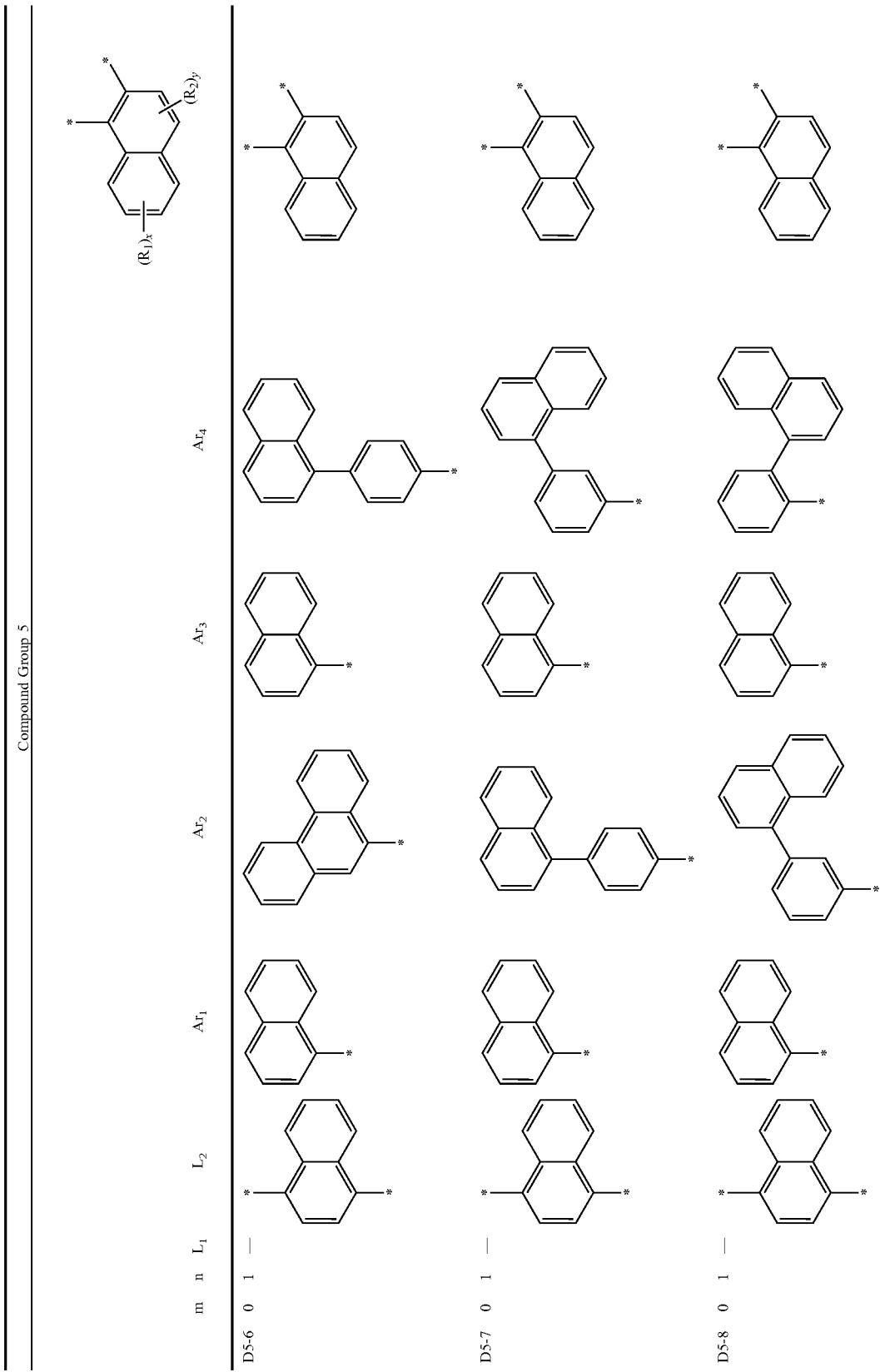

-continued
Compound Group 5
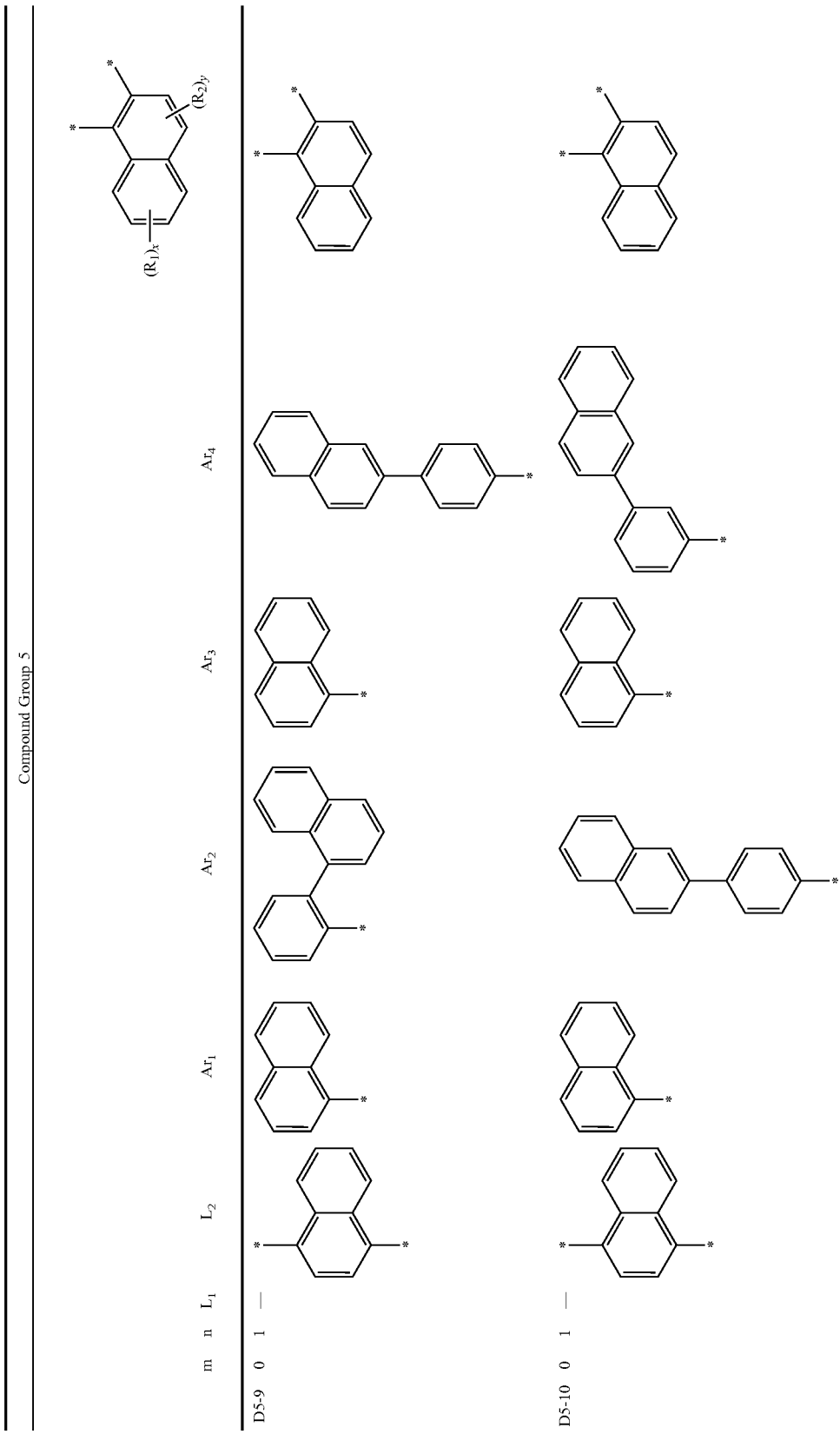

-continued

Compound Group 5

| | m | n | L₁ | L₂ | Ar₁ | Ar₂ | Ar₃ | Ar₄ |
|---|---|---|---|---|---|---|---|---|
| D5-11 | 0 | 1 | — | | | | | |
| D5-12 | 0 | 1 | — | | | | | |
| D5-13 | 0 | 1 | — | | | | | |

-continued
Compound Group 5
| | m | n | L$_1$ | L$_2$ | Ar$_1$ | Ar$_2$ | Ar$_3$ | Ar$_4$ |  |
|---|---|---|---|---|---|---|---|---|---|
| D5-14 | 0 | 1 | — |  | 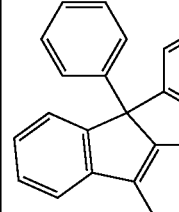 |  |  |  | 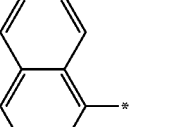 |
| D5-15 | 0 | 1 | — | 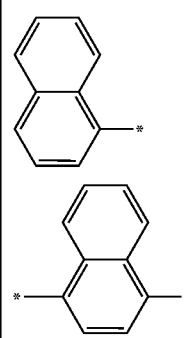 | 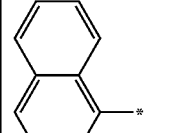 | 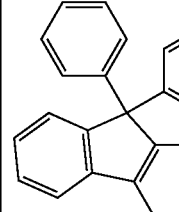 | 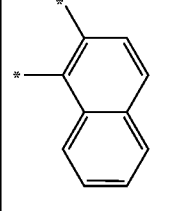 |  | 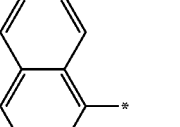 |

-continued
Compound Group 5
| | m | n | L₁ | L₂ | Ar₁ | Ar₂ | Ar₃ | Ar₄ | 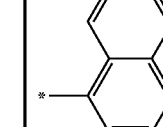 |
|---|---|---|---|---|---|---|---|---|---|
| D5-16 | 0 | 1 | — | 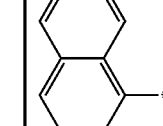 | 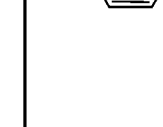 | 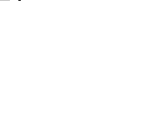 | 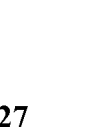 |  |  |
| D5-17 | 0 | 1 | — |  | 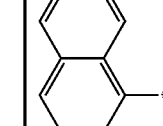 | 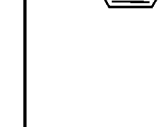 | 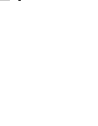 | 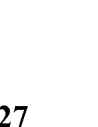 | 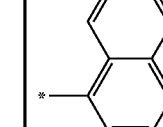 |
| D5-18 | 0 | 1 | — |  |  |  |  |  | 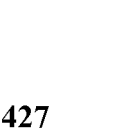 |

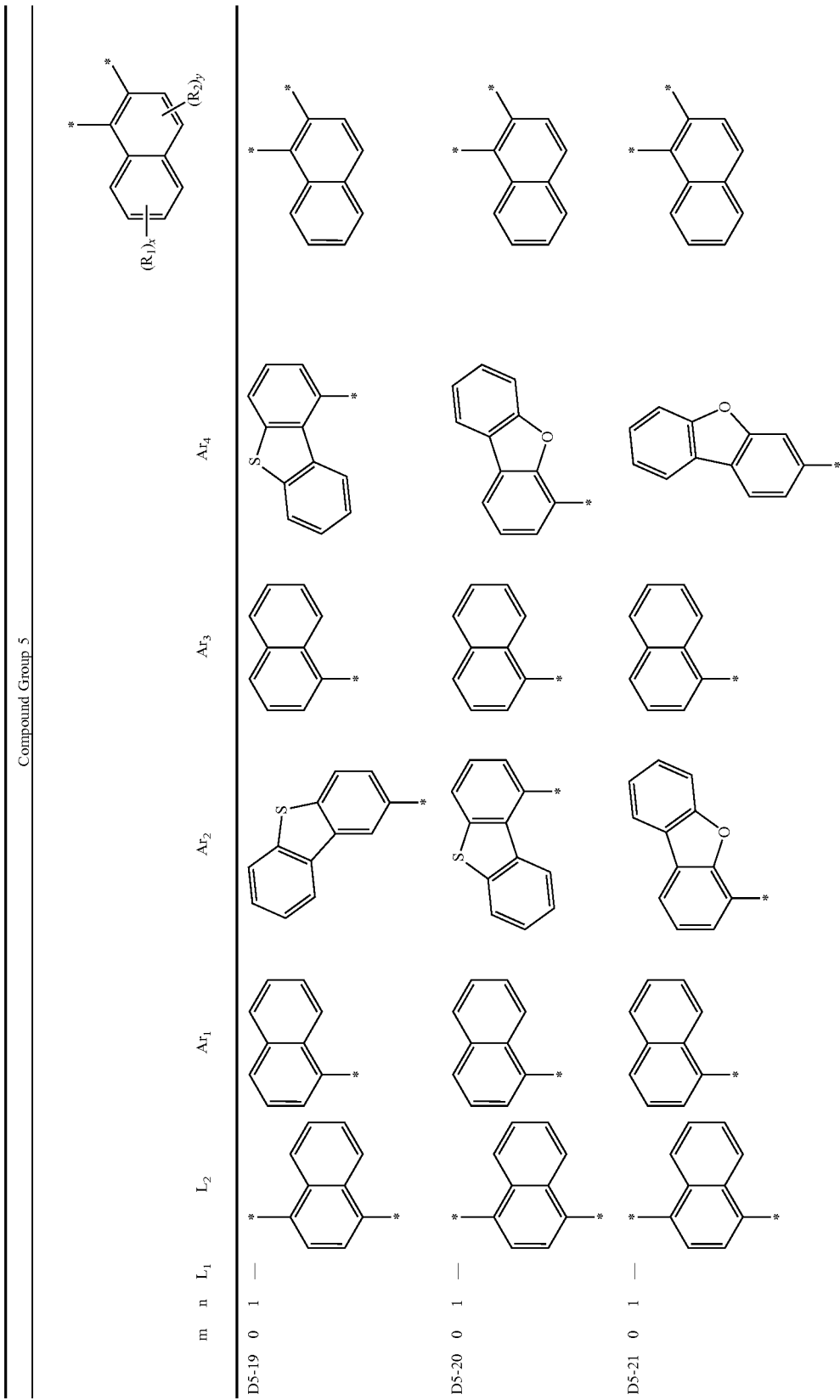

-continued
Compound Group 5
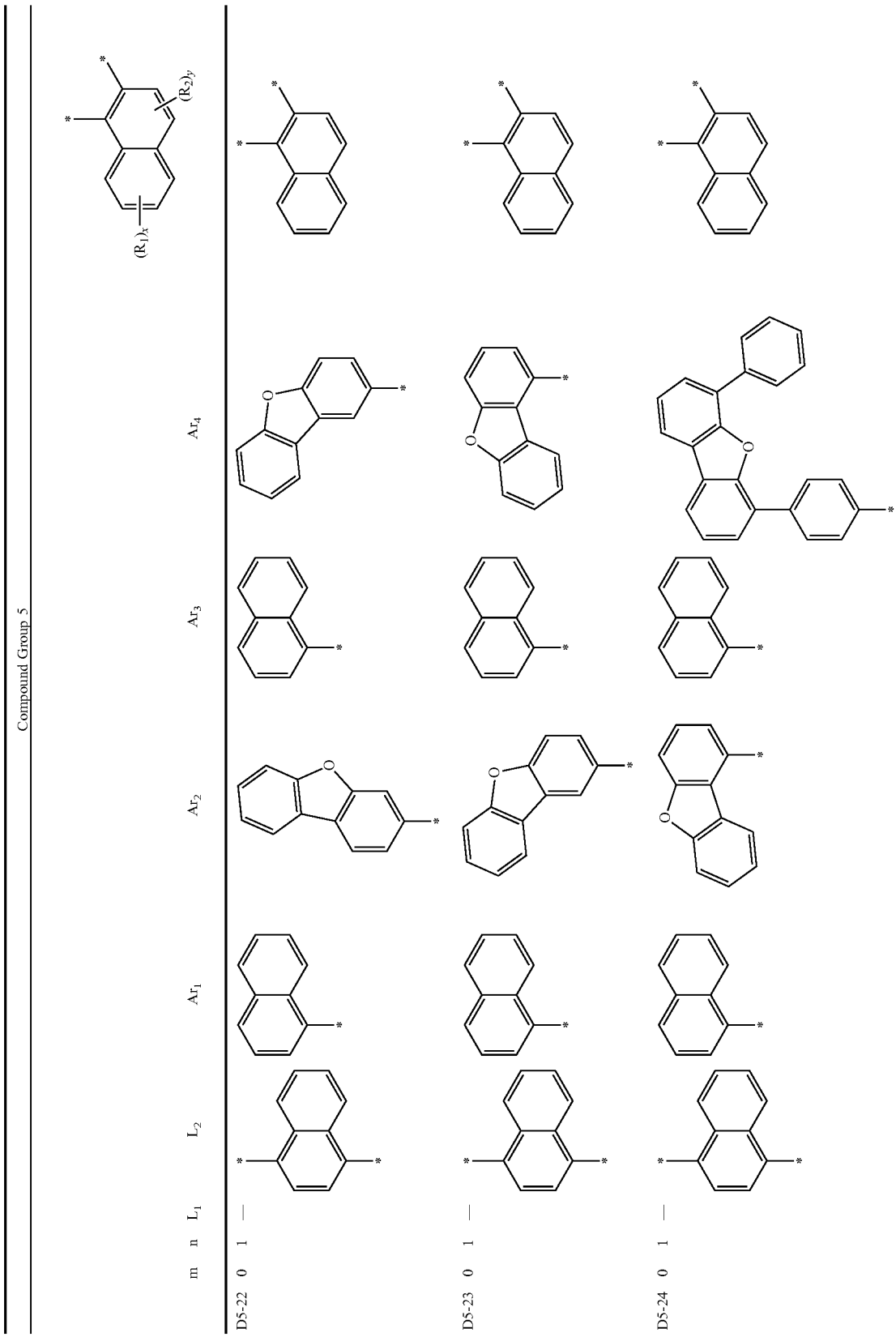

-continued

Compound Group 5

| m | n | L₁ | L₂ | Ar₁ | Ar₂ | Ar₃ | Ar₄ | (R₁)ₓ / (R₂)ᵧ |
|---|---|---|---|---|---|---|---|---|
| D5-25 | 0 | 1 | — | naphthyl | naphthyl | 6-phenyldibenzofuran-4-yl-phenyl | naphthyl | C₆D₅ | naphthyl |
| D5-26 | 0 | 1 | — | naphthyl | naphthyl | C₆D₅ | naphthyl | 4-F-C₆H₄ | naphthyl |
| D5-27 | 0 | 1 | — | naphthyl | naphthyl | 4-F-C₆H₄ | naphthyl | 4-SiPh₃-C₆H₄ | naphthyl |

-continued
Compound Group 5
| | m | n | L₁ | L₂ | Ar₁ | Ar₂ | Ar₃ | Ar₄ | (R₁)ₓ / (R₂)ᵧ |
|---|---|---|---|---|---|---|---|---|---|
| D5-28 | 0 | 1 | — | 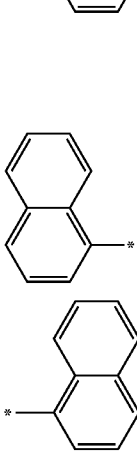 | 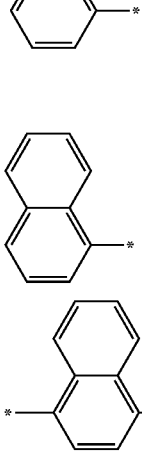 | 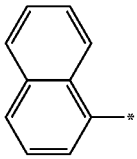 | 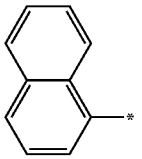 | 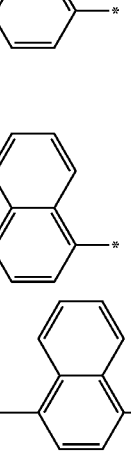 | 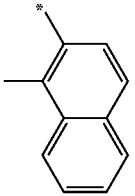 |
| D5-29 | 0 | 1 | — | 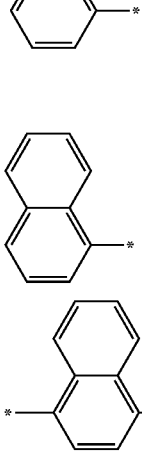 | 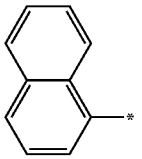 | 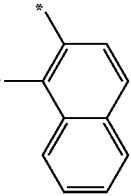 | 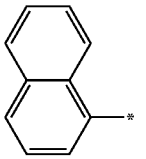 | 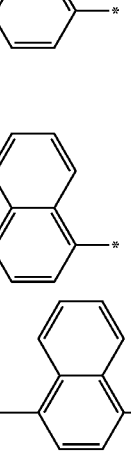 | 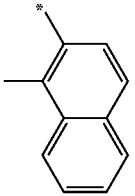 |
| D5-30 | 0 | 1 | — | 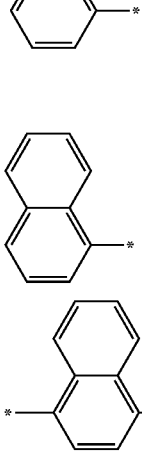 | 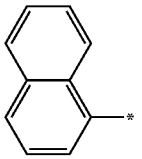 | 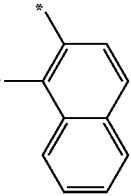 | 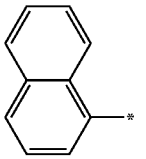 | 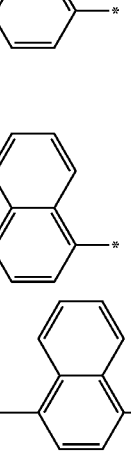 | 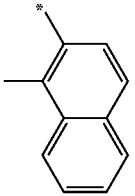 |

-continued
Compound Group 5
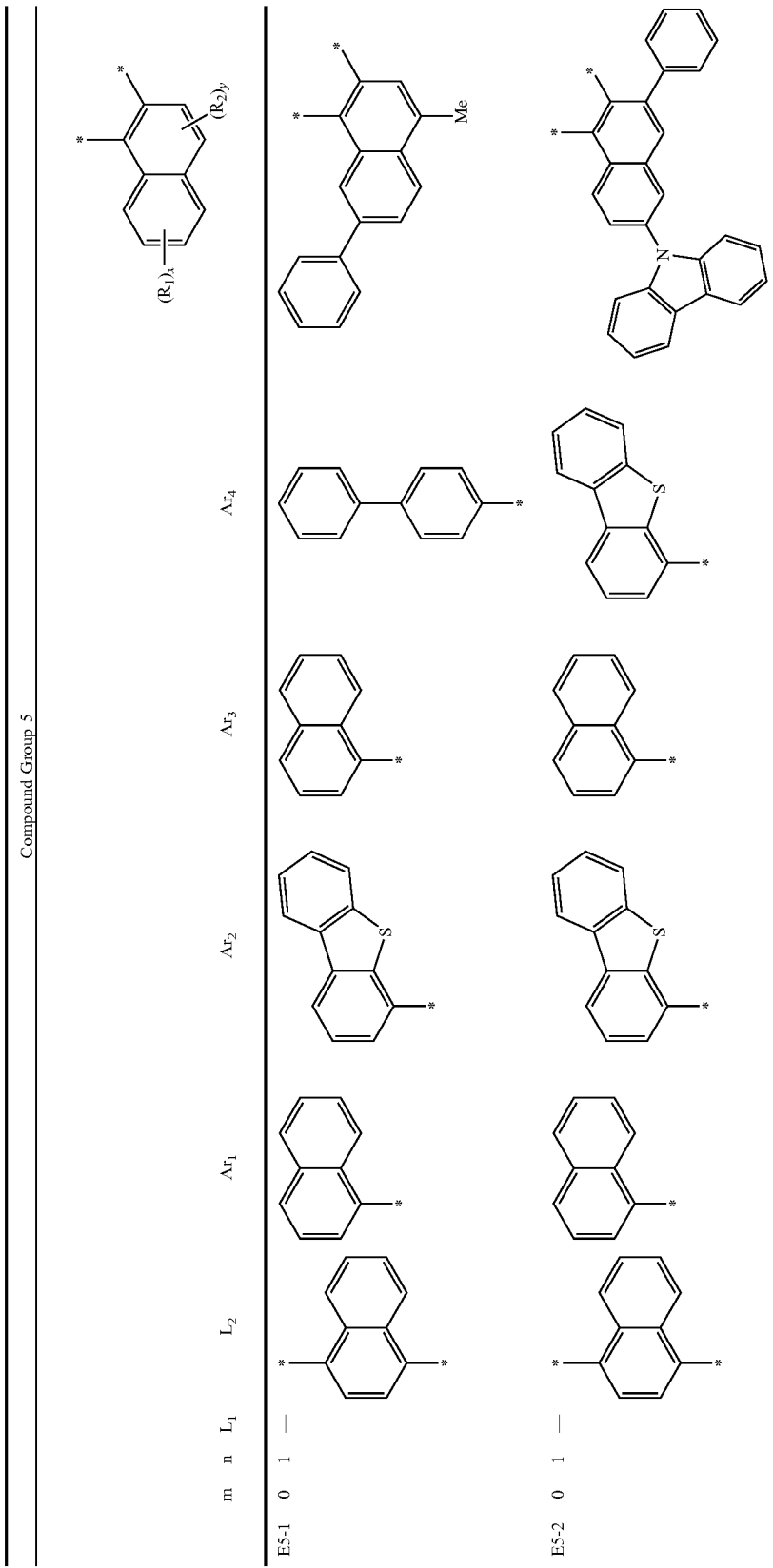

The organic electroluminescence device according to an embodiment of the present disclosure will be explained in more detail with reference to FIG. 1 to FIG. 3.

As described above, the hold transport region HTR may include the above-described diamine compound according to an embodiment of the present disclosure. For example, the hole transport region HTR may include the diamine compound represented by Formula 1.

When the hole transport region HTR has a multilayer structure having a plurality of layers, any layer among the plurality of layers may include the diamine compound represented by Formula 1. For example, the hole transport region HTR may include a hole injection layer HIL disposed on the first electrode EL1 and a hole transport layer HTL disposed on the hole injection layer HIL, and the hole transport layer HTL may include the diamine compound represented by Formula 1. However, embodiments of the present disclosure are not limited thereto. In some embodiments, for example, the hole injection layer HIL may include the diamine compound represented by Formula 1.

The hole transport region HTR may include one, or two or more kinds (structures or examples) of the diamine compound represented by Formula 1. For example, the hole transport region HTR may include at least one selected from the compounds represented in the above-described Compound Groups 1 to 5.

The hole transport region HTR may be formed using any suitable method (such as a vacuum deposition method, a spin coating method, a cast method, a Langmuir-Blodgett (LB) method, an inkjet printing method, a laser printing method, and/or a laser induced thermal imaging (LITI) method).

In some embodiments, the hole transport region may further include additional materials in each layer.

The hole injection layer HIL may include, for example, a phthalocyanine compound (such as copper phthalocyanine); N,N'-diphenyl-N,N'-bis-[4-(phenyl-m-tolyl-amino)-phenyl]-phenyl-4,4'-diamine (DNTPD), 4,4',4"-[tris(3-methylphenyl)phenylamino] triphenylamine (m-MTDATA), 4,4',4"-tris(N,N-diphenylamino)triphenylamine (TDATA), 4,4',4"-tris{N,-2-naphthyl)-N-phenylamino}-triphenylamine (2-TNATA), poly(3,4-ethylene dioxythiophene)/poly(4-styrenesulfonate) (PEDOT/PSS), polyaniline/dodecylbenzenesulfonic acid (PANI/DBSA), polyaniline/camphor sulfonic acid (PANI/CSA), polyaniline/poly(4-styrenesulfonate) (PANI/PSS), N,N'-di(1-naphthalene-1-yl)-N,N'-diphenyl-benzidine (NPD), triphenylamine-containing polyether ketone (TPAPEK), 4-isopropyl-4'-methyldiphenyliodonium [tetrakis(pentafluorophenyl)borate], and/or dipyrazino[2,3-f:2',3'-h]quinoxaline-2,3,6,7,10,11-hexacarbonitrile (HAT-CN).

The hole transport layer HTL may include any suitable material available in the art. For example, the hole transport layer HTL may include carbazole derivatives (such as N-phenyl carbazole and/or polyvinyl carbazole), fluorene-based derivatives, N,N'-bis(3-methylphenyl)-N,N'-diphenyl-[1,1-biphenyl]-4,4'-diamine (TPD), triphenylamine-based derivatives (such as 4,4',4"-tris(N-carbazolyl) triphenylamine (TCTA)), N,N'-di(naphthalene-1-yl)-N,N'-diphenyl-benzidine (NPD), 4,4'-cyclohexylidene bis[N,N-bis(4-methylphenyl)benzeneamine (TAPC), 4,4'-bis[N,N'-(3-tolyl)amino]-3,3'-dimethylbiphenyl (HMTPD), 1,3-bis(N-carbazolyl)benzene (mCP), etc.

The electron blocking layer EBL may include, for example, carbazole derivatives (such as N-phenyl carbazole and/or polyvinyl carbazole), fluorene-based derivatives, triphenylamine-based derivatives (such as N,N'-bis(3-methylphenyl)-N,N'-diphenyl-[1,1-biphenyl]-4,4'-diamine (TPD) and/or 4,4',4"-tris(N-carbazolyl)triphenylamine (TCTA)), N,N'-di(naphthalene-1-yl)-N,N'-diphenyl-benzidine (NPD), 4,4'-cyclohexylidene bis[N,N-bis(4-methylphenyl)benzenamine] (TAPC), 4,4'-bis[N,N'-(3-tolyl)amino]-3,3'-dimethylbiphenyl (HMTPD), and/or mCP.

The thickness of the hole transport region HTR may be about 50 Å to about 15,000 Å, for example, about 100 Å to about 5,000 Å. The thickness of the hole injection region HIL may be, for example, about 30 Å to about 1,000 Å, and the thickness of the hole transport layer HTL may be about 30 Å to about 1,000 Å. For example, the thickness of the electron blocking layer EBL may be about 10 Å to about 1,000 Å. When the thicknesses of the hole transport region HTR, the hole injection layer HIL, the hole transport layer HTL, and the electron blocking layer EBL satisfy the above-described ranges, satisfactory hole transport properties may be achieved without substantial increases in driving voltage.

The hole transport region HTR may further include a charge generating material in addition to the above-described materials to increase conductivity. The charge generating material may be dispersed substantially uniformly or non-uniformly in the hole transport region HTR. The charge generating material may be, for example, a p-dopant. The p-dopant may be a quinone derivative, metal oxide, or cyano group-containing compound, without limitation. Non-limiting examples of the p-dopant include quinone derivatives (such as tetracyanoquinodimethane (TCNQ) and/or 2,3,5,6-tetrafluoro-7,7',8,8'-tetracyanoquinodimethane (F4-TCNQ)), metal halides (such as $MgF_2$, CuI, and/or RbI), metal oxides (such as tungsten oxide and/or molybdenum oxide), and inorganic metal compounds (such as CuI and/or RbI).

As described above, the hole transport region HTR may further include at least one of a hole buffer layer or an electron blocking layer EBL. The hole buffer layer may compensate for an optical resonance distance according to the wavelength of light emitted from an emission layer EML, and may increase light emission efficiency. Materials that may be included in a hole transport region HTR may also be included in the hole buffer layer. The electron blocking layer EBL may prevent or reduce electron injection from the electron transport region ETR to the hole transport region HTR.

The emission layer EML may be provided on the hole transport region HTR. The emission layer EML may have a thickness of, for example, about 100 Å to about 1,000 Å or about 100 Å to about 600 Å. The emission layer EML may have a single layer formed using a single material, a single layer formed using a plurality of different materials, or a multilayer structure having a plurality of layers formed using a plurality of different materials.

Any suitable light-emitting material may be used in the emission layer EML, and may be selected from fluoranthene derivatives, pyrene derivatives, arylacetylene derivatives, anthracene derivatives, fluorene derivatives, perylene derivatives, chrysene derivatives, etc. For example, pyrene derivatives, perylene derivatives, and anthracene derivatives may be used. For example, as the host material of the emission layer EML, an anthracene derivative represented by Formula 10 may be used.

[Formula 10]

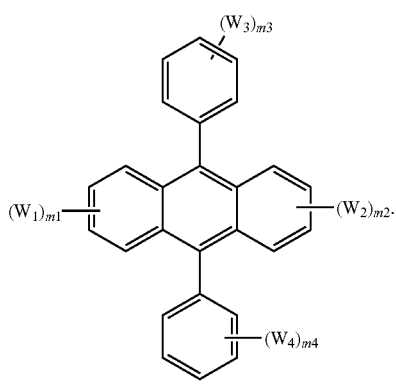

In Formula 10, $W_1$ to $W_4$ may each independently be a hydrogen atom, a deuterium atom, a halogen atom, a substituted or unsubstituted silyl group, a substituted or unsubstituted alkyl group of 1 to 20 carbon atoms, a substituted or unsubstituted aryl group of 6 to 30 carbon atoms for forming a ring, or a substituted or unsubstituted heteroaryl group of 2 to 30 carbon atoms for forming a ring, and/or may be combined with an adjacent group to form a ring. m1 and m2 may each independently be an integer of 0 to 4, and m3 and m4 may each independently be an integer of 0 to 5.

When m1 is 1, $W_1$ may not be a hydrogen atom; when m2 is 1, $W_2$ may not be a hydrogen atom; when m3 is 1, $W_3$ may not be a hydrogen atom; and when m4 is 1, $W_4$ may not be a hydrogen atom.

When m1 is 2 or more, a plurality of $W_1$ groups may be the same or different. When m2 is 2 or more, a plurality of $W_2$ groups may be the same or different. When m3 is 2 or more, a plurality of $W_3$ groups may be the same or different. When m4 is 2 or more, a plurality of $W_4$ groups may be the same or different.

The compound represented by Formula 10 may include, for example, the compounds represented by the structures below. However, the compound represented by Formula 10 is not limited thereto.

a-1

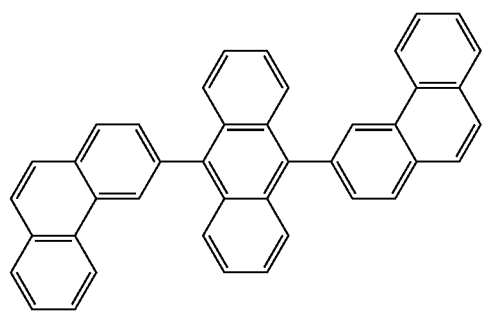

a-2

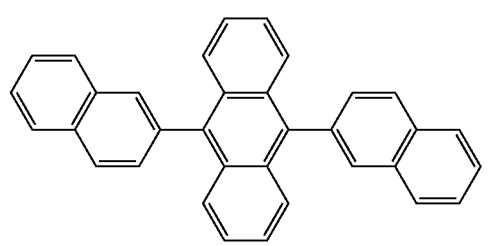

a-3

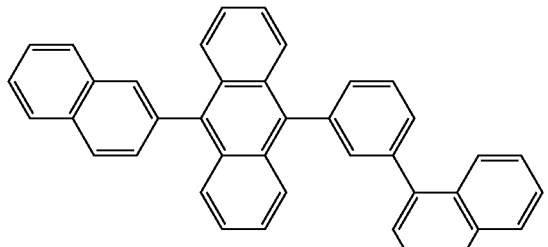

a-4

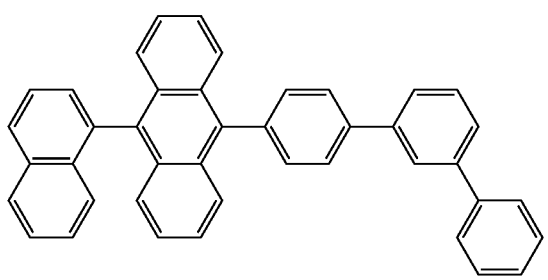

a-5

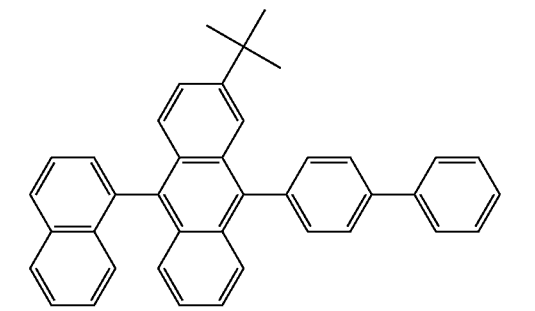

a-6

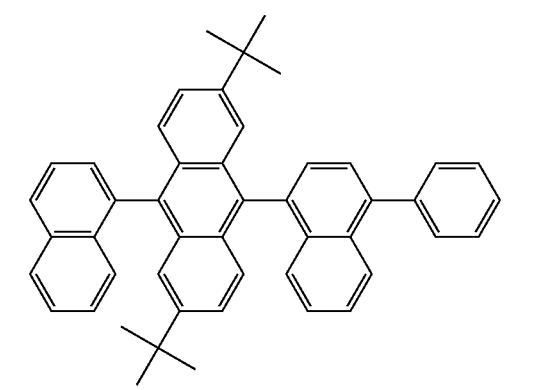

a-7

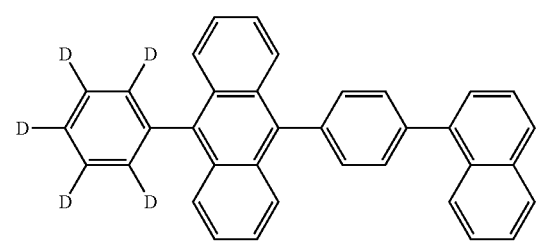

-continued a-8
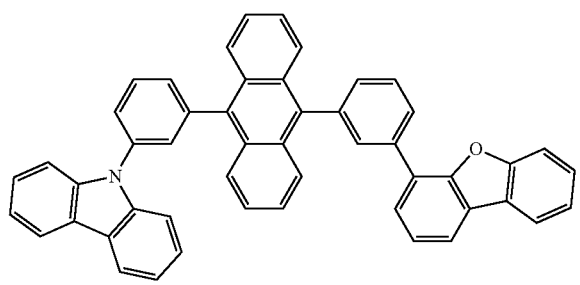

a-9
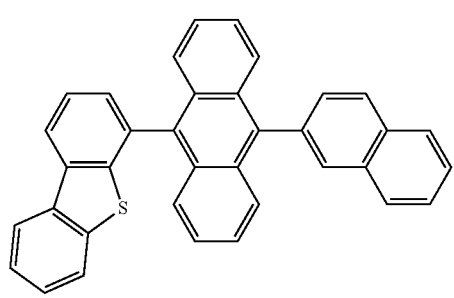

a-10
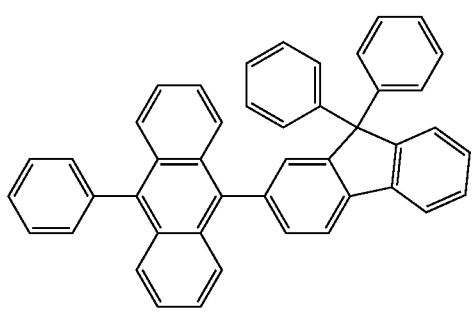

a-11
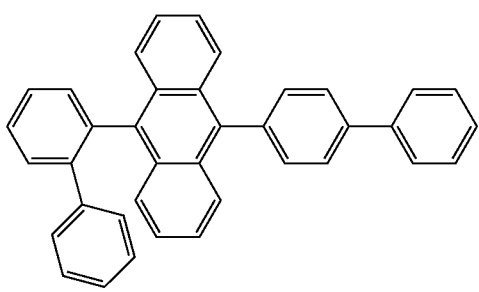

a-12
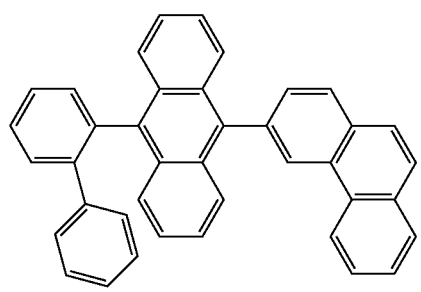

-continued a-13
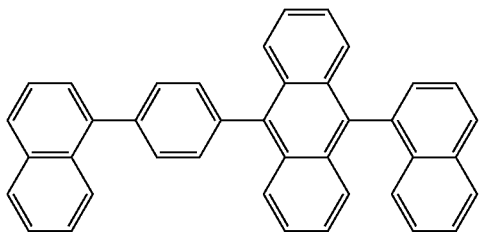

a-14
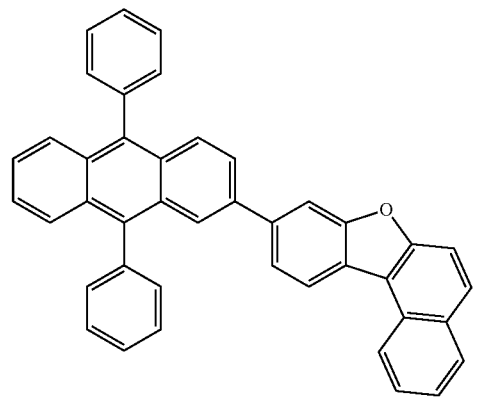

a-15
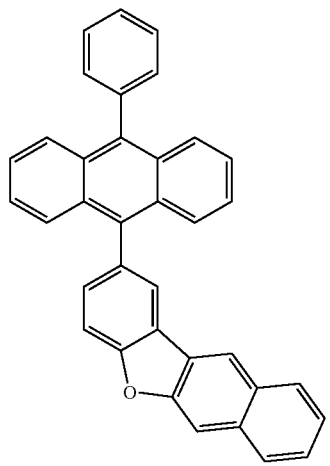

a-16
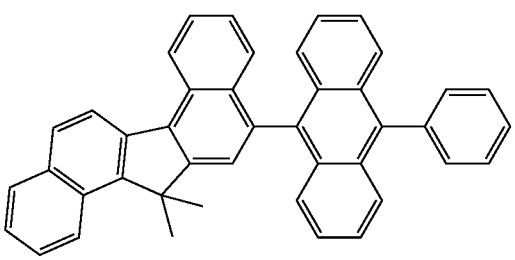

The emission layer EML may include a dopant, and the dopant may be any suitable material. For example, the dopant may be or include at least one among styryl derivatives (for example, 1,4-bis[2-(3-N-ethylcarbazolyl)vinyl]benzene (BCzVB), 4-(di-p-tolylamino)-4"-[(di-p-tolylamino)styryl]stilbene (DPAVB), and/or N-(4-((E)-2-(6-((E)(diphenylamino)styryl)naphthalen-2-yl)vinyl)phenyl)-N-phenylbenzenamine (N-BDAVBi)), perylene and derivatives thereof (for example, 2,5,8,11-tetra-t-butylperylene (TBPe)), pyrene and derivatives thereof (for example, 1,1- dipyrene, 1,4-dipyrenylbenzene, 1,4-bis(N,N-diphenylamino)pyrene), 1,6-bis(N,N-diphenylamino)pyrene, and/or 2,5,8,11-tetra-t-butylperylene (TBP)), and 1,3,5-tris(1-phenyl-1H-benzo[d]imidazole-2-yl)benzene (TPBi), etc.

The emission layer EML may include a host material. For example, the emission layer EML may include as a host material, tris(8-hydroxyquinolino)aluminum (Alq3), bis[2-(diphenylphosphino)phenyl] ether oxide (DPEPO), 4,4'-bis(carbazolyl yl)biphenyl) (CBP), 1,3-bis(carbazol-9-yl)benzene (mCP), 2,8-bis(diphenylphosphoryl)dibenzo[b,d]furan (PPF), 4,4',4"-tris(carbazol-9-yl)-triphenylamine (TCTA), poly(N-vinylcarbazole) (PVK), 9,10-di(naphthalene yl)anthracene (ADN), 3-tert-butyl-9,10-di(naphth-2-yl)anthracene (TBADN), distyrylarylene (DSA), 4,4'-bis(9-carbazolyl)-2,2'-dimethyl-biphenyl (CDBP), 2-methyl-9,10-bis (naphthalen-2-yl)anthracene (MADN), hexaphenyl cyclotriphosphazene (CP1), 1,4-bis(triphenylsilyl)benzene (UGH-2), hexaphenylcyclotrisiloxane (DPSiO3), octaphenylcyclotetrasiloxane (DPSiO4), 2,8-bis(diphenylphosphoryl)dibenzofuran (PPF), and 1,3,5-tris(1-phenyl-1H-benzo[d]imidazole-2-yl)benzene (TPBi), etc. However, an embodiment of the present disclosure is not limited thereto.

When the emission layer EML is to emit red light, the emission layer EML may further include, for example, a fluorescence material including tris(dibenzoylmethanato) phenanthroline europium (PBD:Eu(DBM)$_3$(Phen)) and/or perylene. When the emission layer EML is to emit red light, the dopant included in the emission layer EML may be selected from, for example, a metal complex or an organometallic complex (such as bis(1-phenylisoquinoline)acetylacetonate iridium (PIQIr(acac)), bis(1-phenylquinoline) acetylacetonate iridium (PQIr(acac)), tris(1-phenylquinoline) iridium (PQIr), and/or octaethylporphyrin platinum (PtOEP)), rubrene and derivatives thereof, and 4-dicyanomethylene-2-(p-dimethylaminostyryl)-6-methyl-4H-pyrane (DCM) and derivatives thereof.

When the emission layer EML is to emit green light, the emission layer EML may further include, for example, a fluorescence material including tris(8-hydroxyquinolino) aluminum (Alq3). When the emission layer EML is to emit green light, the dopant included in the emission layer EML may be selected from, for example, a metal complex or an organometallic complex (such as fac-tris(2-phenylpyridine) iridium (Ir(ppy)$_3$), and coumarin and derivatives thereof.

When the emission layer EML is to emit blue light, the emission layer EML may further include a fluorescence material selected from the group consisting of spiro-DPVBi, spiro-6P, distyryl-benzene (DSB), distyryl-arylene (DSA), a polyfluorene (PFO)-based polymer, and a poly(p-phenylene vinylene (PPV)-based polymer. When the emission layer EML is to emit blue light, the dopant included in the emission layer EML may be selected from a metal complex or an organometallic complex (such as (4,6-F2ppy)$_2$Irpic), and perylene and derivatives thereof.

The electron transport region ETR may be provided on the emission layer EML. The electron transport region ETR may include at least one of a hole blocking layer HBL, an electron transport layer ETL, or an electron injection layer ETL, but an embodiment of the present disclosure is not limited thereto.

The electron transport region ETR may have a single layer formed using a single material, a single layer formed using a plurality of different materials, or a multilayer structure having a plurality of layers formed using a plurality of different materials.

For example, the electron transport region ETR may have a single layer structure of an electron injection layer EIL or an electron transport layer ETL, or a single layer structure formed using an electron injection material and an electron transport material. In some embodiments, the electron transport region ETR may have a single layer structure having a plurality of different materials, or a structure stacked from the emission layer EML of electron transport layer ETL/ electron injection layer EIL, or hole blocking layer HBL/ electron transport layer ETL/electron injection layer EIL, without limitation. The thickness of the electron transport region ETR may be, for example, about 100 Å to about 1,500 Å.

The electron transport region ETR may be formed using any suitable method (such as a vacuum deposition method, a spin coating method, a cast method, a Langmuir-Blodgett (LB) method, an inkjet printing method, a laser printing method, and/or a laser induced thermal imaging (LITI) method).

When the electron transport region ETR includes an electron transport layer ETL, the electron transport region ETR may include an anthracene-based compound. The electron transport region may include, for example, tris(8-hydroxyquinolinato)aluminum (Alq3), 1,3,5-tri[(3-pyridyl)-phen-3-yl]benzene, 2,4,6-tris(3'-(pyridin-3-yl)biphenyl-3-yl)-1,3,5-triazine, bis[2-(diphenylphosphino)phenyl]ether oxide (DPEPO), 2-(4-(N-phenylbenzoimidazolyl-1-ylphenyl)-9,10-dinaphthylanthracene, 1,3,5-tri(1-phenyl-1H-benzo[d]imidazol-2-yl)phenyl (TPBi), 2,9-dimethyl-4,7-diphenyl-1,10-phenanthroline (BCP), 4,7-diphenyl-1,10-phenanthroline (Bphen), 3-(4-biphenylyl)-4-phenyl-5-tert-butylphenyl-1,2,4-triazole (TAZ), 4-(naphthalen-1-yl)-3,5-diphenyl-4H-1,2,4-triazole (NTAZ), 2-(4-biphenylyl)-5-(4-tert-butylphenyl)-1,3,4-oxadiazole (tBu-PBD), bis(2-methyl-8-quinolinolato-N1,O8)-(1,1'-biphenyl olato) aluminum (BAlq), beryllium bis(benzoquinolin-10-olate (Bebq$_2$), 9,10-di(naphthalene-2-yl)anthracene (ADN), or a mixture thereof, without limitation. The thickness of the electron transport layer ETL may be about 100 Å to about 1,000 Å and may be, for example, about 150 Å to about 500 Å. When the thickness of the electron transport layer ETL satisfies the above-described range, satisfactory electron transport properties may be obtained without a substantial increase in driving voltage.

When the electron transport region ETR includes the electron injection layer EIL, the electron transport region ETR may include a metal halide (such as LiF, NaCl, CsF, RbCl, RbI, and/or CuI), a lanthanide metal (such as ytterbium (Yb)), a metal oxide (such as Li$_2$O and/or BaO), or lithium quinolate (LiQ). However, an embodiment of the present disclosure is not limited thereto. In some embodiments, the electron injection layer EIL may be formed using a mixture of an electron transport material and an insulating organo metal salt. The organo metal salt may be a material having an energy band gap of about 4 eV or more. The organo metal salt may include, for example, metal acetates, metal benzoates, metal acetoacetates, metal acetylacetonates, and/or metal stearates. The thickness of the electron injection layer EIL may be about 1 Å to about 100 Å, and about 3 Å to about 90 Å. When the thickness of the electron injection layer EIL satisfies the above described range, satisfactory electron injection properties may be obtained without inducing substantial increase of a driving voltage.

The electron transport region ETR may include a hole blocking layer HBL as described above. The hole blocking layer HBL may include, for example, at least one of 2,9-dimethyl-4,7-diphenyl-1,10-phenanthroline (BCP), bis[2-(diphenylphosphino)phenyl]ether oxide (DPEPO), or 4,7- diphenyl-1,10-phenanthroline (Bphen). However, an embodiment of the present disclosure is not limited thereto.

The second electrode EL2 may be provided on the electron transport region ETR. The second electrode EL2 may be a common electrode or a cathode. The second electrode EL2 may be a transmissive electrode, a transflective electrode, or a reflective electrode. When the second electrode EL2 is a transmissive electrode, the second electrode EL2 may include a transparent metal oxide, for example, ITO, IZO, ZnO, ITZO, etc.

When the second electrode EL2 is a transflective electrode or a reflective electrode, the second electrode EL2 may include Ag, Mg, Cu, Al, Pt, Pd, Au, Ni, Nd, Ir, Cr, Li, Ca, LiF/Ca, LiF/Al, Mo, Ti, a compound thereof, or a mixture thereof (for example, a mixture of Ag and Mg). The second electrode EL2 may have a multilayered structure including a reflective layer or a transflective layer formed using the above-described materials and a transparent conductive layer formed using ITO, IZO, ZnO, ITZO, etc.

In some embodiments, the second electrode EL2 may be connected with an auxiliary electrode. When the second electrode EL2 is connected with the auxiliary electrode, the resistance of the second electrode EL2 may decrease.

Referring to FIG. 4, in some embodiments, a capping layer (CPL) may be further disposed on the second electrode EL2 of the organic electroluminescence device 10. The capping layer (CPL) may include, for example, 2,2'-dimethyl-N,N'-di-[(1-naphthyl)-N,N'-diphenyl]-1,1'-biphenyl-4,4'-diamine(α-NPD), N,N'-di(1-naphthyl)-N,N'-diphenyl-(1,1'-biphenyl)-4,4'-diamine (NPB), TPD, m-MTDATA, Alq3, CuPc, N4,N4,N4',N4'-tetra(biphenyl-4-yl) biphenyl-4,4'-diamine (TPD15), 4,4',4''-tris(carbazol-9-yl) triphenylamine (TCTA), etc.

In the organic electroluminescence device 10, when a voltage is applied across the first electrode EL1 and second electrode EL2, holes injected from the first electrode EL1 move through the hole transport region HTR to the emission layer EML, and electrons injected from the second electrode EL2 move through the electron transport region ETR to the emission layer EML. The electrons and holes may recombine in the emission layer EML to produce excitons, and light may be emitted through the transition of the excitons from an excited state to the ground state.

When the organic electroluminescence device 10 is a top emission type, the first electrode EL1 may be a reflective electrode, and the second electrode EL2 may be a transmissive or transflective electrode. When the organic electroluminescence device 10 is a bottom emission type, the first electrode EL1 may be a transmissive or transflective electrode, and the second electrode EL2 may be a reflective electrode.

The organic electroluminescence device 10 according to an embodiment of the present disclosure is characterized in including the diamine compound represented by Formula 1, and accordingly, high efficiency and/or long life (lifespan) may be achieved. In addition, the driving voltage may be decreased.

Hereinafter, the present disclosure will be explained in more detail with reference to embodiments and comparative embodiments. The following embodiments are only illustrations to assist the understanding of the present disclosure, and the scope of the present disclosure is not limited thereto.

SYNTHETIC EXAMPLES

The diamine compound according to an embodiment of the present disclosure may be synthesized, for example, as follows. However, an embodiment of the synthetic method of the diamine compound according to an embodiment of the present disclosure is not limited thereto.

1. Synthesis of Compound A2-3

Synthesis of Compound B

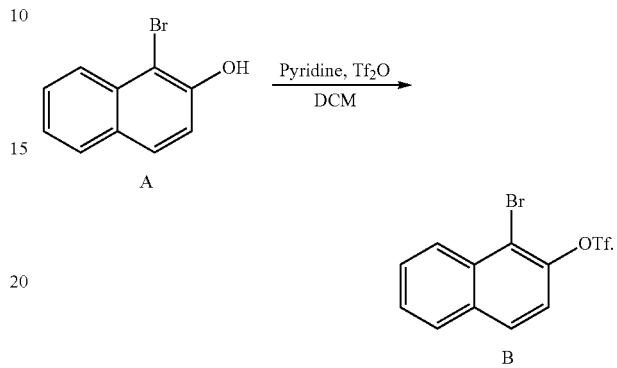

Dichloromethane (DCM, 250 mL) and pyridine (36 mL) were added to the derivative of naphthalene A (50 g, 0.22 mol). The reaction solution was cooled to about 0° C., and trifluoromethanesulfonic anhydride (Tf$_2$O, 55 mL) was added thereto dropwisely over about 1 hour. Then, the reaction solution was stirred at room temperature for about 12 hours. [(Cp*RhCl$_2$)$_2$)] (310 mg, 0.5 mmol) and Cu(OAc)$_2$ (360 mg, 2.0 mol) in a dimethylformaldehyde solution (250 mL) were added, followed by heating and stirring at about 120° C. for about 3 hours. H$_2$O was added to the reaction solution, and the resultant solution was extracted with dichloromethane, washed with an aqueous NaHCO$_3$ solution, H$_2$O, and brine, and dried with MgSO$_4$. The solution thus obtained was concentrated and then separated by silica gel column chromatography to obtain Compound B (99 g, 0.21 mol, 95%, M/S 353.9).

Synthesis of Compound C

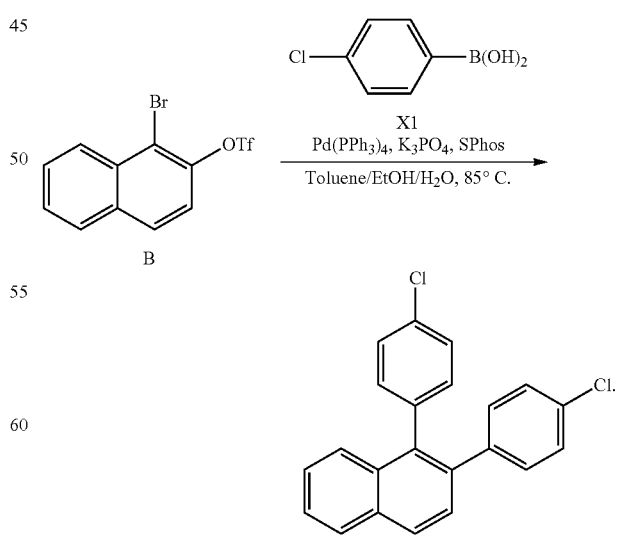

Compound B (15 g, 69 mmol), boronic acid X1 (27 g, 27 mmol), and K₃PO₄ (30 g, 138 mmol) were dissolved in toluene/EtOH/H₂O (v/v/v=4/2/1, 350 mL), and then deaerated. Under an argon atmosphere, 2-dicyclohexylphosphino-2',6'-dimethoxybiphenyl (SPhos, 5.7 g, 14 mmol) and tetrakis(triphenylphosphine) palladium (Pd(PPh₃)₄, 8.0 g, 6.9 mmol) were added, followed by heating and stirring at about 85° C. for about 6 hours. The reaction solution was cooled in the air to room temperature, and then, extracted with toluene, washed with H₂O and brine, and dried with Na₂SO₄. The solution thus obtained was concentrated and separated by column chromatography to obtain Compound C (18 g, 51 mmol, 75%, M/S 348.05).

Synthesis of Compound A2-3

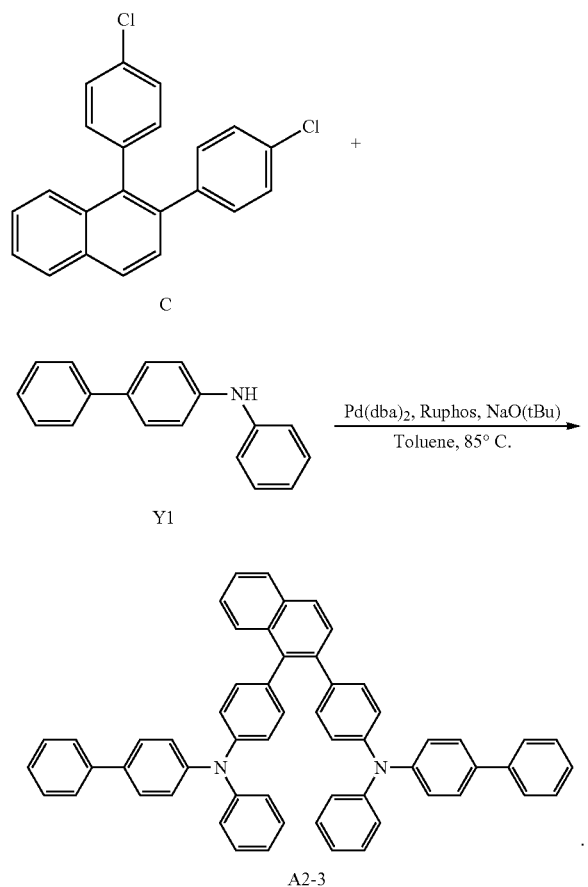

Compound C (10 g, 29 mmol), amine Y1 (16 g, 66 mmol), NaOtBu (6.9 g, 72 mmol), and 2-dicyclohexylphosphino-2',6'-diisopropoxybiphenyl (Ruphos, 2.8 g, 5.7 mmol) were dissolved in toluene (500 mL) and then deaerated. Under an argon atmosphere, bis(dibenzylideneacetone) palladium (0.82 g, 1.4 mmol) was added, followed by heating and stirring at about 85° C. for about 6 hours. The reaction solution was cooled in the air to room temperature, and then, extracted with toluene, washed with H₂O and brine, and dried with Na₂SO₄. The solution thus obtained was concentrated and separated by column chromatography to obtain Compound A2-3 (19 g, 24 mmol, 84%, M/S 766.33).

2. Synthesis of Compound A4-3

Synthesis of Compound D

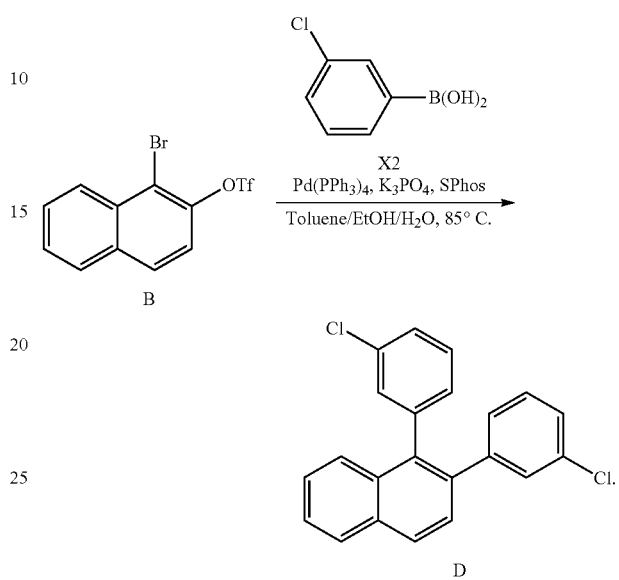

Compound B (15 g, 69 mmol), boronic acid X2 (27 g, 27 mmol), and K₃PO₄ (30 g, 138 mmol) were dissolved in toluene/EtOH/H₂O (v/v/v=4/2/1, 350 mL) and then deaerated. Under an argon atmosphere, 2-dicyclohexylphosphino-2',6'-dimethoxybiphenyl (SPhos, 5.7 g, 14 mmol) and tetrakis(triphenylphosphine) palladium (8.0 g, 6.9 mmol) were added, followed by heating and stirring at about 85° C. for about 6 hours. The reaction solution was cooled in the air to room temperature, and then, extracted with toluene, washed with H₂O and brine, and dried with Na₂SO₄. The solution thus obtained was concentrated and separated by column chromatography to obtain Compound D (20 g, 56 mmol, 81%, M/S 348.05).

Synthesis of Compound A4-3

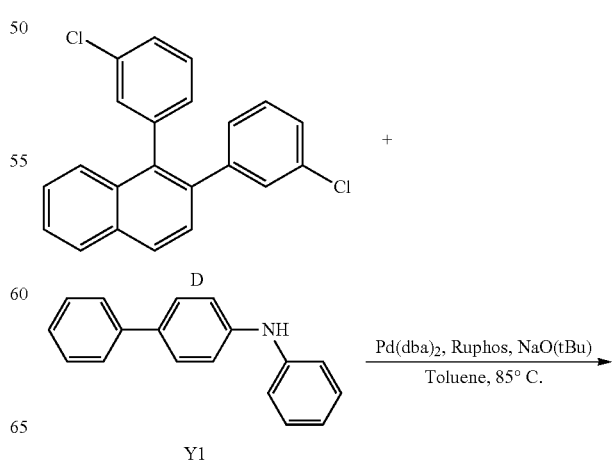

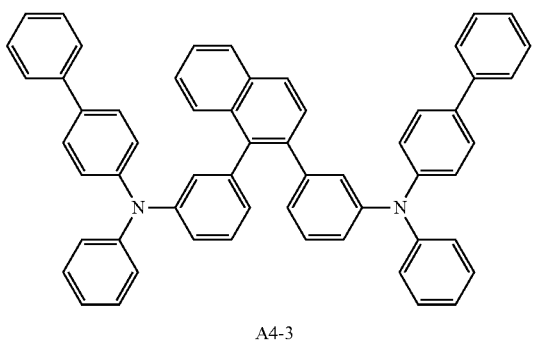

A4-3

Compound D (10 g, 29 mmol), amine Y1 (16 g, 66 mmol), NaOtBu (6.9 g, 72 mmol), and Ruphos (2.8 g, 5.7 mmol) were dissolved in toluene (500 mL), and then deaerated. Under an argon atmosphere, bis(dibenzylideneacetone) palladium (Pd(dba)$_2$, 0.82 g, 1.4 mmol) was added, followed by heating and stirring at about 85° C. for about 6 hours. The reaction solution was cooled in the air to room temperature, and then, extracted with toluene, washed with H$_2$O and brine, and dried with Na$_2$SO$_4$. The solution thus obtained was concentrated and separated by column chromatography to obtain Compound A4-3 (17 g, 22 mmol, 77%, M/S 766.33).

3. Synthesis of Compound E2-3

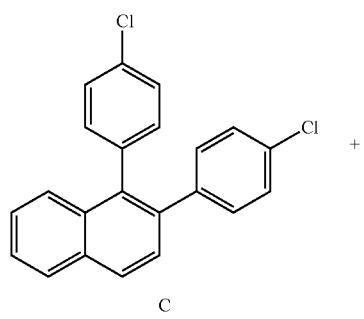

C

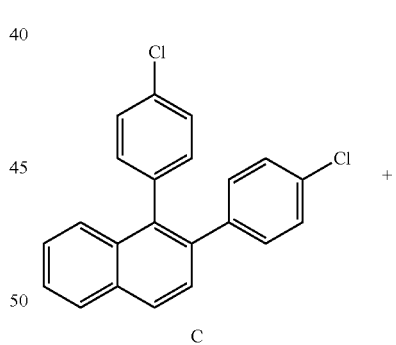

Y2

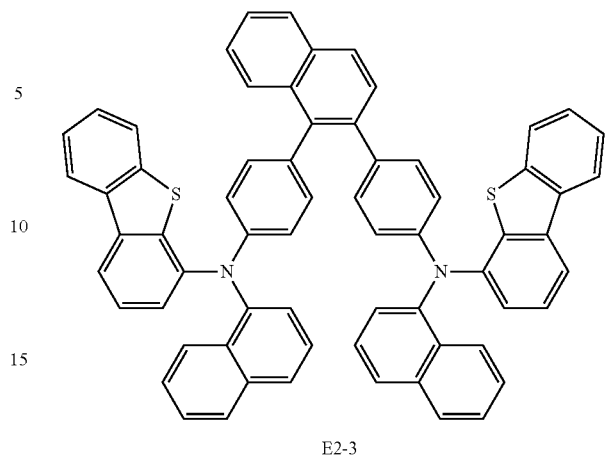

E2-3

Compound C (10 g, 29 mmol), amine Y2 (16 g, 29 mmol), NaOtBu (6.9 g, 72 mmol), and Ruphos (2.8 g, 5.7 mmol) were dissolved in toluene (500 mL) and then deaerated. Under an argon atmosphere, bis(dibenzylideneacetone) palladium (0.82 g, 1.4 mmol) was added, followed by heating and stirring at about 85° C. for about 6 hours. The reaction solution was cooled in the air to room temperature, and then, extracted with toluene, washed with H$_2$O and brine, and dried with Na$_2$SO$_4$. The solution thus obtained was concentrated and separated by column chromatography to obtain Compound E2-3 (18 g, 20 mmol, 69%, M/S 926.28).

4. Synthesis of Compound D2-16

Synthesis of Compound E

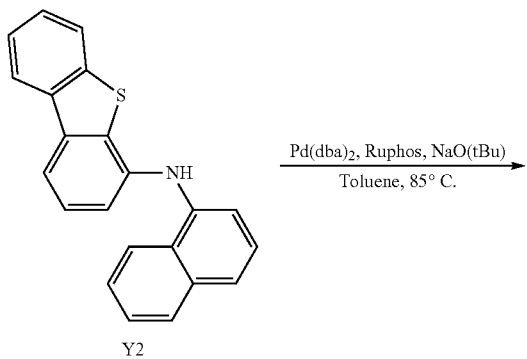

C

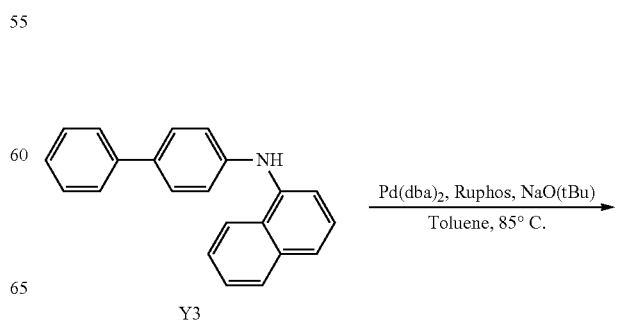

Y3

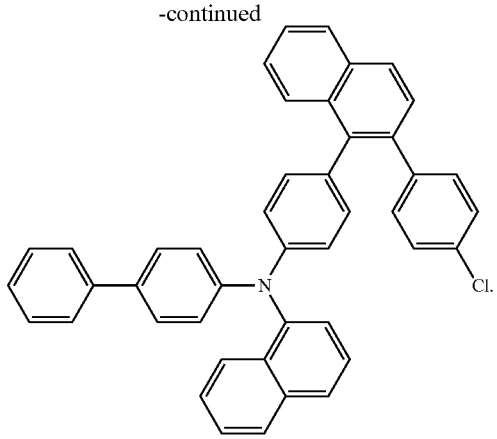

E

Compound C (10 g, 29 mmol), amine Y3 (8.6 g, 29 mmol), NaOtBu (2.8 g, 29 mmol), and Ruphos (2.8 g, 5.7 mmol) were dissolved in toluene (500 mL) and then deaerated. Under an argon atmosphere, bis(dibenzylideneacetone) palladium (0.82 g, 1.4 mmol) was added, followed by heating and stirring at about 85° C. for about 6 hours. The reaction solution was cooled in the air to room temperature, and then, extracted with toluene, washed with H₂O and brine, and dried with Na₂SO₄. The solution thus obtained was concentrated and separated by column chromatography to obtain Compound E (9.2 g, 15 mmol, 52%, M/S 607.21).

Synthesis of Compound D2-16

Compound E (10 g, 16 mmol), amine Y2 (5.3 g, 16 mmol), NaOtBu (2.8 g, 29 mmol), and Ruphos (2.8 g, 5.7 mmol) were dissolved in toluene (500 mL) and then deaerated. Under an argon atmosphere, bis(dibenzylideneacetone) palladium (0.82 g, 1.4 mmol) was added, followed by heating and stirring at about 85° C. for about 6 hours. The reaction solution was cooled in the air to room temperature, and then, extracted with toluene, washed with H₂O and brine, and dried with Na₂SO₄. The solution thus obtained was concentrated and separated by column chromatography to obtain Compound D2-16 (10 g, 10 mmol, 65%, M/S 896.32).

5. Synthesis of Compound A3-3

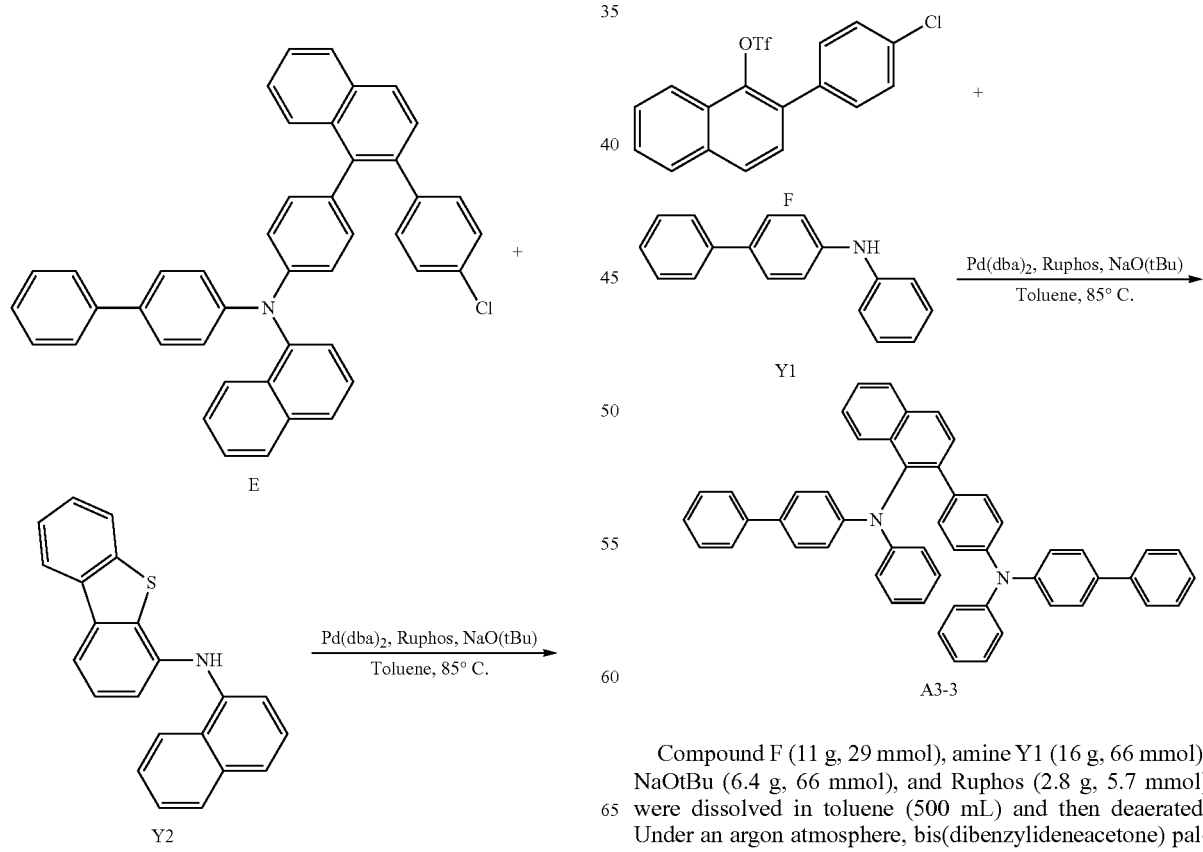

Compound F (11 g, 29 mmol), amine Y1 (16 g, 66 mmol), NaOtBu (6.4 g, 66 mmol), and Ruphos (2.8 g, 5.7 mmol) were dissolved in toluene (500 mL) and then deaerated. Under an argon atmosphere, bis(dibenzylideneacetone) palladium (0.82 g, 1.4 mmol) was added, followed by heating and stirring at about 85° C. for about 6 hours. The reaction solution was cooled in the air to room temperature, and then, extracted with toluene, washed with H₂O and brine, and dried with Na₂SO₄. The solution thus obtained was concentrated and separated by column chromatography to obtain Compound A3-3 (9.8 g, 14 mmol, 49%, M/S 690.3).

6. Synthesis of Compound A1-19

Synthesis of Intermediate Y5

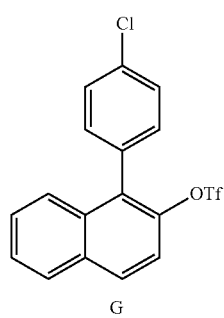

G

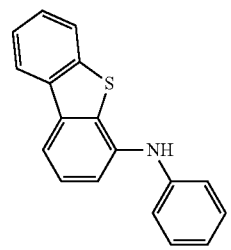

Y4

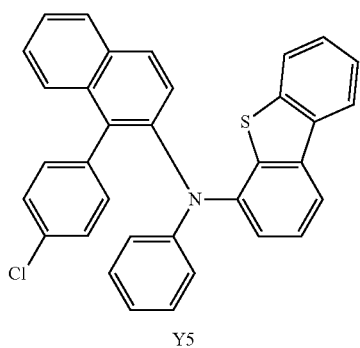

Y5

Compound G (11 g, 29 mmol), amine Y4 (7.9 g, 29 mmol), NaOtBu (2.7 g, 29 mmol), and Ruphos (2.8 g, 5.7 mmol) were dissolved in toluene (500 mL) and then deaerated. Under an argon atmosphere, bis(dibenzylideneacetone) palladium (0.82 g, 1.4 mmol) was added, followed by heating and stirring at about 85° C. for about 6 hours. The reaction solution was cooled in the air to room temperature, and then, extracted with toluene, washed with H₂O and brine, and dried with Na₂SO₄. The solution thus obtained was concentrated and separated by column chromatography to obtain Compound Y5 (4.7 g, 9.2 mmol, 32%, M/S 511.1).

Synthesis of Compound A1-19

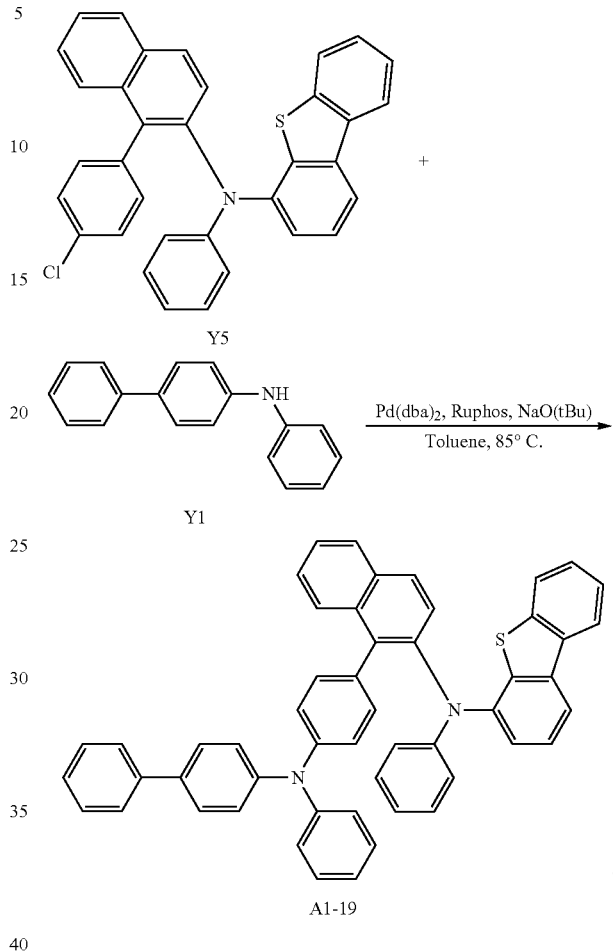

Intermediate Compound Y5 (14 g, 29 mmol), amine Y1 (7.1 g, 29 mmol), NaOtBu (2.7 g, 29 mmol), and Ruphos (2.8 g, 5.7 mmol) were dissolved in toluene (500 mL) and then deaerated. Under an argon atmosphere, bis(dibenzylideneacetone) palladium (0.82 g, 1.4 mmol) was added, followed by heating and stirring at about 85° C. for about 6 hours. The reaction solution was cooled in the air to room temperature, and then, extracted with toluene, washed with H₂O and brine, and dried with Na₂SO₄. The solution thus obtained was concentrated and separated by column chromatography to obtain Compound A1-19 (13 g, 18 mmol, 61%, M/S 720.3).

7. Synthesis of Compound A5-3

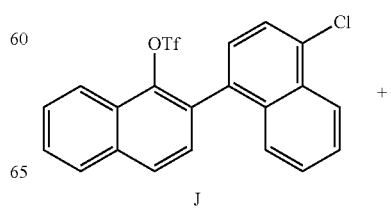

J

-continued

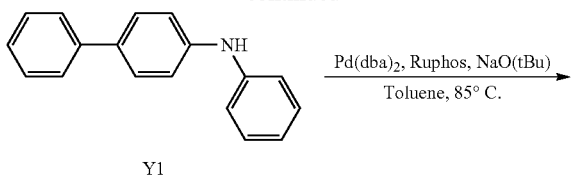

Y1

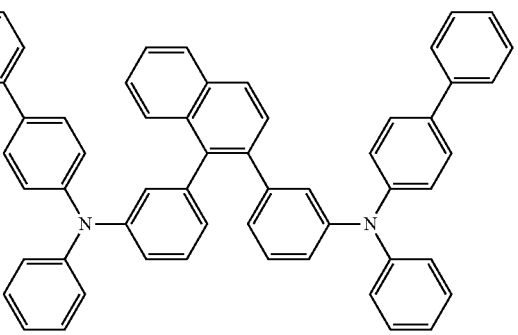

A4-3

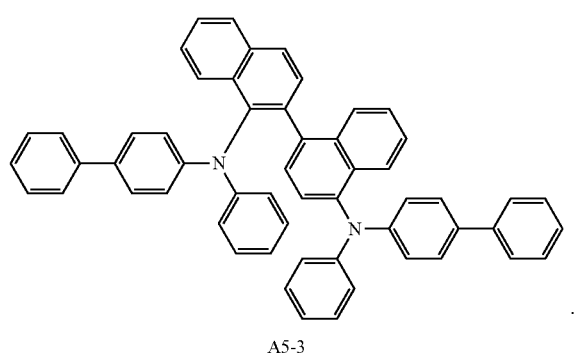

A5-3

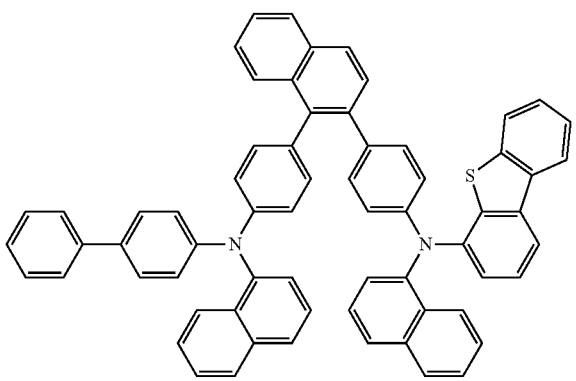

D2-16

Compound J (13 g, 29 mmol), amine Y1 (16 g, 66 mmol), NaOtBu (6.4 g, 66 mmol), and Ruphos (2.8 g, 5.7 mmol) were dissolved in toluene (500 mL) and then deaerated. Under an argon atmosphere, bis(dibenzylideneacetone) palladium (0.82 g, 1.4 mmol) was added, followed by heating and stirring at about 85° C. for about 6 hours. The reaction solution was cooled in the air to room temperature, and then, extracted with toluene, washed with $H_2O$ and brine, and dried with $Na_2SO_4$. The solution thus obtained was concentrated and separated by column chromatography to obtain Compound A5-3 (6.2 g, 8.4 mmol, 29%, M/S 740.3).

DEVICE MANUFACTURING EXAMPLES

Organic electroluminescence devices were manufactured using the Example Compounds and Comparative Compounds below as materials for a hole transport region.

EXAMPLE COMPOUNDS

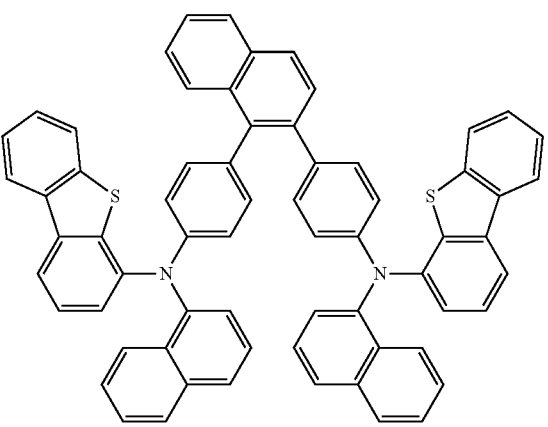

E2-3

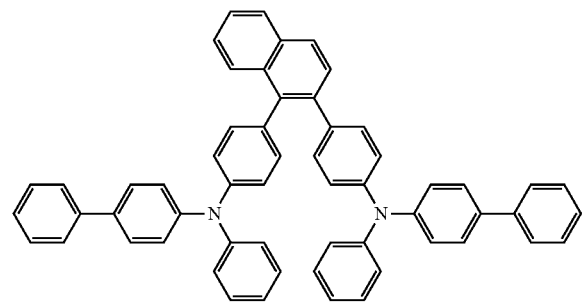

A2-3

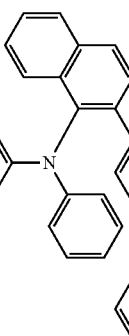

A3-3

-continued

A1-19
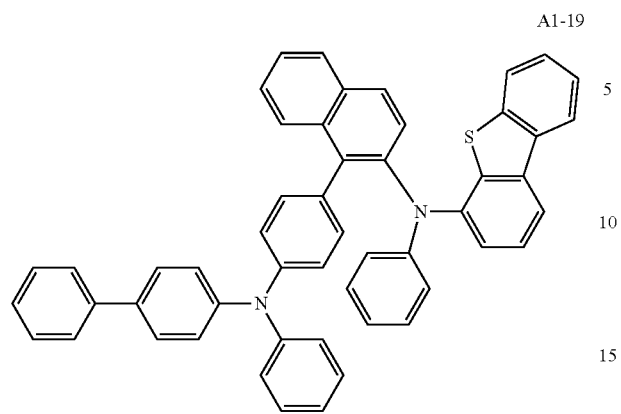

A5-3
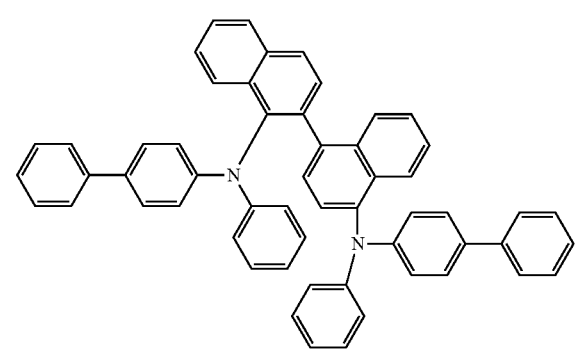

Comparative Compounds

R1
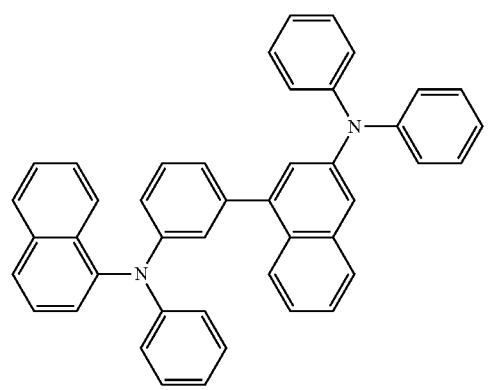

R2
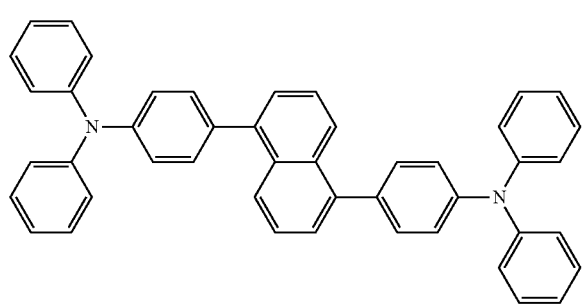

-continued

R3
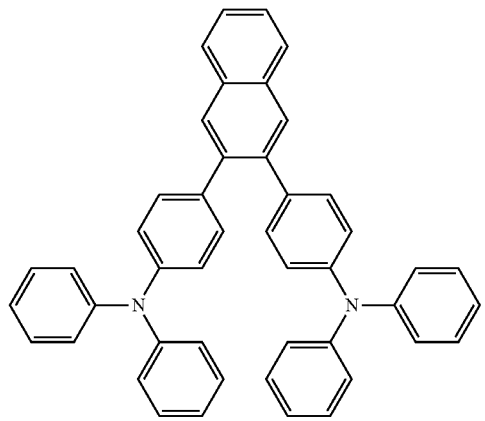

R4
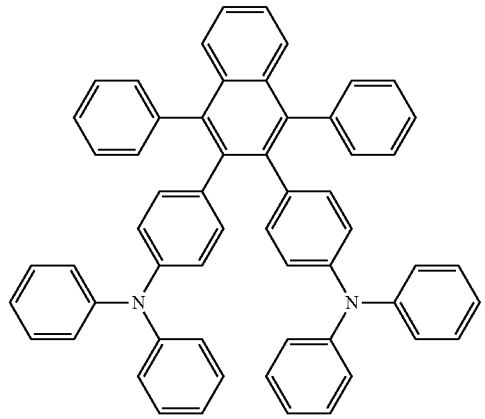

R5
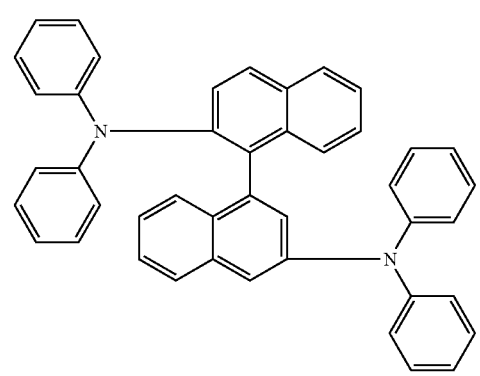

The organic electroluminescence devices of the Examples and Comparative Examples were manufactured by a method below. ITO with a thickness of about 150 nm was patterned on a glass substrate, washed with ultrapure water, and treated with UV-ozone for about 10 minutes to form a first electrode. Then, 2-TNATA was deposited to a thickness of about 60 nm, and the Example Compound or Comparative Compound was deposited to a thickness of about 30 nm to form a hole transport layer. Then, an emission layer with a thickness of about 25 nm was formed using ADN doped with 3% TBP, and on the emission layer, a layer with a thickness of about 25 nm was formed using Alq3, and a layer with a thickness of about 1 nm was formed using LiF to form an electron transport region. After that, a second electrode with a thickness of about 100 nm was formed using aluminum (Al). All layers were formed by a vacuum deposition method.

The emission efficiency of organic electroluminescence devices according to Examples 1 to 7 and Comparative Examples 1 to 5 are shown in Table 1 below. The emission efficiency is a value measured at 10 mA/cm$^2$, and are reported as relative values with respect to Comparative Example 2.

TABLE 1

|  | Hole transport layer | Device efficiency (%) |
| --- | --- | --- |
| Example 1 | Example Compound A2-3 | 109% |
| Example 2 | Example Compound A4-3 | 110% |
| Example 3 | Example Compound D2-16 | 112% |
| Example 4 | Example Compound E2-3 | 112% |
| Example 5 | Example Compound A3-3 | 111% |
| Example 6 | Example Compound A1-19 | 113% |
| Example 7 | Example Compound A5-3 | 111% |
| Comparative Example 1 | Comparative Compound R1 | 103% |
| Comparative Example 2 | Comparative Compound R2 | 100% |
| Comparative Example 3 | Comparative Compound R3 | 102% |
| Comparative Example 4 | Comparative Compound R4 | 104% |
| Comparative Example 5 | Comparative Compound R5 | 104% |

Referring to Table 1, it could be confirmed that Examples 1 to 7 accomplished higher efficiency than Comparative Examples 1 to 5.

The diamine compound according to an embodiment of the present disclosure selectively introduces a linker and an amine group at each of the 1- and 2-positions of naphthalene, and contributes to the increase of the efficiency of an organic electroluminescence device by the effects due to the improvement of orientating factors and electronic delocalization.

In the compounds of Example 1 to Example 7, due to steric repulsion between two amine groups that are substituted at the 1- and 2-positions of naphthalene, those substituents are twisted and intermolecular orientation may be improved. In addition, because the 1-position and 2-position of naphthalene have different electron distributions, when arylamine groups are introduced to the respective positions, effects due to electronic delocalization may be obtained, and transport capacity may be improved. Accordingly, the recombination probability of holes and electrons in an emission layer may be increased, and emission efficiency may be improved.

Examples 3, 4, and 6 each achieved a particularly high device efficiency due to the improvement of the electronic effects of the heteroaryl group of amine.

In Comparative Example 1, arylamine groups were introduced to the 1- and 3-positions of naphthalene. Without being bound by the correctness of any explanation or theory, it is thought that the electron density of naphthalene was relatively low when compared with the compounds of the Examples, so that the efficiency of the device was low.

In Comparative Example 2, it was confirmed that the device efficiency was particularly low. Without being bound by the correctness of any explanation or theory, it is thought that because the amine groups were respectively substituted on different benzene rings of the naphthalene, the electron density of naphthalene was further decreased to decrease the device efficiency.

In Comparative Example 3 and Comparative Example 4, the arylamine groups are introduced at the 2- and 3-positions of naphthalene, such that the electron density of naphthalene was relatively low when compared with the compounds of the Examples, and the device efficiency was low.

In Comparative Example 5, a naphthyl group was introduced at the 1-position of naphthalene, and due to steric repulsion between the two naphthalene groups, electron cloud delocalization was relatively decreased, and device efficiency was low. Without being bound by the correctness of any explanation or theory, it is thought that due to steric repulsion between the arylamine group at the 2-position and the proton at the 8-position, and the arylamine group at the 2'-position and the proton at the 8-position, the dihedral angle between the two connected naphthyl groups was increased, and electron delocalization was decreased.

The diamine compound according to an embodiment of the present disclosure may be used in a hole transport region and may contribute to a decrease in driving voltage, and increase in efficiency and/or life (life span) of an organic electroluminescence device.

The organic electroluminescence device according to an embodiment of the present disclosure may have excellent efficiency.

The diamine compound according to an embodiment of the present disclosure may be used as a material for the hole transport region of an organic electroluminescence device, and by using the diamine compound, the efficiency of the organic electroluminescence device may be improved.

As used herein, the terms "substantially," "about," and similar terms are used as terms of approximation and not as terms of degree, and are intended to account for the inherent deviations in measured or calculated values that would be recognized by those of ordinary skill in the art.

Any numerical range recited herein is intended to include all sub-ranges of the same numerical precision subsumed within the recited range. For example, a range of "1.0 to 10.0" is intended to include all subranges between (and including) the recited minimum value of 1.0 and the recited maximum value of 10.0, that is, having a minimum value equal to or greater than 1.0 and a maximum value equal to or less than 10.0, such as, for example, 2.4 to 7.6. Any maximum numerical limitation recited herein is intended to include all lower numerical limitations subsumed therein and any minimum numerical limitation recited in this specification is intended to include all higher numerical limitations subsumed therein. Accordingly, Applicant reserves the right to amend this specification, including the claims, to expressly recite any sub-range subsumed within the ranges expressly recited herein.

Although the example embodiments of the present disclosure have been described, it is understood that the present disclosure should not be limited to these example embodiments, but various changes and modifications can be made by one ordinary skilled in the art within the spirit and scope of the present disclosure as set forth in the following claims and their equivalents.

What is claimed is:

1. An organic electroluminescence device, comprising:
   a first electrode;
   a hole transport region on the first electrode;
   an emission layer on the hole transport region;
   an electron transport region on the emission layer; and
   a second electrode on the electron transport region,
   wherein the hole transport region comprises a diamine compound represented by Formula 1:

[Formula 1]

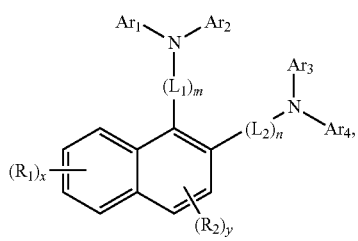

wherein in Formula 1,

Ar$_1$ to Ar$_4$ are each independently a substituted or unsubstituted aryl group of 6 to 30 carbon atoms for forming a ring or a substituted or unsubstituted heteroaryl group of 2 to 30 carbon atoms for forming a ring, L$_1$ is a direct linkage or a substituted or unsubstituted phenylene group, L$_2$ is a direct linkage, a substituted or unsubstituted arylene group of 6 to 30 carbon atoms for forming a ring, or a substituted or unsubstituted heteroarylene group of 2 to 30 carbon atoms for forming a ring, R$_1$ and R$_2$ are each independently a hydrogen atom, a deuterium atom, a halogen atom, a cyano group, a substituted or unsubstituted thiol group, a substituted or unsubstituted oxy group, a substituted or unsubstituted silyl group, a substituted or unsubstituted alkyl group of 1 to 20 carbon atoms, a substituted or unsubstituted aryl group of 6 to 30 carbon atoms for forming a ring, or a substituted or unsubstituted heteroaryl group of 2 to 30 carbon atoms for forming a ring, x is an integer of 0 to 4, y is an integer of 0 to 2, and m and n are each independently an integer of 0 to 4, where m+n is not 0, and L$_1$ and L$_2$ are not both a direct linkage, and wherein i) when L$_2$ is a naphthylene group,
the naphthylene group is represented by

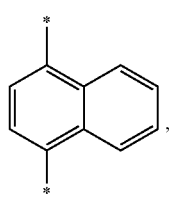

where * represents a bindinq site to a neighboring atom, and ii) when m is 1, n is 1, and L$_1$ and L$_2$ are each an unsubstituted phenylene group represented by

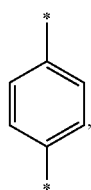

where * represents a bindinq site to a neighboring atom,

R$_1$ and R$_2$ are each independently a hydrogen atom, a deuterium atom, a substituted or unsubstituted alkyl group of 1 to 5 carbon atoms, an unsubstituted phenyl group, or a substituted or unsubstituted carbazole group.

2. The organic electroluminescence device of claim 1, wherein Formula 1 is represented by Formula 2 or Formula 3:

[Formula 2]

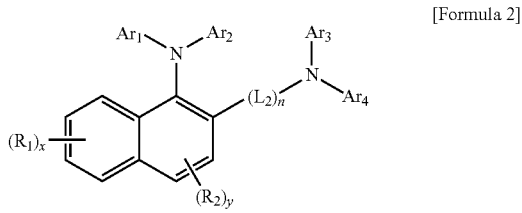

[Formula 3]

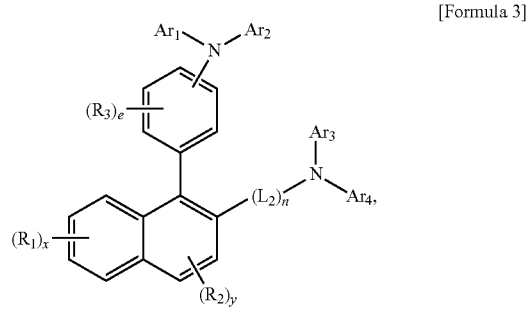

wherein in Formula 2 and Formula 3,

R$_3$ is a hydrogen atom, a deuterium atom, a halogen atom, a substituted or unsubstituted alkyl group of 1 to 20 carbon atoms, a substituted or unsubstituted aryl group of 6 to 30 carbon atoms for forming a ring, or a substituted or unsubstituted heteroaryl group of 2 to 30 carbon atoms for forming a ring, e is an integer of 0 to 4, and Ar$_1$ to Ar$_4$, L$_2$, R$_1$, R$_2$, n, x and y are each independently the same as defined in Formula 1.

3. The organic electroluminescence device of claim 1, wherein L$_2$ is a direct linkage, a substituted or unsubstituted phenylene group, a substituted or unsubstituted biphenylene group, a substituted or unsubstituted naphthylene group, or a substituted or unsubstituted anthracenyl group.

4. The organic electroluminescence device of claim 2, wherein Formula 2 is represented by Formula 2-1 or Formula 2-2:

[Formula 2-1]

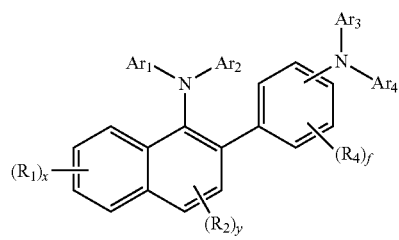

-continued

[Formula 2-2]

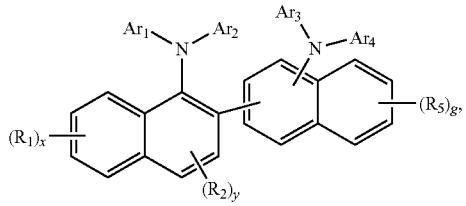

wherein in Formula 2-1 and Formula 2-2,

R$_4$ and R$_5$ are each independently a hydrogen atom, a deuterium atom, a halogen atom, a substituted or unsubstituted alkyl group of 1 to 20 carbon atoms, a substituted or unsubstituted aryl group of 6 to 30 carbon atoms for forming a ring, or a substituted or unsubstituted heteroaryl group of 2 to 30 carbon atoms for forming a ring, f and g are each independently an integer of 0 to 4, and Ar$_1$ to Ar$_4$, R$_1$, R$_2$, x and y are each independently the same as defined in Formula 2.

5. The organic electroluminescence device of claim 2, wherein Formula 3 is represented by any one of Formula 3-1 to Formula 3-3:

[Formula 3-1]

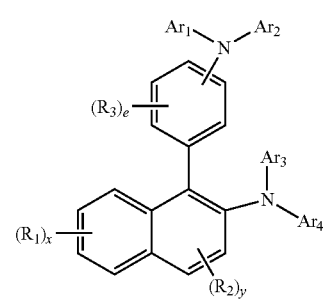

[Formula 3-2]

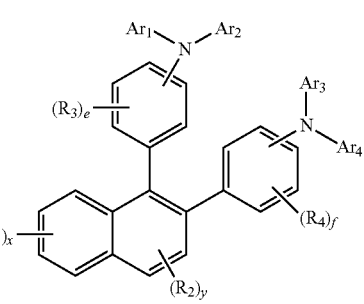

[Formula 3-3]

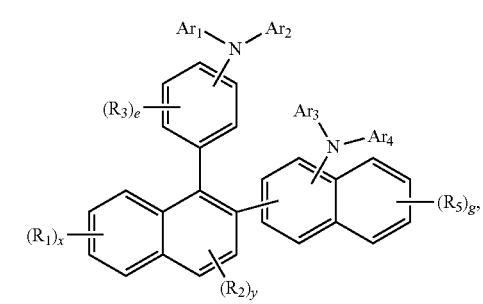

wherein in Formula 3-1 to Formula 3-3,

R$_4$ and R$_5$ are each independently a hydrogen atom, a deuterium atom, a halogen atom, a substituted or unsubstituted alkyl group of 1 to 20 carbon atoms, a substituted or unsubstituted aryl group of 6 to 30 carbon atoms for forming a ring, or a substituted or unsubstituted heteroaryl group of 2 to 30 carbon atoms for forming a ring, f and g are each independently an integer of 0 to 4, and Ar$_1$ to Ar$_4$, R$_1$ to R$_3$, e, x and y are each independently the same as defined in Formula 3.

6. The organic electroluminescence device of claim 2, wherein Formula 3 is represented by Formula 4 or Formula 5:

[Formula 4]

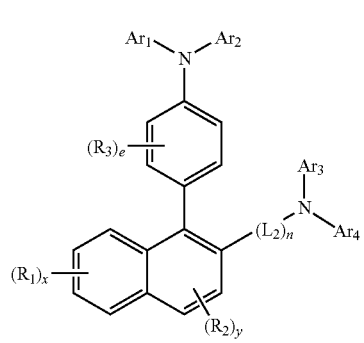

[Formula 5]

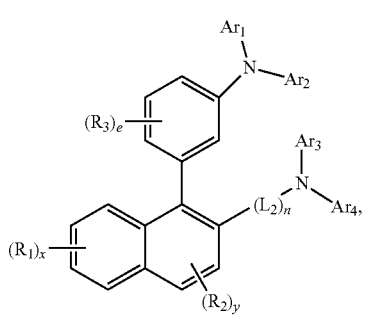

wherein in Formula 4 and Formula 5,

Ar$_1$ to Ar$_4$, L$_2$, R$_1$ to R$_3$, e, n, x and y are each independently the same as defined in Formula 3.

7. The organic electroluminescence device of claim 1, wherein Ar$_1$ and Ar$_3$ are each independently a substituted or unsubstituted phenyl group, a substituted or unsubstituted biphenyl group, a substituted or unsubstituted triphenyl group, or a substituted or unsubstituted naphthyl group.

8. The organic electroluminescence device of claim 1, wherein R$_1$ and R$_2$ are each independently a hydrogen atom, a deuterium atom, a substituted or unsubstituted alkyl group of 1 to 5 carbon atoms, a substituted or unsubstituted phenyl group, or a substituted or unsubstituted carbazole group.

9. The organic electroluminescence device of claim 1, wherein the hole transport region comprises:
a hole injection layer on the first electrode; and
a hole transport layer on the hole injection layer,
wherein the hole transport layer comprises the diamine compound represented by Formula 1.

10. The organic electroluminescence device of claim 9, wherein the hole transport region further comprises an electron blocking layer on the hole transport layer.

11. The organic electroluminescence device of claim 1, wherein the diamine compound represented by Formula 1 is at least one selected among compounds represented in Compound Group 1:

[Compound Group 1]
| | m | n | L₁ | L₂ | Ar₁ | Ar₂ | Ar₃ | Ar₄ | |
|---|---|---|---|---|---|---|---|---|---|
| A1-1 | 1 | 0 |  | — | 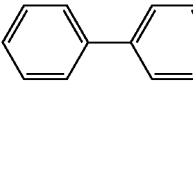 | 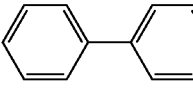 | 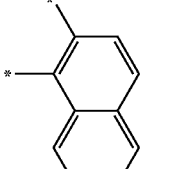 | 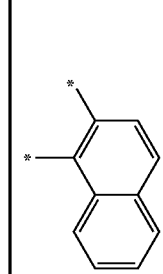 |  |
| A1-2 | 1 | 0 | 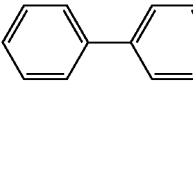 | — | 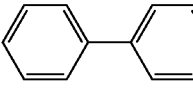 | 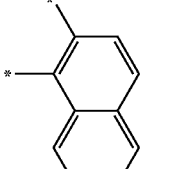 | 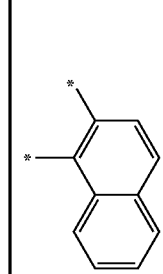 |  | 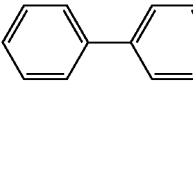 |
| A1-3 | 1 | 0 | 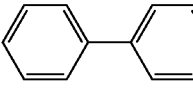 | — | 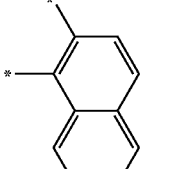 | 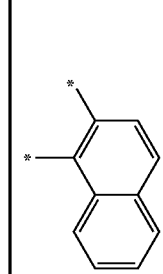 | | | |

-continued
[Compound Group 1]
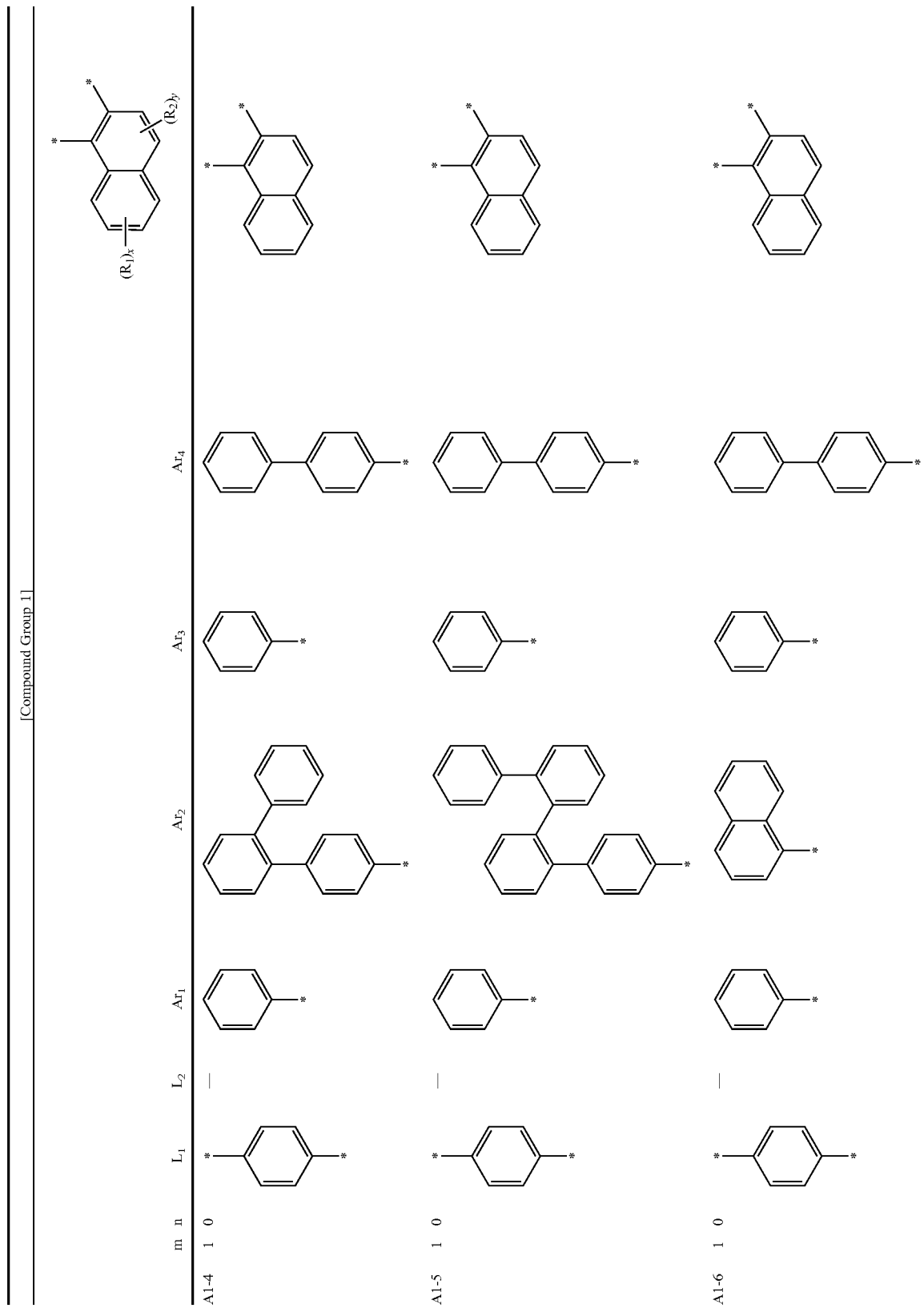

-continued
[Compound Group 1]
| | m | n | $L_1$ | $L_2$ | $Ar_1$ | $Ar_2$ | $Ar_3$ | $Ar_4$ | 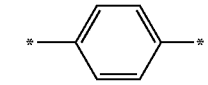 |
|---|---|---|---|---|---|---|---|---|---|
| A1-7 | 1 | 0 | 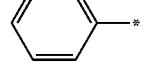 | — | 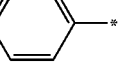 | 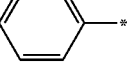 |  |  | 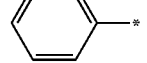 |
| A1-8 | 1 | 0 | 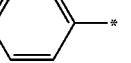 | — | 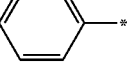 | 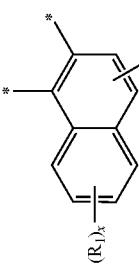 | 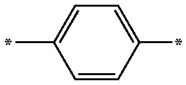 |  | 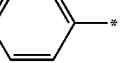 |
| A1-9 | 1 | 0 | 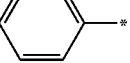 | — | 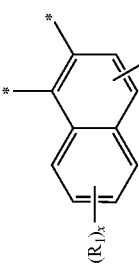 | | | | |

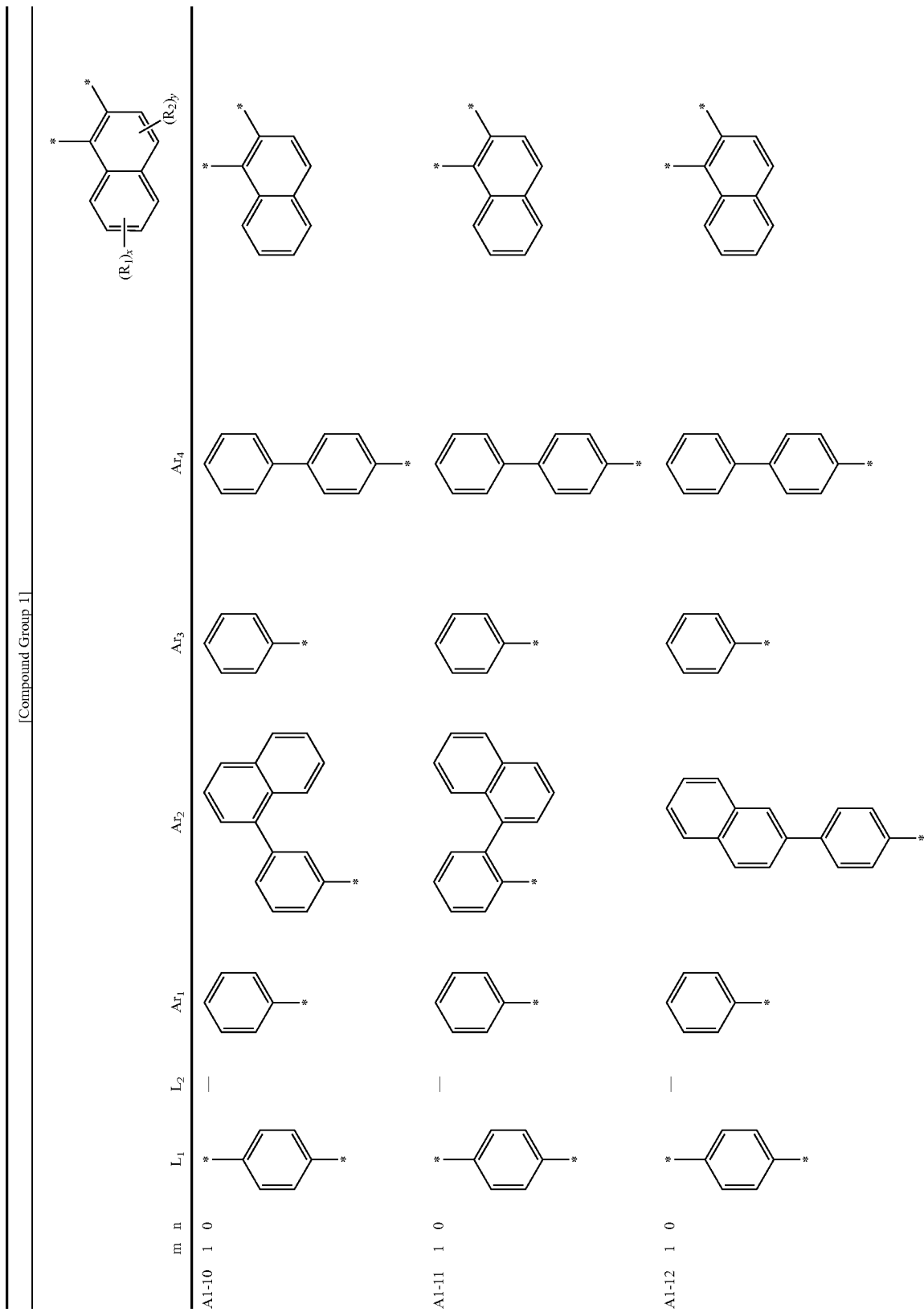

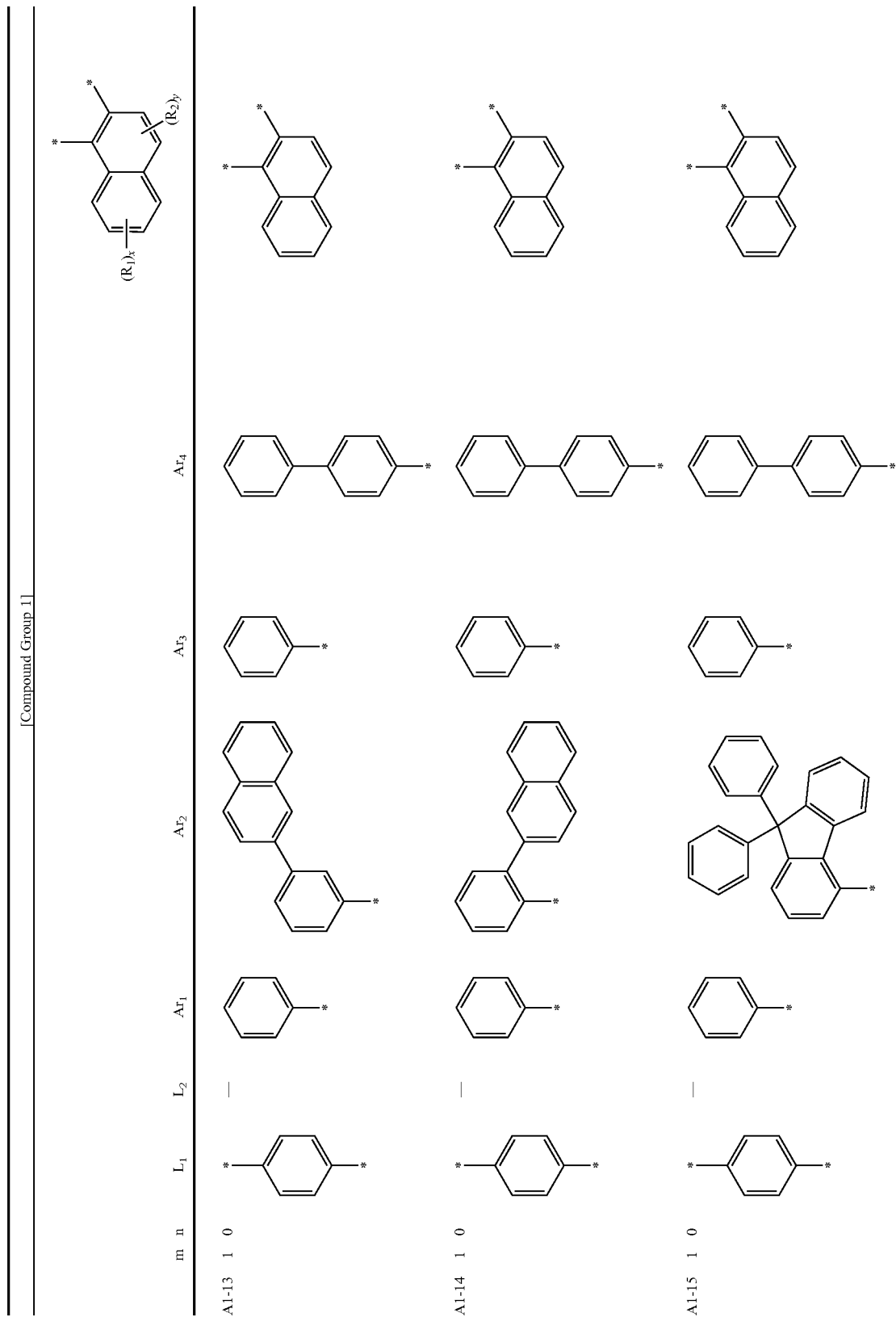

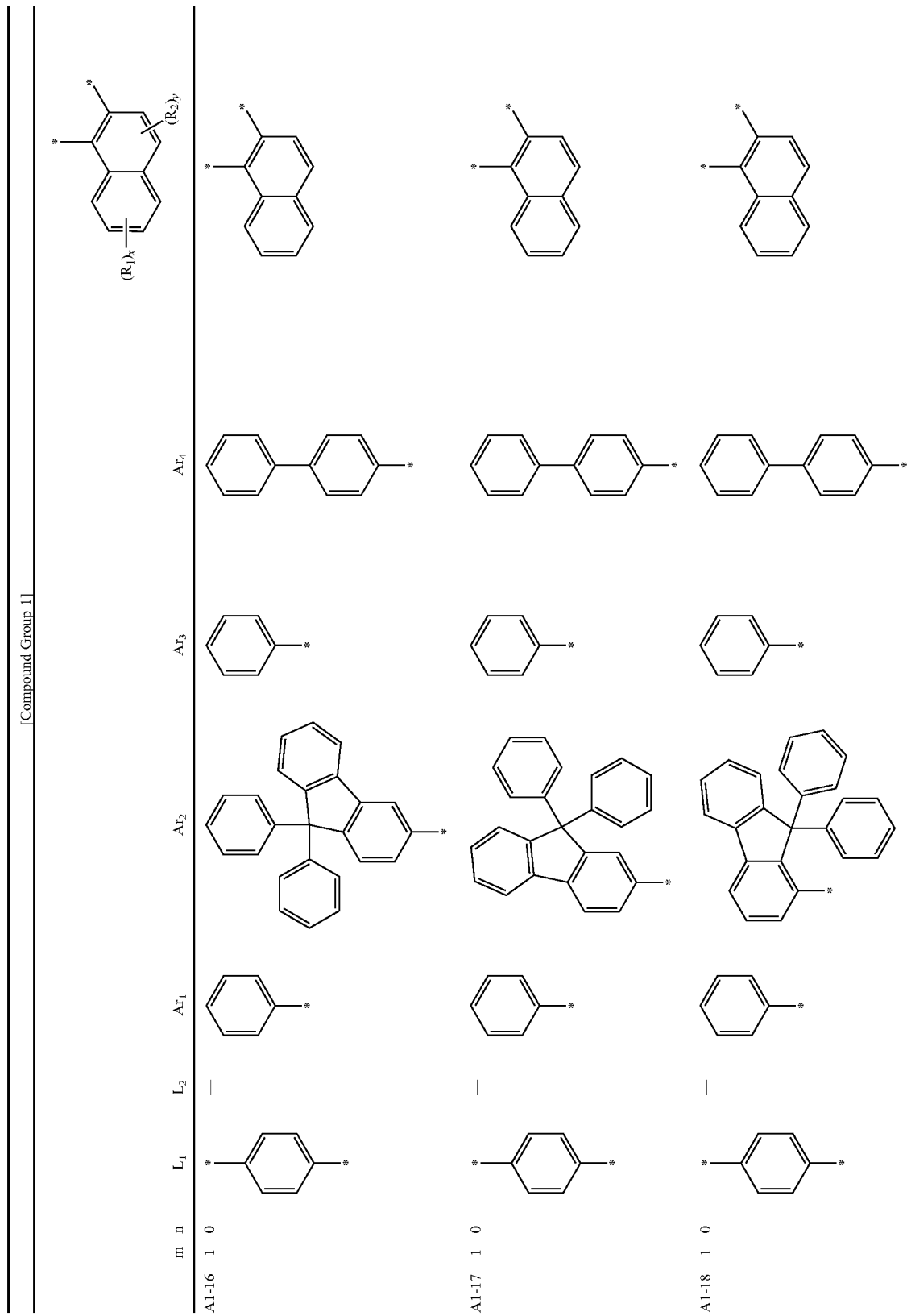

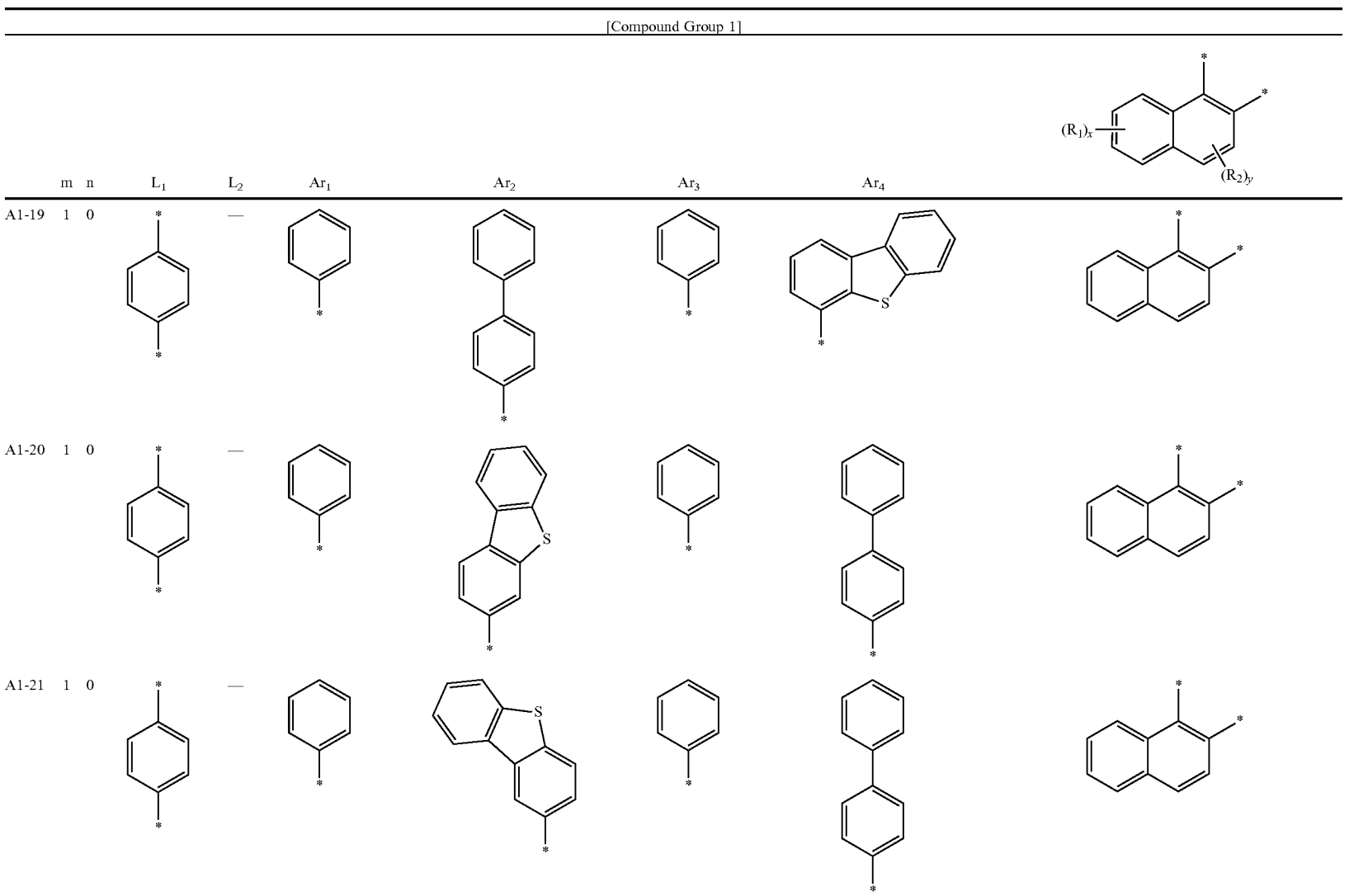

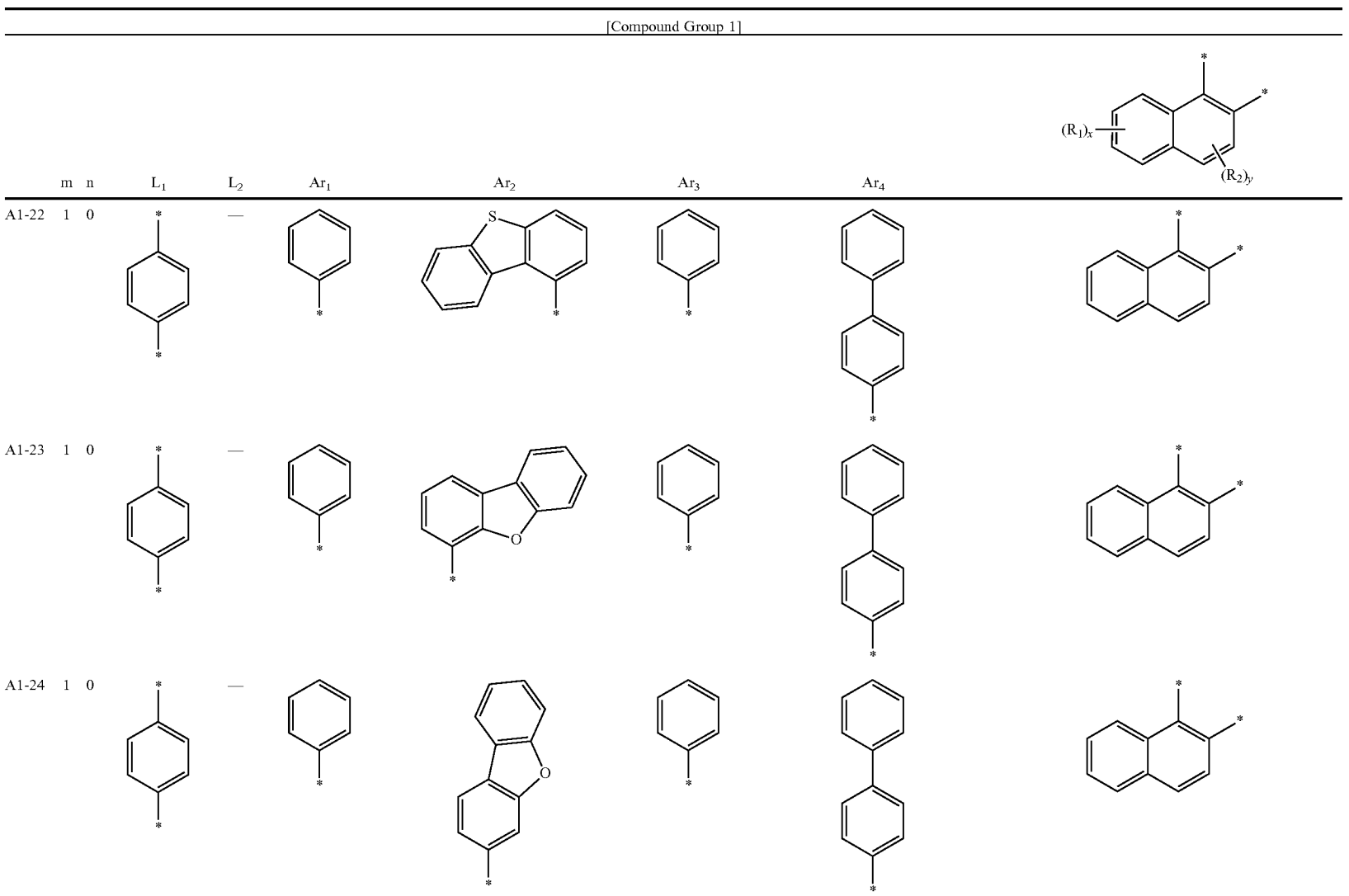

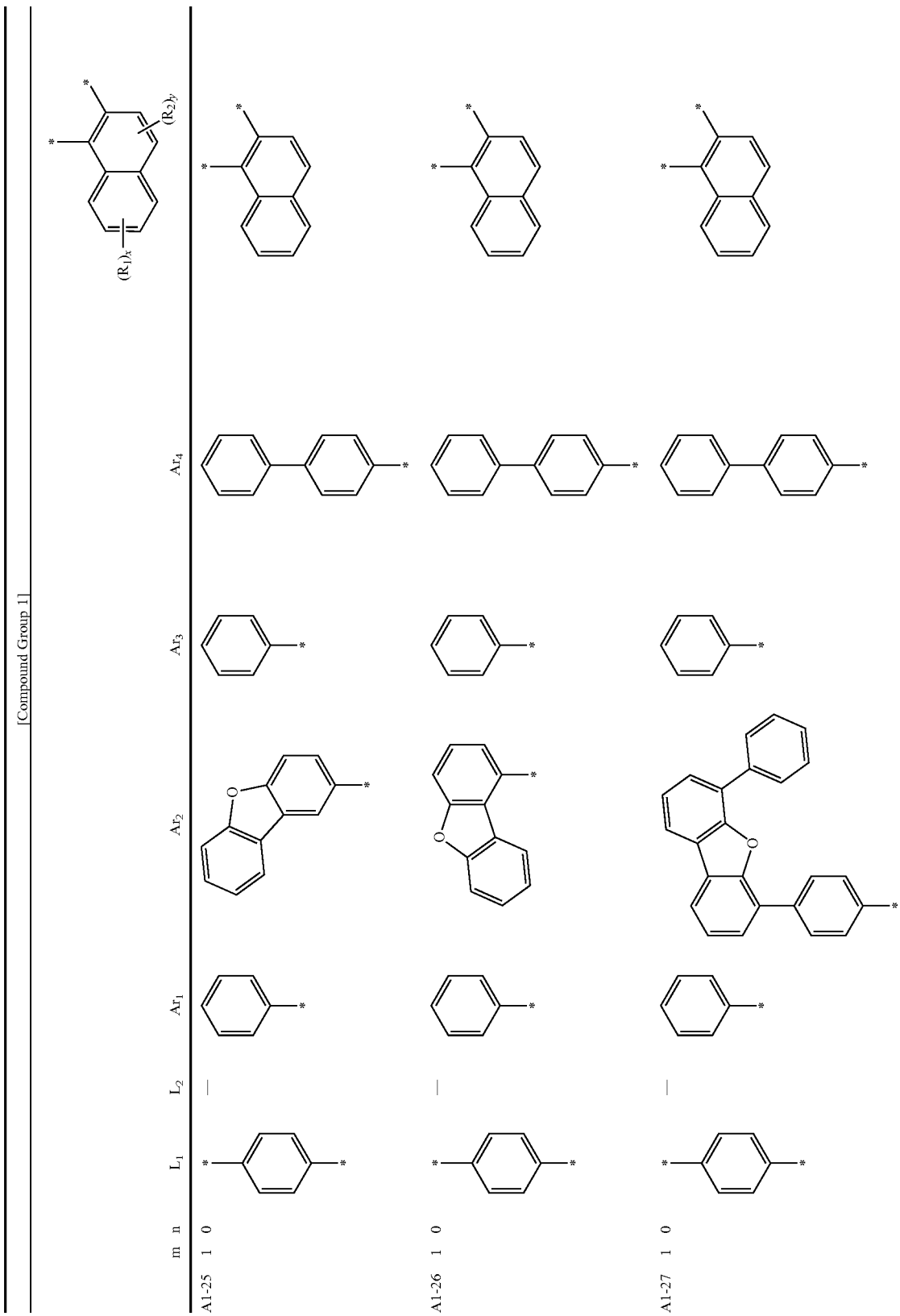

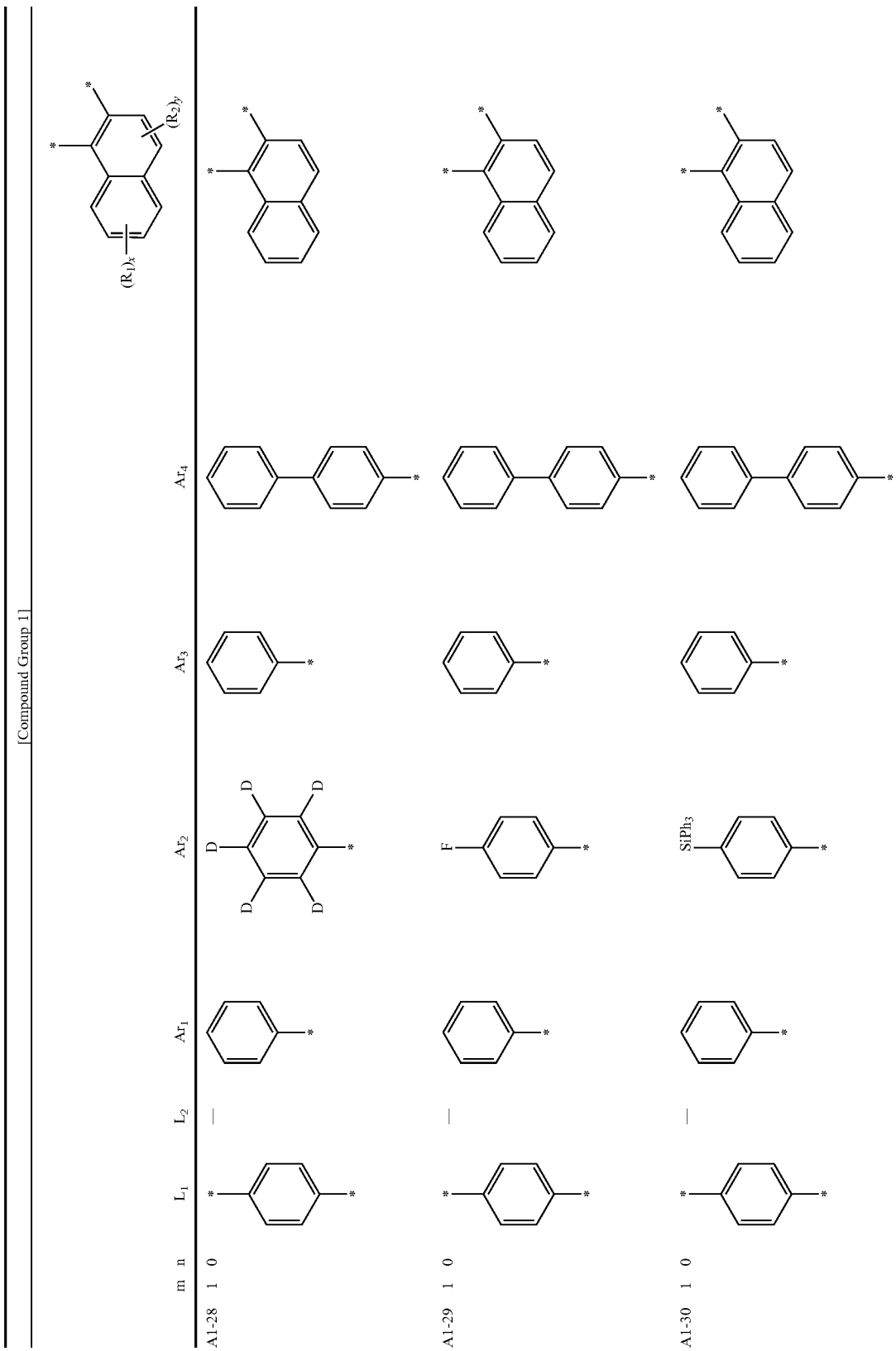

-continued
[Compound Group 1]
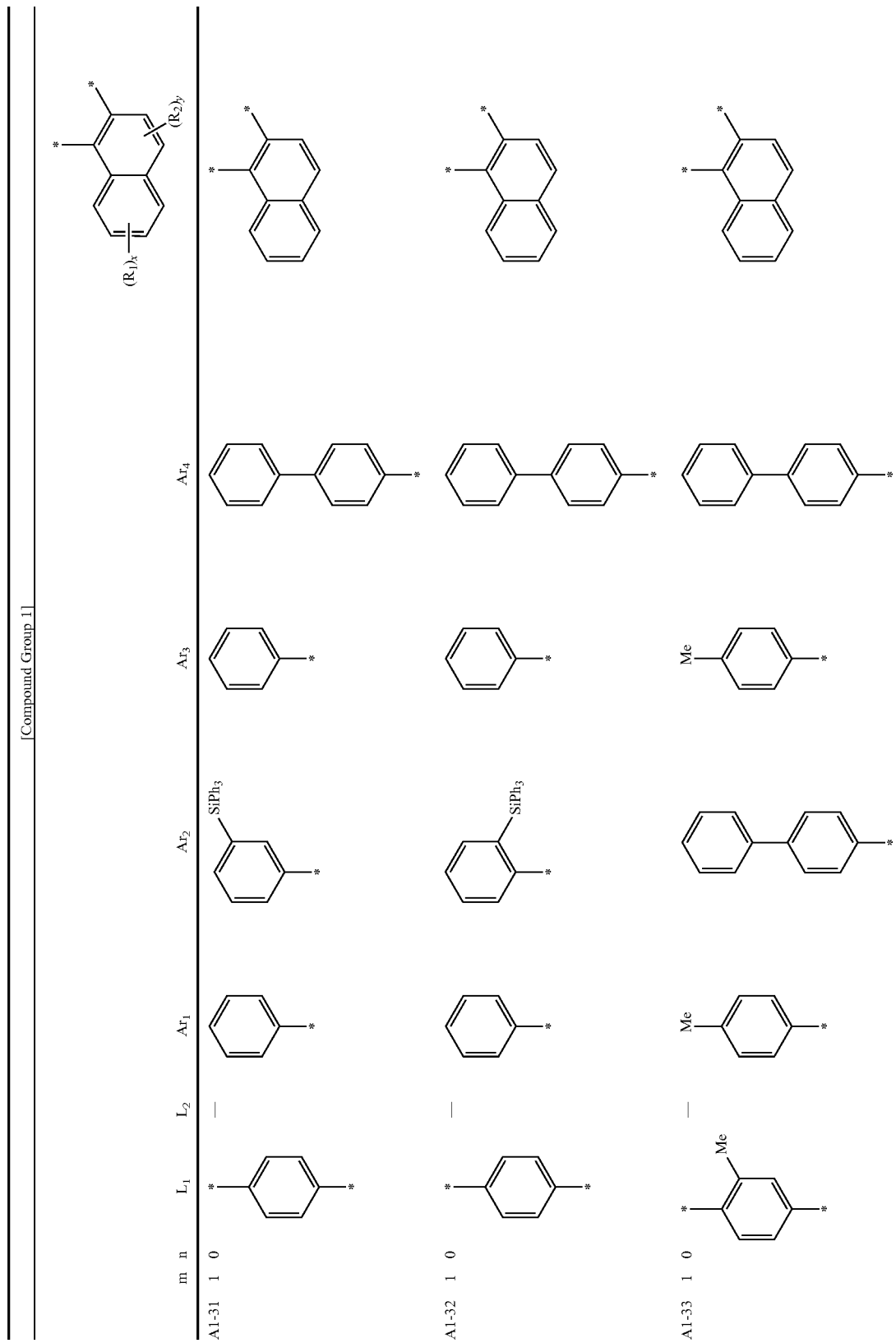

-continued
[Compound Group 1]
| | m | n | L₁ | L₂ | Ar₁ | Ar₂ | Ar₃ | Ar₄ | |
|---|---|---|---|---|---|---|---|---|---|
| B1-1 | 1 | 0 | 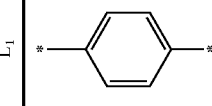 | — | 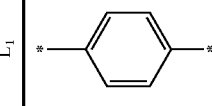 | 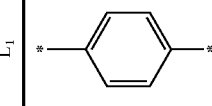 | 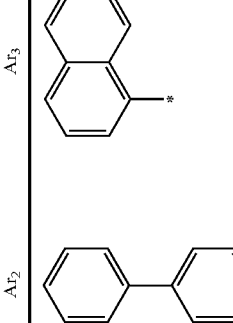 | 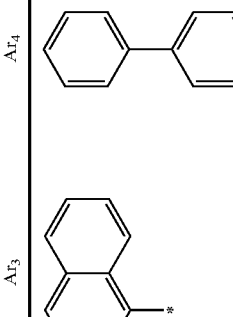 | 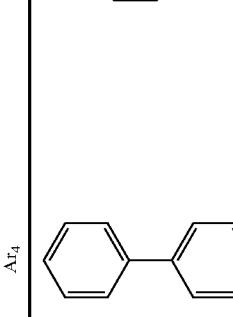 |
| B1-2 | 1 | 0 | 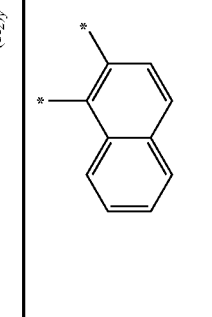 | — | 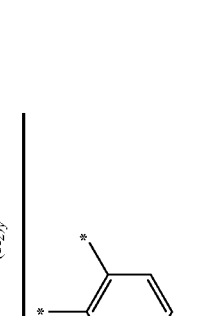 | | | | |
| B1-3 | 1 | 0 | | — | | | | | |

-continued
[Compound Group 1]
| | m | n | L₁ | L₂ | Ar₁ | Ar₂ | Ar₃ | Ar₄ | 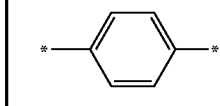 |
|---|---|---|---|---|---|---|---|---|---|
| B1-4 | 1 | 0 | 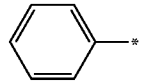 | — | 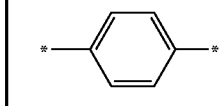 | 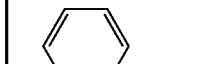 | 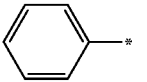 | 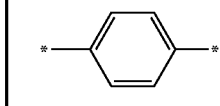 | 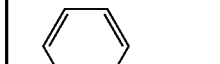 |
| B1-5 | 1 | 0 | 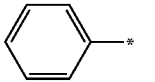 | — |  | 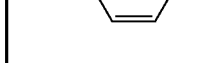 |  | 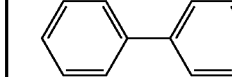 | 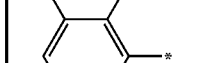 |
| B1-6 | 1 | 0 | 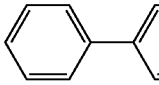 | — | 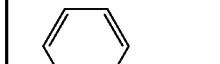 | 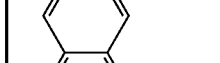 | 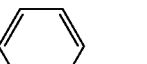 | 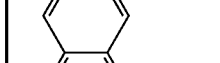 | 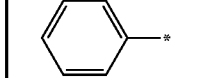 |

-continued
[Compound Group 1]
| | m | n | L₁ | L₂ | Ar₁ | Ar₂ | Ar₃ | Ar₄ | 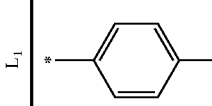 |
|---|---|---|---|---|---|---|---|---|---|
| B1-7 | 1 | 0 | 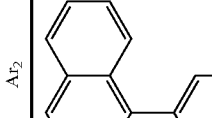 | — | 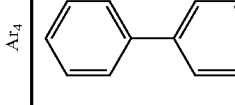 | 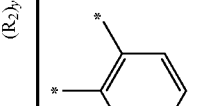 |  | 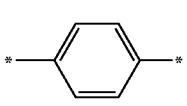 | 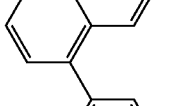 |
| B1-8 | 1 | 0 | 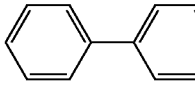 | — | 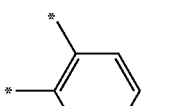 |  | 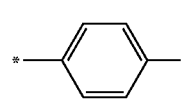 | 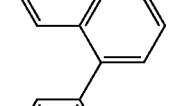 | 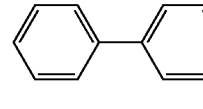 |
| B1-9 | 1 | 0 | 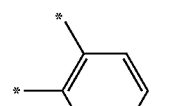 | — |  | | | | |

-continued
[Compound Group 1]
| | m | n | L₁ | L₂ | Ar₁ | Ar₂ | Ar₃ | Ar₄ | |
|---|---|---|---|---|---|---|---|---|---|
| B1-10 | 1 | 0 |  | — |  |  |  |  |  |
| B1-11 | 1 | 0 |  | — |  |  |  |  |  |
| B1-12 | 1 | 0 |  | — |  |  |  |  |  |

-continued

[Compound Group 1]

| | m | n | L₁ | L₂ | Ar₁ | Ar₂ | Ar₃ | Ar₄ | |
|---|---|---|---|---|---|---|---|---|---|
| B1-13 | 1 | 0 | | — | | | | | |
| B1-14 | 1 | 0 | | — | | | | | |
| B1-15 | 1 | 0 | | — | | | | | |

-continued

[Compound Group 1]

| | m | n | L₁ | L₂ | Ar₁ | Ar₂ | Ar₃ | Ar₄ | |
|---|---|---|---|---|---|---|---|---|---|
| B1-16 | 1 | 0 | | — | | | | | |
| B1-17 | 1 | 0 | | — | | | | | |
| B1-18 | 1 | 0 | | — | | | | | |

-continued

[Compound Group 1]

| | m | n | $L_1$ | $L_2$ | $Ar_1$ | $Ar_2$ | $Ar_3$ | $Ar_4$ | |
|---|---|---|---|---|---|---|---|---|---|
| B1-19 | 1 | 0 | | — | | | | | |
| B1-20 | 1 | 0 | | — | | | | | |
| B1-21 | 1 | 0 | | — | | | | | |

-continued

[Compound Group 1]

| | m | n | L₁ | L₂ | Ar₁ | Ar₂ | Ar₃ | Ar₄ | |
|---|---|---|---|---|---|---|---|---|---|
| B1-22 | 1 | 0 | *-⌬-* | — | phenyl | dibenzofuran-3-yl | naphthalen-1-yl | biphenyl-4-yl | naphthalen-1,2-yl |
| B1-23 | 1 | 0 | *-⌬-* | — | phenyl | dibenzofuran-2-yl | naphthalen-1-yl | biphenyl-4-yl | naphthalen-1,2-yl |
| B1-24 | 1 | 0 | *-⌬-* | — | phenyl | dibenzofuran-4-yl | naphthalen-1-yl | biphenyl-4-yl | naphthalen-1,2-yl |

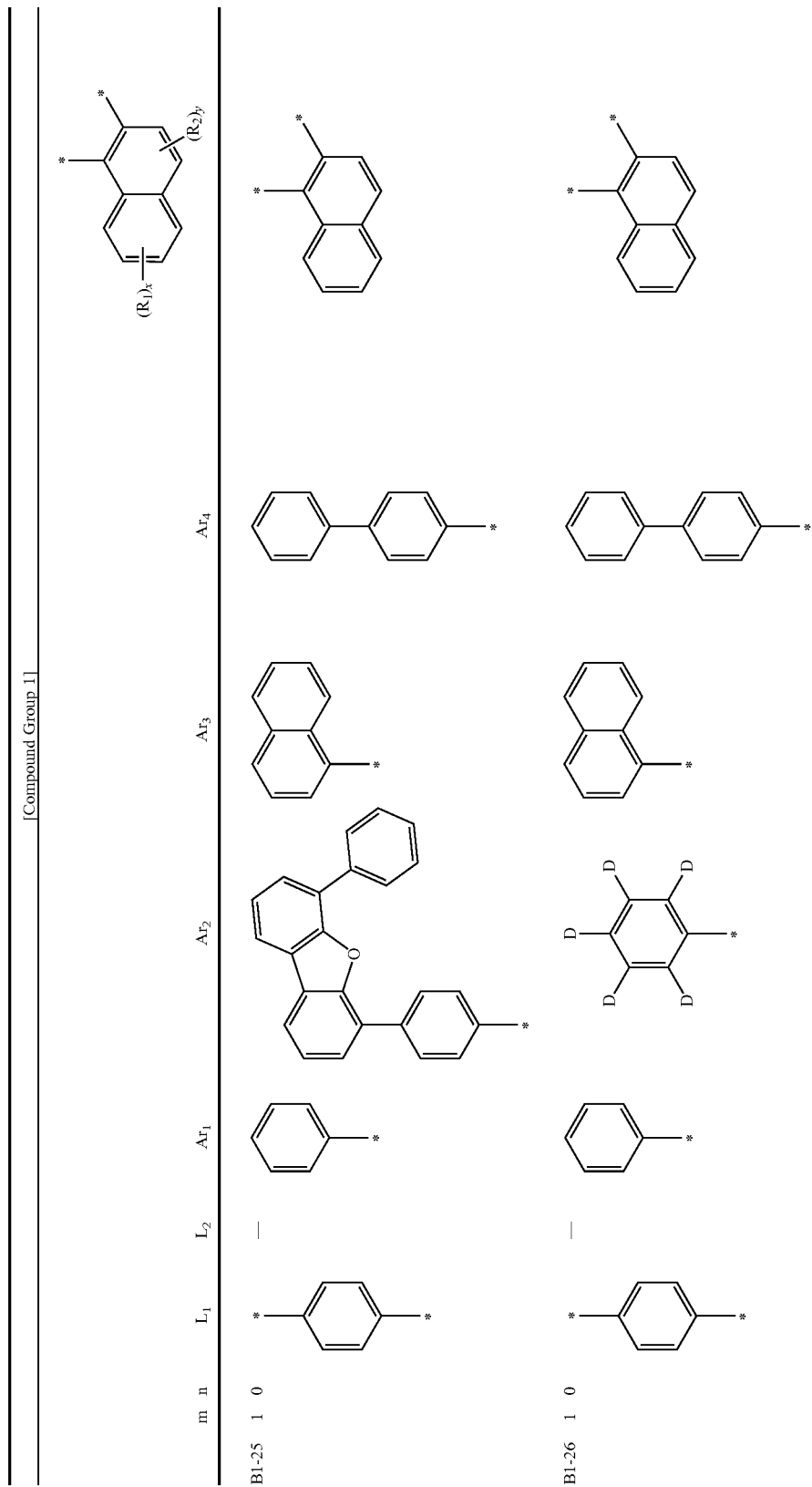

-continued

[Compound Group 1]

| m | n | L₁ | L₂ | Ar₁ | Ar₂ | Ar₃ | Ar₄ | |
|---|---|---|---|---|---|---|---|---|
| B1-27 | 1 | 0 | *–⌬–* | — | Ph | 4-F-C₆H₄ | 1-naphthyl | 4-biphenyl | naphthyl |
| B1-28 | 1 | 0 | *–⌬–* | — | Ph | 4-SiPh₃-C₆H₄ | 1-naphthyl | 4-biphenyl | naphthyl |
| B1-29 | 1 | 0 | *–⌬–* | — | Ph | 3-SiPh₃-C₆H₄ | 1-naphthyl | 4-biphenyl | naphthyl |

-continued
[Compound Group 1]
| | m | n | L₁ | L₂ | Ar₁ | Ar₂ | Ar₃ | Ar₄ | |
|---|---|---|---|---|---|---|---|---|---|
| B1-30 | 1 | 0 | *–⌬–* | — | Ph | o-SiPh₃-C₆H₄ | 1-naphthyl | biphenyl | 1,2-naphthylene |
| C1-1 | 1 | 0 | *–⌬–* | — | 1-naphthyl | biphenyl | Ph | biphenyl | 1,2-naphthylene |
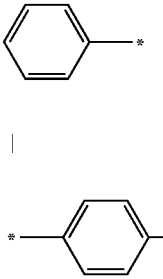

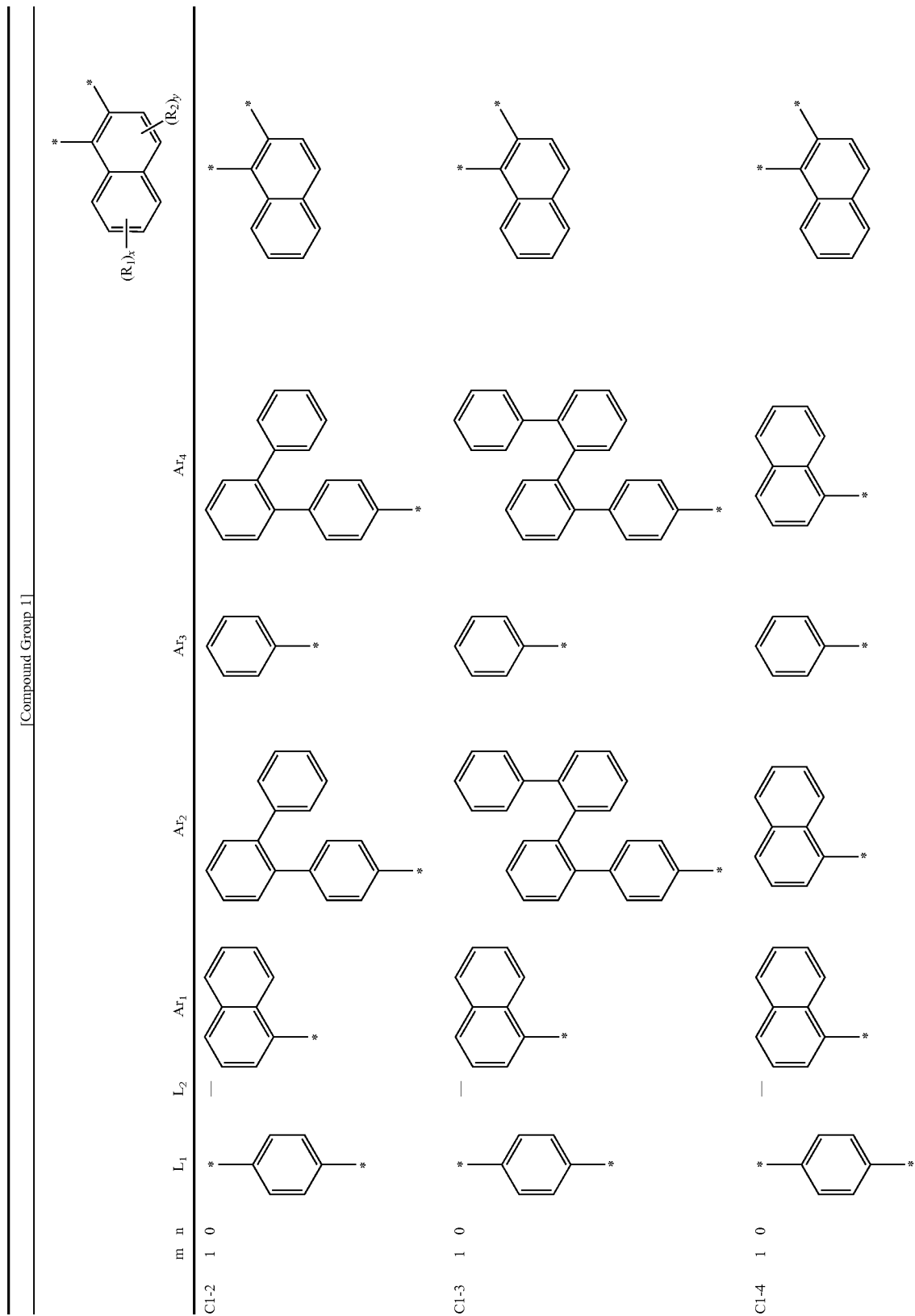

-continued
[Compound Group 1]
| | m | n | L₁ | L₂ | Ar₁ | Ar₂ | Ar₃ | Ar₄ | 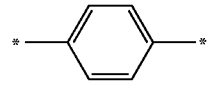 |
|---|---|---|---|---|---|---|---|---|---|
| C1-5 | 1 | 0 |  | — |  |  |  |  |  |
| C1-6 | 1 | 0 |  | — |  |  | 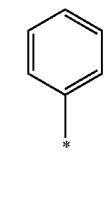 |  |  |
| C1-7 | 1 | 0 |  | — |  |  | 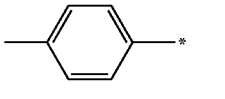 |  |  |

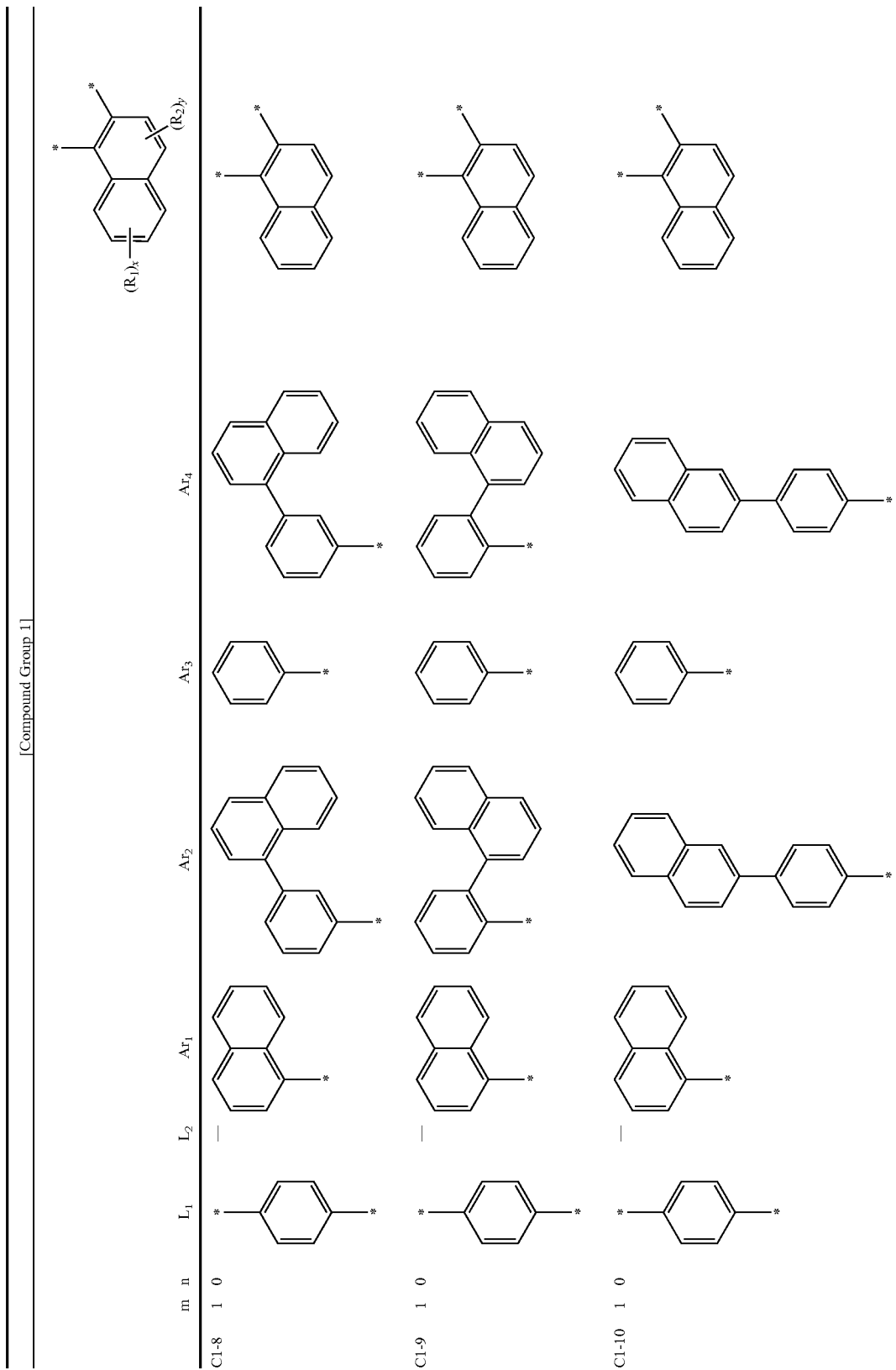

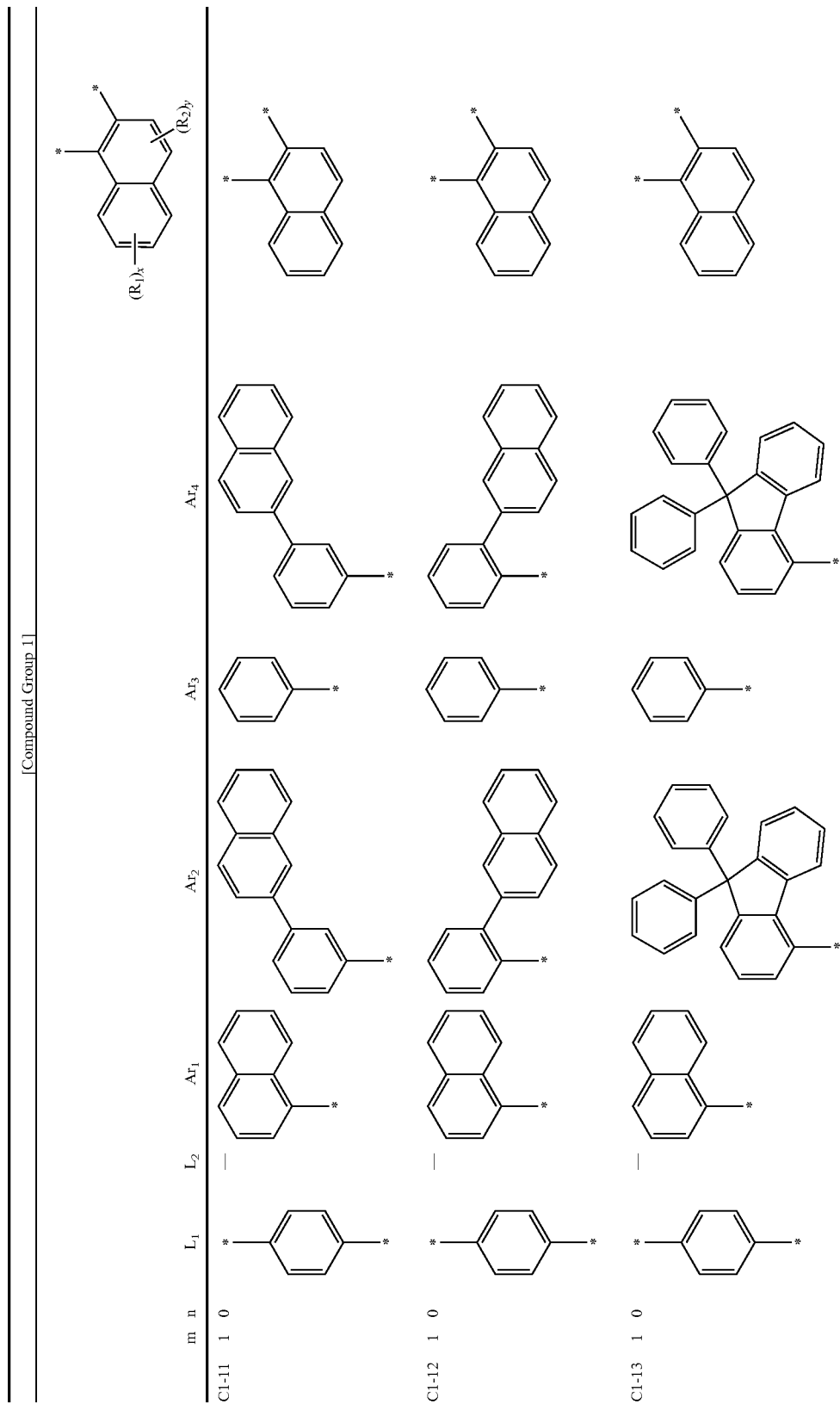

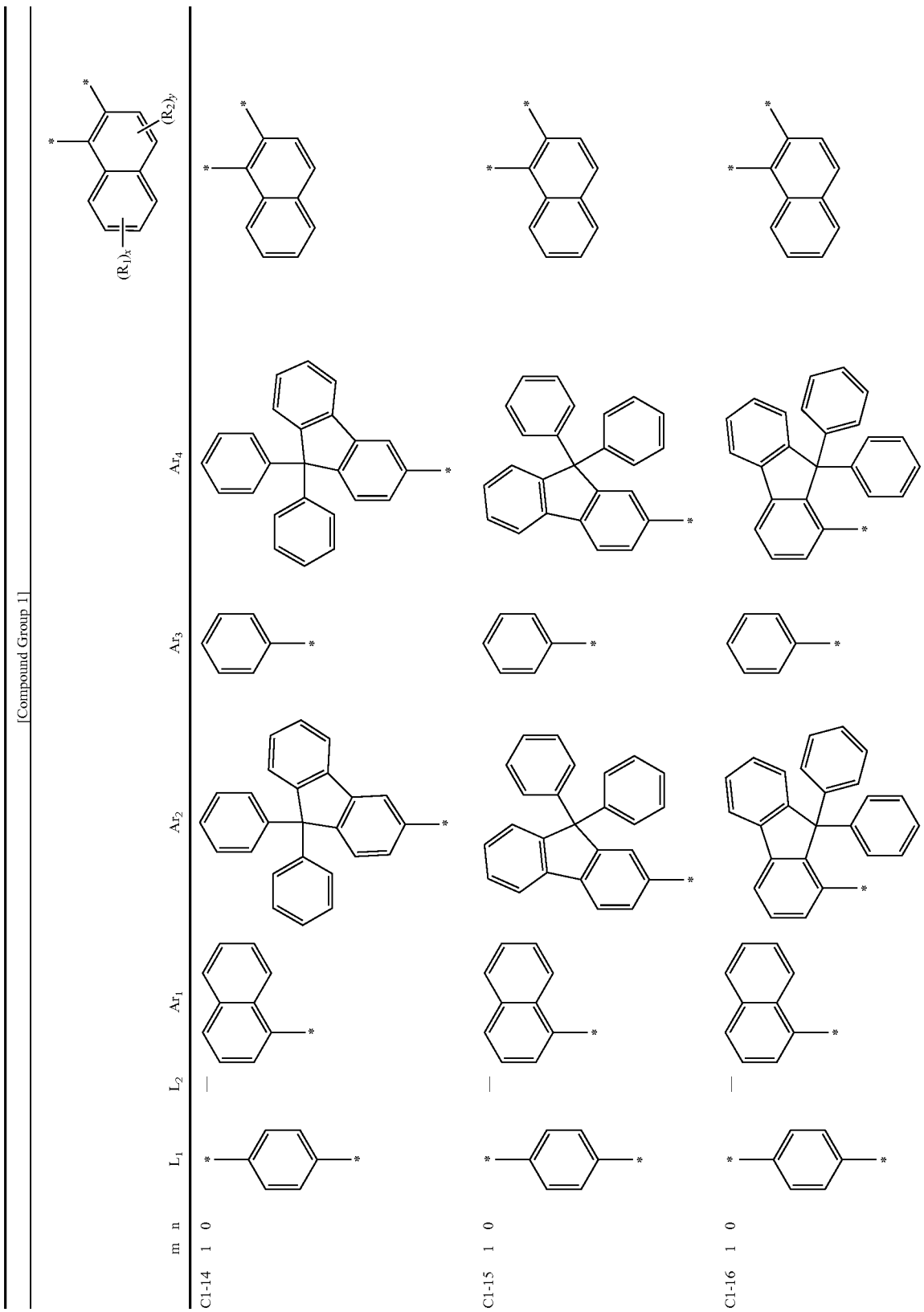

-continued
[Compound Group 1]
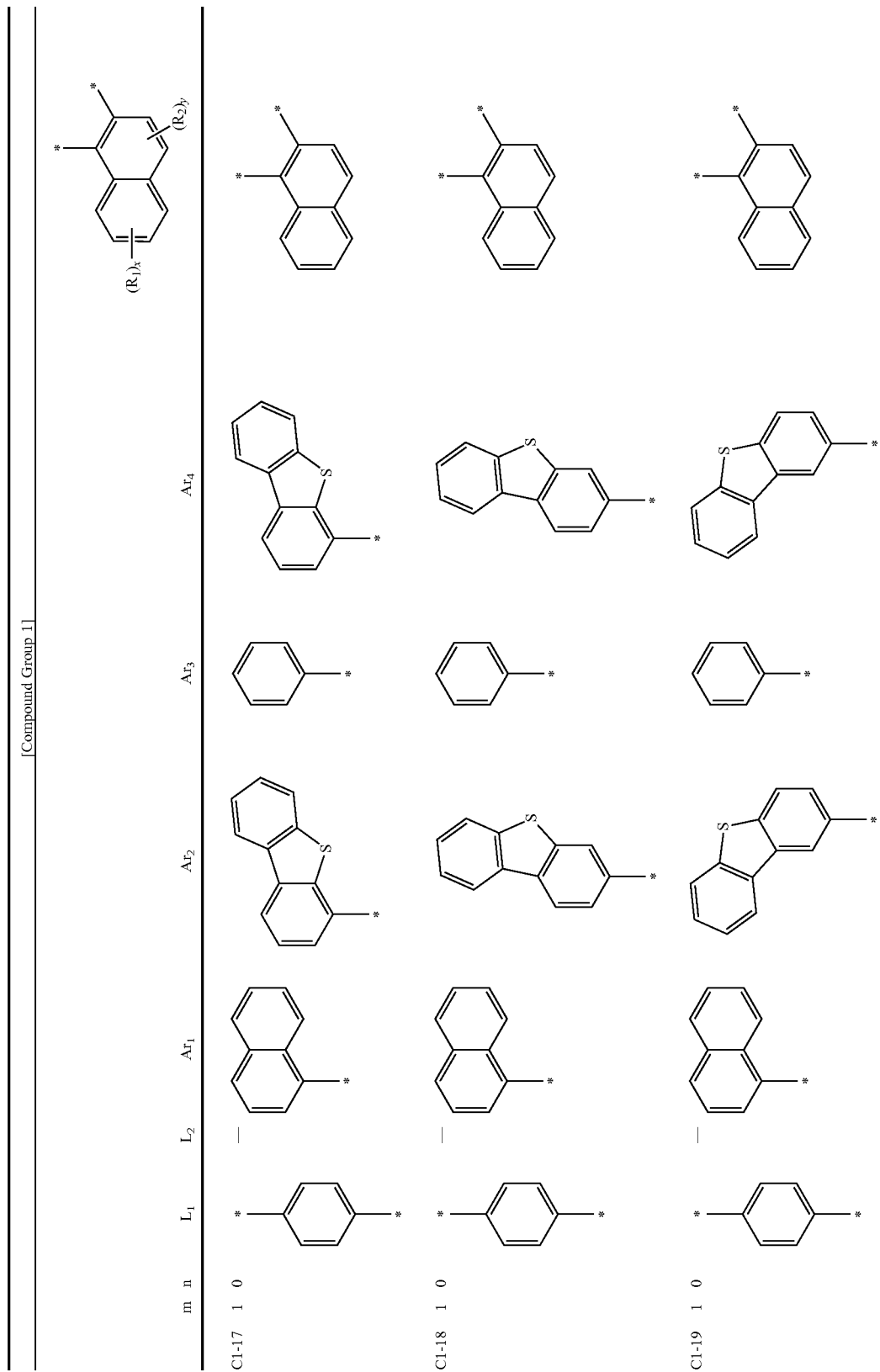

-continued
[Compound Group 1]
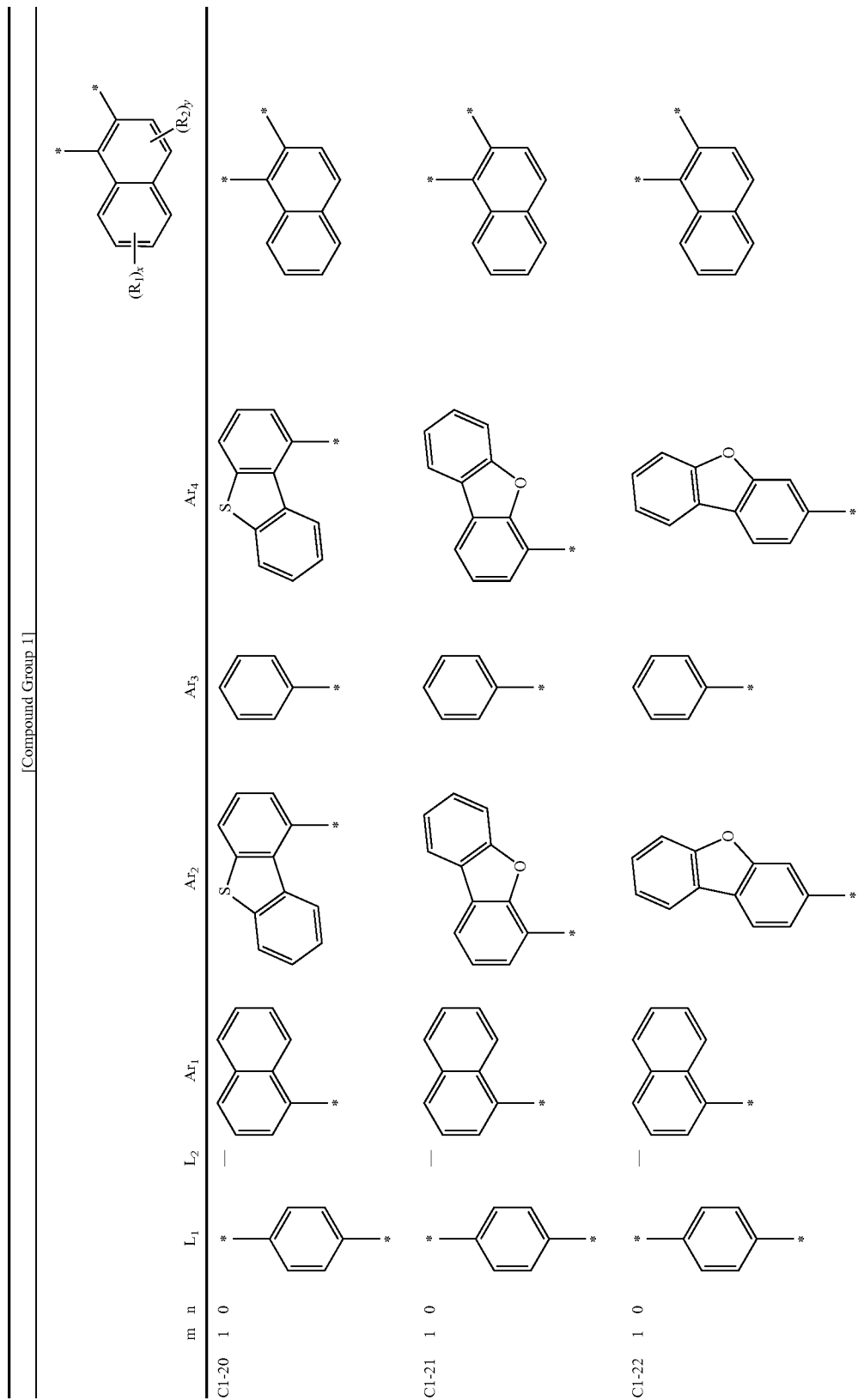

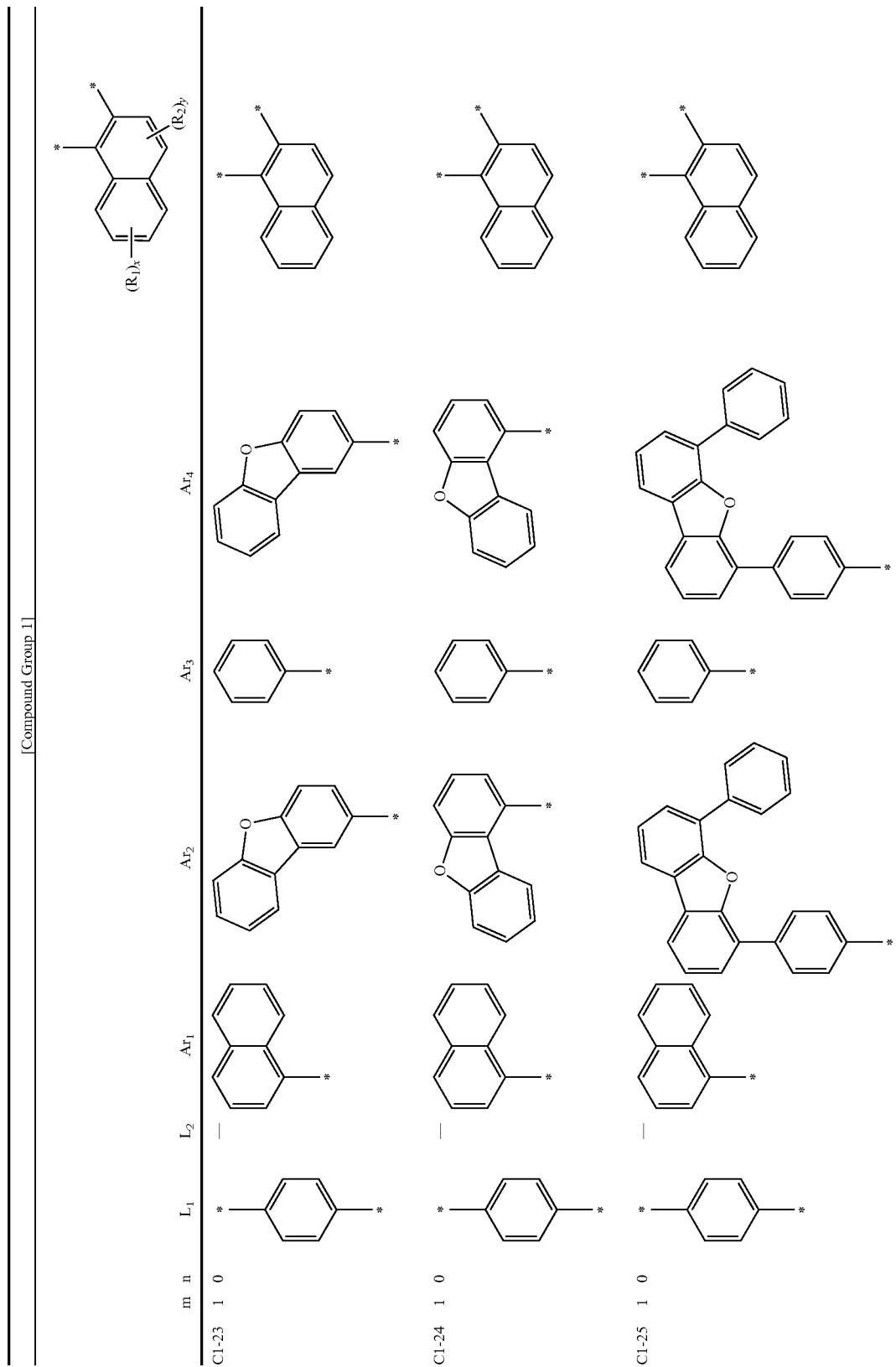

-continued
[Compound Group 1]
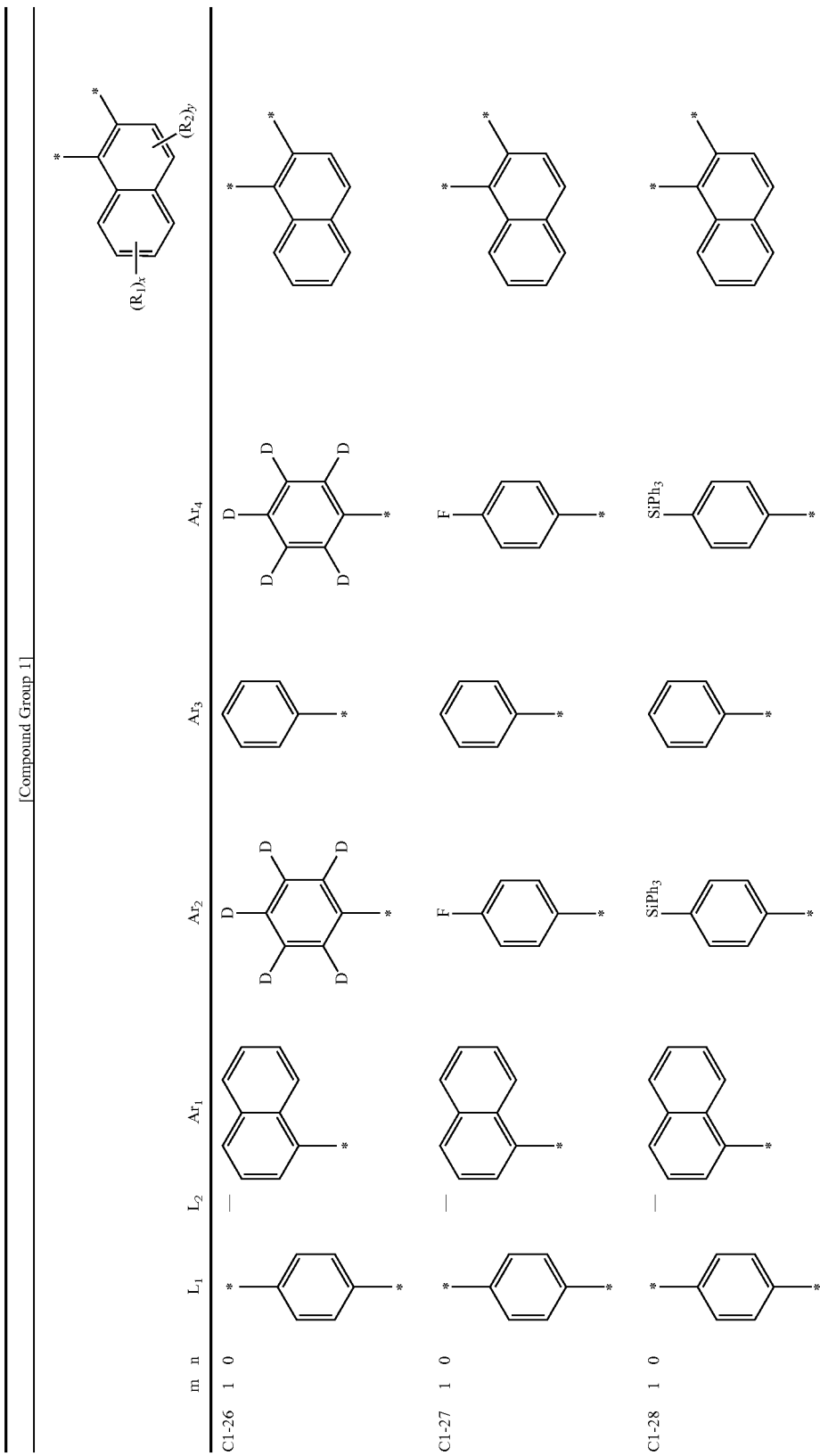

-continued
[Compound Group 1]
| | m | n | L₁ | L₂ | Ar₁ | Ar₂ | Ar₃ | Ar₄ | |
|---|---|---|---|---|---|---|---|---|---|
| C1-29 | 1 | 0 |  | — |  |  |  |  |  |
| C1-30 | 1 | 0 |  | — |  |  |  |  |  |
| D1-1 | 1 | 0 | | | | | | | |

-continued
[Compound Group 1]
| | m | n | $L_1$ | $L_2$ | $Ar_1$ | $Ar_2$ | $Ar_3$ | $Ar_4$ | 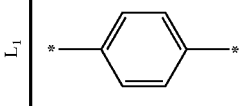 |
|---|---|---|---|---|---|---|---|---|---|
| D1-2 | 1 | 0 | 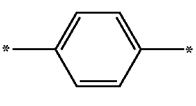 | — | 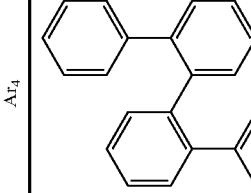 | 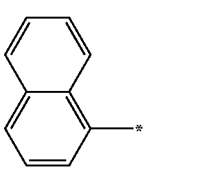 | 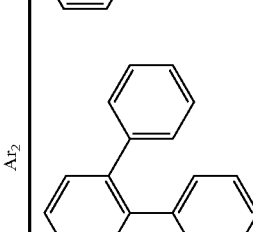 | 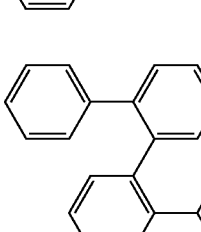 | 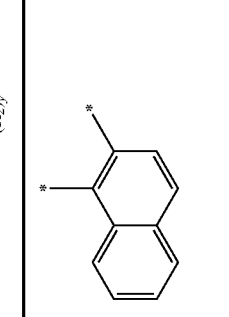 |
| D1-3 | 1 | 0 | 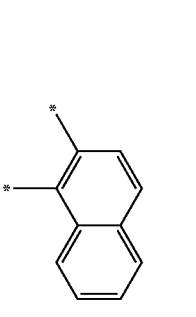 | — | 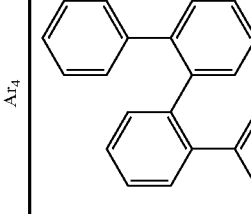 | 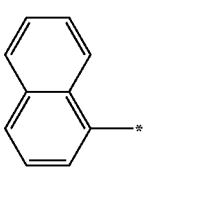 | 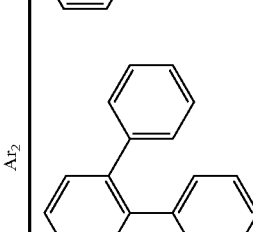 | 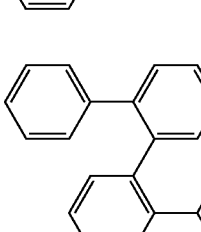 | 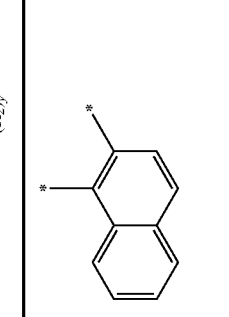 |

-continued

[Compound Group 1]

| | m | n | L₁ | L₂ | Ar₁ | Ar₂ | Ar₃ | Ar₄ | (R₁)ₓ / (R₂)ᵧ naphthalene |
|---|---|---|---|---|---|---|---|---|---|
| D1-4 | 1 | 0 | *–⟨phenyl⟩–* | — | 1-naphthyl | 1-naphthyl | 1-naphthyl | 2-naphthyl | naphthyl |
| D1-5 | 1 | 0 | *–⟨phenyl⟩–* | — | 1-naphthyl | 2-naphthyl | 1-naphthyl | phenanthryl | naphthyl |
| D1-6 | 1 | 0 | *–⟨phenyl⟩–* | — | 1-naphthyl | phenanthryl | 1-naphthyl | naphthyl-phenyl | naphthyl |

-continued

[Compound Group 1]

| | m | n | L₁ | L₂ | Ar₁ | Ar₂ | Ar₃ | Ar₄ | |
|---|---|---|---|---|---|---|---|---|---|
| D1-7 | 1 | 0 | phenylene | — | naphthyl | naphthyl-phenyl | naphthyl | naphthyl-phenyl | naphthyl |
| D1-8 | 1 | 0 | phenylene | — | naphthyl | naphthyl-phenyl | naphthyl | naphthyl-phenyl | naphthyl |
| D1-9 | 1 | 0 | phenylene | — | naphthyl | naphthyl-phenyl | naphthyl | naphthyl-phenyl | naphthyl |

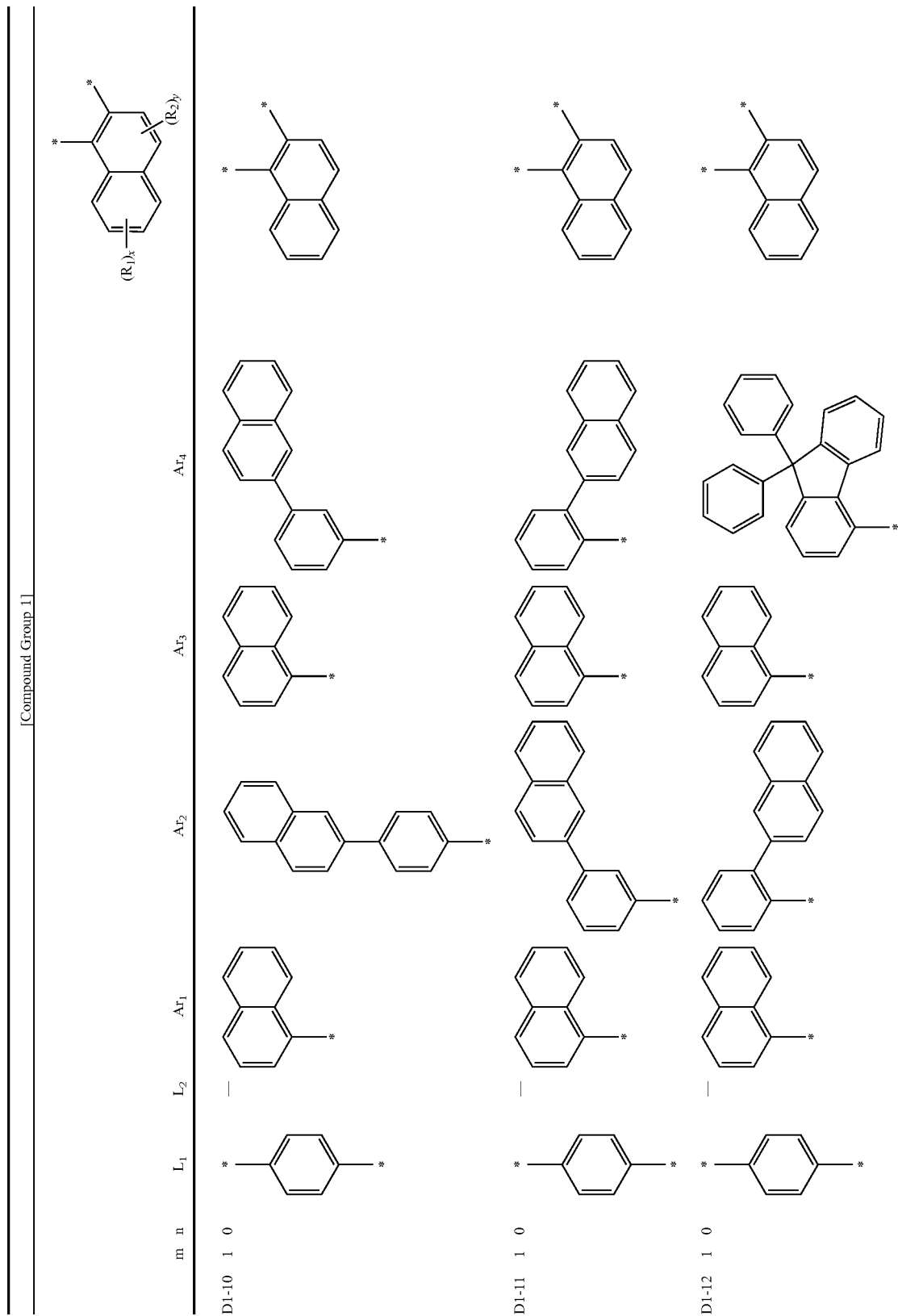

-continued
[Compound Group 1]
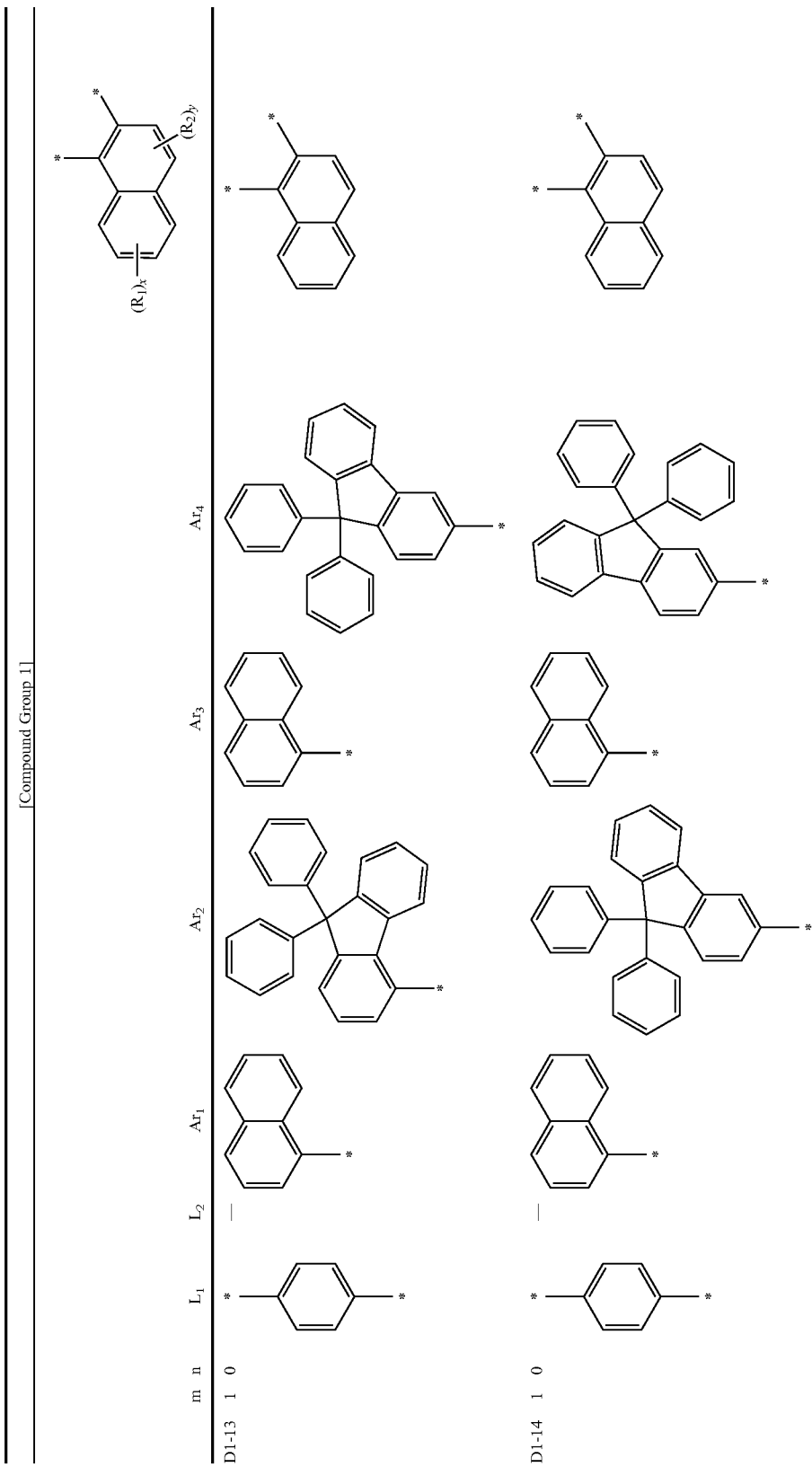

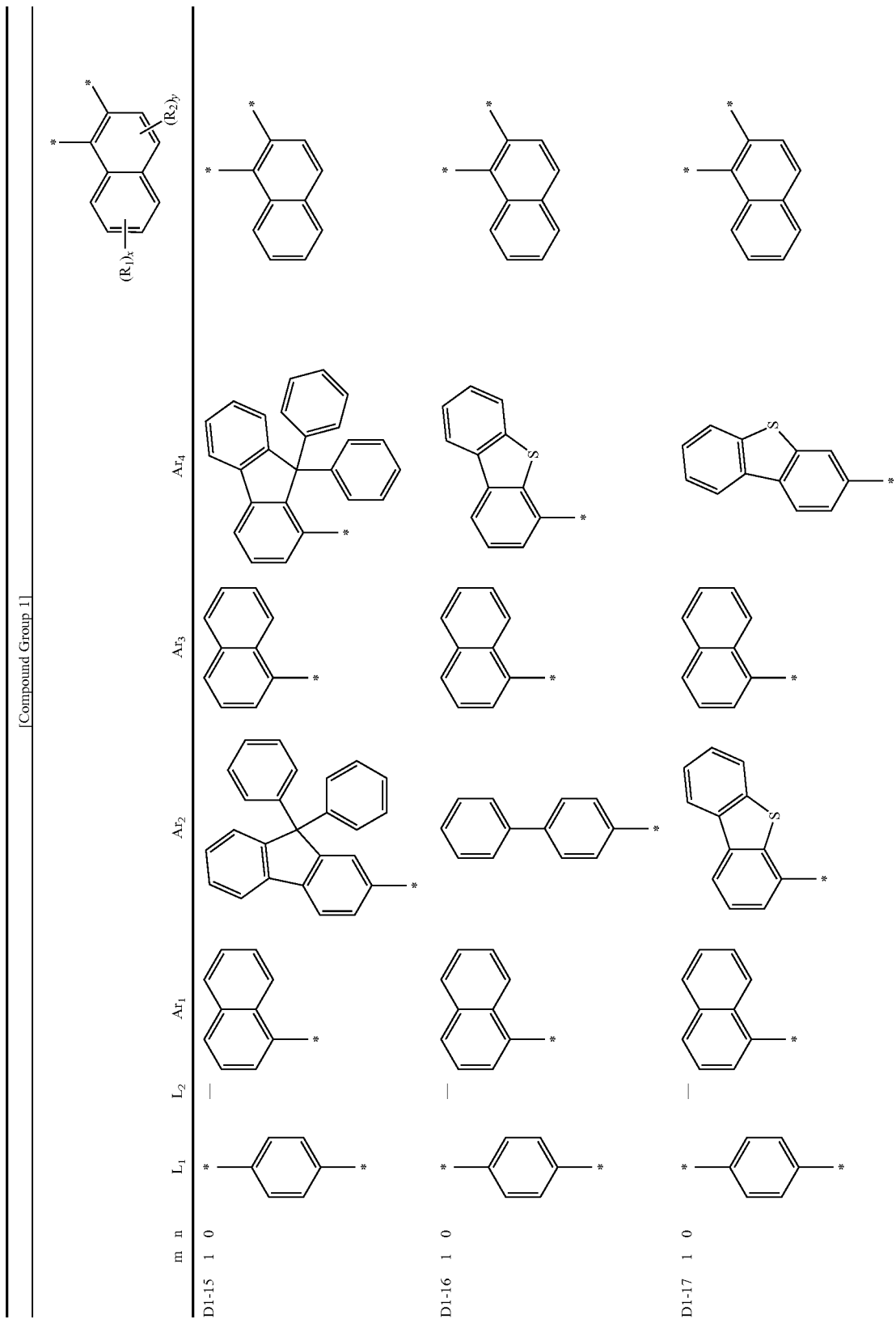

-continued
[Compound Group 1]
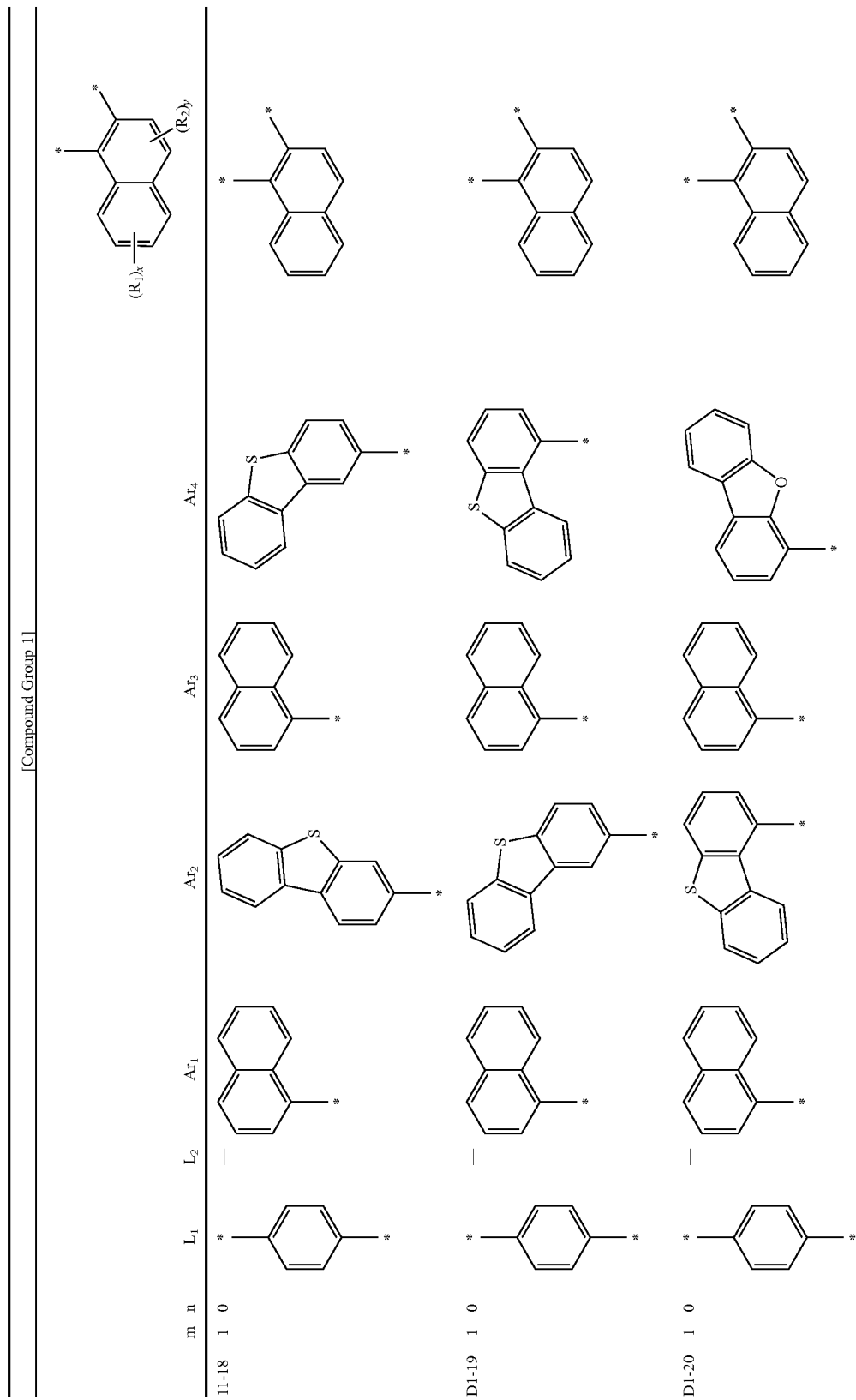

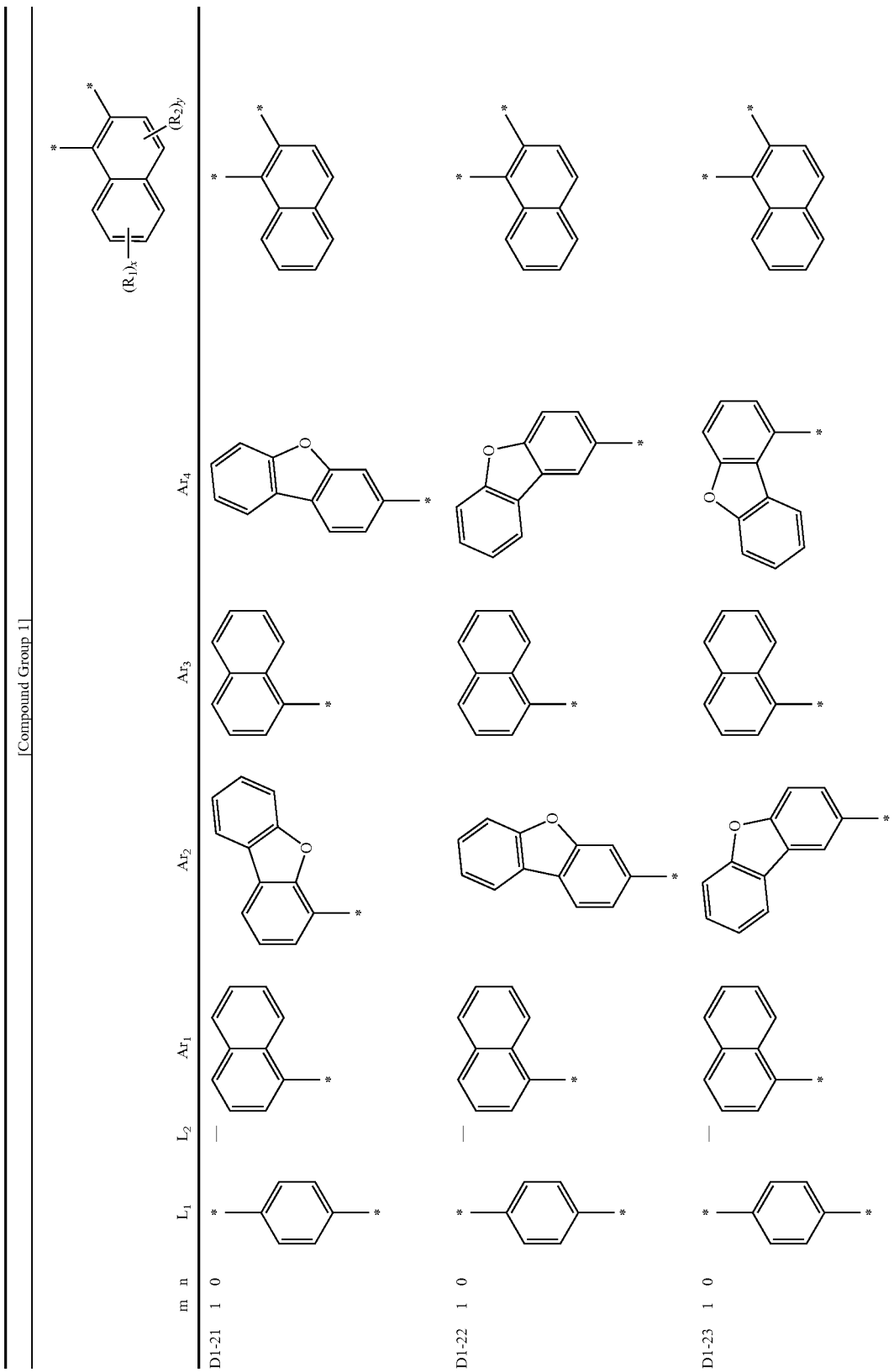

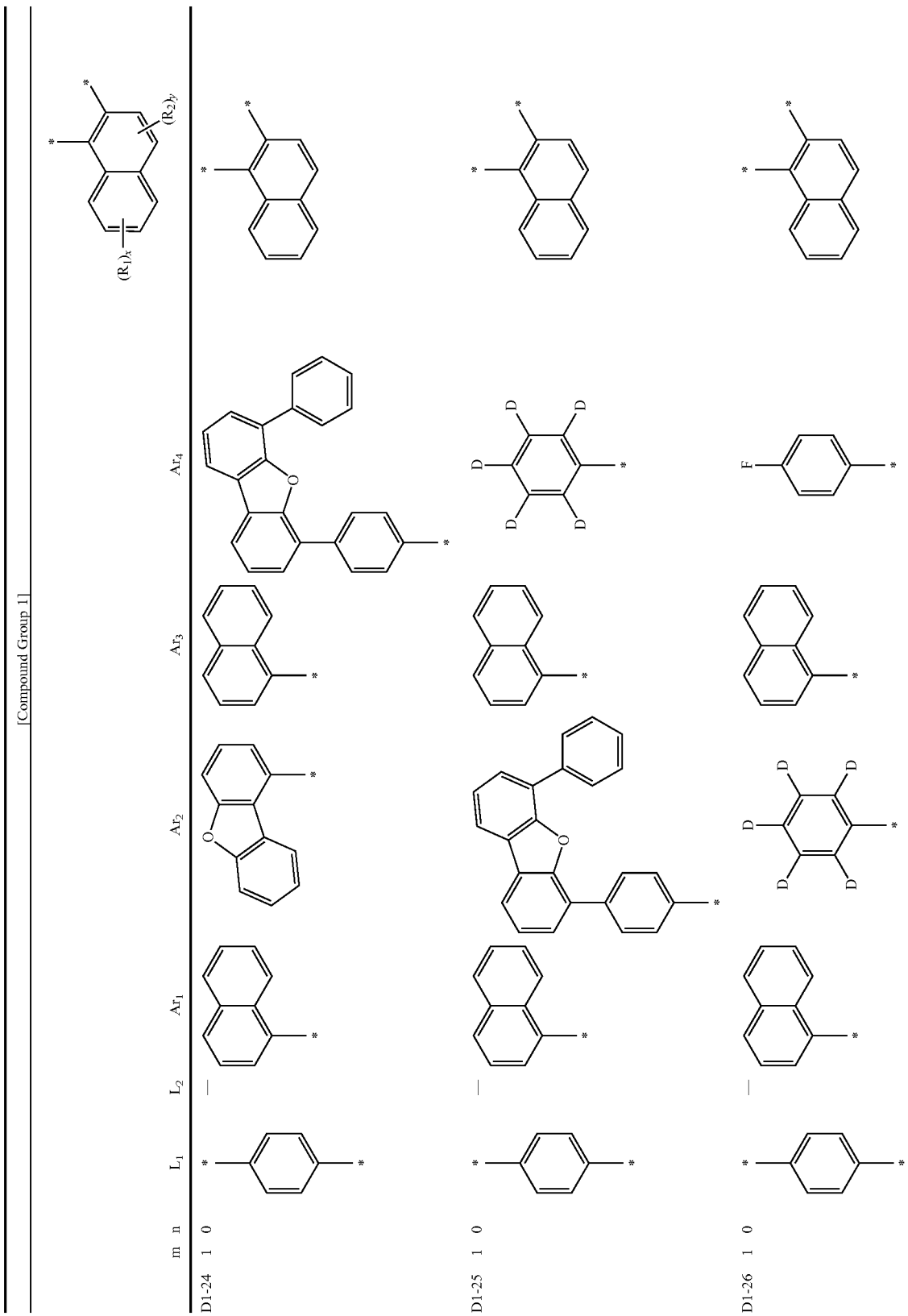

-continued
[Compound Group 1]
| | m | n | L₁ | L₂ | Ar₁ | Ar₂ | Ar₃ | Ar₄ | 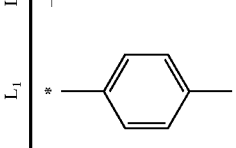 |
|---|---|---|---|---|---|---|---|---|---|
| D1-27 | 1 | 0 | * — *  | — | 1-naphthyl | 4-F-phenyl | 1-naphthyl | 4-SiPh₃-phenyl | 1,2-naphthyl |
| D1-28 | 1 | 0 | * — * | — | 1-naphthyl | 4-SiPh₃-phenyl | 1-naphthyl | 3-SiPh₃-phenyl | 1,2-naphthyl |
| D1-29 | 1 | 0 | * — * | — | 1-naphthyl | 3-SiPh₃-phenyl | 1-naphthyl | 2-SiPh₃-phenyl | 1,2-naphthyl |


12. The organic electroluminescence device of claim 1, wherein the diamine compound represented by Formula 1 is at least one selected among compounds represented in Compound Group 2:

[Compound Group 2]

| | m | n | L₁ | L₂ | Ar₁ | Ar₂ | Ar₃ | Ar₄ | |
|---|---|---|---|---|---|---|---|---|---|
| A2-1 | 1 | 1 | phenylene | phenylene | phenyl | phenyl | phenyl | phenyl | 2-naphthyl (1-subst) |
| A2-2 | 1 | 1 | phenylene | phenylene | biphenyl | biphenyl | biphenyl | biphenyl | 2-naphthyl (1-subst) |
| A2-3 | 1 | 1 | phenylene | phenylene | phenyl | biphenyl | phenyl | biphenyl | 2-naphthyl (1-subst) |

-continued
[Compound Group 2]
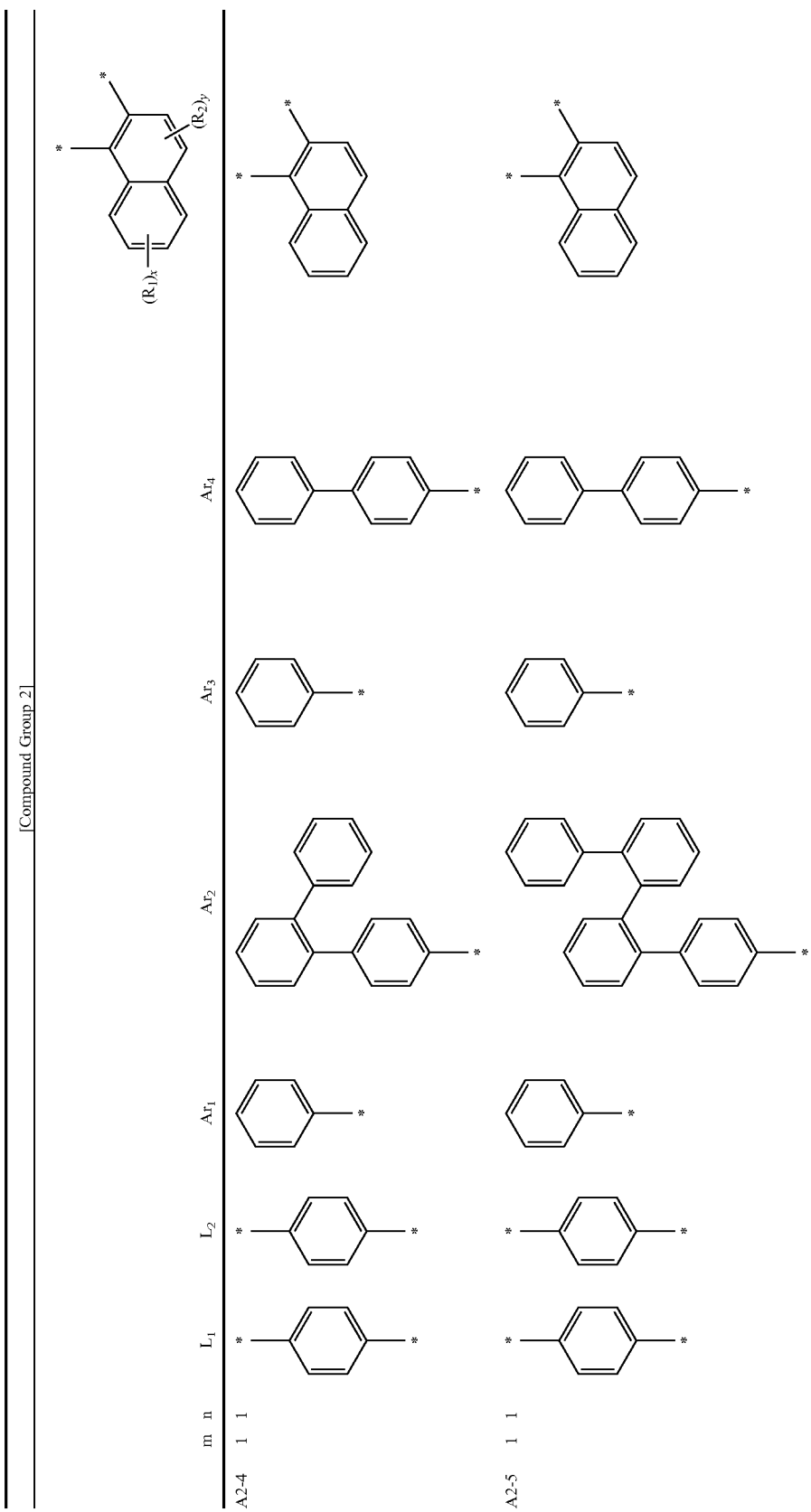

-continued
[Compound Group 2]
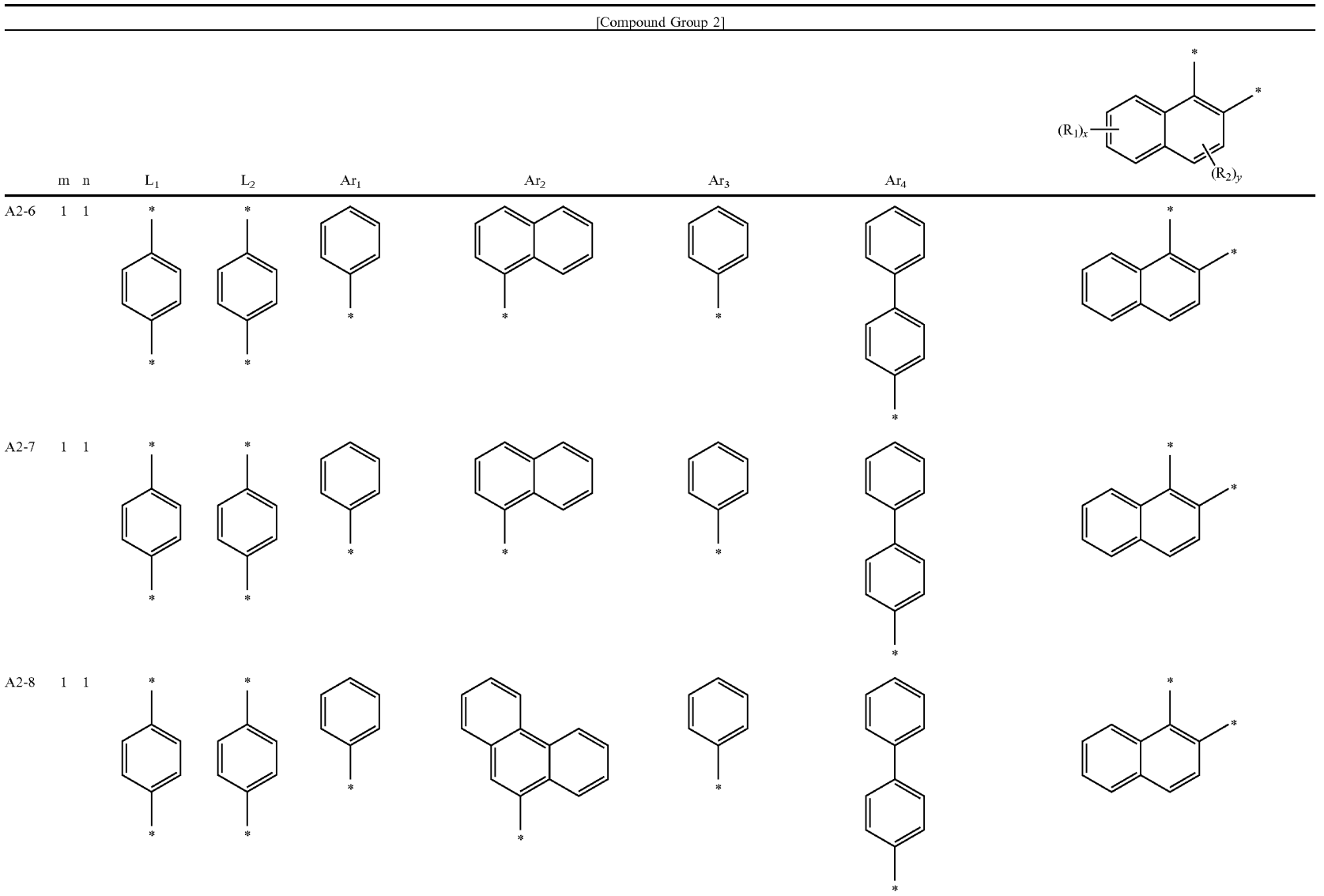

-continued
[Compound Group 2]
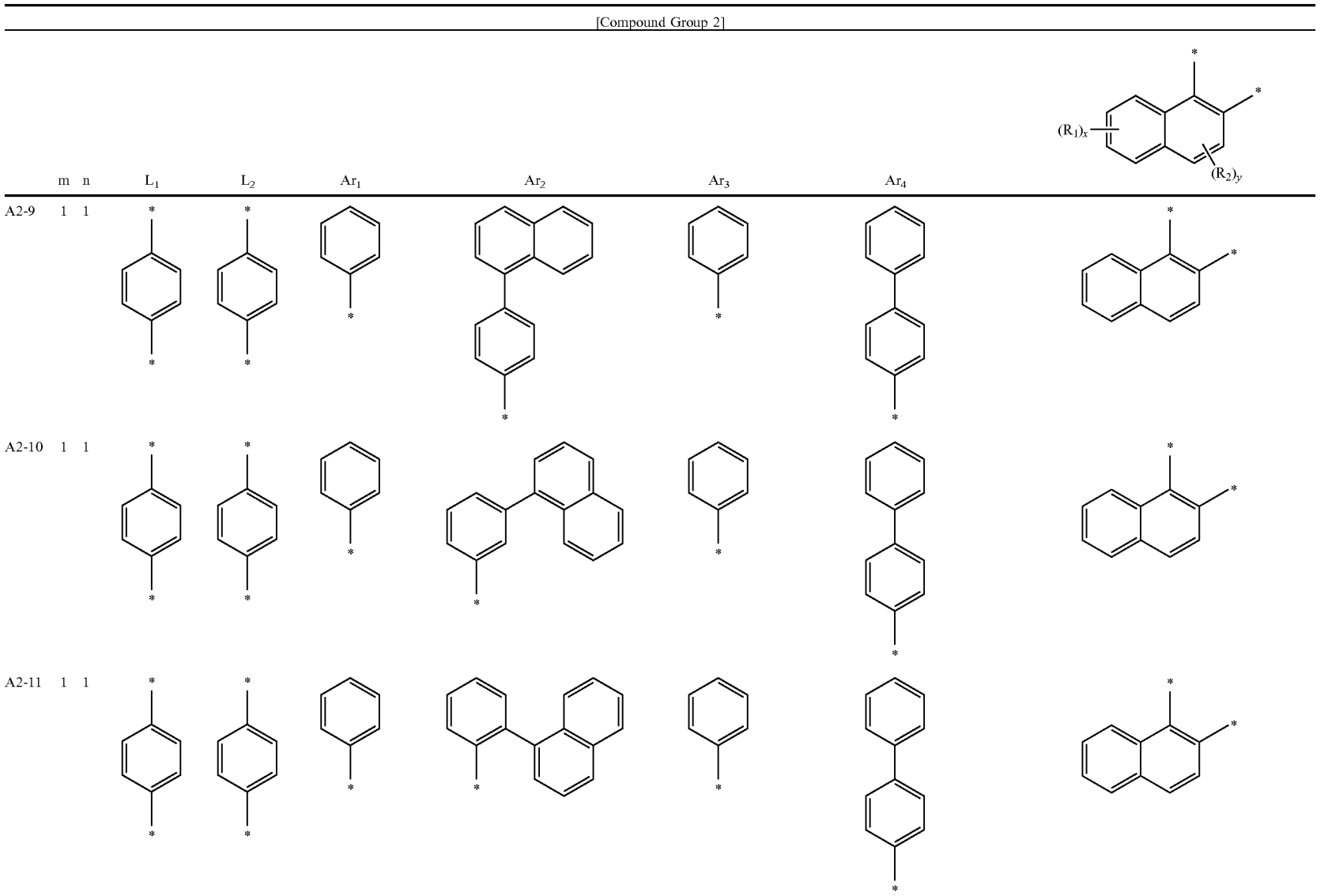

-continued
[Compound Group 2]
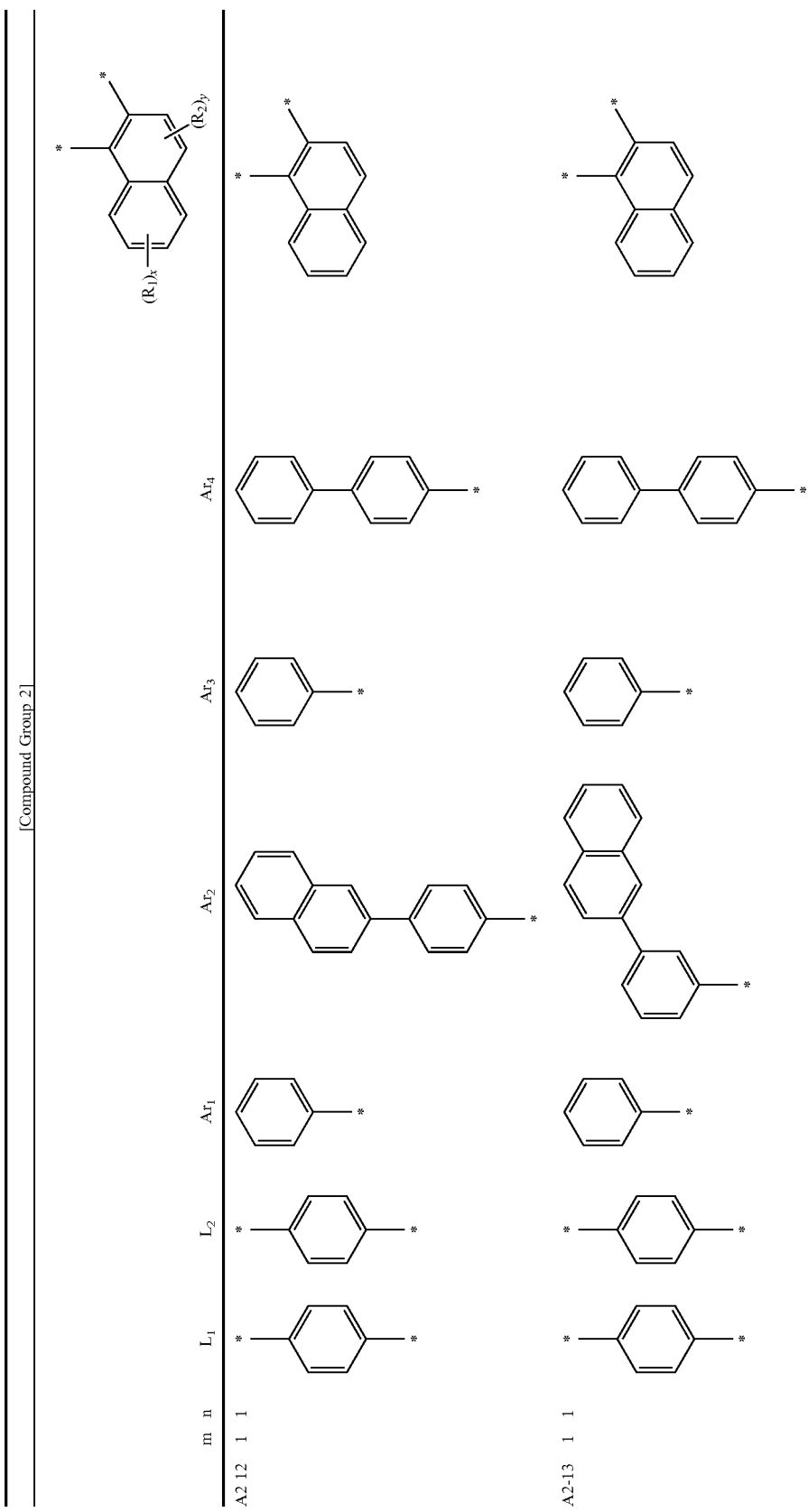

-continued
[Compound Group 2]
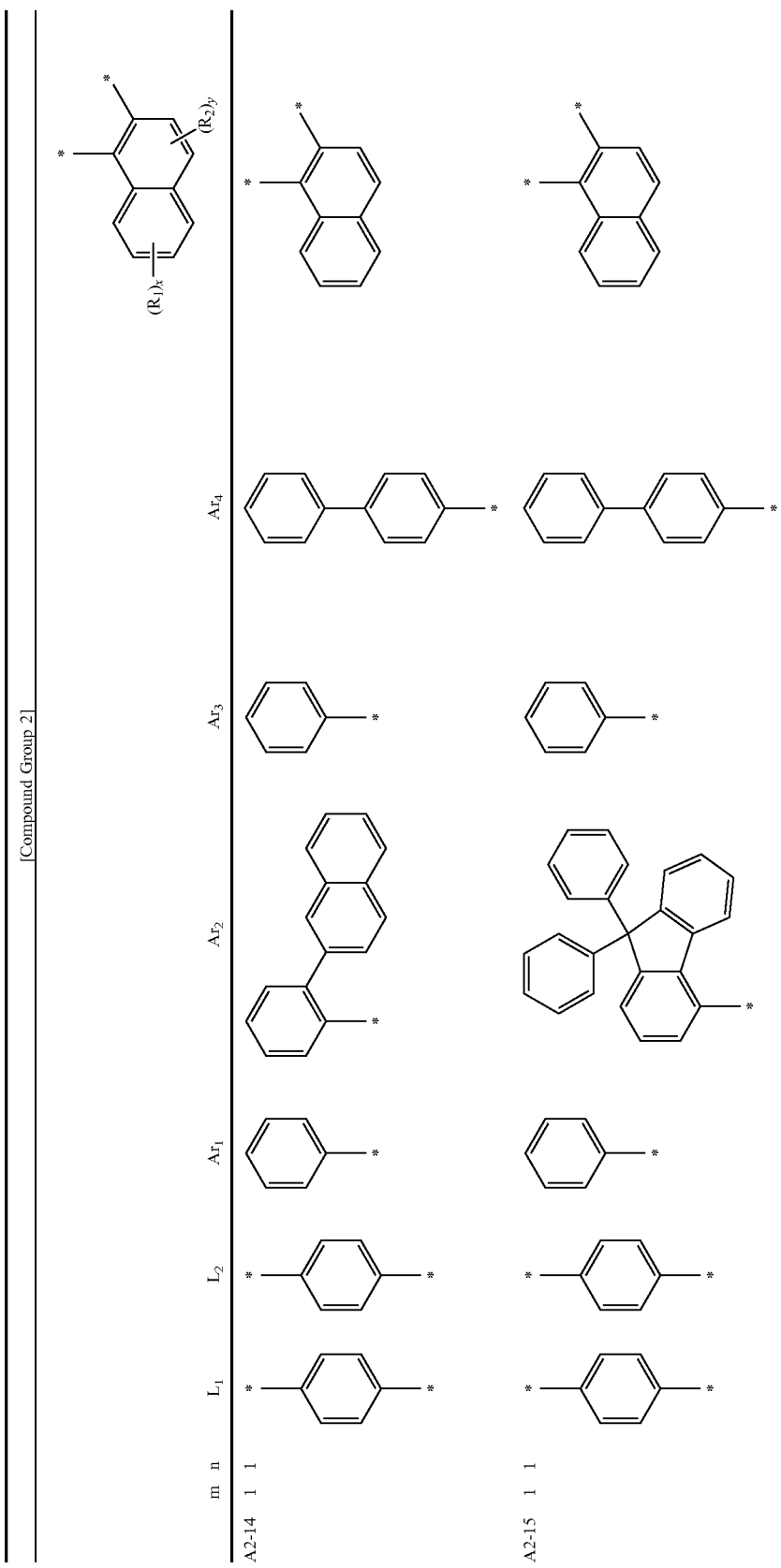

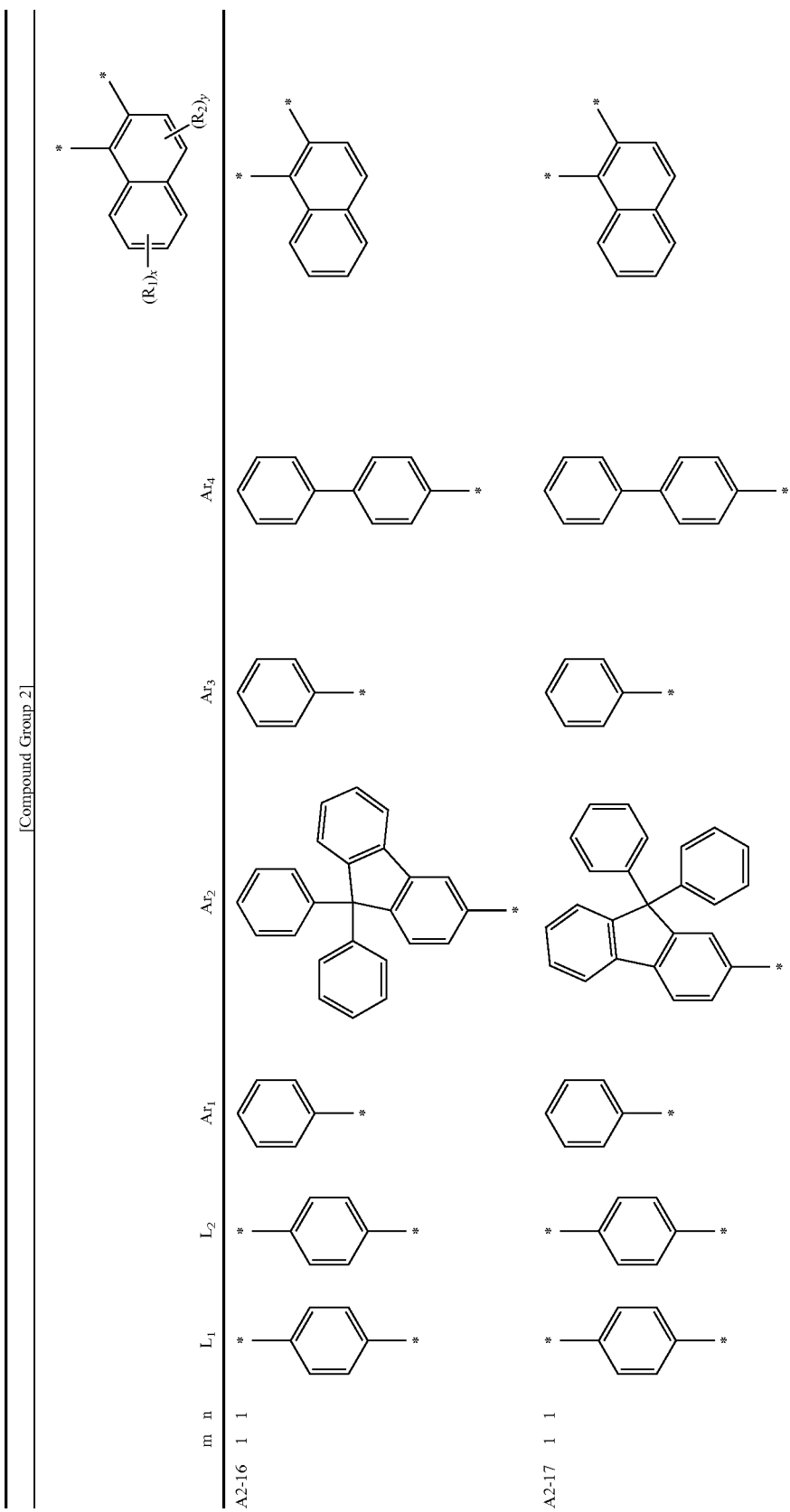

-continued
[Compound Group 2]
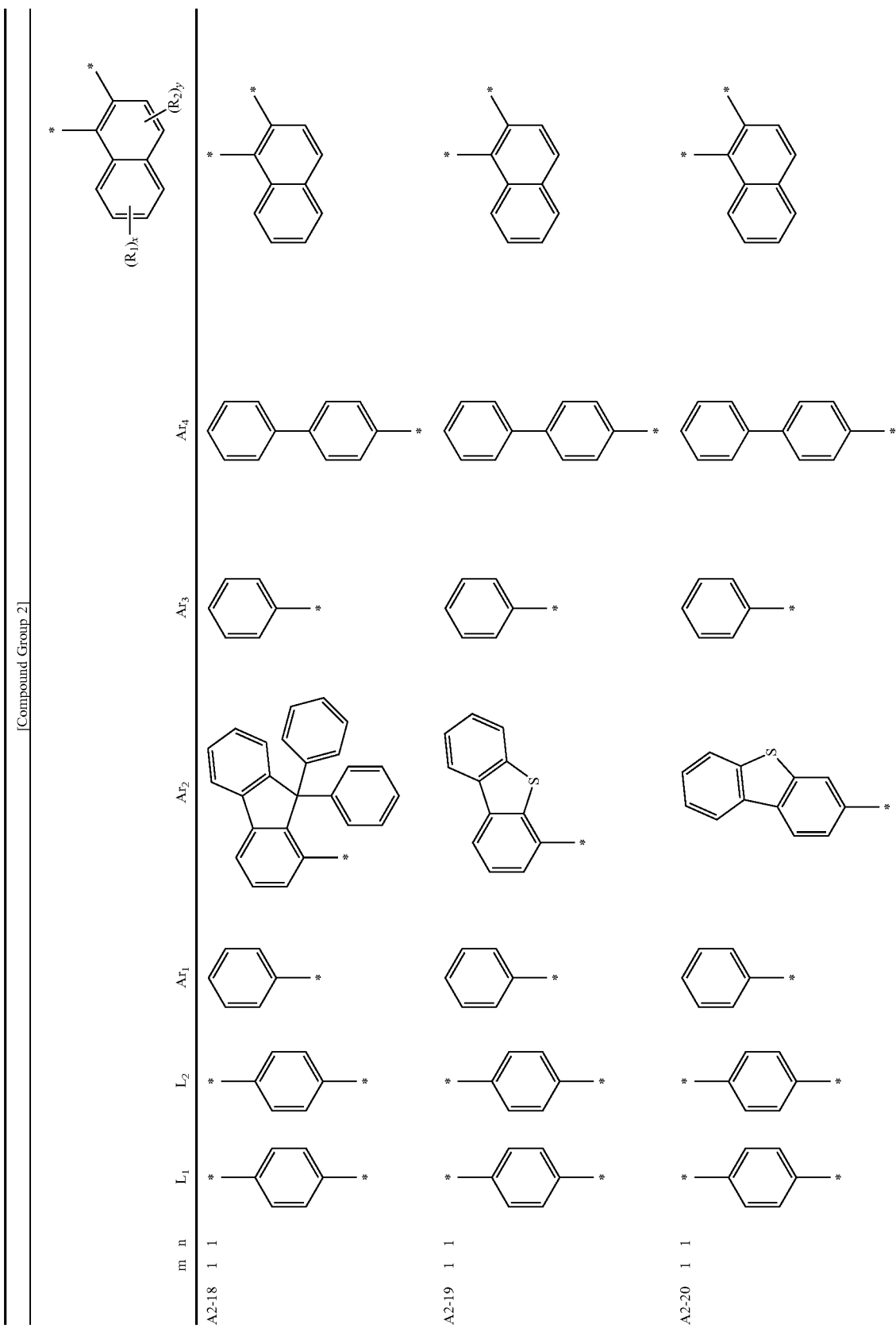

-continued
[Compound Group 2]
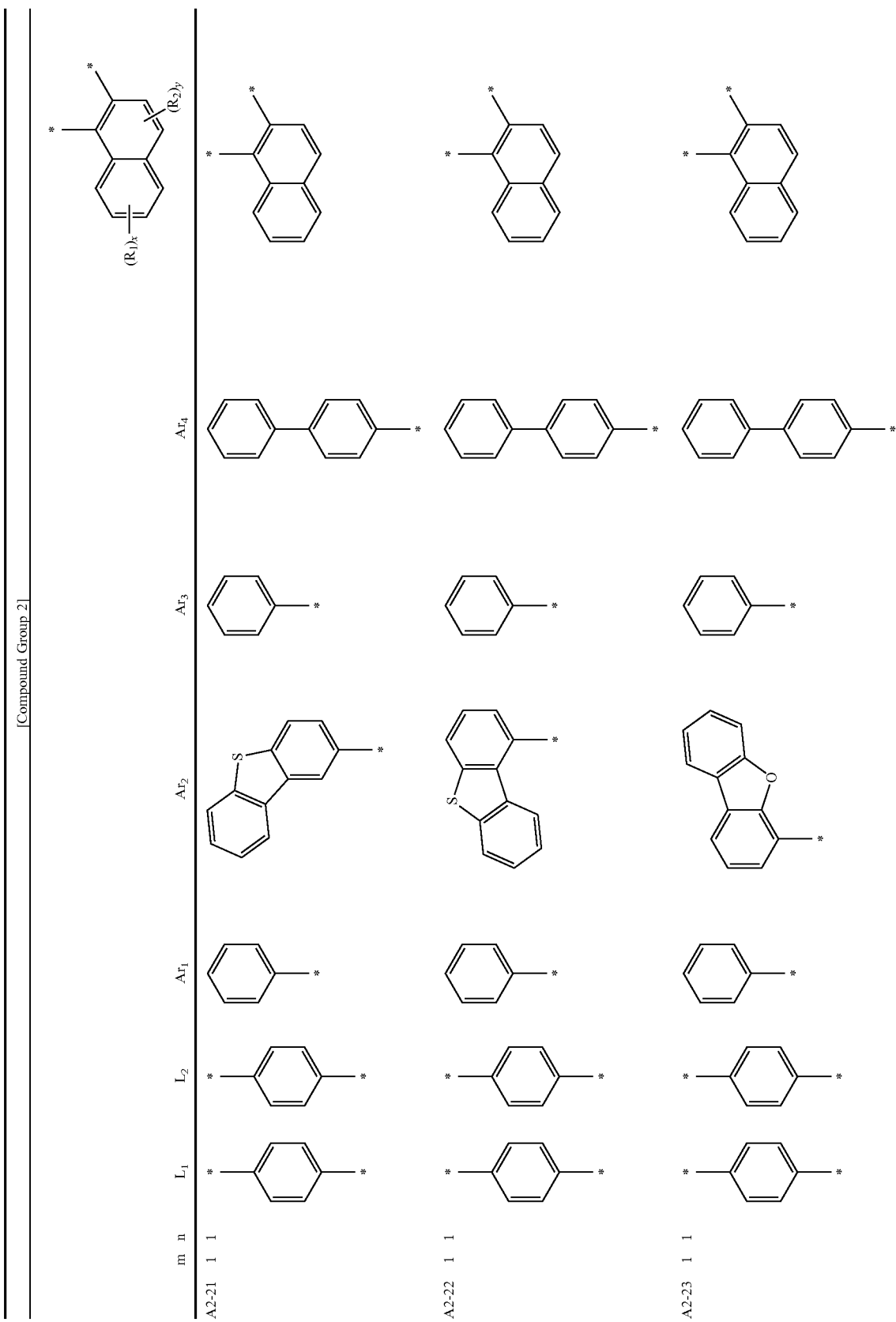

-continued

[Compound Group 2]

| | m | n | L₁ | L₂ | Ar₁ | Ar₂ | Ar₃ | Ar₄ | |
|---|---|---|---|---|---|---|---|---|---|
| A2-24 | 1 | 1 | | | | | | | |
| A2-25 | 1 | 1 | | | | | | | |

-continued
[Compound Group 2]
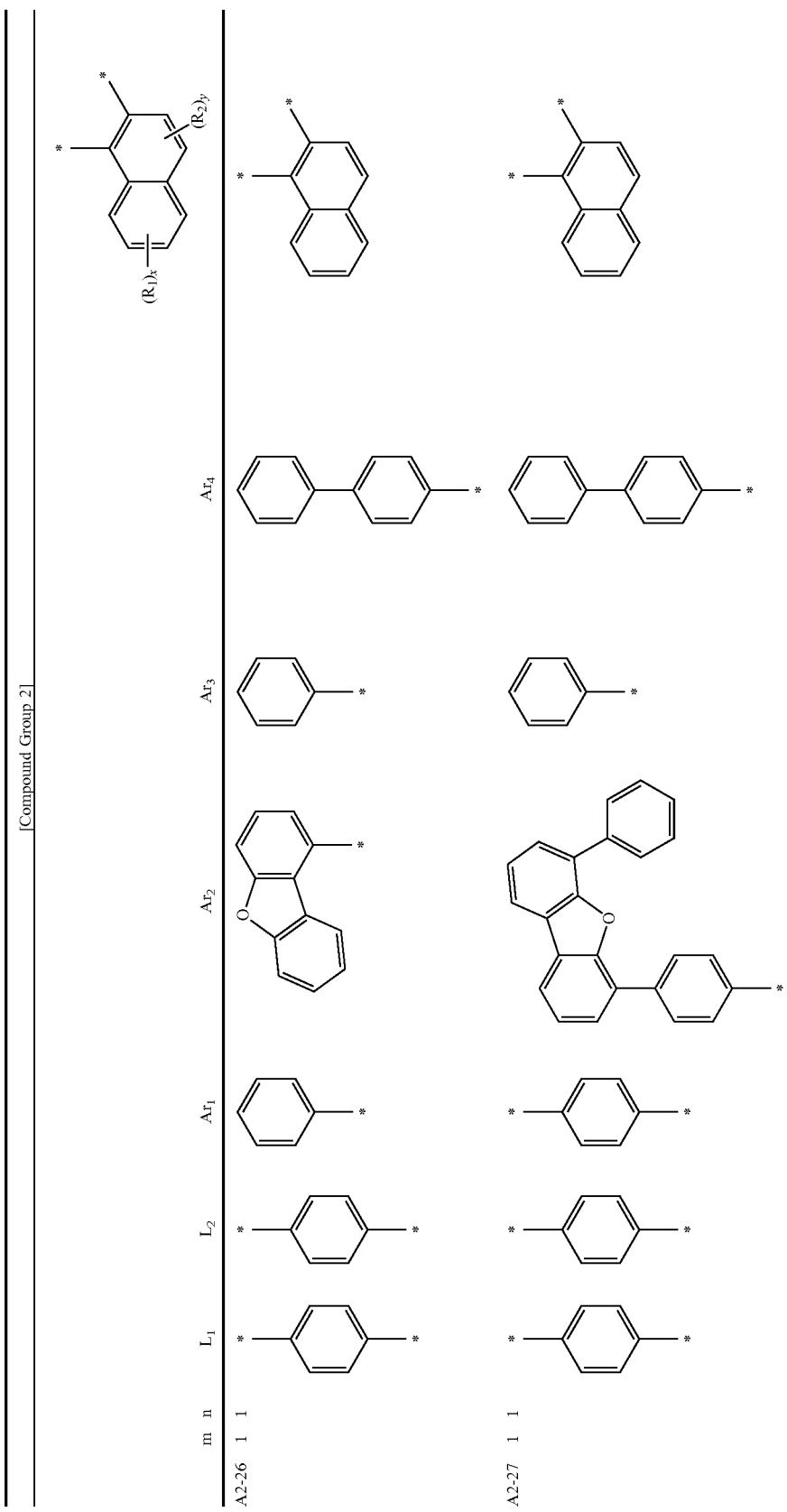

-continued
[Compound Group 2]
| | m | n | L₁ | L₂ | Ar₁ | Ar₂ | Ar₃ | Ar₄ | 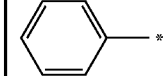 |
|---|---|---|---|---|---|---|---|---|---|
| A2-28 | 1 | 1 | 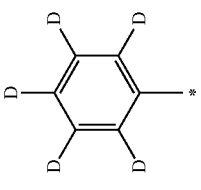 | 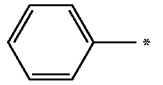 | 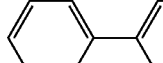 | 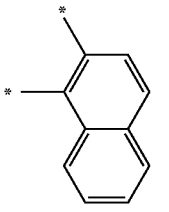 | 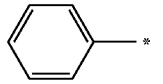 | 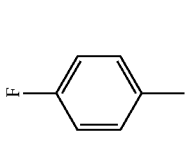 | 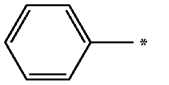 |
| A2-29 | 1 | 1 | 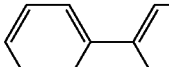 | 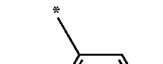 | 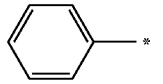 | 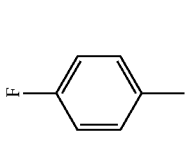 | 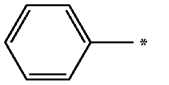 | 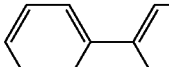 | 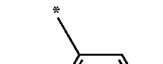 |
| A2-30 | 1 | 1 | | | | | | | |

-continued
[Compound Group 2]
| | m | n | L₁ | L₂ | Ar₁ | Ar₂ | Ar₃ | Ar₄ | 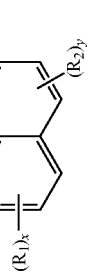 |
|---|---|---|---|---|---|---|---|---|---|
| A2-31 | 1 | 1 | 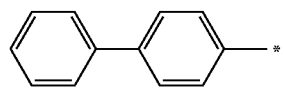 | 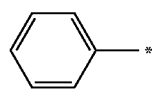 | 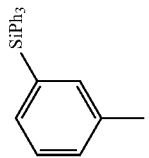 | 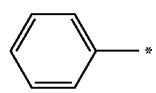 | 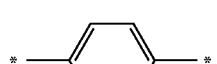 | | 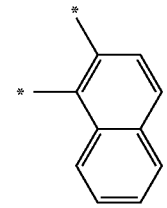 |
| A2-32 | 1 | 1 | 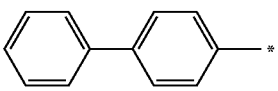 | 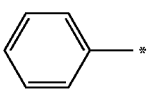 | 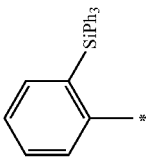 | 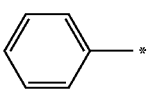 | 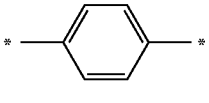 | 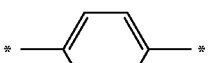 | 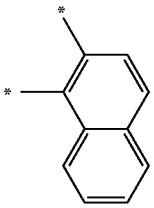 |

-continued

[Compound Group 2]

| m n | L1 | L2 | Ar1 | Ar2 | Ar3 | Ar4 | |
|---|---|---|---|---|---|---|---|
| A2-33 1 0 | | | | | | | |
| B2-1 1 1 | | | | | | | |
| B2-2 1 1 | | | | | | | |

-continued
[Compound Group 2]
| | m | n | L₁ | L₂ | Ar₁ | Ar₂ | Ar₃ | Ar₄ | 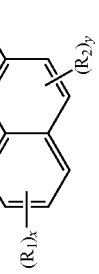 |
|---|---|---|---|---|---|---|---|---|---|
| B2-3 | 1 | 1 | *―⌬―* | *―⌬―* | ⌬―* | terphenyl-* | naphthyl-* | biphenyl-* | naphthyl (1,2-) |
| B2-4 | 1 | 1 | *―⌬―* | *―⌬―* | ⌬―* | naphthyl-* | naphthyl-* | biphenyl-* | naphthyl (1,2-) |

-continued

[Compound Group 2]

| | m | n | L₁ | L₂ | Ar₁ | Ar₂ | Ar₃ | Ar₄ | |
|---|---|---|---|---|---|---|---|---|---|
| B2-5 | 1 | 1 | | | | | | | |
| B2-6 | 1 | 1 | | | | | | | |
| B2-7 | 1 | 1 | | | | | | | |

-continued

[Compound Group 2]

| | m | n | L₁ | L₂ | Ar₁ | Ar₂ | Ar₃ | Ar₄ | |
|---|---|---|---|---|---|---|---|---|---|
| B2-8 | 1 | 1 | phenylene | phenylene | phenyl | 3-(naphthalen-1-yl)phenyl | naphthalen-1-yl | biphenyl | 1-naphthyl |
| B2-9 | 1 | 1 | phenylene | phenylene | phenyl | 2-(naphthalen-1-yl)phenyl | naphthalen-1-yl | biphenyl | 1-naphthyl |

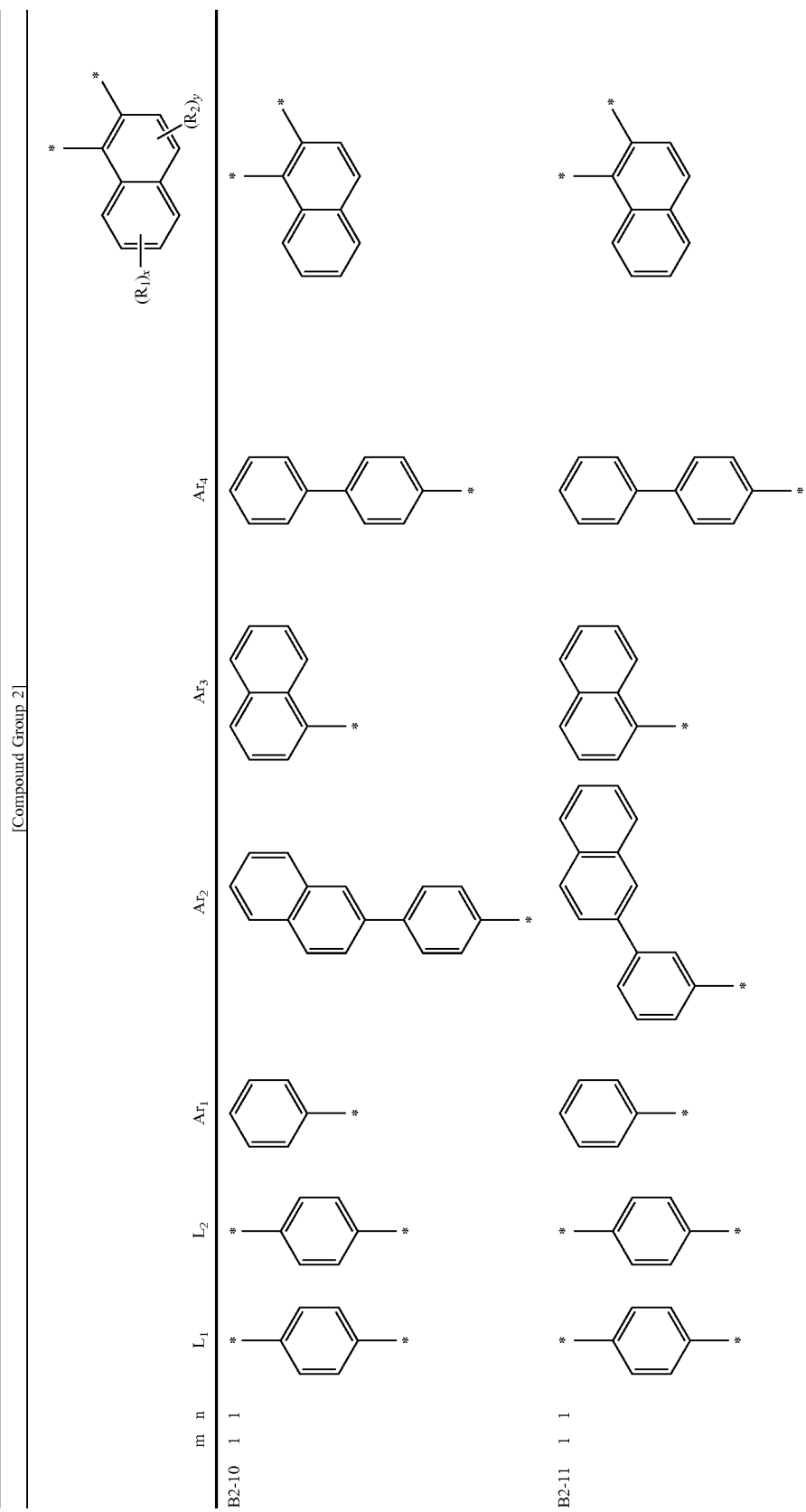

-continued

[Compound Group 2]

| m | n | L₁ | L₂ | Ar₁ | Ar₂ | Ar₃ | Ar₄ | |
|---|---|---|---|---|---|---|---|---|
| B2-12 | 1 | 1 | *–⌬–* | *–⌬–* | ⌬–* | 2-naphthyl-phenyl–* | 1-naphthyl–* | biphenyl–* | 1-naphthyl–* |
| B2-13 | 1 | 1 | *–⌬–* | *–⌬–* | ⌬–* | 9,9-diphenylfluorenyl–* | 1-naphthyl–* | biphenyl–* | 1-naphthyl–* |

-continued
[Compound Group 2]
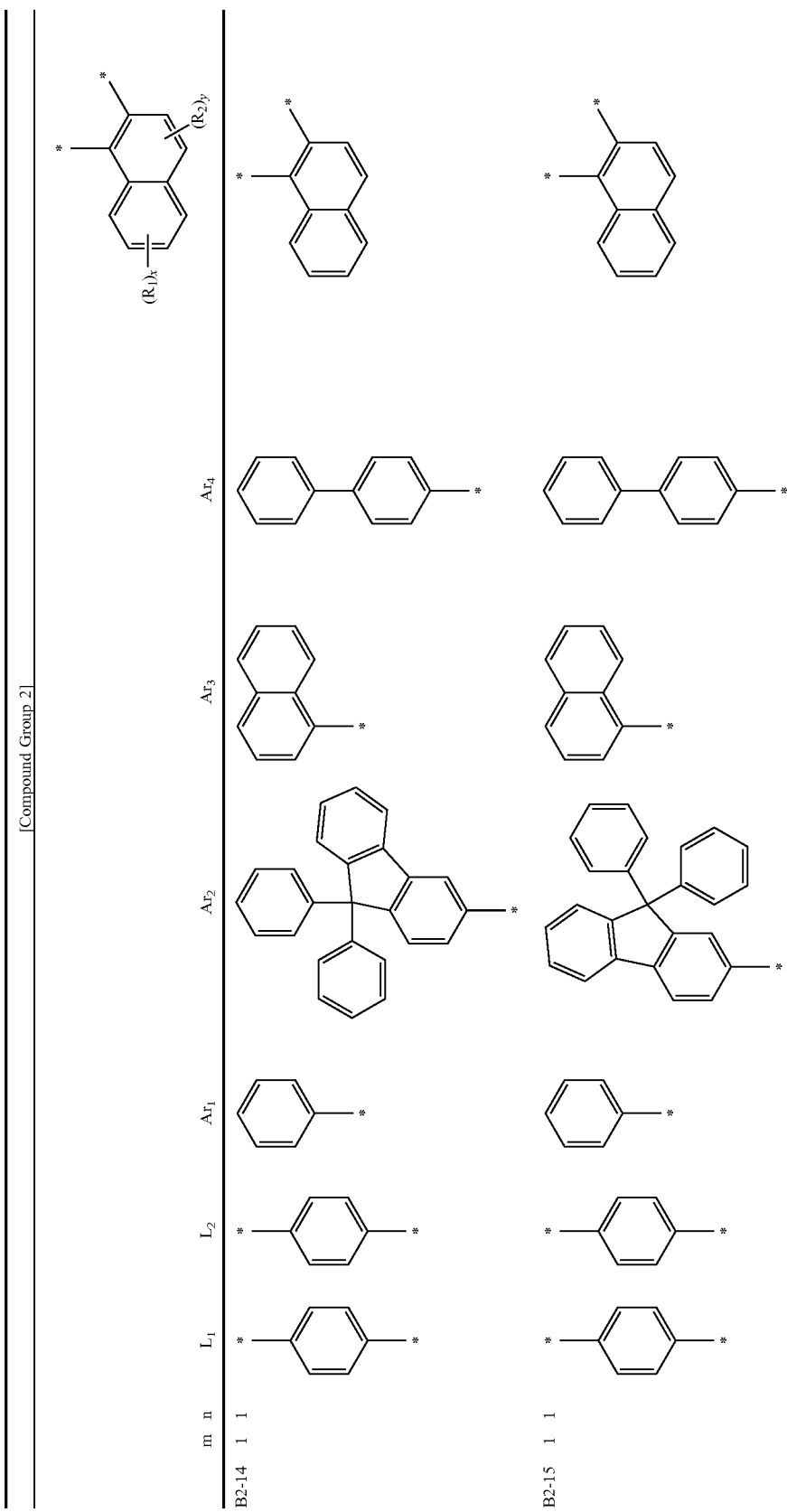

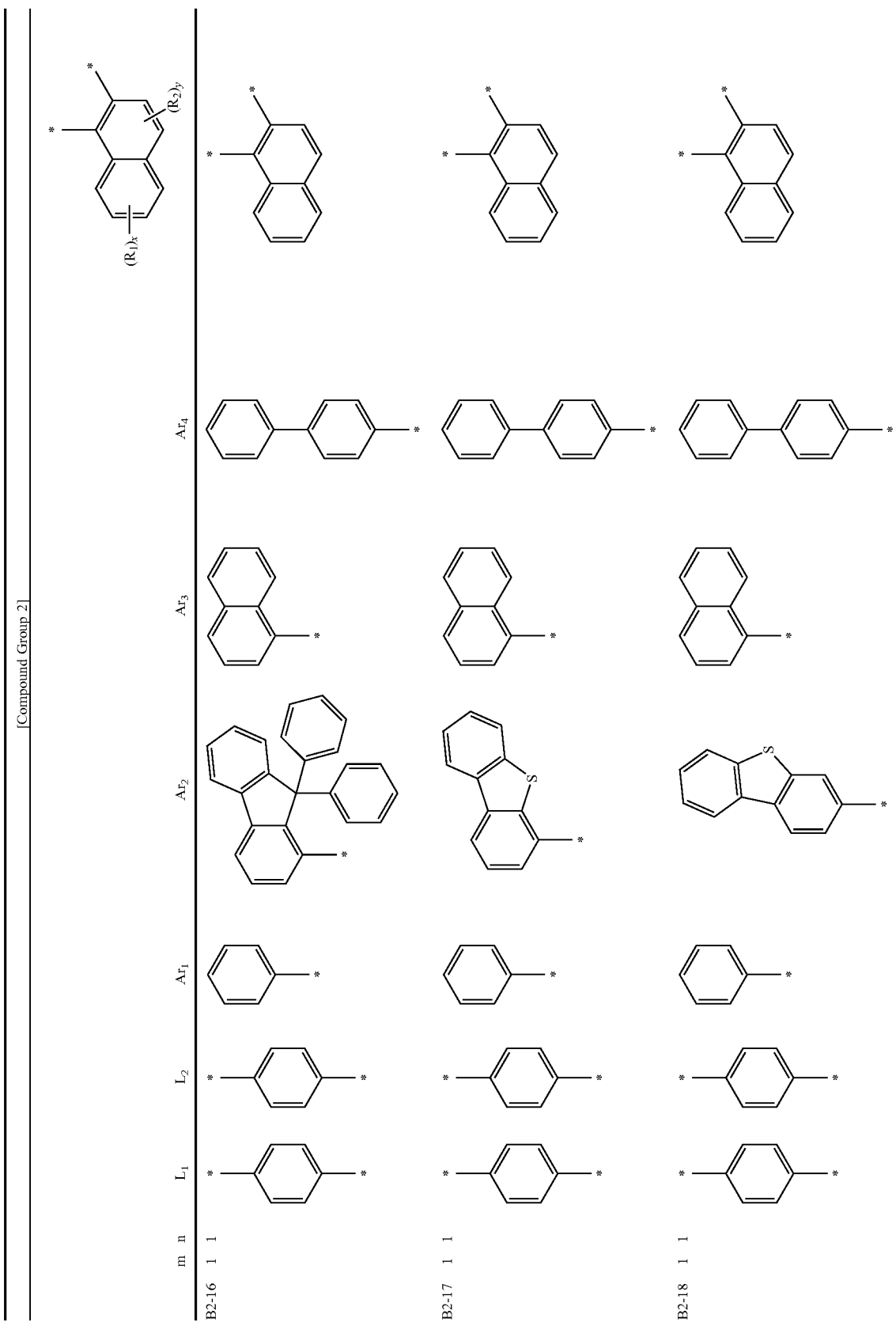

-continued
[Compound Group 2]
| | m | n | L₁ | L₂ | Ar₁ | Ar₂ | Ar₃ | Ar₄ | 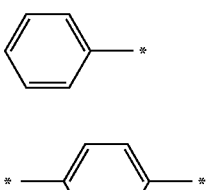 |
|---|---|---|---|---|---|---|---|---|---|
| B2-19 | 1 | 1 | phenylene | phenylene | phenyl | dibenzothiophene | naphthyl | biphenyl | naphthyl |
| B2-20 | 1 | 1 | phenylene | phenylene | phenyl | dibenzothiophene | naphthyl | biphenyl | naphthyl |

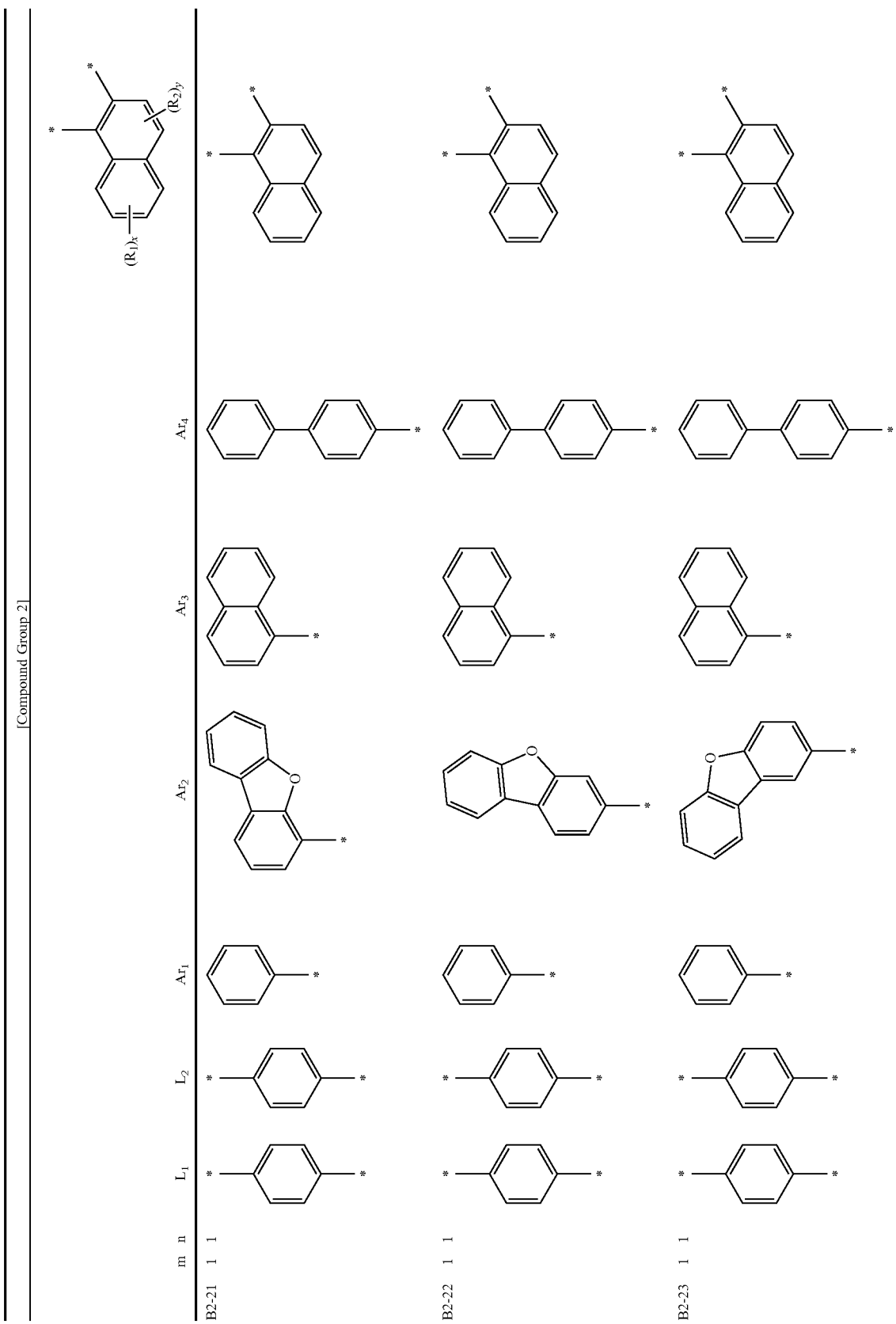

-continued
[Compound Group 2]
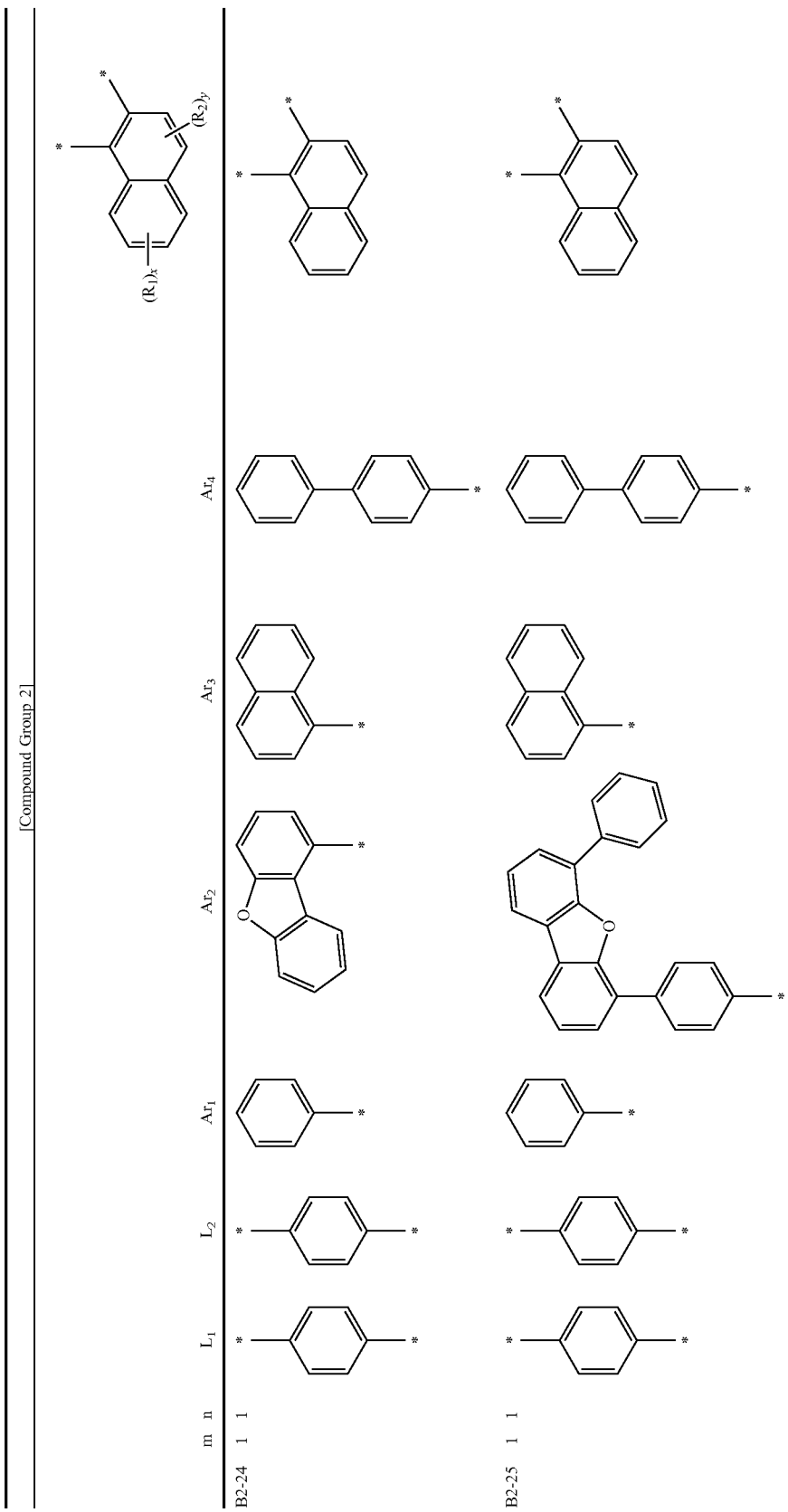

-continued

[Compound Group 2]

| | m | n | L₁ | L₂ | Ar₁ | Ar₂ | Ar₃ | Ar₄ | (structure) |
|---|---|---|---|---|---|---|---|---|---|
| B2-26 | 1 | 1 | *–⟨phenyl⟩–* | *–⟨phenyl⟩–* | ⟨phenyl⟩–* | ⟨C₆D₅⟩–* | 1-naphthyl | biphenyl | 2-naphthyl |
| B2-27 | 1 | 1 | *–⟨phenyl⟩–* | *–⟨phenyl⟩–* | ⟨phenyl⟩–* | 4-F-C₆H₄–* | 1-naphthyl | biphenyl | 1-naphthyl(2-sub) |
| B2-28 | 1 | 1 | *–⟨phenyl⟩–* | *–⟨phenyl⟩–* | ⟨phenyl⟩–* | 4-SiPh₃-C₆H₄–* | 1-naphthyl | biphenyl | 1-naphthyl(2-sub) |

-continued
[Compound Group 2]
| | m | n | L₁ | L₂ | Ar₁ | Ar₂ | Ar₃ | Ar₄ | 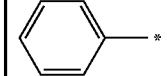 |
|---|---|---|---|---|---|---|---|---|---|
| B2-29 | 1 | 1 | | | | | | | |
| B2-30 | 1 | 1 | | | | | | | |
| C2-1 | 1 | 1 | | | | | | | |

-continued
[Compound Group 2]
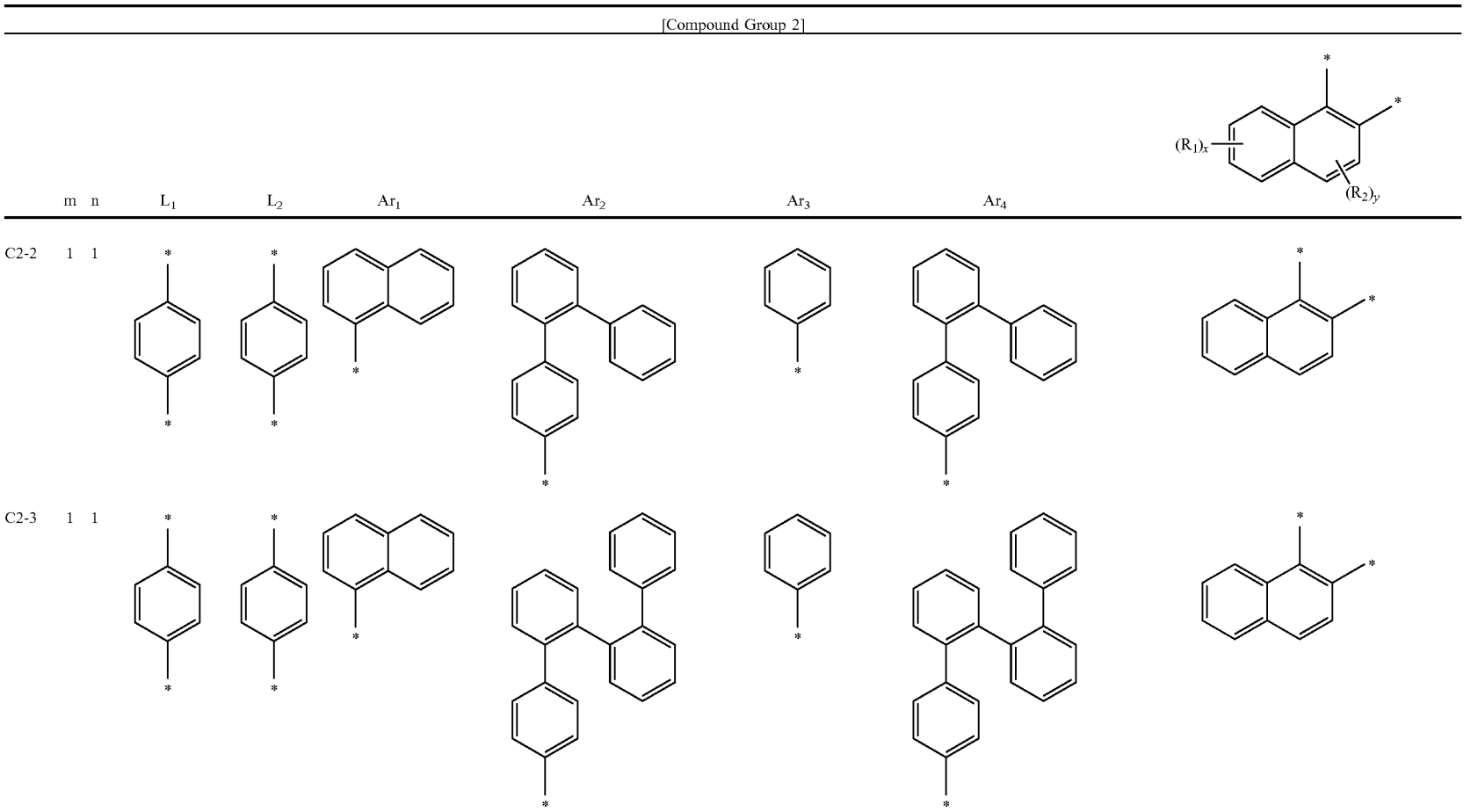

-continued
[Compound Group 2]
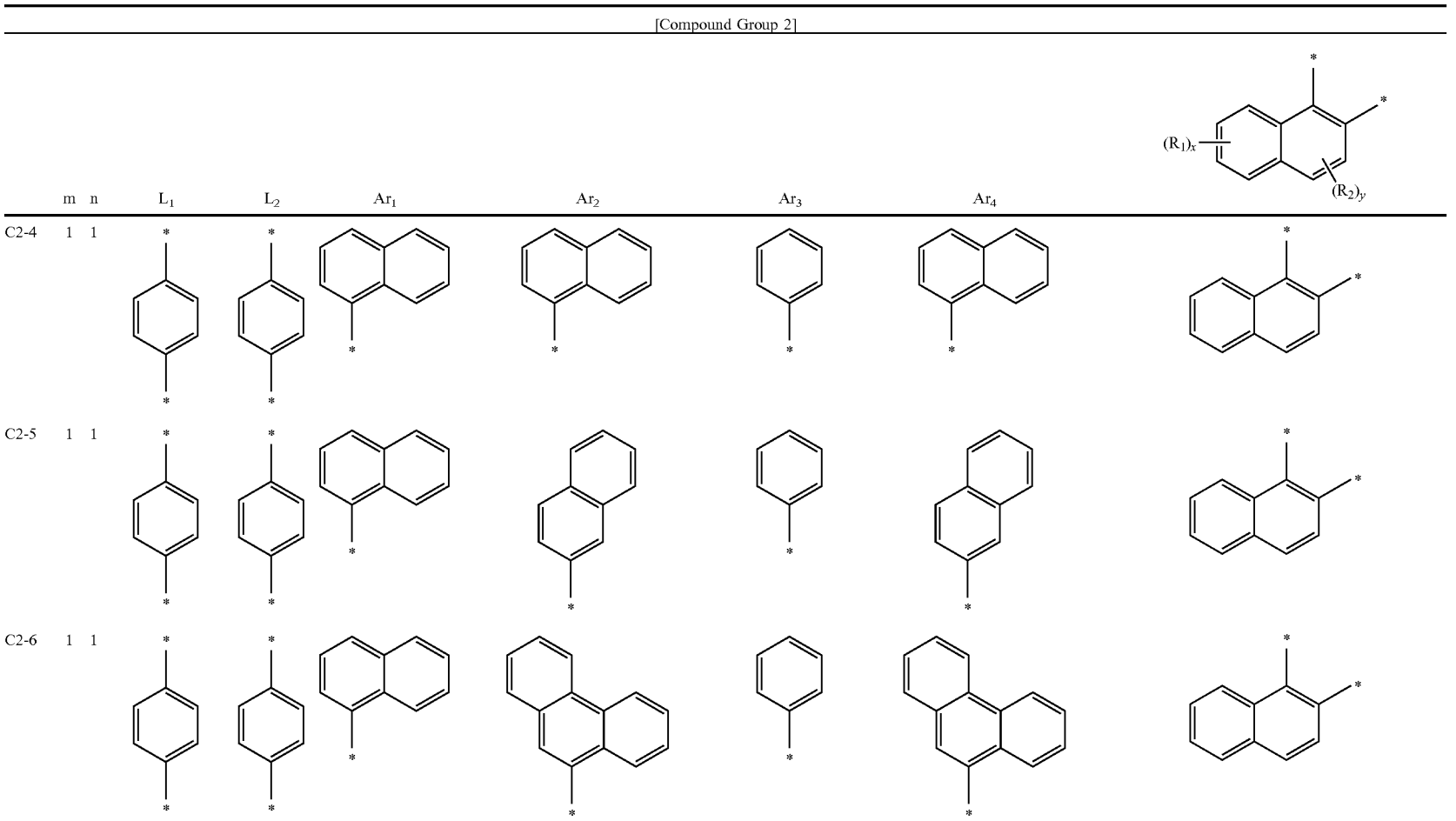

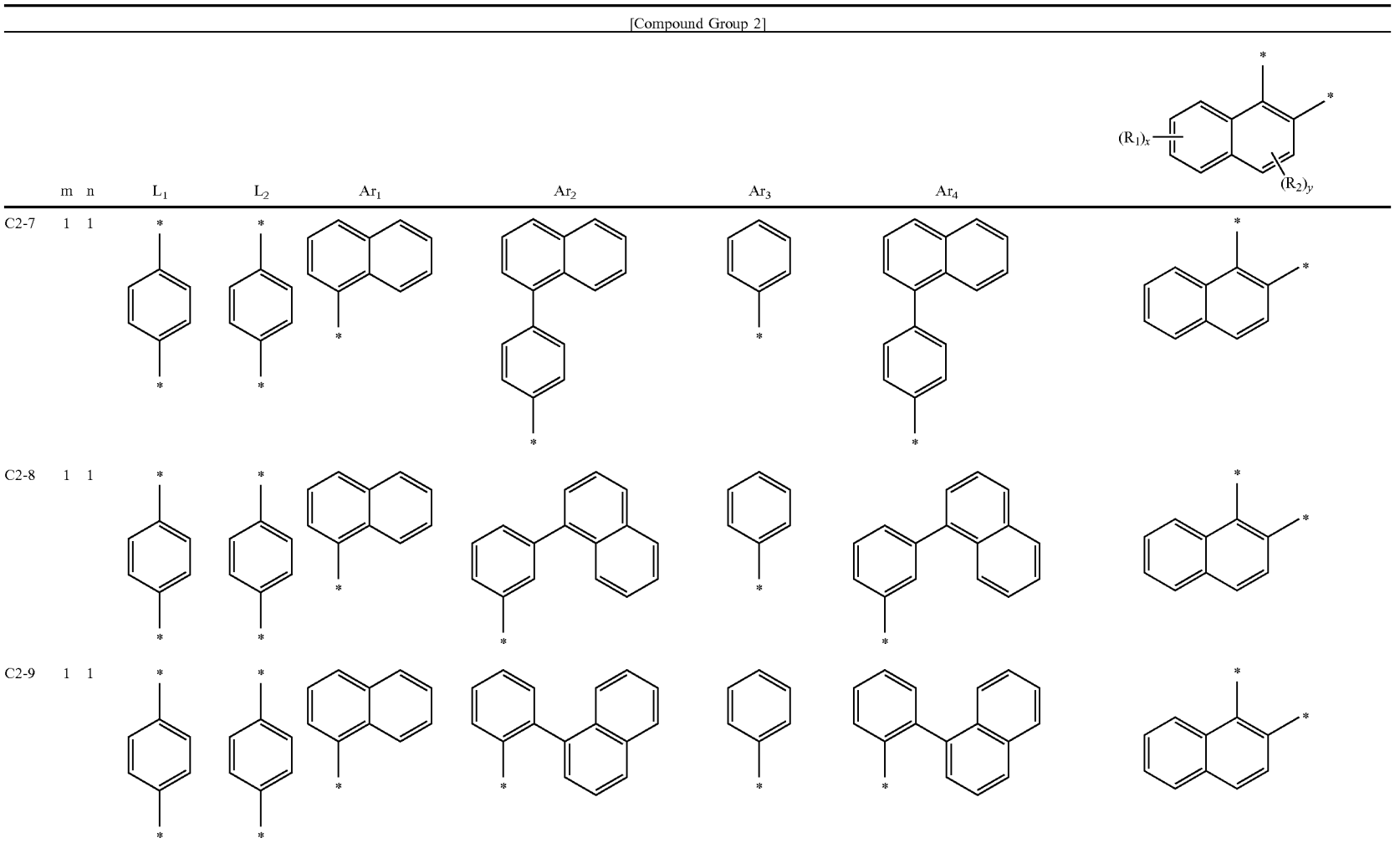

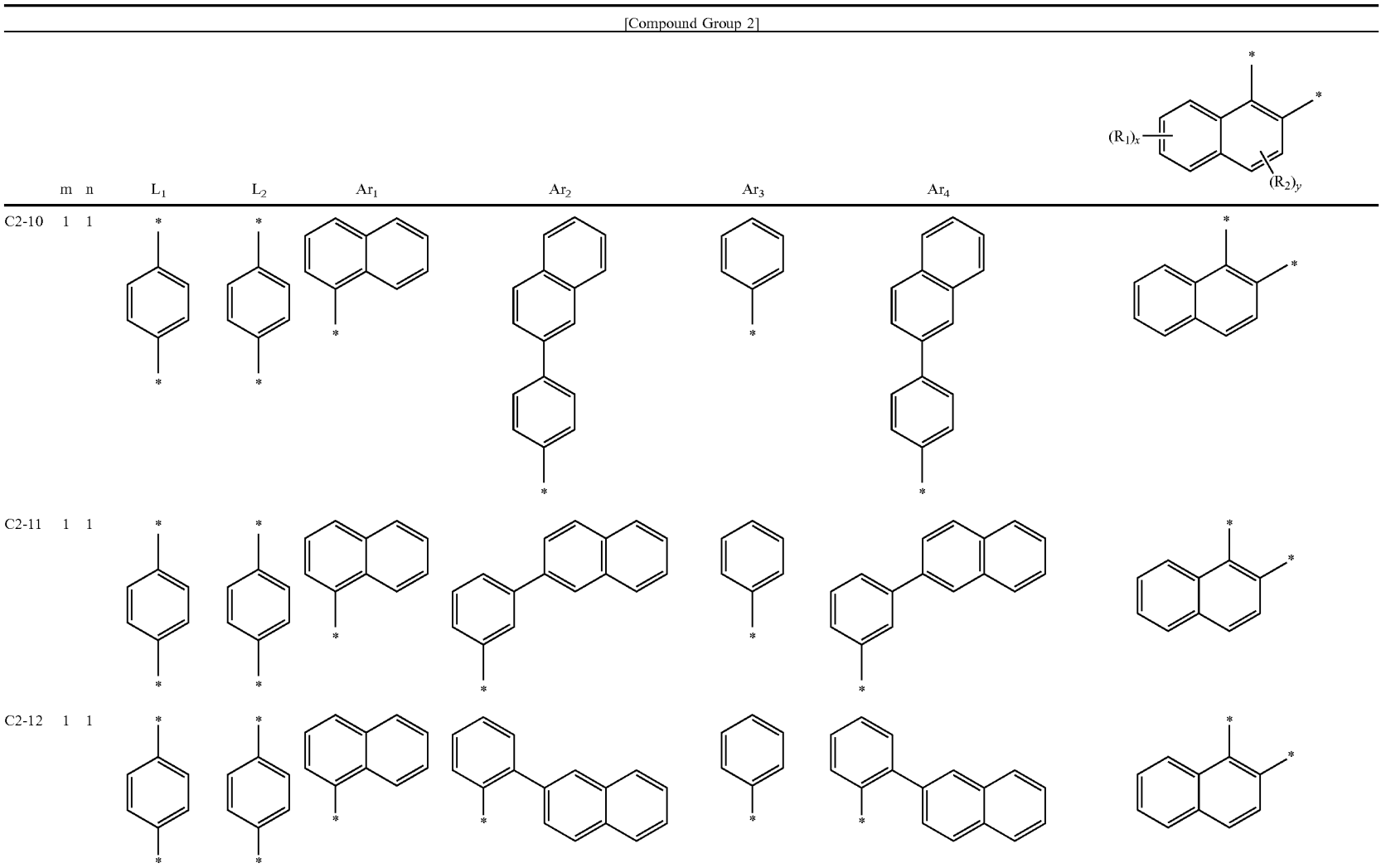

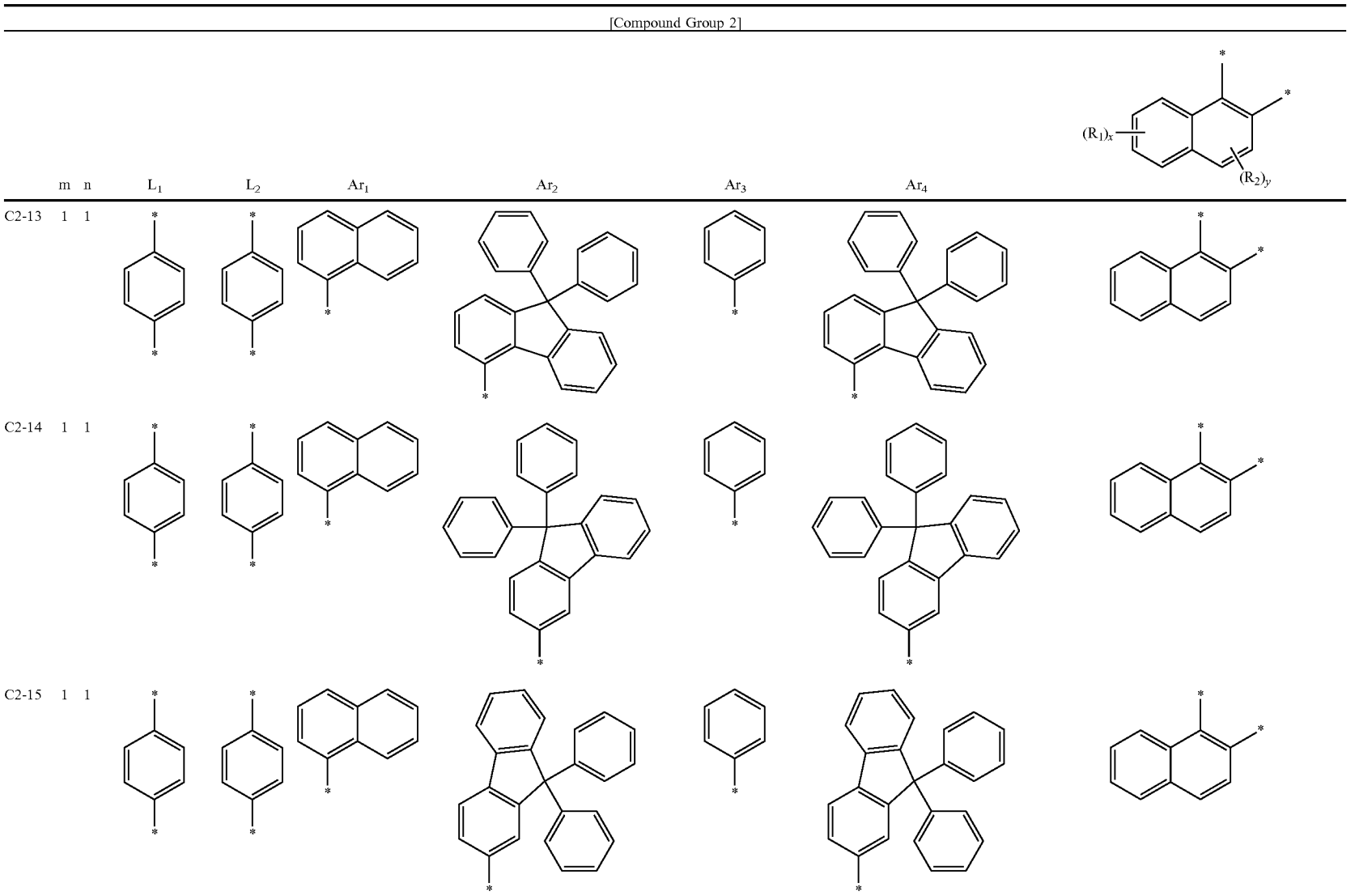

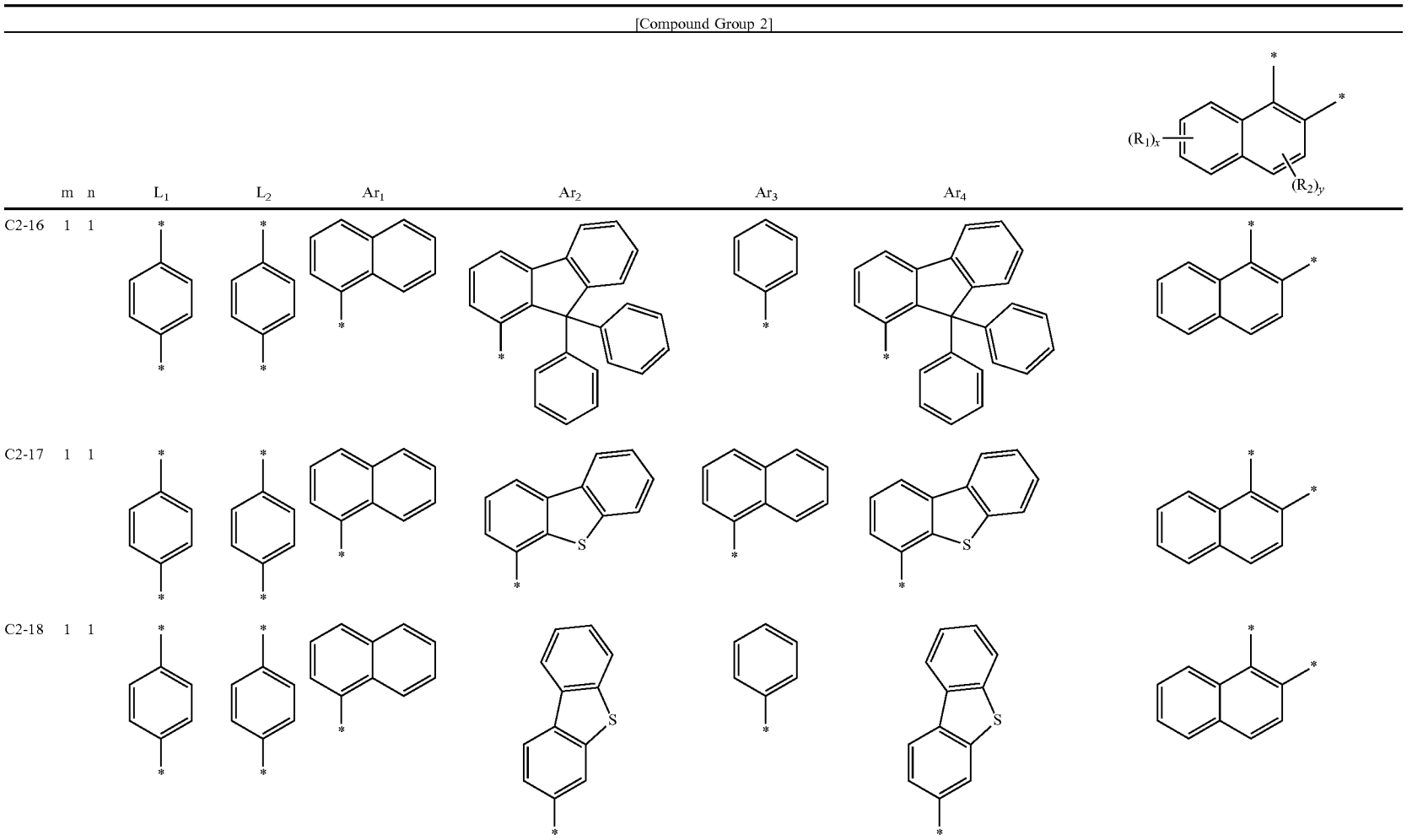

-continued

[Compound Group 2]

| | m | n | L₁ | L₂ | Ar₁ | Ar₂ | Ar₃ | Ar₄ | |
|---|---|---|---|---|---|---|---|---|---|
| C2-19 | 1 | 1 | phenylene | phenylene | naphthyl | dibenzothiophenyl | phenyl | dibenzothiophenyl | |
| C2-20 | 1 | 1 | phenylene | phenylene | naphthyl | dibenzothiophenyl | phenyl | dibenzothiophenyl | |
| C2-21 | 1 | 1 | phenylene | phenylene | naphthyl | dibenzofuranyl | phenyl | dibenzofuranyl | |

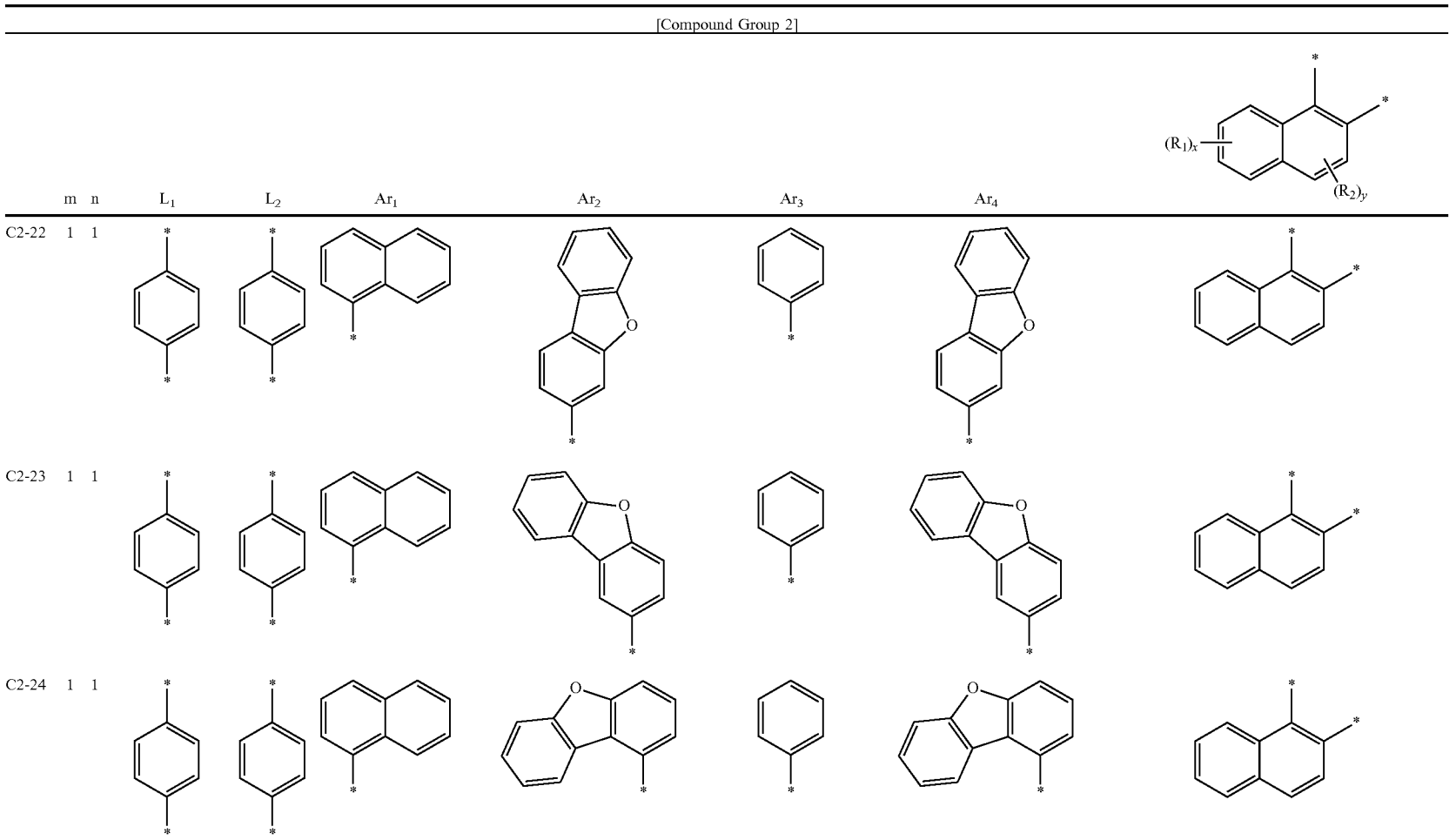

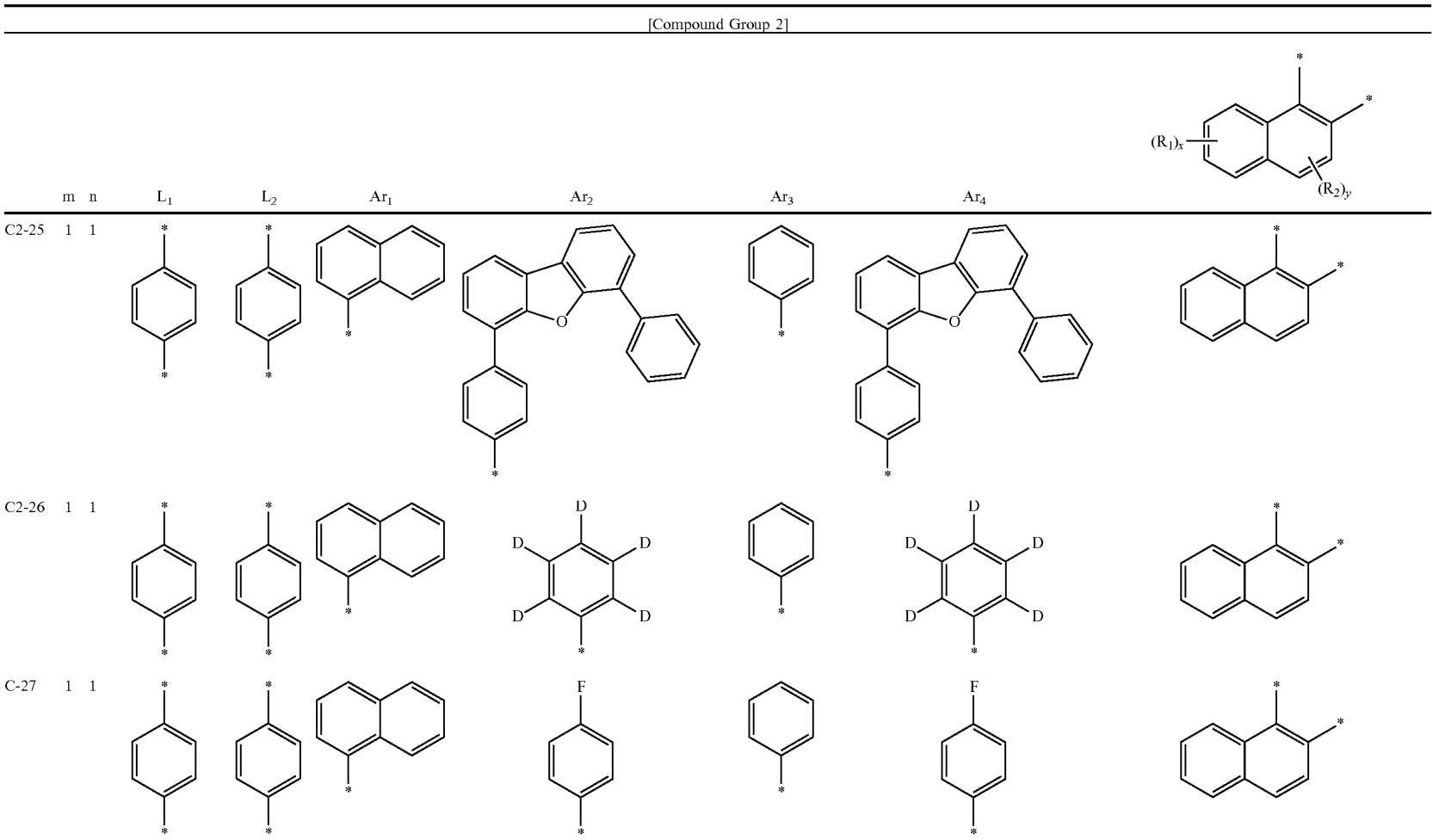

-continued

[Compound Group 2]

| | m | n | L₁ | L₂ | Ar₁ | Ar₂ | Ar₃ | Ar₄ | (naphthyl) |
|---|---|---|---|---|---|---|---|---|---|
| C2-28 | 1 | 1 | phenylene | phenylene | 1-naphthyl | 4-SiPh₃-phenyl | phenyl | 4-SiPh₃-phenyl | naphthyl |
| C2-29 | 1 | 1 | phenylene | phenylene | 1-naphthyl | 3-SiPh₃-phenyl | phenyl | 3-SiPh₃-phenyl | naphthyl |
| C2-30 | 1 | 1 | phenylene | phenylene | 1-naphthyl | 2-SiPh₃-phenyl | phenyl | 2-SiPh₃-phenyl | naphthyl |
| D2-1 | 1 | 1 | phenylene | phenylene | 1-naphthyl | biphenyl | 1-naphthyl | o-terphenyl | naphthyl |

-continued
[Compound Group 2]
| | m | n | L₁ | L₂ | Ar₁ | Ar₂ | Ar₃ | Ar₄ | 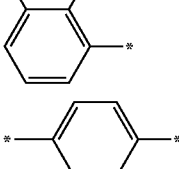 |
|---|---|---|---|---|---|---|---|---|---|
| D2-2 | 1 | 1 | 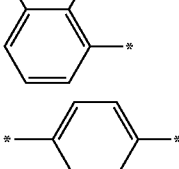 | 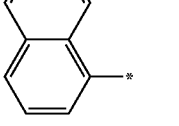 | 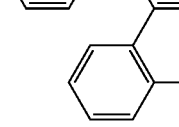 | 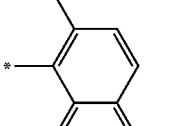 |  |  |  |
| D2-3 | 1 | 1 | 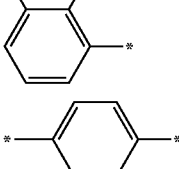 | 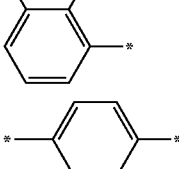 | 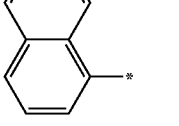 | 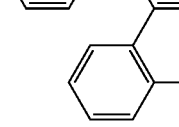 | 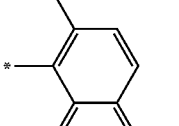 |  |  |

-continued
[Compound Group 2]
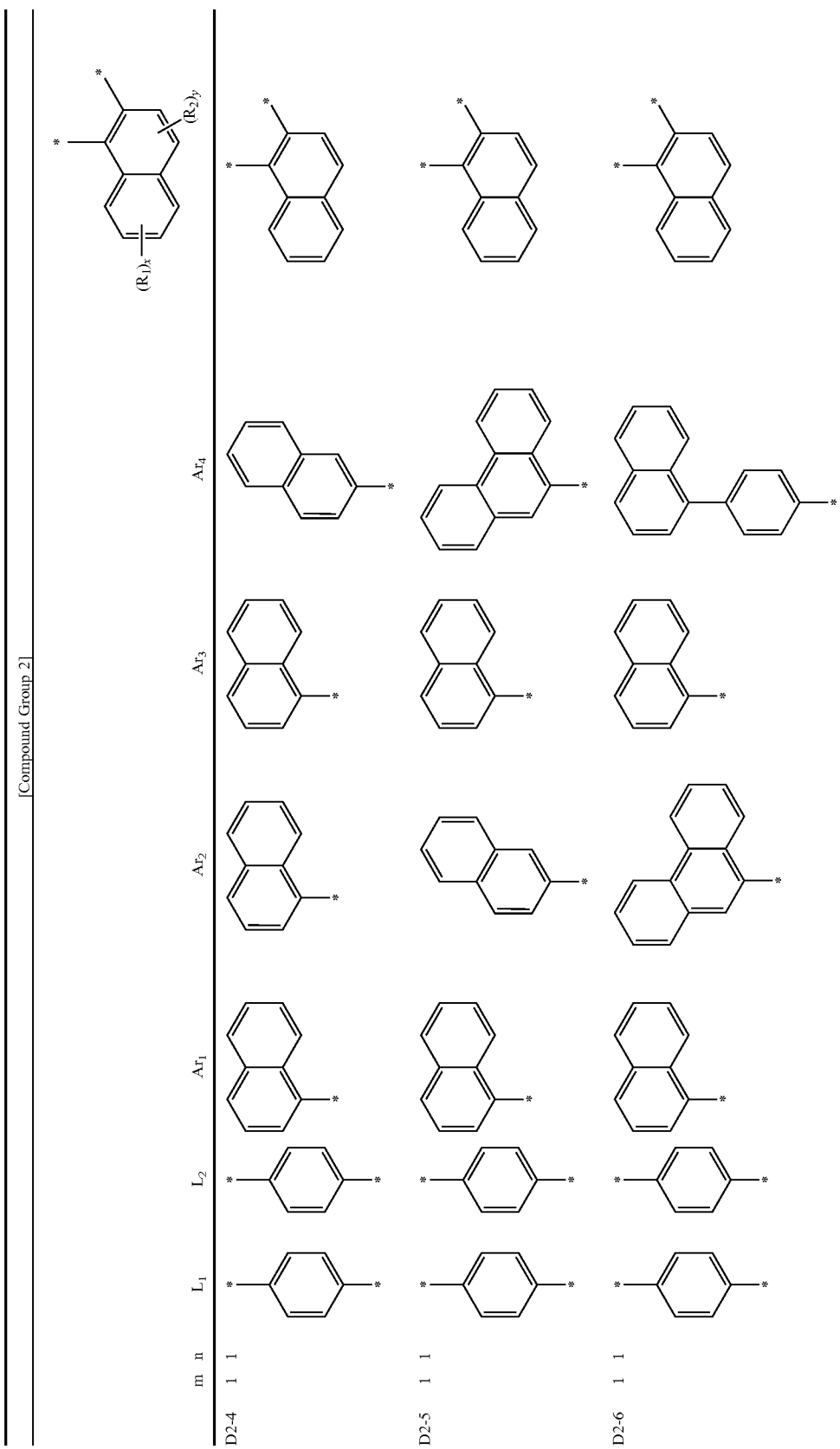

-continued
[Compound Group 2]
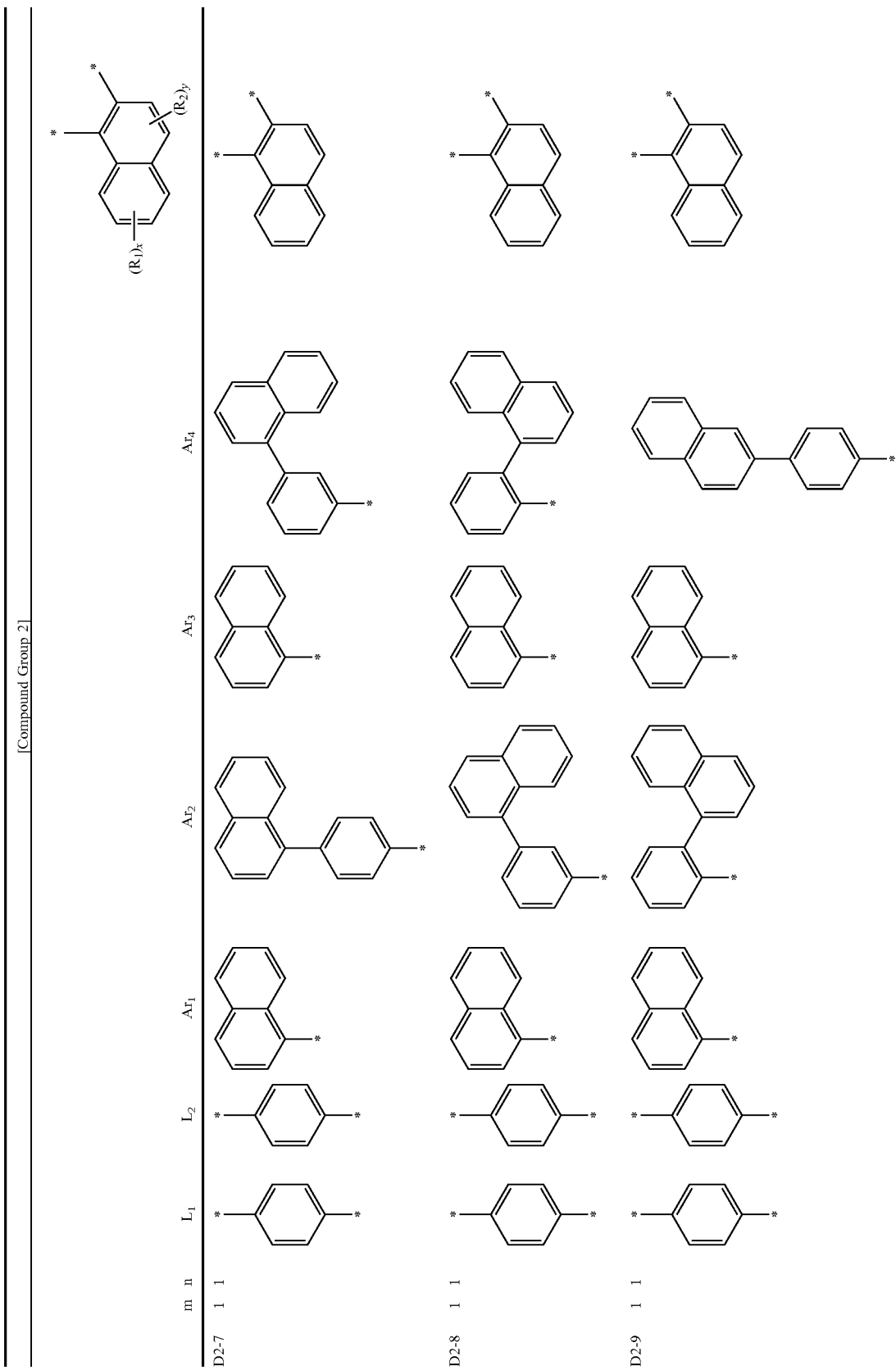

-continued
[Compound Group 2]
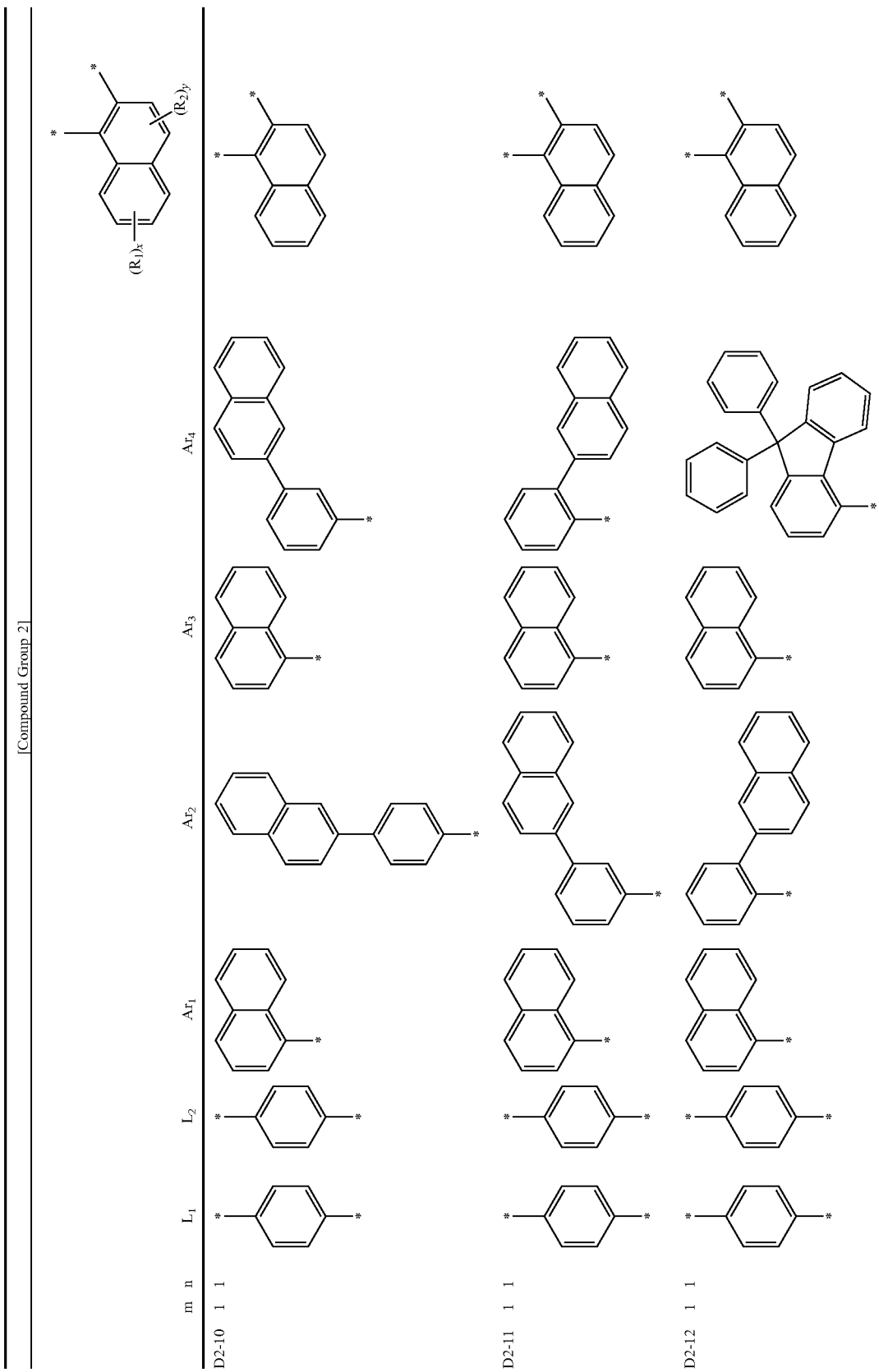

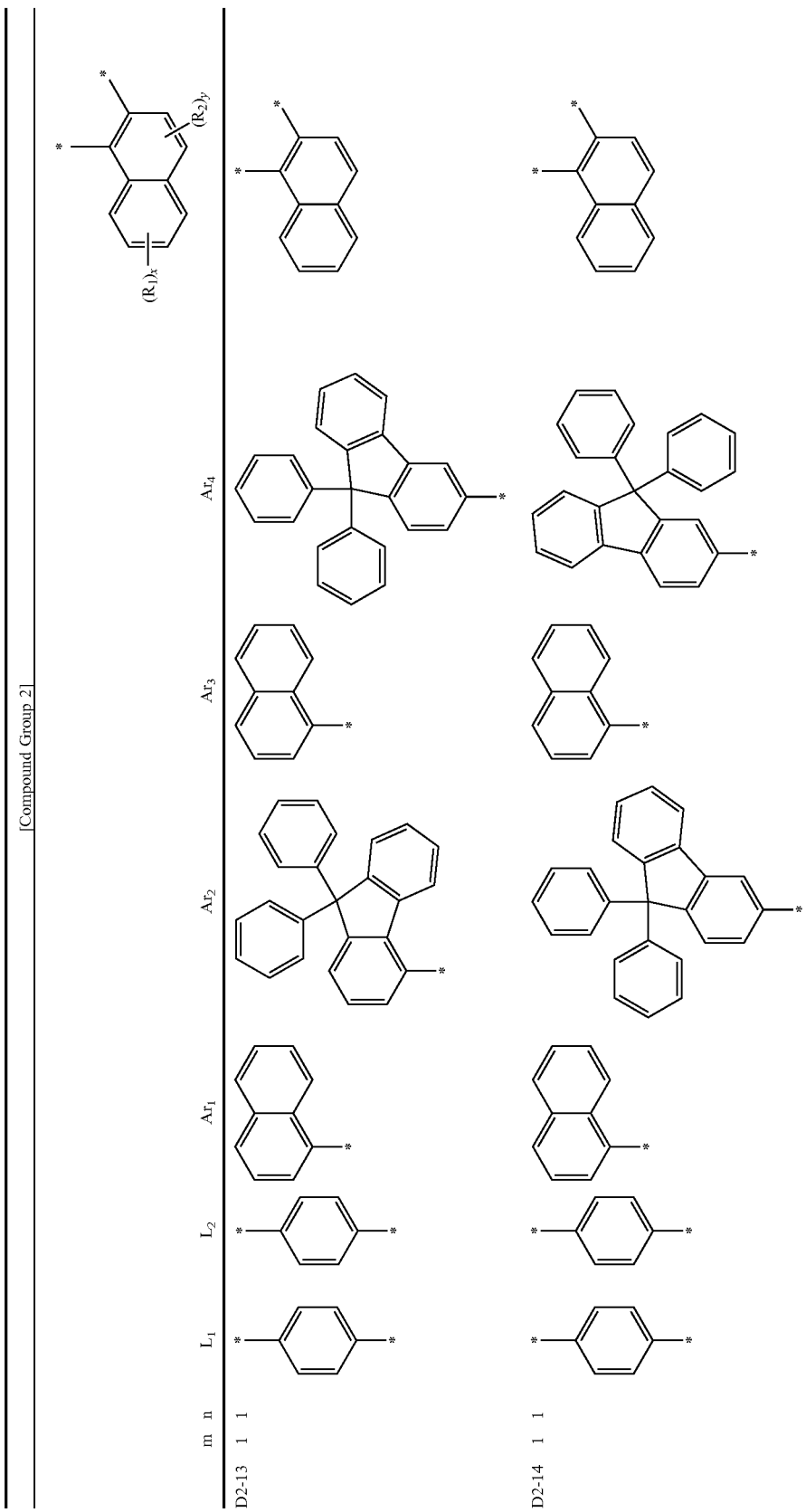

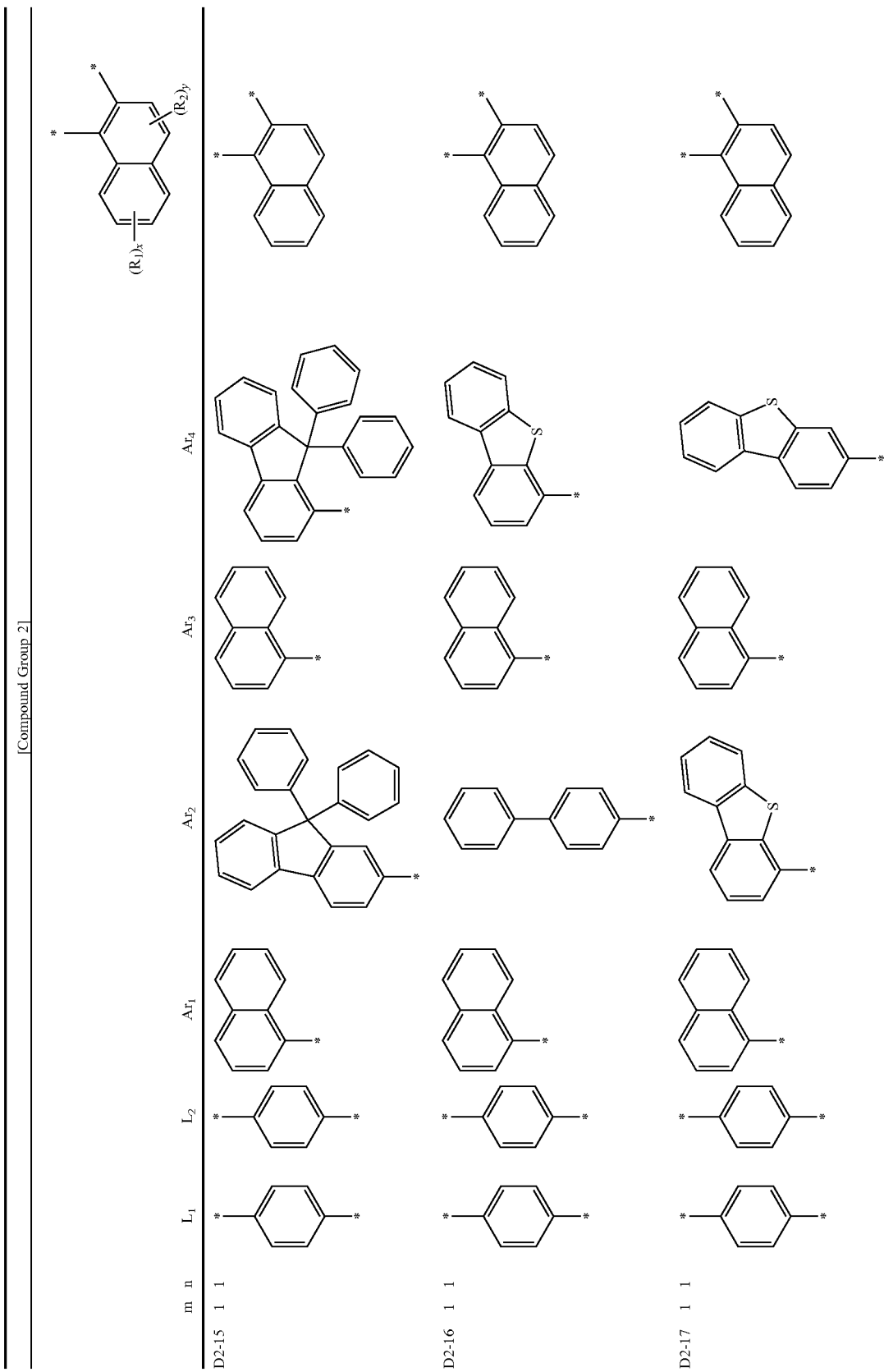

-continued
[Compound Group 2]
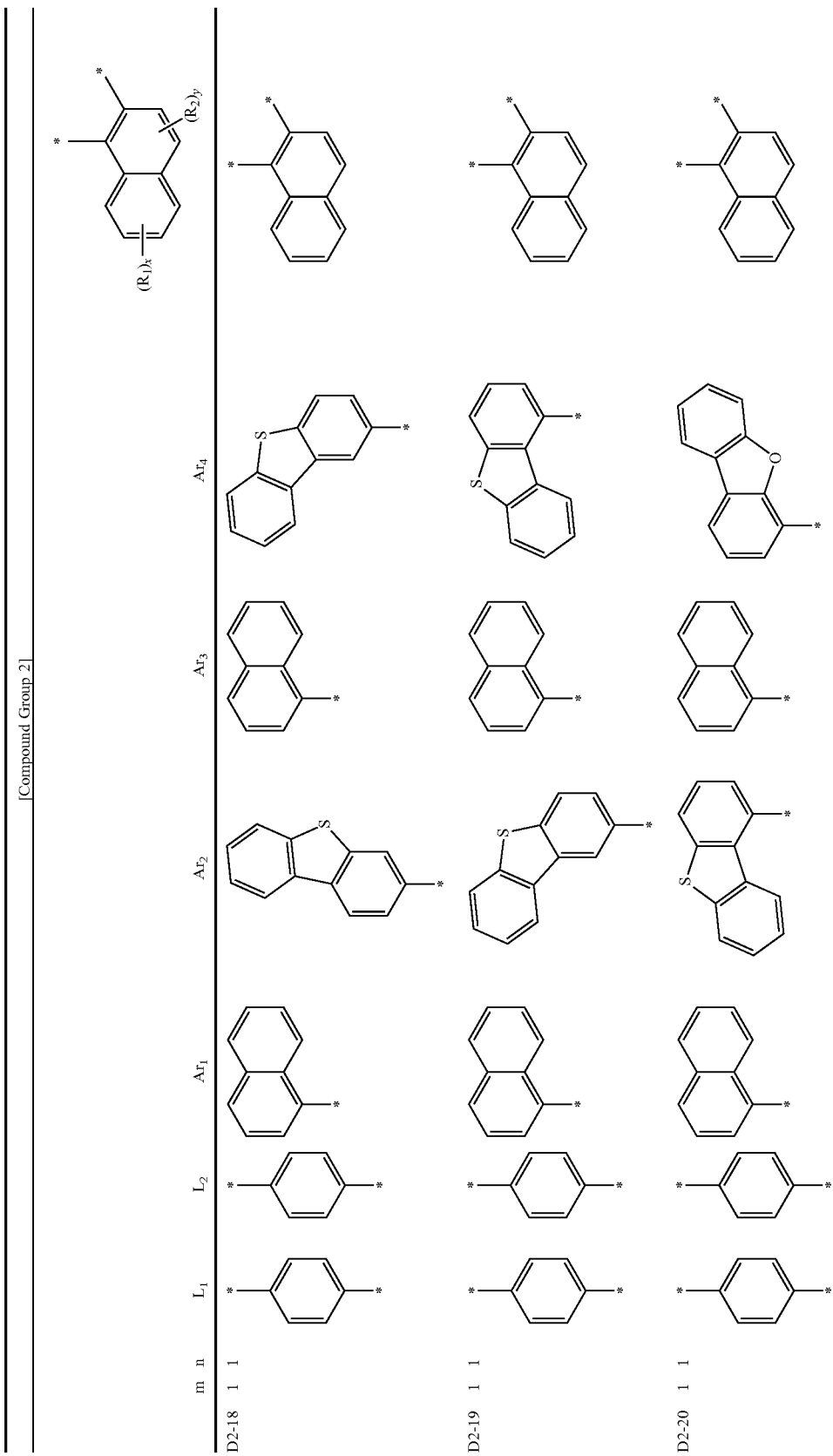

-continued
[Compound Group 2]
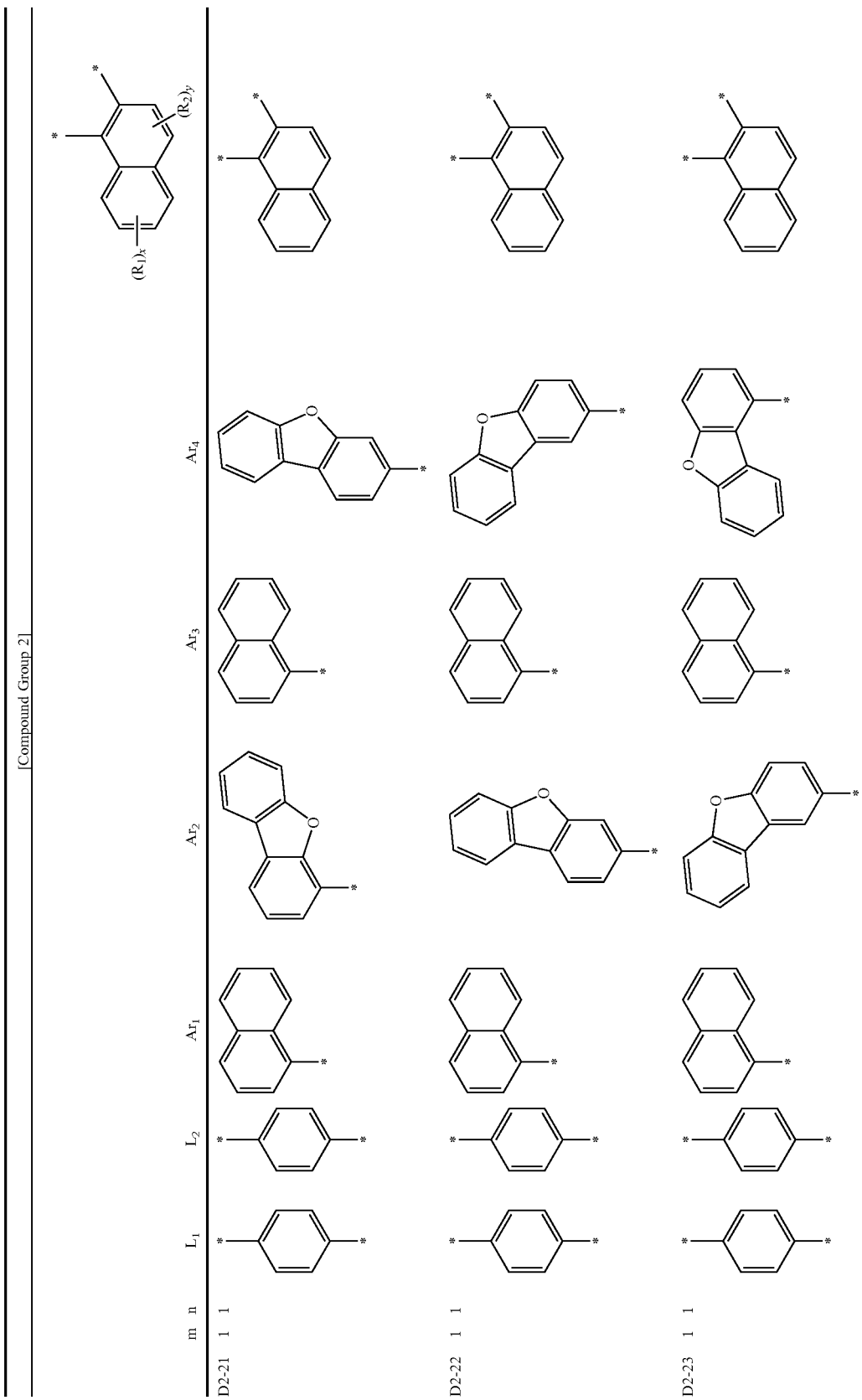

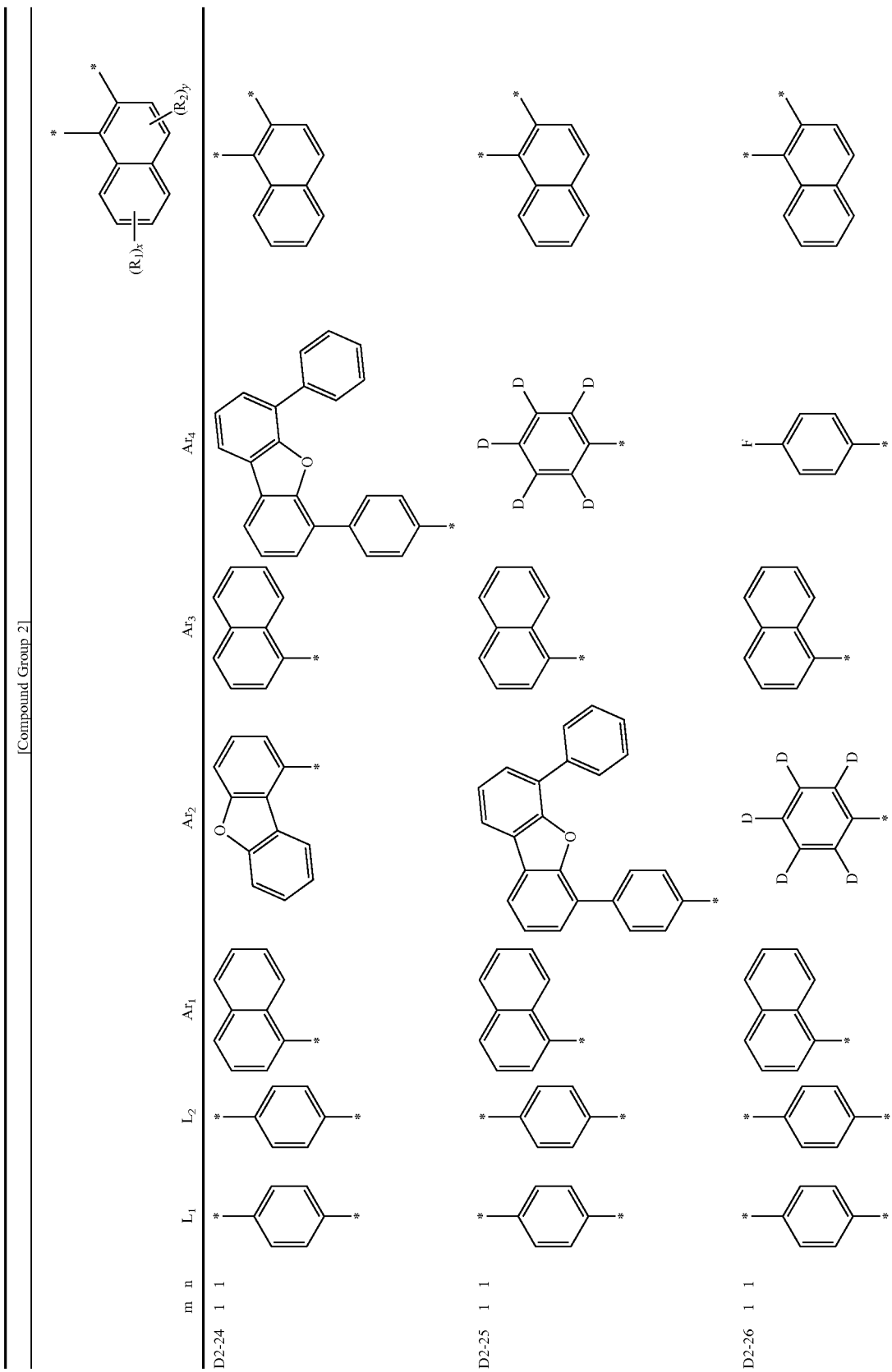

-continued

[Compound Group 2]

| m n | L₁ | L₂ | Ar₁ | Ar₂ | Ar₃ | Ar₄ | (structure with R₁, R₂) |
|---|---|---|---|---|---|---|---|
| D2-27 1 1 | *–C₆H₄–* | *–C₆H₄–* | naphthyl | 4-F-C₆H₄ | naphthyl | 4-SiPh₃-C₆H₄ | naphthyl |
| D2-28 1 1 | *–C₆H₄–* | *–C₆H₄–* | naphthyl | 4-SiPh₃-C₆H₄ | naphthyl | 3-SiPh₃-C₆H₄ | naphthyl |
| D2-29 1 1 | *–C₆H₄–* | *–C₆H₄–* | naphthyl | 3-SiPh₃-C₆H₄ | naphthyl | 2-SiPh₃-C₆H₄ | naphthyl |
| D2-30 1 1 | *–C₆H₄–* | *–C₆H₄–* | naphthyl | 2-SiPh₃-C₆H₄ | naphthyl | biphenyl-phenyl | naphthyl |

-continued

[Compound Group 2]

| m n | L₁ | L₂ | Ar₁ | Ar₂ | Ar₃ | Ar₄ | |
|---|---|---|---|---|---|---|---|
| E2-1  1 1 | *–⌬–* | *–⌬–* | naphthyl | dibenzothiophenyl | naphthyl | biphenyl | naphthyl-Me-phenyl |
| E2-2  1 1 | *–⌬–* | *–⌬–* | naphthyl | dibenzothiophenyl | naphthyl | dibenzothiophenyl | naphthyl-phenyl-carbazolyl |

13. The organic electroluminescence device of claim 1, wherein the diamine compound represented by Formula 1 is at least one selected among compounds represented in Compound Group 3:

[Compound Group 3]
| | m | n | L₁ | L₂ | Ar₁ | Ar₂ | Ar₃ | Ar₄ | 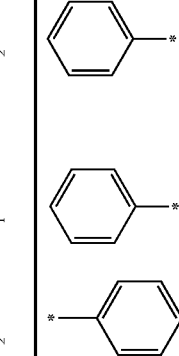 |
|---|---|---|---|---|---|---|---|---|---|
| A3-1 | 0 | 1 | — | phenylene | phenyl | phenyl | phenyl | phenyl | naphthyl |
| A3-2 | 0 | 1 | — | phenylene | biphenyl | biphenyl | biphenyl | biphenyl | naphthyl |
| A3-3 | 0 | 1 | — | phenylene | phenyl | biphenyl | phenyl | biphenyl | naphthyl |

-continued
[Compound Group 3]
| m | n | L$_2$ | Ar$_1$ | Ar$_2$ | Ar$_3$ | Ar$_4$ | |
|---|---|---|---|---|---|---|---|
| A3-4 | 0 | 1 | — | 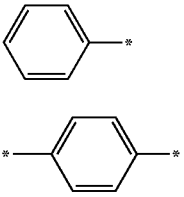 | 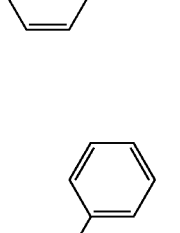 | 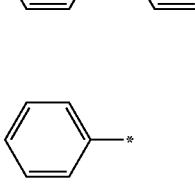 | 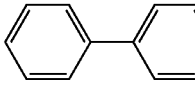 |  |
| A3-5 | 0 | 1 | — | 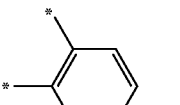 | 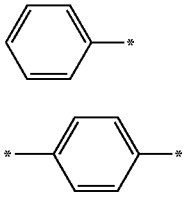 | 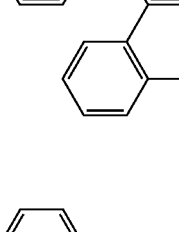 | 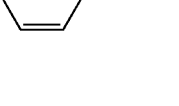 | 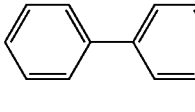 |

-continued

[Compound Group 3]

| | m | n | L₁ | L₂ | Ar₁ | Ar₂ | Ar₃ | Ar₄ | (R₁)x / (R₂)y naphthalene |
|---|---|---|---|---|---|---|---|---|---|
| A3-6 | 0 | 1 | — | * —⌬— * | * —⌬ | * —naphthyl | * —⌬ | * —⌬—⌬ | naphthyl |
| A3-7 | 0 | 1 | — | * —⌬— * | * —⌬ | * —naphthyl | * —⌬ | * —⌬—⌬ | naphthyl |
| A3-8 | 0 | 1 | — | * —⌬— * | * —⌬ | * —phenanthryl | * —⌬ | * —⌬—⌬ | naphthyl |

-continued
[Compound Group 3]
| | m | n | L₁ | L₂ | Ar₁ | Ar₂ | Ar₃ | Ar₄ | |
|---|---|---|---|---|---|---|---|---|---|
| A3-9 | 0 | 1 | — | 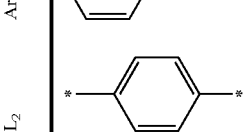 | 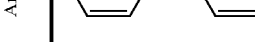 | 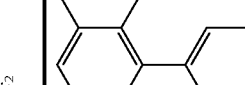 | 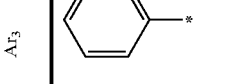 | 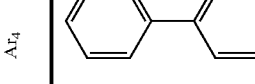 | 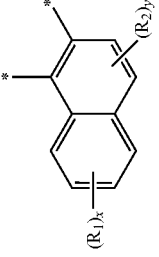 |
| A3-10 | 0 | 1 | — | 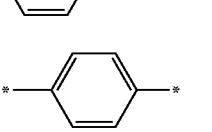 |  | 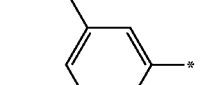 | 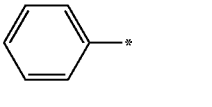 | 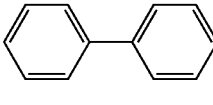 | 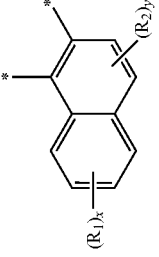 |
| A3-11 | 0 | 1 | — | 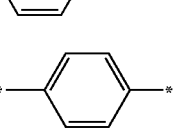 |  | 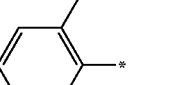 | 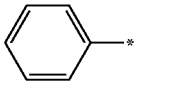 | 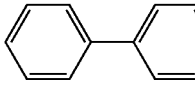 | 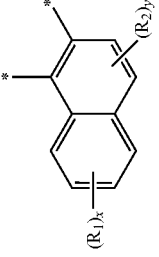 |

-continued
[Compound Group 3]
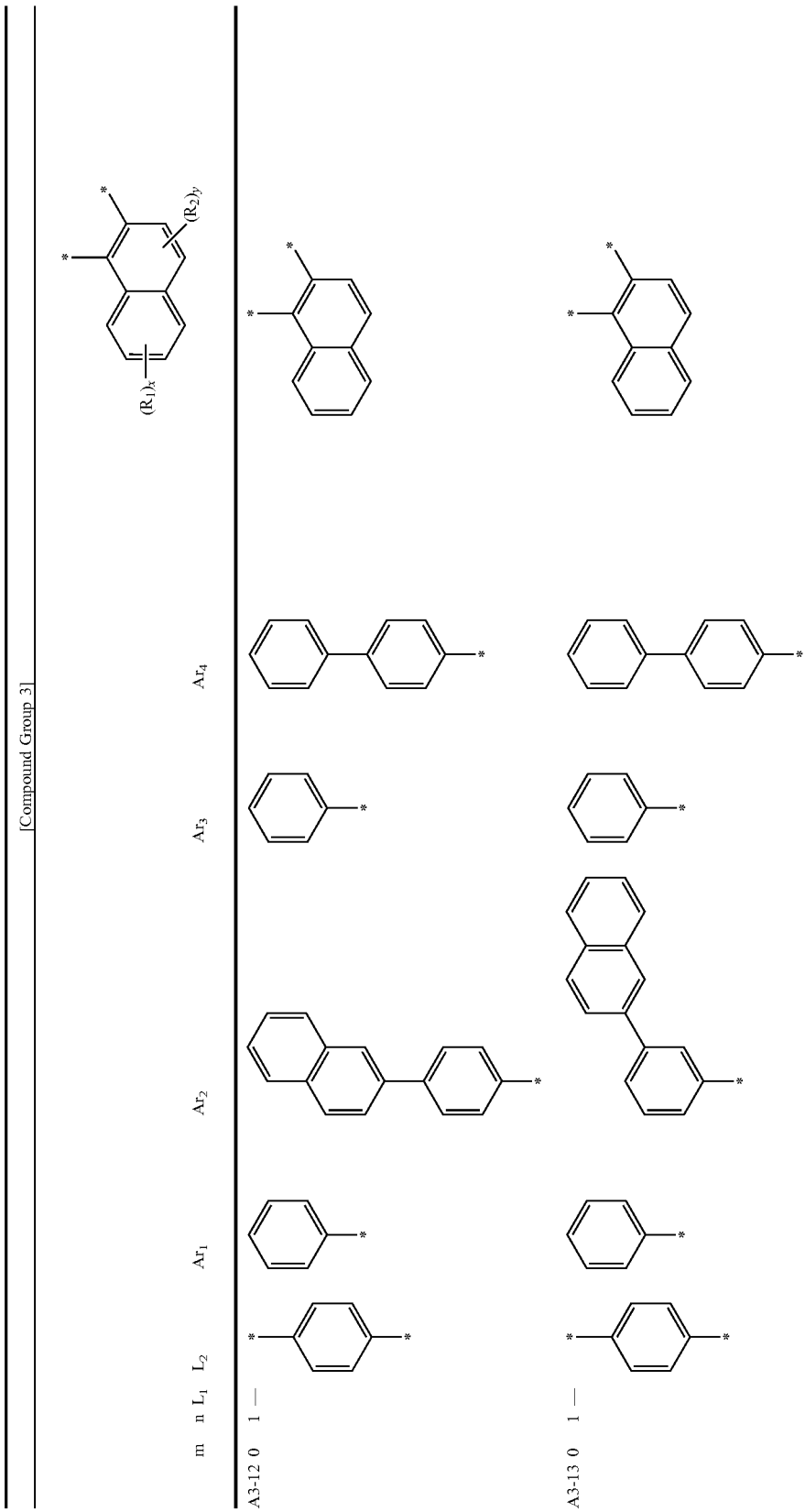

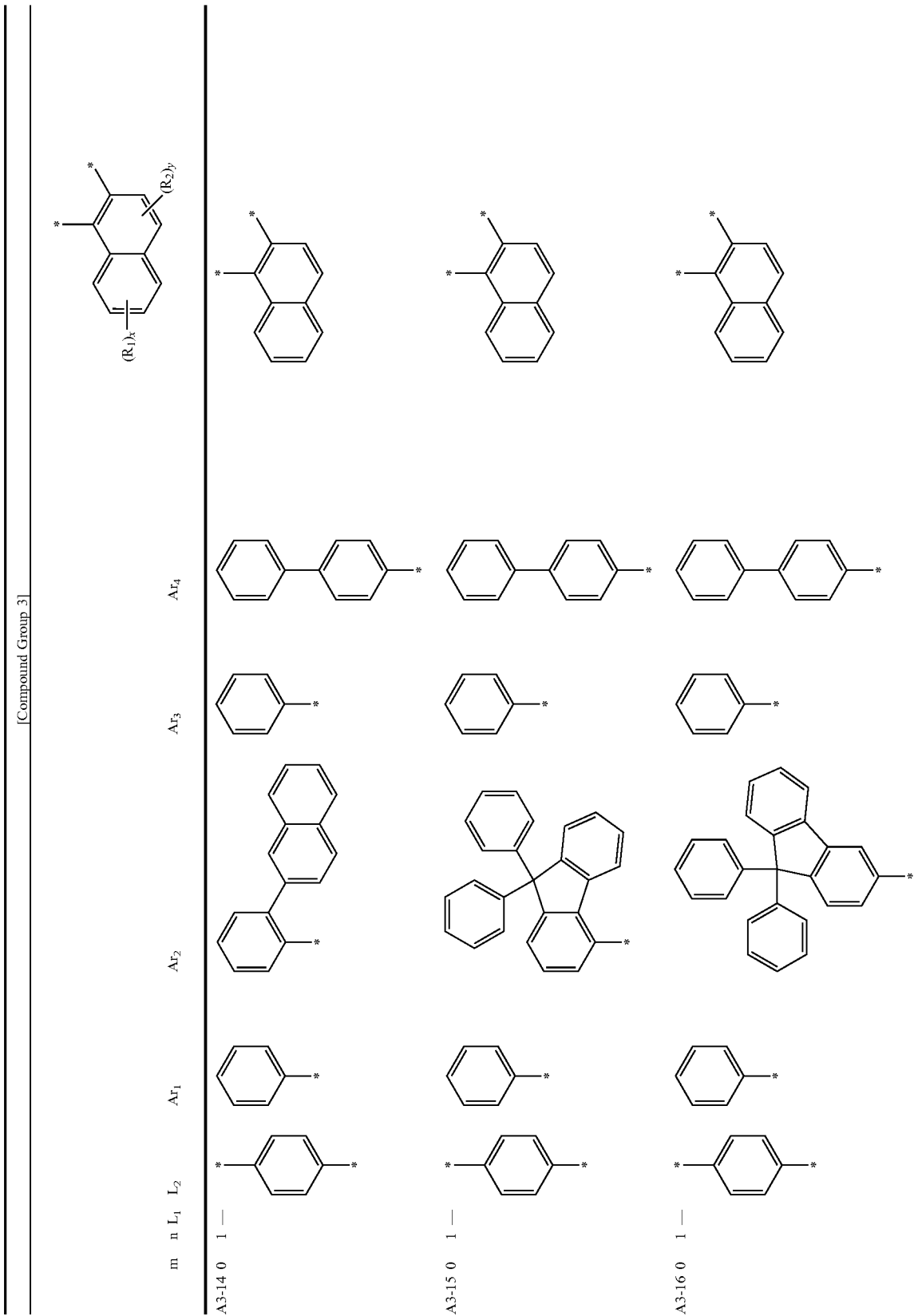

-continued

[Compound Group 3]

| | m | n | L₁ | L₂ | Ar₁ | Ar₂ | Ar₃ | Ar₄ | |
|---|---|---|---|---|---|---|---|---|---|
| A3-17 | 0 | 1 | — | * —⟨ ⟩— * | * —⟨ ⟩ | 9,9-diphenylfluoren-2-yl | * —⟨ ⟩ | biphenyl-4-yl | naphthyl |
| A3-18 | 0 | 1 | — | * —⟨ ⟩— * | * —⟨ ⟩ | 9,9-diphenylfluoren-1-yl | * —⟨ ⟩ | biphenyl-4-yl | naphthyl |
| A3-19 | 0 | 1 | — | * —⟨ ⟩— * | * —⟨ ⟩ | dibenzothiophen-4-yl | * —⟨ ⟩ | biphenyl-4-yl | naphthyl |

-continued
[Compound Group 3]
| | m | n | L₁ | L₂ | Ar₁ | Ar₂ | Ar₃ | Ar₄ | 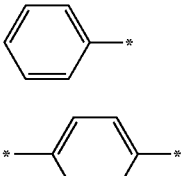 |
|---|---|---|---|---|---|---|---|---|---|
| A3-20 | 0 | 1 | — | 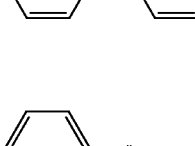 | 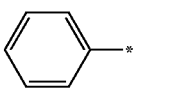 | 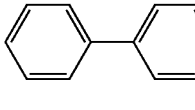 |  | 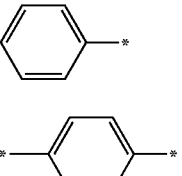 | 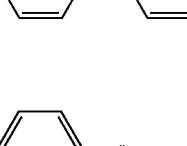 |
| A3-21 | 0 | 1 | — | 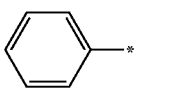 | 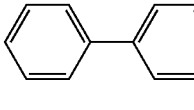 |  | 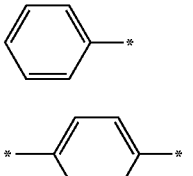 | 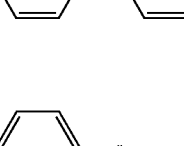 | 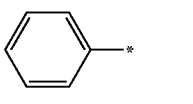 |
| A3-22 | 0 | 1 | — | 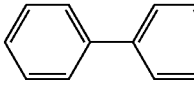 |  |  |  |  |  |

-continued
[Compound Group 3]
| | m | n | L₁ | L₂ | Ar₁ | Ar₂ | Ar₃ | Ar₄ | |
|---|---|---|---|---|---|---|---|---|---|
| A3-23 | 0 | 1 | — | 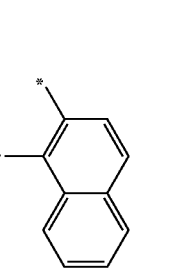 |  | 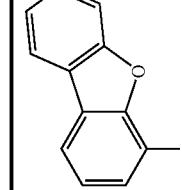 | 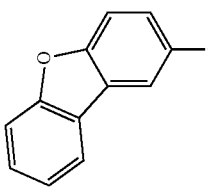 | 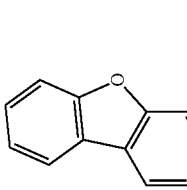 | 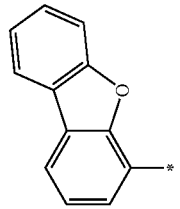 |
| A3-24 | 0 | 1 | — | 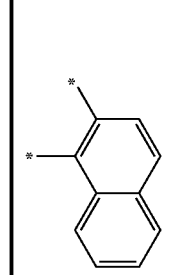 | 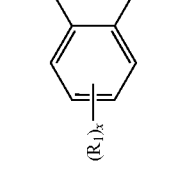 | 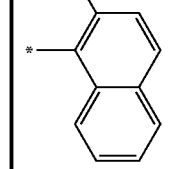 | 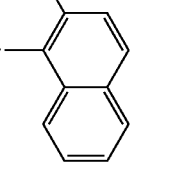 | 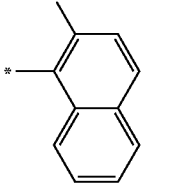 | 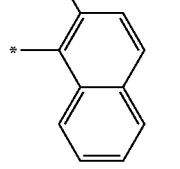 |
| A3-25 | 0 | 1 | — | 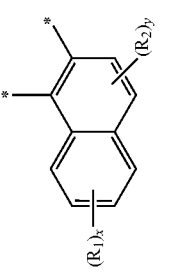 |  |  |  |  |  |

-continued
[Compound Group 3]
| | m | n | L₁ | L₂ | Ar₁ | Ar₂ | Ar₃ | Ar₄ | 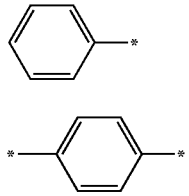 |
|---|---|---|---|---|---|---|---|---|---|
| A3-26 | 0 | 1 | — | 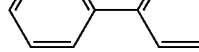 | 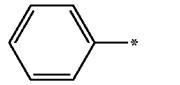 | 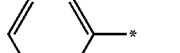 | 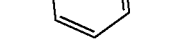 | 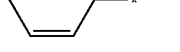 |  |
| A3-27 | 0 | 1 | — | 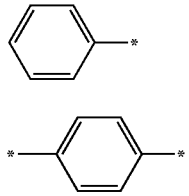 | 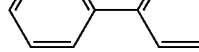 | 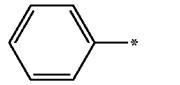 | 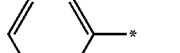 | 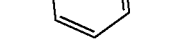 | 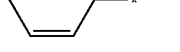 |
| A3-28 | 0 | 1 | — |  | 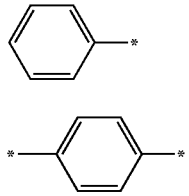 | 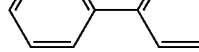 | 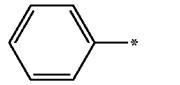 | 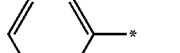 | 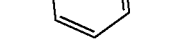 |

-continued
[Compound Group 3]
| | m | n | L₁ | L₂ | Ar₁ | Ar₂ | Ar₃ | Ar₄ | |
|---|---|---|---|---|---|---|---|---|---|
| A3-29 | 0 | 1 | — | 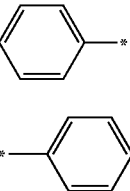 | 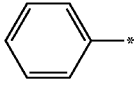 | 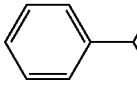 | 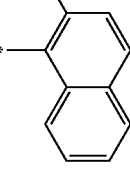 |  |  |
| A3-30 | 0 | 1 | — | 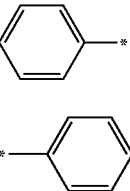 | 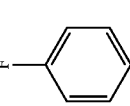 | 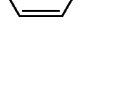 | 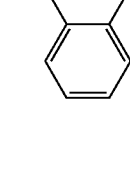 | 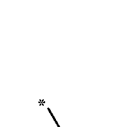 |  |
| A3-31 | 0 | 1 | — | 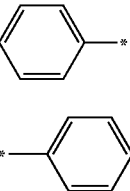 | 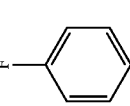 | 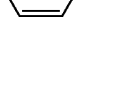 | 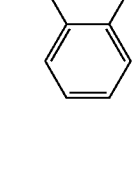 | 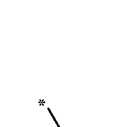 |  |

-continued
[Compound Group 3]
| | m | n | L₁ | L₂ | Ar₁ | Ar₂ | Ar₃ | Ar₄ | 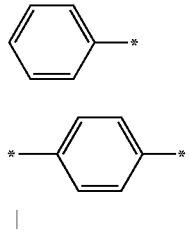 |
|---|---|---|---|---|---|---|---|---|---|
| A3-32 | 0 | 1 | — | | | | | | |
| A3-33 | 0 | 1 | — | | | | | | |
| B3-1 | 0 | 1 | — | | | | | | |

-continued
[Compound Group 3]
| | m | n | L₁ | L₂ | Ar₁ | Ar₂ | Ar₃ | Ar₄ | 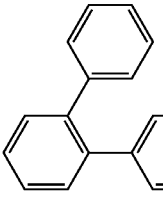 |
|---|---|---|---|---|---|---|---|---|---|
| B3-2 | 0 | 1 | — | 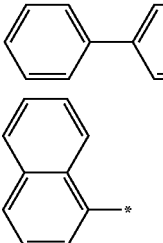 | 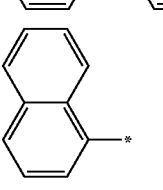 | 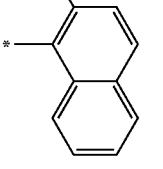 | 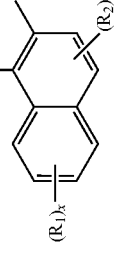 | 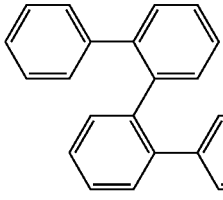 | 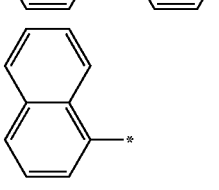 |
| B3-3 | 0 | 1 | — | 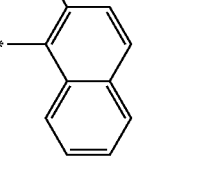 | 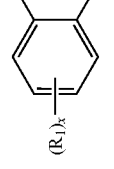 | | | | |

-continued
[Compound Group 3]
| | m | n | L₁ | L₂ | Ar₁ | Ar₂ | Ar₃ | Ar₄ |  |
|---|---|---|---|---|---|---|---|---|---|
| B3-4 | 0 | 1 | — | 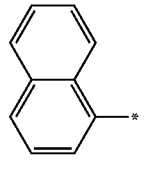 | 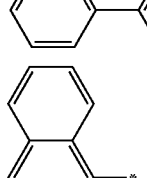 | 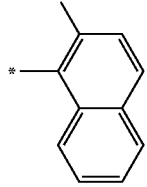 |  | 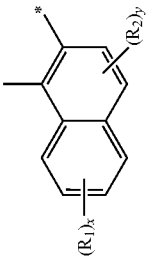 | 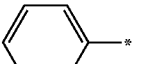 |
| B3-5 | 0 | 1 | — | 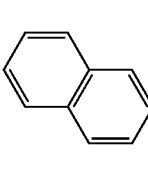 | 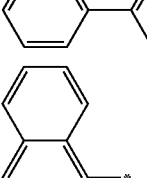 | 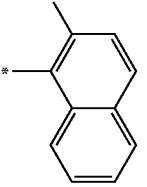 |  | 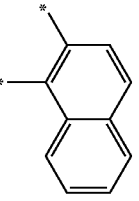 | 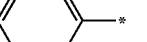 |
| B3-6 | 0 | 1 | — | 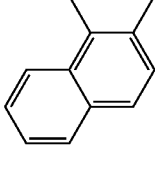 | 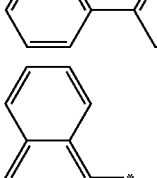 | 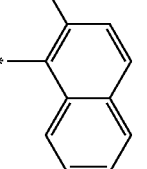 |  | 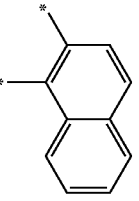 | |

-continued
[Compound Group 3]
| | m | n | $L_1$ | $L_2$ | $Ar_1$ | $Ar_2$ | $Ar_3$ | $Ar_4$ | |
|---|---|---|---|---|---|---|---|---|---|
| B3-7 | 0 | 1 | — | 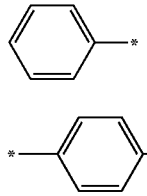 |  | 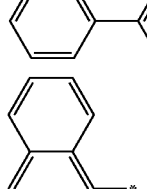 |  | 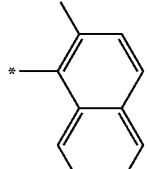 |  |
| B3-8 | 0 | 1 | — | 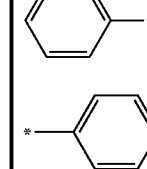 | 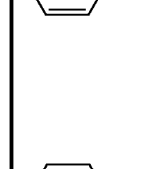 | 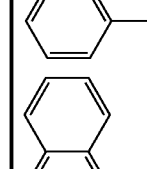 | 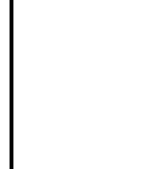 | 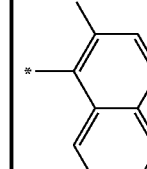 | 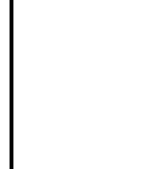 |
| B3-9 | 0 | 1 | — | 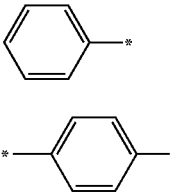 | 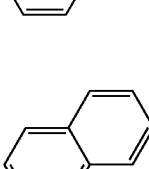 | 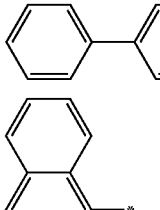 |  | 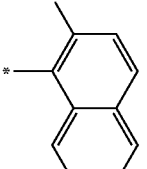 |  |

-continued
[Compound Group 3]
| | m | n | L₁ | L₂ | Ar₁ | Ar₂ | Ar₃ | Ar₄ |
|---|---|---|---|---|---|---|---|---|
| B3-10 | 0 | 1 | — | 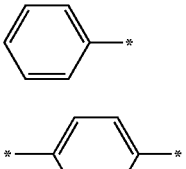 | 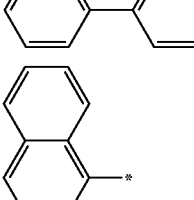 | 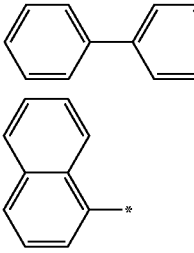 | 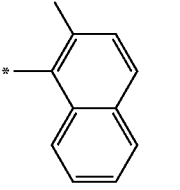 | 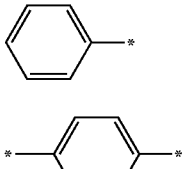 |
| B3-11 | 0 | 1 | — | 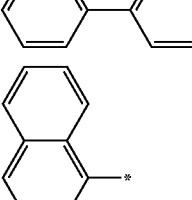 | 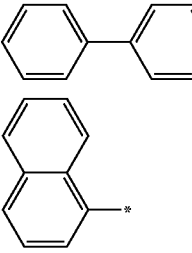 | 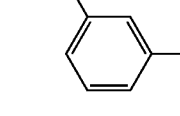 | 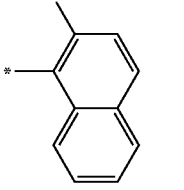 |  |

-continued
[Compound Group 3]
| | m | n | L₁ | L₂ | Ar₁ | Ar₂ | Ar₃ | Ar₄ | |
|---|---|---|---|---|---|---|---|---|---|
| B3-12 | 0 | 1 | — | 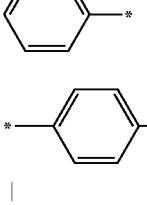 | 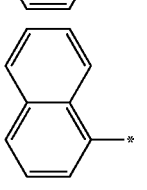 | 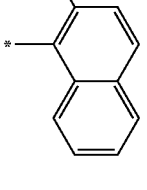 |  |  |  |
| B3-13 | 0 | 1 | — | 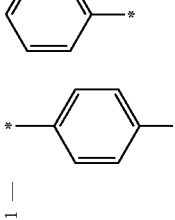 | 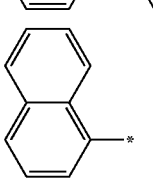 |  |  |  |  |
| B3-14 | 0 | 1 | — | 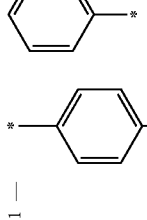 | 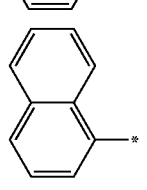 |  |  |  |  |

-continued
[Compound Group 3]
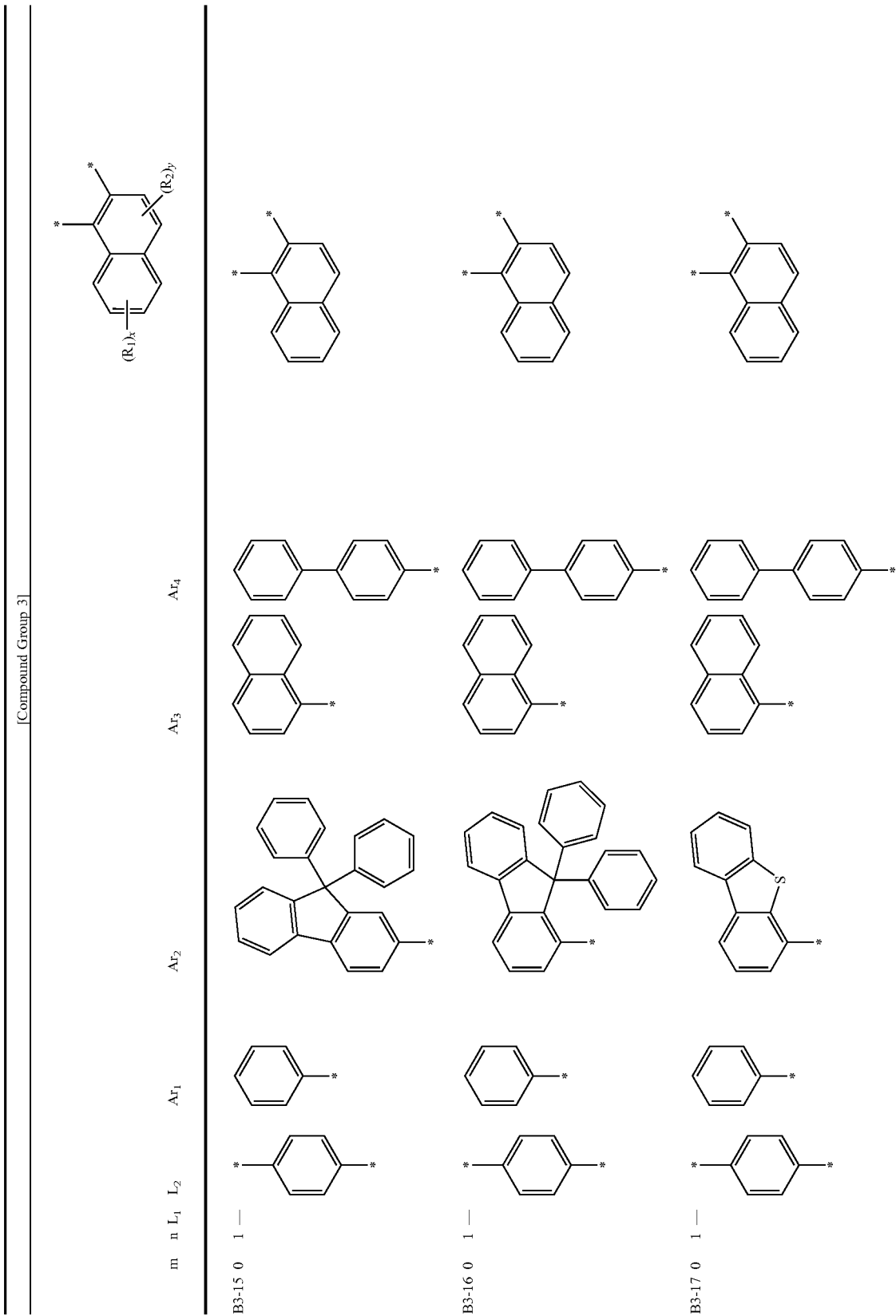

[Compound Group 3]
| | m | n | L₁ | L₂ | Ar₁ | Ar₂ | Ar₃ | Ar₄ | 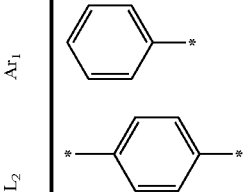 |
|---|---|---|---|---|---|---|---|---|---|
| B3-18 | 0 | 1 | — | 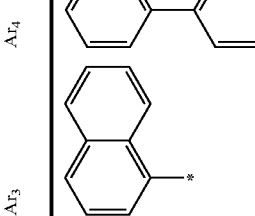 | 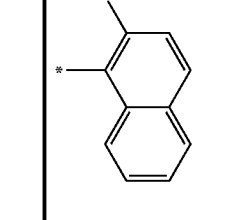 | 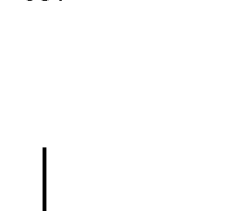 | 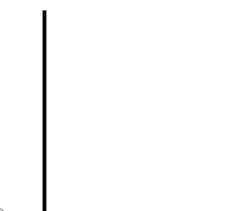 | 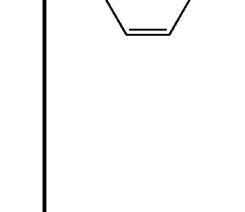 | 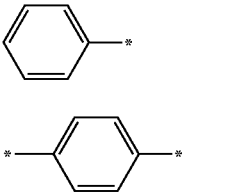 |
| B3-19 | 0 | 1 | — | 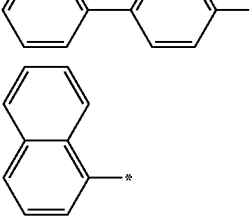 | 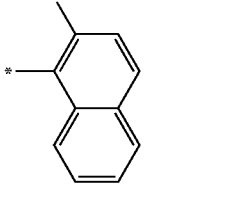 |  |  | 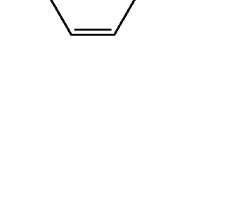 | 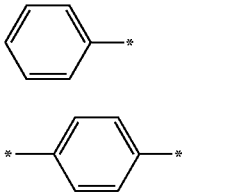 |
| B3-20 | 0 | 1 | — | 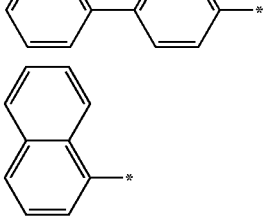 | 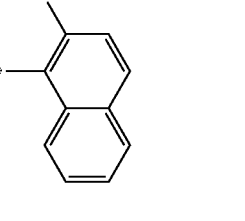 | 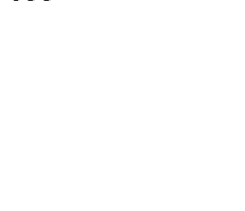 |  | 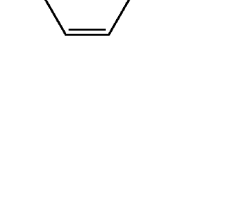 | 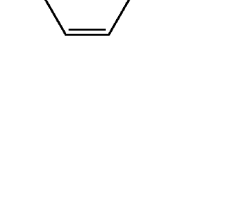 |

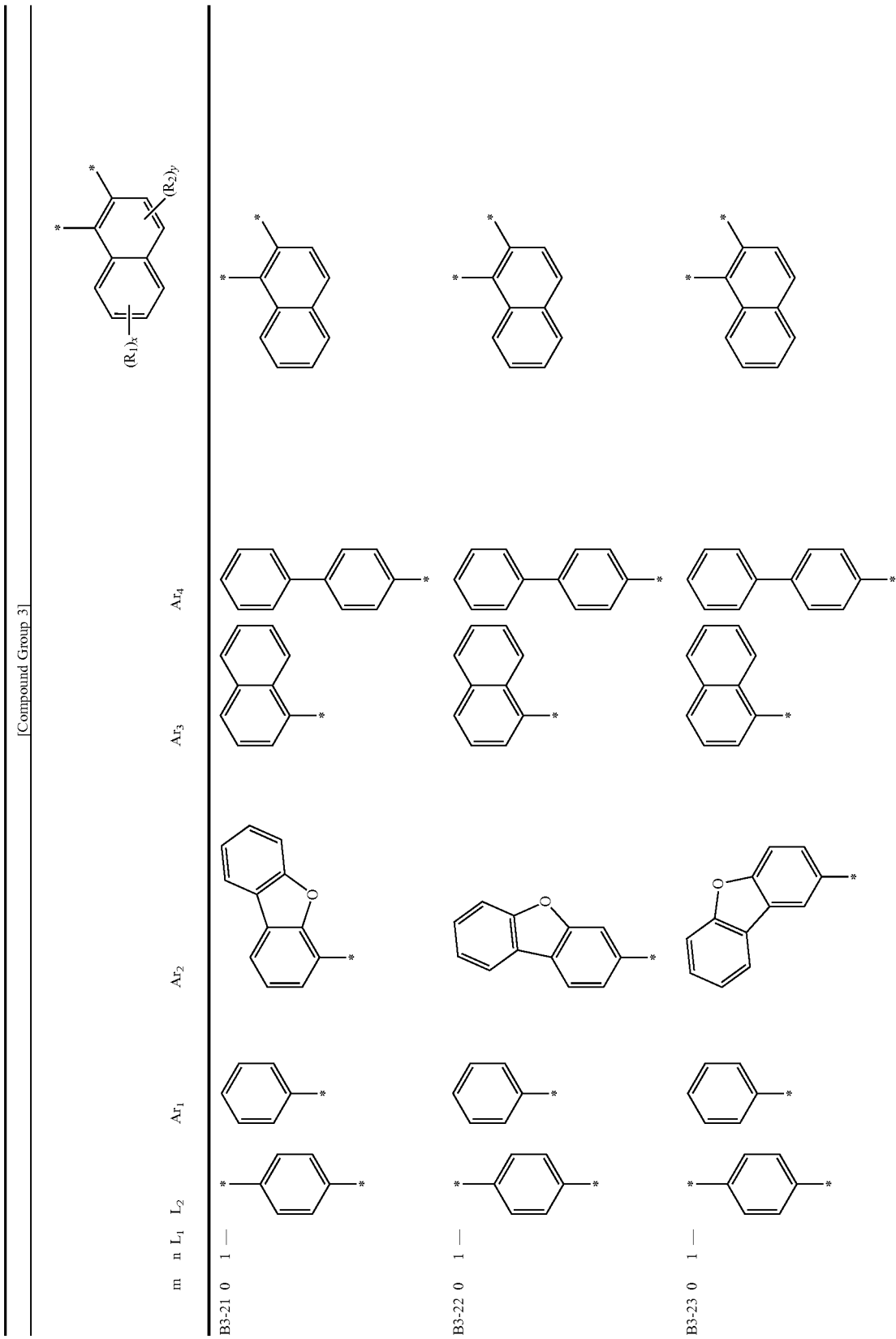

-continued
[Compound Group 3]
| | m | n | L₁ | L₂ | Ar₁ | Ar₂ | Ar₃ | Ar₄ | 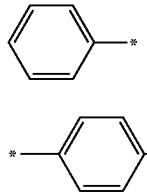 |
|---|---|---|---|---|---|---|---|---|---|
| B3-24 | 0 | 1 | — | * ⌬ * | ⌬* | 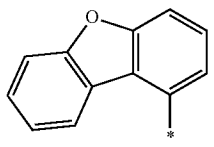 |  |  |  |
| B3-25 | 0 | 1 | — | * ⌬ * | ⌬* | 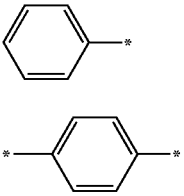 |  |  | 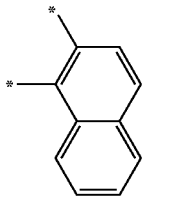 |
| B3-26 | 0 | 1 | — | * ⌬ * | ⌬* |  |  |  |  |

-continued
[Compound Group 3]
| | m | n | L₁ | L₂ | Ar₁ | Ar₂ | Ar₃ | Ar₄ | 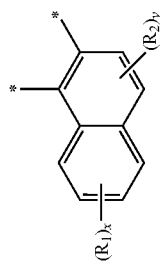 |
|---|---|---|---|---|---|---|---|---|---|
| B3-27 | 0 | 1 | — | 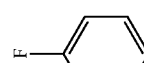 | 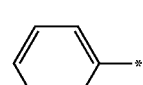 | 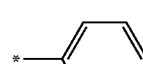 | 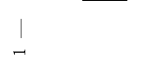 | 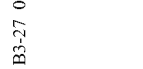 | 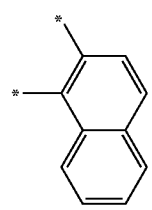 |
| B3-28 | 0 | 1 | — |  | 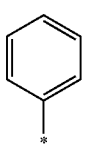 | 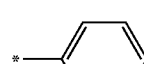 |  |  | 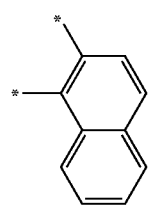 |
| B3-29 | 0 | 1 | — |  | 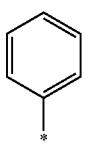 |  |  |  | 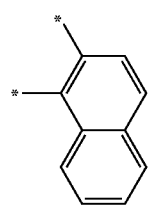 |

-continued
[Compound Group 3]
| | m | n | L₁ | L₂ | Ar₁ | Ar₂ | Ar₃ | Ar₄ |  |
|---|---|---|---|---|---|---|---|---|---|
| B3-30 | 0 | 1 | — |  |  |  |  |  | 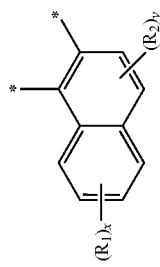 |
| C3-1 | 0 | 1 | — |  |  |  |  |  | 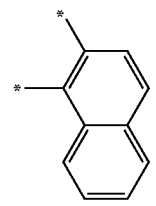 |
| C3-2 | 0 | 1 | — |  | 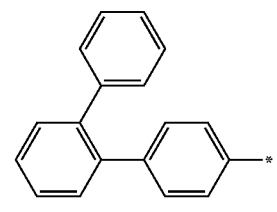 |  |  | 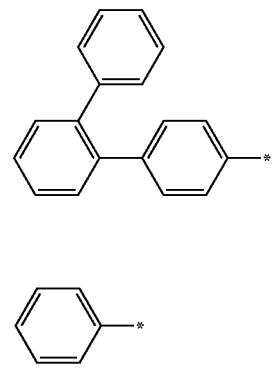 | 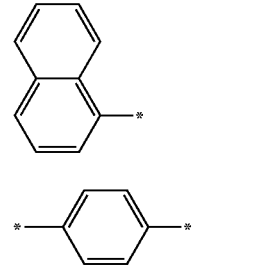 |

-continued
[Compound Group 3]
| | m | n | L₁ | L₂ | Ar₁ | Ar₂ | Ar₃ | Ar₄ | 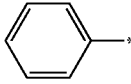 |
|---|---|---|---|---|---|---|---|---|---|
| C3-3 | 0 | 1 | — | 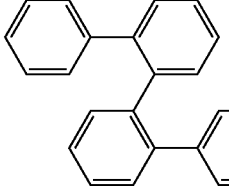 | 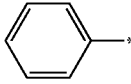 | 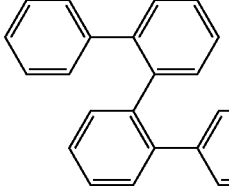 | 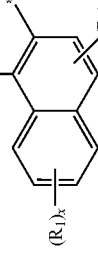 | 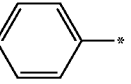 | 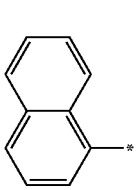 |
| C3-4 | 0 | 1 | — | 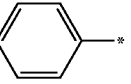 |  |  |  |  |  |
| C3-5 | 0 | 1 | — |  | | | | |  |

-continued
[Compound Group 3]
| | m | n | L₁ | L₂ | Ar₁ | Ar₂ | Ar₃ | Ar₄ | |
|---|---|---|---|---|---|---|---|---|---|
| C3-6 | 0 | 1 | — | 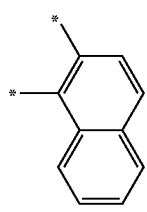 | 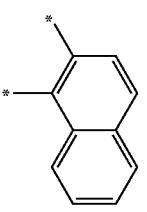 | 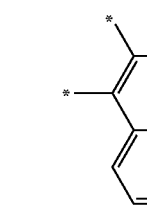 | 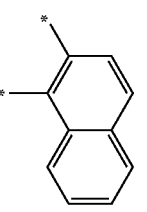 | 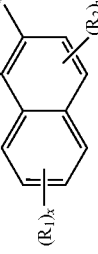 | 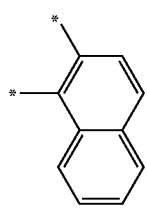 |
| C3-7 | 0 | 1 | — | 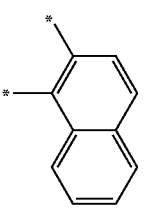 | 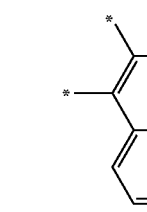 | 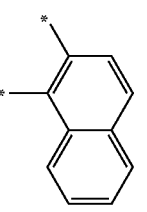 | 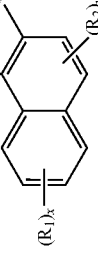 | 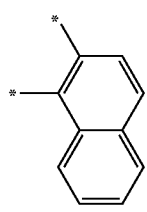 | 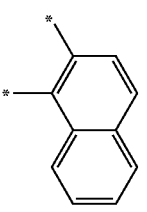 |
| C3-8 | 0 | 1 | — | 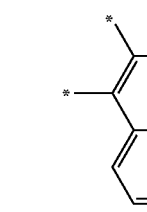 | 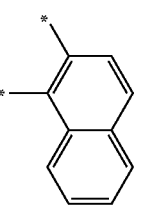 | 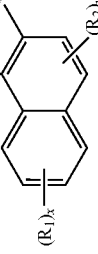 | | | |

-continued

[Compound Group 3]

-continued
[Compound Group 3]
| | m | n | L₁ | L₂ | Ar₁ | Ar₂ | Ar₃ | Ar₄ | 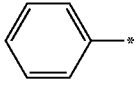 |
|---|---|---|---|---|---|---|---|---|---|
| C3-12 | 0 | 1 | — | 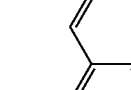 |  |  | 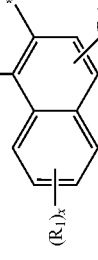 |  | 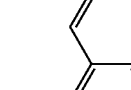 |
| C3-13 | 0 | 1 | — |  |  |  |  |  |  |
| C3-14 | 0 | 1 | — |  |  |  |  |  |  |

-continued
[Compound Group 3]
| | m | n | L₁ | L₂ | Ar₁ | Ar₂ | Ar₃ | Ar₄ | |
|---|---|---|---|---|---|---|---|---|---|
| C3-15 | 0 | 1 | — | 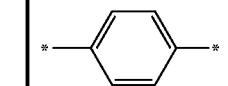 | 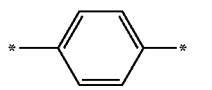 | 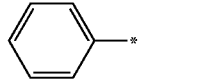 | 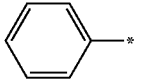 | 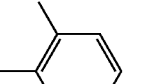 | 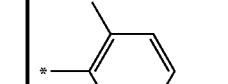 |
| C3-16 | 0 | 1 | — | 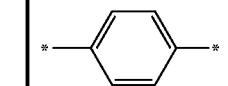 | 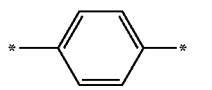 | 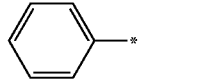 | 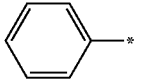 | 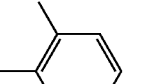 | 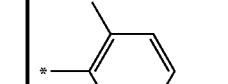 |
| C3-17 | 0 | 1 | — | 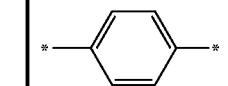 | 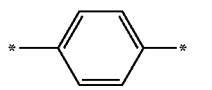 | 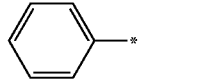 | 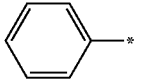 | 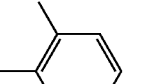 | 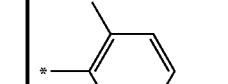 |

-continued

[Compound Group 3]

| | m | n | L₁ | L₂ | Ar₁ | Ar₂ | Ar₃ | Ar₄ | (structure) |
|---|---|---|---|---|---|---|---|---|---|
| C3-18 | 0 | 1 | — | *–⟨phenylene⟩–* | 1-naphthyl | dibenzothiophene | phenyl | dibenzothiophene | 1,2-naphthyl |
| C3-19 | 0 | 1 | — | *–⟨phenylene⟩–* | 1-naphthyl | dibenzothiophene | phenyl | dibenzothiophene | 1,2-naphthyl |
| C3-20 | 0 | 1 | — | *–⟨phenylene⟩–* | 1-naphthyl | dibenzothiophene | phenyl | dibenzothiophene | 1,2-naphthyl |

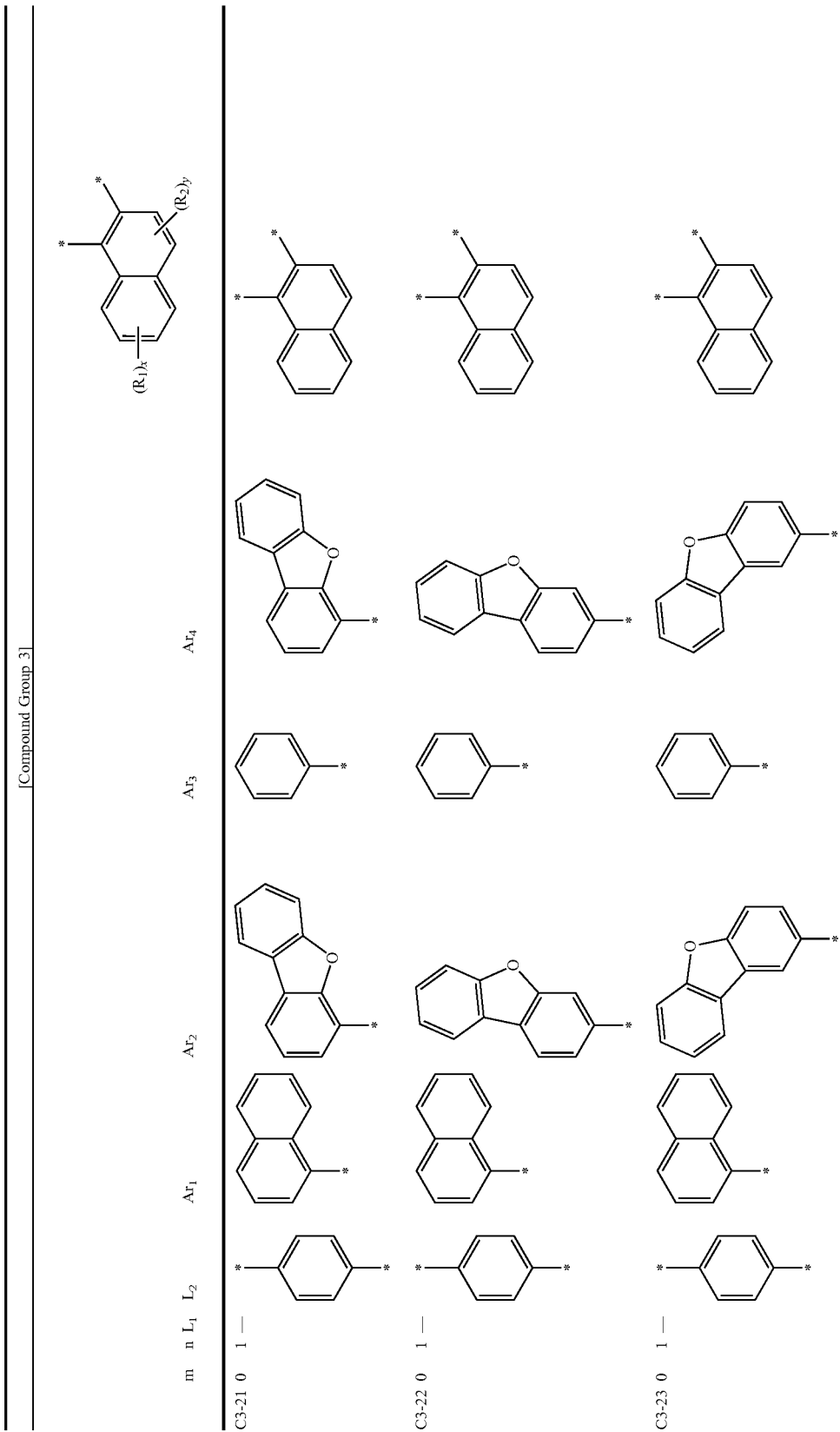

-continued
[Compound Group 3]
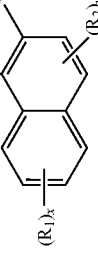

-continued
[Compound Group 3]
| | m | n | $L_1$ | $L_2$ | $Ar_1$ | $Ar_2$ | $Ar_3$ | $Ar_4$ | |
|---|---|---|---|---|---|---|---|---|---|
| C3-27 | 0 | 1 | — | 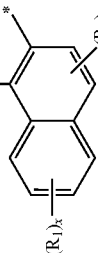 | 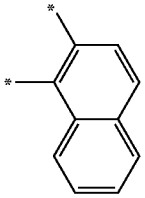 | 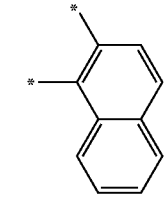 | 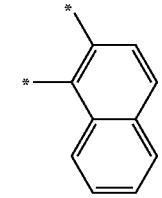 | 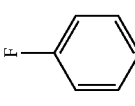 | 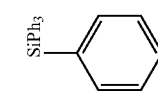 |
| C3-28 | 0 | 1 | — | 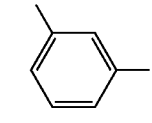 | 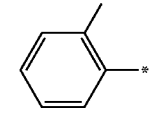 |  | 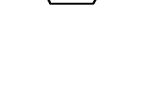 | 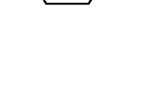 | 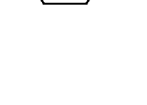 |
| C3-29 | 0 | 1 | — | 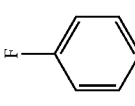 | 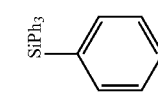 | 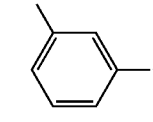 | 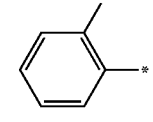 | | |
| C3-30 | 0 | 1 | — | | | | | | |

-continued
[Compound Group 3]
| | m | n | L₁ | L₂ | Ar₁ | Ar₂ | Ar₃ | Ar₄ | |
|---|---|---|---|---|---|---|---|---|---|
| D3-1 | 0 | 1 | — | 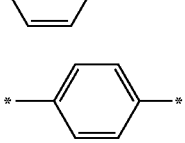 | 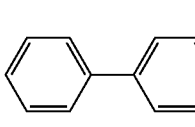 | 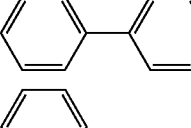 | 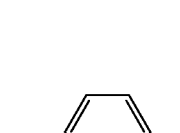 | 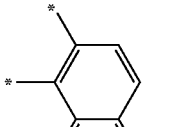 |  |
| D3-2 | 0 | 1 | — | 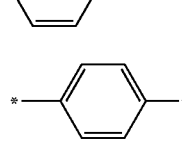 | 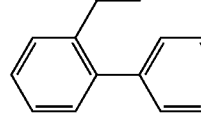 | 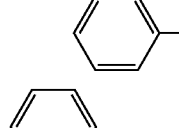 | 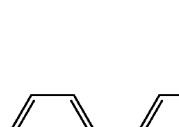 | 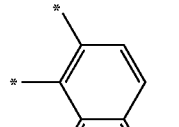 |  |

-continued
[Compound Group 3]
| | m | n | L₁ | L₂ | Ar₁ | Ar₂ | Ar₃ | Ar₄ | 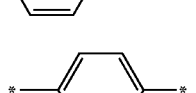 |
|---|---|---|---|---|---|---|---|---|---|
| D3-3 | 0 | 1 | — | 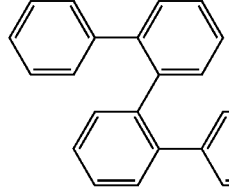 | 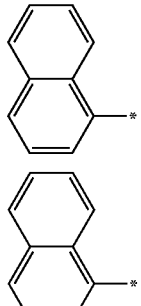 | 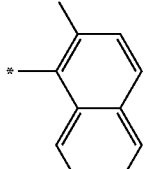 | 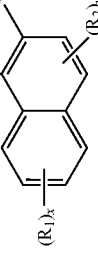 |  | 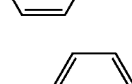 |
| D3-4 | 0 | 1 | — | 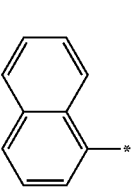 | 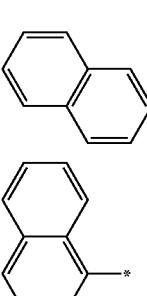 | 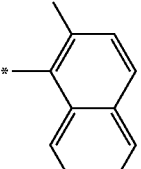 |  |  | 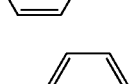 |
| D3-5 | 0 | 1 | — | 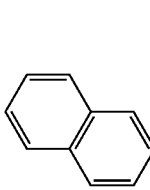 | 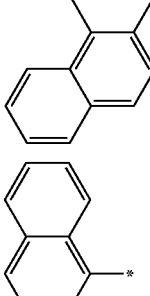 | 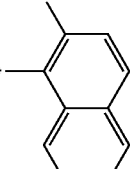 |  |  | |

-continued
[Compound Group 3]
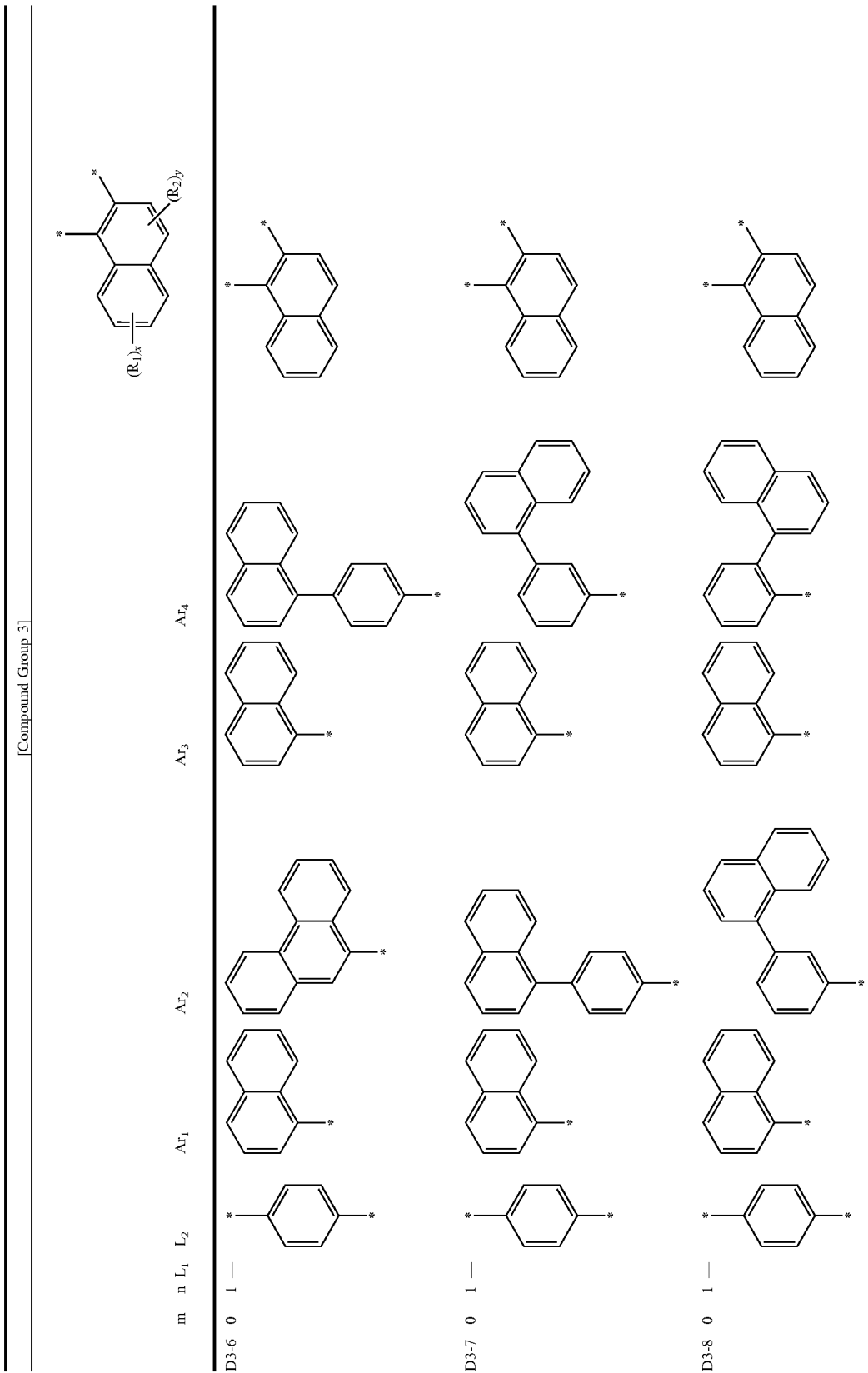

-continued
[Compound Group 3]
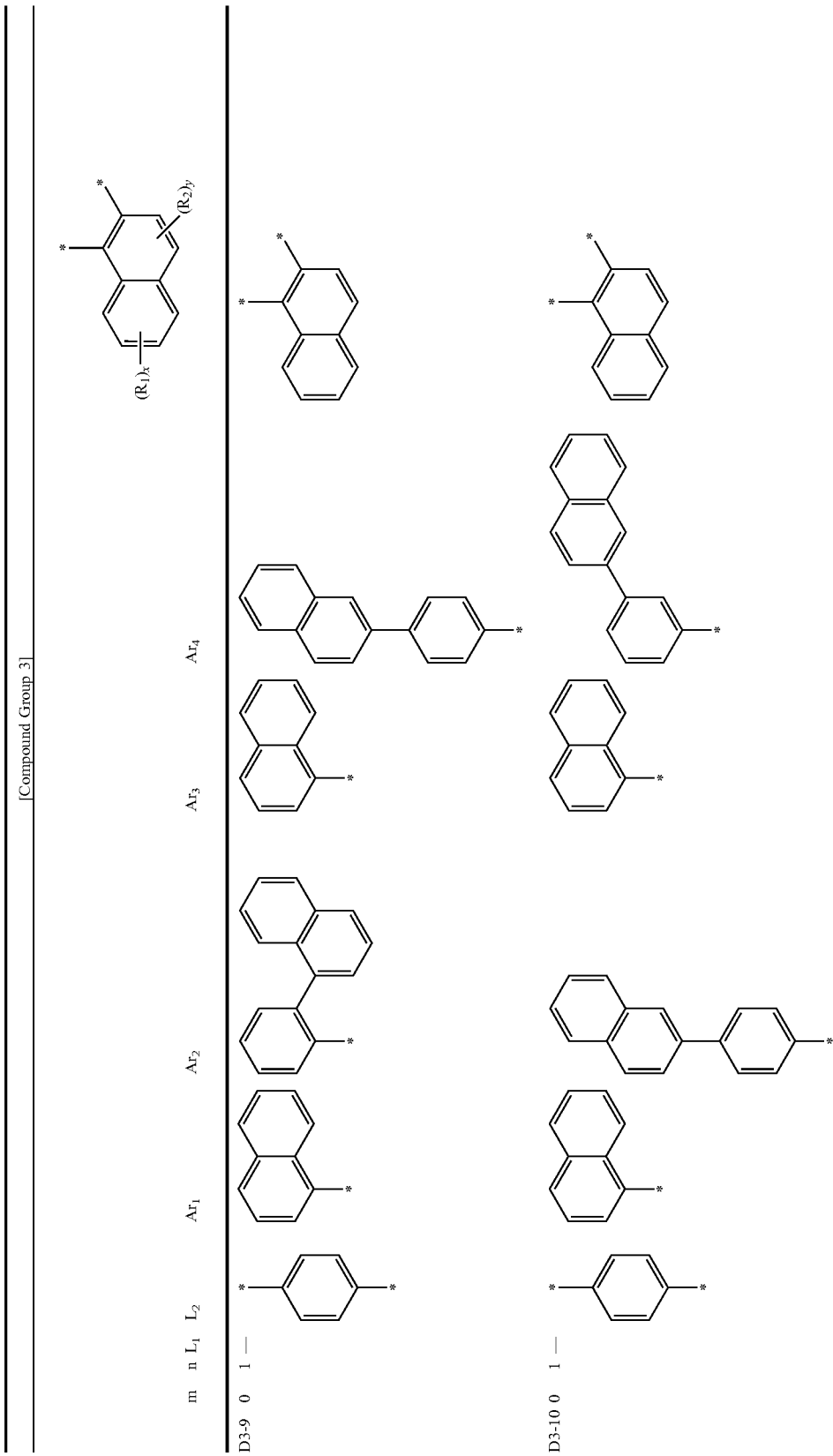

-continued
[Compound Group 3]
| | m | n | L₁ | L₂ | Ar₁ | Ar₂ | Ar₃ | Ar₄ | |
|---|---|---|---|---|---|---|---|---|---|
| D3-11 | 0 | 1 | — | 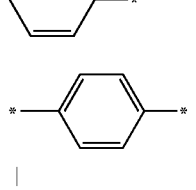 | 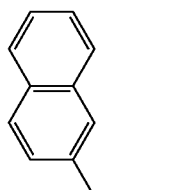 | 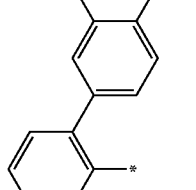 | 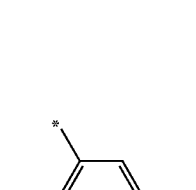 | 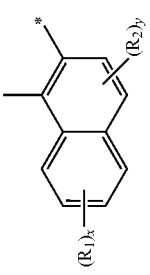 | 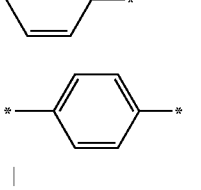 |
| D3-12 | 0 | 1 | — | 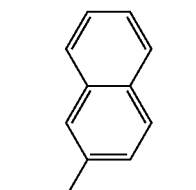 | 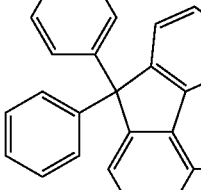 | 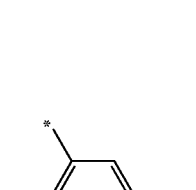 | 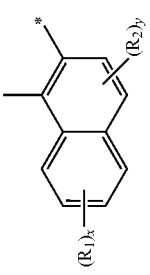 | 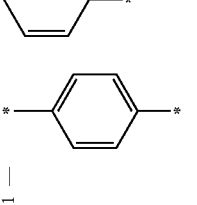 | 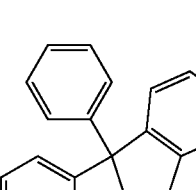 |
| D3-13 | 0 | 1 | — | 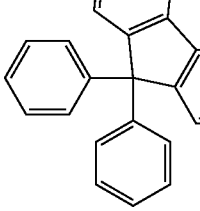 | 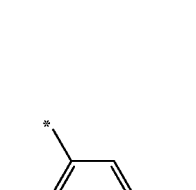 | 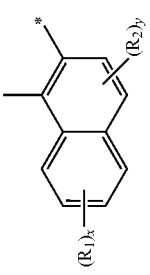 | | | |

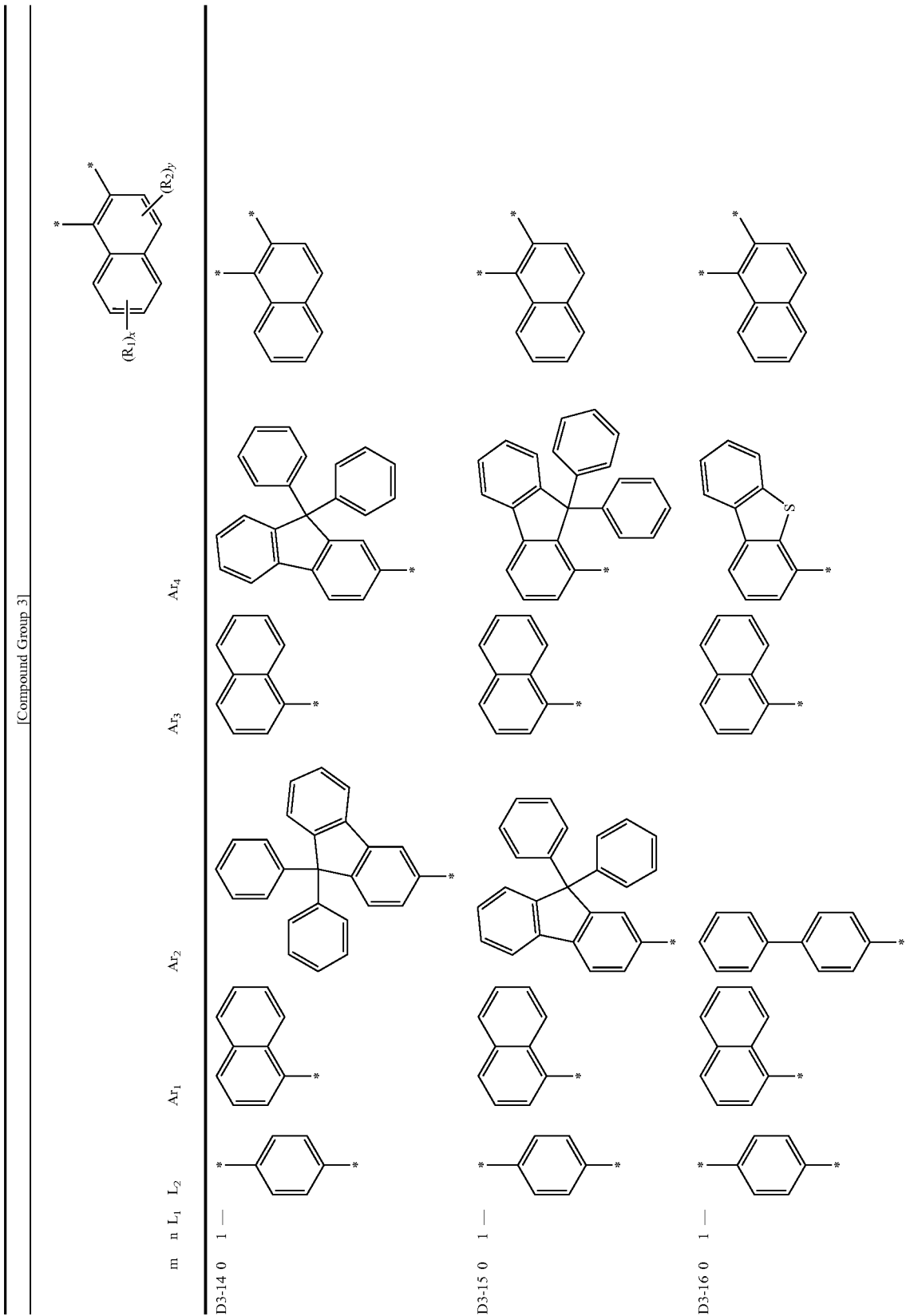

[Compound Group 3]
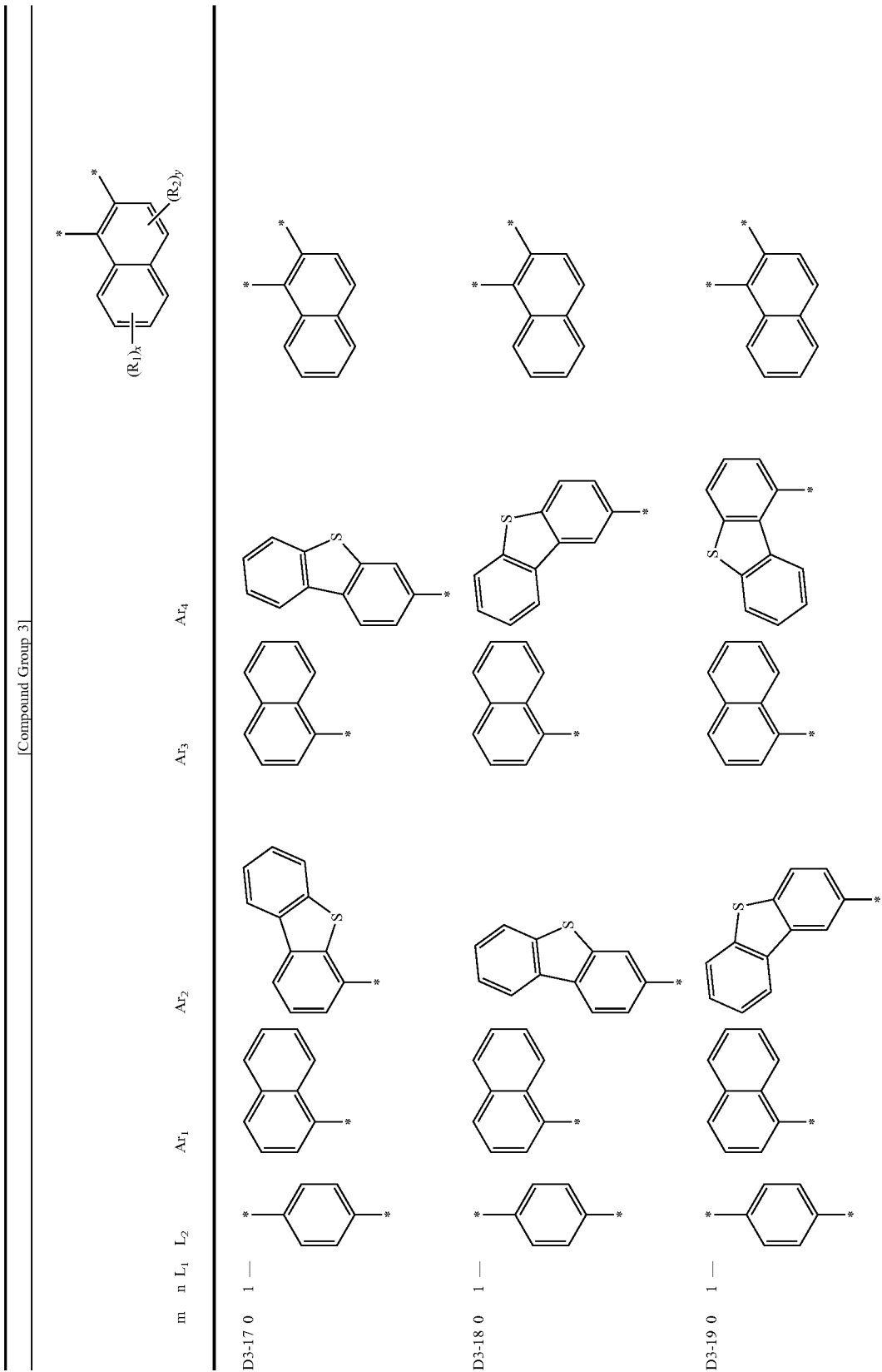

-continued
[Compound Group 3]
| | m | n | L₁ | L₂ | Ar₁ | Ar₂ | Ar₃ | Ar₄ | (R₁)ₓ / (R₂)ᵧ |
|---|---|---|---|---|---|---|---|---|---|
| D3-20 | 0 | 1 | — | 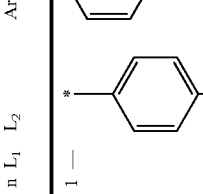 | 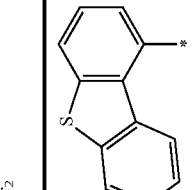 | 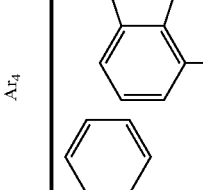 |  | 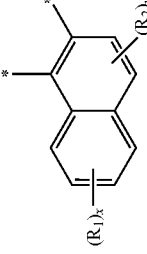 | 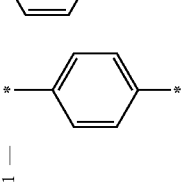 |
| D3-21 | 0 | 1 | — | 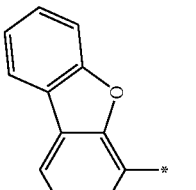 | 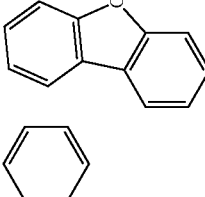 |  | 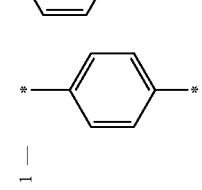 | 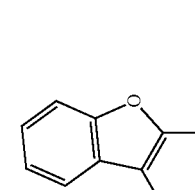 | 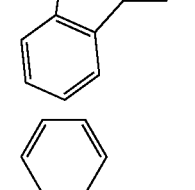 |
| D3-22 | 0 | 1 | — |  |  |  | | | |

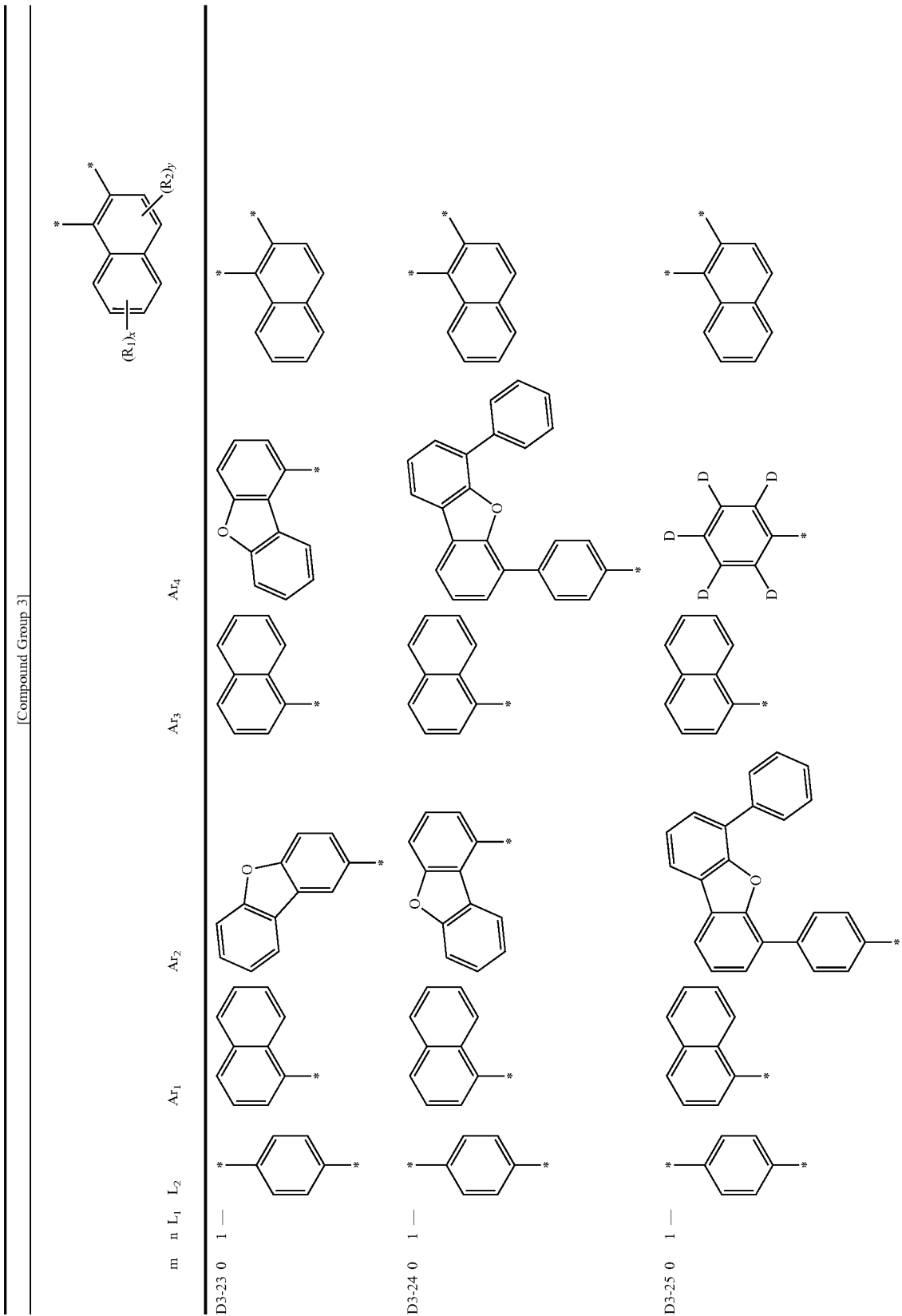

-continued
[Compound Group 3]
| | m | n | L₁ | L₂ | Ar₁ | Ar₂ | Ar₃ | Ar₄ | (R₁)ₓ / (R₂)ᵧ naphthyl |
|---|---|---|---|---|---|---|---|---|---|
| D3-26 | 0 | 1 | — | 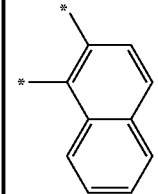 | 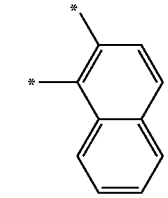 | 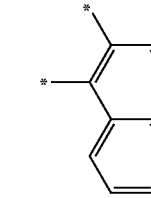 | 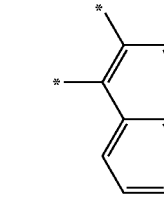 | 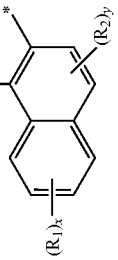 |  |
| D3-27 | 0 | 1 | — | 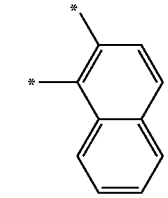 | 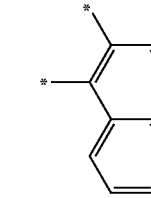 | 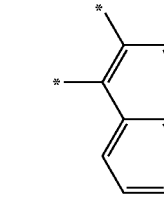 | 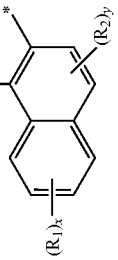 | 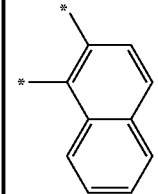 |  |
| D3-28 | 0 | 1 | — | 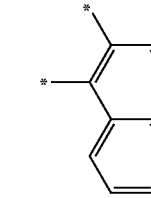 | 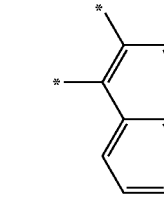 | 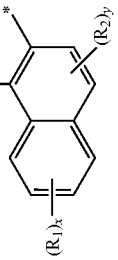 | 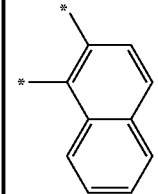 | 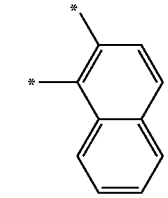 |  |
| D3-29 | 0 | 1 | — | 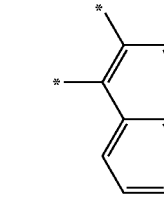 | 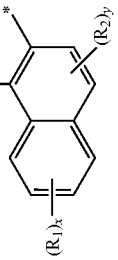 | 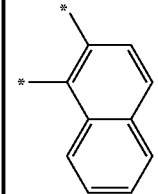 | 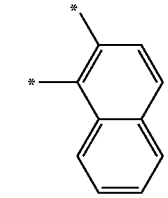 | 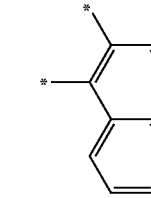 |  |

-continued

[Compound Group 3]

| | m | n | L₁ | L₂ | Ar₁ | Ar₂ | Ar₃ | Ar₄ | |
|---|---|---|---|---|---|---|---|---|---|
| D3-30 | 0 | 1 | — | | | | | | |
| E3-1 | 0 | 1 | — | | | | | | |
| E3-2 | 0 | 1 | — | | | | | | |

14. The organic electroluminescence device of claim 1, wherein the diamine compound represented by Formula 1 is at least one selected among compounds represented in Compound Group 4:

[Compound Group 4]
| | m | n | L₁ | L₂ | Ar₁ | Ar₂ | Ar₃ | Ar₄ | |
|---|---|---|---|---|---|---|---|---|---|
| A4-1 | 1 | 1 | 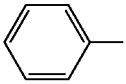 | 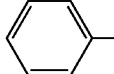 | 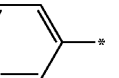 | 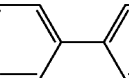 |  | 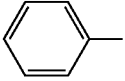 | 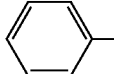 |
| A4-2 | 1 | 1 | 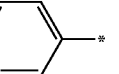 | 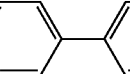 |  | 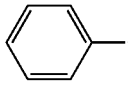 | 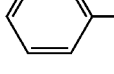 | 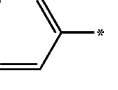 | 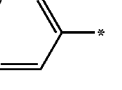 |
| A4-3 | 1 | 1 |  | 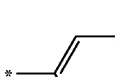 | 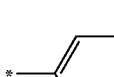 |  |  | 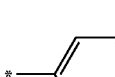 | 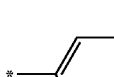 |

-continued
[Compound Group 4]
| | m | n | L₁ | L₂ | Ar₁ | Ar₂ | Ar₃ | Ar₄ | 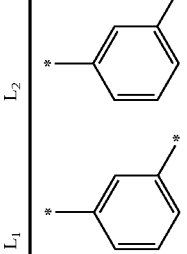 |
|---|---|---|---|---|---|---|---|---|---|
| A4-4 | 1 | 1 | | | | | | | |
| A4-5 | 1 | 1 | | | | | | | |
| A4-6 | 1 | 1 | | | | | | | |

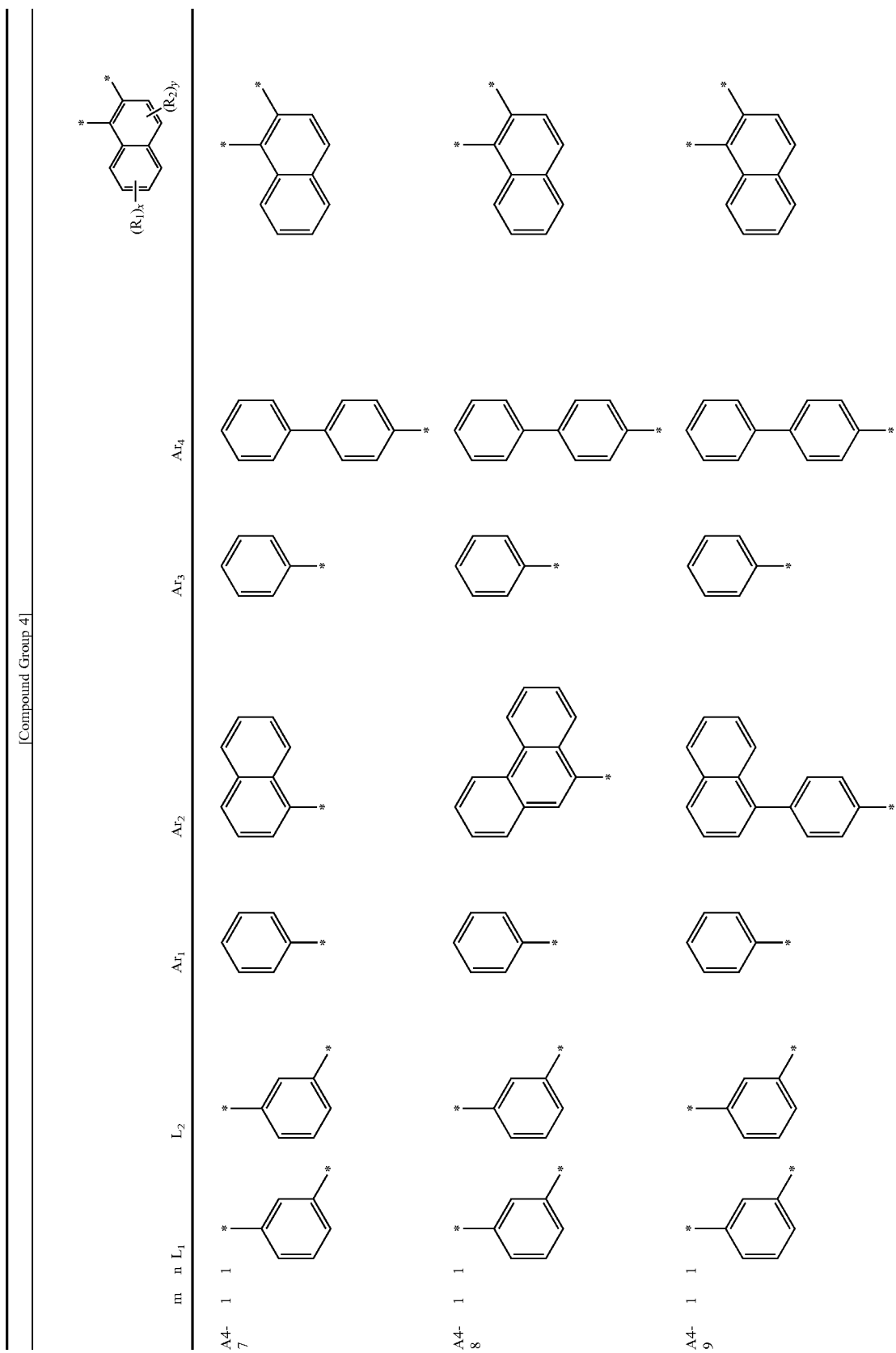

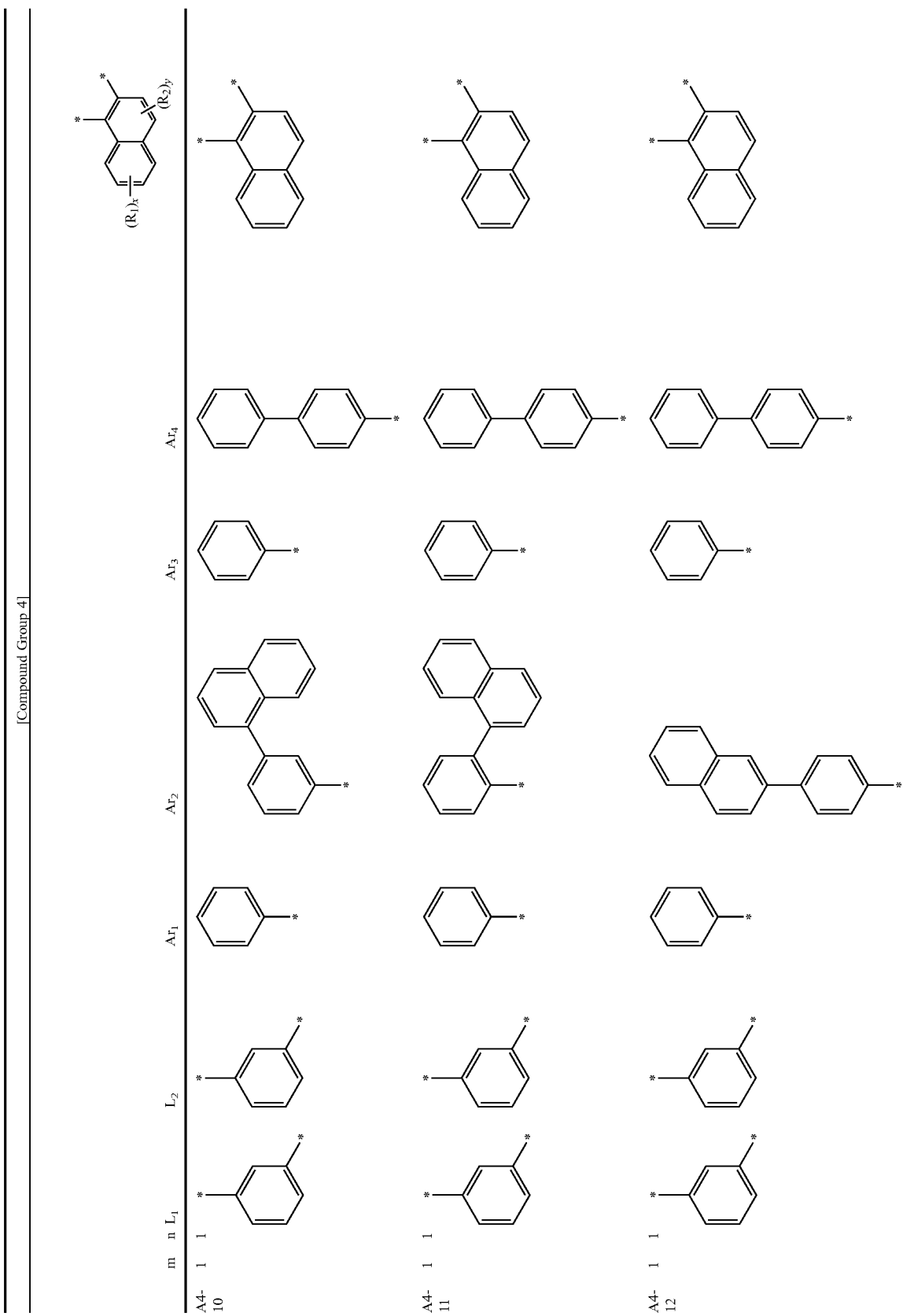

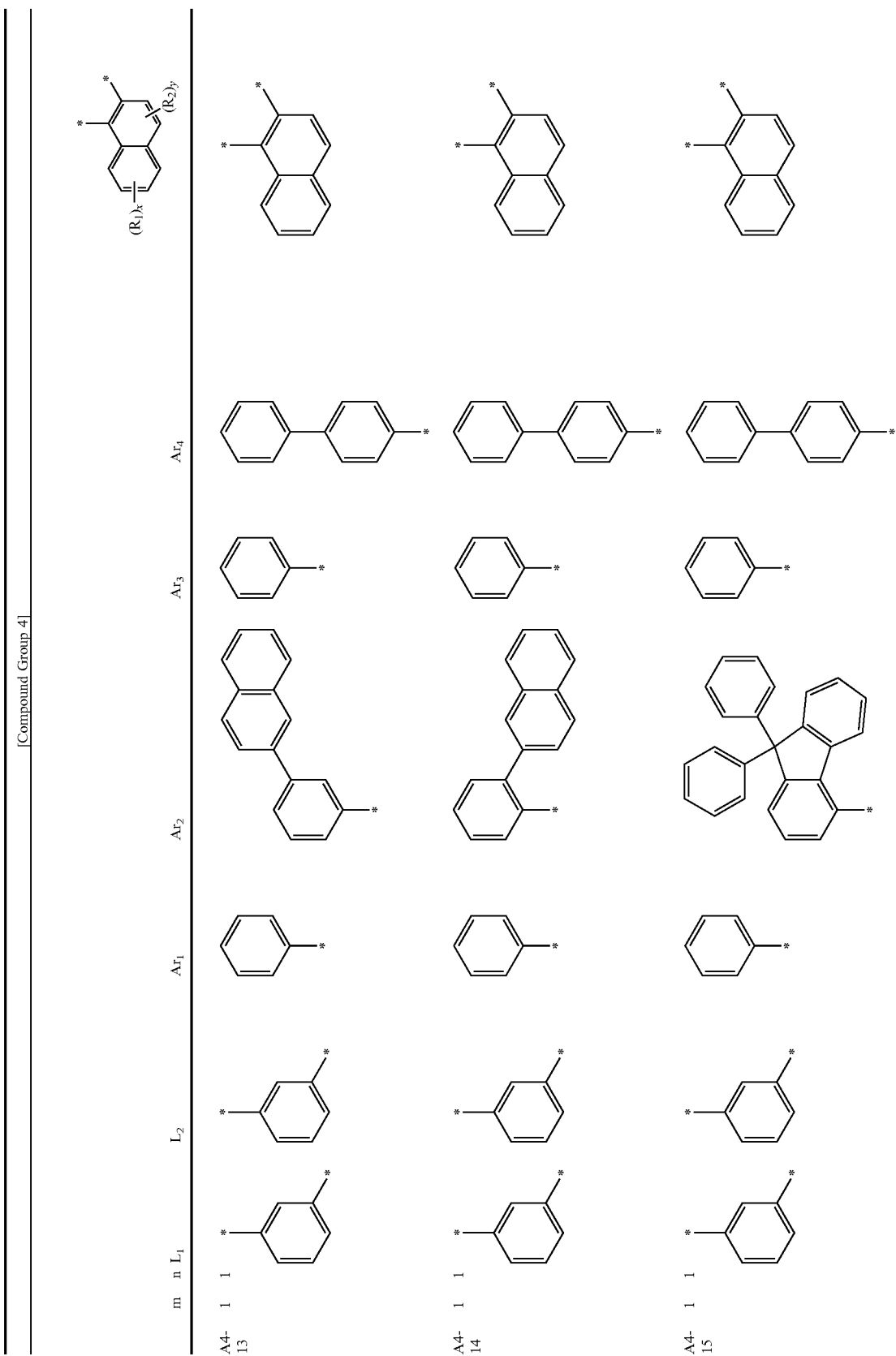

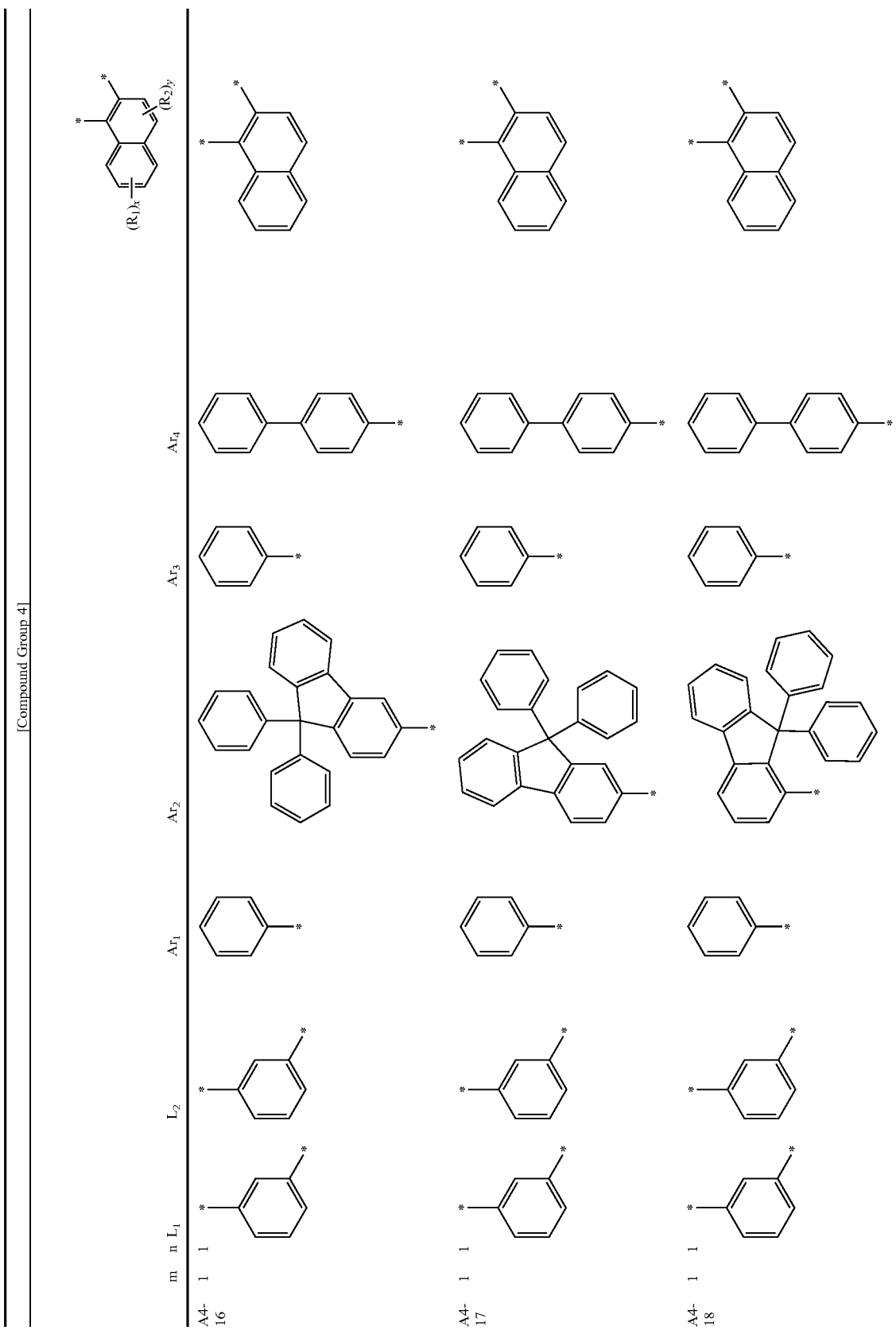

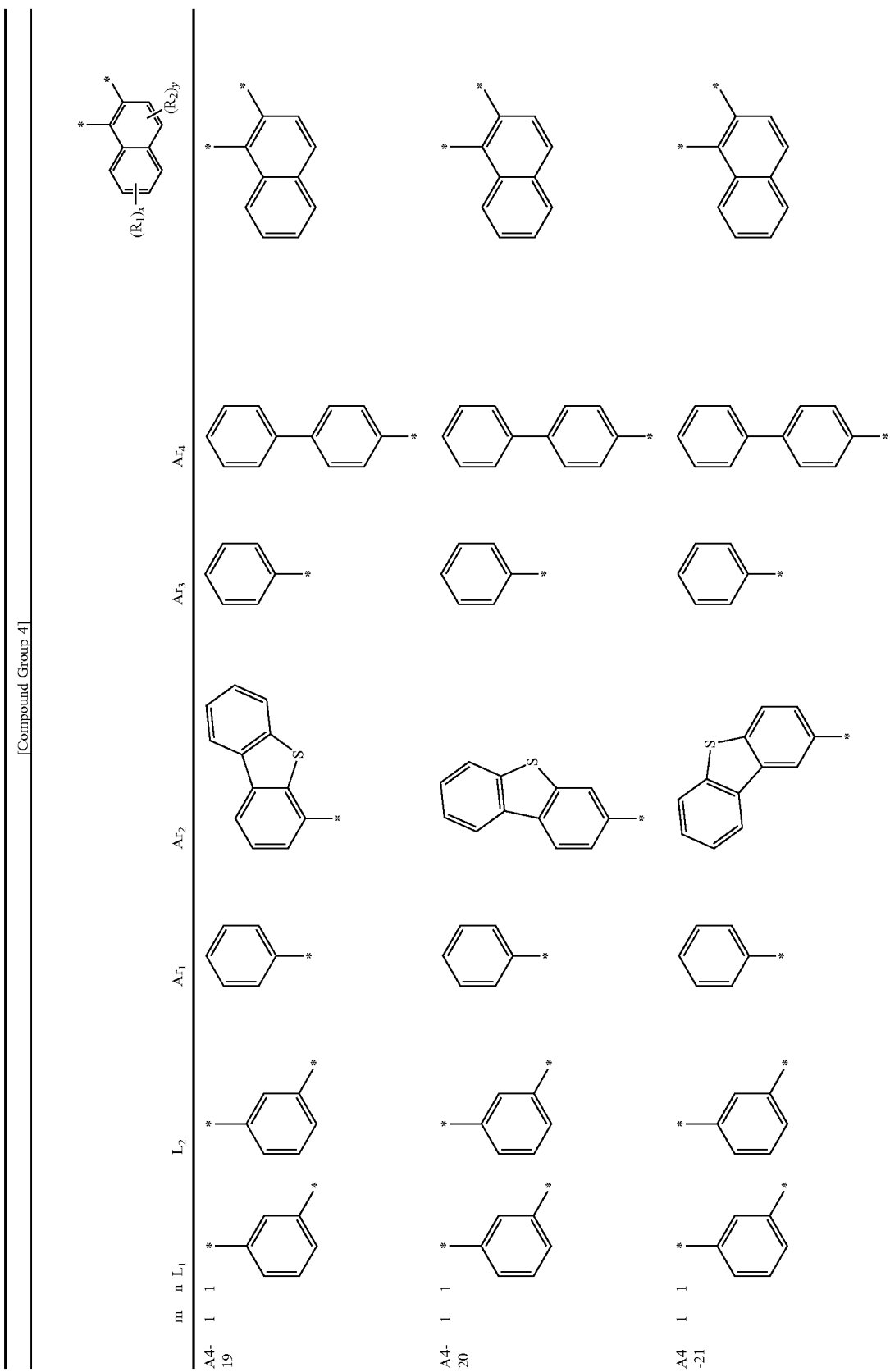

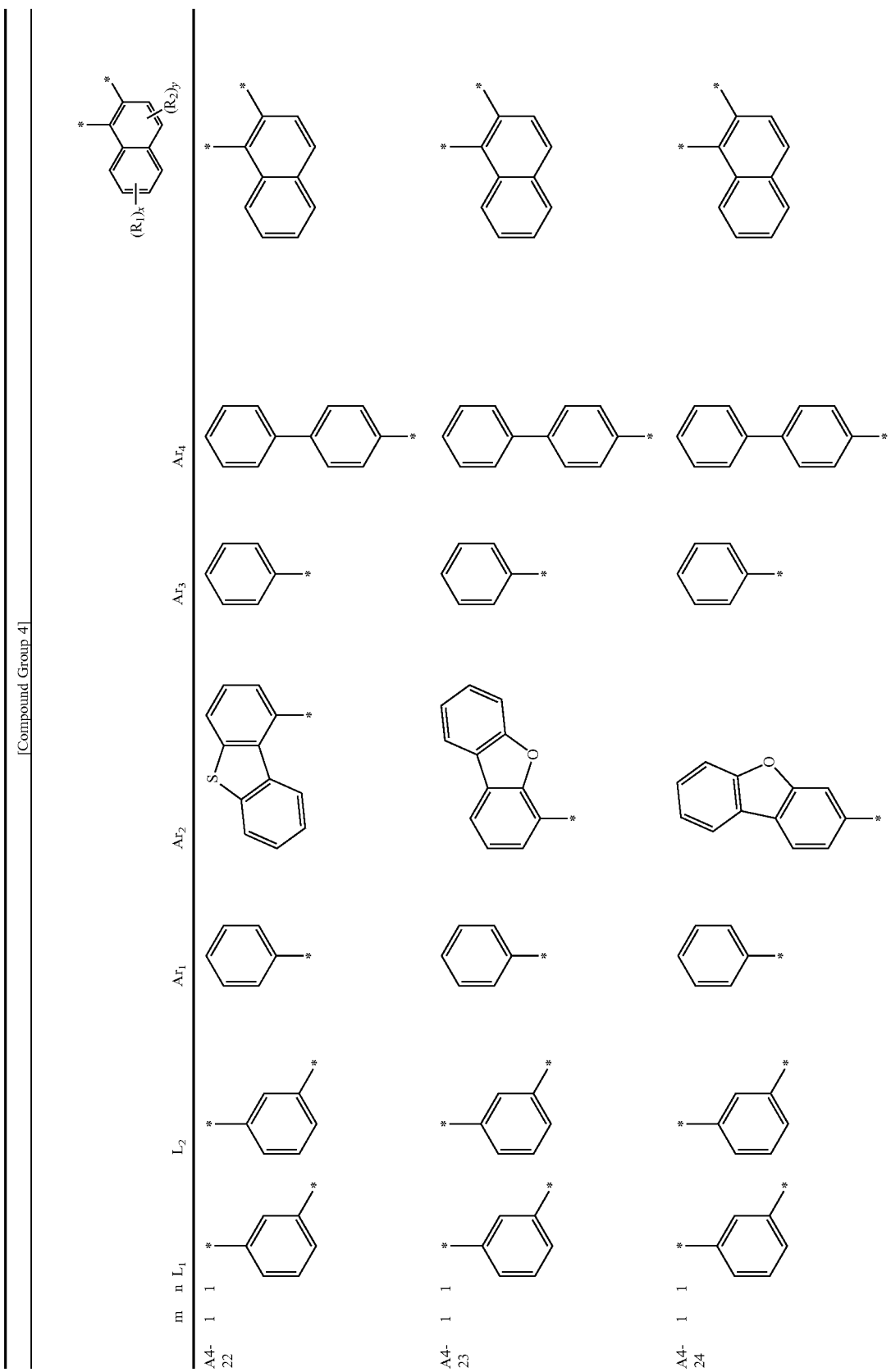

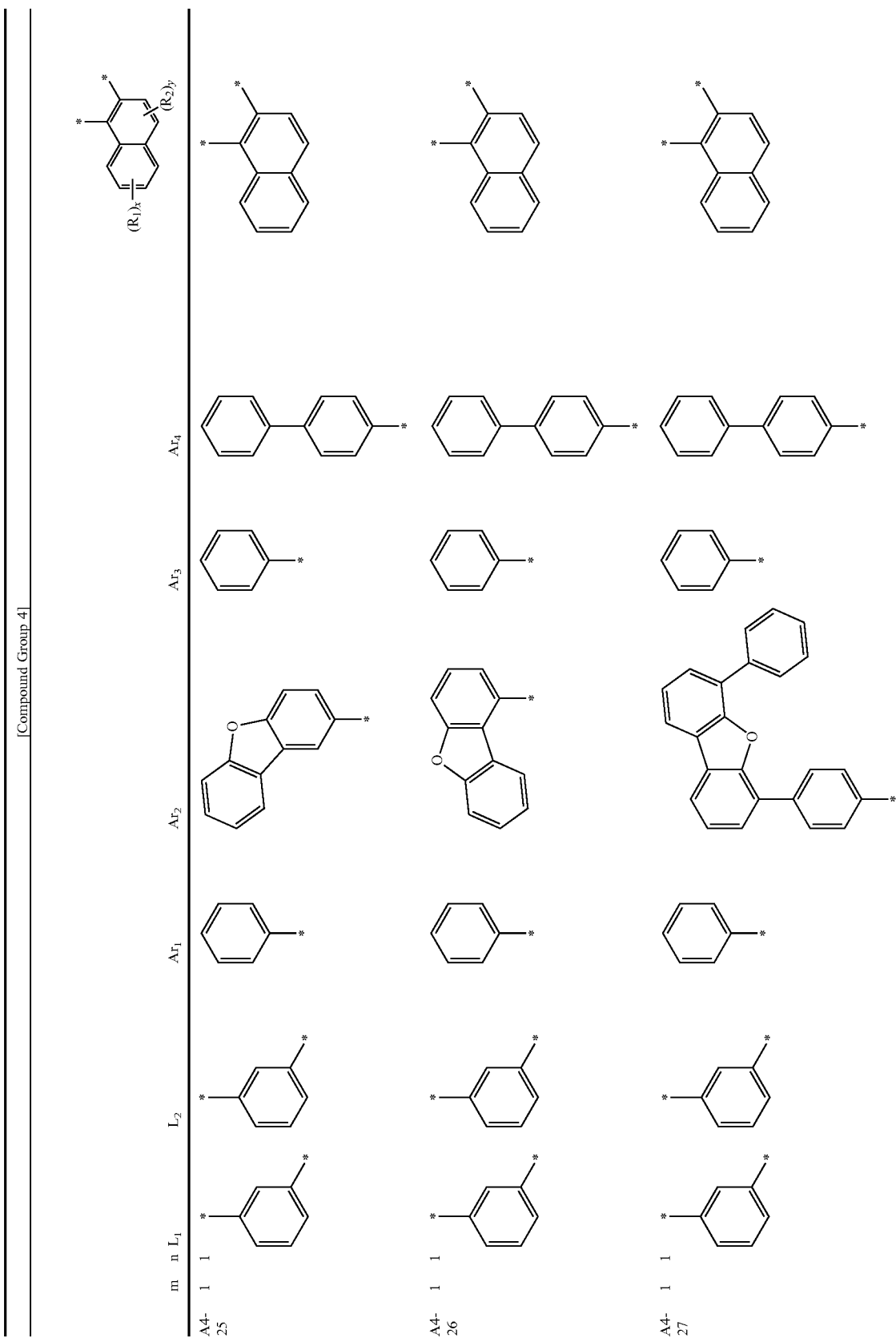

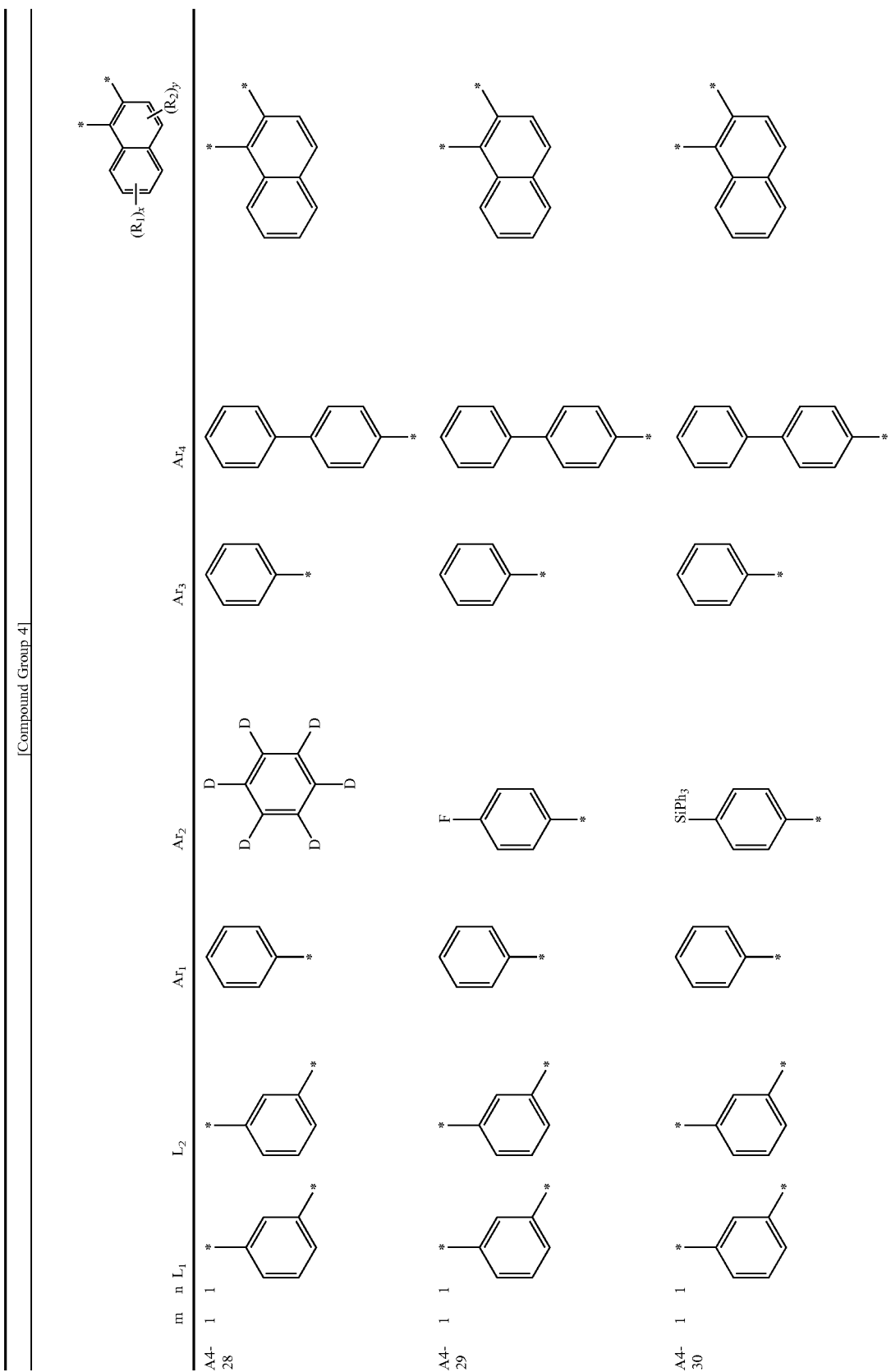

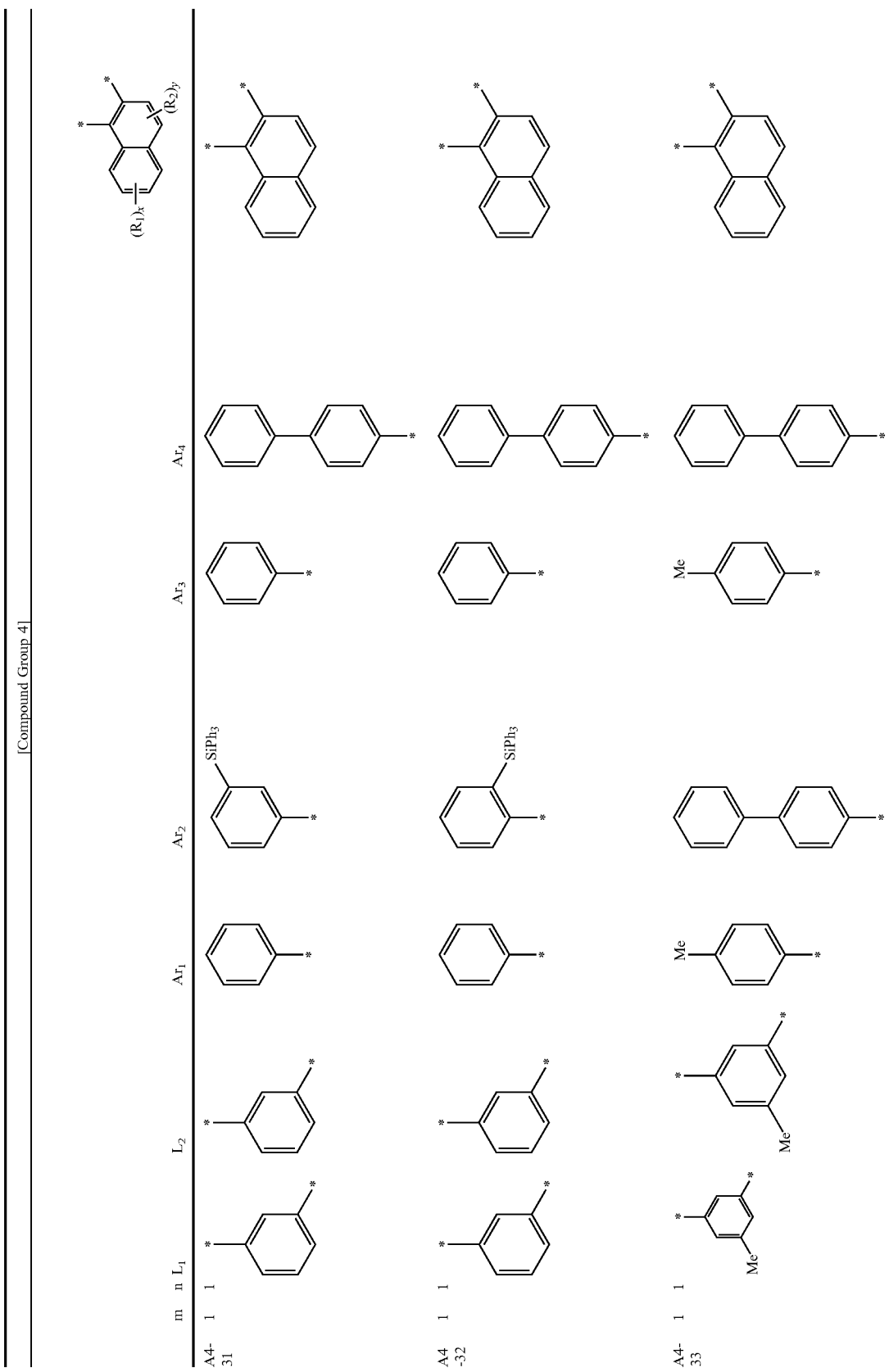

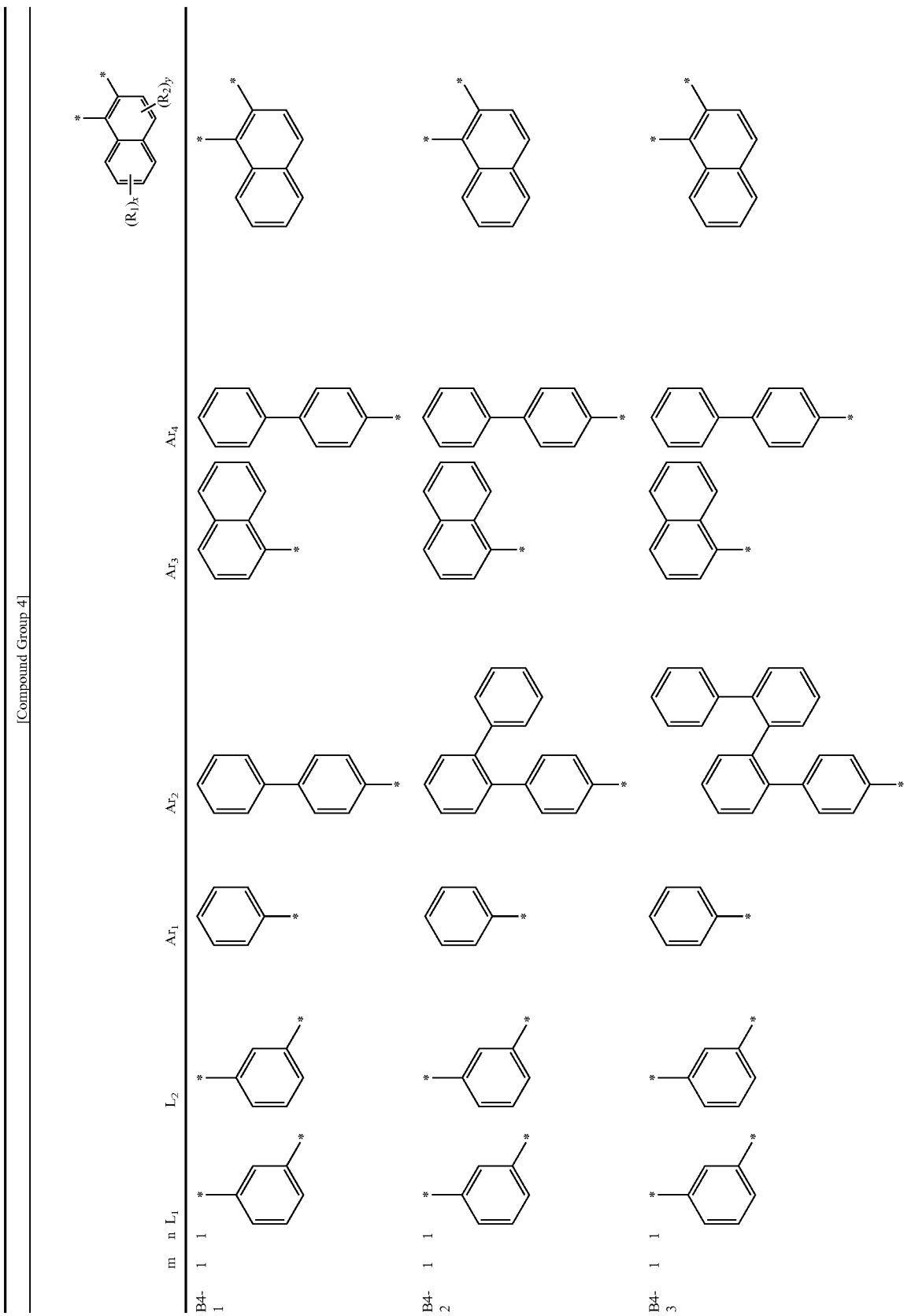

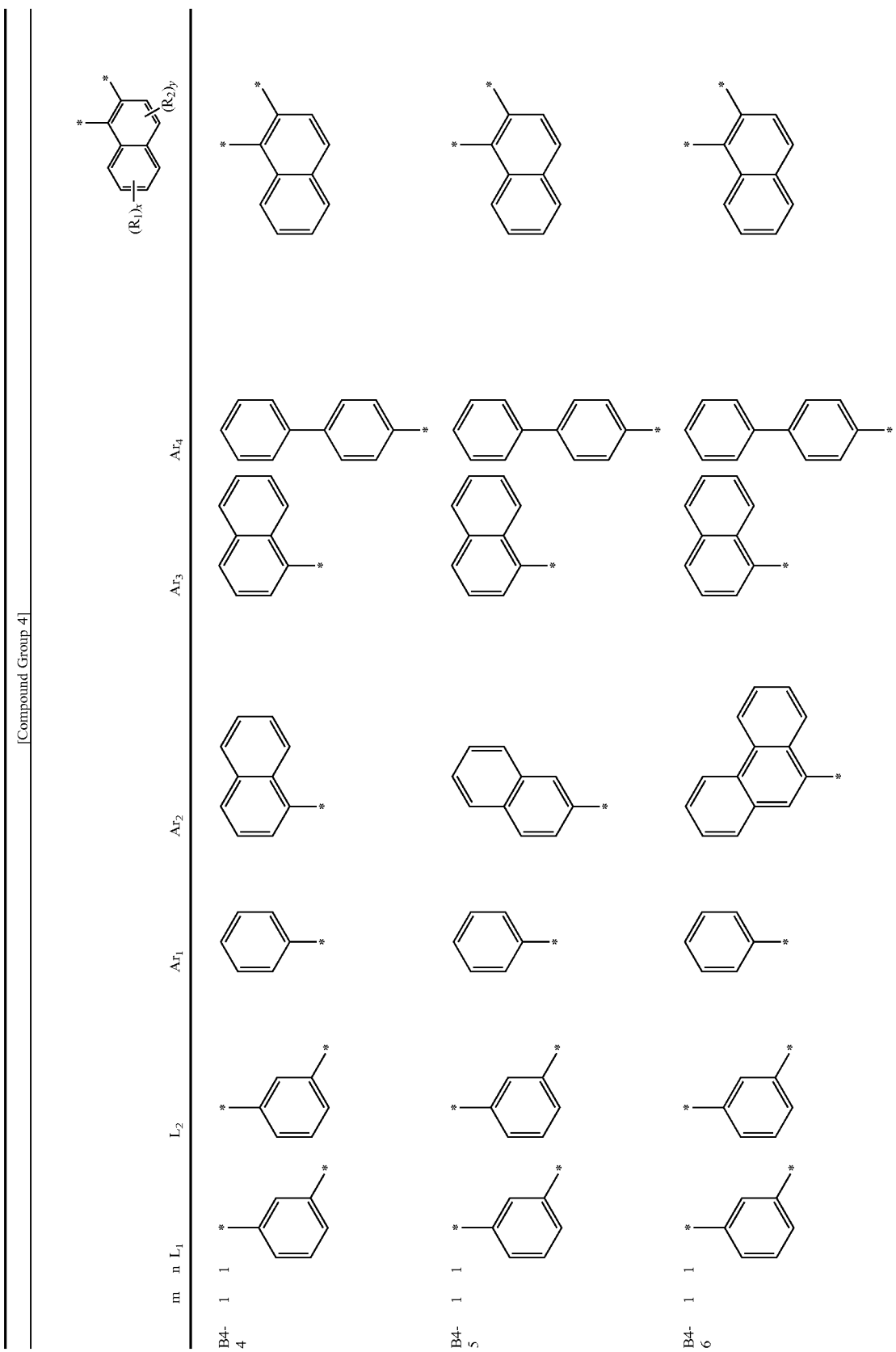

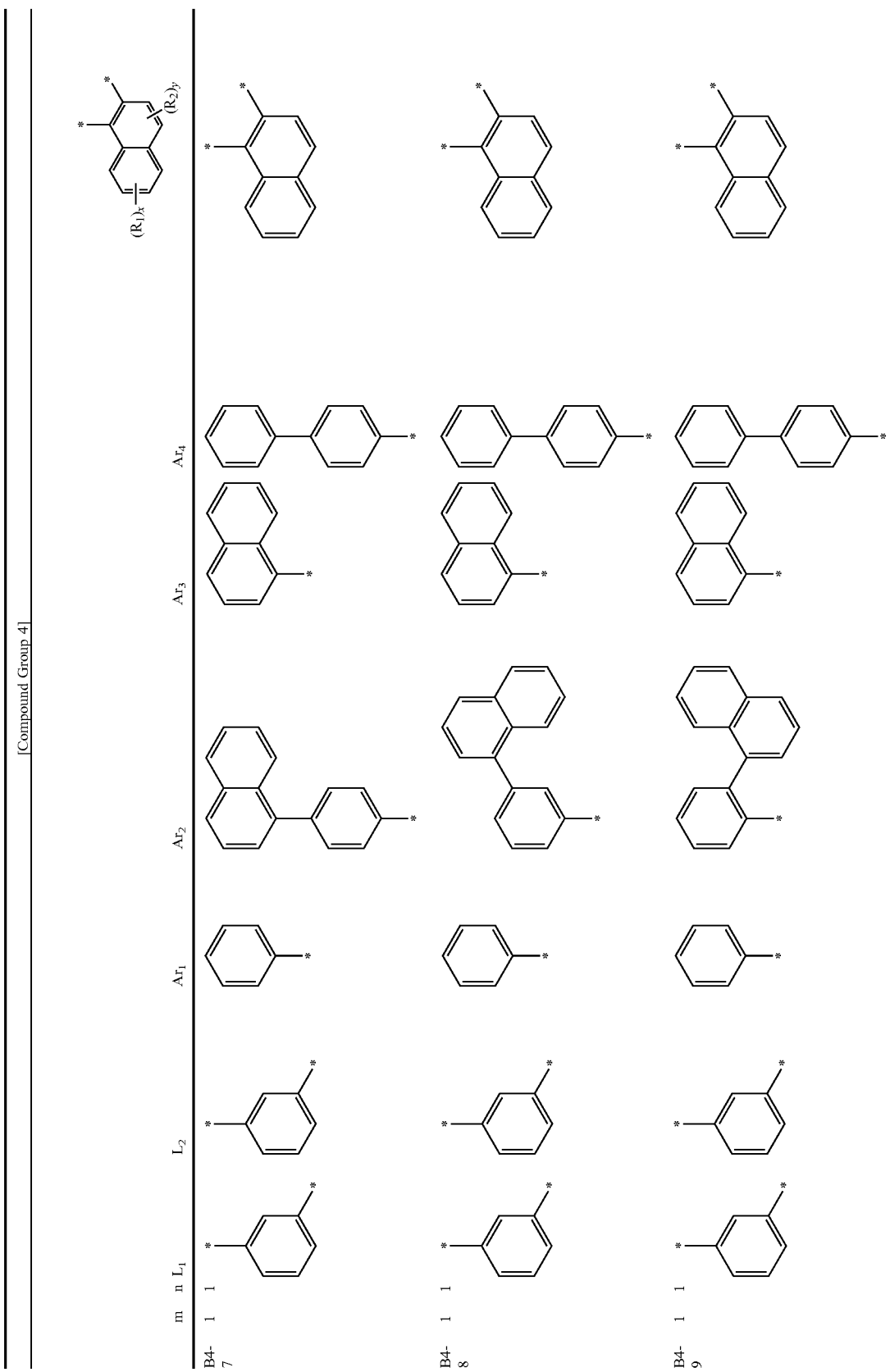

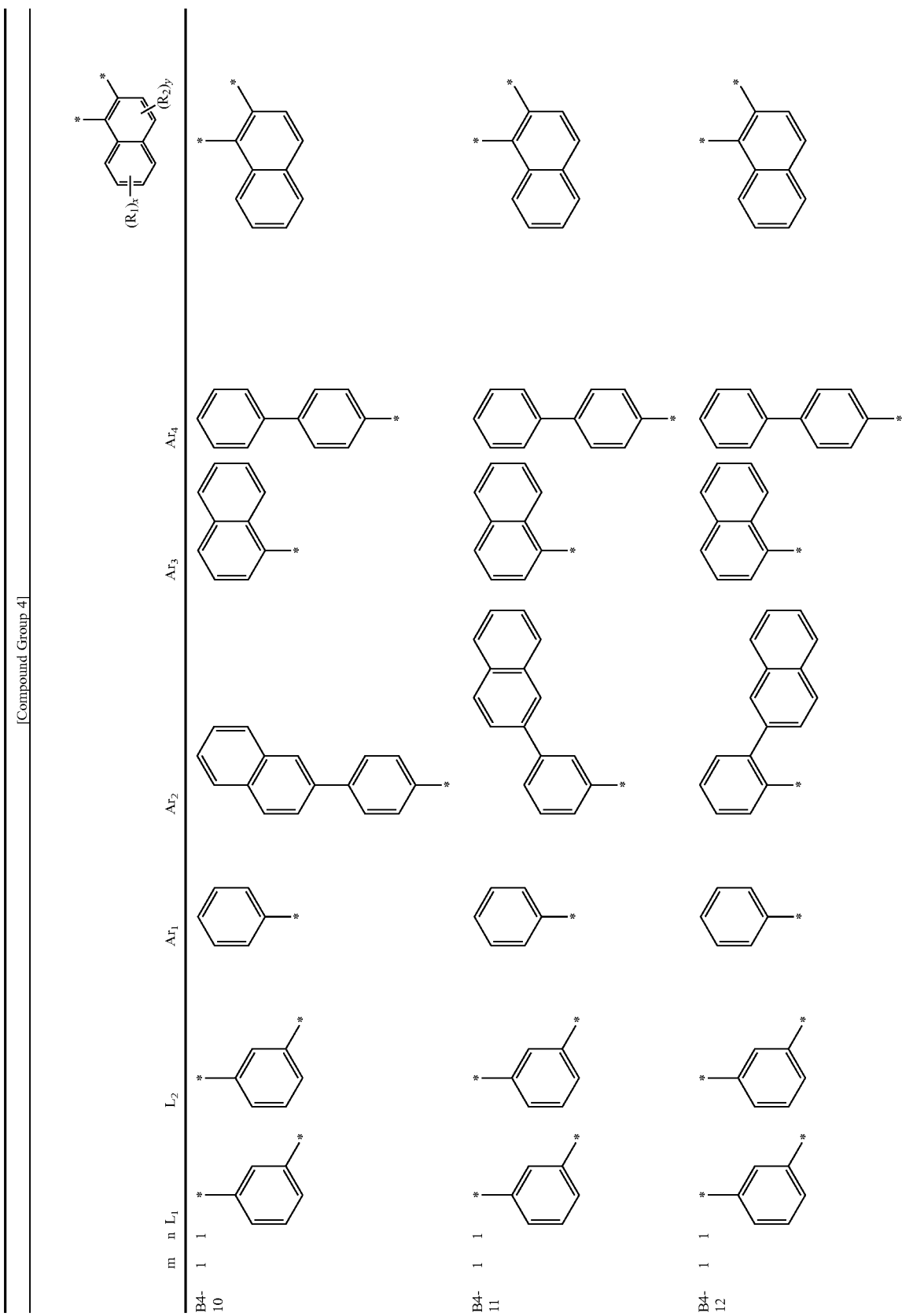

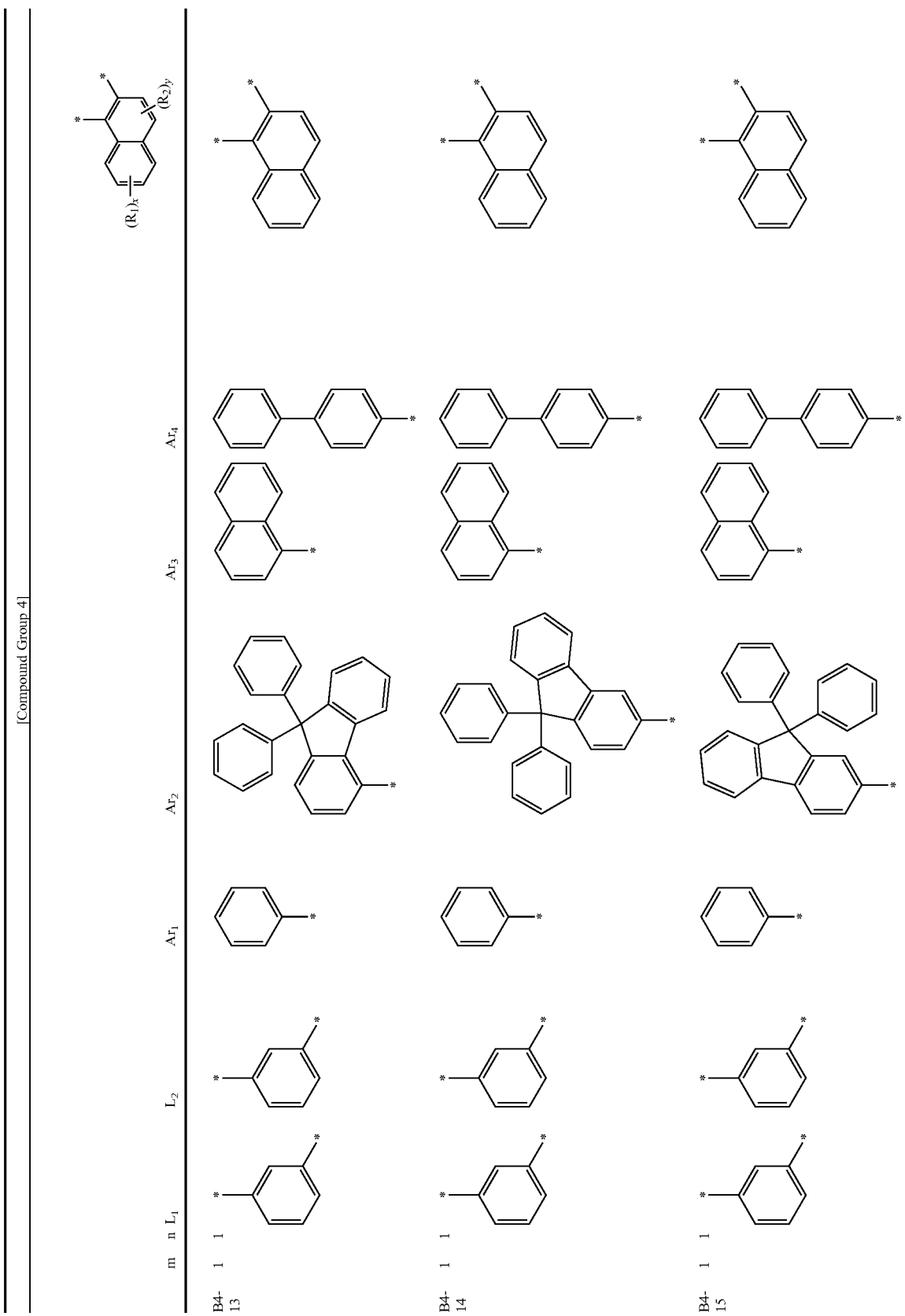

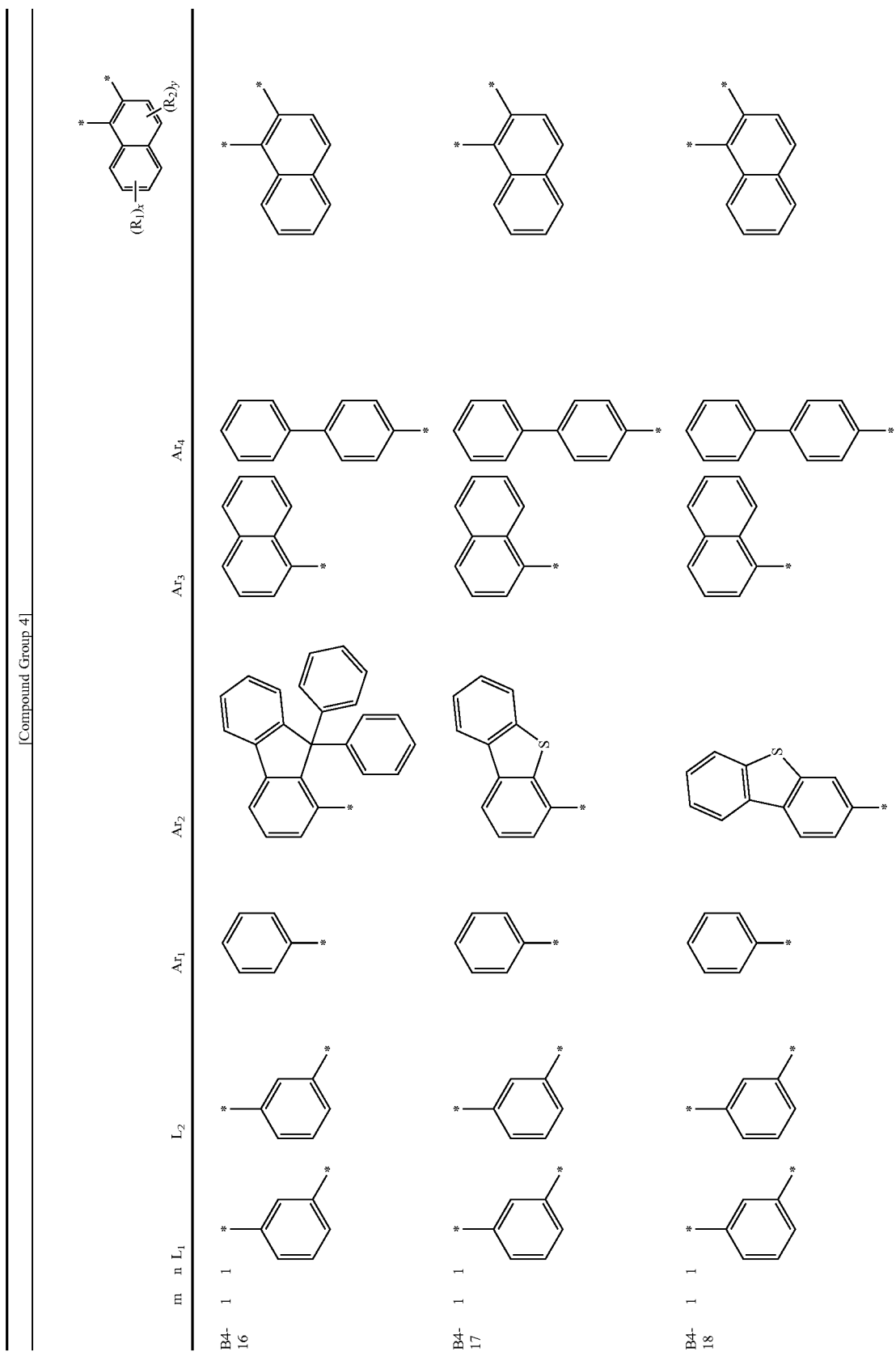

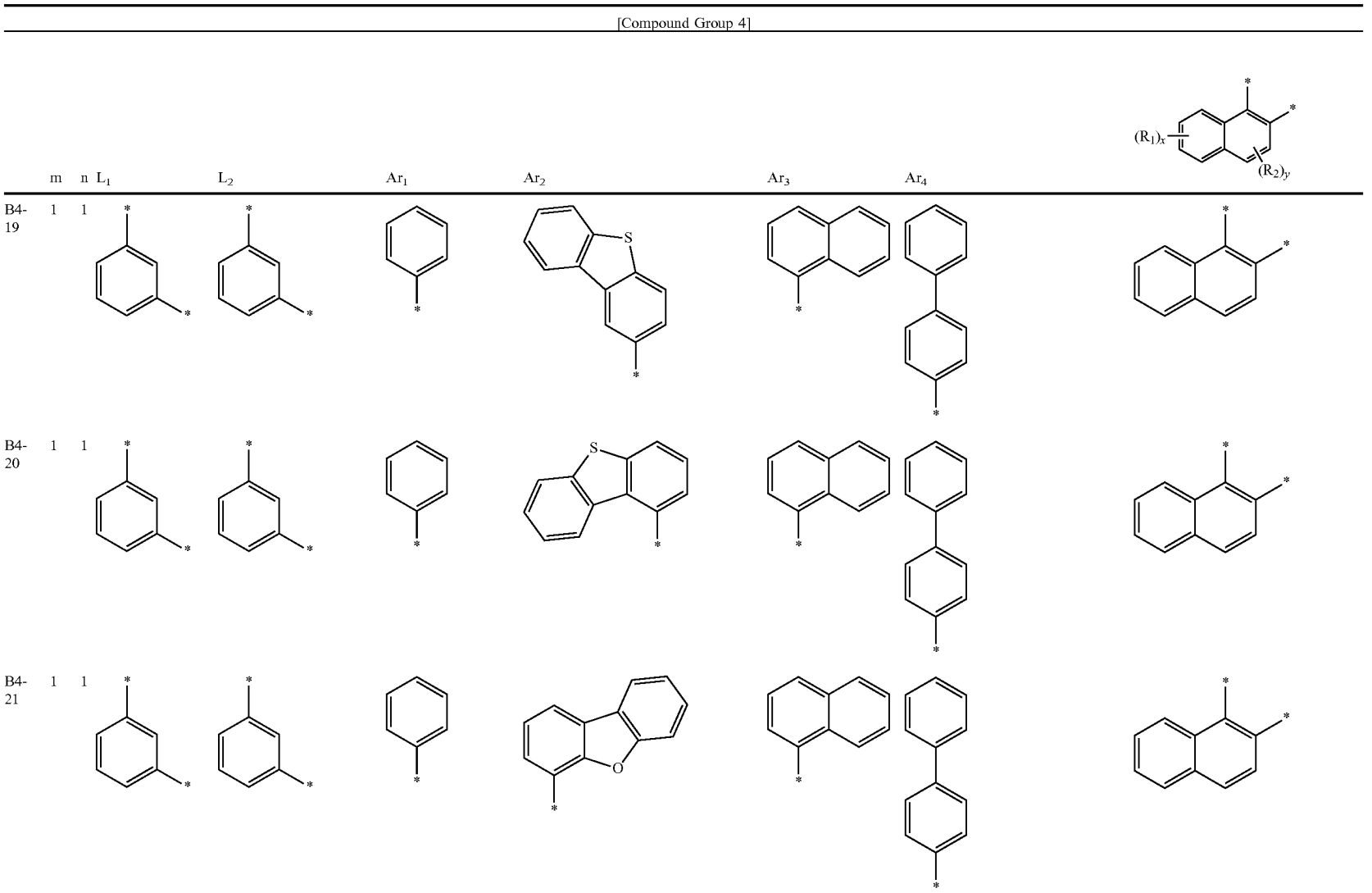

-continued
[Compound Group 4]
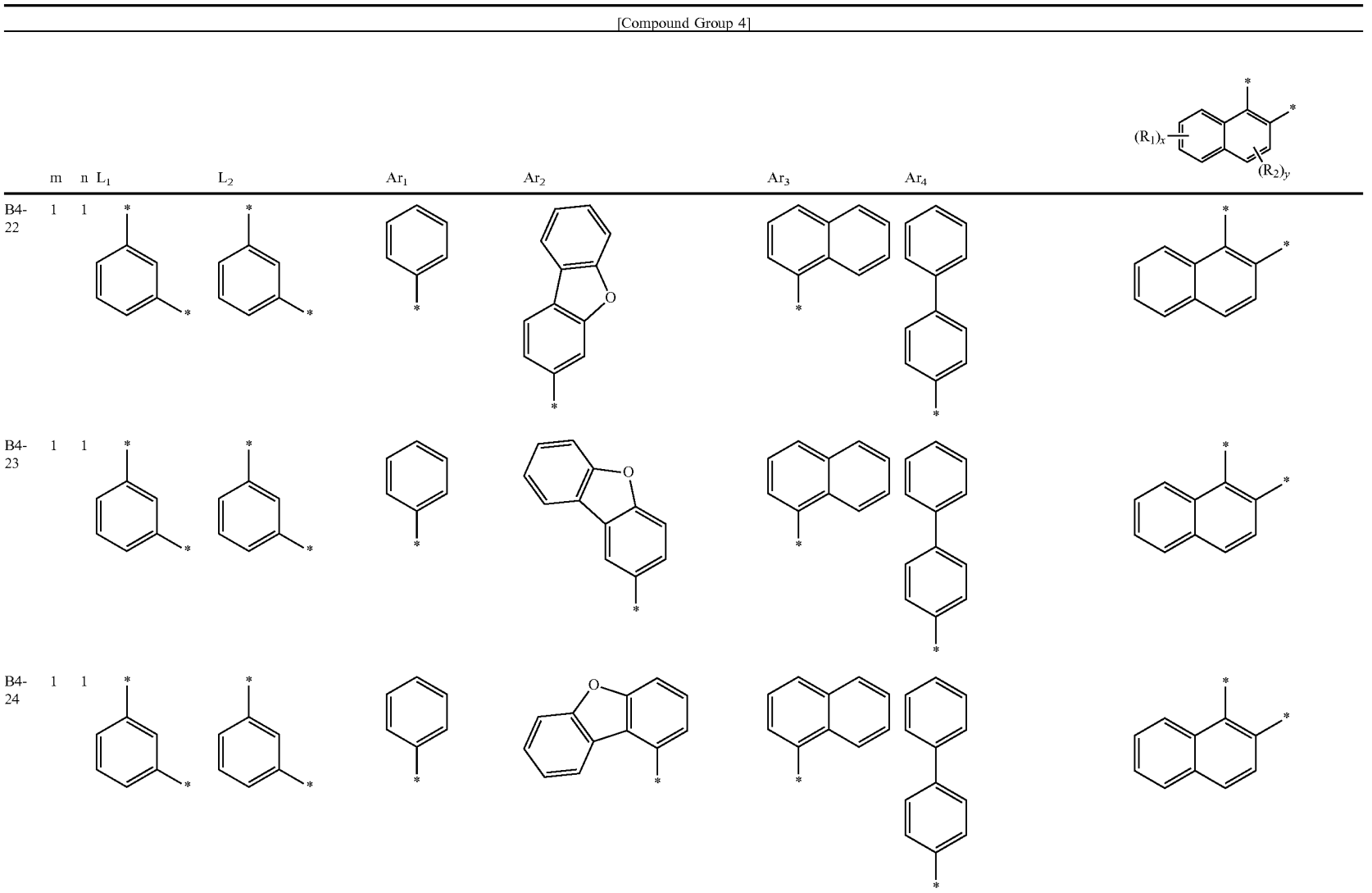

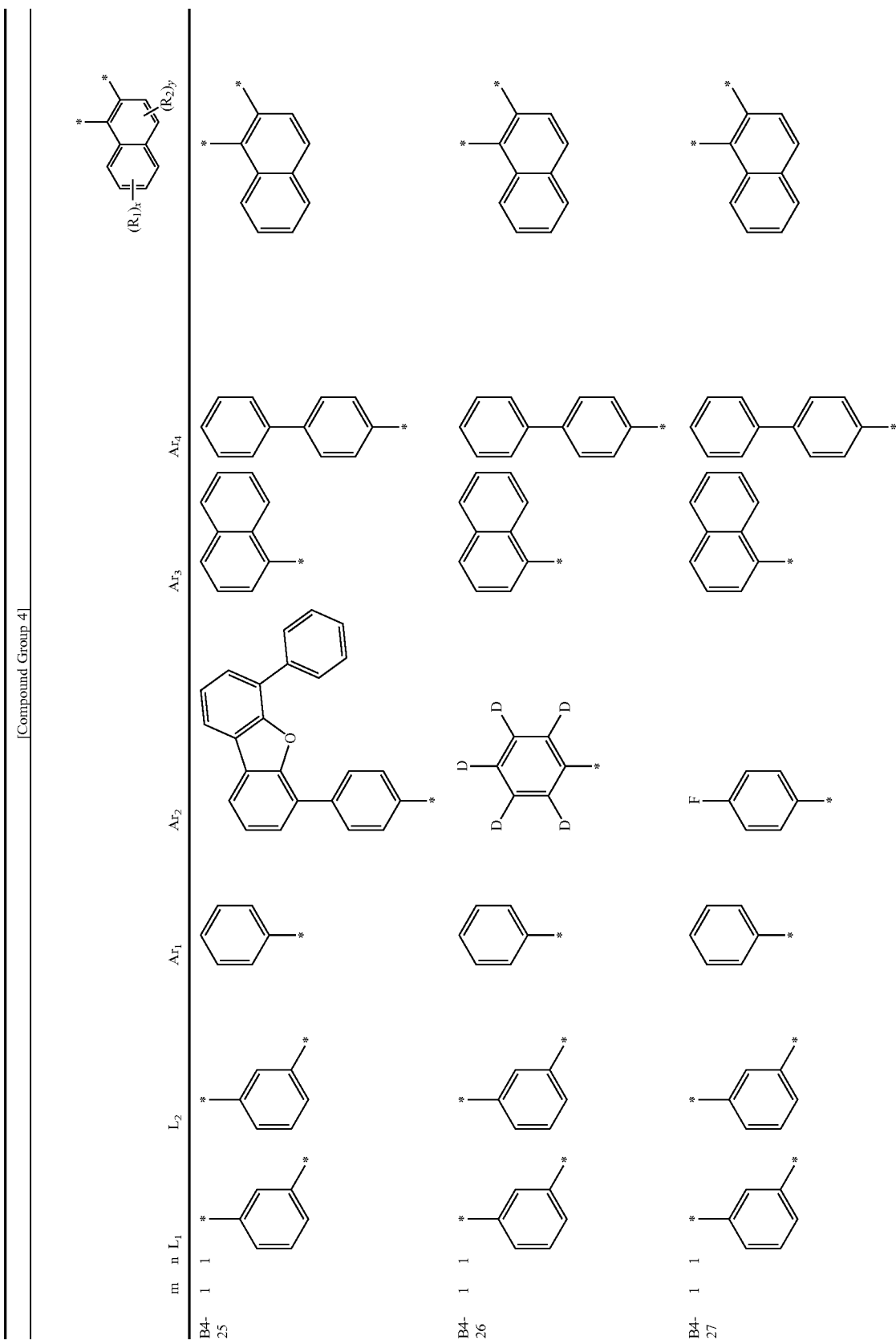

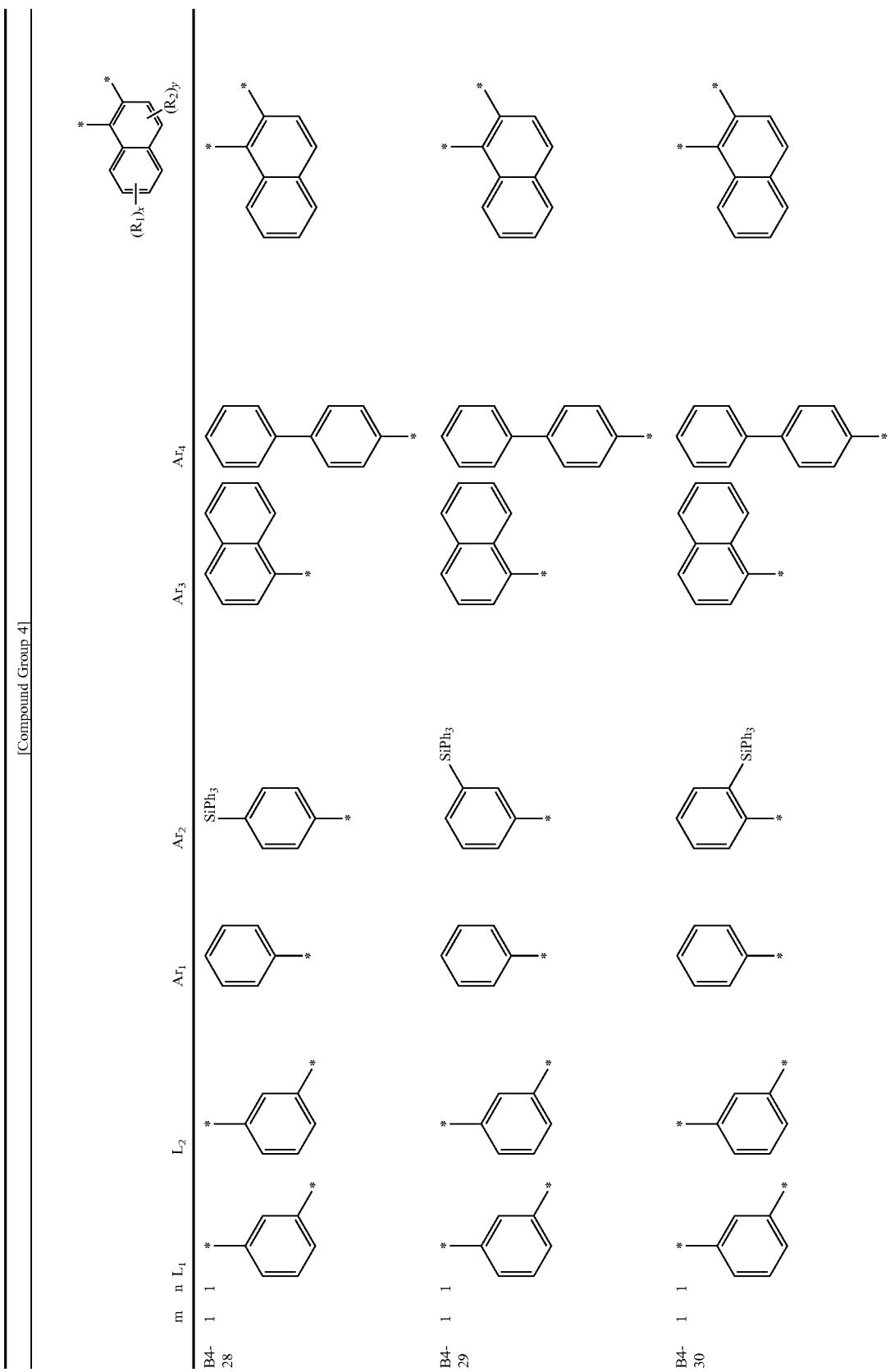

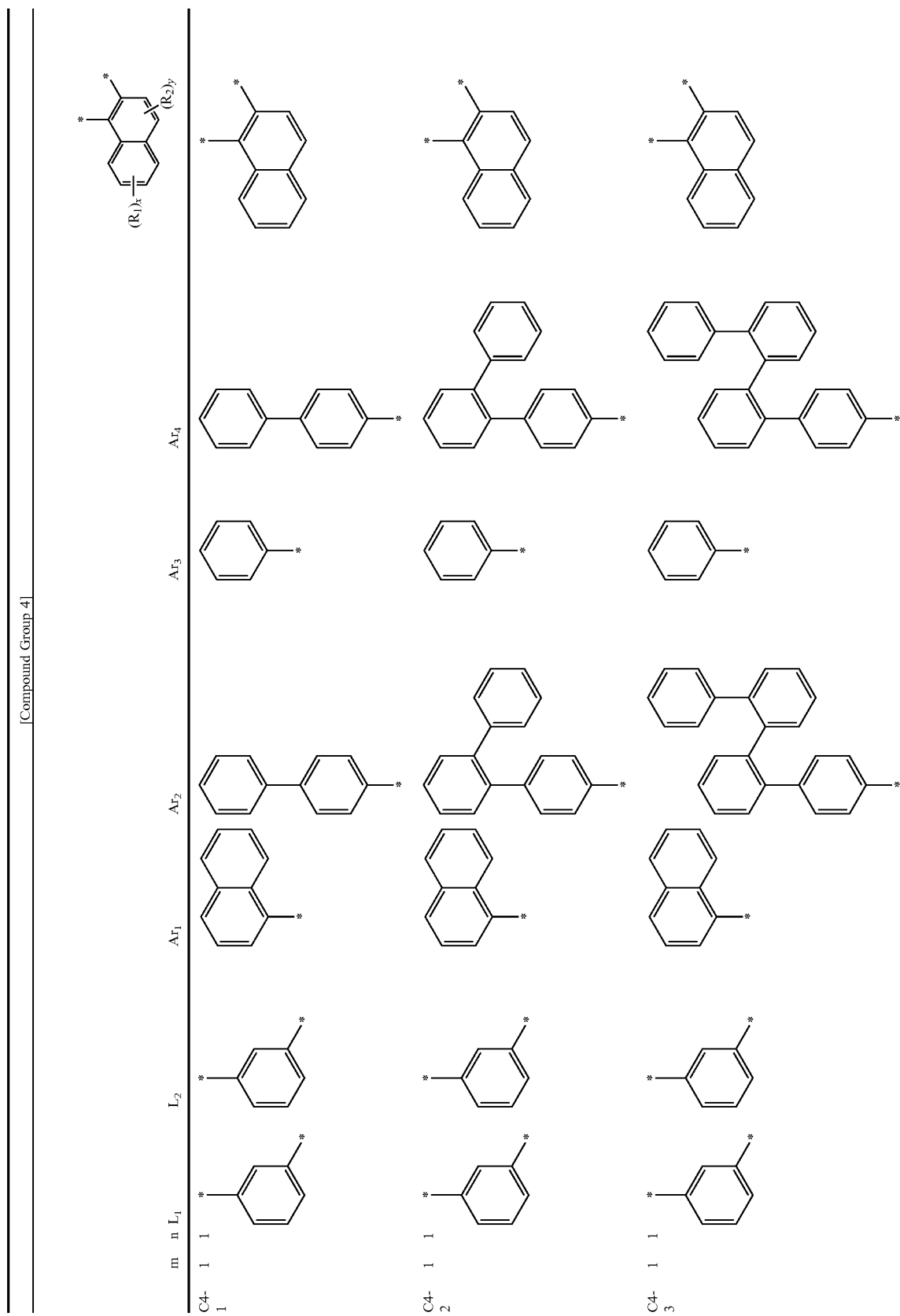

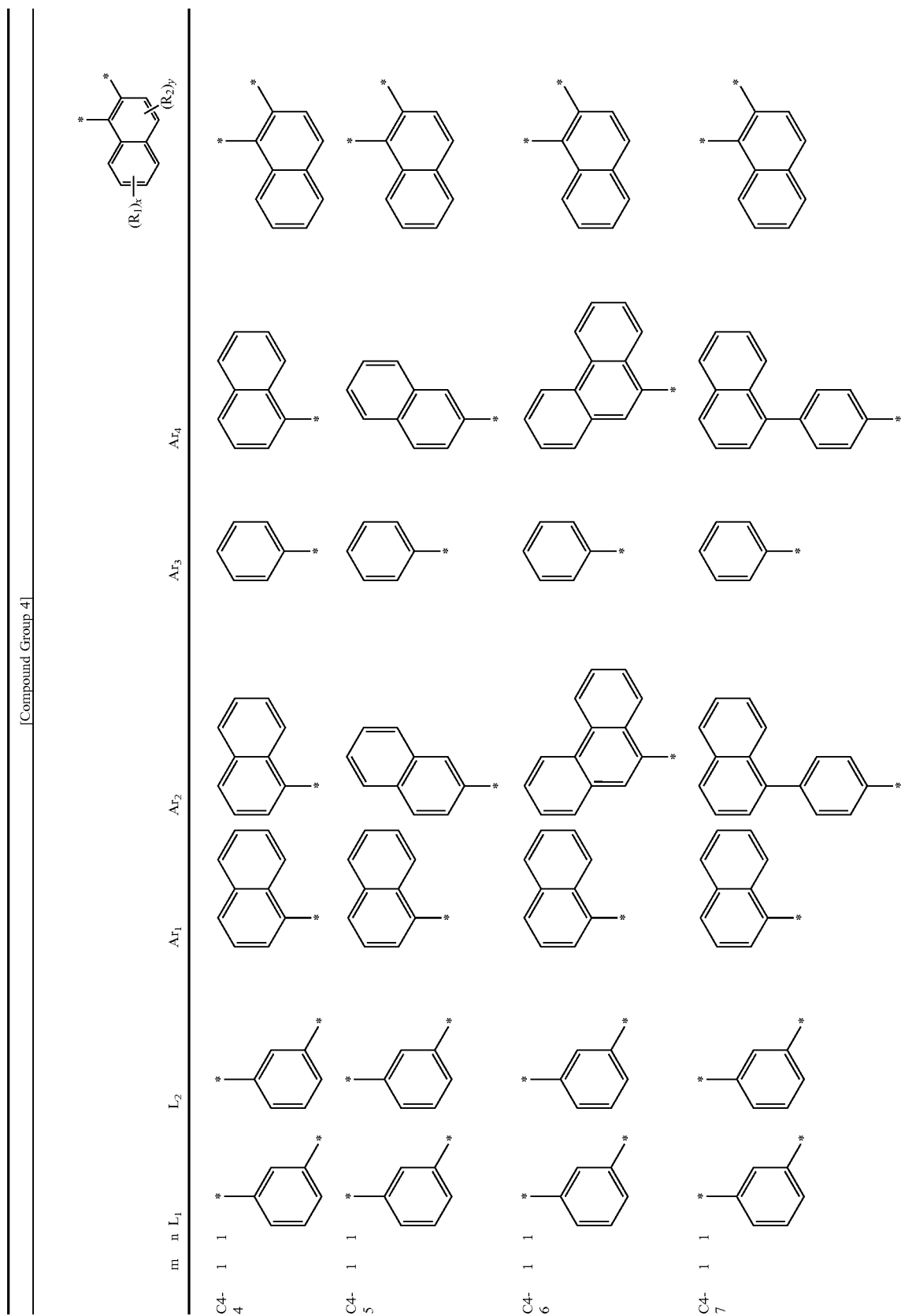

-continued
[Compound Group 4]
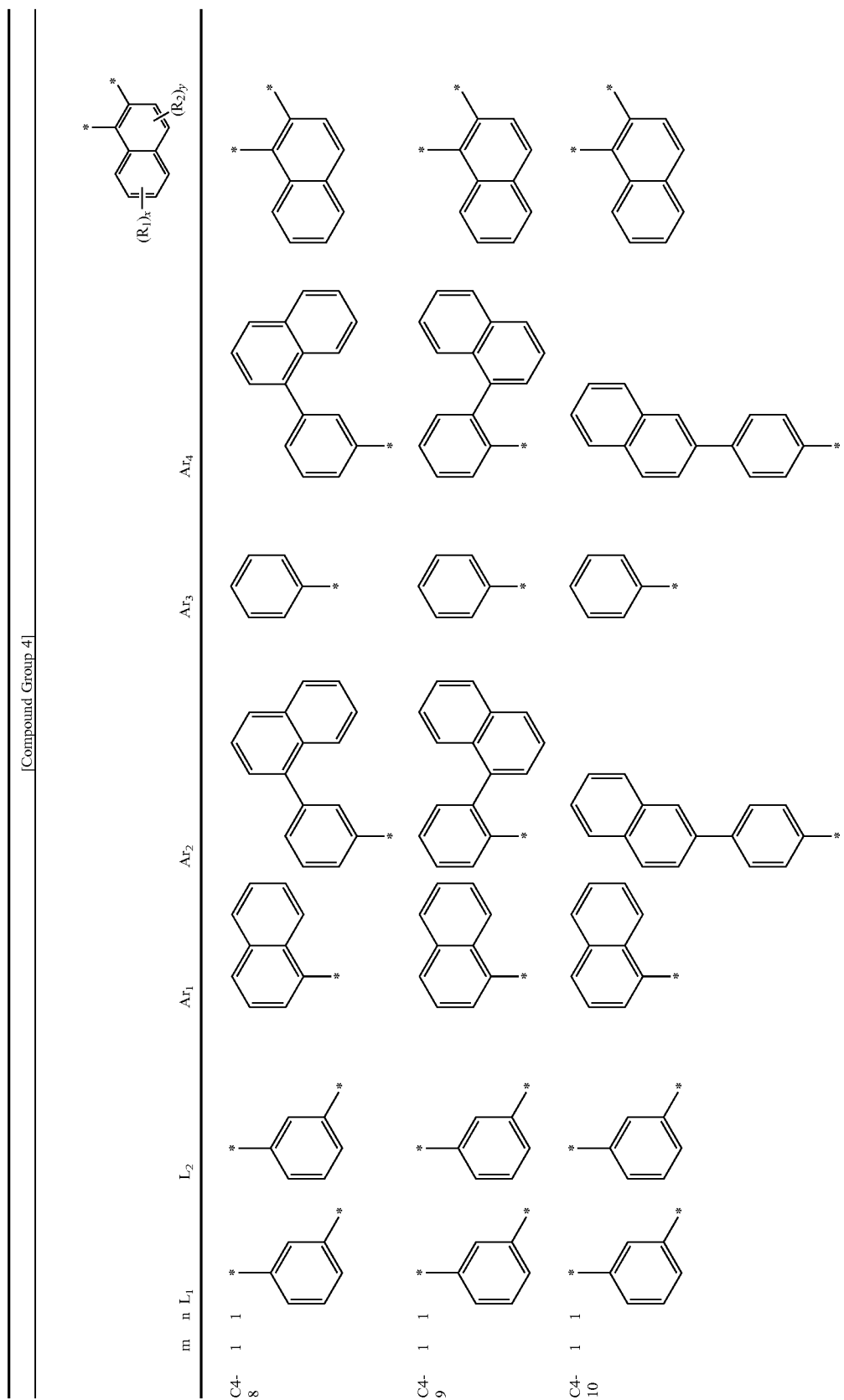

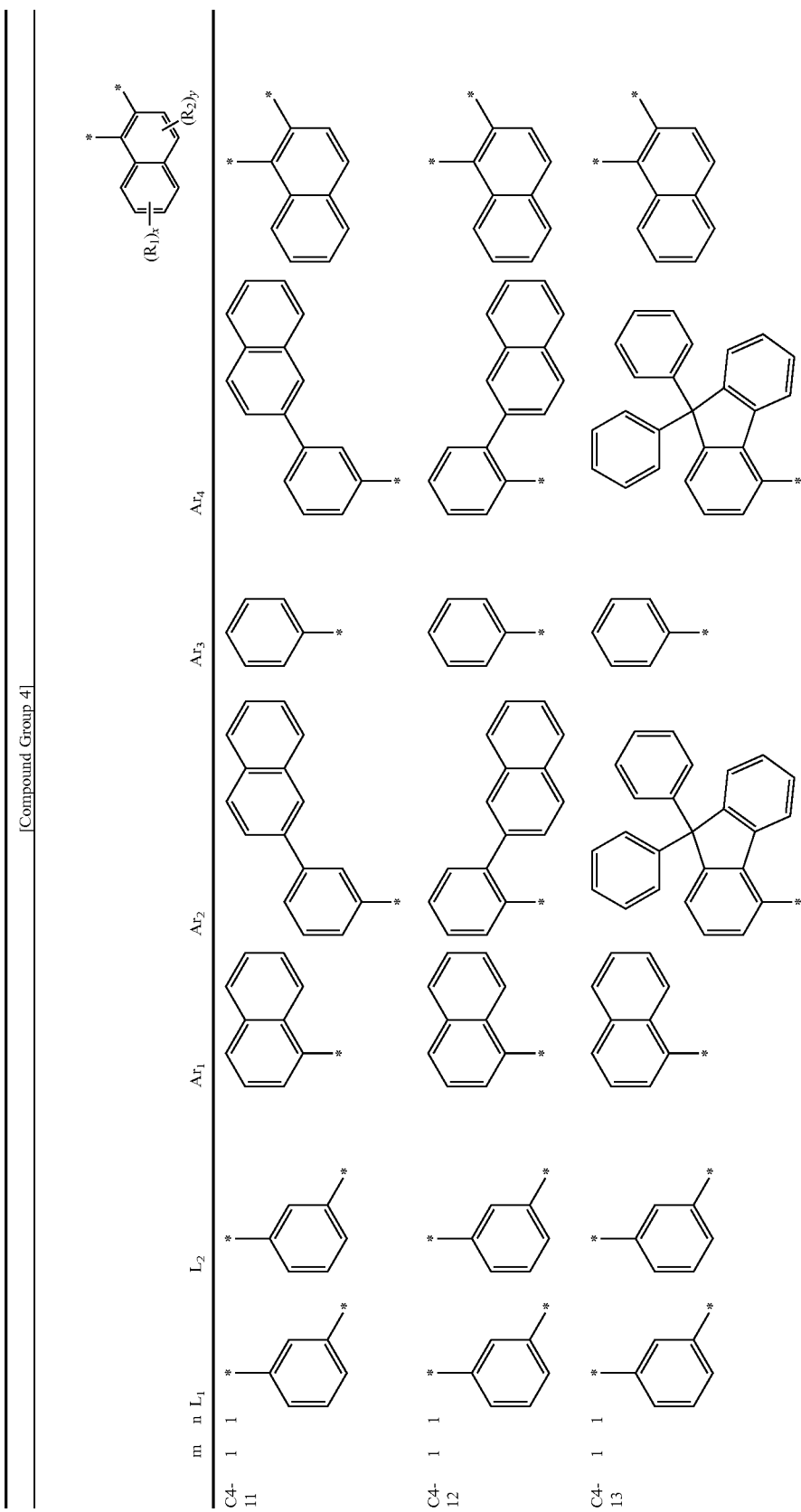

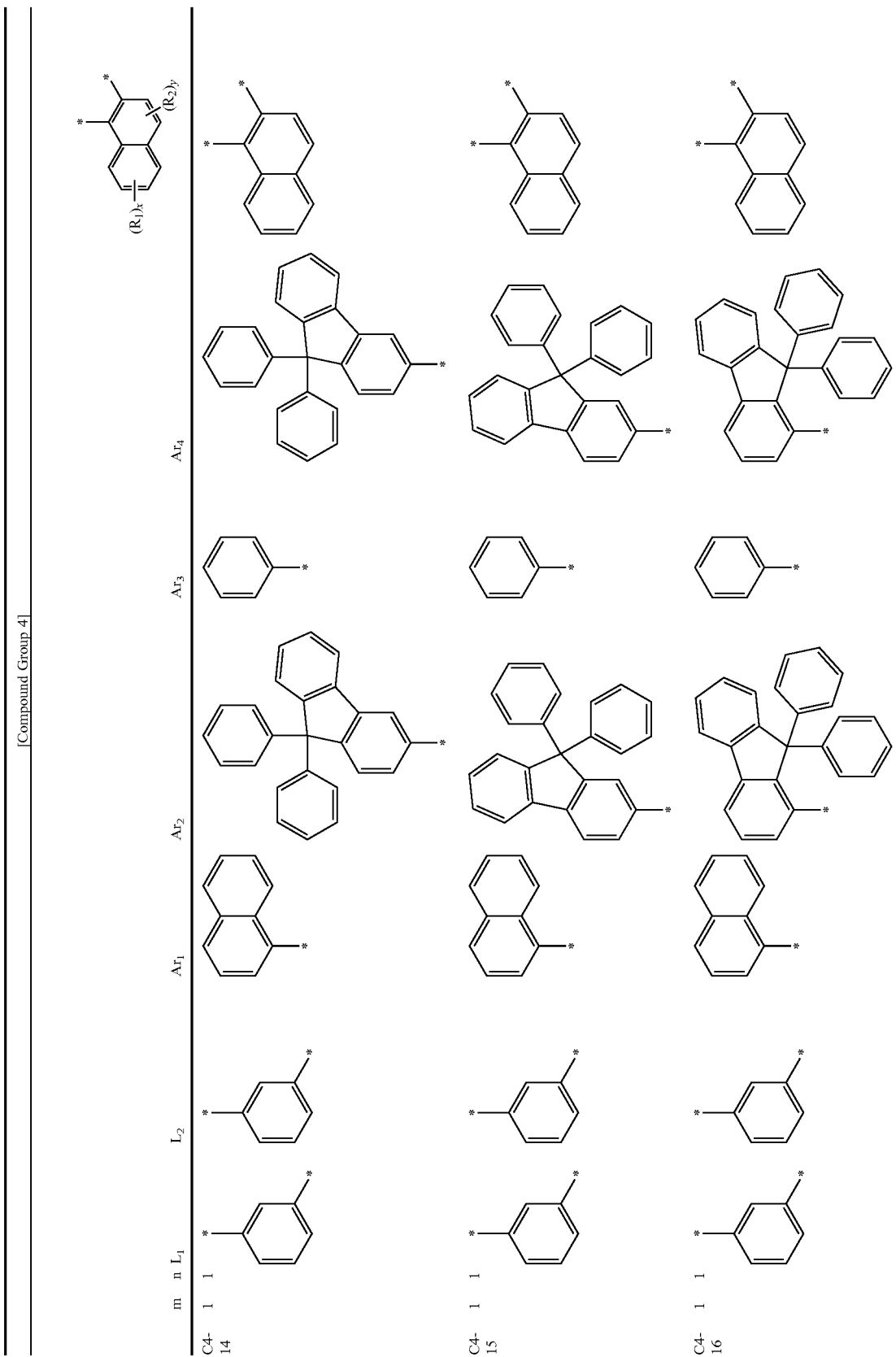

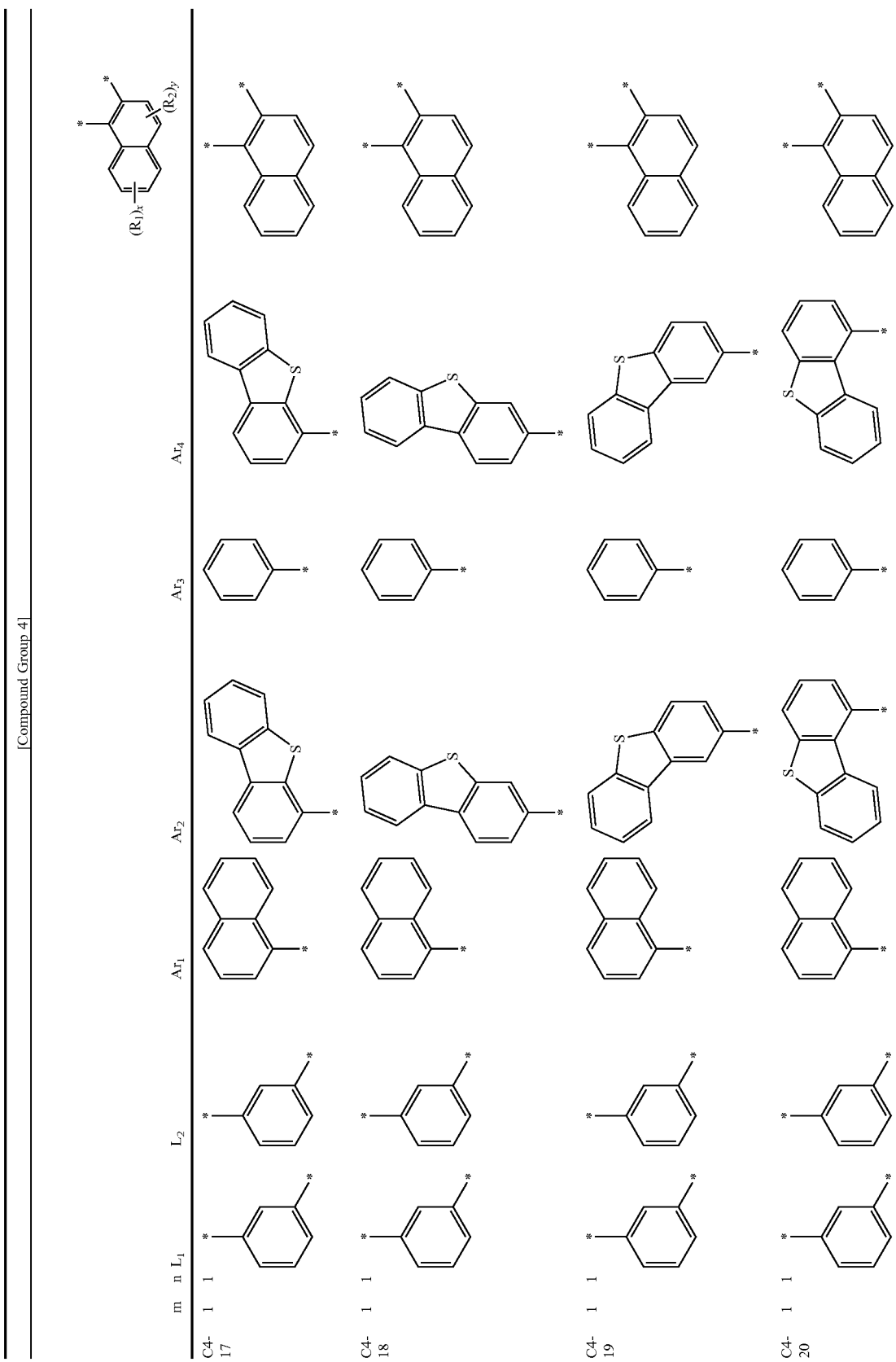

-continued
[Compound Group 4]
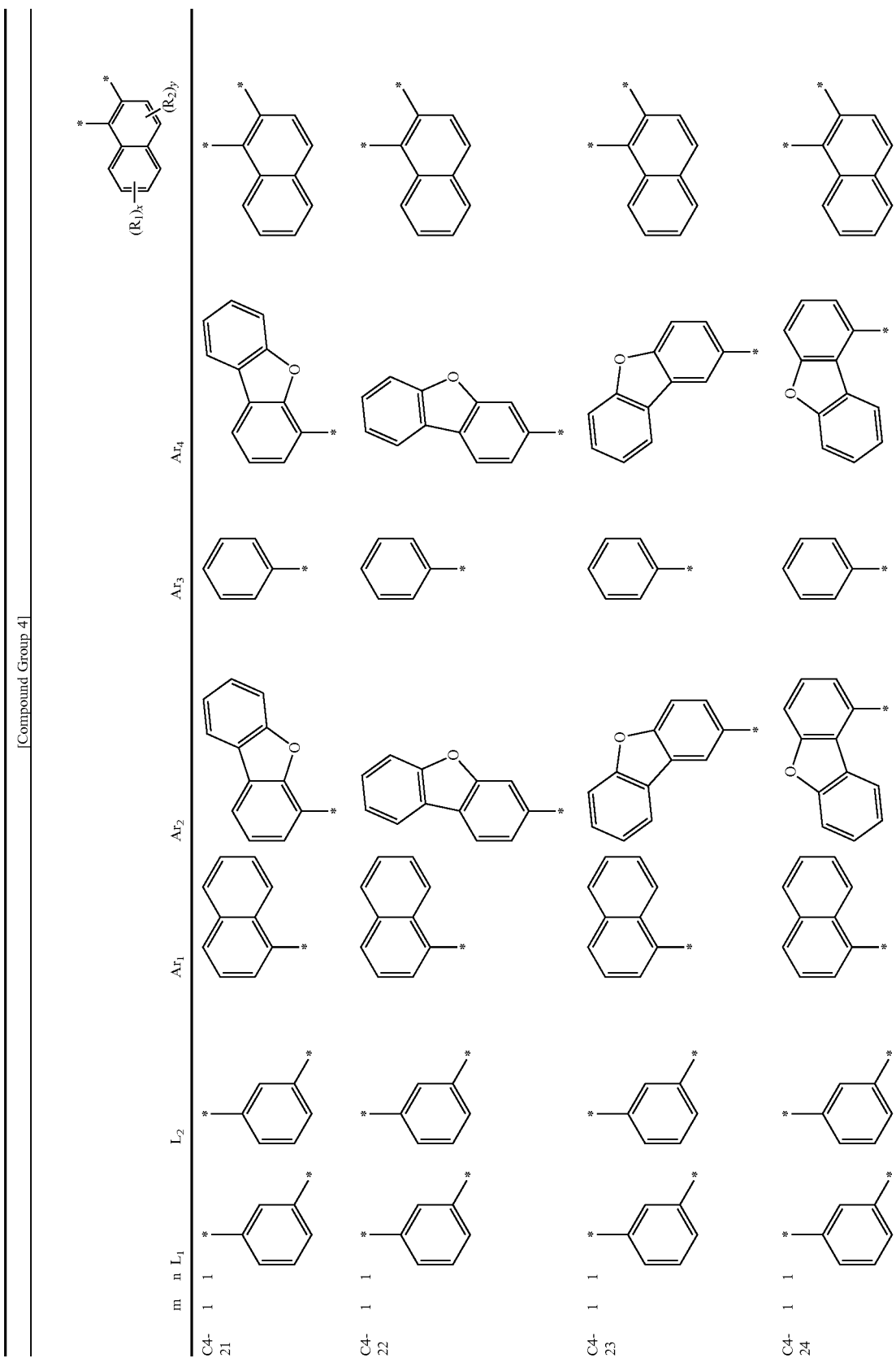

-continued
[Compound Group 4]
| | m | n | L₁ | L₂ | Ar₁ | Ar₂ | Ar₃ | Ar₄ | 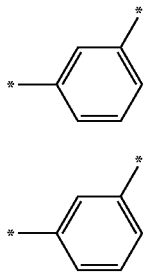 |
|---|---|---|---|---|---|---|---|---|---|
| C4-25 | 1 | 1 | 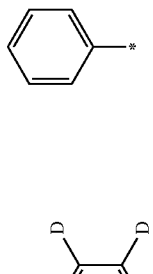 |  |  |  |  |  |  |
| C4-26 | 1 | 1 | 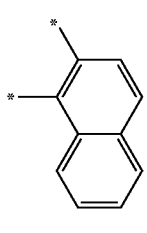 | 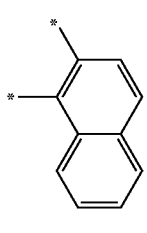 | 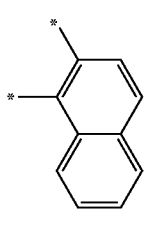 | 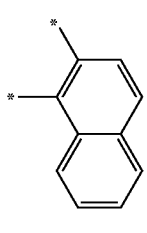 | 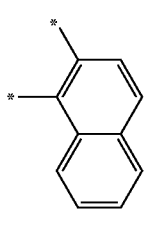 | 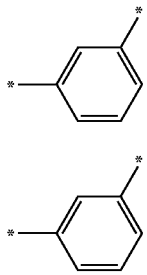 | 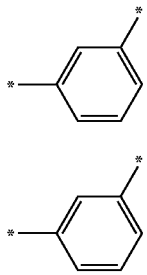 |
| C4-27 | 1 | 1 | 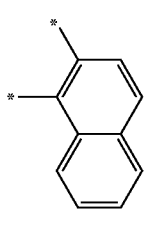 | 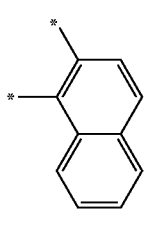 | 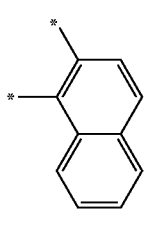 | 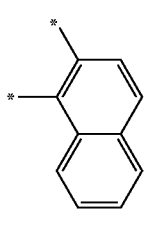 | 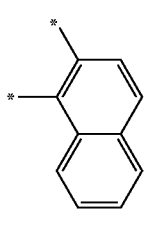 | 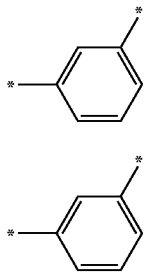 | 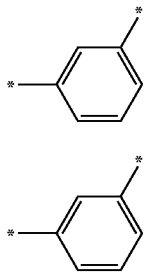 |
| C4-28 | 1 | 1 | 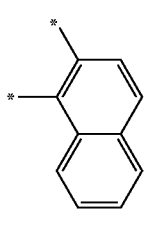 | 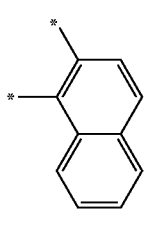 | 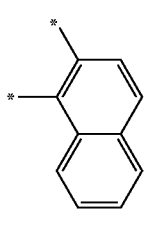 | 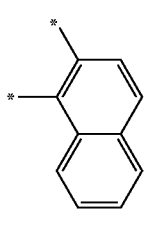 | 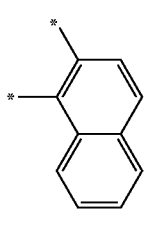 | 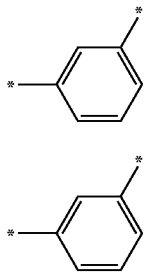 | |

-continued
[Compound Group 4]
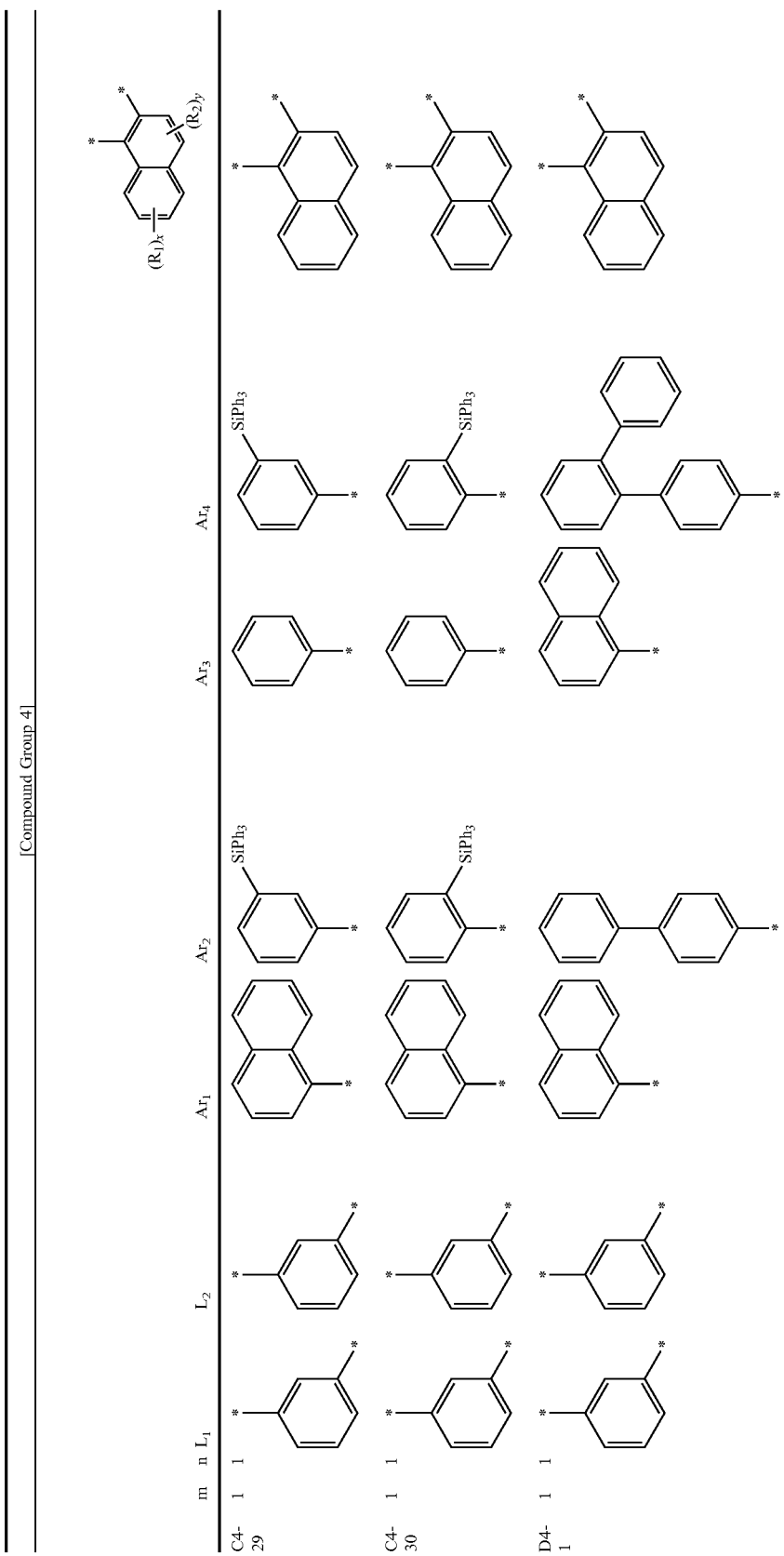

-continued
[Compound Group 4]
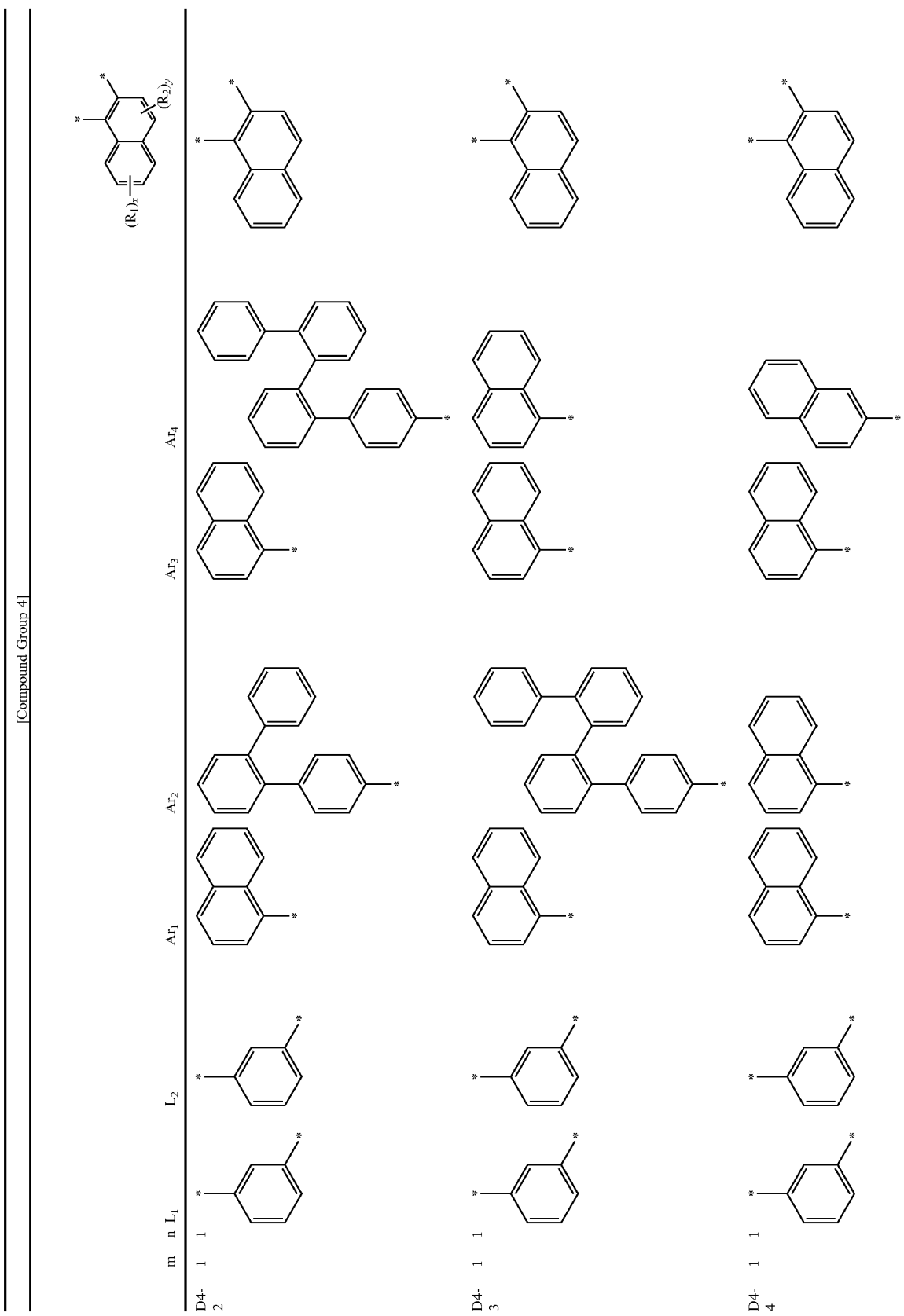

-continued
[Compound Group 4]
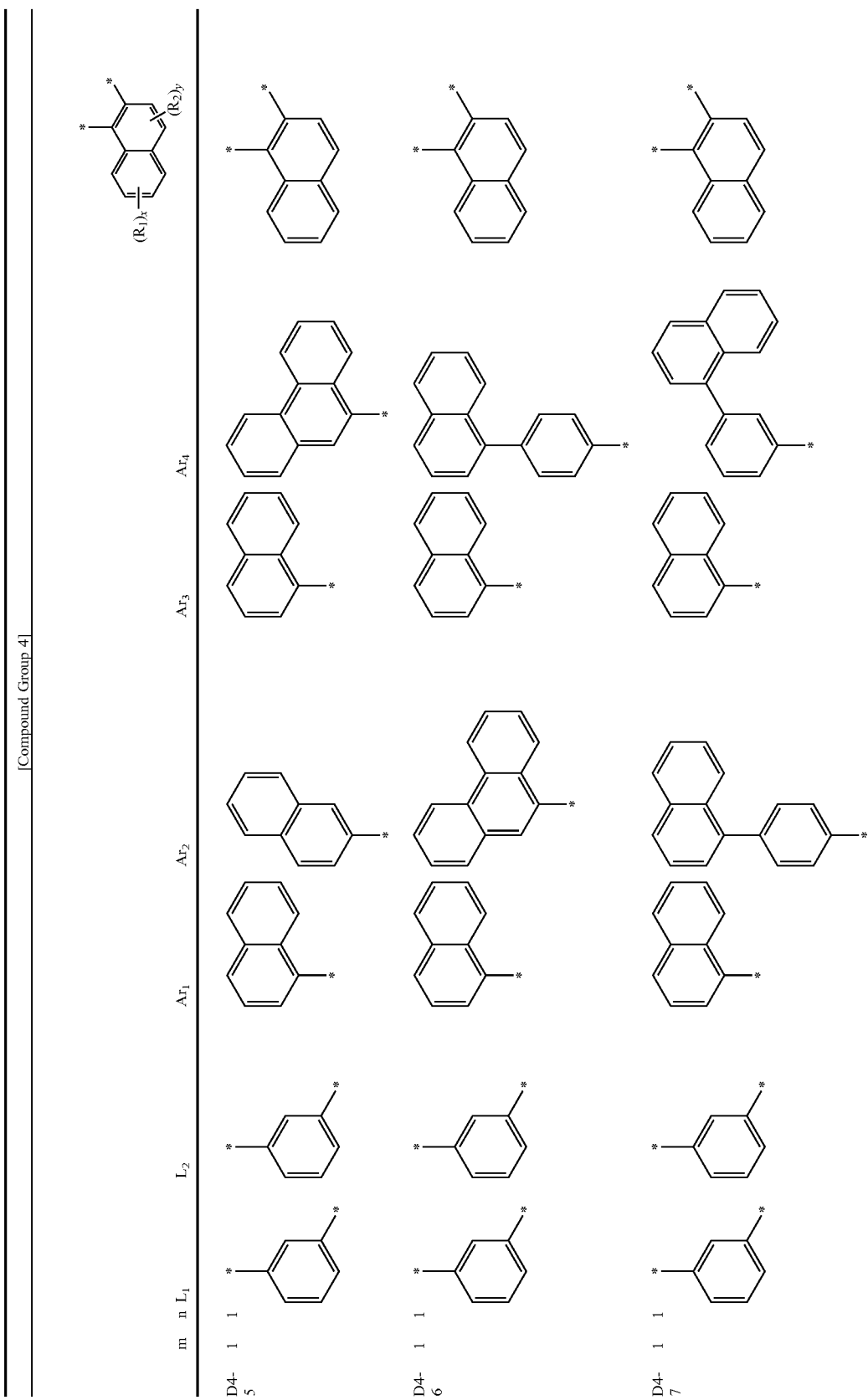

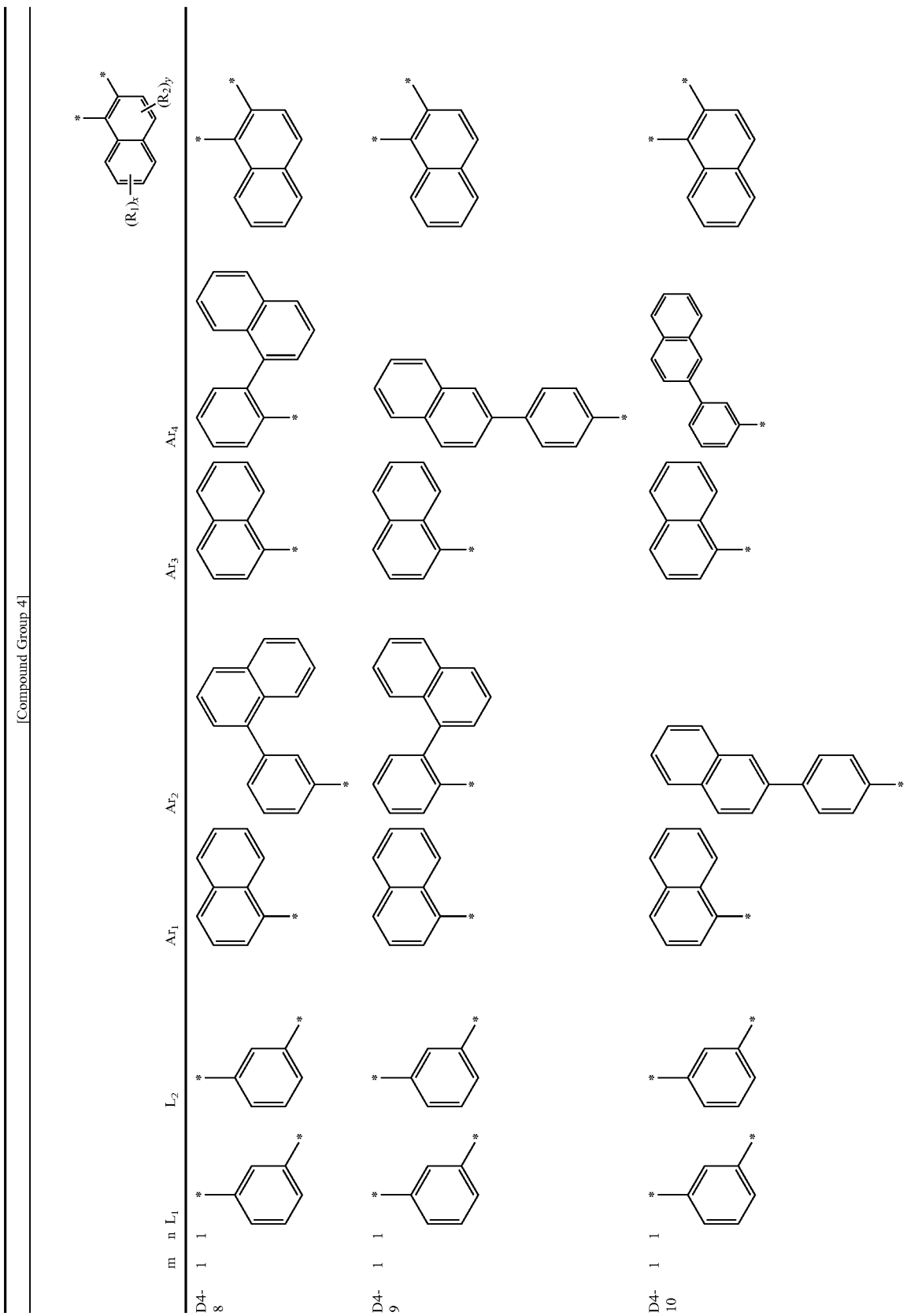

-continued
[Compound Group 4]
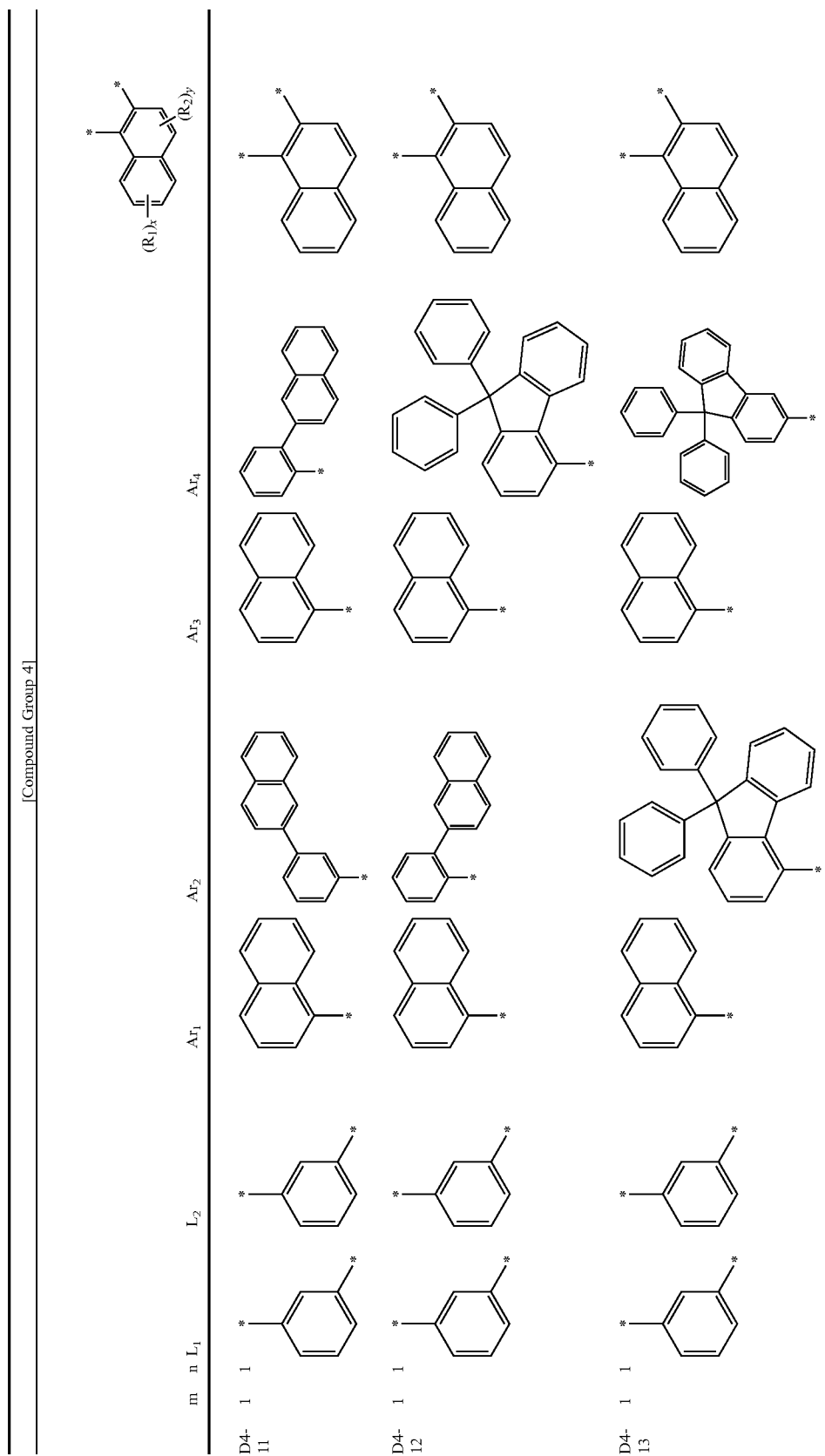

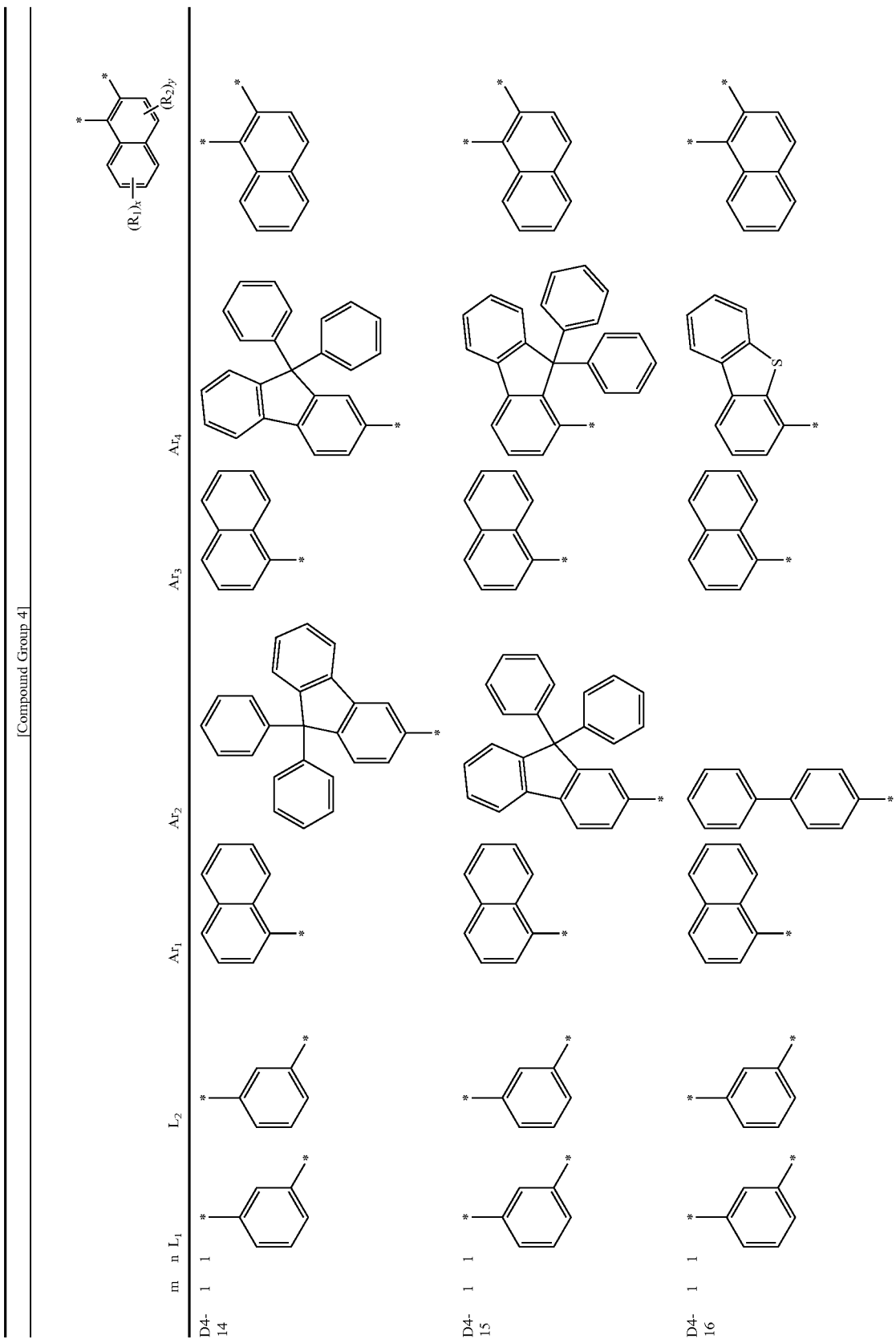

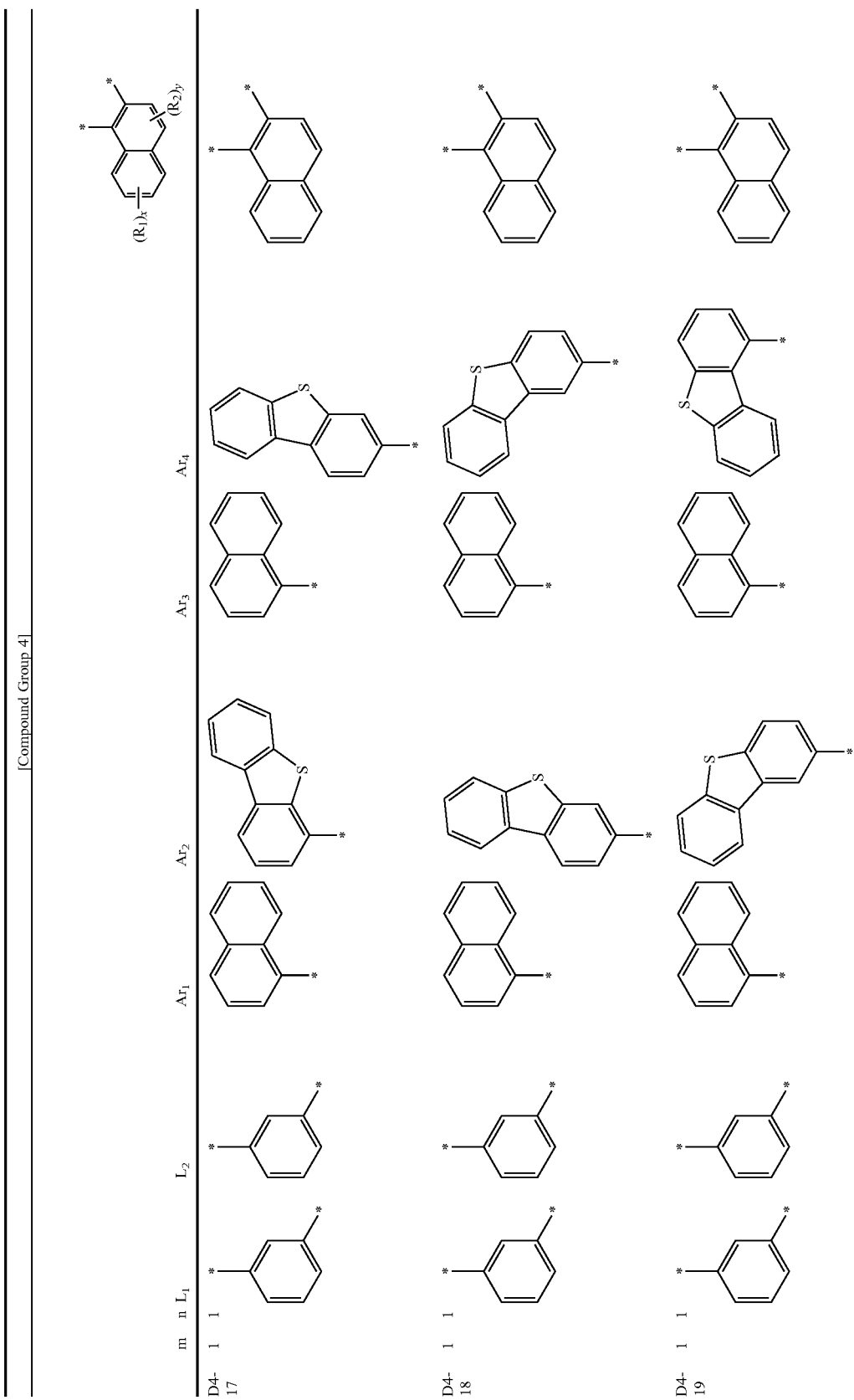

-continued
[Compound Group 4]
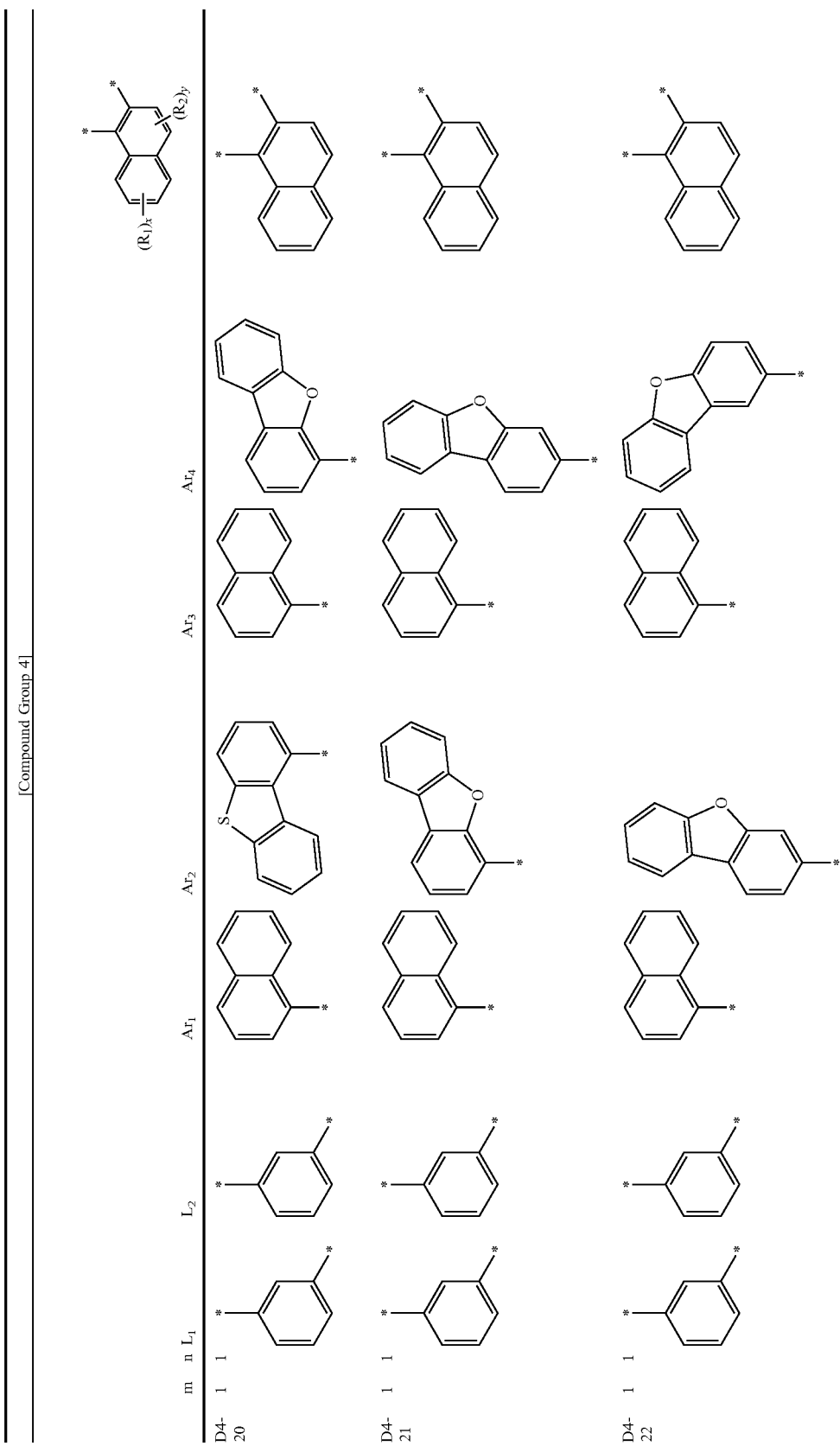

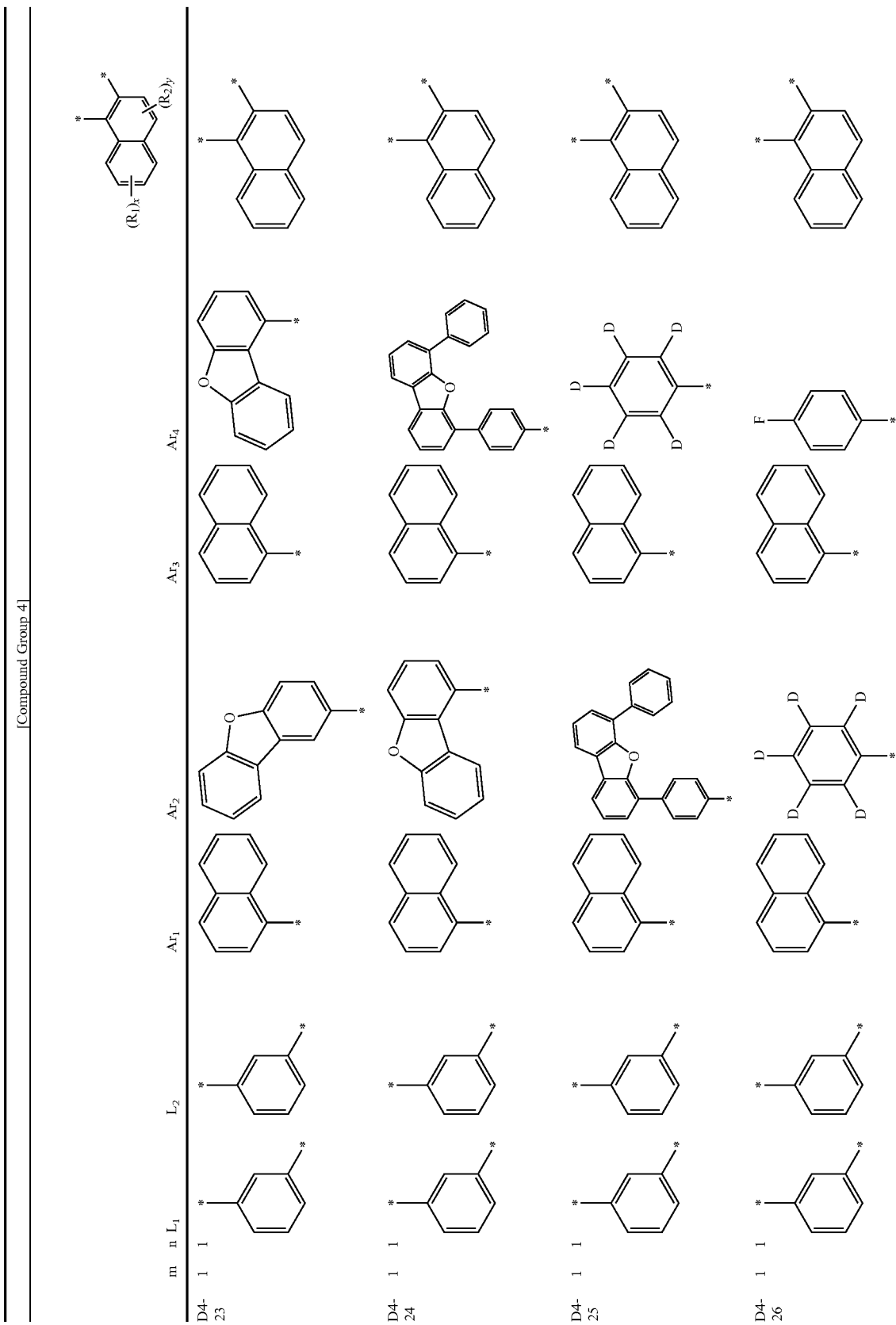

-continued
[Compound Group 4]
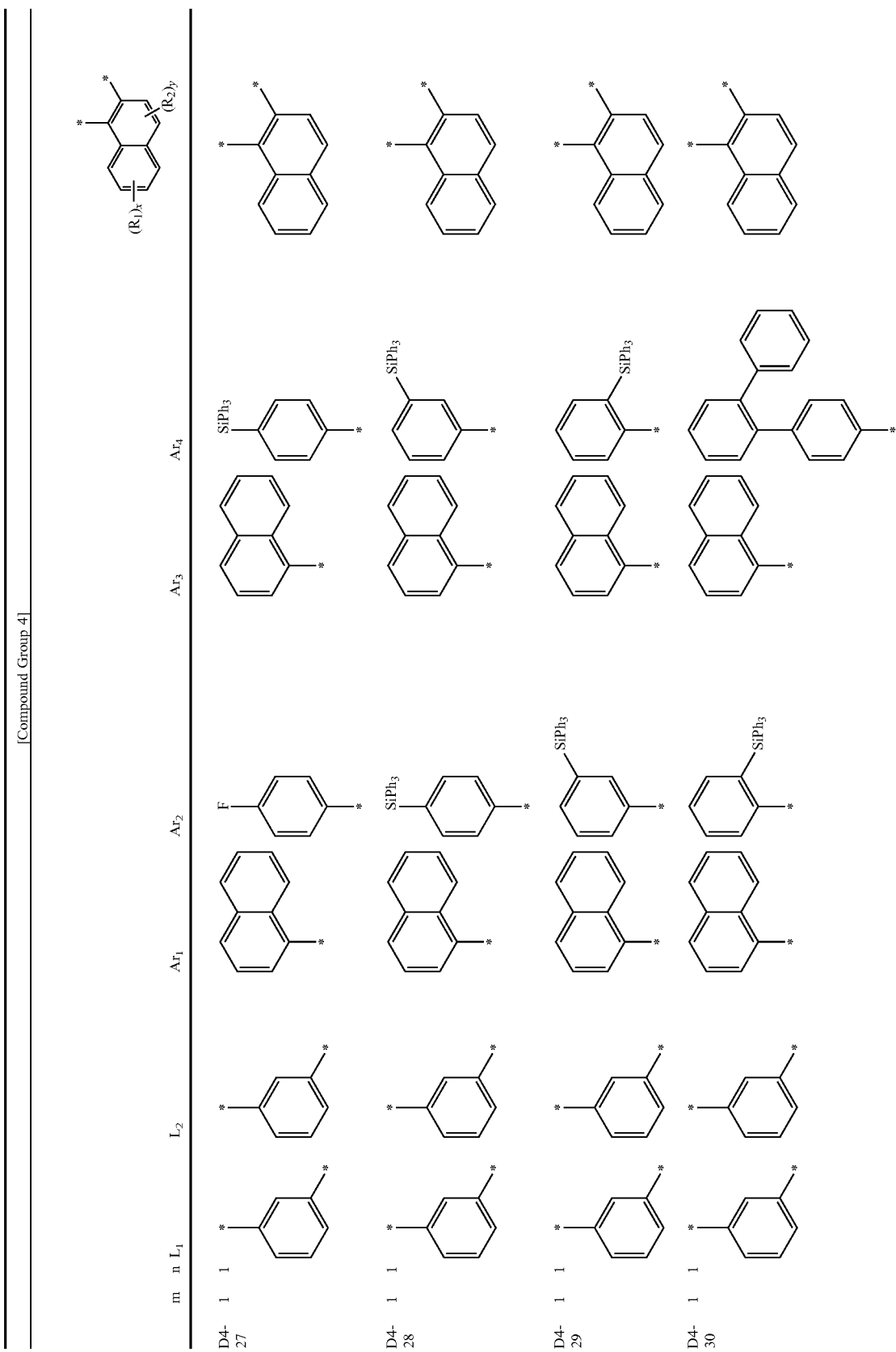

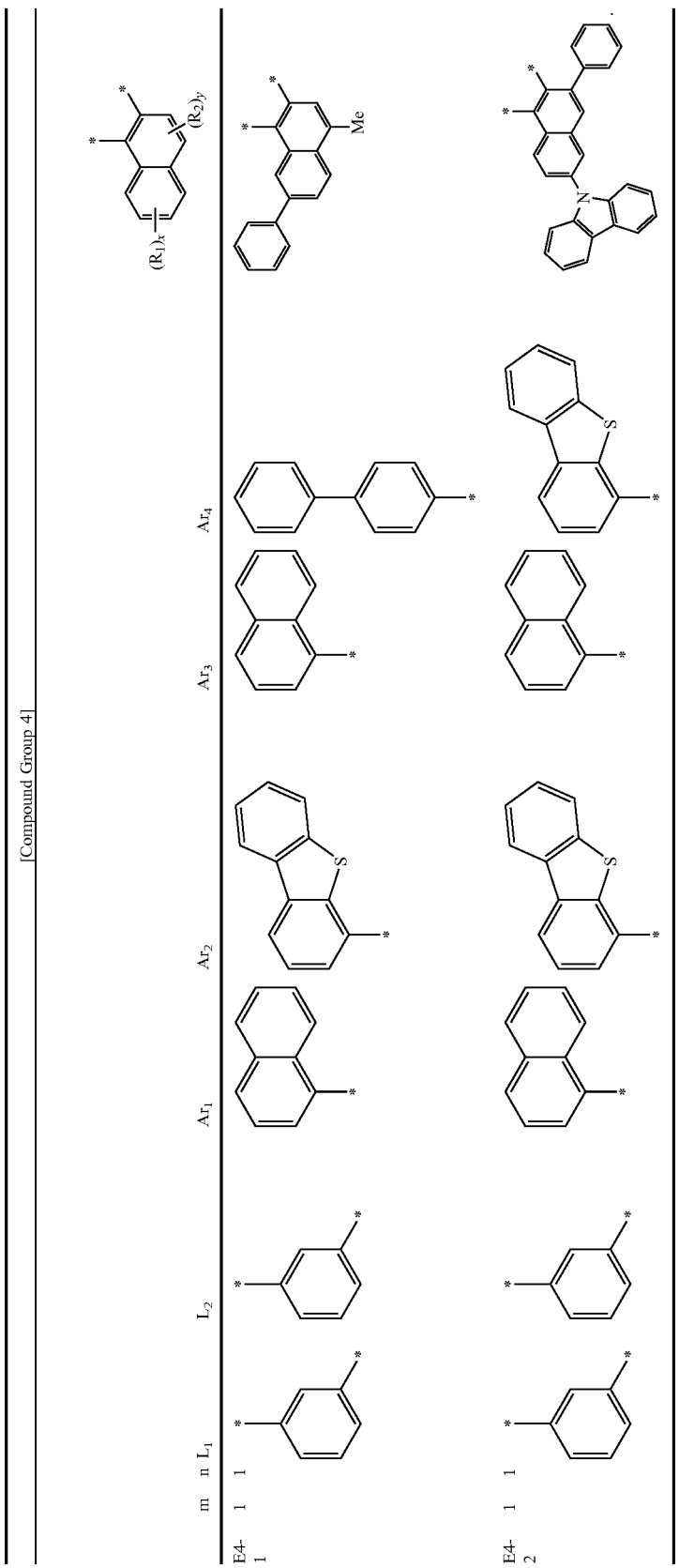

15. The organic electroluminescence device of claim 1, wherein the diamine compound represented by Formula 1 is at least one selected among compounds represented in Compound Group 5:
[Compound Group 5]
| | m | n | $L_1$ | $L_2$ | $Ar_1$ |
|---|---|---|---|---|---|
| A5-1 | 0 | 1 | — | 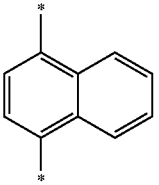 | 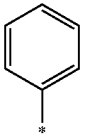 [SMILES: *c1ccccc1] |
| A5-2 | 0 | 1 | — | 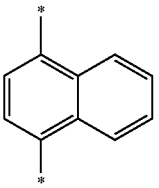 [SMILES: *c1ccc(*)c2ccccc12] | 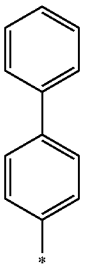 [SMILES: *c1ccc(-c2ccccc2)cc1] |
| A5-3 | 0 | 1 | — | 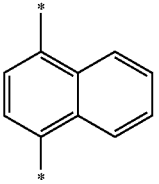 [SMILES: *c1ccc(*)c2ccccc12] | 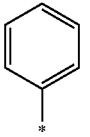 [SMILES: *c1ccccc1] |
| A5-4 | 0 | 1 | — | 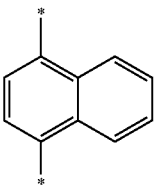 [SMILES: *c1ccc(*)c2ccccc12] | 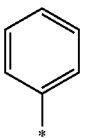 |
| A5-5 | 0 | 1 | — | 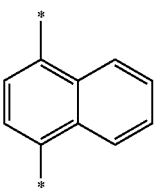 [SMILES: *c1ccc(*)c2ccccc12] | 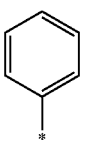 [SMILES: *c1ccccc1] |
| A5-6 | 0 | 1 | — | 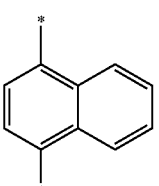 | 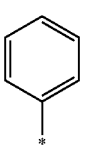 |

[Compound Group 5]
| | | | | | |
|---|---|---|---|---|---|
| A5-7 | 0 | 1 | — | 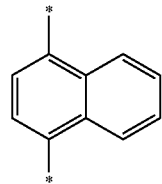 [SMILES: *c1ccc(*)c2ccccc12] | 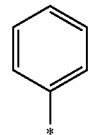 [SMILES: *c1ccccc1] |
| A5-8 | 0 | 1 | — | 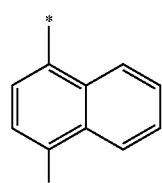 | 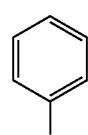 |
| A5-9 | 0 | 1 | — | 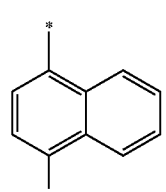 | 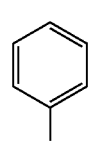 |
| A5-10 | 0 | 1 | — | 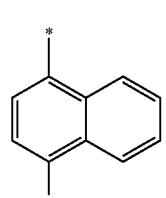 | 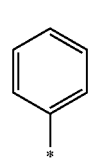 |
| A5-11 | 0 | 1 | — | 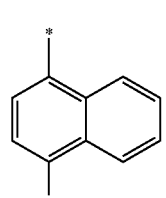 | 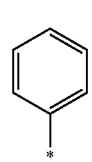 [SMILES: *c1ccccc1] |
| A5-12 | 0 | 1 | — | 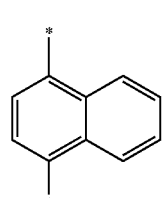 | 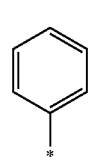 [SMILES: *c1ccccc1] |
| A5-13 | 0 | 1 | — | 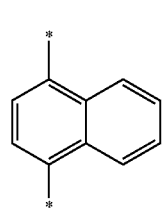 [SMILES: *c1ccc(*)c2ccccc12] | 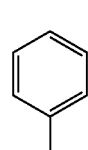 |

-continued
[Compound Group 5]
| A5-14 | 0 | 1 | — | 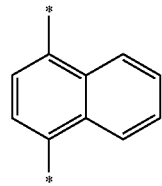 [SMILES: *c1ccc(*)c2ccccc12] | 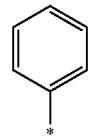 [SMILES: *c1ccccc1] |
| A5-15 | 0 | 1 | — | 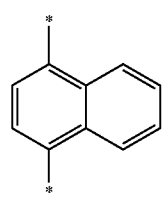 [SMILES: *c1ccc(*)c2ccccc12] | 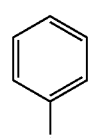 |
| A5-16 | 0 | 1 | — | 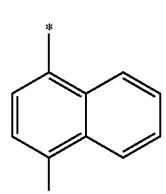 | 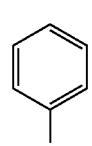 |
| A5-17 | 0 | 1 | — | 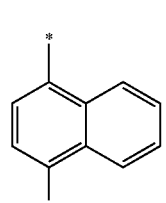 | 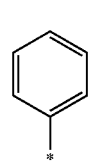 |
| A5-18 | 0 | 1 | — | 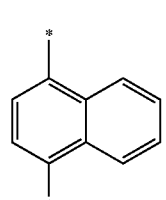 | 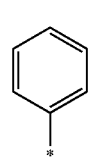 [SMILES: *c1ccccc1] |
| A5-19 | 0 | 1 | — | 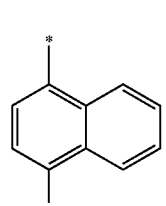 | 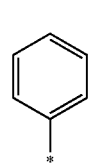 [SMILES: *c1ccccc1] |
| A5-20 | 0 | 1 | — | 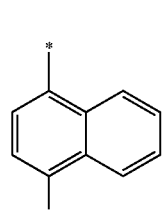 | 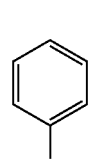 |

-continued
[Compound Group 5]
| A5-21 | 0 | 1 | — | 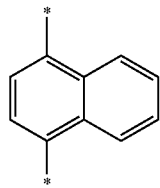 [SMILES: *c1ccc(*)c2ccccc12] | 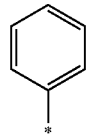 [SMILES: *c1ccccc1] |
| A5-22 | 0 | 1 | — | 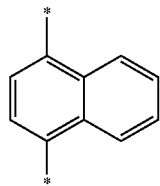 [SMILES: *c1ccc(*)c2ccccc12] | 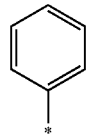 [SMILES: *c1ccccc1] |
| A5-23 | 0 | 1 | — | 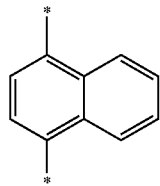 [SMILES: *c1ccc(*)c2ccccc12] | 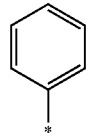 [SMILES: *c1ccccc1] |
| A5-24 | 0 | 1 | — | 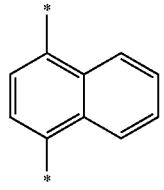 [SMILES: *c1ccc(*)c2ccccc12] | 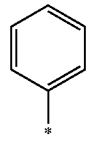 [SMILES: *c1ccccc1] |
| A5-25 | 0 | 1 | — | 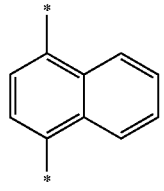 [SMILES: *c1ccc(*)c2ccccc12] | 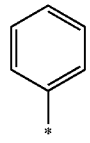 [SMILES: *c1ccccc1] |
| A5-26 | 0 | 1 | — | 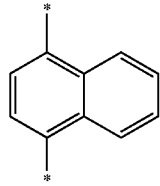 [SMILES: *c1ccc(*)c2ccccc12] | 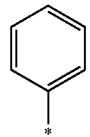 [SMILES: *c1ccccc1] |
| A5-27 | 0 | 1 | — | 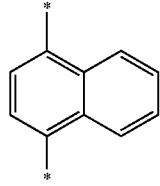 [SMILES: *c1ccc(*)c2ccccc12] | 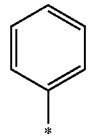 [SMILES: *c1ccccc1] |

-continued
[Compound Group 5]
| A5-28 | 0 | 1 | — | 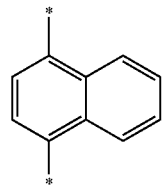 [SMILES: *c1ccc(*)c2ccccc12] | 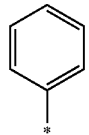 [SMILES: *c1ccccc1] |
| A5-29 | 0 | 1 | — | 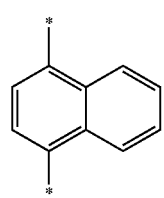 [SMILES: *c1ccc(*)c2ccccc12] | 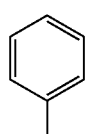 |
| A5-30 | 0 | 1 | — | 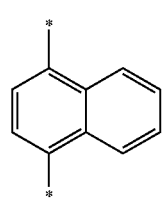 [SMILES: *c1ccc(*)c2ccccc12] | 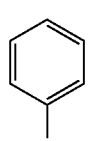 |
| A5-31 | 0 | 1 | — | 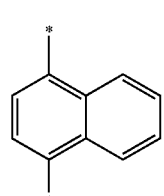 | 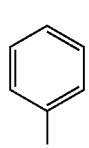 |
| A5-32 | 0 | 1 | — | 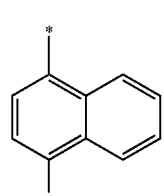 | 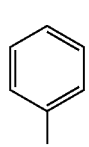 |
| A5-33 | 0 | 1 | — | 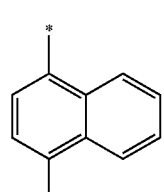 | 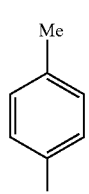 |
| B5-1 | 0 | 1 | — | 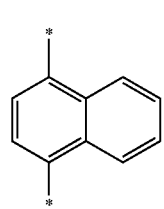 [SMILES: *c1ccc(*)c2ccccc12] | 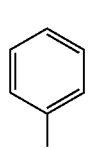 |

-continued
|[Compound Group 5]|
| B5-2 | 0 | 1 | — | 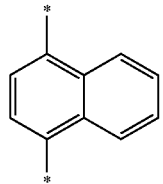 [SMILES: *c1ccc(*)c2ccccc12] | 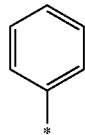 [SMILES: *c1ccccc1] |
| B5-3 | 0 | 1 | — | 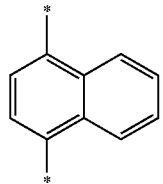 [SMILES: *c1ccc(*)c2ccccc12] | 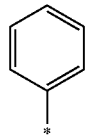 [SMILES: *c1ccccc1] |
| B5-4 | 0 | 1 | — | 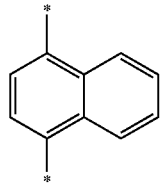 [SMILES: *c1ccc(*)c2ccccc12] | 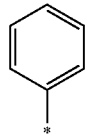 |
| B5-5 | 0 | 1 | — | 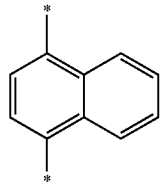 [SMILES: *c1ccc(*)c2ccccc12] | 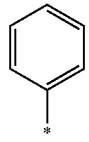 [SMILES: *c1ccccc1] |
| B5-6 | 0 | 1 | — | 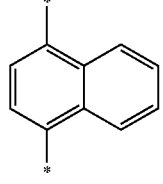 | 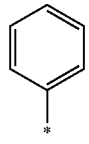 [SMILES: *c1ccccc1] |
| B5-7 | 0 | 1 | — | 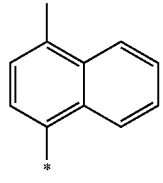 | 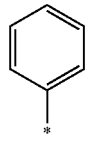 [SMILES: *c1ccccc1] |
| B5-8 | 0 | 1 | — | 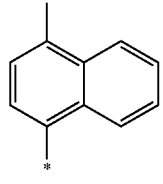 | 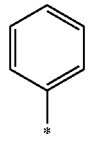 |

|  |  |  |  |  |  |
|---|---|---|---|---|---|
| [Compound Group 5] | | | | | |
| B5-9 | 0 | 1 | — | 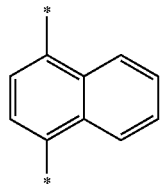 [SMILES: *c1ccc(*)c2ccccc12] | 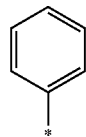 [SMILES: *c1ccccc1] |
| B5-10 | 0 | 1 | — | 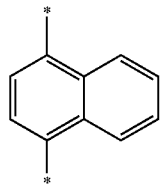 [SMILES: *c1ccc(*)c2ccccc12] | 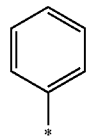 [SMILES: *c1ccccc1] |
| B5-11 | 0 | 1 | — | 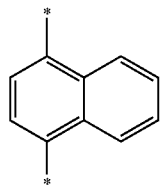 [SMILES: *c1ccc(*)c2ccccc12] | 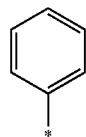 [SMILES: *c1ccccc1] |
| B5-12 | 0 | 1 | — | 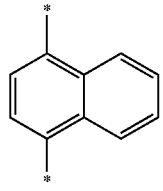 [SMILES: *c1ccc(*)c2ccccc12] | 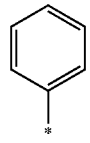 [SMILES: *c1ccccc1] |
| B5-13 | 0 | 1 | — | 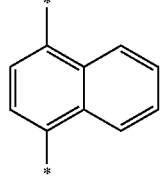 | 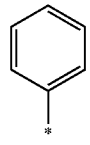 |
| B5-14 | 0 | 1 | — | 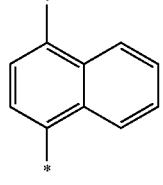 | 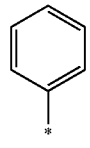 [SMILES: *c1ccccc1] |
| B5-15 | 0 | 1 | — | 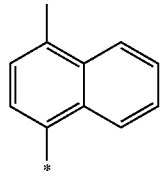 | 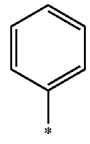 [SMILES: *c1ccccc1] |

-continued
[Compound Group 5]
| | | | | | |
|---|---|---|---|---|---|
| B5-16 | 0 | 1 | — | 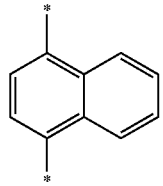 [SMILES: *c1ccc(*)c2ccccc12] | 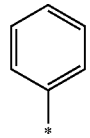 [SMILES: *c1ccccc1] |
| B5-17 | 0 | 1 | — | 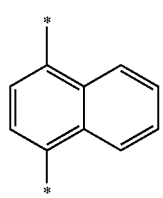 [SMILES: *c1ccc(*)c2ccccc12] | 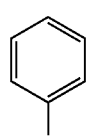 |
| B5-18 | 0 | 1 | — | 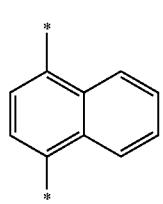 [SMILES: *c1ccc(*)c2ccccc12] | 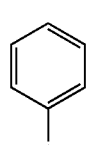 |
| B5-19 | 0 | 1 | — | 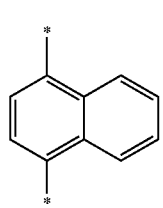 [SMILES: *c1ccc(*)c2ccccc12] | 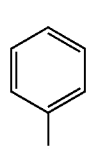 |
| B5-20 | 0 | 1 | — | 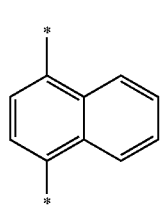 [SMILES: *c1ccc(*)c2ccccc12] | 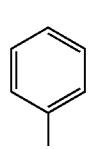 |
| B5-21 | 0 | 1 | — | 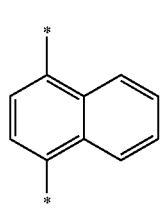 [SMILES: *c1ccc(*)c2ccccc12] | 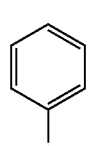 |
| B5-22 | 0 | 1 | — | 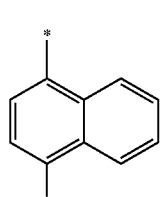 | 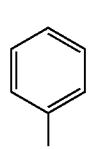 |

-continued
[Compound Group 5]
| | | | | | |
|---|---|---|---|---|---|
| B5-23 | 0 | 1 | — | 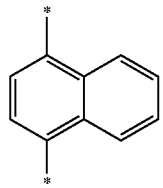 [SMILES: *c1ccc(*)c2ccccc12] | 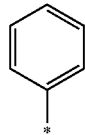 [SMILES: *c1ccccc1] |
| B5-24 | 0 | 1 | — | 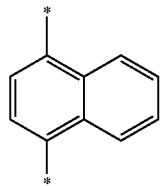 [SMILES: *c1ccc(*)c2ccccc12] | 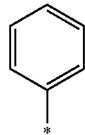 [SMILES: *c1ccccc1] |
| B5-25 | 0 | 1 | — | 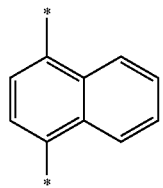 [SMILES: *c1ccc(*)c2ccccc12] | 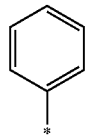 [SMILES: *c1ccccc1] |
| B5-26 | 0 | 1 | — | 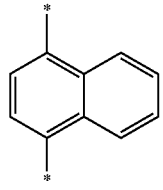 [SMILES: *c1ccc(*)c2ccccc12] | 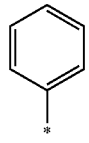 [SMILES: *c1ccccc1] |
| B5-27 | 0 | 1 | — | 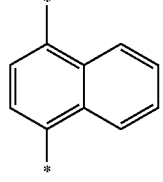 | 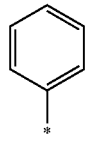 |
| B5-28 | 0 | 1 | — | 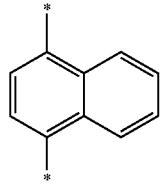 [SMILES: *c1ccc(*)c2ccccc12] | 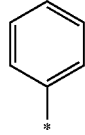 [SMILES: *c1ccccc1] |
| B5-29 | 0 | 1 | — | 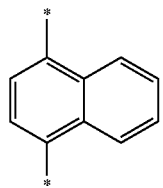 [SMILES: *c1ccc(*)c2ccccc12] | 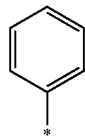 [SMILES: *c1ccccc1] |

-continued
[Compound Group 5]
| B5-30 | 0 | 1 | — | 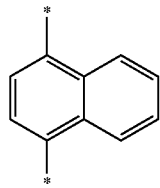 [SMILES: *c1ccc(*)c2ccccc12] | 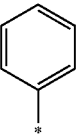 [SMILES: *c1ccccc1] |
| C5-1 | 0 | 1 | — | 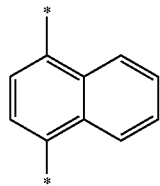 [SMILES: *c1ccc(*)c2ccccc12] | 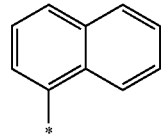 [SMILES: *c1cccc2ccccc12] |
| C5-2 | 0 | 1 | — | 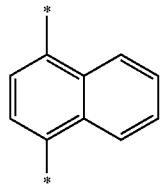 [SMILES: *c1ccc(*)c2ccccc12] | 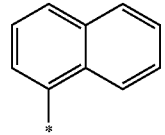 [SMILES: *c1cccc2ccccc12] |
| C5-3 | 0 | 1 | — | 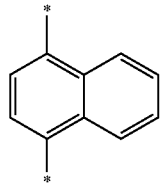 [SMILES: *c1ccc(*)c2ccccc12] | 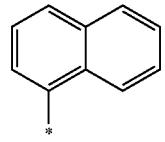 |
| C5-4 | 0 | 1 | — | 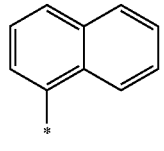 [SMILES: *c1cccc2ccccc12] | 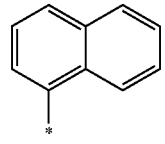 [SMILES: *c1cccc2ccccc12] |
| C5-5 | 0 | 1 | — | 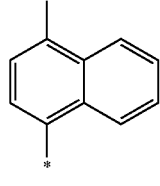 | 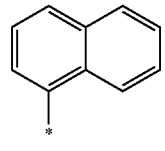 [SMILES: *c1cccc2ccccc12] |
| C5-6 | 0 | 1 | — | 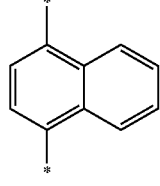 | 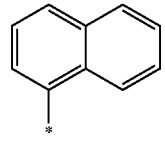 [SMILES: *c1cccc2ccccc12] |

[Compound Group 5]
| | | | | | |
|---|---|---|---|---|---|
| C5-7 | 0 | 1 | — | 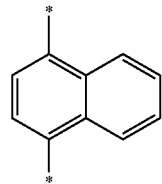 [SMILES: *c1ccc(*)c2ccccc12] | 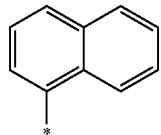 [SMILES: *c1cccc2ccccc12] |
| C5-8 | 0 | 1 | — | 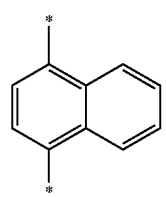 [SMILES: *c1ccc(*)c2ccccc12] | 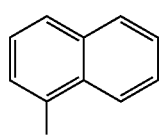 |
| C5-9 | 0 | 1 | — | 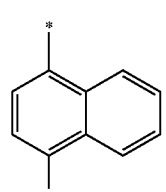 | 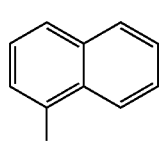 |
| C5-10 | 0 | 1 | — | 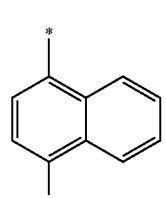 | 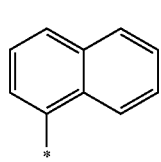 |
| C5-11 | 0 | 1 | — | 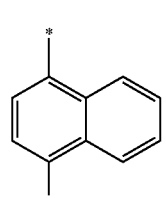 | 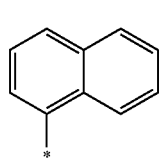 [SMILES: *c1cccc2ccccc12] |
| C5-12 | 0 | 1 | — | 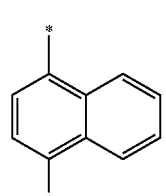 | 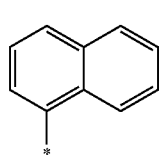 [SMILES: *c1cccc2ccccc12] |
| C5-13 | 0 | 1 | — | 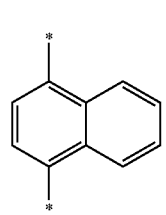 [SMILES: *c1ccc(*)c2ccccc12] | 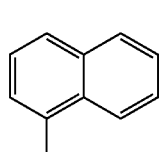 |

-continued
[Compound Group 5]
| | | | | | |
|---|---|---|---|---|---|
| C5-14 | 0 | 1 | — | 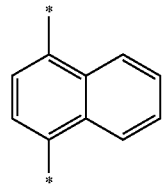 [SMILES: *c1ccc(*)c2ccccc12] | 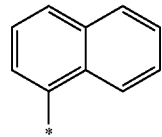 [SMILES: *c1cccc2ccccc12] |
| C5-15 | 0 | 1 | — | 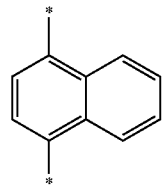 [SMILES: *c1ccc(*)c2ccccc12] | 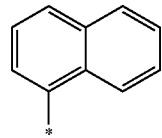 [SMILES: *c1cccc2ccccc12] |
| C5-16 | 0 | 1 | — | 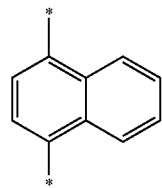 [SMILES: *c1ccc(*)c2ccccc12] | 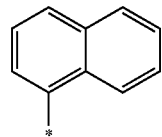 [SMILES: *c1cccc2ccccc12] |
| C5-17 | 0 | 1 | — | 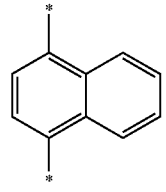 [SMILES: *c1ccc(*)c2ccccc12] | 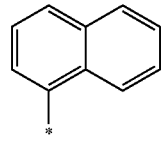 [SMILES: *c1cccc2ccccc12] |
| C5-18 | 0 | 1 | — | 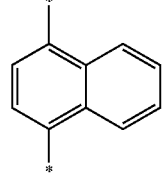 | 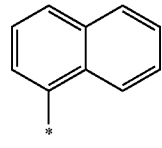 [SMILES: *c1cccc2ccccc12] |
| C5-19 | 0 | 1 | — | 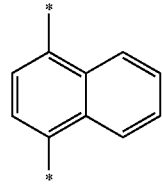 [SMILES: *c1ccc(*)c2ccccc12] | 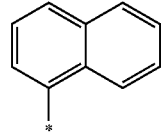 |
| C5-20 | 0 | 1 | — | 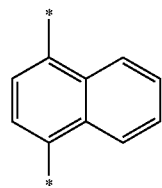 [SMILES: *c1ccc(*)c2ccccc12] | 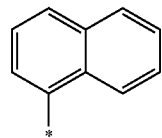 [SMILES: *c1cccc2ccccc12] |

-continued
[Compound Group 5]
| C5-21 | 0 | 1 | — | 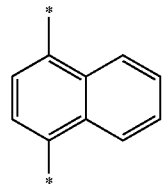 [SMILES: *c1ccc(*)c2ccccc12] | 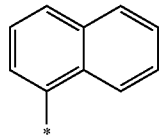 [SMILES: *c1cccc2ccccc12] |
| C5-22 | 0 | 1 | — | 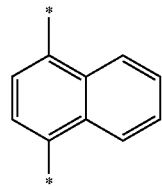 [SMILES: *c1ccc(*)c2ccccc12] | 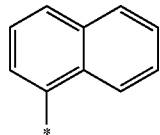 [SMILES: *c1cccc2ccccc12] |
| C5-23 | 0 | 1 | — | 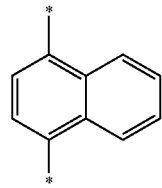 [SMILES: *c1ccc(*)c2ccccc12] | 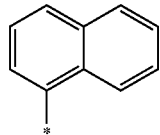 [SMILES: *c1cccc2ccccc12] |
| C5-24 | 0 | 1 | — | 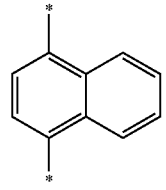 [SMILES: *c1ccc(*)c2ccccc12] | 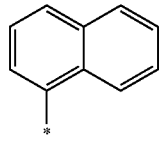 [SMILES: *c1cccc2ccccc12] |
| C5-25 | 0 | 1 | — | 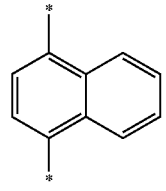 [SMILES: *c1ccc(*)c2ccccc12] | 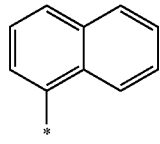 [SMILES: *c1cccc2ccccc12] |
| C5-26 | 0 | 1 | — | 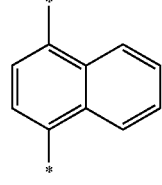 | 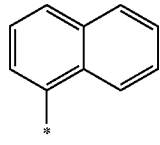 [SMILES: *c1cccc2ccccc12] |
| C5-27 | 0 | 1 | — | 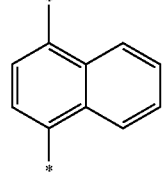 | 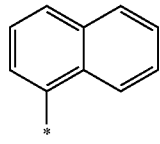 [SMILES: *c1cccc2ccccc12] |

-continued
| [Compound Group 5] | | | | | | |
|---|---|---|---|---|---|---|
| C5-28 | 0 | 1 | — | 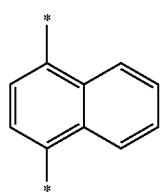 [SMILES: *c1ccc(*)c2ccccc12] | | 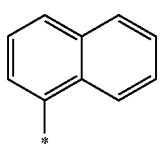 [SMILES: *c1cccc2ccccc12] |
| C5-29 | 0 | 1 | — | 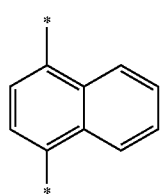 [SMILES: *c1ccc(*)c2ccccc12] | | 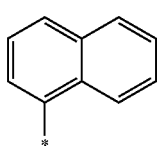 [SMILES: *c1cccc2ccccc12] |
| C5-30 | 0 | 1 | — | 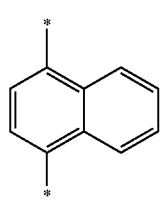 [SMILES: *c1ccc(*)c2ccccc12] | | 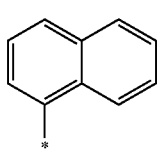 |
| D5-1 | 0 | 1 | — | 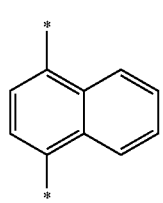 [SMILES: *c1ccc(*)c2ccccc12] | | 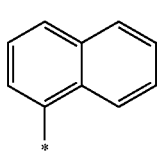 [SMILES: *c1cccc2ccccc12] |
| D5-2 | 0 | 1 | — | 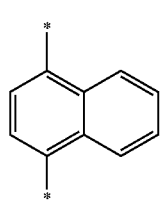 [SMILES: *c1ccc(*)c2ccccc12] | | 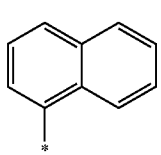 [SMILES: *c1cccc2ccccc12] |
| D5-3 | 0 | 1 | — | 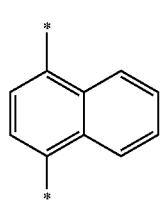 [SMILES: *c1ccc(*)c2ccccc12] | | 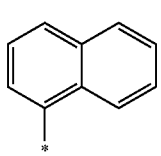 [SMILES: *c1cccc2ccccc12] |
| D5-4 | 0 | 1 | — | 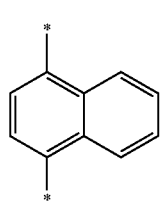 [SMILES: *c1ccc(*)c2ccccc12] | | 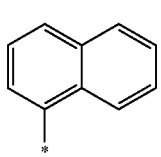 [SMILES: *c1cccc2ccccc12] |

-continued
| [Compound Group 5] | | | | | |
|---|---|---|---|---|---|
| D5-5 | 0 | 1 | — | 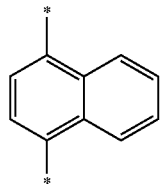 [SMILES: *c1ccc(*)c2ccccc12] | 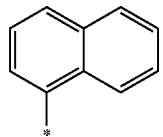 [SMILES: *c1cccc2ccccc12] |
| D5-6 | 0 | 1 | — | 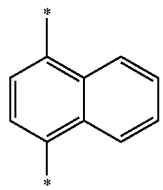 [SMILES: *c1ccc(*)c2ccccc12] | 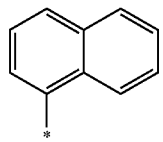 [SMILES: *c1cccc2ccccc12] |
| D5-7 | 0 | 1 | — | 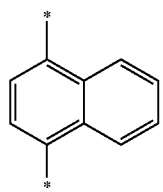 [SMILES: *c1ccc(*)c2ccccc12] | 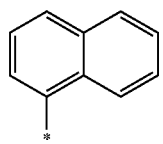 |
| D5-8 | 0 | 1 | — | 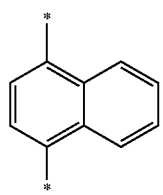 | 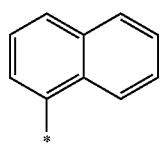 |
| D5-9 | 0 | 1 | — | 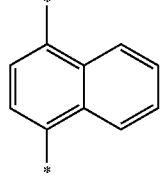 | 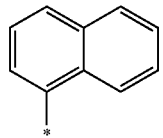 [SMILES: *c1cccc2ccccc12] |
| D5-10 | 0 | 1 | — | 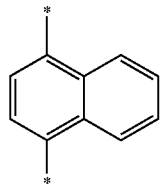 [SMILES: *c1ccc(*)c2ccccc12] | 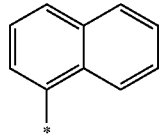 [SMILES: *c1cccc2ccccc12] |
| D5-11 | 0 | 1 | — | 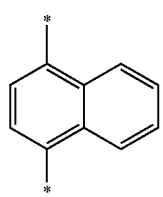 [SMILES: *c1ccc(*)c2ccccc12] | 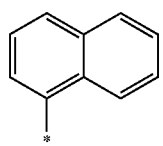 [SMILES: *c1cccc2ccccc12] |

-continued
[Compound Group 5]
| | | | | | |
|---|---|---|---|---|---|
| D5-12 | 0 | 1 | — | 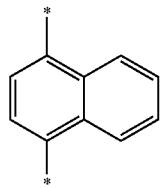 [SMILES: *c1ccc(*)c2ccccc12] | 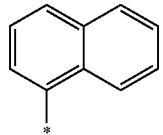 [SMILES: *c1cccc2ccccc12] |
| D5-13 | 0 | 1 | — | 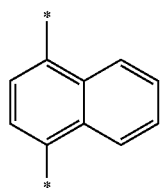 [SMILES: *c1ccc(*)c2ccccc12] | 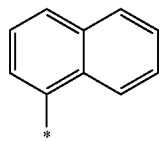 [SMILES: *c1cccc2ccccc12] |
| D5-14 | 0 | 1 | — | 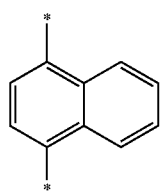 [SMILES: *c1ccc(*)c2ccccc12] | 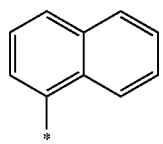 [SMILES: *c1cccc2ccccc12] |
| D5-15 | 0 | 1 | — | 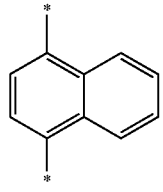 [SMILES: *c1ccc(*)c2ccccc12] | 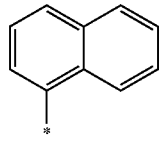 [SMILES: *c1cccc2ccccc12] |
| D5-16 | 0 | 1 | — | 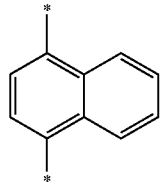 [SMILES: *c1ccc(*)c2ccccc12] | 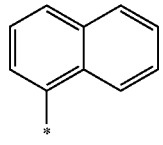 [SMILES: *c1cccc2ccccc12] |
| D5-17 | 0 | 1 | — | 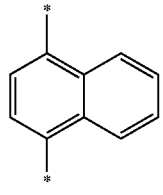 [SMILES: *c1ccc(*)c2ccccc12] | 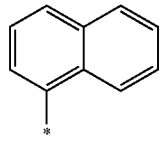 [SMILES: *c1cccc2ccccc12] |
| D5-18 | 0 | 1 | — | 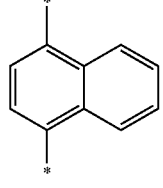 | 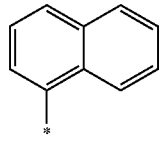 [SMILES: *c1cccc2ccccc12] |

[Compound Group 5]
| | | | | | |
|---|---|---|---|---|---|
| D5-19 | 0 | 1 | — | 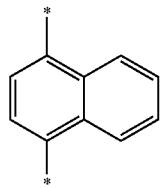 [SMILES: *c1ccc(*)c2ccccc12] | 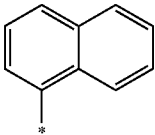 [SMILES: *c1cccc2ccccc12] |
| D5-20 | 0 | 1 | — | 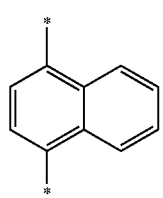 [SMILES: *c1ccc(*)c2ccccc12] | 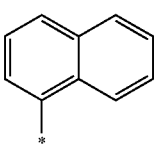 [SMILES: *c1cccc2ccccc12] |
| D5-21 | 0 | 1 | — | 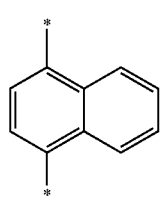 [SMILES: *c1ccc(*)c2ccccc12] | 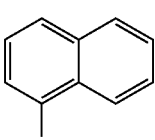 |
| D5-22 | 0 | 1 | — | 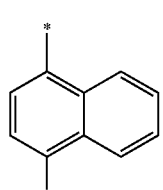 | 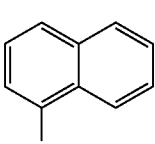 |
| D5-23 | 0 | 1 | — | 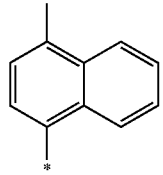 | 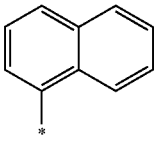 [SMILES: *c1cccc2ccccc12] |
| D5-24 | 0 | 1 | — | 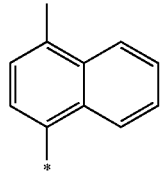 | 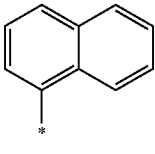 [SMILES: *c1cccc2ccccc12] |
| D5-25 | 0 | 1 | — | 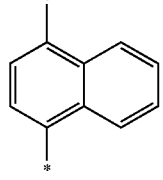 | 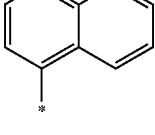 |

-continued
[Compound Group 5]
| D5-26 | 0 | 1 | — | 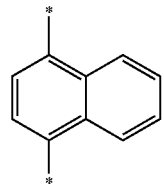 [SMILES: *c1ccc(*)c2ccccc12] | 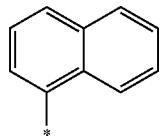 [SMILES: *c1cccc2ccccc12] |
| D5-27 | 0 | 1 | — | 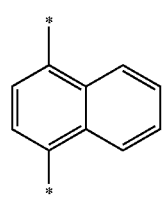 [SMILES: *c1ccc(*)c2ccccc12] | 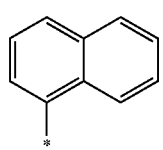 [SMILES: *c1cccc2ccccc12] |
| D5-28 | 0 | 1 | — | 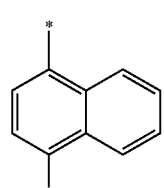 | 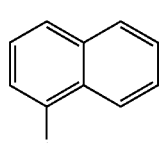 |
| D5-29 | 0 | 1 | — | 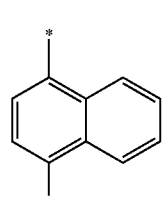 | 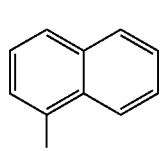 |
| D5-30 | 0 | 1 | — | 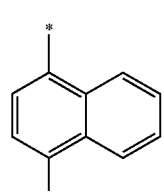 | 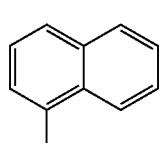 |
| E5-1 | 0 | 1 | — | 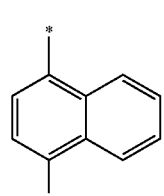 | 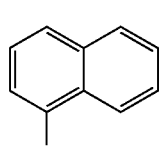 |
| E5-2 | 0 | 1 | — | 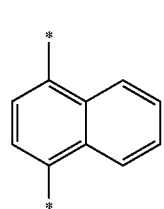 [SMILES: *c1ccc(*)c2ccccc12] | 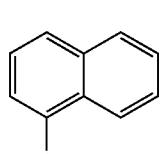 |

-continued
| [Compound Group 5] | | | |
|---|---|---|---|
| Ar₂ | Ar₃ | Ar₄ | 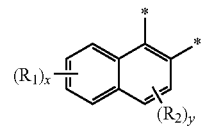 |
| A5-1 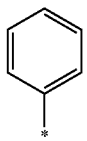 | 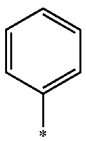 | 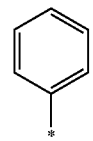 | 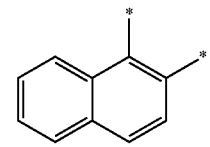 [SMILES: *c1ccc2ccccc2c1*] |
| A5-2 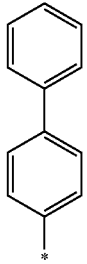 [SMILES: *c1ccc(-c2ccccc2)cc1] | 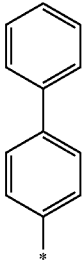 [SMILES: *c1ccc(-c2ccccc2)cc1] | 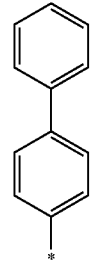 | 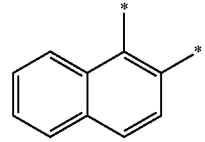 [SMILES: *c1ccc2ccccc2c1*] |
| A5-3 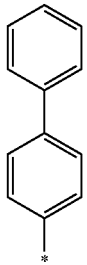 [SMILES: *c1ccc(-c2ccccc2)cc1] | 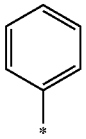 [SMILES: *c1ccccc1] | 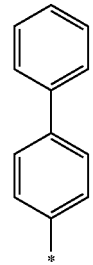 | 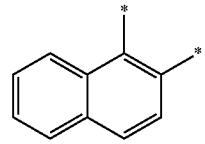 |
| A5-4 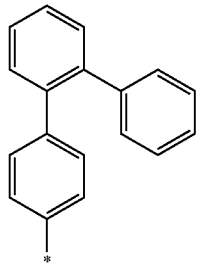 [SMILES: *c1ccc(-c2ccccc2-c2ccccc2)cc1] | 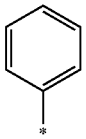 [SMILES: *c1ccccc1] | 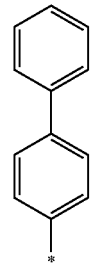 | 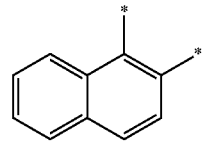 [SMILES: *c1ccc2ccccc2c1*] |
| A5-5 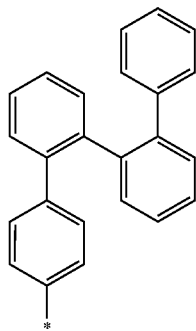 [SMILES: *c1ccc(-c2ccccc2-c2ccccc2-c2ccccc2)cc1] | 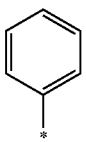 | 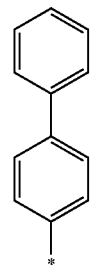 | 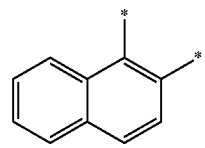 |

-continued
[Compound Group 5]
A5-6 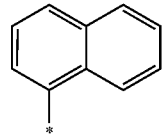 [SMILES: *c1cccc2ccccc12] 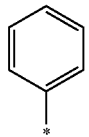 [SMILES: *c1ccccc1] 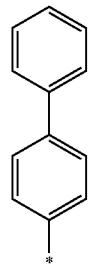 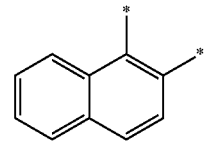
A5-7 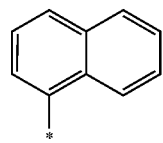 [SMILES: *c1cccc2ccccc12] 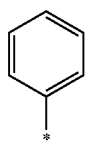 [SMILES: *c1ccccc1] 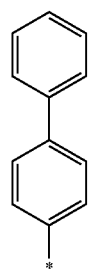 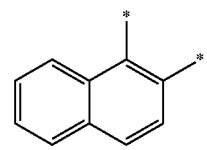
A5-8 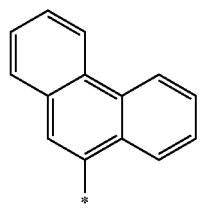 [SMILES: *c1cc2ccccc2c2ccccc12] 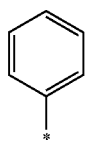 [SMILES: *c1ccccc1] 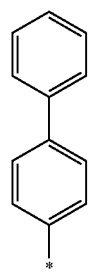 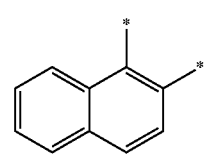
A5-9 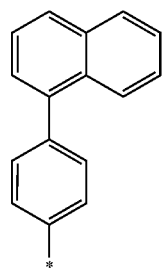 [SMILES: *c1ccc(-c2cccc3ccccc23)cc1] 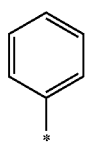 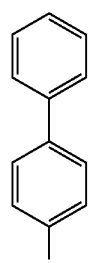 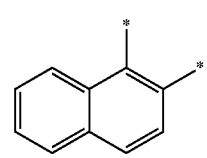
A5-10 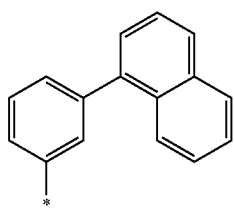 [SMILES: *c1cccc(-c2cccc3ccccc23)c1] 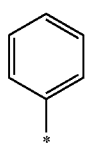 [SMILES: *c1ccccc1] 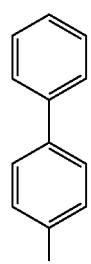 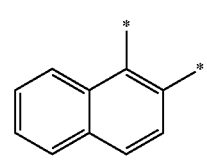

[Compound Group 5]
A5-11 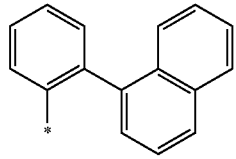 [SMILES: *c1ccccc1-c1cccc2ccccc12] 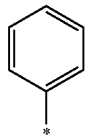 [SMILES: *c1ccccc1] 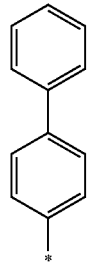 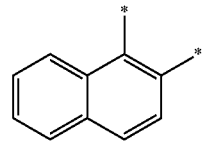
A5-12 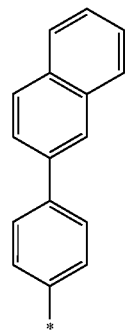 [SMILES: *c1ccc(-c2ccc3ccccc3c2)cc1] 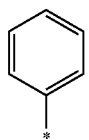 [SMILES: *c1ccccc1] 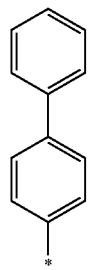 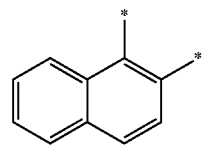
A5-13 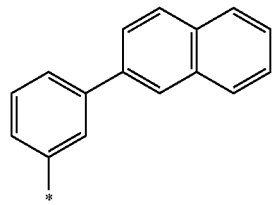 [SMILES: *c1cccc(-c2ccc3ccccc3c2)c1] 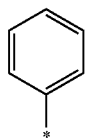 [SMILES: *c1ccccc1] 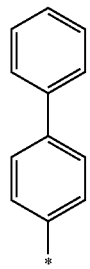 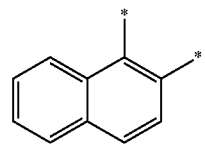
A5-14 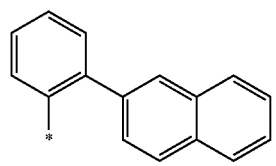 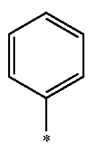 [SMILES: *c1ccccc1] 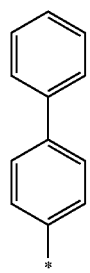 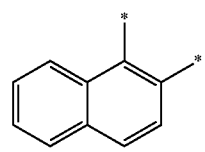
A5-15 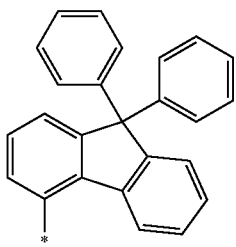 [SMILES: *c1cccc2c1-c1ccccc1C2(c1ccccc1)c1ccccc1] 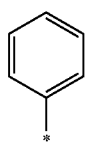 [SMILES: *c1ccccc1] 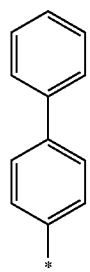 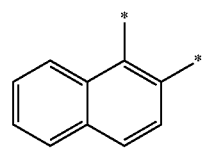

[Compound Group 5]
A5-16 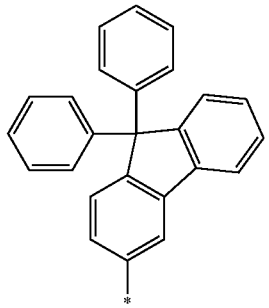 [SMILES: *c1ccc2c(c1)-c1ccccc1C2(c1ccccc1)c1ccccc1] 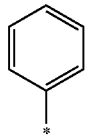 [SMILES: *c1ccccc1] 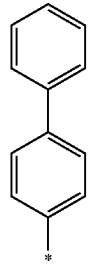 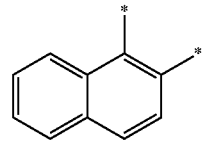
A5-17 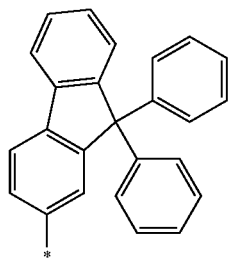 [SMILES: *c1ccc2c(c1)C(c1ccccc1)(c1ccccc1)c1ccccc1-2] 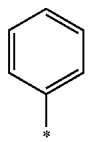 [SMILES: *c1ccccc1] 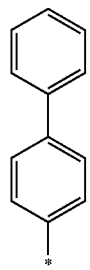 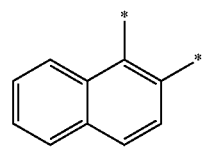
A5-18 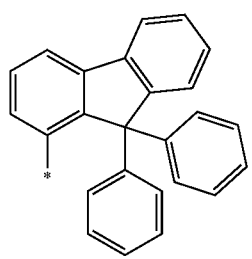 [SMILES: *c1cccc2c1C(c1ccccc1)(c1ccccc1)c1ccccc1-2] 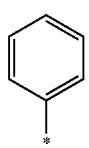 [SMILES: *c1ccccc1] 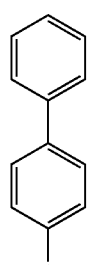 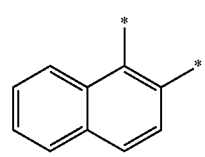
A5-19 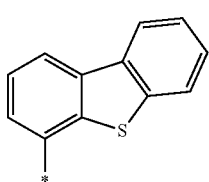 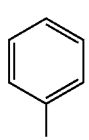 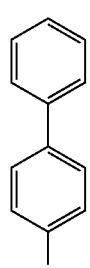 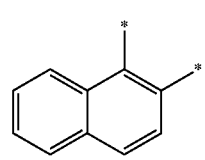 [SMILES: *c1ccc2ccccc2c1*]
A5-20 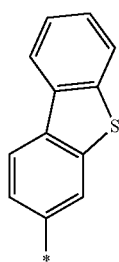 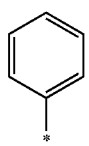 [SMILES: *c1ccccc1] 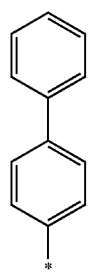 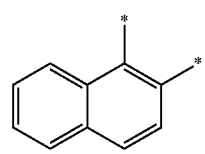

-continued
[Compound Group 5]
A5-21 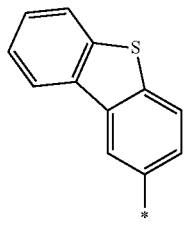 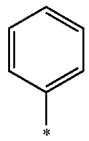 [SMILES: *c1ccccc1] 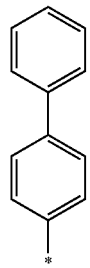 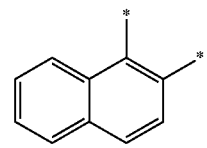
A5-22 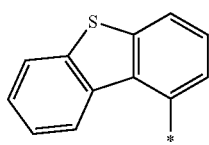 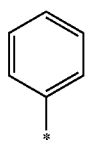 [SMILES: *c1ccccc1] 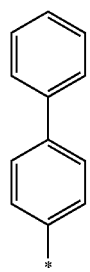 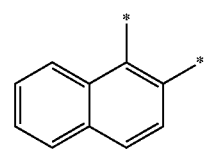
A5-23 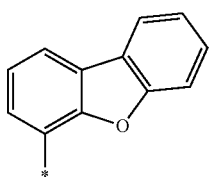 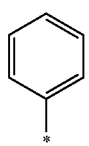 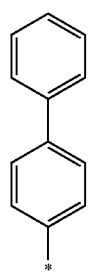 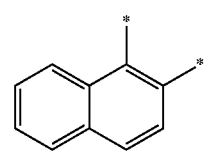
A5-24 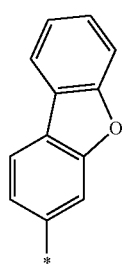 [SMILES: *c1ccc2c(c1)oc1ccccc12] 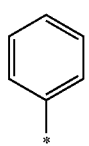 [SMILES: *c1ccccc1] 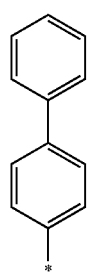 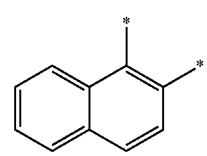
A5-25 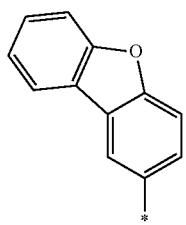 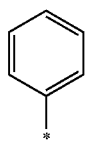 [SMILES: *c1ccccc1] 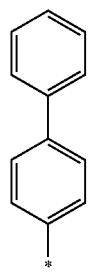 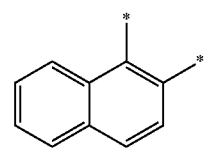

[Compound Group 5]
A5-26 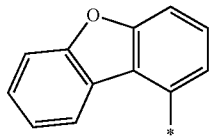 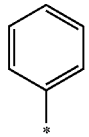 [SMILES: *c1ccccc1] 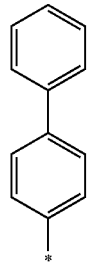 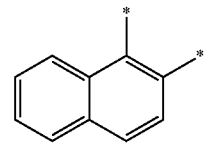
A5-27 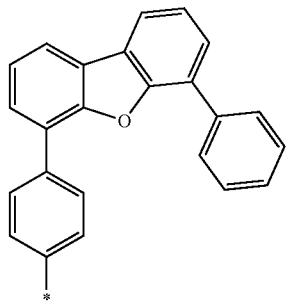 [SMILES: *c1ccc(-c2cccc3c2oc2c(-c4ccccc4)cccc23)cc1] 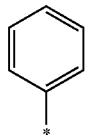 [SMILES: *c1ccccc1] 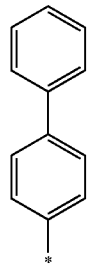 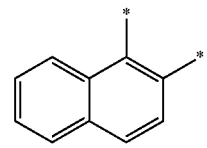
A5-28 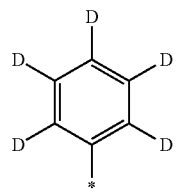 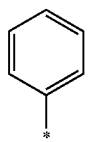 [SMILES: *c1ccccc1] 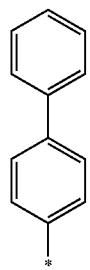 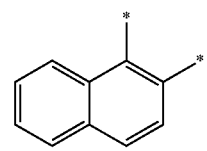
A5-29 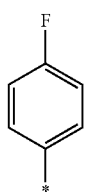 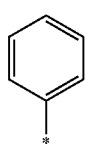 [SMILES: *c1ccccc1] 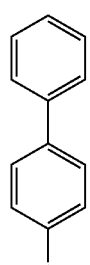 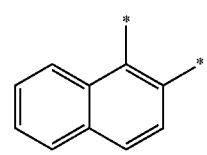 [SMILES: *c1ccc2ccccc2c1*]
A5-30 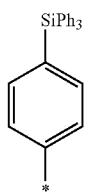 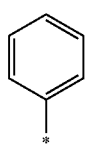 [SMILES: *c1ccccc1] 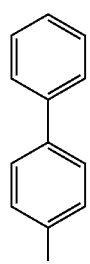 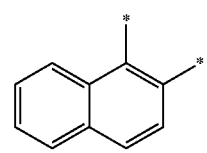 [SMILES: *c1ccc2ccccc2c1*]

-continued
[Compound Group 5]
| | | | | |
|---|---|---|---|---|
| A5-31 | 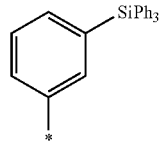 | 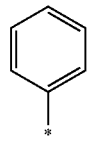 | 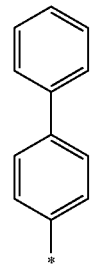 | 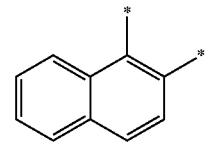 [SMILES: *c1ccc2ccccc2c1*] |
| A5-32 | 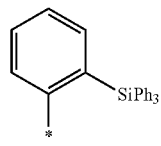 | 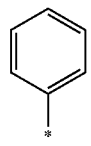 [SMILES: *c1ccccc1] | 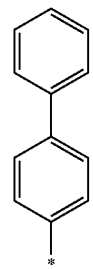 | 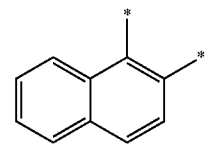 |
| A5-33 | 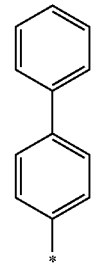 | 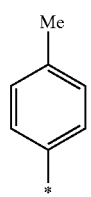 | 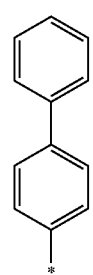 | 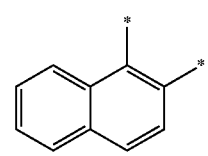 [SMILES: *c1ccc2ccccc2c1*] |
| B5-1 | 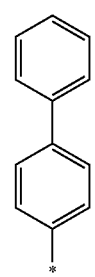 [SMILES: *c1ccc(-c2ccccc2)cc1] | 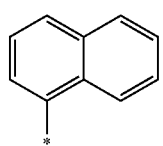 [SMILES: *c1cccc2ccccc12] | 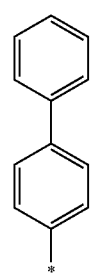 | 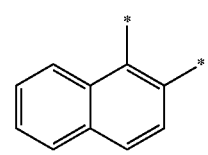 [SMILES: *c1ccc2ccccc2c1*] |
| B5-2 | 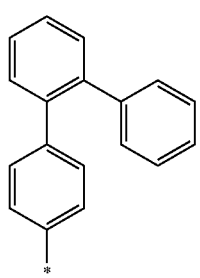 [SMILES: *c1ccc(-c2ccccc2-c2ccccc2)cc1] | 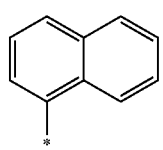 [SMILES: *c1cccc2ccccc12] | 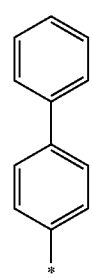 | 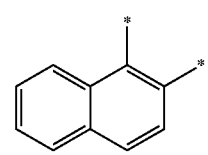 [SMILES: *c1ccc2ccccc2c1*] |

-continued
[Compound Group 5]
B5-3 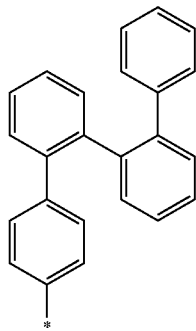 [SMILES: *c1ccc(-c2ccccc2-c2ccccc2-c2ccccc2)cc1] 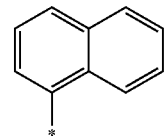 [SMILES: *c1cccc2ccccc12] 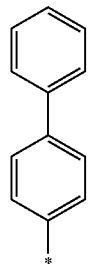 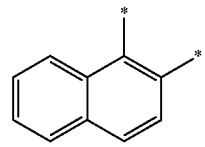 [SMILES: *c1ccc2ccccc2c1*]
B5-4 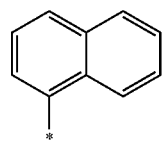 [SMILES: *c1cccc2ccccc12] 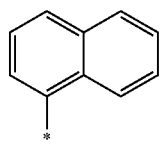 [SMILES: *c1cccc2ccccc12] 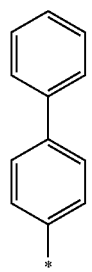 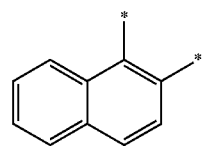 [SMILES: *c1ccc2ccccc2c1*]
B5-5 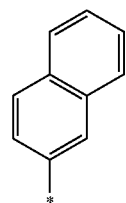 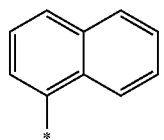 [SMILES: *c1cccc2ccccc12] 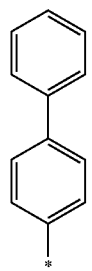 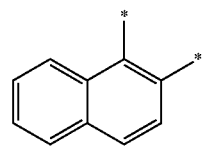 [SMILES: *c1ccc2ccccc2c1*]
B5-6 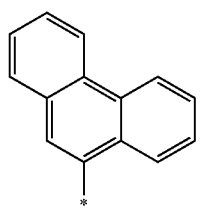 [SMILES: *c1cc2ccccc2c2ccccc12] 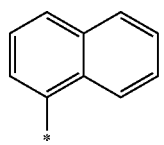 [SMILES: *c1cccc2ccccc12] 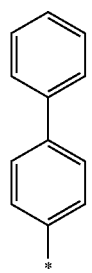 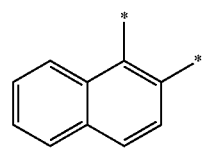 [SMILES: *c1ccc2ccccc2c1*]
B5-7 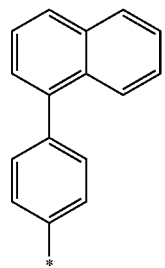 [SMILES: *c1ccc(-c2cccc3ccccc23)cc1] 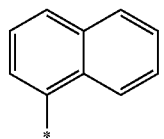 [SMILES: *c1cccc2ccccc12] 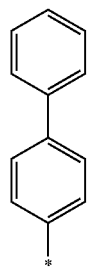 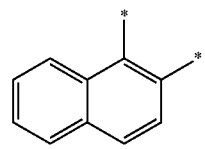

[Compound Group 5]
B5-8 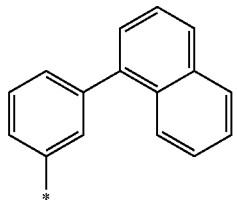 [SMILES: *c1cccc(-c2cccc3ccccc23)c1] 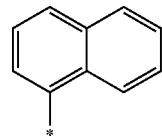 [SMILES: *c1cccc2ccccc12] 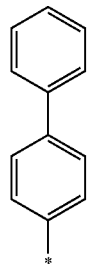 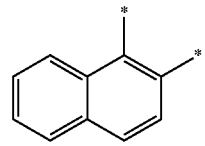 [SMILES: *c1ccc2ccccc2c1*]
B5-9 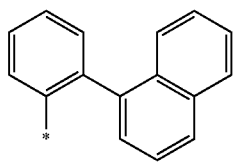 [SMILES: *c1ccccc1-c1cccc2ccccc12] 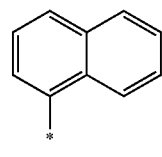 [SMILES: *c1cccc2ccccc12] 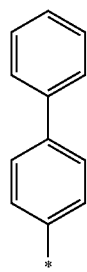 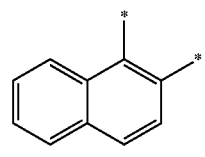 [SMILES: *c1ccc2ccccc2c1*]
B5-10 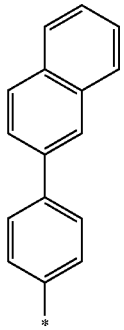 [SMILES: *c1ccc(-c2ccc3ccccc3c2)cc1] 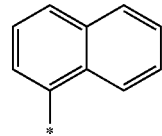 [SMILES: *c1cccc2ccccc12] 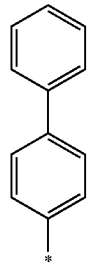 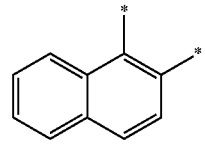 [SMILES: *c1ccc2ccccc2c1*]
B5-11 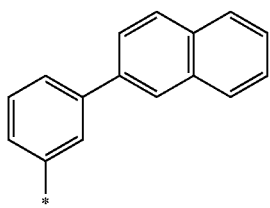 [SMILES: *c1cccc(-c2ccc3ccccc3c2)c1] 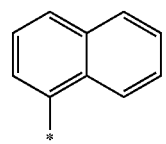 [SMILES: *c1cccc2ccccc12] 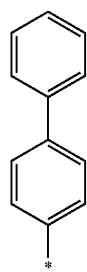 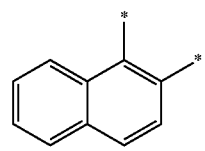
B5-12 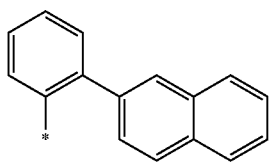 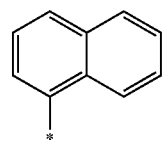 [SMILES: *c1cccc2ccccc12] 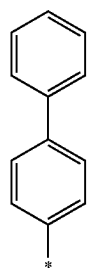 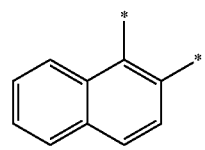 [SMILES: *c1ccc2ccccc2c1*]

-continued
[Compound Group 5]
B5-13 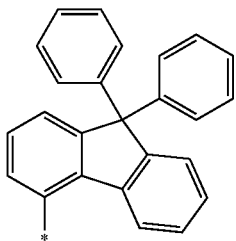 [SMILES: *c1cccc2c1-c1ccccc1C2(c1ccccc1)c1ccccc1] 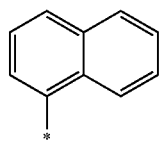 [SMILES: *c1cccc2ccccc12] 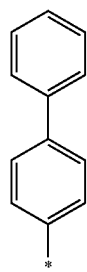 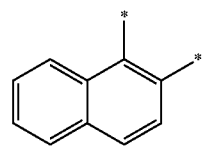 [SMILES: *c1ccc2ccccc2c1*]
B5-14 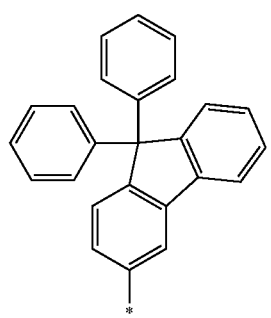 [SMILES: *c1ccc2c(c1)-c1ccccc1C2(c1ccccc1)c1ccccc1] 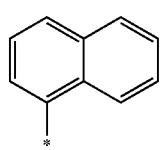 [SMILES: *c1cccc2ccccc12] 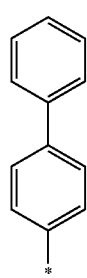 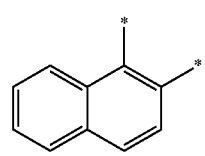 [SMILES: *c1ccc2ccccc2c1*]
B5-15 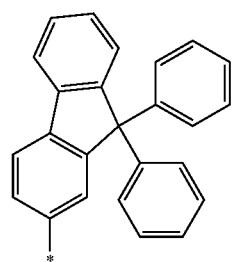 [SMILES: *c1ccc2c(c1)C(c1ccccc1)(c1ccccc1)c1ccccc1-2] 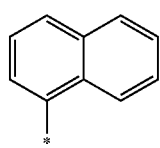 [SMILES: *c1cccc2ccccc12] 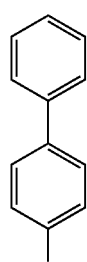 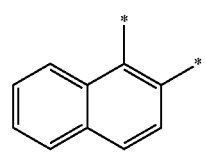 [SMILES: *c1ccc2ccccc2c1*]
B5-16 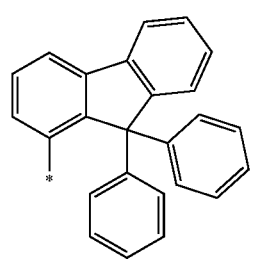 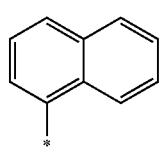 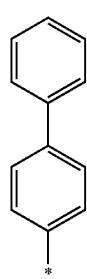 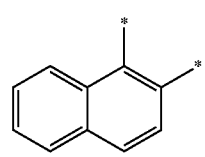
B5-17 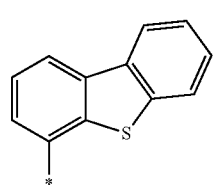 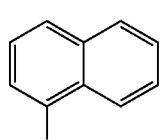 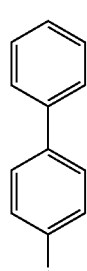 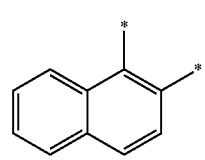

-continued
[Compound Group 5]
B5-18 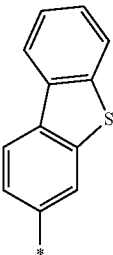 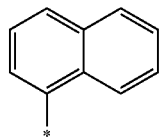 [SMILES: *c1cccc2ccccc12] 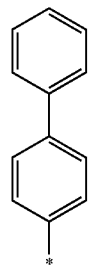 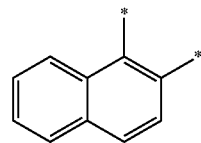 [SMILES: *c1ccc2ccccc2c1*]
B5-19 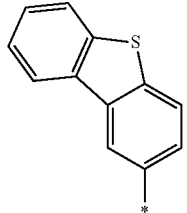 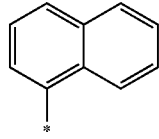 [SMILES: *c1cccc2ccccc12] 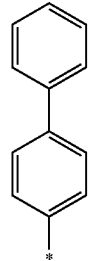 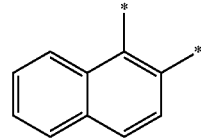 [SMILES: *c1ccc2ccccc2c1*]
B5-20 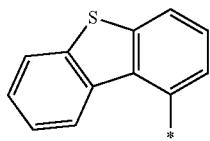 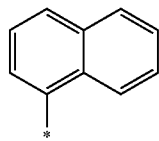 [SMILES: *c1cccc2ccccc12] 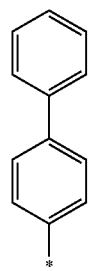 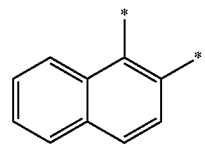
B5-21 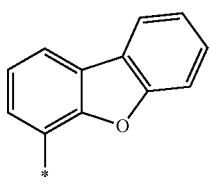 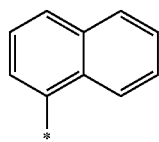 [SMILES: *c1cccc2ccccc12] 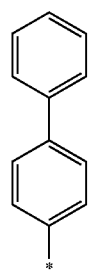 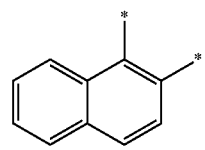
B5-22 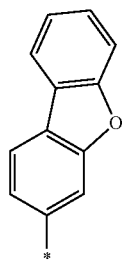 [SMILES: *c1ccc2c(c1)oc1ccccc12] 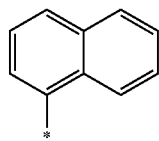 [SMILES: *c1cccc2ccccc12] 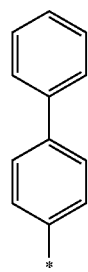 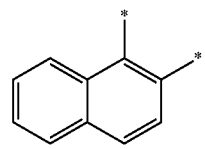

[Compound Group 5]
B5-23 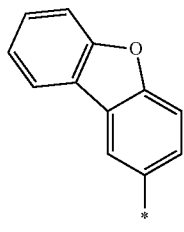 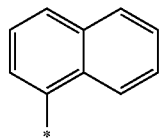 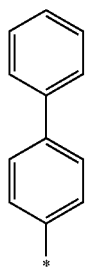 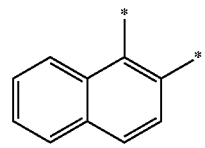
B5-24 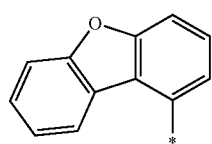 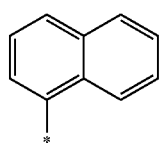 [SMILES: *c1cccc2ccccc12] 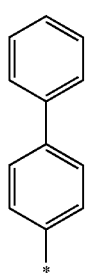 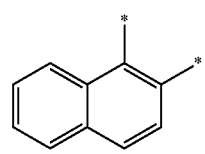
B5-25 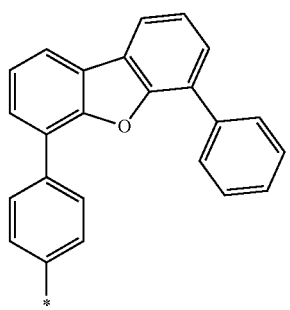 [SMILES: *c1ccc(-c2cccc3c2oc2c(-c4ccccc4)cccc23)cc1] 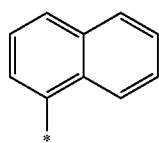 [SMILES: *c1cccc2ccccc12] 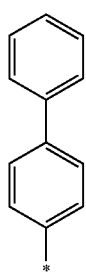 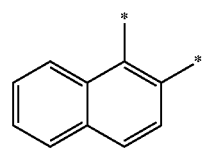
B5-26 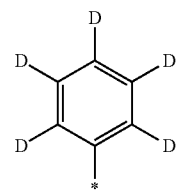 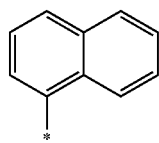 [SMILES: *c1cccc2ccccc12] 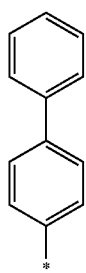 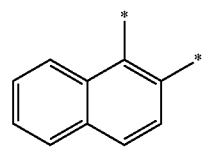
B5-27 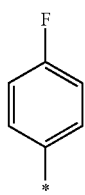 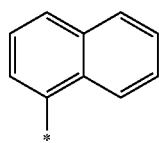 [SMILES: *c1cccc2ccccc12] 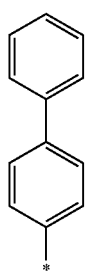 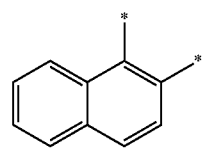

-continued
[Compound Group 5]
B5-28 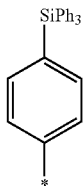 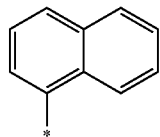 [SMILES: *c1cccc2ccccc12] 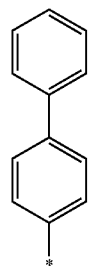 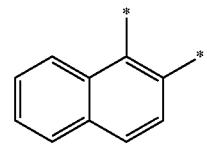
B5-29 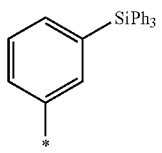 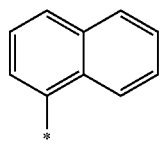 [SMILES: *c1cccc2ccccc12] 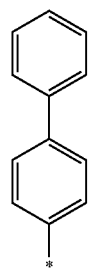 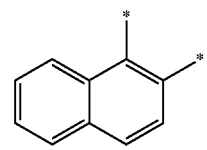
B5-30 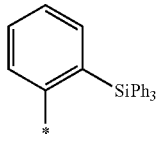 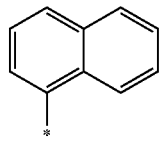 [SMILES: *c1cccc2ccccc12] 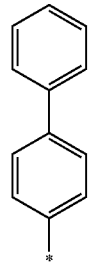 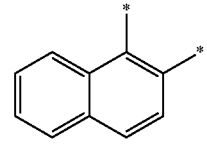
C5-1 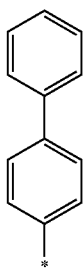 [SMILES: *c1ccc(-c2ccccc2)cc1] 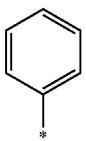 [SMILES: *c1ccccc1] 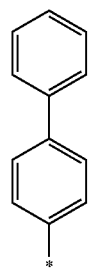 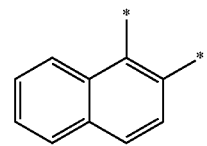
C5-2 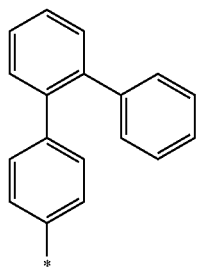 [SMILES: *c1ccc(-c2ccccc2-c2ccccc2)cc1] 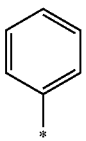 [SMILES: *c1ccccc1] 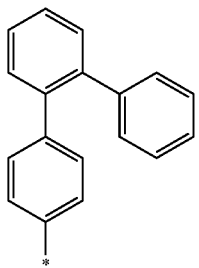 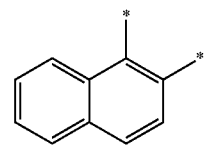

[Compound Group 5]
C5-3 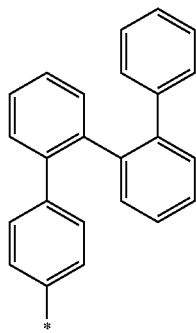 [SMILES: *c1ccc(-c2ccccc2-c2ccccc2-c2ccccc2)cc1] 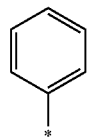 [SMILES: *c1ccccc1] 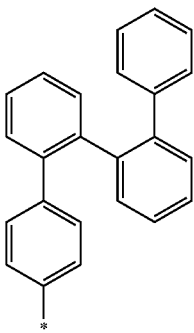 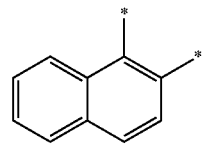 [SMILES: *c1ccc2ccccc2c1*]
C5-4 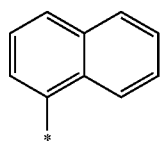 [SMILES: *c1cccc2ccccc12] 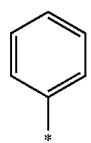 [SMILES: *c1ccccc1] 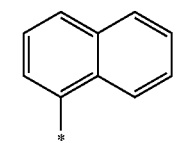 [SMILES: *c1cccc2ccccc12] 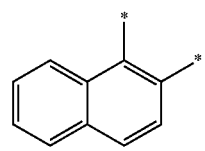
C5-5 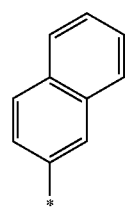 [SMILES: *c1ccc2ccccc2c1] 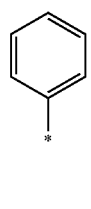 [SMILES: *c1ccccc1] 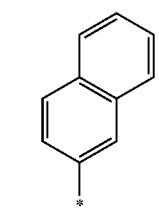 [SMILES: *c1ccc2ccccc2c1] 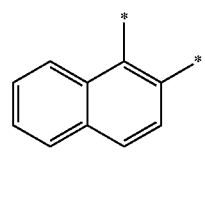 [SMILES: *c1ccc2ccccc2c1*]
C5-6 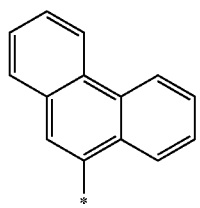 [SMILES: *c1cc2ccccc2c2ccccc12] 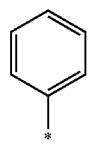 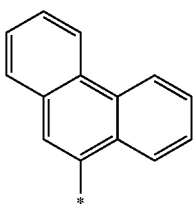 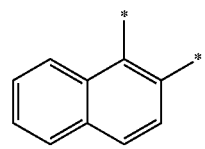 [SMILES: *c1ccc2ccccc2c1*]
C5-7 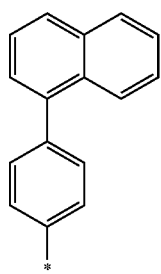 [SMILES: *c1ccc(-c2cccc3ccccc23)cc1] 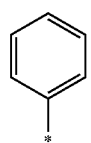 [SMILES: *c1ccccc1] 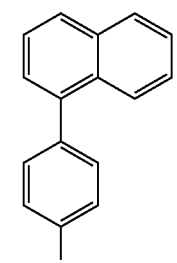 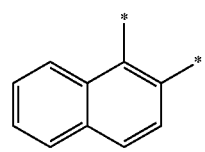 [SMILES: *c1ccc2ccccc2c1*]
C5-8 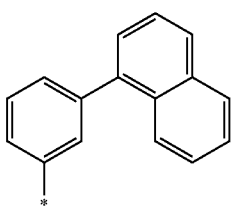 [SMILES: *c1cccc(-c2cccc3ccccc23)c1] 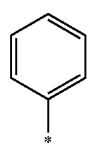 [SMILES: *c1ccccc1] 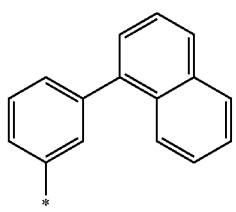 [SMILES: *c1cccc(-c2cccc3ccccc23)c1] 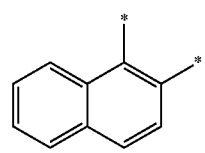 [SMILES: *c1ccc2ccccc2c1*]

[Compound Group 5]
C5-9 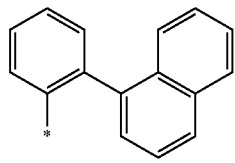 [SMILES: *c1ccccc1-c1cccc2ccccc12] 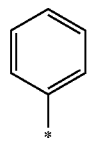 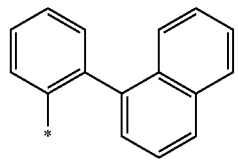 [SMILES: *c1ccccc1-c1cccc2ccccc12] 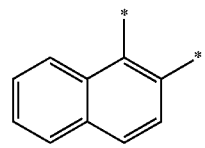 [SMILES: *c1ccc2ccccc2c1*]
C5-10 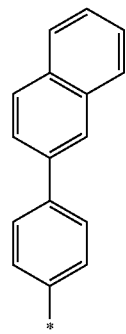 [SMILES: *c1ccc(-c2ccc3ccccc3c2)cc1] 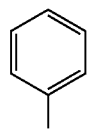 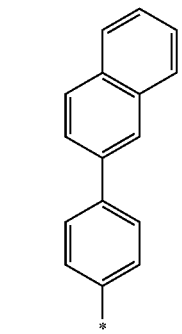 [SMILES: *c1ccc(-c2ccc3ccccc3c2)cc1] 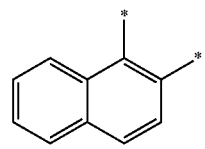
C5-11 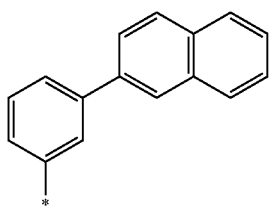 [SMILES: *c1cccc(-c2ccc3ccccc3c2)c1] 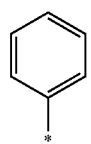 [SMILES: *c1ccccc1] 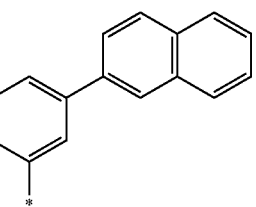 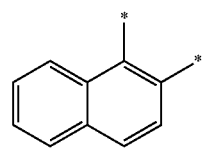 [SMILES: *c1ccc2ccccc2c1*]
C5-12 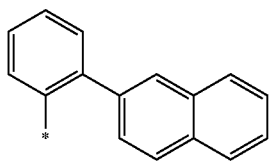 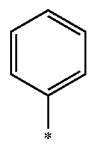 [SMILES: *c1ccccc1] 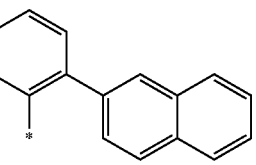 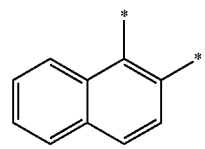 [SMILES: *c1ccc2ccccc2c1*]
C5-13 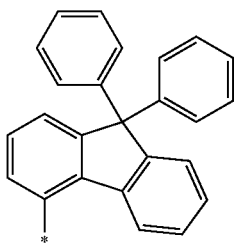 [SMILES: *c1cccc2c1-c1ccccc1C2(c1ccccc1)c1ccccc1] 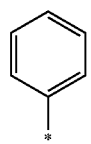 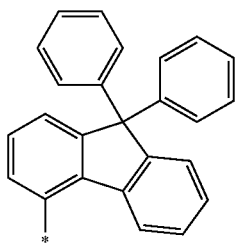 [SMILES: *c1cccc2c1-c1ccccc1C2(c1ccccc1)c1ccccc1] 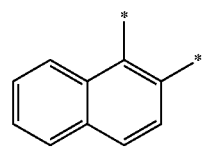 [SMILES: *c1ccc2ccccc2c1*]
C5-14 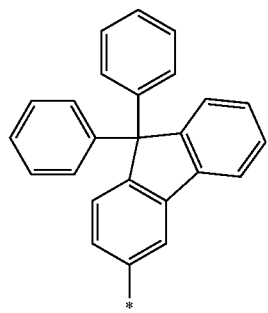 [SMILES: *c1ccc2c(c1)-c1ccccc1C2(c1ccccc1)c1ccccc1] 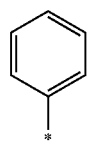 [SMILES: *c1ccccc1] 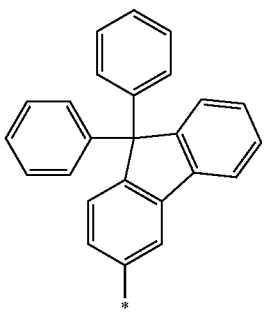 [SMILES: *c1ccc2c(c1)-c1ccccc1C2(c1ccccc1)c1ccccc1] 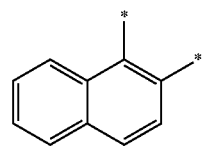 [SMILES: *c1ccc2ccccc2c1*]

[Compound Group 5]
C5-15 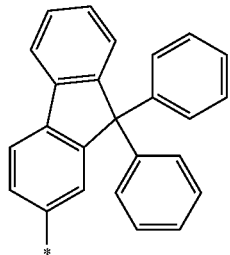 [SMILES: *c1ccc2c(c1)C(c1ccccc1)(c1ccccc1)c1ccccc1-2] 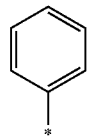 [SMILES: *c1ccccc1] 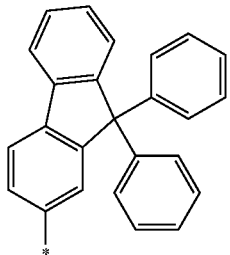 [SMILES: *c1ccc2c(c1)C(c1ccccc1)(c1ccccc1)c1ccccc1-2] 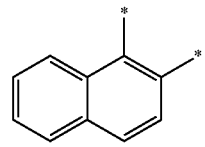 [SMILES: *c1ccc2ccccc2c1*]
C5-16 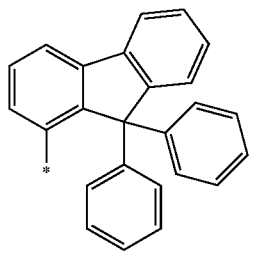 [SMILES: *c1cccc2c1C(c1ccccc1)(c1ccccc1)c1ccccc1-2] 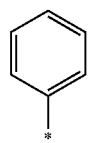 [SMILES: *c1ccccc1] 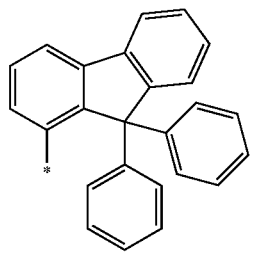 [SMILES: *c1cccc2c1C(c1ccccc1)(c1ccccc1)c1ccccc1-2] 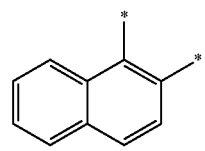 [SMILES: *c1ccc2ccccc2c1*]
C5-17 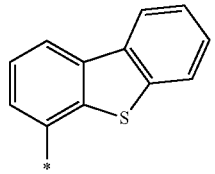 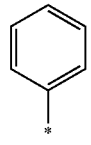 [SMILES: *c1ccccc1] 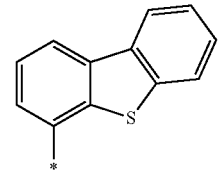 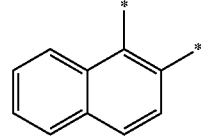 [SMILES: *c1ccc2ccccc2c1*]
C5-18 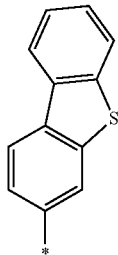 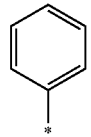 [SMILES: *c1ccccc1] 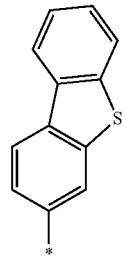 [SMILES: *c1ccc2c(c1)sc1ccccc12] 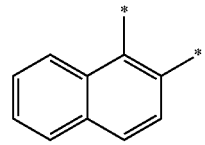 [SMILES: *c1ccc2ccccc2c1*]
C5-19 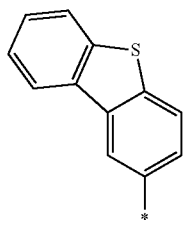 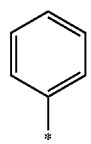 [SMILES: *c1ccccc1] 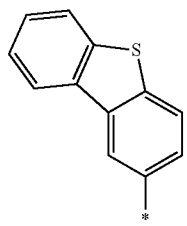 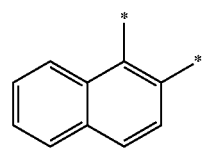 [SMILES: *c1ccc2ccccc2c1*]
C5-20 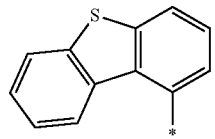 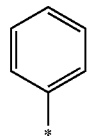 [SMILES: *c1ccccc1] 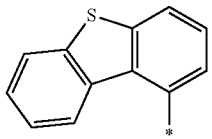 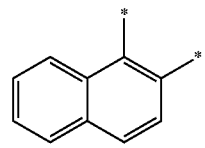

-continued
[Compound Group 5]
| | | | | |
|---|---|---|---|---|
| C5-21 | 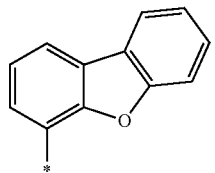 | 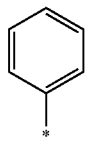 [SMILES: *c1ccccc1] | 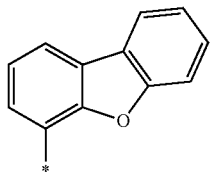 | 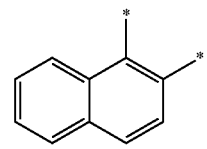 [SMILES: *c1ccc2ccccc2c1*] |
| C5-22 | 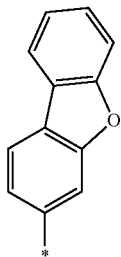 [SMILES: *c1ccc2c(c1)oc1ccccc12] | 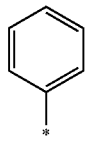 [SMILES: *c1ccccc1] | 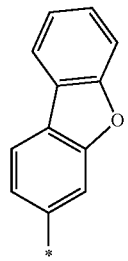 | 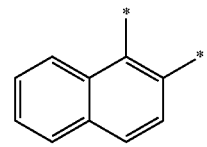 [SMILES: *c1ccc2ccccc2c1*] |
| C5-23 | 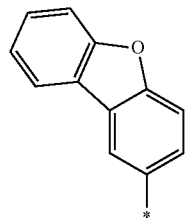 | 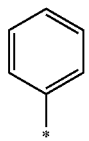 [SMILES: *c1ccccc1] | 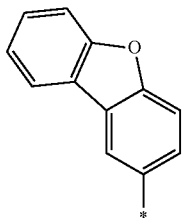 | 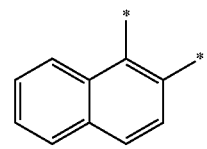 [SMILES: *c1ccc2ccccc2c1*] |
| C5-24 | 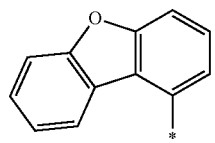 [SMILES: *c1cccc2oc3ccccc3c12] | 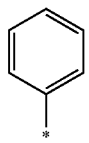 [SMILES: *c1ccccc1] | 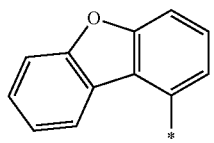 | 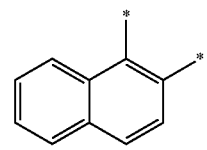 [SMILES: *c1ccc2ccccc2c1*] |
| C5-25 | 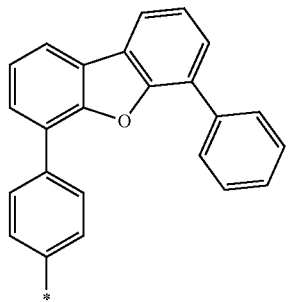 [SMILES: *c1ccc(-c2cccc3c2oc2c(-c4ccccc4)cccc23)cc1] | 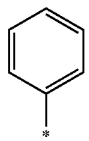 [SMILES: *c1ccccc1] | 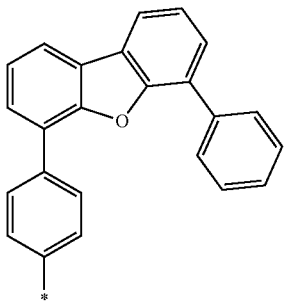 [SMILES: *c1ccc(-c2cccc3c2oc2c(-c4ccccc4)cccc23)cc1] | 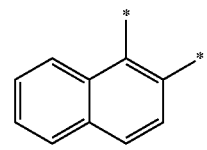 [SMILES: *c1ccc2ccccc2c1*] |
| C5-26 | 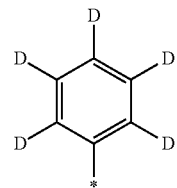 | 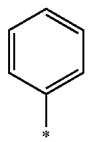 [SMILES: *c1ccccc1] | 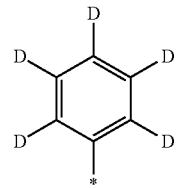 | 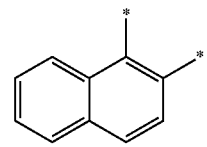 [SMILES: *c1ccc2ccccc2c1*] |

[Compound Group 5]
C5-27 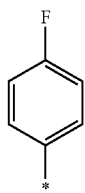 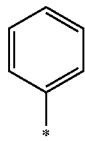 [SMILES: *c1ccccc1] 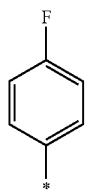 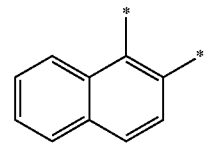
C5-28 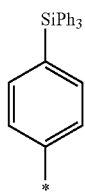 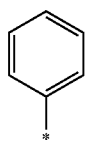 [SMILES: *c1ccccc1] 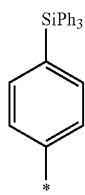 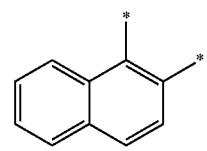 [SMILES: *c1ccc2ccccc2c1*]
C5-29 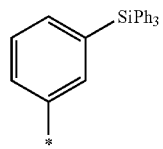 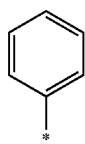 [SMILES: *c1ccccc1] 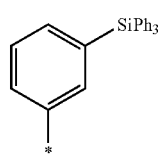 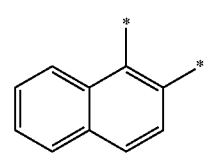
C5-30 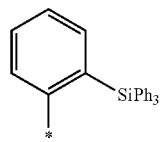 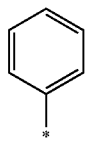 [SMILES: *c1ccccc1] 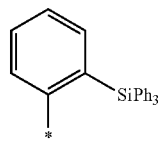 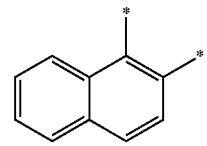 [SMILES: *c1ccc2ccccc2c1*]
D5-1 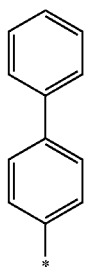 [SMILES: *c1ccc(-c2ccccc2)cc1] 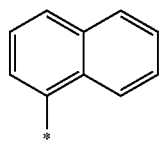 [SMILES: *c1cccc2ccccc12] 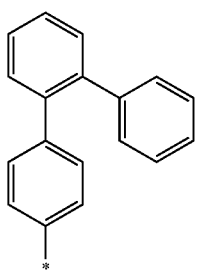 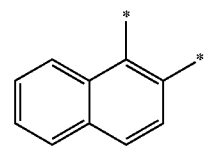 [SMILES: *c1ccc2ccccc2c1*]
D5-2 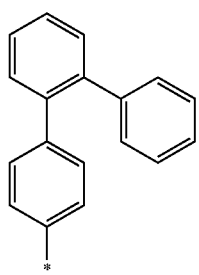 [SMILES: *c1ccc(-c2ccccc2-c2ccccc2)cc1] 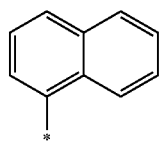 [SMILES: *c1cccc2ccccc12] 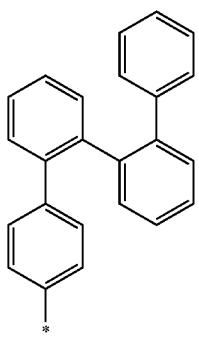 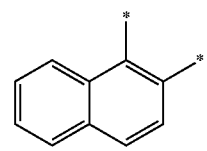 [SMILES: *c1ccc2ccccc2c1*]

[Compound Group 5]
D5-3 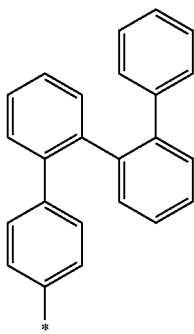 [SMILES: *c1ccc(-c2ccccc2-c2ccccc2-c2ccccc2)cc1] 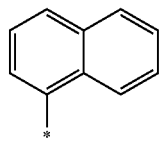 [SMILES: *c1cccc2ccccc12] 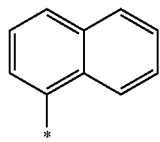 [SMILES: *c1cccc2ccccc12] 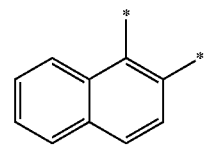 [SMILES: *c1ccc2ccccc2c1*]
D5-4 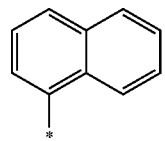 [SMILES: *c1cccc2ccccc12] 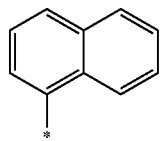 [SMILES: *c1cccc2ccccc12] 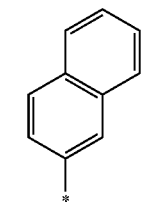 [SMILES: *c1ccc2ccccc2c1] 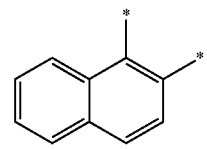 [SMILES: *c1ccc2ccccc2c1*]
D5-5 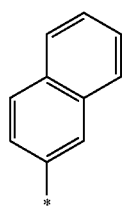 [SMILES: *c1ccc2ccccc2c1] 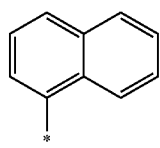 [SMILES: *c1cccc2ccccc12] 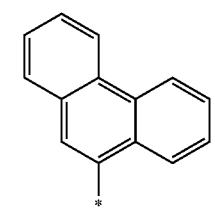 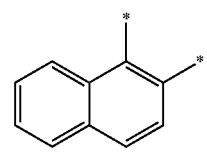 [SMILES: *c1ccc2ccccc2c1*]
D5-6 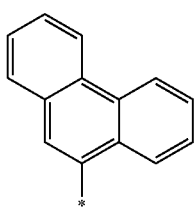 [SMILES: *c1cc2ccccc2c2ccccc12] 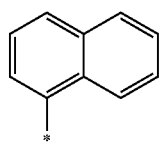 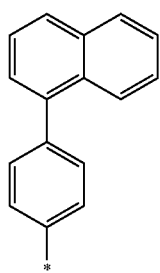 [SMILES: *c1ccc(-c2cccc3ccccc23)cc1] 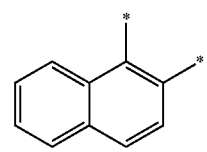 [SMILES: *c1ccc2ccccc2c1*]
D5-7 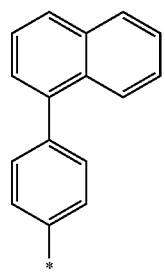 [SMILES: *c1ccc(-c2cccc3ccccc23)cc1] 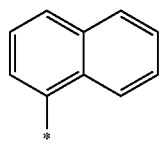 [SMILES: *c1cccc2ccccc12] 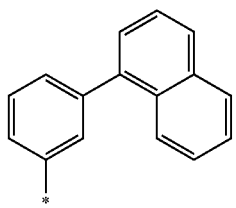 [SMILES: *c1cccc(-c2cccc3ccccc23)c1] 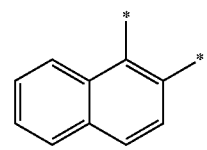 [SMILES: *c1ccc2ccccc2c1*]
D5-8 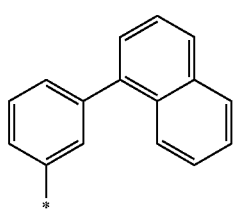 [SMILES: *c1cccc(-c2cccc3ccccc23)c1] 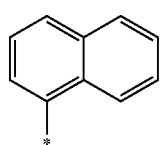 [SMILES: *c1cccc2ccccc12] 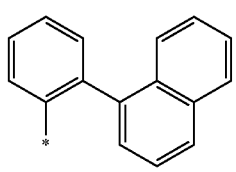 [SMILES: *c1ccccc1-c1cccc2ccccc12] 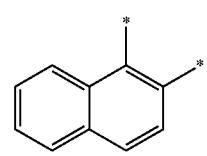 [SMILES: *c1ccc2ccccc2c1*]

[Compound Group 5]
D5-9 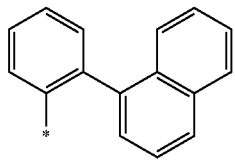 [SMILES: *c1ccccc1-c1cccc2ccccc12] 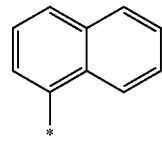 [SMILES: *c1cccc2ccccc12] 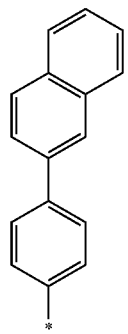 [SMILES: *c1ccc(-c2ccc3ccccc3c2)cc1] 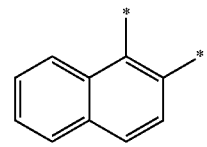
D5-10 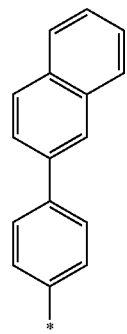 [SMILES: *c1ccc(-c2ccc3ccccc3c2)cc1] 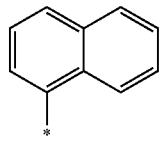 [SMILES: *c1cccc2ccccc12] 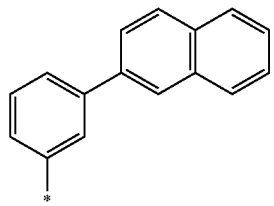 [SMILES: *c1cccc(-c2ccc3ccccc3c2)c1] 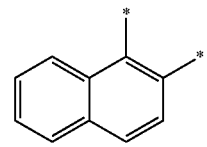 [SMILES: *c1ccc2ccccc2c1*]
D5-11 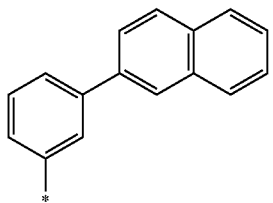 [SMILES: *c1cccc(-c2ccc3ccccc3c2)c1] 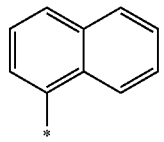 [SMILES: *c1cccc2ccccc12] 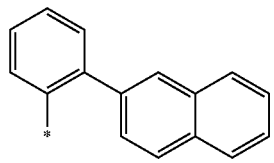 [SMILES: *c1ccccc1-c1ccc2ccccc2c1] 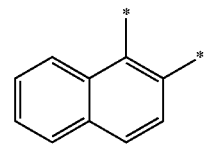
D5-12 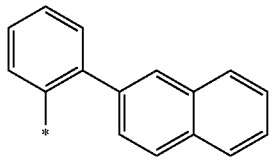 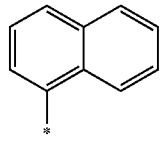 [SMILES: *c1cccc2ccccc12] 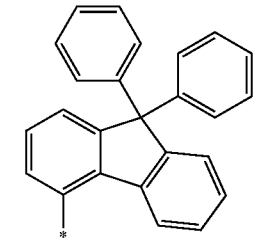 [SMILES: *c1cccc2c1-c1ccccc1C2(c1ccccc1)c1ccccc1] 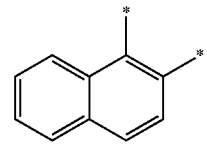 [SMILES: *c1ccc2ccccc2c1*]
D5-13 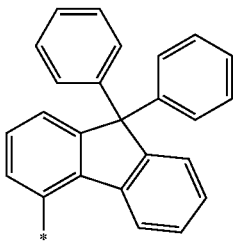 [SMILES: *c1cccc2c1-c1ccccc1C2(c1ccccc1)c1ccccc1] 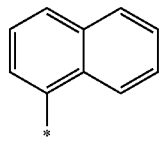 [SMILES: *c1cccc2ccccc12] 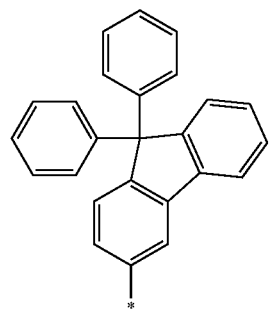 [SMILES: *c1ccc2c(c1)-c1ccccc1C2(c1ccccc1)c1ccccc1] 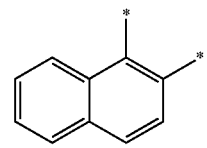 [SMILES: *c1ccc2ccccc2c1*]

[Compound Group 5]
D5-14 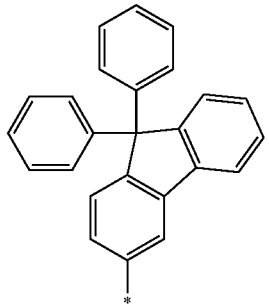 [SMILES: *c1ccc2c(c1)-c1ccccc1C2(c1ccccc1)c1ccccc1] 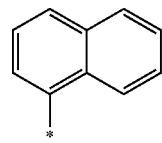 [SMILES: *c1cccc2ccccc12] 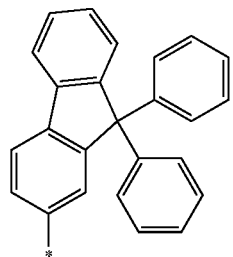 [SMILES: *c1ccc2c(c1)C(c1ccccc1)(c1ccccc1)c1ccccc1-2] 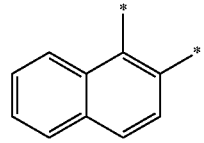 [SMILES: *c1ccc2ccccc2c1*]
D5-15 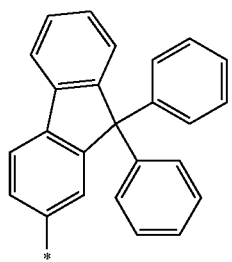 [SMILES: *c1ccc2c(c1)C(c1ccccc1)(c1ccccc1)c1ccccc1-2] 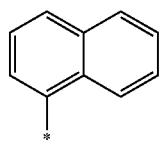 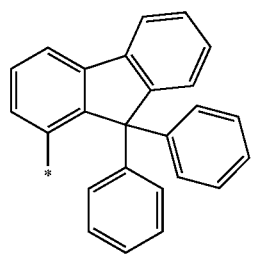 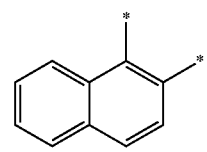
D5-16 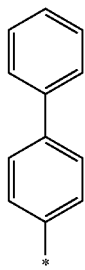 [SMILES: *c1ccc(-c2ccccc2)cc1] 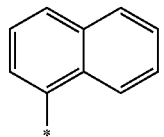 [SMILES: *c1cccc2ccccc12] 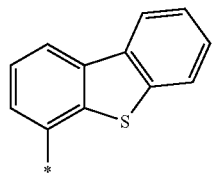 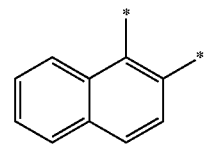 [SMILES: *c1ccc2ccccc2c1*]
D5-17 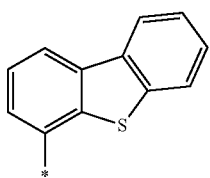 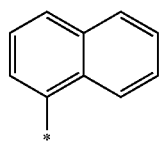 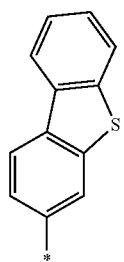 [SMILES: *c1ccc2c(c1)sc1ccccc12] 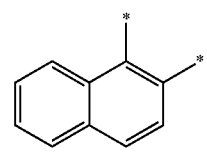
D5-18 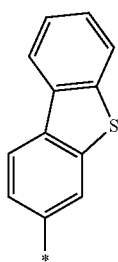 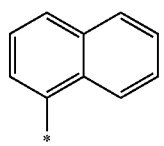 [SMILES: *c1cccc2ccccc12] 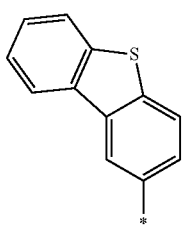 [SMILES: *c1ccc2sc3ccccc3c2c1] 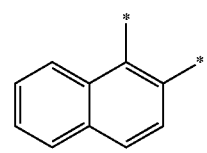

US 11,968,887 B2
897                                               898
-continued
[Compound Group 5]
D5-19 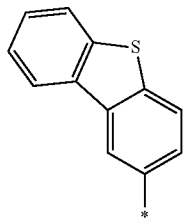 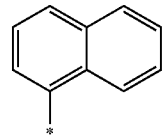 [SMILES: *c1cccc2ccccc12] 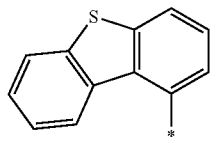 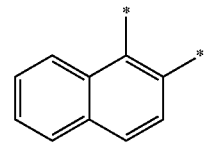
D5-20 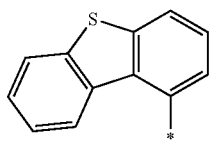 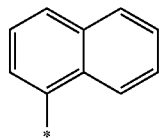 [SMILES: *c1cccc2ccccc12] 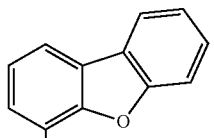 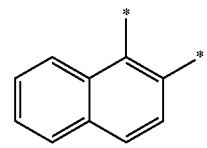
D5-21 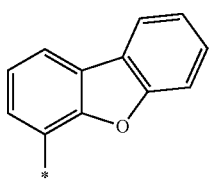 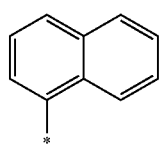 [SMILES: *c1cccc2ccccc12] 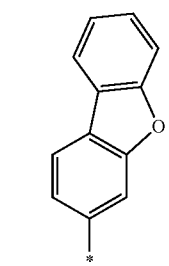 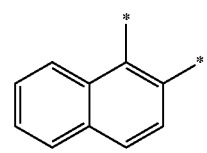 [SMILES: *c1ccc2ccccc2c1*]
D5-22 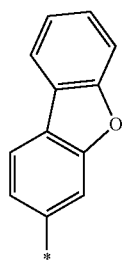 [SMILES: *c1ccc2c(c1)oc1ccccc12] 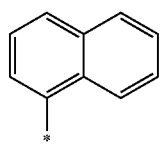 [SMILES: *c1cccc2ccccc12] 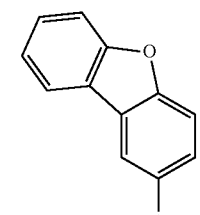 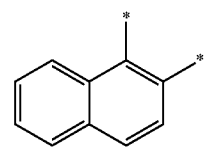
D5-23 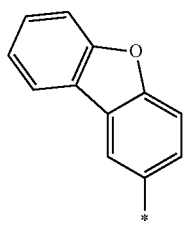 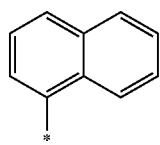 [SMILES: *c1cccc2ccccc12] 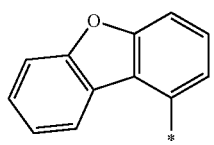 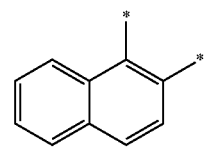 [SMILES: *c1ccc2ccccc2c1*]
D5-24 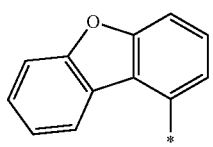 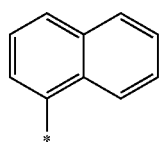 [SMILES: *c1cccc2ccccc12] 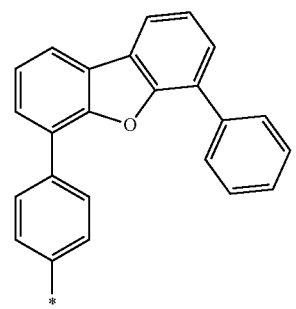 [SMILES: *c1ccc(-c2cccc3c2oc2c(-c4ccccc4)cccc23)cc1] 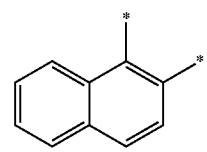 [SMILES: *c1ccc2ccccc2c1*]

-continued
[Compound Group 5]
D5-25 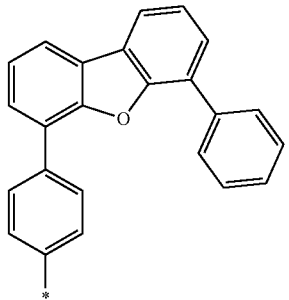 [SMILES: *c1ccc(-c2cccc3c2oc2c(-c4ccccc4)cccc23)cc1] 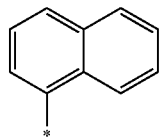 [SMILES: *c1cccc2ccccc12] 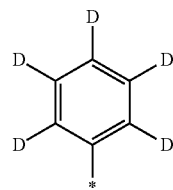 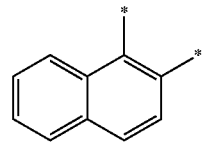
D5-26 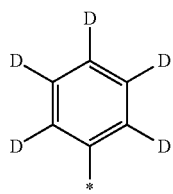 [SMILES: *c1c([2H])c([2H])c([2H])c([2H])c1[2H]] 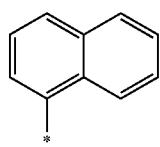 [SMILES: *c1cccc2ccccc12] 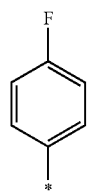 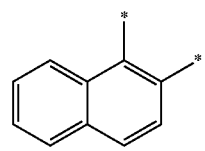 [SMILES: *c1ccc2ccccc2c1*]
D5-27 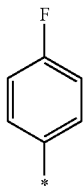 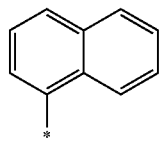 [SMILES: *c1cccc2ccccc12] 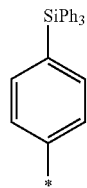 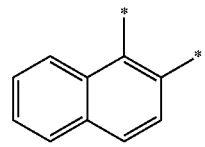 [SMILES: *c1ccc2ccccc2c1*]
D5-28 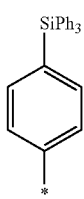 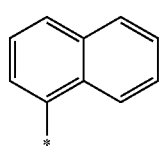 [SMILES: *c1cccc2ccccc12] 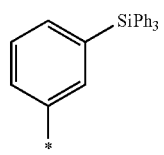 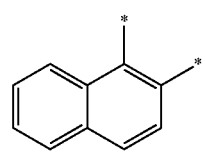 [SMILES: *c1ccc2ccccc2c1*]
D5-29 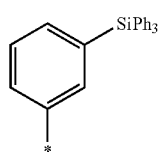 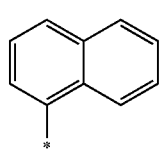 [SMILES: *c1cccc2ccccc12] 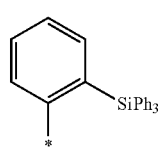 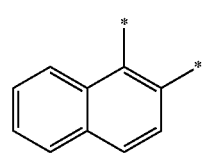 [SMILES: *c1ccc2ccccc2c1*]
D5-30 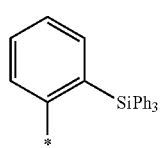 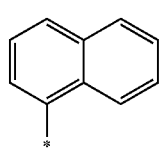 [SMILES: *c1cccc2ccccc12] 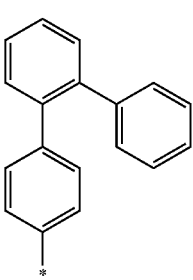 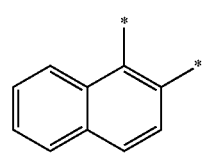 [SMILES: *c1ccc2ccccc2c1*]

[Compound Group 5]

E5-1 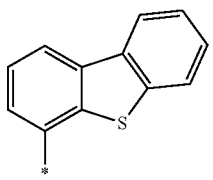 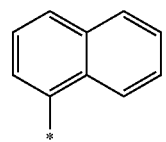 [SMILES: *c1cccc2ccccc12] 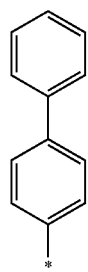 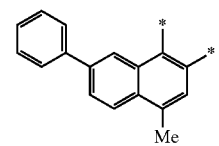 [SMILES: *c1cc(C)c2ccc(-c3ccccc3)cc2c1*]

E5-2 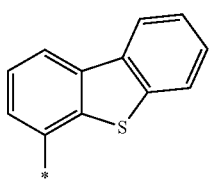 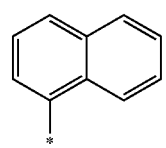 [SMILES: *c1cccc2ccccc12] 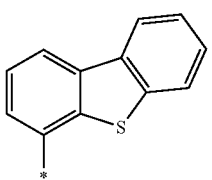 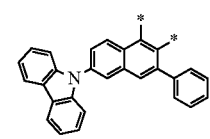

16. A diamine compound represented by Formula 1:

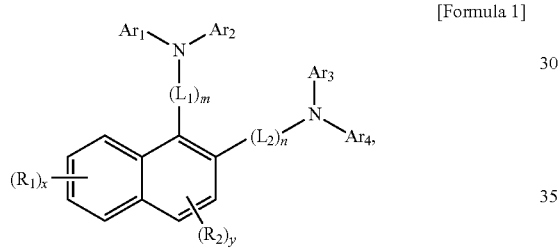

[Formula 1]

wherein in Formula 1,

Ar$_1$ to Ar$_4$ are each independently a substituted or unsubstituted aryl group of 6 to 30 carbon atoms for forming a ring or a substituted or unsubstituted heteroaryl group of 2 to 30 carbon atoms for forming a ring, L$_1$ is a direct linkage or a substituted or unsubstituted phenylene group, L$_2$ is a direct linkage, a substituted or unsubstituted arylene group of 6 to 30 carbon atoms for forming a ring, or a substituted or unsubstituted heteroarylene group of 2 to 30 carbon atoms for forming a ring, R$_1$ and R$_2$ are each independently a hydrogen atom, a deuterium atom, a halogen atom, a cyano group, a substituted or unsubstituted thiol group, a substituted or unsubstituted oxy group, a substituted or unsubstituted silyl group, a substituted or unsubstituted alkyl group of 1 to 20 carbon atoms, a substituted or unsubstituted aryl group of 6 to 30 carbon atoms for forming a ring, or a substituted or unsubstituted heteroaryl group of 2 to 30 carbon atoms for forming a ring, x is an integer of 0 to 4, y is an integer of 0 to 2, and m and n are each independently an integer of 0 to 4, where m+n is not 0, and L$_1$ and L$_2$ are not both a direct linkage, and wherein i) when L$_2$ is a naphthylene group,
  the naphthylene group is represented by

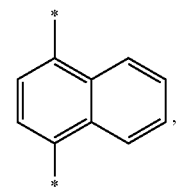

where * represents a bindinq site to a neighboring atom, and ii) when m is 1, n is 1, and L$_1$ and L$_2$ are each an unsubstituted phenylene group represented by

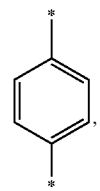

where * represents a bindinq site to a neighboring atom,
R$_1$ and R$_2$ are each independently a hydrogen atom, a deuterium atom, a substituted or unsubstituted alkyl group of 1 to 5 carbon atoms, an unsubstituted phenyl group, or a substituted or unsubstituted carbazole group.

17. The diamine compound of claim 16, wherein Formula 1 is represented by Formula 2 or Formula 3:

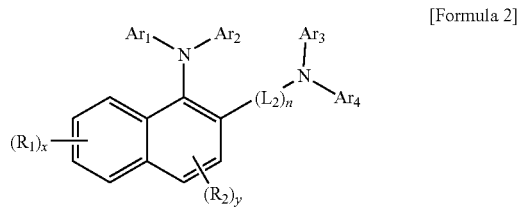

[Formula 2]

[Formula 3]

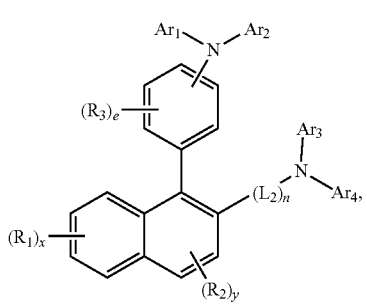

wherein in Formula 2 and Formula 3,

R$_3$ is a hydrogen atom, a deuterium atom, a halogen atom, a substituted or unsubstituted alkyl group of 1 to 20 carbon atoms, a substituted or unsubstituted aryl group of 6 to 30 carbon atoms for forming a ring, or a substituted or unsubstituted heteroaryl group of 2 to 30 carbon atoms for forming a ring, e is an integer of 0 to 4, and Ar$_1$ to Ar$_4$, L$_2$, R$_1$, R$_2$, n, x and y are each independently the same as defined in Formula 1.

18. The diamine compound of claim 17, wherein Formula 2 is represented by Formula 2-1 or Formula 2-2:

[Formula 2-1]

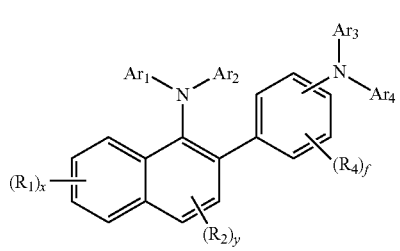

[Formula 2-2]

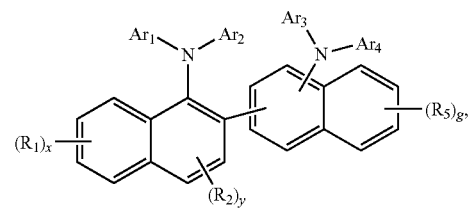

wherein in Formula 2-1 and Formula 2-2,

R$_4$ and R$_5$ are each independently a hydrogen atom, a deuterium atom, a halogen atom, a substituted or unsubstituted alkyl group of 1 to 20 carbon atoms, a substituted or unsubstituted aryl group of 6 to 30 carbon atoms for forming a ring, or a substituted or unsubstituted heteroaryl group of 2 to 30 carbon atoms for forming a ring, f and g are each independently an integer of 0 to 4, and Ar$_1$ to Ar$_4$, R$_1$, R$_2$, x and y are each independently the same as defined in Formula 2.

19. The diamine compound of claim 17, wherein Formula 3 is represented by any one of Formula 3-1 to Formula 3-3:

[Formula 3-1]

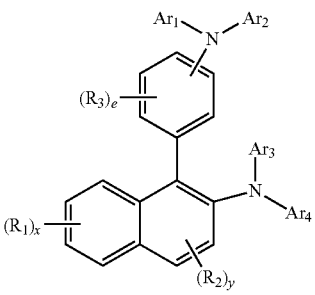

[Formula 3-2]

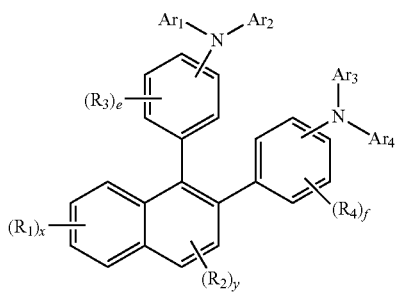

[Formula 3-3]

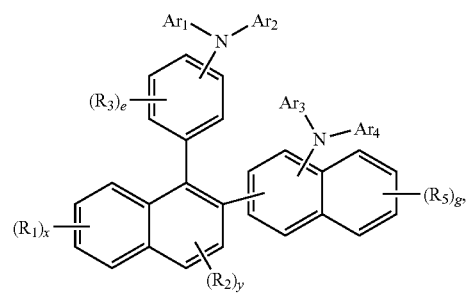

wherein in Formula 3-1 to Formula 3-3,

R$_4$ and R$_5$ are each independently a hydrogen atom, a deuterium atom, a halogen atom, a substituted or unsubstituted alkyl group of 1 to 20 carbon atoms, a substituted or unsubstituted aryl group of 6 to 30 carbon atoms for forming a ring, or a substituted or unsubstituted heteroaryl group of 2 to 30 carbon atoms for forming a ring, f and g are each independently an integer of 0 to 4, and Ar$_1$ to Ar$_4$, R$_1$ to R$_3$, e, x and y are each independently the same as defined in Formula 3.

20. A diamine compound represented by Formula 1:

[Formula 1]

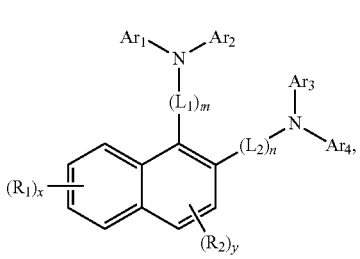

wherein the diamine compound represented by Formula 1 is at least one selected among compounds represented in Compound Group 1:

[Compound Group 1]
| | m | n | L₁ | L₂ | Ar₁ |
|---|---|---|---|---|---|
| A1-1 | 1 | 0 | 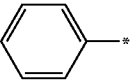 | — | 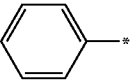 |
| A1-2 | 1 | 0 | 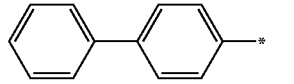 | — | 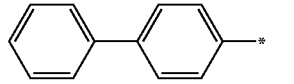 |
| A1-3 | 1 | 0 |  | — |  |
| A1-4 | 1 | 0 |  | — |  |

-continued

[Compound Group 1]

| | | | | |
|---|---|---|---|---|
| A1-5 | 1 | O | *—⟨phenylene⟩—* | — | ⟨phenyl⟩—* |
| A1-6 | 1 | O | *—⟨phenylene⟩—* | — | ⟨phenyl⟩—* |
| A1-7 | 1 | O | *—⟨phenylene⟩—* | — | ⟨phenyl⟩—* |
| A1-8 | 1 | O | *—⟨phenylene⟩—* | — | ⟨phenyl⟩—* |
| A1-9 | 1 | O | *—⟨phenylene⟩—* | — | ⟨phenyl⟩—* |

-continued
[Compound Group 1]
| | | | | |
|---|---|---|---|---|
| 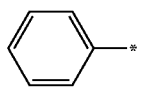 | 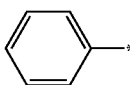 | 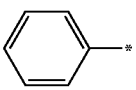 | 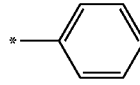 | 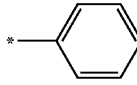 |
| — | — | — | — | — |
| 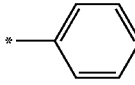 |  |  |  |  |
| 0 | 0 | 0 | 0 | 0 |
| 1 | 1 | 1 | 1 | 1 |
| A1-10 | A1-11 | A1-12 | A1-13 | A1-14 |

-continued
[Compound Group 1]
| | | | | |
|---|---|---|---|---|
| A1-15 | 1 | 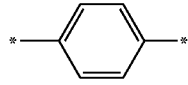 | 0 | 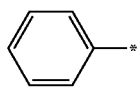 |
| A1-16 | 1 | 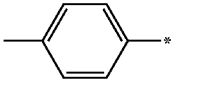 | 0 | 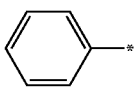 |
| A1-17 | 1 | 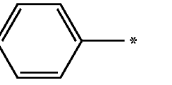 | 0 | 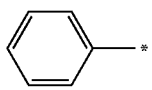 |
| A1-18 | 1 |  | 0 | 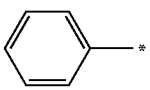 |

-continued
[Compound Group 1]
| | | | | |
|---|---|---|---|---|
| A1-19 | 1 | 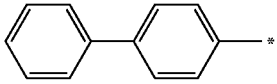 | 0 | 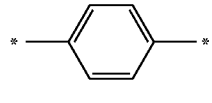 |
| A1-20 | 1 | 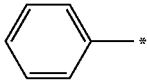 | 0 | 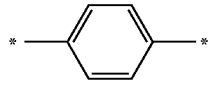 |
| A1-21 | 1 | 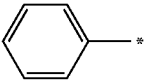 | 0 | 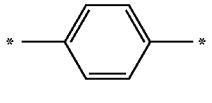 |
| A1-22 | 1 | 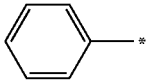 | 0 | 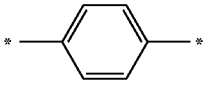 |

-continued
[Compound Group 1]
| | | | | |
|---|---|---|---|---|
| A1-23 | 1 | 0 | 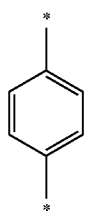 | — | 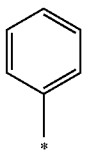 |
| A1-24 | 1 | 0 | 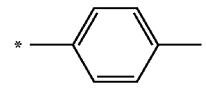 | — | 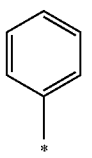 |
| A1-25 | 1 | 0 | 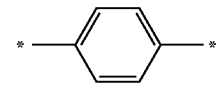 | — |  |
| A1-26 | 1 | 0 | 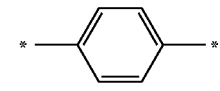 | — | 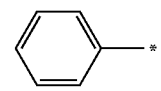 |

-continued
[Compound Group 1]
| | | | | |
|---|---|---|---|---|
| A1-27 | 1 | 0 | 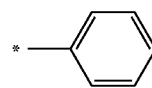 | — | 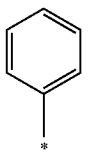 |
| A1-28 | 1 | 0 | 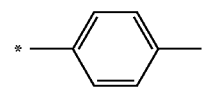 | — | 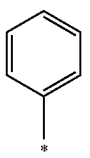 |
| A1-29 | 1 | 0 | 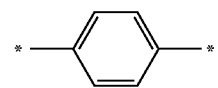 | — | 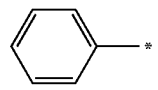 |
| A1-30 | 1 | 0 | 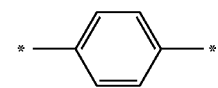 | — | 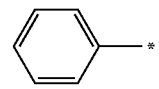 |

-continued
[Compound Group 1]
| | | | | |
|---|---|---|---|---|
| A1-31 | 1 | 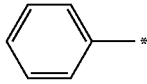 | 0 | 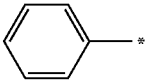 |
| A1-32 | 1 | | 0 | |
| A1-33 | 1 | 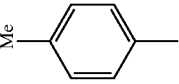 | 0 | |
| B1-1 | 1 | 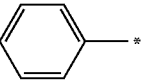 | 0 | |

[Compound Group 1]
| | | | | |
|---|---|---|---|---|
| B1-2 | 1 | 0 |  |  |
| B1-3 | 1 | 0 |  |  |
| B1-4 | 1 | 0 |  |  |
| B1-5 | 1 | 0 |  |  |

-continued
[Compound Group 1]
| | | | | |
|---|---|---|---|---|
| B1-6 | 1 | 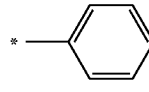 | 0 | 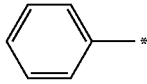 |
| B1-7 | 1 | 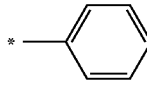 | 0 | 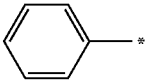 |
| B1-8 | 1 | 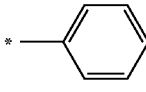 | 0 | 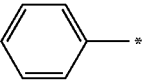 |
| B1-9 | 1 | 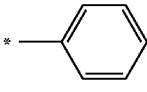 | 0 | 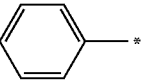 |

-continued

[Compound Group 1]

| | | | | |
|---|---|---|---|---|
| B1-10 | 1 | 0 | *—⟨phenylene⟩—* | —⟨phenyl⟩* |
| B1-11 | 1 | 0 | *—⟨phenylene⟩—* | —⟨phenyl⟩* |
| B1-12 | 1 | 0 | *—⟨phenylene⟩—* | —⟨phenyl⟩* |
| B1-13 | 1 | 0 | *—⟨phenylene⟩—* | —⟨phenyl⟩* |

-continued

[Compound Group 1]

| | | | | |
|---|---|---|---|---|
| B1-14 | 1 | 0 | *─⟨phenylene⟩─* | ─⟨phenyl⟩* |
| B1-15 | 1 | 0 | *─⟨phenylene⟩─* | ─⟨phenyl⟩* |
| B1-16 | 1 | 0 | *─⟨phenylene⟩─* | ─⟨phenyl⟩* |
| B1-17 | 1 | 0 | *─⟨phenylene⟩─* | ─⟨phenyl⟩* |

-continued
[Compound Group 1]
| | | | | |
|---|---|---|---|---|
| B1-18 | 1 | 0 |  | — | 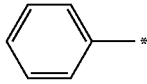 |
| B1-19 | 1 | 0 |  | — | 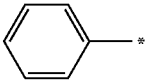 |
| B1-20 | 1 | 0 |  | — | 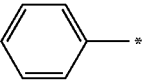 |
| B1-21 | 1 | 0 |  | — | 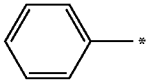 |

-continued

[Compound Group 1]

| | | | | |
|---|---|---|---|---|
| B1-22 | 1 | 0 | *—⟨C6H4⟩—* | —⟨C6H5⟩* |
| B1-23 | 1 | 0 | *—⟨C6H4⟩—* | —⟨C6H5⟩* |
| B1-24 | 1 | 0 | *—⟨C6H4⟩—* | —⟨C6H5⟩* |
| B1-25 | 1 | 0 | *—⟨C6H4⟩—* | —⟨C6H5⟩* |

-continued

[Compound Group 1]

| | | | | |
|---|---|---|---|---|
| B1-26 | 1 | O | *—⟨C6H4⟩—* | ⟨C6H5⟩—* |
| B1-27 | 1 | O | *—⟨C6H4⟩—* | ⟨C6H5⟩—* |
| B1-28 | 1 | O | *—⟨C6H4⟩—* | ⟨C6H5⟩—* |
| B1-29 | 1 | O | *—⟨C6H4⟩—* | ⟨C6H5⟩—* |

-continued

[Compound Group 1]

| | | | |
|---|---|---|---|
| B1-30 | 1 | 0 | *—⟨phenylene⟩—* | — | phenyl-* |
| C1-1 | 1 | 0 | *—⟨phenylene⟩—* | — | naphthyl-* |
| C1-2 | 1 | 0 | *—⟨phenylene⟩—* | — | naphthyl-* |
| C1-3 | 1 | 0 | *—⟨phenylene⟩—* | — | naphthyl-* |

-continued

[Compound Group 1]

| | | | |
|---|---|---|---|
| C1-4 | 1 | *—⟨phenyl⟩—* | 0 | naphthyl-* |
| C1-5 | 1 | *—⟨phenyl⟩—* | 0 | naphthyl-* |
| C1-6 | 1 | *—⟨phenyl⟩—* | 0 | naphthyl-* |
| C1-7 | 1 | *—⟨phenyl⟩—* | 0 | naphthyl-* |

-continued
[Compound Group 1]
| | | | |
|---|---|---|---|
| C1-8 | 1 |  | 0 |  |
| C1-9 | 1 |  | 0 |  |
| C1-10 | 1 |  | 0 |  |
| C1-11 | 1 |  | 0 |  |

-continued

[Compound Group 1]

| | | | |
|---|---|---|---|
| C1-12 | 1 | 0 | *–⟨C6H4⟩–* | — | naphthyl-* |
| C1-13 | 1 | 0 | *–⟨C6H4⟩–* | — | naphthyl-* |
| C1-14 | 1 | 0 | *–⟨C6H4⟩–* | — | naphthyl-* |
| C1-15 | 1 | 0 | *–⟨C6H4⟩–* | — | naphthyl-* |

[Compound Group 1]
| | | | | |
|---|---|---|---|---|
| C1-16 | 1 | 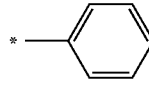 | 0 | 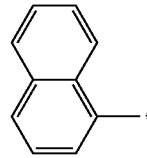 |
| C1-17 | 1 | 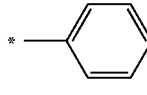 | 0 | 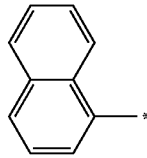 |
| C1-18 | 1 | 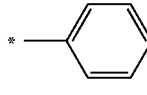 | 0 | 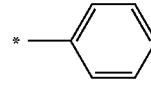 |
| C1-19 | 1 | 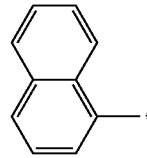 | 0 | 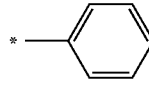 |

-continued
[Compound Group 1]
| | | | | |
|---|---|---|---|---|
| C1-20 | 1 | 0 | 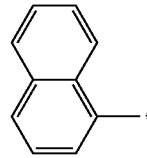 | 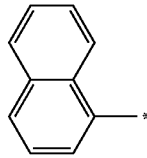 |
| C1-21 | 1 | 0 | 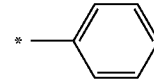 | 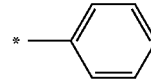 |
| C1-22 | 1 | 0 | 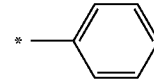 | 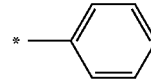 |
| C1-23 | 1 | 0 | 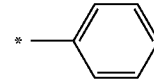 | 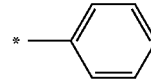 |

-continued

[Compound Group 1]

| | | | | |
|---|---|---|---|---|
| C1-24 | 1 | ―◯― *―⬡―* | 0 | naphthyl-* |
| C1-25 | 1 | ―◯― *―⬡―* | 0 | naphthyl-* |
| C1-26 | 1 | ―◯― *―⬡―* | 0 | naphthyl-* |
| C1-27 | 1 | ―◯― *―⬡―* | 0 | naphthyl-* |

-continued
[Compound Group 1]
| | | | |
|---|---|---|---|
| C1-28 | 1 | 0 | 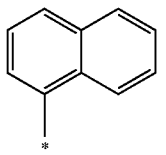 |
| C1-29 | 1 | 0 | 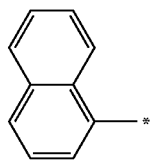 |
| C1-30 | 1 | 0 | 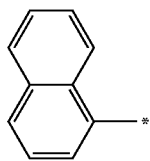 |
| D1-1 | 1 | 0 | 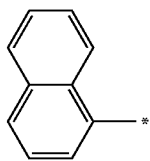 |

[Compound Group 1]
| | | | | |
|---|---|---|---|---|
| D1-2 | 1 | 0 |  |  |
| D1-3 | 1 | 0 | 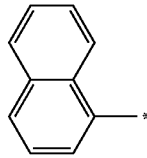 | 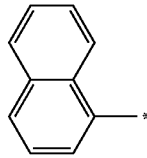 |
| D1-4 | 1 | 0 | 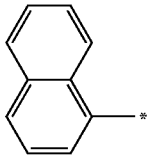 | 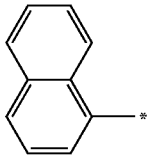 |
| D1-5 | 1 | 0 | 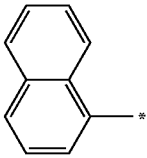 | 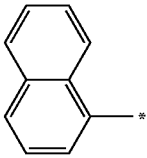 |

-continued
[Compound Group 1]
| D1-6 | 1 | 0 |  | — | 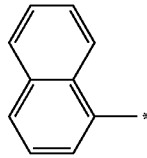 |
| D1-7 | 1 | 0 |  | — | 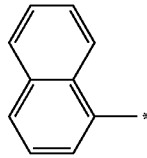 |
| D1-8 | 1 | 0 |  | — | 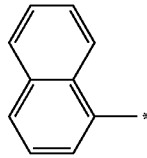 |
| D1-9 | 1 | 0 |  | — | 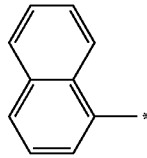 |

-continued
[Compound Group 1]
| | | | |
|---|---|---|---|
| D1-10 | 1 | 0 | 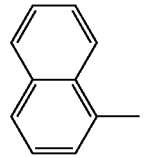 — 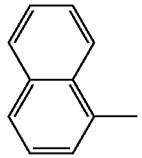 |
| D1-11 | 1 | 0 | 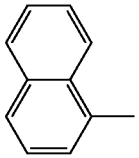 — 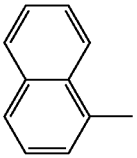 |
| D1-12 | 1 | 0 | — |
| D1-13 | 1 | 0 | — |

-continued
[Compound Group 1]
| | | | | |
|---|---|---|---|---|
| D1-14 | 1 | 0 | 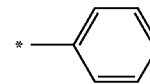 | 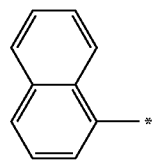 |
| D1-15 | 1 | 0 | 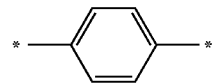 | 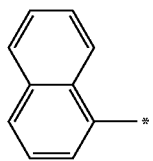 |
| D1-16 | 1 | 0 | 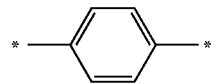 | 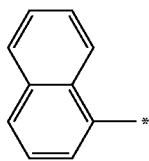 |
| D1-17 | 1 | 0 | 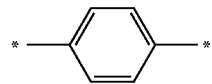 | 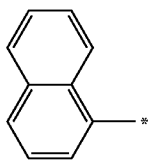 |

-continued

[Compound Group 1]

| | | | |
|---|---|---|---|
| D1-18 | 1 | 0 | *—⟨phenyl⟩—* | — | naphthyl-* |
| D1-19 | 1 | 0 | *—⟨phenyl⟩—* | — | naphthyl-* |
| D1-20 | 1 | 0 | *—⟨phenyl⟩—* | — | naphthyl-* |
| D1-21 | 1 | 0 | *—⟨phenyl⟩—* | — | naphthyl-* |

-continued
[Compound Group 1]
| | | | | |
|---|---|---|---|---|
| D1-22 | 1 | 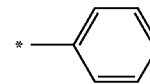 | 0 | 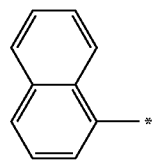 |
| D1-23 | 1 | 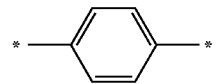 | 0 | 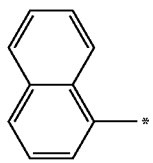 |
| D1-24 | 1 | 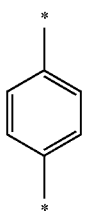 | 0 | 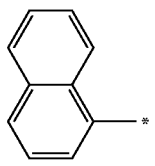 |
| D1-25 | 1 | 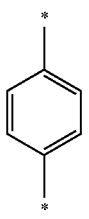 | 0 |  |

-continued

[Compound Group 1]

| | | | | |
|---|---|---|---|---|
| D1-26 | 1 | 0 | *—⟨C6H4⟩—* | —naphthyl* |
| D1-27 | 1 | 0 | *—⟨C6H4⟩—* | —naphthyl* |
| D1-28 | 1 | 0 | *—⟨C6H4⟩—* | —naphthyl* |
| D1-29 | 1 | 0 | *—⟨C6H4⟩—* | —naphthyl* |

-continued

[Compound Group 1]

| | | | |
|---|---|---|---|
| D1-30 | 1 | *—⬡—* (p-phenylene) | naphthyl-* | — |
| E1-1 | 1 | *—⬡—* | naphthyl-* | — |
| E1-2 | 1 | *—⬡—* | naphthyl-* | — |

| | Ar$_2$ | Ar$_3$ | Ar$_4$ | |
|---|---|---|---|---|
| A1-1 | phenyl-* | phenyl-* | phenyl-* | naphthyl with (R$_1$)$_x$, (R$_2$)$_y$ / naphthyl-* |

-continued
[Compound Group 1]
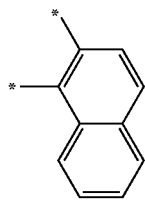
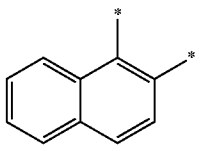 [SMILES: *c1ccc2ccccc2c1*]
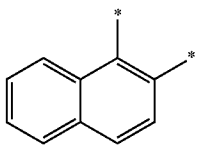 [SMILES: *c1ccc2ccccc2c1*]
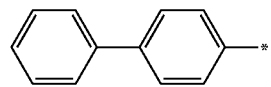
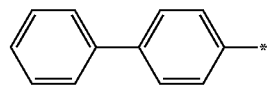
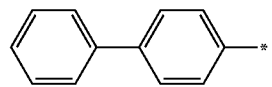
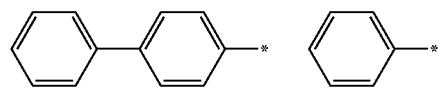
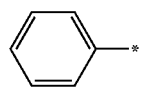
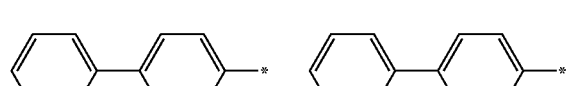
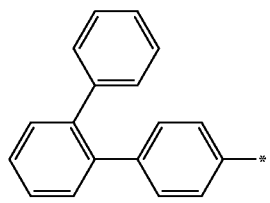
A1-2
A1-3
A1-4

-continued
[Compound Group 1]
A1-5
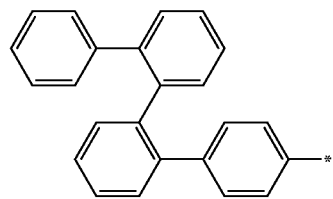 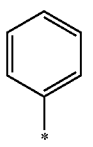 [SMILES: *c1ccccc1] 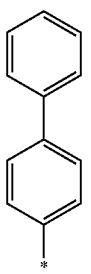 [SMILES: *c1ccc(-c2ccccc2)cc1] 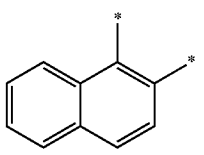 [SMILES: *c1ccc2ccccc2c1*]
A1-6
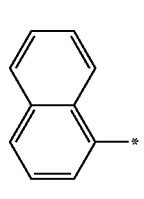 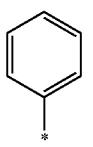 [SMILES: *c1ccccc1] 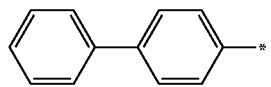 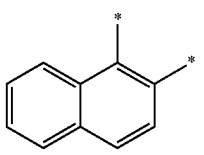 [SMILES: *c1ccc2ccccc2c1*]
A1-7
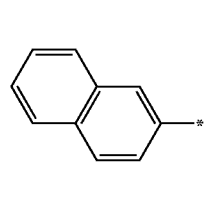 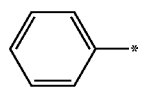 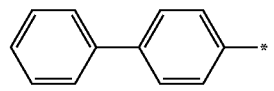 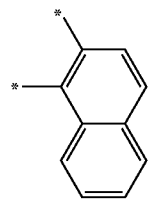

-continued
[Compound Group 1]
A1-8
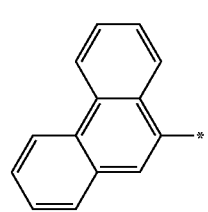
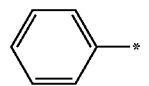
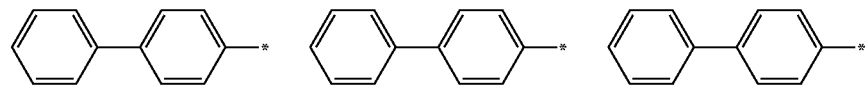
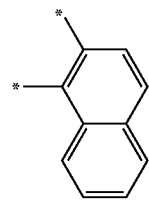
A1-9
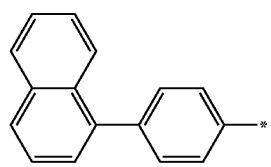
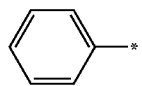
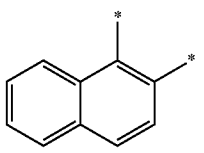 [SMILES: *c1ccc2ccccc2c1*]
A1-10
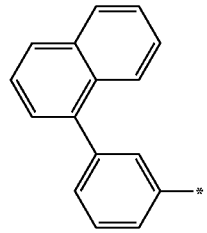
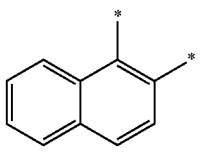 [SMILES: *c1ccc2ccccc2c1*]

-continued
[Compound Group 1]
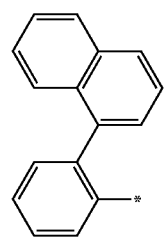 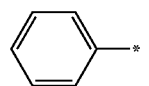 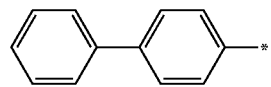 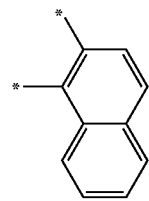
A1-11
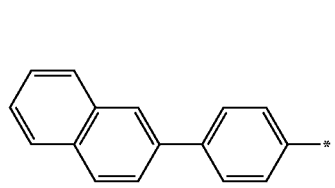 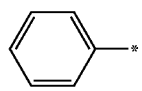 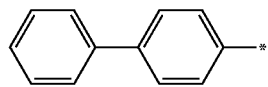 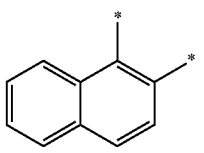 [SMILES: *c1ccc2ccccc2c1*]
A1-12
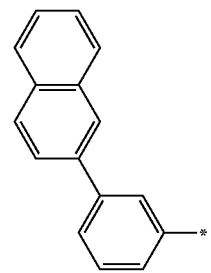 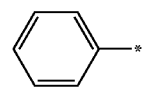 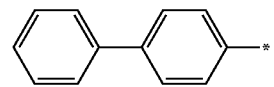 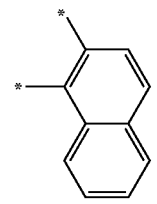
A1-13

-continued
[Compound Group 1]
| | | |
|---|---|---|
| 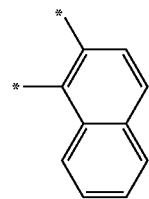 | 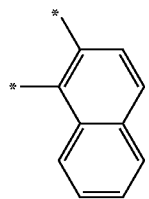 | 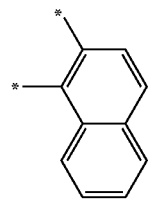 |
| 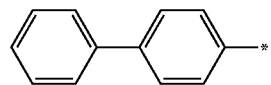 | 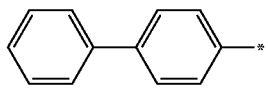 | 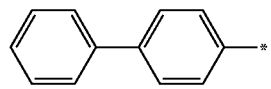 |
| 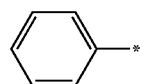 | 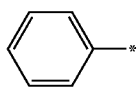 | 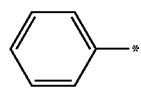 |
| 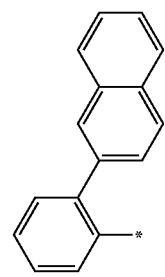 | 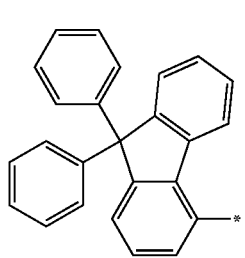 | 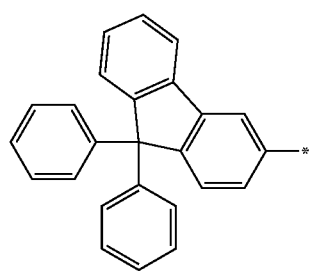 |
| A1-14 | A1-15 | A1-16 |

-continued
[Compound Group 1]
| | | |
|---|---|---|
| 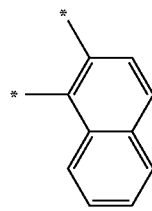 | 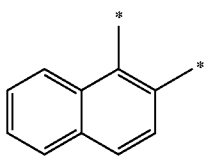 | 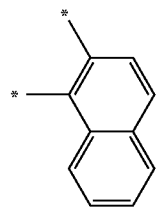 |
| 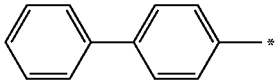 | 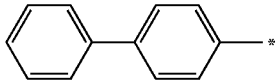 | 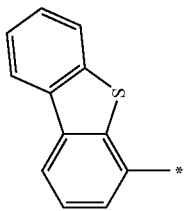 |
| 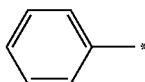 | 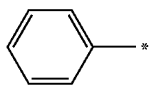 | 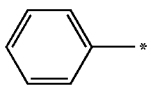 |
| 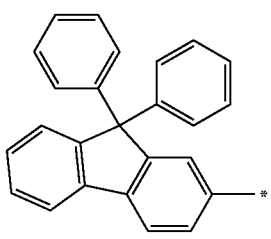 | 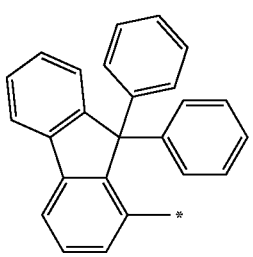 | 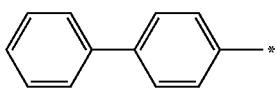 |
| A1-17 | A1-18 | A1-19 |

-continued
[Compound Group 1]
| | | |
|---|---|---|
| 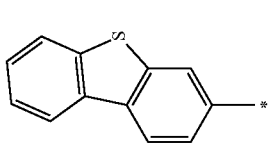 | 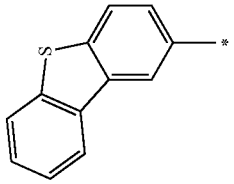 | 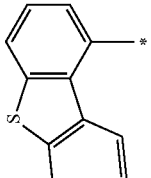 |
|  |  | 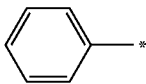 |
| 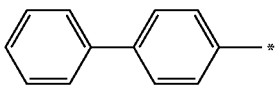 | 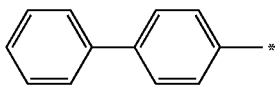 | 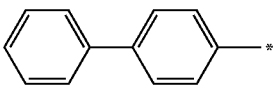 |
| 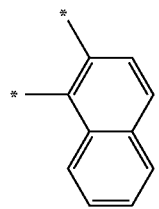 |  |  |
| A1-20 | A1-21 | A1-22 |

-continued
[Compound Group 1]
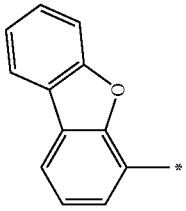 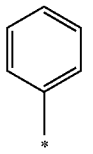 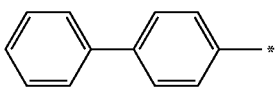 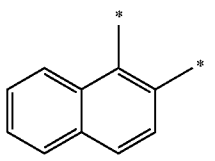
A1-23
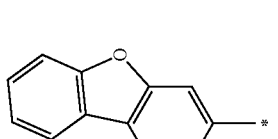 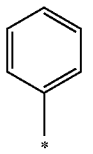 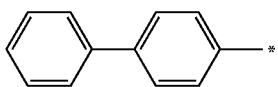 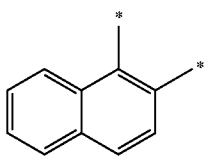
A1-24
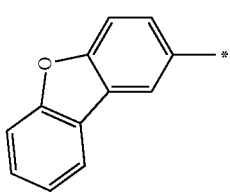 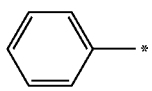 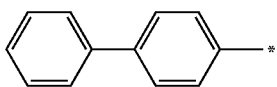 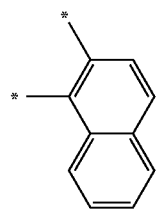
A1-25

-continued
[Compound Group 1]
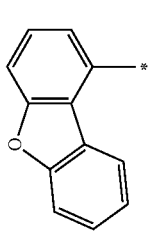 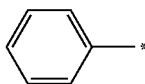 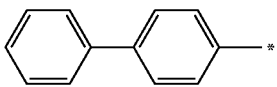 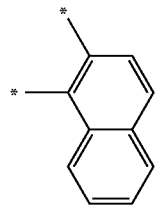
A1-26
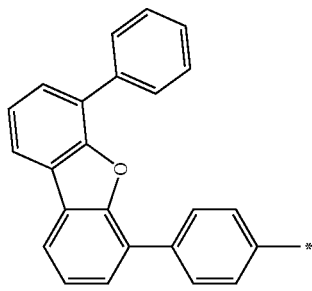 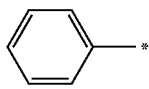 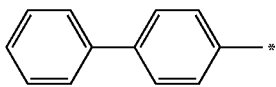
A1-27
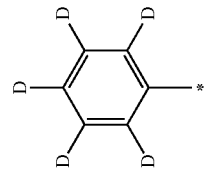 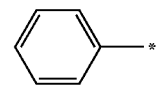 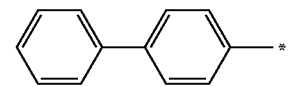
A1-28

-continued
[Compound Group 1]
| | | |
|---|---|---|
| 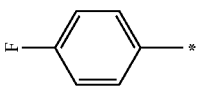 | 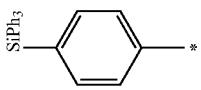 | 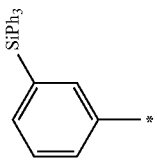 |
|  |  | 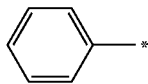 |
| 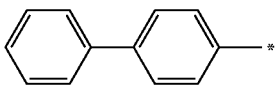 | 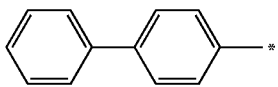 | 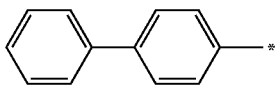 |
| 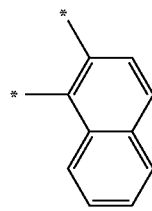 |  | 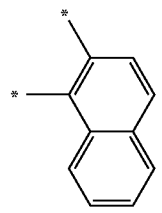 |
| A1-29 | A1-30 | A1-31 |

-continued
[Compound Group 1]
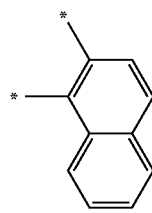 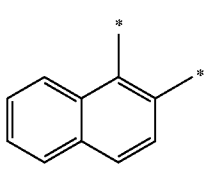 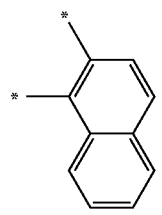
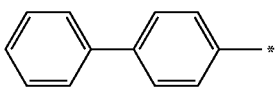
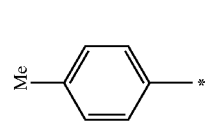 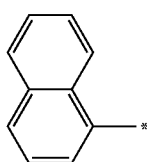
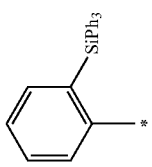  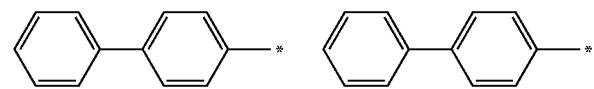
A1-32  A1-33  B1-1

-continued
[Compound Group 1]
| | | | |
|---|---|---|---|
| B1-2 | 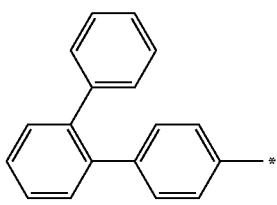 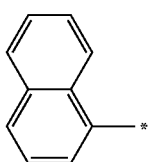 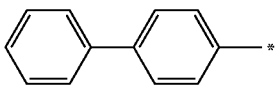 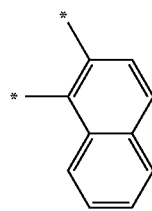 | | |
| B1-3 | 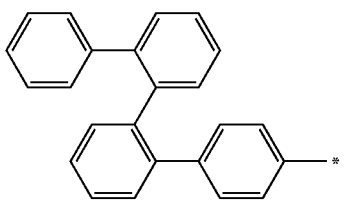 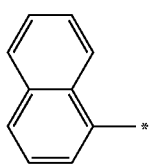 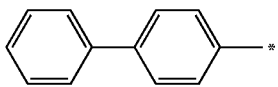 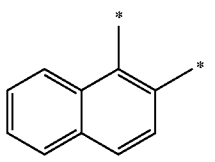 | | |
| B1-4 | 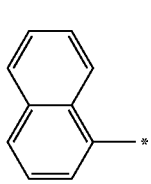 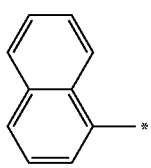 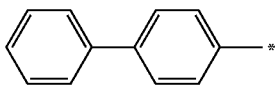 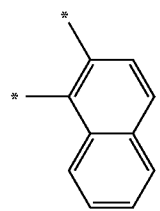 | | |

-continued
[Compound Group 1]
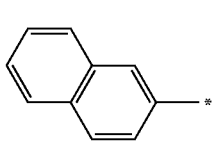 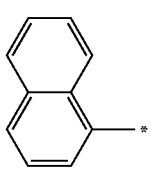 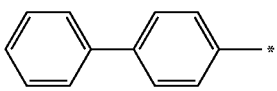 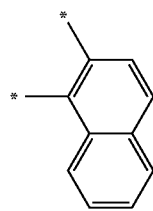
B1-5
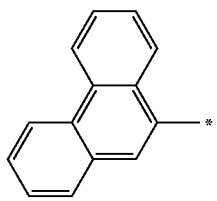 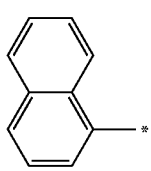 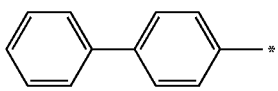 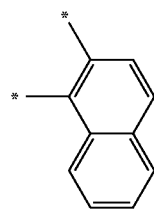
B1-6
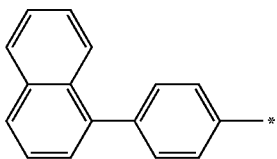 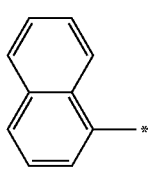 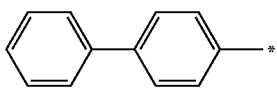 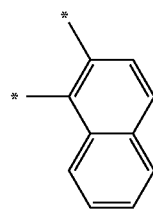
B1-7

-continued
[Compound Group 1]
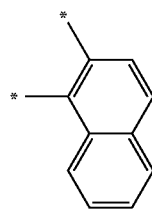 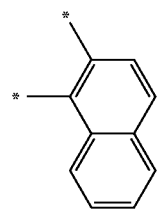 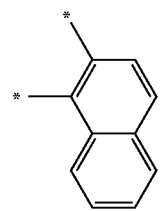
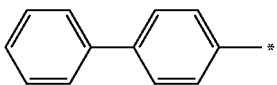 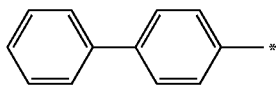 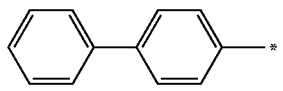
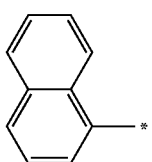 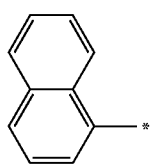 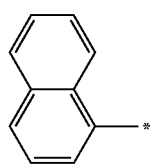
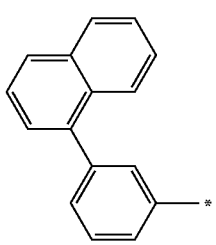 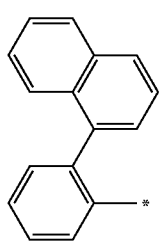 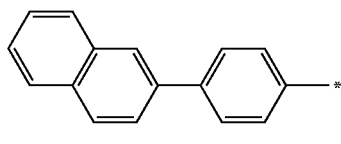
B1-8　　　　　　B1-9　　　　　　B1-10

-continued
[Compound Group 1]
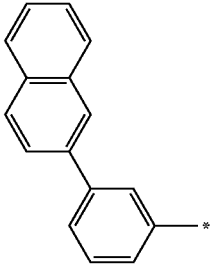
B1-11
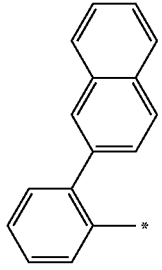
B1-12
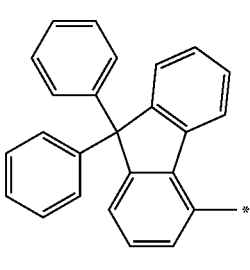
B1-13
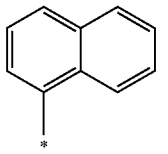
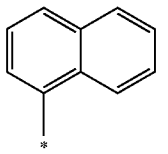
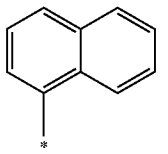
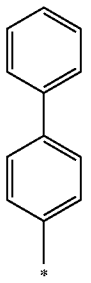
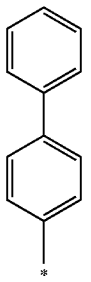
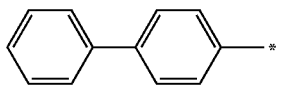
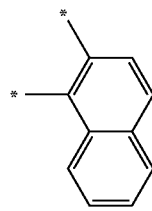
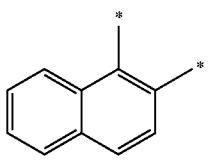
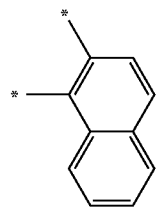

-continued
[Compound Group 1]
B1-14 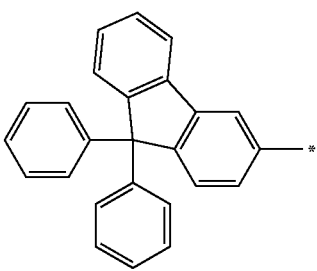 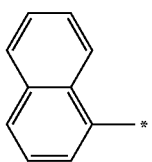 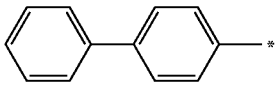 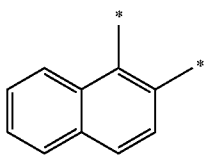
B1-15 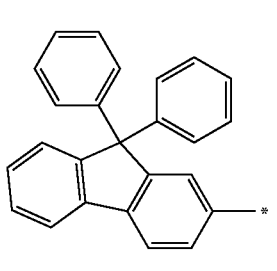 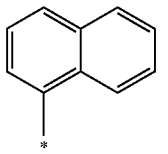 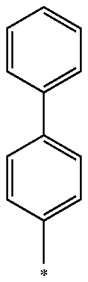 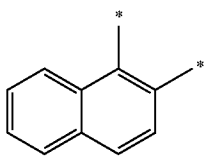
B1-16 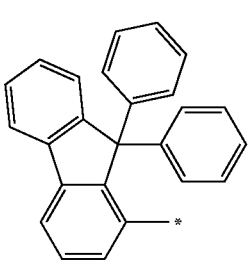 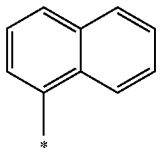 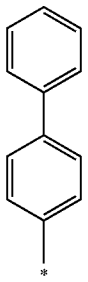 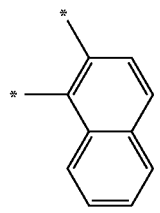

-continued
[Compound Group 1]
B1-17
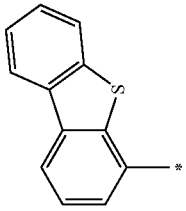
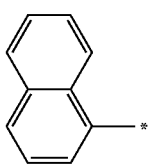
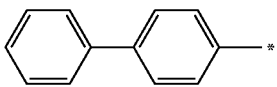
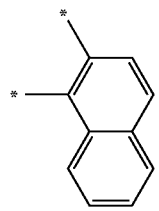
B1-18
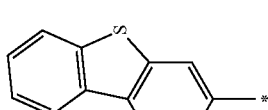
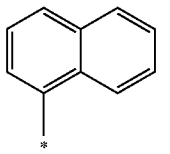
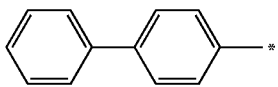
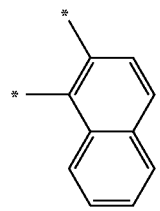
B1-19
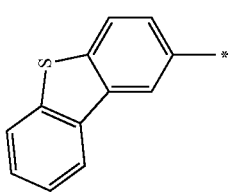
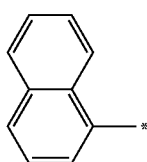
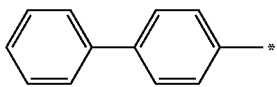
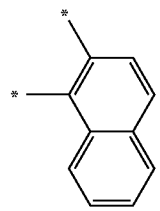

-continued
[Compound Group 1]
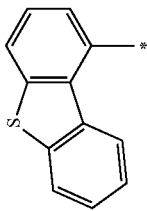
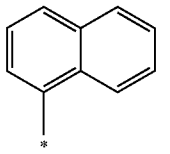
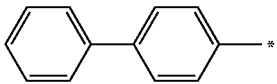
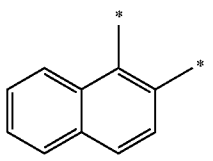
B1-20
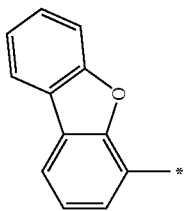
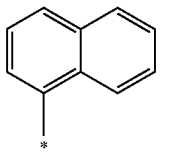
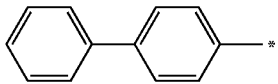
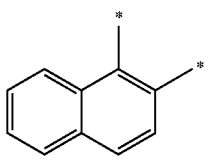
B1-21
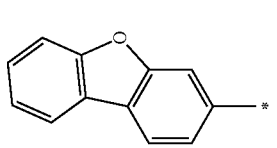
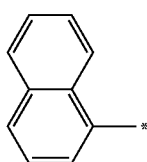
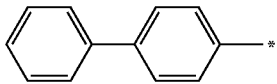
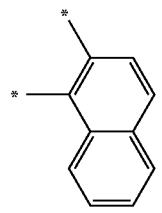
B1-22

-continued
[Compound Group 1]
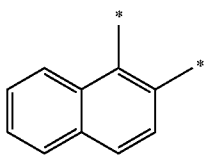 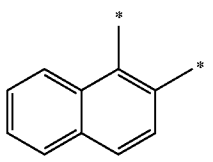 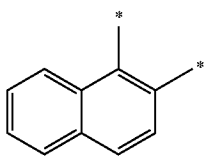
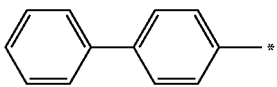 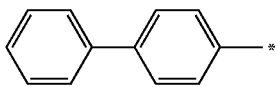 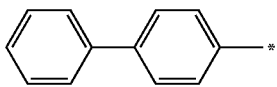
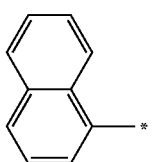 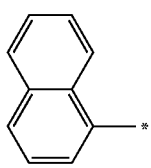 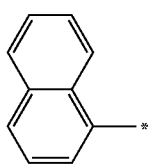
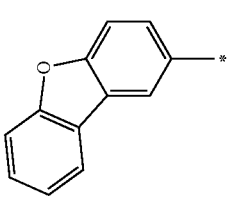 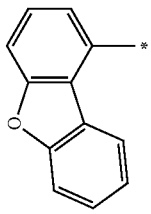 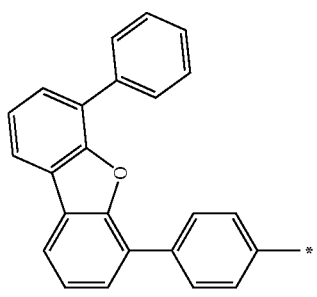
B1-23
B1-24
B1-25

-continued
[Compound Group 1]
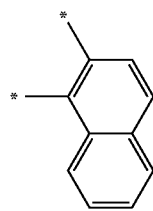 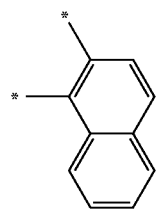 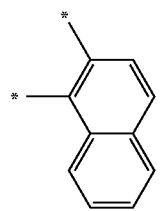
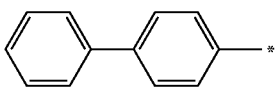 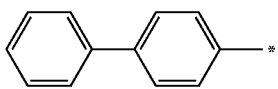 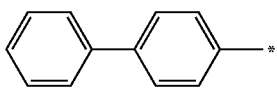
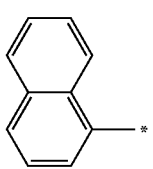 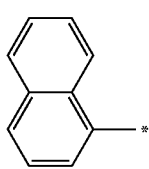 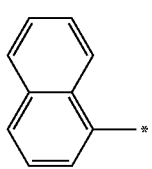
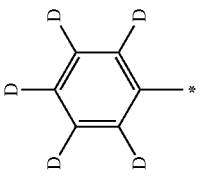 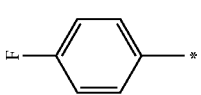 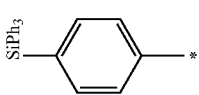
B1-26  B1-27  B1-28

-continued
[Compound Group 1]
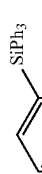
B1-29
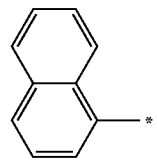
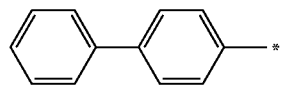
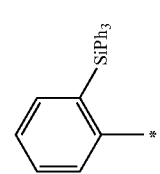
B1-30
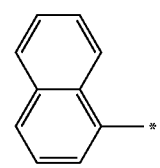
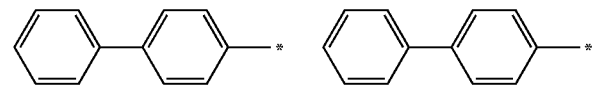
C1-1

-continued
[Compound Group 1]
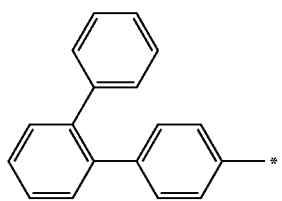
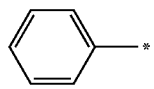
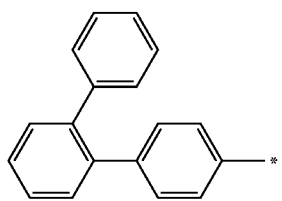
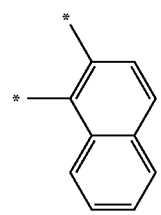
C1-2
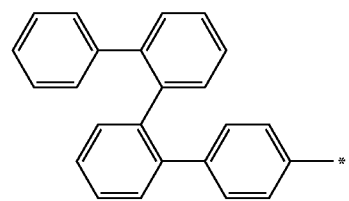
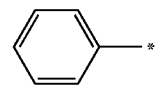
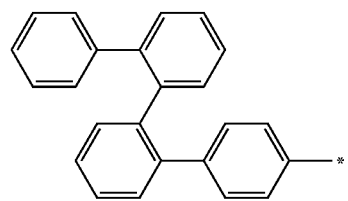
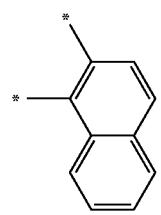
C1-3
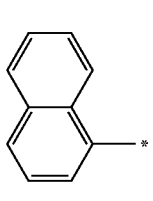
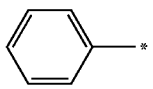
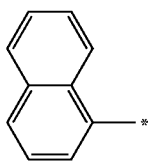
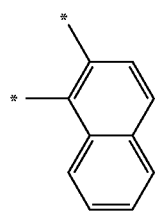
C1-4

-continued
[Compound Group 1]
| | | | |
|---|---|---|---|
| C1-5 | 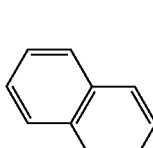 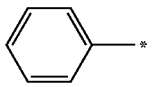 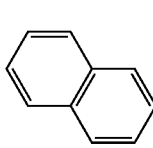 | | |
| C1-6 | 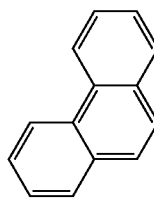 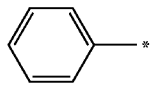 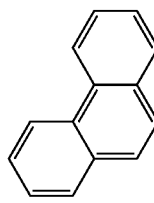 | | |
| C1-7 | 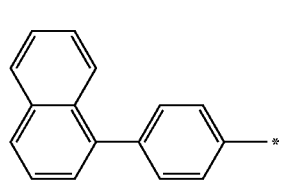 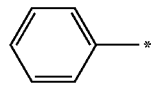 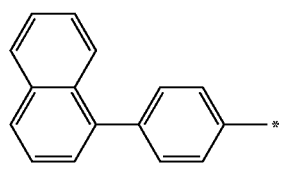 | | |
| C1-8 | 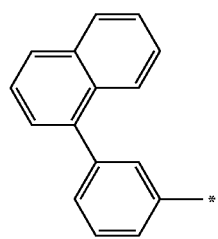 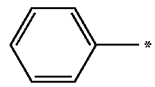 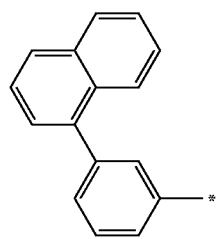 | | |

-continued
[Compound Group 1]
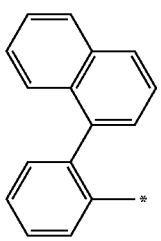 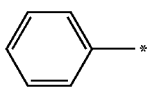 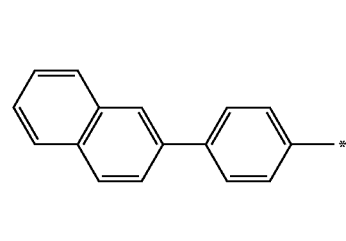 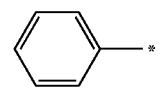 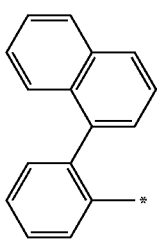 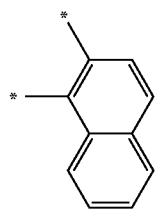 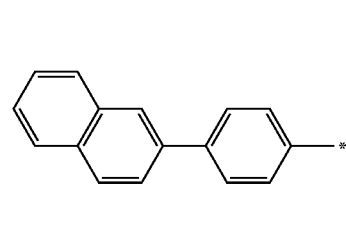 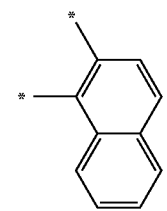
C1-9
C1-10
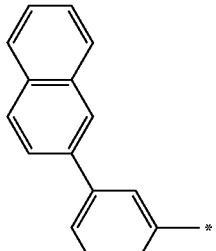 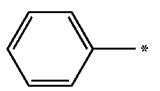 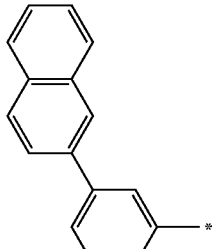 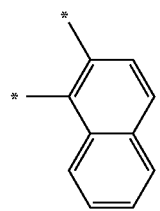 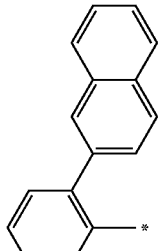 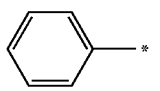 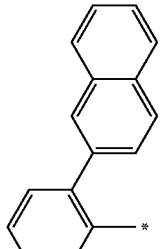 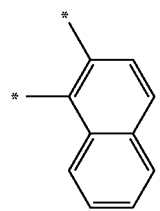
C1-11
C1-12

-continued
[Compound Group 1]
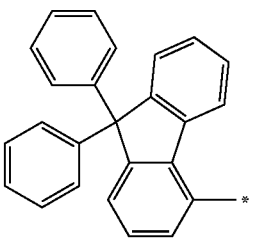
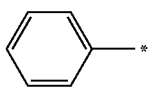
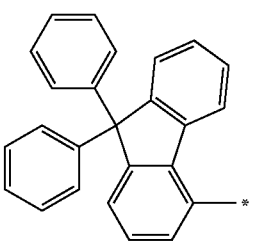
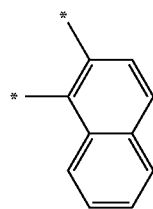
C1-13
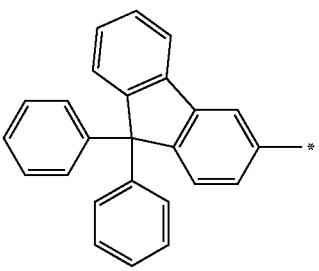
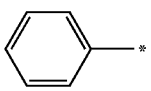
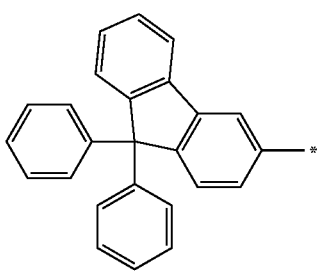
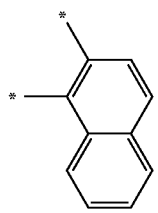
C1-14
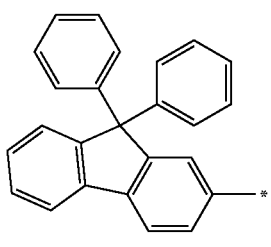
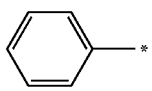
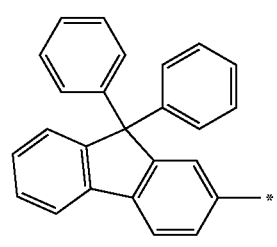
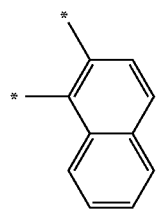
C1-15

-continued
[Compound Group 1]
| | | | |
|---|---|---|---|
| 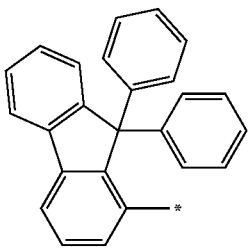 | 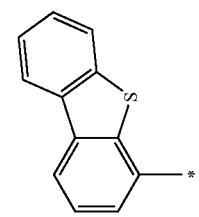 | 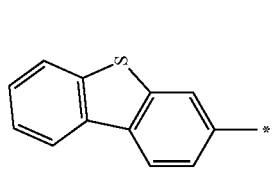 | 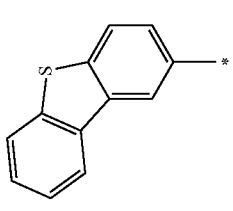 |
| 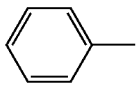 | 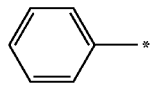 | 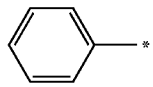 | 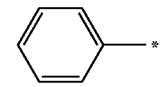 |
| 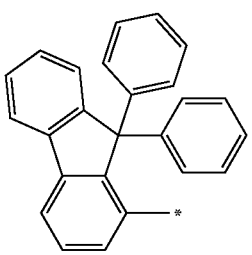 | 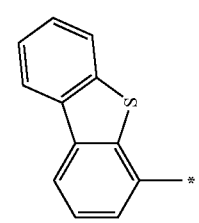 | 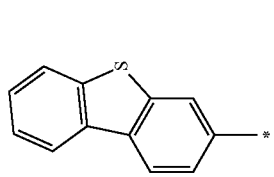 | 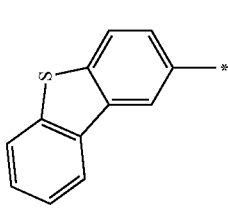 |
| 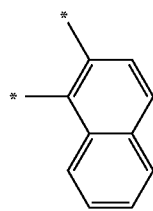 | 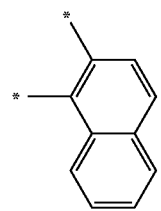 | 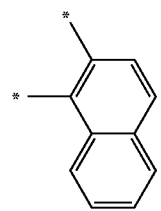 | 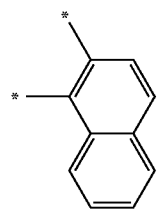 |
| C1-16 | C1-17 | C1-18 | C1-19 |

-continued
[Compound Group 1]
| | | | |
|---|---|---|---|
| 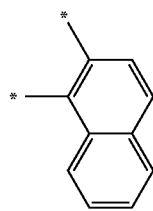 | 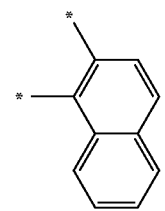 | 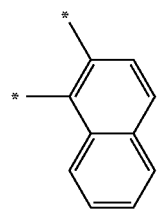 | 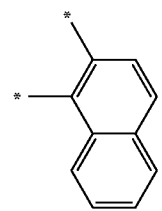 |
| 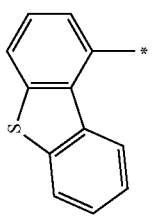 | 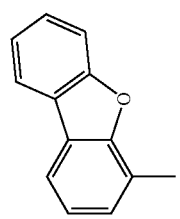 | 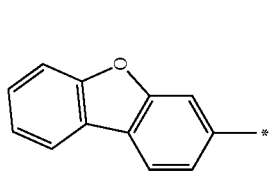 | 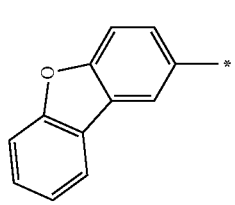 |
| 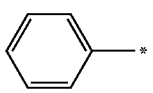 | 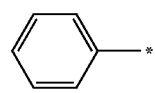 | 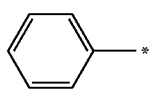 | 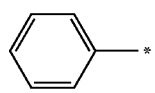 |
| 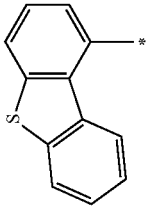 | 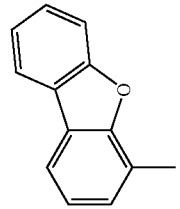 | 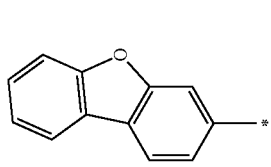 | 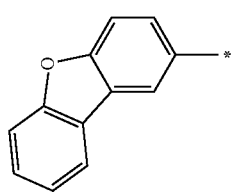 |
| C1-20 | C1-21 | C1-22 | C1-23 |

-continued
[Compound Group 1]
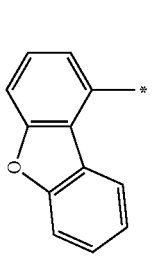
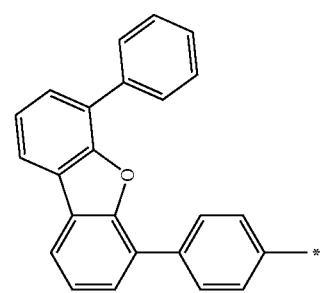
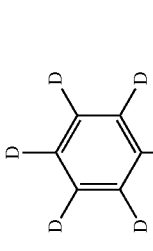
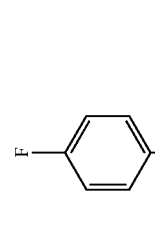
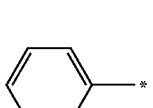
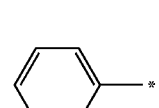
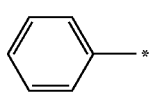
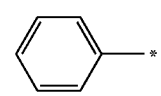
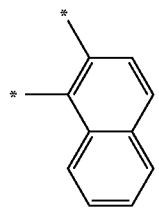
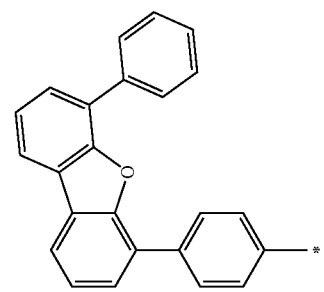
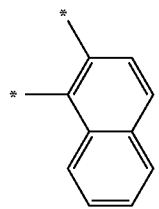
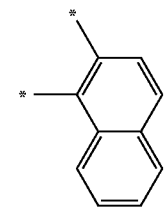
C1-24  C1-25  C1-26  C1-27

[Compound Group 1]
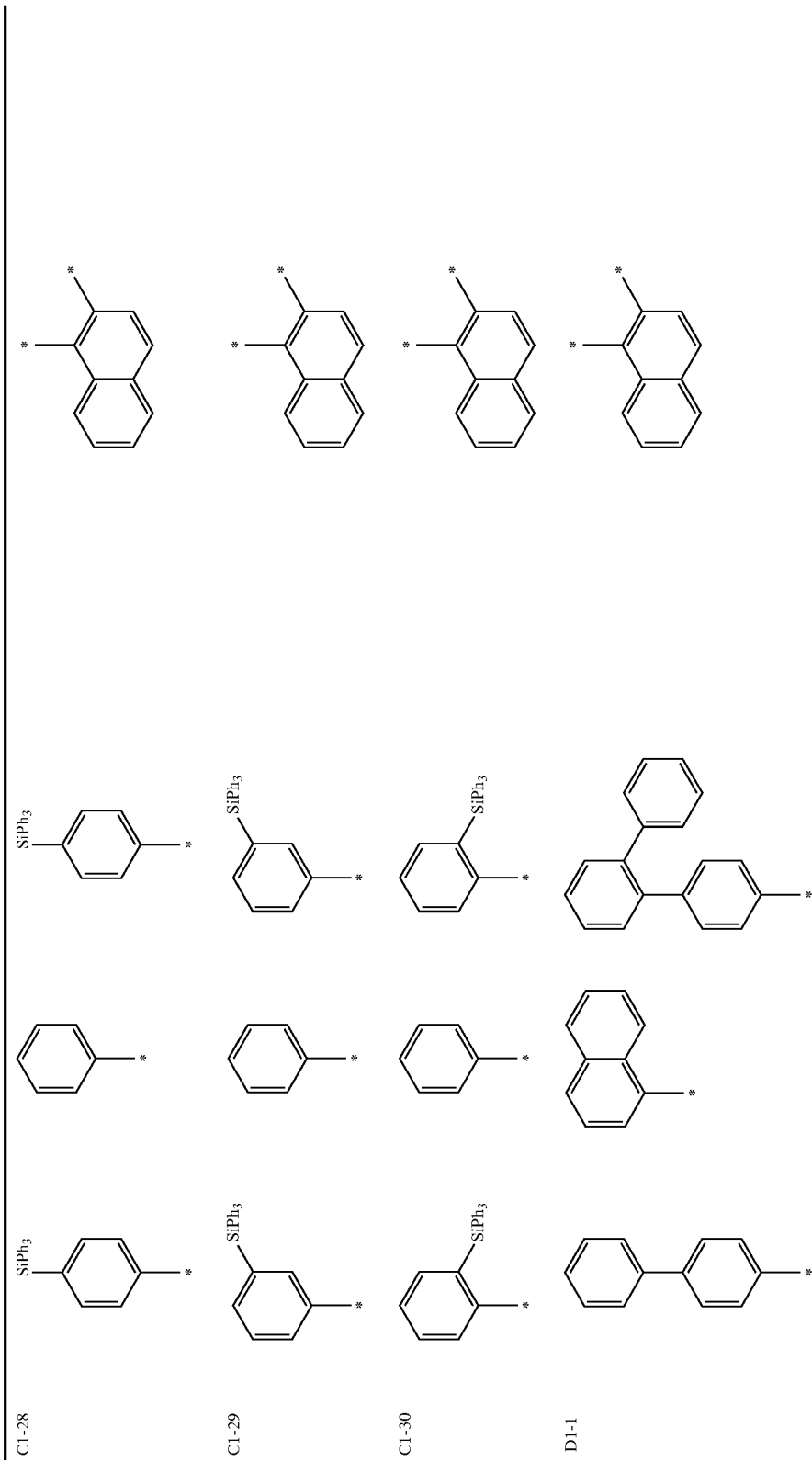

-continued
[Compound Group 1]
D1-2
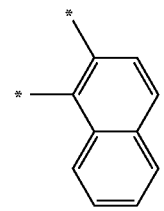 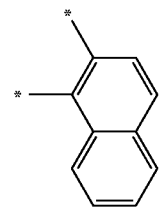 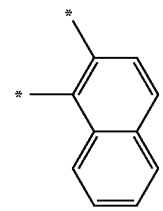
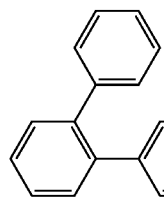 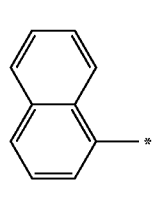 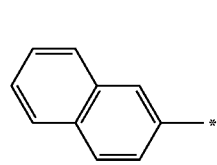
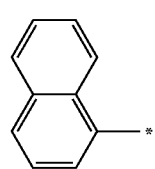 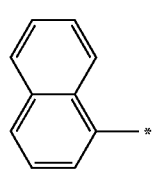 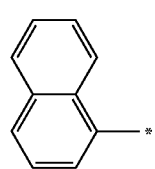
D1-3
D1-4
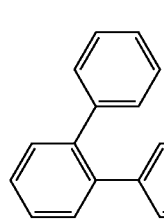 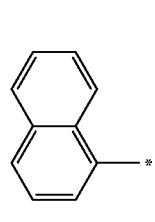

-continued
[Compound Group 1]
| | | | |
|---|---|---|---|
| 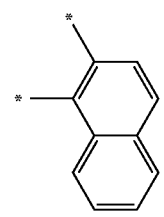 | 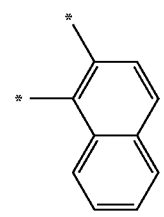 | 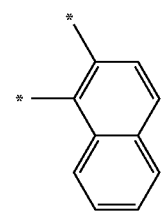 | 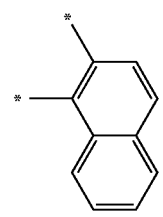 |
| 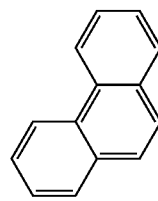 | 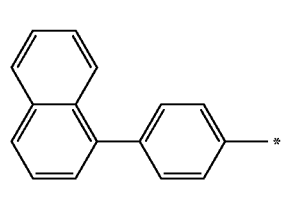 | 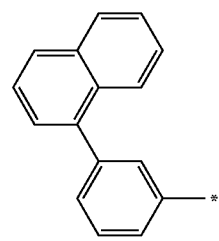 | 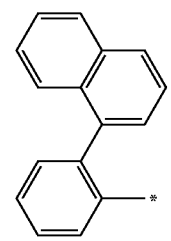 |
| 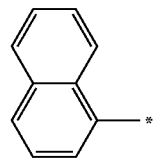 | 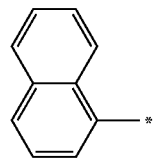 | 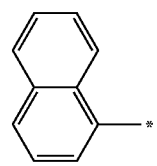 | 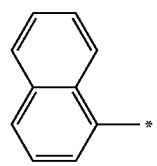 |
| 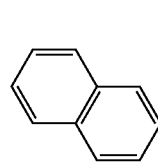 | 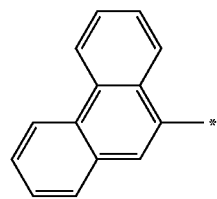 | 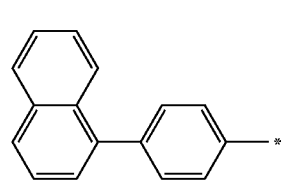 | 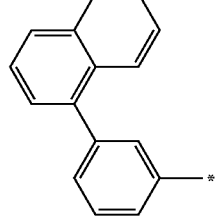 |
| D1-5 | D1-6 | D1-7 | D1-8 |

-continued
[Compound Group 1]
D1-9
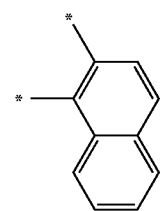
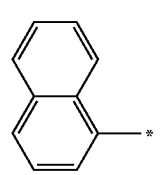
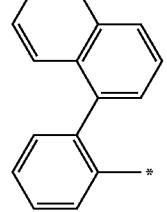
D1-10
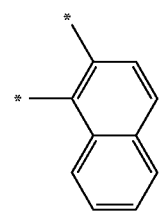
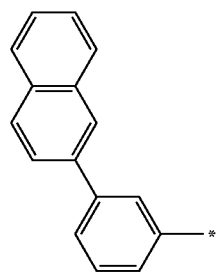
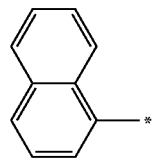
D1-11
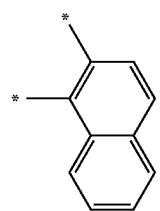
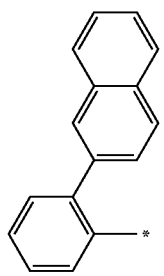
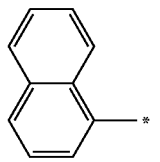

-continued
[Compound Group 1]
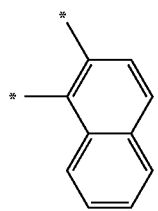
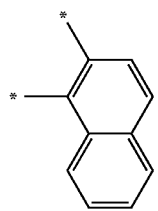
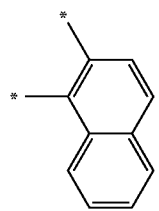
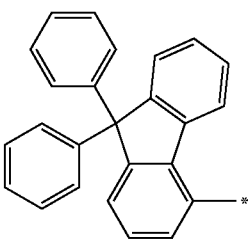
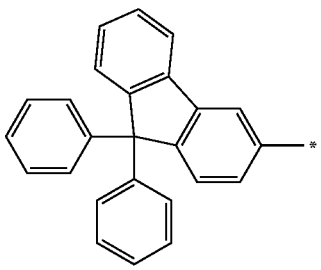
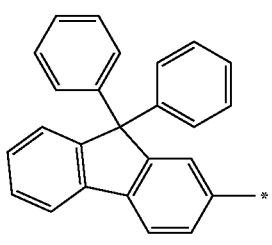
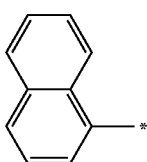
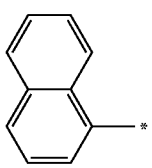
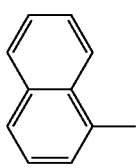
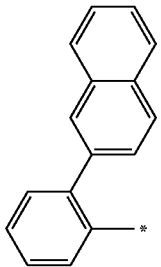
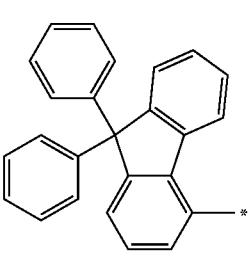
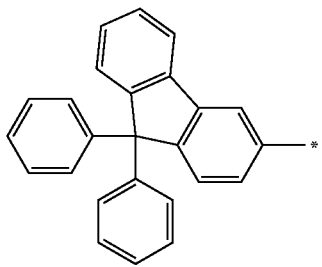
D1-12
D1-13
D1-14

-continued
[Compound Group 1]
| | | |
|---|---|---|
| 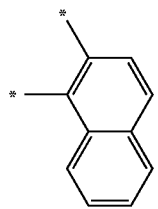 | 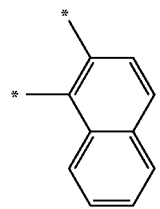 | 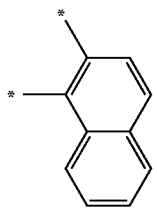 |
| 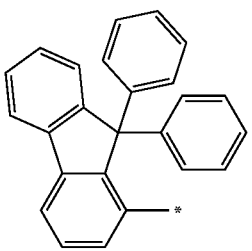 | 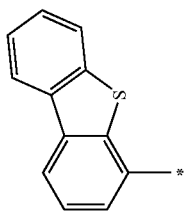 | 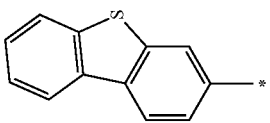 |
| 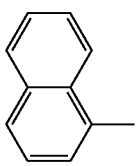 | 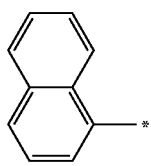 | 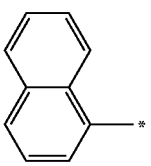 |
| 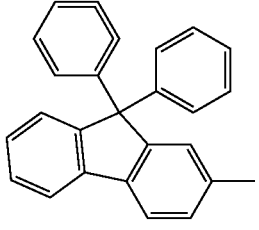 | 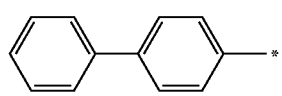 | 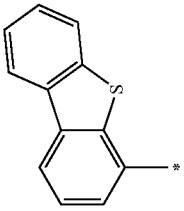 |
| D1-15 | D1-16 | D1-17 |

-continued
[Compound Group 1]
D1-18
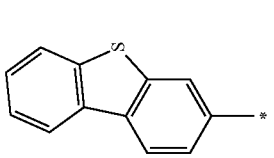
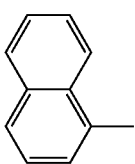
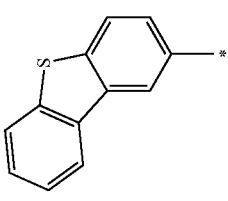
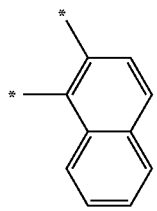
D1-19
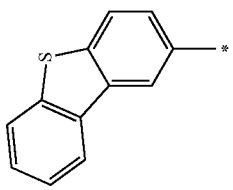
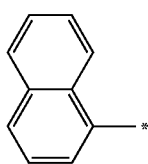
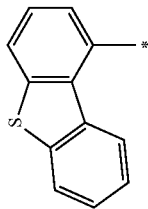
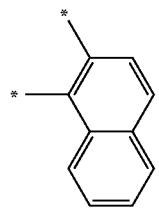
D1-20
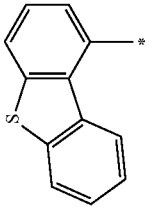
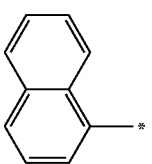
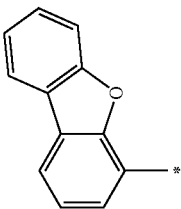
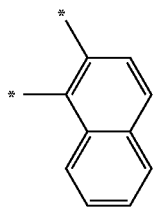
D1-21
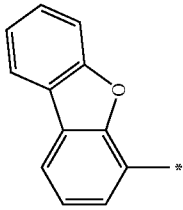
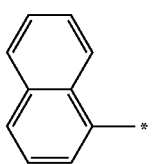
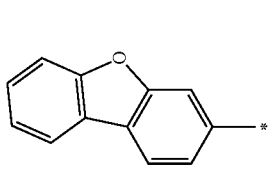
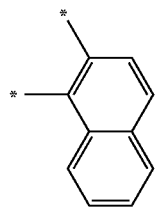

-continued
[Compound Group 1]
D1-22
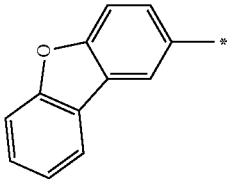 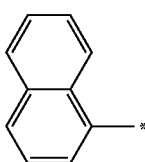 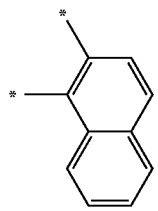
D1-23
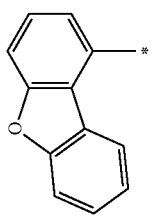 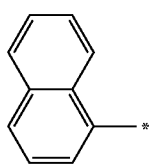 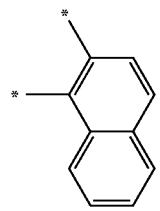
D1-24
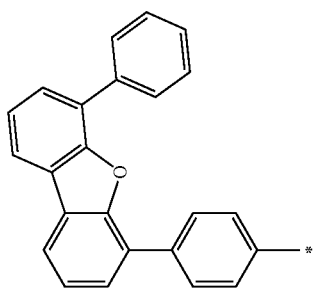 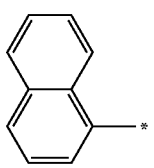 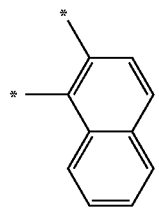
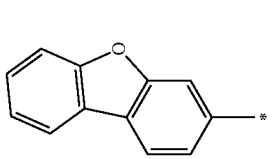 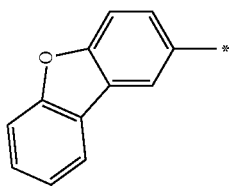 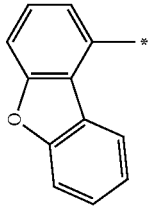

-continued
[Compound Group 1]
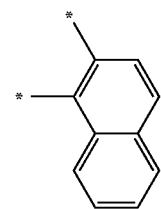
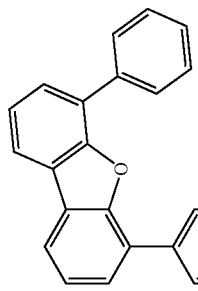
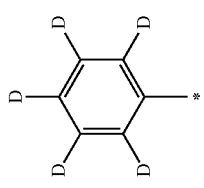
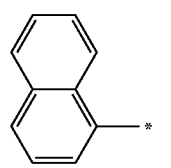
D1-25
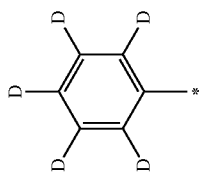
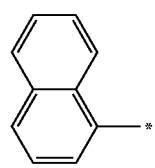
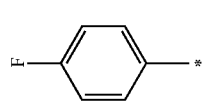
D1-26
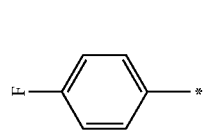
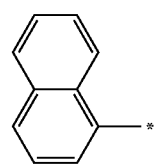
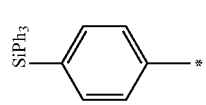
D1-27
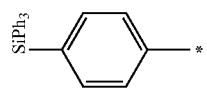
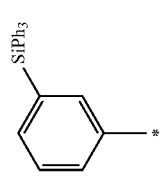
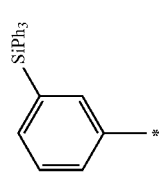
D1-28

-continued
[Compound Group 1]
| D1-29 | 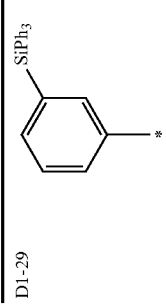 | 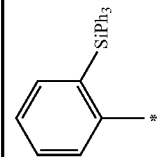 | 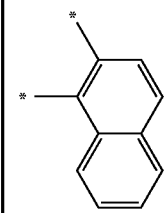 |
| D1-30 | 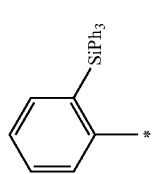 | 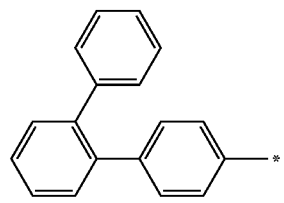 | 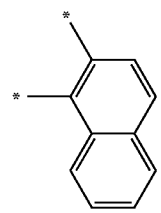 |

-continued
[Compound Group 1]
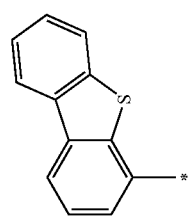
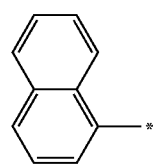
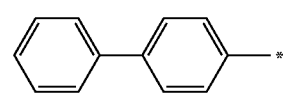
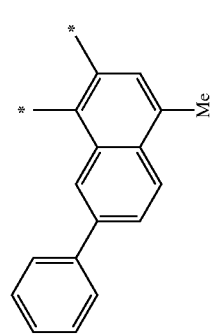
E1-1
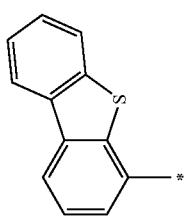
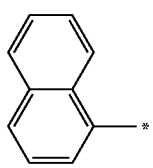
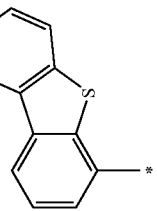
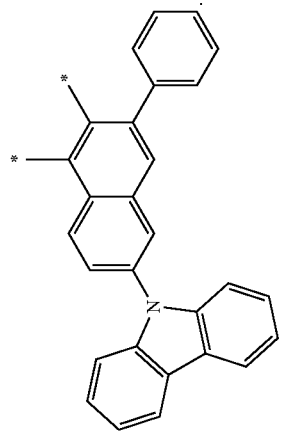
E1-2

21. The diamine compound of claim 16, wherein the diamine compound represented by Formula 1 is at least one selected among compounds represented in Compound Group 2:

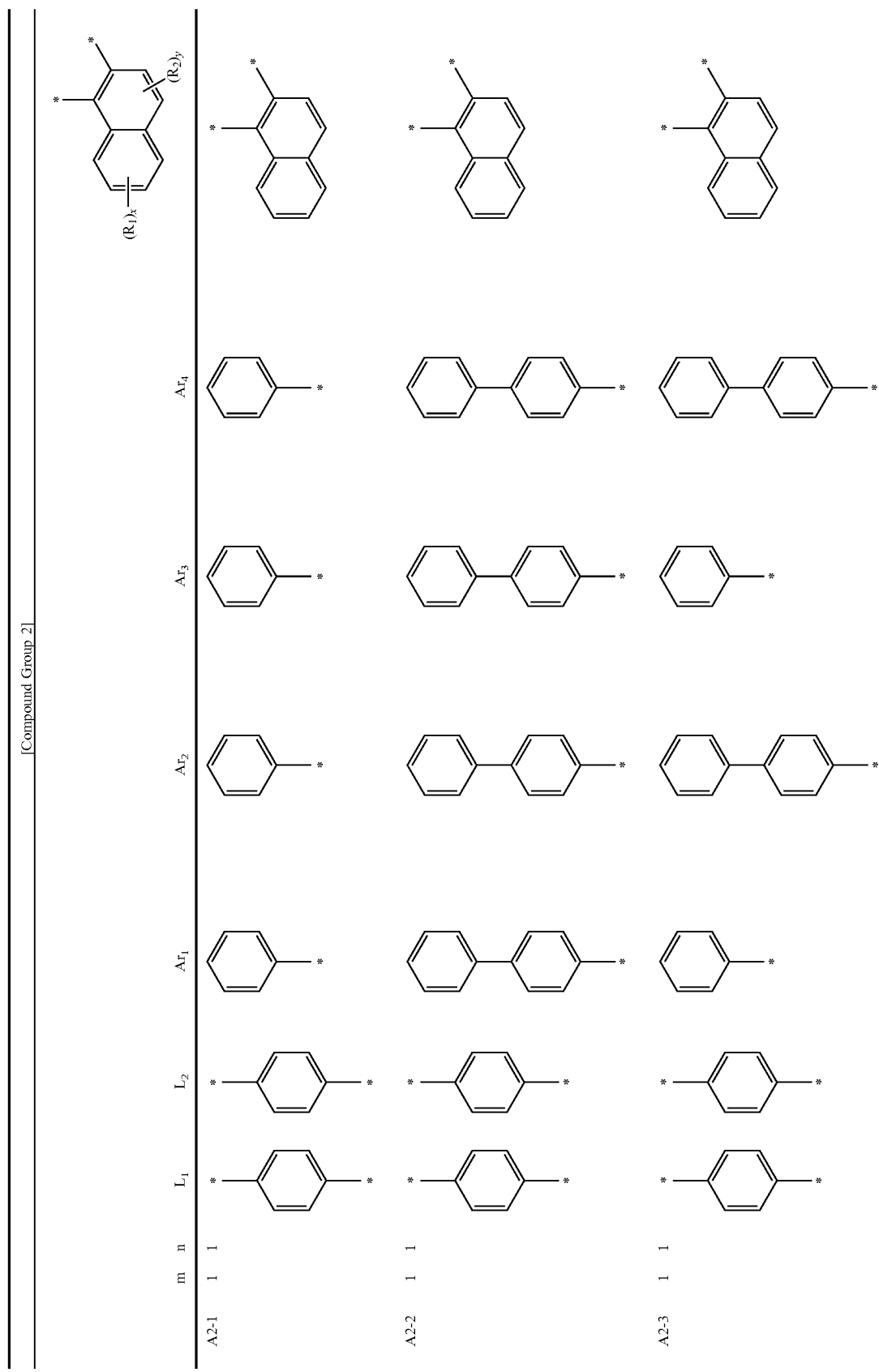

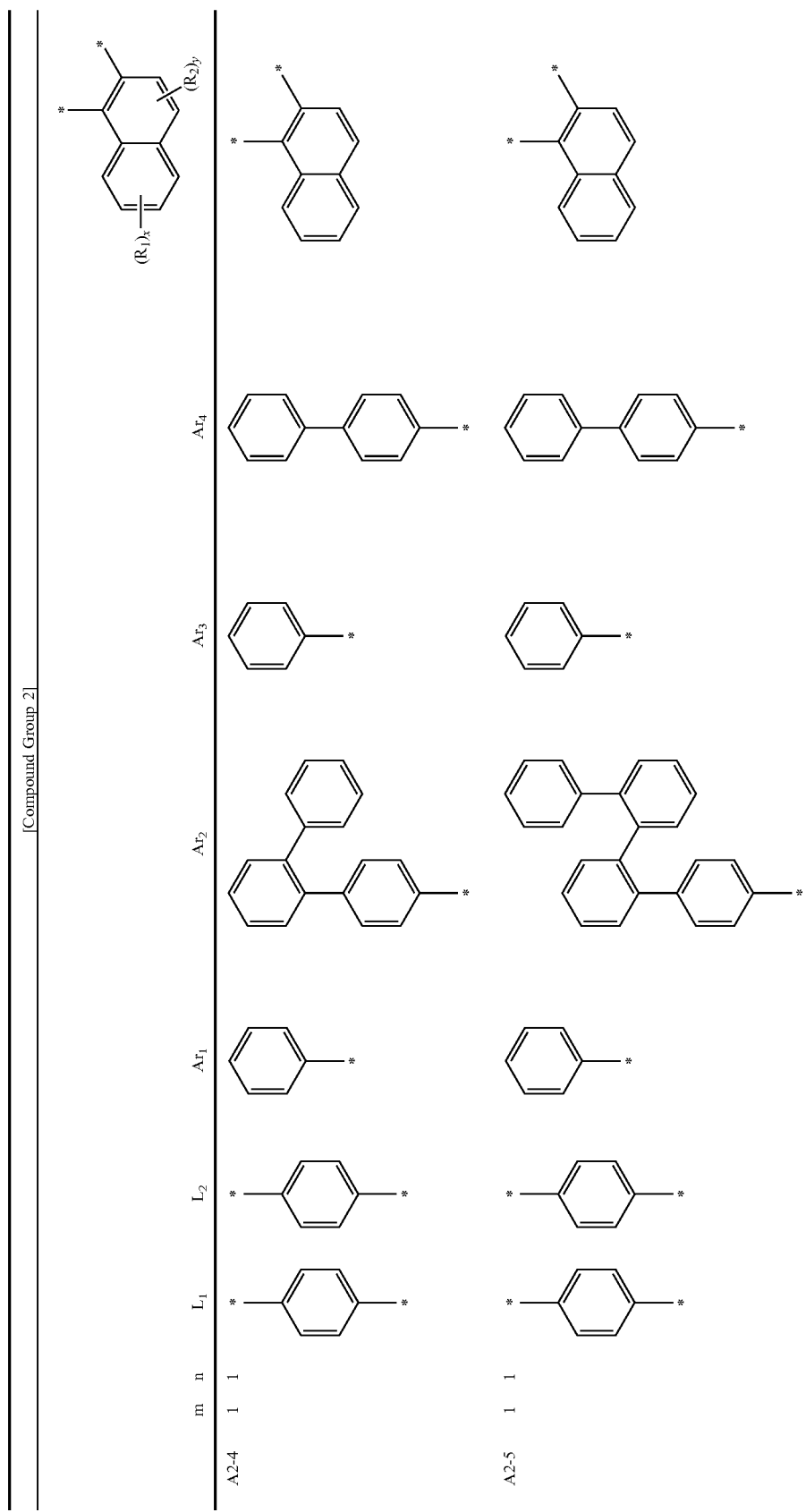

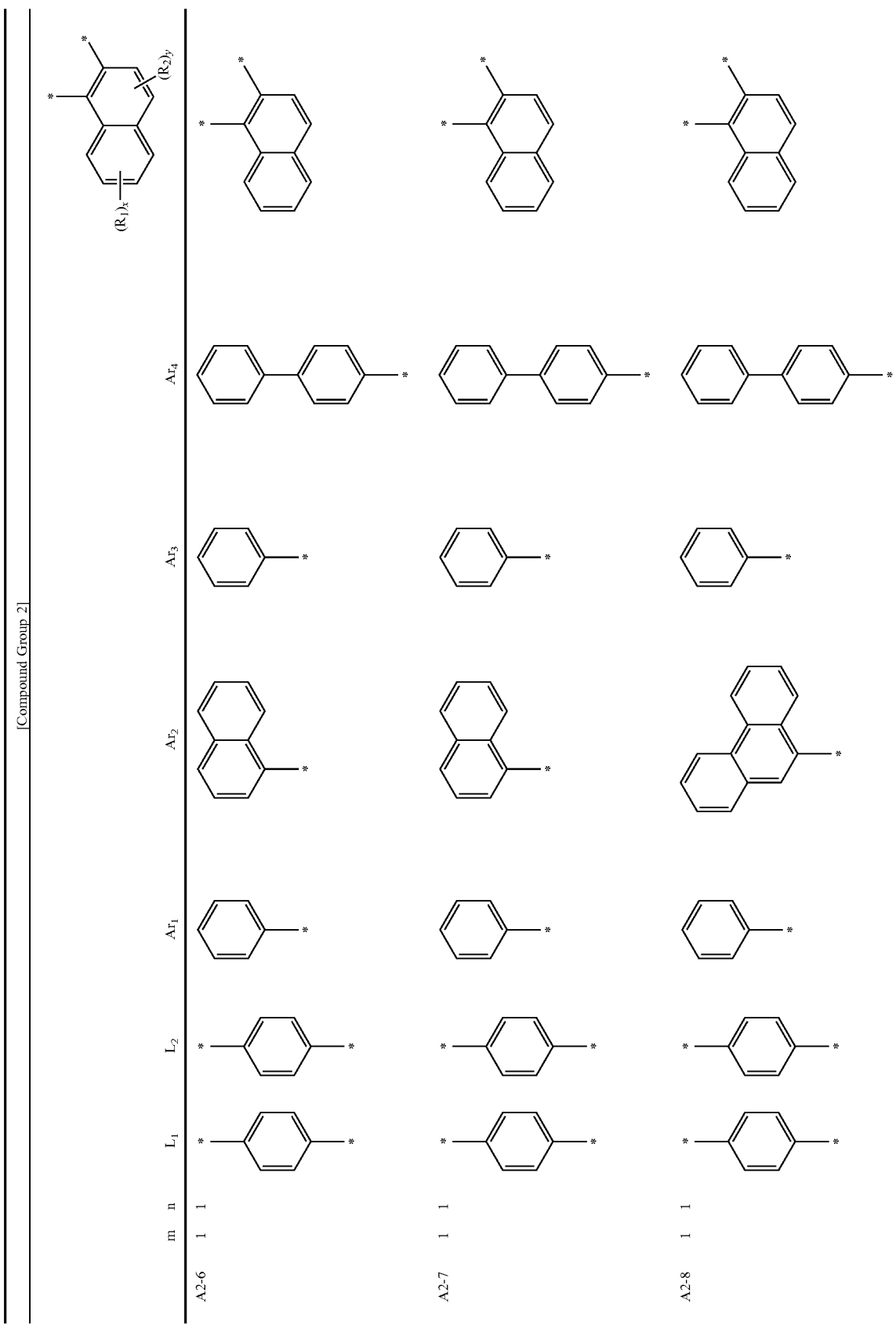

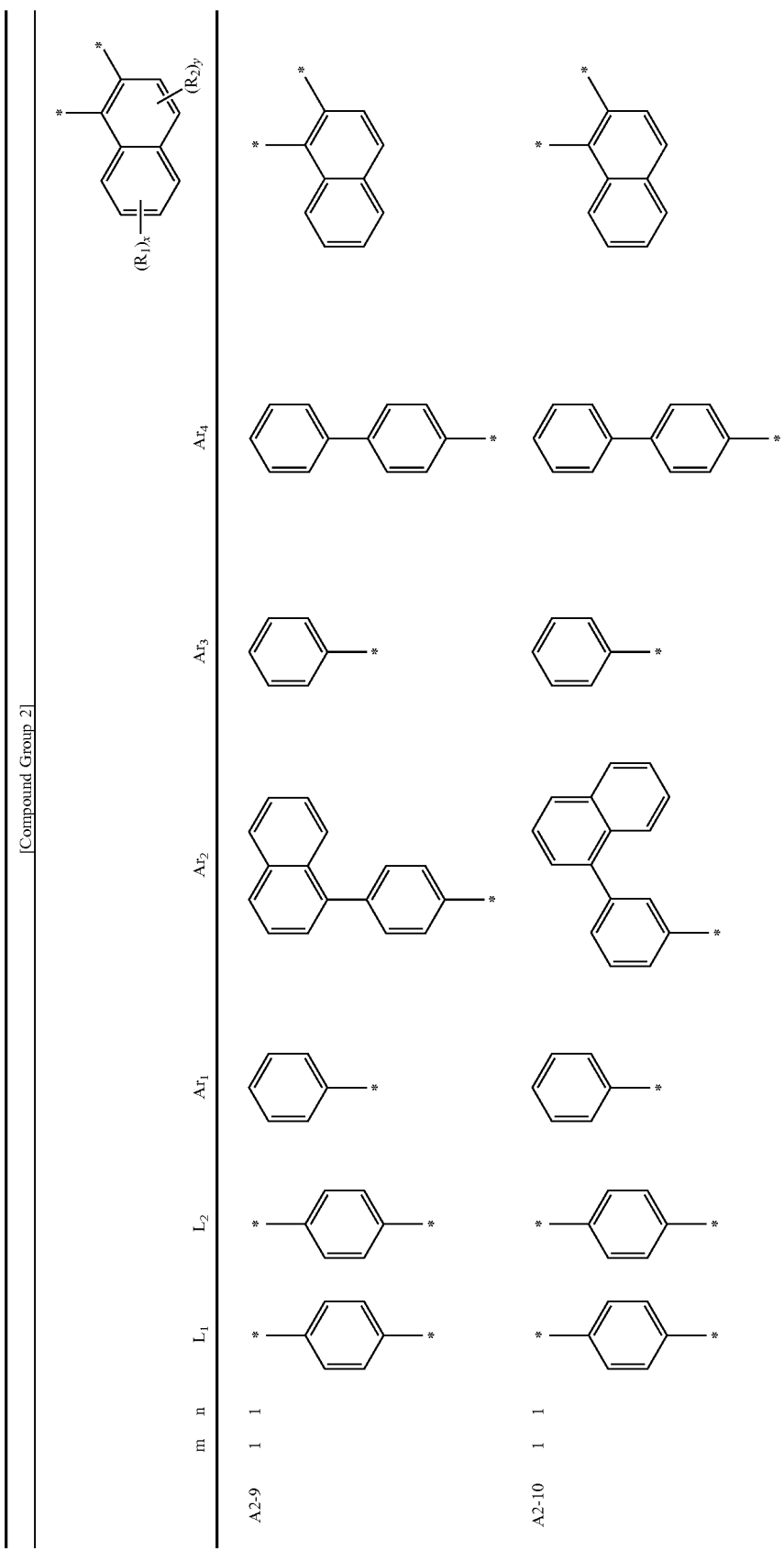

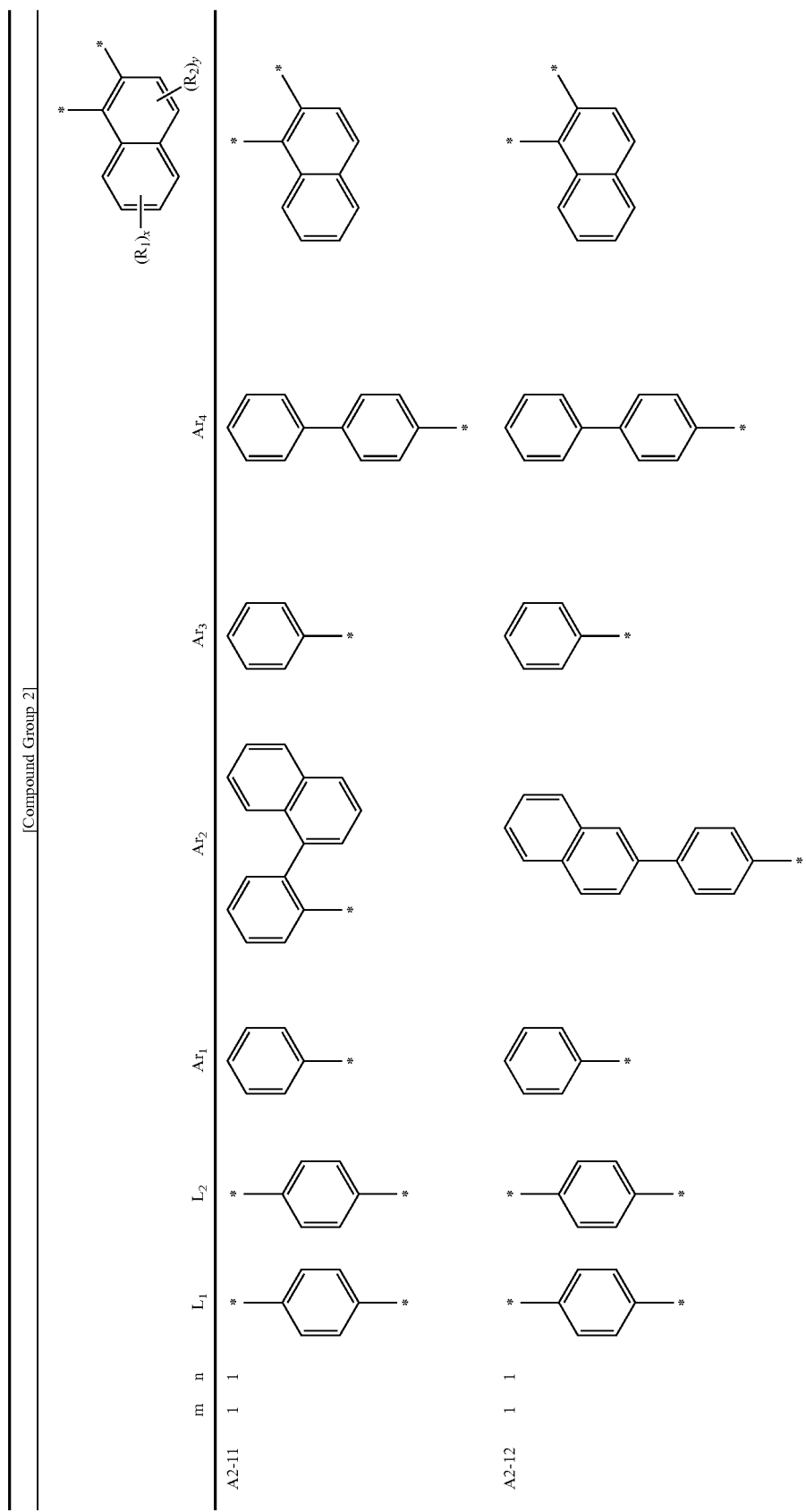

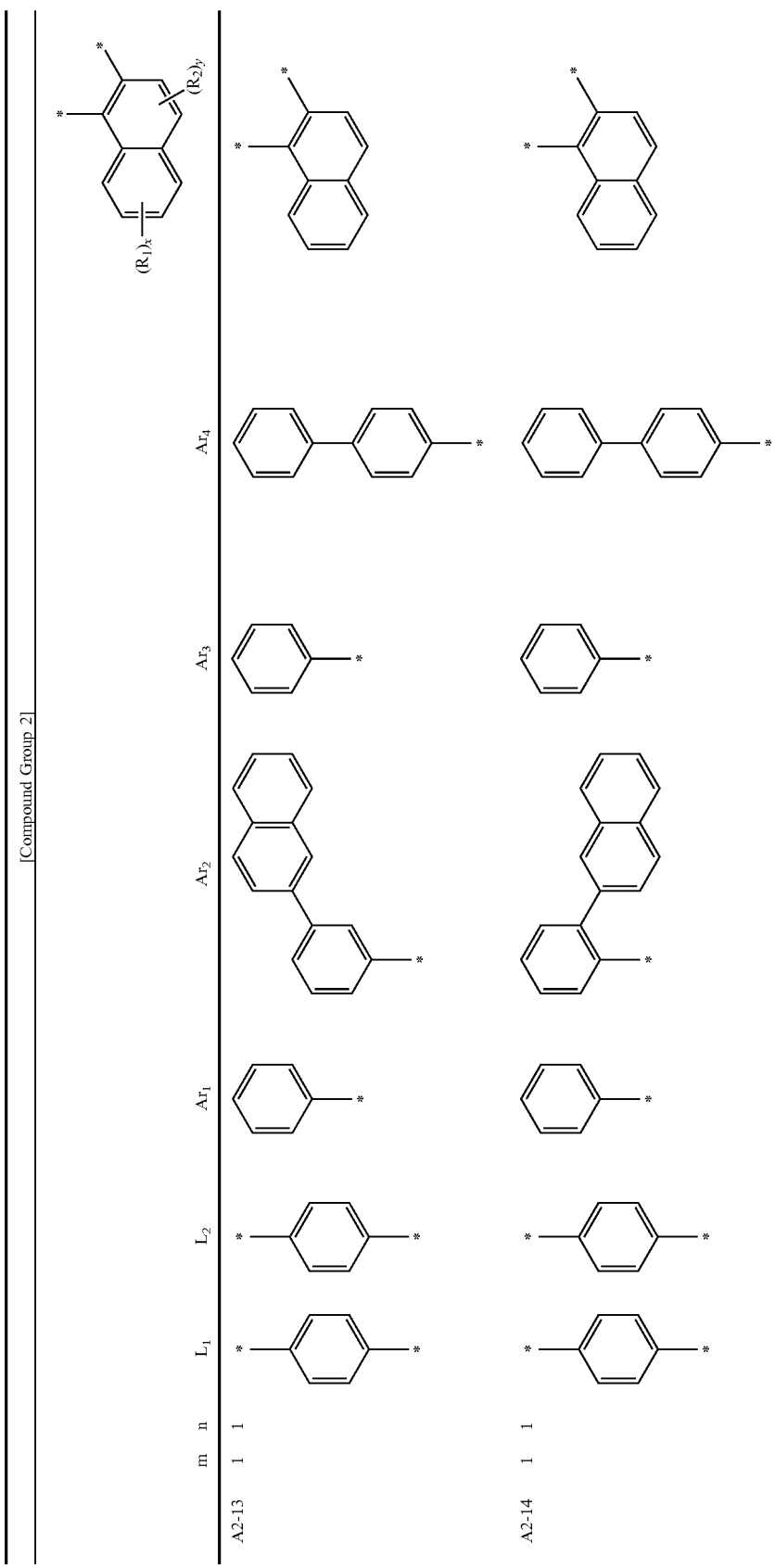

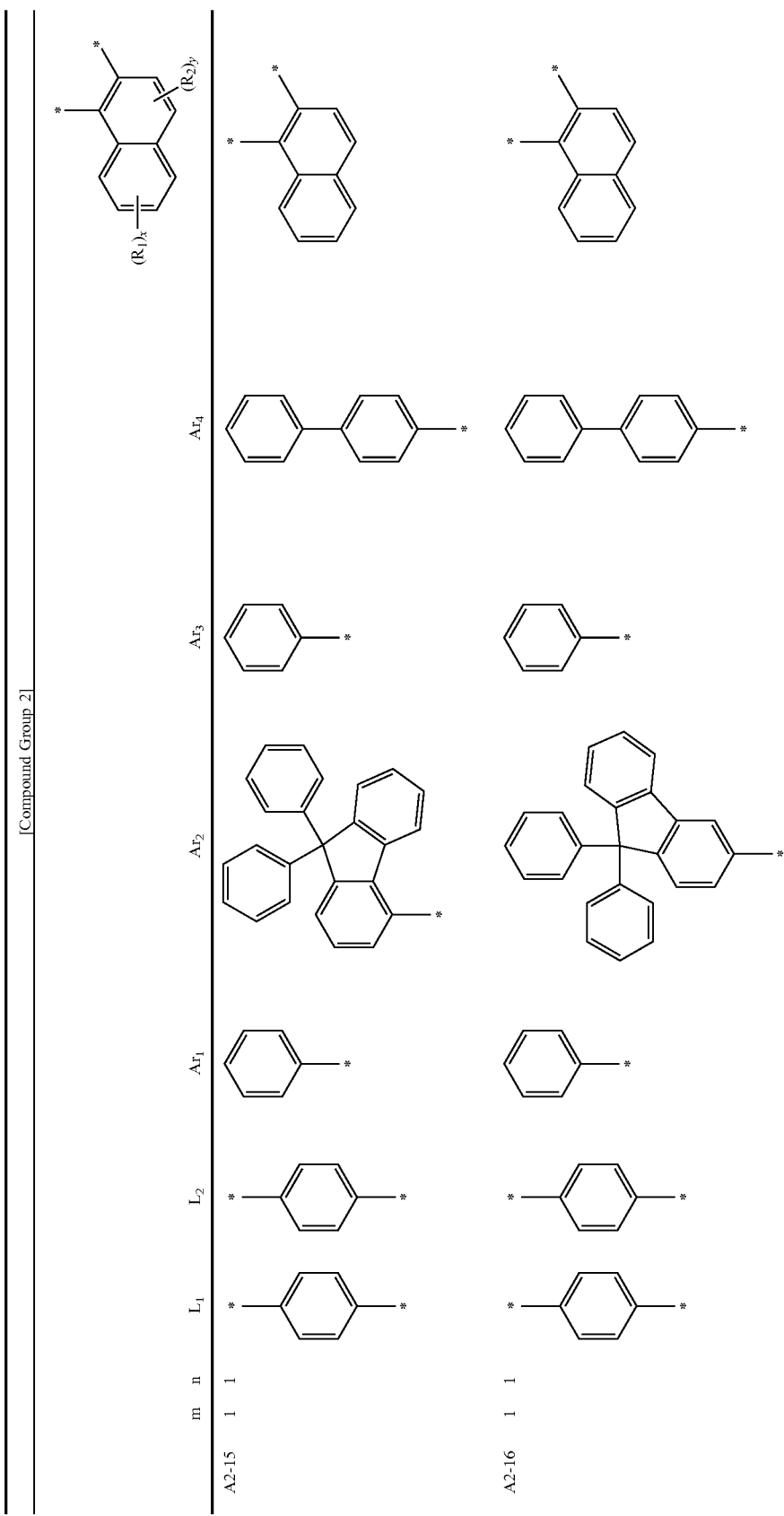

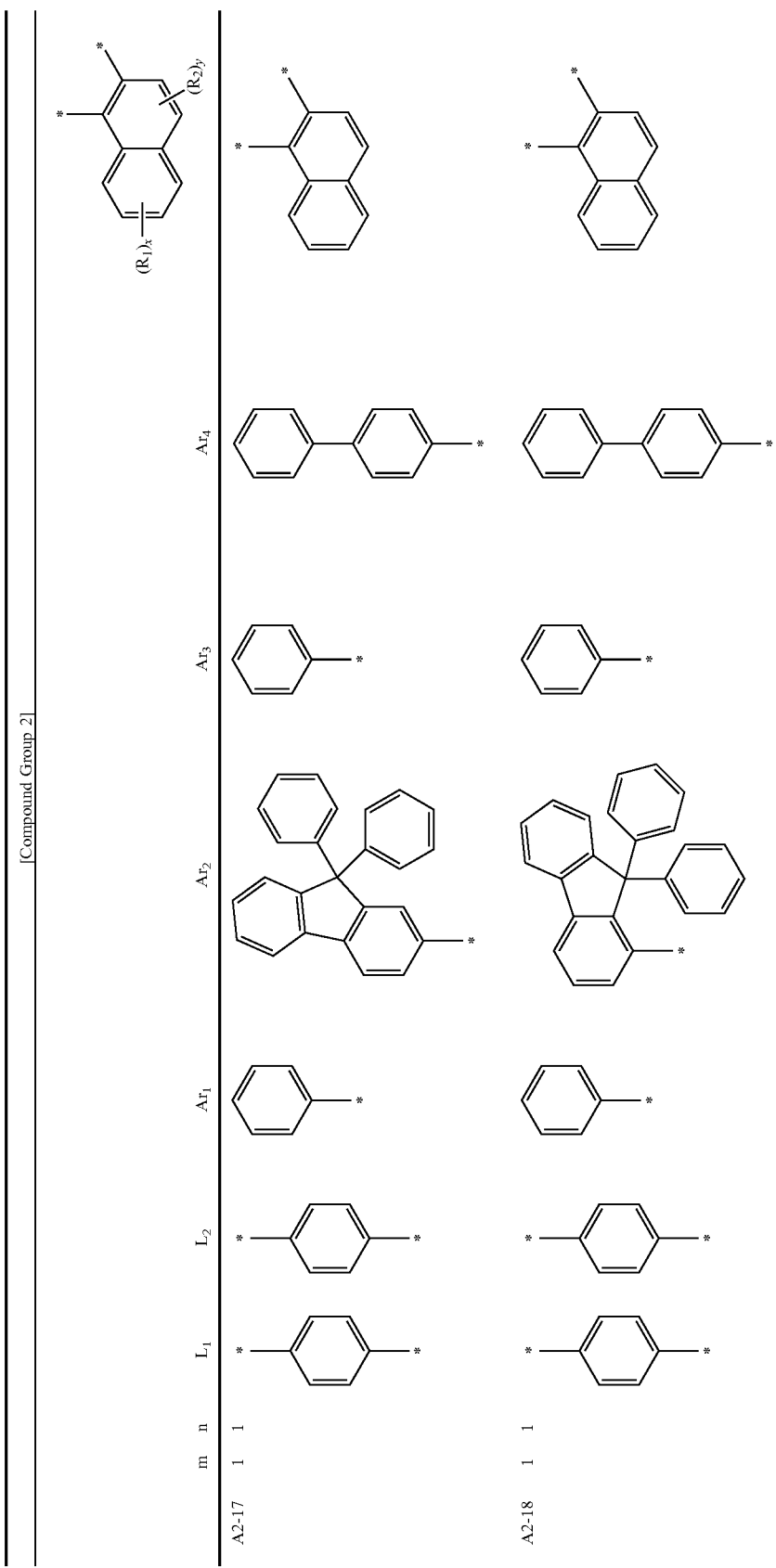

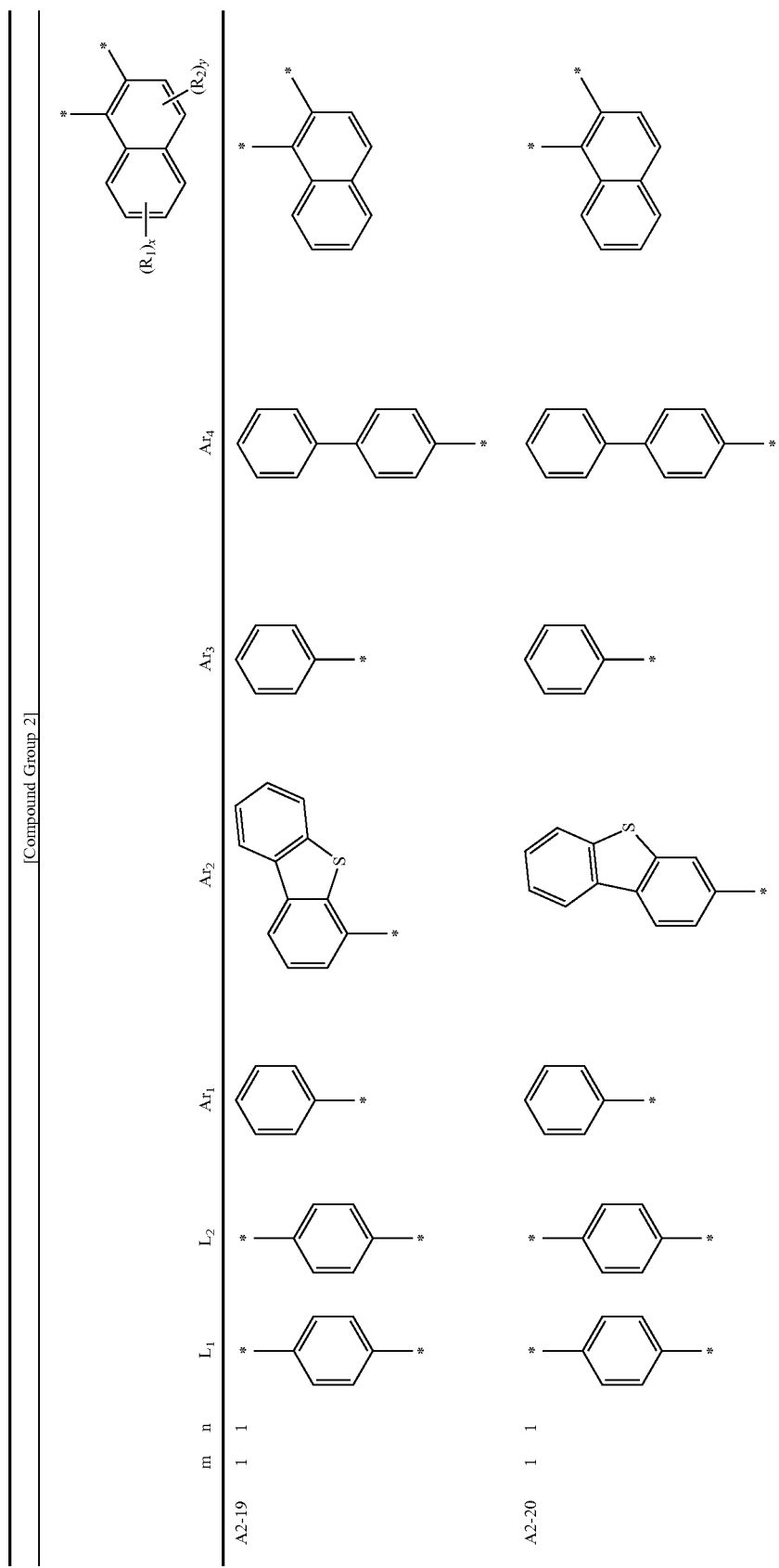

-continued
[Compound Group 2]
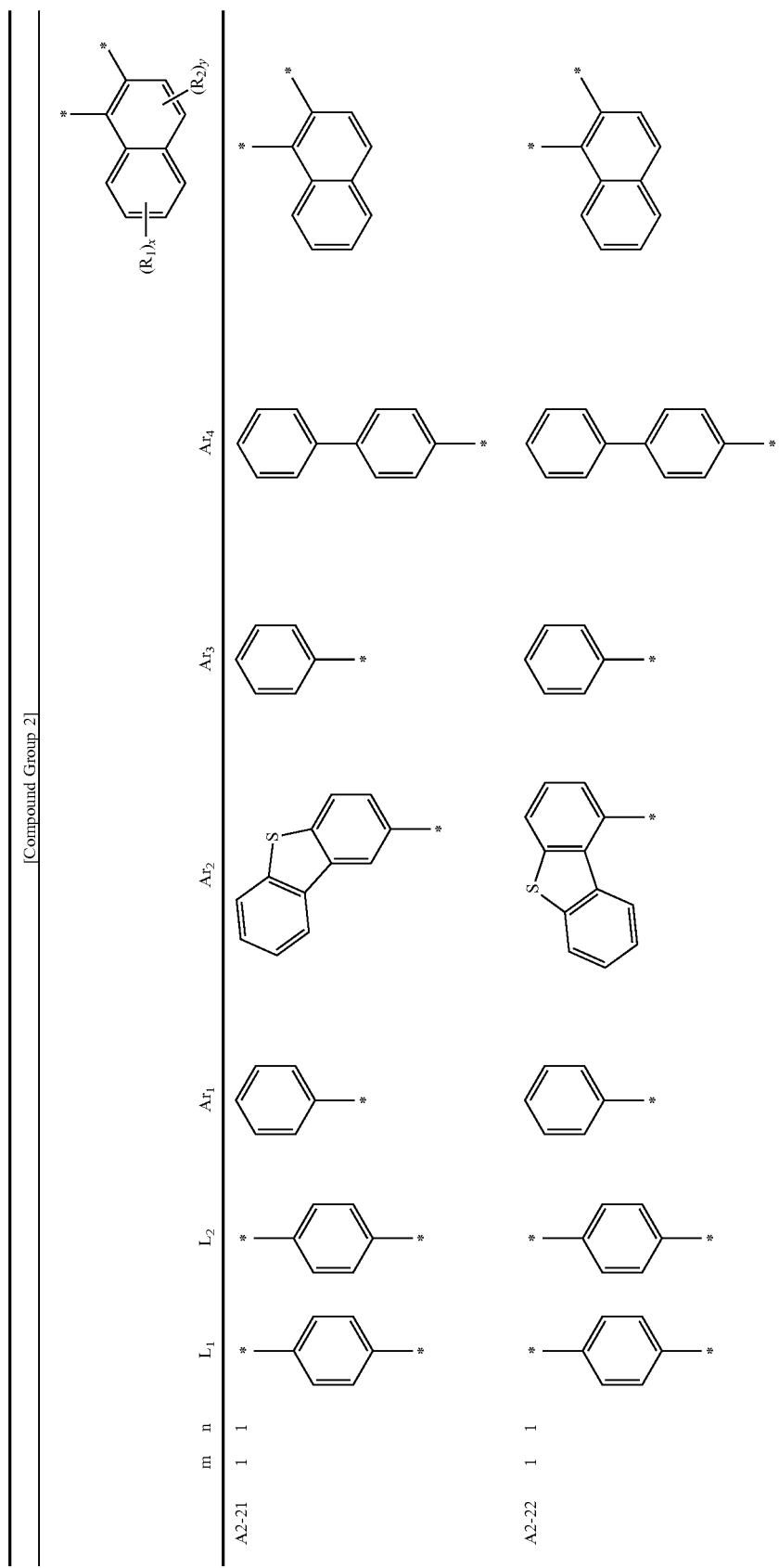

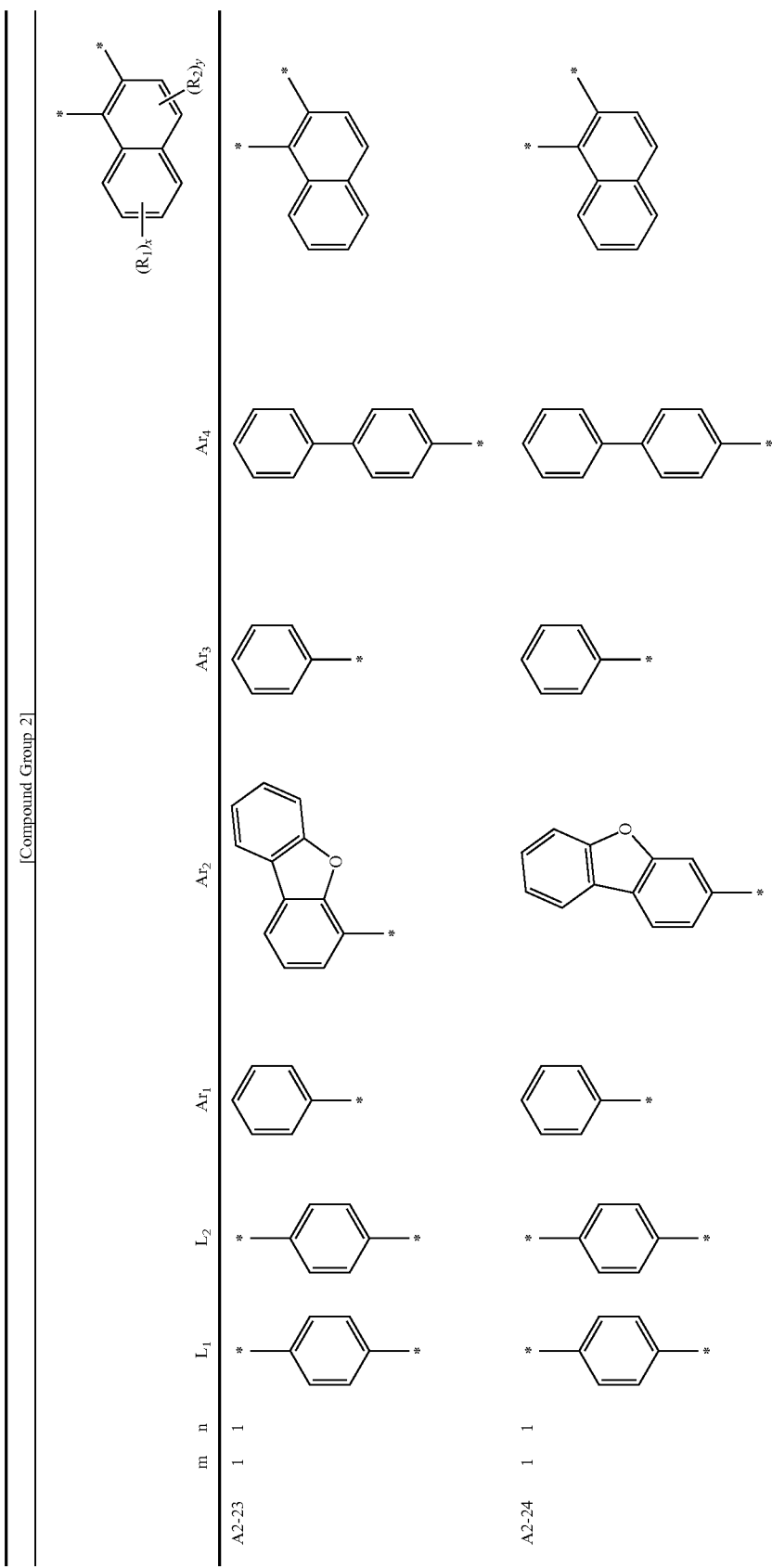

-continued
[Compound Group 2]
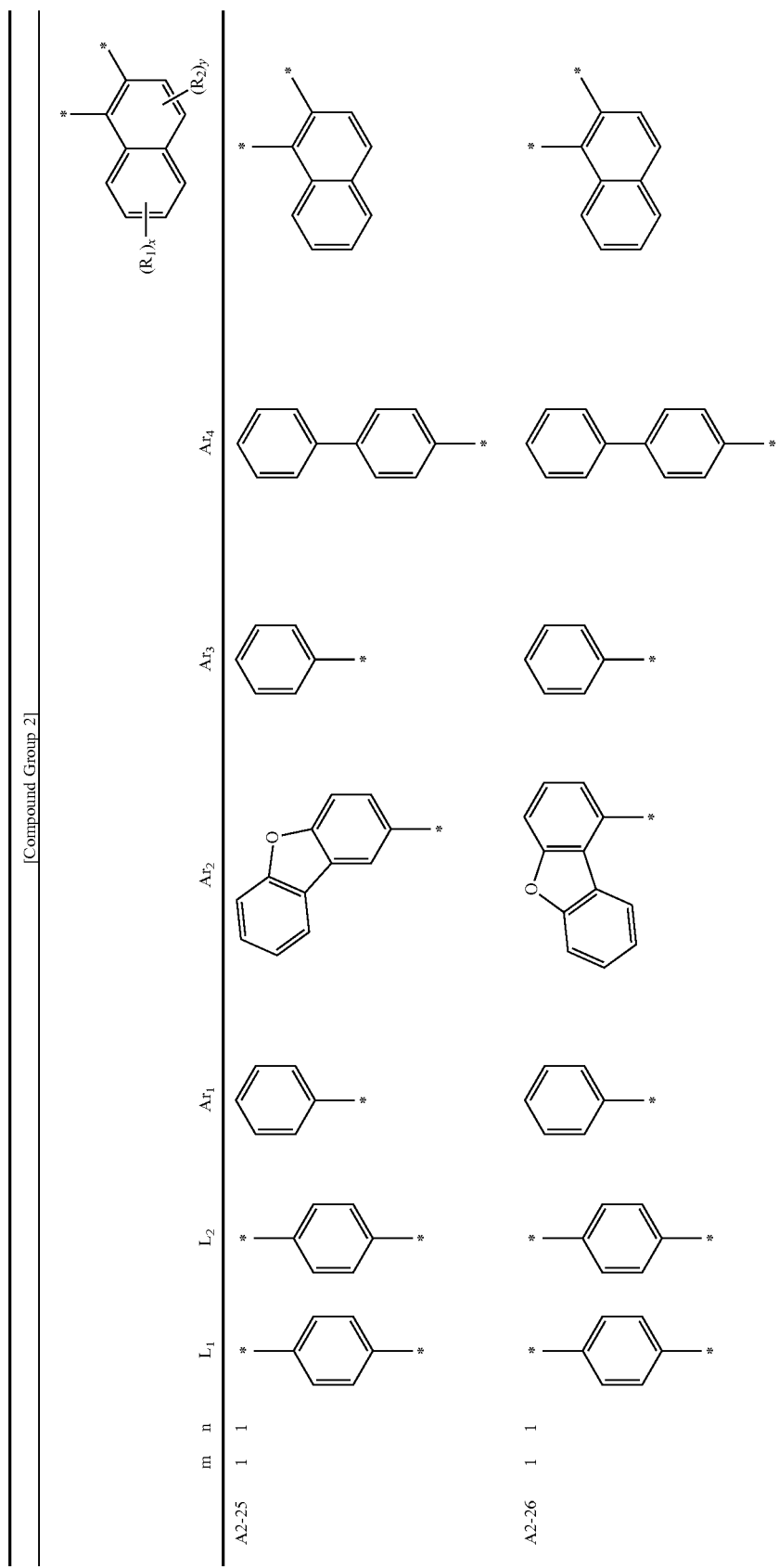

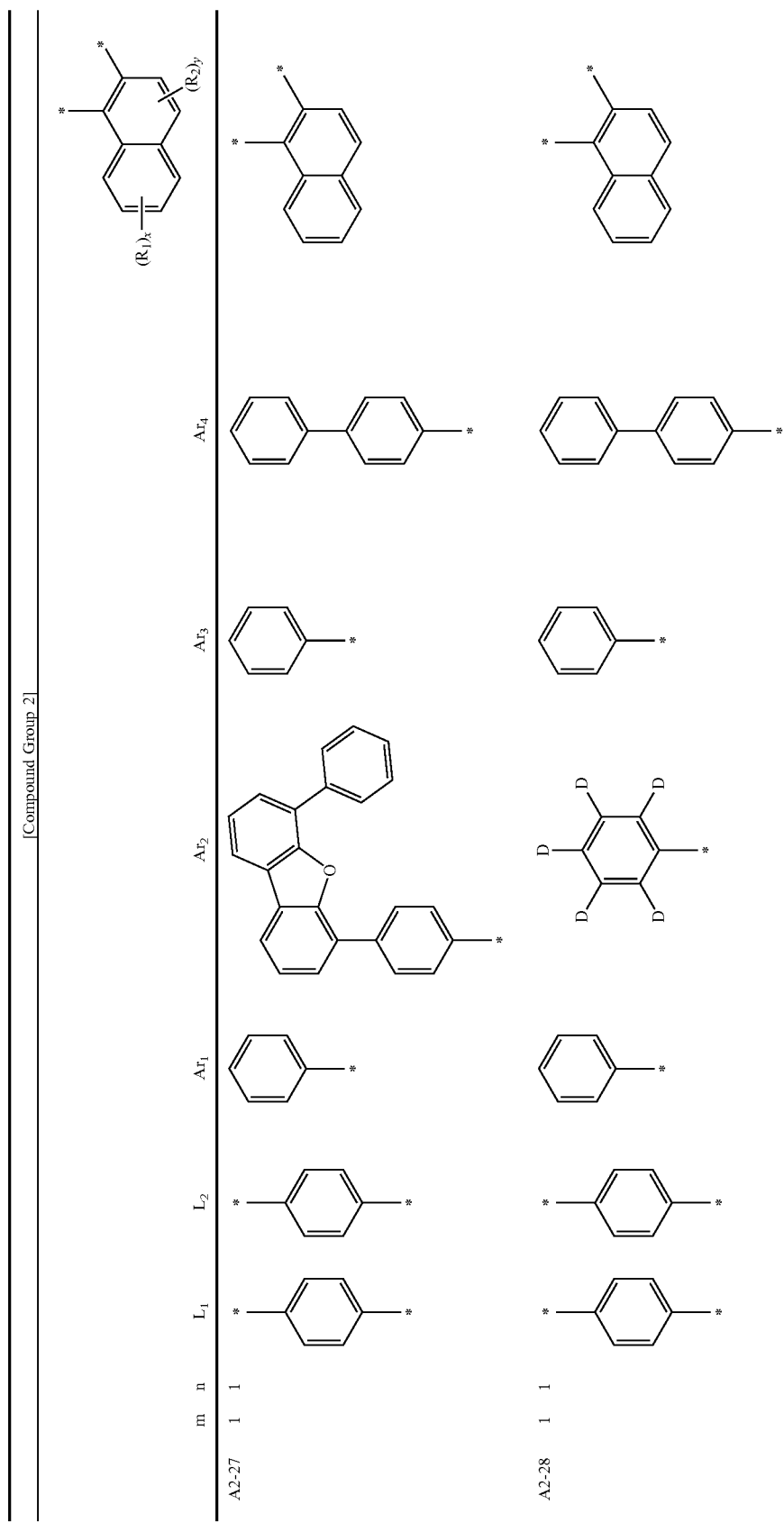

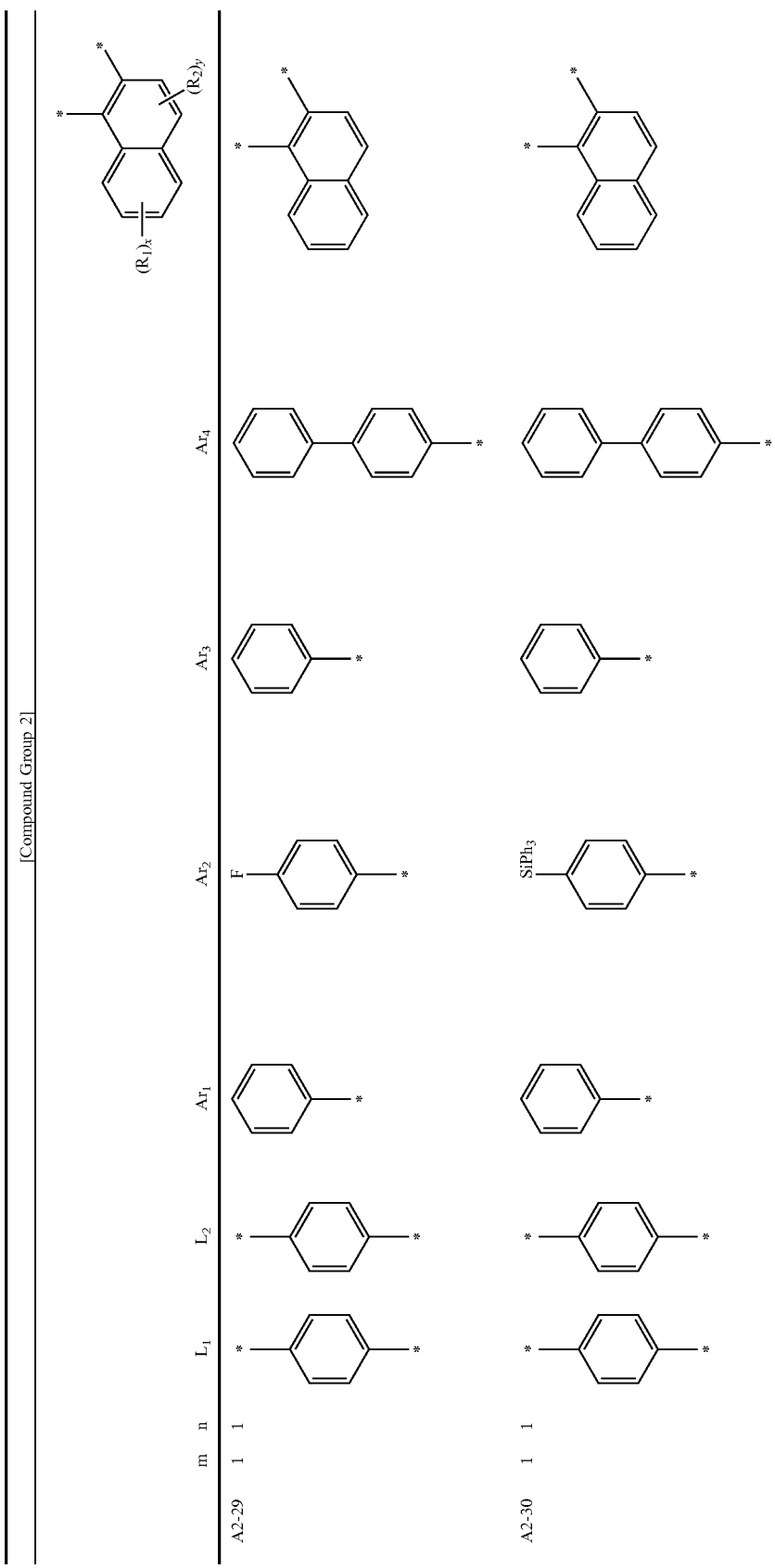

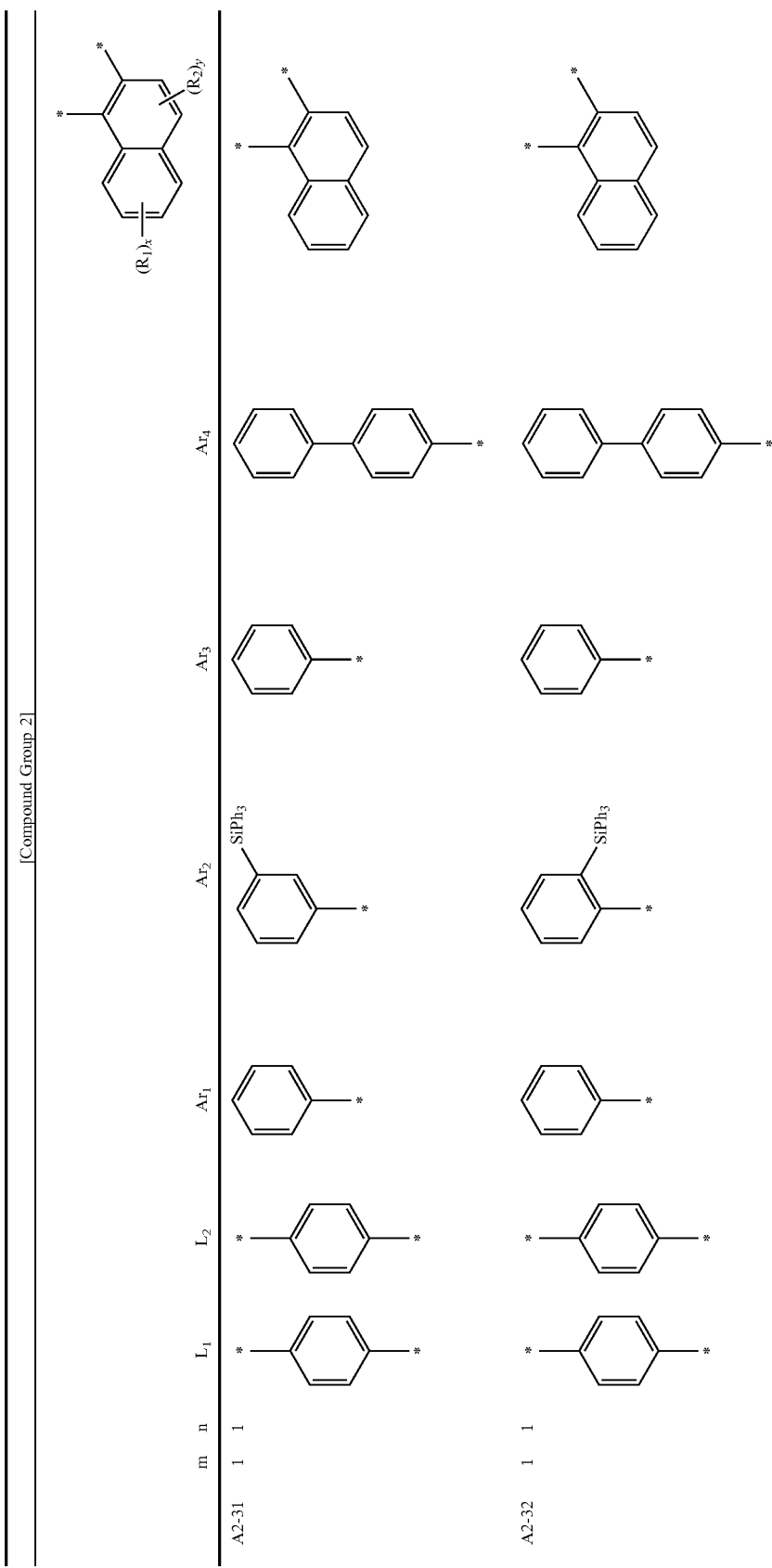

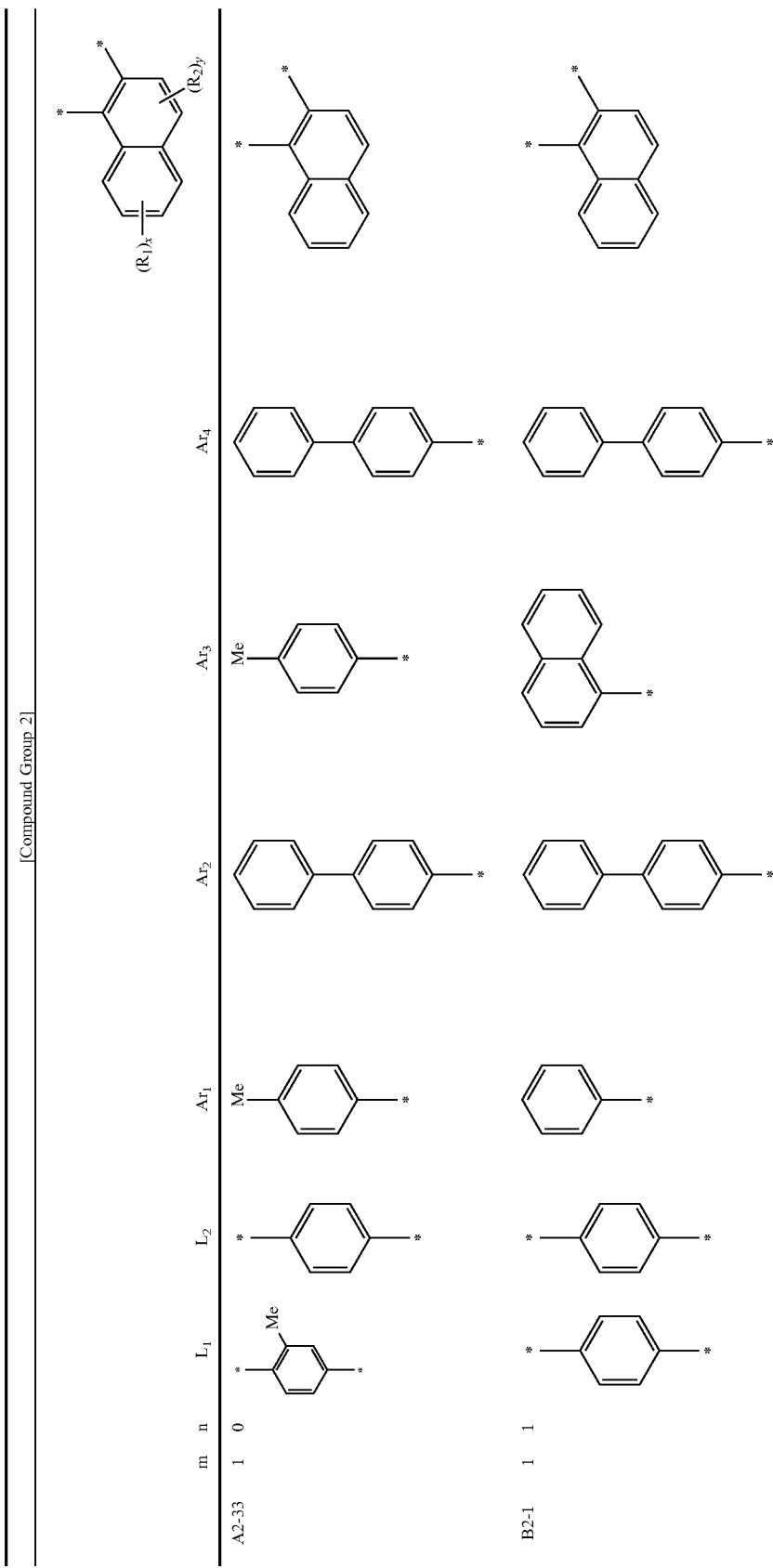

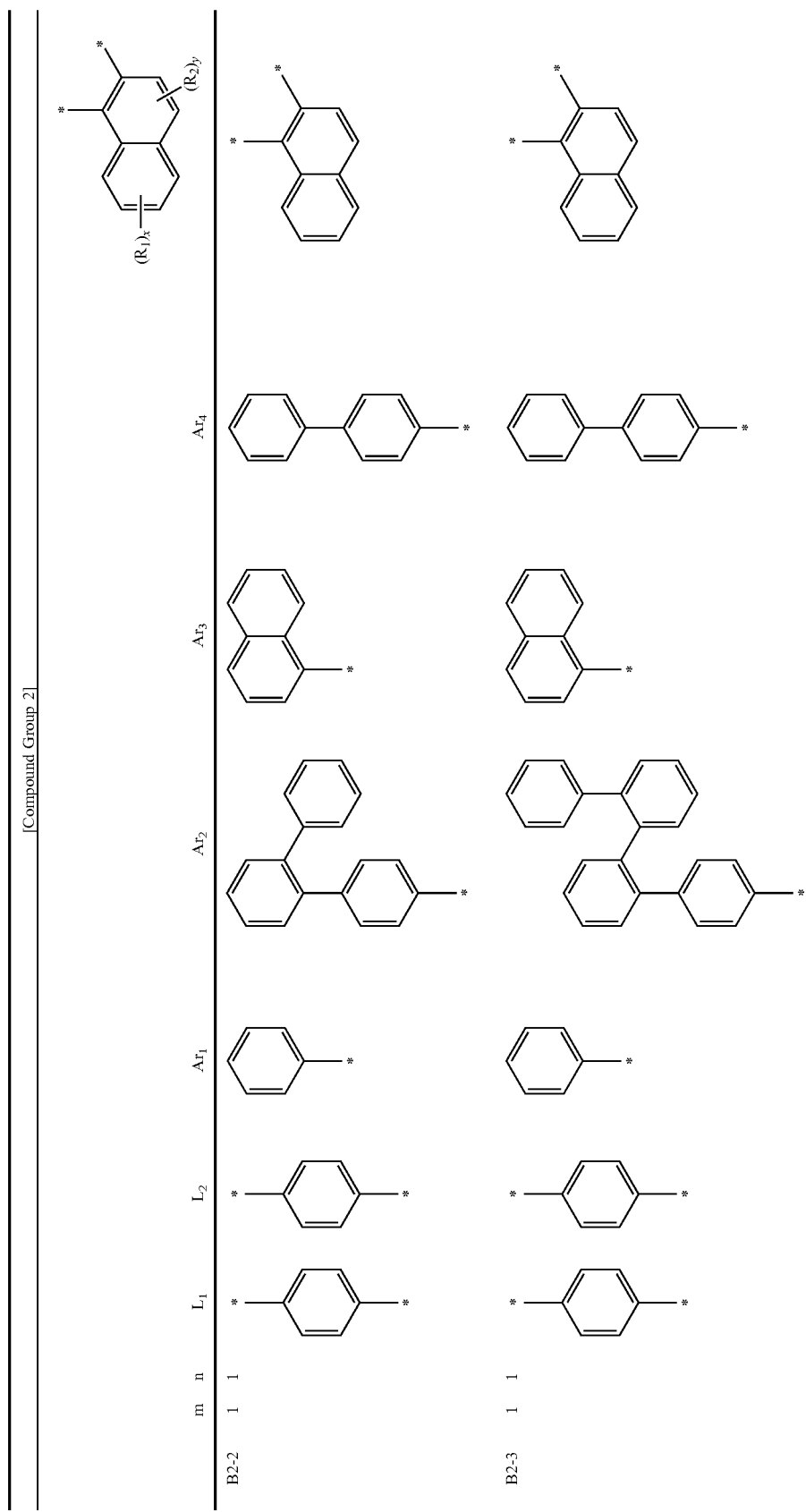

-continued
[Compound Group 2]
| | m | n | L₁ | L₂ | Ar₁ | Ar₂ | Ar₃ | Ar₄ | |
|---|---|---|---|---|---|---|---|---|---|
| B2-4 | 1 | 1 | 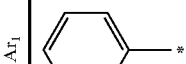 | 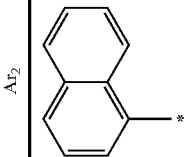 | 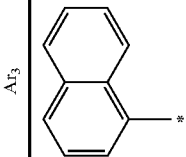 | 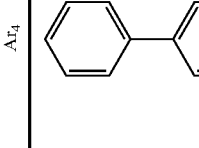 | 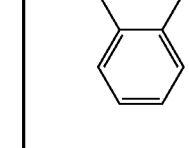 |  | 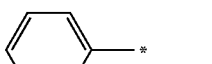 |
| B2-5 | 1 | 1 | 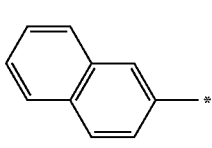 | 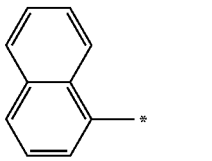 | 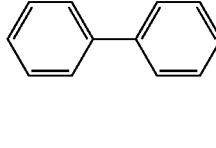 | 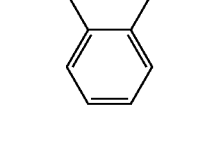 |  | 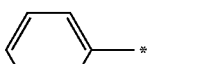 | 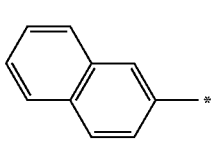 |

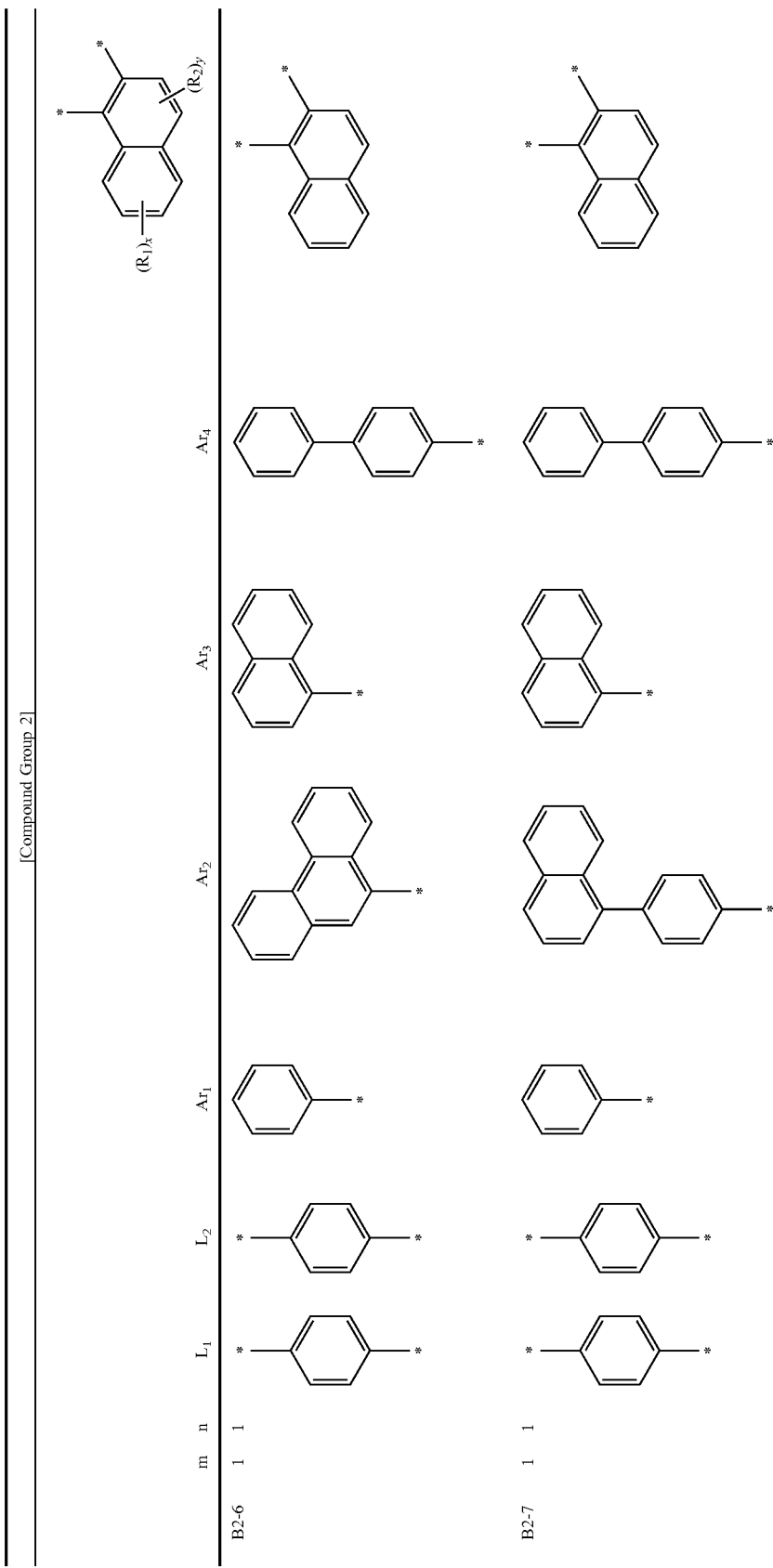

-continued
[Compound Group 2]
| | m | n | L₁ | L₂ | Ar₁ | Ar₂ | Ar₃ | Ar₄ | |
|---|---|---|---|---|---|---|---|---|---|
| B2-8 | 1 | 1 | 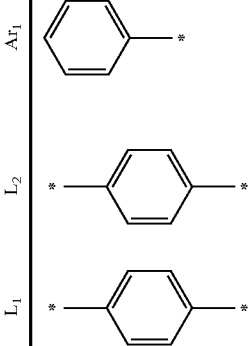 | 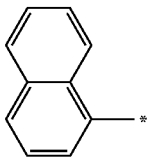 | 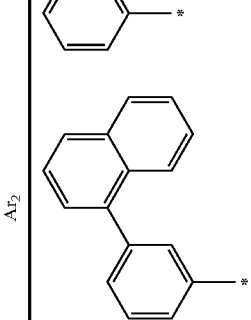 |  | 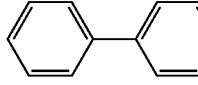 | 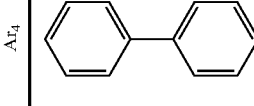 | 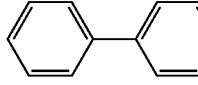 |
| B2-9 | 1 | 1 |  |  |  | 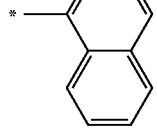 | 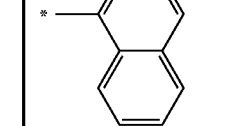 | 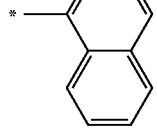 | 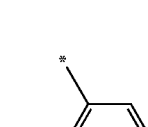 |

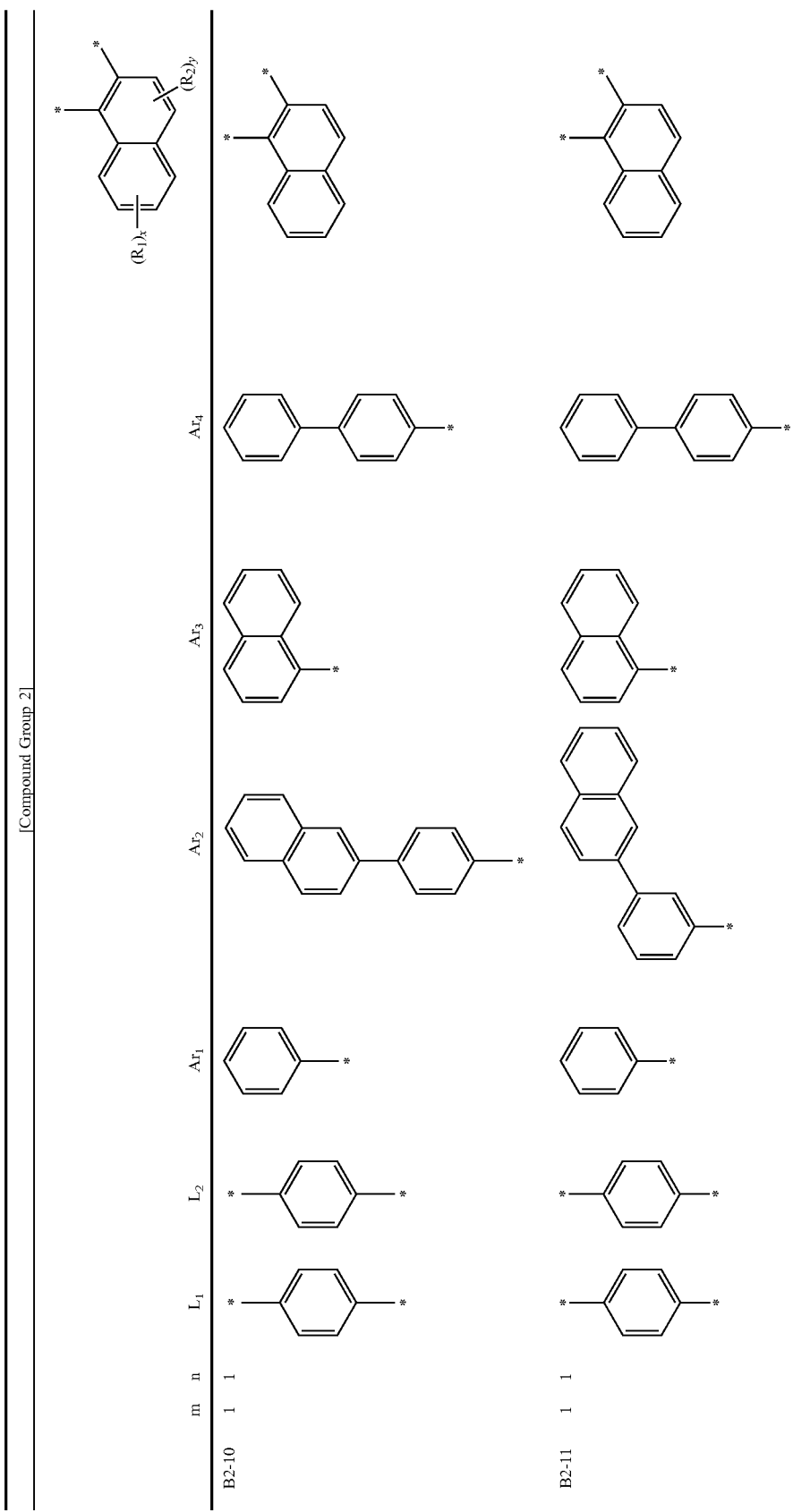

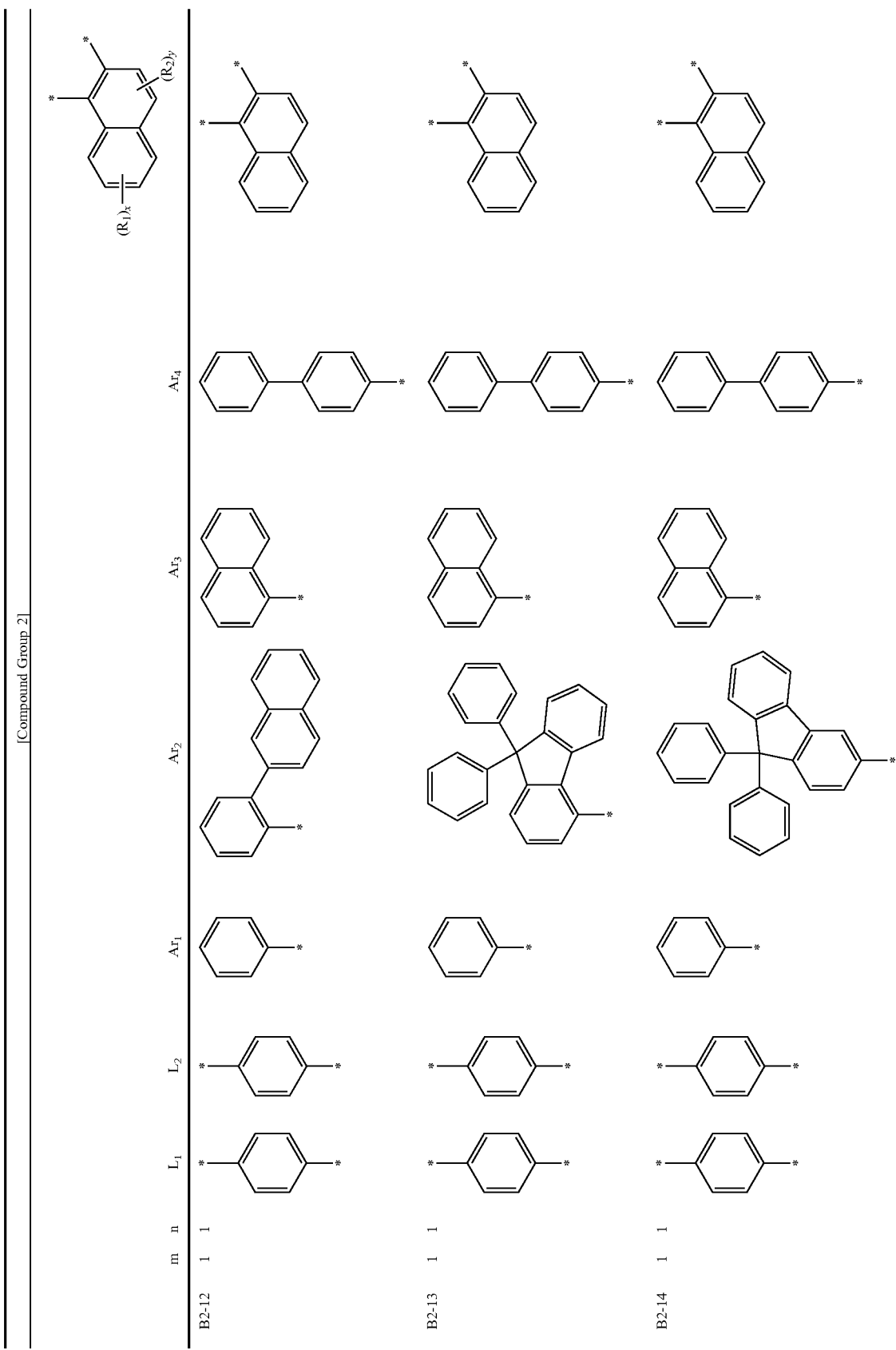

-continued
[Compound Group 2]
| | m | n | L₁ | L₂ | Ar₁ | Ar₂ | Ar₃ | Ar₄ | |
|---|---|---|---|---|---|---|---|---|---|
| B2-15 | 1 | 1 | 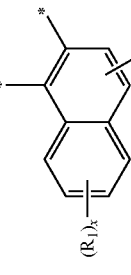 | 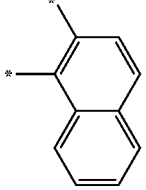 | 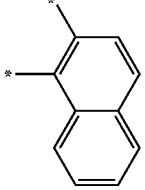 | 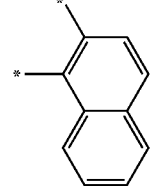 |  | 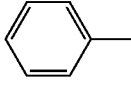 | 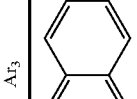 |
| B2-16 | 1 | 1 |  | 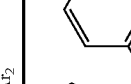 | 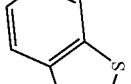 |  |  | 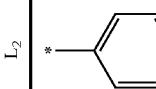 | 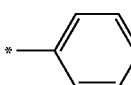 |
| B2-17 | 1 | 1 |  |  |  |  |  | 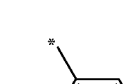 |  |

-continued
[Compound Group 2]
| | m | n | L₁ | L₂ | Ar₁ | Ar₂ | Ar₃ | Ar₄ | |
|---|---|---|---|---|---|---|---|---|---|
| B2-18 | 1 | 1 |  | 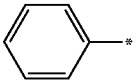 | 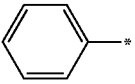 | 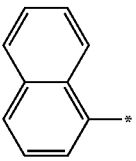 | 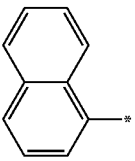 | 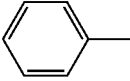 | 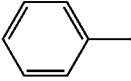 |
| B2-19 | 1 | 1 | 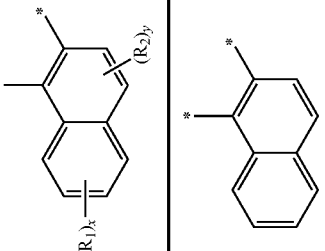 | 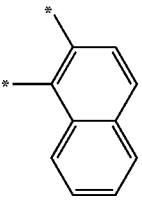 |  | 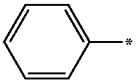 | 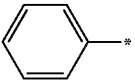 | 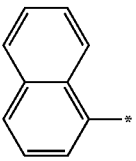 | 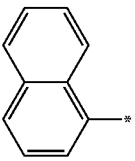 |
| B2-20 | 1 | 1 | 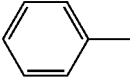 | 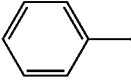 | 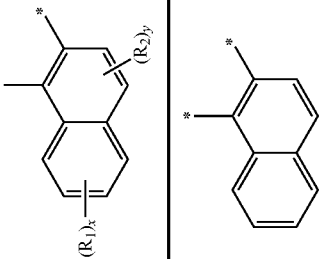 | 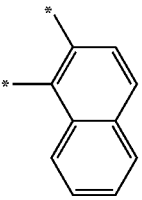 |  | 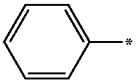 | 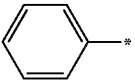 |

-continued
[Compound Group 2]
| | m | n | L₁ | L₂ | Ar₁ | Ar₂ | Ar₃ | Ar₄ |  |
|---|---|---|---|---|---|---|---|---|---|
| B2-21 | 1 | 1 | | | | | | | |
| B2-22 | 1 | 1 | | | | | | | |
| B2-23 | 1 | 1 | | | | | | | |

-continued
[Compound Group 2]
| | m | n | L₁ | L₂ | Ar₁ | Ar₂ | Ar₃ | Ar₄ | 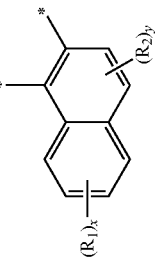 |
|---|---|---|---|---|---|---|---|---|---|
| B2-24 | 1 | 1 | | | | | | | |
| B2-25 | 1 | 1 | | | | | | | |
| B2-26 | 1 | 1 | | | | | | | |

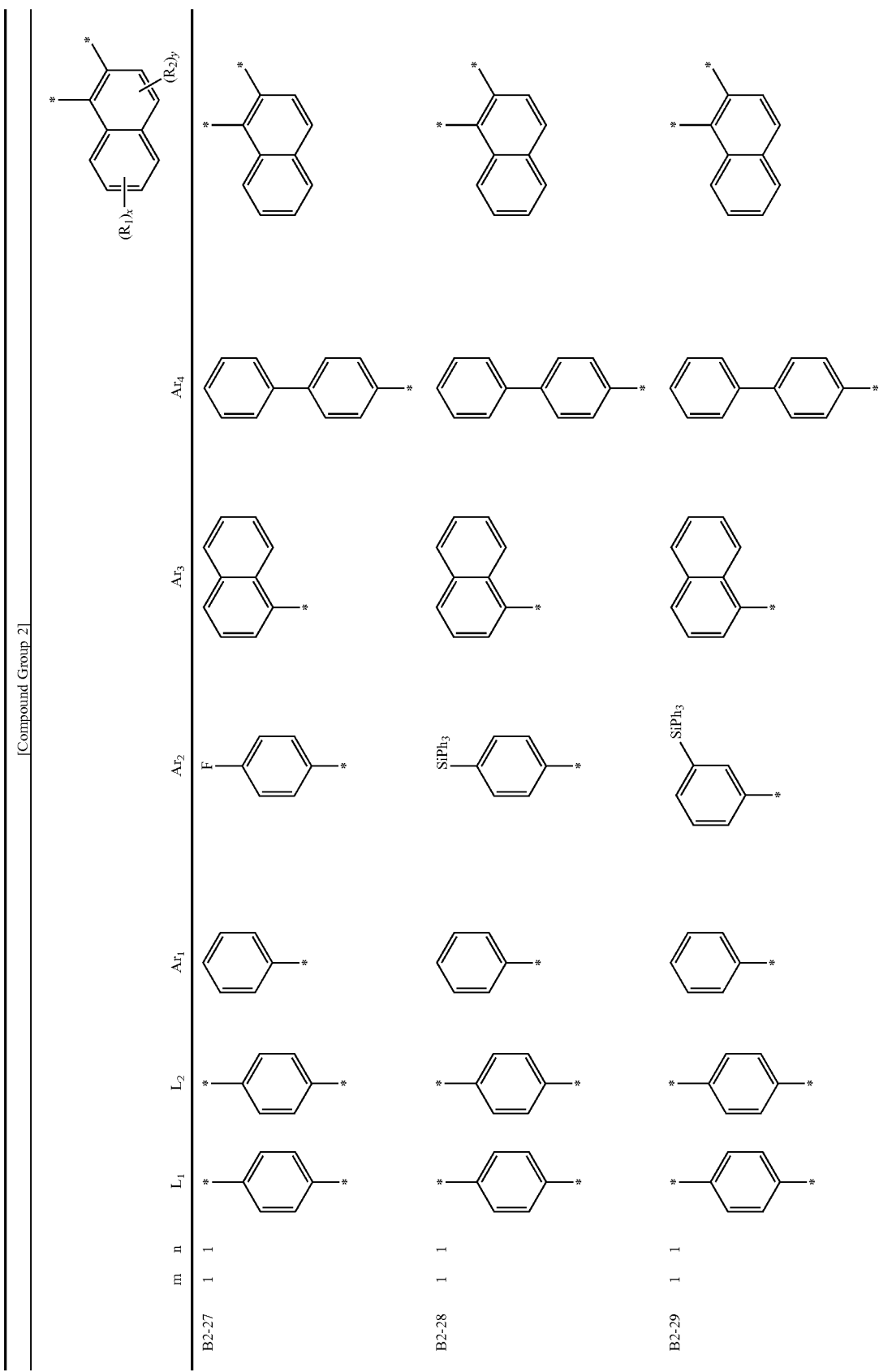

-continued
[Compound Group 2]
| | m | n | L$_1$ | L$_2$ | Ar$_1$ | Ar$_2$ | Ar$_3$ | Ar$_4$ | 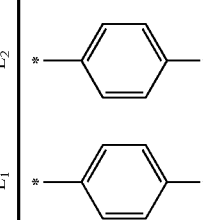 |
|---|---|---|---|---|---|---|---|---|---|
| B2-30 | 1 | 1 | | | | | | | |
| C2-1 | 1 | 1 | | | | | | | |
| C2-2 | 1 | 1 | | | | | | | |

-continued
[Compound Group 2]
| | m | n | L₁ | L₂ | Ar₁ | Ar₂ | Ar₃ | Ar₄ | 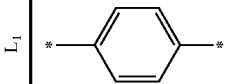 |
|---|---|---|---|---|---|---|---|---|---|
| C2-3 | 1 | 1 | | | | | | | |
| C2-4 | 1 | 1 | | | | | | | |
| C2-5 | 1 | 1 | | | | | | | |

-continued
[Compound Group 2]
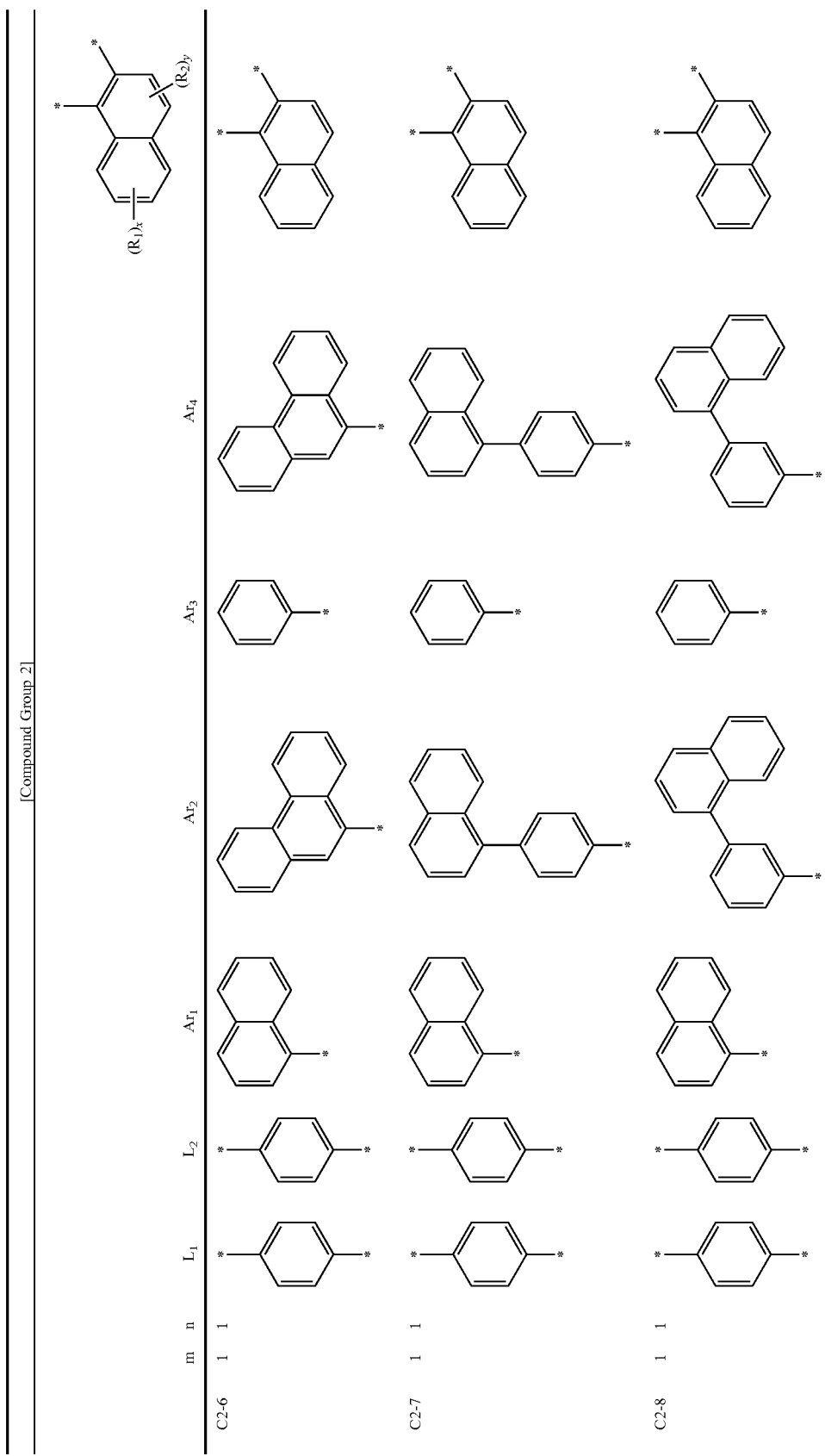

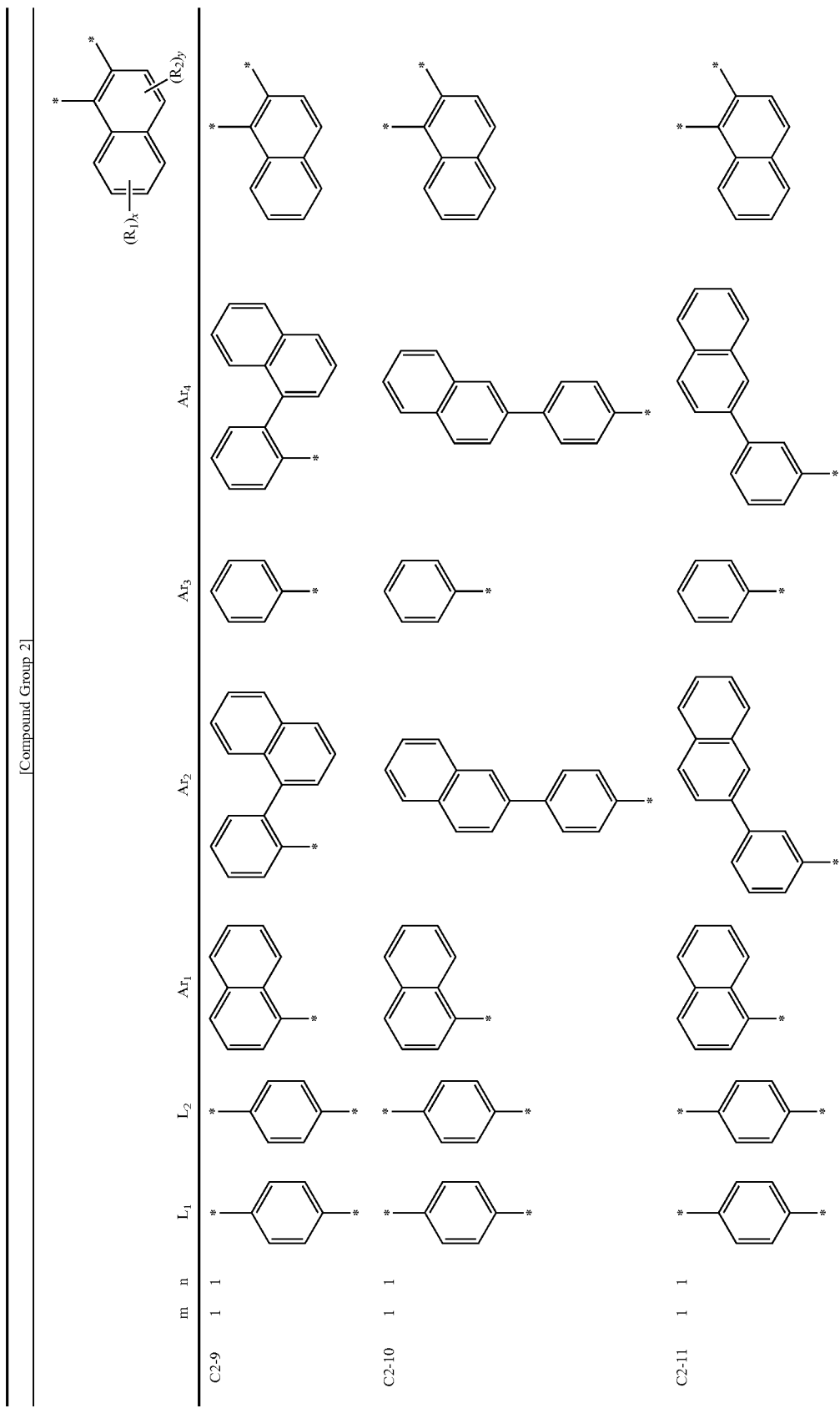

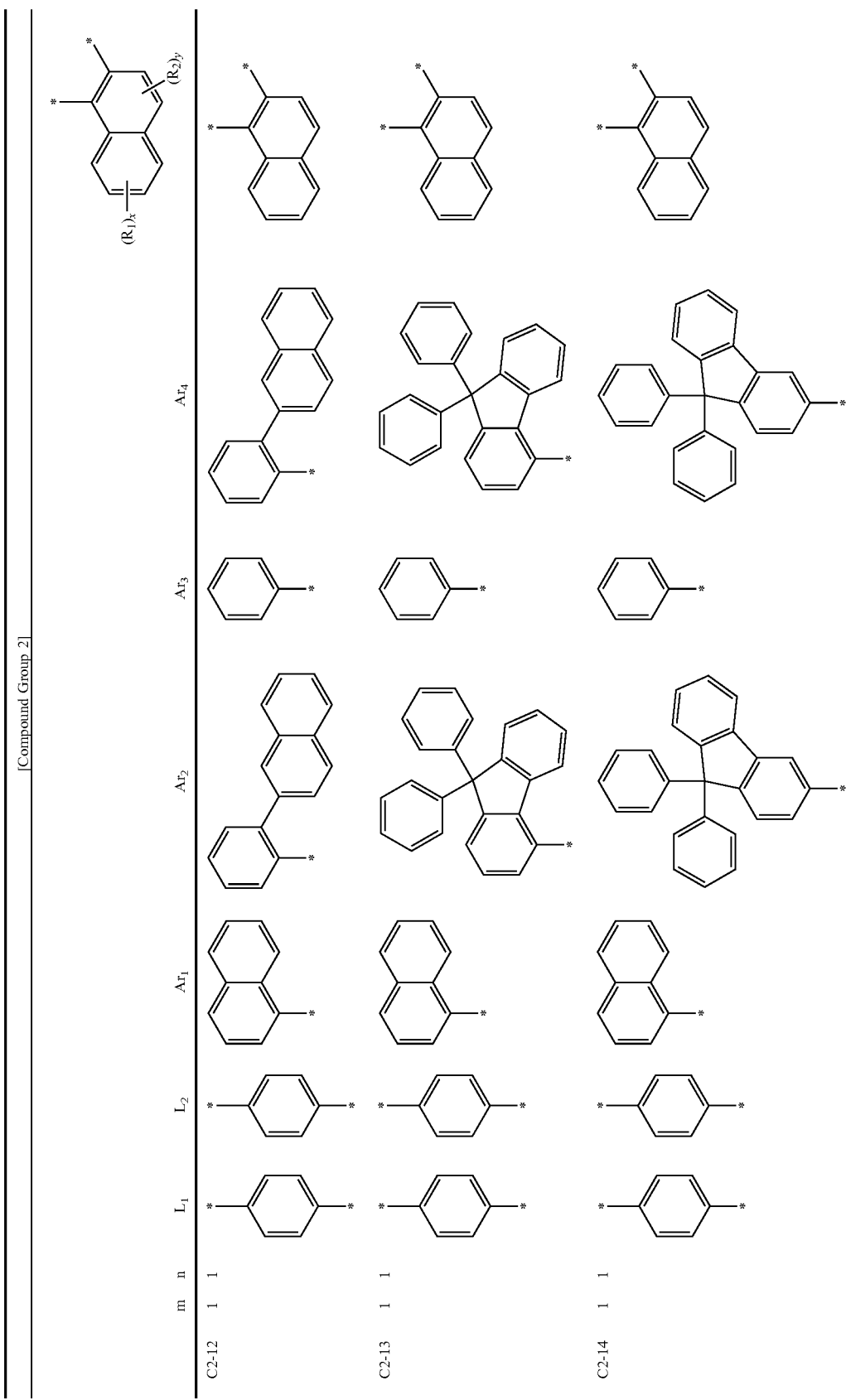

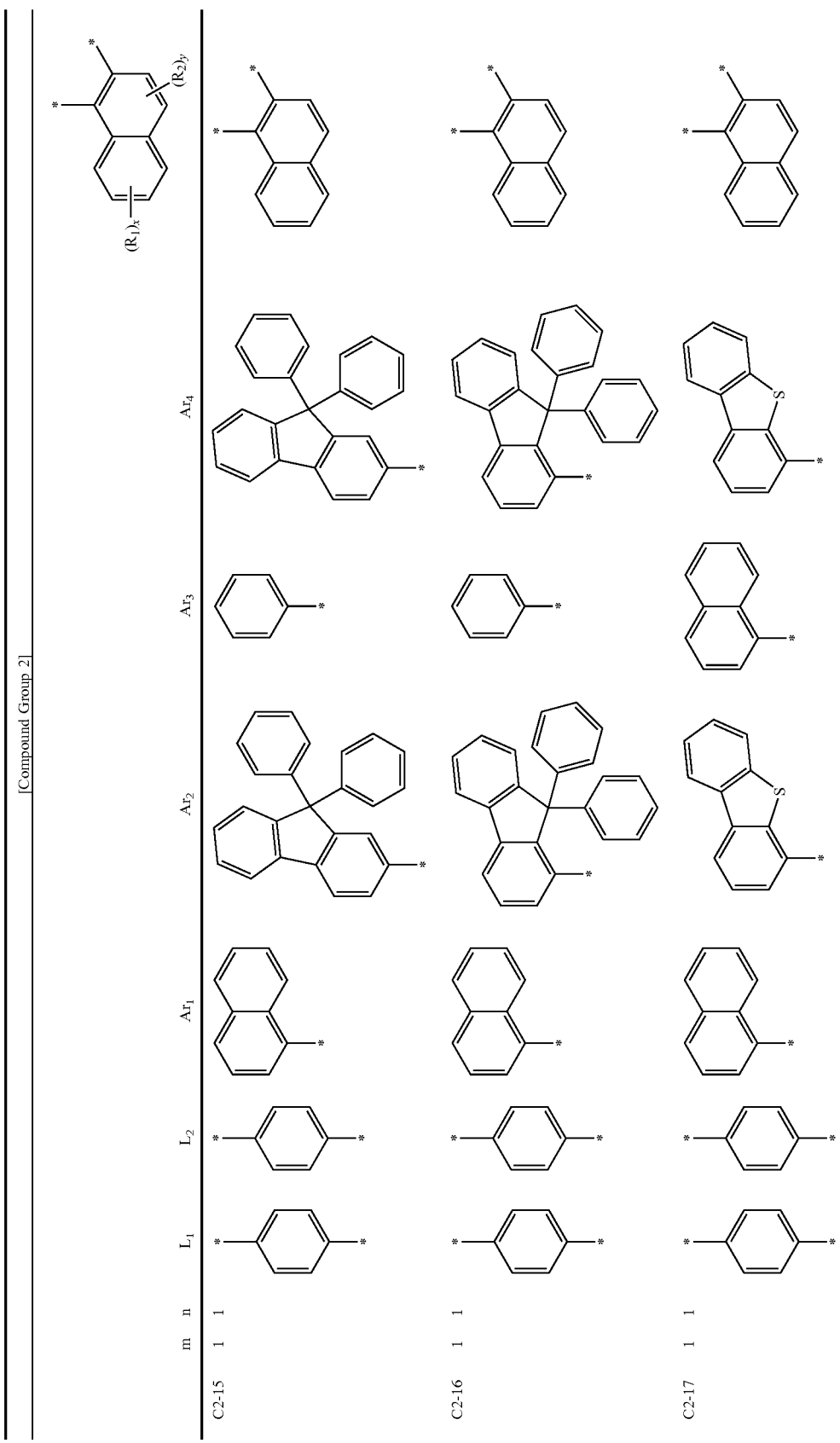

-continued

[Compound Group 2]

| | m | n | L₁ | L₂ | Ar₁ | Ar₂ | Ar₃ | Ar₄ | |
|---|---|---|---|---|---|---|---|---|---|
| C2-18 | 1 | 1 | phenylene | phenylene | 1-naphthyl | dibenzothiophene | phenyl | dibenzothiophene | |
| C2-19 | 1 | 1 | phenylene | phenylene | 1-naphthyl | dibenzothiophene | phenyl | dibenzothiophene | |
| C2-20 | 1 | 1 | phenylene | phenylene | 1-naphthyl | dibenzothiophene | phenyl | dibenzothiophene | |

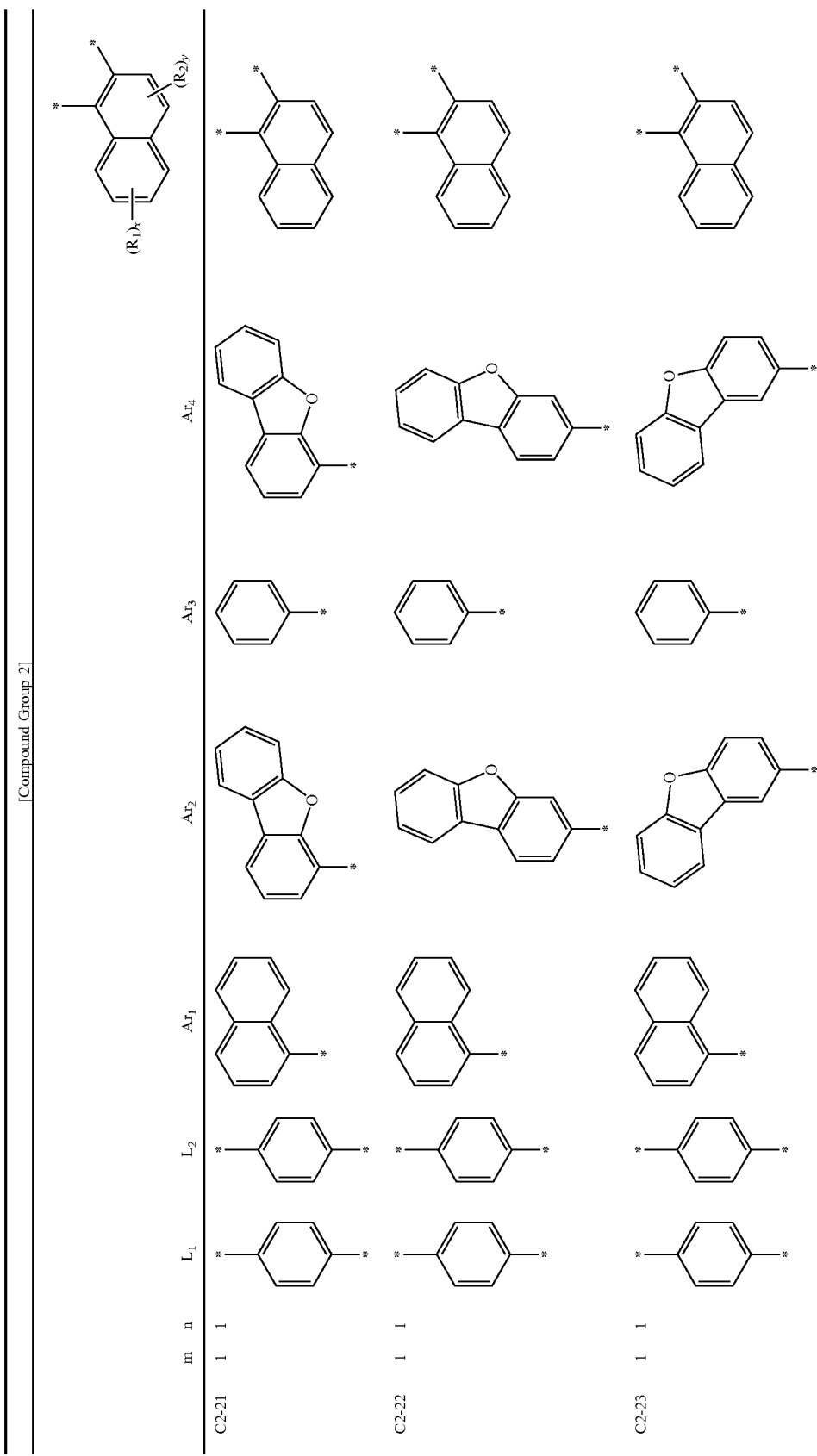

-continued

[Compound Group 2]

| | m | n | L₁ | L₂ | Ar₁ | Ar₂ | Ar₃ | Ar₄ | (structure) |
|---|---|---|---|---|---|---|---|---|---|
| C2-24 | 1 | 1 | *—⟨phenyl⟩—* | *—⟨phenyl⟩—* | 1-naphthyl | dibenzofuran-1-yl | phenyl | dibenzofuran-1-yl | naphthyl |
| C2-25 | 1 | 1 | *—⟨phenyl⟩—* | *—⟨phenyl⟩—* | 1-naphthyl | 4-(dibenzofuran-6-yl)phenyl | phenyl | 4-(dibenzofuran-6-yl)phenyl | naphthyl |
| C2-26 | 1 | 1 | *—⟨phenyl⟩—* | *—⟨phenyl⟩—* | 1-naphthyl | phenyl-d₅ | phenyl | phenyl-d₅ | naphthyl |

-continued
[Compound Group 2]
| | m | n | L₁ | L₂ | Ar₁ | Ar₂ | Ar₃ | Ar₄ | 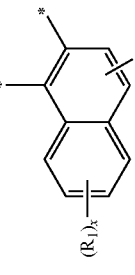 |
|---|---|---|---|---|---|---|---|---|---|
| C2-27 | 1 | 1 | 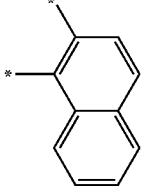 | 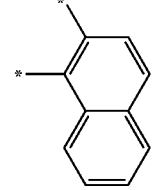 | 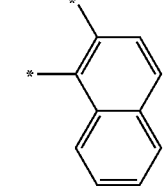 | 4-F-C₆H₄ | 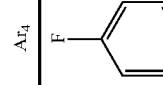 | 4-F-C₆H₄ | 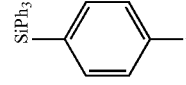 |
| C2-28 | 1 | 1 | 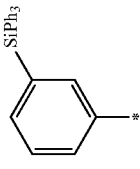 | 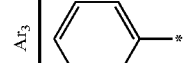 | 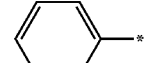 | 4-SiPh₃-C₆H₄ | 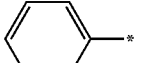 | 4-SiPh₃-C₆H₄ | 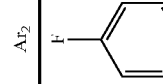 |
| C2-29 | 1 | 1 | 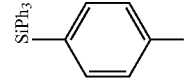 | 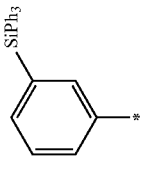 | 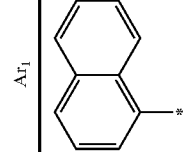 | 3-SiPh₃-C₆H₄ | 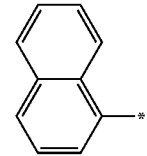 | 3-SiPh₃-C₆H₄ | 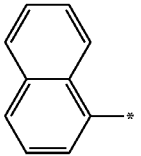 |
| C2-30 | 1 | 1 | 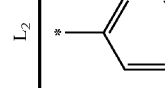 | 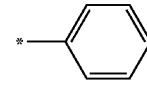 | 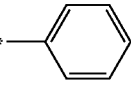 | 2-SiPh₃-C₆H₄ | 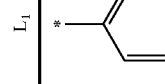 | 2-SiPh₃-C₆H₄ | 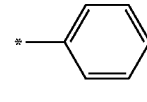 |

-continued
[Compound Group 2]
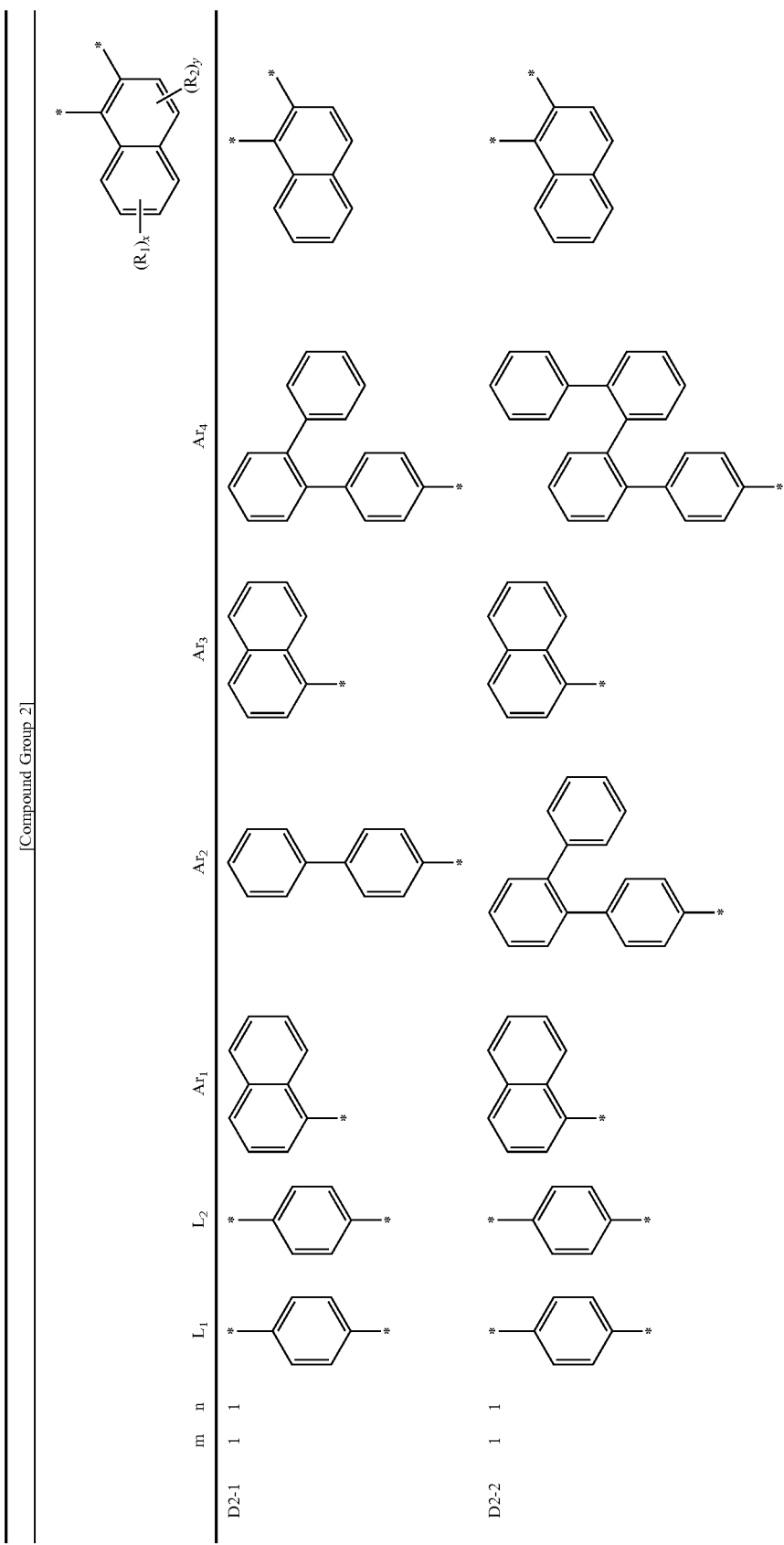

-continued

[Compound Group 2]

| | m | n | L₁ | L₂ | Ar₁ | Ar₂ | Ar₃ | Ar₄ | ![structure] |
|---|---|---|---|---|---|---|---|---|---|
| D2-3 | 1 | 1 | phenylene | phenylene | 1-naphthyl | terphenyl | 1-naphthyl | 1-naphthyl | 1-naphthyl |
| D2-4 | 1 | 1 | phenylene | phenylene | 1-naphthyl | 1-naphthyl | 1-naphthyl | 2-naphthyl | 1-naphthyl |
| D2-5 | 1 | 1 | phenylene | phenylene | 1-naphthyl | 2-naphthyl | 1-naphthyl | 9-phenanthryl | 1-naphthyl |

-continued
[Compound Group 2]
| | m | n | L₁ | L₂ | Ar₁ | Ar₂ | Ar₃ | Ar₄ | 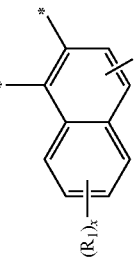 |
|---|---|---|---|---|---|---|---|---|---|
| D2-6 | 1 | 1 | 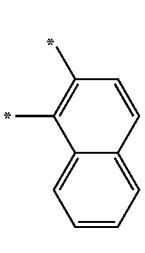 | 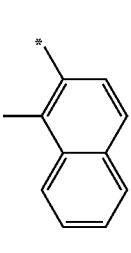 | 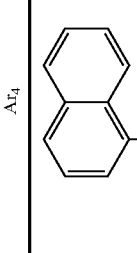 | 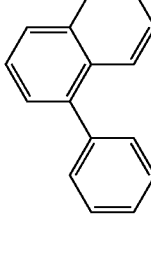 | 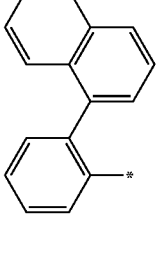 |  | 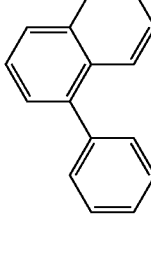 |
| D2-7 | 1 | 1 | 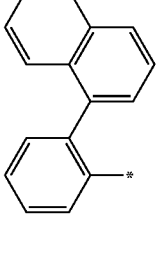 |  | 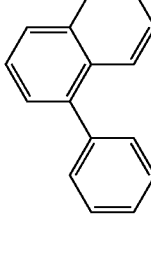 | 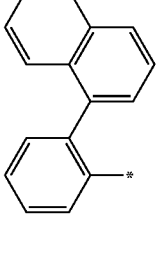 |  | 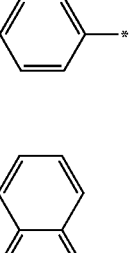 | 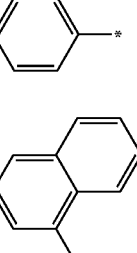 |
| D2-8 | 1 | 1 |  | 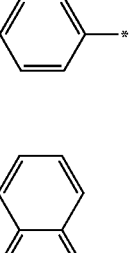 | 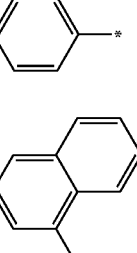 |  | 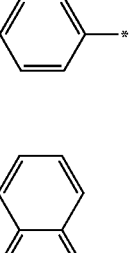 | 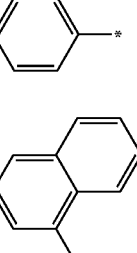 |  |

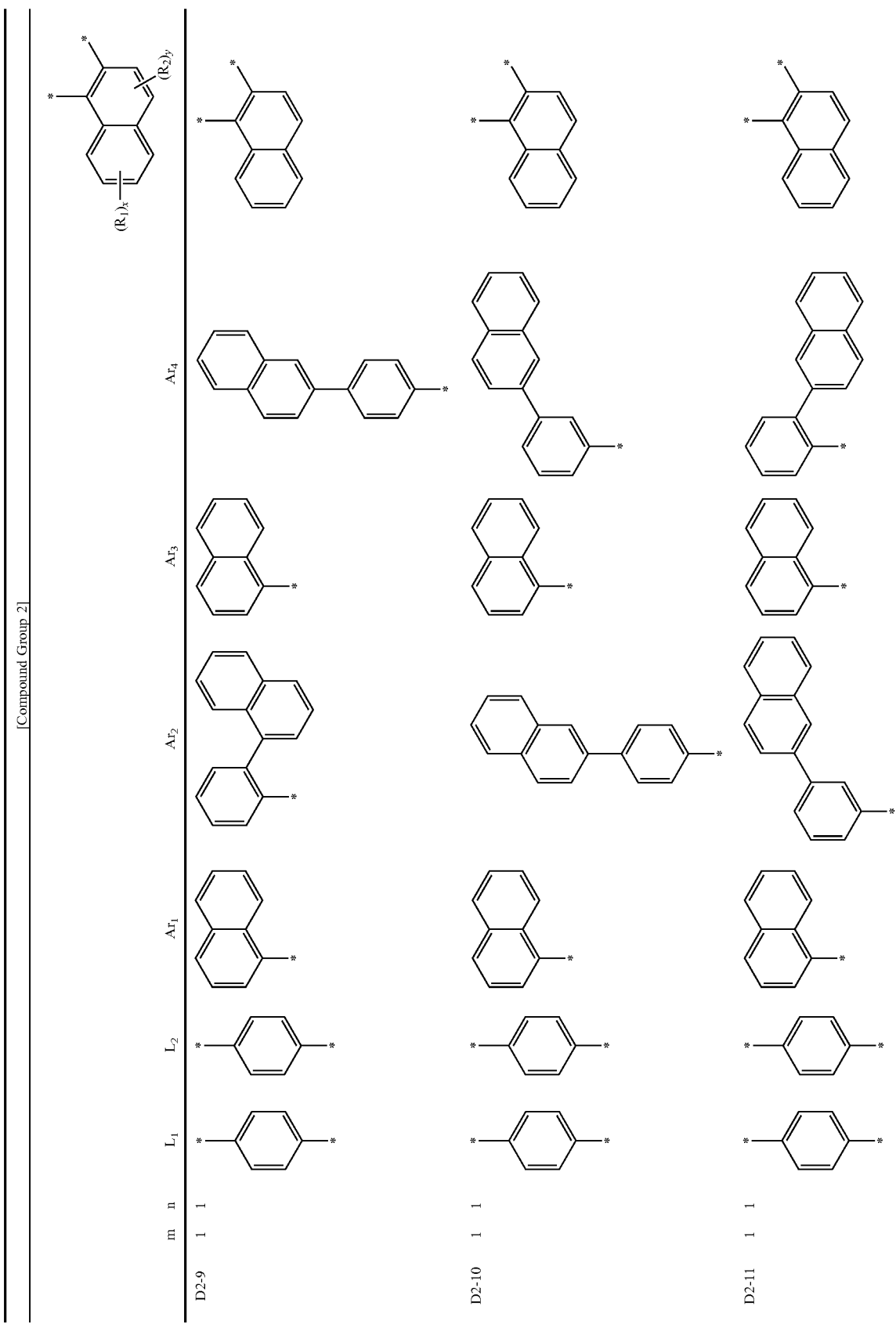

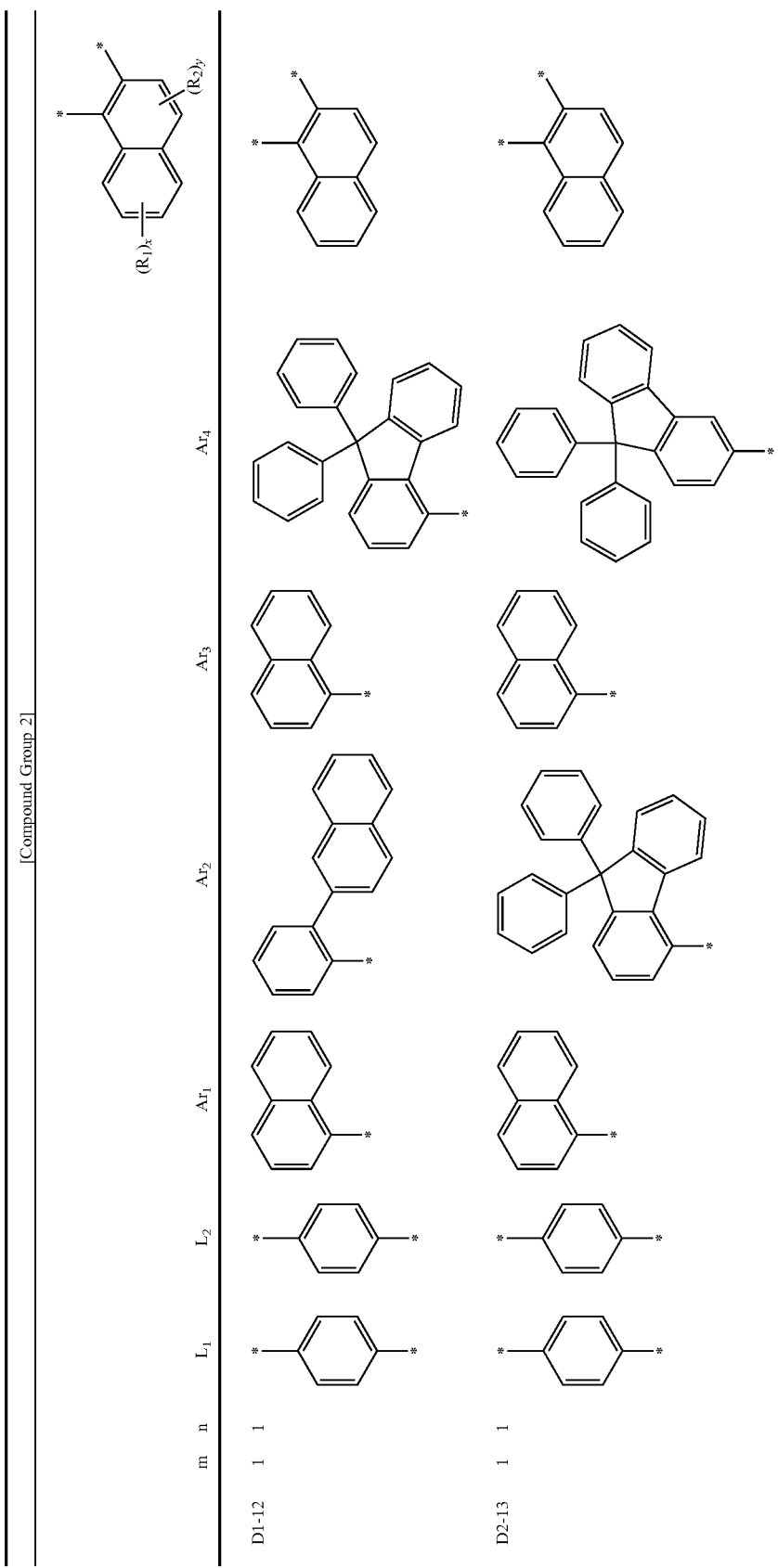

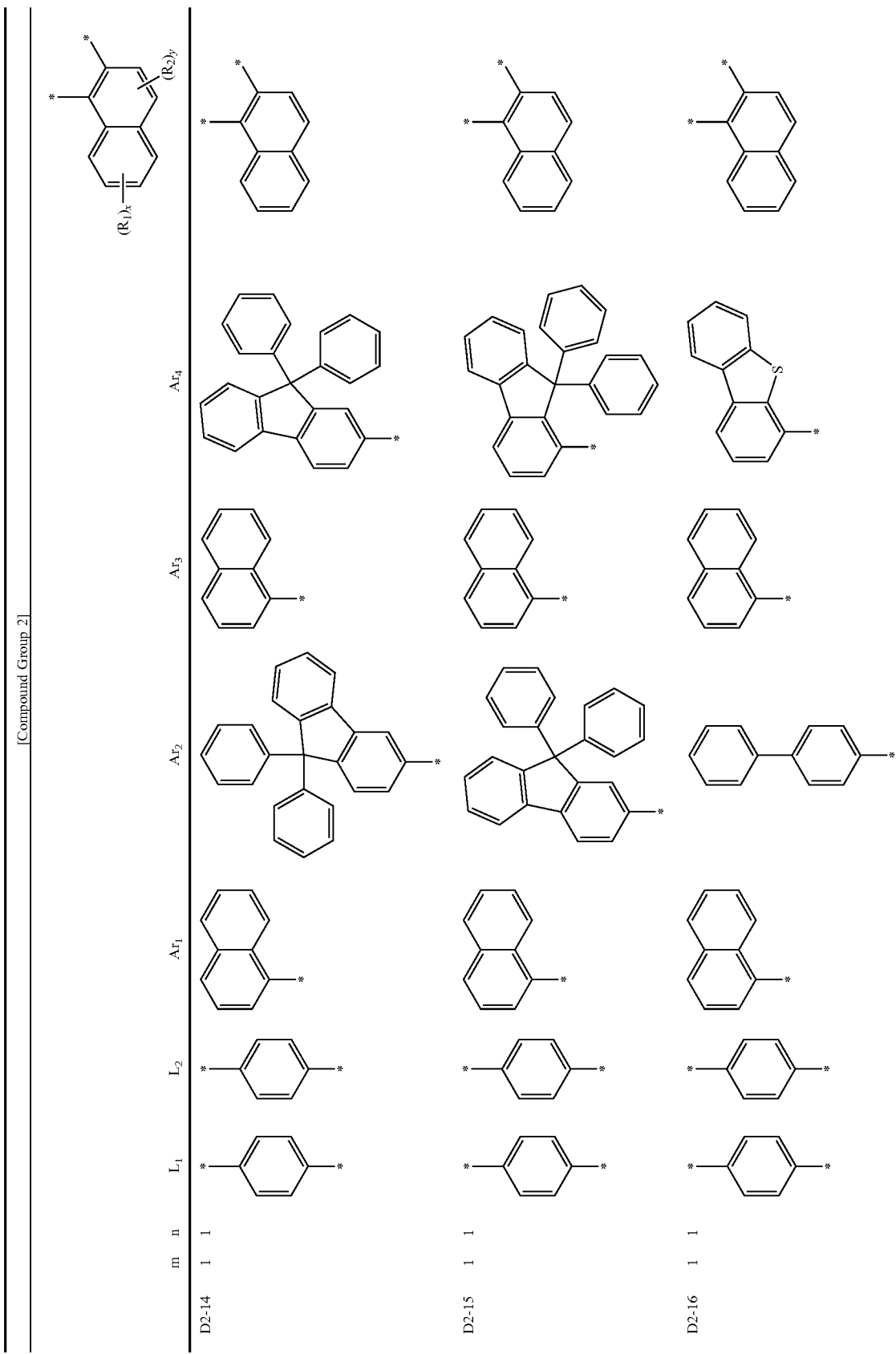

-continued

[Compound Group 2]

| | m | n | L₁ | L₂ | Ar₁ | Ar₂ | Ar₃ | Ar₄ |
|---|---|---|---|---|---|---|---|---|
| D2-17 | 1 | 1 | phenylene | phenylene | 1-naphthyl | dibenzothiophenyl | 1-naphthyl | dibenzothiophenyl |
| D2-18 | 1 | 1 | phenylene | phenylene | 1-naphthyl | dibenzothiophenyl | 1-naphthyl | dibenzothiophenyl |
| D2-19 | 1 | 1 | phenylene | phenylene | 1-naphthyl | dibenzothiophenyl | 1-naphthyl | dibenzothiophenyl |

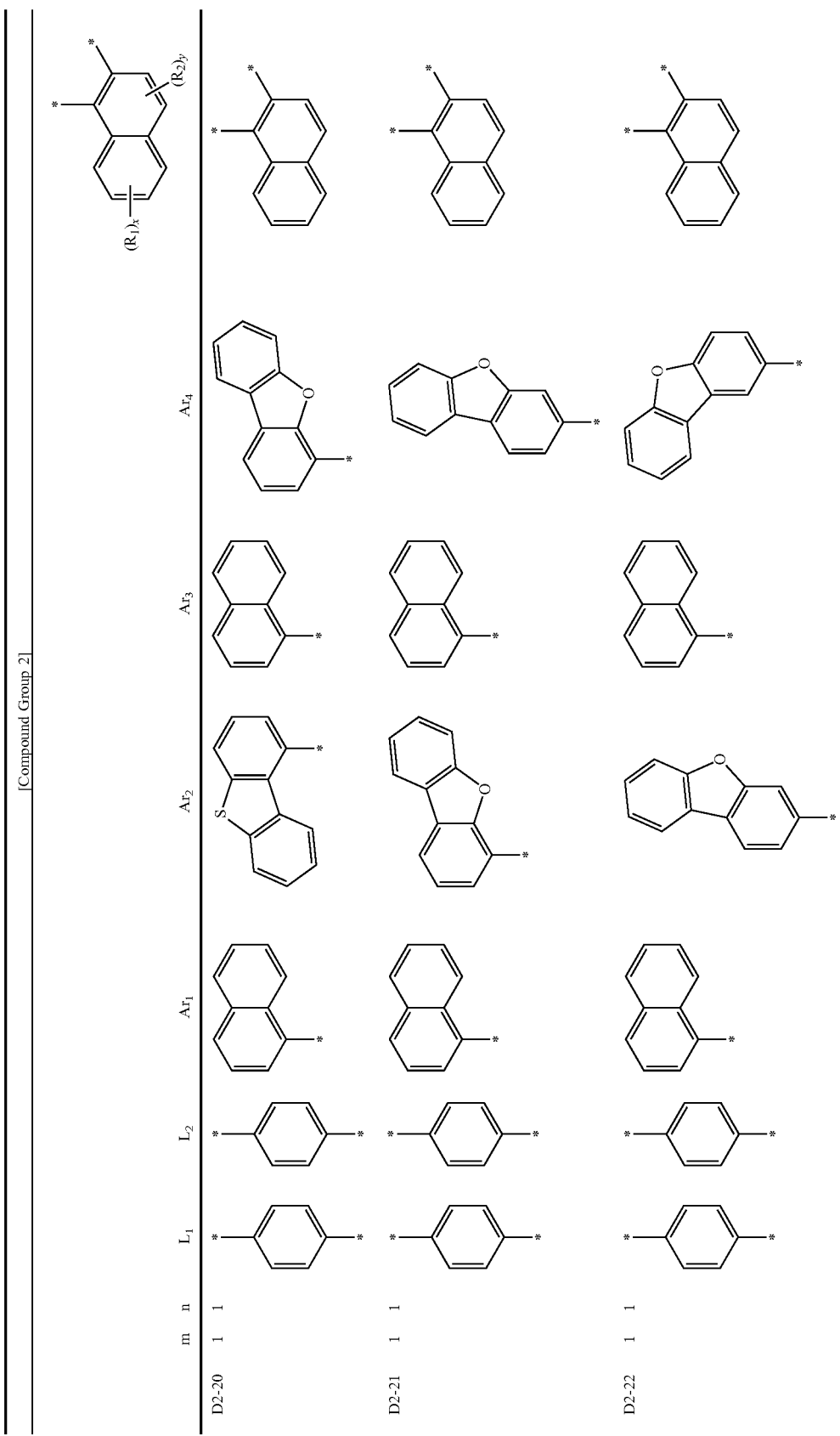

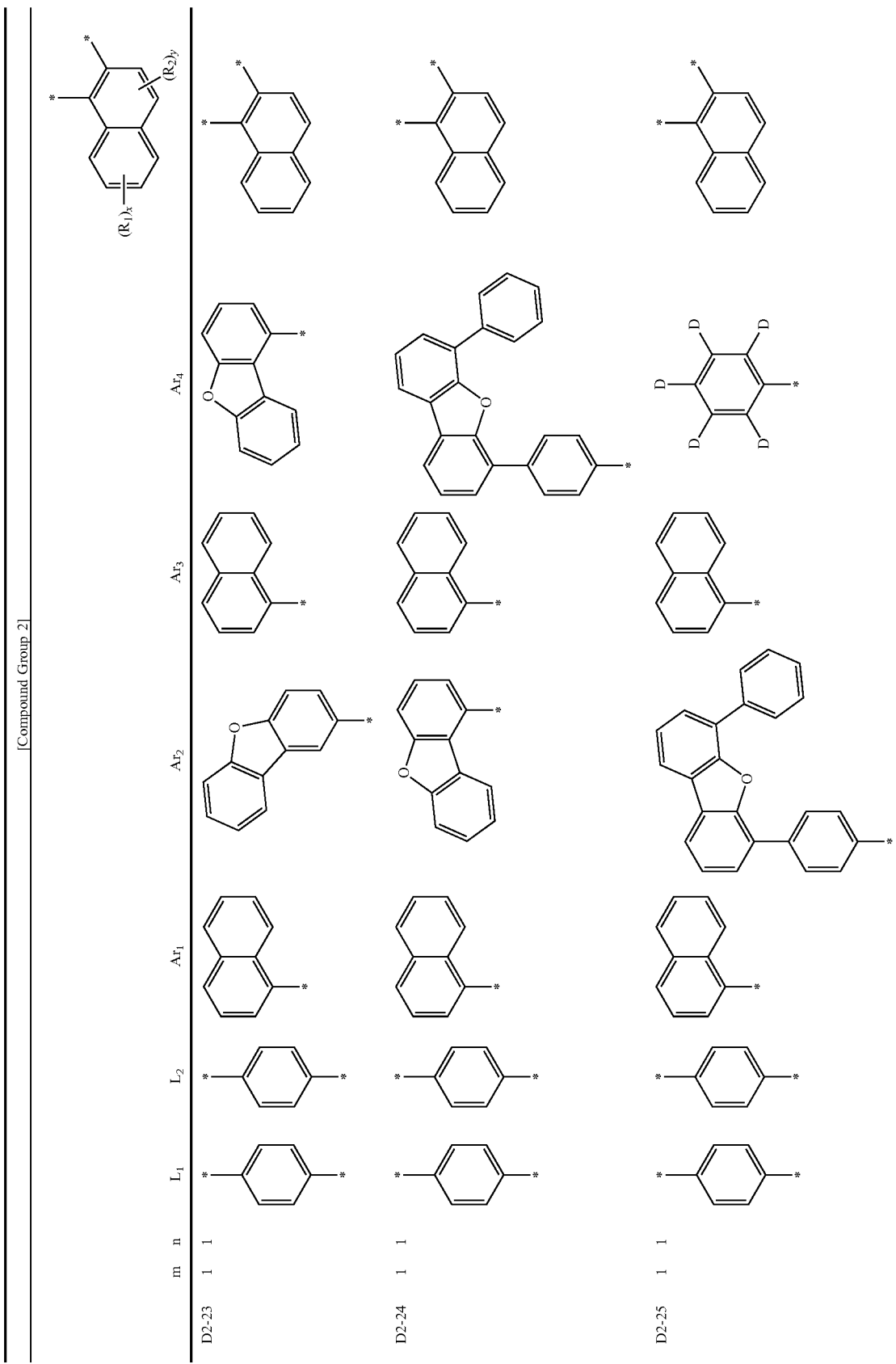

-continued
[Compound Group 2]
| | m | n | L₁ | L₂ | Ar₁ | Ar₂ | Ar₃ | Ar₄ |  |
|---|---|---|---|---|---|---|---|---|---|
| D2-26 | 1 | 1 |  |  |  |  |  |  |  |
| D2-27 | 1 | 1 |  |  |  |  |  |  |  |
| D2-28 | 1 | 1 | | | | | | |  |
| D2-29 | 1 | 1 | | | | | | | |

-continued
[Compound Group 2]
| | m | n | L₁ | L₂ | Ar₁ | Ar₂ | Ar₃ | Ar₄ | 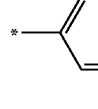 |
|---|---|---|---|---|---|---|---|---|---|
| D2-30 | 1 | 1 | | | | | | | |
| E2-1 | 1 | 1 | | | | | | | |
| E2-2 | 1 | 1 | | | | | | | |

22. The diamine compound of claim 16, wherein the diamine compound represented by Formula 1 is at least one selected among compounds represented in Compound Group 3:

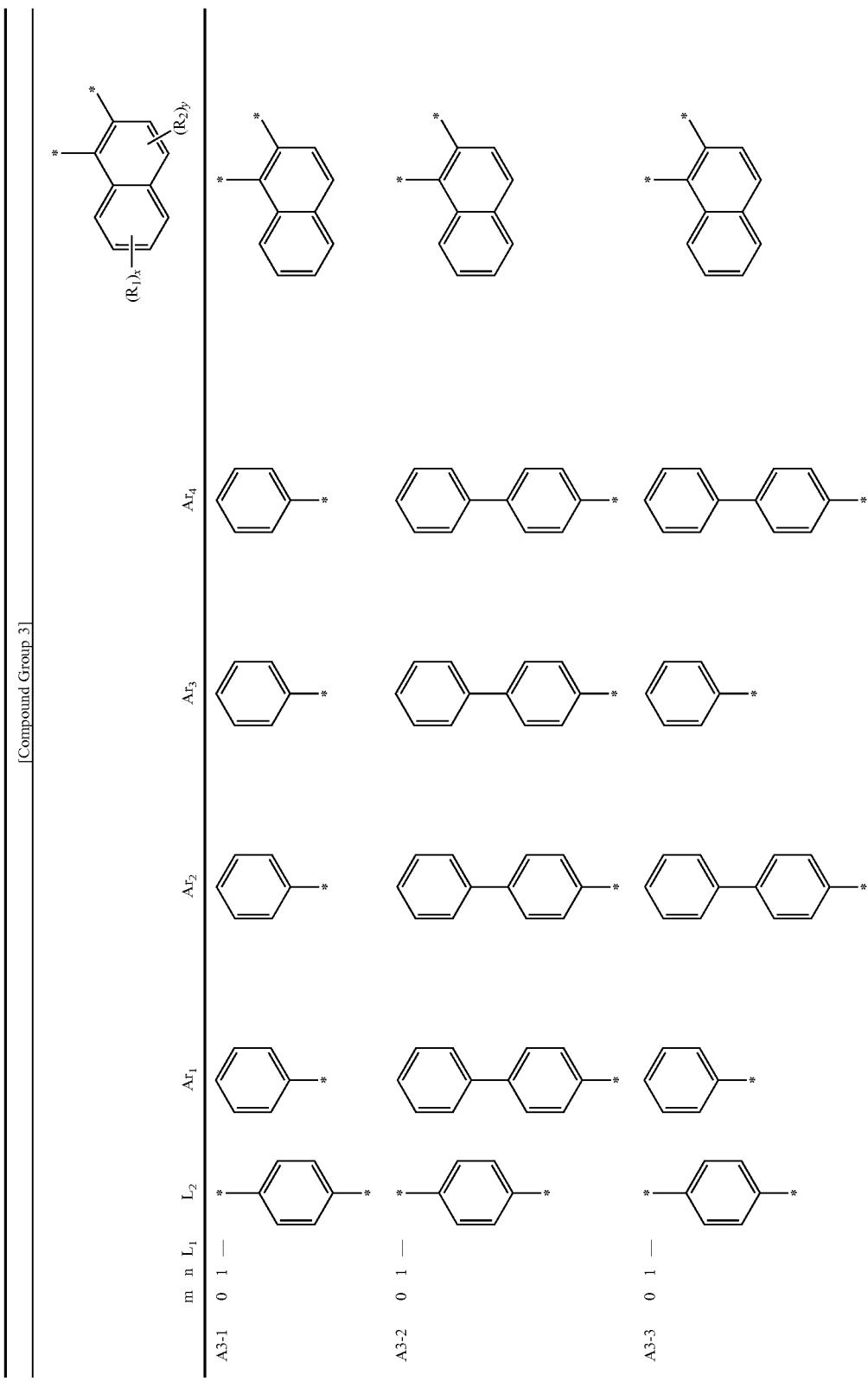

-continued
[Compound Group 3]
| | m | n | L₁ | L₂ | Ar₁ | Ar₂ | Ar₃ | Ar₄ | |
|---|---|---|---|---|---|---|---|---|---|
| A3-4 | 0 | 1 | — | 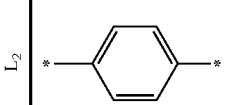 | 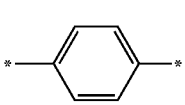 | 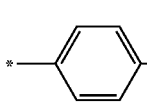 | 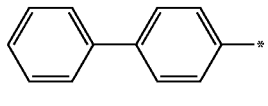 | 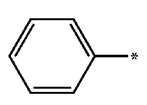 | 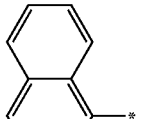 |
| A3-5 | 0 | 1 | — | 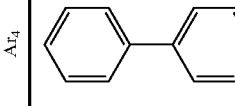 | 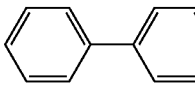 | 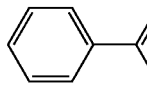 | 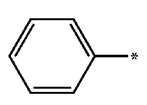 | 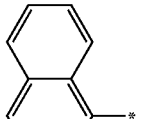 | 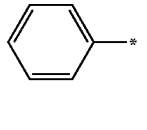 |
| A3-6 | 0 | 1 | — | 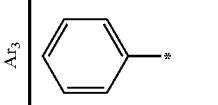 | 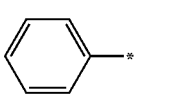 | 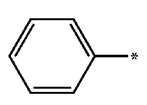 | 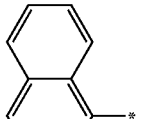 | 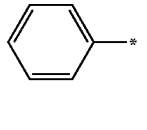 | 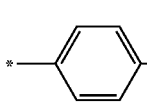 |

-continued
[Compound Group 3]
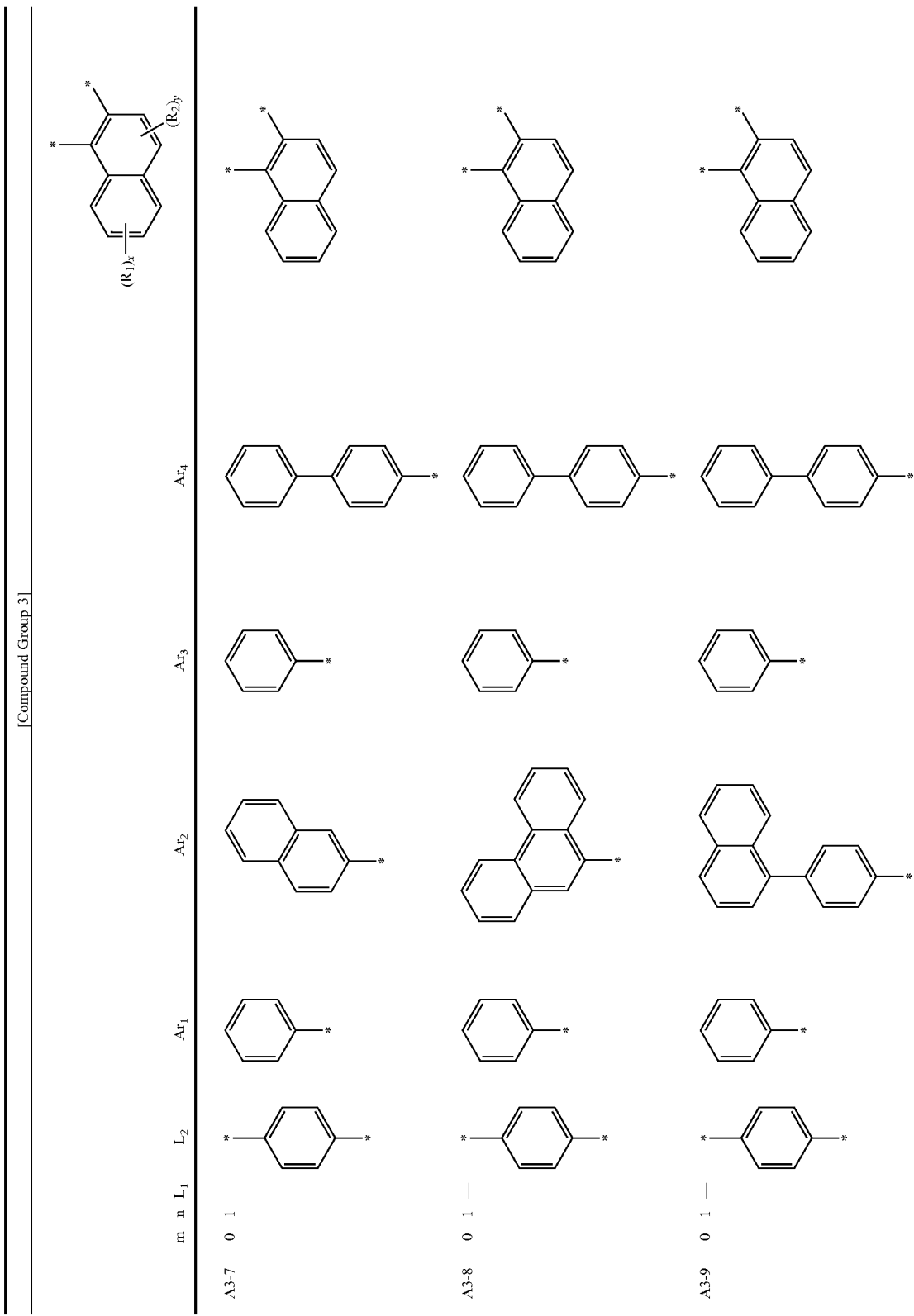

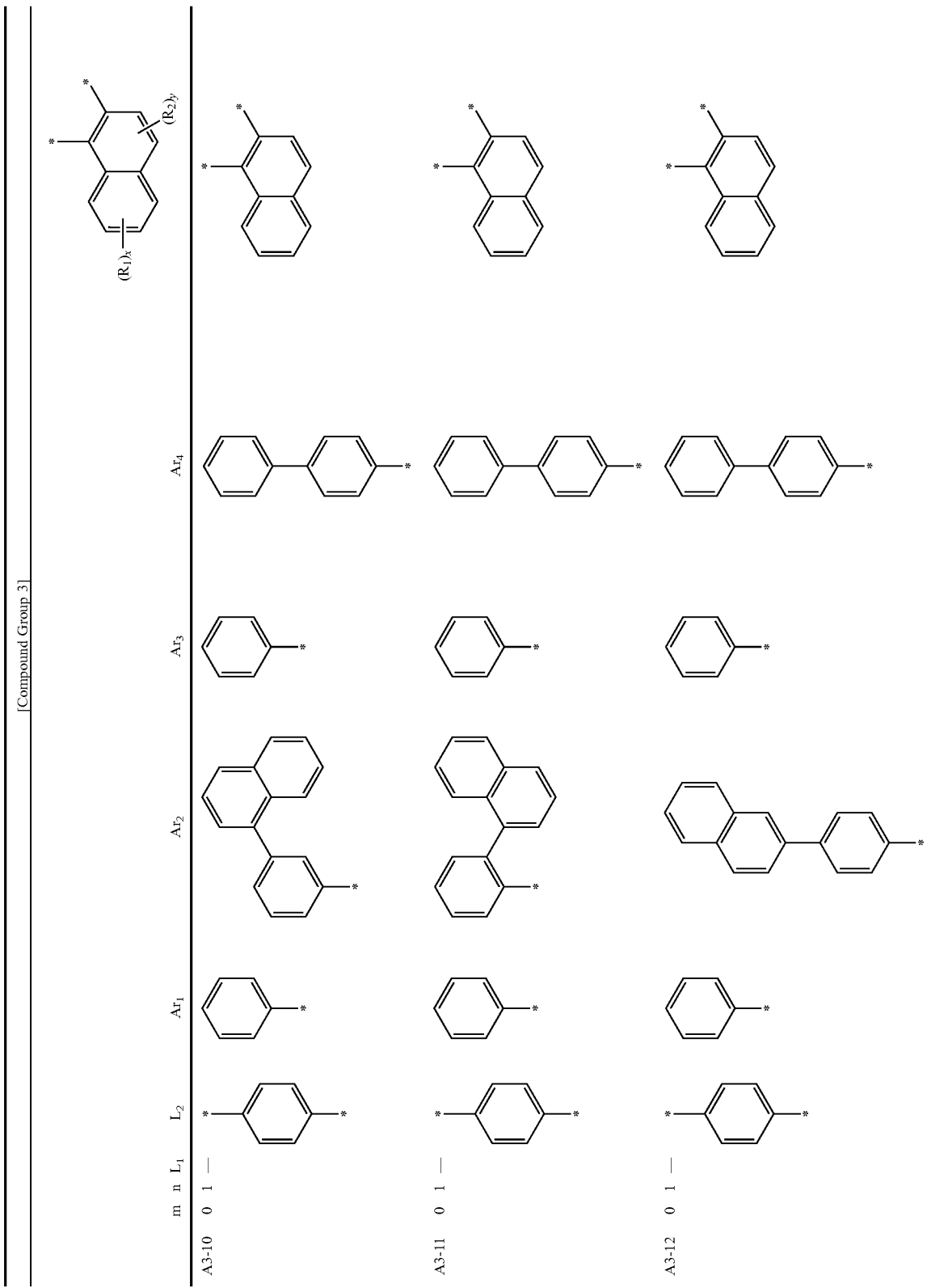

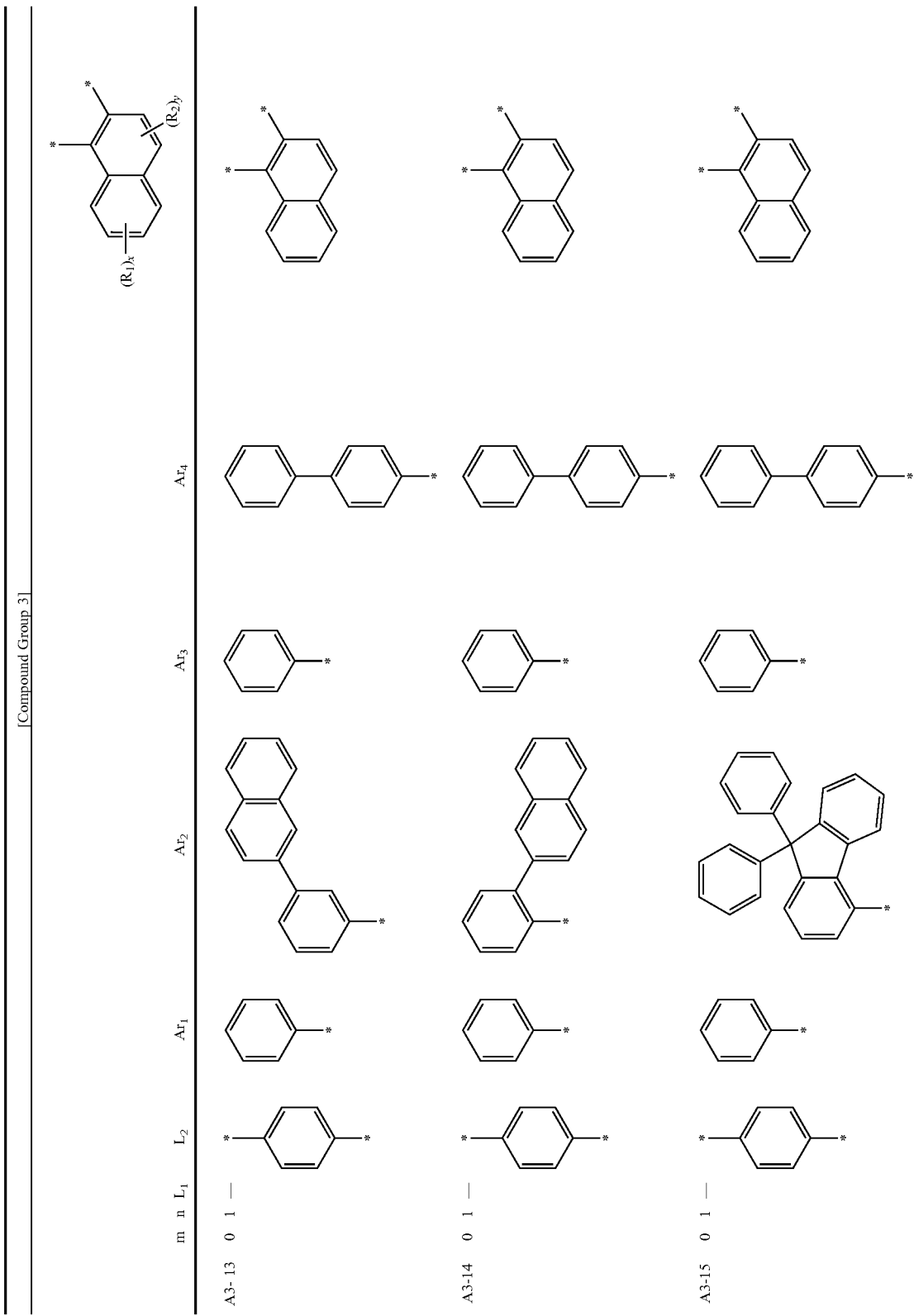

-continued
[Compound Group 3]
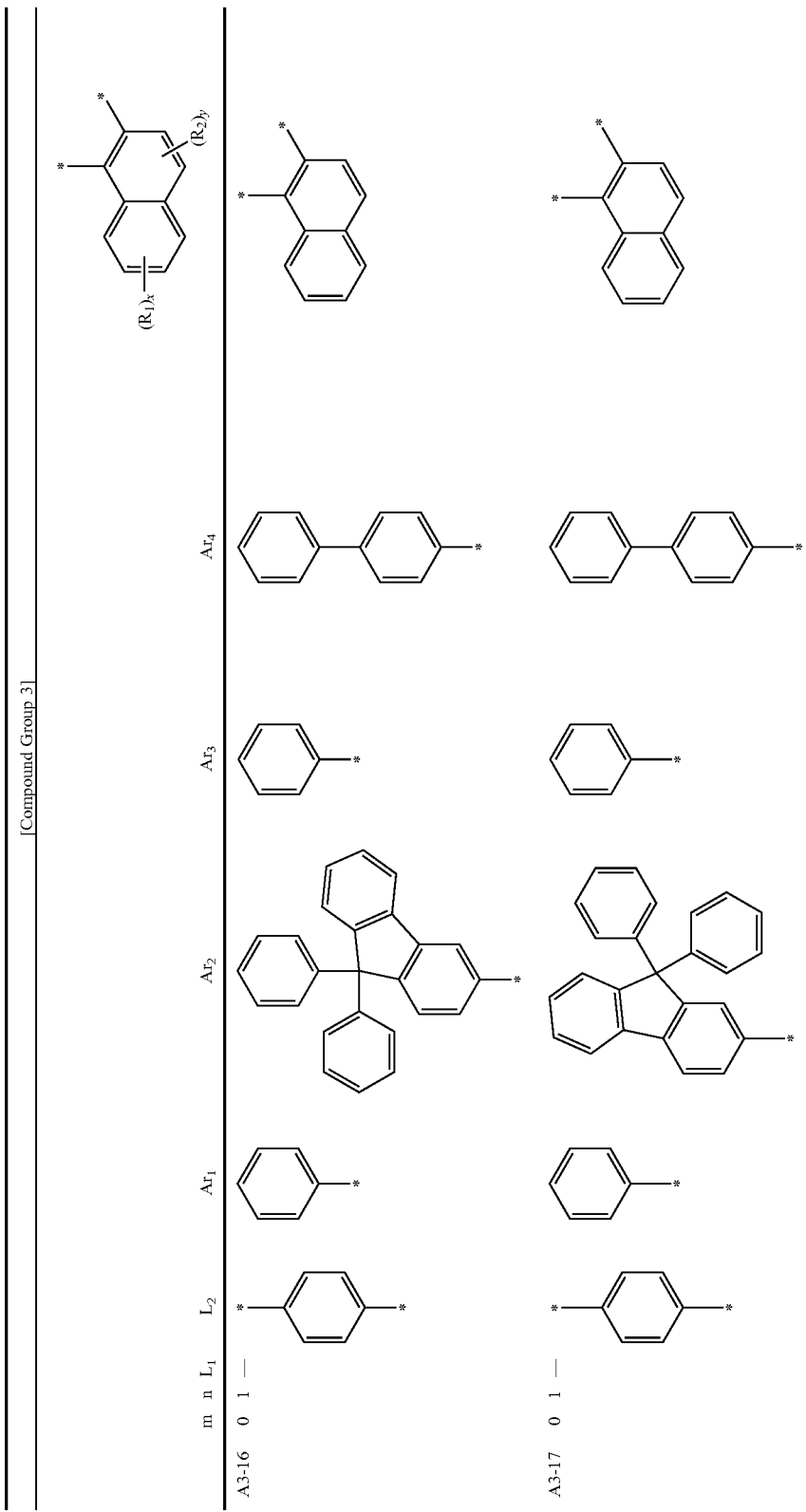

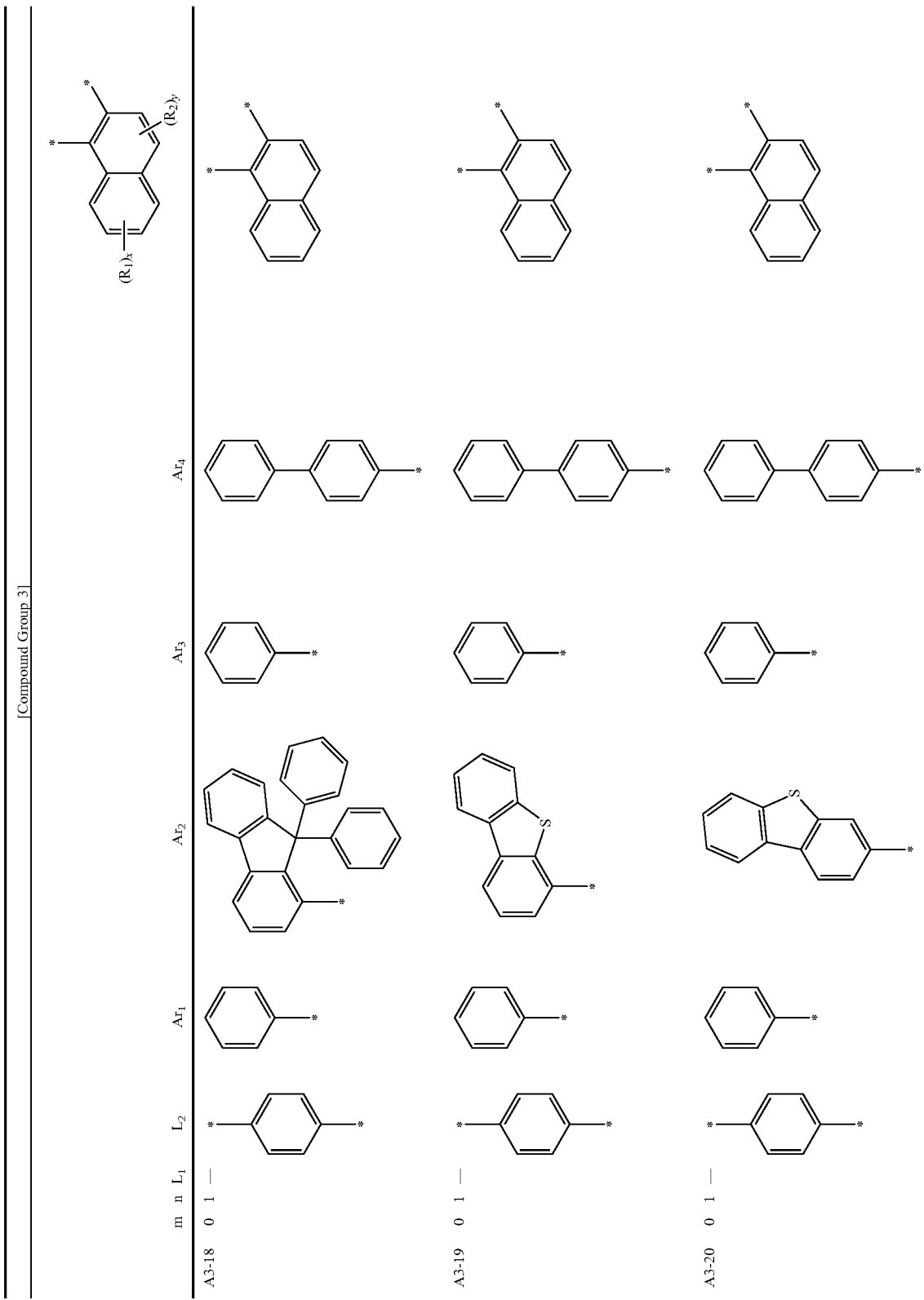

-continued
[Compound Group 3]
| | m | n | L₁ | L₂ | Ar₁ | Ar₂ | Ar₃ | Ar₄ | |
|---|---|---|---|---|---|---|---|---|---|
| A3-21 | 0 | 1 | — | 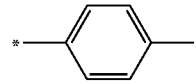 | 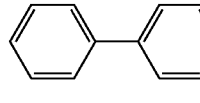 | 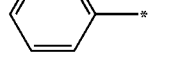 | 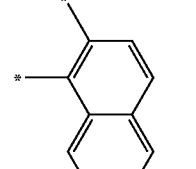 |  | 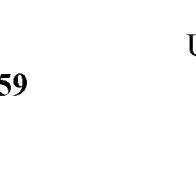 |
| A3-22 | 0 | 1 | — | 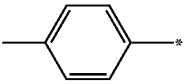 | 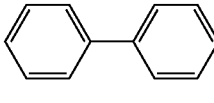 | 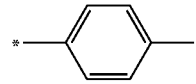 | 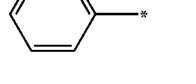 |  | 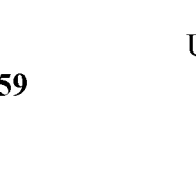 |

-continued
[Compound Group 3]
| | m | n | L₁ | L₂ | Ar₁ | Ar₂ | Ar₃ | Ar₄ | |
|---|---|---|---|---|---|---|---|---|---|
| A3-23 | 0 | 1 | — | 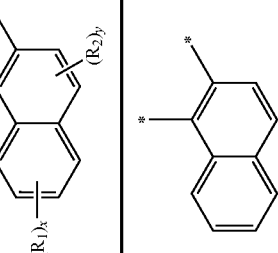 | 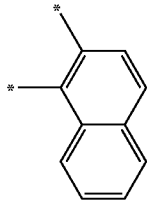 | 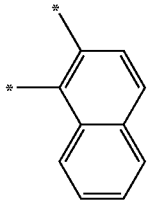 | 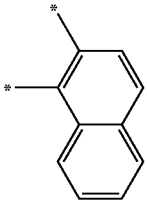 |  |  |
| A3-24 | 0 | 1 | — | 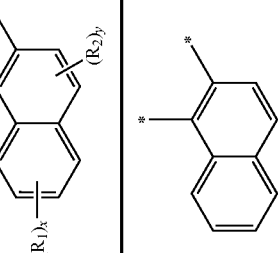 | 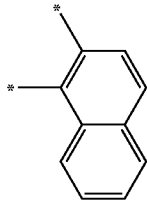 | 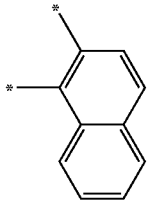 | 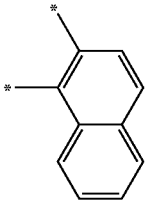 |  |  |
| A3-25 | 0 | 1 | — | 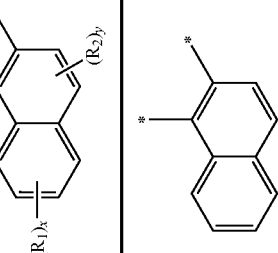 | 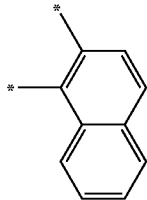 | 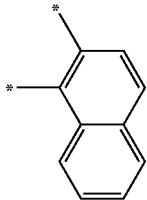 | 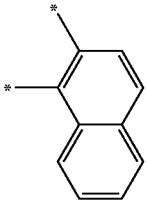 |  |  |

-continued

[Compound Group 3]

| | m | n | L₁ | L₂ | Ar₁ | Ar₂ | Ar₃ | Ar₄ | (structure) |
|---|---|---|---|---|---|---|---|---|---|
| A3-26 | 0 | 1 | — | *–⌬–* | phenyl | dibenzofuranyl | phenyl | biphenyl | 1-naphthyl |
| A3-27 | 0 | 1 | — | *–⌬–* | phenyl | phenyl-dibenzofuranyl-phenyl | phenyl | biphenyl | 1-naphthyl |

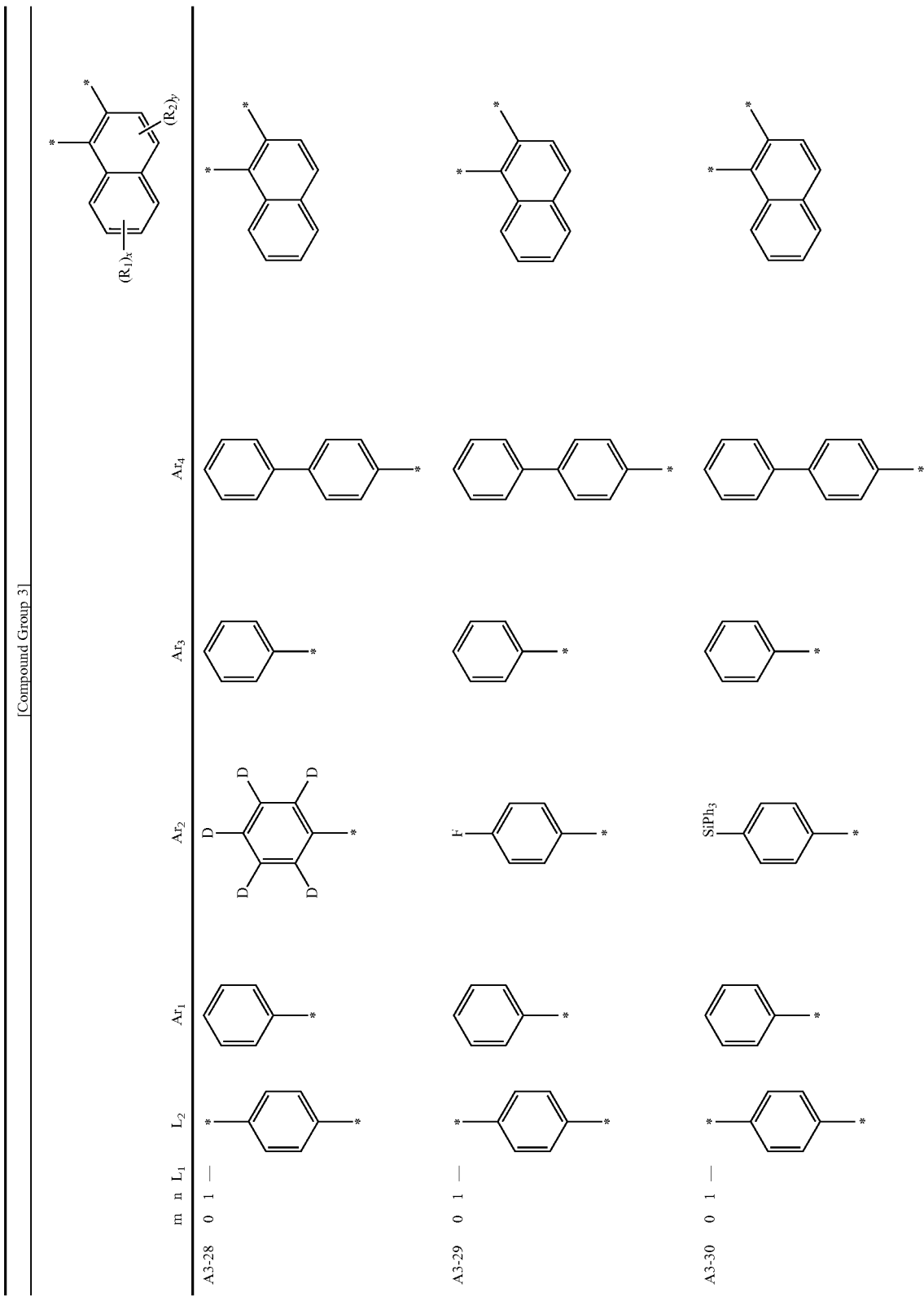

-continued
[Compound Group 3]
| | m | n | L₁ | L₂ | Ar₁ | Ar₂ | Ar₃ | Ar₄ | 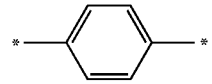 |
|---|---|---|---|---|---|---|---|---|---|
| A3-31 | 0 | 1 | — | 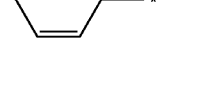 | 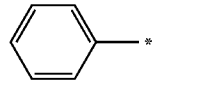 | 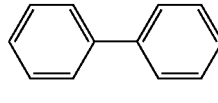 |  | 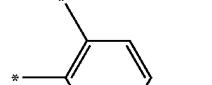 |  |
| A3-32 | 0 | 1 | — |  | 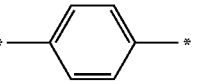 |  | 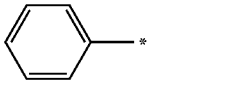 | 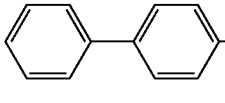 |  |

-continued
[Compound Group 3]
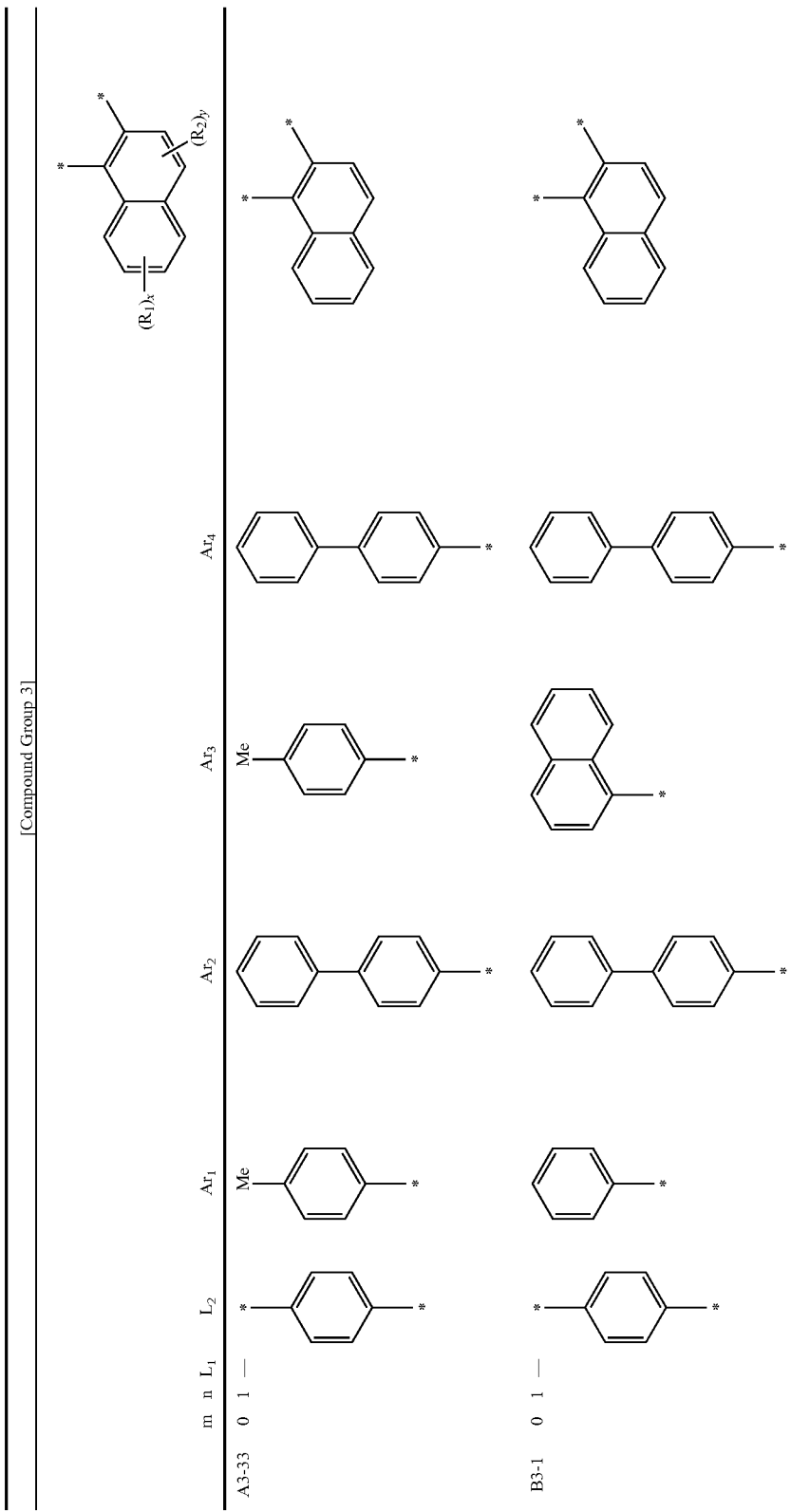

-continued
[Compound Group 3]
| | m | n | L₁ | L₂ | Ar₁ | Ar₂ | Ar₃ | Ar₄ | |
|---|---|---|---|---|---|---|---|---|---|
| B3-2 | 0 | 1 | — |  | 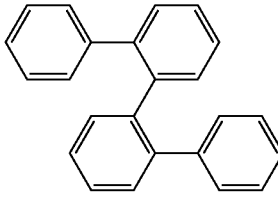 | 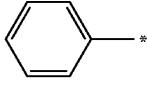 | 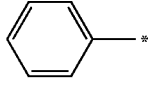 | 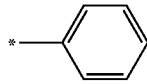 | 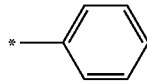 |
| B3-3 | 0 | 1 | — |  |  |  |  | 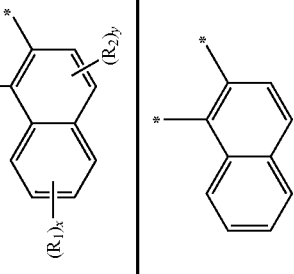 | 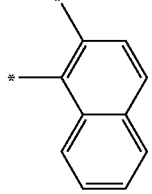 |

-continued
[Compound Group 3]
| | m | n | $L_1$ | $L_2$ | $Ar_1$ | $Ar_2$ | $Ar_3$ | $Ar_4$ | |
|---|---|---|---|---|---|---|---|---|---|
| B3-4 | 0 | 1 | — | 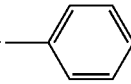 | 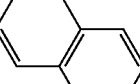 | 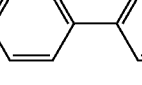 | 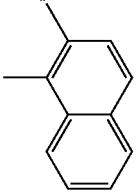 |  |  |
| B3-5 | 0 | 1 | — |  | 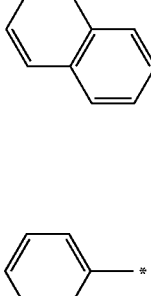 |  |  | 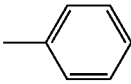 | 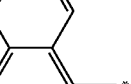 |

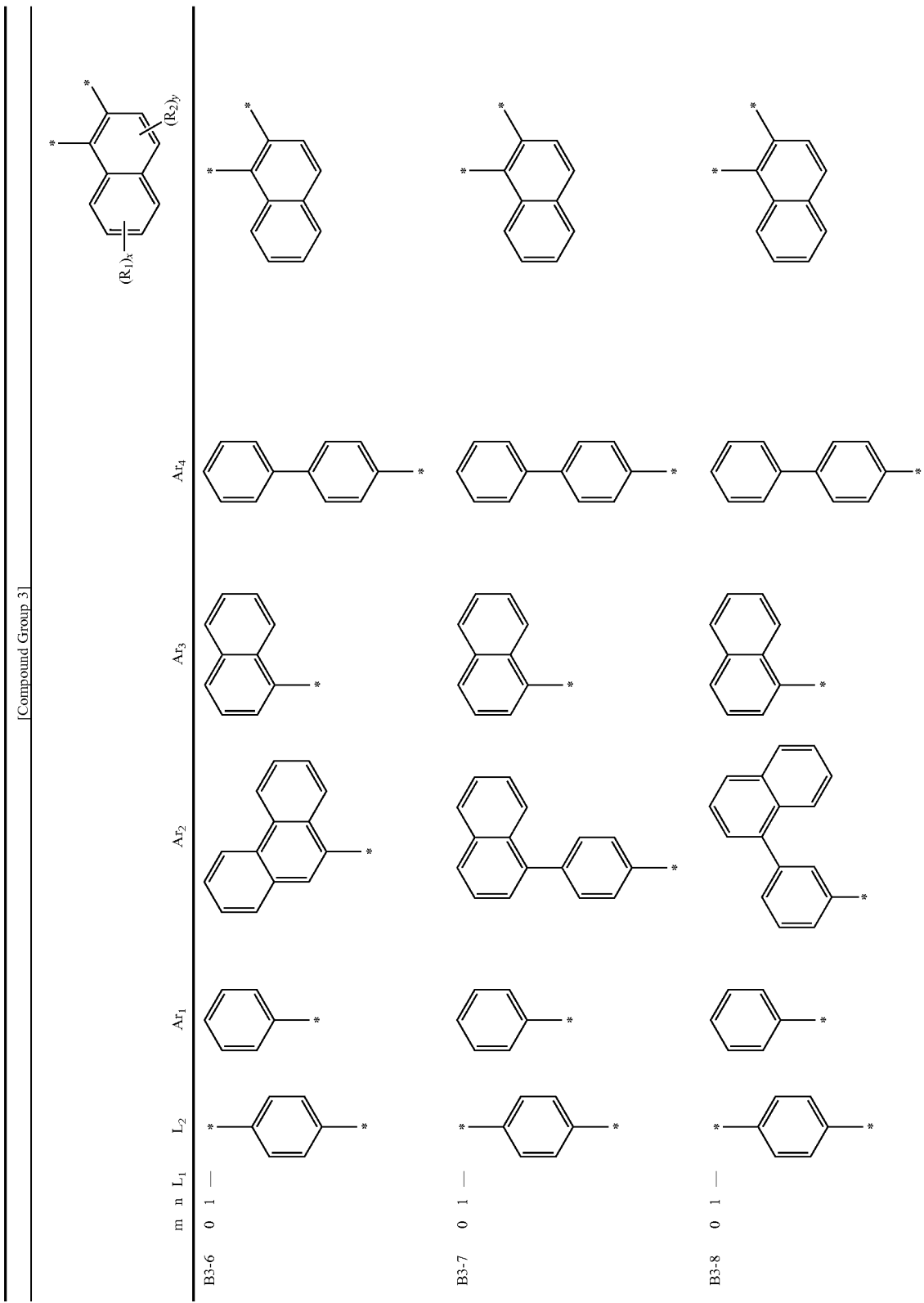

-continued

[Compound Group 3]

| | m | n | L₁ | L₂ | Ar₁ | Ar₂ | Ar₃ | Ar₄ | |
|---|---|---|---|---|---|---|---|---|---|
| B3-9 | 0 | 1 | — | *–⌬–* | *–Ph | 2-biphenyl | 1-naphthyl | 4-biphenyl | 1,2-naphthyl |
| B3-10 | 0 | 1 | — | *–⌬–* | *–Ph | 2-naphthyl-phenyl | 1-naphthyl | 4-biphenyl | 1,2-naphthyl |

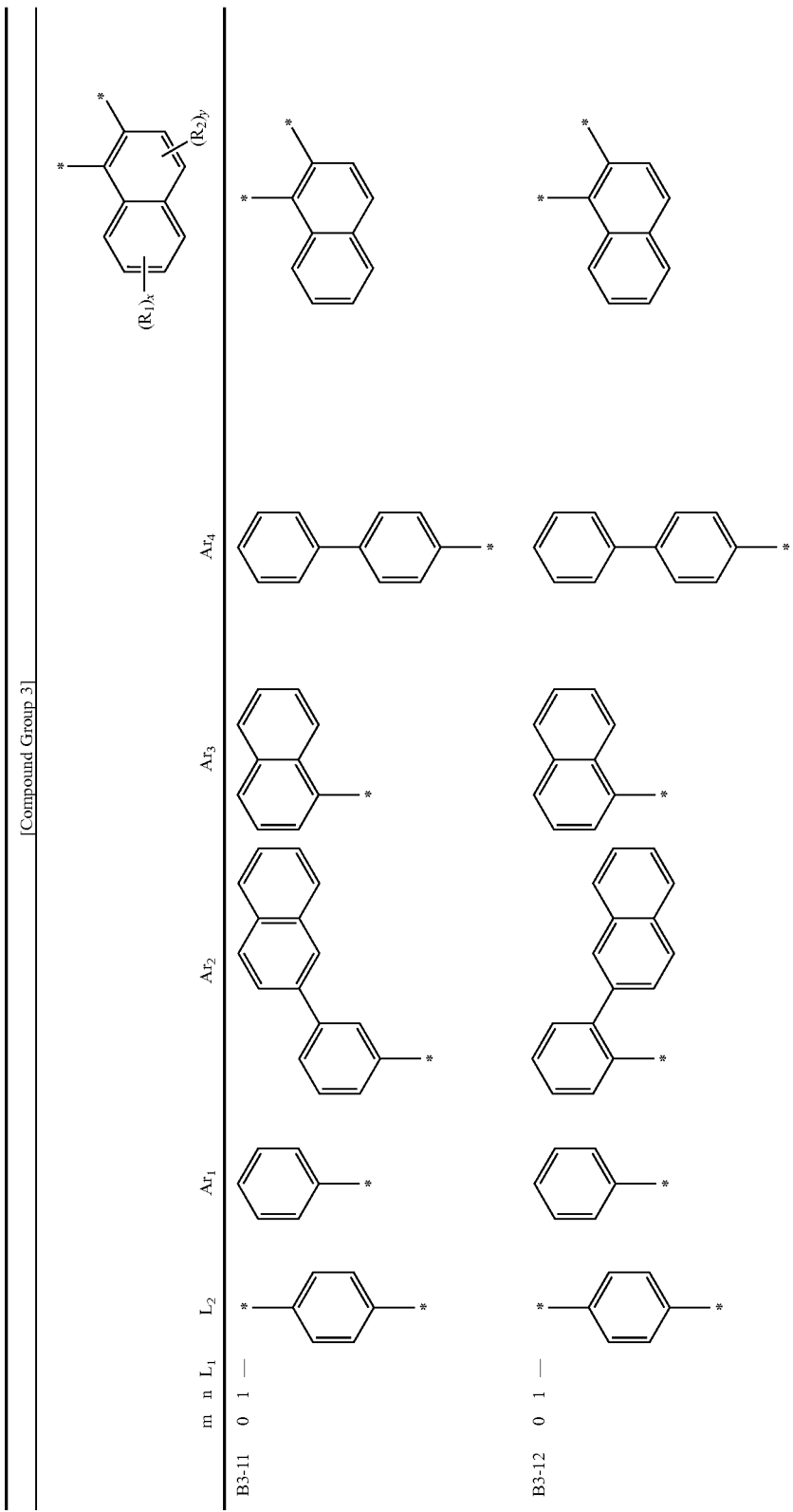

-continued
[Compound Group 3]
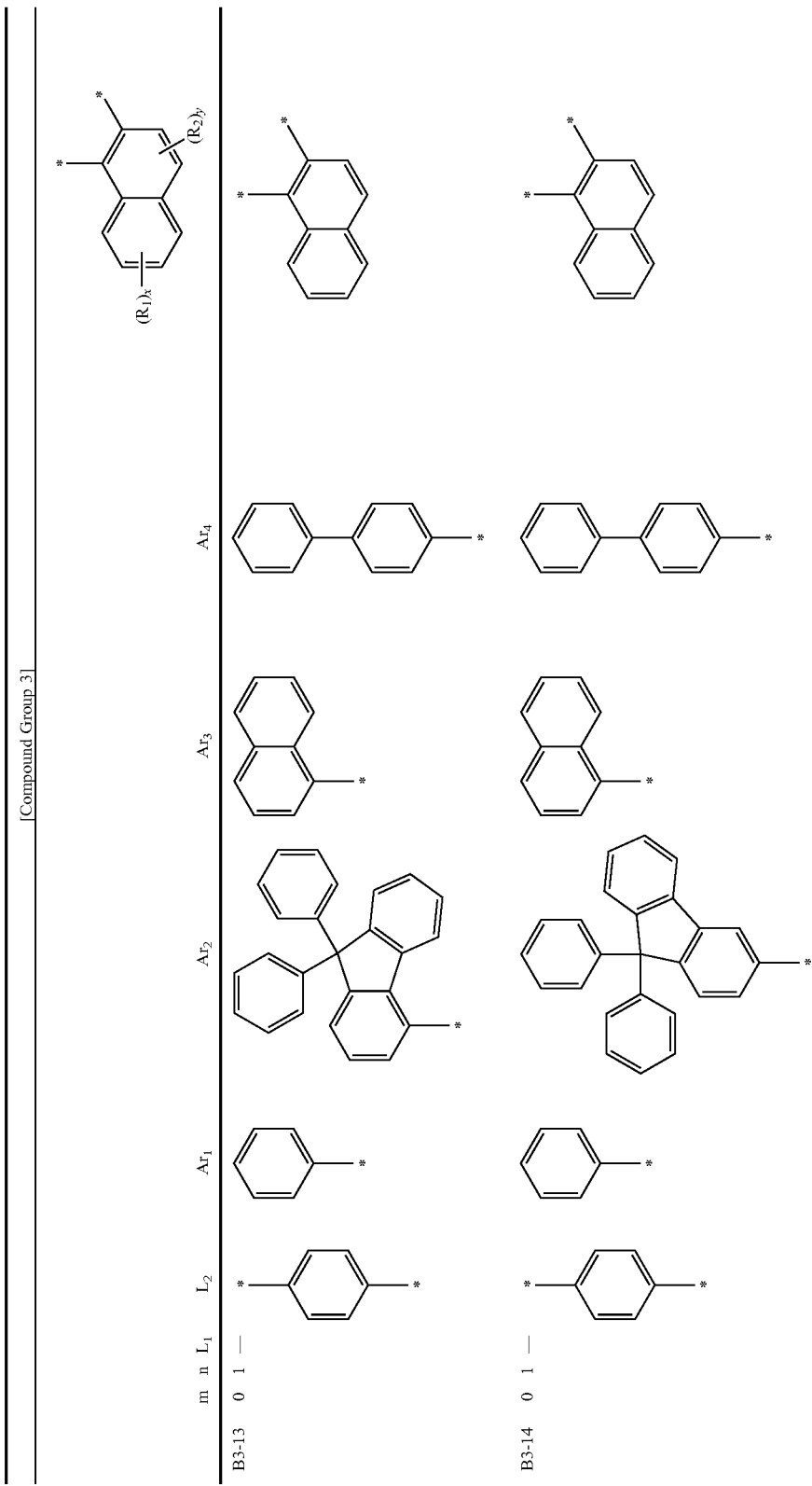

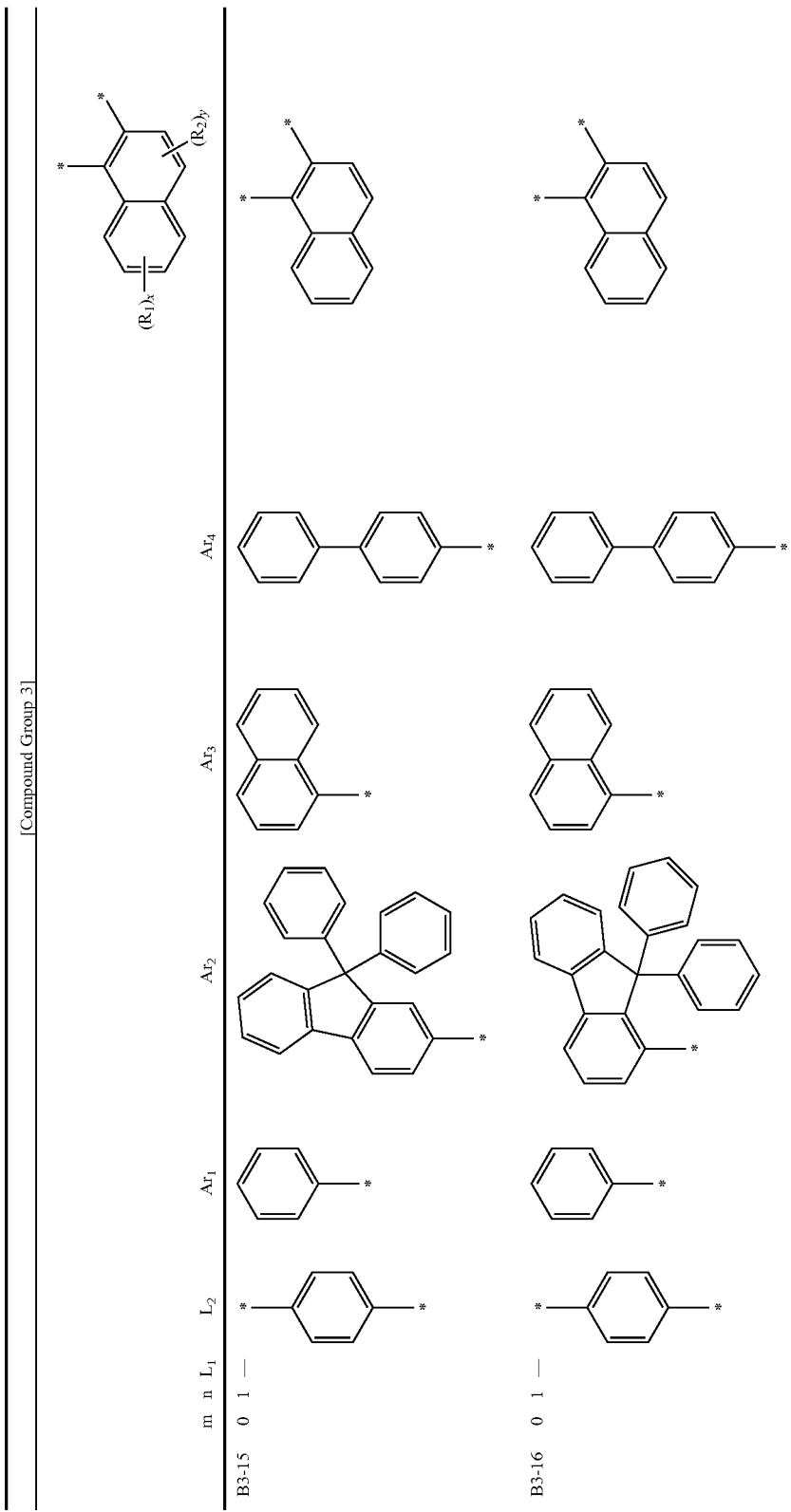

-continued
[Compound Group 3]
| | m | n | L₁ | L₂ | Ar₁ | Ar₂ | Ar₃ | Ar₄ | |
|---|---|---|---|---|---|---|---|---|---|
| B3-17 | 0 | 1 | — | 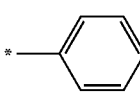 | 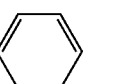 | 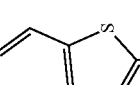 | 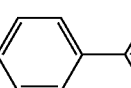 | 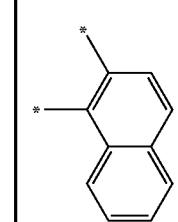 | 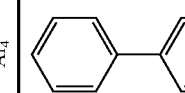 |
| B3-18 | 0 | 1 | — | 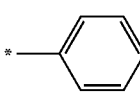 | 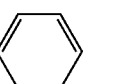 | 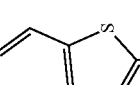 | 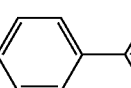 | 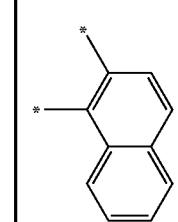 | 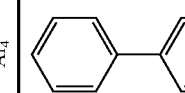 |

-continued
[Compound Group 3]
| | m | n | L₁ | L₂ | Ar₁ | Ar₂ | Ar₃ | Ar₄ | |
|---|---|---|---|---|---|---|---|---|---|
| B3-19 | 0 | 1 | — | 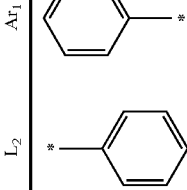 | 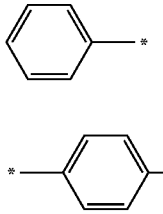 | 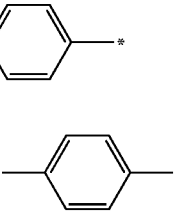 |  | 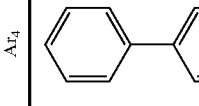 | 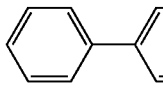 |
| B3-20 | 0 | 1 | — | 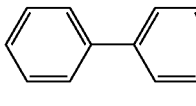 |  | 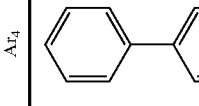 | 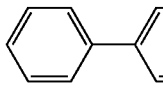 | 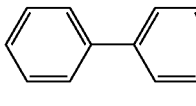 |  |
| B3-21 | 0 | 1 | — | 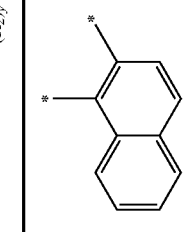 | 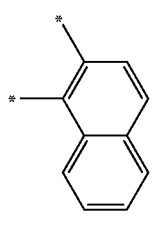 | 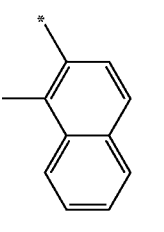 |  | 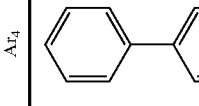 | 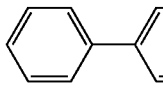 |

-continued
[Compound Group 3]
| | m | n | L$_1$ | L$_2$ | Ar$_1$ | Ar$_2$ | Ar$_3$ | Ar$_4$ |  |
|---|---|---|---|---|---|---|---|---|---|
| B3-22 | 0 | 1 | — | 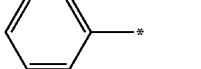 | 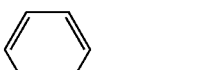 | 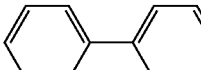 | 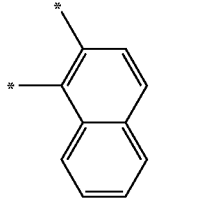 |  |  |
| B3-23 | 0 | 1 | — |  | 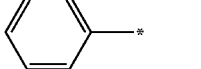 | 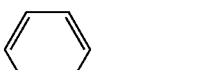 | 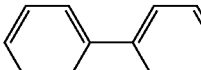 | 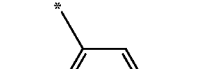 |  |

-continued
[Compound Group 3]
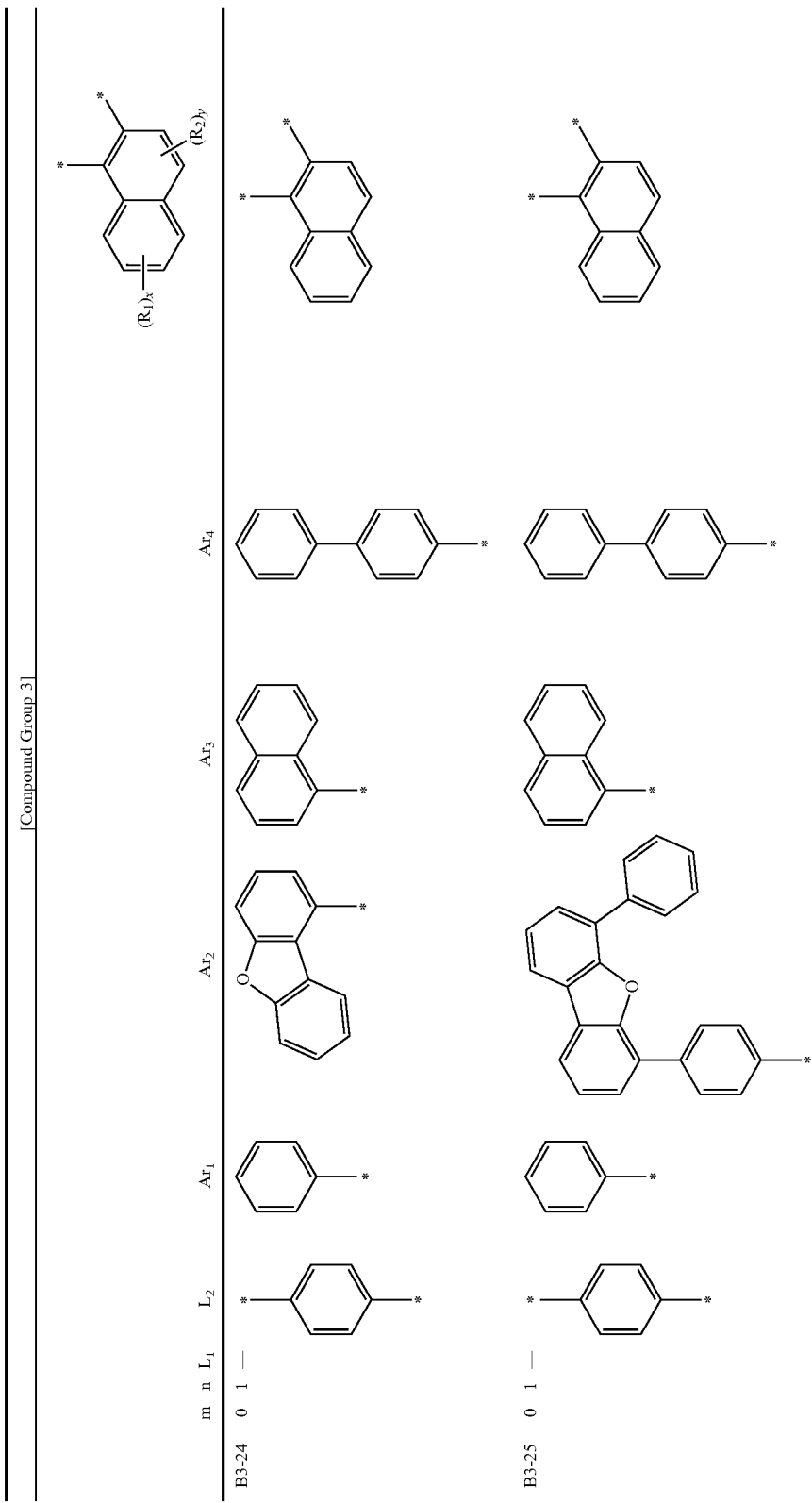

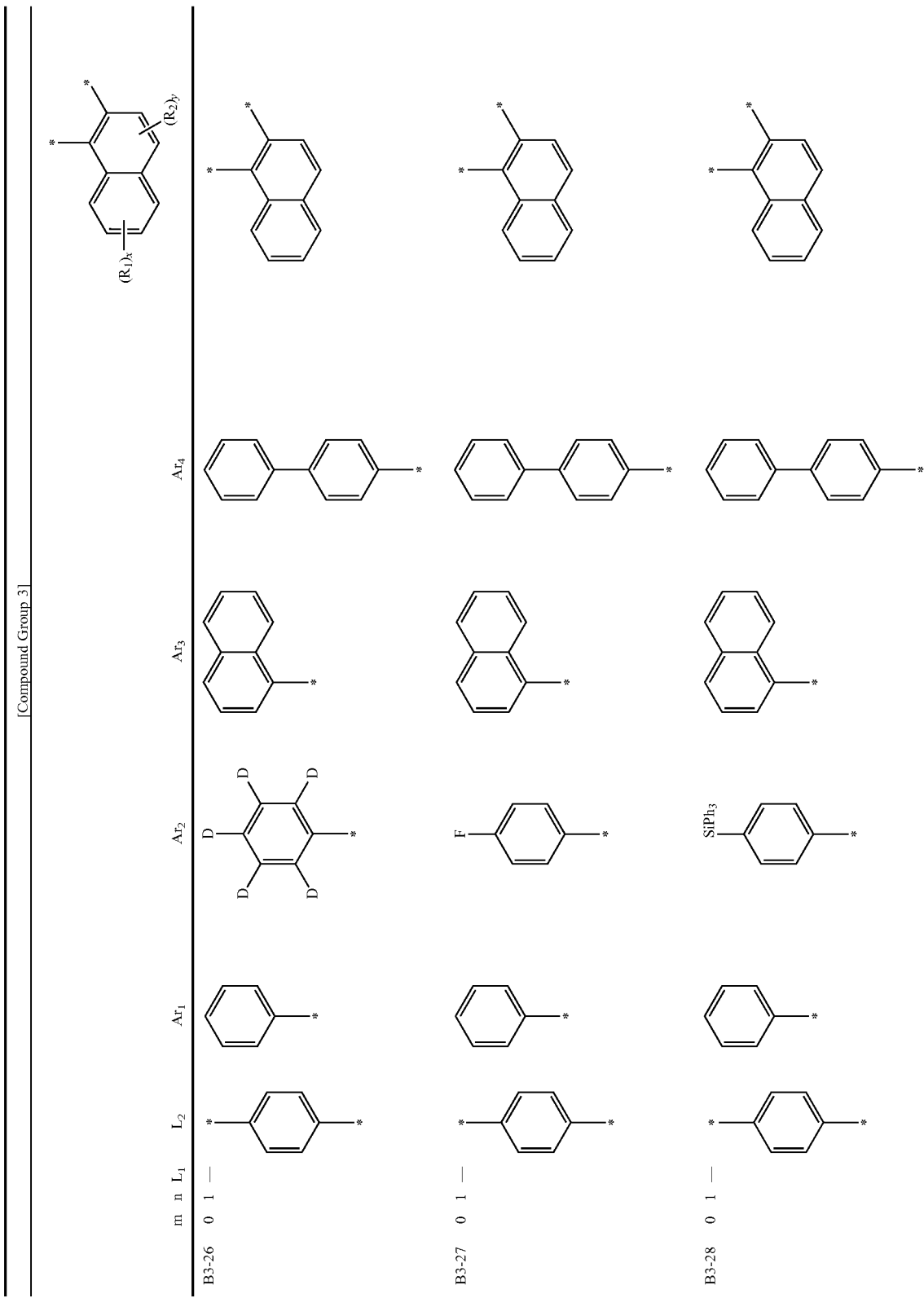

-continued
[Compound Group 3]
| | m | n | L₁ | L₂ | Ar₁ | Ar₂ | Ar₃ | Ar₄ | 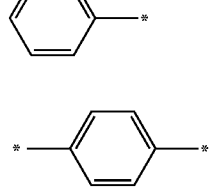 |
|---|---|---|---|---|---|---|---|---|---|
| B3-29 | 0 | 1 | — | 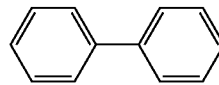 |  | 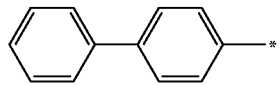 |  | 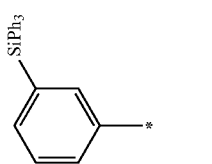 | 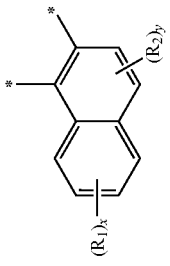 |
| B3-30 | 0 | 1 | — | 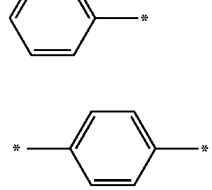 |  |  | 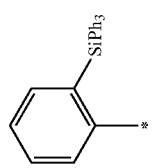 | 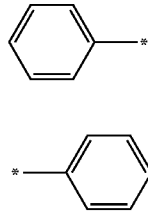 | |

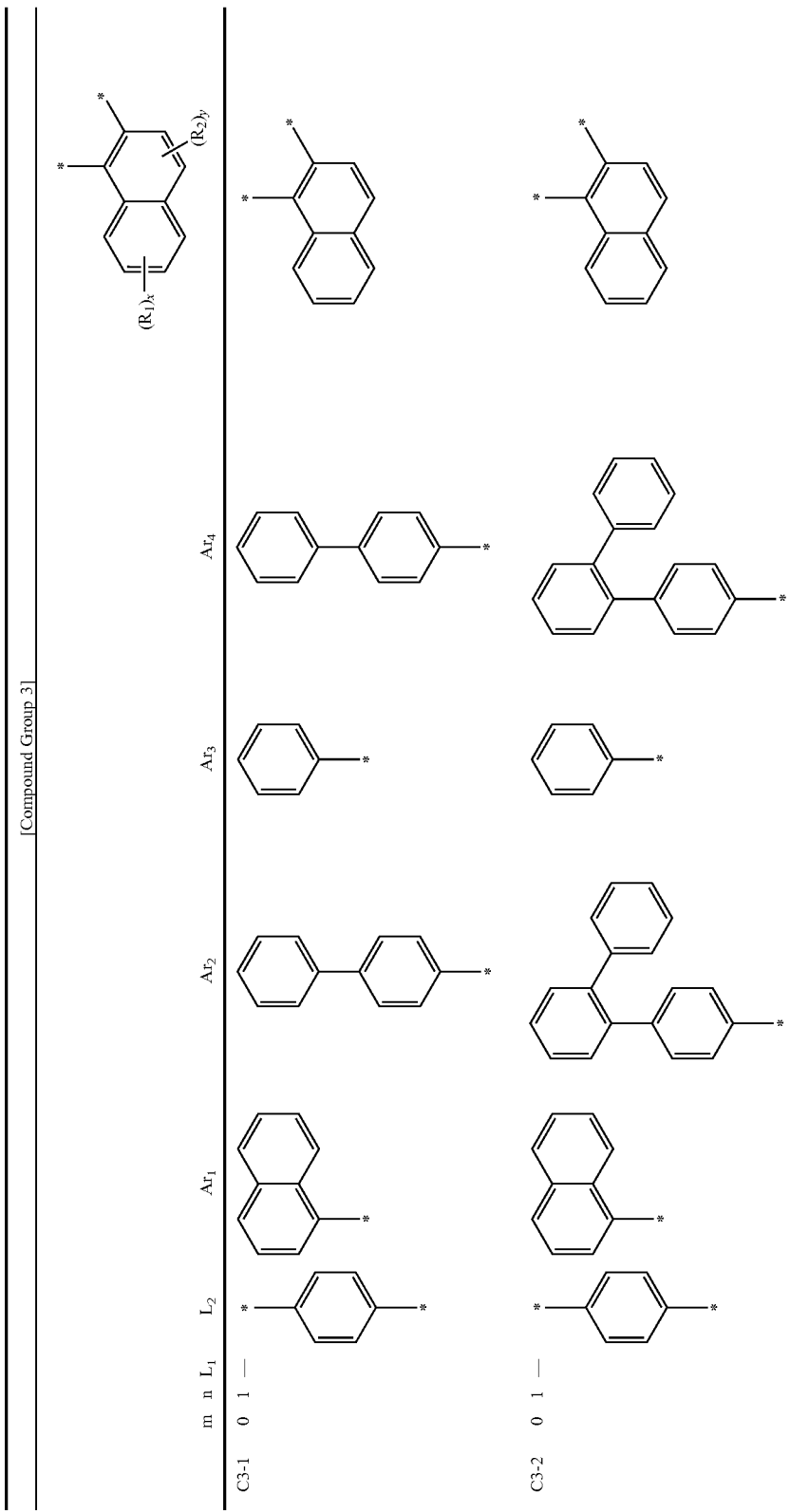

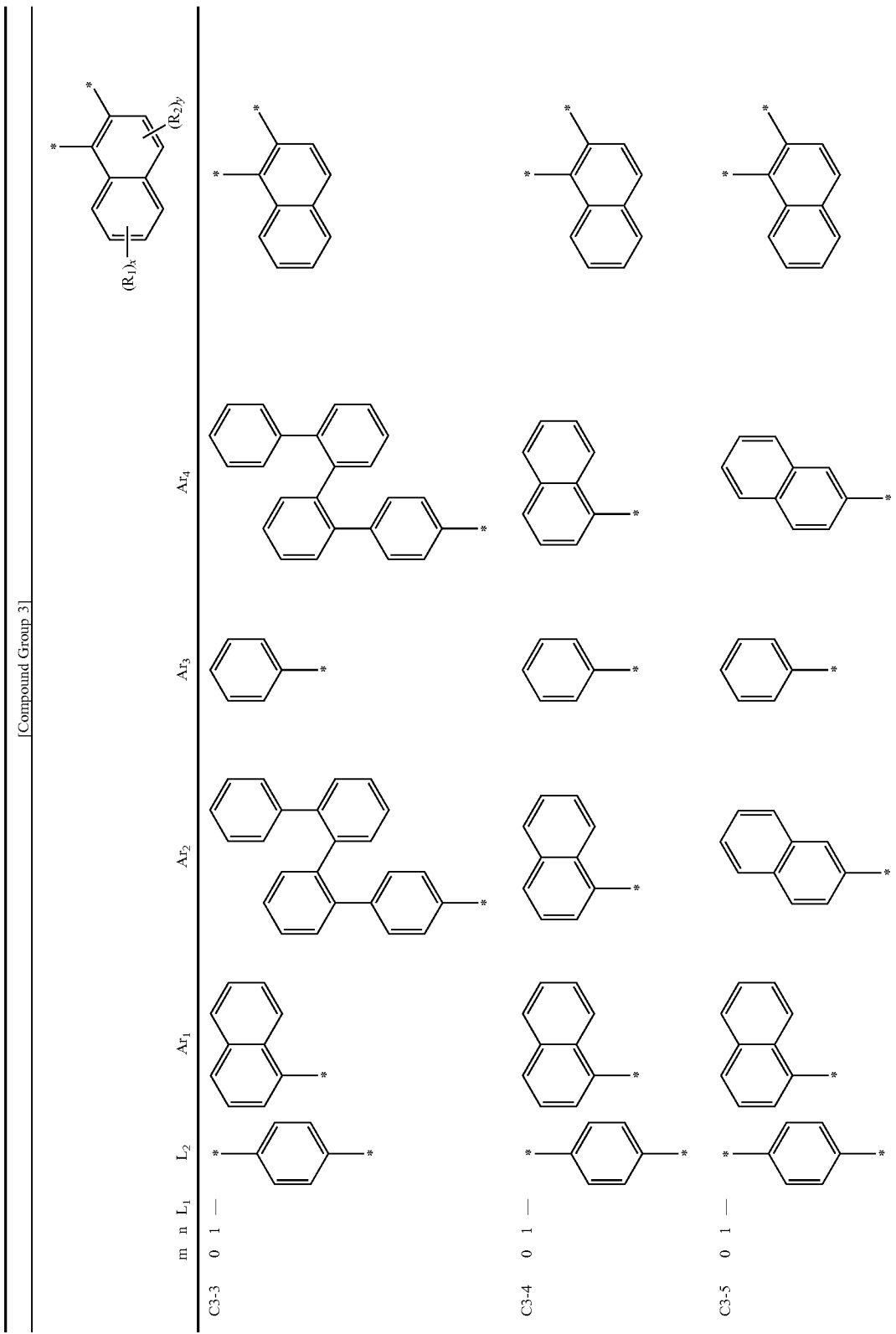

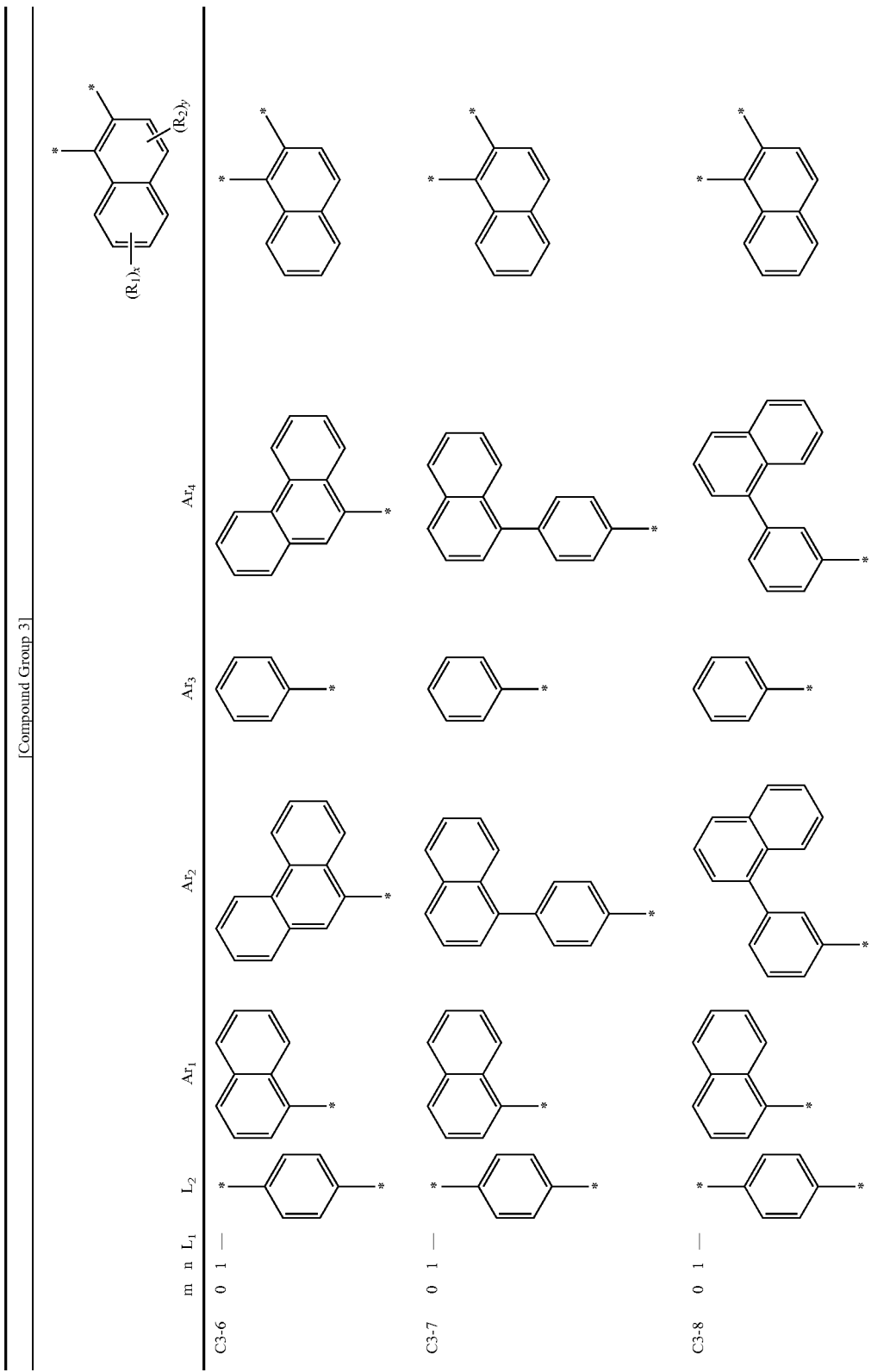

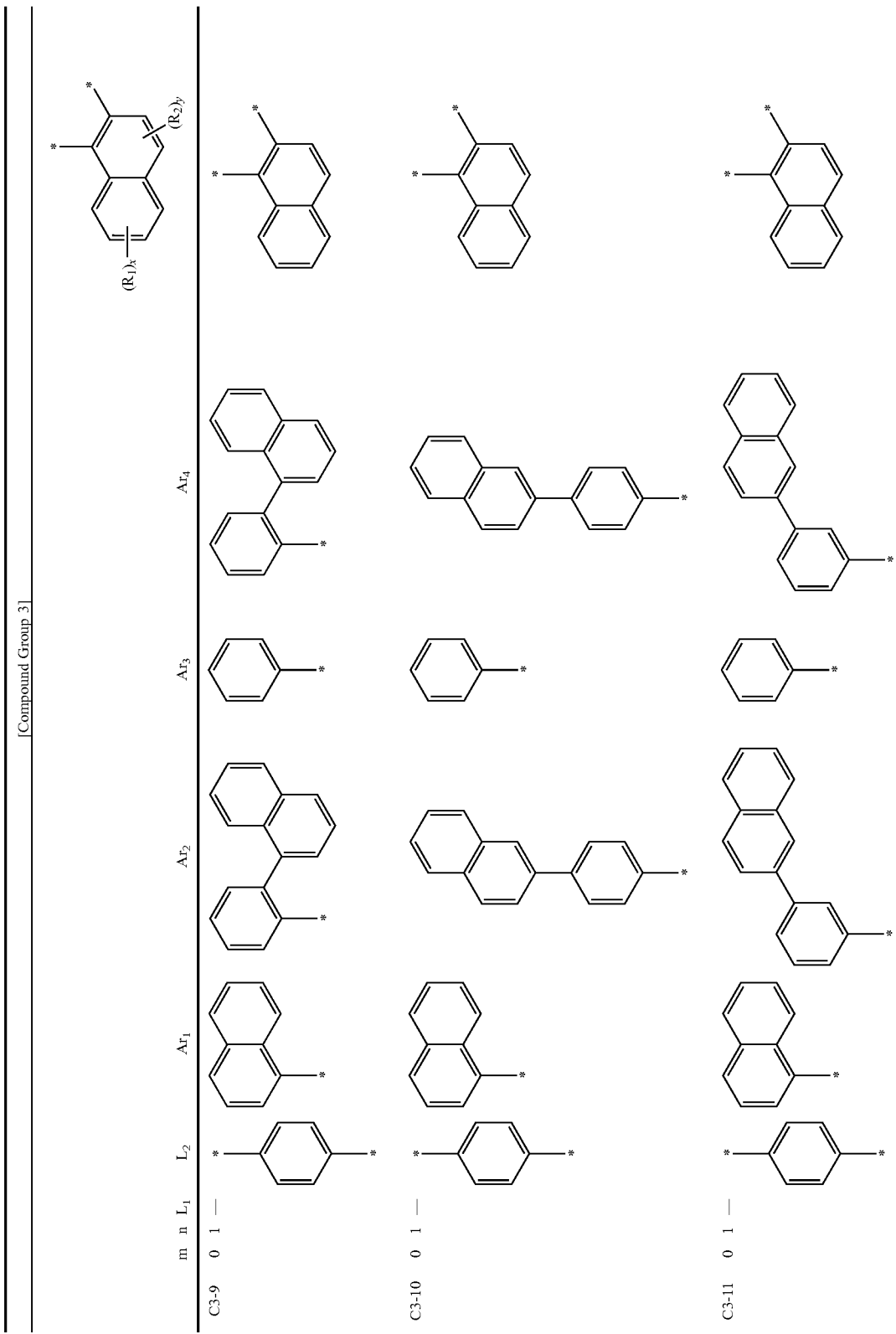

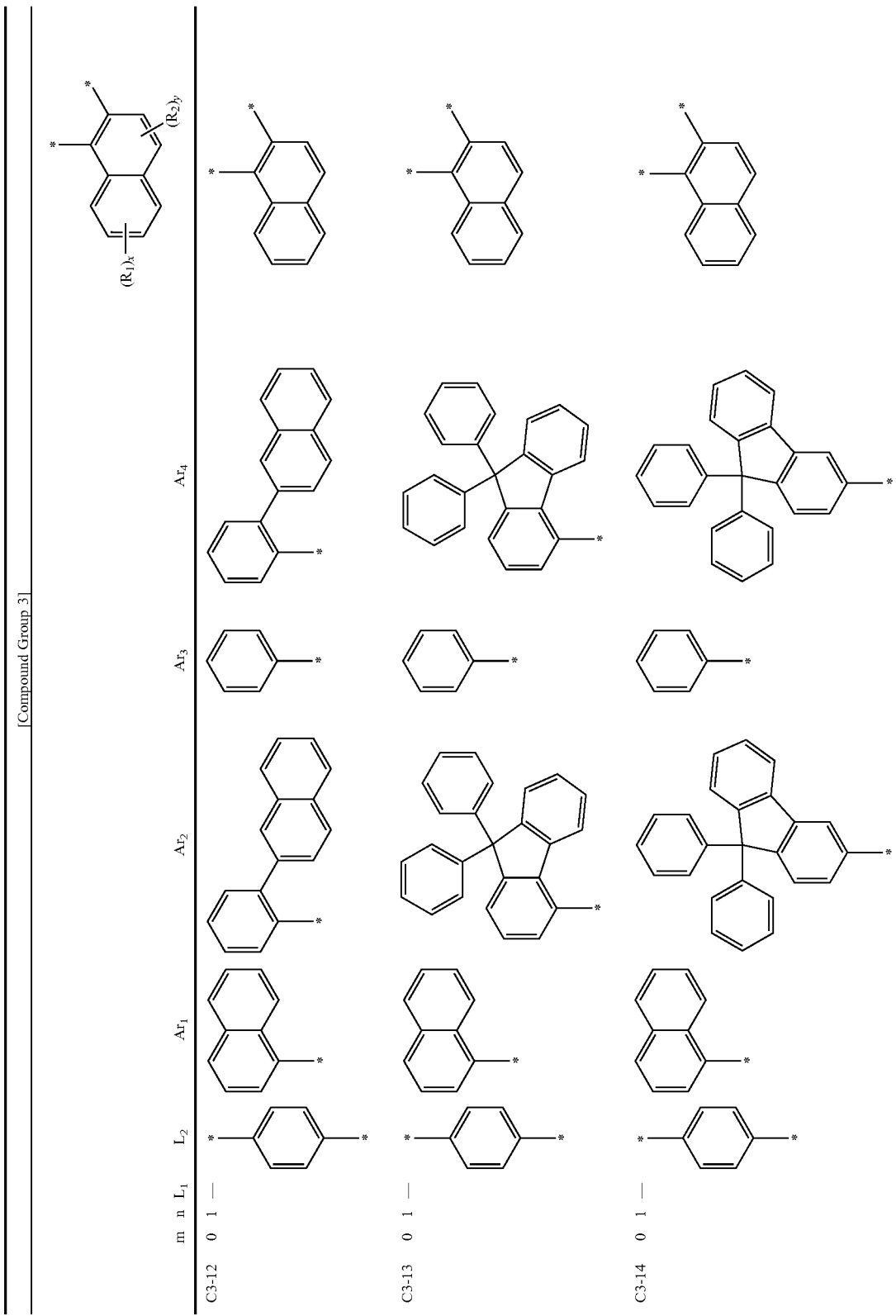

-continued
[Compound Group 3]
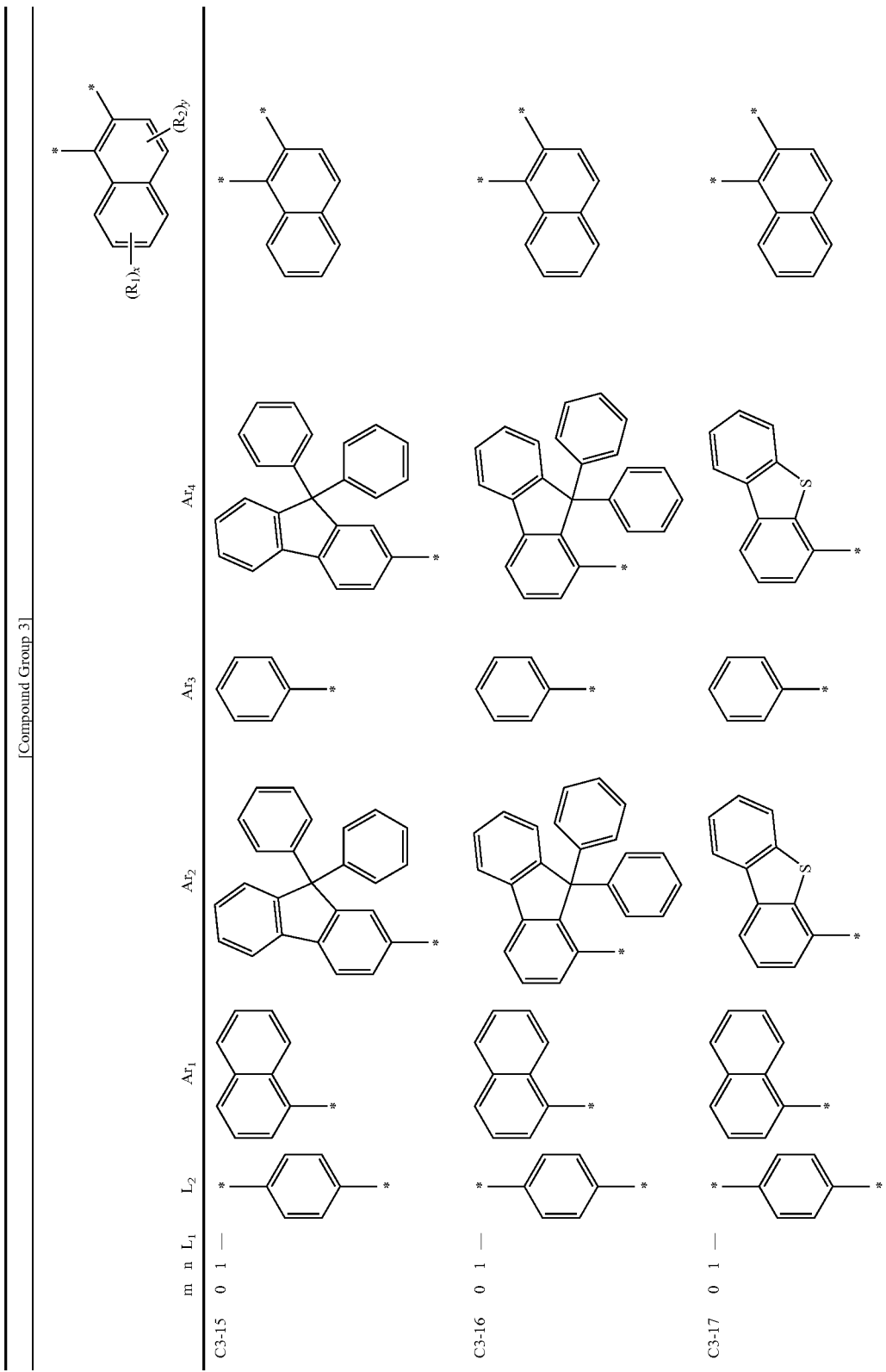

-continued
[Compound Group 3]
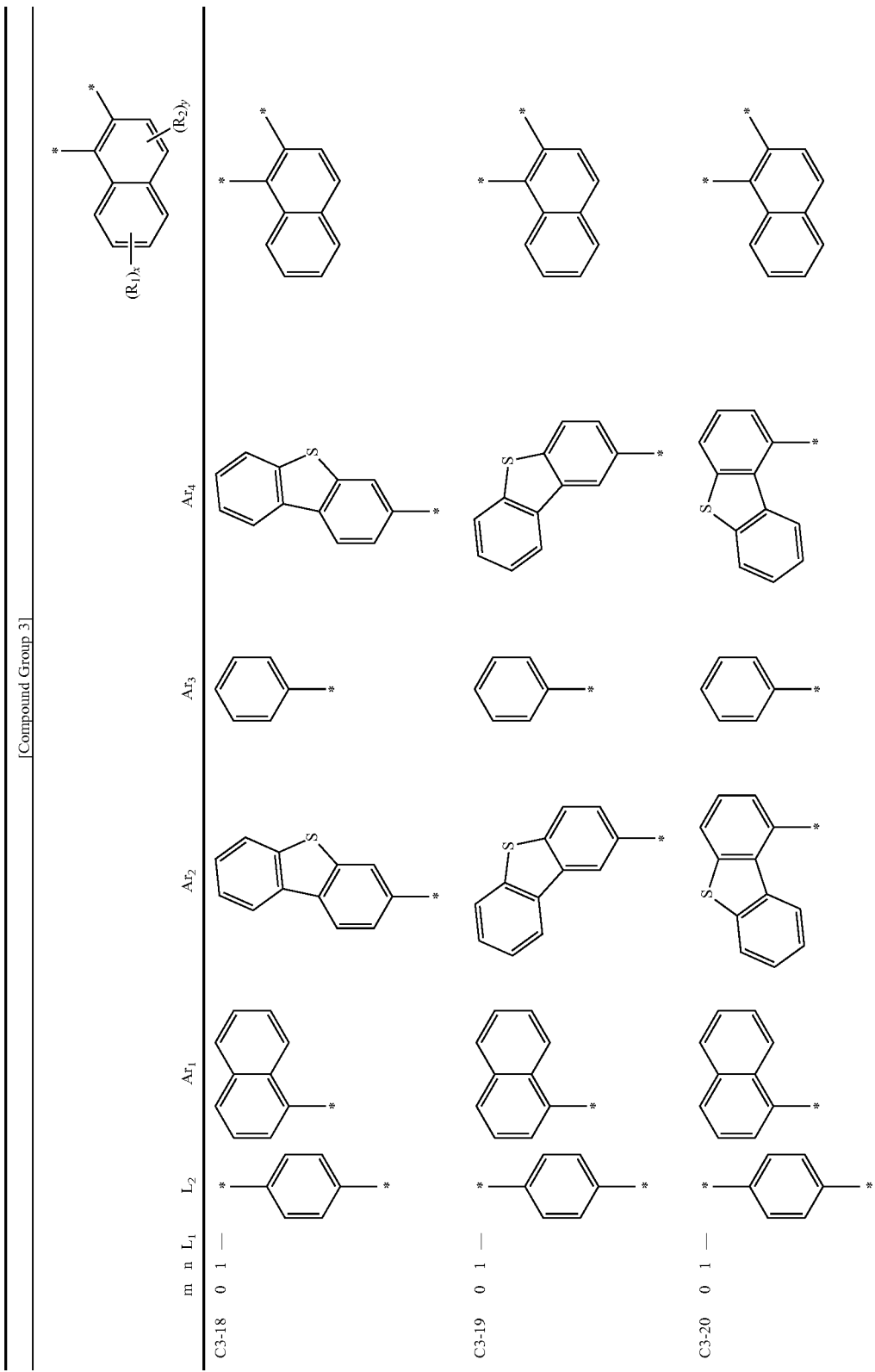

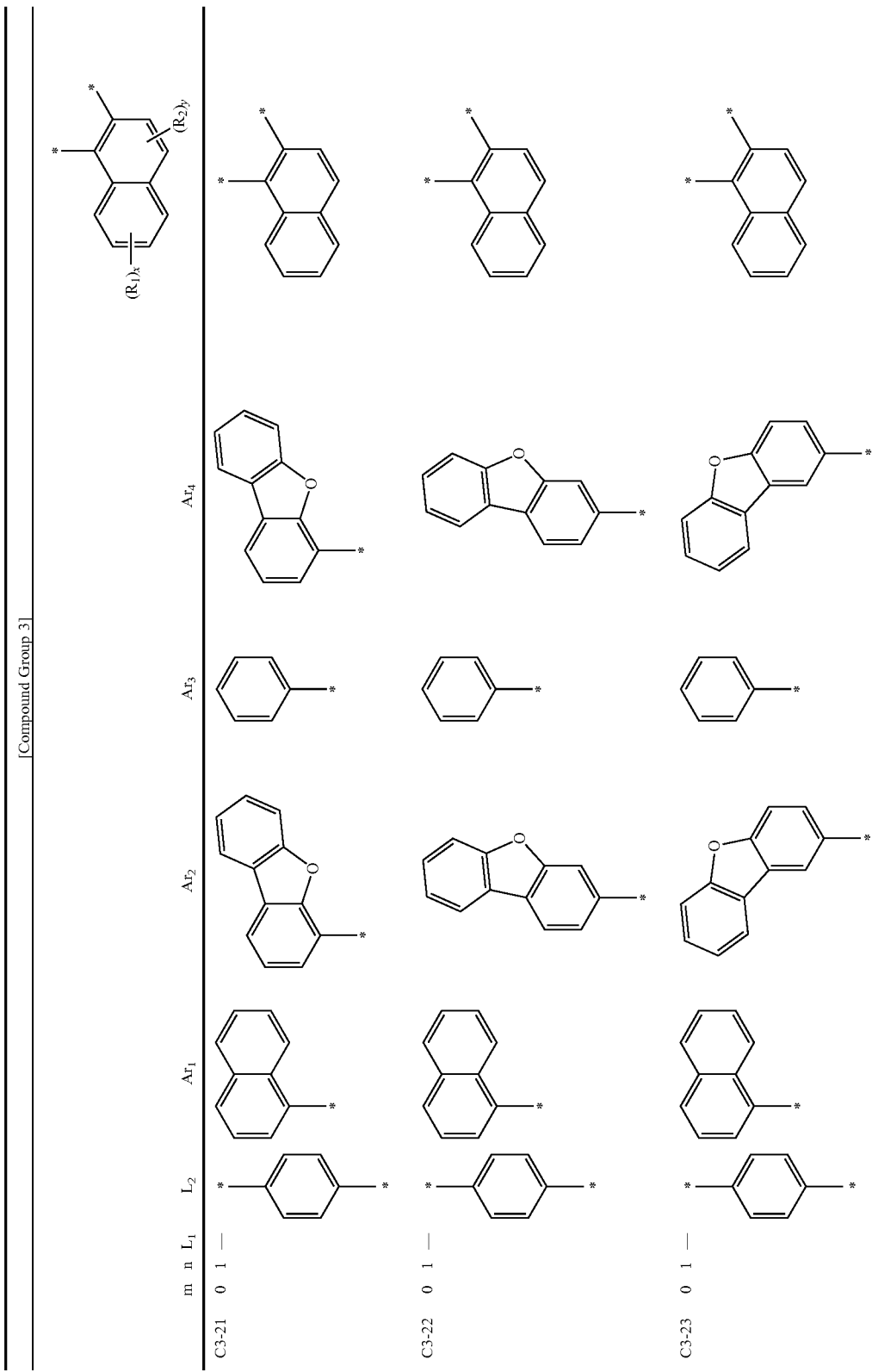

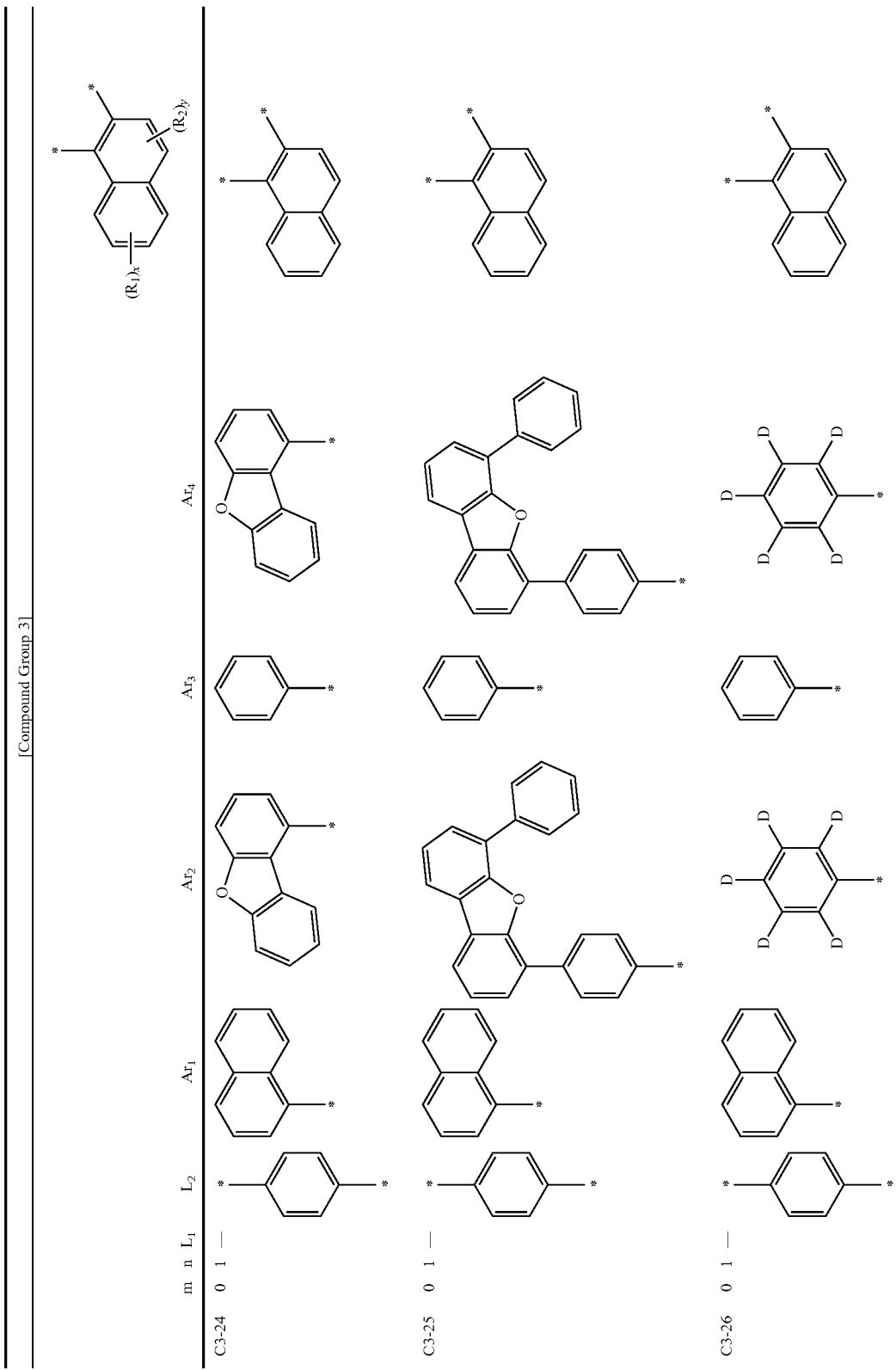

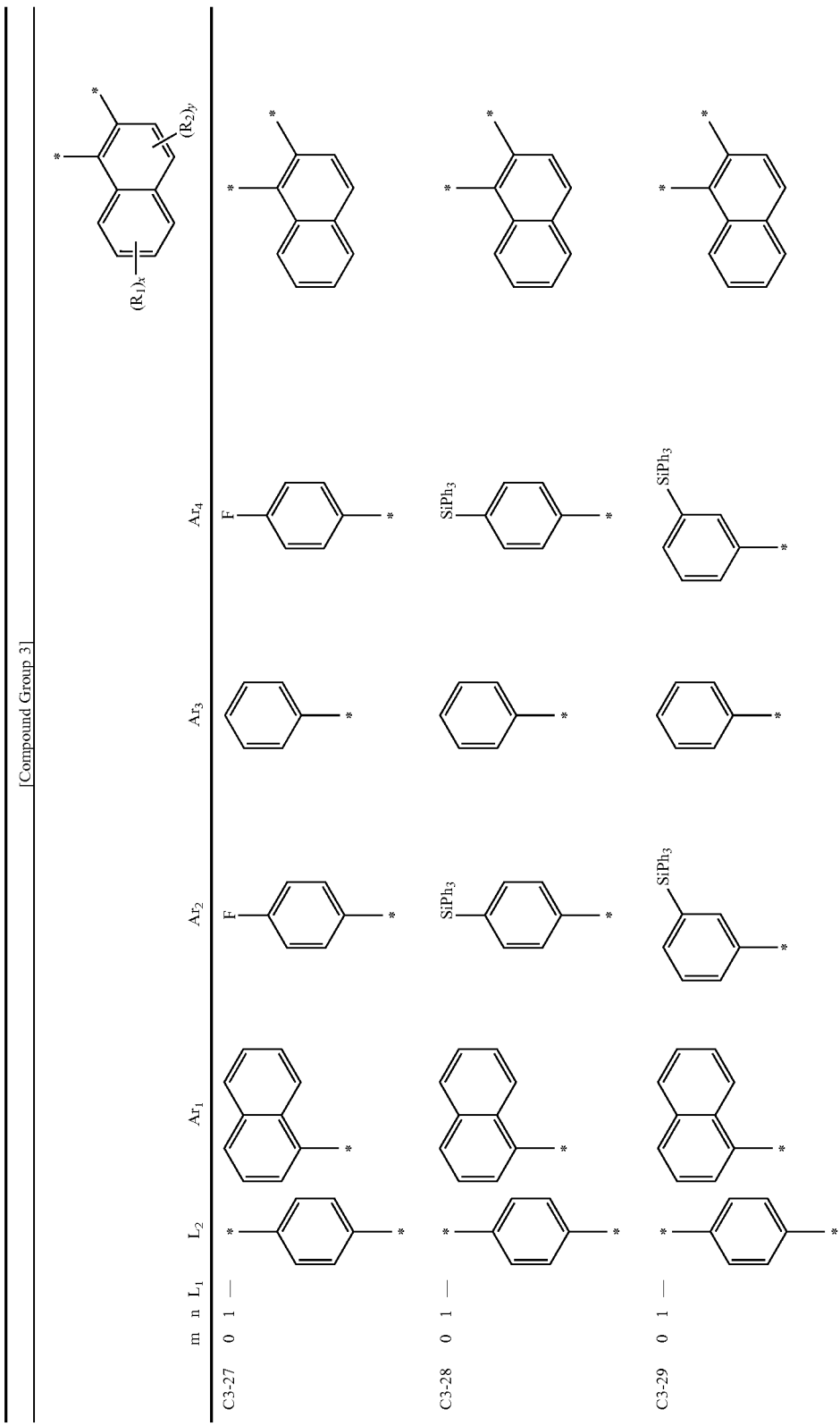

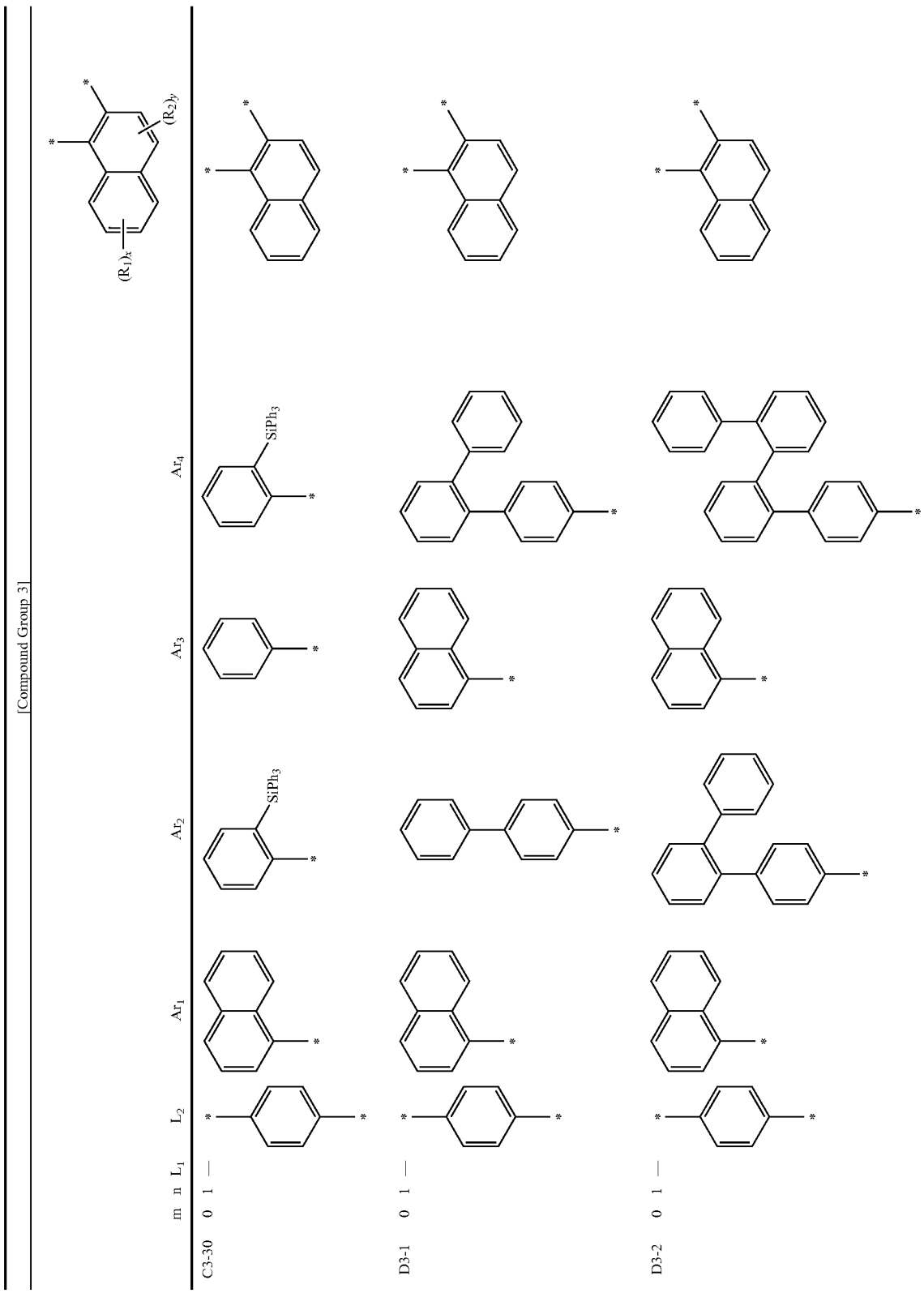

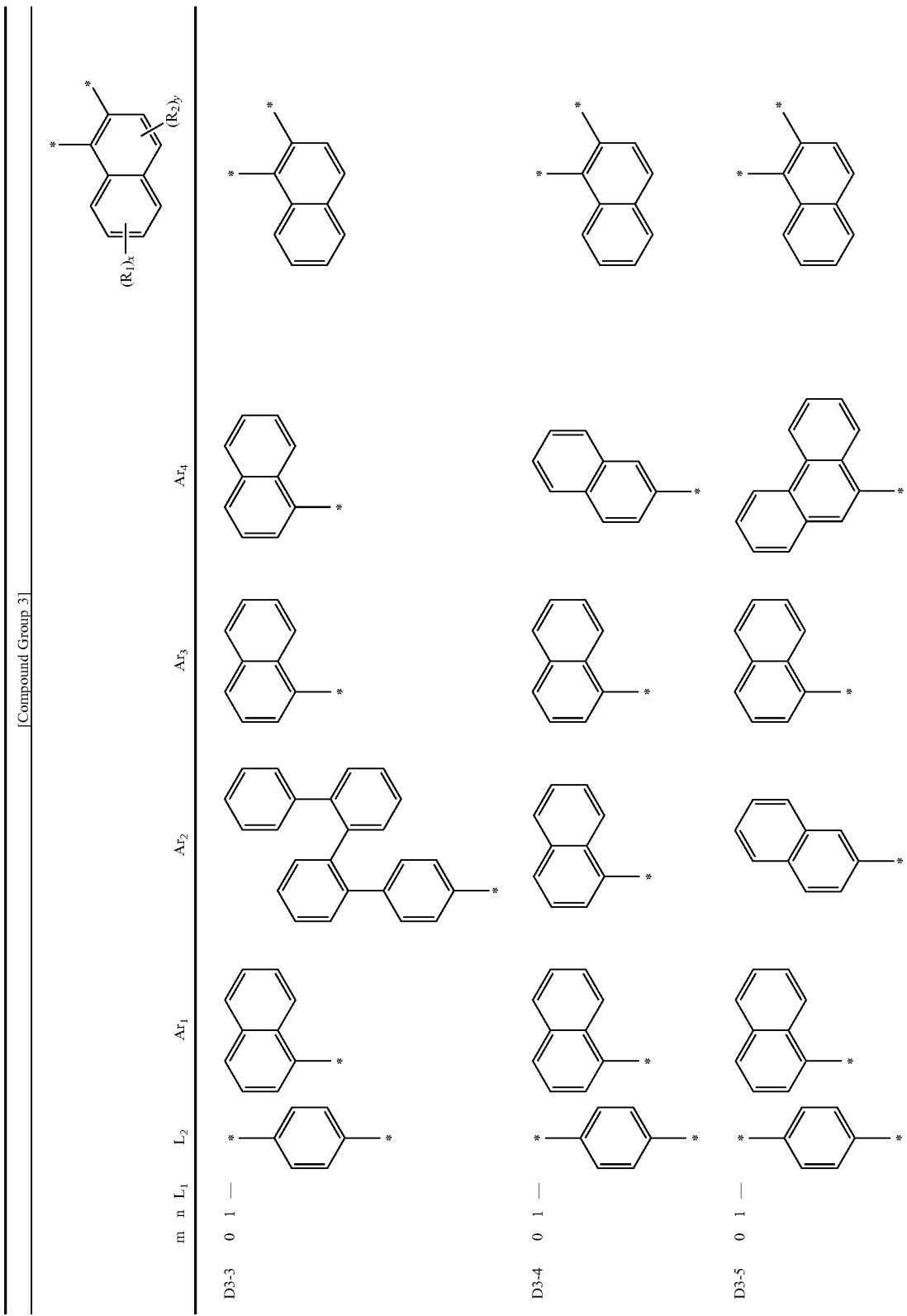

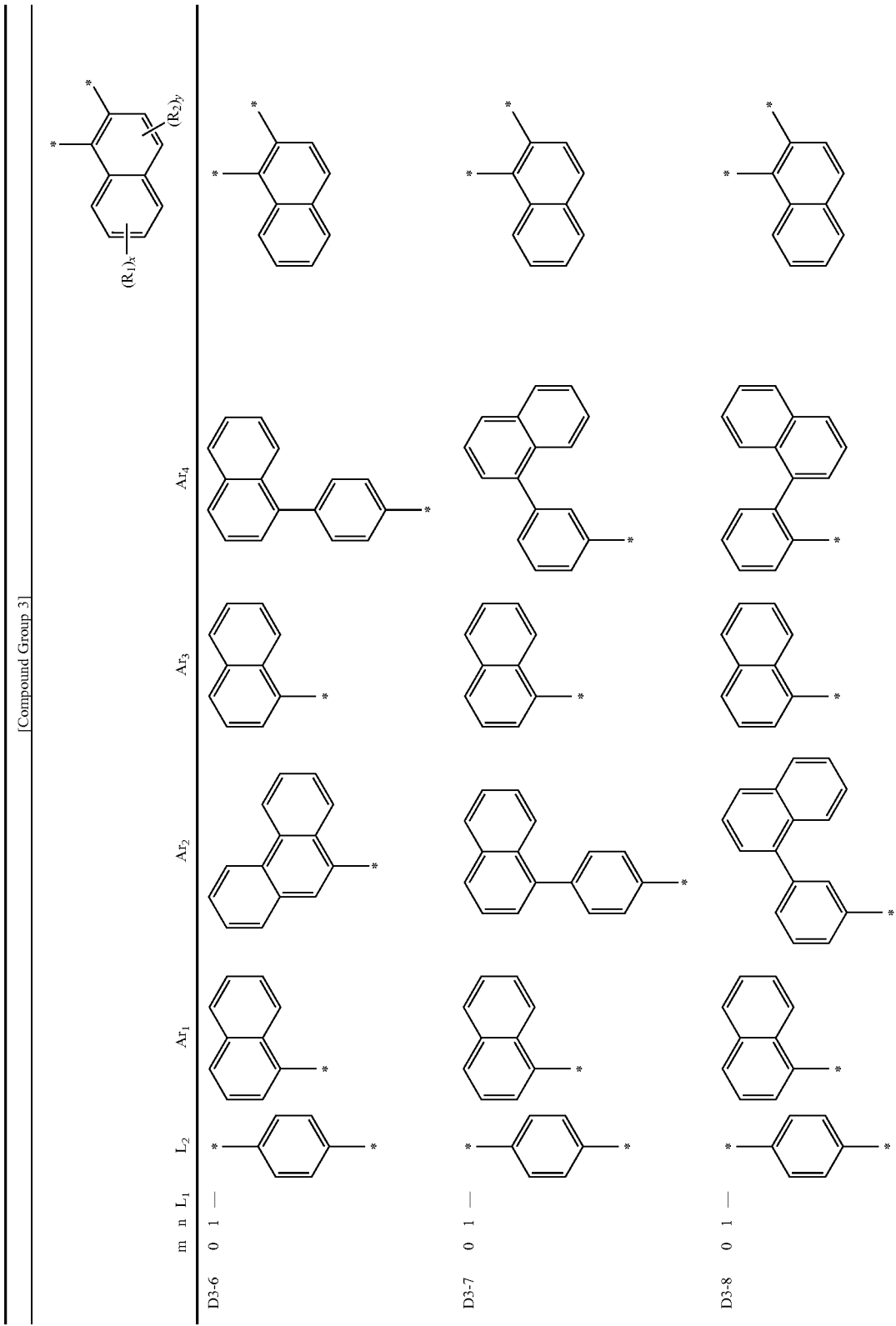

-continued
[Compound Group 3]
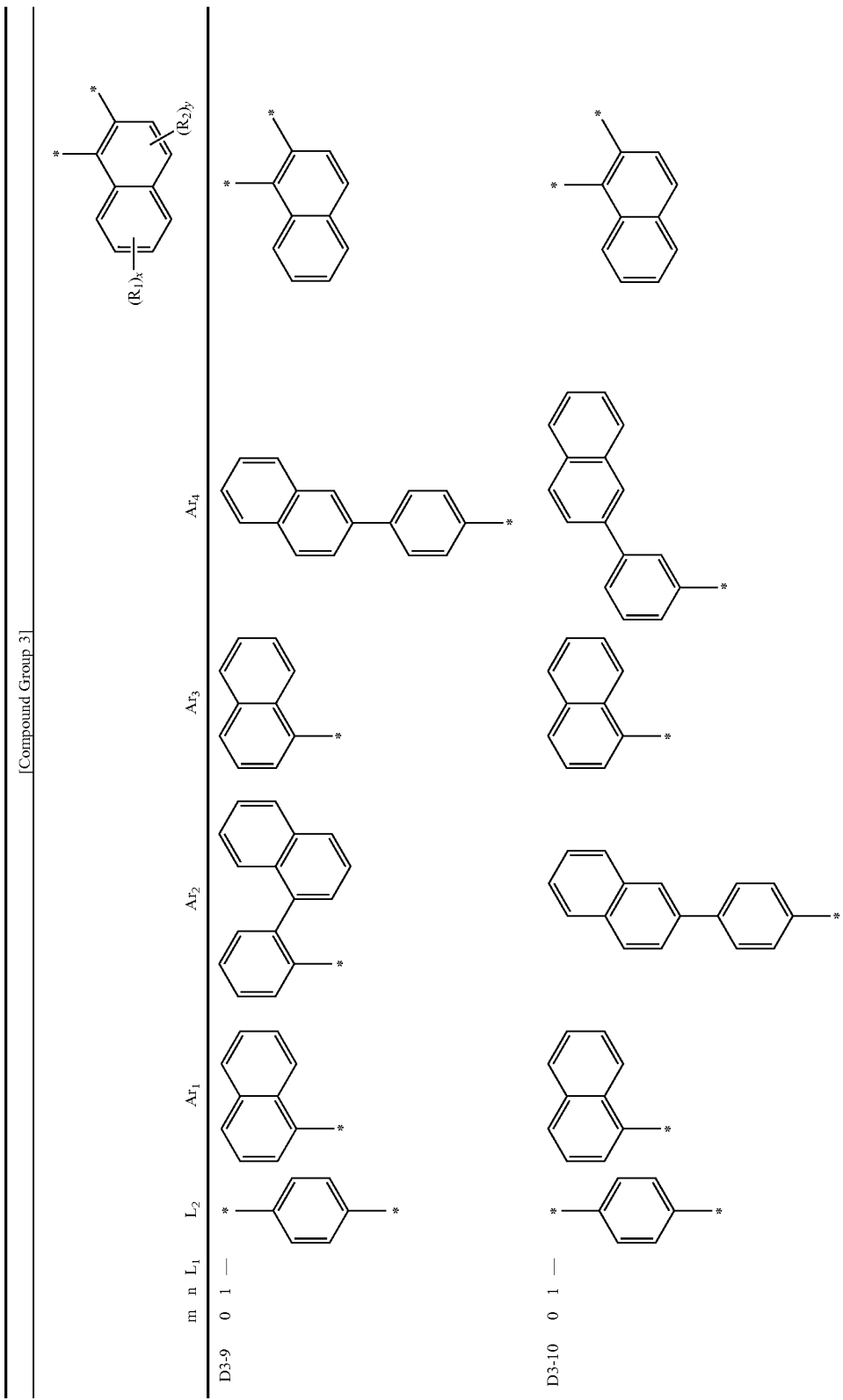

[Compound Group 3]
| | m | n | L₁ | L₂ | Ar₁ | Ar₂ | Ar₃ | Ar₄ |  |
|---|---|---|---|---|---|---|---|---|---|
| D3-11 | 0 | 1 | — |  | 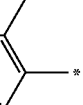 | 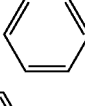 | 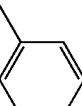 |  | 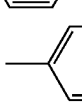 |
| D3-12 | 0 | 1 | — | 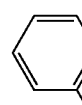 | 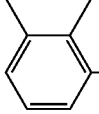 | 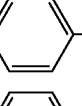 | 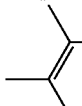 |  | 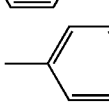 |
| D3-13 | 0 | 1 | — |  | 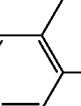 | 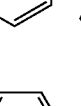 | 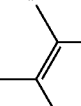 |  | |

-continued
[Compound Group 3]
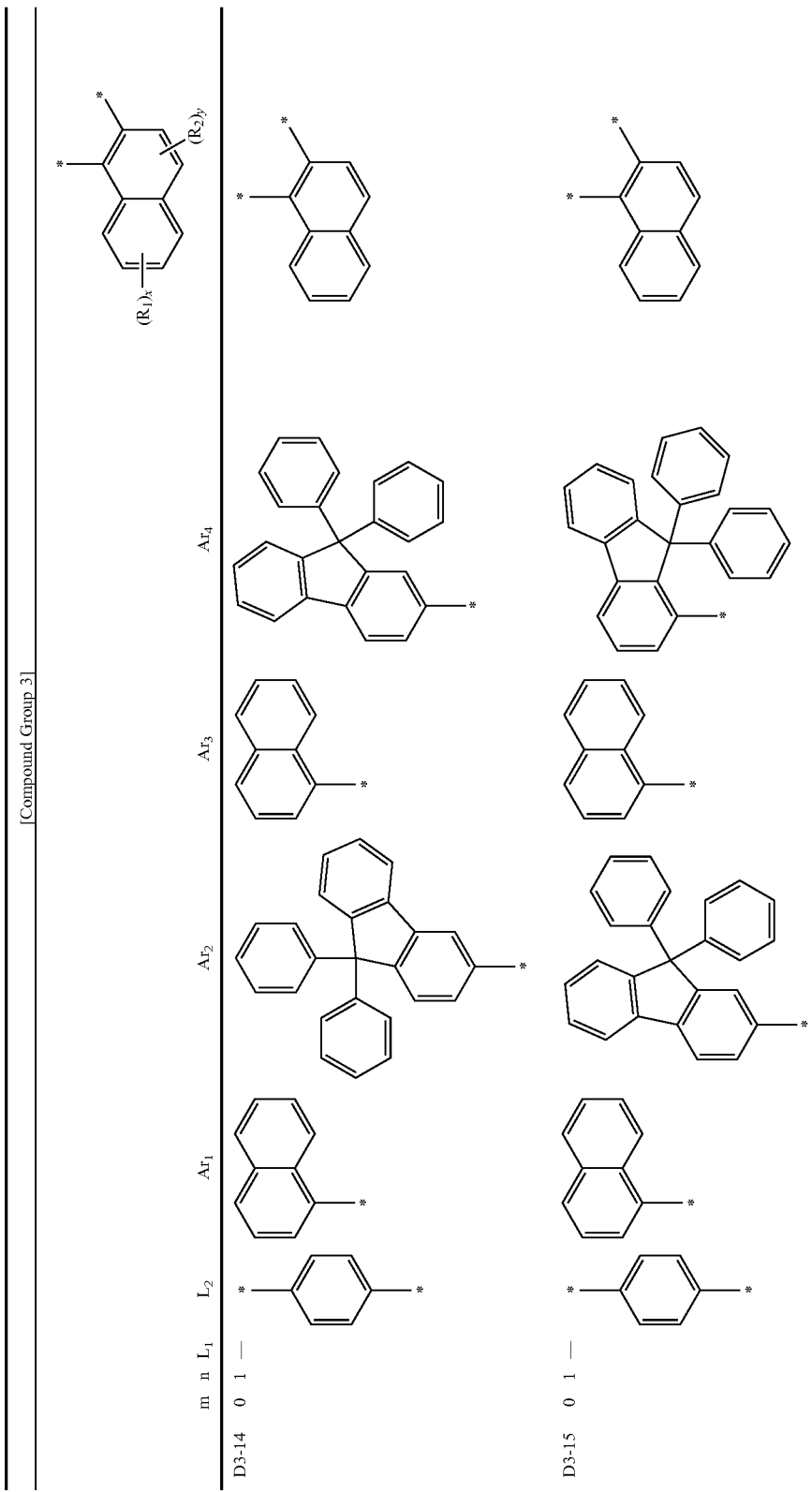

-continued
[Compound Group 3]
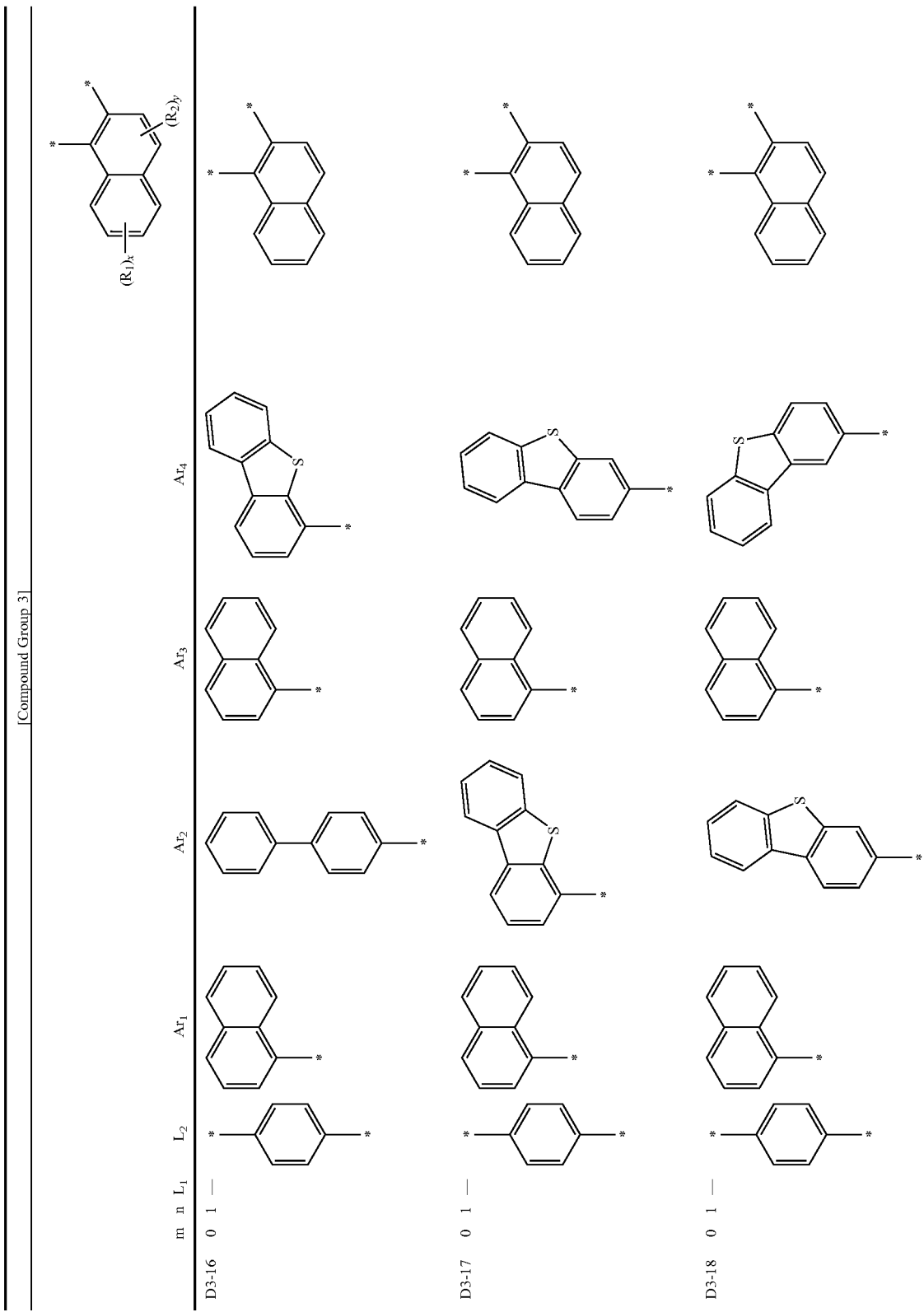

-continued
[Compound Group 3]
| | m | n | L₁ | L₂ | Ar₁ | Ar₂ | Ar₃ | Ar₄ | 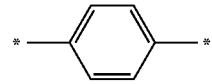 |
|---|---|---|---|---|---|---|---|---|---|
| D3-19 | 0 | 1 | — | 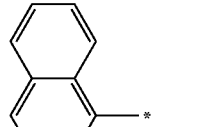 | 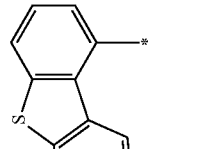 | 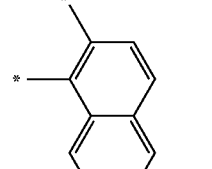 |  |  |  |
| D3-20 | 0 | 1 | — |  | 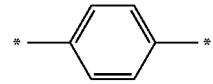 | 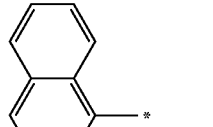 | 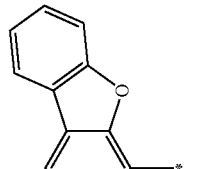 | 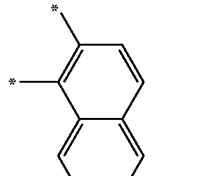 |  |
| D3-21 | 0 | 1 | — |  |  |  | 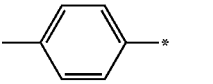 | 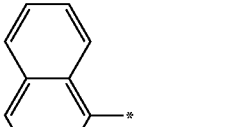 | 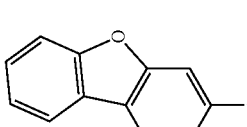 |

-continued
[Compound Group 3]
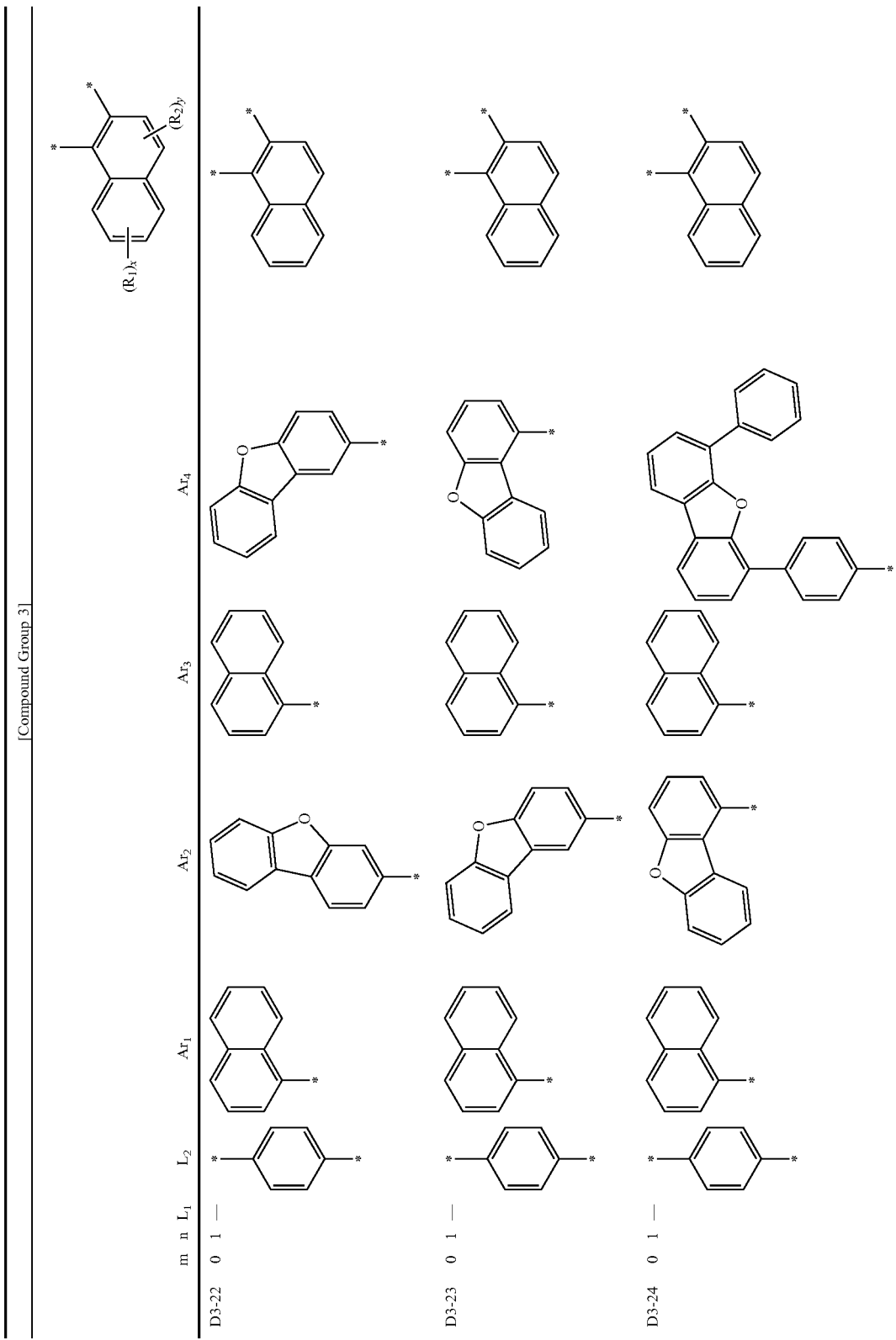

-continued
[Compound Group 3]
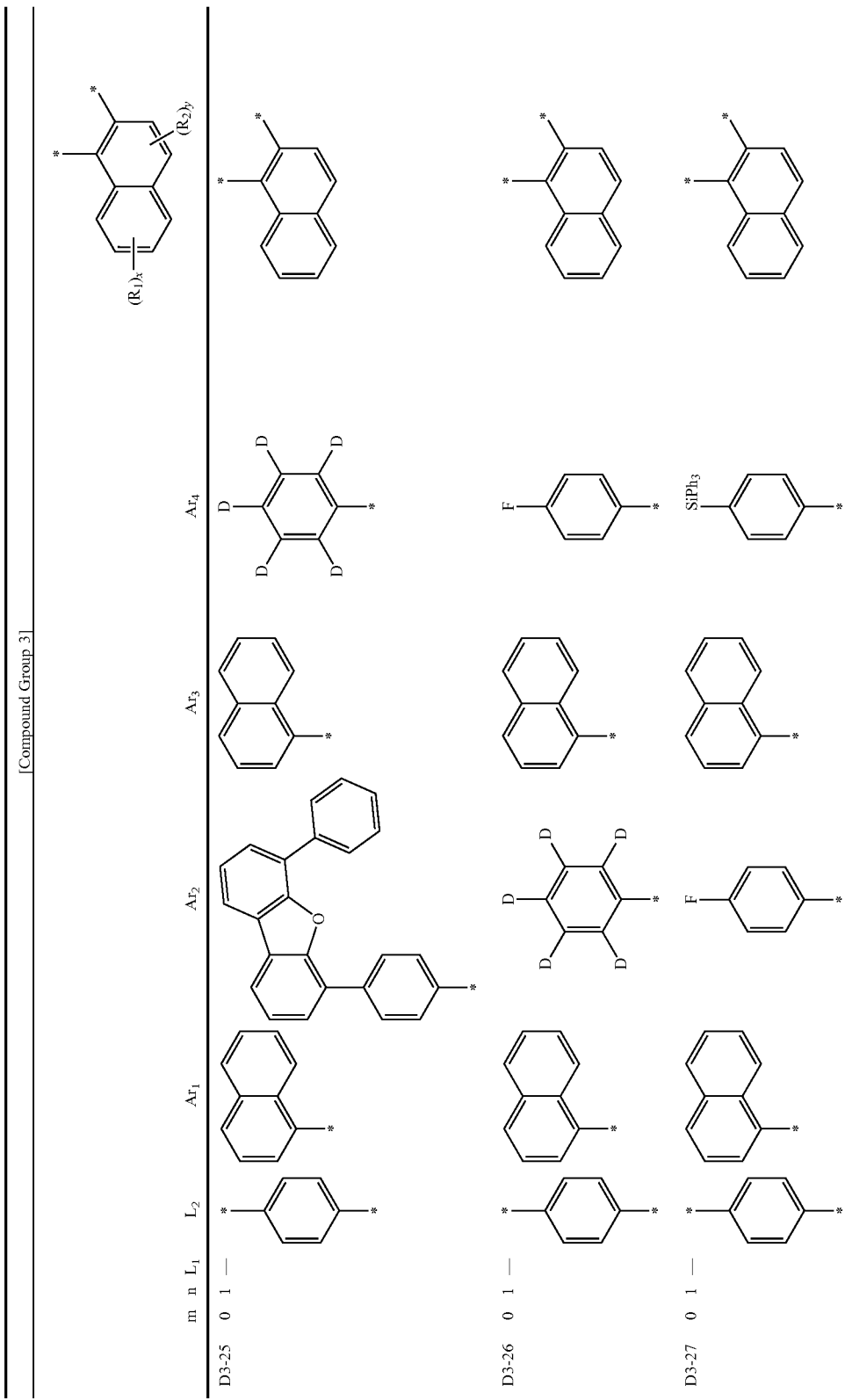

-continued

[Compound Group 3]

| | m | n | L₁ | L₂ | Ar₁ | Ar₂ | Ar₃ | Ar₄ | (R₁)ₓ / (R₂)ᵧ naphthalene |
|---|---|---|---|---|---|---|---|---|---|
| D3-28 | 0 | 1 | — | *—⌬—* | 1-naphthyl | 4-SiPh₃-phenyl | 1-naphthyl | 3-SiPh₃-phenyl | naphthyl |
| D3-29 | 0 | 1 | — | *—⌬—* | 1-naphthyl | 3-SiPh₃-phenyl | 1-naphthyl | 2-SiPh₃-phenyl | naphthyl |
| D3-30 | 0 | 1 | — | *—⌬—* | 1-naphthyl | 2-SiPh₃-phenyl | 1-naphthyl | biphenyl | naphthyl |

-continued
[Compound Group 3]
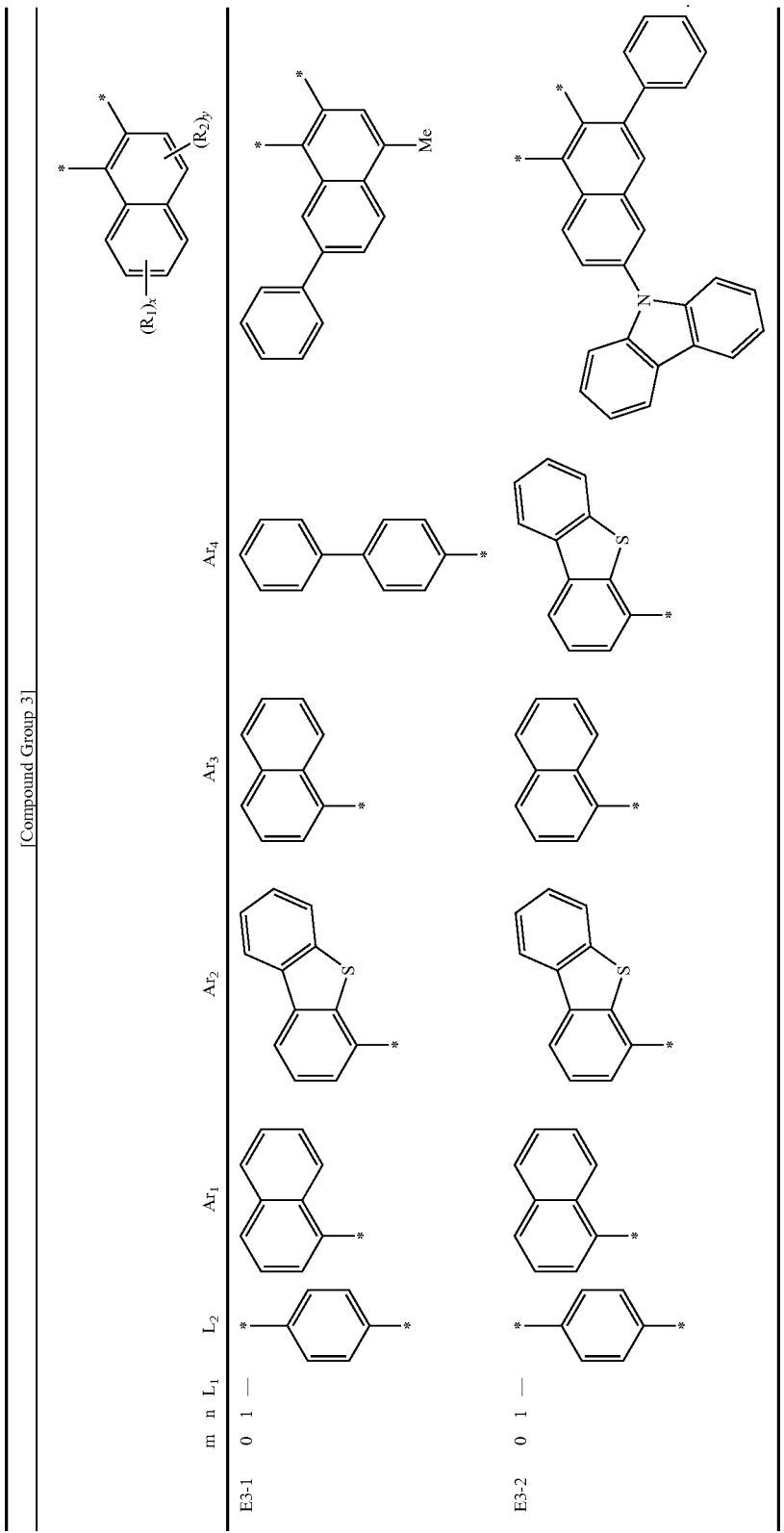

23. The diamine compound of claim 16, wherein the diamine compound represented by Formula 1 is at least one selected among compounds represented in Compound Group 4:

[Compound Group 4]

| | m | n | L$_1$ | L$_2$ | Ar$_1$ | Ar$_2$ |
|---|---|---|---|---|---|---|
| A4-1 | 1 | 1 | | | | |
| A4-2 | 1 | 1 | | | | |
| A4-3 | 1 | 1 | | | | |
| A4-4 | 1 | 1 | | | | |
| A4-5 | 1 | 1 | | | | |
| A4-6 | 1 | 1 | | | | |

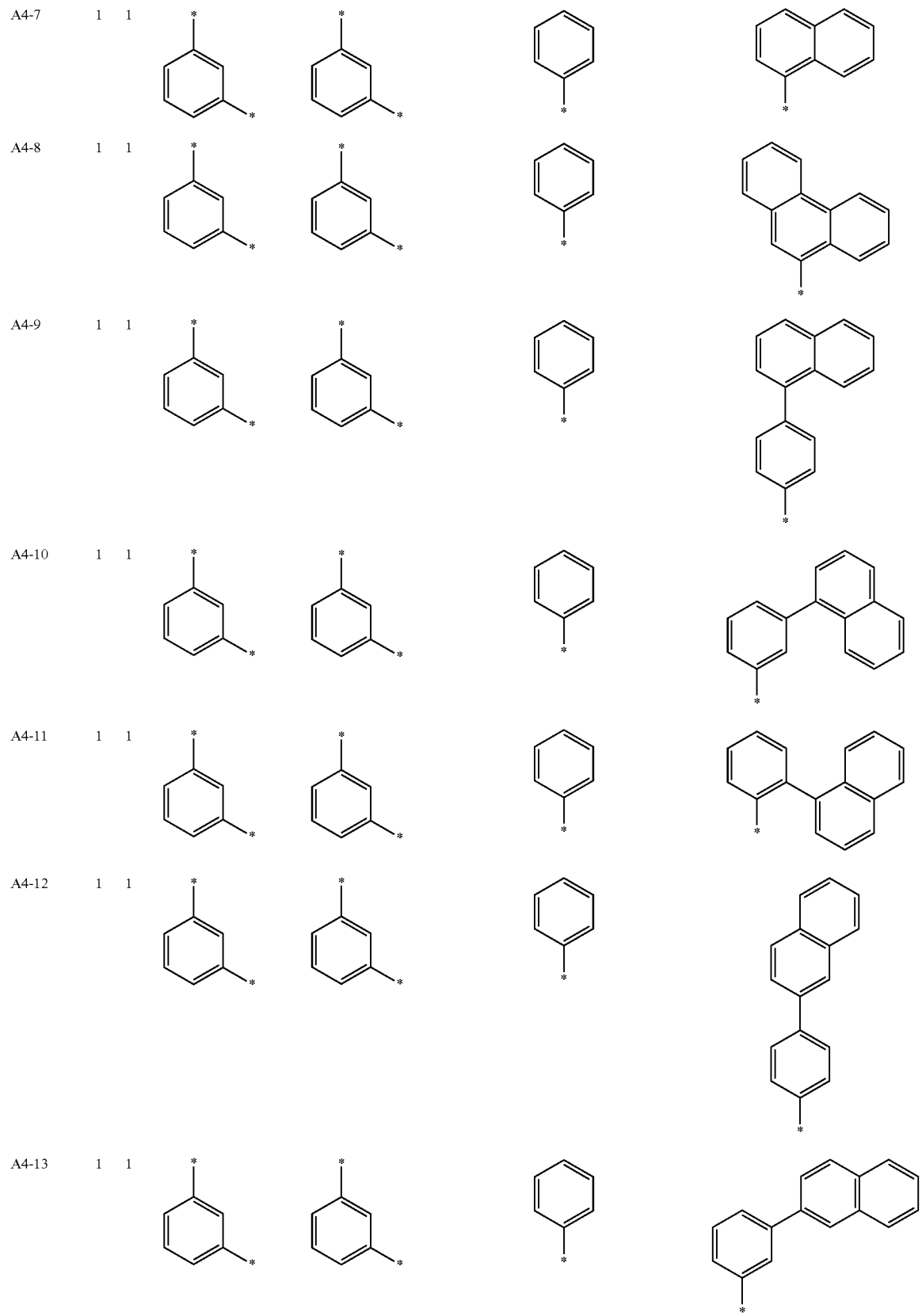

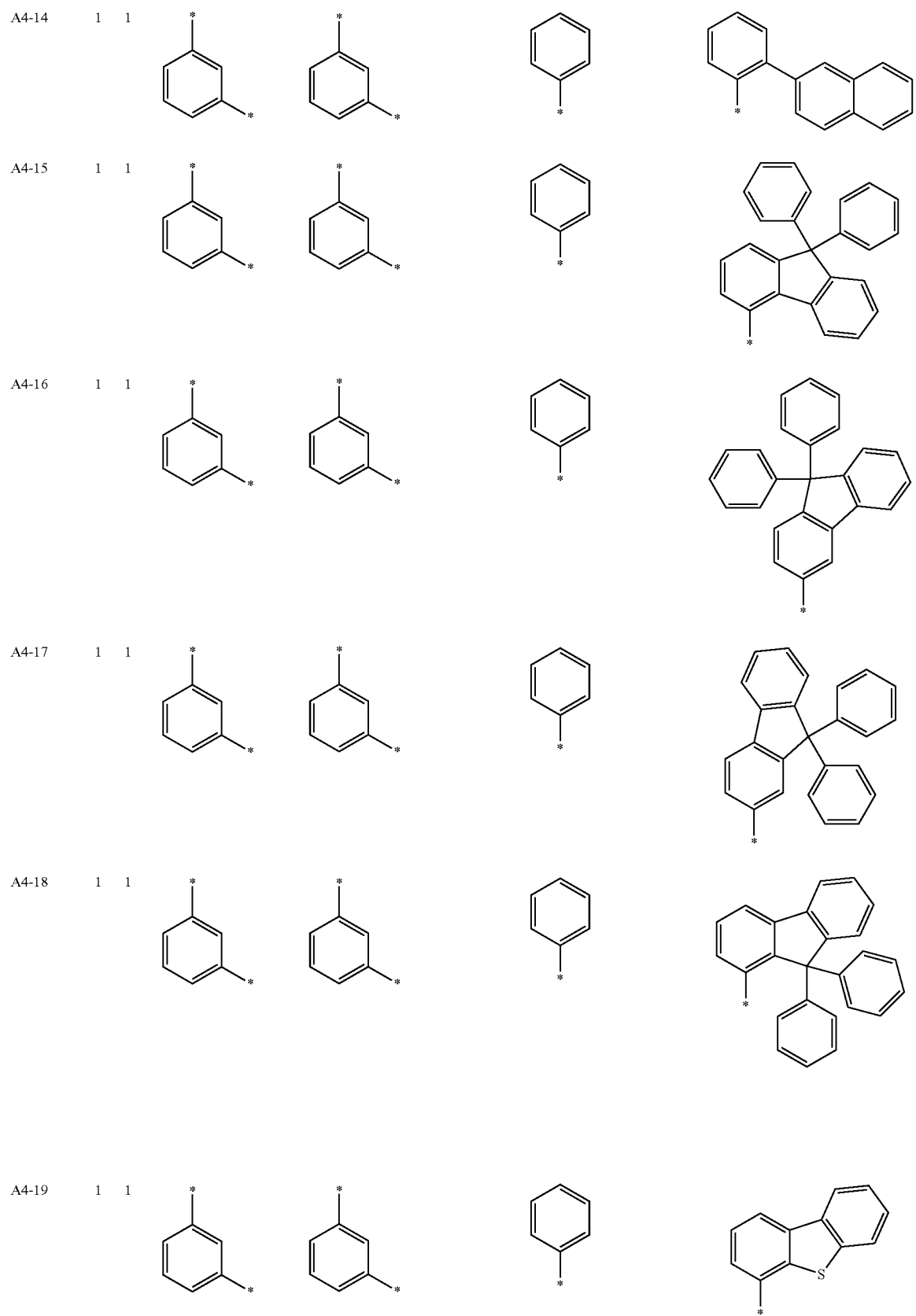

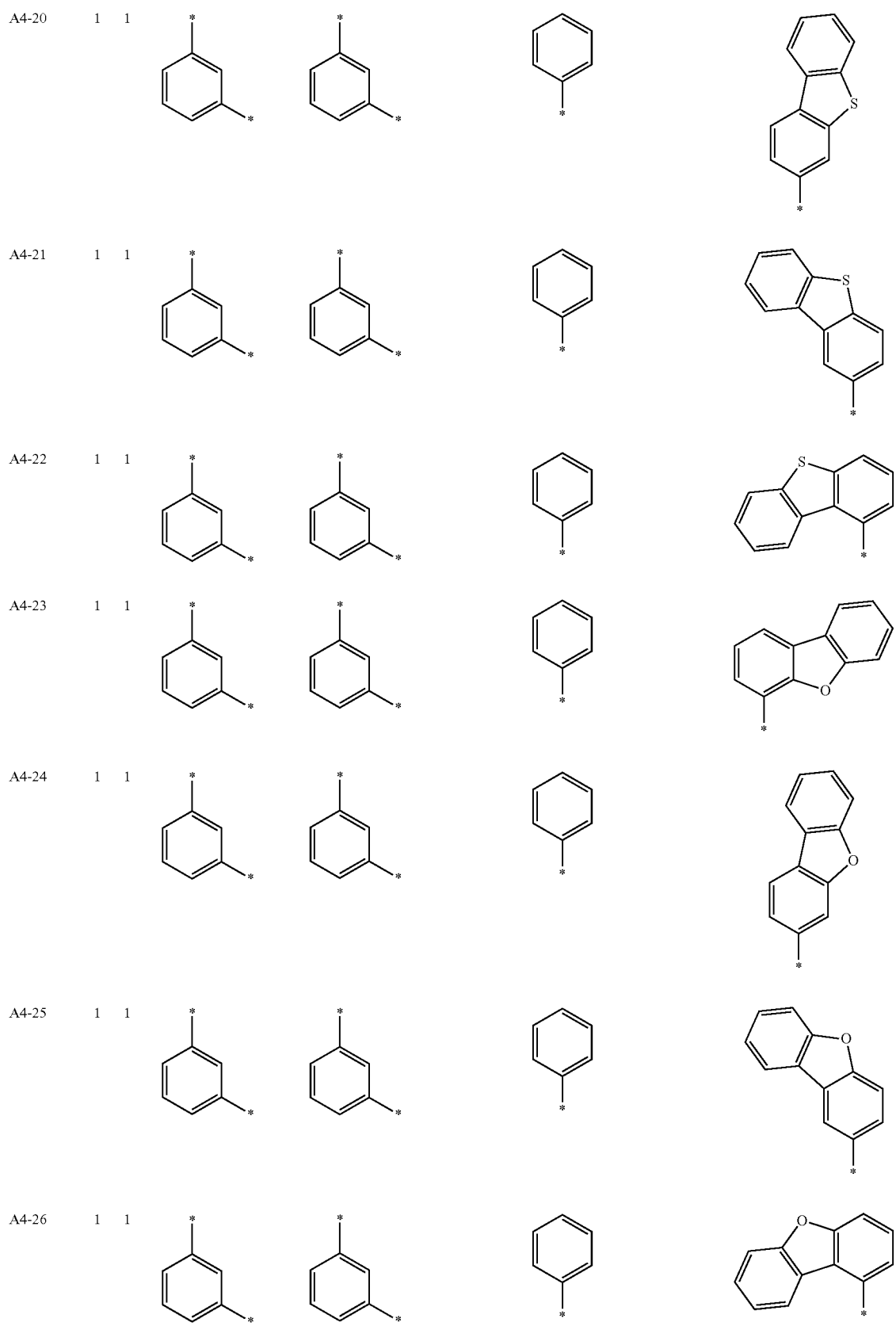

-continued
| | | | | | | |
|---|---|---|---|---|---|---|
| A4-27 | 1 | 1 | 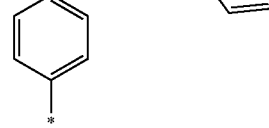 | 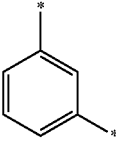 | 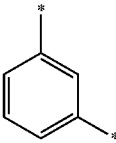 | 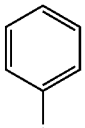 |
| A4-28 | 1 | 1 | 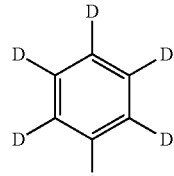 | 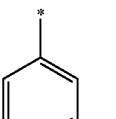 | 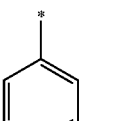 | 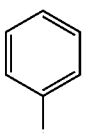 |
| A4-29 | 1 | 1 | 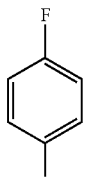 | 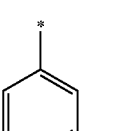 | 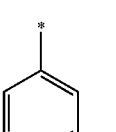 | 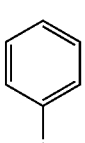 |
| A4-30 | 1 | 1 | 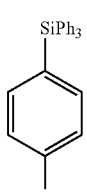 | 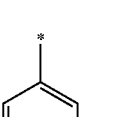 | 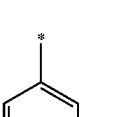 | 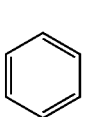 |
| A4-31 | 1 | 1 | 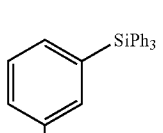 | 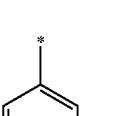 | 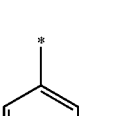 | 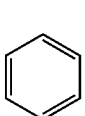 |
| A4-32 | 1 | 1 | 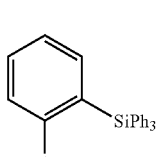 | 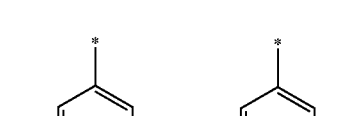 | 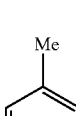 |  |
| A4-33 | 1 | 1 | | | | 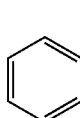 |

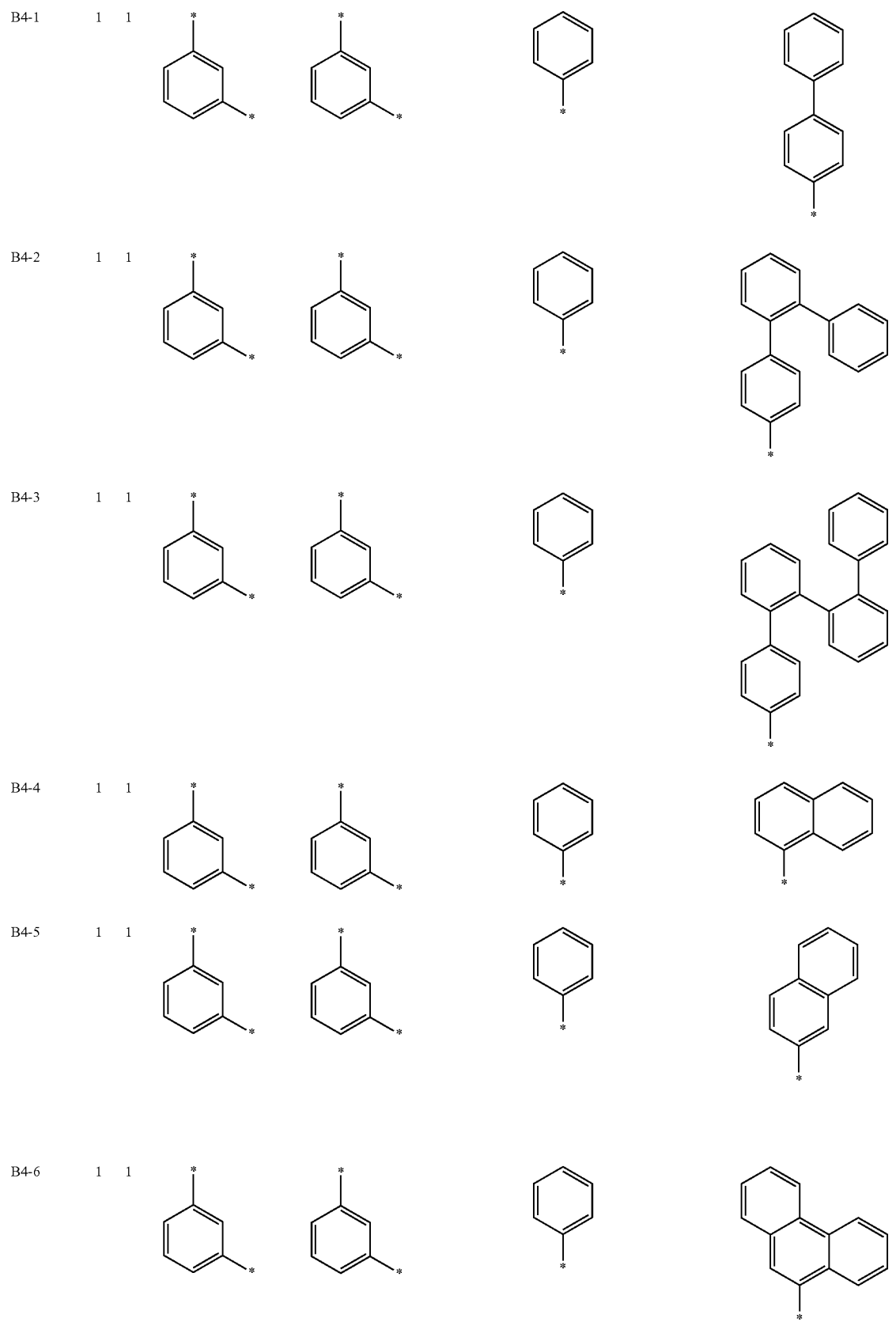

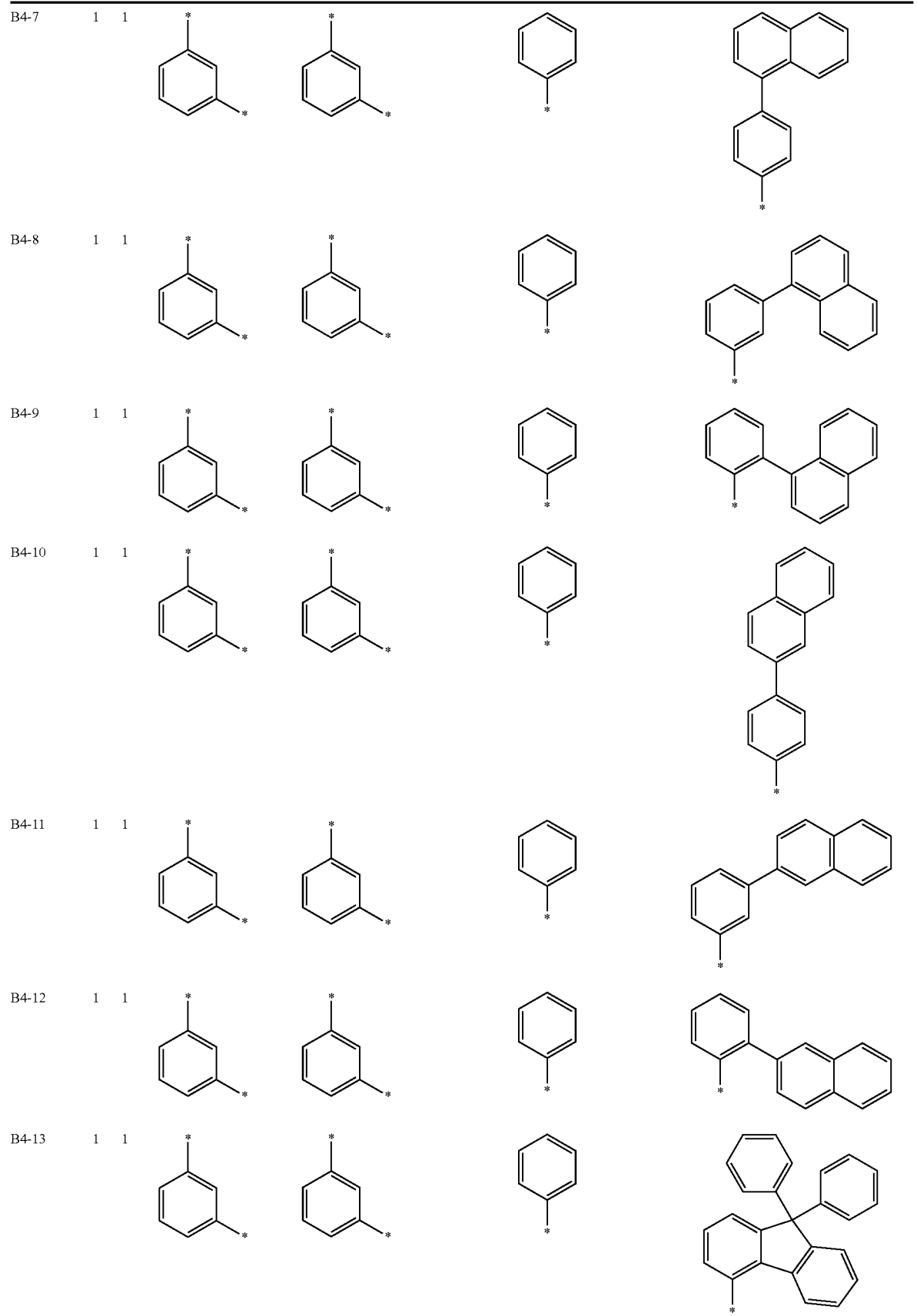

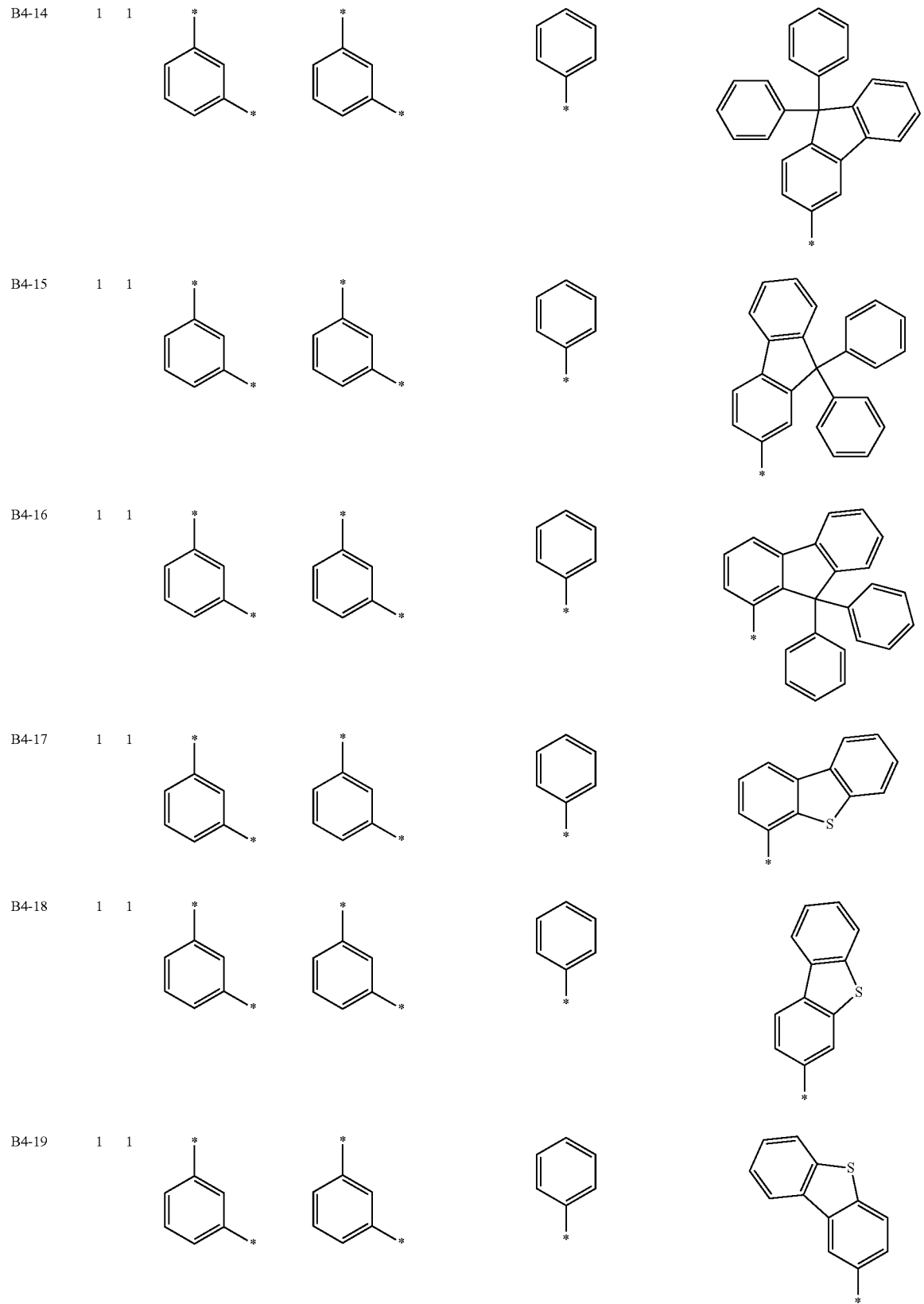

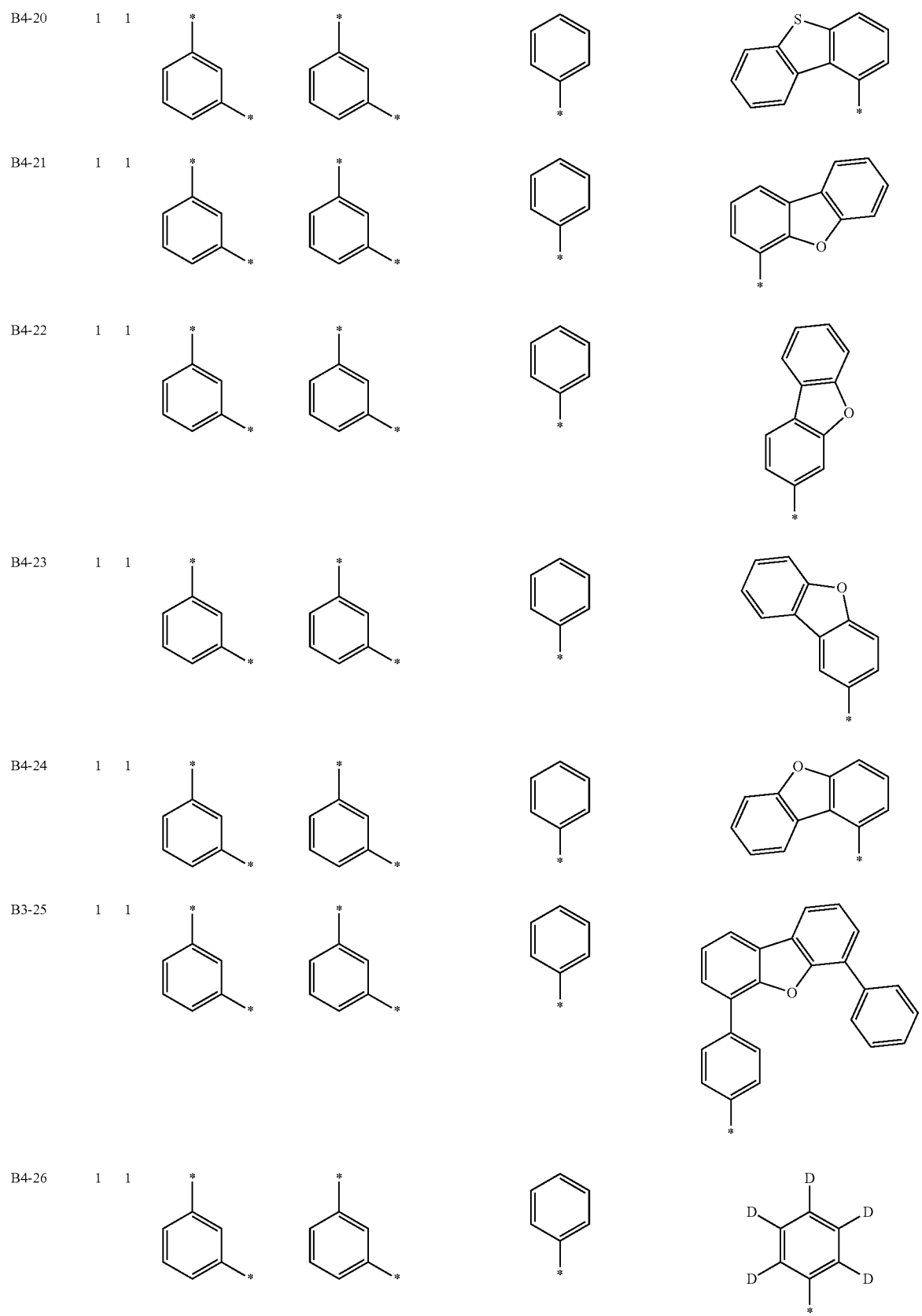

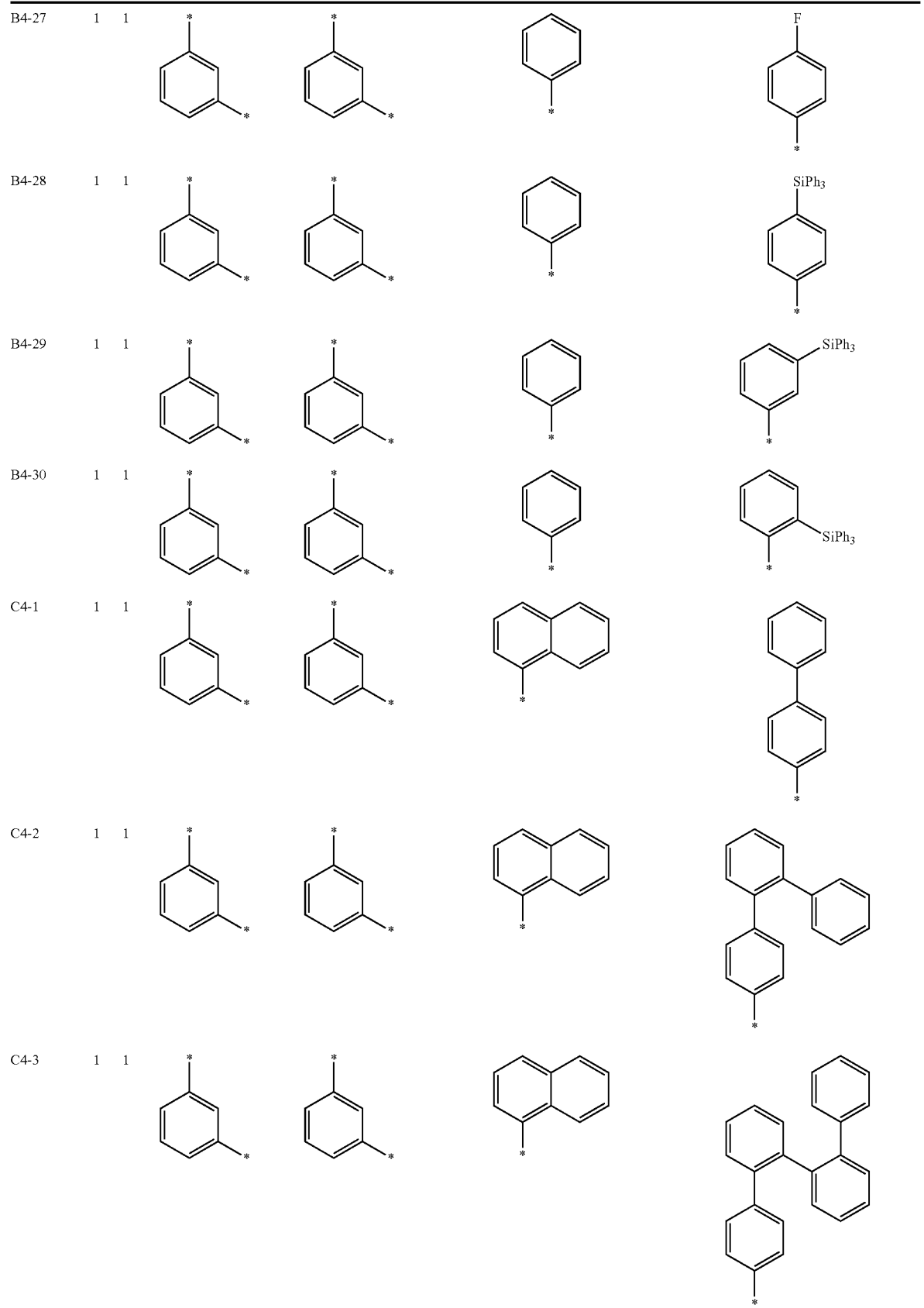

-continued

| | | | | | | |
|---|---|---|---|---|---|---|
| C4-4 | 1 | 1 | (m-phenylene) | (m-phenylene) | 1-naphthyl | 1-naphthyl |
| C4-5 | 1 | 1 | (m-phenylene) | (m-phenylene) | 1-naphthyl | 2-naphthyl |
| C4-6 | 1 | 1 | (m-phenylene) | (m-phenylene) | 1-naphthyl | 9-phenanthryl |
| C4-7 | 1 | 1 | (m-phenylene) | (m-phenylene) | 1-naphthyl | 1-naphthyl-4-phenyl |
| C4-8 | 1 | 1 | (m-phenylene) | (m-phenylene) | 1-naphthyl | 1-(3-phenyl)naphthyl |
| C4-9 | 1 | 1 | (m-phenylene) | (m-phenylene) | 1-naphthyl | 1-(2-naphthyl)naphthyl |
| C4-10 | 1 | 1 | (m-phenylene) | (m-phenylene) | 1-naphthyl | 2-naphthyl-6-phenyl |

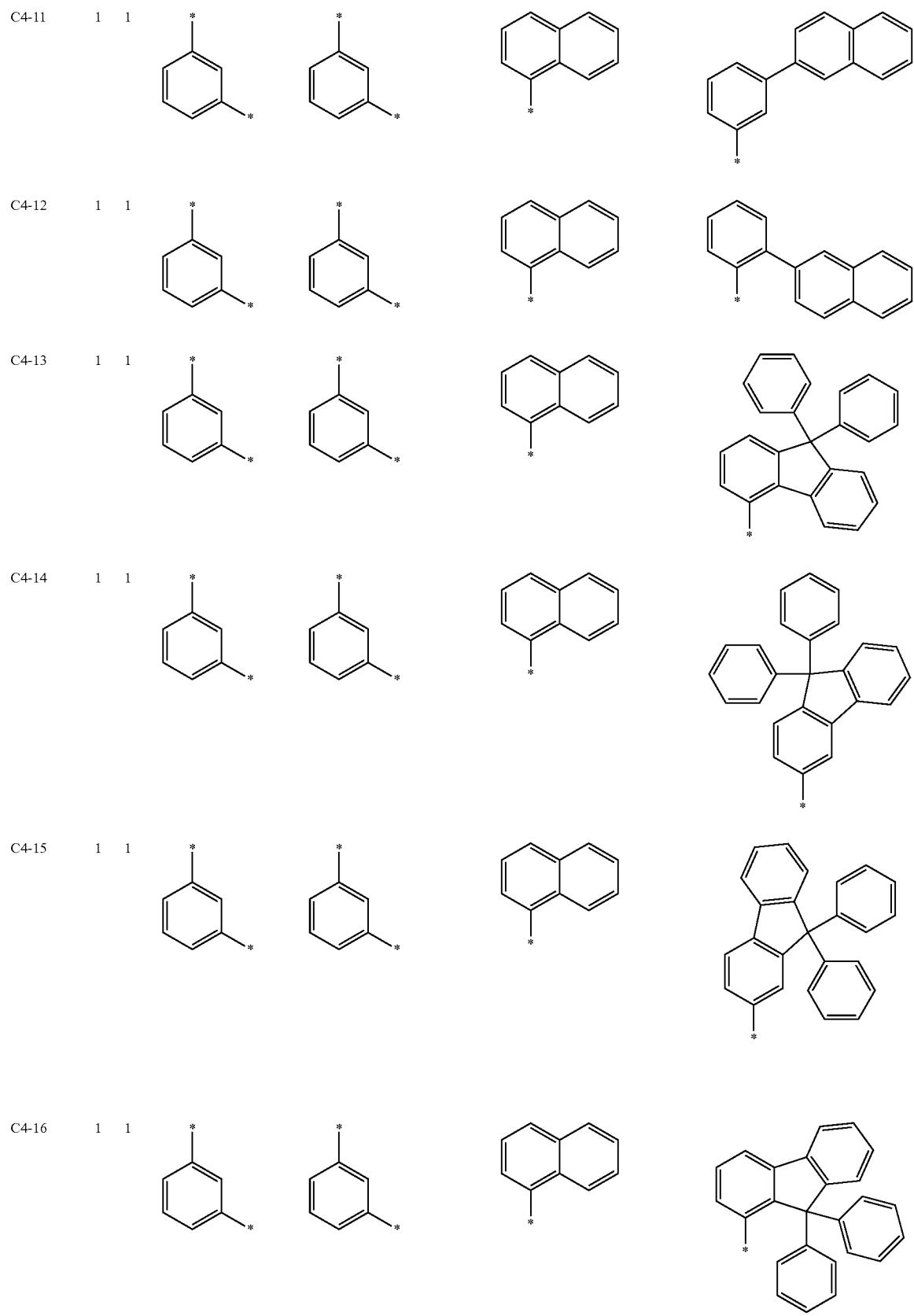

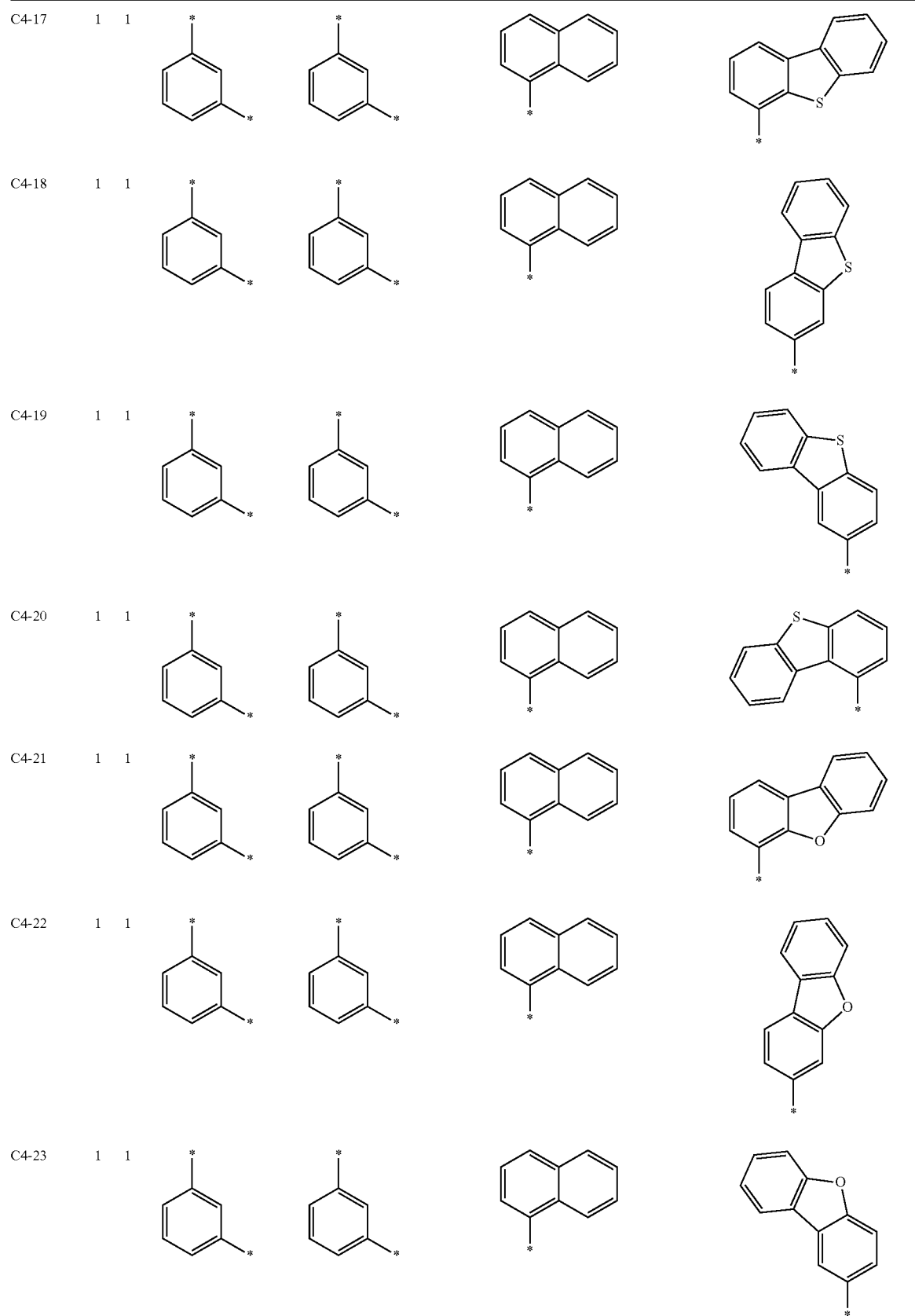

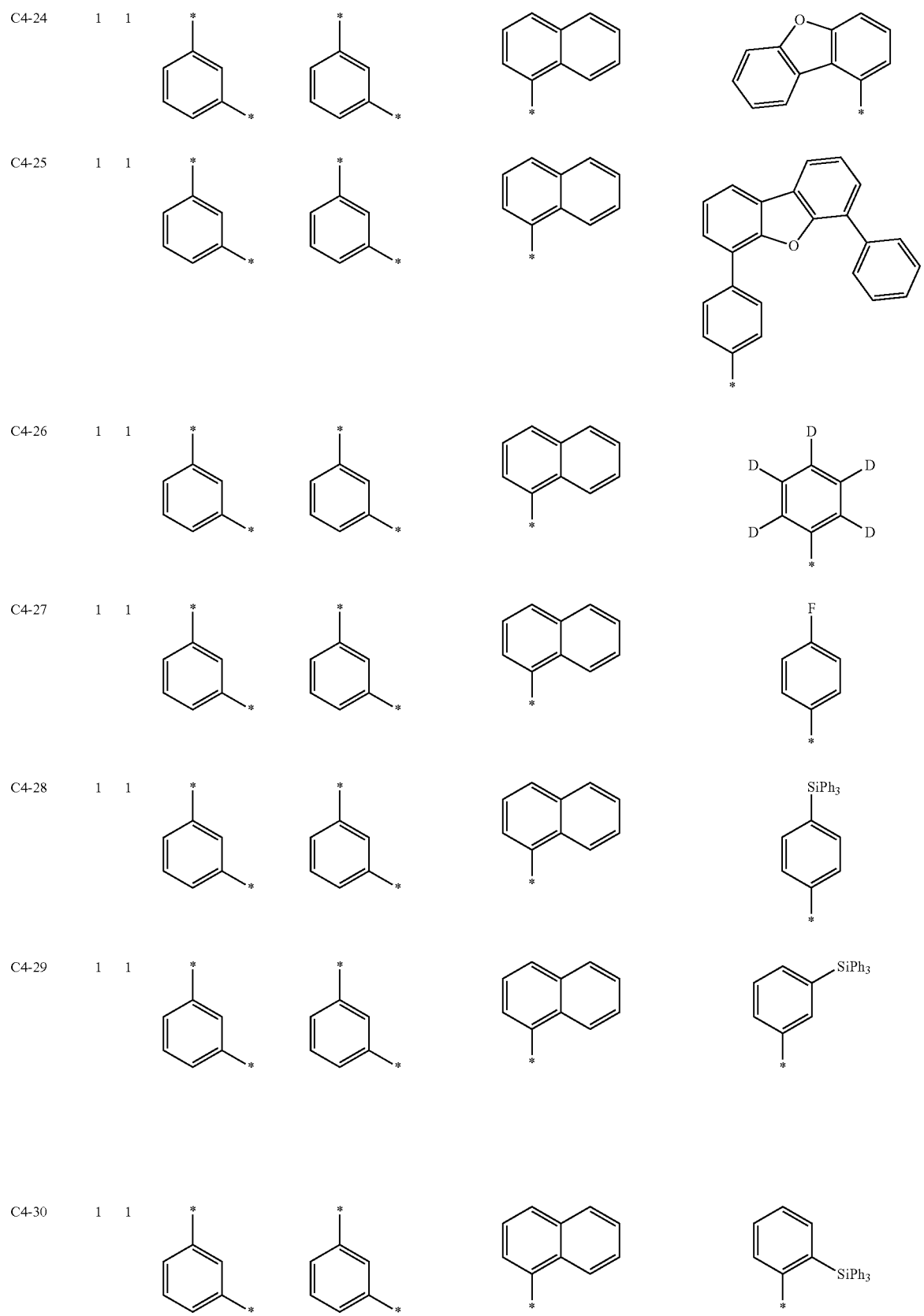

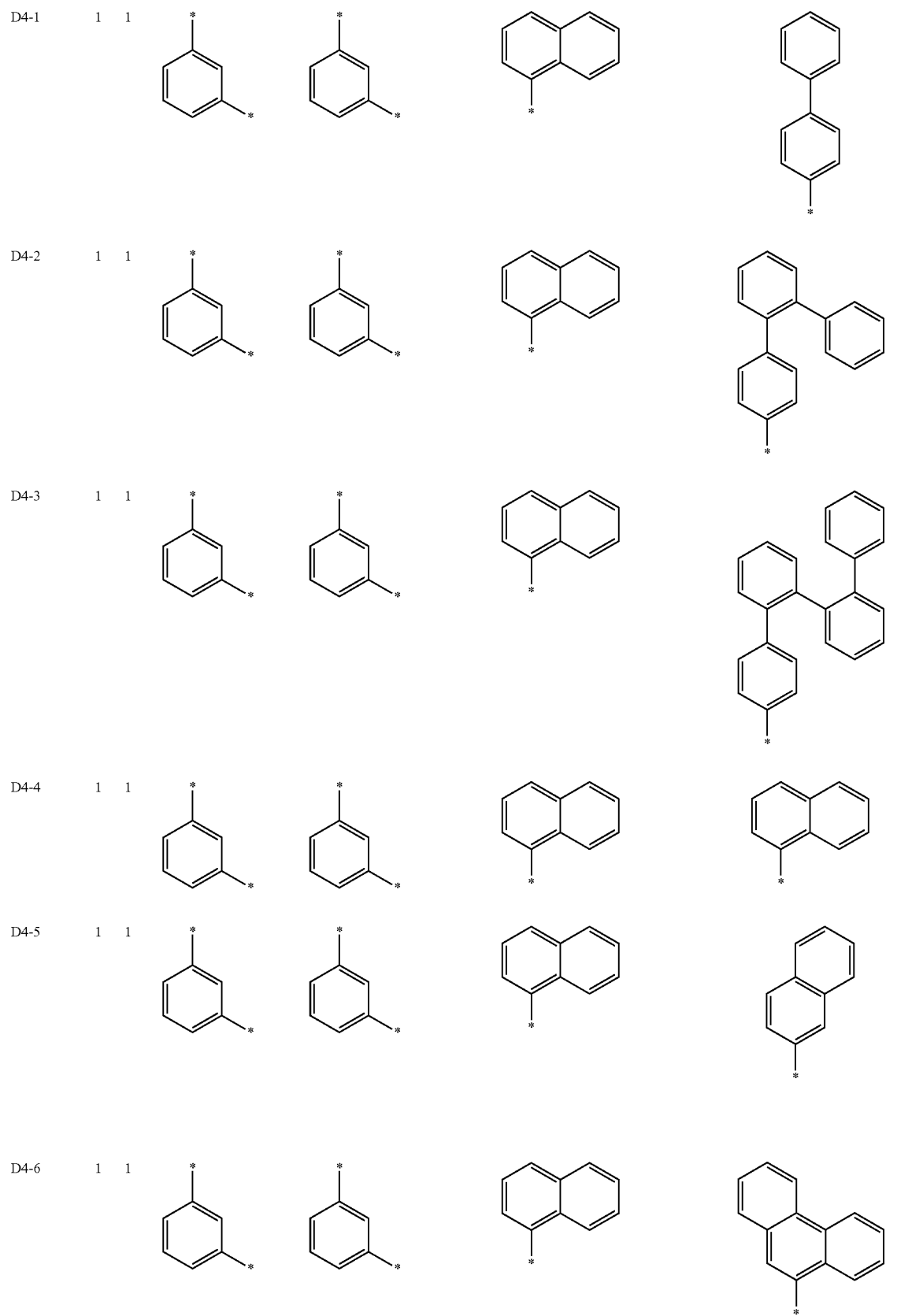

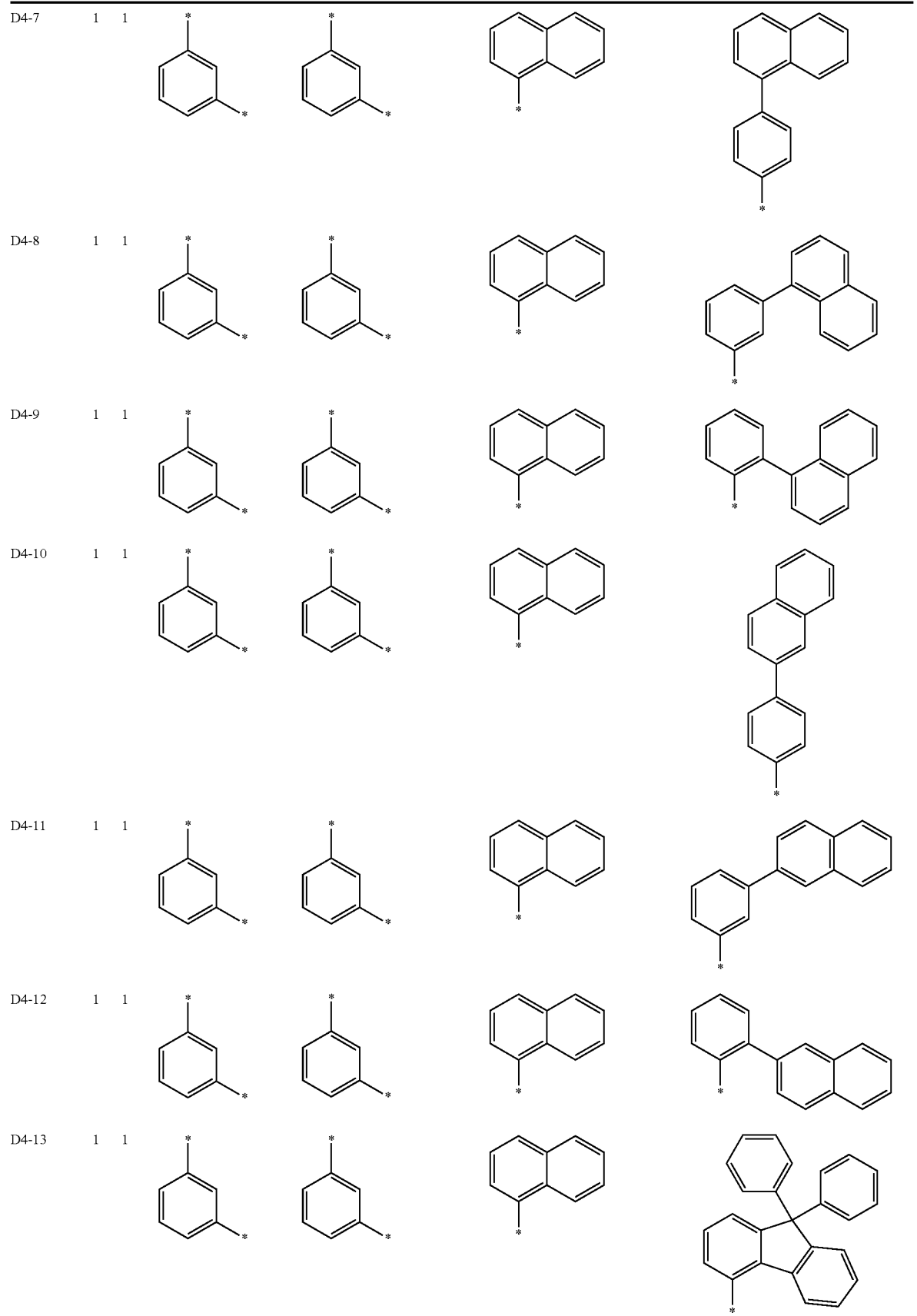

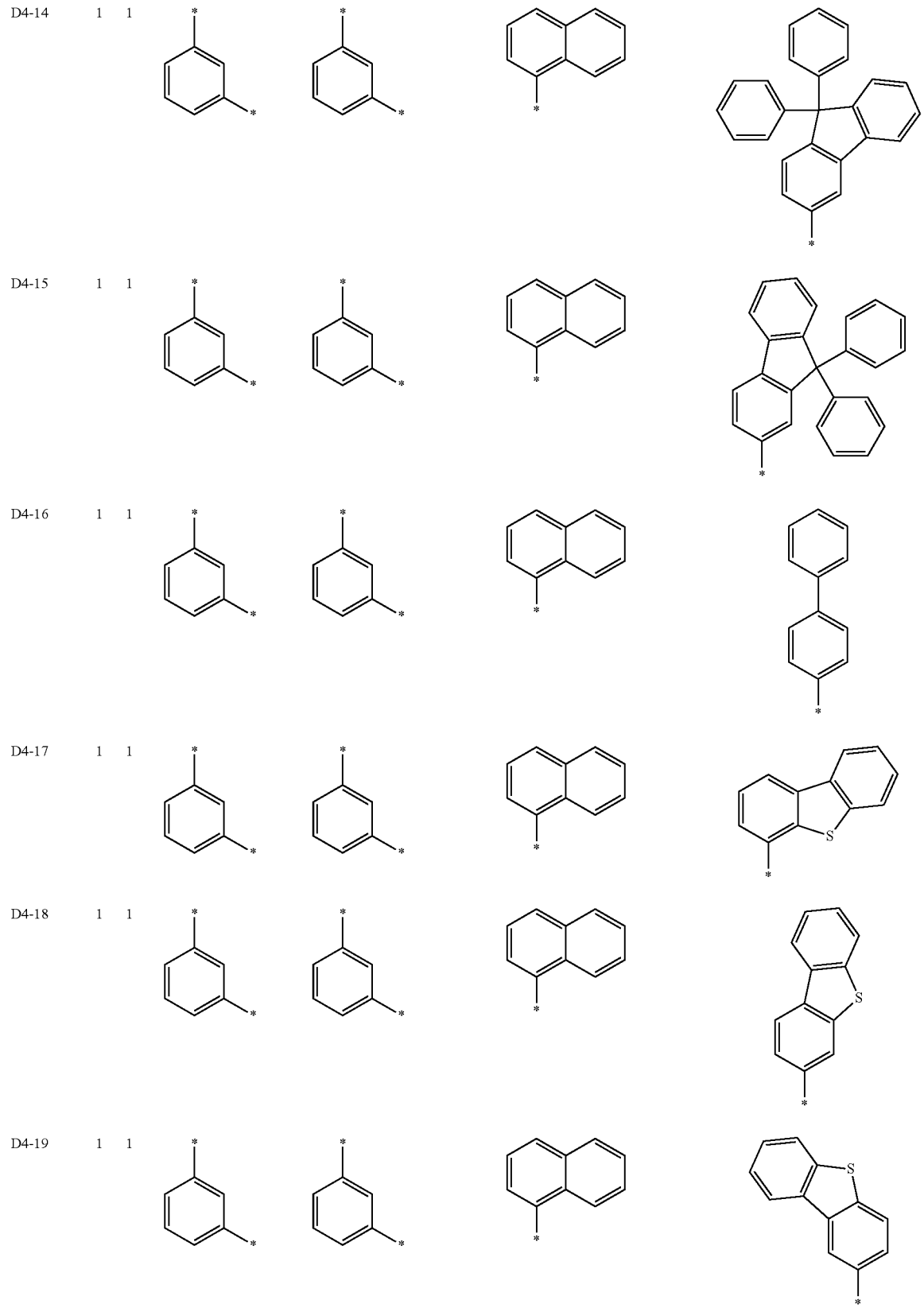

-continued
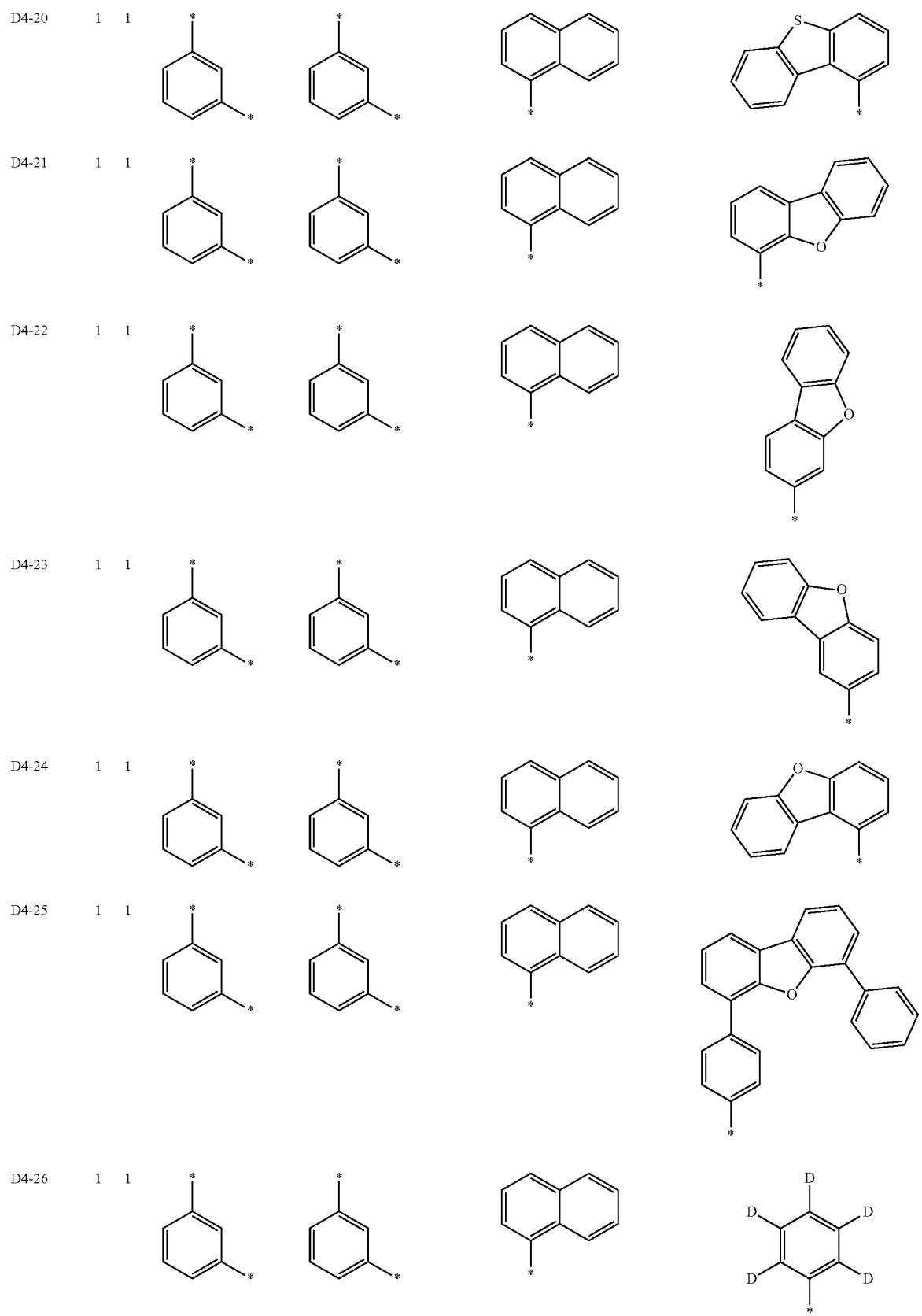

-continued

| ID | | | | | | |
|---|---|---|---|---|---|---|
| D4-27 | 1 | 1 | 1,3-phenylene | 1,3-phenylene | 1-naphthyl | 4-fluorophenyl |
| D4-28 | 1 | 1 | 1,3-phenylene | 1,3-phenylene | 1-naphthyl | 4-(SiPh₃)phenyl |
| D4-29 | 1 | 1 | 1,3-phenylene | 1,3-phenylene | 1-naphthyl | 3-(SiPh₃)phenyl |
| D4-30 | 1 | 1 | 1,3-phenylene | 1,3-phenylene | 1-naphthyl | 2-(SiPh₃)phenyl |
| E4-1 | 1 | 1 | 1,3-phenylene | 1,3-phenylene | 1-naphthyl | dibenzothiophen-4-yl |
| E4-2 | 1 | 1 | 1,3-phenylene | 1,3-phenylene | 1-naphthyl | dibenzothiophen-4-yl |

| | Ar₃ | Ar₄ | |
|---|---|---|---|
| A4-1 | phenyl | phenyl | naphthalene with (R₁)ₓ, (R₂)ᵧ |

-continued
| | | | |
|---|---|---|---|
| A4-2 | 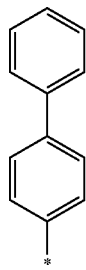 [SMILES: *c1ccc(-c2ccccc2)cc1] | 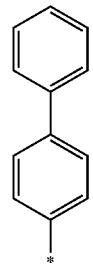 | 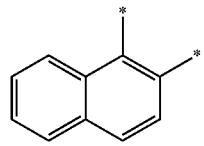 |
| A4-3 | 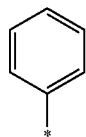 [SMILES: *c1ccccc1] | 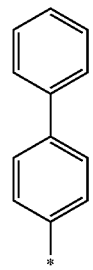 | 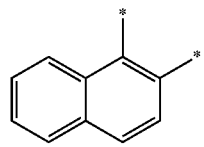 [SMILES: *c1ccc2ccccc2c1*] |
| A4-4 | 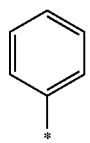 [SMILES: *c1ccccc1] | 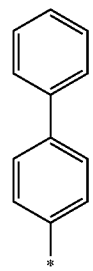 | 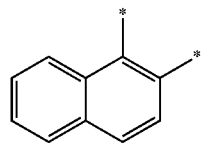 [SMILES: *c1ccc2ccccc2c1*] |
| A4-5 | 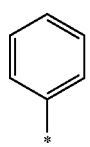 [SMILES: *c1ccccc1] | 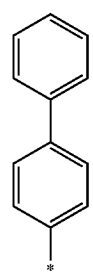 | 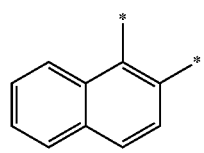 |
| A4-6 | 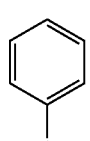 | 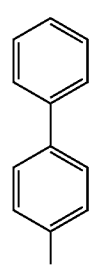 | 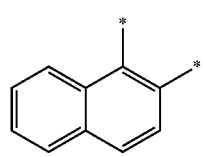 |
| A4-7 | 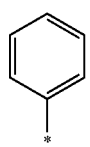 [SMILES: *c1ccccc1] | 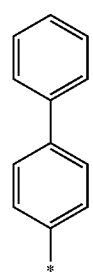 | 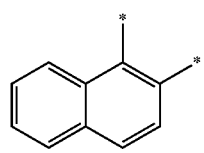 |

1281 1282
-continued
A4-8 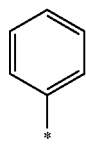 [SMILES: *c1ccccc1] 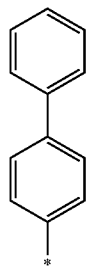 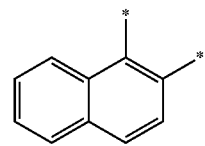
A4-9 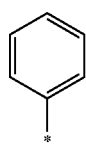 [SMILES: *c1ccccc1] 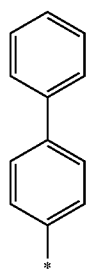 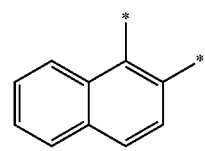 [SMILES: *c1ccc2ccccc2c1*]
A4-10 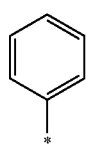 [SMILES: *c1ccccc1] 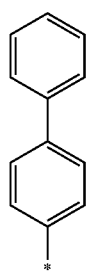 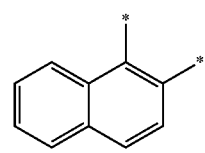
A4-11 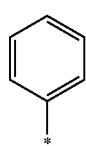 [SMILES: *c1ccccc1] 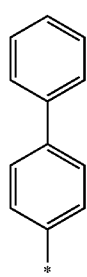 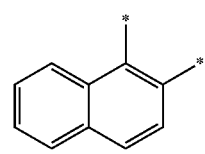
A4-12 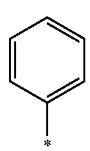 [SMILES: *c1ccccc1] 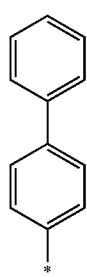 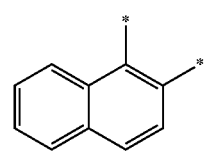

-continued
| | | | |
|---|---|---|---|
| A4-13 | 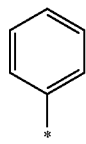 [SMILES: *c1ccccc1] | 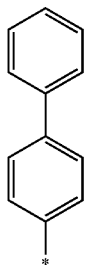 | 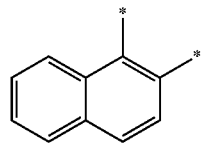 [SMILES: *c1ccc2ccccc2c1*] |
| A4-14 | 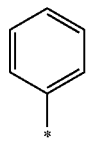 [SMILES: *c1ccccc1] | 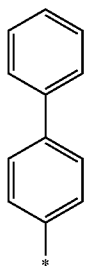 | 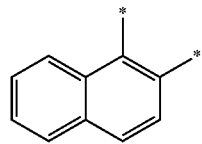 |
| A4-15 | 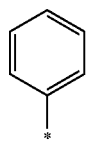 [SMILES: *c1ccccc1] | 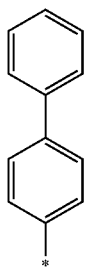 | 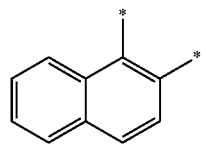 |
| A4-16 | 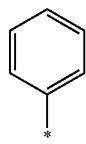 [SMILES: *c1ccccc1] | 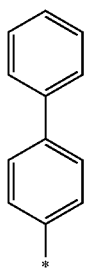 | 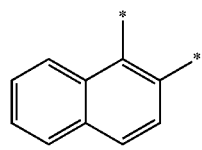 |
| A4-17 | 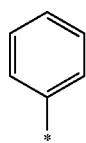 [SMILES: *c1ccccc1] | 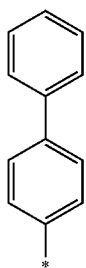 | 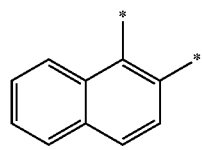 |
| A4-18 | 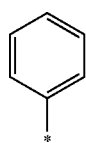 [SMILES: *c1ccccc1] | 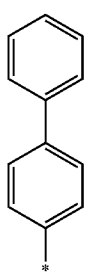 | 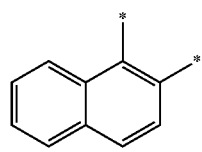 |

| | 1285 | | 1286 |
|---|---|---|---|
| A4-19 | 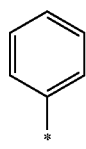 [SMILES: *c1ccccc1] | 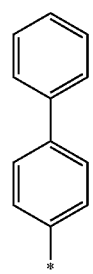 | 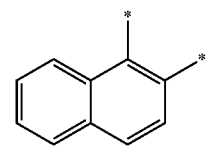 |
| A4-20 | 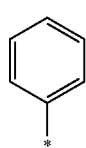 [SMILES: *c1ccccc1] | 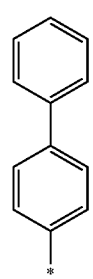 | 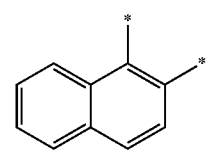 |
| A4-21 | 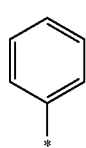 [SMILES: *c1ccccc1] | 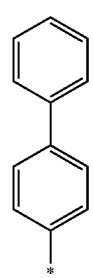 | 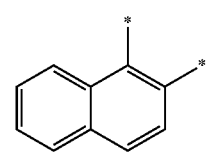 [SMILES: *c1ccc2ccccc2c1*] |
| A4-22 | 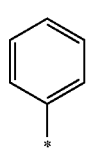 | 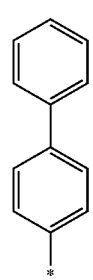 | 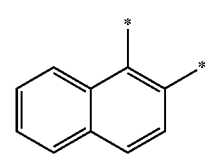 |
| A4-23 | 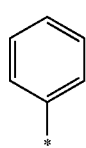 [SMILES: *c1ccccc1] | 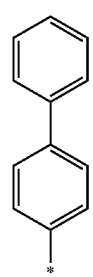 | 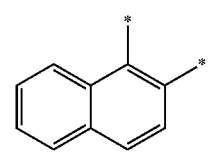 |

-continued
| | 1287 | | 1288 |
|---|---|---|---|
| A4-24 | 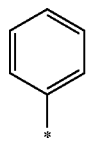 [SMILES: *c1ccccc1] | 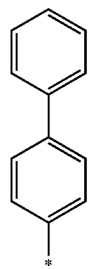 | 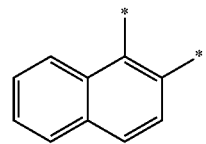 |
| A4-25 | 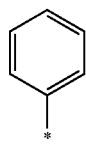 [SMILES: *c1ccccc1] | 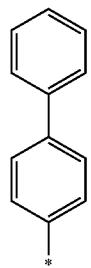 | 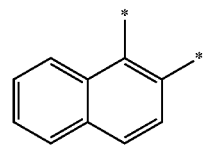 |
| A4-26 | 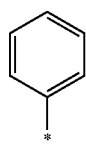 [SMILES: *c1ccccc1] | 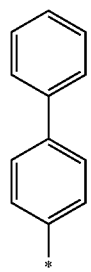 | 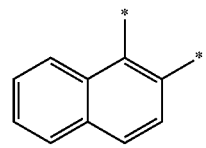 [SMILES: *c1ccc2ccccc2c1*] |
| A4-27 | 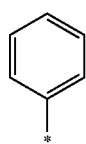 | 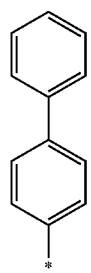 | 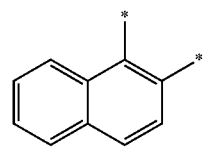 |
| A4-28 | 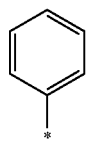 [SMILES: *c1ccccc1] | 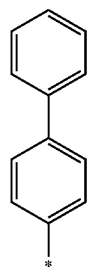 | 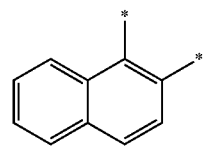 |

-continued
| | | | |
|---|---|---|---|
| A4-29 | 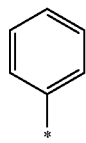 [SMILES: *c1ccccc1] | 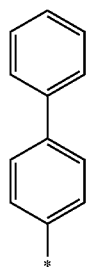 | 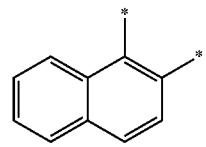 |
| A4-30 | 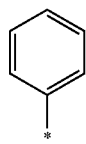 [SMILES: *c1ccccc1] | 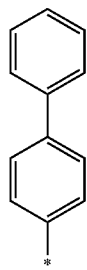 | 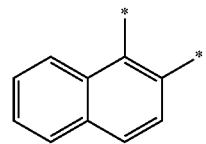 [SMILES: *c1ccc2ccccc2c1*] |
| A4-31 | 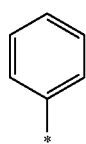 | 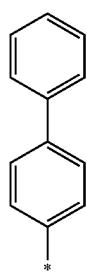 | 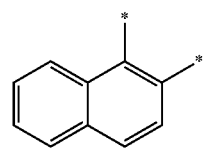 |
| A4-32 | 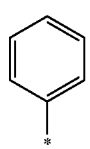 [SMILES: *c1ccccc1] | 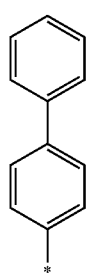 | 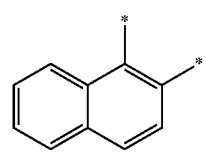 [SMILES: *c1ccc2ccccc2c1*] |
| A4-33 | 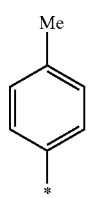 | 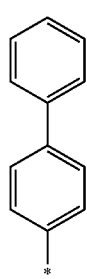 | 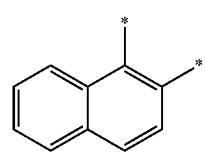 |
| B4-1 | 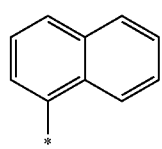 [SMILES: *c1cccc2ccccc12] | 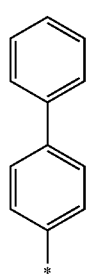 | 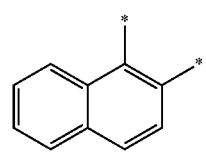 [SMILES: *c1ccc2ccccc2c1*] |

| | 1291 | | 1292 |
|---|---|---|---|
| B4-2 | 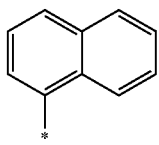 [SMILES: *c1cccc2ccccc12] | 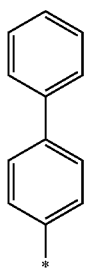 | 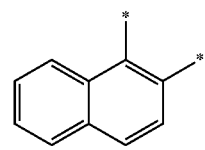 [SMILES: *c1ccc2ccccc2c1*] |
| B4-3 | 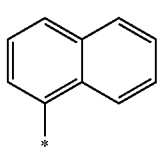 [SMILES: *c1cccc2ccccc12] | 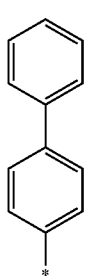 | 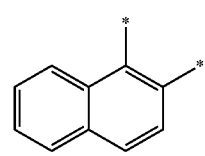 [SMILES: *c1ccc2ccccc2c1*] |
| B4-4 | 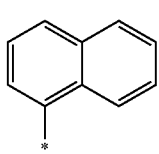 [SMILES: *c1cccc2ccccc12] | 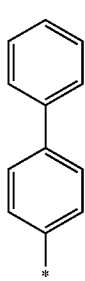 | 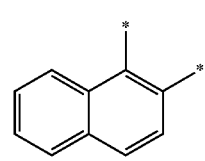 |
| B4-5 | 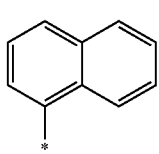 [SMILES: *c1cccc2ccccc12] | 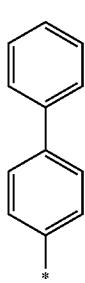 | 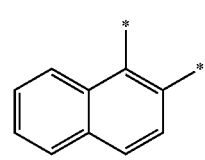 |
| B4-6 | 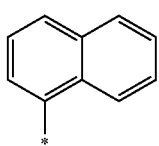 | 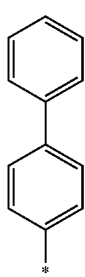 | 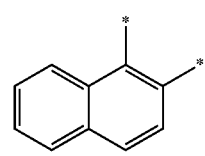 [SMILES: *c1ccc2ccccc2c1*] |

| | | | |
|---|---|---|---|
| B4-7 | 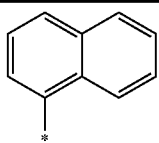 | 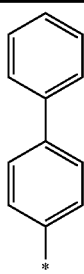 | 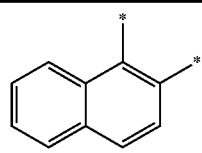 |
| B4-8 | 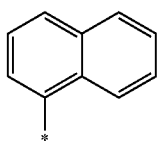 [SMILES: *c1cccc2ccccc12] | 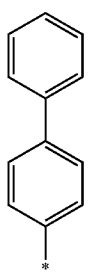 | 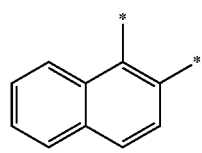 |
| B4-9 | 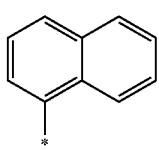 [SMILES: *c1cccc2ccccc12] | 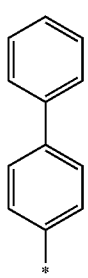 | 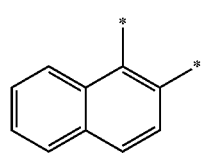 |
| B4-10 | 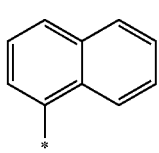 [SMILES: *c1cccc2ccccc12] | 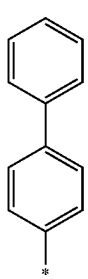 | 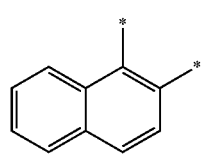 [SMILES: *c1ccc2ccccc2c1*] |
| B4-11 | 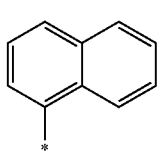 [SMILES: *c1cccc2ccccc12] | 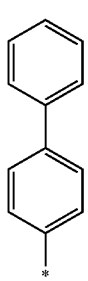 | 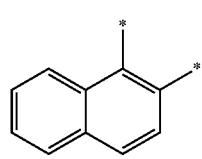 |
| B4-12 | 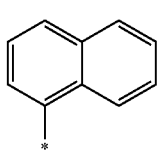 [SMILES: *c1cccc2ccccc12] | 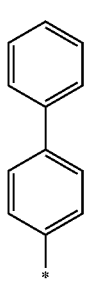 | 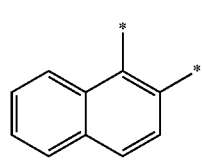 |

-continued
| | | | |
|---|---|---|---|
| B4-13 | 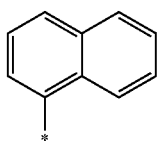 [SMILES: *c1cccc2ccccc12] | 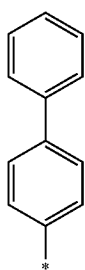 | 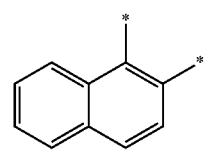 |
| B4-14 | 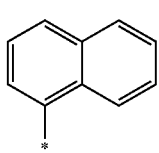 [SMILES: *c1cccc2ccccc12] | 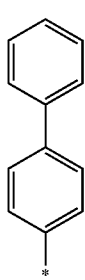 | 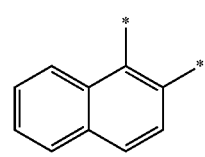 [SMILES: *c1ccc2ccccc2c1*] |
| B4-15 | 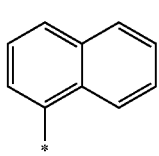 [SMILES: *c1cccc2ccccc12] | 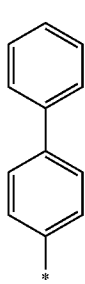 | 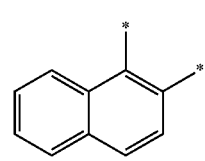 |
| B4-16 | 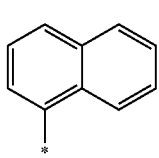 [SMILES: *c1cccc2ccccc12] | 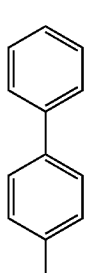 | 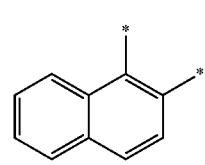 [SMILES: *c1ccc2ccccc2c1*] |
| B4-17 | 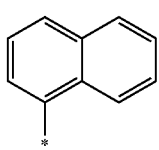 [SMILES: *c1cccc2ccccc12] | 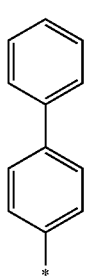 | 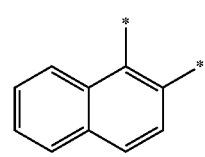 |

-continued
| | | | |
|---|---|---|---|
| B4-18 | 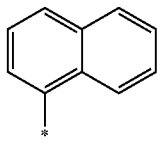 [SMILES: *c1cccc2ccccc12] | 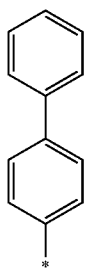 | 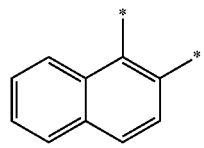 |
| B4-19 | 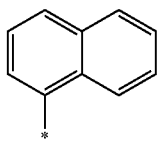 [SMILES: *c1cccc2ccccc12] | 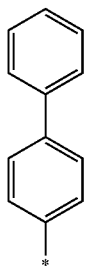 | 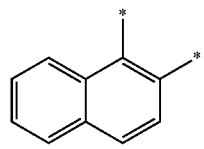 [SMILES: *c1ccc2ccccc2c1*] |
| B4-20 | 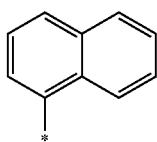 [SMILES: *c1cccc2ccccc12] | 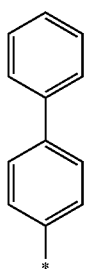 | 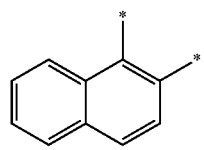 |
| B4-21 | 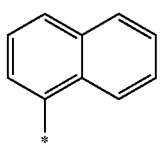 [SMILES: *c1cccc2ccccc12] | 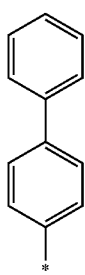 | 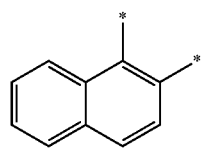 [SMILES: *c1ccc2ccccc2c1*] |
| B4-22 | 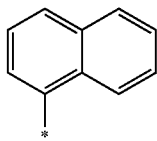 [SMILES: *c1cccc2ccccc12] | 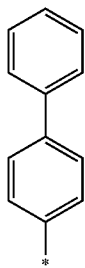 | 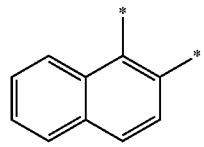 |

US 11,968,887 B2
1299  1300
-continued
B4-23 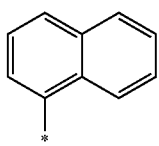 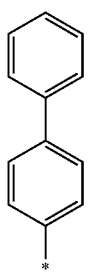 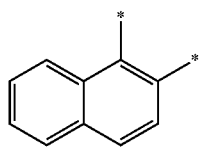
B4-24 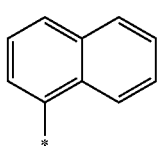 [SMILES: *c1cccc2ccccc12] 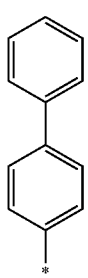 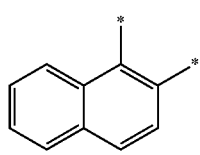
B3-25 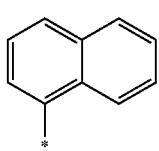 [SMILES: *c1cccc2ccccc12] 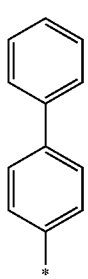 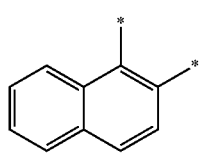
B4-26 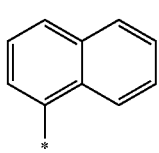 [SMILES: *c1cccc2ccccc12] 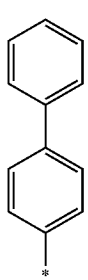 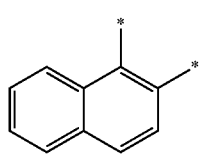 [SMILES: *c1ccc2ccccc2c1*]
B4-27 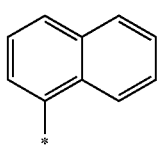 [SMILES: *c1cccc2ccccc12] 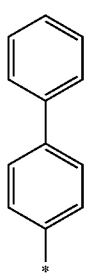 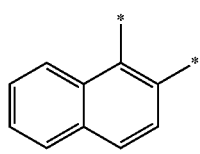

-continued
| | 1301 | | 1302 |
|---|---|---|---|
| B4-28 | 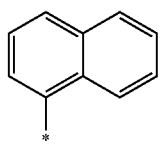 [SMILES: *c1cccc2ccccc12] | 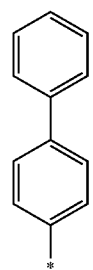 | 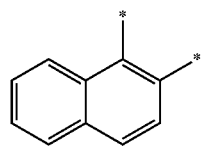 |
| B4-29 | 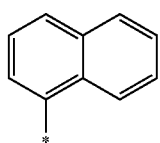 [SMILES: *c1cccc2ccccc12] | 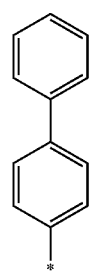 | 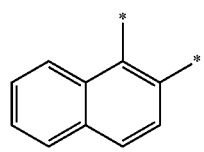 |
| B4-30 | 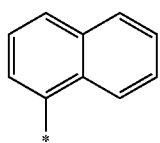 [SMILES: *c1cccc2ccccc12] | 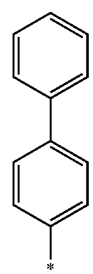 | 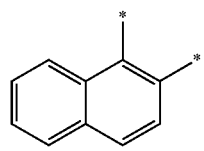 [SMILES: *c1ccc2ccccc2c1*] |
| C4-1 | 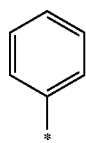 [SMILES: *c1ccccc1] | 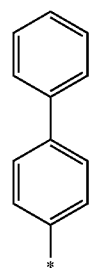 | 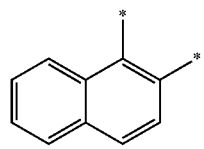 |
| C4-2 | 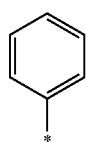 [SMILES: *c1ccccc1] | 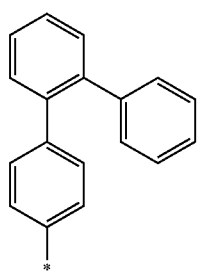 [SMILES: *c1ccc(-c2ccccc2-c2ccccc2)cc1] | 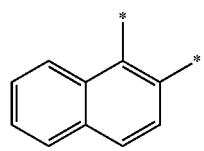 [SMILES: *c1ccc2ccccc2c1*] |

-continued
| | 1303 | | 1304 |
|---|---|---|---|
| C4-3 | 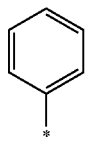 [SMILES: *c1ccccc1] | 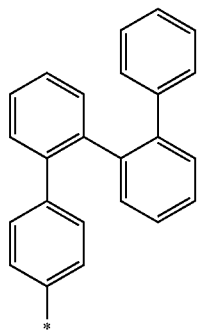 [SMILES: *c1ccc(-c2ccccc2-c2ccccc2-c2ccccc2)cc1] | 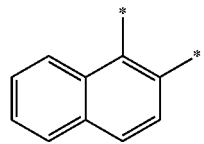 [SMILES: *c1ccc2ccccc2c1*] |
| C4-4 | 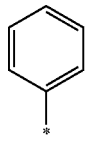 [SMILES: *c1ccccc1] | 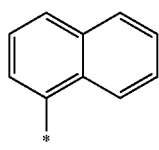 [SMILES: *c1cccc2ccccc12] | 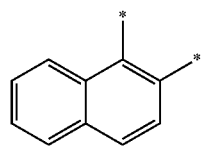 |
| C4-5 | 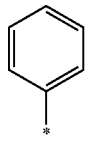 [SMILES: *c1ccccc1] | 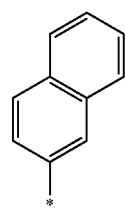 [SMILES: *c1ccc2ccccc2c1] | 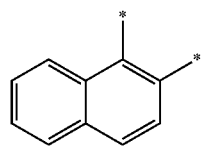 |
| C4-6 | 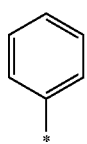 | 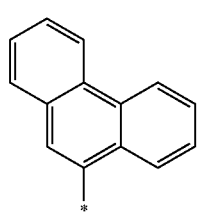 [SMILES: *c1cc2ccccc2c2ccccc12] | 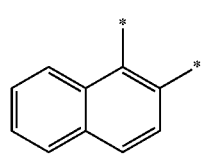 [SMILES: *c1ccc2ccccc2c1*] |
| C4-7 | 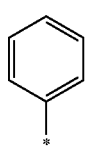 [SMILES: *c1ccccc1] | 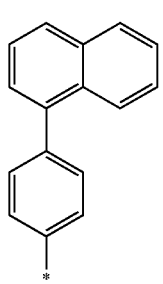 [SMILES: *c1ccc(-c2cccc3ccccc23)cc1] | 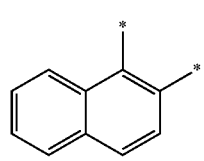 |
| C4-8 | 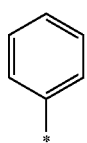 [SMILES: *c1ccccc1] | 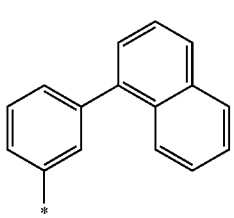 [SMILES: *c1cccc(-c2cccc3ccccc23)c1] | 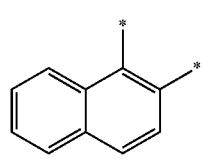 |
| C4-9 | 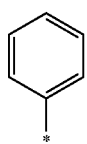 [SMILES: *c1ccccc1] | 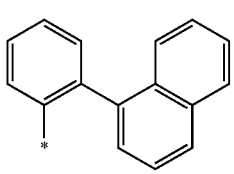 | 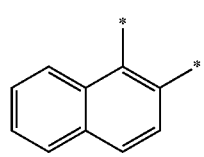 |

-continued
| | 1305 | | 1306 |
|---|---|---|---|
| C4-10 | 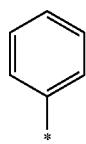 [SMILES: *c1ccccc1] | 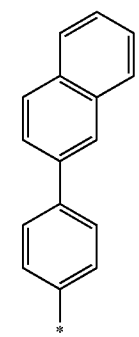 [SMILES: *c1ccc(-c2ccc3ccccc3c2)cc1] | 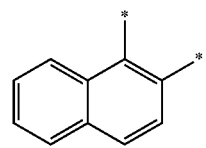 |
| C4-11 | 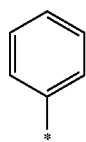 [SMILES: *c1ccccc1] | 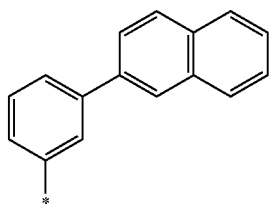 [SMILES: *c1cccc(-c2ccc3ccccc3c2)c1] | 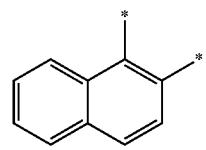 |
| C4-12 | 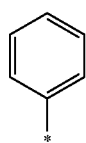 [SMILES: *c1ccccc1] | 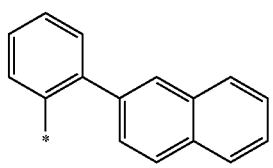 | 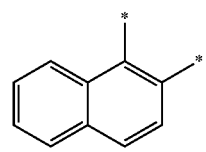 |
| C4-13 | 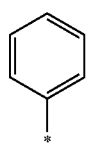 [SMILES: *c1ccccc1] | 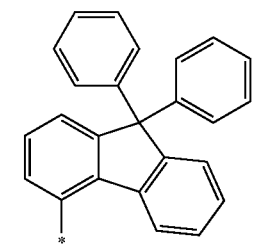 [SMILES: *c1cccc2c1-c1ccccc1C2(c1ccccc1)c1ccccc1] | 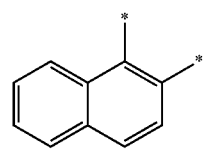 |
| C4-14 | 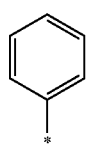 [SMILES: *c1ccccc1] | 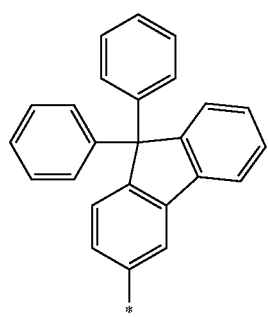 [SMILES: *c1ccc2c(c1)-c1ccccc1C2(c1ccccc1)c1ccccc1] | 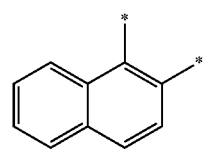 |
| C4-15 | 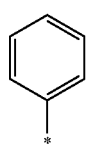 [SMILES: *c1ccccc1] | 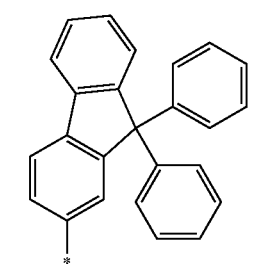 [SMILES: *c1ccc2c(c1)C(c1ccccc1)(c1ccccc1)c1ccccc1-2] | 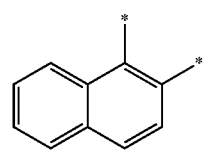 |

-continued
| | 1307 | | | 1308 |
|---|---|---|---|---|
| C4-16 | 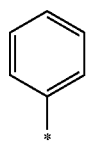 [SMILES: *c1ccccc1] | 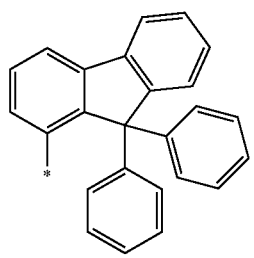 [SMILES: *c1cccc2c1C(c1ccccc1)(c1ccccc1)c1ccccc1-2] | | 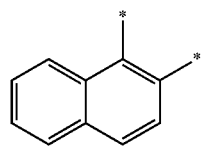 |
| C4-17 | 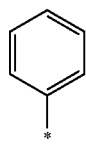 [SMILES: *c1ccccc1] | 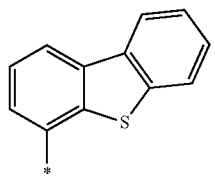 | | 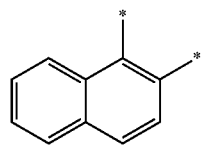 |
| C4-18 | 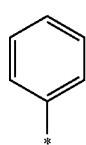 [SMILES: *c1ccccc1] | 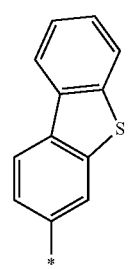 [SMILES: *c1ccc2c(c1)sc1ccccc12] | | 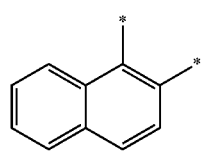 |
| C4-19 | 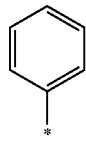 [SMILES: *c1ccccc1] | 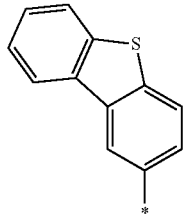 | | 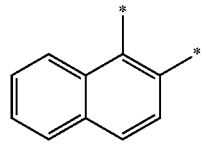 |
| C4-20 | 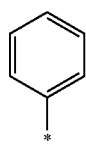 [SMILES: *c1ccccc1] | 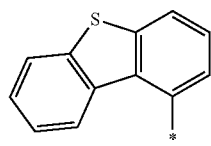 | | 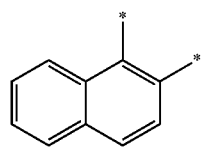 |
| C4-21 | 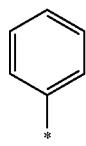 [SMILES: *c1ccccc1] | 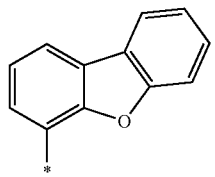 | | 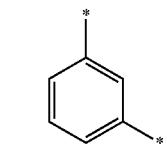 [SMILES: *c1cccc(*)c1] |
| C4-22 | 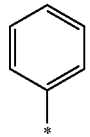 [SMILES: *c1ccccc1] | 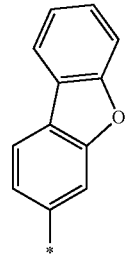 [SMILES: *c1ccc2c(c1)oc1ccccc12] | | 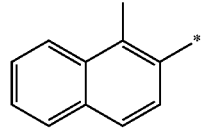 |

-continued
| | 1309 | | 1310 |
|---|---|---|---|
| C4-23 | 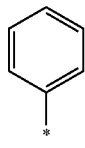 [SMILES: *c1ccccc1] | 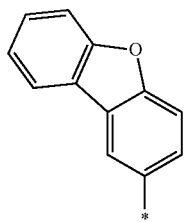 | 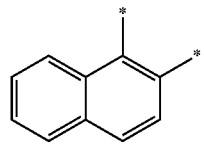 |
| C4-24 | 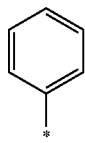 [SMILES: *c1ccccc1] | 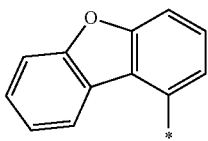 | 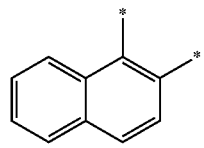 [SMILES: *c1ccc2ccccc2c1*] |
| C4-25 | 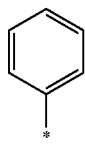 [SMILES: *c1ccccc1] | 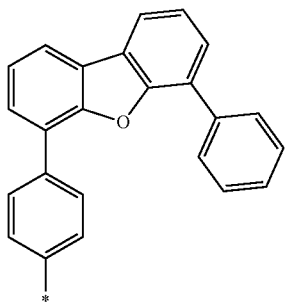 [SMILES: *c1ccc(-c2cccc3c2oc2c(-c4ccccc4)cccc23)cc1] | 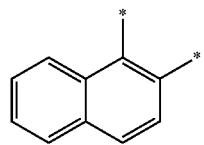 |
| C4-26 | 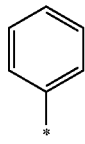 | 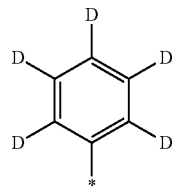 | 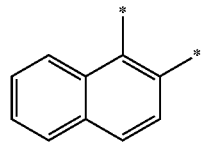 |
| C4-27 | 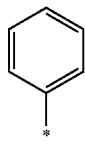 [SMILES: *c1ccccc1] | 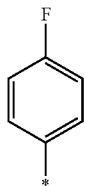 | 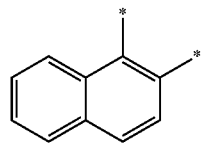 |
| C4-28 | 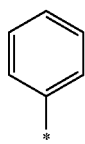 [SMILES: *c1ccccc1] | 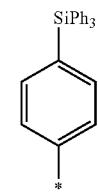 | 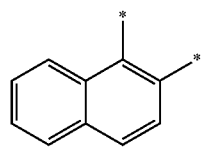 |
| C4-29 | 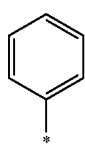 [SMILES: *c1ccccc1] | 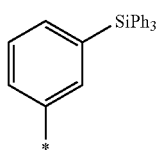 | 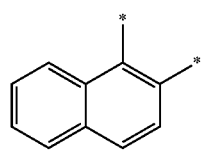 [SMILES: *c1ccc2ccccc2c1*] |
| C4-30 | 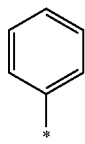 | 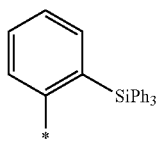 | 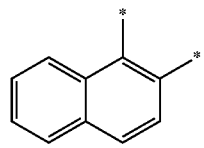 |

| | 1311 | | 1312 |
|---|---|---|---|
| D4-1 | 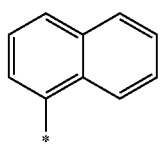 [SMILES: *c1cccc2ccccc12] | 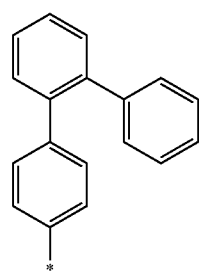 [SMILES: *c1ccc(-c2ccccc2-c2ccccc2)cc1] | 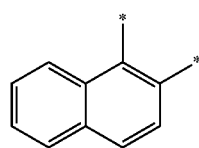 |
| D4-2 | 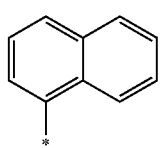 [SMILES: *c1cccc2ccccc12] | 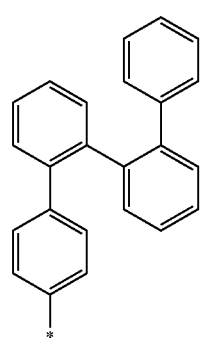 [SMILES: *c1ccc(-c2ccccc2-c2ccccc2-c2ccccc2)cc1] | 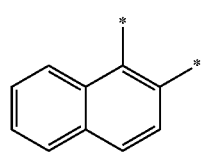 |
| D4-3 | 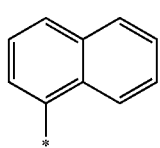 [SMILES: *c1cccc2ccccc12] | 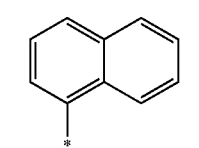 [SMILES: *c1cccc2ccccc12] | 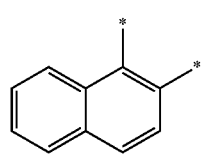 [SMILES: *c1ccc2ccccc2c1*] |
| D4-4 | 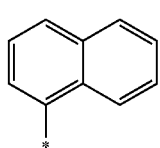 [SMILES: *c1cccc2ccccc12] | 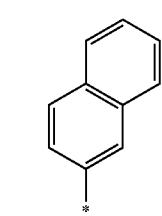 [SMILES: *c1ccc2ccccc2c1] | 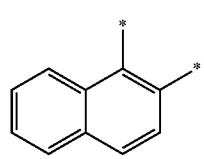 |
| D4-5 | 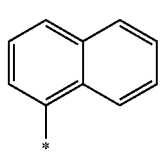 [SMILES: *c1cccc2ccccc12] | 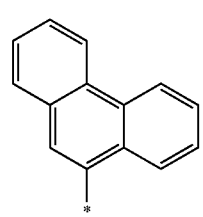 [SMILES: *c1cc2ccccc2c2ccccc12] | 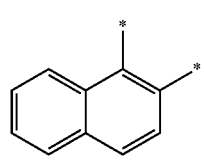 |
| D4-6 | 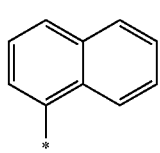 [SMILES: *c1cccc2ccccc12] | 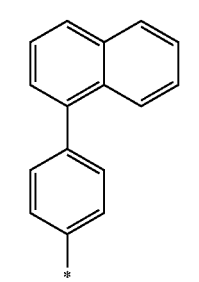 [SMILES: *c1ccc(-c2cccc3ccccc23)cc1] | 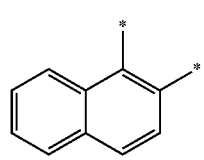 |

-continued
| | 1313 | | 1314 |
|---|---|---|---|
| D4-7 | 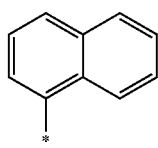 [SMILES: *c1cccc2ccccc12] | 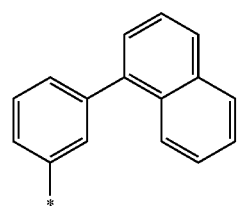 [SMILES: *c1cccc(-c2cccc3ccccc23)c1] | 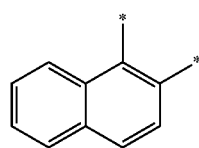 |
| D4-8 | 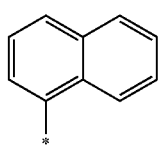 | 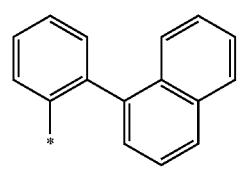 | 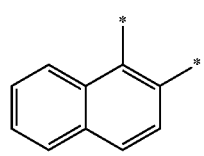 |
| D4-9 | 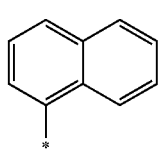 [SMILES: *c1cccc2ccccc12] | 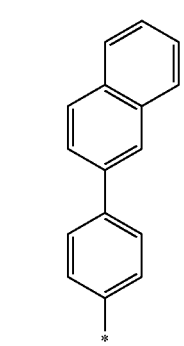 [SMILES: *c1ccc(-c2ccc3ccccc3c2)cc1] | 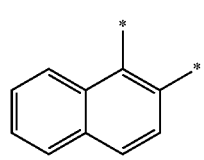 [SMILES: *c1ccc2ccccc2c1*] |
| D4-10 | 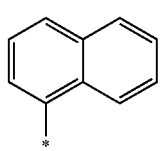 [SMILES: *c1cccc2ccccc12] | 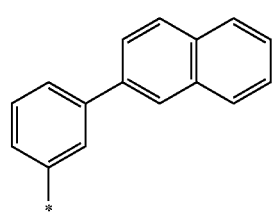 [SMILES: *c1cccc(-c2ccc3ccccc3c2)c1] | 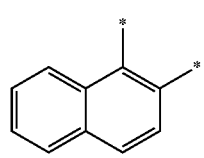 |
| D4-11 | 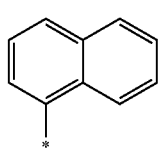 [SMILES: *c1cccc2ccccc12] | 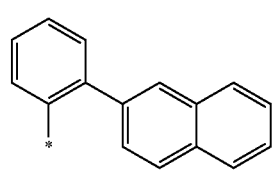 [SMILES: *c1ccccc1-c1ccc2ccccc2c1] | 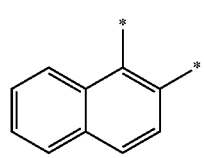 |
| D4-12 | 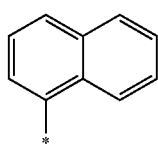 [SMILES: *c1cccc2ccccc12] | 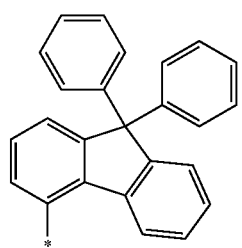 [SMILES: *c1cccc2c1-c1ccccc1C2(c1ccccc1)c1ccccc1] | 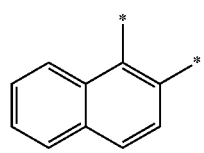 |

-continued
| | | | |
|---|---|---|---|
| D4-13 | 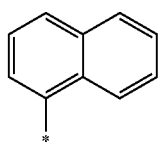 [SMILES: *c1cccc2ccccc12] | 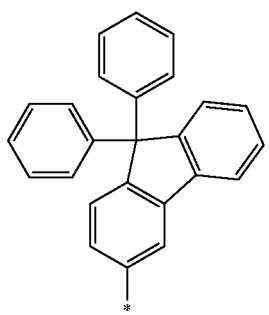 [SMILES: *c1ccc2c(c1)-c1ccccc1C2(c1ccccc1)c1ccccc1] | 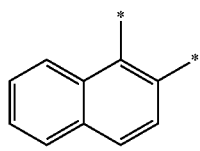 |
| D4-14 | 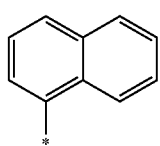 [SMILES: *c1cccc2ccccc12] | 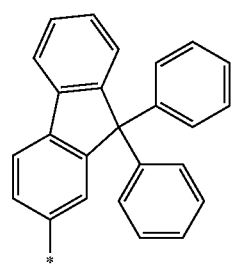 [SMILES: *c1ccc2c(c1)C(c1ccccc1)(c1ccccc1)c1ccccc1-2] | 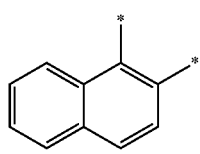 |
| D4-15 | 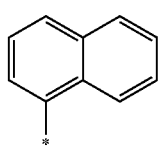 [SMILES: *c1cccc2ccccc12] | 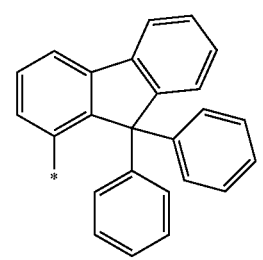 [SMILES: *c1cccc2c1C(c1ccccc1)(c1ccccc1)c1ccccc1-2] | 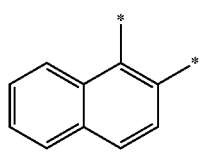 |
| D4-16 | 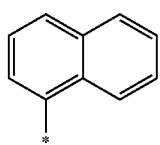 [SMILES: *c1cccc2ccccc12] | 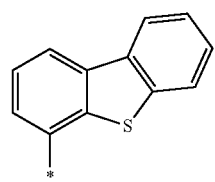 | 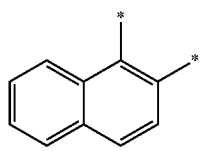 |
| D4-17 | 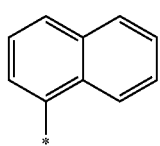 [SMILES: *c1cccc2ccccc12] | 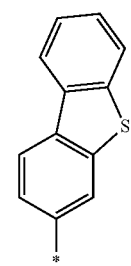 [SMILES: *c1ccc2c(c1)sc1ccccc12] | 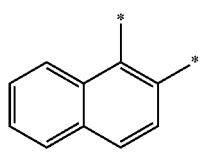 |
| D4-18 | 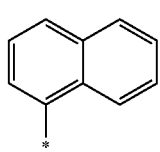 [SMILES: *c1cccc2ccccc12] | 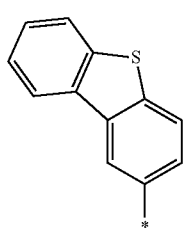 | 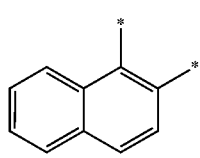 |

-continued
| | | | |
|---|---|---|---|
| D4-19 | 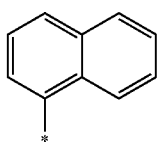 [SMILES: *c1cccc2ccccc12] | 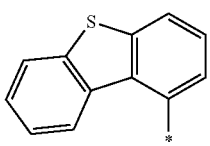 | 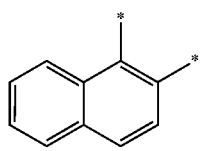 |
| D4-20 | 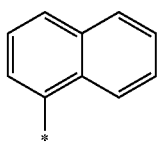 [SMILES: *c1cccc2ccccc12] | 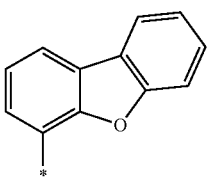 | 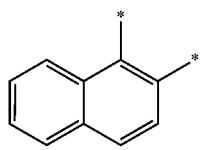 |
| D4-21 | 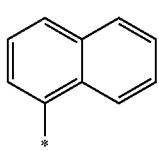 [SMILES: *c1cccc2ccccc12] | 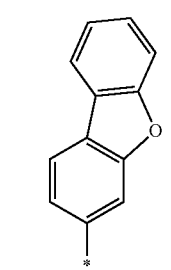 [SMILES: *c1ccc2c(c1)oc1ccccc12] | 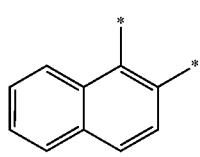 |
| D4-22 | 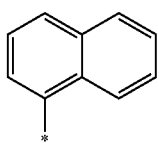 [SMILES: *c1cccc2ccccc12] | 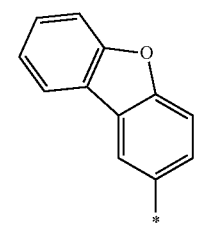 | 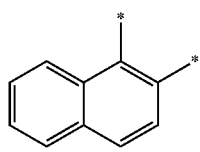 |
| D4-23 | 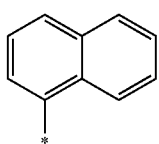 [SMILES: *c1cccc2ccccc12] | 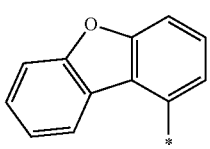 | 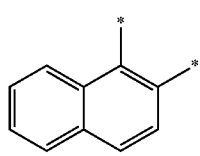 |
| D4-24 | 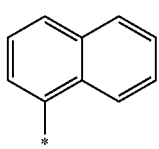 [SMILES: *c1cccc2ccccc12] | 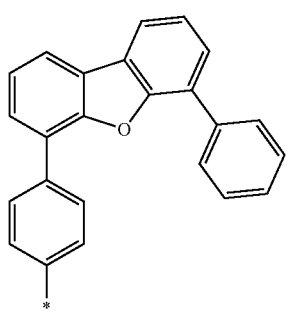 [SMILES: *c1ccc(-c2cccc3c2oc2c(-c4ccccc4)cccc23)cc1] | 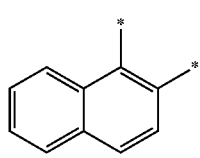 |
| D4-25 | 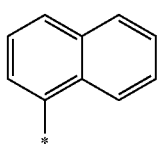 [SMILES: *c1cccc2ccccc12] | 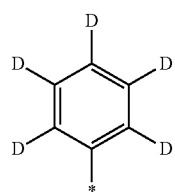 | 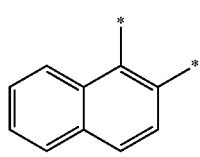 [SMILES: *c1ccc2ccccc2c1*] |

-continued
| | | | |
|---|---|---|---|
| D4-26 | 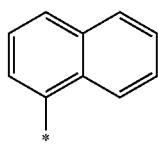 [SMILES: *c1cccc2ccccc12] | 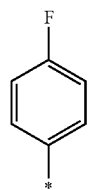 | 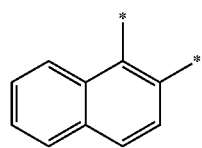 [SMILES: *c1ccc2ccccc2c1*] |
| D4-27 | 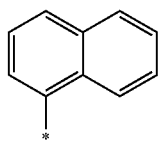 [SMILES: *c1cccc2ccccc12] | 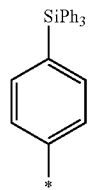 | 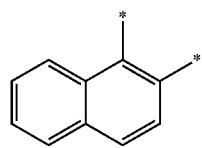 [SMILES: *c1ccc2ccccc2c1*] |
| D4-28 | 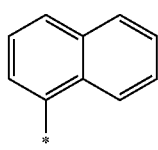 [SMILES: *c1cccc2ccccc12] | 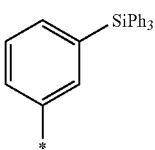 | 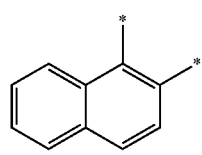 [SMILES: *c1ccc2ccccc2c1*] |
| D4-29 | 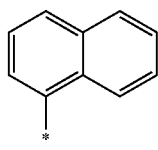 [SMILES: *c1cccc2ccccc12] | 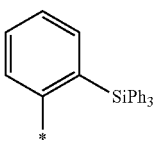 | 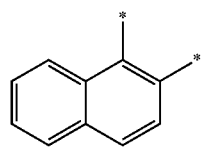 |
| D4-30 | 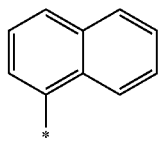 [SMILES: *c1cccc2ccccc12] | 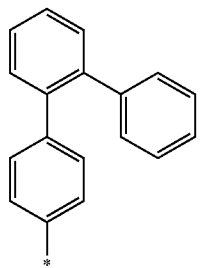 [SMILES: *c1ccc(-c2ccccc2-c2ccccc2)cc1] | 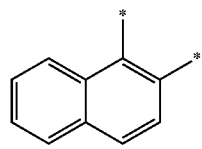 |
| E4-1 | 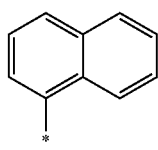 [SMILES: *c1cccc2ccccc12] | 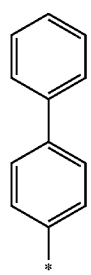 | 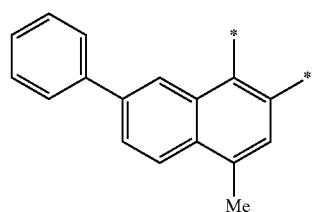 [SMILES: *c1cc(C)c2ccc(-c3ccccc3)cc2c1*] |
| E4-2 | 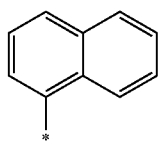 [SMILES: *c1cccc2ccccc12] | 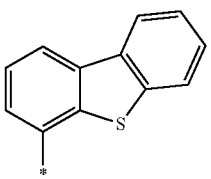 | 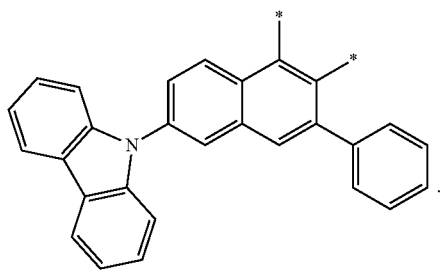 [SMILES: *c1c(-c2ccccc2)cc2cc(-n3c4ccccc4c4ccccc43)ccc2c1*] |

24. The diamine compound of claim 16, wherein the diamine compound represented by Formula 1 is at least one selected among compounds represented in Compound Group 5:
[Compound Group 5]
| | m | n | L₁ | L₂ | Ar₁ | Ar₂ |
|---|---|---|---|---|---|---|
| A5-1 | 0 | 1 | — | 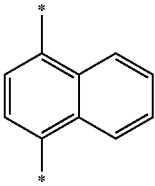 [SMILES: *c1ccc(*)c2ccccc12] | 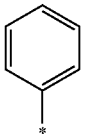 [SMILES: *c1ccccc1] | 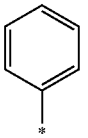 [SMILES: *c1ccccc1] |
| A5-2 | 0 | 1 | — | 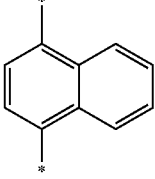 | 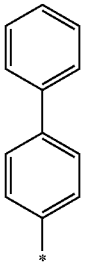 [SMILES: *c1ccc(-c2ccccc2)cc1] | 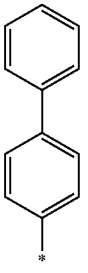 [SMILES: *c1ccc(-c2ccccc2)cc1] |
| A5-3 | 0 | 1 | — | 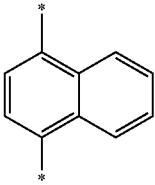 [SMILES: *c1ccc(*)c2ccccc12] | 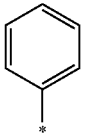 [SMILES: *c1ccccc1] | 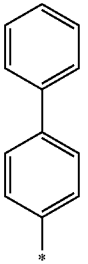 [SMILES: *c1ccc(-c2ccccc2)cc1] |
| A5-4 | 0 | 1 | — | 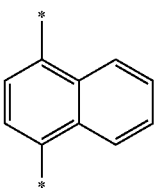 [SMILES: *c1ccc(*)c2ccccc12] | 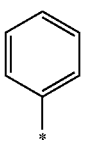 [SMILES: *c1ccccc1] | 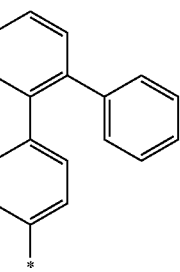 |
| A5-5 | 0 | 1 | — | 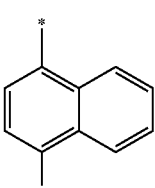 | 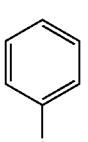 | 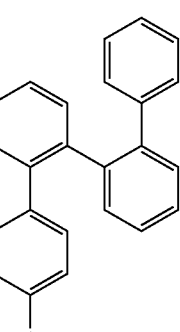 |

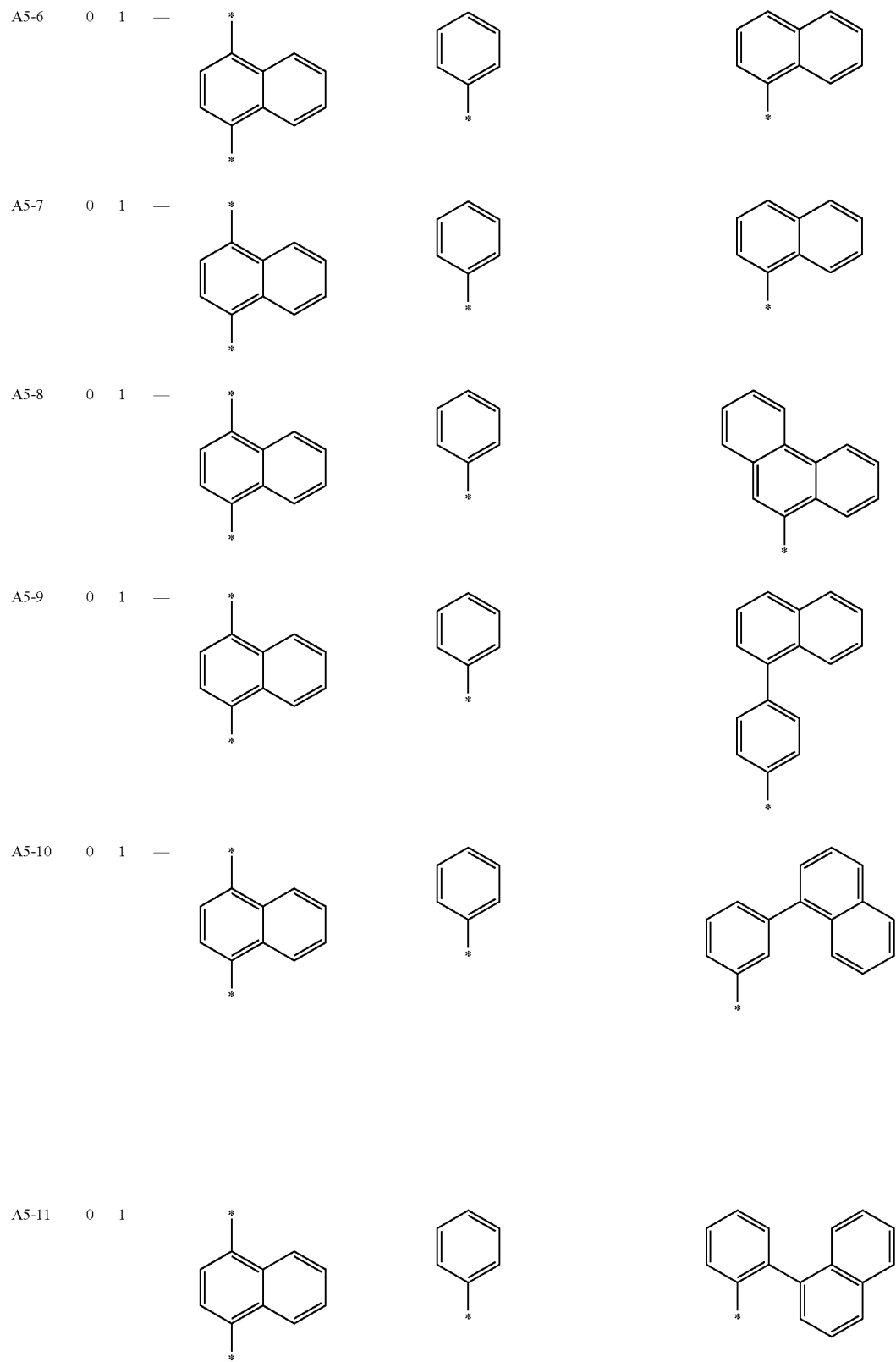

1325                                                                 1326
-continued
[Compound Group 5]
| A5-12 | 0 | 1 | — | 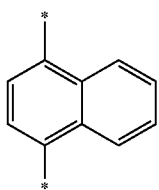 [SMILES: *c1ccc(*)c2ccccc12] | 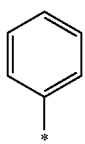 [SMILES: *c1ccccc1] | 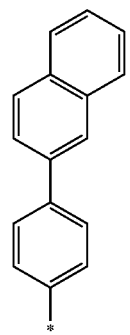 |
| A5-13 | 0 | 1 | — | 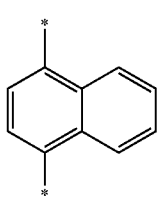 [SMILES: *c1ccc(*)c2ccccc12] | 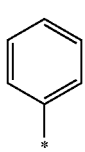 [SMILES: *c1ccccc1] | 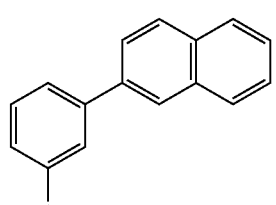 |
| A5-14 | 0 | 1 | — | 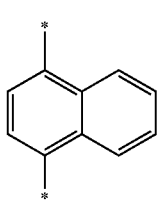 [SMILES: *c1ccc(*)c2ccccc12] | 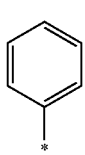 [SMILES: *c1ccccc1] | 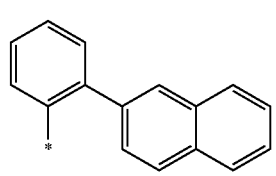 |
| A5-15 | 0 | 1 | — | 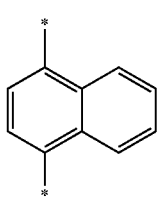 [SMILES: *c1ccc(*)c2ccccc12] | 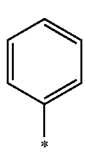 [SMILES: *c1ccccc1] | 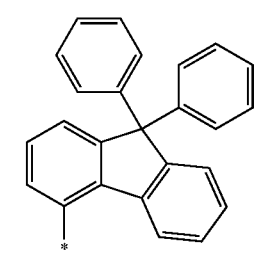 [SMILES: *c1cccc2c1-c1ccccc1C2(c1ccccc1)c1ccccc1] |
| A5-16 | 0 | 1 | — | 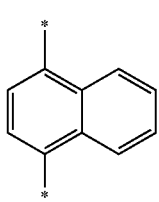 [SMILES: *c1ccc(*)c2ccccc12] | 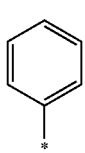 | 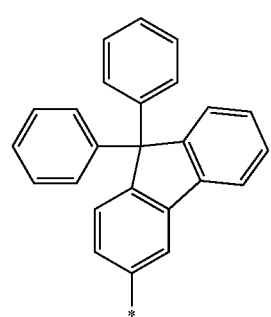 [SMILES: *c1ccc2c(c1)-c1ccccc1C2(c1ccccc1)c1ccccc1] |
| A5-17 | 0 | 1 | — | 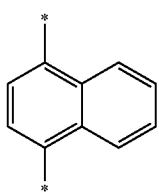 [SMILES: *c1ccc(*)c2ccccc12] | 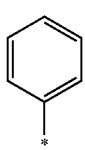 | 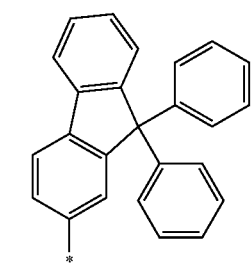 [SMILES: *c1ccc2c(c1)C(c1ccccc1)(c1ccccc1)c1ccccc1-2] |

[Compound Group 5]
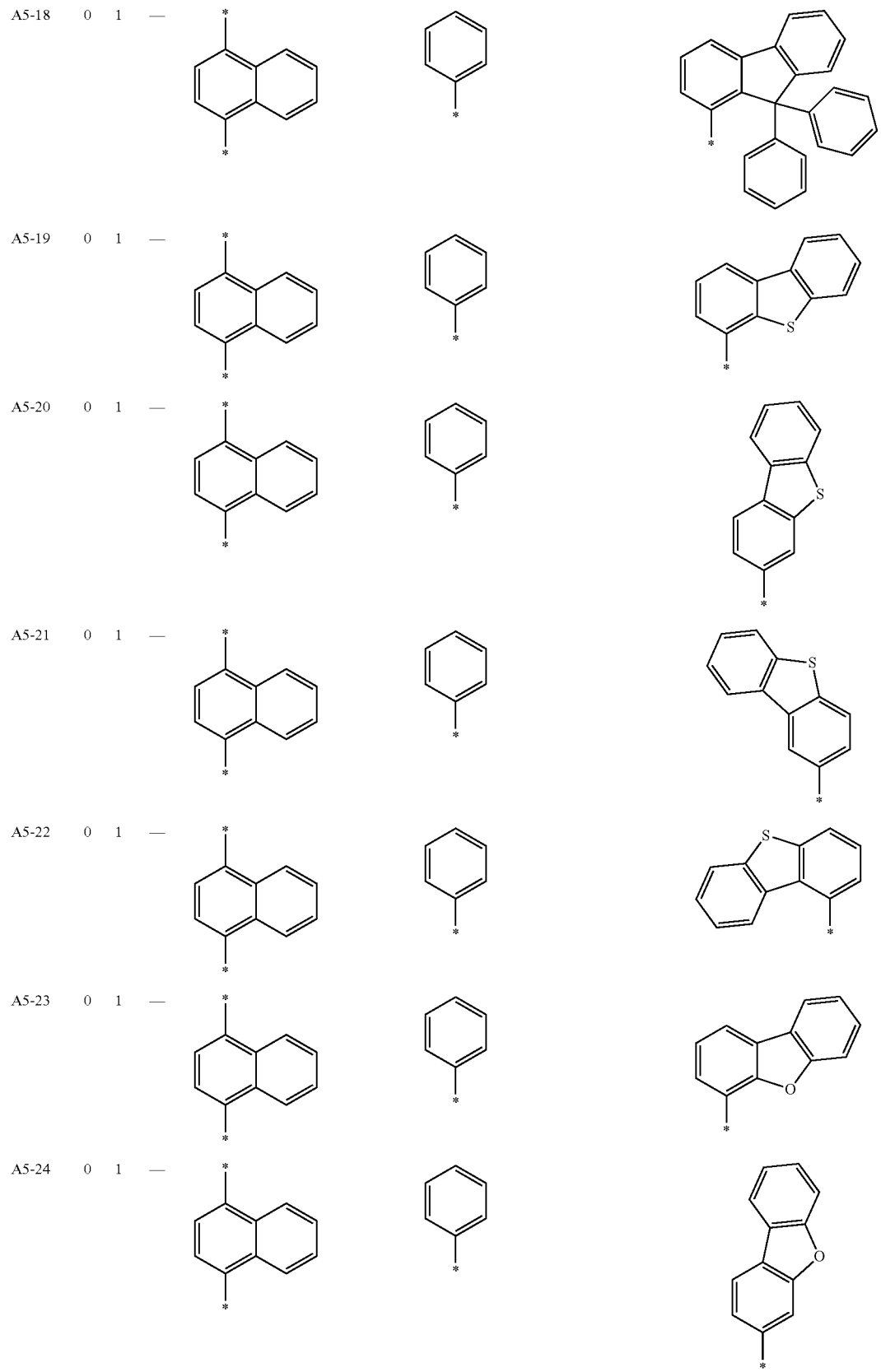

1329 1330
-continued
[Compound Group 5]
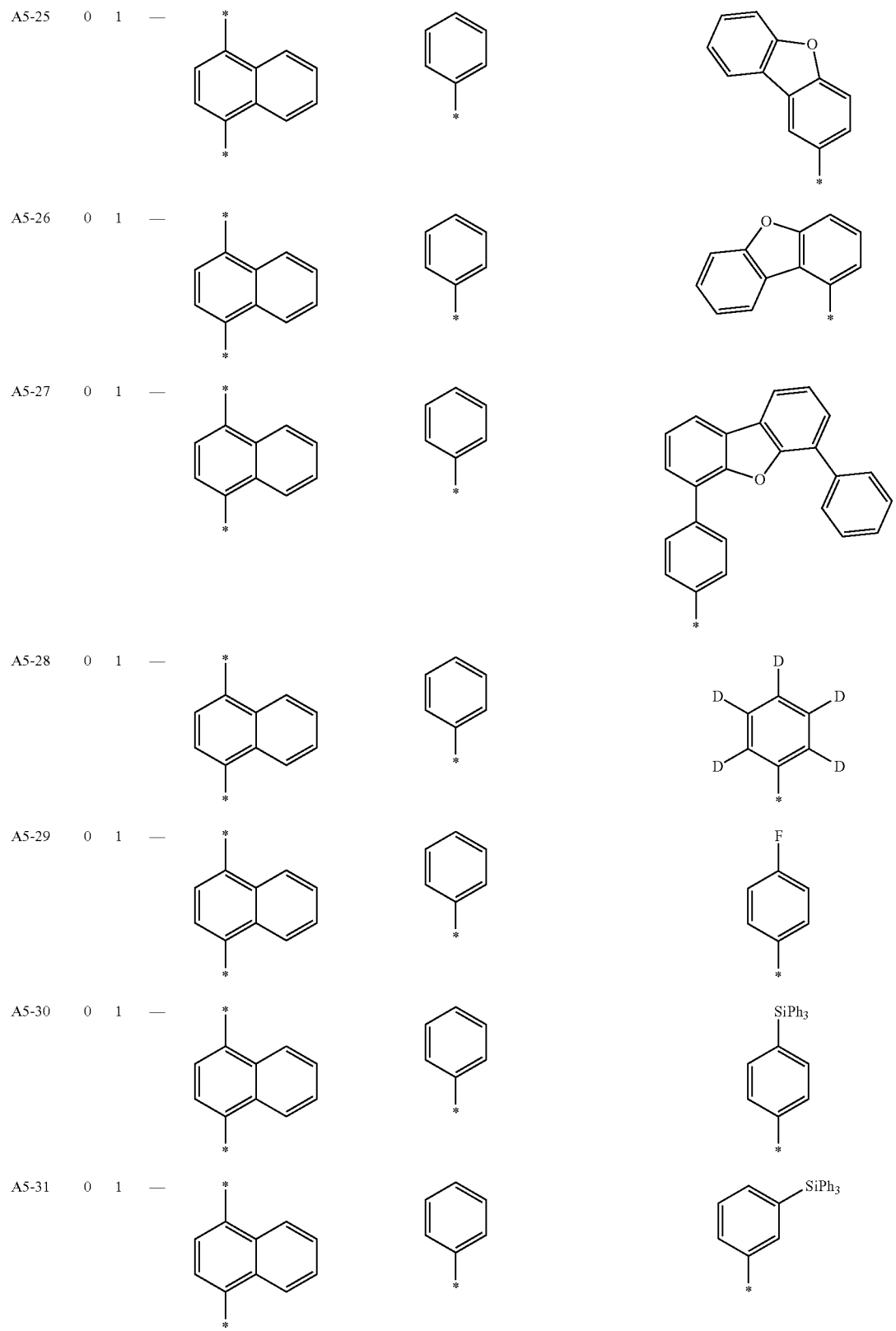

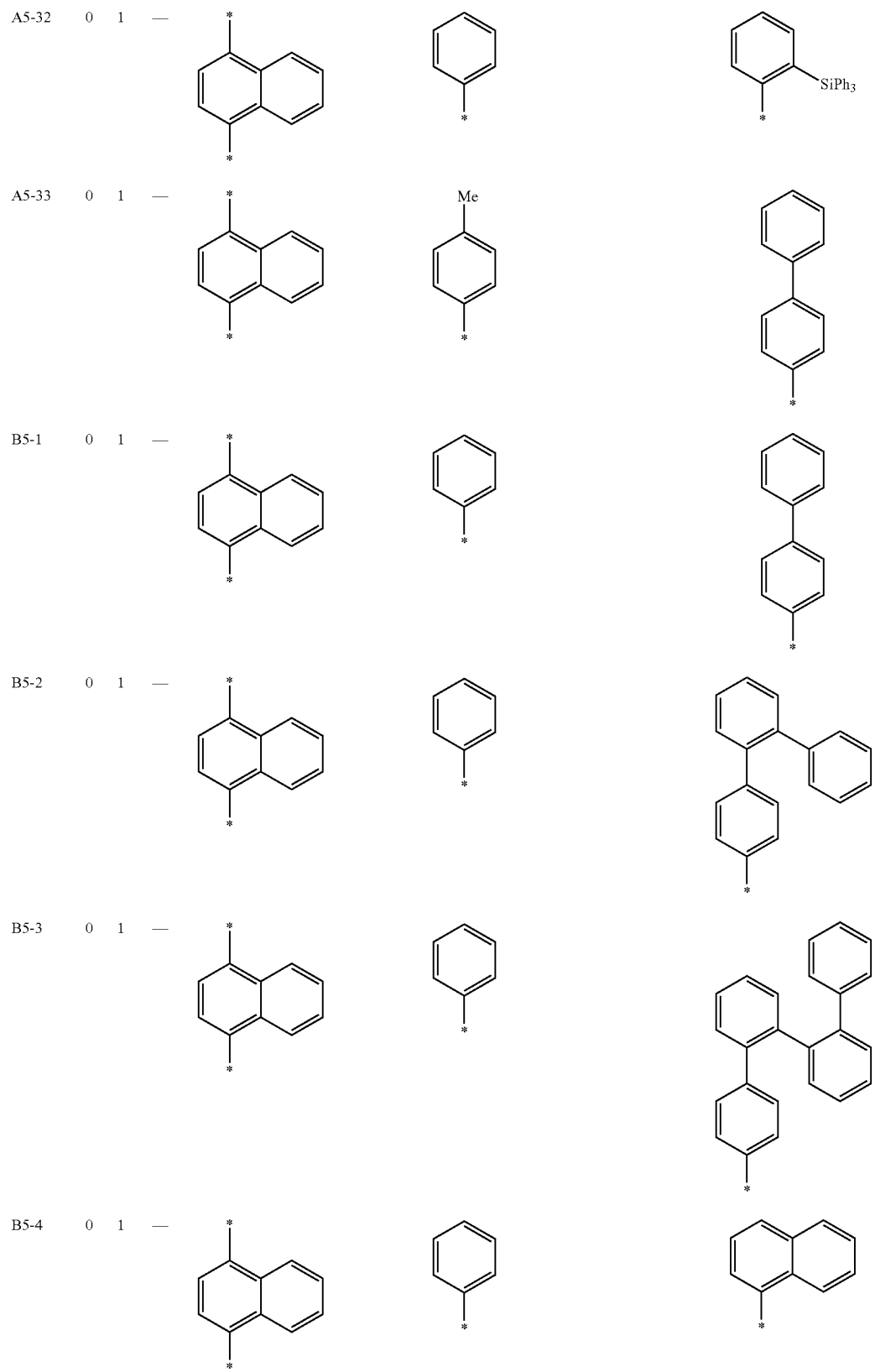

-continued
[Compound Group 5]
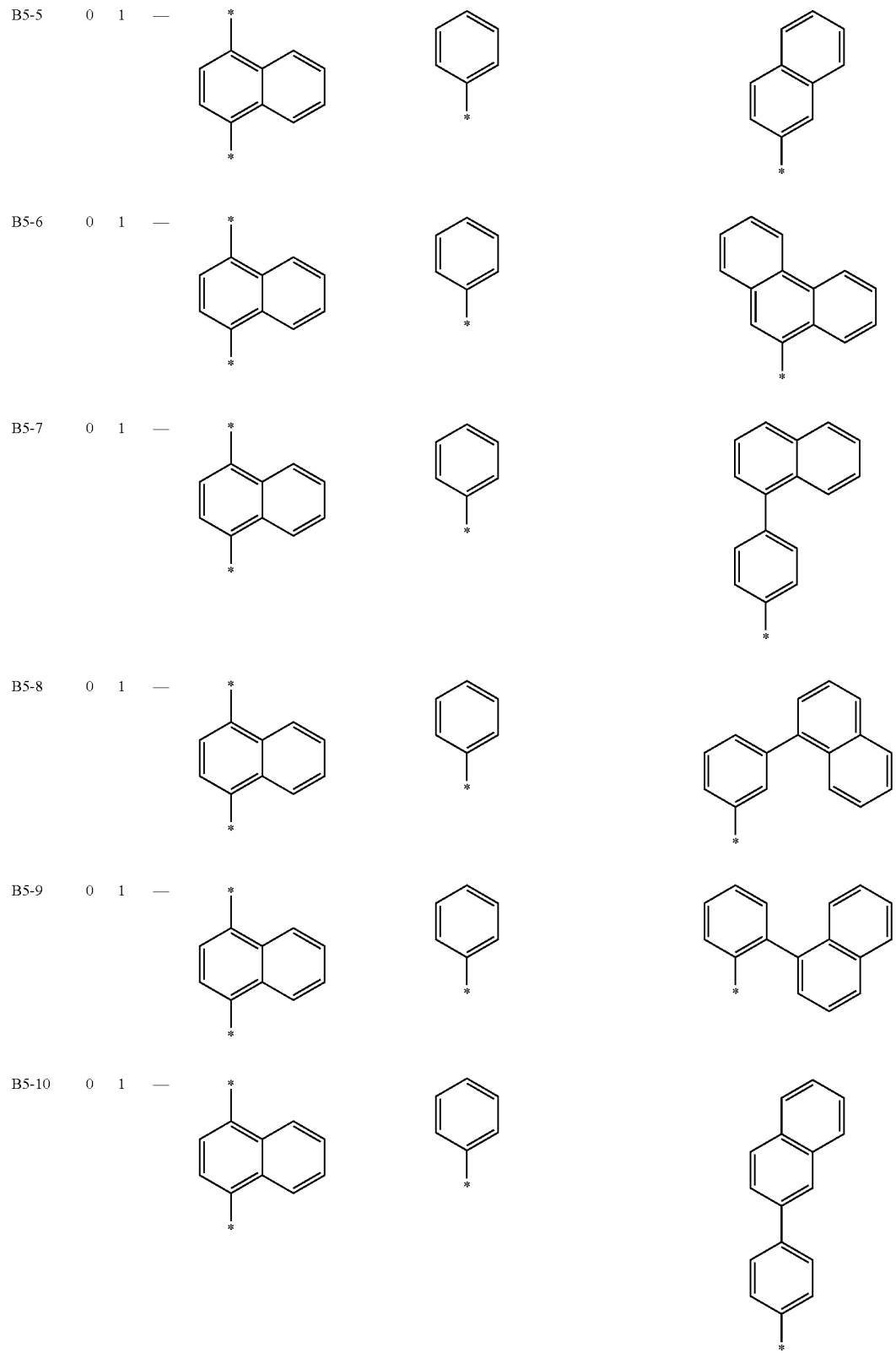

-continued
[Compound Group 5]
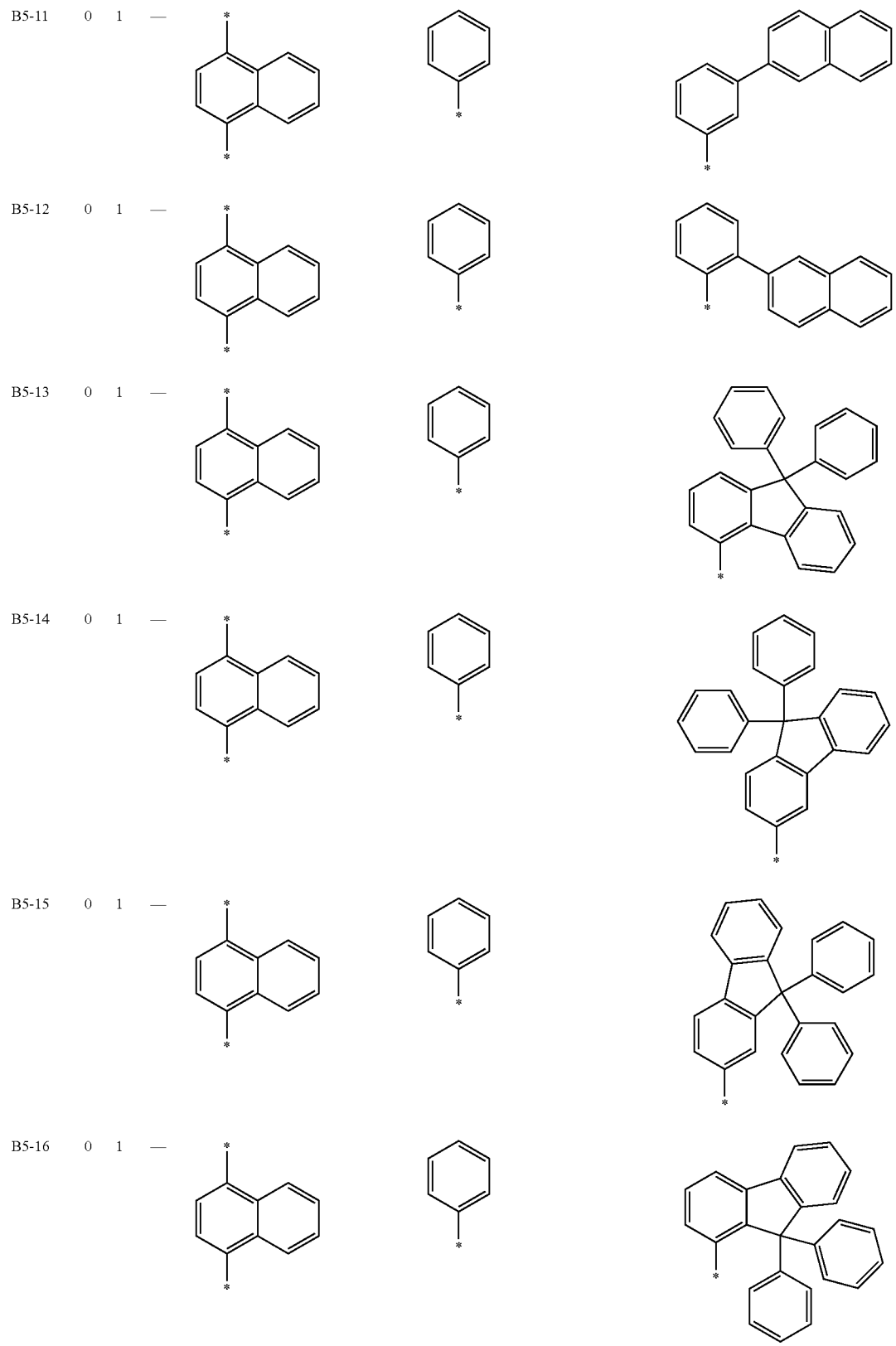

-continued
[Compound Group 5]
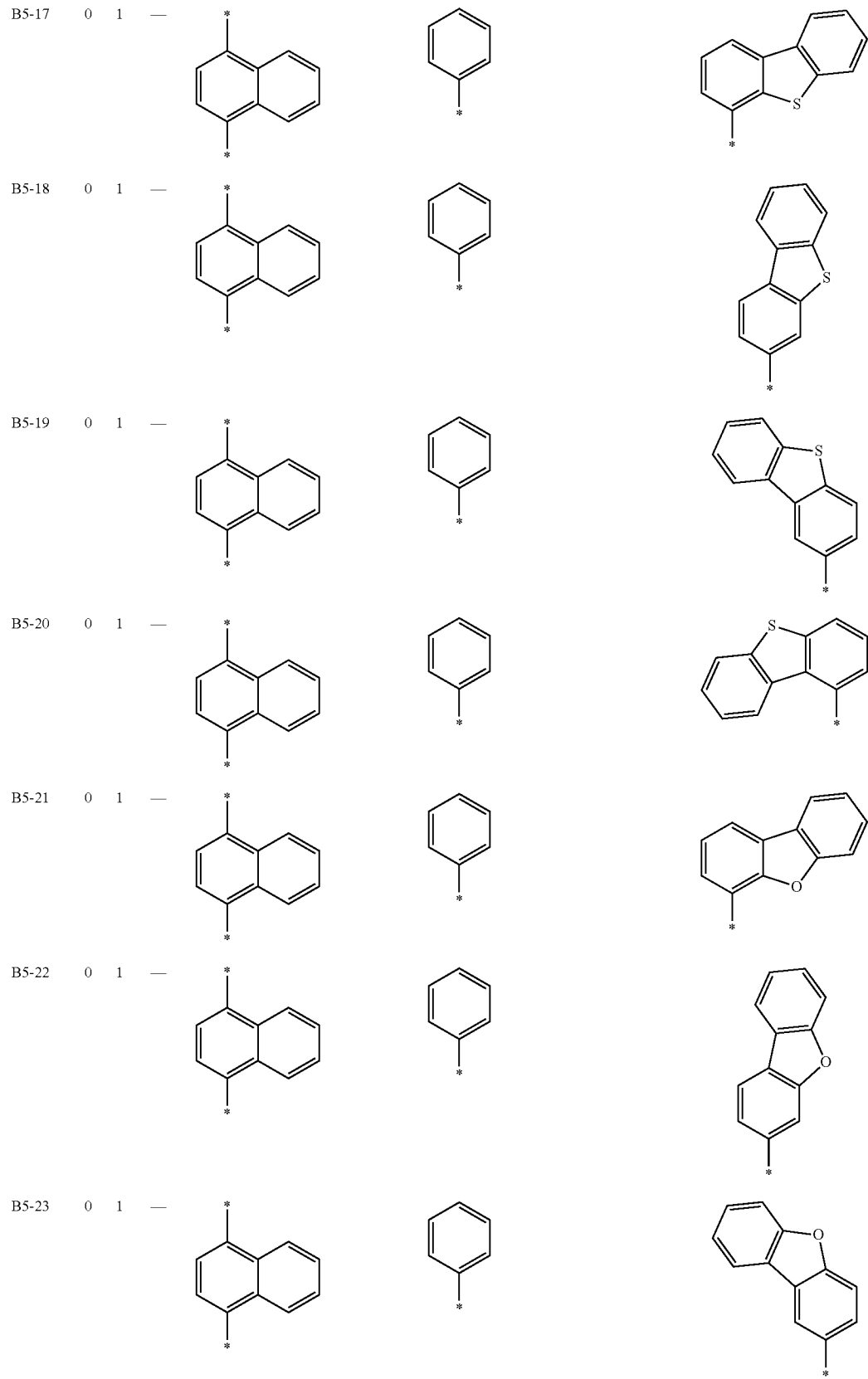

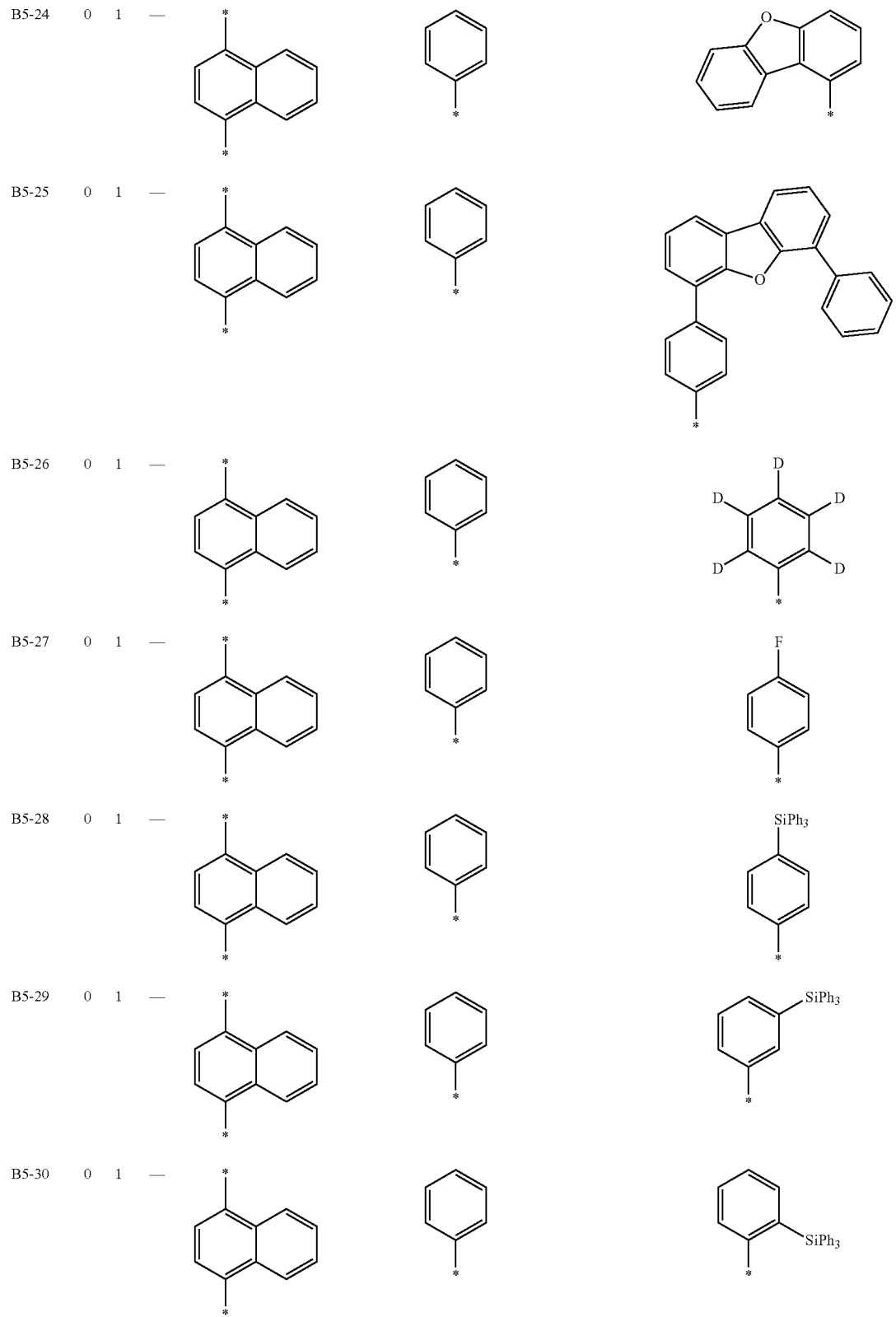

-continued
[Compound Group 5]
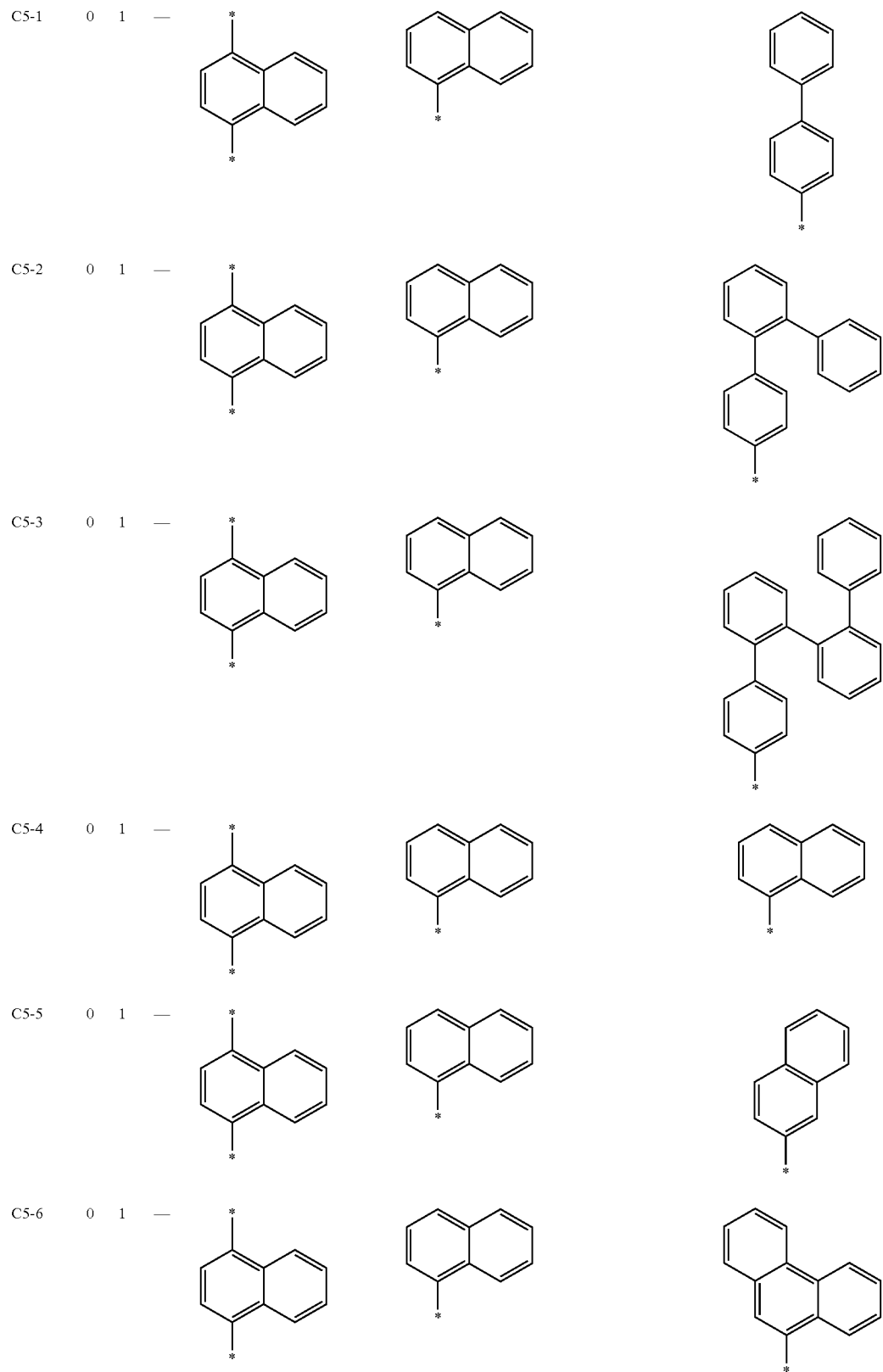

[Compound Group 5]
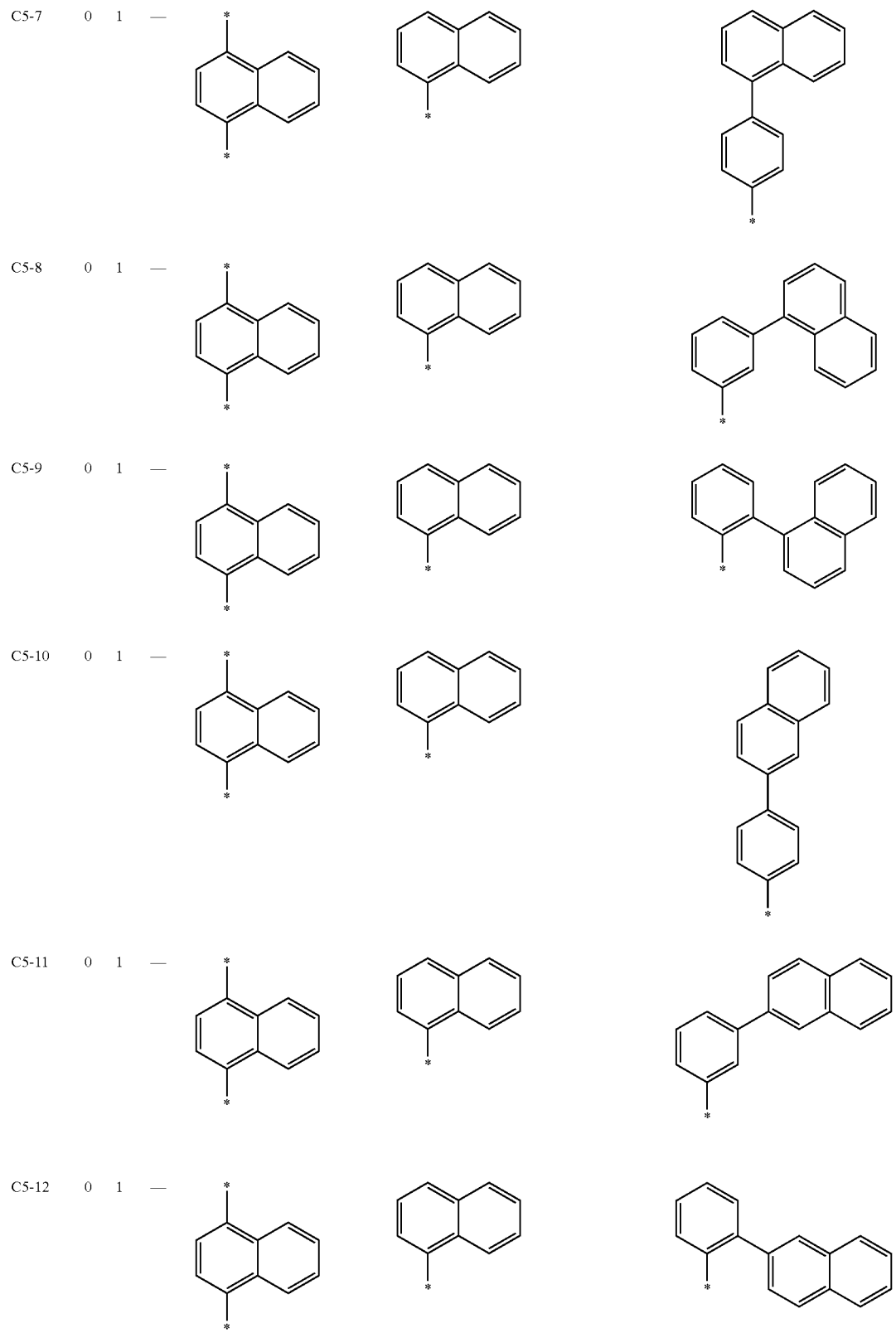

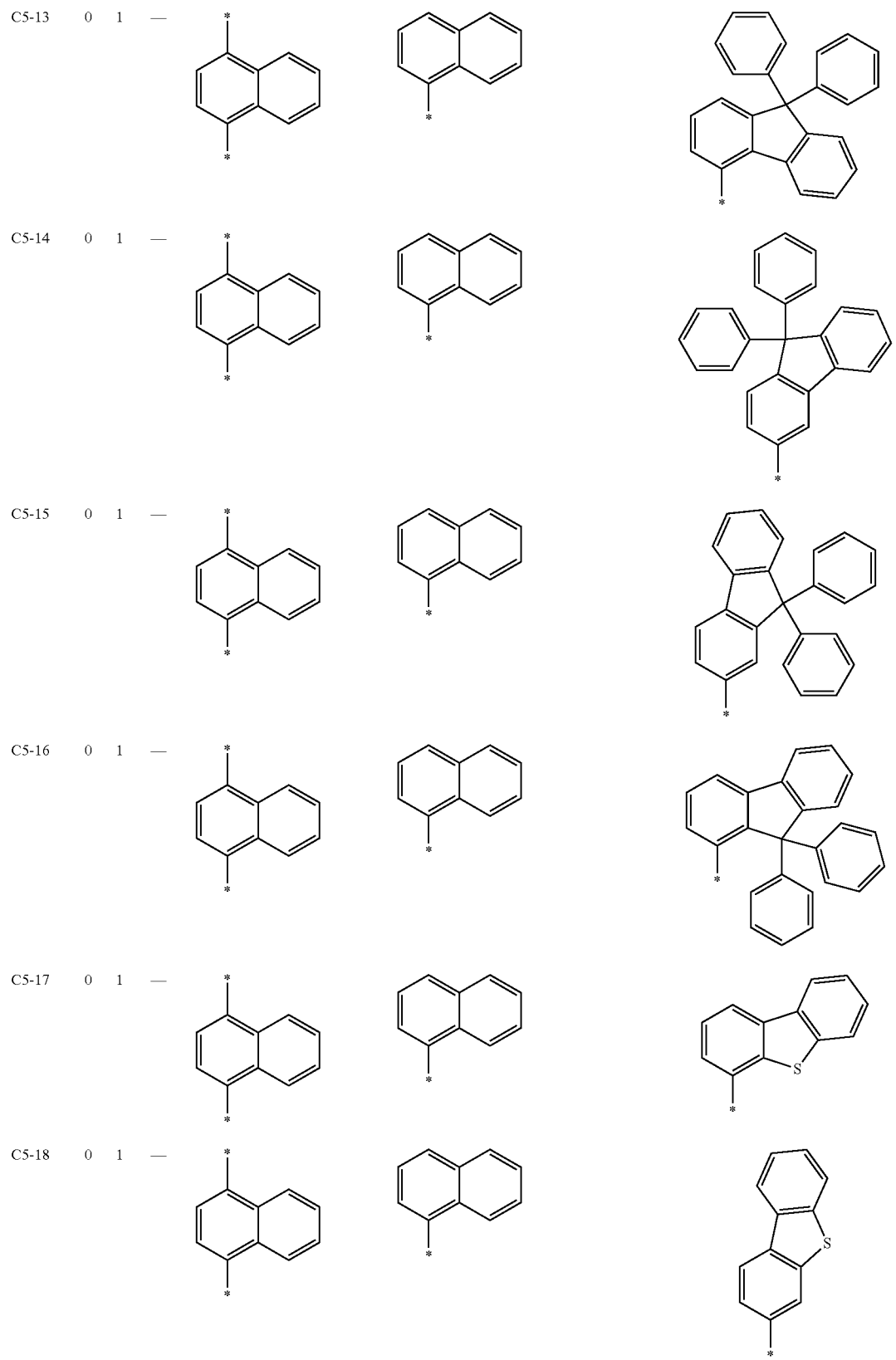

[Compound Group 5]
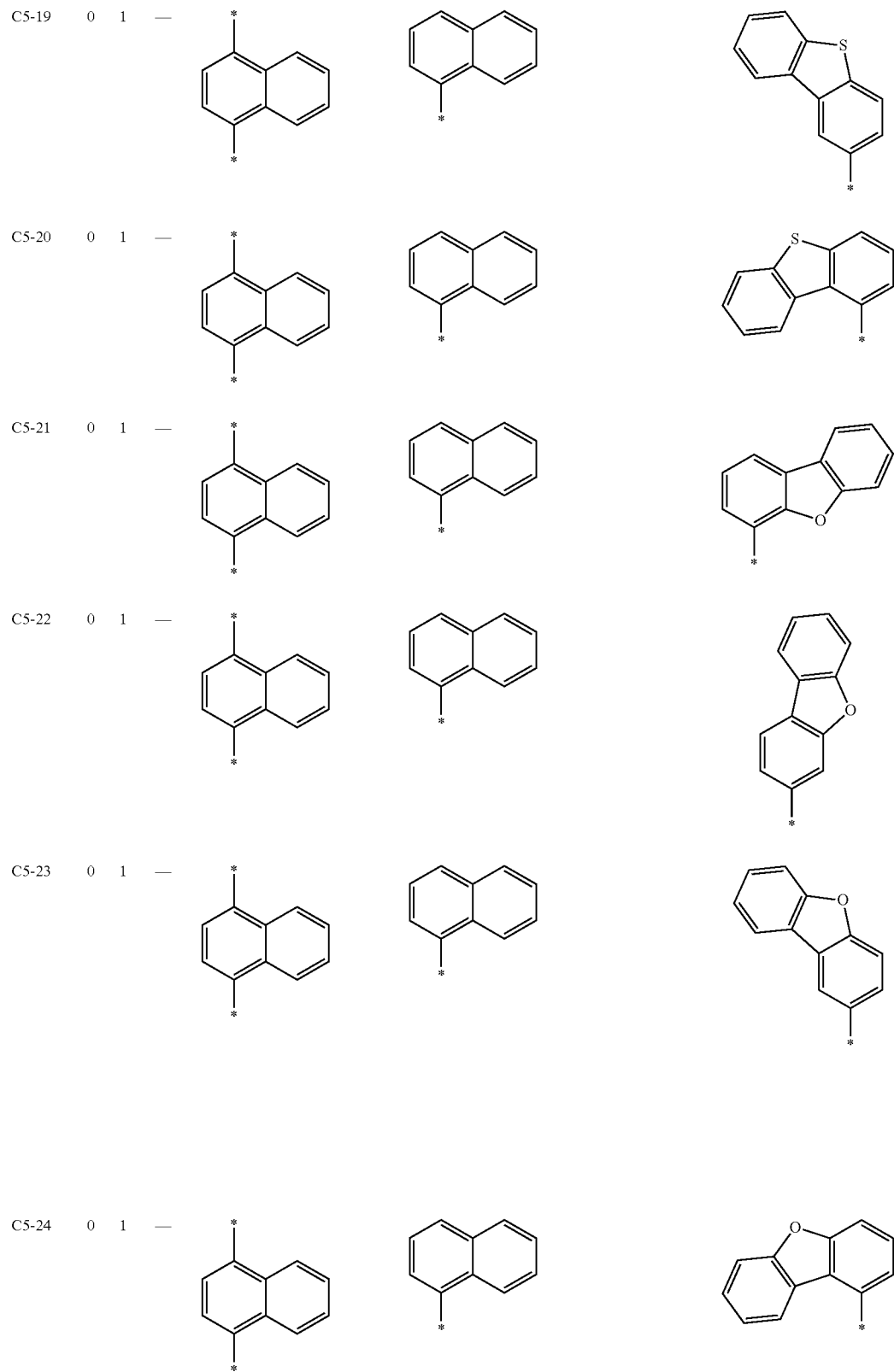

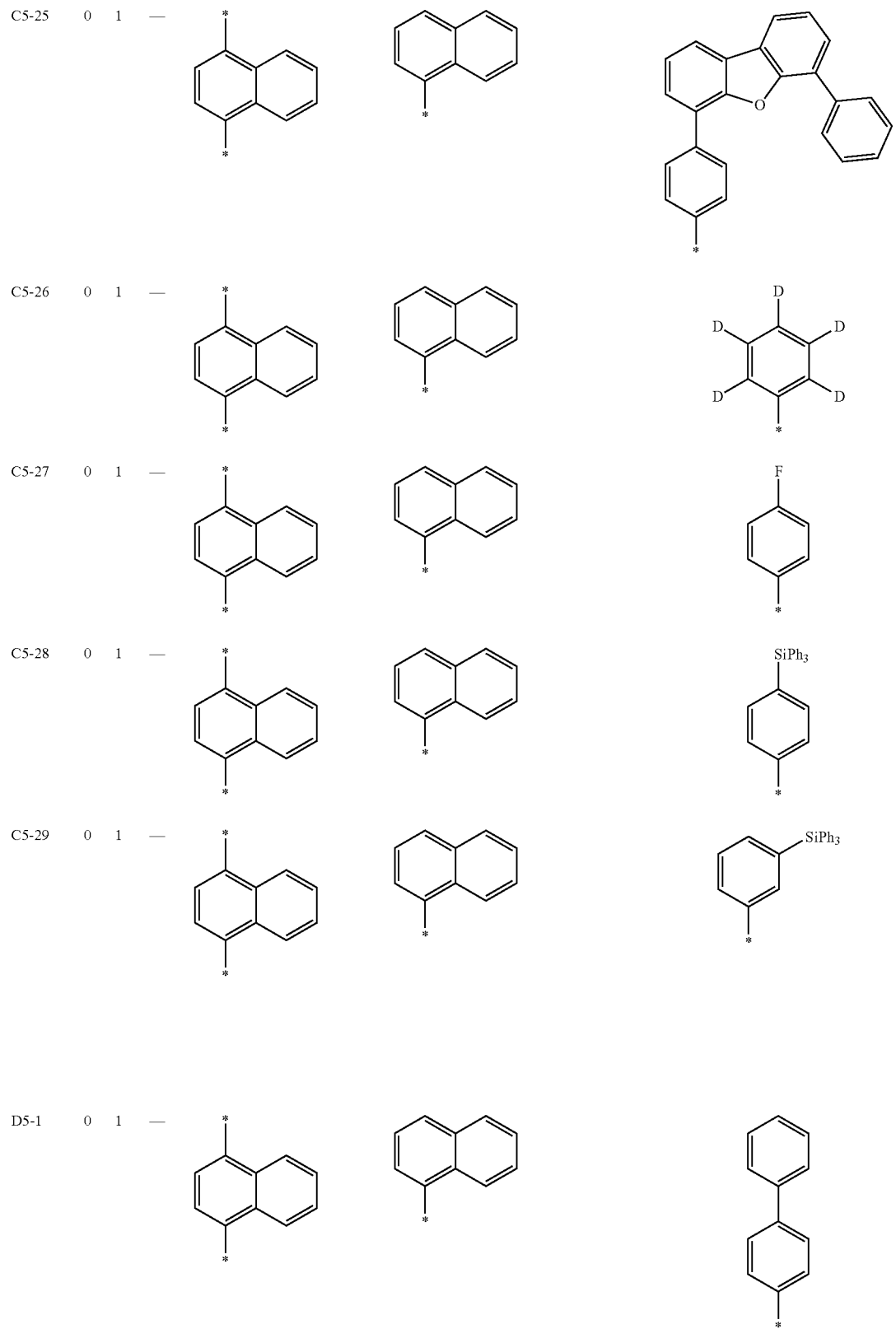

-continued
[Compound Group 5]
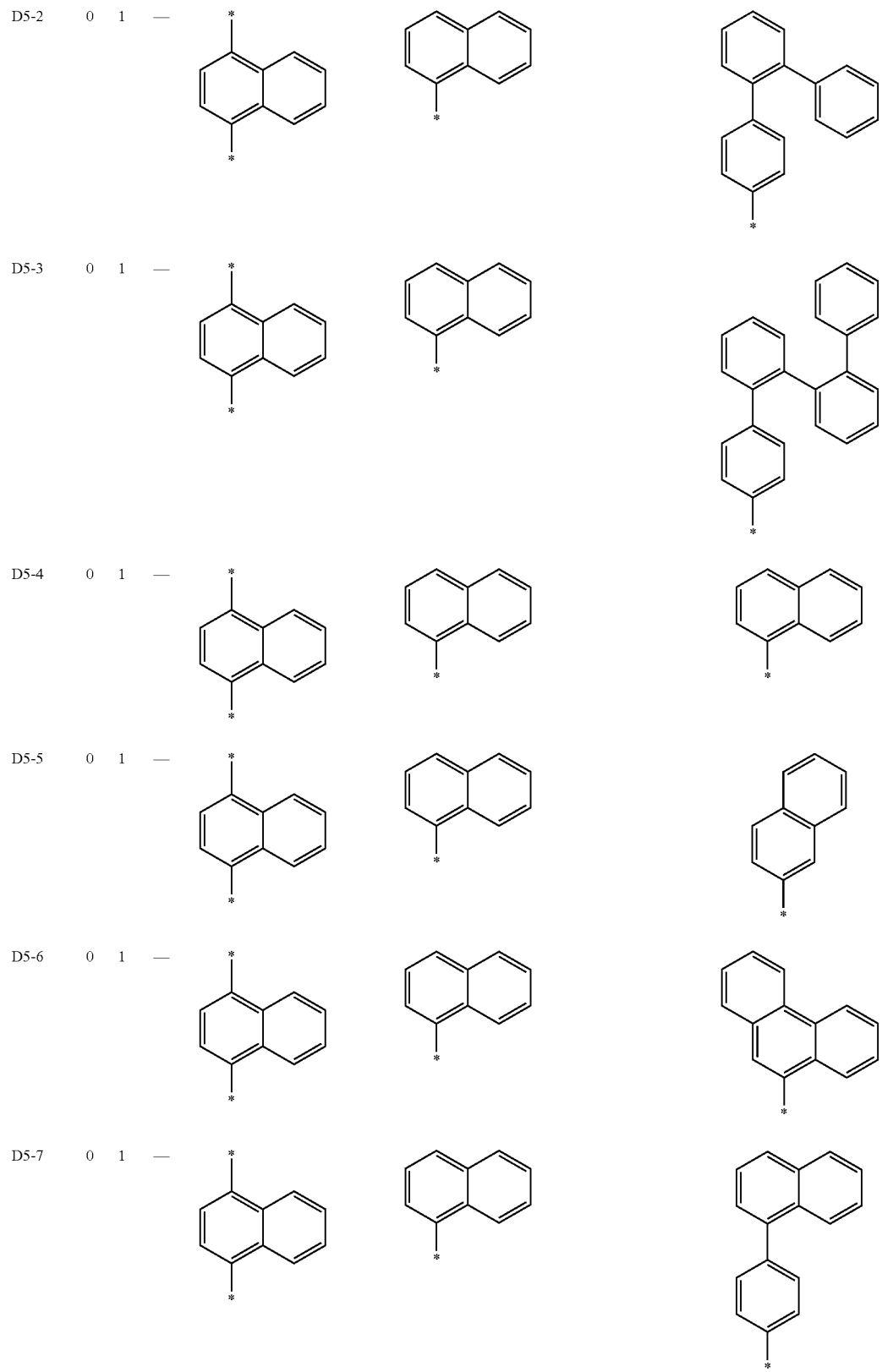

[Compound Group 5]
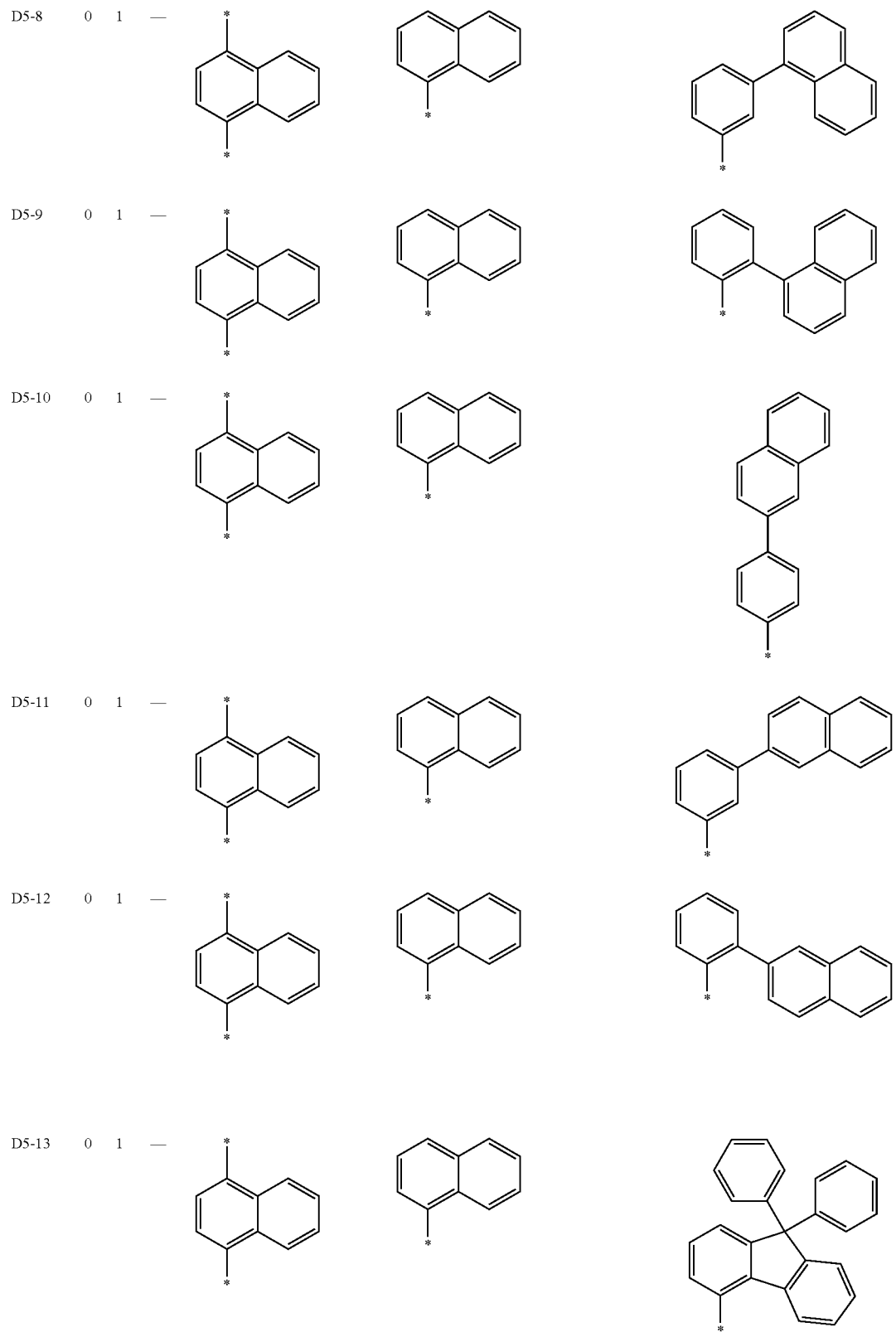

-continued
[Compound Group 5]
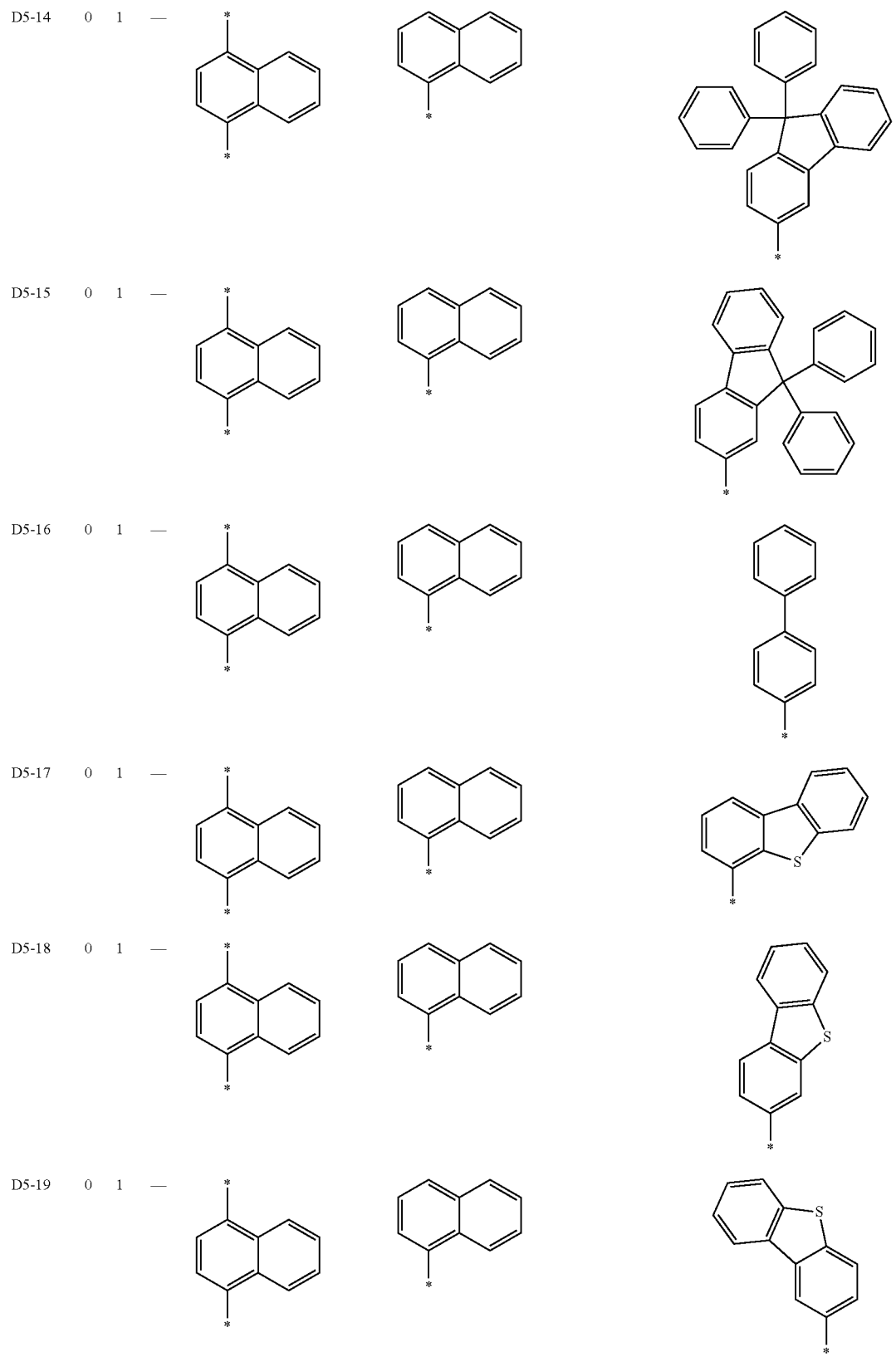

[Compound Group 5]
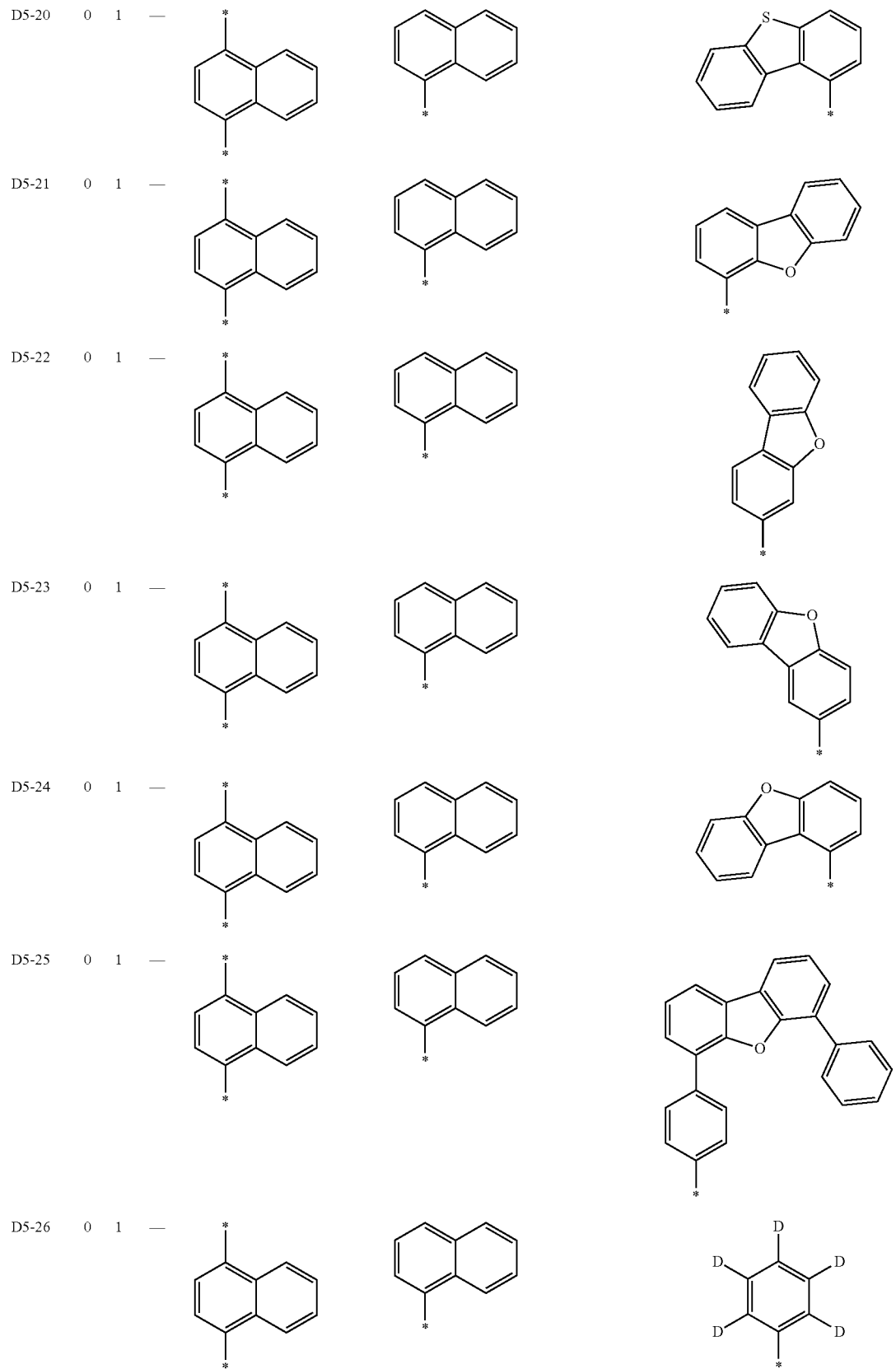

-continued
[Compound Group 5]
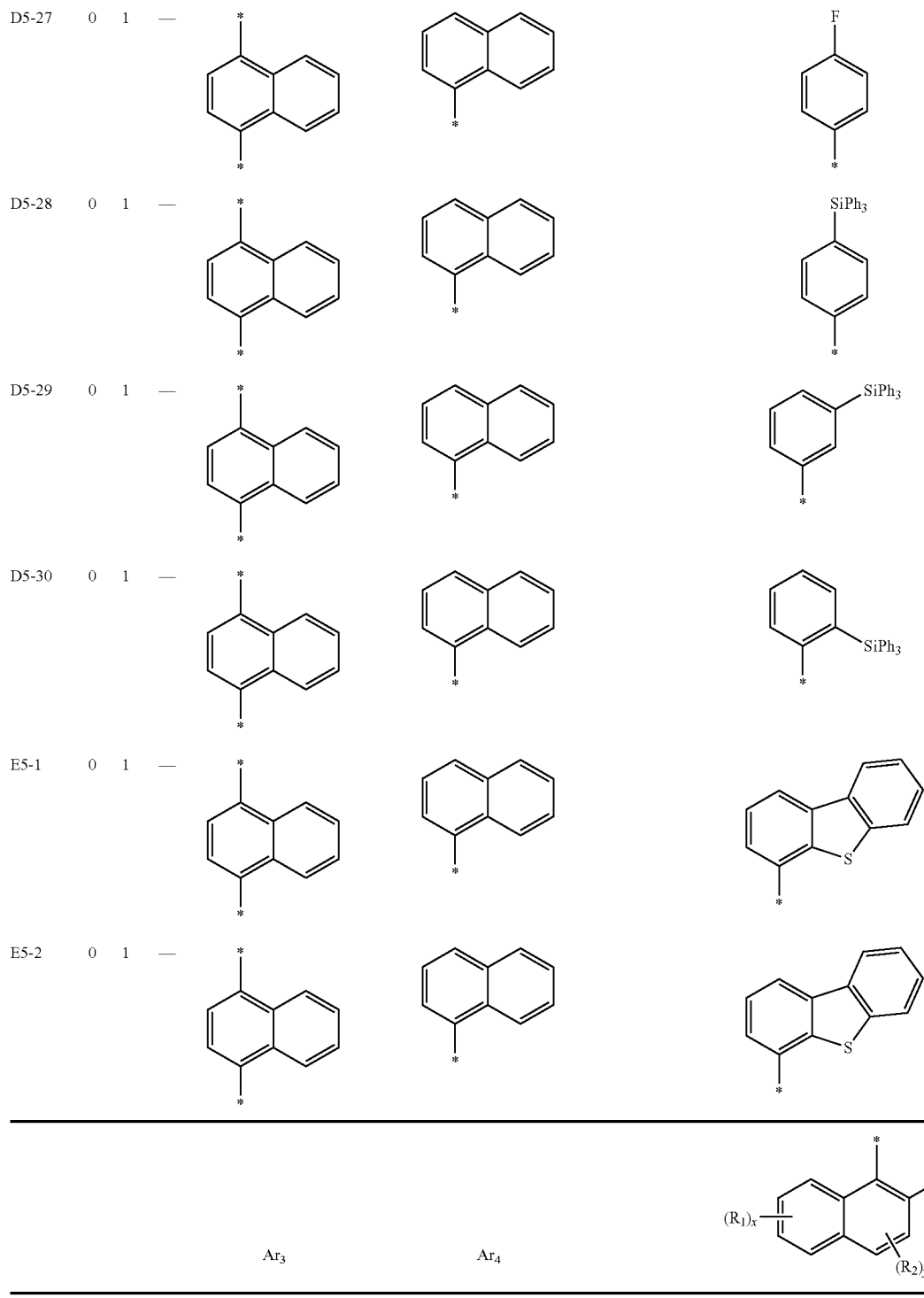
| | | | | Ar₃ | Ar₄ | |
|---|---|---|---|---|---|---|
A5-1
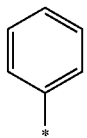 [SMILES: *c1ccccc1] 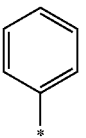 [SMILES: *c1ccccc1] 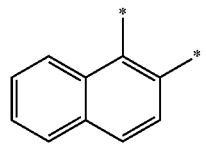

[Compound Group 5]
A5-2 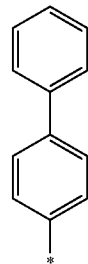 [SMILES: *c1ccc(-c2ccccc2)cc1] 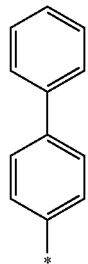 [SMILES: *c1ccc(-c2ccccc2)cc1] 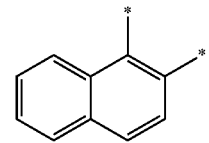
A5-3 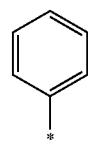 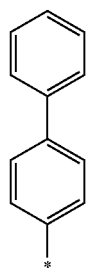 [SMILES: *c1ccc(-c2ccccc2)cc1] 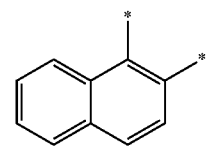
A5-4 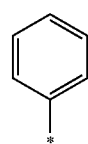 [SMILES: *c1ccccc1] 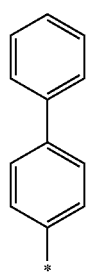 [SMILES: *c1ccc(-c2ccccc2)cc1] 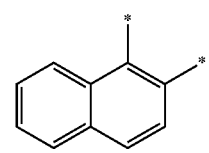
A5-5 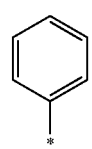 [SMILES: *c1ccccc1] 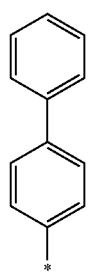 [SMILES: *c1ccc(-c2ccccc2)cc1] 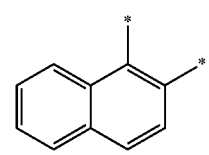
A5-6 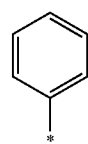 [SMILES: *c1ccccc1] 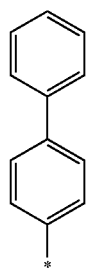 [SMILES: *c1ccc(-c2ccccc2)cc1] 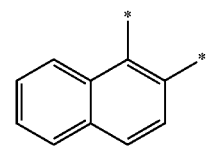

1363 1364
-continued
[Compound Group 5]
A5-7 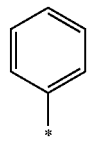 [SMILES: *c1ccccc1] 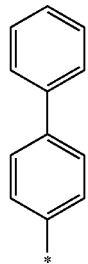 [SMILES: *c1ccc(-c2ccccc2)cc1] 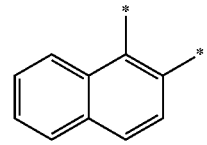 [SMILES: *c1ccc2ccccc2c1*]
A5-8 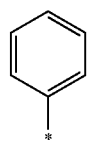 [SMILES: *c1ccccc1] 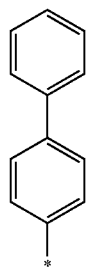 [SMILES: *c1ccc(-c2ccccc2)cc1] 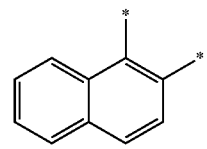
A5-9 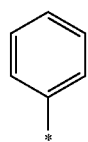 [SMILES: *c1ccccc1] 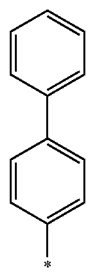 [SMILES: *c1ccc(-c2ccccc2)cc1] 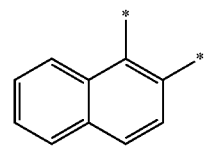
A5-10 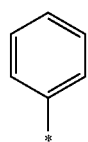 [SMILES: *c1ccccc1] 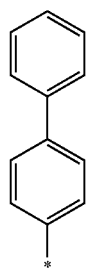 [SMILES: *c1ccc(-c2ccccc2)cc1] 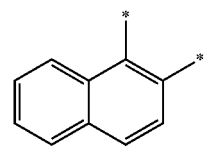
A5-11 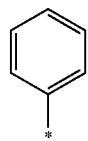 [SMILES: *c1ccccc1] 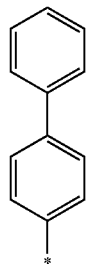 [SMILES: *c1ccc(-c2ccccc2)cc1] 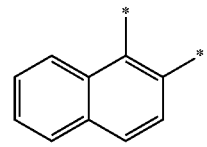

[Compound Group 5]
| | | | |
|---|---|---|---|
| A5-12 | 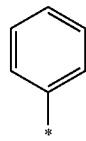 [SMILES: *c1ccccc1] | 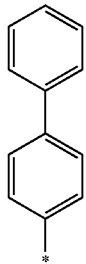 [SMILES: *c1ccc(-c2ccccc2)cc1] | 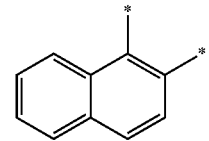 |
| A5-13 | 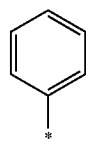 [SMILES: *c1ccccc1] | 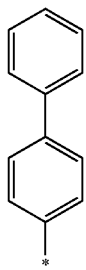 [SMILES: *c1ccc(-c2ccccc2)cc1] | 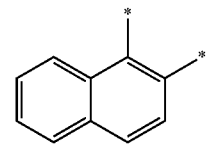 [SMILES: *c1ccc2ccccc2c1*] |
| A5-14 | 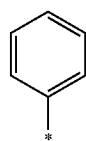 [SMILES: *c1ccccc1] | 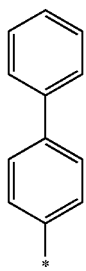 [SMILES: *c1ccc(-c2ccccc2)cc1] | 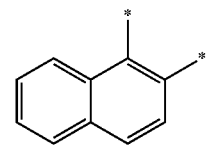 |
| A5-15 | 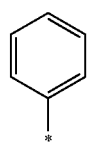 [SMILES: *c1ccccc1] | 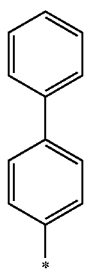 [SMILES: *c1ccc(-c2ccccc2)cc1] | 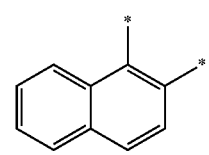 |
| A5-16 | 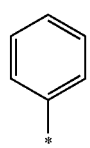 [SMILES: *c1ccccc1] | 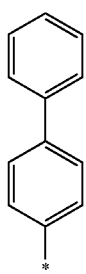 [SMILES: *c1ccc(-c2ccccc2)cc1] | 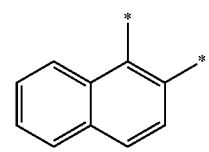 |

-continued
[Compound Group 5]
A5-17 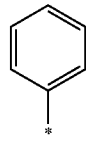 [SMILES: *c1ccccc1] 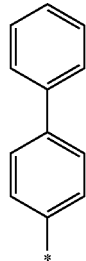 [SMILES: *c1ccc(-c2ccccc2)cc1] 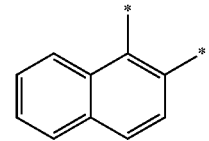
A5-18 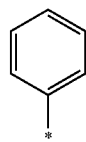 [SMILES: *c1ccccc1] 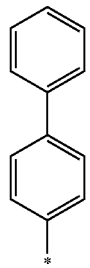 [SMILES: *c1ccc(-c2ccccc2)cc1] 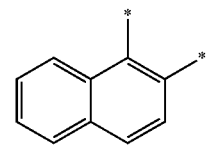 [SMILES: *c1ccc2ccccc2c1*]
A5-20 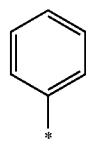 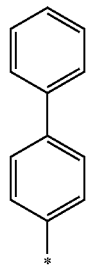 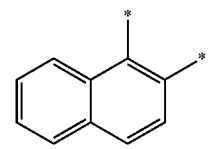
A5-21 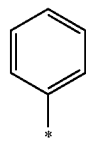 [SMILES: *c1ccccc1] 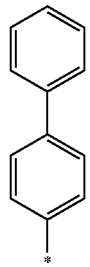 [SMILES: *c1ccc(-c2ccccc2)cc1] 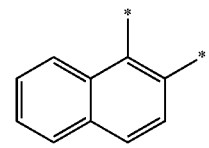
A5-22 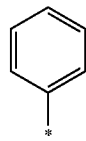 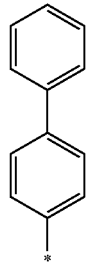 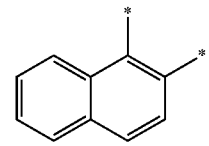

[Compound Group 5]
A5-23 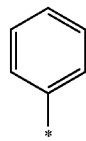 [SMILES: *c1ccccc1] 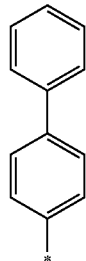 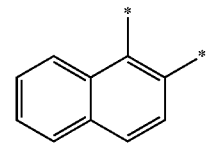
A5-24 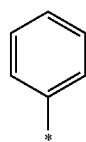 [SMILES: *c1ccccc1] 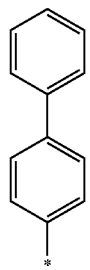 [SMILES: *c1ccc(-c2ccccc2)cc1] 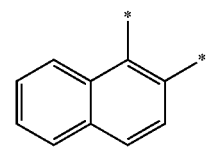 [SMILES: *c1ccc2ccccc2c1*]
A5-25 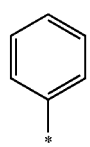 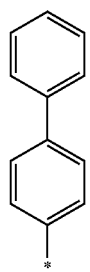 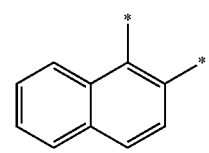
A5-26 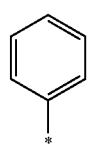 [SMILES: *c1ccccc1] 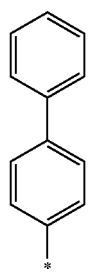 [SMILES: *c1ccc(-c2ccccc2)cc1] 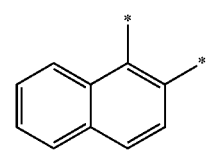
A5-27 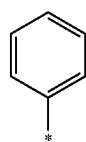 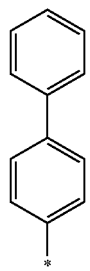 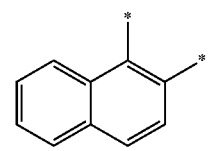

-continued
[Compound Group 5]
A5-28 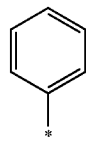 [SMILES: *c1ccccc1] 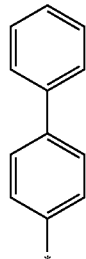 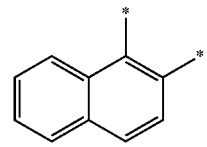
A5-29 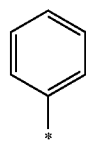 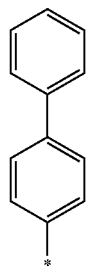 [SMILES: *c1ccc(-c2ccccc2)cc1] 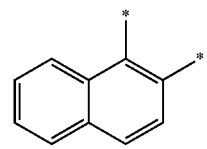 [SMILES: *c1ccc2ccccc2c1*]
A5-30 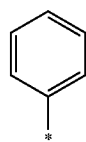 [SMILES: *c1ccccc1] 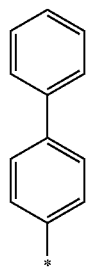 [SMILES: *c1ccc(-c2ccccc2)cc1] 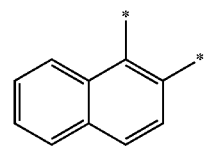
A5-31 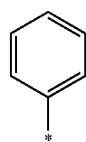 [SMILES: *c1ccccc1] 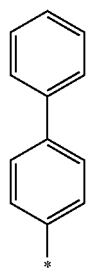 [SMILES: *c1ccc(-c2ccccc2)cc1] 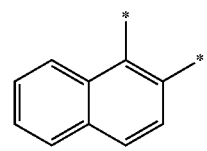
A5-32 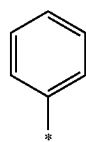 [SMILES: *c1ccccc1] 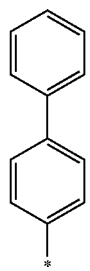 [SMILES: *c1ccc(-c2ccccc2)cc1] 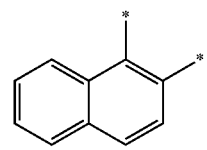

-continued
[Compound Group 5]
| | | | |
|---|---|---|---|
| A5-33 | 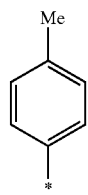 | 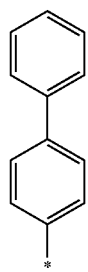 [SMILES: *c1ccc(-c2ccccc2)cc1] | 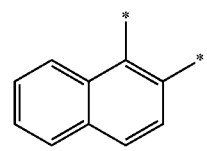 |
| B5-1 | 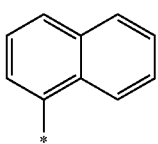 [SMILES: *c1cccc2ccccc12] | 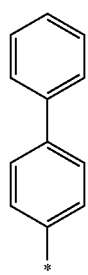 [SMILES: *c1ccc(-c2ccccc2)cc1] | 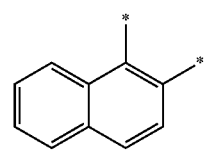 |
| B5-2 | 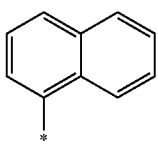 | 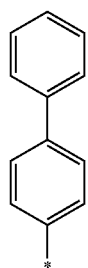 [SMILES: *c1ccc(-c2ccccc2)cc1] | 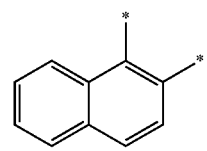 |
| B5-3 | 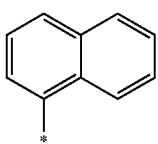 [SMILES: *c1cccc2ccccc12] | 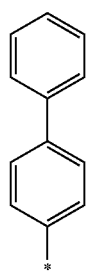 [SMILES: *c1ccc(-c2ccccc2)cc1] | 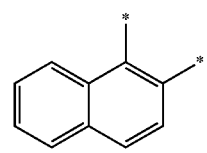 |
| B5-4 | 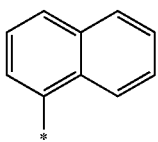 [SMILES: *c1cccc2ccccc12] | 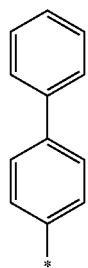 [SMILES: *c1ccc(-c2ccccc2)cc1] | 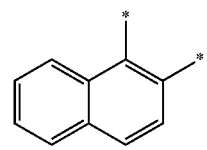 |

-continued
[Compound Group 5]
| | | | |
|---|---|---|---|
| B5-5 | 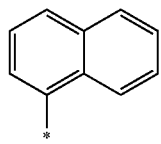 [SMILES: *c1cccc2ccccc12] | 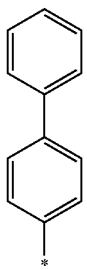 [SMILES: *c1ccc(-c2ccccc2)cc1] | 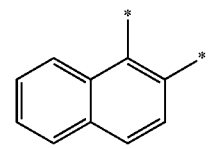 |
| B5-6 | 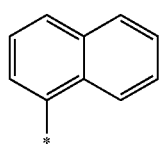 [SMILES: *c1cccc2ccccc12] | 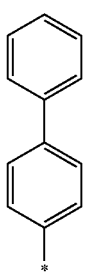 [SMILES: *c1ccc(-c2ccccc2)cc1] | 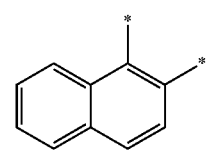 |
| B5-7 | 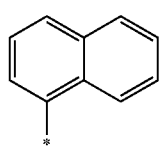 [SMILES: *c1cccc2ccccc12] | 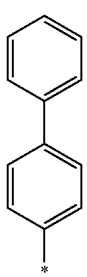 [SMILES: *c1ccc(-c2ccccc2)cc1] | 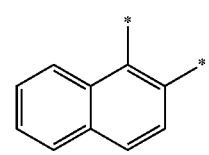 [SMILES: *c1ccc2ccccc2c1*] |
| B5-8 | 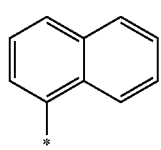 [SMILES: *c1cccc2ccccc12] | 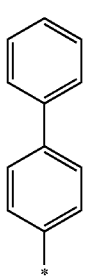 [SMILES: *c1ccc(-c2ccccc2)cc1] | 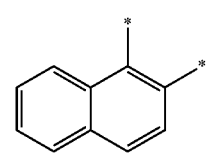 |
| B5-9 | 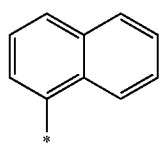 [SMILES: *c1cccc2ccccc12] | 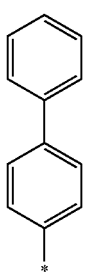 [SMILES: *c1ccc(-c2ccccc2)cc1] | 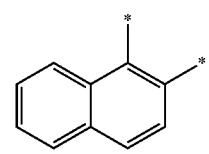 |

-continued
[Compound Group 5]
B5-10 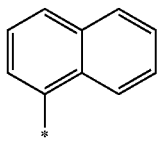 [SMILES: *c1cccc2ccccc12] 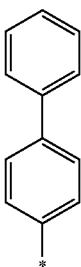 [SMILES: *c1ccc(-c2ccccc2)cc1] 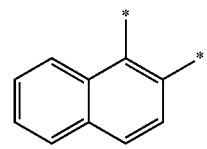
B5-11 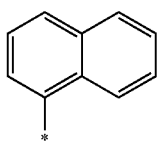 [SMILES: *c1cccc2ccccc12] 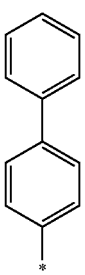 [SMILES: *c1ccc(-c2ccccc2)cc1] 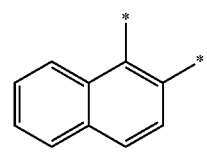
B5-12 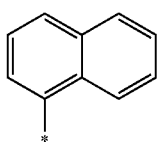 [SMILES: *c1cccc2ccccc12] 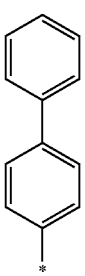 [SMILES: *c1ccc(-c2ccccc2)cc1] 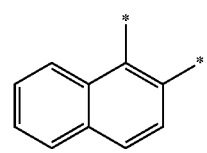 [SMILES: *c1ccc2ccccc2c1*]
B5-13 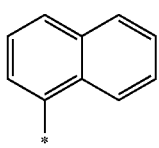 [SMILES: *c1cccc2ccccc12] 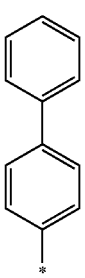 [SMILES: *c1ccc(-c2ccccc2)cc1] 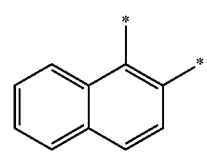
B5-14 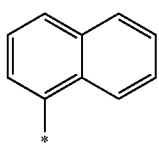 [SMILES: *c1cccc2ccccc12] 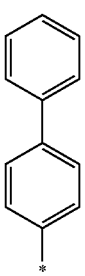 [SMILES: *c1ccc(-c2ccccc2)cc1] 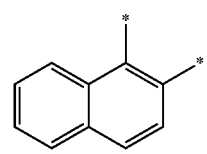

[Compound Group 5]
B5-15 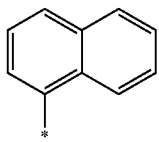 [SMILES: *c1cccc2ccccc12] 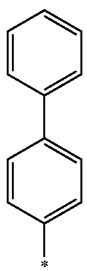 [SMILES: *c1ccc(-c2ccccc2)cc1] 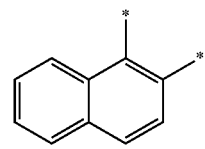
B5-16 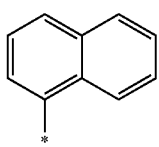 [SMILES: *c1cccc2ccccc12] 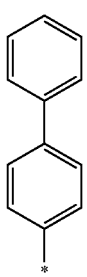 [SMILES: *c1ccc(-c2ccccc2)cc1] 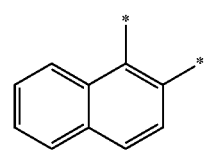
B5-17 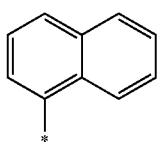 [SMILES: *c1cccc2ccccc12] 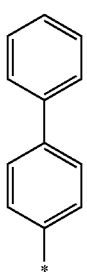 [SMILES: *c1ccc(-c2ccccc2)cc1] 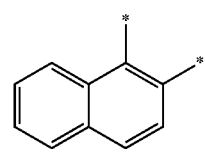 [SMILES: *c1ccc2ccccc2c1*]
B5-18 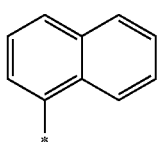 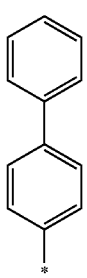 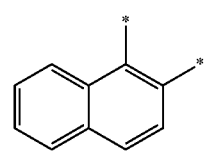
B5-19 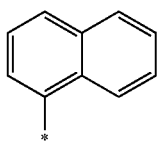 [SMILES: *c1cccc2ccccc12] 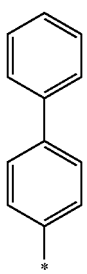 [SMILES: *c1ccc(-c2ccccc2)cc1] 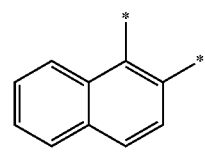

[Compound Group 5]
B5-20 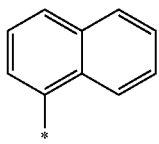 [SMILES: *c1cccc2ccccc12] 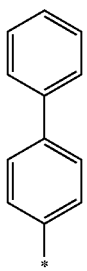 [SMILES: *c1ccc(-c2ccccc2)cc1] 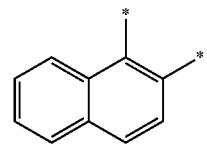
B5-21 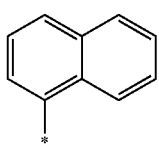 [SMILES: *c1cccc2ccccc12] 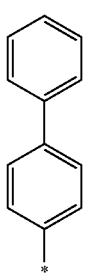 [SMILES: *c1ccc(-c2ccccc2)cc1] 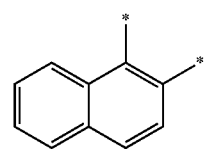
B5-22 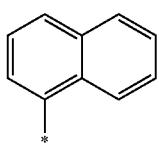 [SMILES: *c1cccc2ccccc12] 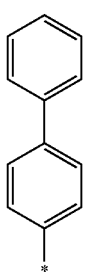 [SMILES: *c1ccc(-c2ccccc2)cc1] 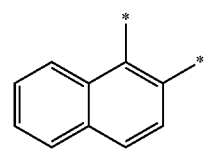 [SMILES: *c1ccc2ccccc2c1*]
B5-23 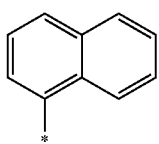 [SMILES: *c1cccc2ccccc12] 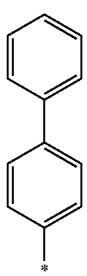 [SMILES: *c1ccc(-c2ccccc2)cc1] 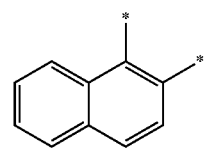
B5-24 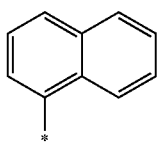 [SMILES: *c1cccc2ccccc12] 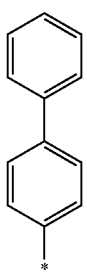 [SMILES: *c1ccc(-c2ccccc2)cc1] 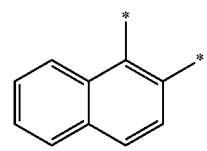

-continued
[Compound Group 5]
B5-25 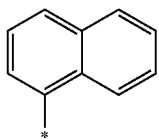 [SMILES: *c1cccc2ccccc12] 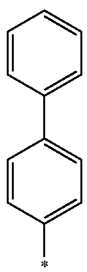 [SMILES: *c1ccc(-c2ccccc2)cc1] 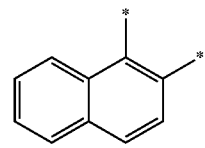
B5-26 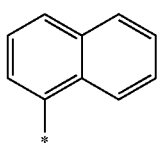 [SMILES: *c1cccc2ccccc12] 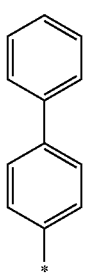 [SMILES: *c1ccc(-c2ccccc2)cc1] 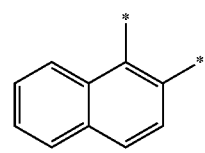
B5-27 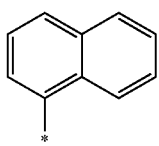 [SMILES: *c1cccc2ccccc12] 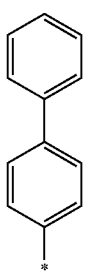 [SMILES: *c1ccc(-c2ccccc2)cc1] 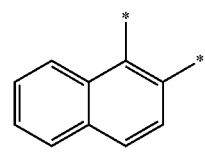
B5-28 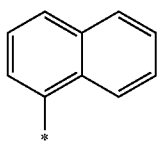 [SMILES: *c1cccc2ccccc12] 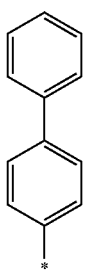 [SMILES: *c1ccc(-c2ccccc2)cc1] 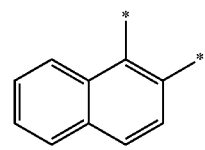
B5-29 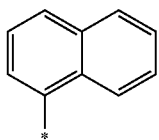 [SMILES: *c1cccc2ccccc12] 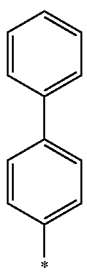 [SMILES: *c1ccc(-c2ccccc2)cc1] 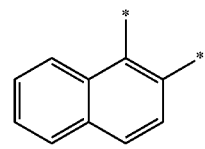

[Compound Group 5]
B5-30 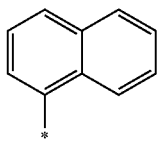 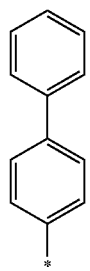 [SMILES: *c1ccc(-c2ccccc2)cc1] 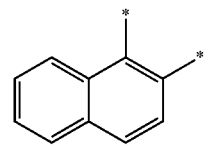
C5-1 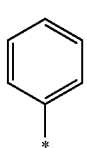 [SMILES: *c1ccccc1] 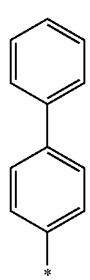 [SMILES: *c1ccc(-c2ccccc2)cc1] 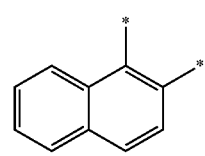 [SMILES: *c1ccc2ccccc2c1*]
C5-2 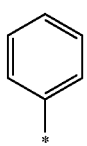 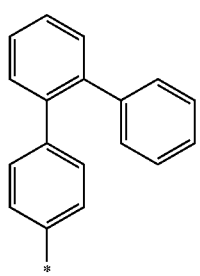 [SMILES: *c1ccc(-c2ccccc2-c2ccccc2)cc1] 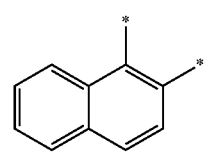
C5-3 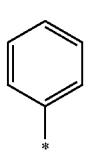 [SMILES: *c1ccccc1] 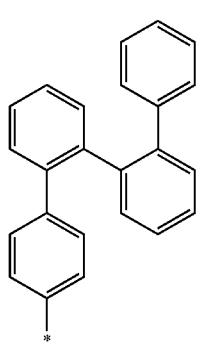 [SMILES: *c1ccc(-c2ccccc2-c2ccccc2-c2ccccc2)cc1] 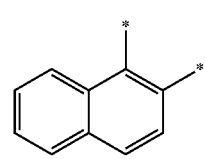 [SMILES: *c1ccc2ccccc2c1*]
C5-4 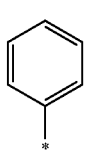 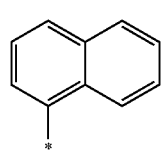 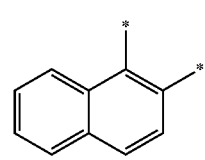
C5-5 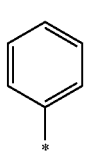 [SMILES: *c1ccccc1] 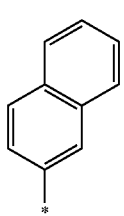 [SMILES: *c1ccc2ccccc2c1] 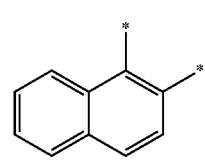

-continued
[Compound Group 5]
C5-6 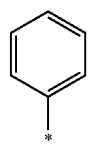 [SMILES: *c1ccccc1] 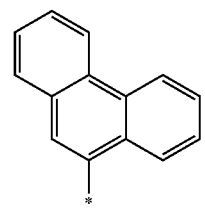 [SMILES: *c1cc2ccccc2c2ccccc12] 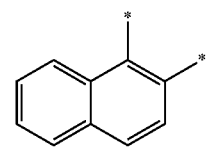
C5-7 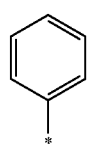 [SMILES: *c1ccccc1] 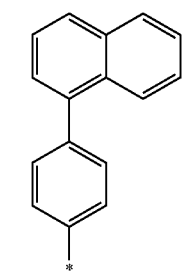 [SMILES: *c1ccc(-c2cccc3ccccc23)cc1] 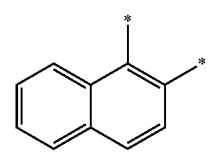
C5-8 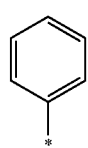 [SMILES: *c1ccccc1] 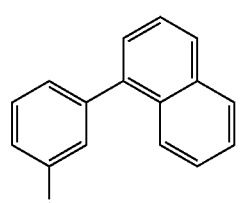 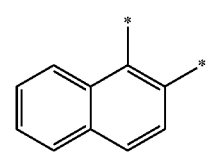
C5-9 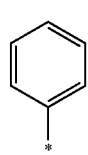 [SMILES: *c1ccccc1] 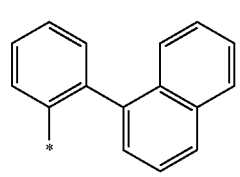 [SMILES: *c1ccccc1-c1cccc2ccccc12] 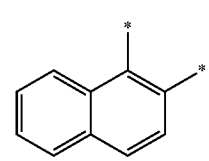
C5-10 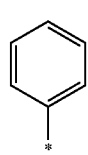 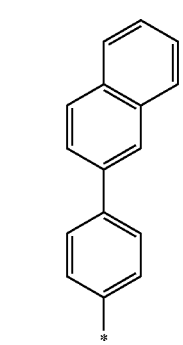 [SMILES: *c1ccc(-c2ccc3ccccc3c2)cc1] 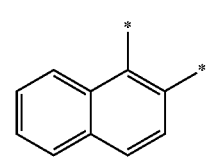
C5-11 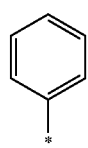 [SMILES: *c1ccccc1] 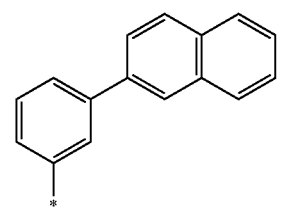 [SMILES: *c1cccc(-c2ccc3ccccc3c2)c1] 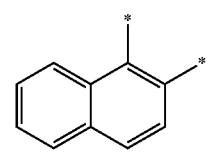
C5-12 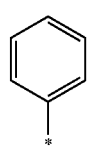 [SMILES: *c1ccccc1] 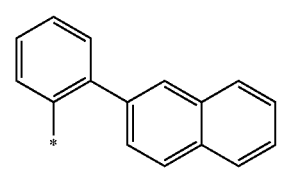 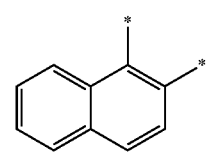

[Compound Group 5]
C5-13 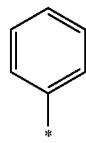 [SMILES: *c1ccccc1] 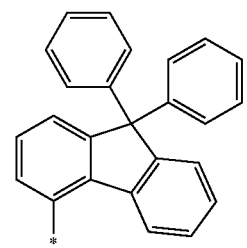 [SMILES: *c1cccc2c1-c1ccccc1C2(c1ccccc1)c1ccccc1] 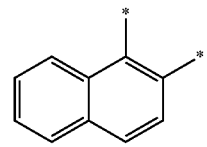
C5-14 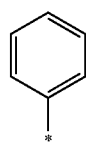 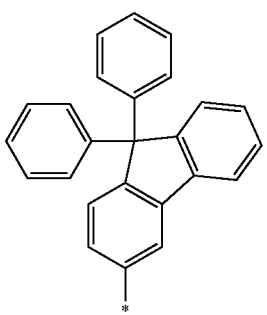 [SMILES: *c1ccc2c(c1)-c1ccccc1C2(c1ccccc1)c1ccccc1] 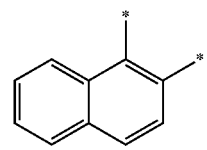
C5-15 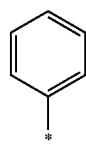 [SMILES: *c1ccccc1] 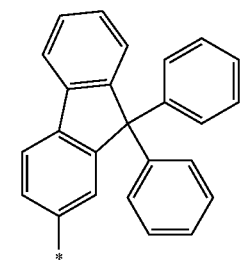 [SMILES: *c1ccc2c(c1)C(c1ccccc1)(c1ccccc1)c1ccccc1-2] 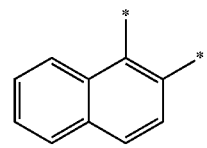 [SMILES: *c1ccc2ccccc2c1*]
C5-16 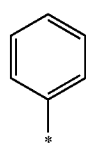 [SMILES: *c1ccccc1] 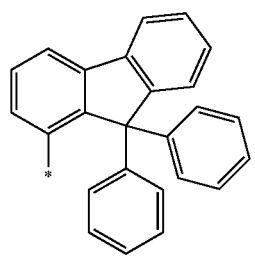 [SMILES: *c1cccc2c1C(c1ccccc1)(c1ccccc1)c1ccccc1-2] 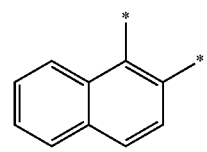 [SMILES: *c1ccc2ccccc2c1*]
C5-17 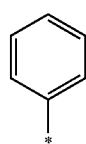 [SMILES: *c1ccccc1] 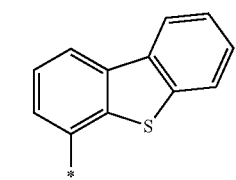 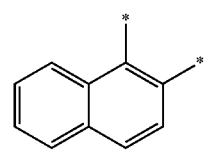
C5-18 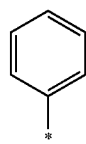 [SMILES: *c1ccccc1] 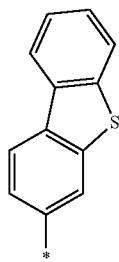 [SMILES: *c1ccc2c(c1)sc1ccccc12] 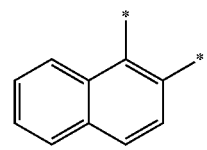

[Compound Group 5]
C5-19 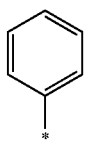 [SMILES: *c1ccccc1] 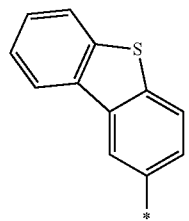 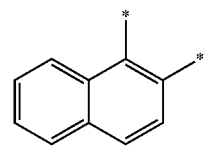 [SMILES: *c1ccc2ccccc2c1*]
C5-20 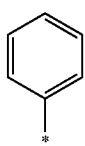 [SMILES: *c1ccccc1] 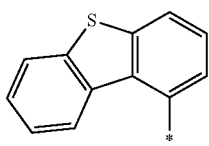 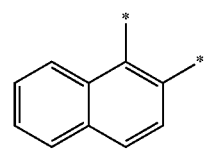
C5-21 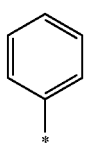 [SMILES: *c1ccccc1] 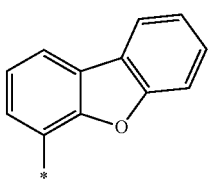 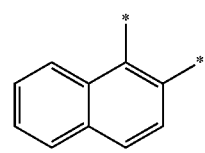
C5-22 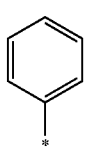 [SMILES: *c1ccccc1] 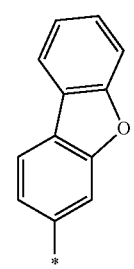 [SMILES: *c1ccc2c(c1)oc1ccccc12] 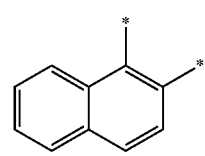
C5-23 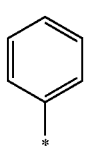 [SMILES: *c1ccccc1] 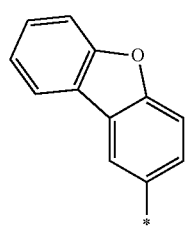 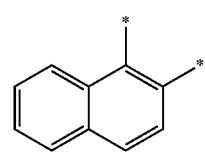
C5-24 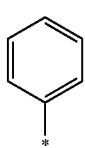 [SMILES: *c1ccccc1] 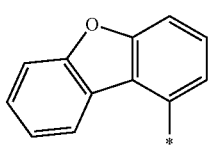 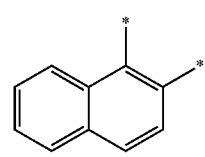
C5-25 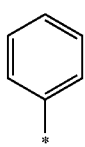 [SMILES: *c1ccccc1] 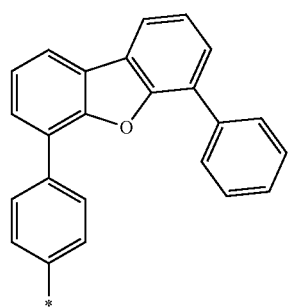 [SMILES: *c1ccc(-c2cccc3c2oc2c(-c4ccccc4)cccc23)cc1] 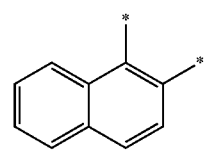

[Compound Group 5]
| | | | |
|---|---|---|---|
| C5-26 | 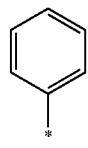 | 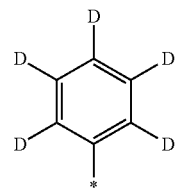 | 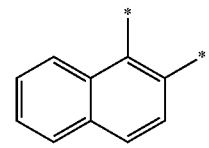 [SMILES: *c1ccc2ccccc2c1*] |
| C5-27 | 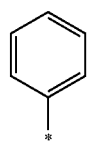 | 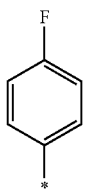 | 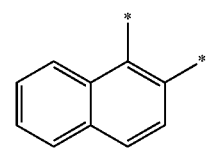 |
| C5-28 | 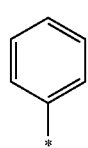 [SMILES: *c1ccccc1] | 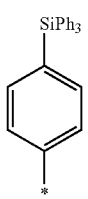 | 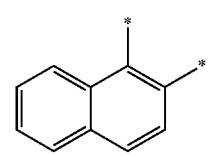 [SMILES: *c1ccc2ccccc2c1*] |
| C5-29 | 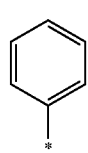 [SMILES: *c1ccccc1] | 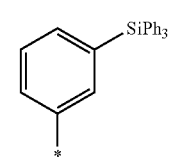 | 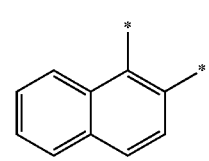 |
| C5-30 | 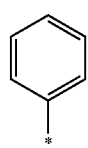 [SMILES: *c1ccccc1] | 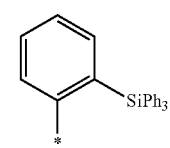 | 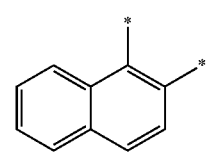 |
| D5-1 | 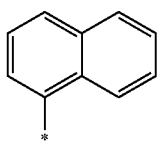 [SMILES: *c1cccc2ccccc12] | 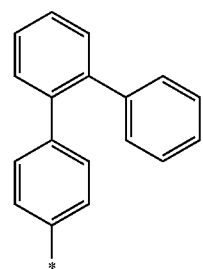 [SMILES: *c1ccc(-c2ccccc2-c2ccccc2)cc1] | 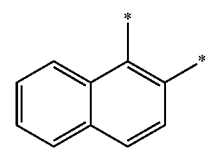 |
| D5-2 | 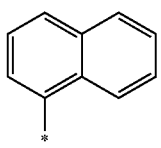 | 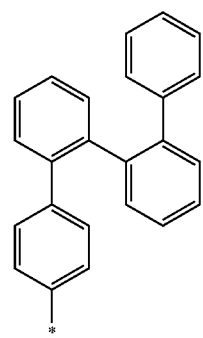 [SMILES: *c1ccc(-c2ccccc2-c2ccccc2-c2ccccc2)cc1] | 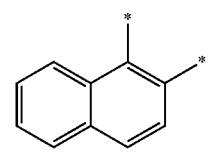 [SMILES: *c1ccc2ccccc2c1*] |

[Compound Group 5]
D5-3 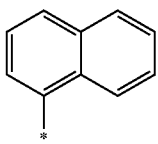 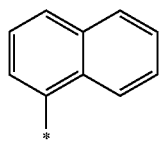 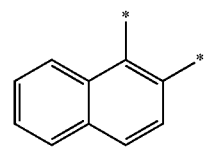 [SMILES: *c1ccc2ccccc2c1*]
D5-4 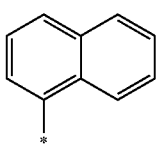 [SMILES: *c1cccc2ccccc12] 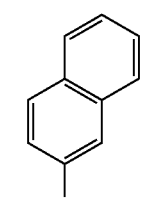 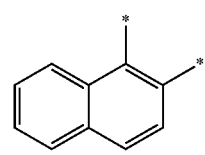 [SMILES: *c1ccc2ccccc2c1*]
D5-5 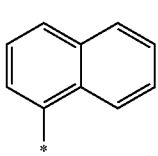 [SMILES: *c1cccc2ccccc12] 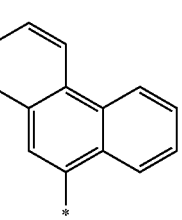 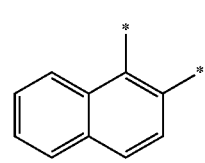
D5-6 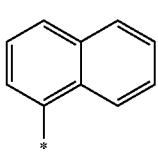 [SMILES: *c1cccc2ccccc12] 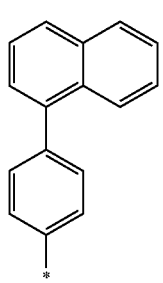 [SMILES: *c1ccc(-c2cccc3ccccc23)cc1] 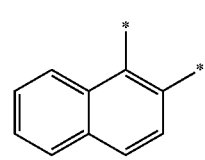 [SMILES: *c1ccc2ccccc2c1*]
D5-7 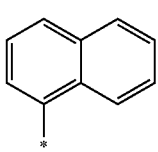 [SMILES: *c1cccc2ccccc12] 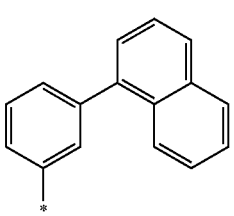 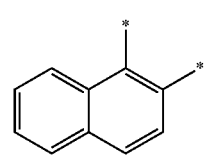
D5-8 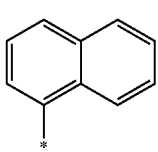 [SMILES: *c1cccc2ccccc12] 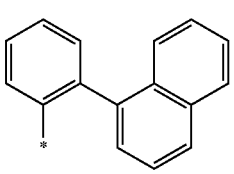 [SMILES: *c1ccccc1-c1cccc2ccccc12] 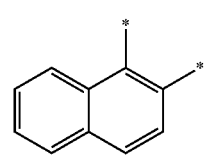
D5-9 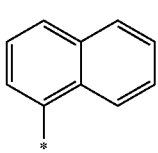 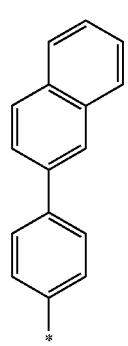 [SMILES: *c1ccc(-c2ccc3ccccc3c2)cc1] 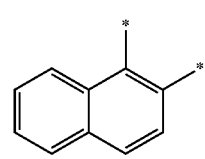

[Compound Group 5]
D5-10 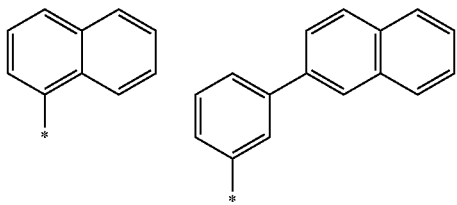 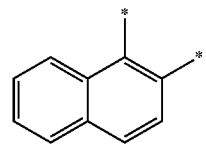
D5-11 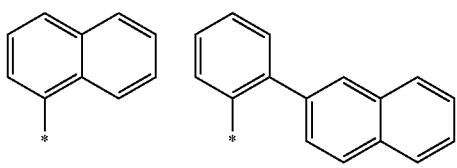 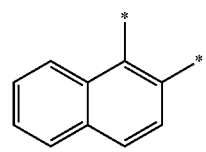
D5-12 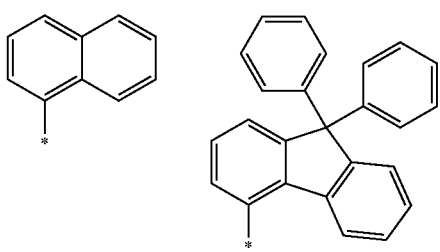 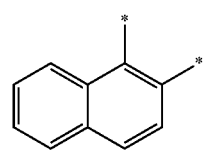
D5-13 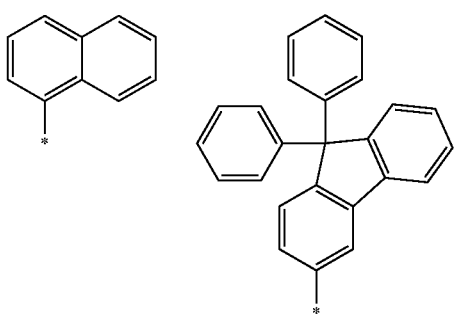 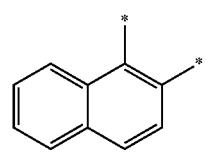
D5-14 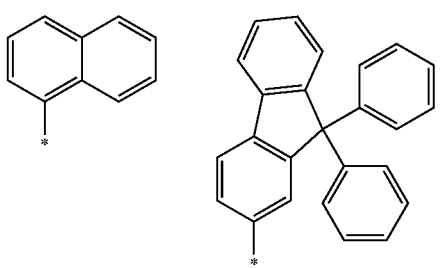 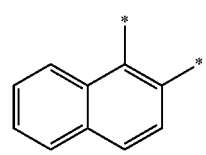
D5-15 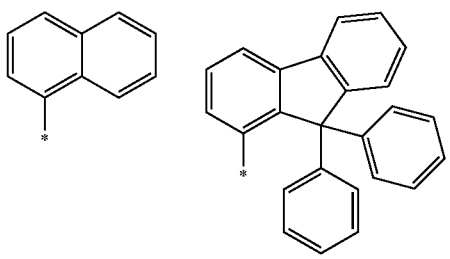 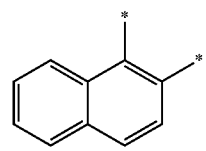

| 1399 | | | 1400 |
|---|---|---|---|
| -continued | | | |
| [Compound Group 5] | | | |
| D5-16 | 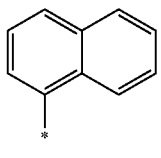 [SMILES: *c1cccc2ccccc12] | 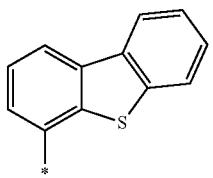 | 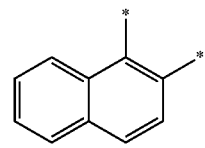 |
| D5-17 | 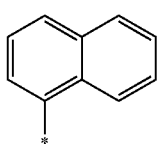 [SMILES: *c1cccc2ccccc12] | 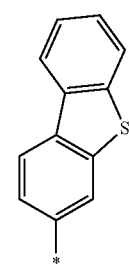 [SMILES: *c1ccc2c(c1)sc1ccccc12] | 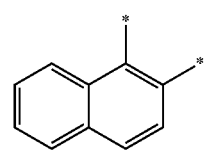 |
| D5-18 | 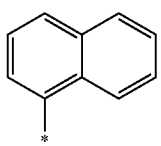 [SMILES: *c1cccc2ccccc12] | 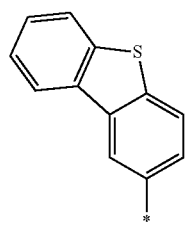 | 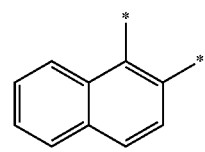 |
| D5-19 | 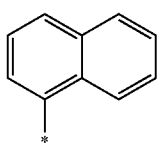 [SMILES: *c1cccc2ccccc12] | 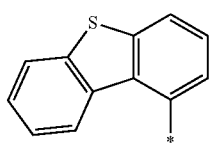 | 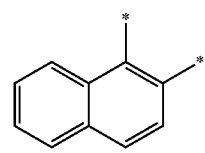 |
| D5-20 | 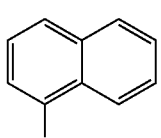 | 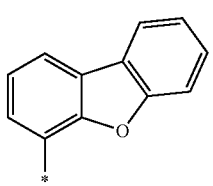 | 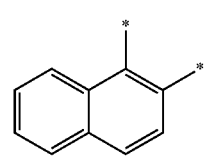 [SMILES: *c1ccc2ccccc2c1*] |
| D5-21 | 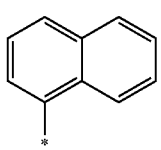 [SMILES: *c1cccc2ccccc12] | 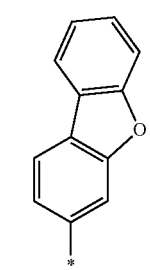 [SMILES: *c1ccc2c(c1)oc1ccccc12] | 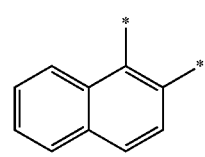 |
| D5-22 | 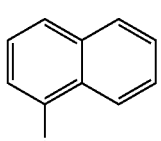 | 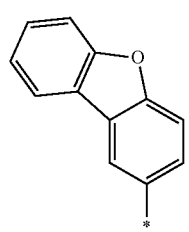 | 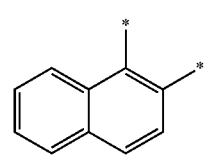 [SMILES: *c1ccc2ccccc2c1*] |

| 1401 | | | 1402 |
|---|---|---|---|
| -continued | | | |
| [Compound Group 5] | | | |
| D5-23 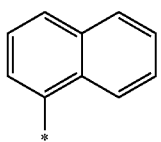 [SMILES: *c1cccc2ccccc12] | 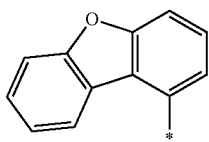 [SMILES: *c1cccc2oc3ccccc3c12] | | 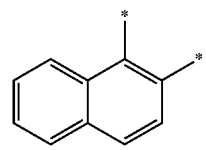 |
| D5-24 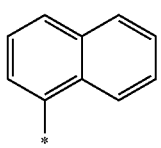 [SMILES: *c1cccc2ccccc12] | 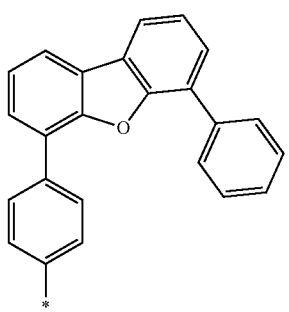 [SMILES: *c1ccc(-c2cccc3c2oc2c(-c4ccccc4)cccc23)cc1] | | 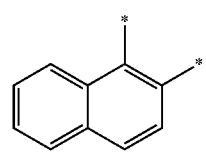 |
| D5-25 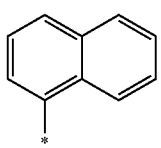 [SMILES: *c1cccc2ccccc12] | 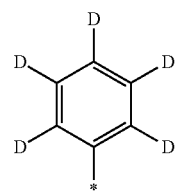 | | 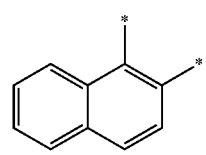 [SMILES: *c1ccc2ccccc2c1*] |
| D5-26 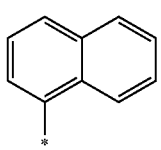 | 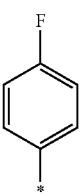 | | 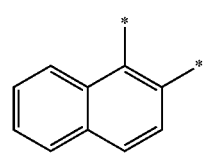 [SMILES: *c1ccc2ccccc2c1*] |
| D5-27 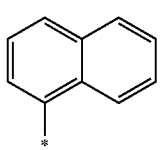 | 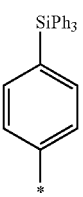 | | 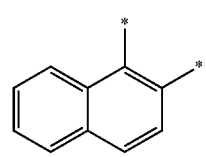 [SMILES: *c1ccc2ccccc2c1*] |
| D5-28 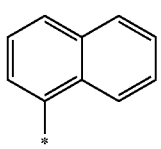 [SMILES: *c1cccc2ccccc12] | 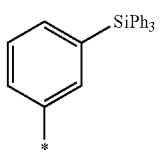 | | 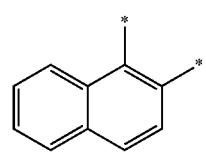 [SMILES: *c1ccc2ccccc2c1*] |
| D5-29 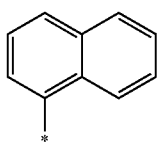 [SMILES: *c1cccc2ccccc12] | 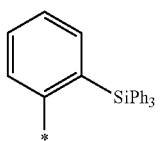 | | 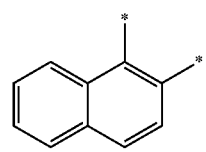 [SMILES: *c1ccc2ccccc2c1*] |

-continued
[Compound Group 5]
D5-30 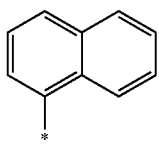 [SMILES: *c1cccc2ccccc12] 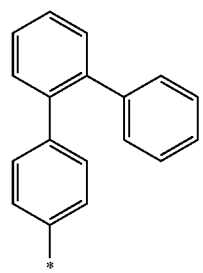 [SMILES: *c1ccc(-c2ccccc2-c2ccccc2)cc1] 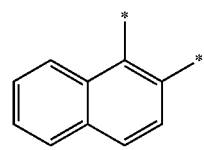
E5-1 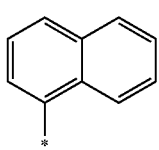 [SMILES: *c1cccc2ccccc12] 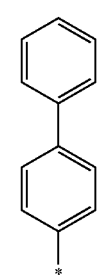 [SMILES: *c1ccc(-c2ccccc2)cc1] 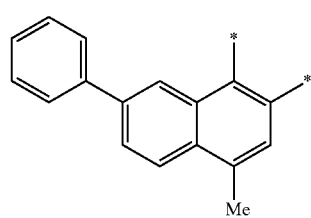 [SMILES: *c1cc(C)c2ccc(-c3ccccc3)cc2c1*]
E5-2 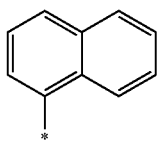 [SMILES: *c1cccc2ccccc12] 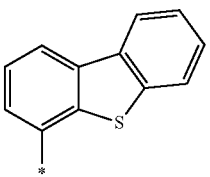 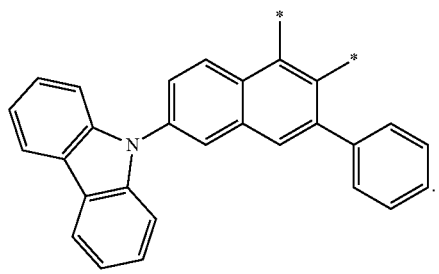 [SMILES: *c1c(-c2ccccc2)cc2cc(-n3c4ccccc4c4ccccc43)ccc2c1*]
* * * * *